US011827699B2

(12) United States Patent
Igawa et al.

(10) Patent No.: US 11,827,699 B2
(45) Date of Patent: Nov. 28, 2023

(54) METHODS FOR PRODUCING ANTIBODIES PROMOTING DISAPPEARANCE OF ANTIGENS HAVING PLURALITY OF BIOLOGICAL ACTIVITIES

(71) Applicant: Chugai Seiyaku Kabushiki Kaisha, Tokyo (JP)

(72) Inventors: Tomoyuki Igawa, Shizuoka (JP); Atsuhiko Maeda, Shizuoka (JP); Shigero Tamba, Shizuoka (JP); Takehisa Kitazawa, Shizuoka (JP); Takeshi Baba, Shizuoka (JP); Yoshinao Ruike, Shizuoka (JP); Junichi Nezu, Shizuoka (JP)

(73) Assignee: Chugai Seiyaku Kabushiki Kaisha, Tokyo (JP)

(*) Notice: Subject to any disclaimer, the term of this patent is extended or adjusted under 35 U.S.C. 154(b) by 0 days.

(21) Appl. No.: 16/028,140

(22) Filed: Jul. 5, 2018

(65) Prior Publication Data

US 2019/0185557 A1 Jun. 20, 2019

Related U.S. Application Data

(63) Continuation of application No. 14/347,034, filed as application No. PCT/JP2012/075083 on Sep. 28, 2012, now abandoned.

(30) Foreign Application Priority Data

Sep. 30, 2011 (JP) ................................ 2011-217043

(51) Int. Cl.

| | |
|---|---|
| ***A61K 39/00*** | (2006.01) |
| ***C07K 16/24*** | (2006.01) |
| ***C07K 16/00*** | (2006.01) |
| ***C07K 16/28*** | (2006.01) |
| ***C07K 16/18*** | (2006.01) |
| ***C07K 16/22*** | (2006.01) |

(52) U.S. Cl.

CPC .............. *C07K 16/24* (2013.01); *C07K 16/00* (2013.01); *C07K 16/18* (2013.01); *C07K 16/22* (2013.01); *C07K 16/248* (2013.01); *C07K 16/2866* (2013.01); *A61K 2039/505* (2013.01); *C07K 2317/20* (2013.01); *C07K 2317/21* (2013.01); *C07K 2317/31* (2013.01); *C07K 2317/52* (2013.01); *C07K 2317/55* (2013.01); *C07K 2317/64* (2013.01); *C07K 2317/70* (2013.01); *C07K 2317/71* (2013.01); *C07K 2317/72* (2013.01); *C07K 2317/76* (2013.01); *C07K 2317/92* (2013.01); *C07K 2317/94* (2013.01)

(58) Field of Classification Search

CPC ........ C07K 16/00; C07K 16/18; C07K 16/22; C07K 16/24; C07K 16/248; C07K 16/2866; C07K 2317/20; C07K 2317/21; C07K 2317/31; C07K 2317/52; C07K 2317/55; C07K 2317/64; C07K 2317/70; C07K 2317/71; C07K 2317/72; C07K 2317/76; C07K 2317/92; C07K 2317/94; A61K 2039/505

See application file for complete search history.

(56) References Cited

U.S. PATENT DOCUMENTS

| | | | |
|---|---|---|---|
| 4,689,299 | A | 8/1987 | Insel et al. |
| 4,801,687 | A | 1/1989 | Ngo |
| 5,202,253 | A | 4/1993 | Esmon et al. |
| 5,322,678 | A | 6/1994 | Morgan et al. |
| 5,501,854 | A | 3/1996 | Raso |
| 5,585,089 | A | 12/1996 | Queen et al. |
| 5,639,641 | A | 6/1997 | Pedersen et al. |
| 5,795,965 | A | 8/1998 | Tsuchiya et al. |
| 5,830,478 | A | 11/1998 | Raso et al. |
| 5,935,935 | A | 8/1999 | Connelly et al. |
| 5,990,286 | A | 11/1999 | Khawli et al. |
| 6,074,642 | A | 6/2000 | Wang et al. |
| 6,329,511 | B1 | 12/2001 | Vasquez et al. |
| 6,485,943 | B2 | 11/2002 | Stevens et al. |
| 6,602,684 | B1 | 8/2003 | Umana et al. |
| 6,677,436 | B1 | 1/2004 | Sato et al. |
| 6,737,056 | B1 | 5/2004 | Presta |
| 6,884,879 | B1 | 4/2005 | Baca et al. |
| 6,913,747 | B1 | 7/2005 | Co et al. |
| 7,052,873 | B2 | 5/2006 | Tsuchiya |
| 7,276,585 | B2 | 10/2007 | Lazar et al. |
| 7,662,925 | B2 | 2/2010 | Lazar et al. |
| 7,955,590 | B2 | 6/2011 | Gillies et al. |
| 7,960,512 | B2 | 6/2011 | Stavenhagen et al. |

(Continued)

FOREIGN PATENT DOCUMENTS

| | | |
|---|---|---|
| AU | 2012/222252 | 10/2013 |
| CA | 2 647 846 | 10/2007 |

(Continued)

OTHER PUBLICATIONS

U.S. Appl. No. 16/264,735, Igawa et al.

(Continued)

*Primary Examiner* — Robert S Landsman
(74) *Attorney, Agent, or Firm* — Fish & Richardson P.C.

(57) ABSTRACT

The present inventors newly discovered that even if an antigen-binding molecule inhibits in vitro some of the physiological activities of an antigen having two or more physiological activities without inhibiting the remaining physiological activities, the molecule can promote elimination of the antigen from blood (from serum or plasma) and as a result reduce the physiological activities in vivo, when the antigen-binding molecule is conferred with the properties: (i) of binding to human FcRn under an acidic pH range condition; (ii) of binding under a neutral pH range condition to human Fc receptor stronger than native human IgG, and (iii) that its antigen-binding activity alters according to the ion concentration.

20 Claims, 70 Drawing Sheets

Specification includes a Sequence Listing.

(56) References Cited

U.S. PATENT DOCUMENTS 8,101,720 B2 1/2012 Lazar et al.
8,188,231 B2 5/2012 Lazar et al.
8,329,867 B2 12/2012 Lazar et al.
8,367,805 B2 2/2013 Chamberlain et al.
8,388,955 B2 3/2013 Lazar et al.
8,562,991 B2 10/2013 Igawa et al.
8,568,726 B2 10/2013 Beaumont et al.
8,735,545 B2 5/2014 Lazar et al.
8,802,820 B2 8/2014 Chamberlain et al.
9,029,515 B2 5/2015 Pons et al.
9,079,949 B1 7/2015 Andrien et al.
9,096,651 B2 8/2015 Igawa et al.
9,107,861 B1 8/2015 Andrien, Jr. et al.
9,200,079 B2 12/2015 Chamberlain et al.
9,765,135 B2 9/2017 Ruike
9,828,429 B2 11/2017 Igawa et al.
9,868,948 B2 1/2018 Igawa et al.
9,890,377 B2 2/2018 Igawa et al.
9,969,800 B2 5/2018 Igawa et al.
10,000,560 B2 6/2018 Ruike et al.
10,024,867 B2 7/2018 Igawa
10,253,100 B2 4/2019 Igawa et al.
10,472,623 B2 11/2019 Igawa et al.
10,618,965 B2 4/2020 Igawa et al.
10,919,953 B2 2/2021 Katada et al.
11,046,784 B2 6/2021 Igawa et al.
11,248,053 B2 2/2022 Igawa et al.
11,267,868 B2 3/2022 Mimoto et al.
11,359,194 B2 6/2022 Igawa et al.
11,371,039 B2 6/2022 Igawa et al.
2002/0098193 A1 7/2002 Ward
2002/0142374 A1 10/2002 Gallo et al.
2002/0164339 A1 11/2002 Do et al.
2003/0059937 A1 3/2003 Ruben et al.
2003/0224397 A1 12/2003 Lowman et al.
2004/0001822 A1 1/2004 Levanon et al.
2004/0001839 A1 1/2004 Levanon et al.
2004/0002450 A1 1/2004 Lazarovits et al.
2004/0081651 A1 4/2004 Karpusas et al.
2004/0110226 A1 6/2004 Lazar et al.
2004/0133357 A1 7/2004 Zhong et al.
2004/0236080 A1 11/2004 Aburatani et al.
2005/0014934 A1 1/2005 Hinton et al.
2005/0032114 A1 2/2005 Hinton et al.
2005/0095243 A1 5/2005 Chan et al.
2005/0244403 A1 11/2005 Lazar et al.
2005/0260213 A1 11/2005 Koenig et al.
2005/0260711 A1 11/2005 Datta et al.
2006/0014156 A1 1/2006 Rabbani et al.
2006/0019342 A1 1/2006 Dall Acqua et al.
2006/0057149 A1 3/2006 Johnson et al.
2006/0063228 A1 3/2006 Kasaian et al.
2006/0067930 A1 3/2006 Adams et al.
2006/0134709 A1 6/2006 Stavenhagen et al.
2006/0141456 A1 6/2006 Edwards et al.
2006/0153860 A1 7/2006 Cho et al.
2007/0009523 A1 1/2007 Presta
2007/0036785 A1 2/2007 Kishimoto et al.
2007/0037734 A1 2/2007 Rossi et al.
2007/0041978 A1 2/2007 Hattori et al.
2007/0059312 A1 3/2007 Baca et al.
2007/0135620 A1 6/2007 Chamberlain et al.
2007/0148164 A1 6/2007 Farrington et al.
2007/0160598 A1 7/2007 Dennis et al.
2007/0224188 A1 9/2007 Allan et al.
2007/0231329 A1 10/2007 Lazar et al.
2007/0237767 A1 10/2007 Lazar et al.
2007/0248602 A1 10/2007 Lazar et al.
2007/0253951 A1 11/2007 Ng et al.
2007/0269371 A1 11/2007 Krummen et al.
2008/0044417 A1 2/2008 Johnson et al.
2008/0089892 A1 4/2008 Allan et al.
2008/0138349 A1 6/2008 Stavenhagen et al.
2008/0166756 A1 7/2008 Tsuchiya et al.
2008/0181890 A1 7/2008 Lazar et al.
2008/0199471 A1 8/2008 Bernett et al.
2009/0035836 A1 2/2009 Datta et al.
2009/0041770 A1 2/2009 Chamberlain et al.
2009/0042291 A1 2/2009 Chu et al.
2009/0053240 A1 2/2009 Lazar et al.
2009/0076251 A1 3/2009 Koenig et al.
2009/0136485 A1 5/2009 Chu et al.
2009/0142340 A1 6/2009 Lazar
2009/0215991 A1 8/2009 Lazar et al.
2009/0263392 A1 10/2009 Igawa et al.
2009/0324589 A1 12/2009 Igawa et al.
2010/0003254 A1 1/2010 Hattori et al.
2010/0098730 A1 4/2010 Lowman et al.
2010/0184959 A1 7/2010 Guler-Gane et al.
2010/0216187 A1 8/2010 Lasters et al.
2010/0239577 A1 9/2010 Igawa et al.
2010/0249482 A1 9/2010 Chung et al.
2010/0292443 A1 11/2010 Sabbadini et al.
2010/0298542 A1 11/2010 Igawa et al.
2011/0044986 A1 2/2011 Biere-Citron et al.
2011/0076275 A1 3/2011 Igawa et al.
2011/0098450 A1 4/2011 Igawa et al.
2011/0111406 A1 5/2011 Igawa et al.
2011/0150888 A1 6/2011 Foltz et al.
2011/0223658 A1 9/2011 Beliard et al.
2011/0229489 A1 9/2011 Pons et al.
2011/0245473 A1 10/2011 Igawa et al.
2012/0009188 A1 1/2012 Behrens et al.
2012/0093818 A1 4/2012 Jackson et al.
2012/0303083 A1 11/2012 Agnetti et al.
2012/0321620 A1 12/2012 Chu et al.
2013/0011866 A1 1/2013 Igawa et al.
2013/0085265 A1 4/2013 Jackson et al.
2013/0131319 A1 5/2013 Igawa et al.
2013/0247234 A1 9/2013 McWhirter et al.
2013/0259876 A1 10/2013 Murphy et al.
2013/0303396 A1 11/2013 Igawa et al.
2013/0336963 A1 12/2013 Igawa et al.
2014/0044730 A1 2/2014 Yancopoulos et al.
2014/0082760 A1 3/2014 McWhirter et al.
2014/0086916 A1 3/2014 Zha
2014/0093496 A1 4/2014 Mimoto et al.
2014/0105889 A1 4/2014 Igawa et al.
2014/0112926 A1 4/2014 Liu
2014/0234340 A1 8/2014 Igawa et al.
2014/0255398 A1 9/2014 Igawa et al.
2014/0335089 A1 11/2014 Igawa et al.
2014/0356371 A1 12/2014 Swergold et al.
2014/0363428 A1 12/2014 Igawa et al.
2015/0050269 A1 2/2015 Igawa et al.
2015/0056182 A1 2/2015 Igawa et al.
2015/0166654 A1 6/2015 Igawa et al.
2015/0203577 A1 7/2015 Igawa et al.
2015/0210763 A1 7/2015 Kuramochi et al.
2015/0252107 A1 9/2015 Stevis et al.
2015/0284465 A1 10/2015 Igawa et al.
2015/0299296 A1 10/2015 Katada et al.
2015/0299313 A1 10/2015 Igawa et al.
2015/0315278 A1 11/2015 Igawa et al.
2015/0353630 A1 12/2015 Igawa et al.
2016/0039912 A1 2/2016 Mimoto et al.
2016/0046693 A1 2/2016 Igawa et al.
2016/0229908 A1 8/2016 Igawa et al.
2016/0244526 A1 8/2016 Igawa et al.
2017/0022270 A1 1/2017 Igawa et al.
2017/0174778 A1 6/2017 Shusta et al.
2017/0226206 A1 8/2017 Igawa et al.
2018/0142027 A1 5/2018 Igawa et al.
2018/0258161 A1 9/2018 Igawa et al.
2019/0112393 A1 4/2019 Igawa et al.
2019/0218309 A1 7/2019 Igawa et al.
2019/0233525 A1 8/2019 Igawa et al.
2019/0359704 A1 11/2019 Igawa et al.
2020/0172610 A1 6/2020 Igawa et al.
2020/0181257 A1 6/2020 Kuramochi et al.
2020/0199241 A1 6/2020 Igawa et al.
2021/0122812 A1 4/2021 Igawa et al.
2021/0261648 A1 8/2021 Katada et al.
2021/0324109 A1 10/2021 Igawa et al.

(56) References Cited

U.S. PATENT DOCUMENTS

| | | | |
|---|---|---|---|
| 2022/0389105 A1 | 12/2022 | Igawa et al. |
| 2022/0389118 A1 | 12/2022 | Igawa et al. |
| 2022/0411483 A1 | 12/2022 | Mimoto et al. |
| 2023/0140797 A1 | 5/2023 | Igawa et al. |

FOREIGN PATENT DOCUMENTS

| | | |
|---|---|---|
| CA | 2 911 000 | 10/2007 |
| CA | 2 700 986 | 4/2009 |
| CA | 2 721 052 | 10/2009 |
| CA | 2 794 860 | 10/2011 |
| CA | 2 827 923 | 8/2012 |
| CA | 2 831 770 | 10/2012 |
| CN | 1274289 | 11/2000 |
| CN | 1763097 | 4/2006 |
| CN | 101001873 | 7/2007 |
| CN | 101014619 | 8/2007 |
| CN | 101098890 | 1/2008 |
| CN | 101932593 | 12/2010 |
| CN | 102056946 | 5/2011 |
| CN | 102149729 | 8/2011 |
| CN | 103492565 | 1/2014 |
| CN | 102633880 | 2/2015 |
| CN | 101874042 | 9/2018 |
| EA | 004317 | 2/2004 |
| EP | 0 091 539 A | 10/1983 |
| EP | 0 182 495 | 5/1986 |
| EP | 0 329 185 | 4/1994 |
| EP | 0 783 893 | 7/1997 |
| EP | 1 069 185 | 1/2001 |
| EP | 1 773 391 | 4/2007 |
| EP | 1 601 697 | 5/2007 |
| EP | 1 787 998 | 5/2007 |
| EP | 1 870 459 | 12/2007 |
| EP | 2 006 381 | 12/2008 |
| EP | 2 009 101 | 12/2008 |
| EP | 2 189 526 | 5/2010 |
| EP | 2 196 541 | 6/2010 |
| EP | 2 202 245 | 6/2010 |
| EP | 2 206 775 A | 7/2010 |
| EP | 2 275 443 | 1/2011 |
| EP | 2 314 618 | 4/2011 |
| EP | 2 366 713 | 9/2011 |
| EP | 2 368 911 | 9/2011 |
| EP | 2 409 990 | 1/2012 |
| EP | 2 543 730 | 1/2013 |
| EP | 2 647 706 | 10/2013 |
| EP | 2 679 681 | 1/2014 |
| EP | 2 698 431 | 2/2014 |
| EP | 2 762 166 | 8/2014 |
| EP | 2 765 192 | 8/2014 |
| EP | 2 818 183 A | 12/2014 |
| EP | 2 889 377 | 7/2015 |
| JP | S61-117457 | 6/1986 |
| JP | S63-52890 | 3/1988 |
| JP | H01-144991 | 6/1989 |
| JP | H02-028200 | 1/1990 |
| JP | H02-501112 | 4/1990 |
| JP | H02-163085 | 6/1990 |
| JP | H03-500644 | 2/1991 |
| JP | H03-504332 | 9/1991 |
| JP | 07-67688 | 3/1995 |
| JP | 2003-512019 | 4/2003 |
| JP | 2004-073210 | 3/2004 |
| JP | 2004-511426 | 4/2004 |
| JP | 2005-501514 | 1/2005 |
| JP | 2005-101105 | 3/2005 |
| JP | 2005-535341 | 11/2005 |
| JP | 2005-378266 | 12/2005 |
| JP | 2007-532139 | 11/2007 |
| JP | 2008-503720 | 2/2008 |
| JP | 2008-505174 | 2/2008 |
| JP | 2008-510466 | 4/2008 |
| JP | 2008-511292 | 4/2008 |
| JP | 2008-519860 | 6/2008 |
| JP | 2010-505436 | 2/2010 |
| JP | 2010-079667 | 3/2010 |
| JP | 2010-514460 | 5/2010 |
| JP | 2010-250830 | 11/2010 |
| JP | 2011-507963 | 3/2011 |
| JP | 4652414 | 3/2011 |
| JP | 2011-184418 | 9/2011 |
| JP | 2012-505833 | 3/2012 |
| JP | 5144499 | 2/2013 |
| JP | 2013-518131 | 5/2013 |
| JP | 2013-521772 | 6/2013 |
| JP | 2013-165716 | 8/2013 |
| JP | 5334319 | 11/2013 |
| JP | 2014-528906 | 10/2014 |
| JP | 2015-130883 | 7/2015 |
| KR | 2010/0074220 | 7/2010 |
| KR | 2011/0004435 | 1/2011 |
| MX | 2013/006109 | 1/2014 |
| RU | 2147442 | 4/2000 |
| RU | 2225721 | 3/2004 |
| RU | 2004/128259 | 8/2005 |
| RU | 2266298 | 12/2005 |
| RU | 2005/112742 | 1/2006 |
| RU | 2337107 | 10/2008 |
| RU | 2007/121679 | 12/2008 |
| RU | 2367667 | 9/2009 |
| RU | 2390527 | 5/2010 |
| RU | 2430111 | 9/2011 |
| RU | 2010/116152 | 11/2011 |
| RU | 2434882 | 11/2011 |
| SG | 183867 | 10/2012 |
| SG | 192945 | 9/2013 |
| TW | 2010/00127 | 1/2010 |
| TW | 2012/02419 | 1/2012 |
| WO | WO 83/03678 | 10/1983 |
| WO | WO 88/04692 | 6/1988 |
| WO | WO 89/01343 | 2/1989 |
| WO | WO 90/07524 | 7/1990 |
| WO | WO 91/12023 | 8/1991 |
| WO | WO 92/19759 | 11/1992 |
| WO | WO 93/17105 | 9/1993 |
| WO | WO 95/02187 | 1/1995 |
| WO | WO 95/14710 | 6/1995 |
| WO | WO 95/29697 | 11/1995 |
| WO | WO 96/11020 | 4/1996 |
| WO | WO 96/12503 | 5/1996 |
| WO | WO 97/20858 | 6/1997 |
| WO | WO 97/34631 | 9/1997 |
| WO | WO 98/03546 | 1/1998 |
| WO | WO 98/46257 | 10/1998 |
| WO | WO 99/18212 | 4/1999 |
| WO | WO 99/51743 | 10/1999 |
| WO | WO 99/58572 | 11/1999 |
| WO | WO 00/014220 | 3/2000 |
| WO | WO 00/42072 | 7/2000 |
| WO | WO 01/30854 | 5/2001 |
| WO | WO 01/82899 | 11/2001 |
| WO | WO 02/060919 | 8/2002 |
| WO | WO 2003/000883 | 1/2003 |
| WO | WO 03/020949 | 3/2003 |
| WO | WO 03/057881 | 7/2003 |
| WO | WO 03/070760 | 8/2003 |
| WO | WO 2003/070760 | 8/2003 |
| WO | WO 03/105757 | 12/2003 |
| WO | WO 2003/107009 | 12/2003 |
| WO | WO 2004/007553 | 1/2004 |
| WO | WO 2004/016740 | 2/2004 |
| WO | WO 2004/029207 | 4/2004 |
| WO | WO 2004/035752 | 4/2004 |
| WO | WO 2004/039826 | 5/2004 |
| WO | WO 2004/068931 | 8/2004 |
| WO | WO 2004/092219 | 10/2004 |
| WO | WO 2004/096273 | 11/2004 |
| WO | WO 2004/099249 | 11/2004 |
| WO | WO 2005/035756 | 4/2005 |
| WO | WO 2005/037867 | 4/2005 |
| WO | WO 2005/047327 | 5/2005 |
| WO | WO 2005/059106 | 6/2005 |
| WO | WO 2005/067620 | 7/2005 |

(56) References Cited

FOREIGN PATENT DOCUMENTS

| | | |
|---|---|---|
| WO | WO 2005/070963 | 8/2005 |
| WO | WO 2005/077981 | 8/2005 |
| WO | WO 2005/080429 | 9/2005 |
| WO | WO 2005/112564 | 12/2005 |
| WO | WO 2005/115452 | 12/2005 |
| WO | WO 2005/121180 | 12/2005 |
| WO | WO 2005/123126 | 12/2005 |
| WO | WO 2005/123780 | 12/2005 |
| WO | WO 2006/004663 | 1/2006 |
| WO | WO 2006/016644 | 2/2006 |
| WO | WO 2006/019447 | 2/2006 |
| WO | WO 2006/020114 | 2/2006 |
| WO | WO 2006/023403 | 3/2006 |
| WO | WO 2006/030200 | 3/2006 |
| WO | WO 2006/030220 | 3/2006 |
| WO | WO 2006/031370 | 3/2006 |
| WO | WO 2006/050166 | 5/2006 |
| WO | WO 2006/050491 | 5/2006 |
| WO | WO 2006/053301 | 5/2006 |
| WO | WO 2006/066598 | 6/2006 |
| WO | WO 2006/067913 | 6/2006 |
| WO | WO 2006/082052 | 8/2006 |
| WO | WO 2006/088478 | 8/2006 |
| WO | WO 2009/095235 | 8/2006 |
| WO | WO 2006/105338 | 10/2006 |
| WO | WO 2006/106905 | 10/2006 |
| WO | WO 2006/109592 | 10/2006 |
| WO | WO 2006/116260 | 11/2006 |
| WO | WO 2006/121852 | 11/2006 |
| WO | WO 2006/130834 | 12/2006 |
| WO | WO 2007/012614 | 2/2007 |
| WO | WO 2007/021841 | 2/2007 |
| WO | WO 2007/024249 | 3/2007 |
| WO | WO 2007/024535 | 3/2007 |
| WO | WO 2007/041635 | 4/2007 |
| WO | WO 2007/060411 | 5/2007 |
| WO | WO 2007/076524 | 7/2007 |
| WO | WO 2007/084253 | 7/2007 |
| WO | WO 2007/114319 | 10/2007 |
| WO | WO 2007/114325 | 10/2007 |
| WO | WO 2007/142325 | 12/2007 |
| WO | WO 2008/002933 | 1/2008 |
| WO | WO 2008/022152 | 2/2008 |
| WO | WO 2008/043822 | 4/2008 |
| WO | WO 2008/060785 | 5/2008 |
| WO | WO 2008/091954 | 7/2008 |
| WO | WO 2008/092117 | 7/2008 |
| WO | WO 2008/143954 | 11/2008 |
| WO | WO 2008/150494 | 12/2008 |
| WO | WO 2009/006338 | 1/2009 |
| WO | WO 2009/008529 | 1/2009 |
| WO | WO 2009/041062 | 4/2009 |
| WO | WO 2009/041643 | 4/2009 |
| WO | WO 2009/053358 | 4/2009 |
| WO | WO 2009/058492 | 5/2009 |
| WO | WO 2009/062083 | 5/2009 |
| WO | WO 2009/086320 | 7/2009 |
| WO | WO 2009/089846 | 7/2009 |
| WO | WO 2009/125825 | 10/2009 |
| WO | WO 2009/131702 | 10/2009 |
| WO | WO 2009/139822 | 11/2009 |
| WO | WO 2009/155513 | 12/2009 |
| WO | WO 2010/015608 | 2/2010 |
| WO | WO 2010/035769 | 4/2010 |
| WO | WO 2010/045193 | 4/2010 |
| WO | WO 2010/058860 | 5/2010 |
| WO | WO 2010/077854 | 7/2010 |
| WO | WO 2010/081173 | 7/2010 |
| WO | WO 2010/085682 | 7/2010 |
| WO | WO 2010/106180 | 9/2010 |
| WO | WO 2010/106812 | 9/2010 |
| WO | WO 2010/107109 | 9/2010 |
| WO | WO 2010/151792 | 12/2010 |
| WO | WO 2011/008517 | 1/2011 |
| WO | WO 2011/043643 | 4/2011 |
| WO | WO 2011/044368 | 4/2011 |
| WO | WO 2011/091078 | 7/2011 |
| WO | WO 2011/094593 | 8/2011 |
| WO | WO 01/70968 | 9/2011 |
| WO | WO 2011/108714 | 9/2011 |
| WO | WO 2011/111007 | 9/2011 |
| WO | WO 2011/122011 | 10/2011 |
| WO | WO 2012/033953 | 3/2012 |
| WO | WO 2012/044831 | 4/2012 |
| WO | WO 2012/073992 | 6/2012 |
| WO | WO 2012/115241 | 8/2012 |
| WO | WO 2012/132067 | 10/2012 |
| WO | WO 2012/133782 | 10/2012 |
| WO | WO 2013/004842 | 1/2013 |
| WO | WO 2013/046704 | 4/2013 |
| WO | WO 2013/047729 | 4/2013 |
| WO | WO 2013/047748 | 4/2013 |
| WO | WO 2013/047752 | 4/2013 |
| WO | WO 2013/081143 | 6/2013 |
| WO | WO 2013/118858 | 8/2013 |
| WO | WO 2013/125667 | 8/2013 |
| WO | WO 2013/138681 | 9/2013 |
| WO | WO 2013/152001 | 10/2013 |
| WO | WO 2013/180200 | 12/2013 |
| WO | WO 2013/180201 | 12/2013 |
| WO | WO 2014/028354 | 2/2014 |
| WO | WO 2014/030728 | 2/2014 |
| WO | WO 2014/140366 | 9/2014 |
| WO | WO 2014/144080 | 9/2014 |
| WO | WO 2014/144575 | 9/2014 |
| WO | WO 2014/144577 | 9/2014 |
| WO | WO 2014/150983 | 9/2014 |
| WO | WO 2014/163101 | 10/2014 |
| WO | WO 2014/164959 | 10/2014 |
| WO | WO 2015/042250 | 3/2015 |
| WO | WO 2015/077491 | 5/2015 |
| WO | WO 2015/134894 | 9/2015 |
| WO | WO 2016/000813 | 1/2016 |
| WO | WO 2016/098356 | 6/2016 |
| WO | WO 2018/167322 | 9/2018 |
| WO | WO 2018/169993 | 9/2018 |

OTHER PUBLICATIONS

Cruse et al., Atlas of Immunology, CRC Press LLC, 2004, Chapter 3: “Antigens and Immunogens”, p. 109.
Decision of the EPO Opposition Division for EP 2 006 381 on Jul. 25, 2018, 17 pages.
Hirose, Nihon Yakurigaku Zasshi, May 2006, 127(5):362-7 (with English translation).
Kamata et al., “Comparison of pH and Ionic Strength Dependence of Interactions between Monoclonal Antibodies and Bovine β-Lactoglobulin,” Biosci Biotechnol Biochem, Jan. 1996, 60(1):25-9.
Sequence alignments and modification scheme (document filed during Oral Proceedings and mentioned in minutes of the Oral Proceedings for EP 2 006 381, posted by EPO on Jul. 25, 2018); 3 pages.
Van Den Abbeele et al., “Antigen-Binding Site Protection During Radiolabeling Leads to a Higher Immunoreactive Fraction,” J Nucl Med, Jan. 1991, 32(1):116-22.
USPTO Final Office Action in U.S. Appl. No. 14/007,947, dated Dec. 10, 2018, 16 pages.
USPTO Final Office Action in U.S. Appl. No. 14/347,448, dated Nov. 13, 2018, 29 pages.
USPTO Notice of Allowance in U.S. Appl. No. 14/347,187, dated Jan. 7, 2019, 13 pages.
Bonvin et al., “De novo isolation of antibodies with pH-dependent binding properties,” mAbs, Mar.-Apr. 2015, 7(2): 294-302.
Declaration of Dr. Anette Henriksen, signed Apr. 17, 2019 (submitted by the Opponent during EPO opposition procedure for EP 2 006 381).
Ferl et al., “A Predictive Model of Therapeutic Monoclonal Antibody Dynamics and Regulation by the Neonatal Fc Receptor (FcRn),” Ann Biomed Eng, Nov. 2005, 33(11):1640-52; and Erratum, Oct. 2011, 39(10):2668.

(56) References Cited

OTHER PUBLICATIONS

Yarilin, Fundamentals of Immunology, M.: Medicina, 1999, pp. 181-184 (with English translation).
USPTO Non-Final Office Action in U.S. Appl. No. 14/377,556, dated Apr. 18, 2019, 9 pages.
U.S. Appl. No. 15/495,026, filed Apr. 24, 2017, Igawa et al.
U.S. Appl. No. 15/952,945, filed Apr. 13, 2018, Igawa et al.
U.S. Appl. No. 15/952,951, filed Apr. 13, 2018, Igawa et al.
U.S. Appl. No. 15/977,757, filed May 11, 2018, Igawa et al.
U.S. Appl. No. 16/108,897, filed Aug. 22, 2018, Igawa et al.
U.S. Appl. No. 61/313,102, filed Mar. 11, 2010, Pons.
Akbarzadeh-Sharbaf et al., "In silico design, construction and cloning of Trastuzumab humanized monoclonal antibody: A possible biosimilar for Herceptin," Adv Biomed Res, Jan.-Mar. 2012, 1(1):1-6. doi: 10. 4103/ 2277-9175. 98122. Epub Jul. 6, 2012.
Alignment of constant region sequences from WO 2009/125825 (document submitted in EP opposition and posted by EPO on Feb. 2, 2018); 1 page.
Alignment of the amino acid sequences of the Fc regions of antibodies exemplified in EP 2275443 (document submitted in EP opposition and posted by EPO on Feb. 2, 2018); 1 page.
Alignment of variable heavy and light chain amino acid sequences from WO 2009/125825 (document submitted in EP opposition and posted by EPO on Feb. 2, 2018); 2 pages.
Antibodies from www.bioinf.org.uk: Dr. Andrew C.R. Martin's Group, downloaded Jul. 11, 2018, nine pages.
Atherton et al., "Acid-base balance: maintenance of plasma pH," Anaesthesia & Intensive Care Medicine, 2009,10(11):557-61 (English abstract only).
Chen et al., "Enhancement and destruction of antibody function by somatic mutation: unequal occurrence is controlled by V gene combinatorial associations," EMBO J, Jun. 15, 1995, 14(12):2784-94.
Claims as granted for Publication No. EP 2275443, dated Jan. 19, 2011 (document submitted in EP opposition); 6 pages.
Datta-Mannan et al., "Humanized IgG1 Variants with Differential Binding Properties to the Neonatal Fc Receptor: Relationship to Pharmacokinetics in Mice and Primates," Drug Metab Dispos, Jan. 2007, 35(1):86-94. Epub Oct. 18, 2006.
Davydov, "Omalizuman (Xolair) for Treatment of Asthma," Am Fam Physician, Jan. 15, 2005, 71(2):341-2.
Declaration of Nimish Gera, Ph.D., CV and Exhibits, Sep. 1, 2016 (submitted in the matter of EP 2275443, Opposition thereto by Alexion Pharmaceuticals, Inc.); 24 pages.
EMA product information: Annexes to file of the tocilizumab preparation RoActemra A126(WC500054890), published Jan. 8, 2010, 109 pages.
EPO Register Extract EP 1915397 (document submitted in EP opposition and posted by EPO on Feb. 2, 2018); 4 pages.
Experimental data characterizing the binding of rituximab to its antigen CD20 and to human FcRn (document submitted in EP opposition and posted by EPO on Feb. 5, 2018); 6 pages.
Expert Declaration by Dr. Madhusudan Natarajan (submitted in EP opposition regarding EP 2552955 and posted by EPO on Feb. 5, 2018); 4 pages.
Fillipovic, Biochemical basis of human life activity, VLADOS, 2005, pp. 38-43 (with English translation).
GE Healthcare, Biacore, Sensor Surface Handbook BR-1005-71, Edition AB, Feb. 2005, pp. 1-100.
Goebl et al., "Neonatal Fe Receptor Mediates Internalization of Fc Transfected Human Endothelial Cells," Molecular Biology of the Cell, Dec. 2008, 19(12):5490-5505.
Gurbaxani et al., "Analysis of a family of antibodies with different half-lives in mice fails to find a correlation between affinity for FcRn and serum half-life," Mol Immunol, Mar. 2006, 43(9):1462-73. Epub Sep. 1, 2005.
Hotzel et al., "A strategy for risk mitigation of antibodies with fast clearance," mAbs, Nov.-Dec. 2012, 4(6):753-60. doi: 10.4161/mabs. 22189.
Hughes et al., "Report of the Use OF Drug Sensitivity Tests in General Practice," Med J Aust, Jan. 18, 1964, 1:72-4.
Irani et al., "Molecular properties of human IgG subclasses and their implications for designing therapeutic monoclonal antibodies against infectious diseases," Mol Immunol, Oct. 2015, 67(2 Pt A):171-82, doi: 10. 1016/j. molimm. 2015. 03. 255. Epub Apr. 18, 2015.
Jaeger, Clinical Immunology and Allergology, M.: Medicina, 1990, 2:484-5 (with English translation).
King, Applications and Engineering of Monoclonal Antibodies, Taylor & Francis, ISBN 0-203-21169-3, 1998, pp. 68-71.
King, Applications and Engineering of Monoclonal Antibodies, Taylor & Francis, ISBN 0-203-21169-3, 2005, pp. 1-236.
Kussie et al., "A single engineered amino acid substitution changes antibody fine specificity," J Immunol, Jan. 1, 1994, 152(1):146-52.
Maxwell et al., "Crystal structure of the human leukocyte Fc receptor, FcγRIIa," Nat Struct Biol, May 1999, 6(5):437-42.
Mellman, "The importance of being acid: the role of acidification in intracellular membrane traffic," J Exp Biol, Nov. 1992, 172-39-45.
Molina et al., "Trastuzumab (Herceptin), a Humanized Anti-HER2 Receptor Monoclonal Antibody, Inhibits Basal and Activated HER2 Ectodomain Cleavage in Breast Cancer Cells," Cancer Res, Jun. 15, 2001, 61(12):4744-9.
O'Donovan et al., "EGFR and HER-2 Antagonists in Breast Cancer," Anticancer Res, May 2007-Jun. 27(3 A):1285-94.
Experimental information regarding off-rate of Xolair Fab for binding to human IgE at pH7.4 and pH5.5 (document submitted in EP opposition and posted by EPO on Feb. 2, 2018); 3 pages.
Official Action dated Oct. 13, 2016, issued for EP Application No. 11714860.1 and submitted as evidence during EP opposition; 3 pages.
Papista et al., "Dysfunctions of the IgA system: a common link between intestinal and renal diseases," Cell Mol Immunol, Mar. 2011, 8(2):126-34. doi:10.1038/cmi.2010.69. Epub Jan. 31, 2011.
Popov et al., "The Stoichiometry and Affinity of the Interaction of Murine Fc Fragments with the MHC Class I-Related Receptor, FcRn," Mol Immunol, Apr. 1996, 33(6):521-30.
Presta, "Molecular engineering and design of therapeutic antibodies," Curr Opin Immunol, Aug. 2008, 20(4):460-70, doi : 10.1016/j.coi.2008. 06.012.
Presta at el., "Humanization of an Anti-Vascular Endothelial Growth Factor Monoclonal Antibody for the Therapy of Solid Tumors and Other Disorders," Cancer Res, Oct. 15, 1997, 57(20):4593-9.
Product labelling information for Rituxan (Rituximab), dated Nov. 1997; 2 pages.
Raghavan et al., "Analysis of the pH Dependence of the Neonatal Fc Receptor/Immunoglobulin G Interaction Using Antibody and Receptor Variants," Biochemistry, Nov. 14, 1995, 34(45):14649-57.
Roitt et al., Immunology, Moscow: Mir, 2000, pp. 373-374 (with English translation).
Ryman et al., "Pharmacokinetics of Monoclonal Antibodies," CPT Pharmacometrics Syst Pharmacol, Sep. 2017, 6(9):576-588. doi: 10.1002/psp4.12224. Epub Jul. 29, 2017.
Sondermann et al., "Molecular Basis for Immune Complex Recognition: A Comparison of Fc-Receptor Structures," J Mol Biol, Jun. 8, 2001, 309(3):737-49.
Sondermann et al., "Crystal structure of the soluble form of the human Fcy-receptor IIb: a new member of the immunoglobulin superfamily at 1.7 A resolution," Embo J Journal, Mar. 1, 1999, 18(5):1095-103.
Stepanov, "Chapter 4, Primary Structure of Protein, 4.1 Primary structure as a level of protein organization," Molecular Biology, Structure and Functions of Proteins, M.:Nauka, 2005, pp. 61-62 (with English abstract).
Supplementary data provided by opponent for EP Application No. 11714860.1 (document submitted in EP opposition and posted by EPO on Feb. 20, 2018); 3 pages.
Summary of information about antibodies in Examples of patent (document submitted in EP opposition and posted by EPO on Apr. 13, 2018); 3 pages.
Tanabe et al., "Characterization of the Monoclonal Antibodies Against Human Protein C Specific for Calcium Ion-induced Conformers," Japanese Journal of Thrombosis and Hemostasis, 1992, 3(1):29-35.

(56) References Cited

OTHER PUBLICATIONS

Vaccaro et al., "Divergent activities of an engineered antibody in murine and human systems have implications for therapeutic antibodies," Proc Natl Acad Sci USA, Dec. 5, 2006, 103(49):18709-14. Epub Nov. 20, 2006.
Waelbroeck et al., "The pH Dependence of Insulin Binding," J Biol Chem, Jul. 25, 1982, 257(14):8284-91.
Ward et al., "Evidence to support the cellular mechanism involved in semm IgG homeostasis in humans," Int Immunol, Feb. 2003, 15(2):187-95.
Welch et al., "Adalimumab (Humira) for the Treatment of Rheumatoid Arthritis" Am Fam Physician, Dec. 15, 2008, 78(12):1406-1408.
Written Submissions by Opponent 1 (Alexion Pharmaceuticals, Inc.) in Opposition of EP 2006381 dated Apr. 13, 2018, 19 pages.
Written Submissions by Opponent 2 (Novo Nordisk A/S) in Opposition of EP 20063 81 dated Apr. 13, 2018, 14 pages.
Written Submissions by Opponent 3 (name Unknown) in Opposition of EP 2006381 dated Apr. 13, 2018, 16 pages.
Wu et al., "Ultra-potent Antibodies Against Respiratory Syncytial Virus: Effects of Binding Kinetics and Binding Valence on Viral Neutralization," J Mol Biol, Jul. 2005, 350:126-144.
Yang et al., "Dataset of the binding kinetic rate constants of anti-PCSK9 antibodies obtained using the Biacore T100, Protean XPR36, Octet RED384, and IBIS MX96 biosensor platforms," Data Brief, Jul. 27, 2016, 8:1173-83. doi: 10. 1016/ J. dib. 2016.07.044. eCollection Sep. 2016.
Yang et al., "Maximizing in vivo target clearance by design of pH-dependent target binding antibodies with altered affinity to FcRn," mAbs, Oct. 2017, 9(7):1105-1117. doi: 10. 1080/19420862. 2017. 1359455. Epub Aug. 8, 2017.
Yarilin, Fundamentals of Immunology, M: Medicina, 1999, pp. 169-172, 354-8 (with English translation).
Yarilin, Fundamentals of Immunology, M: Medicina, 1999, pp. 172-174 (with English translation).
Yarilin, Fundamentals of Immunology, M: Medicina, 1999, pp. 175, 182 (with English translation).
Yeung et al., "A Therapeutic Anti-VEGF Antibody with Increased Potency Independent of Pharmacokinetic Half-life," Cancer Res, Apr. 15, 2010, 70(8):3269-77. doi: 10. 1158/ 0008-5472. CAN-09-4580. Epub Mar. 30, 2010.
YU et al., "Interaction between Bevacizumab and Murine VEGF-A: A Reassessment," Invest Ophthalmol Vis Sci, Feb. 2008, 49(2):522-7 doi: 10.1167/iovs 07-1175.
USPTO Final Office Action in U.S. Appl. No. 13/637,415, dated Mar. 2, 2018, 36 pages.
USPTO Final Office Action in U.S. Appl. No. 14/007,947, dated Apr. 21, 2017, 9 pages.
USPTO Non-Final Office Action in U.S. Appl. No. 14/007,947, dated Apr. 2, 2018, 27 pages.
USPTO Restriction Requirement in U.S. Appl. No. 14/347,034, dated Dec. 18, 2014, 9 pages.
Fish & Richardson P.C., Reply to Restriction Requirement dated Dec. 18, 2014 in U.S. Appl. No. 14/347,034, filed Mar. 18, 2015, 2 pages.
USPTO Non-Final Office Action in U.S. Appl. No. 14/347,034, dated Apr. 16, 2015, 9 pages.
USPTO Interview Summary in U.S. Appl. No. 14/347,034, dated Aug. 17, 2015, 3 pages.
Fish & Richardson P.C., Reply to Non-Final Office Action dated Apr. 16, 2015 in U.S. Appl. No. 14/347,034, filed Sep. 16, 2015, 28 pages.
USPTO Final Office Action in U.S. Appl. No. 14/347,034, dated Oct. 16, 2015, 5 pages.
Fish & Richardson P.C., Reply to Final Office Action dated Oct. 16, 2015 in U.S. Appl. No. 14/347,034, filed Jan. 13, 2016, 28 pages.
USPTO Notice of Allowance in U.S. Appl. No. 14/347,034, dated Feb. 17, 2016, 6 pages.
USPTO Notice of Allowance in U.S. Appl. No. 14/347,034, dated Jun. 3, 2016, 5 pages.
USPTO Non-Final Office Action in U.S. Appl. No. 14/347,034, dated May 25, 2017, 16 pages.
USPTO Non-Final Office Action in U.S. Appl. No. 14/347,034, dated Jan. 8, 2018, 15 pages.
USPTO Notice of Allowance in U.S. Appl. No. 13/595,139, dated Nov. 28, 2017, 17 pages.
USPTO Non-Final Office Action in U.S. Appl. No. 13/595,139, dated Sep. 26, 2018, 32 pages.
USPTO Notice of Allowance in U.S. Appl. No. 13/889,512, dated Nov. 30, 2017, 36 pages.
USPTO Restriction Requirement in U.S. Appl. No. 14/347,448, dated Nov. 24, 2017, 13 pages.
USPTO Non-Final Office Action in U.S. Appl. No. 14/347,448, dated Mar. 9, 2018, 32 pages.
USPTO Final Office Action in U.S. Appl. No. 14/347,187, dated Jan. 19, 2018, 24 pages.
USPTO Applicant-Initiated Interview Summary in U.S. Appl. No. 14/347,187, dated Jul. 10, 2018, 3 pages.
USPTO Non-Final Office Action in U.S. Appl. No. 14/347,187, dated Sep. 4, 2018, 22 pages.
USPTO Restriction Requirement in U.S. Appl. No. 14/404,051, dated Apr. 4, 2016, 13 pages.
USPTO Non-Final Office Action in U.S. Appl. No. 14/404,051, dated Dec. 6, 2016, 22 pages.
USPTO Advisory Action Before the Filing of an Appeal Brief and Notice of Non-Compliant Amendment (37 CFR 1.121) in U.S. Appl. No. 14/404,051, dated Jun. 28, 2018, 4 pages.
USPTO Advisory Action Before the Filing of an Appeal Brief in U.S. Appl. No. 14/404,051, filed Aug. 30, 2018, 3 pages.
USPTO Restriction Requirement in U.S. Appl. No. 15/210,360, dated Oct. 19, 2016, 5 pages.
USPTO Non-Final Office Action in U.S. Appl. No. 15/210,360, dated Mar. 10, 2017, 18 pages.
USPTO Restriction Requirement in U.S. Appl. No. 14/377,556, dated Dec. 15, 2016, 11 pages.
USPTO Non-Final Office Action in U.S. Appl. No. 14/377,556, dated Feb. 27, 2017, 11 pages.
USPTO Final Office Action in U.S. Appl. No. 14/377,556, dated Jul. 7, 2017, 12 pages.
USPTO Non-Final Office Action in U.S. Appl. No. 14/377,556, dated Dec. 12, 2017, 14 pages.
USPTO Final Office Action in U.S. Appl. No. 14/377,556, dated May 11, 2018, 19 pages.
USPTO Non-Final Office Action in U.S. Appl. No. 15/952,945, dated Sep. 20, 2018, 32 pages.
USPTO Restriction Requirement in U.S. Appl. No. 15/210,353, dated Oct. 6, 2016, 5 pages.
USPTO Non-Final Office Action in U.S. Appl. No. 15/210,353, dated Mar. 9, 2017, 16 pages.
Non-Final Office Action for U.S. Appl. No. 15/230,904, dated May 25, 2017, 43 pages.
Reply to Action dated May 25, 2017 in U.S. Appl. No. 15/230,904, filed Nov. 22, 2017, 28 pages.
Non-Final Office Action for U.S. Appl. No. 15/230,904, dated Jan. 8, 2018, 16 pages.
U.S. Appl. No. 13/889,484, filed May 8, 2013, Igawa et al.
U.S. Appl. No. 13/889,512, filed May 8, 2013, Igawa et al.
U.S. Appl. No. 13/990,158, filed May 29, 2013, Igawa et al.
U.S. Appl. No. 14/007,947, filed Sep. 26, 2013, Igawa et al.
U.S. Appl. No. 14/347,187, filed Mar. 25, 2014, Igawa et al.
U.S. Appl. No. 15/210,353, filed Jul. 14, 2016, Igawa et al.
U.S. Appl. No. 15/210,360, filed Jul. 14, 2016, Igawa et al.
U.S. Appl. No. 15/725,692, filed Oct. 5, 2017, Igawa et al.
Adams et al., "Humanization of a recombinant monoclonal antibody to produce a therapeutic HER dimerization inhibitor, pertuzumab," Cancer Immunol Immunother, 2006, 55, 717-727.
Algonomics—TripoleR applications [Online] Retrieved from the Internet on Feb. 29, 2012: http://www.algonomics.com/proteinengineering/tripole_applications.php, 2 pages (Feb. 21, 2009).
Alley et al., "Antibody-drug conjugates: targeted drug delivery for cancer," Curr Opin Chem Biol, Aug. 2010, 14(4):529-37. doi: 10.1016/j.cbpa.2010.06.170. Epub Jul. 17, 2010.

(56) References Cited

OTHER PUBLICATIONS

Almagro et al., "Humanization of antibodies," Front Biosci, Jan. 1, 2008, 13:1619-33.
Amersham Biosciences, "Affinity Chromatography: Principles and Methods," Edition AD, pp. 16-18, 137 (2002).
Amersham Biosciences, "Antibody Purification Handbook," Edition 18-1037-46 [online], [retrieved on Nov. 5, 2015]. Retrieved from the Internet: http://www.promix.ru/manuf/ge/chrom/lit/Antibody_Purification.pdf.
Amigorena et al., "Fc gamma RII expression in resting and activated B lymphocytes," Eur J Immunol, Aug. 1989, 19(8):1379-85.
Amigorena et al., "Cytoplasmic domain heterogeneity and functions of IgG Fc receptors in B lymphocytes," Science, Jun. 26, 1992, 256(5065):1808-12.
Araujo et al., "Increased rheumatoid factor interference observed during immunogenicity assessment of an Fc-engineered therapeutic antibody," J Pharm Biomed Anal, Jul. 15, 2011, 55(5):1041-9. doi: 10.1016/j.jpba.2011.03.008. Epub Mar. 11, 2011.
Armour et al., "Differential binding to human FcgammaRIIa and FcgammaRIIb receptors by human IgG wildtype and mutant antibodies," Mol Immunol, Dec. 2003, 40(9):585-93.
Armour et al., "Recombinant human IgG molecules lacking Fcγ receptor I binding and monocyte triggering activities," Eur J Immunol. Aug. 1999, 29(8):2613-24.
Baeuerle et al., "BiTE: Teaching antibodies to engage T-cells for cancer therapy," Curr Opin Mol Ther, 2009, 11(1):22-30.
Balint et al., "Antibody engineering by parsimonious mutagenesis," Gene, Dec. 27, 1993, 137(1):109-18.
Bartelds et al., "Clinical response to adalimumab: relationship to anti-adalimumab antibodies and serum adalimumab concentrations in rheumatoid arthritis," Ann Rheum Dis, 2007, 66:921-926.
Batra et al., "Pharmacokinetics and biodistribution of genetically engineered antibodies," Curr Opin Biotechnol, Dec. 2002, 13(6):603-8.
Bayry et al., "Immuno affinity purification of foot and mouth disease virus type specific antibodies using recombinant protein absorbed to polystyrene wells," J Virol Methods, Aug. 1999, 81(1-2):21-30.
Beck et al., "Strategies and challenges for the next generation of therapeutic antibodies," Nat Rev Immunol, 2010, 10(5):345-52.
Bender et al., "Immunogenicity, efficacy and adverse events of adalimumab in RA patients," Rheumatol Int, 2007, 27:269-274.
Beringhelli et al., "pH and ionic strength dependence of protein (un)folding and ligand binding to bovine beta-lactoglobulins A and B," Biochemistiy, Dec. 24, 2002, 41(51):15415-22.
Biasini et al., "Immunopurification of pathological prion protein aggregates," PLoS One, Nov. 12, 2009, 4(11):e7816. doi: 10.1371/journal.pone.0007816.
Binz et al., "Engineering novel binding proteins from nonimmunoglobulin domains," Nat Biotechnol, 2005, 23:1257-68.
Blank et al., "Decreased transcription of the human FCGR2B gene mediated by the -343 G/C promoter polymorphism and association with systemic lupus erythematosus," Hum Genet, Jul. 2005, 117(2-3):220-7. Epub May 14, 2005.
Boruchov et al., "Activating and inhibitory IgG Fc receptors on human DCs mediate opposing functions," J Clin Invest, Oct. 2005, 115(10):2914-23. Epub Sep. 15, 2005.
Boumpas et al., "A short course of BG9588 (anti-CD40 ligand antibody) improves serologic activity and decreases hematuria in patients with proliferative lupus glomerulonephritis," Arthritis Rheum, Mar. 2003, 48(3):719-27.
Brown et al., "Tolerance of single, but not multiple, amino acid replacements in antibody $V_H$ CDR2: a means of minimizing B cell wastage from somatic hypermutation?," J Immunol, 1996, 156(9):3285-91.
Brown et al., "A study of the interactions between an IgG-binding domain based on the B domain of staphylococcal protein A and rabbit IgG," Mol Biotechnol, Aug. 1998, 10(1):9-16.
Bruhns et al., "Specificity and affinity of human Fegamma receptors and their polymorphic variants for human IgG subclasses," Blood, Apr. 16, 2009, 113(16):3716-25. doi: 10.1182/blood-2008-09-179754. Epub Nov. 18, 2008.
Bruhns, "Properties of mouse and human IgG receptors and their contribution to disease models," Blood, Jun. 14, 2012, 119(24):5640-9, doi: 10.1182/blood-2012-01-380121. Epub Apr. 25, 2012.
Burmeister et al., "Crystal structure of the complex of rat neonatal Fc receptor with Fc," Nature, Nov. 24, 1994, 372(6504):379-83.
Cartron et al., "Therapeutic activity of humanized anti-CD20 monoclonal antibody and polymorphism in IgG Fc receptor FcgammaRIIIa gene," Blood, 2002, 99(3):754-8.
Cemerski et al., "Suppression of mast cell degranulation through a dual-targeting tandem IgE-IgG Fc domain biologic engineered to bind with high affinity to FcγRIIb," Immunol Lett, Mar. 30, 2012, 143(1):34-43. doi: 10.1016/j.imlet.2012.01.008. Epub Jan. 25, 2012.
Chaparro-Riggers et al., "Increasing serum half-life and extending cholesterol lowering in vivo by engineering antibody with pH-sensitive binding to PCSK9," J Biol Chem, 2012, 287(14):11090-7.
Chau et al., "HuM291(Nuvion), a humanized Fc receptor-nonbinding antibody against CD3, anergizes peripheral blood T cells as partial agonist of the T cell receptor," Transplantation, Apr. 15, 2001, 71(7):941-50.
Chen et al., "Association of a transmembrane polymorphism of Fegamma receptor IIb (FCGR2B) with systemic lupus erythematosus in Taiwanese patients," Arthritis Rheum, Dec. 2006, 54(12):3908-17.
Chen et al., "Generation and Analysis of Random Point Mutations in an Antibody CDR2 Sequence: Many Mutated Antibodies Lose Their Ability to Bind Antigen ," J Exp Med, Sep. 1, 1992, 176(3):855-66.
Chen et al., "Defective Secretion of an Immunoglobulin Caused by Mutations in the Heavy Chain Complementarity Determining Region 2," Exp Med, Aug. 1, 1994, 180(2):577-86.
Chen et al., "Selection and analysis of an optimized anti-VEGF antibody: crystal structure of an affinity-matured Fab in complex with antigen," J Mol Biol, Nov. 5, 1999, 293(4):865-81.
Chirino et al., "Minimizing the immunogenicity of protein therapeutics," Drug Discov Today, 2004, 9:82-90.
Chu et al., "Reduction of total IgE by targeted coengagement of IgE B-cell receptor and FcγRIIb with Fc-engineered antibody," J Allergy Clin Immunol, Apr. 2012, 129(4):1102-15. doi: 10.1016/j.jaci.2011.11.029. Epub Jan. 16, 2012.
Chu et al., "Inhibition of B cell receptor-mediated activation of primary human B cells by coengagement of CD19 and FcgammaRIIb with Fc-engineered antibodies," Mol Immunol, Sep. 2008, 45(15):3926-33, doi: 10.1016/j.molimm.2008.06.027. Epub Aug. 8, 2008.
Chu et al., "Accumulation of Succinimide in a Recombinant Monoclonal Antibody in Mildly Acidic Buffers Under Elevated Temperatures," Pharm Res, Jun. 2007, 24(6):1145-56. Epub Mar. 24, 2007.
Chuntharapai et al., "Isotype-dependent inhibition of tumor growth in vivo by monoclonal antibodies to death receptor 4," J Immunol, Apr. 15, 2001, 166(8):4891-8.
Clark, "IgG effector mechanisms," Chem Immunol, 1997, 65:88-110.
Clark, "An alignment of IgG sequences from Human, Mouse and Rat," Part II Immunoglobulin lectures (v4), pp. 5(i)-(ii) [retrieved on Jul. 25, 2014], Retrieved from the Internet: http://www.path.cam.ac.uk/~mrc7/lecturenotes/handout1a.pdf.
Clarkson et al., "Blockade of clearance of immune complexes by an anti-Fc gamma receptor monoclonal antibody," J Exp Med, Aug. 1, 1986, 164(2):474-89.
Clynes et al., "Fc receptors are required in passive and active immunity to melanoma," Proc Natl Acad Sci USA, 1998, 95(2):652-6.
Clynes et al., "Inhibitory Fc receptors modulate in vivo cytotoxicity against tumor targets," Nat Med, 2000, 6(4):443-6.
Cole et al., "Human IgC2 Variants of Chimeric Anti-CD3 Are Nonmitogenic to T Cells," J Immunol, Oct. 1, 1997, 159(7):3613-21.

(56) References Cited

OTHER PUBLICATIONS

Coloma et al., "Position effects of variable region carbohydrate on the affinity and in vivo behavior of ananti-(1-->6) dextran antibody," J Immunol, Feb. 15, 1999, 162(4):2162-70.
Comper et al., "Charge selectivity in kidney ultrafiltration," Kidney Int, May 1995, 47(5):1242-51.
Cordoba et al., "Non-enzymatic hinge region fragmentation of antibodies in solution," J Chromatogr B Analyt Technol Biomed Life Sci, Apr. 25, 2005, 818(2):115-21.
Couto et al., "Anti-BA46 Monoclonal Antibody Mc3: Humanization Using a Novel Positional Consensus and in Vivo and in Vitro Characterization," Cancer Res, 1995, 55:1717-22.
Cuatrecasas et al., "Affinity Chromatography," Methods Enzymol, 1971, 12:345-78.
Dall'Acqua et al., "Increasing the affinity of a human IgG1 for the neonatal Fc receptor: biological consequences," J Immunol, Nov. 1, 2002, 169(9):5171-80.
Dall'Acqua et al., "Properties of human IgG1s engineered for enhanced binding to the neonatal Fc receptor (FcRn)," J Biol Chem, Aug. 18, 2006, 281(33):23514-24. Epub Jun. 21, 2006.
Dall'Acqua et al., "Antibody humanization by framework shuffling," Methods, 2005, 36(1):43-60.
Damschroder et al., "Framework shuffling of antibodies to reduce immunogenicity and manipulate functional and biophysical properties," Mol Immunol, Apr. 2007, 44(11):3049-60. Epub Jan. 22, 2007.
Datta-Mannan et al., "Monoclonal antibody clearance. Impact of modulating the interaction of IgG with the neonatal Fc receptor," J Biol Chem, Jan. 19, 2007, 282(3):1709-17. Epub Nov. 29, 2006.
Davda et al., "Properties of a general PK/PD model of antibody-ligand interactions for therapeutic antibodies that bind to soluble endogenous targets," mAbs, Sep.-Oct. 2010, 2(5):576-88. doi: 10.4161/mabs.2.5.12833. Epub Sep. 1, 2010.
De Bono et al., "ING-1, a monoclonal antibody targeting Ep-CAM in patients with advanced adenocarcinomas," Clin Cancer Res, 2004, 10(22):7555-65.
De Felice et al., "Formation of amyloid aggregates from human lysozyme and its disease-associated variants using hydrostatic pressure," FASEB J, Jul. 2004, 18(10):1099-101. (doi:10.1096/fj.03-1072fje; PMID 15155566).
Declaration of Nimish Gera, Ph.D., CV and Exhibits, dated Sep. 1, 2016, 24 pages.
De Groot et al., "De-immunization of Therapeutic Proteins by T-cell Epitope Modification," Dev Biol (Basel), Feb. 2005, 122:171-94.
Deen et al., "Structural determinants of glomerular permeability," Am J Physiol Renal Physiol, Oct. 2001, 281(4):F579-96.
Del Rio et al., "An engineered penicillin acylase with altered surface charge is more stable in alkaline pH," Ann N Y Acad Sci, Oct. 12, 1996, 799:61-4.
Deng et al., "Pharmacokinetics of humanized monoclonal anti-tumor necrosis factor-{alpha} antibody and its neonatal Fc receptor variants in mice and cynomolgus monkeys," Drug Metab Dispos, Apr. 2010, 38(4):600-5. doi: 10.1124/dmd.109.031310. Epub Jan. 13, 2010.
Desai et al., "Fc gamma receptor IIB on dendritic cells enforces peripheral tolerance by inhibiting effector T cell responses," J Immunol, May 15, 2007, 178(10):6217-26.
Desjarlais et al., "Optimizing engagement of the immune system by anti-tumor antibodies: an engineer's perspective," Drug Discov Today, Nov. 2007, 12(21-22):898-910. Epub Oct. 22, 2007.
Devanaboyina et al., "The effect of pH dependence of antibody-antigen interactions on subcellular trafficking dynamics," mAbs, 2013, 5(6):851-9.
Dhodapkar et al., "Selective blockade of inhibitory Fegamma receptor enables human dendritic cell maturation with IL-12p70 production and immunity to antibody-coated tumor cells," Proc Natl Acad Sci USA, Feb. 22, 2005, 102(8):2910-5. Epub Feb. 9, 2005.
Drake et al., "Chapter 5: Biophysical Considerations for Development of Antibody-Based Therapeutics," Biophysical Considerations for Development of Antibody-Based Therapeutics, Springer Science + Business Media New York, 95-7 (2012).
Duffau et al., "Platelet CD154 potentiates interferon-alpha secretion by plasmacytoid dendritic cells in systemic lupus erythematosus," Sci Transl Med, Sep. 1, 2010, 2(47):47ra63. doi: 10.1126/scitranslmed.3001001.
Dufner et al., "Harnessing phage and ribosome display for antibody optimization," Trends Biotechnol, Nov. 2006, 24(11):523-9. Epub Sep. 26, 2006.
Durkee et al., "Immunoaffinity Chromatographic Purification of Russell's Viper Venom Factor X Activator Using Elution in High Concentrations of Magnesium Chloride," Protein Expr Purif. Oct. 1993, 4(5):405-11.
Ejima et al., "Effective elution of antibodies by arginine and arginine derivatives in affinity col. chromatography," Anal Biochem, Oct. 15, 2005, 345(2):250-7.
Epstein, "Non-randomness of amino-acid changes in the evolution of homologous proteins," Nature, Jul. 22, 1967, 215(5099):355-9.
Ewert et al., "Stability improvement of antibodies for extracellular and intracellular applications: CDR grafting to stable frameworks and structure-based framework engineering," Methods, 2004, 34:184-199.
Feinberg et al., "Mechanism of pH-dependent N-acetylgalactosamine binding by a functional mimic of the hepatocyte asialoglycoprotein receptor," J Biol Chem, 2000, 275(45):35176-84.
Fiedler et al., "An engineered IN-1 Fab fragment with improved affinity for the Nogo-A axonal growth inhibitor permits immunochemical detection and shows enhanced neutralizing activity," Protein Eng, Nov. 2002, 15(11):931-41.
Fillipovich, Biochemical basis of human life, VLADOS, 2005:49-50 (with English translation).
Finkelman et al., "Anti-cytokine antibodies as carrier proteins. Prolongation of in vivo effects of exogenous cytokines by injection of cytokine-anti-cytokine antibody complexes," J Immunol, 1993, 151(3):1235-44.
Floto et al., "Loss of function of a lupus-associated FcgammaRIIb polymorphism through exclusion from lipid rafts," Nat Med, Oct. 2005, 11(10):1056-8, Epub Sep. 18, 2005.
Foote et al., "Antibody framework residues affecting the conformation of the hypervariable loops," J Mol Biol, Mar. 20, 1992, 224(2):487-99.
Fournier et al., "Activation of human peripheral IgM+ B cells is transiently inhibited by BCR-independent aggregation of Fc gammaRIIB," J Immunol, Oct. 15, 2008, 181(8):5350-9.
Fujii, "Antibody affinity maturation by random mutagenesis," Methods Mol Biol, 2004, 248:345-59.
GE Healthcare. Application note 28-9277-92 AA. "High-throughput screening of elution pH for monoclonal antibodies on MabSelect SuRe using PreDictor plates" [online], [retrieved on Nov. 5, 2015]. Retrieved from the Internet: https://www.gelifesciences.com/gehcls_images/GELS/Related%20Content/Files/1314787424814/litdoc28927792AA_20110831131840.pdf.
Gera et al., "Design of pH Sensitive Binding Proteins from the Hyperthermophilic Sso7d Scaffold," PLoS One, Nov. 2012, 7(11):e48928. doi: 10.1371/journal.pone.0048928. Epub Nov. 7, 2012.
Gerstner et al., "Sequence Plasticity in the Antigen-binding Site of a Therapeutic Anti-HER2 Antibody," J Mol Biol, Aug. 30, 2002, 321(5):851-62.
Gessner et al., "The IgG Fc receptor family," Ann Hematol, Jun. 1998, 76(6):231-48.
Ghetie et al., "Multiple roles for the major histocompatibility complex class I-related receptor FcRn," Annu Rev Immunol, Apr. 2000, 18:739-66.
Ghetie et al., "FcRn: the MHC class I-related receptor that is more than an IgG transporter," Immunol. Today, 1997, 18:592-598.
Ghetie et al., "Increasing the serum persistence of an IgG fragment by random mutagenesis," Nat. Biotechnol, 1997, 15(7):637-40.
Glick et al., Molecular Biotechnology: Principles and Applications of Recombinant DNA, 3rd Edition, Chemical Industry Press, Mar. 2005, p. 168 (with English Translation).

(56) References Cited

OTHER PUBLICATIONS

Gobburu et al., "Pharmacokinetics/dynamics of 5c8, a monoclonal antibody to CD154 (CD40 ligand) suppression of an immune response in monkeys," J Pharmacol Exp Ther, 1998, 286:925-930.
Goode et al., "The glomerular basement membrane charge-selectivity barrier: an oversimplified concept?" Nephrol Dial Transplant, Sep. 1996, 11(9):1714-6.
Graves et al., "Molecular modeling and preclinical evaluation of the humanized NR-LU-13 antibody," Clin Cancer Res, 1999, 5:899-908.
Greenwood et al., "Structural motifs involved in human IgG antibody effector functions," Eur J Immunol, May 1993, 23(5):1098-104.
Guyre et al., "Increased potency of Fc-receptor-targeted antigens," Cancer Immunol Immunother, Nov.-Dec. 1997, 45(3-4):146-8.
Haakenstad et al., "The disappearance kinetics and glomerular deposition of small-latticed soluble immune complexes," Immunology, 1982, 47(3):407-14.
Hamers-Casterman et al., "Naturally occurring antibodies devoid of light chains," Nature, Jun. 3, 1993, 363(6428):446-8.
Hamilton, "Molecular engineering: applications to the clinical laboratory," Clin Chem, 1993, 39(9):1988-97.
Hanson et al., "Catalytic antibodies and their applications," Curr Opin Biotechnol, 2005, 16:631-636.
Haringman et al., "A randomized controlled trial with an anti-CCL2 (anti-monocyte chemotactic protein 1) monoclonal antibody in patients with rheumatoid arthritis," Arthritis Rheum, 2006, 54(8):2387-92.
He et al., "Humanization and pharmacokinetics of a monoclonal antibody with specificity for both E-and P-selectin," J Immunol, 1998, 160:1029-35.
Hebert, "The clearance of immune complexes from the circulation of man and other primates," Am J Kidney Dis, 1991, 17(3):352-61.
Heyman, "Feedback regulation by IgG antibodies," Immunol Lett, Aug. 5, 2003, 88(2):157-61.
Hinton et al., "An engineered human IgG1 antibody with longer serum half-life," J Immunol, 2006, 176(1):346-56.
Hinton et al., "Engineered human IgG antibodies with longer serum half-lives in primates," J Biol Chem, 2004, 279(8):6213-6.
Hird et al., "Tumour localisation with a radioactively labelled reshaped human monoclonal antibody," Br J Cancer, Nov. 1991, 64(5):911-4.
Hironiwa et al., "Calcium-dependent antigen binding as a novel modality for antibody recycling by endosomal antigen dissociation," mAbs, Jan. 2016, 8(1):65-73. doi: 10.1080/19420862.2015.1110660. Epub Oct. 23, 2015.
Hjelm et al., "Antibody-mediated regulation of the immune response," Scand J Immunol, Sep. 2006, 64(3):177-84.
Hong et al., "Enhanced cellular uptake and transport of polyclonal immunoglobulin G and fab after their cationization," J Drug Target, 2000, 8(2):67-77.
Hoogenboom, "Selecting and screening recombinant antibody libraries," Nat Biotechnol, Sep. 2005, 23(9):1105-16.
Horn et al., "Analysis of the binding of pro-urokinase and urokinase-plasminogen activator inhibitor-1 complex to the low density lipoprotein receptor-related protein using a Fab fragment selected from a phage-displayed Fab library," J Biol Chem, May 19, 1995, 270(20):11770-5.
Horton et al., "Potent in vitro and in vivo activity of an Fc-engineered anti-CD19 monoclonal antibody against lymphoma and leukemia," Cancer Res, Oct. 1, 2008, 68(19):8049-57. doi: 10.1158/0008-5472.CAN-08-2268.
Hwang et al., "Use of human germline genes in a CDR homology-based approach to antibody humanization," Methods, 2005, 36:35-42.
Idusogie et al., "Mapping of the C1q binding site on rituxan, a chimeric antibody with a human IgG1 Fc," J Immunol, Apr. 15, 2000, 164(8):4178-84.
Idusogie et al., "Engineered antibodies with increased activity to recruit complement," J Immunol, Feb. 15, 2001, 166(4):2571-5.
Igawa et al., "Antibody recycling by engineered pH-dependent antigen binding improves the duration of antigen neutralization," Nat Biotechnol, Nov. 2010, 28(11):1203-7. doi: 10.1038/nbt.1691. Epub Oct. 17, 2010.
Igawa et al., "Reduced elimination of IgG antibodies by engineering the variable region," Protein Eng Des Sel, 2010, 23(5):385-92.
Igawa et al., "Engineered monoclonal antibody with novel antigen-sweeping activity in vivo," PLoS One, 2013, 8(5):e63236.
Igawa et al., "Antibody optimization technologies for developing next generation antibody therapeutics," Bio Industry, 2011, 28(7):45-21 (with English translation).
Igawa et al., "Engineering the variable region of therapeutic IgG antibodies," mAbs, May-Jun. 2011, 3(3):243-52, Epub May 1, 2011.
Ishii et al., "FcRn, a critical regulator of antibody pharmacokinetics," Folia Pharmacol Jpn, 2010, 136(5):280-284 (with English translation).
Ito et al., "The His-probe method: effects of histidine residues introduced into the complementarity-determining regions of antibodies on antigen-antibody interactions at different pH values," FEBS Lett, Aug. 31, 1992, 309(1):85-8.
Janeway et al., Immunobiology, The Immune System in Health and Disease, 3rd Edition, 1997 Garland Publishing Inc., pp. 3:1-3:11.
Janeway et al., Immunobiology, 5th edition, Jun. 2001, Extract from Chapter 3, pp. 93-122.
Janeway et al., Immunobiology, 5th edition, Jun. 2001, Extract from Chapter 4, pp. 123-154.
Jefferis et al., "Interaction sites on human IgG-Fc for Fc gamma R: current models," Immunol Lett, Jun. 3, 2002, 82(1-2):57-65.
Johnson et al., "Cation exchange-HPLC and mass spectrometry reveal C-terminal amidation of an IgG1 heavy chain," Anal Biochem, 2007, 360:75-83.
Jones et al., "Identification and removal of a promiscuous CD4+ T cell epitope from the C1 domain of factor VIII," Thromb. Haemost, 2005, 3:991-1000.
Junghans et al., "The protection receptor for IgG catabolism is the beta2-microglobulin-containing neonatal intestinal transport receptor," Proc Natl Acad Sci USA, May 28, 1996, 93(11):5512-6.
Juszczak et al., "Ipilimumab: a novel immunomodulating therapy causing autoimmune hypophysitis: a case report and review," Eur J Endocrinol, Jul. 2012, 167(1):1-5. doi: 10.1530/EJE-12-0167. Epub Apr. 10, 2012.
Kamei et al., "Quantitative methods for developing Fc mutants with extended half-lives," Biotechnol Bioeng, Dec. 20, 2005, 92(6):748-60.
Kashmiri et al., "Generation, characterization, and in vivo studies of humanized anticarcinoma antibody CC49," Hybridoma, 1995, 14:461-473.
Katayose et al., "MUC1-specific targeting immunotherapy with bispecific antibodies: inhibition of xenografted human bile duct carcinoma growth," Cancer Res, Sep. 15, 1996, 56(18):4205-12.
Khawli et al., "Improved tumor localization and radioimaging with chemically modified monoclonal antibodies," Cancer Biother Radiopharm, Jun. 1996, 11(3):203-15.
Kim et al., "Lowering of pI by acylation improves the renal uptake of 99mTc-labeled anti-Tac dsFv: effect of different acylating reagents," Nucl Med Biol, Nov. 2002, 29(8):795-801.
Kim et al., "Chemical modification to reduce renal uptake of disulfide-bonded variable region fragment of anti-Tac monoclonal antibody labeled with 99mTc," Bioconjug Chem, May-Jun. 1999, 10(3):447-53.
Kim et al., "Antibody Engineering for the Development of Therapeutic Antibodies," Mol. Cells, 2005, 20:17-29.
Knappik et al., "Fully Synthetic Human Combinatorial Antibody Libraries (HuCAL) Based on Modular Consensus Frameworks and CDRs Randomized with Trinucleotides," J Mol Biol, Feb. 11, 2000, 296(1):57-86.
Kobayashi et al., "A monoclonal antibody specific for a distinct region of hen egg-white lysozyme," Mol Immunol, Apr. 1982, 19(4):619-30.
Kobayashi et al., "The pharmacokinetic characteristics of glycolated humanized anti-Tac Fabs are determined by their isoelectric points," Cancer Res, Jan. 15, 1999, 59(2):422-30.

(56) References Cited

OTHER PUBLICATIONS

Kohrt et al., "Stimulation of natural killer cells with a CD137-specific antibody enhances trastuzumab efficacy in xenotransplant models of breast cancer," J Clin Invest, Mar. 1, 2012, 122(3):1066-75, doi: 10.1172/JCI61226, Epub Feb. 13, 2012.
Komissarov et al., "Site-specific Mutagenesis of a Recombinant Anti-single-stranded DNA Fab Role of Heavy Chain Complementarity—Determining Region 3 Residues in Antigen Interaction," J Biol Chem, Oct. 24, 1997, 272(43):26864-70.
Kuroda et al., "Computer-aided antibody design," Protein Eng Des Sei, Oct. 2012, 25(10):507-21. Epub Jun. 2, 2012.
Laitinen et al., "Brave new (strept)avidins in biotechnology," Trends Biotechnol., Jun. 2007, 25(6):269-77, Epub Apr. 12, 2007.
Lazar et al., "Engineered antibody Fc variants with enhanced effector function," Proc Natl Acad Sci USA, Mar. 14, 2006, 103(11):4005-10. Epub Mar. 6, 2006.
Lee et al., "High-affinity human antibodies from phage-displayed synthetic Fab libraries with a single framework scaffold," J Mol Biol, 2004, 340(5):1073-93.
Leong et al., "Adapting pharmacokinetic properties of a humanized anti-interleukin-8 antibody for therapeutic applications using site-specific pegylation," Cytokine, Nov. 7, 2001, 16(3):106-19.
Lewis et al., "Differential responses of human tumor cell lines to anti-pl85HER2 monoclonal antibodies," Cancer Immunol Immunother, 1993, 37(4):255-63.
Li et al., "Construction and characterization of a humanized anti-human CD3 monoclonal antibody 12F6 with effective immunoregulation functions," Immunology, Dec. 2005, 116(4):487-98.
Li et al., "Inhibitory Fcγ receptor engagement drives adjuvant and anti-tumor activities of agonistic CD40 antibodies," Science, Aug. 19, 2011, 333(6045):1030-4. doi: 10.1126/science.1206954.
Li et al., "CD72 down-modulates BCR-induced signal transduction and diminishes survival in primary mature B lymphocytes," J Immunol, May 1, 2006, 176(9):5321-8.
Li et al., "Apoptotic and antitumor activity of death receptor antibodies require inhibitory Fcγ receptor engagement," Proc Natl Acad Sci USA, Jul. 3, 2012, 109(27):10966-71. doi: 10.1073/pnas.1208698109. Epub Jun. 20, 2012.
Liang et al., "Immunity against a therapeutic xenoprotein/Fc construct delivered by gene transfer is reduced through binding to the inhibitory receptor FcγRIIb," J Gene Med, 2011, 13(9):470-7.
Lin et al., "Preclinical pharmacokinetics, interspecies scaling, and tissue distribution of a humanized monoclonal antibody against vascular endothelial growth factor," J Pharmacol Exp Ther, 1999, 288(1):371-8.
Linder et al., "Design of a pH-dependent cellulose-binding domain," FEBS Lett, Mar. 19, 1999, 447(1):13-6.
Liu et al., "Heterogeneity of Monoclonal Antibodies," J Pharm Sci, Jul. 2008, 97(7):2426-47.
Lobo et al., "Antibody pharmacokinetics and pharmacodynamics," J Pharm Sci, 2004, 93:2645-68.
Lutterbuese et al., "T cell-engaging BiTE antibodies specific for EGFR potently eliminate KRAS- and BRAF-mutated colorectal cancer cells," Proc Natl Acad Sci USA, Jul. 13, 2010, 107(28):12605-10. doi: 10.1073/pnas.1000976107, Epub Jun. 28, 2010.
Luttrell et al., "Reaction coupling of chelation and antigen binding in the calcium ion-dependent antibody binding of cyclic AMP," J Biol Chern, Nov. 15, 1991, 266(32):21626-30.
MacCallum et al., "Antibody-antigen interactions: contact analysis and binding site topography," J Mol Biol, 1996, 262:732-45.
Mackay et al., "Selective dysregulation of the FcgammaIIB receptor on memory B cells in SLE," J Exp Med, Sep. 4, 2006, 203(9):2157-64. Epub Aug. 21, 2006.
Maeda et al., "pH-dependent receptor/ligand dissociation as a determining factor for intracellular sorting of ligands for epidermal growth factor receptors in rat hepatocytes," J Control Release, Jul. 18, 2002, 82(1):71-82.
Maier et al., "Assessment of fully automated antibody homology modeling protocols in molecular operating environment," Proteins, Aug. 2014, 82(8):1599-610. doi: 10.1002/prot.24576. Epub Apr. 23, 2014.
Maini et al., "Double-blind randomized controlled clinical trial of the interleukin-6 receptor antagonist, tocilizumab, in European patients with rheumatoid arthritis who had an incomplete response to methotrexate," Arthritis Rheum, 2006, 54:2817-29.
Malbec et al., "Antibodies against growth factor receptors can inhibit the proliferation of transformed cells via a cis-interaction with inhibitory FcR," Immunol Lett, Mar. 30, 2012, 143(1):28-33.
Manger et al., "Fcgamma receptor IIa polymorphism in Caucasian patients with systemic lupus eiythematosus: association with clinical symptoms," Arthritis Rheum, 1998, 41(7):1181-9.
Marshall et al., "Rational design and engineering of therapeutic proteins," Drug Discov Today, Mar. 1, 2003, 8(5):212-21.
Martin et al., "Crystal structure at 2.8 A of an FcRn/heterodimeric Fc complex: mechanism of pH-dependent binding," Mol Cell, Apr. 2001, 7(4):867-77.
Martin et al., "Preclinical safety and immune-modulating effects of therapeutic monoclonal antibodies to interleukin-6 and tumor necrosis factor-α in cynomolgus macaques," J Immunotoxicol, Jul. 1, 2004, 1(3):131-9. doi:10.1080/15476910490894904.
Matsumiya et al., "Structural comparison of fucosylated and nonfucosylated Fc fragments of human immunoglobulin G1," J Mol Biol, May 4, 2007, 368(3):767-79, Epub Feb. 22, 2007.
Matsunaga et al., "A pH-dependent conformational transition of Abeta peptide and physicochemical properties of the conformers in the glial cell," Biochem J, Feb. 1, 2002, 361(Pt 3):547-56.
Maurer et al., "Antigenicity of polypeptides (poly alpha amino acids): calcium-dependent and independent antibodies," J Immunol, Sep. 1970, 105(3):567-73.
Maxfield et al., "Endocytic recycling," Nat Rev Mol Cell Biol, Feb. 2004, 5(2):121-32.
Merchant et al., "An efficient route to human bispecific IgG," Nat Biotechnol, Jul. 1998, 16:677-681.
Meyer et al., "Bevacizumab immune complexes activate platelets and induce thrombosis in FCGR2A transgenic mice," J Thromb Haemost, Jan. 2009, 7(1):171-81. doi: 10.1111/j.1538-7836.2008.03212.x. Epub Oct. 30, 2008.
Mi et al., "Targeting the neonatal Fc receptor for antigen delivery using engineered Fc fragments," J Immunol, 2008, 181(11):7550-61.
Mimoto et al., "Engineered antibody Fc variant with selectively enhanced FcγRIIb binding over both FcγRIIa(R131) and FcγRIIa(H131)," Protein Eng Des Sei, Oct. 2013, 26(10):589-98. doi: 10.1093/protein/gzt022. Epub Jun. 5, 2013.
Mohan et al., CALBIOCHEM Buffers, "A guide for the preparation and use of buffers in biological systems," by Chandra Mohan, Ph.D., Copyright 2003 EMD Biosciences, Inc., an Affliate of Merck K GaA, Darmastadt, Germany , 37 pages (CALBIOCHEM Buffers Booklet, 2003).
Montero-Julian et al., "Pharmacokinetic study of anti-interleukin-6 (IL-6) therapy with monoclonal antibodies: enhancement of IL-6 clearance by cocktails of anti-IL-6 antibodies," Blood, Feb. 15, 1995, 85(4):917-24.
Moore et al., "Engineered Fc variant antibodies with enhanced ability to recruit complement and mediate effector functions," mAbs, Mar.-Apr. 2010, 2(2):181-9.
Morgan et al., "The N-terminal end of the CH2 domain of chimeric human IgG1 anti-HLA-DR is necessary for C1q, Fc gamma RI and Fc gamma RIII binding," Immunology, Oct. 1995, 86(2):319-24.
Muller et al., "VEGF and the Fab fragment of a humanized neutralizing antibody: crystal structure of the complex at 2.4 Å resolution and mutational analysis of the interface," Structure, Sep. 6, 1998, (9):1153-67.
Murata et al., "Anti-Digoxin Fab Variants Generated by Phage Display," Mol Biotechnol, Jun. 2013, 54(2):269-77. doi: 10. 1007/s12033-012-9564-1.
Murtaugh et al., "A combinatorial histidine scanning library approach to engineer highly pH-dependent protein switches," Protein Sci, 2011, 20(9):1619-31 doi:10.1002/pro 696.

(56) References Cited

OTHER PUBLICATIONS

Muta et al., "A 13-amino-acid motif in the cytoplasmic domain of Fc gamma RIIB modulates B-cell receptor signaling," Nature, Mar. 3, 1994, 368(6466):70-3.
Nakamura et al., "Fegamma receptor IIB-deficient mice develop Goodpasture's syndrome upon immunization with type IV collagen: a novel murine model for autoimmune glomerular basement membrane disease," J Exp Med, Mar. 6, 2000, 191(5):899-906.
Nam et al., "Current evidence for the management of rheumatoid arthritis with biological disease-modifying antirheumatic drugs: a systematic literature review informing the EULAR recommendations for the management of RA," Ann Rheum Dis, Jun. 2010, 69(6):976-86. doi: 10.1136/ard.2009.126573. Epub May 6, 2010.
Nesterova et al., AACR Abstract No. 656 (2007), Los Angeles, CA (Apr. 4-18, 2007), 3 pages.
Nicholas et al., "Regulation of the immune response. I. Reduction in ability of specific antibody to inhibit long-lasting IgG immunological priming after removal of the Fc fragment," J Exp Med, Jun. 1, 1969, 129(6):1183-201.
Niebecker et al., "Safety of therapeutic monoclonal antibodies," Curr Drug Saf, 2010, 5(4):275-86.
Nimmerjahn et al., "Divergent immunoglobulin g subclass activity through selective Fc receptor binding," Science, 2005, 310(5753):1510-2.
Nimmerjahn et al., "Fegamma receptors as regulators of immune responses," Nat Rev Immunol, Jan. 2008, 8(1):34-47.
Nishimoto et al., "Humanized anti-interleukin-6 receptor antibody treatment of multicentric Castleman disease," Blood, 2005, 106:2627-32.
Nishimoto et al., "Interleukin 6: from bench to bedside," Nat Clin Pract Rheumatol, 2006, 2:619-626.
Nishimoto et al., "Mechanisms and pathologic significances in increase in serum interleukin-6 (IL-6) and soluble IL-6 receptor after administration of an anti-IL-6 receptor antibody, tocilizumab, in patients with rheumatoid arthritis and Castleman disease," Blood, Nov. 15, 2008, 112(10):3959-64. doi: 10.1182/blood-2008-05-155846. Epub Sep. 10, 2008.
Nordlund et al., "Introduction of histidine residues into avidin subunit interfaces allows pH-dependent regulation of quaternary structure and biotin binding," FEBS Lett, Dec. 18, 2003, 555(3):449-54.
Ober et al., "Visualizing the Site and Dynamics of IgG Salvage by the MHC Class I-Related Receptor, FcRn," J Immunol, Feb. 15, 2004, 172(4):2021-9.
Olferiev et al., "The role of activating protein 1 in the transcriptional regulation of the human FCGR2B promoter mediated by the -343 G -> C polymorphism associated with systemic lupus eiythematosus," J Biol Chem, Jan. 19, 2007, 282(3):1738-46, Epub Nov. 27, 2006.
Onda et al., "Lowering the Isoelectric Point of the Fv Portion of Recombinant Immunotoxins Leads to Decreased Nonspecific Animal Toxicity without Affecting Antitumor Activity," Cancer Res, 2001, 61:5070-77.
Ono et al., "The humanized anti-HM1.24 antibody effectively kills multiple myeloma cells by human effector cell-mediated cytotoxicity," Mol Immunol, Apr. 1999, 36(6):387-95.
Osbourn et al., "Generation of a panel of related human scFv antibodies with high affinities for human CEA," Immunotechnology, Sep. 1996, 2(3):181-96.
Ozhegov et al., Tolkovyi Slovar Russkogo iazyka: 2004, p. 292 (with an English translation of the relevant passage defining "control").
Pakula et al., "Genetic Analysis of Protein Stability and Function," Annu Rev Genet, 1989, 23:289-310.
Palladino et al., "Anti-TNF-alpha therapies: the next generation," Nat Rev Drug Discov, Sep. 2003, 2(9):736-46.
Pancook et al., In Vitro Affinity Maturation of Human IgM Antibodies Reactive with Tumor-Associated Antigens, Hybrid Hybridomics, Oct. 2001, 20(5-6):383-96.
Pardridge et al., "Enhanced Endocytosis in Cultured Human Breast Carcinoma Cells and In Vivo Biodistribution in Rats of a Humanized Monoclonal Antibody after Cationization of the Protein," J Pharmacol Exp Ther, Jul. 1998, 286(1):548-54.
Pardridge et al., "Enhanced cellular uptake and in vivo biodistribution of a monoclonal antibody following cationization," J Pharm Sci, Aug. 1995, 84(8):943-8.
Patton et al., "An acid dissociation bridging ELISA for detection of antibodies directed against therapeutic proteins in the presence of antigen," J Immunol Methods, Sep. 2005, 304(1-2):189-95.
Pavlinkova et al., "Charge-Modified Single Chain Antibody Constructs of Monoclonal Antibody CC49: Generation, Characterization, Pharmacokinetics, and Biodistribution Analysis," Nucl Med Biol, Jan. 1999, 26(1):27-34.
Pavlou et al., "The therapeutic antibodies market to 2008," Eur J Pharm Biopharm., Apr. 2005, 59(3):389-96.
Pejchal et al., "A Conformational Switch in Human Immunodeficiency Vims gp41 Revealed by the Structures of Overlapping Epitopes Recognized by Neutralizing Antibodies," J Virol, Sep. 2009, 83(17):8451-62, doi: 10.1128/JVI. 00685-09, Epub Jun. 10, 2009.
Petkova et al., "Enhanced half-life of genetically engineered human IgG1 antibodies in a humanized FcRn mouse model: potential application in humorally mediated autoimmune disease," Int Immunol, 2006, 18(12):1759-69.
Poduslo et al., "Polyamine modification increases the permeability of proteins at the blood-nerve and blood-brain barriers," J Neurochem, 1996, 66:1599-1609.
Pons et al., "Energetic analysis of an antigen/antibody interface: Alanine scanning mutagenesis and double mutant cycles on the HyHEL-10/lysozyme interaction," Protein Sci, May 1999, 8(5):958-68.
Presta, "Engineering of therapeutic antibodies to minimize immunogenicity and optimize function," Adv Drug Deliv Rev, Aug. 7, 2006, 58(5-6):640-56, Epub May 23, 2006.
Prickett et al., "A calcium-dependent antibody for identification and purification of recombinant proteins," Biotechniques, Jun. 1989, 7(6):580-9.
Qiao et al., "Dependence of antibody-mediated presentation of antigen on FcRn," Proc Natl Acad Sci USA, 2008, 105(27):9337-42.
Radaev et al., "The role of Fc glycosylation and the binding of peptide inhibitors," J Biol Chem, May 11, 2001, 276(19):16478-83. Epub Jan. 31, 2001.
Radaev et al., "The structure of a human type III Fegamma receptor in complex with Fc," J Biol Chem, May 11, 2001, 276(19):16469-77. Epub Jan. 31, 2001.
Rajpal et al., A general method for greatly improving the affinity of antibodies by using combinatorial libraries, Proc Natl Acad Sci USA, 2005, 102:8466-71.
Ramos et al., "Evaluation of CA-125 and soluble CD-23 in patients with pelvic endometriosis: a case-control study," Rev Assoc Med Bras, Jan.-Feb. 2012, 58(1):26-32.
Raposo et al., "Epitope-specific antibody response is controlled by immunoglobulin Vh polymorphisms," J Exp Med, Mar. 10, 2014, 211(3):405-11.doi:10.1084/jem.20130968. Epub Feb. 17, 2014.
Rathanaswami et al., "Demonstration of an in vivo generated sub-picomolar affinity fully human monoclonal antibody to interleukin-8," Biochem Biophys Res Commun, 2005, 334:1004-13.
Ravetch et al., "Immune inhibitory receptors," Science, Oct. 6, 2000, 290(5489):84-9.
Reddy et al., "Elimination of Fc Receptor-Dependent Effector Functions of a Modified IgG4 Monoclonal Antibody to Human CD4," J Immunol, Feb. 15, 2000, 164(4):1925-33.
Reichert et al., "Development trends for monoclonal antibody cancer therapeutics," Nat Rev Drug Discovery, May 2007, 6(5):349-56.
Reichert et al., "Monoclonal antibody successes in the clinic," Nat Biotechnol, Sep. 2005, 23(9):1073-8.
Reimann et al., "A humanized form of a CD4-specific monoclonal antibody exhibits decreased antigenicity and prolonged plasma half-life in rhesus monkeys while retaining its unique biological and antiviral properties," AIDS Res Hum Retroviruses, Jul. 20, 1997, 13(11):933-43.

(56) References Cited

OTHER PUBLICATIONS

Reverberi et al., "Factors affecting the antigen-antibody reaction," Blood Transfus, Nov. 2007, 5(4):227-40. doi: 10.2450/2007.0047-07.
Rich et al., "Grading the commercial optical biosensor literature—Class of 2008: 'The Mighty Binders'," J Mol Recognit, 2010, 23(1):1-64. doi: 10.1002/jmr.1004.
Richards et al., "Optimization of antibody binding to FegammaRIIa enhances macrophage phagocytosis of tumor cells," Mol Cancer Ther, Aug. 2008, 7(8):2517-27. doi: 10.1158/1535-7163.MCT-08-0201.
Riechelmann et al., "Phase I trial with the CD44v6-targeting immunoconjugate bivatuzumab mertansine in head and neck squamous cell carcinoma," Oral Oncol, Sep. 2008, 44(9):823-9. doi: 10,1016/j.oraloncology.2007.10.009. Epub Jan. 18, 2008.
Robles-Carrillo et al., "Anti-CD40L immune complexes potently activate platelets in vitro and cause thrombosis in FCGR2A transgenic mice," J Immunol, Aug. 1, 2010, 185(3):1577-83. doi: 10.4049/jimmunol.0903888. Epub Jun. 28, 2010.
Roitt et al., Immunology, M., Mir, (2000), pp. 110-111 (in Russian, with what is believed to be a published English equivalent of those pages taken from Roitt et al., "Antibody Structure and Function," Immunology, Fifth Ed., (1998), pp. 80-81).
Rojas et al., "Formation, distribution, and elimination of infliximab and anti-infliximab immune complexes in cynomolgus monkeys," J Pharmacol Exp Ther, May 2005, 313(2):578-85. Epub Jan. 12, 2005.
Roopenian et al., "FcRn: the neonatal Fc receptor comes of age," Nat Rev Immunol, 2007, 7(9):715-25.
Rothe et al., "Ribosome display for improved biotherapeutic molecules," Expert Opin Biol Ther, 2006, 6:177-187.
Rudikoff et al., "Single amino acid substitution altering antigen-binding specificity," Proc Natl Acad Sci USA, Mar. 1982, 79(6):1979-83.
Rudge et al.,, "VEGF Trap complex formation measures production rates of VEGF, providing a biomarker for predicting efficacious angiogenic blockade," Proc Natl Acad Sci USA, 2007, 104(47):18363-70.
Salfeld et al., "Isotype selection in antibody engineering," Nat Biotechnol, 2007, 25:1369-72.
Salmon et al., "Fc gamma RIIA alleles are heritable risk factors for lupus nephritis in African Americans," J Clin Invest, Mar. 1, 1996, 97(5):1348-54.
Sarkar et al., "Rational cytokine design for increased lifetime and enhanced potency using pH-activated 'histidine switching'," Nat Biotechnol, Sep. 2002, 20(9):908-13. Epub Aug. 5, 2002.
Sato et al., "Reshaping a human antibody to inhibit the interleukin 6-dependent tumor cell growth," Cancer Res, 1993, 53:851-856.
Satoh et al., "Non-fucosylated therapeutic antibodies as next-generation therapeutic antibodies," Expert Opin Biol Ther, 2006, 6(11):1161-73.
Scappaticci et al., "Arterial thromboembolic events in patients with metastatic carcinoma treated with chemotherapy and bevacizumab," J Natl Cancer Inst, Aug. 15, 2007, 99(16):1232-9. Epub Aug. 8, 2007.
Schaeffer et al., "The rat glomerular filtration bamer does not show negative charge selectivity," Microcirculation, Oct. 2002, 9(5):329-42.
Schier et al., "Isolation of Picomolar Affinity Anti-c-erbB-2 Single-chain Fv by Molecular Evolution of the Complementarity Determining Regions in the Center of the Antibody Binding Site," J Mol Biol. Nov. 8, 1996, 263(4):551-67.
Schmitz et al., "Phage display: a molecular tool for the generation of antibodies—a review," Placenta, Mar. 2000, 21 Suppl A:S106-12.
Schulke et al., "The homodimer of prostate-specific membrane antigen is a functional target for cancer therapy," Proc Natl Acad Sci USA, Oct. 28, 2003, 100(22):12590-5.
Schuster et al., "Signaling of human ciliary neurotrophic factor (CNTF) revisited. The interleukin-6 receptor can serve as an alpha-receptor for Ctnf," J Biol Chem, Mar. 14, 2003, 278(11):9528-35.
Schroeder et al., "Similarity and divergence in the development and expression of the mouse and human antibody repertoires," Dev Comp Immunol, 2006, 30(1-2):119-35.
Schroter et al., "A generic approach to engineer antibody pH-switches using combinatorial histidine scanning libraries and yeast display," mAbs, 2015, 7(1):138-51. doi: 10.4161/19420862.2014.985993.
Seda et al., "B-cell receptor signalling and its crosstalk with other pathways in normal and malignant cells," Eur J Haematol, Mar. 2015, 94(3):193-205. doi: 10.1111/ejh.12427. Epub Sep. 13, 2014.
Sharifi et al., "Improving monoclonal antibody pharmacokinetics via chemical modification," Q J Nucl Med, Dec. 1998, 42(4):242-9.
Shields et al., "High resolution mapping of the binding site on human IgGl for Fc gamma RI, Fc gamma RII, Fc gamma RIII, and FcRn and design of IgGl variants with improved binding to the Fc gamma R," J Biol Chem, Mar. 2, 2001, 276(9):6591-604, Epub Nov. 28, 2000.
Shinkawa et al., "The absence of fucose but not the presence of galactose or bisecting N-acetylglucosamine of human IgG1 complex-type oligosaccharides shows the critical role of enhancing antibody-dependent cellular cytotoxicity," J Biol Chem, Jan. 31, 2003, 278(5):3466-73. Epub Nov. 8, 2002.
Shire et al., "Challenges in the development of high protein concentration formulations," J Pharm Sci, 2004, 93:1390-1402.
Sigma-Aldrich, "Product Information: Monoclonal Anti-Flag ® M1, Clone M1 produced in mouse, purified immunoglobulin," Sigma-Aldrich.com, Catalog No. F3040. Retrieved from the Internet on Nov. 5, 2013 at: http://www.sigmaaldrich.com/content/dam/sigma-aldrich/does/Sigma/Datasheet/f3040dat.pdf.
Sims et al., "HMGB1 and RAGE in inflammation and cancer," Annu Rev Immunol, 2010, 28:367-88.
Singer et al., "1.3 Structure of Proteins," Genes & Genomes, 1991, pp. 67-69.
Smith et al., "FcgammaRIIB in autoimmunity and infection: evolutionary and therapeutic implications," Nat Rev Immunol, May 2010, 10(5):328-43, doi: 10.1038/nri2762.
Sondermann et al., "The 3.2-A crystal structure of the human IgG1 Fc fragment-Fc gammaRIII complex," Nature, Jul. 20, 2000, 406(6793):267-73.
Stearns et al., "The interaction of a Ca2+-dependent monoclonal antibody with the protein C activation peptide region. Evidence for obligatory Ca2+ binding to both antigen and antibody," J Biol Chem, Jan. 15, 1988, 263(2):826-32.
Stewart et al., "Site-directed mutagenesis of a catalytic antibody: an arginine and a histidine residue play key roles," Biochemistiy, 1994, 33(8):1994-2003.
Strand et al., "Biologic therapies in rheumatology: lessons learned, future directions," Nat Rev Drug Discov, 2007, 6:75-92.
Strohl WR, Optimization of Fc-mediated effector functions of monoclonal antibodies, Curr Opin Biotechnol, Dec. 2009, 20(6):685-91. doi: 10.1016/j.copbio.2009.10.011. Epub Nov. 4, 2009.
Su et al., Expression profile of FcgammaRIIb on leukocytes and its dysregulation in systemic lupus eiythematosus, J Immunol, Mar. 1, 2007, 178(5):3272-80.
Suzuki et al., "Importance of neonatal FcR in regulating the semm half-life of therapeutic proteins containing the Fc domain of human IgG1: a comparative study of the affinity of monoclonal antibodies and Fc-fusion proteins to human neonatal FcR," J Immunol, 2010, 184(4):1968-76.
Tabrizi et al., "Elimination mechanisms of therapeutic monoclonal antibodies," Drug Discov Today, Jan. 2006, 11(1-2):81-8.
Takeuchi et al., "The Japanese experience with biologic therapies for rheumatoid arthritis," Nat Rev Rheumatol, Nov. 2010, 6(11):644-52, doi: 10.1038/nrrheum.2010.154. Epub Sep. 28, 2010.
Tan et al., "Engineering the isoelectric point of a renal cell carcinoma targeting antibody greatly enhances scFv solubility," Immunotechnology, Oct. 1998, 4(2):107-14.
Tanzi et al., "Twenty years of the Alzheimer's disease amyloid hypothesis: a genetic perspective," Cell, Feb. 2005, 120(4):545-55. (doi:10.1016/j.cell.2005.02.008;PMID 15734686).
Tarditi et al., "Selective high-performance liquid chromatographic purification of bispecific monoclonal antibodies," J Chromatogr, 1992, 599(1-2):13-20.

(56) References Cited

OTHER PUBLICATIONS

Teeling et al., "The Biological Activity of Human CD20 Monoclonal Antibodies Is Linked to Unique Epitopes on CD20," J Immunol, Jul. 1, 2006, 177(1):362-71.
Ten Kate et al., "Effect of isoelectric point on biodistribution and inflammation: imaging with indium-111-labelled IgG,"Eur J Nucl Med, Jun. 1990, 17(6-8):305-9 (abstract) [Database BIOSIS Accession No. 1991910742 20].
Trinh et al., "Ipilimumab in the treatment of melanoma," Expert Opin Biol Ther, Jun. 2012, 12(6):773-82, doi: 10.1517/14712598.2012.675325. Epub Apr. 14, 2012.
Tsuchiya, Credit Suisse Seminar, "Therapeutic Antibody," at Fuji-Gotemba Laboratories, p. 21 (2006) (English translation).
Tsurushita et al., "Design of humanized antibodies: From anti-Tac to Zenapax," Methods, 2005, 36:69-83.
Vaccaro et al., "Engineering the Fc region of immunoglobulin G to modulate in vivo antibody levels," Nat Biotechnol, Oct. 2005, 23(10): 1283-8, Epub Sep. 25, 2005.
Vaisitti et al., "Cationization of monoclonal antibodies: Another step towards the "Magic Bullet"?" J Biol Regul Homeost Agents. Jul.-Dec. 2005, 19(3-4):105-12.
Vajdos et al., "Comprehensive Functional Maps of the Antigen-binding Site of an Anti-ErbB2 Antibody Obtained with Shotgun Scanning Mutagenesis," J Mol Biol, Jul. 5, 2002, 320(2):415-28.
Van Walle et al., "Immunogenicity screening in protein drug development," Expert Opin Biol Ther, Mar. 2007, 7(3):405-18.
Vaughn et al., "Structural basis of pH-dependent antibody binding by the neonatal Fc receptor," Structure, 1998, 6(1):63-73.
Verhoeyen et al., "Construction of a reshaped HMFG1 antibody and comparison of its fine specificity with that of the parent mouse antibody," Immunology, Mar. 1993, 78(3):364-70.
Verhoeyen et al., "Monoclonal Antibodies in Clinical Oncology," 1991, Edited by AA Epenetos, Chapter 5, pp. 37-43, Chapman and Hall.
Veri et al., "Therapeutic control of B cell activation via recruitment of Fcgamma receptor IIb (CD32B) inhibitory function with a novel bispecific antibody scaffold," Arthritis Rheum, Jul. 2010, 62(7):1933-43. doi: 10.1002/art.27477.
Veri et al., "Monoclonal antibodies capable of discriminating the human inhibitory Fcgamma-receptor IIB (CD32B) from the activating Fcgamma-receptor IIa (CD32A): biochemical, biological and functional characterization," Immunology, 2007, 121(3):392-404.
Vidarsson et al., "IgG subclasses and allotypes: from structure to effector functions," Front Immunol, Oct. 20, 2014, 5:520. doi: 10.3389/fimmu.2014.00520. eCollection 2014.
Wang et al., "HMG-1 as a late mediator of endotoxin lethality in mice," Science, 1999, 285(5425):248-51.
Wang et al., "Monoclonal Antibodies with Identical Fc Sequences Can Bind to FcRn Differentially with Pharmacokinetic Consequences," Dmg Metabolism and Disposition, Sep. 2011, 39(9):1469-77. doi: 10.1124/dmd.111.039453. Epub May 24, 2011.
Ward et al., "A calcium-binding monoclonal antibody that recognizes a non-calcium-binding epitope in the short consensus repeat units (SCRs) of complement C1r," Mol Immunol, Jan. 1992, 29(1):83-93.
Warmerdam et al., Molecular basis for a polymorphism of human Fc gamma receptor II (CD32), J Exp Med, Jul. 1, 1990, 172(1):19-25.
Weiner et al., "Monoclonal antibodies: versatile platforms for cancer immunotherapy," Nat Rev Immunol, May 2010, 10(5):317-27, doi: 10.1038/nri2744.
Wenink et al., "The inhibitory Fc gamma IIb receptor dampens TLR4-mediated immune responses and is selectively up-regulated on dendritic cells from rheumatoid arthritis patients with quiescent disease," J Immunol, Oct. 1, 2009, 183(7):4509-20. doi: 10.4049/jimmunol.0900153. Epub Sep. 4, 2009.
Wernersson et al., "IgG-mediated enhancement of antibody responses is low in Fc receptor gamma chain-deficient mice and increased in Fc gamma RII-deficient mice," J Immunol, Jul. 15, 1999, 163(2):618-22.
Wiens et al., "Somatic Mutation in VH Complementarity-Determining Region 2 and Framework Region 2," J Immunol, Aug. 1, 1997, 159(3):1293-302.
Wiens et al., "Mutation of a Single Conserved Residue in VH Complementarity-Determining Region 2 Results in a Severe Ig Secretion Defect," J Immunol, Aug. 15, 2001, 167(4):2179-86.
Wikipedia, "Chaotropic agent" [online], [retrieved on Nov. 2, 2015], Retrieved from the Inernet: https://en.wikipedia.org/wiki/Chaotropic_agent, 3 pages.
Wilson et al., "An Fcγ receptor-dependent mechanism drives antibody-mediated target-receptor signaling in cancer cells," Cancer Cell, Jan. 18, 2011, 19(1):101-13, doi: 10.1016/j.ccr.2010.11.012.
Wojciak et al., "The crystal structure of sphingo sine-1-phosphate in complex with a Fab fragment reveals metal bridging of an antibody and its antigen," Proc Natl Acad Sci USA, 2009, 106(42):17717-22.
Wolf et al., "BiTEs: bispecific antibody constmcts with unique anti-tumor activity," Drag Discov Today, Sep. 15, 2005, 10(18):1237-44.
Wu et al., "Development of motavizumab, an ultra-potent antibody for the prevention of respiratory syncytial vims infection in the upper and lower respiratory tract," J Mol Biol, 2007, 368:652-665.
Wu et al., "Humanization of a murine monoclonal antibody by simultaneous optimization of framework and CDR residues," J Mol Biol, Nov. 19, 1999, 294(1):151-62.
Wu et al., "Stepwise in vitro affinity maturation of Vitaxin, an αvβ33-specific humanized mAb," Proc Natl Acad Sci USA, May 26, 1998, 95(11):6037-42.
Xiang et al., "Study of B72.3 combining sites by molecular modeling and site-directed mutagenesis," Protein Eng, 2000, 13(5):339-44.
Xiao et al., "Pharmacokinetics of anti-hepcidin monoclonal antibody Ab 12B9m and hepcidin in cynomolgus monkeys," AAPS J, Dec. 2010, 12(4):646-57. doi: 10.1208/s12248-010-9222-0. Epub Aug. 25, 2010.
Xolair (omalizumab) Prescribing Information, https://www.gene.com/download/pdf/xolair_prescribing.pdf, Jul. 2016, 27 pages.
Xu et al., "Fc gamma Rs modulate cytotoxicity of anti-Fas antibodies: implications for agonistic antibody-based therapeutics," J Immunol, Jul. 15, 2003, 171(2):562-8.
Yamamoto et al., "Molecular studies of pH-dependent ligand interactions with the low-density lipoprotein receptor," Biochemistry, 2008, 47(44):11647-52.
Yamasaki et al., "Pharmacokinetic analysis of in vivo disposition of succinylated proteins targeted to liver nonparenchymal cells via scavenger receptors: importance of molecular size and negative charge density for in vivo recognition by receptors," J Pharmacol Exp Ther, 2002, 301:467-477.
Yang et al., "CDR walking mutagenesis for the affinity maturation of a potent human anti-HIV-1 antibody into the picomolar range," J Mol Biol, 1995, 254(3):392-403.
Yang et al., "Tailoring structure-function and pharmacokinetic properties of single-chain Fv proteins by site-specific PEGylation," Protein Eng, Oct. 2003, 16(10):761-70.
Yarmush et al., "Immunoadsorption: strategies for antigen elution and production of reusable adsorbents," Biotechnol Prog, May-Jun. 1992, 8(3):168-78.
Yeung et al., "Engineering human IgG1 affinity to human neonatal Fc receptor: impact of affinity improvement on pharmacokinetics in primates," J Immunol, Jun. 15, 2009, 182(12):7663-71. doi: 10.4049/jimmunol.0804182.
Yuasa et al., "Deletion of Fcgamma receptor IIB renders H-2(b) mice susceptible to collagen-induced arthritis," J Exp Med, Jan. 4, 1999, 189(1):187-94.
Zalevsky et al., "Enhanced antibody half-life improves in vivo activity," Nat Biotechnol, 2010, 28(2):157-9.
Zalevsky et al., "The impact of Fc engineering on an anti-CD19 antibody: increased Fcgamma receptor affinity enhances B-cell clearing in nonhuman primates," Blood, 2009, 113(16):3735-43. Epub Dec. 24, 2008.
Zhang et al., "Effective therapy for a murine model of human anaplastic large-cell lymphoma with the anti-CD30 monoclonal antibody, HeFi-1,does not require activating Fc receptors," Blood, Jul. 15, 2006, 108(2):705-10. Epub Mar. 21, 2006.

(56) References Cited

OTHER PUBLICATIONS

Zhang et al., "Immune complex/Ig negatively regulate TLR4-triggered inflammatory response in macrophages through Fc gamma RIIb-dependent PGE2 production," J Immunol, Jan. 1, 2009, 182(1):554-62.
Zheng et al., "Translational pharmacokinetics and pharmacodynamics of an FcRn-variant anti-CD4 monoclonal antibody from preclinical model to phase I study," Clin Pharmacol Ther, Feb. 2011, 89(2):283-90, doi: 10.1038/clpt.2010.311. Epub Dec. 29, 2010.
Zhou et al., "Interfacial metal and antibody recognition," Proc Natl Acad Sci USA, (2005) 102(41):14575-80.
Zhu et al., "MHC class I-related neonatal Fc receptor for IgG is functionally expressed in monocytes, intestinal macrophages, and dendritic cells," J Immunol, 2001, 166(5):3266-76.
Zuckier et al., "Chimeric human-mouse IgG antibodies with shuffled constant region exons demonstrate that multiple domains contribute to in vivo half-life," Cancer Res, 1998, 58:3905-08.
Zwick et al., "The Long Third Complementarity-Determining Region of the Heavy Chain Is Important in the Activity of the Broadly Neutralizing Anti-Human Immunodeficiency Virus Type 1 Antibody 2F5," J Virol, Mar. 2004, 78(6):3155-61.
USPTO Restriction Requirement in U.S. Appl. No. 13/637,415, dated Dec. 31, 2014, 8 pages.
Fish & Richardson P.C., Reply to Restriction Requirement dated Dec. 31, 2014 in U.S. Appl. No. 13/637,415, filed Feb. 25, 2015, 1 page.
USPTO Non-Final Office Action in U.S. Appl. No. 13/637,415, dated May 13, 2015, 24 pages.
Fish & Richardson P.C., Reply to Non-Final Office Action dated May 13, 2015 in U.S. Appl. No. 13/637,415, filed Aug. 13, 2015, 21 pages.
USPTO Final Office Action in U.S. Appl. No. 13/637,415, dated Nov. 13, 2015, 20 pages.
Fish & Richardson P.C., Reply to Final Office Action dated Nov. 13, 2015 in U.S. Appl. No. 13/637,415, filed May 12, 2016, 22 pages.
USPTO Restriction Requirement in U.S. Appl. No. 13/637,415, dated Dec. 1, 2016.
USPTO Non-Final Office Action in U.S. Appl. No. 13/637,415, dated May 23, 2017, 27 pages.
International Search Report for App. Ser. No. PCT/JP2011/001888, dated Nov. 2, 2011, 7 pages.
USPTO Restriction Requirement in U.S. Appl. No. 14/007,947, dated Nov. 30, 2015, 9 pages.
Fish & Richardson P.C., Reply to Restriction Requirement dated Nov. 30, 2015 in U.S. Appl. No. 14/007,947, filed Apr. 26, 2016, 1 page.
USPTO Non-Final Office Action in U.S. Appl. No. 14/007,947, dated Aug. 22, 2016, 31 pages.
Fish & Richardson P.C. Reply to Final Office Action dated Apr. 21, 2017 in U.S. Appl. No. 14/007,947, filed Oct. 23, 2017, 28 pages.
International Preliminary Report on Patentability for App. Ser. No. PCT/JP2012/058603, dated Oct. 8, 2013, 11 pages.
International Search Report for App. Ser. No. PCT/JP2012/058603, dated May 29, 2012, 2 pages.
International Search Report for App. Ser. No. PCT/JP2012/075083, dated Oct. 23, 2012, 2 pages.
International Preliminary Report on Patentability for App. Ser. No. PCT/JP2012/075083, dated Apr. 1, 2014, 8 pages.
International Search Report for App. Ser. No. PCT/JP2012/006218, dated Mar. 26, 2013, 11 pages.
USPTO Non-Final Office Action in U.S. App. U.S. Appl. No. 13/595,139, dated Nov. 14, 2012, 10 pages.
Fish & Richardson P.C., Amendment in Reply to Office Action dated Nov. 14, 2012 in U.S. Appl. No. 13/595,139, filed May 14, 2013, 19 pages.
USPTO Final Office Action in U.S. Appl. No. 13/595,139, dated Aug. 1, 2013, 8 pages.
USPTO Notice of Allowance in U.S. Appl. No. 13/595,139, dated Oct. 11, 2013, 15 pages.
USPTO Non-Final Office Action in U.S. Appl. No. 13/595,139, dated Mar. 13, 2015, 12 pages.
Fish & Richardson P.C., Amendment and Reply to Office Action dated Mar. 13, 2015 in U.S. Appl. No. 13/595,139, filed Jun. 11, 2015, 19 pages.
USPTO Non-Final Office Action in U.S. Appl. No. 13/595,139, dated Aug. 3, 2015, 13 pages.
FISH & Richardson P.C., Reply to Office Action dated Aug. 3, 2015 in U.S. Appl. No. 13/595,139, filed Dec. 2, 2015, 28 pages.
USPTO Final Office Action in U.S. Appl. No. 13/595,139, dated Feb. 12, 2016, 12 pages.
Fish & Richardson P.C., Reply to Office Action dated Feb. 12, 2016 in U.S. Appl. No. 13/595,139, filed Jul. 11, 2016, 4 pages.
USPTO Non-Final Office Action in U.S. Appl. No. 13/595,139, dated Nov. 23, 2016, 11 pages.
Fish & Richardson P.C., Reply to Office Action dated Nov. 23, 2016 in U.S. Appl. No. 13/595,139, filed Mar. 22, 2016, 29 pages.
USPTO Final Office Action in U.S. Appl. No. 13/595,139, dated May 30, 2017, 23 pages.
Fish & Richardson P.C., Reply to Office Action dated May 30, 2017 in U.S. Appl. No. 13/595,139, filed Sep. 21, 2017, 36 pages.
USPTO Notice of Allowance in U.S. Appl. No. 13/595,139, dated Oct. 3, 2017, 7 pages.
International Search Report for App. Ser. No. PCT/JP2011/077619, dated Feb. 28, 2012, 4 pages.
International Preliminary Report on Patentability for App. Ser. No. PCT/JP2011/077619, dated Jun. 4, 2013, 8 pages.
International Search Report for App. Ser. No. PCT/JP2012/081185, dated Feb. 26, 2013, 9 pages.
International Preliminary Report on Patentability for App. Ser. No. PCT/JP2012/081185, dated Jun. 3, 2014, 9 pages.
International Search Report for App. Ser. No. PCT/JP2013/054461, dated May 7, 2013, 7 pages.
International Preliminary Report on Patentability for App. Ser. No. PCT/JP2013/054461, dated Aug. 26, 2014, 6 pages.
USPTO Restriction Requirement in U.S. Appl. No. 14/347,321, dated Dec. 17, 2015, 10 pages.
Fish & Richardson P.C., Reply to Restriction Requirement dated Dec. 17, 2015 in U.S. Appl. No. 14/347,321, filed Feb. 16, 2016, 3 pages.
Fish & Richardson P.C., Reply to Office Action dated May 2, 2016 in U.S. Appl. No. 14/347,321, filed Nov. 2, 2016, 35 pages.
USPTO Non-Final Office Action in U.S. Appl. No. 14/347,321, dated May 2, 2016, 34 pages.
USPTO Final Office Action in U.S. Appl. No. 14/347,321 dated Jan. 9, 2017, 60 pages.
USPTO Non-Final Office Action in U.S. Appl. No. 14/347,321, dated Nov. 13, 2017, 64 pages.
International Search Report for App. Ser. No. PCT/JP2012/075092, dated Dec. 25, 2012, 4 pages.
International Preliminary Report on Patentability for App. Ser. No. PCT/JP2012/075092, dated Apr. 1, 2014, 10 pages.
International Search Report for App. Ser. No. PCT/JP2013/072507, dated Oct. 29, 2013, 4 pages.
International Preliminary Report on Patentability for App. Ser. No. PCT/JP2013/072507, dated Feb. 24, 2015, 6 pages.
USPTO Non-Final Office Action in U.S. Appl. No. 13/889,512, dated Mar. 26, 2015, 12 pages.
Fish & Richardson P.C., Amendment and Reply to Office Action dated Mar. 26, 2015 in U.S. Appl. No. 13/889,512, filed Jun. 25, 2015, 10 pages.
USPTO Non-Final Office Action in U.S. Appl. No. 13/889,512, dated Aug. 4, 2015, 12 pages.
Fish & Richardson P.C., Amendment and Reply to Office Action dated Aug. 4, 2015 in U.S. Appl. No. 13/889,512, filed Nov. 2, 2015, 13 pages.
USPTO Final Office Action in U.S. Appl. No. 13/889,512, dated Dec. 17, 2015, 11 pages.
Fish & Richardson P.C., Reply to Final Office Action dated Dec. 17, 2015 in U.S. Appl. No. 13/889,512, filed Jul. 15, 2016, 4 pages.
USPTO Non-Final Office Action in U.S. Appl. No. 13/889,512, dated Nov. 28, 2016, 10 pages.

(56) References Cited

OTHER PUBLICATIONS

Fish & Richardson P.C., Reply to Non-Final Office Action dated Nov. 28, 2016 in U.S. Appl. No. 13/889,512, filed Mar. 27, 2017, 16 pages.
USPTO Final Office Action in U.S. Appl. No. 13/889,512, dated May 31, 2017, 15 pages.
Fish & Richardson P.C., Supplemental Reply to Final Office Action dated May 31, 2017 in U.S. Appl. No. 13/889,512, filed Oct. 24, 2017, 15 pages.
USPTO Notice of Allowance in U.S. Appl. No. 13/889,512, dated Oct. 23, 2017, 7 pages.
USPTO Non-Final Office Action in U.S. Appl. No. 13/889,484, dated Apr. 6, 2015, 12 pages.
Fish & Richardson P.C., Amendment and Reply to Office Action dated Apr. 6, 2015 in U.S. Appl. No. 13/889,484, filed Jul. 6, 2015, 14 pages.
USPTO Final Office Action in U.S. Appl. No. 13/889,484, dated Aug. 4, 2015, 12 pages.
Fish & Richardson P.C., Reply to Final Office Action dated Aug. 4, 2015 in U.S. Appl. No. 13/889,484, filed Dec. 2, 2015, 104 pages.
USPTO Advisory Action in U.S. Appl. No. 13/889,484, dated Jan. 7, 2016, 3 pages.
USPTO Non-Final Office Action in U.S. Appl. No. 13/889,484, dated Nov. 25, 2016, 12 pages.
USPTO Reply to Non-Final Office Action in U.S. Appl. No. 13/889,484, dated May 25, 2017, 16 pages.
USPTO Final Office Action in U.S. Appl. No. 13/889,484, dated Aug. 16, 2017, 14 pages.
Fish & Richardson P.C. Reply to Final Office Action dated Aug. 16, 2017 in U.S. Appl. No. 13/889,484, filed Oct. 19, 2017, 28 pages.
USPTO Notice of Allowance in U.S. Appl. No. 13/889,484, dated Nov. 16, 2017, 18 pages.
International Search Report for App. Ser. No. PCT/JP2014/059706, dated Jul. 15, 2014, 4 pages.
International Preliminary Report on Patentability for App. Ser. No. PCT/JP2014/059706, dated Oct. 6, 2015, 10 pages.
USPTO Restriction Requirement in U.S. Appl. No. 14/347,448, dated Dec. 21, 2015, 8 pages.
Fish & Richardson P.C., Reply to Restriction Requirement dated Dec. 21, 2015 in U.S. Appl. No. 14/347,448, filed Mar. 21, 2016, 13 pages.
USPTO Office Action in U.S. Appl. No. 14/347,448, dated May 26, 2016, 54 pages.
Fish & Richardson P.C., Reply to Office Action dated May 26, 2016 in U.S. Appl. No. 14/347,448, filed Nov. 28, 2016, 27 pages.
USPTO Final Office Action in U.S. Appl. No. 14/347,448, dated Feb. 21, 2017, 45 pages.
USPTO Interview Summary in U.S. Appl. No. 14/347,448, dated Aug. 16, 2017, 4 pages.
USPTO Restriction Requirement in U.S. Appl. No. 13/990,158, dated Jan. 6, 2016, 9 pages.
USPTO Non-Final Office Action in U.S. Appl. No. 13/990,158, dated Aug. 19, 2016, 36 pages.
Fish & Richardson P.C, Reply to Non-Final Office Action dated Aug. 19, 2016 in U.S. Appl. No. 13/990,158, filed Feb. 17, 2017, 19 pages.
USPTO Final Office Action in U.S. Appl. No. 13/990,158, dated May 2, 2017, 42 pages.
USPTO Restriction Requirement in U.S. Appl. No. 14/361,013, dated Mar. 16, 2016, 15 pages.
Fish & Richardson P.C., Response to Restriction Requirement dated Mar. 16, 2016 in U.S. Appl. No. 14/361,013, filed Aug. 1, 2016, 21 pages.
USPTO Non-Final Office Action in U.S. Appl. No. 14/361,013, dated Oct. 28, 2016, 33 pages.
Fish & Richardson P.C., USPTO Response Non-Final Office Action in U.S. Appl. No. 14/361,013, dated Apr. 26, 2017, 117 pages.
USPTO Final Office Action in U.S. Appl. No. 14/361,013, dated Jul. 24, 2017, 43 pages.
USPTO Restriction Requirement in U.S. Appl. No. 14/347,187, dated Jan. 26, 2017, 9 pages.
Fish & Richardson P.C., Reply to Restriction Requirement dated Jan. 26, 2017 in U.S. Appl. No. 14/347,187, filed Mar. 27, 2017, 2 pages.
USPTO Non-Final Office Action in U.S. Appl. No. 14/347,187, dated Jun. 14, 2017, 23 pages.
Fish & Richardson P.C., Reply to Non-Final Office Action dated Jun. 14, 2017, in U.S. Appl. No. 14/347,187, filed Oct. 16, 2017, 36 pages.
USPTO Final Office Action in U.S. Appl. No. 14/404,051, dated Oct. 18, 2017, 15 pages.
USPTO Notice of Allowance and Examiner-Initiated Interview Summary in U.S. Appl. No. 14/007,947, dated Apr. 3, 2019, 10 pages.
U.S. Appl. No. 14/377,556, Kuramochi et al., filed Aug. 8, 2014.
U.S. Appl. No. 16/361,498, filed Mar. 22, 2019, Igawa et al.
Aboud-Pirak et al., "Binding and Endocytosis of a Monoclonal Antibody to a High Molecular Weight Human Milk Fat Globule Membrane-associated Antigen by Cultured MCFG-7 Breast Carcinoma Cells," Cancer Res, Jun. 1, 1988, 48(11):3188-96.
Anchin et al., "Recognition of Superpotent Sweetener Ligands by a Library of Monoclonal Antibodies," J Mol Recognit, Sep.-Oct. 1997, 10(5):235-42.
Binding data for Rituximab (submitted by the Opponent during EP opposition procedure for EP 2 708 558 and posted by EPO on Jan. 15, 2019), 6 pages.
Chang et al., "Practical Approaches to Protein Formulation Development," Pharm Biotechnol, 2002, 13:1-25.
Concordance table showing Kabat numbering for antibody Hyb C1 (document submitted in EP opposition 2 275 443 and posted by EPO on Sep. 7, 2016), 6 pages.
Concordance table showing Kabat numbering for antibody 300N (document submitted in EP opposition 2 275 443 and posted by EPO on Sep. 7, 2016), 5 pages.
Cunningham et al., "The Covalent Structure of a Human γG-Immunoglobulin. VII. Amino Acid Sequence of Heavy-Chain Cyanogen Bromide Fragments $H_1$-$H_4$," Biochemistry, Aug. 4, 1970, 9(16):3161-70.
Declaration by Madhusudan Natarajan, Ph.D. (submitted by the Opponent during EP opposition procedure for EP 2 708 558 and posted by EPO on Jan. 15, 2019), 3 pages.
Edwards et al., "The Remarkable Flexibility of the Human Antibody Repertoire; Isolation of Over One Thousand Different Antibodies to a Single Protein, BLyS," J Mol Biol, Nov. 14, 2003, 334(1):103-18.
Examination Report No. 1 for AU 2013306700 (IP Australia) dated Jun. 7, 2018, 3 pages.
Fan et al., "Self-Association of Human PCSK9 Correlates with Its LDLR-Degrading Activity," Biochemistry, Feb. 12, 2008, 47(6):1631-9. doi: 10.1021/bi7016359. Epub Jan. 16, 2008.
Fisher et al., "Affinity purification of antibodies using antigens immobilized on solid supports," Biochem Soc Trans, Apr. 1988, 16(2):134-8.
Goel et al., "Plasticity within the Antigen-Combining Site May Manifest as Molecular Mimicry in the Humoral Immune Response," J Immunol, Dec. 15, 2004, 173(12):7358-67.
Gopferich et al., Chapter 15 "Drug Delivery from Bioerodible Polymers," Formulation and Delivery of Proteins and Peptides, American Chemical Society, eds. Cleland et al., 1994, pp. 242-277.
Hughes-Jones et al., "The Effect of pH and Ionic Strength on the Reaction between Anti-D and Erythrocytes," Immunology, Jan. 1964, 7:72-81.
Huse et al., "Purification of antibodies by affinity chromatography," J Biochem Biophys Methods, May 31, 2002, 51(3):217-31.
Jain et al., "Engineering antibodies for clinical applications," Trends Biotechnol, Jul. 2007, 25(7):307-16, Epub May 21, 2007.
Kakita et al., "Isolation of a Human Monoclonal Antibody with Strong Neutralizing Activity against Diphtheria Toxin," Infect Immun, Jun. 2006, 74(6):3682-3.
Kanyavuz et al., "Breaking the law: unconventional strategies for antibody diversification," Nat Rev Immunol, Jun. 2019, 19(6):355-368. doi: 10.1038/s41577-019-0126-7.

(56) References Cited

OTHER PUBLICATIONS

King, "Preparation, structure and function of monoclonal antibodies," Applications and Engineering of Monoclonal Antibodies, CRC Press, 1998, pp. 2 and 13-4.
King, "Antibody engineering: design for specific applications," Applications and Engineering of Monoclonal Antibodies, CRC Press, 1998, pp. 27-75.
Kipriyanov et al., "Generation of Recombinant Antibodies," Mol Biotechnol, Sep. 1999, 12(2):173-201.
Kranz et al., "Mechanisms of Ligand Binding by Monoclonal Anti-fluorescyl Antibodies," J Biol Chem, Jun. 25, 1982, 257(12):6987-95.
Kurki et al., "Desmin antibodies in acute infectious myopericarditis," APMIS, Jun. 1989, 97(6):527-32.
Lloyd et al., "Modelling the human immune response: performance of a $10^{11}$ human antibody repertoire against a broad panel of therapeutically relevant antigens," Protein Eng Des Sel, Mar. 2009, 22(3):159-68. doi: 10.1093/protein/gzn058. Epub Oct. 29, 2008.
Male et al., Chapter 3 "Antibodies," Immunology, 2006, published by Elsevier Ltd., pp. 59-86.
Medesan et al., "Comparative studies of rat IgG to further delineate the Fc:FcRn interaction site," Eur J Immunol, Jul. 1998, 28(7):2092-100.
Narhi et al., "Effect of Three Elution Buffers on the Recovery and Structure of Monoclonal Antibodies," Anal Biochem, Nov. 15, 1997, 253(2):236-45.
Originally Filed Claims of EP Application No. 13195713.6 (EP Publication No. 2 708 558) (submitted by the Opponent during EP opposition procedure for EP 2 708 558 and posted by EPO on Jan. 15, 2019), 2 pages.
Originally Filed Description of EP Application No. 13195713.6 (EP Publication No. 2 708 558) (submitted by the Opponent during EP opposition procedure for EP 2 708 558 and posted by EPO on Jan. 15, 2019), 153 pages.
Patel et al., "A Forgotten Cause of Kidney Injury in Chronic Myelomonocytic Leukemia," Am J Kidney Dis, Jul. 2009, 54(1):159-64. doi: 10.1053/j.ajkd.2008.11.013. Epub Jan. 29, 2009.
Perng et al., "Desmin Aggregate Formation by R120G αB-Crystallin Is Caused by Altered Filament Interactions and Is Dependent upon Network Status in Cells," Mol Biol Cell, May 2004, 15(5):2335-46.
Product Information Sheet from SIGMA-H-Y Medium (1998) and document establishing that it was published in 1998 (submitted by the Opponent during EP opposition procedure for EP 2 708 558 and posted by EPO on Jan. 15, 2019), 4 pages.
Promega Protocols and Applications Guide, 1991, 2nd Edition (submitted by the Opponent during EP opposition procedure for EP 2 708 558 and posted by EPO on Jan. 14, 2019), 3 pages.
Raso, "Intracellular Targeting Using Bispecific Antibodies," Methods in Molecular Medicine, 2000, vol. 25, pp. 37-50.
Raso et al., "Intracellular Targeting with Low pH-triggered Bispecific Antibodies," J Biol Chem, Oct. 31, 1997, 272(44):27623-8.
Raso et al., "Antibodies Capable of Releasing Diphtheria Toxin in Response to the Low pH Found in Endosomes," J Biol Chem, Oct. 31, 1997, 272(44):27618-22.
Rituximab (Wikipedia), accessed on Oct. 24, 2018 (submitted by the Opponent during EP opposition procedure for EP 2 708 558 and posted by EPO on Jan. 15, 2019), 15 pages (with English translation).
Rituximab biologic license application approval, dated Nov. 26, 1997 (submitted by the Opponent during EP opposition procedure for EP 2 708 558 and posted by EPO on Jan. 15, 2019), 2 pages.
Rituximab product information, IDEC, 1997 (submitted by the Opponent during EP opposition procedure for EP 2 708 558 and posted by EPO on Jan. 15, 2019), 2 pages.
Roitt et al., Immunology, Moscow: Mir, 2000, pp. 97-113 (in Russian, including what are believed to be corresponding pages from an English language edition of Immunology).
Sada et al., "Effect of histidine residues in antigenic sites on pH dependence of immuno-adsorption equilibrium," Appl Microbiol Biotechnol, 1988, 27:528-32.
Sazinsky et al., "Aglycosylated immunoglobulin G1 variants productively engage activating Fc receptors," Proc Natl Acad Sci USA, Dec. 23, 2008, 105(51):20167-72. doi: 10.1073/pnas.0809257105. Epub Dec. 12, 2008.
Shadduck et al., "Fractionation of Antibodies to L-Cell Colony-Stimulating Factor by Affinity Chromatography," Blood, Jun. 1979, 53(6):1182-90.
Singer et al., Genes & Genomes, Moscow, Mir, 1998, 1:63-64 (in Russian, including what are believed to be corresponding pages from an English language edition of Genes & Genomes).
Travis et al., "Isolation of Albumin from Whole Human Plasma and Fractionation of Albumin-Depleted Plasma," Biochem J, Aug. 1, 1976, 157(2):301-6.
Venturi et al., "The Monoclonal Antibody 1F6 Identifies a pH-dependent Conformational Change in the Hydrophilic $NH_2$ Terminus of NhaA $Na^+/H^+$ Antiporter of *Escherichia coli*," J Biol Chem, Feb. 18, 2000, 275(7):4734-42.
Wang, "Instability, stabilization, and formulation of liquid protein pharmaceuticals," Int J Pharm, Aug. 20, 1999, 185(2):129-88.
Weiss et al., "Rapid mapping of protein functional epitopes by combinatorial alanine scanning," Proc Natl Acad Sci USA, Aug. 1, 2000, 97(16):8950-4.
Barrabes et al., "Effect of sialic acid content on glycoprotein pI analyzed by two-dimensional electrophoresis," Electrophoresis, Sep. 2010, 31(17):2903-12, doi: 10.1002/elps.200900764.
Decision of the Opposition Division in EP 2 275 443, dated Apr. 26, 2018 (submitted on May 24, 2019 by the Patentee during EPO Opposition Procedure for EP 2 202 245), 29 pages.
Declaration of Taichi Kuramochi (submitted on May 24, 2019 by the Patentee during EPO Opposition Procedure for EP 2 202 245), 11 pages.
Granted claims of EP 2 275 443 (submitted on May 24, 2019 by the Patentee during EPO Opposition Procedure for EP 2 202 245), 1 page.
Supplemental Material to Raposo et al., "Epitope-specific antibody response is controlled by immunoglobulin VH polymorphisms," J Exp Med, Mar. 10, 2014, 211(3):405-11. doi: 10.1084/jem.20130968. Epub Feb. 17, 2014 (submitted on May 24, 2019 by the Patentee during EPO Opposition Procedure for EP 2 202 245), 4 pages.
U.S. Appl. No. 15/050,145, Igawa te al. filed Feb. 22, 2016.
U.S. Appl. No. 14/007,947, Igawa et al., filed Dec. 30, 2013.
U.S. Appl. No. 14/404,051, Igawa et al., filed Nov. 26, 2014.
U.S. Appl. No. 14/423,269, Katada et al., filed Feb. 23, 2015.
U.S. Appl. No. 16/795,676, filed Feb. 20, 2020, Kuramochi et al.
U.S. Appl. No. 16/806,027, filed Mar. 2, 2020, Igawa et al.
Annotated amino acid sequence of the variable heavy (VH) and variable light (VL) domains of the monoclonal antibodies bevacizumab/Avastin, adalimumab/Humira, omalizumab/Xolair, and rituximab/Mabthera, dated Jul. 2019, 10 pages (submitted to the EPO with the written submission to attend oral proceedings on Sep. 6, 2019 by Opponent 1 in EP 11714860.1).
Diamond et al., "Somatic mutation of the T15 heavy chain gives rise to an antibody with autoantibody specificity," Proc Natl Acad Sci USA, Sep. 1984, 81(18):5841-4.
Evidence for the publication date of Zalevsky et al., Nat Biotechnol, Feb. 2010, 28(2):157-9, 1 page (submitted to the EPO with the written submission to attend oral proceedings on Sep. 6, 2019 by Opponent 1 in EP 11714860.1).
Expert Declaration of J. Boucneau, dated Sep. 6, 2019, 13 pages (submitted to the EPO with the written submission to attend oral proceedings on Sep. 6, 2019 by Opponent 1 in EP 11714860.1).
Hasemann et al., "Mutational Analysis of Arsonate Binding by a $CRI_{A+}$ Antibody-$V_H$ and $V_L$ Junctional Diversity are Essential for Binding Activity," J Biol Chem, Apr. 25, 1991, 266(12):7626-32.
Ohno et al., "Antigen-binding specificities of antibodies are primarily determined by seven residues of $V_H$," Proc Natl Acad Sci USA, May 1985, 82(9):2945-9.

(56) References Cited

OTHER PUBLICATIONS

Proprietor's (Chugai Seiyaku Kabushiki Kaisha) Submission dated Sep. 5, 2016 in EP11714860.1, 6 pages (submitted to the EPO with the written submission to attend oral proceedings on Sep. 6, 2019 by Opponent 1 in EP 11714860.1).

Proprietor's (Chugai Seiyaku Kabushiki Kaisha) Submission dated Sep. 19, 2016 in EP11714860.1, 3 pages (submitted to the EPO with the written submission to attend oral proceedings on Sep. 6, 2019 by Opponent 1 EP 11714860.1).

Proprietor's (Chugai Seiyaku Kabushiki Kaisha) Submission dated Feb. 20, 2017 in EP 2 275 443, 35 pages (submitted to the EPO with the written submission to attend oral proceedings on Sep. 6, 2019 by Opponent 5 in EP 11714860.1).

Rich et al., "A global benchmark study using affinity-based biosensors," Anal Biochem, Mar. 15, 2009, 386(2):194-216. doi: 10.1016/j.ab.2008.11.021. Epub Nov. 27, 2008.

Roitt et al., "Overview: Antibody—a flexible adaptor," Immunology, Moscow: Mir, 2000, p. 9 (with what is believed to be the corresponding page from an English version of Immunology).

Sigma product information for ACES buffer, 1 page (submitted to the EPO with the written submission to attend oral proceedings on Sep. 6, 2019 by Opponent 1 in EP 11714860.1).

Table summarizing lack of novelty over WO 2009/086320A, dated Jul. 9, 2009, 4 pages (submitted to the EPO with the written submission to attend oral proceedings on Sep. 6, 2019 by Opponent 1 in EP 11714860.1).

Yang et al., "Comparison of biosensor platforms in the evaluation of high affinity antibody-antigen binding kinetics," Anal Biochem, Sep. 1, 2016, 508:78-96. doi: 10.1016/j.ab.2016.06.024. Epub Jun. 27, 2016.

Abelev, "Monoclonal antibodies," Sorosovkii Educational Journal, No. 1, 1998, pp. 16-20 (with English translation).

English translation of JP 2010-266121 (priority document for EP 2 647 706), submitted to European Patent Office on May 25, 2020, by Applicant during the examination procedure for EP 3 517 550.

English translation of JP 2011-217886 (priority document for EP 2 647 706), submitted to European Patent Office on May 25, 2020, by Applicant during the examination procedure for EP 3 517 550.

Finlay et al., "Affinity Maturation of a Humanized Rat Antibody for Anti-RAGE Therapy: Comprehensive Mutagenesis Reveals a High Level of Mutational Plasticity Both Inside and Outside the Complementarity-Determining Regions," J Mol Biol, May 8, 2009, 388(3):541-558.

Safdari et al., "Antibody humanization methods—a review and update," Biotechnol Genet Eng Rev, 2013, 29:175-186.

Curtiss, "Selectivity and Specificity Are the Keys to Cost-Effective Use of Omalizumab for Allergic Asthma," J Manag Care Pharm, Nov.-Dec. 2005, 11(9):774-776.

Decision of the Opposition Division dated Dec. 19, 2019 in EP 2 552 955 (submitted by Patentee (Chugai Seiyaku Kabushiki Kaisha) in the grounds of appeal on Apr. 28, 2020 in EP 2 552 955).

Expert Declaration of Joachim Boucneau, signed Mar. 11, 2020 (submitted by the Opponents in Mar. 2020 in the Oppositions of EP 2 708 558 and EP 2 708 559).

Guidance on the use of International Nonproprietary Names (INNs) for Pharmaceutical Substances, World Health Organization, 2017, 55 pages (submitted by the Opponents in Mar. 2020 in Oppositions of EP 2 708 558 and EP 2 708 559).

Ito et al., "Molecular Designs of Antibodies and Peptides by Phage Display," Seibutsubutsuri, 2008, 48(5), 294-298 (with English translation).

Roche Media Release, dated Jan. 5, 2011, 4 pages (retrieved from the internet https://www.roche.com/media/releases/med-cor-2011-01-05.htm), (submitted by the Opponents in Mar. 2020 in the Oppositions of EP 2 708 558 and EP 2 708 559).

Van Assche et al., "Adalimumab in Crohn's disease," Biologies, Dec. 2007, 1(4):355-65.

Yu et al., "Development and Validation of a Cell-Based Fluorescent Method for Measuring Antibody Affinity," J Immunol Methods, Mar. 2017, 442:49-53. doi: 10.1016/j.jim.2016.12.004. Epub Dec. 24, 2016.

U.S. Appl. No. 12/295,039, Igawa et al., filed Jan. 20, 2009.

U.S. Appl. No. 15/725,692, Igawa et al., filed Oct. 5, 2017.

U.S. Appl. No. 15/988,348, Igawa et al., filed May 24, 2018.

U.S. Appl. No. 15/977,757, Igawa et al., filed May 11, 2018.

U.S. Appl. No. 14/781,069, Mimoto et al., filed Sep. 29, 2015.

U.S. Appl. No. 17/020,497, filed Sep. 14, 2020, Igawa et al.

U.S. Appl. No. 17/020,543, filed Sep. 14, 2020, Igawa et al.

U.S. Appl. No. 17/028,210, filed Sep. 22, 2020, Katada et al.

U.S. Appl. No. 17/144,342, filed Jan. 8, 2021.

Abe et al., "Effect of $\beta_2$-microglobulin adsorption column on dialysis-related amyloidosis," Kidney Int, Oct. 2003, 64(4):1522-1528. doi: 10.1046/j.1523-1755.2003.00235.x.

"Alexa Fluor® 488 anti-β-Amyloid, 1-16 Antibody 6E10," Catalog 803013, Biolegend, Sep. 10, 2018, 3 pages, <https://www.biolegend.com/en-us/global-elements/pdf-popup/alexa-fluor-488-antibeta-amyloid--1-16-antibody-10833?filename=Alexa%20Fluorreg%20488%20anti-beta-Amyloid%201-16%20Antibody.pdf&pdfgen=true>.

"Anti-Huntingtin antibody [EPR5526] ab109115," Abeam, 11 pages, printed from the internet Apr. 13, 2020, <https://www.abcam.com/huntingtin-antibody-epr5526-ab109115.pdf.

"Anti-Glial Fibrillary Acidic Protein (GFAP) Mouse mAb (G-A-5)," IF03L, Millipore Sigma, Aug. 27, 2007, 3 pages, <https://www.emdmillipore.com/US/en/product/Anti-Glial-Fibrillary-Acidic-Protein-GFAP-Mouse-mAb-G-A-5,EMD_BIO-IF03L#anchor_PDS>.

Arnoux et al., "Metformin reverses early cortical network dysfunction and behavior changes in Huntington's disease," Elife, Sep. 4, 2018, 7. pii: e38744. doi: 10.7554/eLife.38744.

Example antibody family tree, 4 pages (submitted with the Written Submission for Opposition against EP 2 708 559 on Mar. 12, 2020).

"GD-IgA1 (KM55) anti-human rat monoclonal antibody," Catalog No. 10777, IBL America, 6 pages, printed from the internet Apr. 13, 2020, <https://www.ibl-america.com/gd-igal-km55-antihuman-rat-igg-moab/>.

Jones et al., "Mutations in GFAP Disrupt the Distribution and Function of Organelles in Human Astrocytes," Cell Rep, Oct. 23, 2018, 25(4):947-958.e4. doi: 10.1016/j.celrep.2018.09.083.

Kabat et al., "Sequences of Proteins of Immunological Interest," 1991, National Institute of Health Publication No. 91(3242), pp. 103, 310.

Kontermann et al., Chapter 4 "Mouse Immune Libraries for the Generation of ScFv Fragments Directed Against Human Cell Surface Antigens," 1:47-62 and Chapter 27 "Engineering of the Fc Region for Improved PK (FcRn Interaction)," 1:415-427, Antibody Engineering, 2010.

Kroetsch et al., "Engineered pH-dependent recycling antibodies enhance elimination of Staphylococcal enterotoxin B superantigen in mice," mAbs, Feb./Mar. 2019, 11(2):411-421.

"Monoclonal Mouse Anti-Human Desmin (Concentrate) Clone D33," Code No. M0760, Agilent Dako, 3 pages, printed from the internet Apr. 13, 2020 <https://www.agilent.com/en/product/immunohistochemistry/antibodies-controls/primaryantibodies/desmin-(concentrate)-76523>.

Poosarla et al., "Computational de novo Design of Antibodies binding to a Peptide with High Affinity," Biotechn Bioeng, Jun. 2017, 114(6):1331-1342.

Schrama et al., "Antibody targeted drugs as cancer therapeutics," Nat Rev Drug Discov, Feb. 2006, 5(2):147-159.

Suzuki et al., "IgA nephropathy and IgA vasculitis with nephritis have a shared feature involving galactose-deficient IgA1-oriented pathogenesis," Kidney Int, Mar. 2018, 93(3):700-705. doi: 10.1016/j.kint.2017.10.019. Epub Jan. 10, 2018.

Torres et al., "The immunoglobulin constant region contributes to affinity and specificity," Trend Immunol, Feb. 2008, 29(2):91-97.

Yang et al., "Effect of anti-CD20 antibody Fab' fragment on apoptosis of B lymphoma cells and intracellular calcium," Tumor, Feb. 2006, 26(2):116-119 (with English translation).

(56) References Cited

OTHER PUBLICATIONS

Zhang et al., "Monoclonal antibodies as therapeutic agents in oncology and antibody gene therapy," Cell Res, Feb. 2007, 17(2):89-99.
USPTO Final Office Action in U.S. Appl. No. 13/637,415, dated Mar. 3, 2020, 26 pages.
USPTO Final Office Action in U.S. Appl. No. 14/404,051, dated Jul. 14, 2020, 31 pages.
Almagro et al., "Design and validation of a synthetic $V_H$ repertoire with tailored diversity for protein recognition," J Mol Recognit, Sep.-Oct. 2006, 19(5):413-422.
Amendment and Reply to Action of May 30, 2017 in U.S. Appl. No. 13/595,139, dated Sep. 21, 2017, 29 pages (submitted on Dec. 20, 2017 in opposition against EP 2 275 443).
Annex 1 Accompanying Response to Statement of Grounds of Appeal of Opponent 2 (Alexion Pharmaceuticals, Inc.), dated Sep. 16, 2020 in opposition against EP 2 552 955, 29 pages.
Annex A to Statement of Grounds of Appeal of Patentee (Chugai Seiyaku Kabushiki Kaisha), dated Apr. 28, 2020 in opposition against EP 2 552 955, 82 pages.
Bazin et al., "Use of hu-IgG-SCID mice to evaluate the in vivo stability of human monoclonal IgG antibodies," J Immunol Methods, Jun. 24, 1994, 172(2):209-217.
Birn et al., "Renal albumin absorption in physiology and pathology," Kidney Int, Feb. 2006, 69(3):440-449.
Chaudhury et al., "The Major Histocompatibility Complex-related Fc Receptor for IgG (FcRn) Binds Albumin and Prolongs Its Lifespan," J Exp Med, Feb. 3, 2003, 197(3) 315-322.
Chilukuri et al., "Polyethylene glycosylation prolongs the circulatory stability of recombinant humanbutyiylcholinesterase," ChemBiol Interact, Dec. 15, 2005, 157-158:115-121, Epub Oct. 25, 2005.
Chuang et al., "Pharmaceutical Strategies Utilizing Recombinant Human Semm Albumin," Pharm Res, May 2002, 19(5):569-577.
Colman et al., "Effects of amino acid sequence changes on antibody-antigen interactions," Res Immunol, Jan. 1994, 145(1):33-36.
Coloma et al., "Design and production of novel tetravalent bispecific antibodies," Nat Biotechnol, Feb. 1997, 15(2):159-163.
Declaration of Susannah Davis with Curriculum Vitae, dated Dec. 13, 2017, 6 pages (submitted on Dec. 20, 2017 in the opposition against EP 2 275 443).
Declaration of Dr. Roland Kontermann with Curriculum Vitae, dated Nov. 20, 2017, 24 pages (submitted on Dec. 20, 2017 in the opposition against EP 2 275 443).
Declaration of Jan-Terje Andersen with Curriculum Vitae, dated Dec. 12, 2012, 5 pages (submitted on Dec. 20, 2017 in the opposition against EP 2 275 443) 5 pages.
Dennis et al., "Albumin Binding as a General Strategy for Improving the Pharmacokinetics of Proteins," J Biol Chem, Sep. 20, 2002, 277(38) 35035-35043. Epub Jul. 15, 2002.
Dirnberger et al., "Secretion of biologically active glycoforms of bovine follicle stimulating hormone in plants," Eur J Biochem, Aug. 2001, 268(16):4570-4579.
EUTM register extract—BIACORE, 4 pages (document downloaded on Aug. 26, 2020, submitted in opposition against EP 2 552 955, and posted by EPO on Sep. 15, 2020).
Experimental Results by Fuji Gotemba Research Labs, dated Mar. 21, 2017, 4 pages (submitted on Dec. 22, 2017 in opposition against EP 2 275 443).
Experimental Results by Kamakura Research Labs, dated Mar. 22, 2017, 10 pages (submitted on Dec. 22, 2017 in opposition against EP 2 275 443).
Final Written Submissions of Opponent 2 (Alexion Pharmaceuticals, Inc.), dated Sep. 6, 2019, submitted in opposition against EP 2 552 955, 26 pages.
First priority application of the opposed patent, JP 2008-104147 (submitted on Sep. 6, 2018 in appeal of EP 2 575 443) (with English translation).
Fischer et al., "Bispecific Antibodies: Molecules That Enable Novel Therapeutic Strategies," Pathobiology, 2007, 74(1):3-14.
Franks, "Conformational Stability of Proteins," Protein Biotechnology, 1993, pp. 395-436.
Gekle, "Renal Tubule Albumin Transport," Annu Rev Physiol, Mar. 17, 2005, 67:573-94.
Guasch et al., "Charge Selectivity of the Clomerular Filtration Barrier in Healthy and Nephrotic Humans," J Clin Invest, Nov. 1993, 92(5):2274-2282.
Harris et al., "Identification of multiple sources of charge heterogeneity in a recombinant antibody," Chromatography B, Mar. 10, 2001, 752:233-245.
Holt et al., "Anti-serum albumin domain antibodies for extending the half-lives of short lived drugs," Protein Eng Des Sel, May 2008, 21 (5)283-288. doi: 10.1093/protein/gzm067. Epub Apr. 2, 2008.
Henne et al., "Anti-PCSK9 Antibody Pharmacokinetics and Low-Density Lipoprotein-Cholesterol Pharmacodynamics in Nonhuman Primates Are Antigen Affinity-Dependent and Exhibit Limited Sensitivity to Neonatal Fc Receptor-Binding Enhancement," J Pharmacol and Exp Ther, Apr. 2015, 353:119-131.
Ho et al., "In vitro antibody evolution targeting germline hot spots to increase activity of an anti-CD22 immunotoxin," J Biol Chem, Jan. 7, 2005, 280(1):607-617. doi: 10.1074/jbc.M409783200. Epub Oct. 18, 2004.
Huang et al., "Recombinant human butyrylcholinesterase from milk of transgenic animals to protect against organophosphate poisoning," Proc Natl Acad Sci USA, Aug. 21, 2007, 104(34):13603-13608. Epub Jul. 27, 2007.
Inoue et al., "Synthesis of a Superoxide Dismutase Derivative That Circulates Bound to Albumin And Accumulates in Tissues Whose pH is Decreased," Biochemistry, Aug. 8, 1989, 28(16):6619-6624.
Kawamoto et al., "Circulatory Stability and Plasma Lidocaine Levels during Continuous and Intermittent Thoracic Epidural Analgesia," J Anesth, Apr. 1991, 5(2):166-171.
Kim et al., "The Glycosylation and Pharmacokinetics of CTLA4Ig Produced in Rice Cells," Biol PharmBull, Oct. 2007, 30(10):1913-1917.
Knudsen et al., "Potent Derivatives of Glucagon-like Peptide-1 with Pharmacokinetic Properties Suitable for Once Daily Administration," J Med Chem, May 4, 2000, 43(9):1664-1669.
Kratz, "Albumin as a drug carrier: Design of prodrugs, drug conjugates and nanoparticles," Journal of Controlled Release, Dec. 18, 2008, 132(3):171-183. doi: 10.1016/j.jconrel.2008.05.010 Epub May 17, 2008.
Kurtzhals et al., "Albumin Binding and Time Action of Acylated Insulins in Various Species," J Pharm Sci, Mar. 1996, 85(3):304-308.
Kurtzhals et al., "Effect of Fatty Acids and Selected Drugs on the Albumin Binding of a Long-Acting, Acylated Insulin Analogue," J Pharm Sci, Dec. 1997, 86(12):1365-1368.
Lescar et al., "Crystal Structure of a Cross-reaction Complex between Fab F9.13.7 and Guinea Fowl Lysozyme," J Biol Chem, Jul. 28, 1995, 270(30):18067-18076.
Liberti et al., "Antigenicity of Polypeptides (Poly-α-amino Acids). Physicochemical Studies of a Calcium-Dependent Antigen-Antibody Reaction," Biochemistry, Apr. 27, 1971, 10(9):1632-1639.
Makrides et al., "Extended in Vivo Half-Life of Human Soluble Complement Receptor Type 1 Fused to a Serum Albumin-Binding Receptor," J Pharmacol Exp Ther. Apr. 1996, 277(1):534-542.
Manning et al., "Stability of Protein Pharmaceuticals," Pharm Res, Nov. 1989, 6(11):903-918.
Muller et al., Chapter 2 "Bispecific Antibodies," Handbook of Therapeutic Antibodies, 2007, 2:345-378.
Notice of Opposition of Opponent 1 (Ablynx N.V.), dated Feb. 2, 2018, against EP 2 552 955, 50 pages.
O'Hear et al., "Antibody buffering of a ligand in vivo," Proc Natl Acad Sci USA, Jan. 4, 2005, 102(1):40-44. Epub Dec. 22, 2004.
Opposition of Opponent 5 (Shire Human Genetic Therapies, Inc.), dated Feb. 5, 2018, against EP 2 552 955, 70 pages.
Patentee's (Chugai Seiyaku Kabushiki Kaisha) Response to Article 94(3) EPC Communication, filed on Oct. 20, 2020, in EP 19154335.4 (EP 3 521 311).
Peters et al., Chapter 3 Ligand Binding by Albumin, All about Albumin, Academic Press, 1996, pp. 76-79.

(56) References Cited

OTHER PUBLICATIONS

Rehlaender et al., "Antibodies as Carrier Proteins," Pharm Res, Nov. 1998, 15(11):1652-1656.
Reply from Opponent 5 (Shire Human Genetic Therapies, Inc.), dated Sep. 6, 2019, submitted in opposition against EP 2 552 955, 15 pages.
Response by Opponent 1 (Ablynx N.V.), dated Sep. 6, 2019, submitted in opposition against EP 2 552 955, 57 pages.
Saxena et al., "Role of Oligosaccharides in the Pharmacokinetics of Tissue-Derived and Genetically Engineered Cholinesterases," Mol Pharmacol, Jan. 1998, 53(1):112-122.
Schulze et al., "Turnover of Plasma Proteins," Elsevier, 1966, p. 476.
Schuster et al., "The human interleukin-6 (IL-6) receptor exists as a preformed dimer in the plasma membrane," FEBS Lett, Mar. 13, 2003, 538(1-3):113-116.
Siberil et al., "Molecular aspects of human FcKR interactions with IgG: Functional and therapeutic consequences," Immunol Lett, Aug. 15, 2006, 106(2):111-118, Epub Jun. 12, 2006.
Statement of Facts and Arguments in Support of Opposition by Opponent 2 (Alexion Pharmaceuticals, Inc.), dated Feb. 2, 2018, submitted in opposition against EP 2 552 955, 39 pages.
Stork et al., "A novel tri-functional antibody fusion protein with improved pharmacokinetic properties generated by fusing a bispecific single-chain diabody with an albumin-binding domain form streptococcal protein G," Protein Eng Des Sel, Nov. 2007, 20(11):569-576, Epub Nov. 3, 2007.
Summary of Exp. Evidence of Patent and Ito et al., FEBS, vol. 309, No. 1, pp. 85-88 (submitted on Feb. 20, 2018 in Opposition against EP 2 275 443).
Summary of lineages of antibodies of working example, 4 pages (document submitted on Jan. 23, 2019 during appeal procedure of EP 2 275,443).
Third-Party Preissuance Submission Under 35 U.S.C. §122(e) and 37 C.F.R. §1.290, submitted Apr. 2, 2019, in U.S. Appl. No. 15/952,951, 137 pages.
Third-Party Preissuance Submission Under 35 U.S.C. §122(e) and 37 C.F.R. §1.290 submitted Jan. 17, 2019, in U.S. Appl. No. 15/952,951, 121 pages.
Yoon et al., "Construction, Affinity Maturation, and Biological Characterization of an Anti-tumor-associated Glycoprotein-72 Humanized Antibody," J Biol Chem, Mar. 17, 2006, 281(11):6985-6992.
USPTO Non-Final Office Action in U.S. Appl. No. 13/637,415, dated Feb. 10, 2021, 32 pages.
U.S. Appl. No. 17/359,867, Igawa et al., filed Jun. 28, 2021.
U.S. Pat. No. 9,096,651, Igawa et al., issued Aug. 4, 2015.
U.S. Pat. No. 9,828,429, Igawa et al., issued Nov. 28, 2017.
US Pat. No. 11,248,053, Igawa et al., issued Feb. 15, 2022.
U.S. Appl. No. 17/578,524, Igawa et al., filed Jan. 19, 2022.
U.S. Appl. No. 12/936,587, Igawa et al., filed Jan. 3, 2011 (abandoned).
U.S. Appl. No. 13/595,139, Igawa et al., filed Aug. 27, 2012 (abandoned).
U.S. Pat. No. 9,868,948, Igawa et al., issued Jan. 16, 2018.
U.S. Appl. No. 13/637,415, Igawa et al., filed Feb. 4, 2013.
U.S. Appl. No. 15/050,145, Igawa et al., filed Feb. 22, 2016.
U.S. Appl. No. 13/990,158, Igawa et al., filed Mar. 28, 2014 (abandoned).
U.S. Appl. No. 15/988,347, Igawa et al., filed May 24, 2018.
U.S. Pat. No. 10,618,965, Igawa et al., issued Apr. 14, 2020.
U.S. Appl. No. 16/806,027, Igawa et al., filed Mar. 2, 2020.
U.S. Appl. No. 14/347,034, Igawa et al., filed Mar. 25, 2014 (abandoned).
U.S. Appl. No. 15/230,904, Igawa et al., filed Aug. 8, 2016 (abandoned).
U.S. Appl. No. 14/347,321, Igawa et al., filed Mar. 26, 2014 (abandoned).
U.S. Appl. No. 15/977,757, Igawa et al., filed May 11, 2018 (abandoned).
U.S. Appl. No. 17/561,207, Igawa et al., filed Dec. 23, 2021.
U.S. Pat. No. 10,253,100, Igawa et al., issued Apr. 9, 2019.
U.S. Appl. No. 16/264,735, Igawa et al., filed Feb. 1, 2019.
U.S. Appl. No. 14/361,013, Igawa et al., filed May 28, 2014 (abandoned).
U.S. Appl. No. 16/108,897, Igawa et al., filed Aug. 22, 2018.
U.S. Appl. No. 14/377,556, Kuramochi et al., filed Aug. 8, 2014 (abandoned).
U.S. Appl. No. 16/795,676, Kuramochi et al., filed Feb. 20, 2020.
U.S. Appl. No. 14/379,825, Igawa et al., filed Aug. 20, 2014.
U.S. Appl. No. 14/404,051, Igawa et al., filed Nov. 26, 2014 (abandoned).
U.S. Appl. No. 17/144,342, Igawa et al., filed Jan. 8, 2021.
U.S. Pat. No. 10,919,953, Katada et al., issued Feb. 16, 2021.
U.S. Appl. No. 17/028,210, Katada et al., filed Sep. 22, 2020.
U.S. Pat. No. 11,267,868, Mimoto et al., filed Mar. 8, 2022.
U.S. Appl. No. 17/671,185, Mimoto et al., filed Feb. 14, 2022.
U.S. Appl. No. 15/210,360, Igawa et al., filed Jul. 14, 2016.
U.S. Appl. No. 15,210,353, Igawa et al., filed Jul. 14, 2016.
U.S. Appl. No. 15/495,026, Igawa et al., filed Apr. 24, 2017.
U.S. Pat. No. 10,472,623, Igawa et al., issued Nov. 12, 2019.
U.S. Appl. No. 15/952,951, Igawa et al., filed Apr. 13, 2018.
U.S. Appl. No. 16/361,498, Igawa et al., filed Mar. 22, 2019.
U.S. Appl. No. 17/020,497, Igawa et al., filed Sep. 14, 2020.
U.S. Appl. No. 17/020,543, Igawa et al., filed Sep. 14, 2020.
U.S. Appl. No. 16/539,765, Igawa et al, filed Aug. 13, 2019.
U.S. Appl. No. 17/671,185, Mimoto et al., Feb. 14, 2022.
Anderson et al., "Perspective—FcRn transports albumin: relevance to immunology and medicine," Trends Immunol, Jul. 2006, 27(7):343-348. Epub May 30, 2006.
Annex from opponent 2's submission of Jun. 7, 2018, 13 pages (document cited by the opponent in the EPO opposition proceedings of EP 2 202 245 on May 19, 2021).
Antibodies in Example 29 of EP 2 202 245, 2 pages (document cited by the opponent in the EPO opposition proceedings of EP 2 202 245 on May 19, 2020).
Application as filed for EP 2 698 431, 375 pages (document cited in EPO opposition proceedings of EP 2 698 431 on Jun. 23, 2021).
Borrok et al., "pH-dependent Binding Engineering Reveals an FcRn Affinity Threshold That Governs IgG Recycling," J Chem, Feb. 13, 2015, 290(7):4282-4290. doi: 10.1074/jbc.M114.603712. Epub Dec. 23, 2014.
Ellison et al., "Linkage and sequence homology of two human immunoglobulin γ heavy chain constant region genes," Proc Natl Acad Sci USA, Mar. 1982, 79(6):1984-1988.
English translation of PCT/JP2011/072550, 283 pages (corresponding to WO 2012/132067, which was cited in IDS filed on Sep. 24, 2018). The translation was submitted in the EPO opposition proceedings of EP 2 698 431 on Jun. 23, 2021.
English translation of PCT/JP2012/054624, 110 pages (corresponding to WO 2012/115241, which was cited in IDS filed on Sep. 24, 2018). The translation was submitted in the EPO opposition proceedings of EP 2 698 431 on Jun. 23, 2021.
Han et al., "Monoclonal antibodies: interspecies scaling with minimal preclinical information," Ther Deliv, Mar. 2011, 2(3):359-368.
Huck et al., "Sequence of a human immunoglobulin gamma 3 heavy chain constant region gene: comparison with the other human C gamma genes," Nucleic Acids Res, Feb. 25, 1986, 14(4):1779-1789.
Jung et al., "Aglycosylated IgG variants expressed in bacteria that selectively bind FcγRI potentiate tumor cell killing by monocyte-dendritic cells," Proc Natl Acad Sci USA, Jan. 12, 2010, 107(2):604-609.
NCBI database: GenBank Accession No. AAC82527.1, Jun. 10, 2016, "immunoglobulin gamma-1 heavy chain constant region, partial [*Homo sapiens*]," (https://www.ncbi.nlm.nih.gov/protein/AAC82527.1).
NCBI database: GenBank Accession No. AAB59393.1, Aug. 1, 2016, "immunoglobulin gamma-2 heavy chain, partial [*Homo sapiens*]," (https://www.ncbi.nlm.nih.gov/protein/AAB59393.1).
NCBI database: GenBank Accession No. AAB59394.1, Aug. 1, 2016, "immunoglobulin gamma-4 heavy chain, partial [*Homo sapiens*]," (https://www.ncbi.nlm.nih.gov/protein/AAB59394.1).

(56) References Cited

OTHER PUBLICATIONS

NCBI database: GenBank Accession No. CAA27268.1, Jul. 25, 2016, "C gamma 3, partial [*Homo sapiens*]," (https://www.ncbi.nlm.nih.gov/protein/CAA27268.1).
PCT/JP2011/001888, 203 pages (document cited in EPO opposition proceedings of EP 2 698 431 on Jun. 23, 2021).
Presta et al., "Engineering therapeutic antibodies for improved function," Biochem Soc Trans, Aug. 2002, 30(4):487-490.
Screenshots of Genetyx software, 3 pages (document cited by opponent during the EPO opposition proceedings of EP 2 202 245 on May 22, 2020).
Screenshots of the web-based calculator, 9 pages (document cited by opponent during the EPO opposition proceedings of EP 2 202 245 on May 22, 2020).
Sections of the Genetyx manual pertaining to isoelectric point, 5 pages (document cited by opponent during the EPO opposition proceedings of EP 2 202 245 on May 22, 2020) (with English translation).
Smith et al., "Prolonged in Vivo Residence Times of Antibody Fragments Associated with Albumin," Bioconjug Chem, Sep. 2001-Oct. 12(5):750-756.
Takahashi et al., "Structure of human immunoglobulin gamma genes: implications for evolution of a gene family," Cell, Jun. 1982, 29(2):671-679.
Wines et al., "The IgG Fc Contains Distinct Fc Receptor (FcR) Binding Sites: The Leukocyte Receptors FcγRI and FcγRIIa Bind to a Region in the Fc Distinct from That Recognized by Neonatal FcR and Protein A," J Immunol, May 15, 2000, 164(10):5313-5318.
USPTO Final Office Action in U.S. Appl. No. 13/637,415, dated Oct. 4, 2021, 32 pages.
USPTO Final Office Action in U.S. Appl. No. 15/952,951, dated Jul. 16, 2021, 15 pages.
USPTO Non-Final Office Action in U.S. Appl. No. 17/020,497, dated Jan. 29, 2021, 23 pages.
USPTO Non-Final Office Action in U.S. Appl. No. 17/020,497, dated Sep. 21, 2021, 21 pages.
Beranger et al., "IMGT Scientific Chart," Jun. 8, 2016, 7 pages.
Fillipovic, Biochemical basis of human life, VLADOS, 2005:70 (with English translation).
U.S. Appl. No. 17/854,023, Igawa et al., filed Jun. 30, 2022.
Attwood, "The Babel of Bioinformatics," Science, Oct. 20, 2000, 290(5491):471-473. doi: 10.1126/science.290.5491.471. PMID: 11183771.
Skolnick et al., "From genes to protein structure and function: novel applications of computational approaches in the genomic era," Trends Biotechnol, Jan. 2000, 18(1):34-39. doi: 10.1016/s0167-7799(99)01398-0. PMID: 10631780.
U.S. Appl. No. 18/052,258, Igawa et al., Nov. 3, 2022.
U.S. Appl. No. 18/298,743, Igawa et al., filed Apr. 11, 2023.
Perrakis et al., "AI revolutions in biology—The joys and perils of AlphaFold," EMBO Rep, Nov. 4, 2021, 22(11):e54046, 6 pages.
U.S. Appl. No. 18/156,138, Igawa et al., Jan. 18, 2023.

HMG481-IgG1

HMG487-IgG1

BLACK CRYSTAL STRUCTURE OF Fc(P238D)/FcγRIIb EXTRACELLULAR REGION COMPLEX
GRAY MODEL STRUCTURE OF Fc(WT)/FcγRIIb EXTRACELLULAR REGION COMPLEX

THIN LINE: X-RAY CRYSTAL STRUCTURE OF Fc(P238D)/FcγRIIb EXTRACELLULAR REGION COMPLEX
HEAVY LINE: X-RAY CRYSTAL STRUCTURE OF Fc(P208)/FcγRIIb EXTRACELLULAR REGION COMPLEX

THIN LINE : Fc(P208)
HEAVY LINE : FcγRIIb EXTRACELLULAR REGION

BLACK: X-RAY CRYSTAL STRUCTURE OF Fc(P208)/FcγRIIaR EXTRACELLULAR REGION COMPLEX
GRAY: X-RAY CRYSTAL STRUCTURE OF Fc(P208)/FcγRIIb EXTRACELLULAR REGION COMPLEX

THIN LINE: Fc(P208)

HEAVY LINE: FcγRIIaR or FcγRIIb EXTRACELLULAR REGION

LEFT: X-RAY CRYSTAL STRUCTURE OF Fc(P208)/FcγRIIaR EXTRACELLULAR REGION COMPLEX

RIGHT: X-RAY CRYSTAL STRUCTURE OF Fc(P208)/FcγRIIb EXTRACELLULAR REGION COMPLEX

THIN LINE: Fc(P208)
HEAVY LINE: FcγRIIaR or FcγRIIb EXTRACELLULAR REGION

LEFT: X-RAY CRYSTAL STRUCTURE OF Fc(P208)/FcγRIIaR EXTRACELLULAR REGION COMPLEX

RIGHT: X-RAY CRYSTAL STRUCTURE OF Fc(P208)/FcγRIIb EXTRACELLULAR REGION COMPLEX (i) CRYSTAL STRUCTURE IN THE PRESENCE OF CALCIUM ION (ii) CRYSTAL STRUCTURE IN THE ABSENCE OF CALCIUM ION

SEQUENCE LISTING

<160> NUMBER OF SEQ ID NOS: 169

<210> SEQ ID NO 1
<211> LENGTH: 452
<212> TYPE: PRT
<213> ORGANISM: Homo sapiens

<400> SEQUENCE: 1

```
Gln Val Gln Leu Val Gln Ser Gly Ala Glu Val Lys Lys Pro Gly Ser
1               5                   10                  15

Ser Val Lys Val Ser Cys Lys Ala Ser Gly Gly Thr Phe Ser Ser Tyr
            20                  25                  30

Ala Ile Ser Trp Val Arg Gln Ala Pro Gly Gln Gly Leu Glu Trp Met
        35                  40                  45

Gly Gly Ile Ile Pro Ile Phe Gly Thr Ala Asn Tyr Ala Gln Lys Phe
    50                  55                  60

Gln Gly Arg Val Thr Ile Thr Ala Asp Glu Ser Thr Ser Thr Ala Tyr
65                  70                  75                  80

Met Glu Leu Ser Ser Leu Arg Ser Glu Asp Thr Ala Val Tyr Tyr Cys
                85                  90                  95

Ala Arg Asp Ser Pro Val Pro Gly Val Tyr Tyr Tyr Tyr Gly Met Asp
            100                 105                 110

Val Trp Gly Gln Gly Thr Met Val Thr Val Ser Ser Ala Ser Thr Lys
        115                 120                 125

Gly Pro Ser Val Phe Pro Leu Ala Pro Ser Ser Lys Ser Thr Ser Gly
    130                 135                 140

Gly Thr Ala Ala Leu Gly Cys Leu Val Lys Asp Tyr Phe Pro Glu Pro
145                 150                 155                 160

Val Thr Val Ser Trp Asn Ser Gly Ala Leu Thr Ser Gly Val His Thr
                165                 170                 175

Phe Pro Ala Val Leu Gln Ser Ser Gly Leu Tyr Ser Leu Ser Ser Val
            180                 185                 190

Val Thr Val Pro Ser Ser Ser Leu Gly Thr Gln Thr Tyr Ile Cys Asn
        195                 200                 205

Val Asn His Lys Pro Ser Asn Thr Lys Val Asp Lys Lys Val Glu Pro
    210                 215                 220

Lys Ser Cys Asp Lys Thr His Thr Cys Pro Pro Cys Pro Ala Pro Glu
225                 230                 235                 240

Leu Leu Gly Gly Pro Ser Val Phe Leu Phe Pro Pro Lys Pro Lys Asp
                245                 250                 255

Thr Leu Met Ile Ser Arg Thr Pro Glu Val Thr Cys Val Val Val Asp
            260                 265                 270

Val Ser His Glu Asp Pro Glu Val Lys Phe Asn Trp Tyr Val Asp Gly
        275                 280                 285

Val Glu Val His Asn Ala Lys Thr Lys Pro Arg Glu Glu Gln Tyr Asn
    290                 295                 300

Ser Thr Tyr Arg Val Val Ser Val Leu Thr Val Leu His Gln Asp Trp
305                 310                 315                 320

Leu Asn Gly Lys Glu Tyr Lys Cys Lys Val Ser Asn Lys Ala Leu Pro
                325                 330                 335

Ala Pro Ile Glu Lys Thr Ile Ser Lys Ala Lys Gly Gln Pro Arg Glu
            340                 345                 350

Pro Gln Val Tyr Thr Leu Pro Pro Ser Arg Asp Glu Leu Thr Lys Asn
        355                 360                 365
```

```
Gln Val Ser Leu Thr Cys Leu Val Lys Gly Phe Tyr Pro Ser Asp Ile
    370                 375                 380

Ala Val Glu Trp Glu Ser Asn Gly Gln Pro Glu Asn Asn Tyr Lys Thr
385                 390                 395                 400

Thr Pro Pro Val Leu Asp Ser Asp Gly Ser Phe Phe Leu Tyr Ser Lys
                405                 410                 415

Leu Thr Val Asp Lys Ser Arg Trp Gln Gln Gly Asn Val Phe Ser Cys
            420                 425                 430

Ser Val Met His Glu Ala Leu His Asn His Tyr Thr Gln Lys Ser Leu
        435                 440                 445

Ser Leu Ser Pro
    450


<210> SEQ ID NO 2
<211> LENGTH: 215
<212> TYPE: PRT
<213> ORGANISM: Homo sapiens

<400> SEQUENCE: 2

Glu Ile Val Leu Thr Gln Ser Pro Ala Thr Leu Ser Val Ser Pro Gly
1               5                   10                  15

Glu Arg Val Thr Leu Ser Cys Arg Ala Ser Gln Ser Val Ala Asn His
            20                  25                  30

Leu Ala Trp Tyr Gln Gln Lys Pro Gly Gln Pro Pro Ser Leu Leu Ile
        35                  40                  45

Tyr Asp Ala Ser Thr Arg Ala Thr Asp Val Pro Ala Arg Phe Ser Gly
    50                  55                  60

Ser Gly Ser Gly Thr Glu Phe Thr Leu Ser Ile Ser Gly Leu Gln Ser
65                  70                  75                  80

Glu Asp Phe Ala Val Tyr Tyr Cys Gln Gln Tyr Lys Asp Trp Pro Pro
                85                  90                  95

Leu Thr Phe Gly Gly Gly Thr Lys Val Glu Phe Lys Arg Thr Val Ala
            100                 105                 110

Ala Pro Ser Val Phe Ile Phe Pro Pro Ser Asp Glu Gln Leu Lys Ser
        115                 120                 125

Gly Thr Ala Ser Val Val Cys Leu Leu Asn Asn Phe Tyr Pro Arg Glu
    130                 135                 140

Ala Lys Val Gln Trp Lys Val Asp Asn Ala Leu Gln Ser Gly Asn Ser
145                 150                 155                 160

Gln Glu Ser Val Thr Glu Gln Asp Ser Lys Asp Ser Thr Tyr Ser Leu
                165                 170                 175

Ser Ser Thr Leu Thr Leu Ser Lys Ala Asp Tyr Glu Lys His Lys Val
            180                 185                 190

Tyr Ala Cys Glu Val Thr His Gln Gly Leu Ser Ser Pro Val Thr Lys
        195                 200                 205

Ser Phe Asn Arg Gly Glu Cys
    210                 215


<210> SEQ ID NO 3
<211> LENGTH: 452
<212> TYPE: PRT
<213> ORGANISM: Artificial Sequence
<220> FEATURE:
<223> OTHER INFORMATION: an artificially synthesized sequence

<400> SEQUENCE: 3

Gln Val Gln Leu Val Gln Ser Gly Ala Glu Val Lys Lys Pro Gly Ser
```

-continued

```
1               5                   10                  15

Ser Val Lys Val Ser Cys Lys Ala Ser Gly Gly Thr Phe Ser Ser Tyr
            20                  25                  30

Ala Ile Ser Trp Val Arg Gln Ala Pro Gly Gln Gly Leu Glu Trp Met
        35                  40                  45

Gly Gly Ile Ile Pro Ile Phe Gly Thr Ala Asn Tyr Ala Gln Lys Phe
    50                  55                  60

Gln Gly Arg Val Thr Ile Thr Ala Asp Glu Ser Thr Ser Thr Ala Tyr
65                  70                  75                  80

Met Glu Leu Ser Ser Leu Arg Ser Glu Asp Thr Ala Val Tyr Tyr Cys
                85                  90                  95

Ala Arg Asp Ser Pro Val Pro Gly Val Tyr Tyr Tyr Tyr Gly Met Asp
            100                 105                 110

Val Trp Gly Gln Gly Thr Met Val Thr Val Ser Ser Ala Ser Thr Lys
        115                 120                 125

Gly Pro Ser Val Phe Pro Leu Ala Pro Ser Ser Lys Ser Thr Ser Gly
    130                 135                 140

Gly Thr Ala Ala Leu Gly Cys Leu Val Lys Asp Tyr Phe Pro Glu Pro
145                 150                 155                 160

Val Thr Val Ser Trp Asn Ser Gly Ala Leu Thr Ser Gly Val His Thr
                165                 170                 175

Phe Pro Ala Val Leu Gln Ser Ser Gly Leu Tyr Ser Leu Ser Ser Val
            180                 185                 190

Val Thr Val Pro Ser Ser Ser Leu Gly Thr Gln Thr Tyr Ile Cys Asn
        195                 200                 205

Val Asn His Lys Pro Ser Asn Thr Lys Val Asp Lys Lys Val Glu Pro
    210                 215                 220

Lys Ser Cys Asp Lys Thr His Thr Cys Pro Pro Cys Pro Ala Pro Glu
225                 230                 235                 240

Leu Leu Gly Gly Pro Ser Val Phe Leu Phe Pro Pro Lys Pro Lys Asp
                245                 250                 255

Thr Leu Met Ile Ser Arg Thr Pro Glu Val Thr Cys Val Val Val Asp
            260                 265                 270

Val Ser His Glu Asp Pro Glu Val Lys Phe Asn Trp Tyr Val Asp Gly
        275                 280                 285

Val Glu Val His Asn Ala Lys Thr Lys Pro Arg Glu Glu Gln Tyr Asn
    290                 295                 300

Ser Thr Tyr Arg Val Val Ser Val Leu Thr Val Leu His Gln Asp Trp
305                 310                 315                 320

Leu Asn Gly Lys Glu Tyr Lys Cys Lys Val Ser Asn Lys Ala Leu Pro
                325                 330                 335

Ala Pro Val Glu Lys Thr Ile Ser Lys Ala Lys Gly Gln Pro Arg Glu
            340                 345                 350

Pro Gln Val Tyr Thr Leu Pro Pro Ser Arg Asp Glu Leu Thr Lys Asn
        355                 360                 365

Gln Val Ser Leu Thr Cys Leu Val Lys Gly Phe Tyr Pro Ser Asp Ile
    370                 375                 380

Ala Val Glu Trp Glu Ser Asn Gly Gln Pro Glu Asn Asn Tyr Lys Thr
385                 390                 395                 400

Thr Pro Pro Val Leu Asp Ser Asp Gly Ser Phe Phe Leu Tyr Ser Lys
                405                 410                 415

Leu Thr Val Asp Lys Ser Arg Trp Gln Gln Gly Asn Val Phe Ser Cys
            420                 425                 430
```

```
Ser Val Met His Glu Ala Leu His Tyr His Tyr Thr Gln Lys Ser Leu
        435                 440                 445

Ser Leu Ser Pro
    450


<210> SEQ ID NO 4
<211> LENGTH: 447
<212> TYPE: PRT
<213> ORGANISM: Artificial Sequence
<220> FEATURE:
<223> OTHER INFORMATION: an artificially synthesized sequence

<400> SEQUENCE: 4

Gln Val Gln Leu Gln Glu Ser Gly Pro Gly Leu Val Lys Pro Ser Glu
1               5                   10                  15

Thr Leu Ser Leu Thr Cys Ala Val Ser Gly His Ser Ile Ser His Asp
            20                  25                  30

His Ala Trp Ser Trp Val Arg Gln Pro Pro Gly Glu Gly Leu Glu Trp
        35                  40                  45

Ile Gly Phe Ile Ser Tyr Ser Gly Ile Thr Asn Tyr Asn Pro Ser Leu
    50                  55                  60

Gln Gly Arg Val Thr Ile Ser Arg Asp Asn Ser Lys Asn Thr Leu Tyr
65                  70                  75                  80

Leu Gln Met Asn Ser Leu Arg Ala Glu Asp Thr Ala Val Tyr Tyr Cys
                85                  90                  95

Ala Arg Ser Leu Ala Arg Thr Thr Ala Met Asp Tyr Trp Gly Glu Gly
            100                 105                 110

Thr Leu Val Thr Val Ser Ser Ala Ser Thr Lys Gly Pro Ser Val Phe
        115                 120                 125

Pro Leu Ala Pro Ser Ser Lys Ser Thr Ser Gly Gly Thr Ala Ala Leu
    130                 135                 140

Gly Cys Leu Val Lys Asp Tyr Phe Pro Glu Pro Val Thr Val Ser Trp
145                 150                 155                 160

Asn Ser Gly Ala Leu Thr Ser Gly Val His Thr Phe Pro Ala Val Leu
                165                 170                 175

Gln Ser Ser Gly Leu Tyr Ser Leu Ser Ser Val Val Thr Val Pro Ser
            180                 185                 190

Ser Ser Leu Gly Thr Gln Thr Tyr Ile Cys Asn Val Asn His Lys Pro
        195                 200                 205

Ser Asn Thr Lys Val Asp Lys Lys Val Glu Pro Lys Ser Cys Asp Lys
    210                 215                 220

Thr His Thr Cys Pro Pro Cys Pro Ala Pro Glu Leu Leu Gly Gly Pro
225                 230                 235                 240

Ser Val Phe Leu Phe Pro Pro Lys Pro Lys Asp Thr Leu Met Ile Ser
                245                 250                 255

Arg Thr Pro Glu Val Thr Cys Val Val Val Asp Val Ser His Glu Asp
            260                 265                 270

Pro Glu Val Lys Phe Asn Trp Tyr Val Asp Gly Val Glu Val His Asn
        275                 280                 285

Ala Lys Thr Lys Pro Arg Glu Glu Gln Tyr Asn Ser Thr Tyr Arg Val
    290                 295                 300

Val Ser Val Leu Thr Val Leu His Gln Asp Trp Leu Asn Gly Lys Glu
305                 310                 315                 320

Tyr Lys Cys Lys Val Ser Asn Lys Ala Leu Pro Ala Pro Ile Glu Lys
                325                 330                 335
```

Thr Ile Ser Lys Ala Lys Gly Gln Pro Arg Glu Pro Gln Val Tyr Thr
340 345 350

Leu Pro Pro Ser Arg Asp Glu Leu Thr Lys Asn Gln Val Ser Leu Thr
355 360 365

Cys Leu Val Lys Gly Phe Tyr Pro Ser Asp Ile Ala Val Glu Trp Glu
370 375 380

Ser Asn Gly Gln Pro Glu Asn Asn Tyr Lys Thr Thr Pro Pro Val Leu
385 390 395 400

Asp Ser Asp Gly Ser Phe Phe Leu Tyr Ser Lys Leu Thr Val Asp Lys
405 410 415

Ser Arg Trp Gln Gln Gly Asn Val Phe Ser Cys Ser Val Met His Glu
420 425 430

Ala Leu His Asn His Tyr Thr Gln Lys Ser Leu Ser Leu Ser Pro
435 440 445

<210> SEQ ID NO 5
<211> LENGTH: 214
<212> TYPE: PRT
<213> ORGANISM: Artificial Sequence
<220> FEATURE:
<223> OTHER INFORMATION: an artificially synthesized sequence

<400> SEQUENCE: 5

Asp Ile Gln Met Thr Gln Ser Pro Ser Ser Leu Ser Ala Ser Val Gly
1 5 10 15

Asp Arg Val Thr Ile Thr Cys Arg Ala Ser Gln Asp Ile Ser Ser Tyr
20 25 30

Leu Asn Trp Tyr Gln Gln Lys Pro Gly Lys Ala Pro Lys Leu Leu Ile
35 40 45

Tyr Tyr Thr Ser Arg Leu His Ser Gly Val Pro Ser Arg Phe Ser Gly
50 55 60

Ser Gly Ser Gly Thr Asp Phe Thr Phe Thr Ile Ser Ser Leu Gln Pro
65 70 75 80

Glu Asp Ile Ala Thr Tyr Tyr Cys Gln Gln Gly Asn Thr Leu Pro Tyr
85 90 95

Thr Phe Gly Gln Gly Thr Lys Val Glu Ile Lys Arg Thr Val Ala Ala
100 105 110

Pro Ser Val Phe Ile Phe Pro Pro Ser Asp Glu Gln Leu Lys Ser Gly
115 120 125

Thr Ala Ser Val Val Cys Leu Leu Asn Asn Phe Tyr Pro Arg Glu Ala
130 135 140

Lys Val Gln Trp Lys Val Asp Asn Ala Leu Gln Ser Gly Asn Ser Gln
145 150 155 160

Glu Ser Val Thr Glu Gln Asp Ser Lys Asp Ser Thr Tyr Ser Leu Ser
165 170 175

Ser Thr Leu Thr Leu Ser Lys Ala Asp Tyr Glu Lys His Lys Val Tyr
180 185 190

Ala Cys Glu Val Thr His Gln Gly Leu Ser Ser Pro Val Thr Lys Ser
195 200 205

Phe Asn Arg Gly Glu Cys
210

<210> SEQ ID NO 6
<211> LENGTH: 447
<212> TYPE: PRT
<213> ORGANISM: Artificial Sequence
<220> FEATURE:
<223> OTHER INFORMATION: an artificially synthesized sequence

<400> SEQUENCE: 6

```
Gln Val Gln Leu Gln Glu Ser Gly Pro Gly Leu Val Lys Pro Ser Glu
1               5                   10                  15

Thr Leu Ser Leu Thr Cys Ala Val Ser Gly His Ser Ile Ser His Asp
            20                  25                  30

His Ala Trp Ser Trp Val Arg Gln Pro Pro Gly Glu Gly Leu Glu Trp
        35                  40                  45

Ile Gly Phe Ile Ser Tyr Ser Gly Ile Thr Asn Tyr Asn Pro Ser Leu
    50                  55                  60

Gln Gly Arg Val Thr Ile Ser Arg Asp Asn Ser Lys Asn Thr Leu Tyr
65                  70                  75                  80

Leu Gln Met Asn Ser Leu Arg Ala Glu Asp Thr Ala Val Tyr Tyr Cys
                85                  90                  95

Ala Arg Ser Leu Ala Arg Thr Thr Ala Met Asp Tyr Trp Gly Glu Gly
            100                 105                 110

Thr Leu Val Thr Val Ser Ser Ala Ser Thr Lys Gly Pro Ser Val Phe
        115                 120                 125

Pro Leu Ala Pro Ser Ser Lys Ser Thr Ser Gly Gly Thr Ala Ala Leu
    130                 135                 140

Gly Cys Leu Val Lys Asp Tyr Phe Pro Glu Pro Val Thr Val Ser Trp
145                 150                 155                 160

Asn Ser Gly Ala Leu Thr Ser Gly Val His Thr Phe Pro Ala Val Leu
                165                 170                 175

Gln Ser Ser Gly Leu Tyr Ser Leu Ser Ser Val Val Thr Val Pro Ser
            180                 185                 190

Ser Ser Leu Gly Thr Gln Thr Tyr Ile Cys Asn Val Asn His Lys Pro
        195                 200                 205

Ser Asn Thr Lys Val Asp Lys Lys Val Glu Pro Lys Ser Cys Asp Lys
    210                 215                 220

Thr His Thr Cys Pro Pro Cys Pro Ala Pro Glu Leu Leu Gly Gly Pro
225                 230                 235                 240

Ser Val Phe Leu Phe Pro Pro Lys Pro Lys Asp Thr Leu Met Ile Ser
                245                 250                 255

Arg Thr Pro Glu Val Thr Cys Val Val Val Asp Val Ser His Glu Asp
            260                 265                 270

Pro Glu Val Lys Phe Asn Trp Tyr Val Asp Gly Val Glu Val His Asn
        275                 280                 285

Ala Lys Thr Lys Pro Arg Glu Glu Gln Tyr Asn Ser Thr Tyr Arg Val
    290                 295                 300

Val Ser Val Leu Thr Val Leu His Gln Asp Trp Leu Asn Gly Lys Glu
305                 310                 315                 320

Tyr Lys Cys Lys Val Ser Asn Lys Ala Leu Pro Ala Pro Val Glu Lys
                325                 330                 335

Thr Ile Ser Lys Ala Lys Gly Gln Pro Arg Glu Pro Gln Val Tyr Thr
            340                 345                 350

Leu Pro Pro Ser Arg Asp Glu Leu Thr Lys Asn Gln Val Ser Leu Thr
        355                 360                 365

Cys Leu Val Lys Gly Phe Tyr Pro Ser Asp Ile Ala Val Glu Trp Glu
    370                 375                 380

Ser Asn Gly Gln Pro Glu Asn Asn Tyr Lys Thr Thr Pro Pro Val Leu
385                 390                 395                 400
```

```
Asp Ser Asp Gly Ser Phe Phe Leu Tyr Ser Lys Leu Thr Val Asp Lys
                405                 410                 415

Ser Arg Trp Gln Gln Gly Asn Val Phe Ser Cys Ser Val Met His Glu
            420                 425                 430

Ala Leu His Tyr His Tyr Thr Gln Lys Ser Leu Ser Leu Ser Pro
        435                 440                 445


<210> SEQ ID NO 7
<211> LENGTH: 215
<212> TYPE: PRT
<213> ORGANISM: Homo sapiens

<400> SEQUENCE: 7

Met Gly Lys Gly Asp Pro Lys Lys Pro Arg Gly Lys Met Ser Ser Tyr
1               5                   10                  15

Ala Phe Phe Val Gln Thr Cys Arg Glu Glu His Lys Lys Lys His Pro
            20                  25                  30

Asp Ala Ser Val Asn Phe Ser Glu Phe Ser Lys Lys Cys Ser Glu Arg
        35                  40                  45

Trp Lys Thr Met Ser Ala Lys Glu Lys Gly Lys Phe Glu Asp Met Ala
    50                  55                  60

Lys Ala Asp Lys Ala Arg Tyr Glu Arg Glu Met Lys Thr Tyr Ile Pro
65                  70                  75                  80

Pro Lys Gly Glu Thr Lys Lys Lys Phe Lys Asp Pro Asn Ala Pro Lys
                85                  90                  95

Arg Pro Pro Ser Ala Phe Phe Leu Phe Cys Ser Glu Tyr Arg Pro Lys
            100                 105                 110

Ile Lys Gly Glu His Pro Gly Leu Ser Ile Gly Asp Val Ala Lys Lys
        115                 120                 125

Leu Gly Glu Met Trp Asn Asn Thr Ala Ala Asp Asp Lys Gln Pro Tyr
    130                 135                 140

Glu Lys Lys Ala Ala Lys Leu Lys Glu Lys Tyr Glu Lys Asp Ile Ala
145                 150                 155                 160

Ala Tyr Arg Ala Lys Gly Lys Pro Asp Ala Ala Lys Lys Gly Val Val
                165                 170                 175

Lys Ala Glu Lys Ser Lys Lys Lys Lys Glu Glu Glu Glu Asp Glu Glu
            180                 185                 190

Asp Glu Glu Asp Glu Glu Glu Glu Glu Asp Glu Glu Asp Glu Asp Glu
        195                 200                 205

Glu Glu Asp Asp Asp Asp Glu
    210                 215


<210> SEQ ID NO 8
<211> LENGTH: 20
<212> TYPE: DNA
<213> ORGANISM: Artificial Sequence
<220> FEATURE:
<223> OTHER INFORMATION: an artificially synthesized primer sequence

<400> SEQUENCE: 8

agracccagc atggacayva                                                20


<210> SEQ ID NO 9
<211> LENGTH: 25
<212> TYPE: DNA
<213> ORGANISM: Artificial Sequence
<220> FEATURE:
<223> OTHER INFORMATION: an artificially synthesized primer sequence
```

<400> SEQUENCE: 9
ggayrgwatt tattygccac rcaca 25

<210> SEQ ID NO 10
<211> LENGTH: 20
<212> TYPE: DNA
<213> ORGANISM: Artificial Sequence
<220> FEATURE:
<223> OTHER INFORMATION: an artificially synthesized primer sequence

<400> SEQUENCE: 10
agacrctcac catggagact 20

<210> SEQ ID NO 11
<211> LENGTH: 17
<212> TYPE: DNA
<213> ORGANISM: Artificial Sequence
<220> FEATURE:
<223> OTHER INFORMATION: an artificially synthesized primer sequence

<400> SEQUENCE: 11
actggctccg ggaggta 17

<210> SEQ ID NO 12
<211> LENGTH: 17
<212> TYPE: DNA
<213> ORGANISM: Artificial Sequence
<220> FEATURE:
<223> OTHER INFORMATION: an artificially synthesized primer sequence

<400> SEQUENCE: 12
caccatggag actgggc 17

<210> SEQ ID NO 13
<211> LENGTH: 15
<212> TYPE: DNA
<213> ORGANISM: Artificial Sequence
<220> FEATURE:
<223> OTHER INFORMATION: an artificially synthesized primer sequence

<400> SEQUENCE: 13
ggaggagacg gtgac 15

<210> SEQ ID NO 14
<211> LENGTH: 16
<212> TYPE: DNA
<213> ORGANISM: Artificial Sequence
<220> FEATURE:
<223> OTHER INFORMATION: an artificially synthesized primer sequence

<400> SEQUENCE: 14
atggacacga gggccc 16

<210> SEQ ID NO 15
<211> LENGTH: 19
<212> TYPE: DNA
<213> ORGANISM: Artificial Sequence
<220> FEATURE:
<223> OTHER INFORMATION: an artificially synthesized primer sequence

<400> SEQUENCE: 15
tttgaccacc acctcggtc 19

<210> SEQ ID NO 16

-continued

<211> LENGTH: 1893
<212> TYPE: DNA
<213> ORGANISM: Homo sapiens

<400> SEQUENCE: 16

```
gaaggatatt aaagagcacc tgcaggaatt ttttaagggg atgccggggg aagggcttga     60
aggaggaact aaggaggctt ccagaagatt ttgattaaca gcgagcgcta gggaaggcca    120
cggggataca gaggggtagg aggaggatcc agagacctcc aagttgtgga ctccggaggc    180
atcgagttcc tttcccagtt ttgtcaagaa ttccctgagc ggcagacacc ctcaaagtaa    240
aaaacgggaa ccacagagaa ggaaaaagaa gaaccacaag cgttttgaga aacaaacagg    300
ctgggcctag ggcctggggt gtgccctgca actgggggt ggggctggat gttcttggag    360
tcagggagca gcagcctccc acaggatgtg agagaggaac tggggtctcc agtcacggga    420
gccaggagcc ggccagggcc gcaggcagga agggagcgag gctgaaggga acgtcgtcct    480
ctcagcatgg gggtcccgcg gcctcagccc tgggcgctgg ggctcctgct ctttctcctt    540
cctgggagcc tgggcgcaga aagccacctc tccctcctgt accaccttac cgcggtgtcc    600
tcgcctgccc cggggactcc tgccttctgg gtgtccggct ggctgggccc gcagcagtac    660
ctgagctaca atagcctgcg gggcgaggcg gagccctgtg gagcttgggt ctgggaaaac    720
caggtgtcct ggtattggga gaaagagacc acagatctga ggatcaagga gaagctcttt    780
ctggaagctt tcaaagcttt ggggggaaaa ggtccctaca ctctgcaggg cctgctgggc    840
tgtgaactgg gccctgacaa cacctcggtg cccaccgcca agttcgccct gaacggcgag    900
gagttcatga atttcgacct caagcagggc acctggggtg gggactggcc cgaggccctg    960
gctatcagtc agcggtggca gcagcaggac aaggcggcca acaaggagct caccttcctg   1020
ctattctcct gcccgcaccg cctgcgggag cacctggaga ggggccgcgg aaacctggag   1080
tggaaggagc ccccctccat gcgcctgaag gcccgaccca gcagccctgg cttttccgtg   1140
cttacctgca gcgccttctc cttctaccct ccggagctgc aacttcggtt cctgcggaat   1200
gggctggccg ctggcaccgg ccagggtgac ttcggcccca acagtgacgg atccttccac   1260
gcctcgtcgt cactaacagt caaaagtggc gatgagcacc actactgctg cattgtgcag   1320
cacgcggggc tggcgcagcc cctcagggtg gagctggaat ctccagccaa gtcctccgtg   1380
ctcgtggtgg gaatcgtcat cggtgtcttg ctactcacgg cagcggctgt aggaggagct   1440
ctgttgtgga gaaggatgag gagtgggctg ccagcccctt ggatctccct tcgtggagac   1500
gacaccgggg tcctcctgcc caccccaggg gaggcccagg atgctgattt gaaggatgta   1560
aatgtgattc cagccaccgc ctgaccatcc gccattccga ctgctaaaag cgaatgtagt   1620
caggcccctt tcatgctgtg agacctcctg gaacactggc atctctgagc ctccagaagg   1680
ggttctgggc ctagttgtcc tccctctgga gccccgtcct gtggtctgcc tcagtttccc   1740
ctcctaatac atatggctgt tttccacctc gataatataa cacgagtttg ggcccgaatc   1800
agtgtgttct catcattttt caggcagggg aggtaaggga ataagtcggg ggactgaatg   1860
gcggctgggc ctcggatctc tcctacaggt aac                                1893
```

<210> SEQ ID NO 17
<211> LENGTH: 365
<212> TYPE: PRT
<213> ORGANISM: Homo sapiens

<400> SEQUENCE: 17

Met Gly Val Pro Arg Pro Gln Pro Trp Ala Leu Gly Leu Leu Leu Phe

```
1               5                   10                  15

Leu Leu Pro Gly Ser Leu Gly Ala Glu Ser His Leu Ser Leu Leu Tyr
            20                  25                  30

His Leu Thr Ala Val Ser Ser Pro Ala Pro Gly Thr Pro Ala Phe Trp
        35                  40                  45

Val Ser Gly Trp Leu Gly Pro Gln Gln Tyr Leu Ser Tyr Asn Ser Leu
    50                  55                  60

Arg Gly Glu Ala Glu Pro Cys Gly Ala Trp Val Trp Glu Asn Gln Val
65                  70                  75                  80

Ser Trp Tyr Trp Glu Lys Glu Thr Thr Asp Leu Arg Ile Lys Glu Lys
                85                  90                  95

Leu Phe Leu Glu Ala Phe Lys Ala Leu Gly Gly Lys Gly Pro Tyr Thr
            100                 105                 110

Leu Gln Gly Leu Leu Gly Cys Glu Leu Gly Pro Asp Asn Thr Ser Val
        115                 120                 125

Pro Thr Ala Lys Phe Ala Leu Asn Gly Glu Glu Phe Met Asn Phe Asp
    130                 135                 140

Leu Lys Gln Gly Thr Trp Gly Gly Asp Trp Pro Glu Ala Leu Ala Ile
145                 150                 155                 160

Ser Gln Arg Trp Gln Gln Gln Asp Lys Ala Ala Asn Lys Glu Leu Thr
                165                 170                 175

Phe Leu Leu Phe Ser Cys Pro His Arg Leu Arg Glu His Leu Glu Arg
            180                 185                 190

Gly Arg Gly Asn Leu Glu Trp Lys Glu Pro Pro Ser Met Arg Leu Lys
        195                 200                 205

Ala Arg Pro Ser Ser Pro Gly Phe Ser Val Leu Thr Cys Ser Ala Phe
    210                 215                 220

Ser Phe Tyr Pro Pro Glu Leu Gln Leu Arg Phe Leu Arg Asn Gly Leu
225                 230                 235                 240

Ala Ala Gly Thr Gly Gln Gly Asp Phe Gly Pro Asn Ser Asp Gly Ser
                245                 250                 255

Phe His Ala Ser Ser Ser Leu Thr Val Lys Ser Gly Asp Glu His His
            260                 265                 270

Tyr Cys Cys Ile Val Gln His Ala Gly Leu Ala Gln Pro Leu Arg Val
        275                 280                 285

Glu Leu Glu Ser Pro Ala Lys Ser Ser Val Leu Val Val Gly Ile Val
    290                 295                 300

Ile Gly Val Leu Leu Leu Thr Ala Ala Ala Val Gly Gly Ala Leu Leu
305                 310                 315                 320

Trp Arg Arg Met Arg Ser Gly Leu Pro Ala Pro Trp Ile Ser Leu Arg
                325                 330                 335

Gly Asp Asp Thr Gly Val Leu Leu Pro Thr Pro Gly Glu Ala Gln Asp
            340                 345                 350

Ala Asp Leu Lys Asp Val Asn Val Ile Pro Ala Thr Ala
        355                 360                 365
```

<210> SEQ ID NO 18
<211> LENGTH: 1738
<212> TYPE: DNA
<213> ORGANISM: Mus musculus

<400> SEQUENCE: 18

```
aggagctagt gggtggagtt ggatgccctc agagttctcc agtcctaact gtgtacagac      60

aggatgtaag agaagaactg gaggctctaa gcagaggatc catcggctgc aggcagaggg     120
```

```
aagagggcct ctgtgaggaa caggctgagc gtcagaggag gaggcccagg cctggttctc    180
tagctctgta attaattaac taaagtggat caaatgagaa ggtgaaagtt cacagaggaa    240
cactcctgtc tgtcgtcttg gactgggtct ccatcccacc atccagcgtc ctggtctacg    300
aagagtccac agggaccttg tgaagaatca acaaggcggg gtccagagga gtcacgtgtc    360
ccttccactc cgggtcaccc tgtcggaatg gggatgccac tgccctgggc cctcagcctc    420
ttgttggtcc tcctgcctca gacctggggc tcagagaccc gcccccccact gatgtatcat    480
ctcacggctg tgtcaaaccc atctacgggg cttccctctt tctgggctac aggctggttg    540
ggtcctcagc agtatctgac ctacaacagc ctgcggcagg aagctgaccc ctgtggggcc    600
tggatgtggg aaaatcaggt gtcttggtat tgggagaagg agaccacaga cctcaaaagc    660
aaagaacagc tcttcttgga ggccctcaag accctggaga agatattaaa tgggacctac    720
acactgcagg gcctgctggg ctgtgaactg gcctcggata attcctcagt gcccacggct    780
gtgtttgccc tcaatggtga ggagtttatg aaattcaacc caagaatcgg caattggact    840
ggggagtggc ctgagacgga aatcgttgct aatctgtgga tgaagcagcc tgatgcggcc    900
aggaaggaga gcgagttcct gctaaactct tgtccggagc gactgctagg ccacctggag    960
aggggccgac ggaacctgga gtggaaggag ccgccgtcta tgcgcctgaa ggcccgtcct   1020
ggcaactctg gctcctccgt gctgacctgt gctgctttct ccttctaccc accggagctc   1080
aagttccgat tcctgcgcaa tggctagcc tcaggctccg ggaattgcag cactggtccc   1140
aatggagatg gctctttcca cgcatggtca ttgctggagg tcaaacgtgg agatgagcac   1200
cattatcaat gtcaagtgga gcatgagggg ctggcacagc ctctcactgt ggacctagat   1260
tcatcagcca gatcttctgt gcctgtggtt ggaatcgttc ttggtttatt gctggtggta   1320
gtggccatcg caggcggtgt gctgttgtgg ggcaggatgc gcagcggtct gccagcccca   1380
tggctttctc tcagcggcga tgactctggt gacctgttgc ctggtgggaa cttgccccca   1440
gaagctgaac ctcaaggtgc aaatgccttt ccagccactt cctgatgcag actcgggccc   1500
cctgcccact gcagcctttc gggctgtgtg acctcctgaa ctgtctccga gcctcctgag   1560
ggagcctggg cccgatgtcc tcccatggat ccctgctttt gtggcctgct tcagtttccc   1620
ttcttaatgt acatggttgt tttccatctc cacataaatt tggccccaaa tctgtgtgtg   1680
catcgttatt ctcaagtttc aagcagctgg aataaattga acgcgtctgg gaaagatc     1738
```

```
<210> SEQ ID NO 19
<211> LENGTH: 365
<212> TYPE: PRT
<213> ORGANISM: Mus musculus

<400> SEQUENCE: 19

Met Gly Met Pro Leu Pro Trp Ala Leu Ser Leu Leu Leu Val Leu Leu
1               5                   10                  15

Pro Gln Thr Trp Gly Ser Glu Thr Arg Pro Pro Leu Met Tyr His Leu
            20                  25                  30

Thr Ala Val Ser Asn Pro Ser Thr Gly Leu Pro Ser Phe Trp Ala Thr
        35                  40                  45

Gly Trp Leu Gly Pro Gln Gln Tyr Leu Thr Tyr Asn Ser Leu Arg Gln
    50                  55                  60

Glu Ala Asp Pro Cys Gly Ala Trp Met Trp Glu Asn Gln Val Ser Trp
65                  70                  75                  80

Tyr Trp Glu Lys Glu Thr Thr Asp Leu Lys Ser Lys Glu Gln Leu Phe
```

-continued

```
                85                  90                  95

Leu Glu Ala Leu Lys Thr Leu Glu Lys Ile Leu Asn Gly Thr Tyr Thr
            100                 105                 110

Leu Gln Gly Leu Leu Gly Cys Glu Leu Ala Ser Asp Asn Ser Ser Val
        115                 120                 125

Pro Thr Ala Val Phe Ala Leu Asn Gly Glu Glu Phe Met Lys Phe Asn
    130                 135                 140

Pro Arg Ile Gly Asn Trp Thr Gly Glu Trp Pro Glu Thr Glu Ile Val
145                 150                 155                 160

Ala Asn Leu Trp Met Lys Gln Pro Asp Ala Ala Arg Lys Glu Ser Glu
                165                 170                 175

Phe Leu Leu Asn Ser Cys Pro Glu Arg Leu Leu Gly His Leu Glu Arg
            180                 185                 190

Gly Arg Arg Asn Leu Glu Trp Lys Glu Pro Pro Ser Met Arg Leu Lys
        195                 200                 205

Ala Arg Pro Gly Asn Ser Gly Ser Ser Val Leu Thr Cys Ala Ala Phe
    210                 215                 220

Ser Phe Tyr Pro Pro Glu Leu Lys Phe Arg Phe Leu Arg Asn Gly Leu
225                 230                 235                 240

Ala Ser Gly Ser Gly Asn Cys Ser Thr Gly Pro Asn Gly Asp Gly Ser
                245                 250                 255

Phe His Ala Trp Ser Leu Leu Glu Val Lys Arg Gly Asp Glu His His
            260                 265                 270

Tyr Gln Cys Gln Val Glu His Glu Gly Leu Ala Gln Pro Leu Thr Val
        275                 280                 285

Asp Leu Asp Ser Ser Ala Arg Ser Ser Val Pro Val Val Gly Ile Val
    290                 295                 300

Leu Gly Leu Leu Leu Val Val Val Ala Ile Ala Gly Gly Val Leu Leu
305                 310                 315                 320

Trp Gly Arg Met Arg Ser Gly Leu Pro Ala Pro Trp Leu Ser Leu Ser
                325                 330                 335

Gly Asp Asp Ser Gly Asp Leu Leu Pro Gly Gly Asn Leu Pro Pro Glu
            340                 345                 350

Ala Glu Pro Gln Gly Ala Asn Ala Phe Pro Ala Thr Ser
        355                 360                 365
```

<210> SEQ ID NO 20
<211> LENGTH: 1552
<212> TYPE: DNA
<213> ORGANISM: Rattus norvegicus

<400> SEQUENCE: 20

```
tcagttctgt aattaattaa ctaacgtgga tcaaatgaga aggtgaaagt tcacacagga      60

gcactcctgt cgtcttggac tgggtctcca tcccaccatc cagtgccctg gtctacgaag     120

agtccacagg gaccttgtga agaatcaaca aggcggggtc cagaggagtc acgtgtgcct     180

tccactccgg gtcgccctgt caggatgggg atgtcccagc ccggggtcct cctcagcctc     240

ttattggtcc tcctgcctca gacctgggga gcggagcccc gtctcccact gatgtatcat     300

cttgcagctg tgtctgactt atcaacgggg cttccctctt tctgggccac gggctggctg     360

ggtgctcagc aatatctgac ctacaacaac ctgcggcagg aggctgaccc ctgtggggcc     420

tggatatggg aaaaccaggt gtcttggtat tgggagaagg agaccacgga tctgaaaagc     480

aaagaacagc tcttcttgga ggccatcagg accctggaga accaaataaa tgggaccttc     540
```

-continued

```
acactgcagg gcctgctggg ctgtgaactg gcccctgata attcttcatt gcccacggct    600

gtgtttgccc tcaatggtga ggagttcatg cggttcaacc caagaacggg caactggagt    660

ggggagtggc cggagacaga tatcgttggt aatctgtgga tgaagcaacc tgaggcggcc    720

aggaaggaga gcgagttcct gctaacttct tgtcctgagc ggctgctagg ccacctggag    780

aggggccgtc agaacctgga gtggaaggag ccgccatcta tgcgcctgaa ggcccgtcct    840

ggcaactctg gctcctcagt actgacctgt gctgctttct ccttctaccc gccggagctc    900

aagtttcgat tcctgcgcaa tgggctagcc tcaggctctg ggaattgcag cactggtccc    960

aatggtgatg gatctttcca tgcatggtca ttgctagagg tcaaacgtgg agatgaacac   1020

cattaccaat gtcaagtgga gcatgagggg ctggcccagc ctctcactgt ggacctagat   1080

tcgcccgcca gatcttctgt gcctgtggtc ggaatcattc ttggtttatt gctggtggta   1140

gtggccatcg caggggtgt gctgctatgg aacaggatgc gaagtgggct gccagcccca   1200

tggctttctc tcagtggtga tgactctggc gacctattgc ctggtgggaa cttgcccccg   1260

gaggctgaac ctcaaggtgt aaatgccttt ccggccactt cctgatgcca acccaggccc   1320

catacccatt gcagcctgtg ggctgtgtg acctcctgaa ctgtctctga gcctcccgag   1380

ggagccctgg gctggatgtc ctcctcgtgg atcccttctt ttgtggcctg cttcagtttc   1440

ccctcttaat gtcaatggct atttccatct ccacataaat ttgggcccaa atctgtgtgt   1500

gcatcgttat tctcaggttt caggcagccg gaataaattg aacaagtttg ag           1552
```

<210> SEQ ID NO 21
<211> LENGTH: 366
<212> TYPE: PRT
<213> ORGANISM: Rattus norvegicus

<400> SEQUENCE: 21

```
Met Gly Met Ser Gln Pro Gly Val Leu Leu Ser Leu Leu Leu Val Leu
1               5                   10                  15

Leu Pro Gln Thr Trp Gly Ala Glu Pro Arg Leu Pro Leu Met Tyr His
            20                  25                  30

Leu Ala Ala Val Ser Asp Leu Ser Thr Gly Leu Pro Ser Phe Trp Ala
        35                  40                  45

Thr Gly Trp Leu Gly Ala Gln Gln Tyr Leu Thr Tyr Asn Asn Leu Arg
    50                  55                  60

Gln Glu Ala Asp Pro Cys Gly Ala Trp Ile Trp Glu Asn Gln Val Ser
65                  70                  75                  80

Trp Tyr Trp Glu Lys Glu Thr Thr Asp Leu Lys Ser Lys Glu Gln Leu
                85                  90                  95

Phe Leu Glu Ala Ile Arg Thr Leu Glu Asn Gln Ile Asn Gly Thr Phe
            100                 105                 110

Thr Leu Gln Gly Leu Leu Gly Cys Glu Leu Ala Pro Asp Asn Ser Ser
        115                 120                 125

Leu Pro Thr Ala Val Phe Ala Leu Asn Gly Glu Glu Phe Met Arg Phe
    130                 135                 140

Asn Pro Arg Thr Gly Asn Trp Ser Gly Glu Trp Pro Glu Thr Asp Ile
145                 150                 155                 160

Val Gly Asn Leu Trp Met Lys Gln Pro Glu Ala Ala Arg Lys Glu Ser
                165                 170                 175

Glu Phe Leu Leu Thr Ser Cys Pro Glu Arg Leu Leu Gly His Leu Glu
            180                 185                 190

Arg Gly Arg Gln Asn Leu Glu Trp Lys Glu Pro Pro Ser Met Arg Leu
```

```
        195                 200                 205

Lys Ala Arg Pro Gly Asn Ser Gly Ser Ser Val Leu Thr Cys Ala Ala
    210                 215                 220

Phe Ser Phe Tyr Pro Pro Glu Leu Lys Phe Arg Phe Leu Arg Asn Gly
225                 230                 235                 240

Leu Ala Ser Gly Ser Gly Asn Cys Ser Thr Gly Pro Asn Gly Asp Gly
            245                 250                 255

Ser Phe His Ala Trp Ser Leu Leu Glu Val Lys Arg Gly Asp Glu His
            260                 265                 270

His Tyr Gln Cys Gln Val Glu His Glu Gly Leu Ala Gln Pro Leu Thr
        275                 280                 285

Val Asp Leu Asp Ser Pro Ala Arg Ser Ser Val Pro Val Val Gly Ile
    290                 295                 300

Ile Leu Gly Leu Leu Leu Val Val Val Ala Ile Ala Gly Gly Val Leu
305                 310                 315                 320

Leu Trp Asn Arg Met Arg Ser Gly Leu Pro Ala Pro Trp Leu Ser Leu
            325                 330                 335

Ser Gly Asp Asp Ser Gly Asp Leu Leu Pro Gly Gly Asn Leu Pro Pro
            340                 345                 350

Glu Ala Glu Pro Gln Gly Val Asn Ala Phe Pro Ala Thr Ser
        355                 360                 365


<210> SEQ ID NO 22
<211> LENGTH: 3428
<212> TYPE: DNA
<213> ORGANISM: Homo sapiens

<400> SEQUENCE: 22

tggagagtaa tgttacagag cggagagagt gaggaggctg cgtctggctc ccgctctcac     60

agccattgca gtacattgag ctccatagag acagcgccgg ggcaagtgag agccggacgg    120

gcactgggcg actctgtgcc tcgctgagga aaaataacta aacatgggca aaggagatcc    180

taagaagccg agaggcaaaa tgtcatcata tgcatttttt gtgcaaactt gtcgggagga    240

gcataagaag aagcacccag atgcttcagt caacttctca gagttttcta agaagtgctc    300

agagaggtgg aagaccatgt ctgctaaaga gaaaggaaaa tttgaagata tggcaaaagc    360

ggacaaggcc cgttatgaaa gagaaatgaa aacctatatc cctcccaaag gggagacaaa    420

aaagaagttc aaggatccca atgcacccaa gaggcctcct tcggccttct tcctcttctg    480

ctctgagtat cgcccaaaaa tcaaaggaga acatcctggc ctgtccattg gtgatgttgc    540

gaagaaactg ggagagatgt ggaataacac tgctgcagat gacaagcagc cttatgaaaa    600

gaaggctgcg aagctgaagg aaaaatacga aaaggatatt gctgcatatc gagctaaagg    660

aaagcctgat gcagcaaaaa agggagttgt caaggctgaa aaaagcaaga aaaagaagga    720

agaggaggaa gatgaggaag atgaagagga tgaggaggag gaggaagatg aagaagatga    780

agatgaagaa gaagatgatg atgatgaata agttggttct agcgcagttt tttttttctt    840

gtctataaag catttaaccc ccctgtacac aactcactcc ttttaaagaa aaaaattgaa    900

atgtaaggct gtgtaagatt tgtttttaaa ctgtacagtg tctttttttg tatagttaac    960

acactaccga atgtgtcttt agatagccct gtcctggtgg tattttcaat agccactaac   1020

cttgcctggt acagtatggg ggttgtaaat tggcatggaa atttaaagca ggttcttgtt   1080

ggtgcacagc acaaattagt tatatatggg gatggtagtt ttttcatctt cagttgtctc   1140

tgatgcagct tatacgaaat aattgttgtt ctgttaactg aataccactc tgtaattgca   1200
```

-continued

```
aaaaaaaaaa aaaagttgca gctgttttgt tgacattctg aatgcttcta agtaaataca   1260
atttttttta ttagtattgt tgtccttttc ataggtctga aatttttctt cttgagggga   1320
agctagtctt ttgcttttgc ccattttgaa tcacatgaat tattacagtg tttatccttt   1380
catatagtta gctaataaaa agcttttgtc tacacaccct gcatatcata atgggggtaa   1440
agttaagttg agatagtttt catccataac tgaacatcca aaatcttgat cagttaagaa   1500
atttcacata gcccacttac atttacaaac tgaagagtaa tcaatctact caaagcatgg   1560
gattattaga atcaaacatt ttgaaagtct gtccttgaag gactaataga aaagtatgtt   1620
ctaaccttta catgaggact ctattcttta actcccatta ccatgtaatg gcagttatat   1680
tttgcagttc ccacattaaa gaagacctga gaatgtatcc ccaaaagcgt gagcttaaaa   1740
tacaagactg ccatattaaa ttttttgttg acattagtct cagtgaagac tatgaaaatg   1800
ctggctatag atgtcttttc ccatttatct aaatatggac tgctcaggaa acgagacttt   1860
ccattacaag tatttttaat taattgggcc agcttttcaa acaaagatgc cacattcaaa   1920
atagggtata ttttcctata ttacggtttg cccctttata aatccaagta gataggaaga   1980
aagaagacaa actttgcatc tcagtatgaa ttattcaatt tatttgaatg atttttcttt   2040
acaaaacaaa ctcattcatt agtcatgttt atctgcttag gagtttaggg aacaatttgg   2100
caattttgtg gttttcgaga ttatcgtttt cttaaagtgc cagtatttta aaatagcgtt   2160
cttgtaattt tacacgcttt tgtgatggag tgctgttttg ttatataatt tagacttgga   2220
ttctttccat ttgcatttgt ttatgtaatt tcaggaggaa tactgaacat ctgagtcctg   2280
gatgatacta ataaactaat aattgcagag gttttaaata ctagttaaat ggctttcact   2340
taagaactta agattttgtt acatattttt aaatcttgtt tctaataata cctcttagca   2400
gtacctttta aataagtata agggatggca aagtttttcc ctttaaaaat actcacttta   2460
tgcttataaa taggttaatg ggctgataaa aggttttgtc aaacattgca agtattcggt   2520
gctatatata aaggaggaaa aactagtttt actttcagaa tgatttaaac aagattttta   2580
aaaacaagat acatgcaagc gaacagcagg gttagtgata ggctgcaatt gtgtcgaaca   2640
tcagattttt tgttaagagg agcaaatgac tcaatctgat ttagatggaa gtttctactg   2700
tatagaaatc accattaatc accaacatta ataattctga tccatttaaa atgaattctg   2760
gctcaaggag aatttgtaac tttagtaggt acgtcatgac aactaccatt tttttaagat   2820
gttgagaatg ggaacagttt ttttagggtt tattcttgac cacagatctt aagaaaatgg   2880
acaaaacccc tcttcaatct gaagattagt atggtttggt gttctaacag tatcccctag   2940
aagttggatg tctaaaactc aagtaaatgg aagtgggagg caatttagat aagtgtaaag   3000
ccttgtaact gaagatgatt ttttttagaa agtgtataga aactatttta atgccaagat   3060
agttacagtg ctgtggggtt taaagacttt gttgacatca agaaaagact aaatctataa   3120
ttaattgggc caacttttaa aatgaagatg ctttttaaaa ctaatgaact aagatgtata   3180
aatcttagtt tttttgtatt ttaaagatag gcatatggca tattgattaa cgagtcaaat   3240
ttcctaactt tgctgtgcaa aggttgagag ctattgctga ttagttacca cagttctgat   3300
gatcgtccca tcacagtgtt gttaatgttt gctgtattta ttaattttct taaagtgaaa   3360
tctgaaaaat gaaatttgtg tgtcctgtgt acccgagggg taatgattaa atgataaaga   3420
taagaaaa                                                            3428
```

<210> SEQ ID NO 23

```
<211> LENGTH: 215
<212> TYPE: PRT
<213> ORGANISM: Homo sapiens

<400> SEQUENCE: 23

Met Gly Lys Gly Asp Pro Lys Lys Pro Arg Gly Lys Met Ser Ser Tyr
1               5                   10                  15

Ala Phe Phe Val Gln Thr Cys Arg Glu Glu His Lys Lys Lys His Pro
            20                  25                  30

Asp Ala Ser Val Asn Phe Ser Glu Phe Ser Lys Lys Cys Ser Glu Arg
        35                  40                  45

Trp Lys Thr Met Ser Ala Lys Glu Lys Gly Lys Phe Glu Asp Met Ala
    50                  55                  60

Lys Ala Asp Lys Ala Arg Tyr Glu Arg Glu Met Lys Thr Tyr Ile Pro
65                  70                  75                  80

Pro Lys Gly Glu Thr Lys Lys Lys Phe Lys Asp Pro Asn Ala Pro Lys
                85                  90                  95

Arg Pro Pro Ser Ala Phe Phe Leu Phe Cys Ser Glu Tyr Arg Pro Lys
            100                 105                 110

Ile Lys Gly Glu His Pro Gly Leu Ser Ile Gly Asp Val Ala Lys Lys
        115                 120                 125

Leu Gly Glu Met Trp Asn Asn Thr Ala Ala Asp Asp Lys Gln Pro Tyr
    130                 135                 140

Glu Lys Lys Ala Ala Lys Leu Lys Glu Lys Tyr Glu Lys Asp Ile Ala
145                 150                 155                 160

Ala Tyr Arg Ala Lys Gly Lys Pro Asp Ala Ala Lys Lys Gly Val Val
                165                 170                 175

Lys Ala Glu Lys Ser Lys Lys Lys Lys Glu Glu Glu Glu Asp Glu Glu
            180                 185                 190

Asp Glu Glu Asp Glu Glu Glu Glu Glu Asp Glu Glu Asp Glu Asp Glu
        195                 200                 205

Glu Glu Asp Asp Asp Asp Glu
    210                 215


<210> SEQ ID NO 24
<211> LENGTH: 2327
<212> TYPE: DNA
<213> ORGANISM: Mus musculus

<400> SEQUENCE: 24

gttacagagc ggagagagtg aggaggctgc gtctggctcc cgctctcaca gccattgcag     60

tacattgagc tccatagaga cagcgccggg gcaagcgcga gccggacggg cactgggcga    120

ctctgtgcct cgcggaggaa aatcaactaa acatgggcaa aggagatcct aaaaagccga    180

gaggcaaaat gtcctcatat gcattctttg tgcaaacttg ccgggaggag cacaagaaga    240

agcacccgga tgcttctgtc aacttctcag agttctccaa gaagtgctca gagaggtgga    300

agaccatgtc tgctaaagaa aaggggaaat ttgaagatat ggcaaaggct gacaaggctc    360

gttatgaaag agaaatgaaa acctacatcc cccccaaagg ggagaccaaa aagaagttca    420

aggaccccaa tgcacccaag aggcctcctt cggccttctt cttgttctgt tctgagtacc    480

gccccaaaat caaaggcgag catcctggct tatccattgg tgatgttgca aagaaactag    540

gagagatgtg gaacaacact gcagcagatg acaagcagcc ctatgagaag aaagctgcca    600

agctgaagga gaagtatgag aaggatattg ctgcctacag agctaaagga aaacctgatg    660

cagcgaaaaa gggggtggtc aaggctgaaa agagcaagaa aaagaaggaa gaggaagatg    720
```

atgaggagga tgaagaggat gaggaagagg aggaagaaga ggaagacgaa gatgaagaag 780
aagatgatga tgatgaataa gttggttcta gcgcagtttt tttttcttgt ctataaagca 840
tttaaccccc ctgtacacaa ctcactcctt ttaaagaaaa aaattgaaat gtaaggctgt 900
gtaagatttg tttttaaact gtacagtgtc ttttttgta tagttaacac actaccgaat 960
gtgtctttag atagccctgt cctggtggta ttttcaatag ccactaacct tgcctggtac 1020
agtctggggg ttgtaaattg gcatggaaat ttaaagcagg ttcttgttgg tgcacagcac 1080
aaattagtta tatatgggga cagtagtttg gttttttgtt tttttttttt tttcttttgg 1140
ttttcttttt gggttttatt tttttcatct tcagttgtct ctgatgcagc ttatacgaag 1200
ataattgttg ttctgttaac tgaataccac tctgtaattg caaaaaaaaa attgcggctg 1260
ttttgttgac attctgaatg cttctaagta aatacaattt tttttattag tattgttgtc 1320
cttttcatag gtctgaaagt tttcttctca aggggaagct agtcttttgc tttgcccatt 1380
ttgggtcaca tggattatta gtgtgttatc tttcatctag ttagctggaa gagagctttt 1440
gtccacatgc cctgccattg tggtagggta acattttcat ccatagttga agaatctcct 1500
aaatcgtgat agttggataa gagatattat ataacctact tggcaaagca aggagtgatc 1560
aatactgtca caccgtggga ctattaggat caagcaatct gaacgtctgt ccttgaagga 1620
ctgatagaaa agtaccttct aatccttaca cgaggactct cctttaaccg ccattactgt 1680
gtaatgacag ttatatttg cagtttcccc tactaaagaa gacctgagaa tgtatcccca 1740
aaagtgtgag cttaaaatac aagactgctg tactatttgt tgaccttagt cccagcgaag 1800
gctatcacaa gaacgctggc tgtaaagcct ttgcccttct atctagatat ggattgctca 1860
ggaaacttga ctgtttaaag gtatttttaa ttacttgagc cagcttttaa aattatgcca 1920
catttaaaat gaagggtata ttttcctata ctgtggtttg tccctttatg aatcagatac 1980
aagaggataa actttgcata ttagtaccat ttgtccaata catttgcttt ttctttataa 2040
aacccaaact cattcattaa tcaggtttaa tctgcttagt ttagggaaca atttggcaat 2100
tttgtggatt tttttttgag attatcgttc tcttaaagtg ccagtgtttt aaatagcgtt 2160
cttgtaattt cacgcgcttt tgtgatggag tgctgttata taattttgac ttgggttctt 2220
tacatttgcg ttgttaatgt aatttgagga ggaatactga acatgagtcc tggatgatac 2280
taataaacta ataattacag aggttttaaa aaaaaaaaaa aaaaaaa 2327

<210> SEQ ID NO 25
<211> LENGTH: 215
<212> TYPE: PRT
<213> ORGANISM: Mus musculus

<400> SEQUENCE: 25

Met Gly Lys Gly Asp Pro Lys Lys Pro Arg Gly Lys Met Ser Ser Tyr
1 5 10 15

Ala Phe Phe Val Gln Thr Cys Arg Glu Glu His Lys Lys Lys His Pro
20 25 30

Asp Ala Ser Val Asn Phe Ser Glu Phe Ser Lys Lys Cys Ser Glu Arg
35 40 45

Trp Lys Thr Met Ser Ala Lys Glu Lys Gly Lys Phe Glu Asp Met Ala
50 55 60

Lys Ala Asp Lys Ala Arg Tyr Glu Arg Glu Met Lys Thr Tyr Ile Pro
65 70 75 80

Pro Lys Gly Glu Thr Lys Lys Lys Phe Lys Asp Pro Asn Ala Pro Lys

-continued

```
                85                  90                  95

Arg Pro Pro Ser Ala Phe Phe Leu Phe Cys Ser Glu Tyr Arg Pro Lys
            100                 105                 110

Ile Lys Gly Glu His Pro Gly Leu Ser Ile Gly Asp Val Ala Lys Lys
        115                 120                 125

Leu Gly Glu Met Trp Asn Asn Thr Ala Ala Asp Asp Lys Gln Pro Tyr
    130                 135                 140

Glu Lys Lys Ala Ala Lys Leu Lys Glu Lys Tyr Glu Lys Asp Ile Ala
145                 150                 155                 160

Ala Tyr Arg Ala Lys Gly Lys Pro Asp Ala Ala Lys Lys Gly Val Val
                165                 170                 175

Lys Ala Glu Lys Ser Lys Lys Lys Lys Glu Glu Glu Asp Asp Glu Glu
            180                 185                 190

Asp Glu Glu Asp Glu Glu Glu Glu Glu Glu Glu Glu Asp Glu Asp Glu
        195                 200                 205

Glu Glu Asp Asp Asp Asp Glu
    210                 215


<210> SEQ ID NO 26
<211> LENGTH: 2256
<212> TYPE: DNA
<213> ORGANISM: Rattus norvegicus

<400> SEQUENCE: 26

cgagagccgg acgggcactg ggcgactctg tgcctcgcgg aggaaaatca actaaacatg      60

ggcaaaggag atcctaagaa gccgagaggc aaaatgtcct catatgcatt ctttgtgcaa     120

acctgccggg aggagcacaa gaagaagcac ccggatgctt ctgtcaactt ctcagagttc     180

tccaagaagt gctcagagag gtggaagacc atgtctgcta aagaaaaggg gaaatttgaa     240

gatatggcaa aggctgacaa ggctcgttat gaaagagaaa tgaaaaccta catccccccc     300

aaaggggaga ccaaaaagaa gttcaaggac cccaatgccc ccaagaggcc tccttcggcc     360

ttcttcttgt tctgttctga gtaccgccca aaaatcaaag gcgagcatcc tggcttatcc     420

attggtgatg ttgcgaagaa actaggagag atgtggaaca acactgctgc ggatgacaag     480

cagccctatg aaaagaaggc cgccaagctg aaggagaagt atgagaagga tattgctgcc     540

tacagagcta aggaaaaacc tgatgcagcg aaaaaggggg tggtcaaggc tgagaagagc     600

aagaaaaaga aggaagagga agacgacgag gaggatgaag aggatgagga agaggaggaa     660

gaggaggaag acgaagatga agaagaagat gatgatgatg aataagttgg ttctagcgca     720

gttttttttt cttgtctata aagcatttaa cccccctgta cacaactcac tccttttaaa     780

gaaaaaaatt gaaatgtaag gctgtgtaag atttgttttt aaactgtaca gtgtcttttt     840

ttgtatagtt aacacactac cgaatgtgtc tttagctagc cctgtcctgg tggtattttc     900

aatagccact aaccttgcct ggtacagtct gggggttgta aattggcatg gaaattaaag     960

caggttcttg ttggtgcaca gcacaaatta gttatatatg gggacagtag tttggttttt    1020

ggtttctttt tttttttttt tttggttttg tttttttttcc ttttgttttt tttttccatc    1080

ttcagttgtc tctgatgcag cttatacgaa ggtaattgtt gttctgttaa ctgaatacca    1140

ctctgtaatt gcaaaaaaat ggcggctgtt ttgttgacat tctgaatgct tctaagtaaa    1200

tacaattttt tttattagta ctgttgtcct tttcataggt ctgaaagttt tcttctcaag    1260

gggaagctag tcttttgctt ttgcccattt tgggtcacat ggattattag tgtgtatctt    1320

catatagttg gaaaaatctt ttgtccacac accctgcata ttgtggtagg ggtaacattt    1380
```

```
tcatctacag ttgaagaatt ctccaaaatt gtgatcagtt ggataagaga tactctactt   1440

agcaaagcaa ggagtgatca attctgtcac accatgggat tattagatca aacagtctga   1500

aagtctgtcc ttgaaggact aatagaaaag tatgttctgc tccttacctg aggactcctt   1560

taactgccat tactgtgtaa tgacagttat attttgcagt ttcccctact aaagacctga   1620

gaatgtatcc ccaaaagcgt gagcttaaaa tacaagattg ctgtactatt tgttgacctt   1680

agtcccagcg aaggctatca tgagaagctg gctgtaatgc ctttgccctt ctatctaaat   1740

acggattgct caggaaactt gactgtttaa aggtatattt aattagttga gccagctttt   1800

aaaattatgc cacatttaaa atgaagggta tattttccta tattgtggtt tgtcccttta   1860

taaatcagat acaaggaaag cggataaact ttgcatatta gtaccagttg tccaagccat   1920

ttgctttttc tttataaagc ccgaactcat tcattaatca tgtttaatct gcttagttta   1980

gggaacaatt tggcaatttt gtgggttttc tttttttctt tttctttttt tttttttttt   2040

gagattatca ttctcttaaa gtgccagtgt tttaaaatag cgttcttgta attttccgcg   2100

cttttgtgat ggagtgctgt tatatcattt tgacttgggt tctttacagt tgcctttgtt   2160

ctgtaatttg aggaggaata ctgaacatga gtcctggatg atactaataa actaataatt   2220

gcagaggttt taaaaaaaaa aaaaaaaaaa aaaaaa                              2256
```

<210> SEQ ID NO 27
<211> LENGTH: 215
<212> TYPE: PRT
<213> ORGANISM: Rattus norvegicus

<400> SEQUENCE: 27

```
Met Gly Lys Gly Asp Pro Lys Lys Pro Arg Gly Lys Met Ser Ser Tyr
1               5                   10                  15

Ala Phe Phe Val Gln Thr Cys Arg Glu Glu His Lys Lys Lys His Pro
            20                  25                  30

Asp Ala Ser Val Asn Phe Ser Glu Phe Ser Lys Lys Cys Ser Glu Arg
        35                  40                  45

Trp Lys Thr Met Ser Ala Lys Glu Lys Gly Lys Phe Glu Asp Met Ala
    50                  55                  60

Lys Ala Asp Lys Ala Arg Tyr Glu Arg Glu Met Lys Thr Tyr Ile Pro
65                  70                  75                  80

Pro Lys Gly Glu Thr Lys Lys Lys Phe Lys Asp Pro Asn Ala Pro Lys
                85                  90                  95

Arg Pro Pro Ser Ala Phe Phe Leu Phe Cys Ser Glu Tyr Arg Pro Lys
            100                 105                 110

Ile Lys Gly Glu His Pro Gly Leu Ser Ile Gly Asp Val Ala Lys Lys
        115                 120                 125

Leu Gly Glu Met Trp Asn Asn Thr Ala Ala Asp Asp Lys Gln Pro Tyr
    130                 135                 140

Glu Lys Lys Ala Ala Lys Leu Lys Glu Lys Tyr Glu Lys Asp Ile Ala
145                 150                 155                 160

Ala Tyr Arg Ala Lys Gly Lys Pro Asp Ala Ala Lys Lys Gly Val Val
                165                 170                 175

Lys Ala Glu Lys Ser Lys Lys Lys Lys Glu Glu Glu Asp Asp Glu Glu
            180                 185                 190

Asp Glu Glu Asp Glu Glu Glu Glu Glu Glu Glu Glu Asp Glu Asp Glu
        195                 200                 205

Glu Glu Asp Asp Asp Asp Glu
```

210 215

<210> SEQ ID NO 28
<211> LENGTH: 2358
<212> TYPE: DNA
<213> ORGANISM: Homo sapiens

<400> SEQUENCE: 28
aaactcacac aacaactctt ccccgctgag aggagacagc cagtgcgact ccaccctcca 60
gctcgacggc agccgccccg gccgacagcc ccgagacgac agcccggcgc gtcccggtcc 120
ccacctccga ccaccgccag cgctccaggc cccgccgctc cccgctcgcc gccaccgcgc 180
cctccgctcc gcccgcagtg ccaaccatga ccgccgccag tatgggcccc gtccgcgtcg 240
ccttcgtggt cctcctcgcc ctctgcagcc ggccggccgt cggccagaac tgcagcgggc 300
cgtgccggtg cccggacgag ccggcgccgc gctgcccggc gggcgtgagc ctcgtgctgg 360
acggctgcgg ctgctgccgc gtctgcgcca agcagctggg cgagctgtgc accgagcgcg 420
acccctgcga cccgcacaag ggcctcttct gtgacttcgg ctccccggcc aaccgcaaga 480
tcggcgtgtg caccgccaaa gatggtgctc cctgcatctt cggtggtacg gtgtaccgca 540
gcggagagtc cttccagagc agctgcaagt accagtgcac gtgcctggac ggggcggtgg 600
gctgcatgcc cctgtgcagc atggacgttc gtctgcccag ccctgactgc cccttcccga 660
ggagggtcaa gctgcccggg aaatgctgcg aggagtgggt gtgtgacgag cccaaggacc 720
aaaccgtggt tgggcctgcc ctcgcggctt accgactgga agacacgttt ggcccagacc 780
caactatgat tagagccaac tgcctggtcc agaccacaga gtggagcgcc tgttccaaga 840
cctgtgggat gggcatctcc acccgggtta ccaatgacaa cgcctcctgc aggctagaga 900
agcagagccg cctgtgcatg gtcaggcctt gcgaagctga cctggaagag aacattaaga 960
agggcaaaaa gtgcatccgt actcccaaaa tctccaagcc tatcaagttt gagctttctg 1020
gctgcaccag catgaagaca taccgagcta aattctgtgg agtatgtacc gacggccgat 1080
gctgcacccc ccacagaacc accaccctgc cggtggagtt caagtgccct gacggcgagg 1140
tcatgaagaa gaacatgatg ttcatcaaga cctgtgcctg ccattacaac tgtcccggag 1200
acaatgacat ctttgaatcg ctgtactaca ggaagatgta cggagacatg gcatgaagcc 1260
agagagtgag agacattaac tcattagact ggaacttgaa ctgattcaca tctcattttt 1320
ccgtaaaaat gatttcagta gcacaagtta tttaaatctg tttttctaac tgggggaaaa 1380
gattcccacc caattcaaaa cattgtgcca tgtcaaacaa atagtctatc aaccccagac 1440
actggtttga agaatgttaa gacttgacag tggaactaca ttagtacaca gcaccagaat 1500
gtatattaag gtgtggcttt aggagcagtg ggagggtacc agcagaaagg ttagtatcat 1560
cagatagcat cttatacgag taatatgcct gctatttgaa gtgtaattga gaaggaaaat 1620
tttagcgtgc tcactgacct gcctgtagcc ccagtgacag ctaggatgtg cattctccag 1680
ccatcaagag actgagtcaa gttgttcctt aagtcagaac agcagactca gctctgacat 1740
tctgattcga atgacactgt tcaggaatcg gaatcctgtc gattagactg gacagcttgt 1800
ggcaagtgaa tttgcctgta acaagccaga ttttttaaaa tttatattgt aaatattgtg 1860
tgtgtgtgtg tgtgtgtata tatatatata tgtacagtta tctaagttaa tttaaagttg 1920
tttgtgcctt tttatttttg tttttaatgc tttgatattt caatgttagc ctcaatttct 1980
gaacaccata ggtagaatgt aaagcttgtc tgatcgttca aagcatgaaa tggatactta 2040
tatggaaatt ctgctcagat agaatgacag tccgtcaaaa cagattgttt gcaaagggga 2100

```
ggcatcagtg tccttggcag gctgatttct aggtaggaaa tgtggtagcc tcacttttaa   2160

tgaacaaatg gcctttatta aaaactgagt gactctatat agctgatcag tttttttcacc   2220

tggaagcatt tgtttctact ttgatatgac tgtttttcgg acagtttatt tgttgagagt   2280

gtgaccaaaa gttacatgtt tgcacctttc tagttgaaaa taaagtgtat atttttttcta   2340

taaaaaaaaa aaaaaaaa                                                  2358


<210> SEQ ID NO 29
<211> LENGTH: 349
<212> TYPE: PRT
<213> ORGANISM: Homo sapiens

<400> SEQUENCE: 29

Met Thr Ala Ala Ser Met Gly Pro Val Arg Val Ala Phe Val Val Leu
1               5                   10                  15

Leu Ala Leu Cys Ser Arg Pro Ala Val Gly Gln Asn Cys Ser Gly Pro
            20                  25                  30

Cys Arg Cys Pro Asp Glu Pro Ala Pro Arg Cys Pro Ala Gly Val Ser
        35                  40                  45

Leu Val Leu Asp Gly Cys Gly Cys Cys Arg Val Cys Ala Lys Gln Leu
    50                  55                  60

Gly Glu Leu Cys Thr Glu Arg Asp Pro Cys Asp Pro His Lys Gly Leu
65                  70                  75                  80

Phe Cys Asp Phe Gly Ser Pro Ala Asn Arg Lys Ile Gly Val Cys Thr
                85                  90                  95

Ala Lys Asp Gly Ala Pro Cys Ile Phe Gly Gly Thr Val Tyr Arg Ser
            100                 105                 110

Gly Glu Ser Phe Gln Ser Ser Cys Lys Tyr Gln Cys Thr Cys Leu Asp
        115                 120                 125

Gly Ala Val Gly Cys Met Pro Leu Cys Ser Met Asp Val Arg Leu Pro
    130                 135                 140

Ser Pro Asp Cys Pro Phe Pro Arg Arg Val Lys Leu Pro Gly Lys Cys
145                 150                 155                 160

Cys Glu Glu Trp Val Cys Asp Glu Pro Lys Asp Gln Thr Val Val Gly
                165                 170                 175

Pro Ala Leu Ala Ala Tyr Arg Leu Glu Asp Thr Phe Gly Pro Asp Pro
            180                 185                 190

Thr Met Ile Arg Ala Asn Cys Leu Val Gln Thr Thr Glu Trp Ser Ala
        195                 200                 205

Cys Ser Lys Thr Cys Gly Met Gly Ile Ser Thr Arg Val Thr Asn Asp
    210                 215                 220

Asn Ala Ser Cys Arg Leu Glu Lys Gln Ser Arg Leu Cys Met Val Arg
225                 230                 235                 240

Pro Cys Glu Ala Asp Leu Glu Glu Asn Ile Lys Lys Gly Lys Lys Cys
                245                 250                 255

Ile Arg Thr Pro Lys Ile Ser Lys Pro Ile Lys Phe Glu Leu Ser Gly
            260                 265                 270

Cys Thr Ser Met Lys Thr Tyr Arg Ala Lys Phe Cys Gly Val Cys Thr
        275                 280                 285

Asp Gly Arg Cys Cys Thr Pro His Arg Thr Thr Thr Leu Pro Val Glu
    290                 295                 300

Phe Lys Cys Pro Asp Gly Glu Val Met Lys Lys Asn Met Met Phe Ile
305                 310                 315                 320
```

-continued

```
Lys Thr Cys Ala Cys His Tyr Asn Cys Pro Gly Asp Asn Asp Ile Phe
                325                 330                 335

Glu Ser Leu Tyr Tyr Arg Lys Met Tyr Gly Asp Met Ala
            340                 345
```

<210> SEQ ID NO 30
<211> LENGTH: 2418
<212> TYPE: DNA
<213> ORGANISM: Mus musculus

<400> SEQUENCE: 30

```
agttctttgg cgagccggct cccgggagcg tataaaagcc agcgccgccc gcctagtctc     60

acacagctct tctctccaag aagactcagc cagatccact ccagctccga ccccaggaga    120

ccgacctcct ccagacggca gcagccccag cccagccgac aaccccagac gccaccgcct    180

ggagcgtcca gacaccaacc tccgcccctg tccgaatcca ggctccggcc gcgcctctcg    240

tcgcctctgc accctgctgt gcatcctcct accgcgtccc gatcatgctc gcctccgtcg    300

caggtcccat cagcctcgcc ttggtgctcc tcgctctctg cacccggcct gctatgggcc    360

aggactgcag cgcgcaatgt cagtgcgcag ccgaagcagc gccgcactgc cccgccggcg    420

tgagcctggt gctggacggc tgcggctgct gccgcgtctg cgccaagcag ctgggagaac    480

tgtgtacgga gcgtgacccc tgcgacccac acaagggcct cttctgcgat ttcggctccc    540

ccgccaaccg caagatcgga gtgtgcactg ccaaagatgg tgcaccctgt gtcttcggtg    600

ggtcggtgta ccgcagcggt gagtccttcc aaagcagctg caaataccaa tgcacttgcc    660

tggatggggc cgtgggctgc gtgcccctgt gcagcatgga cgtgcgcctg cccagccctg    720

actgcccctt cccgagaagg gtcaagctgc ctgggaaatg ctgcgaggag tgggtgtgtg    780

acgagcccaa ggaccgcaca gcagttggcc ctgccctagc tgcctaccga ctggaagaca    840

catttggccc agacccaact atgatgcgag ccaactgcct ggtccagacc acagagtgga    900

gcgcctgttc taagacctgt gggatgggca tctccacccg agttaccaat gacaatacct    960

tctgcagact ggagaagcag agccgcctct gcatggtcag gccctgcgaa gctgacctgg   1020

aggaaaacat taagaagggc aaaaagtgca tccggacacc taaaatcgcc aagcctgtca   1080

agtttgagct ttctggctgc accagtgtga agacatacag ggctaagttc tgcggggtgt   1140

gcacagacgg ccgctgctgc acaccgcaca gaaccaccac tctgccagtg gagttcaaat   1200

gccccgatgg cgagatcatg aaaaagaata tgatgttcat caagacctgt gcctgccatt   1260

acaactgtcc tggggacaat gacatctttg agtccctgta ctacaggaag atgtacggag   1320

acatggcgta aagccaggaa gtaagggaca cgaactcatt agactataac ttgaactgag   1380

ttgcatctca ttttcttctg taaaaacaat tacagtagca cattaattta aatctgtgtt   1440

tttaactacc gtgggaggaa ctatcccacc aaagtgagaa cgttatgtca tggccataca   1500

agtagtctgt caacctcaga cactggtttc gagacagttt acacttgaca gttgttcatt   1560

agcgcacagt gccagaatgc acactgaggt gagtctcctg gaacagtgga gatgccagga   1620

gaaagaaaga caggtactag ctgaggttat tttaaaagca gcagtgtgcc tactttttgg   1680

agtgtaaccg gggagggaaa ttatagcatg cttgcagaca gacctgctct agcgagagct   1740

gagcatgtgt cctccactag atgaggctga gtccagctgt tctttaagaa cagcagtttc   1800

agctctgacc attctgattc cagtgacact tgtcaggagt cagagccttg tctgttagac   1860

tggacagctt gtggcaagta agtttgcctg taacaagcca gatttttatt gatattgtaa   1920

atattgtgga tatatatata tatatatata tatatatttg tacagttatc taagttaatt   1980
```

```
taaagtcatt tgtttttgtt ttaagtgctt ttgggatttt aaactgatag cctcaaactc   2040

caaacaccat aggtaggaca cgaagcttat ctgtgattca aaacaaagga gatactgcag   2100

tgggaattgt gacctgagtg actctctgtc agaacaaatg ctgtgcaggt gataaagcta   2160

tgtattggaa gtcagatttc tagtaggaaa tgtggtcaaa tccctgttgg tgaacaaatg   2220

gcctttatta agaaatggct ggctcagggt aaggtccgat tcctaccagg aagtgcttgc   2280

tgcttctttg attatgactg gtttggggtg gggggcagtt tatttgttga gagtgtgacc   2340

aaaagttaca tgtttgcacc tttctagttg aaaataaagt atatatatat tttttatatg   2400

aaaaaaaaaa aaaaaaaa                                                 2418
```

<210> SEQ ID NO 31
<211> LENGTH: 348
<212> TYPE: PRT
<213> ORGANISM: Mus musculus

<400> SEQUENCE: 31

```
Met Leu Ala Ser Val Ala Gly Pro Ile Ser Leu Ala Leu Val Leu Leu
1               5                   10                  15

Ala Leu Cys Thr Arg Pro Ala Met Gly Gln Asp Cys Ser Ala Gln Cys
            20                  25                  30

Gln Cys Ala Ala Glu Ala Ala Pro His Cys Pro Ala Gly Val Ser Leu
        35                  40                  45

Val Leu Asp Gly Cys Gly Cys Cys Arg Val Cys Ala Lys Gln Leu Gly
    50                  55                  60

Glu Leu Cys Thr Glu Arg Asp Pro Cys Asp Pro His Lys Gly Leu Phe
65                  70                  75                  80

Cys Asp Phe Gly Ser Pro Ala Asn Arg Lys Ile Gly Val Cys Thr Ala
                85                  90                  95

Lys Asp Gly Ala Pro Cys Val Phe Gly Gly Ser Val Tyr Arg Ser Gly
            100                 105                 110

Glu Ser Phe Gln Ser Ser Cys Lys Tyr Gln Cys Thr Cys Leu Asp Gly
        115                 120                 125

Ala Val Gly Cys Val Pro Leu Cys Ser Met Asp Val Arg Leu Pro Ser
    130                 135                 140

Pro Asp Cys Pro Phe Pro Arg Arg Val Lys Leu Pro Gly Lys Cys Cys
145                 150                 155                 160

Glu Glu Trp Val Cys Asp Glu Pro Lys Asp Arg Thr Ala Val Gly Pro
                165                 170                 175

Ala Leu Ala Ala Tyr Arg Leu Glu Asp Thr Phe Gly Pro Asp Pro Thr
            180                 185                 190

Met Met Arg Ala Asn Cys Leu Val Gln Thr Thr Glu Trp Ser Ala Cys
        195                 200                 205

Ser Lys Thr Cys Gly Met Gly Ile Ser Thr Arg Val Thr Asn Asp Asn
    210                 215                 220

Thr Phe Cys Arg Leu Glu Lys Gln Ser Arg Leu Cys Met Val Arg Pro
225                 230                 235                 240

Cys Glu Ala Asp Leu Glu Glu Asn Ile Lys Lys Gly Lys Lys Cys Ile
                245                 250                 255

Arg Thr Pro Lys Ile Ala Lys Pro Val Lys Phe Glu Leu Ser Gly Cys
            260                 265                 270

Thr Ser Val Lys Thr Tyr Arg Ala Lys Phe Cys Gly Val Cys Thr Asp
        275                 280                 285
```

```
Gly Arg Cys Cys Thr Pro His Arg Thr Thr Thr Leu Pro Val Glu Phe
    290                 295                 300

Lys Cys Pro Asp Gly Glu Ile Met Lys Lys Asn Met Met Phe Ile Lys
305                 310                 315                 320

Thr Cys Ala Cys His Tyr Asn Cys Pro Gly Asp Asn Asp Ile Phe Glu
                325                 330                 335

Ser Leu Tyr Tyr Arg Lys Met Tyr Gly Asp Met Ala
            340                 345


<210> SEQ ID NO 32
<211> LENGTH: 2349
<212> TYPE: DNA
<213> ORGANISM: Rattus norvegicus

<400> SEQUENCE: 32

cacagctctt ctctccaaga agactcagcc agacccactc cagctccgac cctaggagac     60

cgacctcctc cagacggcag cagccccagc ccagtggaca accccaggag ccaccacctg    120

gagcgtccgg acaccaacct ccgccccgag accgagtcca ggctccggcc gcgcccctcg    180

tcgcctctgc accccgctgt gcgtcctcct gccgcgcccc gaccatgctc gcctccgtcg    240

cgggtcccgt tagcctcgcc ttggtgctcc tcctctgcac ccggcctgcc accggccagg    300

actgcagcgc gcagtgtcag tgcgcagctg aagcggcgcc gcgctgcccc gccggcgtga    360

gcctggtgct ggacggctgc ggctgctgcc gcgtctgcgc caagcagctg ggagaactgt    420

gcacggagcg tgatccctgc gacccacaca agggtctctt ctgcgacttc ggctcccccg    480

ccaaccgcaa gattggcgtg tgcactgcca aagatggtgc accctgtgtc ttcggtgggt    540

ccgtgtaccg cagcggcgag tccttccaaa gcagttgcaa ataccagtgc acttgcctgg    600

atggggccgt gggctgtgtg cccctgtgca gcatggacgt gcgcctgccc agccctgact    660

gcccctttccc gagaagggtc aagctgcccg ggaaatgctg tgaggagtgg gtgtgtgatg   720

agcccaagga ccgcacagtg gttggccctg ccctagctgc ctaccgactg gaagacacat    780

ttggccctga cccaactatg atgcgagcca actgcctggt ccagaccaca gagtggagcg    840

cctgttctaa gacctgtggg atgggcatct ccacccgggt taccaatgac aatacctttct   900

gcaggctgga gaagcagagt cgtctctgca tggtcaggcc ctgtgaagct gacctagagg    960

aaaacattaa gaagggcaaa aagtgcatcc ggacgcctaa aattgccaag cctgtcaagt   1020

ttgagctttc tggctgcacc agtgtgaaga cctaccgggc taagttctgt ggggtgtgca   1080

cggacggccg ctgctgcaca ccgcacagaa ccaccacact gccggtggag ttcaagtgcc   1140

ccgatggcga gatcatgaaa aagaacatga tgttcatcaa gacctgtgcc tgccattaca   1200

actgtcccgg ggacaatgac atctttgagt ccttgtacta caggaagatg tatggagaca   1260

tggcgtaaag ccagggagta agggacacga actcatttag actataactt gaactgagtt   1320

acatctcatt ttcttctgta aaaaaacaaa aaggattaca gtagcacatt aatttaaatc   1380

tgggttccta actgctgtgg gagaaaacac ccccaccgaag tgagaaccgt gtgtcattgt   1440

catgcaaata gcctgtcaat ctcagacact ggtttcgaga cagtttagac ttgacagttg   1500

ttcactagcg cacagtgaca gaacgcacac taaggtgagc ctcctggaag agtggagatg   1560

ccaggagaaa gacaggtact agctgaggtc attttaaaag cagcgatatg cctacttttt   1620

ggagtgtgac aggggaggga cattatagct tgcttgcaga cagacctgct ctagcaagag   1680

ctgggtgtgt gtcctccact cggtgaggct gaagccagct attctttcag taagaacagc   1740

agtttcagcg ctgacattct gattccagtg acactggtcg ggagtcagaa ccttgtctat   1800
```

```
tagactggac agcttgtggc aagtgaattt gccggtaaca agccagattt ttatggatct   1860

tgtaaatatt gtggataaat atatatattt gtacagttat ctaagttaat ttaaagacgt   1920

ttgtgcctat tgttcttgtt ttaagtgctt ttggaatttt taaactgata gcctcaaact   1980

ccaaacacca tcgataggac ataaagcttg tctgtgattc aaaacaaagg agatactgca   2040

gtggaaactg taacctgagt gactgtctgt cagaacatat ggtacgtaga cggtaaagca   2100

atggatcaga agtcagattt ctagtaggaa atgtaaaatc actgttggcg aacaaatggc   2160

ctttattaag aaatggcttg ctcagggtaa ctggtcagat ttccacgagg aagtgtttgc   2220

tgcttctttg actatgactg gtttgggagg cagtttattt gttgagagtg tgaccaaaag   2280

ttacatgttt gcacctttct agttgaaaat aaagtatata tattttttat atgaaaaaaa   2340

aaaaaaaaa                                                           2349
```

<210> SEQ ID NO 33
<211> LENGTH: 347
<212> TYPE: PRT
<213> ORGANISM: Rattus norvegicus

<400> SEQUENCE: 33

```
Met Leu Ala Ser Val Ala Gly Pro Val Ser Leu Ala Leu Val Leu Leu
1               5                   10                  15

Leu Cys Thr Arg Pro Ala Thr Gly Gln Asp Cys Ser Ala Gln Cys Gln
            20                  25                  30

Cys Ala Ala Glu Ala Ala Pro Arg Cys Pro Ala Gly Val Ser Leu Val
        35                  40                  45

Leu Asp Gly Cys Gly Cys Cys Arg Val Cys Ala Lys Gln Leu Gly Glu
    50                  55                  60

Leu Cys Thr Glu Arg Asp Pro Cys Asp Pro His Lys Gly Leu Phe Cys
65                  70                  75                  80

Asp Phe Gly Ser Pro Ala Asn Arg Lys Ile Gly Val Cys Thr Ala Lys
                85                  90                  95

Asp Gly Ala Pro Cys Val Phe Gly Gly Ser Val Tyr Arg Ser Gly Glu
            100                 105                 110

Ser Phe Gln Ser Ser Cys Lys Tyr Gln Cys Thr Cys Leu Asp Gly Ala
        115                 120                 125

Val Gly Cys Val Pro Leu Cys Ser Met Asp Val Arg Leu Pro Ser Pro
    130                 135                 140

Asp Cys Pro Phe Pro Arg Arg Val Lys Leu Pro Gly Lys Cys Cys Glu
145                 150                 155                 160

Glu Trp Val Cys Asp Glu Pro Lys Asp Arg Thr Val Val Gly Pro Ala
                165                 170                 175

Leu Ala Ala Tyr Arg Leu Glu Asp Thr Phe Gly Pro Asp Pro Thr Met
            180                 185                 190

Met Arg Ala Asn Cys Leu Val Gln Thr Thr Glu Trp Ser Ala Cys Ser
        195                 200                 205

Lys Thr Cys Gly Met Gly Ile Ser Thr Arg Val Thr Asn Asp Asn Thr
    210                 215                 220

Phe Cys Arg Leu Glu Lys Gln Ser Arg Leu Cys Met Val Arg Pro Cys
225                 230                 235                 240

Glu Ala Asp Leu Glu Glu Asn Ile Lys Lys Gly Lys Lys Cys Ile Arg
                245                 250                 255

Thr Pro Lys Ile Ala Lys Pro Val Lys Phe Glu Leu Ser Gly Cys Thr
            260                 265                 270
```

Ser Val Lys Thr Tyr Arg Ala Lys Phe Cys Gly Val Cys Thr Asp Gly
        275                 280                 285

Arg Cys Cys Thr Pro His Arg Thr Thr Thr Leu Pro Val Glu Phe Lys
    290                 295                 300

Cys Pro Asp Gly Glu Ile Met Lys Lys Asn Met Met Phe Ile Lys Thr
305                 310                 315                 320

Cys Ala Cys His Tyr Asn Cys Pro Gly Asp Asn Asp Ile Phe Glu Ser
                325                 330                 335

Leu Tyr Tyr Arg Lys Met Tyr Gly Asp Met Ala
            340                 345

<210> SEQ ID NO 34
<211> LENGTH: 1920
<212> TYPE: DNA
<213> ORGANISM: Homo sapiens

<400> SEQUENCE: 34
ggatccctgc cacggggtcc ccagctcccc catccaggcc ccccaggctg atgggcgctg 60
gcctgaggct ggcactgact aggttctgtc ctcacagcct ccacacagag cccatccgtc 120
ttccccttga cccgctgctg caaaaacatt ccctccaatg ccacctccgt gactctgggc 180
tgcctggcca cgggctactt cccggagccg gtgatggtga cctgggacac aggctccctc 240
aacgggacaa ctatgacctt accagccacc accctcacgc tctctggtca ctatgccacc 300
atcagcttgc tgaccgtctc gggtgcgtgg gccaagcaga tgttcacctg ccgtgtggca 360
cacactccat cgtccacaga ctgggtcgac aacaaaacct tcagcggtaa gagagggcca 420
agctcagaga ccacagttcc caggagtgcc aggctgaggg ctggcagagt gggcaggggt 480
tgagggggtg ggtgggctca aacgtgggaa cacccagcat gcctggggac ccgggccagg 540
acgtgggggc aagaggaggg cacacagagc tcagagaggc caacaaccct catgaccacc 600
agctctcccc cagtctgctc cagggacttc accccgccca ccgtgaagat cttacagtcg 660
tcctgcgacg gcggcgggca cttccccccg accatccagc tcctgtgcct cgtctctggg 720
tacaccccag ggactatcaa catcacctgg ctggaggacg ggcaggtcat ggacgtggac 780
ttgtccaccg cctctaccac gcaggagggt gagctggcct ccacacaaag cgagctcacc 840
ctcagccaga agcactggct gtcagaccgc acctacacct gccaggtcac ctatcaaggt 900
cacacctttg aggacagcac caagaagtgt gcaggtacgt tcccacctgc cctggtggcc 960
gccacggagg ccagagaaga ggggcgggtg ggcctcacac agccctccgg tgtaccacag 1020
attccaaccc gagaggggtg agcgcctacc taagccggcc cagcccgttc gacctgttca 1080
tccgcaagtc gcccacgatc acctgtctgg tggtggacct ggcacccagc aaggggaccg 1140
tgaacctgac ctggtcccgg gccagtggga agcctgtgaa ccactccacc agaaaggagg 1200
agaagcagcg caatggcacg ttaaccgtca cgtccaccct gccggtgggc acccgagact 1260
ggatcgaggg ggagacctac cagtgcaggg tgacccaccc ccacctgccc agggccctca 1320
tgcggtccac gaccaagacc agcggtgagc catgggcagg ccggggtcgt gggggaaggg 1380
agggagcgag tgagcggggc ccgggctgac cccacgtctg gccacaggcc cgcgtgctgc 1440
cccggaagtc tatgcgtttg cgacgccgga gtggccgggg agccgggaca agcgcaccct 1500
cgcctgcctg atccagaact tcatgcctga ggacatctcg gtgcagtggc tgcacaacga 1560
ggtgcagctc ccggacgccc ggcacagcac gacgcagccc cgcaagacca agggctccgg 1620
cttcttcgtc ttcagccgcc tggaggtgac cagggccgaa tgggagcaga aagatgagtt 1680
catctgccgt gcagtccatg aggcagcgag cccctcacag accgtccagc gagcggtgtc 1740
tgtaaatccc ggtaaatgac gtactcctgc ctccctccct cccagggctc catccagctg 1800
tgcagtgggg aggactggcc agaccttctg tccactgttg caatgacccc aggaagctac 1860
ccccaataaa ctgtgcctgc tcagagcccc agtacaccca ttcttgggag cgggcagggc 1920

<210> SEQ ID NO 35
<211> LENGTH: 2435
<212> TYPE: DNA
<213> ORGANISM: Mus musculus

<400> SEQUENCE: 35
gaatctaacc atctgtctcc tagactggaa tggggtcccc agagccctgc tcctgtcaca 60
gctgccctta accagttccc cacgctgcag gtatgtagtg atataaataa gtctaaccta 120
ggtccttcct ttctcacagc ctctatcagg aaccctcagc tctacccctt aaagccctgt 180
aaaggcactg cttccatgac cctaggctgc ctagtaaagg actacttccc taatcctgtg 240
actgtgacct ggtattcaga ctccctgaac atgagcactg tgaacttccc tgccctcggt 300
tctgaactca aggtcaccac cagccaagtg accagctggg gcaagtcagc caagaacttc 360
acatgccacg tgacacatcc tccatcattc aacgaaagta ggactatcct aggtaagtag 420
ggatgggctg acagttacac tgtgtattct ccccttggaga tggaacagtt tctgtctaat 480
caggaacttg tcacaatttc ctttcataga ggacttcata agagattttt tttctacttc 540
tatcatgttt agtgatccaa atagatttta aaaactggtt gagtgcatat tacttttagc 600
ctcagaagac atcacgcaca tttaagaggc atttaactat tgtaaattat tctgatgact 660
taaaaaatgc tcacgactga gtcgtatatt tttaaataaa ttttattagt ttagtttaaa 720
aaaagaaaag aaaattatta attttattaa aaaatctcct atatttaaaa aaaaaagaga 780
aaaaggcaga gctgggctgg ctacggttac cacaggaaca tggtcagagg aggaagggac 840
tcttatacaa cctatgacag gagaacggga gacccaacat actcgggggc ctaccttcag 900
agaacacaag gccagggcaa tactcacgag accagttgtt cgccctgccc ctagttcgac 960
ctgtcaacat cactgagccc accttggagc tactccattc atcctgcgac cccaatgcat 1020
tccactccac catccagctg tactgcttca tttatggcca catcctaaat gatgtctctg 1080
tcagctggct aatggacgat cgggagataa ctgatacact tgcacaaact gttctaatca 1140
aggaggaagg caaactagcc tctacctgca gtaaactcaa catcactgag cagcaatgga 1200
tgtctgaaag caccttcacc tgcaaggtca cctcccaagg cgtagactat ttggcccaca 1260
ctcggagatg cccaggtagg tctacactcg cctgatgccc agacctcaga gtccctgagg 1320
gaaaggcagg ttcacacagc ccttcctccc cgacagatca tgagccacgg ggtgtgatta 1380
cctacctgat cccacccagc cccctggacc tgtatcaaaa cggtgctccc aagcttacct 1440
gtctggtggt ggacctggaa agcgagaaga atgtcaatgt gacgtggaac caagagaaga 1500
agacttcagt ctcagcatcc cagtggtaca ctaagcacca caataacgcc acaactagta 1560
tcacctccat cctgcctgta gttgccaagg actggattga aggctacggc tatcagtgca 1620
tagtggacca ccctgatttt cccaagccca ttgtgcgttc catcaccaag accccaggtg 1680
agtacaggag gtggagagtg gccagccctt ctcatgttca gagaacatgg ttaactggtt 1740
aagtcatgtc gtcccacagg ccagcgctca gcccccgagg tatatgtgtt cccaccacca 1800
gaggaggaga gcgaggacaa acgcacactc acctgtttga tccagaactt cttccctgag 1860

```
gatatctctg tgcagtggct gggggatggc aaactgatct caaacagcca gcacagtacc   1920

acaacacccc tgaaatccaa tggctccaat caaggcttct tcatcttcag tcgcctagag   1980

gtcgccaaga cactctggac acagagaaaa cagttcacct gccaagtgat ccatgaggca   2040

cttcagaaac ccaggaaact ggagaaaaca atatccacaa gccttggtaa cacctccctc   2100

cgtccctcct aggcctccat gtagctgtgg tggggaaggt ggatgacaga catccgctca   2160

ctgttgtaac accaggaagc taccccaata aacactcagt gcctgattag agccctgggc   2220

gcccgttctt cggggaaggc agggttcatg ggcagaaata tctcggcctg aaagaaggga   2280

cacccaagag aaggacagga gtgaagcacg gctcacccat ctgtctctgt gttgaatatt   2340

taacacatag gcgtcacagg acttcagcag tggtccttca gcgtcccctg atccttcgct   2400

gctcttcact ggatatcatg cgcctgatct ctaga                              2435
```

<210> SEQ ID NO 36
<211> LENGTH: 447
<212> TYPE: PRT
<213> ORGANISM: Artificial Sequence
<220> FEATURE:
<223> OTHER INFORMATION: an artificially synthesized sequence

<400> SEQUENCE: 36

```
Glu Val Gln Leu Leu Glu Ser Gly Gly Gly Leu Val Gln Pro Gly Gly
1               5                   10                  15

Ser Leu Arg Leu Ser Cys Ala Ala Ser Gly Phe Thr Phe Ser Trp Tyr
            20                  25                  30

Asp Met Thr Trp Val Arg Gln Ala Pro Gly Lys Gly Leu Glu Trp Val
        35                  40                  45

Ser Ser Ile Ser Pro Ser Gly Gly Tyr Thr Lys Tyr Ala Asp Ser Val
    50                  55                  60

Lys Gly Arg Phe Thr Ile Ser Arg Asp Asn Ser Lys Asn Thr Leu Tyr
65                  70                  75                  80

Leu Gln Met Asn Ser Leu Arg Ala Glu Asp Thr Ala Val Tyr Tyr Cys
                85                  90                  95

Thr Thr Glu Phe Tyr Asp Tyr Leu Asp Val Trp Gly Lys Gly Thr Thr
            100                 105                 110

Val Thr Val Ser Ser Ala Ser Thr Lys Gly Pro Ser Val Phe Pro Leu
        115                 120                 125

Ala Pro Ser Ser Lys Ser Thr Ser Gly Gly Thr Ala Ala Leu Gly Cys
    130                 135                 140

Leu Val Lys Asp Tyr Phe Pro Glu Pro Val Thr Val Ser Trp Asn Ser
145                 150                 155                 160

Gly Ala Leu Thr Ser Gly Val His Thr Phe Pro Ala Val Leu Gln Ser
                165                 170                 175

Ser Gly Leu Tyr Ser Leu Ser Ser Val Val Thr Val Pro Ser Ser Ser
            180                 185                 190

Leu Gly Thr Gln Thr Tyr Ile Cys Asn Val Asn His Lys Pro Ser Asn
        195                 200                 205

Thr Lys Val Asp Lys Lys Val Glu Pro Lys Ser Cys Asp Lys Thr His
    210                 215                 220

Thr Cys Pro Pro Cys Pro Ala Pro Glu Leu Leu Gly Gly Pro Ser Val
225                 230                 235                 240

Phe Leu Phe Pro Pro Lys Pro Lys Asp Thr Leu Met Ile Ser Arg Thr
                245                 250                 255

Pro Glu Val Thr Cys Val Val Val Asp Val Ser His Glu Asp Pro Glu
```

260 265 270

Val Lys Phe Asn Trp Tyr Val Asp Gly Val Glu Val His Asn Ala Lys
275 280 285

Thr Lys Pro Arg Glu Glu Gln Tyr Asn Ser Thr Tyr Arg Val Val Ser
290 295 300

Val Leu Thr Val Leu His Gln Asp Trp Leu Asn Gly Lys Glu Tyr Lys
305 310 315 320

Cys Lys Val Ser Asn Lys Ala Leu Pro Ala Pro Ile Glu Lys Thr Ile
325 330 335

Ser Lys Ala Lys Gly Gln Pro Arg Glu Pro Gln Val Tyr Thr Leu Pro
340 345 350

Pro Ser Arg Asp Glu Leu Thr Lys Asn Gln Val Ser Leu Thr Cys Leu
355 360 365

Val Lys Gly Phe Tyr Pro Ser Asp Ile Ala Val Glu Trp Glu Ser Asn
370 375 380

Gly Gln Pro Glu Asn Asn Tyr Lys Thr Thr Pro Pro Val Leu Asp Ser
385 390 395 400

Asp Gly Ser Phe Phe Leu Tyr Ser Lys Leu Thr Val Asp Lys Ser Arg
405 410 415

Trp Gln Gln Gly Asn Val Phe Ser Cys Ser Val Met His Glu Ala Leu
420 425 430

His Asn His Tyr Thr Gln Lys Ser Leu Ser Leu Ser Pro Gly Lys
435 440 445

<210> SEQ ID NO 37
<211> LENGTH: 217
<212> TYPE: PRT
<213> ORGANISM: Artificial Sequence
<220> FEATURE:
<223> OTHER INFORMATION: an artificially synthesized sequence

<400> SEQUENCE: 37

Asp Ile Gln Met Thr Gln Ser Pro Gly Thr Leu Ser Leu Ser Pro Gly
1 5 10 15

Glu Gly Ala Thr Leu Ser Cys Arg Ala Ser Gln Ser Val Ser Ser Thr
20 25 30

Tyr Leu Ala Trp Tyr Gln Gln Lys Pro Gly Gln Ala Pro Arg Leu Leu
35 40 45

Ile Tyr Glu Ala Ser Lys Arg Ala Thr Gly Thr Pro Ala Arg Phe Ser
50 55 60

Gly Ser Gly Ser Gly Thr Asp Phe Thr Leu Ser Ile Ser Ser Leu Glu
65 70 75 80

Pro Glu Asp Phe Ala Val Tyr Tyr Cys Gln His Arg His Asn Trp Pro
85 90 95

Pro Gln Trp Thr Phe Gly Gln Gly Thr Lys Val Glu Val Lys Arg Thr
100 105 110

Val Ala Ala Pro Ser Val Phe Ile Phe Pro Pro Ser Asp Glu Gln Leu
115 120 125

Lys Ser Gly Thr Ala Ser Val Val Cys Leu Leu Asn Asn Phe Tyr Pro
130 135 140

Arg Glu Ala Lys Val Gln Trp Lys Val Asp Asn Ala Leu Gln Ser Gly
145 150 155 160

Asn Ser Gln Glu Ser Val Thr Glu Gln Asp Ser Lys Asp Ser Thr Tyr
165 170 175

Ser Leu Ser Ser Thr Leu Thr Leu Ser Lys Ala Asp Tyr Glu Lys His

```
            180                 185                 190

Lys Val Tyr Ala Cys Glu Val Thr His Gln Gly Leu Ser Ser Pro Val
        195                 200                 205

Thr Lys Ser Phe Asn Arg Gly Glu Cys
    210                 215


<210> SEQ ID NO 38
<211> LENGTH: 119
<212> TYPE: PRT
<213> ORGANISM: Homo sapiens

<400> SEQUENCE: 38

Met Ser Arg Ser Val Ala Leu Ala Val Leu Ala Leu Leu Ser Leu Ser
1               5                   10                  15

Gly Leu Glu Ala Ile Gln Arg Thr Pro Lys Ile Gln Val Tyr Ser Arg
            20                  25                  30

His Pro Ala Glu Asn Gly Lys Ser Asn Phe Leu Asn Cys Tyr Val Ser
        35                  40                  45

Gly Phe His Pro Ser Asp Ile Glu Val Asp Leu Leu Lys Asn Gly Glu
    50                  55                  60

Arg Ile Glu Lys Val Glu His Ser Asp Leu Ser Phe Ser Lys Asp Trp
65                  70                  75                  80

Ser Phe Tyr Leu Leu Tyr Tyr Thr Glu Phe Thr Pro Thr Glu Lys Asp
                85                  90                  95

Glu Tyr Ala Cys Arg Val Asn His Val Thr Leu Ser Gln Pro Lys Ile
            100                 105                 110

Val Lys Trp Asp Arg Asp Met
        115


<210> SEQ ID NO 39
<211> LENGTH: 1125
<212> TYPE: DNA
<213> ORGANISM: Homo sapiens

<400> SEQUENCE: 39

atgtggttct tgacaactct gctcctttgg gttccagttg atgggcaagt ggacaccaca      60

aaggcagtga tcactttgca gcctccatgg gtcagcgtgt tccaagagga aaccgtaacc     120

ttgcactgtg aggtgctcca tctgcctggg agcagctcta cacagtggtt tctcaatggc     180

acagccactc agacctcgac ccccagctac agaatcacct ctgccagtgt caatgacagt     240

ggtgaataca ggtgccagag aggtctctca gggcgaagtg accccataca gctggaaatc     300

cacagaggct ggctactact gcaggtctcc agcagagtct tcacggaagg agaacctctg     360

gccttgaggt gtcatgcgtg gaaggataag ctggtgtaca atgtgcttta ctatcgaaat     420

ggcaaagcct ttaagttttt ccactggaat tctaacctca ccattctgaa aaccaacata     480

agtcacaatg gcacctacca ttgctcaggc atgggaaagc atcgctacac atcagcagga     540

atatctgtca ctgtgaaaga gctatttcca gctccagtgc tgaatgcatc tgtgacatcc     600

ccactcctgg aggggaatct ggtcaccctg agctgtgaaa caaagttgct cttgcagagg     660

cctggtttgc agctttactt ctccttctac atgggcagca agaccctgcg aggcaggaac     720

acatcctctg aataccaaat actaactgct agaagagaag actctgggtt atactggtgc     780

gaggctgcca cagaggatgg aaatgtcctt aagcgcagcc ctgagttgga gcttcaagtg     840

cttggcctcc agttaccaac tcctgtctgg tttcatgtcc ttttctatct ggcagtggga     900

ataatgtttt tagtgaacac tgttctctgg gtgacaatac gtaaagaact gaaaagaaag     960
```

aaaaagtggg atttagaaat ctctttggat tctggtcatg agaagaaggt aatttccagc 1020
cttcaagaag acagacattt agaagaagag ctgaaatgtc aggaacaaaa agaagaacag 1080
ctgcaggaag gggtgcaccg gaaggagccc caggggggcca cgtag 1125

<210> SEQ ID NO 40
<211> LENGTH: 374
<212> TYPE: PRT
<213> ORGANISM: Homo sapiens

<400> SEQUENCE: 40

Met Trp Phe Leu Thr Thr Leu Leu Leu Trp Val Pro Val Asp Gly Gln
1 5 10 15

Val Asp Thr Thr Lys Ala Val Ile Thr Leu Gln Pro Pro Trp Val Ser
20 25 30

Val Phe Gln Glu Glu Thr Val Thr Leu His Cys Glu Val Leu His Leu
35 40 45

Pro Gly Ser Ser Ser Thr Gln Trp Phe Leu Asn Gly Thr Ala Thr Gln
50 55 60

Thr Ser Thr Pro Ser Tyr Arg Ile Thr Ser Ala Ser Val Asn Asp Ser
65 70 75 80

Gly Glu Tyr Arg Cys Gln Arg Gly Leu Ser Gly Arg Ser Asp Pro Ile
85 90 95

Gln Leu Glu Ile His Arg Gly Trp Leu Leu Leu Gln Val Ser Ser Arg
100 105 110

Val Phe Thr Glu Gly Glu Pro Leu Ala Leu Arg Cys His Ala Trp Lys
115 120 125

Asp Lys Leu Val Tyr Asn Val Leu Tyr Tyr Arg Asn Gly Lys Ala Phe
130 135 140

Lys Phe Phe His Trp Asn Ser Asn Leu Thr Ile Leu Lys Thr Asn Ile
145 150 155 160

Ser His Asn Gly Thr Tyr His Cys Ser Gly Met Gly Lys His Arg Tyr
165 170 175

Thr Ser Ala Gly Ile Ser Val Thr Val Lys Glu Leu Phe Pro Ala Pro
180 185 190

Val Leu Asn Ala Ser Val Thr Ser Pro Leu Leu Glu Gly Asn Leu Val
195 200 205

Thr Leu Ser Cys Glu Thr Lys Leu Leu Leu Gln Arg Pro Gly Leu Gln
210 215 220

Leu Tyr Phe Ser Phe Tyr Met Gly Ser Lys Thr Leu Arg Gly Arg Asn
225 230 235 240

Thr Ser Ser Glu Tyr Gln Ile Leu Thr Ala Arg Arg Glu Asp Ser Gly
245 250 255

Leu Tyr Trp Cys Glu Ala Ala Thr Glu Asp Gly Asn Val Leu Lys Arg
260 265 270

Ser Pro Glu Leu Glu Leu Gln Val Leu Gly Leu Gln Leu Pro Thr Pro
275 280 285

Val Trp Phe His Val Leu Phe Tyr Leu Ala Val Gly Ile Met Phe Leu
290 295 300

Val Asn Thr Val Leu Trp Val Thr Ile Arg Lys Glu Leu Lys Arg Lys
305 310 315 320

Lys Lys Trp Asp Leu Glu Ile Ser Leu Asp Ser Gly His Glu Lys Lys
325 330 335

Val Ile Ser Ser Leu Gln Glu Asp Arg His Leu Glu Glu Glu Leu Lys 340 345 350

Cys Gln Glu Gln Lys Glu Glu Gln Leu Gln Glu Gly Val His Arg Lys
355 360 365

Glu Pro Gln Gly Ala Thr
370

<210> SEQ ID NO 41
<211> LENGTH: 951
<212> TYPE: DNA
<213> ORGANISM: Homo sapiens

<400> SEQUENCE: 41
atgactatgg agacccaaat gtctcagaat gtatgtccca gaaacctgtg gctgcttcaa 60
ccattgacag ttttgctgct gctggcttct gcagacagtc aagctgctcc cccaaaggct 120
gtgctgaaac ttgagccccc gtggatcaac gtgctccagg aggactctgt gactctgaca 180
tgccaggggg ctcgcagccc tgagagcgac tccattcagt ggttccacaa tgggaatctc 240
attcccaccc acacgcagcc cagctacagg ttcaaggcca acaacaatga cagcggggag 300
tacacgtgcc agactggcca gaccagcctc agcgaccctg tgcatctgac tgtgctttcc 360
gaatggctgg tgctccagac ccctcacctg gagttccagg agggagaaac catcatgctg 420
aggtgccaca gctggaagga caagcctctg gtcaaggtca cattcttcca gaatggaaaa 480
tcccagaaat tctcccattt ggatcccacc ttctccatcc cacaagcaaa ccacagtcac 540
agtggtgatt accactgcac aggaaacata ggctacacgc tgttctcatc caagcctgtg 600
accatcactg tccaagtgcc cagcatgggc agctcttcac caatgggggt cattgtggct 660
gtggtcattg cgactgctgt agcagccatt gttgctgctg tagtggcctt gatctactgc 720
aggaaaaagc ggatttcagc caattccact gatcctgtga aggctgccca atttgagcca 780
cctggacgtc aaatgattgc catcagaaag agacaacttg aagaaaccaa caatgactat 840
gaaacagctg acggcggcta catgactctg aaccccaggg cacctactga cgatgataaa 900
aacatctacc tgactcttcc tcccaacgac catgtcaaca gtaataacta a 951

<210> SEQ ID NO 42
<211> LENGTH: 316
<212> TYPE: PRT
<213> ORGANISM: Homo sapiens

<400> SEQUENCE: 42

Met Thr Met Glu Thr Gln Met Ser Gln Asn Val Cys Pro Arg Asn Leu
1 5 10 15

Trp Leu Leu Gln Pro Leu Thr Val Leu Leu Leu Leu Ala Ser Ala Asp
20 25 30

Ser Gln Ala Ala Pro Pro Lys Ala Val Leu Lys Leu Glu Pro Pro Trp
35 40 45

Ile Asn Val Leu Gln Glu Asp Ser Val Thr Leu Thr Cys Gln Gly Ala
50 55 60

Arg Ser Pro Glu Ser Asp Ser Ile Gln Trp Phe His Asn Gly Asn Leu
65 70 75 80

Ile Pro Thr His Thr Gln Pro Ser Tyr Arg Phe Lys Ala Asn Asn Asn
85 90 95

Asp Ser Gly Glu Tyr Thr Cys Gln Thr Gly Gln Thr Ser Leu Ser Asp
100 105 110

Pro Val His Leu Thr Val Leu Ser Glu Trp Leu Val Leu Gln Thr Pro
115 120 125

His Leu Glu Phe Gln Glu Gly Glu Thr Ile Met Leu Arg Cys His Ser
    130                 135                 140

Trp Lys Asp Lys Pro Leu Val Lys Val Thr Phe Phe Gln Asn Gly Lys
145                 150                 155                 160

Ser Gln Lys Phe Ser His Leu Asp Pro Thr Phe Ser Ile Pro Gln Ala
                165                 170                 175

Asn His Ser His Ser Gly Asp Tyr His Cys Thr Gly Asn Ile Gly Tyr
            180                 185                 190

Thr Leu Phe Ser Ser Lys Pro Val Thr Ile Thr Val Gln Val Pro Ser
        195                 200                 205

Met Gly Ser Ser Ser Pro Met Gly Val Ile Val Ala Val Val Ile Ala
    210                 215                 220

Thr Ala Val Ala Ala Ile Val Ala Ala Val Val Ala Leu Ile Tyr Cys
225                 230                 235                 240

Arg Lys Lys Arg Ile Ser Ala Asn Ser Thr Asp Pro Val Lys Ala Ala
                245                 250                 255

Gln Phe Glu Pro Pro Gly Arg Gln Met Ile Ala Ile Arg Lys Arg Gln
            260                 265                 270

Leu Glu Glu Thr Asn Asn Asp Tyr Glu Thr Ala Asp Gly Gly Tyr Met
        275                 280                 285

Thr Leu Asn Pro Arg Ala Pro Thr Asp Asp Asp Lys Asn Ile Tyr Leu
    290                 295                 300

Thr Leu Pro Pro Asn Asp His Val Asn Ser Asn Asn
305                 310                 315

<210> SEQ ID NO 43
<211> LENGTH: 876
<212> TYPE: DNA
<213> ORGANISM: Homo sapiens

<400> SEQUENCE: 43
atgggaatcc tgtcattctt acctgtcctt gccactgaga gtgactgggc tgactgcaag 60
tccccccagc cttggggtca tatgcttctg tggacagctg tgctattcct ggctcctgtt 120
gctgggacac ctgcagctcc cccaaaggct gtgctgaaac tcgagcccca gtggatcaac 180
gtgctccagg aggactctgt gactctgaca tgccggggga ctcacagccc tgagagcgac 240
tccattcagt ggttccacaa tgggaatctc attcccaccc acacgcagcc cagctacagg 300
ttcaaggcca acaacaatga cagcggggag tacacgtgcc agactggcca gaccagcctc 360
agcgaccctg tgcatctgac tgtgctttct gagtggctgg tgctccagac ccctcacctg 420
gagttccagg agggagaaac catcgtgctg aggtgccaca gctggaagga caagcctctg 480
gtcaaggtca cattcttcca gaatggaaaa tccaagaaat tttcccgttc ggatcccaac 540
ttctccatcc cacaagcaaa ccacagtcac agtggtgatt accactgcac aggaaacata 600
ggctacacgc tgtactcatc caagcctgtg accatcactg tccaagctcc cagctcttca 660
ccgatgggga tcattgtggc tgtggtcact gggattgctg tagcggccat tgttgctgct 720
gtagtggcct tgatctactg caggaaaaag cggatttcag ccaatcccac taatcctgat 780
gaggctgaca aagttggggc tgagaacaca atcacctatt cacttctcat gcacccggat 840
gctctggaag agcctgatga ccagaaccgt atttag 876

<210> SEQ ID NO 44
<211> LENGTH: 291
<212> TYPE: PRT

<213> ORGANISM: Homo sapiens

<400> SEQUENCE: 44

```
Met Gly Ile Leu Ser Phe Leu Pro Val Leu Ala Thr Glu Ser Asp Trp
1               5                   10                  15

Ala Asp Cys Lys Ser Pro Gln Pro Trp Gly His Met Leu Leu Trp Thr
            20                  25                  30

Ala Val Leu Phe Leu Ala Pro Val Ala Gly Thr Pro Ala Ala Pro Pro
        35                  40                  45

Lys Ala Val Leu Lys Leu Glu Pro Gln Trp Ile Asn Val Leu Gln Glu
    50                  55                  60

Asp Ser Val Thr Leu Thr Cys Arg Gly Thr His Ser Pro Glu Ser Asp
65                  70                  75                  80

Ser Ile Gln Trp Phe His Asn Gly Asn Leu Ile Pro Thr His Thr Gln
                85                  90                  95

Pro Ser Tyr Arg Phe Lys Ala Asn Asn Asn Asp Ser Gly Glu Tyr Thr
            100                 105                 110

Cys Gln Thr Gly Gln Thr Ser Leu Ser Asp Pro Val His Leu Thr Val
        115                 120                 125

Leu Ser Glu Trp Leu Val Leu Gln Thr Pro His Leu Glu Phe Gln Glu
    130                 135                 140

Gly Glu Thr Ile Val Leu Arg Cys His Ser Trp Lys Asp Lys Pro Leu
145                 150                 155                 160

Val Lys Val Thr Phe Phe Gln Asn Gly Lys Ser Lys Lys Phe Ser Arg
                165                 170                 175

Ser Asp Pro Asn Phe Ser Ile Pro Gln Ala Asn His Ser His Ser Gly
            180                 185                 190

Asp Tyr His Cys Thr Gly Asn Ile Gly Tyr Thr Leu Tyr Ser Ser Lys
        195                 200                 205

Pro Val Thr Ile Thr Val Gln Ala Pro Ser Ser Ser Pro Met Gly Ile
    210                 215                 220

Ile Val Ala Val Val Thr Gly Ile Ala Val Ala Ala Ile Val Ala Ala
225                 230                 235                 240

Val Val Ala Leu Ile Tyr Cys Arg Lys Lys Arg Ile Ser Ala Asn Pro
                245                 250                 255

Thr Asn Pro Asp Glu Ala Asp Lys Val Gly Ala Glu Asn Thr Ile Thr
            260                 265                 270

Tyr Ser Leu Leu Met His Pro Asp Ala Leu Glu Glu Pro Asp Asp Gln
        275                 280                 285

Asn Arg Ile
    290
```

<210> SEQ ID NO 45
<211> LENGTH: 765
<212> TYPE: DNA
<213> ORGANISM: Homo sapiens

<400> SEQUENCE: 45

```
atgtggcagc tgctcctccc aactgctctg ctacttctag tttcagctgg catgcggact     60

gaagatctcc caaaggctgt ggtgttcctg gagcctcaat ggtacagggt gctcgagaag    120

gacagtgtga ctctgaagtg ccagggagcc tactcccctg aggacaattc cacacagtgg    180

tttcacaatg agagcctcat ctcaagccag gcctcgagct acttcattga cgctgccaca    240

gttgacgaca gtggagagta caggtgccag acaaacctct ccaccctcag tgacccggtg    300
```

```
cagctagaag tccatatcgg ctggctgttg ctccaggccc ctcggtgggt gttcaaggag    360

gaagacccta ttcacctgag gtgtcacagc tggaagaaca ctgctctgca taaggtcaca    420

tatttacaga atggcaaagg caggaagtat tttcatcata attctgactt ctacattcca    480

aaagccacac tcaaagacag cggctcctac ttctgcaggg ggcttgttgg gagtaaaaat    540

gtgtcttcag agactgtgaa catcaccatc actcaaggtt tgtcagtgtc aaccatctca    600

tcattctttc cacctgggta ccaagtctct ttctgcttgg tgatggtact cctttttgca    660

gtggacacag gactatattt ctctgtgaag acaaacattc gaagctcaac aagagactgg    720

aaggaccata aatttaaatg gagaaaggac cctcaagaca aatga                    765


<210> SEQ ID NO 46
<211> LENGTH: 254
<212> TYPE: PRT
<213> ORGANISM: Homo sapiens

<400> SEQUENCE: 46

Met Trp Gln Leu Leu Leu Pro Thr Ala Leu Leu Leu Leu Val Ser Ala
1               5                   10                  15

Gly Met Arg Thr Glu Asp Leu Pro Lys Ala Val Val Phe Leu Glu Pro
            20                  25                  30

Gln Trp Tyr Arg Val Leu Glu Lys Asp Ser Val Thr Leu Lys Cys Gln
        35                  40                  45

Gly Ala Tyr Ser Pro Glu Asp Asn Ser Thr Gln Trp Phe His Asn Glu
    50                  55                  60

Ser Leu Ile Ser Ser Gln Ala Ser Ser Tyr Phe Ile Asp Ala Ala Thr
65                  70                  75                  80

Val Asp Asp Ser Gly Glu Tyr Arg Cys Gln Thr Asn Leu Ser Thr Leu
                85                  90                  95

Ser Asp Pro Val Gln Leu Glu Val His Ile Gly Trp Leu Leu Leu Gln
            100                 105                 110

Ala Pro Arg Trp Val Phe Lys Glu Glu Asp Pro Ile His Leu Arg Cys
        115                 120                 125

His Ser Trp Lys Asn Thr Ala Leu His Lys Val Thr Tyr Leu Gln Asn
    130                 135                 140

Gly Lys Gly Arg Lys Tyr Phe His His Asn Ser Asp Phe Tyr Ile Pro
145                 150                 155                 160

Lys Ala Thr Leu Lys Asp Ser Gly Ser Tyr Phe Cys Arg Gly Leu Val
                165                 170                 175

Gly Ser Lys Asn Val Ser Ser Glu Thr Val Asn Ile Thr Ile Thr Gln
            180                 185                 190

Gly Leu Ser Val Ser Thr Ile Ser Ser Phe Phe Pro Pro Gly Tyr Gln
        195                 200                 205

Val Ser Phe Cys Leu Val Met Val Leu Leu Phe Ala Val Asp Thr Gly
    210                 215                 220

Leu Tyr Phe Ser Val Lys Thr Asn Ile Arg Ser Ser Thr Arg Asp Trp
225                 230                 235                 240

Lys Asp His Lys Phe Lys Trp Arg Lys Asp Pro Gln Asp Lys
                245                 250


<210> SEQ ID NO 47
<211> LENGTH: 702
<212> TYPE: DNA
<213> ORGANISM: Homo sapiens

<400> SEQUENCE: 47
```

```
atgtggcagc tgctcctccc aactgctctg ctacttctag tttcagctgg catgcggact      60

gaagatctcc caaaggctgt ggtgttcctg gagcctcaat ggtacagcgt gcttgagaag     120

gacagtgtga ctctgaagtg ccagggagcc tactcccctg aggacaattc cacacagtgg     180

tttcacaatg agagcctcat ctcaagccag gcctcgagct acttcattga cgctgccaca     240

gtcaacgaca gtggagagta caggtgccag acaaacctct ccaccctcag tgacccggtg     300

cagctagaag tccatatcgg ctggctgttg ctccaggccc ctcggtgggt gttcaaggag     360

gaagacccta ttcacctgag gtgtcacagc tggaagaaca ctgctctgca taaggtcaca     420

tatttacaga atggcaaaga caggaagtat tttcatcata attctgactt ccacattcca     480

aaagccacac tcaaagatag cggctcctac ttctgcaggg ggcttgttgg gagtaaaaat     540

gtgtcttcag agactgtgaa catcaccatc actcaaggtt tggcagtgtc aaccatctca     600

tcattctctc cacctgggta ccaagtctct ttctgcttgg tgatggtact cctttttgca     660

gtggacacag gactatattt ctctgtgaag acaaacattt ga                       702
```

```
<210> SEQ ID NO 48
<211> LENGTH: 233
<212> TYPE: PRT
<213> ORGANISM: Homo sapiens

<400> SEQUENCE: 48

Met Trp Gln Leu Leu Leu Pro Thr Ala Leu Leu Leu Leu Val Ser Ala
1               5                   10                  15

Gly Met Arg Thr Glu Asp Leu Pro Lys Ala Val Val Phe Leu Glu Pro
            20                  25                  30

Gln Trp Tyr Ser Val Leu Glu Lys Asp Ser Val Thr Leu Lys Cys Gln
        35                  40                  45

Gly Ala Tyr Ser Pro Glu Asp Asn Ser Thr Gln Trp Phe His Asn Glu
    50                  55                  60

Ser Leu Ile Ser Ser Gln Ala Ser Ser Tyr Phe Ile Asp Ala Ala Thr
65                  70                  75                  80

Val Asn Asp Ser Gly Glu Tyr Arg Cys Gln Thr Asn Leu Ser Thr Leu
                85                  90                  95

Ser Asp Pro Val Gln Leu Glu Val His Ile Gly Trp Leu Leu Leu Gln
            100                 105                 110

Ala Pro Arg Trp Val Phe Lys Glu Glu Asp Pro Ile His Leu Arg Cys
        115                 120                 125

His Ser Trp Lys Asn Thr Ala Leu His Lys Val Thr Tyr Leu Gln Asn
    130                 135                 140

Gly Lys Asp Arg Lys Tyr Phe His His Asn Ser Asp Phe His Ile Pro
145                 150                 155                 160

Lys Ala Thr Leu Lys Asp Ser Gly Ser Tyr Phe Cys Arg Gly Leu Val
                165                 170                 175

Gly Ser Lys Asn Val Ser Ser Glu Thr Val Asn Ile Thr Ile Thr Gln
            180                 185                 190

Gly Leu Ala Val Ser Thr Ile Ser Ser Phe Ser Pro Pro Gly Tyr Gln
        195                 200                 205

Val Ser Phe Cys Leu Val Met Val Leu Leu Phe Ala Val Asp Thr Gly
    210                 215                 220

Leu Tyr Phe Ser Val Lys Thr Asn Ile
225                 230
```

<210> SEQ ID NO 49
<211> LENGTH: 330
<212> TYPE: PRT
<213> ORGANISM: Homo sapiens

<400> SEQUENCE: 49

```
Ala Ser Thr Lys Gly Pro Ser Val Phe Pro Leu Ala Pro Ser Ser Lys
1               5                   10                  15

Ser Thr Ser Gly Gly Thr Ala Ala Leu Gly Cys Leu Val Lys Asp Tyr
            20                  25                  30

Phe Pro Glu Pro Val Thr Val Ser Trp Asn Ser Gly Ala Leu Thr Ser
        35                  40                  45

Gly Val His Thr Phe Pro Ala Val Leu Gln Ser Ser Gly Leu Tyr Ser
    50                  55                  60

Leu Ser Ser Val Val Thr Val Pro Ser Ser Ser Leu Gly Thr Gln Thr
65                  70                  75                  80

Tyr Ile Cys Asn Val Asn His Lys Pro Ser Asn Thr Lys Val Asp Lys
                85                  90                  95

Lys Val Glu Pro Lys Ser Cys Asp Lys Thr His Thr Cys Pro Pro Cys
            100                 105                 110

Pro Ala Pro Glu Leu Leu Gly Gly Pro Ser Val Phe Leu Phe Pro Pro
        115                 120                 125

Lys Pro Lys Asp Thr Leu Met Ile Ser Arg Thr Pro Glu Val Thr Cys
    130                 135                 140

Val Val Val Asp Val Ser His Glu Asp Pro Glu Val Lys Phe Asn Trp
145                 150                 155                 160

Tyr Val Asp Gly Val Glu Val His Asn Ala Lys Thr Lys Pro Arg Glu
                165                 170                 175

Glu Gln Tyr Asn Ser Thr Tyr Arg Val Val Ser Val Leu Thr Val Leu
            180                 185                 190

His Gln Asp Trp Leu Asn Gly Lys Glu Tyr Lys Cys Lys Val Ser Asn
        195                 200                 205

Lys Ala Leu Pro Ala Pro Ile Glu Lys Thr Ile Ser Lys Ala Lys Gly
    210                 215                 220

Gln Pro Arg Glu Pro Gln Val Tyr Thr Leu Pro Pro Ser Arg Asp Glu
225                 230                 235                 240

Leu Thr Lys Asn Gln Val Ser Leu Thr Cys Leu Val Lys Gly Phe Tyr
                245                 250                 255

Pro Ser Asp Ile Ala Val Glu Trp Glu Ser Asn Gly Gln Pro Glu Asn
            260                 265                 270

Asn Tyr Lys Thr Thr Pro Pro Val Leu Asp Ser Asp Gly Ser Phe Phe
        275                 280                 285

Leu Tyr Ser Lys Leu Thr Val Asp Lys Ser Arg Trp Gln Gln Gly Asn
    290                 295                 300

Val Phe Ser Cys Ser Val Met His Glu Ala Leu His Asn His Tyr Thr
305                 310                 315                 320

Gln Lys Ser Leu Ser Leu Ser Pro Gly Lys
                325                 330
```

<210> SEQ ID NO 50
<211> LENGTH: 326
<212> TYPE: PRT
<213> ORGANISM: Homo sapiens

<400> SEQUENCE: 50

```
Ala Ser Thr Lys Gly Pro Ser Val Phe Pro Leu Ala Pro Cys Ser Arg
```

-continued

```
1               5                   10                  15

Ser Thr Ser Glu Ser Thr Ala Ala Leu Gly Cys Leu Val Lys Asp Tyr
            20                  25                  30

Phe Pro Glu Pro Val Thr Val Ser Trp Asn Ser Gly Ala Leu Thr Ser
        35                  40                  45

Gly Val His Thr Phe Pro Ala Val Leu Gln Ser Ser Gly Leu Tyr Ser
    50                  55                  60

Leu Ser Ser Val Val Thr Val Pro Ser Ser Asn Phe Gly Thr Gln Thr
65                  70                  75                  80

Tyr Thr Cys Asn Val Asp His Lys Pro Ser Asn Thr Lys Val Asp Lys
                85                  90                  95

Thr Val Glu Arg Lys Cys Cys Val Glu Cys Pro Pro Cys Pro Ala Pro
            100                 105                 110

Pro Val Ala Gly Pro Ser Val Phe Leu Phe Pro Pro Lys Pro Lys Asp
        115                 120                 125

Thr Leu Met Ile Ser Arg Thr Pro Glu Val Thr Cys Val Val Val Asp
    130                 135                 140

Val Ser His Glu Asp Pro Glu Val Gln Phe Asn Trp Tyr Val Asp Gly
145                 150                 155                 160

Val Glu Val His Asn Ala Lys Thr Lys Pro Arg Glu Glu Gln Phe Asn
                165                 170                 175

Ser Thr Phe Arg Val Val Ser Val Leu Thr Val Val His Gln Asp Trp
            180                 185                 190

Leu Asn Gly Lys Glu Tyr Lys Cys Lys Val Ser Asn Lys Gly Leu Pro
        195                 200                 205

Ala Pro Ile Glu Lys Thr Ile Ser Lys Thr Lys Gly Gln Pro Arg Glu
    210                 215                 220

Pro Gln Val Tyr Thr Leu Pro Pro Ser Arg Glu Glu Met Thr Lys Asn
225                 230                 235                 240

Gln Val Ser Leu Thr Cys Leu Val Lys Gly Phe Tyr Pro Ser Asp Ile
                245                 250                 255

Ala Val Glu Trp Glu Ser Asn Gly Gln Pro Glu Asn Asn Tyr Lys Thr
            260                 265                 270

Thr Pro Pro Met Leu Asp Ser Asp Gly Ser Phe Phe Leu Tyr Ser Lys
        275                 280                 285

Leu Thr Val Asp Lys Ser Arg Trp Gln Gln Gly Asn Val Phe Ser Cys
    290                 295                 300

Ser Val Met His Glu Ala Leu His Asn His Tyr Thr Gln Lys Ser Leu
305                 310                 315                 320

Ser Leu Ser Pro Gly Lys
                325


<210> SEQ ID NO 51
<211> LENGTH: 377
<212> TYPE: PRT
<213> ORGANISM: Homo sapiens

<400> SEQUENCE: 51

Ala Ser Thr Lys Gly Pro Ser Val Phe Pro Leu Ala Pro Cys Ser Arg
1               5                   10                  15

Ser Thr Ser Gly Gly Thr Ala Ala Leu Gly Cys Leu Val Lys Asp Tyr
            20                  25                  30

Phe Pro Glu Pro Val Thr Val Ser Trp Asn Ser Gly Ala Leu Thr Ser
        35                  40                  45
```

```
Gly Val His Thr Phe Pro Ala Val Leu Gln Ser Ser Gly Leu Tyr Ser
    50                  55                  60

Leu Ser Ser Val Val Thr Val Pro Ser Ser Ser Leu Gly Thr Gln Thr
65                  70                  75                  80

Tyr Thr Cys Asn Val Asn His Lys Pro Ser Asn Thr Lys Val Asp Lys
                85                  90                  95

Arg Val Glu Leu Lys Thr Pro Leu Gly Asp Thr Thr His Thr Cys Pro
            100                 105                 110

Arg Cys Pro Glu Pro Lys Ser Cys Asp Thr Pro Pro Pro Cys Pro Arg
        115                 120                 125

Cys Pro Glu Pro Lys Ser Cys Asp Thr Pro Pro Pro Cys Pro Arg Cys
    130                 135                 140

Pro Glu Pro Lys Ser Cys Asp Thr Pro Pro Pro Cys Pro Arg Cys Pro
145                 150                 155                 160

Ala Pro Glu Leu Leu Gly Gly Pro Ser Val Phe Leu Phe Pro Pro Lys
                165                 170                 175

Pro Lys Asp Thr Leu Met Ile Ser Arg Thr Pro Glu Val Thr Cys Val
            180                 185                 190

Val Val Asp Val Ser His Glu Asp Pro Glu Val Gln Phe Lys Trp Tyr
        195                 200                 205

Val Asp Gly Val Glu Val His Asn Ala Lys Thr Lys Pro Arg Glu Glu
    210                 215                 220

Gln Tyr Asn Ser Thr Phe Arg Val Val Ser Val Leu Thr Val Leu His
225                 230                 235                 240

Gln Asp Trp Leu Asn Gly Lys Glu Tyr Lys Cys Lys Val Ser Asn Lys
                245                 250                 255

Ala Leu Pro Ala Pro Ile Glu Lys Thr Ile Ser Lys Thr Lys Gly Gln
            260                 265                 270

Pro Arg Glu Pro Gln Val Tyr Thr Leu Pro Pro Ser Arg Glu Glu Met
        275                 280                 285

Thr Lys Asn Gln Val Ser Leu Thr Cys Leu Val Lys Gly Phe Tyr Pro
    290                 295                 300

Ser Asp Ile Ala Val Glu Trp Glu Ser Ser Gly Gln Pro Glu Asn Asn
305                 310                 315                 320

Tyr Asn Thr Thr Pro Pro Met Leu Asp Ser Asp Gly Ser Phe Phe Leu
                325                 330                 335

Tyr Ser Lys Leu Thr Val Asp Lys Ser Arg Trp Gln Gln Gly Asn Ile
            340                 345                 350

Phe Ser Cys Ser Val Met His Glu Ala Leu His Asn Arg Phe Thr Gln
        355                 360                 365

Lys Ser Leu Ser Leu Ser Pro Gly Lys
    370                 375


<210> SEQ ID NO 52
<211> LENGTH: 327
<212> TYPE: PRT
<213> ORGANISM: Homo sapiens

<400> SEQUENCE: 52

Ala Ser Thr Lys Gly Pro Ser Val Phe Pro Leu Ala Pro Cys Ser Arg
1               5                   10                  15

Ser Thr Ser Glu Ser Thr Ala Ala Leu Gly Cys Leu Val Lys Asp Tyr
            20                  25                  30

Phe Pro Glu Pro Val Thr Val Ser Trp Asn Ser Gly Ala Leu Thr Ser
        35                  40                  45
```

Gly Val His Thr Phe Pro Ala Val Leu Gln Ser Ser Gly Leu Tyr Ser
50 55 60

Leu Ser Ser Val Val Thr Val Pro Ser Ser Ser Leu Gly Thr Lys Thr
65 70 75 80

Tyr Thr Cys Asn Val Asp His Lys Pro Ser Asn Thr Lys Val Asp Lys
85 90 95

Arg Val Glu Ser Lys Tyr Gly Pro Pro Cys Pro Ser Cys Pro Ala Pro
100 105 110

Glu Phe Leu Gly Gly Pro Ser Val Phe Leu Phe Pro Pro Lys Pro Lys
115 120 125

Asp Thr Leu Met Ile Ser Arg Thr Pro Glu Val Thr Cys Val Val Val
130 135 140

Asp Val Ser Gln Glu Asp Pro Glu Val Gln Phe Asn Trp Tyr Val Asp
145 150 155 160

Gly Val Glu Val His Asn Ala Lys Thr Lys Pro Arg Glu Glu Gln Phe
165 170 175

Asn Ser Thr Tyr Arg Val Val Ser Val Leu Thr Val Leu His Gln Asp
180 185 190

Trp Leu Asn Gly Lys Glu Tyr Lys Cys Lys Val Ser Asn Lys Gly Leu
195 200 205

Pro Ser Ser Ile Glu Lys Thr Ile Ser Lys Ala Lys Gly Gln Pro Arg
210 215 220

Glu Pro Gln Val Tyr Thr Leu Pro Pro Ser Gln Glu Glu Met Thr Lys
225 230 235 240

Asn Gln Val Ser Leu Thr Cys Leu Val Lys Gly Phe Tyr Pro Ser Asp
245 250 255

Ile Ala Val Glu Trp Glu Ser Asn Gly Gln Pro Glu Asn Asn Tyr Lys
260 265 270

Thr Thr Pro Pro Val Leu Asp Ser Asp Gly Ser Phe Phe Leu Tyr Ser
275 280 285

Arg Leu Thr Val Asp Lys Ser Arg Trp Gln Glu Gly Asn Val Phe Ser
290 295 300

Cys Ser Val Met His Glu Ala Leu His Asn His Tyr Thr Gln Lys Ser
305 310 315 320

Leu Ser Leu Ser Leu Gly Lys
325

<210> SEQ ID NO 53
<211> LENGTH: 328
<212> TYPE: PRT
<213> ORGANISM: Artificial sequence
<220> FEATURE:
<223> OTHER INFORMATION: an artificially synthesized sequence

<400> SEQUENCE: 53

Ala Ser Thr Lys Gly Pro Ser Val Phe Pro Leu Ala Pro Ser Ser Lys
1 5 10 15

Ser Thr Ser Gly Gly Thr Ala Ala Leu Gly Cys Leu Val Lys Asp Tyr
20 25 30

Phe Pro Glu Pro Val Thr Val Ser Trp Asn Ser Gly Ala Leu Thr Ser
35 40 45

Gly Val His Thr Phe Pro Ala Val Leu Gln Ser Ser Gly Leu Tyr Ser
50 55 60

Leu Ser Ser Val Val Thr Val Pro Ser Ser Ser Leu Gly Thr Gln Thr
65 70 75 80

-continued

```
Tyr Ile Cys Asn Val Asn His Lys Pro Ser Asn Thr Lys Val Asp Lys
                85                  90                  95

Lys Val Glu Pro Lys Ser Cys Asp Lys Thr His Thr Cys Pro Pro Cys
            100                 105                 110

Pro Ala Pro Glu Leu Leu Gly Gly Pro Ser Val Phe Leu Phe Pro Pro
        115                 120                 125

Lys Pro Lys Asp Thr Leu Met Ile Ser Arg Thr Pro Glu Val Thr Cys
    130                 135                 140

Val Val Val Asp Val Ser His Glu Asp Pro Glu Val Lys Phe Asn Trp
145                 150                 155                 160

Tyr Val Asp Gly Val Glu Val His Asn Ala Lys Thr Lys Pro Arg Glu
                165                 170                 175

Glu Gln Tyr Asn Ser Thr Tyr Arg Val Val Ser Val Leu Thr Val Leu
            180                 185                 190

His Gln Asp Trp Leu Asn Gly Lys Glu Tyr Lys Cys Lys Val Ser Asn
        195                 200                 205

Lys Ala Leu Pro Ala Pro Ile Glu Lys Thr Ile Ser Lys Ala Lys Gly
    210                 215                 220

Gln Pro Arg Glu Pro Gln Val Tyr Thr Leu Pro Pro Ser Arg Asp Glu
225                 230                 235                 240

Leu Thr Lys Asn Gln Val Ser Leu Thr Cys Leu Val Lys Gly Phe Tyr
                245                 250                 255

Pro Ser Asp Ile Ala Val Glu Trp Glu Ser Asn Gly Gln Pro Glu Asn
            260                 265                 270

Asn Tyr Lys Thr Thr Pro Pro Val Leu Asp Ser Asp Gly Ser Phe Phe
        275                 280                 285

Leu Tyr Ser Lys Leu Thr Val Asp Lys Ser Arg Trp Gln Gln Gly Asn
    290                 295                 300

Val Phe Ser Cys Ser Val Met His Glu Ala Leu His Asn His Tyr Thr
305                 310                 315                 320

Gln Lys Ser Leu Ser Leu Ser Pro
                325


<210> SEQ ID NO 54
<211> LENGTH: 107
<212> TYPE: PRT
<213> ORGANISM: Artificial sequence
<220> FEATURE:
<223> OTHER INFORMATION: an artificially synthesized sequence

<400> SEQUENCE: 54

Arg Thr Val Ala Ala Pro Ser Val Phe Ile Phe Pro Pro Ser Asp Glu
1               5                   10                  15

Gln Leu Lys Ser Gly Thr Ala Ser Val Val Cys Leu Leu Asn Asn Phe
            20                  25                  30

Tyr Pro Arg Glu Ala Lys Val Gln Trp Lys Val Asp Asn Ala Leu Gln
        35                  40                  45

Ser Gly Asn Ser Gln Glu Ser Val Thr Glu Gln Asp Ser Lys Asp Ser
    50                  55                  60

Thr Tyr Ser Leu Ser Ser Thr Leu Thr Leu Ser Lys Ala Asp Tyr Glu
65                  70                  75                  80

Lys His Lys Val Tyr Ala Cys Glu Val Thr His Gln Gly Leu Ser Ser
                85                  90                  95

Pro Val Thr Lys Ser Phe Asn Arg Gly Glu Cys
            100                 105
```

<210> SEQ ID NO 55
<211> LENGTH: 443
<212> TYPE: PRT
<213> ORGANISM: Artificial sequence
<220> FEATURE:
<223> OTHER INFORMATION: an artificially synthesized sequence

<400> SEQUENCE: 55

```
Gln Val Gln Leu Val Gln Ser Gly Ala Glu Val Lys Lys Pro Gly Ala
1               5                   10                  15

Ser Val Lys Val Ser Cys Lys Ala Ser Gly Tyr Thr Phe Thr Asp Tyr
            20                  25                  30

Glu Met His Trp Val Arg Gln Ala Pro Gly Gln Gly Leu Glu Trp Met
        35                  40                  45

Gly Ala Leu Asp Pro Lys Thr Gly Asp Thr Ala Tyr Ser Gln Lys Phe
    50                  55                  60

Lys Gly Arg Val Thr Leu Thr Ala Asp Lys Ser Thr Ser Thr Ala Tyr
65                  70                  75                  80

Met Glu Leu Ser Ser Leu Thr Ser Glu Asp Thr Ala Val Tyr Tyr Cys
                85                  90                  95

Thr Arg Phe Tyr Ser Tyr Thr Tyr Trp Gly Gln Gly Thr Leu Val Thr
            100                 105                 110

Val Ser Ser Ala Ser Thr Lys Gly Pro Ser Val Phe Pro Leu Ala Pro
        115                 120                 125

Ser Ser Lys Ser Thr Ser Gly Gly Thr Ala Ala Leu Gly Cys Leu Val
    130                 135                 140

Lys Asp Tyr Phe Pro Glu Pro Val Thr Val Ser Trp Asn Ser Gly Ala
145                 150                 155                 160

Leu Thr Ser Gly Val His Thr Phe Pro Ala Val Leu Gln Ser Ser Gly
                165                 170                 175

Leu Tyr Ser Leu Ser Ser Val Val Thr Val Pro Ser Ser Ser Leu Gly
            180                 185                 190

Thr Gln Thr Tyr Ile Cys Asn Val Asn His Lys Pro Ser Asn Thr Lys
        195                 200                 205

Val Asp Lys Lys Val Glu Pro Lys Ser Cys Asp Lys Thr His Thr Cys
    210                 215                 220

Pro Pro Cys Pro Ala Pro Glu Leu Leu Gly Gly Pro Ser Val Phe Leu
225                 230                 235                 240

Phe Pro Pro Lys Pro Lys Asp Thr Leu Met Ile Ser Arg Thr Pro Glu
                245                 250                 255

Val Thr Cys Val Val Val Asp Val Ser His Glu Asp Pro Glu Val Lys
            260                 265                 270

Phe Asn Trp Tyr Val Asp Gly Val Glu Val His Asn Ala Lys Thr Lys
        275                 280                 285

Pro Arg Glu Glu Gln Tyr Asn Ser Thr Tyr Arg Val Val Ser Val Leu
    290                 295                 300

Thr Val Leu His Gln Asp Trp Leu Asn Gly Lys Glu Tyr Lys Cys Lys
305                 310                 315                 320

Val Ser Asn Lys Ala Leu Pro Ala Pro Ile Glu Lys Thr Ile Ser Lys
                325                 330                 335

Ala Lys Gly Gln Pro Arg Glu Pro Gln Val Tyr Thr Leu Pro Pro Ser
            340                 345                 350

Arg Asp Glu Leu Thr Lys Asn Gln Val Ser Leu Thr Cys Leu Val Lys
        355                 360                 365
```

Gly Phe Tyr Pro Ser Asp Ile Ala Val Glu Trp Glu Ser Asn Gly Gln
    370                 375                 380

Pro Glu Asn Asn Tyr Lys Thr Thr Pro Pro Val Leu Asp Ser Asp Gly
385                 390                 395                 400

Ser Phe Phe Leu Tyr Ser Lys Leu Thr Val Asp Lys Ser Arg Trp Gln
                405                 410                 415

Gln Gly Asn Val Phe Ser Cys Ser Val Met His Glu Ala Leu His Asn
            420                 425                 430

His Tyr Thr Gln Lys Ser Leu Ser Leu Ser Pro
        435                 440

<210> SEQ ID NO 56
<211> LENGTH: 219
<212> TYPE: PRT
<213> ORGANISM: Artificial sequence
<220> FEATURE:
<223> OTHER INFORMATION: an artificially synthesized sequence

<400> SEQUENCE: 56

Asp Val Val Met Thr Gln Ser Pro Leu Ser Leu Pro Val Thr Pro Gly
1               5                   10                  15

Glu Pro Ala Ser Ile Ser Cys Arg Ser Ser Gln Ser Leu Val His Ser
            20                  25                  30

Asn Arg Asn Thr Tyr Leu His Trp Tyr Leu Gln Lys Pro Gly Gln Ser
        35                  40                  45

Pro Gln Leu Leu Ile Tyr Lys Val Ser Asn Arg Phe Ser Gly Val Pro
    50                  55                  60

Asp Arg Phe Ser Gly Ser Gly Ser Gly Thr Asp Phe Thr Leu Lys Ile
65                  70                  75                  80

Ser Arg Val Glu Ala Glu Asp Val Gly Val Tyr Tyr Cys Ser Gln Asn
                85                  90                  95

Thr His Val Pro Pro Thr Phe Gly Gln Gly Thr Lys Leu Glu Ile Lys
            100                 105                 110

Arg Thr Val Ala Ala Pro Ser Val Phe Ile Phe Pro Pro Ser Asp Glu
        115                 120                 125

Gln Leu Lys Ser Gly Thr Ala Ser Val Val Cys Leu Leu Asn Asn Phe
    130                 135                 140

Tyr Pro Arg Glu Ala Lys Val Gln Trp Lys Val Asp Asn Ala Leu Gln
145                 150                 155                 160

Ser Gly Asn Ser Gln Glu Ser Val Thr Glu Gln Asp Ser Lys Asp Ser
                165                 170                 175

Thr Tyr Ser Leu Ser Ser Thr Leu Thr Leu Ser Lys Ala Asp Tyr Glu
            180                 185                 190

Lys His Lys Val Tyr Ala Cys Glu Val Thr His Gln Gly Leu Ser Ser
        195                 200                 205

Pro Val Thr Lys Ser Phe Asn Arg Gly Glu Cys
    210                 215

<210> SEQ ID NO 57
<211> LENGTH: 214
<212> TYPE: PRT
<213> ORGANISM: Artificial sequence
<220> FEATURE:
<223> OTHER INFORMATION: an artificially synthesized sequence

<400> SEQUENCE: 57

Glu Thr Thr Leu Thr Gln Ser Pro Ala Phe Met Ser Ala Thr Pro Gly

-continued

```
1               5                   10                  15

Asp Lys Val Asn Ile Ser Cys Lys Ala Ser Gln Asp Ile Asp Asp Asp
            20                  25                  30

Met Asn Trp Tyr Gln Gln Lys Pro Gly Glu Ala Ala Ile Phe Ile Ile
        35                  40                  45

Gln Glu Ala Thr Thr Leu Val Pro Gly Ile Ser Pro Arg Phe Ser Gly
    50                  55                  60

Ser Gly Tyr Gly Thr Asp Phe Thr Leu Thr Ile Asn Asn Ile Glu Ser
65                  70                  75                  80

Glu Asp Ala Ala Tyr Tyr Phe Cys Leu Gln His Asp Asn Phe Pro Tyr
                85                  90                  95

Thr Phe Gly Gln Gly Thr Lys Leu Glu Ile Lys Arg Thr Val Ala Ala
            100                 105                 110

Pro Ser Val Phe Ile Phe Pro Pro Ser Asp Glu Gln Leu Lys Ser Gly
        115                 120                 125

Thr Ala Ser Val Val Cys Leu Leu Asn Asn Phe Tyr Pro Arg Glu Ala
    130                 135                 140

Lys Val Gln Trp Lys Val Asp Asn Ala Leu Gln Ser Gly Asn Ser Gln
145                 150                 155                 160

Glu Ser Val Thr Glu Gln Asp Ser Lys Asp Ser Thr Tyr Ser Leu Ser
                165                 170                 175

Ser Thr Leu Thr Leu Ser Lys Ala Asp Tyr Glu Lys His Lys Val Tyr
            180                 185                 190

Ala Cys Glu Val Thr His Gln Gly Leu Ser Ser Pro Val Thr Lys Ser
        195                 200                 205

Phe Asn Arg Gly Glu Cys
    210
```

<210> SEQ ID NO 58
<211> LENGTH: 107
<212> TYPE: PRT
<213> ORGANISM: Artificial sequence
<220> FEATURE:
<223> OTHER INFORMATION: an artificially synthesized sequence

<400> SEQUENCE: 58

```
Asp Ile Gln Met Thr Gln Ser Pro Ser Ser Leu Ser Ala Ser Val Gly
1               5                   10                  15

Asp Arg Val Thr Ile Thr Cys Arg Ala Ser Gln Ser Ile Ser Ser Tyr
            20                  25                  30

Leu Asn Trp Tyr Gln Gln Lys Pro Gly Lys Ala Pro Lys Leu Leu Ile
        35                  40                  45

Tyr Ala Ala Ser Ser Leu Gln Ser Gly Val Pro Ser Arg Phe Ser Gly
    50                  55                  60

Ser Gly Ser Gly Thr Asp Phe Thr Leu Thr Ile Ser Ser Leu Gln Pro
65                  70                  75                  80

Glu Asp Phe Ala Thr Tyr Tyr Cys Gln Gln Ser Tyr Ser Thr Pro Phe
                85                  90                  95

Thr Phe Gly Pro Gly Thr Lys Val Asp Ile Lys
            100                 105
```

<210> SEQ ID NO 59
<211> LENGTH: 112
<212> TYPE: PRT
<213> ORGANISM: Artificial sequence
<220> FEATURE:
<223> OTHER INFORMATION: an artificially synthesized sequence

<400> SEQUENCE: 59

Asp Ile Val Met Thr Gln Ser Pro Leu Ser Leu Pro Val Thr Pro Gly
1 5 10 15

Glu Pro Ala Ser Ile Ser Cys Arg Ser Ser Gln Ser Leu Leu His Ser
20 25 30

Asn Gly Asp Asn Tyr Leu Asp Trp Tyr Leu Gln Lys Pro Gly Gln Ser
35 40 45

Pro Gln Leu Leu Ile Tyr Leu Gly Ser Asn Arg Ala Ser Gly Val Pro
50 55 60

Asp Arg Phe Ser Gly Ser Gly Ser Gly Thr Asp Phe Thr Leu Lys Ile
65 70 75 80

Ser Arg Val Glu Ala Glu Asp Val Gly Val Tyr Tyr Cys Met Gln Val
85 90 95

Leu Arg Asn Pro Leu Thr Phe Gly Gly Gly Thr Lys Val Glu Ile Gln
100 105 110

<210> SEQ ID NO 60
<211> LENGTH: 107
<212> TYPE: PRT
<213> ORGANISM: Artificial sequence
<220> FEATURE:
<223> OTHER INFORMATION: an artificially synthesized sequence

<400> SEQUENCE: 60

Glu Ile Val Met Thr Gln Ser Pro Ala Thr Leu Ser Leu Ser Pro Gly
1 5 10 15

Glu Arg Ala Thr Leu Ser Cys Arg Ala Ser Gln Ser Val Ser Ser Tyr
20 25 30

Leu Ala Trp Tyr Gln Gln Lys Pro Gly Gln Ala Pro Arg Leu Leu Ile
35 40 45

Tyr Asp Ala Ser Asn Arg Ala Thr Gly Ile Pro Ala Arg Phe Ser Gly
50 55 60

Ser Gly Ser Gly Thr Asp Phe Thr Leu Thr Ile Ser Ser Leu Glu Pro
65 70 75 80

Glu Asp Phe Ala Val Tyr Tyr Cys Gln Gln Arg Ser Asn Trp Pro Pro
85 90 95

Thr Phe Gly Gln Gly Thr Lys Val Glu Ile Lys
100 105

<210> SEQ ID NO 61
<211> LENGTH: 112
<212> TYPE: PRT
<213> ORGANISM: Artificial sequence
<220> FEATURE:
<223> OTHER INFORMATION: an artificially synthesized sequence

<400> SEQUENCE: 61

Asp Ile Val Met Thr Gln Ser Pro Glu Ser Leu Val Leu Ser Leu Gly
1 5 10 15

Gly Thr Ala Thr Ile Asn Cys Arg Ser Ser Gln Ser Val Leu Tyr Ser
20 25 30

Ser Asn Asn Lys Asn Tyr Leu Thr Trp Tyr Gln Gln Lys Pro Gly Gln
35 40 45

Pro Pro Thr Leu Leu Phe Ser Trp Ala Ser Ile Arg Asp Ser Gly Val
50 55 60

Pro Asp Arg Phe Ser Ala Ser Gly Ser Gly Thr Glu Phe Thr Leu Thr
65 70 75 80

```
Ile Ser Asp Leu Gln Ala Glu Asp Ala Ala Val Tyr Tyr Cys Gln Gln
                85                  90                  95

Tyr Tyr Arg Ala Pro Ser Phe Gly Gln Gly Thr Lys Leu Gln Ile Lys
            100                 105                 110


<210> SEQ ID NO 62
<211> LENGTH: 107
<212> TYPE: PRT
<213> ORGANISM: Artificial sequence
<220> FEATURE:
<223> OTHER INFORMATION: an artificially synthesized sequence

<400> SEQUENCE: 62

Glu Thr Thr Leu Thr Gln Ser Pro Ala Phe Met Ser Ala Thr Pro Gly
1               5                   10                  15

Asp Lys Val Asn Ile Ser Cys Lys Ala Ser Gln Asp Ile Asp Asp Asp
            20                  25                  30

Met Asn Trp Tyr Gln Gln Lys Pro Gly Glu Ala Ala Ile Phe Ile Ile
        35                  40                  45

Gln Glu Ala Thr Thr Leu Val Pro Gly Ile Ser Pro Arg Phe Ser Gly
    50                  55                  60

Ser Gly Tyr Gly Thr Asp Phe Thr Leu Thr Ile Asn Asn Ile Glu Ser
65                  70                  75                  80

Glu Asp Ala Ala Tyr Tyr Phe Cys Leu Gln His Asp Asn Phe Pro Tyr
                85                  90                  95

Thr Phe Gly Gln Gly Thr Lys Leu Glu Ile Lys
            100                 105


<210> SEQ ID NO 63
<211> LENGTH: 128
<212> TYPE: PRT
<213> ORGANISM: Artificial sequence
<220> FEATURE:
<223> OTHER INFORMATION: an artificially synthesized sequence

<400> SEQUENCE: 63

Gln Val Gln Leu Val Gln Ser Gly Ala Glu Val Lys Lys Pro Gly Ala
1               5                   10                  15

Ser Val Lys Val Ser Cys Lys Ala Ser Gly Tyr Thr Phe Thr Ser Tyr
            20                  25                  30

Tyr Met His Trp Val Arg Gln Ala Pro Gly Gln Gly Leu Glu Trp Met
        35                  40                  45

Gly Ile Ile Asn Pro Ser Gly Gly Ser Thr Ser Tyr Ala Gln Lys Phe
    50                  55                  60

Gln Gly Arg Val Thr Met Thr Arg Asp Thr Ser Thr Ser Thr Val Tyr
65                  70                  75                  80

Met Glu Leu Ser Ser Leu Arg Ser Glu Asp Thr Ala Val Tyr Tyr Cys
                85                  90                  95

Ala Arg Asp Gly Thr Leu Tyr Asp Phe Trp Ser Gly Tyr Tyr Ser Tyr
            100                 105                 110

Asp Ala Phe Asp Ile Trp Gly Gln Gly Thr Met Val Thr Val Ser Ser
        115                 120                 125


<210> SEQ ID NO 64
<211> LENGTH: 122
<212> TYPE: PRT
<213> ORGANISM: Artificial sequence
<220> FEATURE:
<223> OTHER INFORMATION: an artificially synthesized sequence
```

<400> SEQUENCE: 64

Gln Met Gln Leu Val Gln Ser Gly Ala Glu Val Lys Lys Pro Gly Ser
1 5 10 15

Ser Val Lys Val Ser Cys Lys Ala Ser Gly Gly Thr Phe Ser Ser Tyr
20 25 30

Ala Ile Ser Trp Val Arg Gln Ala Pro Gly Gln Gly Leu Glu Trp Met
35 40 45

Gly Gly Ile Ile Pro Ile Phe Gly Thr Ala Asn Tyr Ala Gln Lys Phe
50 55 60

Gln Gly Arg Val Thr Ile Thr Ala Asp Glu Ser Thr Ser Thr Ala Tyr
65 70 75 80

Met Glu Leu Ser Ser Leu Arg Ser Glu Asp Thr Ala Val Tyr Tyr Cys
85 90 95

Ala Arg Asp Leu Asp Thr Gly Pro Tyr Tyr Tyr Gly Met Asp Val Trp
100 105 110

Gly Gln Gly Thr Met Val Thr Val Ser Ser
115 120

<210> SEQ ID NO 65
<211> LENGTH: 124
<212> TYPE: PRT
<213> ORGANISM: Artificial sequence
<220> FEATURE:
<223> OTHER INFORMATION: an artificially synthesized sequence

<400> SEQUENCE: 65

Gln Val Gln Leu Val Gln Ser Gly Ala Glu Val Lys Lys Pro Gly Ser
1 5 10 15

Ser Val Lys Val Ser Cys Lys Ala Ser Gly Gly Thr Phe Ser Ser Tyr
20 25 30

Ala Ile Ser Trp Val Arg Gln Ala Pro Gly Gln Gly Leu Glu Trp Met
35 40 45

Gly Gly Ile Ile Pro Ile Phe Gly Thr Ala Asn Tyr Ala Gln Lys Phe
50 55 60

Gln Gly Arg Val Thr Ile Thr Ala Asp Glu Ser Thr Ser Thr Ala Tyr
65 70 75 80

Met Glu Leu Ser Ser Leu Arg Ser Glu Asp Thr Ala Val Tyr Tyr Cys
85 90 95

Ala Arg Asp Ser Pro Val Pro Gly Val Tyr Tyr Tyr Tyr Gly Met Asp
100 105 110

Val Trp Gly Gln Gly Thr Met Val Thr Val Ser Ser
115 120

<210> SEQ ID NO 66
<211> LENGTH: 119
<212> TYPE: PRT
<213> ORGANISM: Artificial sequence
<220> FEATURE:
<223> OTHER INFORMATION: an artificially synthesized sequence

<400> SEQUENCE: 66

Gln Val Gln Leu Val Gln Ser Gly Ala Glu Val Lys Lys Pro Gly Glu
1 5 10 15

Ser Leu Lys Ile Ser Cys Lys Gly Ser Gly Tyr Ser Phe Thr Ser Tyr
20 25 30

Trp Ile Gly Trp Val Arg Gln Met Pro Gly Lys Gly Leu Glu Trp Met
35 40 45

```
Gly Ile Ile Tyr Pro Gly Asp Ser Asp Thr Arg Tyr Ser Pro Ser Phe
    50                  55                  60

Gln Gly Gln Val Thr Ile Ser Ala Asp Lys Ser Ile Ser Thr Ala Tyr
65                  70                  75                  80

Leu Gln Trp Ser Ser Leu Lys Ala Ser Asp Thr Ala Met Tyr Tyr Cys
                85                  90                  95

Ala Arg His Arg Ala Gly Asp Leu Gly Gly Asp Tyr Trp Gly Gln Gly
            100                 105                 110

Thr Leu Val Thr Val Ser Ser
        115


<210> SEQ ID NO 67
<211> LENGTH: 445
<212> TYPE: PRT
<213> ORGANISM: Artificial sequence
<220> FEATURE:
<223> OTHER INFORMATION: an artificially synthesized sequence

<400> SEQUENCE: 67

Gln Val Gln Leu Val Gln Ser Gly Ala Glu Val Lys Lys Pro Gly Ala
1               5                   10                  15

Ser Val Lys Val Ser Cys Lys Ala Ser Gly Tyr Thr Phe Thr Gly Tyr
            20                  25                  30

Ile Met Asn Trp Val Arg Gln Ala Pro Gly Gln Gly Leu Glu Trp Met
        35                  40                  45

Gly Leu Ile Asn Pro Tyr Asn Gly Gly Thr Asp Tyr Asn Pro Gln Phe
    50                  55                  60

Gln Asp Arg Val Thr Ile Thr Ala Asp Lys Ser Thr Ser Thr Ala Tyr
65                  70                  75                  80

Met Glu Leu Ser Ser Leu Arg Ser Glu Asp Thr Ala Val Tyr Tyr Cys
                85                  90                  95

Ala Arg Asp Gly Tyr Asp Asp Gly Pro Tyr Thr Leu Glu Thr Trp Gly
            100                 105                 110

Gln Gly Thr Leu Val Thr Val Ser Ser Ala Ser Thr Lys Gly Pro Ser
        115                 120                 125

Val Phe Pro Leu Ala Pro Ser Ser Lys Ser Thr Ser Gly Gly Thr Ala
    130                 135                 140

Ala Leu Gly Cys Leu Val Lys Asp Tyr Phe Pro Glu Pro Val Thr Val
145                 150                 155                 160

Ser Trp Asn Ser Gly Ala Leu Thr Ser Gly Val His Thr Phe Pro Ala
                165                 170                 175

Val Leu Gln Ser Ser Gly Leu Tyr Ser Leu Ser Ser Val Val Thr Val
            180                 185                 190

Pro Ser Ser Asn Phe Gly Thr Gln Thr Tyr Thr Cys Asn Val Asp His
        195                 200                 205

Lys Pro Ser Asn Thr Lys Val Asp Lys Thr Val Glu Arg Lys Ser Cys
    210                 215                 220

Val Glu Cys Pro Pro Cys Pro Ala Pro Pro Val Ala Gly Pro Ser Val
225                 230                 235                 240

Phe Leu Phe Pro Pro Lys Pro Lys Asp Thr Leu Met Ile Ser Arg Thr
                245                 250                 255

Pro Glu Val Thr Cys Val Val Val Asp Val Ser Gln Glu Asp Pro Glu
            260                 265                 270

Val Gln Phe Asn Trp Tyr Val Asp Gly Val Glu Val His Asn Ala Lys
        275                 280                 285
```

Thr Lys Pro Arg Glu Glu Gln Phe Asn Ser Thr Phe Arg Val Val Ser
290 295 300

Val Leu Thr Val Val His Gln Asp Trp Leu Asn Gly Lys Glu Tyr Lys
305 310 315 320

Cys Lys Val Ser Asn Lys Gly Leu Pro Ala Pro Ile Glu Lys Thr Ile
325 330 335

Ser Lys Thr Lys Gly Gln Pro Arg Glu Pro Gln Val Tyr Thr Leu Pro
340 345 350

Pro Ser Gln Glu Glu Met Thr Lys Asn Gln Val Ser Leu Thr Cys Leu
355 360 365

Val Lys Gly Phe Tyr Pro Ser Asp Ile Ala Val Glu Trp Glu Ser Asn
370 375 380

Gly Gln Pro Glu Asn Asn Tyr Lys Thr Thr Pro Pro Met Leu Asp Ser
385 390 395 400

Asp Gly Ser Phe Phe Leu Tyr Ser Lys Leu Thr Val Asp Lys Ser Arg
405 410 415

Trp Gln Glu Gly Asn Val Phe Ser Cys Ser Val Met His Glu Ala Leu
420 425 430

His Asn His Tyr Thr Gln Lys Ser Leu Ser Leu Ser Pro
435 440 445

<210> SEQ ID NO 68
<211> LENGTH: 214
<212> TYPE: PRT
<213> ORGANISM: Artificial sequence
<220> FEATURE:
<223> OTHER INFORMATION: an artificially synthesized sequence

<400> SEQUENCE: 68

Glu Thr Thr Leu Thr Gln Ser Pro Ala Phe Met Ser Ala Thr Pro Gly
1 5 10 15

Asp Lys Val Asn Ile Ser Cys Lys Ala Ser Gln Asp Ile Asp Asp Asp
20 25 30

Met Asn Trp Tyr Gln Gln Lys Pro Gly Glu Ala Ala Ile Phe Ile Ile
35 40 45

Gln Glu Ala Thr Thr Leu Val Pro Gly Ile Pro Pro Arg Phe Ser Gly
50 55 60

Ser Gly Tyr Gly Thr Asp Phe Thr Leu Thr Ile Asn Asn Ile Glu Ser
65 70 75 80

Glu Asp Ala Ala Tyr Tyr Phe Cys Leu Gln His Asp Asn Phe Pro Leu
85 90 95

Thr Phe Gly Gln Gly Thr Lys Val Glu Ile Lys Arg Thr Val Ala Ala
100 105 110

Pro Ser Val Phe Ile Phe Pro Pro Ser Asp Glu Gln Leu Lys Ser Gly
115 120 125

Thr Ala Ser Val Val Cys Leu Leu Asn Asn Phe Tyr Pro Arg Glu Ala
130 135 140

Lys Val Gln Trp Lys Val Asp Asn Ala Leu Gln Ser Gly Asn Ser Gln
145 150 155 160

Glu Ser Val Thr Glu Gln Asp Ser Lys Asp Ser Thr Tyr Ser Leu Ser
165 170 175

Ser Thr Leu Thr Leu Ser Lys Ala Asp Tyr Glu Lys His Lys Val Tyr
180 185 190

Ala Cys Glu Val Thr His Gln Gly Leu Ser Ser Pro Val Thr Lys Ser
195 200 205

```
Phe Asn Arg Gly Glu Cys
    210


<210> SEQ ID NO 69
<211> LENGTH: 214
<212> TYPE: PRT
<213> ORGANISM: Artificial sequence
<220> FEATURE:
<223> OTHER INFORMATION: an artificially synthesized sequence

<400> SEQUENCE: 69

Glu Thr Thr Leu Thr Gln Ser Pro Ala Phe Met Ser Ala Thr Pro Gly
1               5                   10                  15

Asp Lys Val Asn Ile Ser Cys Lys Ala Ser Gln Asp Ile Glu Asp Asp
            20                  25                  30

Met Asn Trp Tyr Gln Gln Lys Pro Gly Glu Ala Ala Ile Phe Ile Ile
        35                  40                  45

Gln Glu Ala Thr Thr Leu Val Pro Gly Ile Ser Pro Arg Phe Ser Gly
    50                  55                  60

Ser Gly Tyr Gly Thr Asp Phe Thr Leu Thr Ile Asn Asn Ile Glu Ser
65                  70                  75                  80

Glu Asp Ala Ala Tyr Tyr Phe Cys Leu Gln His Asp Asn Phe Pro Leu
                85                  90                  95

Thr Phe Gly Gln Gly Thr Lys Val Glu Ile Lys Arg Thr Val Ala Ala
            100                 105                 110

Pro Ser Val Phe Ile Phe Pro Pro Ser Asp Glu Gln Leu Lys Ser Gly
        115                 120                 125

Thr Ala Ser Val Val Cys Leu Leu Asn Asn Phe Tyr Pro Arg Glu Ala
    130                 135                 140

Lys Val Gln Trp Lys Val Asp Asn Ala Leu Gln Ser Gly Asn Ser Gln
145                 150                 155                 160

Glu Ser Val Thr Glu Gln Asp Ser Lys Asp Ser Thr Tyr Ser Leu Ser
                165                 170                 175

Ser Thr Leu Thr Leu Ser Lys Ala Asp Tyr Glu Lys His Lys Val Tyr
            180                 185                 190

Ala Cys Glu Val Thr His Gln Gly Leu Ser Ser Pro Val Thr Lys Ser
        195                 200                 205

Phe Asn Arg Gly Glu Cys
    210


<210> SEQ ID NO 70
<211> LENGTH: 214
<212> TYPE: PRT
<213> ORGANISM: Artificial sequence
<220> FEATURE:
<223> OTHER INFORMATION: an artificially synthesized sequence

<400> SEQUENCE: 70

Glu Thr Thr Leu Thr Gln Ser Pro Ala Phe Met Ser Ala Thr Pro Gly
1               5                   10                  15

Asp Lys Val Thr Ile Ser Cys Lys Ala Ser Gln Asp Ile Asp Asp Asp
            20                  25                  30

Met Asn Trp Tyr Gln Gln Lys Pro Gly Glu Ala Ala Ile Phe Ile Ile
        35                  40                  45

Gln Glu Ala Thr Thr Leu Val Pro Gly Ile Ser Pro Arg Phe Ser Gly
    50                  55                  60

Ser Gly Tyr Gly Thr Asp Phe Thr Leu Thr Ile Asn Asn Ile Glu Ser
```

65 70 75 80

Glu Asp Ala Ala Tyr Tyr Phe Cys Leu Gln His Asp Asn Phe Pro Tyr
85 90 95

Thr Phe Gly Gln Gly Thr Lys Leu Glu Ile Lys Arg Thr Val Ala Ala
100 105 110

Pro Ser Val Phe Ile Phe Pro Pro Ser Asp Glu Gln Leu Lys Ser Gly
115 120 125

Thr Ala Ser Val Val Cys Leu Leu Asn Asn Phe Tyr Pro Arg Glu Ala
130 135 140

Lys Val Gln Trp Lys Val Asp Asn Ala Leu Gln Ser Gly Asn Ser Gln
145 150 155 160

Glu Ser Val Thr Glu Gln Asp Ser Lys Asp Ser Thr Tyr Ser Leu Ser
165 170 175

Ser Thr Leu Thr Leu Ser Lys Ala Asp Tyr Glu Lys His Lys Val Tyr
180 185 190

Ala Cys Glu Val Thr His Gln Gly Leu Ser Ser Pro Val Thr Lys Ser
195 200 205

Phe Asn Arg Gly Glu Cys
210

<210> SEQ ID NO 71
<211> LENGTH: 107
<212> TYPE: PRT
<213> ORGANISM: Artificial sequence
<220> FEATURE:
<223> OTHER INFORMATION: an artificially synthesized sequence

<400> SEQUENCE: 71

Asp Ile Gln Met Thr Gln Ser Pro Ser Ser Leu Ser Ala Ser Val Gly
1 5 10 15

Asp Arg Val Thr Ile Thr Cys Lys Ala Ser Gln Asp Ile Asp Asp Asp
20 25 30

Met Asn Trp Tyr Gln Gln Lys Pro Gly Lys Ala Pro Lys Leu Leu Ile
35 40 45

Tyr Glu Ala Thr Thr Leu Val Pro Gly Val Pro Ser Arg Phe Ser Gly
50 55 60

Ser Gly Ser Gly Thr Asp Phe Thr Leu Thr Ile Ser Ser Leu Gln Pro
65 70 75 80

Glu Asp Phe Ala Thr Tyr Tyr Cys Leu Gln His Asp Asn Phe Pro Tyr
85 90 95

Thr Phe Gly Gln Gly Thr Lys Val Glu Ile Lys
100 105

<210> SEQ ID NO 72
<211> LENGTH: 107
<212> TYPE: PRT
<213> ORGANISM: Artificial sequence
<220> FEATURE:
<223> OTHER INFORMATION: an artificially synthesized sequence

<400> SEQUENCE: 72

Asp Ile Val Met Thr Gln Ser Pro Leu Ser Leu Pro Val Thr Pro Gly
1 5 10 15

Glu Pro Ala Ser Ile Ser Cys Lys Ala Ser Gln Asp Ile Asp Asp Asp
20 25 30

Met Asn Trp Tyr Leu Gln Lys Pro Gly Gln Ser Pro Gln Leu Leu Ile
35 40 45

```
Tyr Glu Ala Thr Thr Leu Val Pro Gly Val Pro Asp Arg Phe Ser Gly
    50                  55                  60

Ser Gly Ser Gly Thr Asp Phe Thr Leu Lys Ile Ser Arg Val Glu Ala
65                  70                  75                  80

Glu Asp Val Gly Val Tyr Tyr Cys Leu Gln His Asp Asn Phe Pro Tyr
                85                  90                  95

Thr Phe Gly Gln Gly Thr Lys Leu Glu Ile Lys
            100                 105


<210> SEQ ID NO 73
<211> LENGTH: 107
<212> TYPE: PRT
<213> ORGANISM: Artificial sequence
<220> FEATURE:
<223> OTHER INFORMATION: an artificially synthesized sequence

<400> SEQUENCE: 73

Glu Ile Val Leu Thr Gln Ser Pro Gly Thr Leu Ser Leu Ser Pro Gly
1               5                   10                  15

Glu Arg Ala Thr Leu Ser Cys Lys Ala Ser Gln Asp Ile Asp Asp Asp
            20                  25                  30

Met Asn Trp Tyr Gln Gln Lys Pro Gly Gln Ala Pro Arg Leu Leu Ile
        35                  40                  45

Tyr Glu Ala Thr Thr Leu Val Pro Gly Ile Pro Asp Arg Phe Ser Gly
    50                  55                  60

Ser Gly Ser Gly Thr Asp Phe Thr Leu Thr Ile Ser Arg Leu Glu Pro
65                  70                  75                  80

Glu Asp Phe Ala Val Tyr Tyr Cys Leu Gln His Asp Asn Phe Pro Tyr
                85                  90                  95

Thr Phe Gly Gln Gly Thr Lys Val Glu Ile Lys
            100                 105


<210> SEQ ID NO 74
<211> LENGTH: 107
<212> TYPE: PRT
<213> ORGANISM: Artificial sequence
<220> FEATURE:
<223> OTHER INFORMATION: an artificially synthesized sequence

<400> SEQUENCE: 74

Asp Ile Val Met Thr Gln Ser Pro Asp Ser Leu Ala Val Ser Leu Gly
1               5                   10                  15

Glu Arg Ala Thr Ile Asn Cys Lys Ala Ser Gln Asp Ile Asp Asp Asp
            20                  25                  30

Met Asn Trp Tyr Gln Gln Lys Pro Gly Gln Pro Pro Lys Leu Leu Ile
        35                  40                  45

Tyr Glu Ala Thr Thr Leu Val Pro Gly Val Pro Asp Arg Phe Ser Gly
    50                  55                  60

Ser Gly Ser Gly Thr Asp Phe Thr Leu Thr Ile Ser Ser Leu Gln Ala
65                  70                  75                  80

Glu Asp Val Ala Val Tyr Tyr Cys Leu Gln His Asp Asn Phe Pro Tyr
                85                  90                  95

Thr Phe Gly Gln Gly Thr Lys Leu Glu Ile Lys
            100                 105


<210> SEQ ID NO 75
<211> LENGTH: 214
<212> TYPE: PRT
<213> ORGANISM: Artificial sequence
```

<220> FEATURE:
<223> OTHER INFORMATION: an artificially synthesized sequence

<400> SEQUENCE: 75

Glu Thr Thr Leu Thr Gln Ser Pro Ala Phe Met Ser Ala Thr Pro Gly
1               5                   10                  15

Asp Lys Val Thr Ile Ser Cys Lys Ala Ser Gln Asp Ile Ala Asp Asp
            20                  25                  30

Met Asn Trp Tyr Gln Gln Lys Pro Gly Glu Ala Ala Ile Phe Ile Ile
        35                  40                  45

Gln Glu Ala Thr Thr Leu Val Pro Gly Ile Ser Pro Arg Phe Ser Gly
    50                  55                  60

Ser Gly Tyr Gly Thr Asp Phe Thr Leu Thr Ile Asn Asn Ile Glu Ser
65                  70                  75                  80

Glu Asp Ala Ala Tyr Tyr Phe Cys Leu Gln His Asp Asn Phe Pro Tyr
                85                  90                  95

Thr Phe Gly Gln Gly Thr Lys Leu Glu Ile Lys Arg Thr Val Ala Ala
            100                 105                 110

Pro Ser Val Phe Ile Phe Pro Pro Ser Asp Glu Gln Leu Lys Ser Gly
        115                 120                 125

Thr Ala Ser Val Val Cys Leu Leu Asn Asn Phe Tyr Pro Arg Glu Ala
    130                 135                 140

Lys Val Gln Trp Lys Val Asp Asn Ala Leu Gln Ser Gly Asn Ser Gln
145                 150                 155                 160

Glu Ser Val Thr Glu Gln Asp Ser Lys Asp Ser Thr Tyr Ser Leu Ser
                165                 170                 175

Ser Thr Leu Thr Leu Ser Lys Ala Asp Tyr Glu Lys His Lys Val Tyr
            180                 185                 190

Ala Cys Glu Val Thr His Gln Gly Leu Ser Ser Pro Val Thr Lys Ser
        195                 200                 205

Phe Asn Arg Gly Glu Cys
    210

<210> SEQ ID NO 76
<211> LENGTH: 214
<212> TYPE: PRT
<213> ORGANISM: Artificial sequence
<220> FEATURE:
<223> OTHER INFORMATION: an artificially synthesized sequence

<400> SEQUENCE: 76

Glu Thr Thr Leu Thr Gln Ser Pro Ala Phe Met Ser Ala Thr Pro Gly
1               5                   10                  15

Asp Lys Val Thr Ile Ser Cys Lys Ala Ser Gln Asp Ile Asp Ala Asp
            20                  25                  30

Met Asn Trp Tyr Gln Gln Lys Pro Gly Glu Ala Ala Ile Phe Ile Ile
        35                  40                  45

Gln Glu Ala Thr Thr Leu Val Pro Gly Ile Ser Pro Arg Phe Ser Gly
    50                  55                  60

Ser Gly Tyr Gly Thr Asp Phe Thr Leu Thr Ile Asn Asn Ile Glu Ser
65                  70                  75                  80

Glu Asp Ala Ala Tyr Tyr Phe Cys Leu Gln His Asp Asn Phe Pro Tyr
                85                  90                  95

Thr Phe Gly Gln Gly Thr Lys Leu Glu Ile Lys Arg Thr Val Ala Ala
            100                 105                 110

Pro Ser Val Phe Ile Phe Pro Pro Ser Asp Glu Gln Leu Lys Ser Gly

```
        115                 120                 125

Thr Ala Ser Val Val Cys Leu Leu Asn Asn Phe Tyr Pro Arg Glu Ala
    130                 135                 140

Lys Val Gln Trp Lys Val Asp Asn Ala Leu Gln Ser Gly Asn Ser Gln
145                 150                 155                 160

Glu Ser Val Thr Glu Gln Asp Ser Lys Asp Ser Thr Tyr Ser Leu Ser
            165                 170                 175

Ser Thr Leu Thr Leu Ser Lys Ala Asp Tyr Glu Lys His Lys Val Tyr
            180                 185                 190

Ala Cys Glu Val Thr His Gln Gly Leu Ser Ser Pro Val Thr Lys Ser
        195                 200                 205

Phe Asn Arg Gly Glu Cys
    210


<210> SEQ ID NO 77
<211> LENGTH: 214
<212> TYPE: PRT
<213> ORGANISM: Artificial sequence
<220> FEATURE:
<223> OTHER INFORMATION: an artificially synthesized sequence

<400> SEQUENCE: 77

Glu Thr Thr Leu Thr Gln Ser Pro Ala Phe Met Ser Ala Thr Pro Gly
1               5                   10                  15

Asp Lys Val Thr Ile Ser Cys Lys Ala Ser Gln Asp Ile Asp Asp Ala
            20                  25                  30

Met Asn Trp Tyr Gln Gln Lys Pro Gly Glu Ala Ala Ile Phe Ile Ile
        35                  40                  45

Gln Glu Ala Thr Thr Leu Val Pro Gly Ile Ser Pro Arg Phe Ser Gly
    50                  55                  60

Ser Gly Tyr Gly Thr Asp Phe Thr Leu Thr Ile Asn Asn Ile Glu Ser
65                  70                  75                  80

Glu Asp Ala Ala Tyr Tyr Phe Cys Leu Gln His Asp Asn Phe Pro Tyr
                85                  90                  95

Thr Phe Gly Gln Gly Thr Lys Leu Glu Ile Lys Arg Thr Val Ala Ala
            100                 105                 110

Pro Ser Val Phe Ile Phe Pro Pro Ser Asp Glu Gln Leu Lys Ser Gly
        115                 120                 125

Thr Ala Ser Val Val Cys Leu Leu Asn Asn Phe Tyr Pro Arg Glu Ala
    130                 135                 140

Lys Val Gln Trp Lys Val Asp Asn Ala Leu Gln Ser Gly Asn Ser Gln
145                 150                 155                 160

Glu Ser Val Thr Glu Gln Asp Ser Lys Asp Ser Thr Tyr Ser Leu Ser
                165                 170                 175

Ser Thr Leu Thr Leu Ser Lys Ala Asp Tyr Glu Lys His Lys Val Tyr
            180                 185                 190

Ala Cys Glu Val Thr His Gln Gly Leu Ser Ser Pro Val Thr Lys Ser
        195                 200                 205

Phe Asn Arg Gly Glu Cys
    210


<210> SEQ ID NO 78
<211> LENGTH: 214
<212> TYPE: PRT
<213> ORGANISM: Artificial sequence
<220> FEATURE:
<223> OTHER INFORMATION: an artificially synthesized sequence
```

<400> SEQUENCE: 78

Glu Thr Thr Leu Thr Gln Ser Pro Ala Phe Met Ser Ala Thr Pro Gly
1 5 10 15

Asp Lys Val Thr Ile Ser Cys Lys Ala Ser Gln Asp Ile Asp Asp Asp
20 25 30

Met Asn Trp Tyr Gln Gln Lys Pro Gly Glu Ala Ala Ile Phe Ile Ile
35 40 45

Gln Ala Ala Thr Thr Leu Val Pro Gly Ile Ser Pro Arg Phe Ser Gly
50 55 60

Ser Gly Tyr Gly Thr Asp Phe Thr Leu Thr Ile Asn Asn Ile Glu Ser
65 70 75 80

Glu Asp Ala Ala Tyr Tyr Phe Cys Leu Gln His Asp Asn Phe Pro Tyr
85 90 95

Thr Phe Gly Gln Gly Thr Lys Leu Glu Ile Lys Arg Thr Val Ala Ala
100 105 110

Pro Ser Val Phe Ile Phe Pro Pro Ser Asp Glu Gln Leu Lys Ser Gly
115 120 125

Thr Ala Ser Val Val Cys Leu Leu Asn Asn Phe Tyr Pro Arg Glu Ala
130 135 140

Lys Val Gln Trp Lys Val Asp Asn Ala Leu Gln Ser Gly Asn Ser Gln
145 150 155 160

Glu Ser Val Thr Glu Gln Asp Ser Lys Asp Ser Thr Tyr Ser Leu Ser
165 170 175

Ser Thr Leu Thr Leu Ser Lys Ala Asp Tyr Glu Lys His Lys Val Tyr
180 185 190

Ala Cys Glu Val Thr His Gln Gly Leu Ser Ser Pro Val Thr Lys Ser
195 200 205

Phe Asn Arg Gly Glu Cys
210

<210> SEQ ID NO 79
<211> LENGTH: 214
<212> TYPE: PRT
<213> ORGANISM: Artificial sequence
<220> FEATURE:
<223> OTHER INFORMATION: an artificially synthesized sequence

<400> SEQUENCE: 79

Glu Thr Thr Leu Thr Gln Ser Pro Ala Phe Met Ser Ala Thr Pro Gly
1 5 10 15

Asp Lys Val Thr Ile Ser Cys Lys Ala Ser Gln Asp Ile Ala Asp Ala
20 25 30

Met Asn Trp Tyr Gln Gln Lys Pro Gly Glu Ala Ala Ile Phe Ile Ile
35 40 45

Gln Glu Ala Thr Thr Leu Val Pro Gly Ile Ser Pro Arg Phe Ser Gly
50 55 60

Ser Gly Tyr Gly Thr Asp Phe Thr Leu Thr Ile Asn Asn Ile Glu Ser
65 70 75 80

Glu Asp Ala Ala Tyr Tyr Phe Cys Leu Gln His Asp Asn Phe Pro Tyr
85 90 95

Thr Phe Gly Gln Gly Thr Lys Leu Glu Ile Lys Arg Thr Val Ala Ala
100 105 110

Pro Ser Val Phe Ile Phe Pro Pro Ser Asp Glu Gln Leu Lys Ser Gly
115 120 125

```
Thr Ala Ser Val Val Cys Leu Leu Asn Asn Phe Tyr Pro Arg Glu Ala
    130                 135                 140

Lys Val Gln Trp Lys Val Asp Asn Ala Leu Gln Ser Gly Asn Ser Gln
145                 150                 155                 160

Glu Ser Val Thr Glu Gln Asp Ser Lys Asp Ser Thr Tyr Ser Leu Ser
                165                 170                 175

Ser Thr Leu Thr Leu Ser Lys Ala Asp Tyr Glu Lys His Lys Val Tyr
            180                 185                 190

Ala Cys Glu Val Thr His Gln Gly Leu Ser Ser Pro Val Thr Lys Ser
        195                 200                 205

Phe Asn Arg Gly Glu Cys
    210


<210> SEQ ID NO 80
<211> LENGTH: 214
<212> TYPE: PRT
<213> ORGANISM: Artificial sequence
<220> FEATURE:
<223> OTHER INFORMATION: an artificially synthesized sequence

<400> SEQUENCE: 80

Glu Thr Thr Leu Thr Gln Ser Pro Ala Phe Met Ser Ala Thr Pro Gly
1               5                   10                  15

Asp Lys Val Thr Ile Ser Cys Lys Ala Ser Gln Asp Ile Ala Asp Asp
            20                  25                  30

Met Asn Trp Tyr Gln Gln Lys Pro Gly Glu Ala Ala Ile Phe Ile Ile
        35                  40                  45

Gln Ala Ala Thr Thr Leu Val Pro Gly Ile Ser Pro Arg Phe Ser Gly
    50                  55                  60

Ser Gly Tyr Gly Thr Asp Phe Thr Leu Thr Ile Asn Asn Ile Glu Ser
65                  70                  75                  80

Glu Asp Ala Ala Tyr Tyr Phe Cys Leu Gln His Asp Asn Phe Pro Tyr
                85                  90                  95

Thr Phe Gly Gln Gly Thr Lys Leu Glu Ile Lys Arg Thr Val Ala Ala
            100                 105                 110

Pro Ser Val Phe Ile Phe Pro Pro Ser Asp Glu Gln Leu Lys Ser Gly
        115                 120                 125

Thr Ala Ser Val Val Cys Leu Leu Asn Asn Phe Tyr Pro Arg Glu Ala
    130                 135                 140

Lys Val Gln Trp Lys Val Asp Asn Ala Leu Gln Ser Gly Asn Ser Gln
145                 150                 155                 160

Glu Ser Val Thr Glu Gln Asp Ser Lys Asp Ser Thr Tyr Ser Leu Ser
                165                 170                 175

Ser Thr Leu Thr Leu Ser Lys Ala Asp Tyr Glu Lys His Lys Val Tyr
            180                 185                 190

Ala Cys Glu Val Thr His Gln Gly Leu Ser Ser Pro Val Thr Lys Ser
        195                 200                 205

Phe Asn Arg Gly Glu Cys
    210


<210> SEQ ID NO 81
<211> LENGTH: 214
<212> TYPE: PRT
<213> ORGANISM: Artificial sequence
<220> FEATURE:
<223> OTHER INFORMATION: an artificially synthesized sequence

<400> SEQUENCE: 81
```

```
Glu Thr Thr Leu Thr Gln Ser Pro Ala Phe Met Ser Ala Thr Pro Gly
1               5                   10                  15

Asp Lys Val Thr Ile Ser Cys Lys Ala Ser Gln Asp Ile Ala Asp Ala
            20                  25                  30

Met Asn Trp Tyr Gln Gln Lys Pro Gly Glu Ala Ala Ile Phe Ile Ile
        35                  40                  45

Gln Ala Ala Thr Thr Leu Val Pro Gly Ile Ser Pro Arg Phe Ser Gly
    50                  55                  60

Ser Gly Tyr Gly Thr Asp Phe Thr Leu Thr Ile Asn Asn Ile Glu Ser
65                  70                  75                  80

Glu Asp Ala Ala Tyr Tyr Phe Cys Leu Gln His Asp Asn Phe Pro Tyr
                85                  90                  95

Thr Phe Gly Gln Gly Thr Lys Leu Glu Ile Lys Arg Thr Val Ala Ala
            100                 105                 110

Pro Ser Val Phe Ile Phe Pro Pro Ser Asp Glu Gln Leu Lys Ser Gly
        115                 120                 125

Thr Ala Ser Val Val Cys Leu Leu Asn Asn Phe Tyr Pro Arg Glu Ala
    130                 135                 140

Lys Val Gln Trp Lys Val Asp Asn Ala Leu Gln Ser Gly Asn Ser Gln
145                 150                 155                 160

Glu Ser Val Thr Glu Gln Asp Ser Lys Asp Ser Thr Tyr Ser Leu Ser
                165                 170                 175

Ser Thr Leu Thr Leu Ser Lys Ala Asp Tyr Glu Lys His Lys Val Tyr
            180                 185                 190

Ala Cys Glu Val Thr His Gln Gly Leu Ser Ser Pro Val Thr Lys Ser
        195                 200                 205

Phe Asn Arg Gly Glu Cys
    210
```

<210> SEQ ID NO 82
<211> LENGTH: 214
<212> TYPE: PRT
<213> ORGANISM: Artificial sequence
<220> FEATURE:
<223> OTHER INFORMATION: an artificially synthesized sequence

<400> SEQUENCE: 82

```
Glu Thr Thr Leu Thr Gln Ser Pro Ala Phe Met Ser Ala Thr Pro Gly
1               5                   10                  15

Asp Lys Val Thr Ile Ser Cys Lys Ala Ser Gln Asp Ile Asp Asp Asp
            20                  25                  30

Met Asn Trp Tyr Gln Gln Lys Pro Gly Glu Ala Ala Ile Phe Ile Ile
        35                  40                  45

Gln Glu Ala Thr Thr Leu Val Pro Gly Ile Ser Pro Arg Phe Ser Gly
    50                  55                  60

Ser Gly Tyr Gly Thr Asp Phe Thr Leu Thr Ile Asn Asn Ile Glu Ser
65                  70                  75                  80

Glu Asp Ala Ala Tyr Tyr Phe Cys Leu Gln His Ala Asn Phe Pro Tyr
                85                  90                  95

Thr Phe Gly Gln Gly Thr Lys Leu Glu Ile Lys Arg Thr Val Ala Ala
            100                 105                 110

Pro Ser Val Phe Ile Phe Pro Pro Ser Asp Glu Gln Leu Lys Ser Gly
        115                 120                 125

Thr Ala Ser Val Val Cys Leu Leu Asn Asn Phe Tyr Pro Arg Glu Ala
    130                 135                 140
```

Lys Val Gln Trp Lys Val Asp Asn Ala Leu Gln Ser Gly Asn Ser Gln
145 150 155 160

Glu Ser Val Thr Glu Gln Asp Ser Lys Asp Ser Thr Tyr Ser Leu Ser
165 170 175

Ser Thr Leu Thr Leu Ser Lys Ala Asp Tyr Glu Lys His Lys Val Tyr
180 185 190

Ala Cys Glu Val Thr His Gln Gly Leu Ser Ser Pro Val Thr Lys Ser
195 200 205

Phe Asn Arg Gly Glu Cys
210

<210> SEQ ID NO 83
<211> LENGTH: 214
<212> TYPE: PRT
<213> ORGANISM: Artificial sequence
<220> FEATURE:
<223> OTHER INFORMATION: an artificially synthesized sequence

<400> SEQUENCE: 83

Asp Ile Gln Met Thr Gln Ser Pro Ser Ser Leu Ser Ala Ser Val Gly
1 5 10 15

Asp Arg Val Thr Ile Thr Cys Arg Ala Ser Gln Ser Ile Asp Asp Asp
20 25 30

Leu Asn Trp Tyr Gln Gln Lys Pro Gly Lys Ala Pro Lys Leu Leu Ile
35 40 45

Tyr Glu Ala Ser Ser Leu Gln Ser Gly Val Pro Ser Arg Phe Ser Gly
50 55 60

Ser Gly Ser Gly Thr Asp Phe Thr Leu Thr Ile Ser Ser Leu Gln Pro
65 70 75 80

Glu Asp Phe Ala Thr Tyr Tyr Cys Gln Gln Ser Asp Ser Thr Pro Tyr
85 90 95

Thr Phe Gly Gln Gly Thr Lys Val Glu Ile Lys Arg Thr Val Ala Ala
100 105 110

Pro Ser Val Phe Ile Phe Pro Pro Ser Asp Glu Gln Leu Lys Ser Gly
115 120 125

Thr Ala Ser Val Val Cys Leu Leu Asn Asn Phe Tyr Pro Arg Glu Ala
130 135 140

Lys Val Gln Trp Lys Val Asp Asn Ala Leu Gln Ser Gly Asn Ser Gln
145 150 155 160

Glu Ser Val Thr Glu Gln Asp Ser Lys Asp Ser Thr Tyr Ser Leu Ser
165 170 175

Ser Thr Leu Thr Leu Ser Lys Ala Asp Tyr Glu Lys His Lys Val Tyr
180 185 190

Ala Cys Glu Val Thr His Gln Gly Leu Ser Ser Pro Val Thr Lys Ser
195 200 205

Phe Asn Arg Gly Glu Cys
210

<210> SEQ ID NO 84
<211> LENGTH: 214
<212> TYPE: PRT
<213> ORGANISM: Artificial sequence
<220> FEATURE:
<223> OTHER INFORMATION: an artificially synthesized sequence

<400> SEQUENCE: 84

Asp Ile Gln Met Thr Gln Ser Pro Ser Ser Leu Ser Ala Ser Val Gly

-continued

```
1               5                   10                  15

Asp Arg Val Thr Ile Thr Cys Arg Ala Ser Gln Ser Ile Ser Ser Tyr
            20                  25                  30

Leu Asn Trp Tyr Gln Gln Lys Pro Gly Lys Ala Pro Lys Leu Leu Ile
        35                  40                  45

Tyr Ala Ala Ser Ser Leu Gln Ser Gly Val Pro Ser Arg Phe Ser Gly
    50                  55                  60

Ser Gly Ser Gly Thr Asp Phe Thr Leu Thr Ile Ser Ser Leu Gln Pro
65                  70                  75                  80

Glu Asp Phe Ala Thr Tyr Tyr Cys Gln Gln Ser Tyr Ser Thr Pro Tyr
                85                  90                  95

Thr Phe Gly Gln Gly Thr Lys Val Glu Ile Lys Arg Thr Val Ala Ala
            100                 105                 110

Pro Ser Val Phe Ile Phe Pro Pro Ser Asp Glu Gln Leu Lys Ser Gly
        115                 120                 125

Thr Ala Ser Val Val Cys Leu Leu Asn Asn Phe Tyr Pro Arg Glu Ala
    130                 135                 140

Lys Val Gln Trp Lys Val Asp Asn Ala Leu Gln Ser Gly Asn Ser Gln
145                 150                 155                 160

Glu Ser Val Thr Glu Gln Asp Ser Lys Asp Ser Thr Tyr Ser Leu Ser
                165                 170                 175

Ser Thr Leu Thr Leu Ser Lys Ala Asp Tyr Glu Lys His Lys Val Tyr
            180                 185                 190

Ala Cys Glu Val Thr His Gln Gly Leu Ser Ser Pro Val Thr Lys Ser
        195                 200                 205

Phe Asn Arg Gly Glu Cys
    210
```

<210> SEQ ID NO 85
<211> LENGTH: 214
<212> TYPE: PRT
<213> ORGANISM: Artificial sequence
<220> FEATURE:
<223> OTHER INFORMATION: an artificially synthesized sequence

<400> SEQUENCE: 85

```
Asp Ile Gln Met Thr Gln Ser Pro Ser Ser Leu Ser Ala Ser Val Gly
1               5                   10                  15

Asp Arg Val Thr Ile Thr Cys Arg Ala Ser Gln Ser Ile Ala Asp Asp
            20                  25                  30

Leu Asn Trp Tyr Gln Gln Lys Pro Gly Lys Ala Pro Lys Leu Leu Ile
        35                  40                  45

Tyr Glu Ala Ser Ser Leu Gln Ser Gly Val Pro Ser Arg Phe Ser Gly
    50                  55                  60

Ser Gly Ser Gly Thr Asp Phe Thr Leu Thr Ile Ser Ser Leu Gln Pro
65                  70                  75                  80

Glu Asp Phe Ala Thr Tyr Tyr Cys Gln Gln Ser Asp Ser Thr Pro Tyr
                85                  90                  95

Thr Phe Gly Gln Gly Thr Lys Val Glu Ile Lys Arg Thr Val Ala Ala
            100                 105                 110

Pro Ser Val Phe Ile Phe Pro Pro Ser Asp Glu Gln Leu Lys Ser Gly
        115                 120                 125

Thr Ala Ser Val Val Cys Leu Leu Asn Asn Phe Tyr Pro Arg Glu Ala
    130                 135                 140

Lys Val Gln Trp Lys Val Asp Asn Ala Leu Gln Ser Gly Asn Ser Gln
```

145 150 155 160

Glu Ser Val Thr Glu Gln Asp Ser Lys Asp Ser Thr Tyr Ser Leu Ser
165 170 175

Ser Thr Leu Thr Leu Ser Lys Ala Asp Tyr Glu Lys His Lys Val Tyr
180 185 190

Ala Cys Glu Val Thr His Gln Gly Leu Ser Ser Pro Val Thr Lys Ser
195 200 205

Phe Asn Arg Gly Glu Cys
210

<210> SEQ ID NO 86
<211> LENGTH: 214
<212> TYPE: PRT
<213> ORGANISM: Artificial sequence
<220> FEATURE:
<223> OTHER INFORMATION: an artificially synthesized sequence

<400> SEQUENCE: 86

Asp Ile Gln Met Thr Gln Ser Pro Ser Ser Leu Ser Ala Ser Val Gly
1 5 10 15

Asp Arg Val Thr Ile Thr Cys Arg Ala Ser Gln Ser Ile Asp Ala Asp
20 25 30

Leu Asn Trp Tyr Gln Gln Lys Pro Gly Lys Ala Pro Lys Leu Leu Ile
35 40 45

Tyr Glu Ala Ser Ser Leu Gln Ser Gly Val Pro Ser Arg Phe Ser Gly
50 55 60

Ser Gly Ser Gly Thr Asp Phe Thr Leu Thr Ile Ser Ser Leu Gln Pro
65 70 75 80

Glu Asp Phe Ala Thr Tyr Tyr Cys Gln Gln Ser Asp Ser Thr Pro Tyr
85 90 95

Thr Phe Gly Gln Gly Thr Lys Val Glu Ile Lys Arg Thr Val Ala Ala
100 105 110

Pro Ser Val Phe Ile Phe Pro Pro Ser Asp Glu Gln Leu Lys Ser Gly
115 120 125

Thr Ala Ser Val Val Cys Leu Leu Asn Asn Phe Tyr Pro Arg Glu Ala
130 135 140

Lys Val Gln Trp Lys Val Asp Asn Ala Leu Gln Ser Gly Asn Ser Gln
145 150 155 160

Glu Ser Val Thr Glu Gln Asp Ser Lys Asp Ser Thr Tyr Ser Leu Ser
165 170 175

Ser Thr Leu Thr Leu Ser Lys Ala Asp Tyr Glu Lys His Lys Val Tyr
180 185 190

Ala Cys Glu Val Thr His Gln Gly Leu Ser Ser Pro Val Thr Lys Ser
195 200 205

Phe Asn Arg Gly Glu Cys
210

<210> SEQ ID NO 87
<211> LENGTH: 214
<212> TYPE: PRT
<213> ORGANISM: Artificial sequence
<220> FEATURE:
<223> OTHER INFORMATION: an artificially synthesized sequence

<400> SEQUENCE: 87

Asp Ile Gln Met Thr Gln Ser Pro Ser Ser Leu Ser Ala Ser Val Gly
1 5 10 15

Asp Arg Val Thr Ile Thr Cys Arg Ala Ser Gln Ser Ile Asp Asp Ala
20 25 30

Leu Asn Trp Tyr Gln Gln Lys Pro Gly Lys Ala Pro Lys Leu Leu Ile
35 40 45

Tyr Glu Ala Ser Ser Leu Gln Ser Gly Val Pro Ser Arg Phe Ser Gly
50 55 60

Ser Gly Ser Gly Thr Asp Phe Thr Leu Thr Ile Ser Ser Leu Gln Pro
65 70 75 80

Glu Asp Phe Ala Thr Tyr Tyr Cys Gln Gln Ser Asp Ser Thr Pro Tyr
85 90 95

Thr Phe Gly Gln Gly Thr Lys Val Glu Ile Lys Arg Thr Val Ala Ala
100 105 110

Pro Ser Val Phe Ile Phe Pro Pro Ser Asp Glu Gln Leu Lys Ser Gly
115 120 125

Thr Ala Ser Val Val Cys Leu Leu Asn Asn Phe Tyr Pro Arg Glu Ala
130 135 140

Lys Val Gln Trp Lys Val Asp Asn Ala Leu Gln Ser Gly Asn Ser Gln
145 150 155 160

Glu Ser Val Thr Glu Gln Asp Ser Lys Asp Ser Thr Tyr Ser Leu Ser
165 170 175

Ser Thr Leu Thr Leu Ser Lys Ala Asp Tyr Glu Lys His Lys Val Tyr
180 185 190

Ala Cys Glu Val Thr His Gln Gly Leu Ser Ser Pro Val Thr Lys Ser
195 200 205

Phe Asn Arg Gly Glu Cys
210

<210> SEQ ID NO 88
<211> LENGTH: 214
<212> TYPE: PRT
<213> ORGANISM: Artificial sequence
<220> FEATURE:
<223> OTHER INFORMATION: an artificially synthesized sequence

<400> SEQUENCE: 88

Asp Ile Gln Met Thr Gln Ser Pro Ser Ser Leu Ser Ala Ser Val Gly
1 5 10 15

Asp Arg Val Thr Ile Thr Cys Arg Ala Ser Gln Ser Ile Ser Asp Asp
20 25 30

Leu Asn Trp Tyr Gln Gln Lys Pro Gly Lys Ala Pro Lys Leu Leu Ile
35 40 45

Tyr Glu Ala Ser Ser Leu Gln Ser Gly Val Pro Ser Arg Phe Ser Gly
50 55 60

Ser Gly Ser Gly Thr Asp Phe Thr Leu Thr Ile Ser Ser Leu Gln Pro
65 70 75 80

Glu Asp Phe Ala Thr Tyr Tyr Cys Gln Gln Ser Asp Ser Thr Pro Tyr
85 90 95

Thr Phe Gly Gln Gly Thr Lys Val Glu Ile Lys Arg Thr Val Ala Ala
100 105 110

Pro Ser Val Phe Ile Phe Pro Pro Ser Asp Glu Gln Leu Lys Ser Gly
115 120 125

Thr Ala Ser Val Val Cys Leu Leu Asn Asn Phe Tyr Pro Arg Glu Ala
130 135 140

Lys Val Gln Trp Lys Val Asp Asn Ala Leu Gln Ser Gly Asn Ser Gln
145 150 155 160

-continued

```
Glu Ser Val Thr Glu Gln Asp Ser Lys Asp Ser Thr Tyr Ser Leu Ser
                165                 170                 175

Ser Thr Leu Thr Leu Ser Lys Ala Asp Tyr Glu Lys His Lys Val Tyr
            180                 185                 190

Ala Cys Glu Val Thr His Gln Gly Leu Ser Ser Pro Val Thr Lys Ser
        195                 200                 205

Phe Asn Arg Gly Glu Cys
    210


<210> SEQ ID NO 89
<211> LENGTH: 456
<212> TYPE: PRT
<213> ORGANISM: Artificial sequence
<220> FEATURE:
<223> OTHER INFORMATION: an artificially synthesized sequence

<400> SEQUENCE: 89

Gln Val Gln Leu Gln Glu Ser Gly Pro Gly Leu Val Lys Pro Ser Glu
1               5                   10                  15

Thr Leu Ser Leu Thr Cys Thr Val Ser Gly Gly Ser Ile Ser Ser Ser
            20                  25                  30

Ser Tyr Tyr Trp Gly Trp Ile Arg Gln Pro Pro Gly Lys Gly Leu Glu
        35                  40                  45

Trp Ile Gly Ser Ile Tyr Tyr Ser Gly Ser Thr Tyr Tyr Asn Pro Ser
    50                  55                  60

Leu Lys Ser Arg Val Thr Ile Ser Val Asp Thr Ser Lys Asn Gln Phe
65                  70                  75                  80

Ser Leu Lys Leu Ser Ser Val Thr Ala Ala Asp Thr Ala Val Tyr Tyr
                85                  90                  95

Cys Ala Arg Val Pro Pro Tyr Ser Ser Ser Ser Tyr Tyr Tyr Tyr Tyr
            100                 105                 110

Tyr Tyr Met Asp Val Trp Gly Lys Gly Thr Thr Val Thr Val Ser Ser
        115                 120                 125

Ala Ser Thr Lys Gly Pro Ser Val Phe Pro Leu Ala Pro Ser Ser Lys
    130                 135                 140

Ser Thr Ser Gly Gly Thr Ala Ala Leu Gly Cys Leu Val Lys Asp Tyr
145                 150                 155                 160

Phe Pro Glu Pro Val Thr Val Ser Trp Asn Ser Gly Ala Leu Thr Ser
                165                 170                 175

Gly Val His Thr Phe Pro Ala Val Leu Gln Ser Ser Gly Leu Tyr Ser
            180                 185                 190

Leu Ser Ser Val Val Thr Val Pro Ser Ser Ser Leu Gly Thr Gln Thr
        195                 200                 205

Tyr Ile Cys Asn Val Asn His Lys Pro Ser Asn Thr Lys Val Asp Lys
    210                 215                 220

Lys Val Glu Pro Lys Ser Cys Asp Lys Thr His Thr Cys Pro Pro Cys
225                 230                 235                 240

Pro Ala Pro Glu Leu Leu Gly Gly Pro Ser Val Phe Leu Phe Pro Pro
                245                 250                 255

Lys Pro Lys Asp Thr Leu Met Ile Ser Arg Thr Pro Glu Val Thr Cys
            260                 265                 270

Val Val Val Asp Val Ser His Glu Asp Pro Glu Val Lys Phe Asn Trp
        275                 280                 285

Tyr Val Asp Gly Val Glu Val His Asn Ala Lys Thr Lys Pro Arg Glu
    290                 295                 300
```

```
Glu Gln Tyr Asn Ser Thr Tyr Arg Val Val Ser Val Leu Thr Val Leu
305                 310                 315                 320

His Gln Asp Trp Leu Asn Gly Lys Glu Tyr Lys Cys Lys Val Ser Asn
                325                 330                 335

Lys Ala Leu Pro Ala Pro Ile Glu Lys Thr Ile Ser Lys Ala Lys Gly
            340                 345                 350

Gln Pro Arg Glu Pro Gln Val Tyr Thr Leu Pro Pro Ser Arg Asp Glu
        355                 360                 365

Leu Thr Lys Asn Gln Val Ser Leu Thr Cys Leu Val Lys Gly Phe Tyr
    370                 375                 380

Pro Ser Asp Ile Ala Val Glu Trp Glu Ser Asn Gly Gln Pro Glu Asn
385                 390                 395                 400

Asn Tyr Lys Thr Thr Pro Pro Val Leu Asp Ser Asp Gly Ser Phe Phe
                405                 410                 415

Leu Tyr Ser Lys Leu Thr Val Asp Lys Ser Arg Trp Gln Gln Gly Asn
            420                 425                 430

Val Phe Ser Cys Ser Val Met His Glu Ala Leu His Asn His Tyr Thr
        435                 440                 445

Gln Lys Ser Leu Ser Leu Ser Pro
    450                 455


<210> SEQ ID NO 90
<211> LENGTH: 452
<212> TYPE: PRT
<213> ORGANISM: Artificial sequence
<220> FEATURE:
<223> OTHER INFORMATION: an artificially synthesized sequence

<400> SEQUENCE: 90

Glu Val Gln Leu Val Glu Ser Gly Gly Gly Leu Val Gln Pro Gly Gly
1               5                   10                  15

Ser Leu Arg Leu Ser Cys Ala Ala Ser Gly Phe Thr Phe Ser Ser Tyr
            20                  25                  30

Ala Met Ser Trp Val Arg Gln Ala Pro Gly Lys Gly Leu Glu Trp Val
        35                  40                  45

Ser Ala Ile Ser Gly Ser Gly Gly Ser Thr Tyr Tyr Ala Asp Ser Val
    50                  55                  60

Lys Gly Arg Phe Thr Ile Ser Arg Asp Asn Ser Lys Asn Thr Leu Tyr
65                  70                  75                  80

Leu Gln Met Asn Ser Leu Arg Ala Glu Asp Thr Ala Val Tyr Tyr Cys
                85                  90                  95

Ala Lys Ala Pro Gly Ile Gln Leu Trp Leu Arg Pro Ser Tyr Phe Asp
            100                 105                 110

Tyr Trp Gly Gln Gly Thr Leu Val Thr Val Ser Ser Ala Ser Thr Lys
        115                 120                 125

Gly Pro Ser Val Phe Pro Leu Ala Pro Ser Ser Lys Ser Thr Ser Gly
    130                 135                 140

Gly Thr Ala Ala Leu Gly Cys Leu Val Lys Asp Tyr Phe Pro Glu Pro
145                 150                 155                 160

Val Thr Val Ser Trp Asn Ser Gly Ala Leu Thr Ser Gly Val His Thr
                165                 170                 175

Phe Pro Ala Val Leu Gln Ser Ser Gly Leu Tyr Ser Leu Ser Ser Val
            180                 185                 190

Val Thr Val Pro Ser Ser Ser Leu Gly Thr Gln Thr Tyr Ile Cys Asn
        195                 200                 205
```

```
Val Asn His Lys Pro Ser Asn Thr Lys Val Asp Lys Lys Val Glu Pro
    210                 215                 220

Lys Ser Cys Asp Lys Thr His Thr Cys Pro Pro Cys Pro Ala Pro Glu
225                 230                 235                 240

Leu Leu Gly Gly Pro Ser Val Phe Leu Phe Pro Pro Lys Pro Lys Asp
                245                 250                 255

Thr Leu Met Ile Ser Arg Thr Pro Glu Val Thr Cys Val Val Val Asp
            260                 265                 270

Val Ser His Glu Asp Pro Glu Val Lys Phe Asn Trp Tyr Val Asp Gly
        275                 280                 285

Val Glu Val His Asn Ala Lys Thr Lys Pro Arg Glu Glu Gln Tyr Asn
    290                 295                 300

Ser Thr Tyr Arg Val Val Ser Val Leu Thr Val Leu His Gln Asp Trp
305                 310                 315                 320

Leu Asn Gly Lys Glu Tyr Lys Cys Lys Val Ser Asn Lys Ala Leu Pro
                325                 330                 335

Ala Pro Ile Glu Lys Thr Ile Ser Lys Ala Lys Gly Gln Pro Arg Glu
            340                 345                 350

Pro Gln Val Tyr Thr Leu Pro Pro Ser Arg Asp Glu Leu Thr Lys Asn
        355                 360                 365

Gln Val Ser Leu Thr Cys Leu Val Lys Gly Phe Tyr Pro Ser Asp Ile
    370                 375                 380

Ala Val Glu Trp Glu Ser Asn Gly Gln Pro Glu Asn Asn Tyr Lys Thr
385                 390                 395                 400

Thr Pro Pro Val Leu Asp Ser Asp Gly Ser Phe Phe Leu Tyr Ser Lys
                405                 410                 415

Leu Thr Val Asp Lys Ser Arg Trp Gln Gln Gly Asn Val Phe Ser Cys
            420                 425                 430

Ser Val Met His Glu Ala Leu His Asn His Tyr Thr Gln Lys Ser Leu
        435                 440                 445

Ser Leu Ser Pro
    450
```

<210> SEQ ID NO 91
<211> LENGTH: 447
<212> TYPE: PRT
<213> ORGANISM: Artificial sequence
<220> FEATURE:
<223> OTHER INFORMATION: an artificially synthesized sequence

<400> SEQUENCE: 91

```
Gln Val Gln Leu Gln Glu Ser Gly Pro Gly Leu Val Lys Pro Trp Glu
1               5                   10                  15

Thr Leu Ser Leu Thr Cys Thr Val Ala Gly Asp Ser Ile Lys Tyr Ser
            20                  25                  30

Ser Asp Tyr Trp Gly Trp Val Arg Gln Ser Pro Gly Lys Gly Leu Glu
        35                  40                  45

Trp Ile Gly Ser Ser Tyr Leu Ser Gly Thr Thr Gln Tyr Asn Pro Ser
    50                  55                  60

Leu Lys Ser Arg Val Thr Met Ser Val Asp Thr Ser Lys Asn Gln Phe
65                  70                  75                  80

Ser Leu Arg Leu Ser Ser Val Thr Ala Ala Asp Thr Ala Val Tyr Tyr
                85                  90                  95

Cys Ala Arg His Arg Gly Pro Thr Gly Val Asp Gln Trp Gly Gln Gly
            100                 105                 110
```

```
Thr Leu Val Thr Val Ser Ser Ala Ser Thr Lys Gly Pro Ser Val Phe
        115                 120                 125

Pro Leu Ala Pro Ser Ser Lys Ser Thr Ser Gly Gly Thr Ala Ala Leu
    130                 135                 140

Gly Cys Leu Val Lys Asp Tyr Phe Pro Glu Pro Val Thr Val Ser Trp
145                 150                 155                 160

Asn Ser Gly Ala Leu Thr Ser Gly Val His Thr Phe Pro Ala Val Leu
                165                 170                 175

Gln Ser Ser Gly Leu Tyr Ser Leu Ser Ser Val Val Thr Val Pro Ser
            180                 185                 190

Ser Ser Leu Gly Thr Gln Thr Tyr Ile Cys Asn Val Asn His Lys Pro
        195                 200                 205

Ser Asn Thr Lys Val Asp Lys Lys Val Glu Pro Lys Ser Cys Asp Lys
    210                 215                 220

Thr His Thr Cys Pro Pro Cys Pro Ala Pro Glu Leu Leu Gly Gly Pro
225                 230                 235                 240

Ser Val Phe Leu Phe Pro Pro Lys Pro Lys Asp Thr Leu Met Ile Ser
                245                 250                 255

Arg Thr Pro Glu Val Thr Cys Val Val Val Asp Val Ser His Glu Asp
            260                 265                 270

Pro Glu Val Lys Phe Asn Trp Tyr Val Asp Gly Val Glu Val His Asn
        275                 280                 285

Ala Lys Thr Lys Pro Arg Glu Glu Gln Tyr Asn Ser Thr Tyr Arg Val
    290                 295                 300

Val Ser Val Leu Thr Val Leu His Gln Asp Trp Leu Asn Gly Lys Glu
305                 310                 315                 320

Tyr Lys Cys Lys Val Ser Asn Lys Ala Leu Pro Ala Pro Ile Glu Lys
                325                 330                 335

Thr Ile Ser Lys Ala Lys Gly Gln Pro Arg Glu Pro Gln Val Tyr Thr
            340                 345                 350

Leu Pro Pro Ser Arg Asp Glu Leu Thr Lys Asn Gln Val Ser Leu Thr
        355                 360                 365

Cys Leu Val Lys Gly Phe Tyr Pro Ser Asp Ile Ala Val Glu Trp Glu
    370                 375                 380

Ser Asn Gly Gln Pro Glu Asn Asn Tyr Lys Thr Thr Pro Pro Val Leu
385                 390                 395                 400

Asp Ser Asp Gly Ser Phe Phe Leu Tyr Ser Lys Leu Thr Val Asp Lys
                405                 410                 415

Ser Arg Trp Gln Gln Gly Asn Val Phe Ser Cys Ser Val Met His Glu
            420                 425                 430

Ala Leu His Asn His Tyr Thr Gln Lys Ser Leu Ser Leu Ser Pro
        435                 440                 445
```

<210> SEQ ID NO 92
<211> LENGTH: 449
<212> TYPE: PRT
<213> ORGANISM: Artificial sequence
<220> FEATURE:
<223> OTHER INFORMATION: an artificially synthesized sequence

<400> SEQUENCE: 92

```
Glu Val Gln Leu Val Gln Ser Gly Gly Gly Leu Val Gln Pro Gly Arg
1               5                   10                  15

Ser Leu Thr Leu Ser Cys Val Gly Tyr Gly Phe Thr Phe His Glu Asn
            20                  25                  30
```

-continued

```
Asp Met His Trp Leu Arg Gln Pro Leu Gly Lys Gly Leu Glu Trp Val
        35                  40                  45

Ser His Ile Gly Trp Asn Asn Asn Arg Val Ala Tyr Ala Asp Ser Val
    50                  55                  60

Lys Gly Arg Phe Ala Val Ser Arg Asp Asn Ala Lys Asn Ser Leu Phe
65                  70                  75                  80

Leu His Met Asn Ser Leu Arg Pro Asp Asp Thr Ala Leu Tyr Tyr Cys
                85                  90                  95

Ala Lys Asp Leu Gly Asn Pro Ile Tyr Asp Val Phe Asp Val Trp Gly
            100                 105                 110

Gln Gly Thr Met Val Thr Val Ser Ser Ala Ser Thr Lys Gly Pro Ser
        115                 120                 125

Val Phe Pro Leu Ala Pro Ser Ser Lys Ser Thr Ser Gly Gly Thr Ala
    130                 135                 140

Ala Leu Gly Cys Leu Val Lys Asp Tyr Phe Pro Glu Pro Val Thr Val
145                 150                 155                 160

Ser Trp Asn Ser Gly Ala Leu Thr Ser Gly Val His Thr Phe Pro Ala
                165                 170                 175

Val Leu Gln Ser Ser Gly Leu Tyr Ser Leu Ser Ser Val Val Thr Val
            180                 185                 190

Pro Ser Ser Ser Leu Gly Thr Gln Thr Tyr Ile Cys Asn Val Asn His
        195                 200                 205

Lys Pro Ser Asn Thr Lys Val Asp Lys Lys Val Glu Pro Lys Ser Cys
    210                 215                 220

Asp Lys Thr His Thr Cys Pro Pro Cys Pro Ala Pro Glu Leu Leu Gly
225                 230                 235                 240

Gly Pro Ser Val Phe Leu Phe Pro Pro Lys Pro Lys Asp Thr Leu Met
                245                 250                 255

Ile Ser Arg Thr Pro Glu Val Thr Cys Val Val Val Asp Val Ser His
            260                 265                 270

Glu Asp Pro Glu Val Lys Phe Asn Trp Tyr Val Asp Gly Val Glu Val
        275                 280                 285

His Asn Ala Lys Thr Lys Pro Arg Glu Glu Gln Tyr Asn Ser Thr Tyr
    290                 295                 300

Arg Val Val Ser Val Leu Thr Val Leu His Gln Asp Trp Leu Asn Gly
305                 310                 315                 320

Lys Glu Tyr Lys Cys Lys Val Ser Asn Lys Ala Leu Pro Ala Pro Ile
                325                 330                 335

Glu Lys Thr Ile Ser Lys Ala Lys Gly Gln Pro Arg Glu Pro Gln Val
            340                 345                 350

Tyr Thr Leu Pro Pro Ser Arg Asp Glu Leu Thr Lys Asn Gln Val Ser
        355                 360                 365

Leu Thr Cys Leu Val Lys Gly Phe Tyr Pro Ser Asp Ile Ala Val Glu
    370                 375                 380

Trp Glu Ser Asn Gly Gln Pro Glu Asn Asn Tyr Lys Thr Thr Pro Pro
385                 390                 395                 400

Val Leu Asp Ser Asp Gly Ser Phe Phe Leu Tyr Ser Lys Leu Thr Val
                405                 410                 415

Asp Lys Ser Arg Trp Gln Gln Gly Asn Val Phe Ser Cys Ser Val Met
            420                 425                 430

His Glu Ala Leu His Asn His Tyr Thr Gln Lys Ser Leu Ser Leu Ser
        435                 440                 445

Pro
```

<210> SEQ ID NO 93
<211> LENGTH: 452
<212> TYPE: PRT
<213> ORGANISM: Artificial sequence
<220> FEATURE:
<223> OTHER INFORMATION: an artificially synthesized sequence

<400> SEQUENCE: 93

Gln Pro Ala Leu Ala Gln Met Gln Leu Val Glu Ser Gly Gly Gly Leu
1 5 10 15

Val Gln Pro Gly Arg Ser Leu Arg Leu Ser Cys Ala Ala Ser Gly Phe
20 25 30

Thr Phe Asp Asp Tyr Ala Met His Trp Val Arg Gln Ala Pro Gly Lys
35 40 45

Gly Leu Glu Trp Val Ser Gly Ile Ser Trp Asn Ser Gly Ser Ile Gly
50 55 60

Tyr Ala Asp Ser Val Lys Gly Arg Phe Thr Ile Ser Arg Asp Asn Ala
65 70 75 80

Lys Asn Ser Leu Tyr Leu Gln Met Asn Ser Leu Arg Ala Glu Asp Thr
85 90 95

Ala Leu Tyr Tyr Cys Ala Arg Glu Gly Val Leu Gly Asp Ala Phe Asp
100 105 110

Ile Trp Gly Gln Gly Thr Met Val Thr Val Ser Ser Ala Ser Thr Lys
115 120 125

Gly Pro Ser Val Phe Pro Leu Ala Pro Ser Ser Lys Ser Thr Ser Gly
130 135 140

Gly Thr Ala Ala Leu Gly Cys Leu Val Lys Asp Tyr Phe Pro Glu Pro
145 150 155 160

Val Thr Val Ser Trp Asn Ser Gly Ala Leu Thr Ser Gly Val His Thr
165 170 175

Phe Pro Ala Val Leu Gln Ser Ser Gly Leu Tyr Ser Leu Ser Ser Val
180 185 190

Val Thr Val Pro Ser Ser Ser Leu Gly Thr Gln Thr Tyr Ile Cys Asn
195 200 205

Val Asn His Lys Pro Ser Asn Thr Lys Val Asp Lys Lys Val Glu Pro
210 215 220

Lys Ser Cys Asp Lys Thr His Thr Cys Pro Pro Cys Pro Ala Pro Glu
225 230 235 240

Leu Leu Gly Gly Pro Ser Val Phe Leu Phe Pro Pro Lys Pro Lys Asp
245 250 255

Thr Leu Met Ile Ser Arg Thr Pro Glu Val Thr Cys Val Val Val Asp
260 265 270

Val Ser His Glu Asp Pro Glu Val Lys Phe Asn Trp Tyr Val Asp Gly
275 280 285

Val Glu Val His Asn Ala Lys Thr Lys Pro Arg Glu Glu Gln Tyr Asn
290 295 300

Ser Thr Tyr Arg Val Val Ser Val Leu Thr Val Leu His Gln Asp Trp
305 310 315 320

Leu Asn Gly Lys Glu Tyr Lys Cys Lys Val Ser Asn Lys Ala Leu Pro
325 330 335

Ala Pro Ile Glu Lys Thr Ile Ser Lys Ala Lys Gly Gln Pro Arg Glu
340 345 350

Pro Gln Val Tyr Thr Leu Pro Pro Ser Arg Asp Glu Leu Thr Lys Asn
355 360 365

Gln Val Ser Leu Thr Cys Leu Val Lys Gly Phe Tyr Pro Ser Asp Ile
370 375 380

Ala Val Glu Trp Glu Ser Asn Gly Gln Pro Glu Asn Asn Tyr Lys Thr
385 390 395 400

Thr Pro Pro Val Leu Asp Ser Asp Gly Ser Phe Phe Leu Tyr Ser Lys
405 410 415

Leu Thr Val Asp Lys Ser Arg Trp Gln Gln Gly Asn Val Phe Ser Cys
420 425 430

Ser Val Met His Glu Ala Leu His Asn His Tyr Thr Gln Lys Ser Leu
435 440 445

Ser Leu Ser Pro
450

<210> SEQ ID NO 94
<211> LENGTH: 454
<212> TYPE: PRT
<213> ORGANISM: Artificial sequence
<220> FEATURE:
<223> OTHER INFORMATION: an artificially synthesized sequence

<400> SEQUENCE: 94

Gln Val Gln Leu Gln Gln Ser Gly Pro Gly Leu Val Lys Pro Ser Gln
1 5 10 15

Thr Leu Ser Leu Thr Cys Ala Ile Ser Gly Asp Ser Val Ser Ser Asn
20 25 30

Ser Ala Ala Trp Asn Trp Ile Arg Gln Ser Pro Ser Arg Gly Leu Glu
35 40 45

Trp Leu Gly Arg Thr Tyr Tyr Arg Ser Lys Trp Tyr Asn Asp Tyr Ala
50 55 60

Val Ser Val Lys Ser Arg Ile Thr Ile Asn Pro Asp Thr Ser Lys Asn
65 70 75 80

Gln Phe Ser Leu Gln Leu Asn Ser Val Thr Pro Glu Asp Thr Ala Val
85 90 95

Tyr Tyr Cys Ala Arg Arg Val Arg Ser Gly Ser Tyr Tyr Tyr Tyr Gly
100 105 110

Met Asp Val Trp Gly Gln Gly Thr Thr Val Thr Val Ser Ser Ala Ser
115 120 125

Thr Lys Gly Pro Ser Val Phe Pro Leu Ala Pro Ser Ser Lys Ser Thr
130 135 140

Ser Gly Gly Thr Ala Ala Leu Gly Cys Leu Val Lys Asp Tyr Phe Pro
145 150 155 160

Glu Pro Val Thr Val Ser Trp Asn Ser Gly Ala Leu Thr Ser Gly Val
165 170 175

His Thr Phe Pro Ala Val Leu Gln Ser Ser Gly Leu Tyr Ser Leu Ser
180 185 190

Ser Val Val Thr Val Pro Ser Ser Ser Leu Gly Thr Gln Thr Tyr Ile
195 200 205

Cys Asn Val Asn His Lys Pro Ser Asn Thr Lys Val Asp Lys Lys Val
210 215 220

Glu Pro Lys Ser Cys Asp Lys Thr His Thr Cys Pro Pro Cys Pro Ala
225 230 235 240

Pro Glu Leu Leu Gly Gly Pro Ser Val Phe Leu Phe Pro Pro Lys Pro
245 250 255

Lys Asp Thr Leu Met Ile Ser Arg Thr Pro Glu Val Thr Cys Val Val
260 265 270

Val Asp Val Ser His Glu Asp Pro Glu Val Lys Phe Asn Trp Tyr Val
        275                 280                 285

Asp Gly Val Glu Val His Asn Ala Lys Thr Lys Pro Arg Glu Glu Gln
    290                 295                 300

Tyr Asn Ser Thr Tyr Arg Val Val Ser Val Leu Thr Val Leu His Gln
305                 310                 315                 320

Asp Trp Leu Asn Gly Lys Glu Tyr Lys Cys Lys Val Ser Asn Lys Ala
                325                 330                 335

Leu Pro Ala Pro Ile Glu Lys Thr Ile Ser Lys Ala Lys Gly Gln Pro
            340                 345                 350

Arg Glu Pro Gln Val Tyr Thr Leu Pro Pro Ser Arg Asp Glu Leu Thr
        355                 360                 365

Lys Asn Gln Val Ser Leu Thr Cys Leu Val Lys Gly Phe Tyr Pro Ser
    370                 375                 380

Asp Ile Ala Val Glu Trp Glu Ser Asn Gly Gln Pro Glu Asn Asn Tyr
385                 390                 395                 400

Lys Thr Thr Pro Pro Val Leu Asp Ser Asp Gly Ser Phe Phe Leu Tyr
                405                 410                 415

Ser Lys Leu Thr Val Asp Lys Ser Arg Trp Gln Gln Gly Asn Val Phe
            420                 425                 430

Ser Cys Ser Val Met His Glu Ala Leu His Asn His Tyr Thr Gln Lys
        435                 440                 445

Ser Leu Ser Leu Ser Pro
    450

<210> SEQ ID NO 95
<211> LENGTH: 450
<212> TYPE: PRT
<213> ORGANISM: Artificial sequence
<220> FEATURE:
<223> OTHER INFORMATION: an artificially synthesized sequence

<400> SEQUENCE: 95

Gln Val Gln Leu Gln Glu Ser Gly Pro Gly Leu Val Lys Pro Ser Gln
1               5                   10                  15

Thr Leu Ser Leu Thr Cys Ala Ile Ser Gly Asp Ser Val Ser Ser Asn
            20                  25                  30

Ser Ala Ala Trp Asn Trp Ile Arg Gln Ser Pro Ser Arg Gly Leu Glu
        35                  40                  45

Trp Leu Gly Arg Thr Tyr Tyr Arg Ser Lys Trp Tyr Asn Asp Tyr Ala
    50                  55                  60

Val Ser Val Lys Ser Arg Ile Thr Ile Ile Pro Asp Thr Ser Lys Asn
65                  70                  75                  80

Gln Phe Ser Leu Gln Leu Asn Ser Val Thr Pro Glu Asp Thr Ala Val
                85                  90                  95

Tyr Tyr Cys Ala Arg Lys Asp Pro Arg Val Trp Ala Phe Asp Ile Trp
            100                 105                 110

Gly Gln Gly Thr Met Val Thr Val Ser Ser Ala Ser Thr Lys Gly Pro
        115                 120                 125

Ser Val Phe Pro Leu Ala Pro Ser Ser Lys Ser Thr Ser Gly Gly Thr
    130                 135                 140

Ala Ala Leu Gly Cys Leu Val Lys Asp Tyr Phe Pro Glu Pro Val Thr
145                 150                 155                 160

Val Ser Trp Asn Ser Gly Ala Leu Thr Ser Gly Val His Thr Phe Pro
                165                 170                 175

```
Ala Val Leu Gln Ser Ser Gly Leu Tyr Ser Leu Ser Ser Val Val Thr
            180                 185                 190

Val Pro Ser Ser Ser Leu Gly Thr Gln Thr Tyr Ile Cys Asn Val Asn
        195                 200                 205

His Lys Pro Ser Asn Thr Lys Val Asp Lys Lys Val Glu Pro Lys Ser
    210                 215                 220

Cys Asp Lys Thr His Thr Cys Pro Pro Cys Pro Ala Pro Glu Leu Leu
225                 230                 235                 240

Gly Gly Pro Ser Val Phe Leu Phe Pro Pro Lys Pro Lys Asp Thr Leu
                245                 250                 255

Met Ile Ser Arg Thr Pro Glu Val Thr Cys Val Val Val Asp Val Ser
            260                 265                 270

His Glu Asp Pro Glu Val Lys Phe Asn Trp Tyr Val Asp Gly Val Glu
        275                 280                 285

Val His Asn Ala Lys Thr Lys Pro Arg Glu Glu Gln Tyr Asn Ser Thr
    290                 295                 300

Tyr Arg Val Val Ser Val Leu Thr Val Leu His Gln Asp Trp Leu Asn
305                 310                 315                 320

Gly Lys Glu Tyr Lys Cys Lys Val Ser Asn Lys Ala Leu Pro Ala Pro
                325                 330                 335

Ile Glu Lys Thr Ile Ser Lys Ala Lys Gly Gln Pro Arg Glu Pro Gln
            340                 345                 350

Val Tyr Thr Leu Pro Pro Ser Arg Asp Glu Leu Thr Lys Asn Gln Val
        355                 360                 365

Ser Leu Thr Cys Leu Val Lys Gly Phe Tyr Pro Ser Asp Ile Ala Val
    370                 375                 380

Glu Trp Glu Ser Asn Gly Gln Pro Glu Asn Asn Tyr Lys Thr Thr Pro
385                 390                 395                 400

Pro Val Leu Asp Ser Asp Gly Ser Phe Phe Leu Tyr Ser Lys Leu Thr
                405                 410                 415

Val Asp Lys Ser Arg Trp Gln Gln Gly Asn Val Phe Ser Cys Ser Val
            420                 425                 430

Met His Glu Ala Leu His Asn His Tyr Thr Gln Lys Ser Leu Ser Leu
        435                 440                 445

Ser Pro
    450


<210> SEQ ID NO 96
<211> LENGTH: 449
<212> TYPE: PRT
<213> ORGANISM: Artificial sequence
<220> FEATURE:
<223> OTHER INFORMATION: an artificially synthesized sequence

<400> SEQUENCE: 96

Glu Val Gln Leu Val Gln Ser Gly Ala Glu Val Lys Lys Pro Gly Ser
1               5                   10                  15

Ser Val Lys Val Ser Cys Lys Ala Ser Gly Gly Thr Phe Ser Ser Tyr
            20                  25                  30

Ala Ile Ser Trp Val Arg Gln Ala Pro Gly Gln Gly Leu Glu Trp Met
        35                  40                  45

Gly Arg Ile Ile Pro Val Leu Ala Ile Ala Asn Tyr Ala Gln Lys Phe
    50                  55                  60

Gln Gly Arg Val Thr Ile Thr Ala Asp Lys Ser Thr His Thr Ala Tyr
65                  70                  75                  80
```

```
Met Glu Leu Ser Ser Leu Arg Ser Gly Asp Thr Ala Val Tyr Tyr Cys
                85                  90                  95

Ala Arg Asp Ser Gly Tyr Ser Ala Gly Tyr Gly Gly Asp Tyr Trp Gly
            100                 105                 110

Gln Gly Thr Leu Val Thr Val Ser Ser Ala Ser Thr Lys Gly Pro Ser
        115                 120                 125

Val Phe Pro Leu Ala Pro Ser Ser Lys Ser Thr Ser Gly Gly Thr Ala
    130                 135                 140

Ala Leu Gly Cys Leu Val Lys Asp Tyr Phe Pro Glu Pro Val Thr Val
145                 150                 155                 160

Ser Trp Asn Ser Gly Ala Leu Thr Ser Gly Val His Thr Phe Pro Ala
                165                 170                 175

Val Leu Gln Ser Ser Gly Leu Tyr Ser Leu Ser Ser Val Val Thr Val
            180                 185                 190

Pro Ser Ser Ser Leu Gly Thr Gln Thr Tyr Ile Cys Asn Val Asn His
        195                 200                 205

Lys Pro Ser Asn Thr Lys Val Asp Lys Lys Val Glu Pro Lys Ser Cys
    210                 215                 220

Asp Lys Thr His Thr Cys Pro Pro Cys Pro Ala Pro Glu Leu Leu Gly
225                 230                 235                 240

Gly Pro Ser Val Phe Leu Phe Pro Pro Lys Pro Lys Asp Thr Leu Met
                245                 250                 255

Ile Ser Arg Thr Pro Glu Val Thr Cys Val Val Val Asp Val Ser His
            260                 265                 270

Glu Asp Pro Glu Val Lys Phe Asn Trp Tyr Val Asp Gly Val Glu Val
        275                 280                 285

His Asn Ala Lys Thr Lys Pro Arg Glu Glu Gln Tyr Asn Ser Thr Tyr
    290                 295                 300

Arg Val Val Ser Val Leu Thr Val Leu His Gln Asp Trp Leu Asn Gly
305                 310                 315                 320

Lys Glu Tyr Lys Cys Lys Val Ser Asn Lys Ala Leu Pro Ala Pro Ile
                325                 330                 335

Glu Lys Thr Ile Ser Lys Ala Lys Gly Gln Pro Arg Glu Pro Gln Val
            340                 345                 350

Tyr Thr Leu Pro Pro Ser Arg Asp Glu Leu Thr Lys Asn Gln Val Ser
        355                 360                 365

Leu Thr Cys Leu Val Lys Gly Phe Tyr Pro Ser Asp Ile Ala Val Glu
    370                 375                 380

Trp Glu Ser Asn Gly Gln Pro Glu Asn Asn Tyr Lys Thr Thr Pro Pro
385                 390                 395                 400

Val Leu Asp Ser Asp Gly Ser Phe Phe Leu Tyr Ser Lys Leu Thr Val
                405                 410                 415

Asp Lys Ser Arg Trp Gln Gln Gly Asn Val Phe Ser Cys Ser Val Met
            420                 425                 430

His Glu Ala Leu His Asn His Tyr Thr Gln Lys Ser Leu Ser Leu Ser
        435                 440                 445

Pro
```

<210> SEQ ID NO 97
<211> LENGTH: 447
<212> TYPE: PRT
<213> ORGANISM: Artificial sequence
<220> FEATURE:
<223> OTHER INFORMATION: an artificially synthesized sequence

<400> SEQUENCE: 97

```
Glu Val Gln Leu Val Glu Ser Gly Gly Asp Leu Val Gln Pro Gly Gly
1               5                   10                  15

Ser Leu Arg Leu Ser Cys Ala Ala Ser Gly Phe Thr Phe Lys Thr Tyr
            20                  25                  30

Trp Met Asn Trp Val Arg Gln Ala Pro Gly Lys Gly Leu Glu Trp Val
        35                  40                  45

Ala Asn Ile Arg Ala Asp Gly Gly Gln Met Tyr Tyr Ala Asp Ser Val
    50                  55                  60

Lys Gly Arg Phe Thr Ile Ser Arg Asp Asn Ala Lys Asp Ser Leu Tyr
65                  70                  75                  80

Leu Gln Met Ile Ser Leu Arg Pro Glu Asp Thr Ala Leu Tyr Tyr Cys
                85                  90                  95

Ala Arg Asp Pro Phe Ala Ser Gly Gly Leu Asp Gln Trp Gly Gln Gly
            100                 105                 110

Thr Met Val Thr Val Ser Ser Ala Ser Thr Lys Gly Pro Ser Val Phe
        115                 120                 125

Pro Leu Ala Pro Ser Ser Lys Ser Thr Ser Gly Gly Thr Ala Ala Leu
    130                 135                 140

Gly Cys Leu Val Lys Asp Tyr Phe Pro Glu Pro Val Thr Val Ser Trp
145                 150                 155                 160

Asn Ser Gly Ala Leu Thr Ser Gly Val His Thr Phe Pro Ala Val Leu
                165                 170                 175

Gln Ser Ser Gly Leu Tyr Ser Leu Ser Ser Val Val Thr Val Pro Ser
            180                 185                 190

Ser Ser Leu Gly Thr Gln Thr Tyr Ile Cys Asn Val Asn His Lys Pro
        195                 200                 205

Ser Asn Thr Lys Val Asp Lys Lys Val Glu Pro Lys Ser Cys Asp Lys
    210                 215                 220

Thr His Thr Cys Pro Pro Cys Pro Ala Pro Glu Leu Leu Gly Gly Pro
225                 230                 235                 240

Ser Val Phe Leu Phe Pro Pro Lys Pro Lys Asp Thr Leu Met Ile Ser
                245                 250                 255

Arg Thr Pro Glu Val Thr Cys Val Val Val Asp Val Ser His Glu Asp
            260                 265                 270

Pro Glu Val Lys Phe Asn Trp Tyr Val Asp Gly Val Glu Val His Asn
        275                 280                 285

Ala Lys Thr Lys Pro Arg Glu Glu Gln Tyr Asn Ser Thr Tyr Arg Val
    290                 295                 300

Val Ser Val Leu Thr Val Leu His Gln Asp Trp Leu Asn Gly Lys Glu
305                 310                 315                 320

Tyr Lys Cys Lys Val Ser Asn Lys Ala Leu Pro Ala Pro Ile Glu Lys
                325                 330                 335

Thr Ile Ser Lys Ala Lys Gly Gln Pro Arg Glu Pro Gln Val Tyr Thr
            340                 345                 350

Leu Pro Pro Ser Arg Asp Glu Leu Thr Lys Asn Gln Val Ser Leu Thr
        355                 360                 365

Cys Leu Val Lys Gly Phe Tyr Pro Ser Asp Ile Ala Val Glu Trp Glu
    370                 375                 380

Ser Asn Gly Gln Pro Glu Asn Asn Tyr Lys Thr Thr Pro Pro Val Leu
385                 390                 395                 400

Asp Ser Asp Gly Ser Phe Phe Leu Tyr Ser Lys Leu Thr Val Asp Lys
```

```
                405                 410                 415

Ser Arg Trp Gln Gln Gly Asn Val Phe Ser Cys Ser Val Met His Glu
            420                 425                 430

Ala Leu His Asn His Tyr Thr Gln Lys Ser Leu Ser Leu Ser Pro
        435                 440                 445


<210> SEQ ID NO 98
<211> LENGTH: 450
<212> TYPE: PRT
<213> ORGANISM: Artificial sequence
<220> FEATURE:
<223> OTHER INFORMATION: an artificially synthesized sequence

<400> SEQUENCE: 98

Glu Val Gln Leu Val Glu Ser Gly Gly Gly Val Val Gln Pro Gly Arg
1               5                   10                  15

Ser Leu Arg Leu Ser Cys Ala Ala Ser Gly Phe Thr Phe Ser Ser Tyr
            20                  25                  30

Gly Met Glu Trp Val Arg Gln Ala Pro Gly Lys Gly Leu Glu Trp Val
        35                  40                  45

Ala Leu Ile Ser His Asp Gly Asn Asn Lys Tyr Tyr Ala Asp Ser Val
    50                  55                  60

Glu Gly Arg Phe Thr Ile Ser Arg Asp Asn Ser Arg Asn Thr Leu Tyr
65                  70                  75                  80

Leu Gln Met Asn Ser Leu Arg Ala Glu Asp Thr Ala Val Tyr Tyr Cys
                85                  90                  95

Ala Lys Asp Arg Val Arg Tyr Phe Asp Ser Tyr Gly Met Asp Val Trp
            100                 105                 110

Gly His Gly Thr Thr Val Thr Val Ser Ser Ala Ser Thr Lys Gly Pro
        115                 120                 125

Ser Val Phe Pro Leu Ala Pro Ser Ser Lys Ser Thr Ser Gly Gly Thr
    130                 135                 140

Ala Ala Leu Gly Cys Leu Val Lys Asp Tyr Phe Pro Glu Pro Val Thr
145                 150                 155                 160

Val Ser Trp Asn Ser Gly Ala Leu Thr Ser Gly Val His Thr Phe Pro
                165                 170                 175

Ala Val Leu Gln Ser Ser Gly Leu Tyr Ser Leu Ser Ser Val Val Thr
            180                 185                 190

Val Pro Ser Ser Ser Leu Gly Thr Gln Thr Tyr Ile Cys Asn Val Asn
        195                 200                 205

His Lys Pro Ser Asn Thr Lys Val Asp Lys Lys Val Glu Pro Lys Ser
    210                 215                 220

Cys Asp Lys Thr His Thr Cys Pro Pro Cys Pro Ala Pro Glu Leu Leu
225                 230                 235                 240

Gly Gly Pro Ser Val Phe Leu Phe Pro Pro Lys Pro Lys Asp Thr Leu
                245                 250                 255

Met Ile Ser Arg Thr Pro Glu Val Thr Cys Val Val Val Asp Val Ser
            260                 265                 270

His Glu Asp Pro Glu Val Lys Phe Asn Trp Tyr Val Asp Gly Val Glu
        275                 280                 285

Val His Asn Ala Lys Thr Lys Pro Arg Glu Glu Gln Tyr Asn Ser Thr
    290                 295                 300

Tyr Arg Val Val Ser Val Leu Thr Val Leu His Gln Asp Trp Leu Asn
305                 310                 315                 320

Gly Lys Glu Tyr Lys Cys Lys Val Ser Asn Lys Ala Leu Pro Ala Pro
```

```
                325                 330                 335

Ile Glu Lys Thr Ile Ser Lys Ala Lys Gly Gln Pro Arg Glu Pro Gln
            340                 345                 350

Val Tyr Thr Leu Pro Pro Ser Arg Asp Glu Leu Thr Lys Asn Gln Val
        355                 360                 365

Ser Leu Thr Cys Leu Val Lys Gly Phe Tyr Pro Ser Asp Ile Ala Val
    370                 375                 380

Glu Trp Glu Ser Asn Gly Gln Pro Glu Asn Asn Tyr Lys Thr Thr Pro
385                 390                 395                 400

Pro Val Leu Asp Ser Asp Gly Ser Phe Phe Leu Tyr Ser Lys Leu Thr
                405                 410                 415

Val Asp Lys Ser Arg Trp Gln Gln Gly Asn Val Phe Ser Cys Ser Val
            420                 425                 430

Met His Glu Ala Leu His Asn His Tyr Thr Gln Lys Ser Leu Ser Leu
        435                 440                 445

Ser Pro
    450


<210> SEQ ID NO 99
<211> LENGTH: 449
<212> TYPE: PRT
<213> ORGANISM: Artificial sequence
<220> FEATURE:
<223> OTHER INFORMATION: an artificially synthesized sequence

<400> SEQUENCE: 99

Glu Val Gln Leu Val Gln Ser Gly Ala Glu Val Lys Lys Pro Gly Glu
1               5                   10                  15

Ser Leu Arg Ile Ser Cys Lys Gly Ser Gly Tyr Ser Phe Thr Ser Phe
            20                  25                  30

Trp Ile Asn Trp Val Arg Gln Met Pro Gly Lys Gly Leu Glu Trp Met
        35                  40                  45

Gly Asn Ile Asp Pro Ser Asp Ser Tyr Thr Asn Tyr Ser Pro Ser Phe
    50                  55                  60

Gln Gly His Val Ala Ile Ser Ala Asp Lys Ser Ile Ser Thr Ala Tyr
65                  70                  75                  80

Leu His Trp Asn Ser Leu Lys Ala Ser Asp Thr Ala Met Tyr Tyr Cys
                85                  90                  95

Ala Arg His Arg Tyr Leu Gly Gln Leu Ala Pro Phe Asp Pro Trp Gly
            100                 105                 110

Gln Gly Thr Leu Val Thr Val Ser Ser Ala Ser Thr Lys Gly Pro Ser
        115                 120                 125

Val Phe Pro Leu Ala Pro Ser Ser Lys Ser Thr Ser Gly Gly Thr Ala
    130                 135                 140

Ala Leu Gly Cys Leu Val Lys Asp Tyr Phe Pro Glu Pro Val Thr Val
145                 150                 155                 160

Ser Trp Asn Ser Gly Ala Leu Thr Ser Gly Val His Thr Phe Pro Ala
                165                 170                 175

Val Leu Gln Ser Ser Gly Leu Tyr Ser Leu Ser Ser Val Val Thr Val
            180                 185                 190

Pro Ser Ser Ser Leu Gly Thr Gln Thr Tyr Ile Cys Asn Val Asn His
        195                 200                 205

Lys Pro Ser Asn Thr Lys Val Asp Lys Lys Val Glu Pro Lys Ser Cys
    210                 215                 220

Asp Lys Thr His Thr Cys Pro Pro Cys Pro Ala Pro Glu Leu Leu Gly
```

225 230 235 240

Gly Pro Ser Val Phe Leu Phe Pro Pro Lys Pro Lys Asp Thr Leu Met
245 250 255

Ile Ser Arg Thr Pro Glu Val Thr Cys Val Val Val Asp Val Ser His
260 265 270

Glu Asp Pro Glu Val Lys Phe Asn Trp Tyr Val Asp Gly Val Glu Val
275 280 285

His Asn Ala Lys Thr Lys Pro Arg Glu Glu Gln Tyr Asn Ser Thr Tyr
290 295 300

Arg Val Val Ser Val Leu Thr Val Leu His Gln Asp Trp Leu Asn Gly
305 310 315 320

Lys Glu Tyr Lys Cys Lys Val Ser Asn Lys Ala Leu Pro Ala Pro Ile
325 330 335

Glu Lys Thr Ile Ser Lys Ala Lys Gly Gln Pro Arg Glu Pro Gln Val
340 345 350

Tyr Thr Leu Pro Pro Ser Arg Asp Glu Leu Thr Lys Asn Gln Val Ser
355 360 365

Leu Thr Cys Leu Val Lys Gly Phe Tyr Pro Ser Asp Ile Ala Val Glu
370 375 380

Trp Glu Ser Asn Gly Gln Pro Glu Asn Asn Tyr Lys Thr Thr Pro Pro
385 390 395 400

Val Leu Asp Ser Asp Gly Ser Phe Phe Leu Tyr Ser Lys Leu Thr Val
405 410 415

Asp Lys Ser Arg Trp Gln Gln Gly Asn Val Phe Ser Cys Ser Val Met
420 425 430

His Glu Ala Leu His Asn His Tyr Thr Gln Lys Ser Leu Ser Leu Ser
435 440 445

Pro

<210> SEQ ID NO 100
<211> LENGTH: 214
<212> TYPE: PRT
<213> ORGANISM: Artificial sequence
<220> FEATURE:
<223> OTHER INFORMATION: an artificially synthesized sequence

<400> SEQUENCE: 100

Asp Ile Gln Met Thr Gln Ser Pro Ser Ser Leu Ser Ala Ser Val Gly
1 5 10 15

Asp Arg Val Thr Ile Thr Cys Arg Ala Ser Gln Ser Ile Glu Asp Asp
20 25 30

Leu Ala Trp Tyr Gln Gln Lys Pro Gly Lys Ala Pro Lys Leu Leu Ile
35 40 45

Tyr Glu Ala Ser Ser Leu Gln Ser Gly Val Pro Ser Arg Phe Ser Gly
50 55 60

Ser Gly Ser Gly Thr Asp Phe Thr Leu Thr Ile Ser Ser Leu Gln Pro
65 70 75 80

Glu Asp Phe Ala Thr Tyr Tyr Cys Gln Gln Arg Asp Asn Tyr Pro Leu
85 90 95

Thr Phe Gly Gln Gly Thr Lys Val Glu Ile Lys Arg Thr Val Ala Ala
100 105 110

Pro Ser Val Phe Ile Phe Pro Pro Ser Asp Glu Gln Leu Lys Ser Gly
115 120 125

Thr Ala Ser Val Val Cys Leu Leu Asn Asn Phe Tyr Pro Arg Glu Ala
130 135 140

Lys Val Gln Trp Lys Val Asp Asn Ala Leu Gln Ser Gly Asn Ser Gln
145 150 155 160

Glu Ser Val Thr Glu Gln Asp Ser Lys Asp Ser Thr Tyr Ser Leu Ser
165 170 175

Ser Thr Leu Thr Leu Ser Lys Ala Asp Tyr Glu Lys His Lys Val Tyr
180 185 190

Ala Cys Glu Val Thr His Gln Gly Leu Ser Ser Pro Val Thr Lys Ser
195 200 205

Phe Asn Arg Gly Glu Cys
210

<210> SEQ ID NO 101
<211> LENGTH: 214
<212> TYPE: PRT
<213> ORGANISM: Artificial sequence
<220> FEATURE:
<223> OTHER INFORMATION: an artificially synthesized sequence

<400> SEQUENCE: 101

Asp Ile Gln Met Thr Gln Ser Pro Ser Ser Leu Ser Ala Ser Val Gly
1 5 10 15

Asp Arg Val Thr Ile Thr Cys Arg Ala Ser Gln Ser Ile Glu Asp Asp
20 25 30

Leu Ala Trp Tyr Gln Gln Lys Pro Gly Lys Ala Pro Lys Leu Leu Ile
35 40 45

Tyr His Ala Ser Thr Leu Gln Ser Gly Val Pro Ser Arg Phe Ser Gly
50 55 60

Ser Gly Ser Gly Thr Asp Phe Thr Leu Thr Ile Ser Ser Leu Gln Pro
65 70 75 80

Glu Asp Phe Ala Thr Tyr Tyr Cys Gln Gln Ser Asp Ser Ser Pro Leu
85 90 95

Thr Phe Gly Gln Gly Thr Lys Val Glu Ile Lys Arg Thr Val Ala Ala
100 105 110

Pro Ser Val Phe Ile Phe Pro Pro Ser Asp Glu Gln Leu Lys Ser Gly
115 120 125

Thr Ala Ser Val Val Cys Leu Leu Asn Asn Phe Tyr Pro Arg Glu Ala
130 135 140

Lys Val Gln Trp Lys Val Asp Asn Ala Leu Gln Ser Gly Asn Ser Gln
145 150 155 160

Glu Ser Val Thr Glu Gln Asp Ser Lys Asp Ser Thr Tyr Ser Leu Ser
165 170 175

Ser Thr Leu Thr Leu Ser Lys Ala Asp Tyr Glu Lys His Lys Val Tyr
180 185 190

Ala Cys Glu Val Thr His Gln Gly Leu Ser Ser Pro Val Thr Lys Ser
195 200 205

Phe Asn Arg Gly Glu Cys
210

<210> SEQ ID NO 102
<211> LENGTH: 214
<212> TYPE: PRT
<213> ORGANISM: Artificial sequence
<220> FEATURE:
<223> OTHER INFORMATION: an artificially synthesized sequence

<400> SEQUENCE: 102

Asp Ile Gln Met Thr Gln Ser Pro Ser Ser Leu Ser Ala Ser Val Gly

```
1               5                   10                  15

Asp Arg Val Thr Ile Thr Cys Arg Ala Ser Gln Ser Ile Glu Asp Asp
            20                  25                  30

Leu Ala Trp Tyr Gln Gln Lys Pro Gly Lys Ala Pro Lys Leu Leu Ile
        35                  40                  45

Tyr Glu Ala Ser Ser Leu Gln Ser Gly Val Pro Ser Arg Phe Ser Gly
    50                  55                  60

Ser Gly Ser Gly Thr Asp Phe Thr Leu Thr Ile Ser Ser Leu Gln Pro
65                  70                  75                  80

Glu Asp Phe Ala Thr Tyr Tyr Cys Gln Gln Ser Ser Asn Tyr Pro Leu
                85                  90                  95

Thr Phe Gly Gln Gly Thr Lys Val Glu Ile Lys Arg Thr Val Ala Ala
            100                 105                 110

Pro Ser Val Phe Ile Phe Pro Pro Ser Asp Glu Gln Leu Lys Ser Gly
        115                 120                 125

Thr Ala Ser Val Val Cys Leu Leu Asn Asn Phe Tyr Pro Arg Glu Ala
    130                 135                 140

Lys Val Gln Trp Lys Val Asp Asn Ala Leu Gln Ser Gly Asn Ser Gln
145                 150                 155                 160

Glu Ser Val Thr Glu Gln Asp Ser Lys Asp Ser Thr Tyr Ser Leu Ser
                165                 170                 175

Ser Thr Leu Thr Leu Ser Lys Ala Asp Tyr Glu Lys His Lys Val Tyr
            180                 185                 190

Ala Cys Glu Val Thr His Gln Gly Leu Ser Ser Pro Val Thr Lys Ser
        195                 200                 205

Phe Asn Arg Gly Glu Cys
    210


<210> SEQ ID NO 103
<211> LENGTH: 214
<212> TYPE: PRT
<213> ORGANISM: Artificial sequence
<220> FEATURE:
<223> OTHER INFORMATION: an artificially synthesized sequence

<400> SEQUENCE: 103

Asp Ile Gln Met Thr Gln Ser Pro Ser Ser Leu Ser Ala Ser Val Gly
1               5                   10                  15

Asp Arg Val Thr Ile Thr Cys Arg Ala Ser Gln Ser Ile Glu Asp Asp
            20                  25                  30

Leu Ala Trp Tyr Gln Gln Lys Pro Gly Lys Ala Pro Lys Leu Leu Ile
        35                  40                  45

Tyr Glu Ala Ser Ser Leu Gln Ser Gly Val Pro Ser Arg Phe Ser Gly
    50                  55                  60

Ser Gly Ser Gly Thr Asp Phe Thr Leu Thr Ile Ser Ser Leu Gln Pro
65                  70                  75                  80

Glu Asp Phe Ala Thr Tyr Tyr Cys Gln Gln Ser Asp Gly Tyr Pro Tyr
                85                  90                  95

Thr Phe Gly Gln Gly Thr Lys Val Glu Ile Lys Arg Thr Val Ala Ala
            100                 105                 110

Pro Ser Val Phe Ile Phe Pro Pro Ser Asp Glu Gln Leu Lys Ser Gly
        115                 120                 125

Thr Ala Ser Val Val Cys Leu Leu Asn Asn Phe Tyr Pro Arg Glu Ala
    130                 135                 140

Lys Val Gln Trp Lys Val Asp Asn Ala Leu Gln Ser Gly Asn Ser Gln
```

```
145                 150                 155                 160

Glu Ser Val Thr Glu Gln Asp Ser Lys Asp Ser Thr Tyr Ser Leu Ser
                165                 170                 175

Ser Thr Leu Thr Leu Ser Lys Ala Asp Tyr Glu Lys His Lys Val Tyr
            180                 185                 190

Ala Cys Glu Val Thr His Gln Gly Leu Ser Ser Pro Val Thr Lys Ser
        195                 200                 205

Phe Asn Arg Gly Glu Cys
    210


<210> SEQ ID NO 104
<211> LENGTH: 214
<212> TYPE: PRT
<213> ORGANISM: Artificial sequence
<220> FEATURE:
<223> OTHER INFORMATION: an artificially synthesized sequence

<400> SEQUENCE: 104

Asp Ile Gln Met Thr Gln Ser Pro Ser Ser Leu Ser Ala Ser Val Gly
1               5                   10                  15

Asp Arg Val Thr Ile Thr Cys Arg Ala Ser Gln Ser Ile Glu Asp Asp
            20                  25                  30

Leu Asn Trp Tyr Gln Gln Lys Pro Gly Lys Ala Pro Lys Leu Leu Ile
        35                  40                  45

Tyr Glu Ala Ser Asn Leu Gln Ser Gly Val Pro Ser Arg Phe Ser Gly
    50                  55                  60

Ser Gly Ser Gly Thr Asp Phe Thr Leu Thr Ile Ser Ser Leu Gln Pro
65                  70                  75                  80

Glu Asp Phe Ala Thr Tyr Tyr Cys Gln Gln His Ser Ser Ser Pro Tyr
                85                  90                  95

Thr Phe Gly Gln Gly Thr Lys Val Glu Ile Lys Arg Thr Val Ala Ala
            100                 105                 110

Pro Ser Val Phe Ile Phe Pro Pro Ser Asp Glu Gln Leu Lys Ser Gly
        115                 120                 125

Thr Ala Ser Val Val Cys Leu Leu Asn Asn Phe Tyr Pro Arg Glu Ala
    130                 135                 140

Lys Val Gln Trp Lys Val Asp Asn Ala Leu Gln Ser Gly Asn Ser Gln
145                 150                 155                 160

Glu Ser Val Thr Glu Gln Asp Ser Lys Asp Ser Thr Tyr Ser Leu Ser
                165                 170                 175

Ser Thr Leu Thr Leu Ser Lys Ala Asp Tyr Glu Lys His Lys Val Tyr
            180                 185                 190

Ala Cys Glu Val Thr His Gln Gly Leu Ser Ser Pro Val Thr Lys Ser
        195                 200                 205

Phe Asn Arg Gly Glu Cys
    210


<210> SEQ ID NO 105
<211> LENGTH: 214
<212> TYPE: PRT
<213> ORGANISM: Artificial sequence
<220> FEATURE:
<223> OTHER INFORMATION: an artificially synthesized sequence

<400> SEQUENCE: 105

Asp Ile Gln Met Thr Gln Ser Pro Ser Ser Leu Ser Ala Ser Val Gly
1               5                   10                  15
```

-continued

```
Asp Arg Val Thr Ile Thr Cys Arg Ala Ser Gln Ser Ile Glu Asp Asp
            20                  25                  30

Leu Ala Trp Tyr Gln Gln Lys Pro Gly Lys Ala Pro Lys Leu Leu Ile
        35                  40                  45

Tyr Glu Ala Ser Asn Leu Gln Ser Gly Val Pro Ser Arg Phe Ser Gly
    50                  55                  60

Ser Gly Ser Gly Thr Asp Phe Thr Leu Thr Ile Ser Ser Leu Gln Pro
65                  70                  75                  80

Glu Asp Phe Ala Thr Tyr Tyr Cys Gln Gln Tyr Asp Ser Tyr Pro Tyr
                85                  90                  95

Thr Phe Gly Gln Gly Thr Lys Val Glu Ile Lys Arg Thr Val Ala Ala
            100                 105                 110

Pro Ser Val Phe Ile Phe Pro Pro Ser Asp Glu Gln Leu Lys Ser Gly
        115                 120                 125

Thr Ala Ser Val Val Cys Leu Leu Asn Asn Phe Tyr Pro Arg Glu Ala
    130                 135                 140

Lys Val Gln Trp Lys Val Asp Asn Ala Leu Gln Ser Gly Asn Ser Gln
145                 150                 155                 160

Glu Ser Val Thr Glu Gln Asp Ser Lys Asp Ser Thr Tyr Ser Leu Ser
                165                 170                 175

Ser Thr Leu Thr Leu Ser Lys Ala Asp Tyr Glu Lys His Lys Val Tyr
            180                 185                 190

Ala Cys Glu Val Thr His Gln Gly Leu Ser Ser Pro Val Thr Lys Ser
        195                 200                 205

Phe Asn Arg Gly Glu Cys
    210


<210> SEQ ID NO 106
<211> LENGTH: 214
<212> TYPE: PRT
<213> ORGANISM: Artificial sequence
<220> FEATURE:
<223> OTHER INFORMATION: an artificially synthesized sequence

<400> SEQUENCE: 106

Asp Ile Gln Met Thr Gln Ser Pro Ser Ser Leu Ser Ala Ser Val Gly
1               5                   10                  15

Asp Arg Val Thr Ile Thr Cys Arg Ala Ser Gln Ser Ile Ser Asp Asp
            20                  25                  30

Leu Ala Trp Tyr Gln Gln Lys Pro Gly Lys Ala Pro Lys Leu Leu Ile
        35                  40                  45

Tyr His Ala Ser His Leu Gln Ser Gly Val Pro Ser Arg Phe Ser Gly
    50                  55                  60

Ser Gly Ser Gly Thr Asp Phe Thr Leu Thr Ile Ser Ser Leu Gln Pro
65                  70                  75                  80

Glu Asp Phe Ala Thr Tyr Tyr Cys Gln Gln Tyr Asp Asn Ser Pro Leu
                85                  90                  95

Thr Phe Gly Gln Gly Thr Lys Val Glu Ile Lys Arg Thr Val Ala Ala
            100                 105                 110

Pro Ser Val Phe Ile Phe Pro Pro Ser Asp Glu Gln Leu Lys Ser Gly
        115                 120                 125

Thr Ala Ser Val Val Cys Leu Leu Asn Asn Phe Tyr Pro Arg Glu Ala
    130                 135                 140

Lys Val Gln Trp Lys Val Asp Asn Ala Leu Gln Ser Gly Asn Ser Gln
145                 150                 155                 160
```

Glu Ser Val Thr Glu Gln Asp Ser Lys Asp Ser Thr Tyr Ser Leu Ser
165 170 175

Ser Thr Leu Thr Leu Ser Lys Ala Asp Tyr Glu Lys His Lys Val Tyr
180 185 190

Ala Cys Glu Val Thr His Gln Gly Leu Ser Ser Pro Val Thr Lys Ser
195 200 205

Phe Asn Arg Gly Glu Cys
210

<210> SEQ ID NO 107
<211> LENGTH: 214
<212> TYPE: PRT
<213> ORGANISM: Artificial sequence
<220> FEATURE:
<223> OTHER INFORMATION: an artificially synthesized sequence

<400> SEQUENCE: 107

Asp Ile Gln Met Thr Gln Ser Pro Ser Ser Leu Ser Ala Ser Val Gly
1 5 10 15

Asp Arg Val Thr Ile Thr Cys Arg Ala Ser Gln Ser Ile Ser Asp Asp
20 25 30

Leu Ala Trp Tyr Gln Gln Lys Pro Gly Lys Ala Pro Lys Leu Leu Ile
35 40 45

Tyr His Ala Ser Asn Leu Gln Ser Gly Val Pro Ser Arg Phe Ser Gly
50 55 60

Ser Gly Ser Gly Thr Asp Phe Thr Leu Thr Ile Ser Ser Leu Gln Pro
65 70 75 80

Glu Asp Phe Ala Thr Tyr Tyr Cys Gln Gln Tyr Asp Asn Tyr Pro Tyr
85 90 95

Thr Phe Gly Gln Gly Thr Lys Val Glu Ile Lys Arg Thr Val Ala Ala
100 105 110

Pro Ser Val Phe Ile Phe Pro Pro Ser Asp Glu Gln Leu Lys Ser Gly
115 120 125

Thr Ala Ser Val Val Cys Leu Leu Asn Asn Phe Tyr Pro Arg Glu Ala
130 135 140

Lys Val Gln Trp Lys Val Asp Asn Ala Leu Gln Ser Gly Asn Ser Gln
145 150 155 160

Glu Ser Val Thr Glu Gln Asp Ser Lys Asp Ser Thr Tyr Ser Leu Ser
165 170 175

Ser Thr Leu Thr Leu Ser Lys Ala Asp Tyr Glu Lys His Lys Val Tyr
180 185 190

Ala Cys Glu Val Thr His Gln Gly Leu Ser Ser Pro Val Thr Lys Ser
195 200 205

Phe Asn Arg Gly Glu Cys
210

<210> SEQ ID NO 108
<211> LENGTH: 214
<212> TYPE: PRT
<213> ORGANISM: Artificial sequence
<220> FEATURE:
<223> OTHER INFORMATION: an artificially synthesized sequence

<400> SEQUENCE: 108

Asp Ile Gln Met Thr Gln Ser Pro Ser Ser Leu Ser Ala Ser Val Gly
1 5 10 15

Asp Arg Val Thr Ile Thr Cys Arg Ala Ser Gln Ser Ile Glu Asp Asp
20 25 30

```
Leu Asn Trp Tyr Gln Gln Lys Pro Gly Lys Ala Pro Lys Leu Leu Ile
        35                  40                  45

Tyr Glu Ala Ser Ser Leu Gln Ser Gly Val Pro Ser Arg Phe Ser Gly
    50                  55                  60

Ser Gly Ser Gly Thr Asp Phe Thr Leu Thr Ile Ser Ser Leu Gln Pro
65                  70                  75                  80

Glu Asp Phe Ala Thr Tyr Tyr Cys Gln Gln Arg Asp Ser Ser Pro Tyr
                85                  90                  95

Thr Phe Gly Gln Gly Thr Lys Val Glu Ile Lys Arg Thr Val Ala Ala
            100                 105                 110

Pro Ser Val Phe Ile Phe Pro Pro Ser Asp Glu Gln Leu Lys Ser Gly
        115                 120                 125

Thr Ala Ser Val Val Cys Leu Leu Asn Asn Phe Tyr Pro Arg Glu Ala
    130                 135                 140

Lys Val Gln Trp Lys Val Asp Asn Ala Leu Gln Ser Gly Asn Ser Gln
145                 150                 155                 160

Glu Ser Val Thr Glu Gln Asp Ser Lys Asp Ser Thr Tyr Ser Leu Ser
                165                 170                 175

Ser Thr Leu Thr Leu Ser Lys Ala Asp Tyr Glu Lys His Lys Val Tyr
            180                 185                 190

Ala Cys Glu Val Thr His Gln Gly Leu Ser Ser Pro Val Thr Lys Ser
        195                 200                 205

Phe Asn Arg Gly Glu Cys
    210


<210> SEQ ID NO 109
<211> LENGTH: 214
<212> TYPE: PRT
<213> ORGANISM: Artificial sequence
<220> FEATURE:
<223> OTHER INFORMATION: an artificially synthesized sequence

<400> SEQUENCE: 109

Asp Ile Gln Met Thr Gln Ser Pro Ser Ser Leu Ser Ala Ser Val Gly
1               5                   10                  15

Asp Arg Val Thr Ile Thr Cys Arg Ala Ser Gln Ser Ile Glu Asp Asp
            20                  25                  30

Leu Asn Trp Tyr Gln Gln Lys Pro Gly Lys Ala Pro Lys Leu Leu Ile
        35                  40                  45

Tyr Glu Ala Ser Ser Leu Gln Ser Gly Val Pro Ser Arg Phe Ser Gly
    50                  55                  60

Ser Gly Ser Gly Thr Asp Phe Thr Leu Thr Ile Ser Ser Leu Gln Pro
65                  70                  75                  80

Glu Asp Phe Ala Thr Tyr Tyr Cys Gln Gln Ser Asn Asp Tyr Pro Tyr
                85                  90                  95

Thr Phe Gly Gln Gly Thr Lys Val Glu Ile Lys Arg Thr Val Ala Ala
            100                 105                 110

Pro Ser Val Phe Ile Phe Pro Pro Ser Asp Glu Gln Leu Lys Ser Gly
        115                 120                 125

Thr Ala Ser Val Val Cys Leu Leu Asn Asn Phe Tyr Pro Arg Glu Ala
    130                 135                 140

Lys Val Gln Trp Lys Val Asp Asn Ala Leu Gln Ser Gly Asn Ser Gln
145                 150                 155                 160

Glu Ser Val Thr Glu Gln Asp Ser Lys Asp Ser Thr Tyr Ser Leu Ser
                165                 170                 175
```

```
Ser Thr Leu Thr Leu Ser Lys Ala Asp Tyr Glu Lys His Lys Val Tyr
            180                 185                 190

Ala Cys Glu Val Thr His Gln Gly Leu Ser Ser Pro Val Thr Lys Ser
        195                 200                 205

Phe Asn Arg Gly Glu Cys
    210


<210> SEQ ID NO 110
<211> LENGTH: 214
<212> TYPE: PRT
<213> ORGANISM: Artificial sequence
<220> FEATURE:
<223> OTHER INFORMATION: an artificially synthesized sequence

<400> SEQUENCE: 110

Asp Ile Gln Met Thr Gln Ser Pro Ser Ser Leu Ser Ala Ser Val Gly
1               5                   10                  15

Asp Arg Val Thr Ile Thr Cys Arg Ala Ser Gln Ser Ile Glu Asp Asp
            20                  25                  30

Leu Ala Trp Tyr Gln Gln Lys Pro Gly Lys Ala Pro Lys Leu Leu Ile
        35                  40                  45

Tyr Glu Ala Ser Ser Leu Gln Ser Gly Val Pro Ser Arg Phe Ser Gly
    50                  55                  60

Ser Gly Ser Gly Thr Asp Phe Thr Leu Thr Ile Ser Ser Leu Gln Pro
65                  70                  75                  80

Glu Asp Phe Ala Thr Tyr Tyr Cys Gln Gln His Asp Asn Tyr Pro Tyr
                85                  90                  95

Thr Phe Gly Gln Gly Thr Lys Val Glu Ile Lys Arg Thr Val Ala Ala
            100                 105                 110

Pro Ser Val Phe Ile Phe Pro Pro Ser Asp Glu Gln Leu Lys Ser Gly
        115                 120                 125

Thr Ala Ser Val Val Cys Leu Leu Asn Asn Phe Tyr Pro Arg Glu Ala
    130                 135                 140

Lys Val Gln Trp Lys Val Asp Asn Ala Leu Gln Ser Gly Asn Ser Gln
145                 150                 155                 160

Glu Ser Val Thr Glu Gln Asp Ser Lys Asp Ser Thr Tyr Ser Leu Ser
                165                 170                 175

Ser Thr Leu Thr Leu Ser Lys Ala Asp Tyr Glu Lys His Lys Val Tyr
            180                 185                 190

Ala Cys Glu Val Thr His Gln Gly Leu Ser Ser Pro Val Thr Lys Ser
        195                 200                 205

Phe Asn Arg Gly Glu Cys
    210


<210> SEQ ID NO 111
<211> LENGTH: 447
<212> TYPE: PRT
<213> ORGANISM: Artificial sequence
<220> FEATURE:
<223> OTHER INFORMATION: an artificially synthesized sequence

<400> SEQUENCE: 111

Gln Val Gln Leu Gln Glu Ser Gly Pro Gly Leu Val Arg Pro Ser Gln
1               5                   10                  15

Thr Leu Ser Leu Thr Cys Thr Val Ser Gly Tyr Ser Ile Thr Ser Asp
            20                  25                  30

His Ala Trp Ser Trp Val Arg Gln Pro Pro Gly Arg Gly Leu Glu Trp
```

```
        35                  40                  45

Ile Gly Tyr Ile Ser Tyr Ser Gly Ile Thr Thr Tyr Asn Pro Ser Leu
    50                  55                  60

Lys Ser Arg Val Thr Met Leu Arg Asp Thr Ser Lys Asn Gln Phe Ser
65                  70                  75                  80

Leu Arg Leu Ser Ser Val Thr Ala Ala Asp Thr Ala Val Tyr Tyr Cys
                85                  90                  95

Ala Arg Ser Leu Ala Arg Thr Thr Ala Met Asp Tyr Trp Gly Gln Gly
            100                 105                 110

Ser Leu Val Thr Val Ser Ser Ala Ser Thr Lys Gly Pro Ser Val Phe
        115                 120                 125

Pro Leu Ala Pro Ser Ser Lys Ser Thr Ser Gly Gly Thr Ala Ala Leu
    130                 135                 140

Gly Cys Leu Val Lys Asp Tyr Phe Pro Glu Pro Val Thr Val Ser Trp
145                 150                 155                 160

Asn Ser Gly Ala Leu Thr Ser Gly Val His Thr Phe Pro Ala Val Leu
                165                 170                 175

Gln Ser Ser Gly Leu Tyr Ser Leu Ser Ser Val Val Thr Val Pro Ser
            180                 185                 190

Ser Ser Leu Gly Thr Gln Thr Tyr Ile Cys Asn Val Asn His Lys Pro
        195                 200                 205

Ser Asn Thr Lys Val Asp Lys Lys Val Glu Pro Lys Ser Cys Asp Lys
    210                 215                 220

Thr His Thr Cys Pro Pro Cys Pro Ala Pro Glu Leu Leu Gly Gly Pro
225                 230                 235                 240

Ser Val Phe Leu Phe Pro Pro Lys Pro Lys Asp Thr Leu Met Ile Ser
                245                 250                 255

Arg Thr Pro Glu Val Thr Cys Val Val Val Asp Val Ser His Glu Asp
            260                 265                 270

Pro Glu Val Lys Phe Asn Trp Tyr Val Asp Gly Val Glu Val His Asn
        275                 280                 285

Ala Lys Thr Lys Pro Arg Glu Glu Gln Tyr Asn Ser Thr Tyr Arg Val
    290                 295                 300

Val Ser Val Leu Thr Val Leu His Gln Asp Trp Leu Asn Gly Lys Glu
305                 310                 315                 320

Tyr Lys Cys Lys Val Ser Asn Lys Ala Leu Pro Ala Pro Ile Glu Lys
                325                 330                 335

Thr Ile Ser Lys Ala Lys Gly Gln Pro Arg Glu Pro Gln Val Tyr Thr
            340                 345                 350

Leu Pro Pro Ser Arg Asp Glu Leu Thr Lys Asn Gln Val Ser Leu Thr
        355                 360                 365

Cys Leu Val Lys Gly Phe Tyr Pro Ser Asp Ile Ala Val Glu Trp Glu
    370                 375                 380

Ser Asn Gly Gln Pro Glu Asn Asn Tyr Lys Thr Thr Pro Pro Val Leu
385                 390                 395                 400

Asp Ser Asp Gly Ser Phe Phe Leu Tyr Ser Lys Leu Thr Val Asp Lys
                405                 410                 415

Ser Arg Trp Gln Gln Gly Asn Val Phe Ser Cys Ser Val Met His Glu
            420                 425                 430

Ala Leu His Asn His Tyr Thr Gln Lys Ser Leu Ser Leu Ser Pro
        435                 440                 445
```

<210> SEQ ID NO 112

<211> LENGTH: 214
<212> TYPE: PRT
<213> ORGANISM: Artificial sequence
<220> FEATURE:
<223> OTHER INFORMATION: an artificially synthesized sequence

<400> SEQUENCE: 112

```
Asp Ile Gln Met Thr Gln Ser Pro Ser Ser Leu Ser Ala Ser Val Gly
1               5                   10                  15

Asp Arg Val Thr Ile Thr Cys Arg Ala Ser Gln Asp Ile Ser Ser Tyr
            20                  25                  30

Leu Asn Trp Tyr Gln Gln Lys Pro Gly Lys Ala Pro Lys Leu Leu Ile
        35                  40                  45

Tyr Tyr Thr Ser Arg Leu His Ser Gly Val Pro Ser Arg Phe Ser Gly
    50                  55                  60

Ser Gly Ser Gly Thr Asp Phe Thr Phe Thr Ile Ser Ser Leu Gln Pro
65                  70                  75                  80

Glu Asp Ile Ala Thr Tyr Tyr Cys Gln Gln Gly Asn Thr Leu Pro Tyr
                85                  90                  95

Thr Phe Gly Gln Gly Thr Lys Val Glu Ile Lys Arg Thr Val Ala Ala
            100                 105                 110

Pro Ser Val Phe Ile Phe Pro Pro Ser Asp Glu Gln Leu Lys Ser Gly
        115                 120                 125

Thr Ala Ser Val Val Cys Leu Leu Asn Asn Phe Tyr Pro Arg Glu Ala
    130                 135                 140

Lys Val Gln Trp Lys Val Asp Asn Ala Leu Gln Ser Gly Asn Ser Gln
145                 150                 155                 160

Glu Ser Val Thr Glu Gln Asp Ser Lys Asp Ser Thr Tyr Ser Leu Ser
                165                 170                 175

Ser Thr Leu Thr Leu Ser Lys Ala Asp Tyr Glu Lys His Lys Val Tyr
            180                 185                 190

Ala Cys Glu Val Thr His Gln Gly Leu Ser Ser Pro Val Thr Lys Ser
        195                 200                 205

Phe Asn Arg Gly Glu Cys
    210
```

<210> SEQ ID NO 113
<211> LENGTH: 447
<212> TYPE: PRT
<213> ORGANISM: Artificial sequence
<220> FEATURE:
<223> OTHER INFORMATION: an artificially synthesized sequence

<400> SEQUENCE: 113

```
Gln Val Gln Leu Gln Glu Ser Gly Pro Gly Leu Val Lys Pro Ser Glu
1               5                   10                  15

Thr Leu Ser Leu Thr Cys Ala Val Ser Gly Tyr Ser Ile Ser Asp Asp
            20                  25                  30

Gln Ala Trp Ser Trp Val Arg Gln Pro Pro Gly Glu Gly Leu Glu Trp
        35                  40                  45

Ile Gly Tyr Ile Ser Tyr Ser Gly Ile Thr Asn Tyr Asn Pro Ser Leu
    50                  55                  60

Lys Gly Arg Val Thr Ile Ser Arg Asp Thr Ser Lys Asn Gln Phe Ser
65                  70                  75                  80

Leu Lys Leu Ser Ser Val Thr Ala Ala Asp Thr Ala Ala Tyr Tyr Cys
                85                  90                  95

Ala Arg Ser Leu Ala Arg Thr Thr Ala Met Asp Tyr Trp Gly Glu Gly
```

```
            100                 105                 110

Thr Leu Val Thr Val Ser Ser Ala Ser Thr Lys Gly Pro Ser Val Phe
        115                 120                 125

Pro Leu Ala Pro Ser Ser Lys Ser Thr Ser Gly Gly Thr Ala Ala Leu
    130                 135                 140

Gly Cys Leu Val Lys Asp Tyr Phe Pro Glu Pro Val Thr Val Ser Trp
145                 150                 155                 160

Asn Ser Gly Ala Leu Thr Ser Gly Val His Thr Phe Pro Ala Val Leu
                165                 170                 175

Gln Ser Ser Gly Leu Tyr Ser Leu Ser Ser Val Val Thr Val Pro Ser
            180                 185                 190

Ser Ser Leu Gly Thr Gln Thr Tyr Ile Cys Asn Val Asn His Lys Pro
        195                 200                 205

Ser Asn Thr Lys Val Asp Lys Lys Val Glu Pro Lys Ser Cys Asp Lys
    210                 215                 220

Thr His Thr Cys Pro Pro Cys Pro Ala Pro Glu Leu Leu Gly Gly Pro
225                 230                 235                 240

Ser Val Phe Leu Phe Pro Pro Lys Pro Lys Asp Thr Leu Met Ile Ser
                245                 250                 255

Arg Thr Pro Glu Val Thr Cys Val Val Val Asp Val Ser His Glu Asp
            260                 265                 270

Pro Glu Val Lys Phe Asn Trp Tyr Val Asp Gly Val Glu Val His Asn
        275                 280                 285

Ala Lys Thr Lys Pro Arg Glu Glu Gln Tyr Asn Ser Thr Tyr Arg Val
    290                 295                 300

Val Ser Val Leu Thr Val Leu His Gln Asp Trp Leu Asn Gly Lys Glu
305                 310                 315                 320

Tyr Lys Cys Lys Val Ser Asn Lys Ala Leu Pro Ala Pro Ile Glu Lys
                325                 330                 335

Thr Ile Ser Lys Ala Lys Gly Gln Pro Arg Glu Pro Gln Val Tyr Thr
            340                 345                 350

Leu Pro Pro Ser Arg Asp Glu Leu Thr Lys Asn Gln Val Ser Leu Thr
        355                 360                 365

Cys Leu Val Lys Gly Phe Tyr Pro Ser Asp Ile Ala Val Glu Trp Glu
    370                 375                 380

Ser Asn Gly Gln Pro Glu Asn Asn Tyr Lys Thr Thr Pro Pro Val Leu
385                 390                 395                 400

Asp Ser Asp Gly Ser Phe Phe Leu Tyr Ser Lys Leu Thr Val Asp Lys
                405                 410                 415

Ser Arg Trp Gln Gln Gly Asn Val Phe Ser Cys Ser Val Met His Glu
            420                 425                 430

Ala Leu His Asn His Tyr Thr Gln Lys Ser Leu Ser Leu Ser Pro
        435                 440                 445


<210> SEQ ID NO 114
<211> LENGTH: 214
<212> TYPE: PRT
<213> ORGANISM: Artificial sequence
<220> FEATURE:
<223> OTHER INFORMATION: an artificially synthesized sequence

<400> SEQUENCE: 114

Asp Ile Gln Met Thr Gln Ser Pro Ser Ser Leu Ser Ala Ser Val Gly
1               5                   10                  15

Asp Ser Val Thr Ile Thr Cys Gln Ala Ser Gln Asp Ile Ser Ser Tyr
```

```
            20                  25                  30

Leu Asn Trp Tyr Gln Gln Lys Pro Gly Lys Ala Pro Glu Leu Leu Ile
        35                  40                  45

Tyr Tyr Gly Ser Glu Leu His Ser Gly Val Pro Ser Arg Phe Ser Gly
    50                  55                  60

Ser Gly Ser Gly Thr Asp Phe Thr Phe Thr Ile Ser Ser Leu Glu Ala
65                  70                  75                  80

Glu Asp Ala Ala Thr Tyr Tyr Cys Gln Gln Gly Asn Ser Leu Pro Tyr
                85                  90                  95

Thr Phe Gly Gln Gly Thr Lys Val Glu Ile Glu Arg Thr Val Ala Ala
            100                 105                 110

Pro Ser Val Phe Ile Phe Pro Pro Ser Asp Glu Gln Leu Lys Ser Gly
        115                 120                 125

Thr Ala Ser Val Val Cys Leu Leu Asn Asn Phe Tyr Pro Arg Glu Ala
    130                 135                 140

Lys Val Gln Trp Lys Val Asp Asn Ala Leu Gln Ser Gly Asn Ser Gln
145                 150                 155                 160

Glu Ser Val Thr Glu Gln Asp Ser Lys Asp Ser Thr Tyr Ser Leu Ser
                165                 170                 175

Ser Thr Leu Thr Leu Ser Lys Ala Asp Tyr Glu Lys His Lys Val Tyr
            180                 185                 190

Ala Cys Glu Val Thr His Gln Gly Leu Ser Ser Pro Val Thr Lys Ser
        195                 200                 205

Phe Asn Arg Gly Glu Cys
    210


<210> SEQ ID NO 115
<211> LENGTH: 453
<212> TYPE: PRT
<213> ORGANISM: Artificial sequence
<220> FEATURE:
<223> OTHER INFORMATION: an artificially synthesized sequence

<400> SEQUENCE: 115

Gln Val Gln Leu Val Gln Ser Gly Ala Glu Val Lys Lys Pro Gly Ser
1               5                   10                  15

Ser Val Lys Val Ser Cys Lys Ala Ser Gly Gly Thr Phe Ser Ser Tyr
            20                  25                  30

Ala Ile Ser Trp Val Arg Gln Ala Pro Gly Gln Gly Leu Glu Trp Met
        35                  40                  45

Gly Gly Ile Ile Pro Ile Phe Gly Thr Ala Asn Tyr Ala Gln Lys Phe
    50                  55                  60

Gln Gly Arg Val Thr Ile Thr Ala Asp Glu Ser Thr Ser Thr Ala Tyr
65                  70                  75                  80

Met Glu Leu Ser Ser Leu Arg Ser Glu Asp Thr Ala Val Tyr Tyr Cys
                85                  90                  95

Ala Arg Glu Arg Asp Tyr Tyr Asp Ser Ser Gly Tyr Tyr Asp Ala Phe
            100                 105                 110

Asp Ile Trp Gly Gln Gly Thr Met Val Thr Val Ser Ser Ala Ser Thr
        115                 120                 125

Lys Gly Pro Ser Val Phe Pro Leu Ala Pro Ser Ser Lys Ser Thr Ser
    130                 135                 140

Gly Gly Thr Ala Ala Leu Gly Cys Leu Val Lys Asp Tyr Phe Pro Glu
145                 150                 155                 160

Pro Val Thr Val Ser Trp Asn Ser Gly Ala Leu Thr Ser Gly Val His
```

```
                165                 170                 175

Thr Phe Pro Ala Val Leu Gln Ser Ser Gly Leu Tyr Ser Leu Ser Ser
            180                 185                 190

Val Val Thr Val Pro Ser Ser Ser Leu Gly Thr Gln Thr Tyr Ile Cys
        195                 200                 205

Asn Val Asn His Lys Pro Ser Asn Thr Lys Val Asp Lys Lys Val Glu
    210                 215                 220

Pro Lys Ser Cys Asp Lys Thr His Thr Cys Pro Pro Cys Pro Ala Pro
225                 230                 235                 240

Glu Leu Leu Gly Gly Pro Ser Val Phe Leu Phe Pro Pro Lys Pro Lys
                245                 250                 255

Asp Thr Leu Met Ile Ser Arg Thr Pro Glu Val Thr Cys Val Val Val
            260                 265                 270

Asp Val Ser His Glu Asp Pro Glu Val Lys Phe Asn Trp Tyr Val Asp
        275                 280                 285

Gly Val Glu Val His Asn Ala Lys Thr Lys Pro Arg Glu Glu Gln Tyr
    290                 295                 300

Asn Ser Thr Tyr Arg Val Val Ser Val Leu Thr Val Leu His Gln Asp
305                 310                 315                 320

Trp Leu Asn Gly Lys Glu Tyr Lys Cys Lys Val Ser Asn Lys Ala Leu
                325                 330                 335

Pro Ala Pro Ile Glu Lys Thr Ile Ser Lys Ala Lys Gly Gln Pro Arg
            340                 345                 350

Glu Pro Gln Val Tyr Thr Leu Pro Pro Ser Arg Asp Glu Leu Thr Lys
        355                 360                 365

Asn Gln Val Ser Leu Thr Cys Leu Val Lys Gly Phe Tyr Pro Ser Asp
    370                 375                 380

Ile Ala Val Glu Trp Glu Ser Asn Gly Gln Pro Glu Asn Asn Tyr Lys
385                 390                 395                 400

Thr Thr Pro Pro Val Leu Asp Ser Asp Gly Ser Phe Phe Leu Tyr Ser
                405                 410                 415

Lys Leu Thr Val Asp Lys Ser Arg Trp Gln Gln Gly Asn Val Phe Ser
            420                 425                 430

Cys Ser Val Met His Glu Ala Leu His Asn His Tyr Thr Gln Lys Ser
        435                 440                 445

Leu Ser Leu Ser Pro
    450


<210> SEQ ID NO 116
<211> LENGTH: 214
<212> TYPE: PRT
<213> ORGANISM: Artificial sequence
<220> FEATURE:
<223> OTHER INFORMATION: an artificially synthesized sequence

<400> SEQUENCE: 116

Glu Thr Thr Val Thr Gln Ser Pro Ser Phe Leu Ser Ala Ser Val Gly
1               5                   10                  15

Asp Arg Val Thr Ile Thr Cys Ile Thr Thr Thr Asp Ile Asp Asp Asp
            20                  25                  30

Met Asn Trp Phe Gln Gln Glu Pro Gly Lys Ala Pro Lys Leu Leu Ile
        35                  40                  45

Ser Glu Gly Asn Ile Leu Arg Pro Gly Val Pro Ser Arg Phe Ser Ser
    50                  55                  60

Ser Gly Tyr Gly Thr Asp Phe Thr Leu Thr Ile Ser Lys Leu Gln Pro
```

65 70 75 80

Glu Asp Phe Ala Thr Tyr Tyr Cys Leu Gln Ser Asp Asn Leu Pro Phe
85 90 95

Thr Phe Gly Gln Gly Thr Lys Leu Glu Ile Lys Arg Thr Val Ala Ala
100 105 110

Pro Ser Val Phe Ile Phe Pro Pro Ser Asp Glu Gln Leu Lys Ser Gly
115 120 125

Thr Ala Ser Val Val Cys Leu Leu Asn Asn Phe Tyr Pro Arg Glu Ala
130 135 140

Lys Val Gln Trp Lys Val Asp Asn Ala Leu Gln Ser Gly Asn Ser Gln
145 150 155 160

Glu Ser Val Thr Glu Gln Asp Ser Lys Asp Ser Thr Tyr Ser Leu Ser
165 170 175

Ser Thr Leu Thr Leu Ser Lys Ala Asp Tyr Glu Lys His Lys Val Tyr
180 185 190

Ala Cys Glu Val Thr His Gln Gly Leu Ser Ser Pro Val Thr Lys Ser
195 200 205

Phe Asn Arg Gly Glu Cys
210

<210> SEQ ID NO 117
<211> LENGTH: 449
<212> TYPE: PRT
<213> ORGANISM: Artificial sequence
<220> FEATURE:
<223> OTHER INFORMATION: an artificially synthesized sequence

<400> SEQUENCE: 117

Gln Val Gln Leu Val Gln Ser Gly Ala Glu Val Lys Lys Pro Gly Ala
1 5 10 15

Ser Val Lys Val Ser Cys Lys Ala Ser Gly Tyr Thr Phe Thr Ser Tyr
20 25 30

Tyr Met His Trp Val Arg Gln Ala Pro Gly Gln Gly Leu Glu Trp Met
35 40 45

Gly Ile Ile Asn Pro Ser Gly Gly Ser Thr Ser Tyr Ala Gln Lys Phe
50 55 60

Gln Gly Arg Val Thr Met Thr Arg Asp Thr Ser Thr Ser Thr Val Tyr
65 70 75 80

Met Glu Leu Ser Ser Leu Arg Ser Glu Asp Thr Ala Val Tyr Tyr Cys
85 90 95

Ala Arg Asp Asp Pro Gly Gly Gly Glu Tyr Tyr Phe Asp Tyr Trp Gly
100 105 110

Gln Gly Thr Leu Val Thr Val Ser Ser Ala Ser Thr Lys Gly Pro Ser
115 120 125

Val Phe Pro Leu Ala Pro Ser Ser Lys Ser Thr Ser Gly Gly Thr Ala
130 135 140

Ala Leu Gly Cys Leu Val Lys Asp Tyr Phe Pro Glu Pro Val Thr Val
145 150 155 160

Ser Trp Asn Ser Gly Ala Leu Thr Ser Gly Val His Thr Phe Pro Ala
165 170 175

Val Leu Gln Ser Ser Gly Leu Tyr Ser Leu Ser Ser Val Val Thr Val
180 185 190

Pro Ser Ser Ser Leu Gly Thr Gln Thr Tyr Ile Cys Asn Val Asn His
195 200 205

Lys Pro Ser Asn Thr Lys Val Asp Lys Lys Val Glu Pro Lys Ser Cys

```
    210                 215                 220

Asp Lys Thr His Thr Cys Pro Pro Cys Pro Ala Pro Glu Leu Leu Gly
225                 230                 235                 240

Gly Pro Ser Val Phe Leu Phe Pro Pro Lys Pro Lys Asp Thr Leu Met
                245                 250                 255

Ile Ser Arg Thr Pro Glu Val Thr Cys Val Val Val Asp Val Ser His
            260                 265                 270

Glu Asp Pro Glu Val Lys Phe Asn Trp Tyr Val Asp Gly Val Glu Val
        275                 280                 285

His Asn Ala Lys Thr Lys Pro Arg Glu Glu Gln Tyr Asn Ser Thr Tyr
    290                 295                 300

Arg Val Val Ser Val Leu Thr Val Leu His Gln Asp Trp Leu Asn Gly
305                 310                 315                 320

Lys Glu Tyr Lys Cys Lys Val Ser Asn Lys Ala Leu Pro Ala Pro Ile
                325                 330                 335

Glu Lys Thr Ile Ser Lys Ala Lys Gly Gln Pro Arg Glu Pro Gln Val
            340                 345                 350

Tyr Thr Leu Pro Pro Ser Arg Asp Glu Leu Thr Lys Asn Gln Val Ser
        355                 360                 365

Leu Thr Cys Leu Val Lys Gly Phe Tyr Pro Ser Asp Ile Ala Val Glu
    370                 375                 380

Trp Glu Ser Asn Gly Gln Pro Glu Asn Asn Tyr Lys Thr Thr Pro Pro
385                 390                 395                 400

Val Leu Asp Ser Asp Gly Ser Phe Phe Leu Tyr Ser Lys Leu Thr Val
                405                 410                 415

Asp Lys Ser Arg Trp Gln Gln Gly Asn Val Phe Ser Cys Ser Val Met
            420                 425                 430

His Glu Ala Leu His Asn His Tyr Thr Gln Lys Ser Leu Ser Leu Ser
        435                 440                 445

Pro


<210> SEQ ID NO 118
<211> LENGTH: 217
<212> TYPE: PRT
<213> ORGANISM: Artificial sequence
<220> FEATURE:
<223> OTHER INFORMATION: an artificially synthesized sequence

<400> SEQUENCE: 118

Gln Ser Val Leu Thr Gln Pro Pro Ser Val Ser Gly Ala Pro Gly Gln
1               5                   10                  15

Arg Val Thr Ile Ser Cys Thr Gly Ser Arg Ser Asn Met Gly Ala Gly
            20                  25                  30

Tyr Asp Val His Trp Tyr Gln Leu Leu Pro Gly Ala Ala Pro Lys Leu
        35                  40                  45

Leu Ile Ser His Asn Thr His Arg Pro Ser Gly Val Pro Asp Arg Phe
    50                  55                  60

Ser Gly Ser Lys Ser Gly Ala Ser Ala Ser Leu Ala Ile Thr Gly Leu
65                  70                  75                  80

Gln Ala Glu Asp Glu Ala Asp Tyr Tyr Cys Gln Ser His Asp Ser Ser
                85                  90                  95

Leu Ser Ala Val Val Phe Gly Gly Gly Thr Lys Leu Thr Val Leu Ser
            100                 105                 110

Gln Pro Lys Ala Ala Pro Ser Val Thr Leu Phe Pro Pro Ser Ser Glu
        115                 120                 125
```

Glu Leu Gln Ala Asn Lys Ala Thr Leu Val Cys Leu Ile Ser Asp Phe
    130                 135                 140

Tyr Pro Gly Ala Val Thr Val Ala Trp Lys Ala Asp Ser Ser Pro Val
145                 150                 155                 160

Lys Ala Gly Val Glu Thr Thr Thr Pro Ser Lys Gln Ser Asn Asn Lys
                165                 170                 175

Tyr Ala Ala Ser Ser Tyr Leu Ser Leu Thr Pro Glu Gln Trp Lys Ser
            180                 185                 190

His Arg Ser Tyr Ser Cys Gln Val Thr His Glu Gly Ser Thr Val Glu
        195                 200                 205

Lys Thr Val Ala Pro Thr Glu Cys Ser
    210                 215

<210> SEQ ID NO 119
<211> LENGTH: 126
<212> TYPE: PRT
<213> ORGANISM: Artificial sequence
<220> FEATURE:
<223> OTHER INFORMATION: an artificially synthesized sequence

<400> SEQUENCE: 119

Glu Val Gln Leu Val Glu Ser Gly Gly Gly Leu Val Gln Pro Gly Gly
1               5                   10                  15

Ser Leu Arg Leu Ser Cys Ala Ala Ser Gly Phe Thr Phe Ser Ser Tyr
            20                  25                  30

Glu Met Asn Trp Val Arg Gln Ala Pro Gly Lys Gly Leu Glu Trp Val
        35                  40                  45

Ser Tyr Ile Ser Ser Ser Gly Ser Thr Ile Tyr Tyr Ala Asp Ser Val
    50                  55                  60

Lys Gly Arg Phe Thr Ile Ser Arg Asp Asn Ala Lys Asn Ser Leu Tyr
65                  70                  75                  80

Leu Gln Met Asn Ser Leu Arg Ala Glu Asp Thr Ala Val Tyr Tyr Cys
                85                  90                  95

Ala Arg Asp Ala Pro Tyr Tyr Tyr Asp Ser Ser Gly Tyr Thr Asp Ala
            100                 105                 110

Phe Asp Ile Trp Gly Gln Gly Thr Met Val Thr Val Ser Ser
        115                 120                 125

<210> SEQ ID NO 120
<211> LENGTH: 106
<212> TYPE: PRT
<213> ORGANISM: Artificial sequence
<220> FEATURE:
<223> OTHER INFORMATION: an artificially synthesized sequence

<400> SEQUENCE: 120

Glu Ile Val Leu Thr Gln Ser Pro Ala Thr Leu Ser Leu Ser Pro Gly
1               5                   10                  15

Glu Arg Ala Thr Leu Ser Cys Arg Ala Ser Gln Ser Val Ser Ser Tyr
            20                  25                  30

Leu Ala Trp Tyr Gln Gln Lys Pro Gly Gln Ala Pro Arg Leu Leu Ile
        35                  40                  45

Phe Asp Ala Ser Asn Arg Ala Ala Gly Ile Pro Ala Arg Phe Ser Gly
    50                  55                  60

Ser Gly Ser Gly Thr Asp Phe Thr Leu Thr Ile Ser Ser Leu Glu Pro
65                  70                  75                  80

Glu Asp Phe Ala Val Tyr Tyr Cys Gln Gln Phe Asp Lys Trp Val Thr

```
                85                  90                  95

Phe Gly Gly Gly Thr Thr Val Glu Ile Arg
            100                 105


<210> SEQ ID NO 121
<211> LENGTH: 454
<212> TYPE: PRT
<213> ORGANISM: Artificial sequence
<220> FEATURE:
<223> OTHER INFORMATION: an artificially synthesized sequence

<400> SEQUENCE: 121

Glu Val Gln Leu Val Glu Ser Gly Gly Gly Leu Val Gln Pro Gly Gly
1               5                   10                  15

Ser Leu Arg Leu Ser Cys Ala Ala Ser Gly Phe Thr Phe Ser Ser Tyr
            20                  25                  30

Glu Met Asn Trp Val Arg Gln Ala Pro Gly Lys Gly Leu Glu Trp Val
        35                  40                  45

Ser Tyr Ile Ser Ser Ser Gly Ser Thr Ile Tyr Tyr Ala Asp Ser Val
    50                  55                  60

Lys Gly Arg Phe Thr Ile Ser Arg Asp Asn Ala Lys Asn Ser Leu Tyr
65                  70                  75                  80

Leu Gln Met Asn Ser Leu Arg Ala Glu Asp Thr Ala Val Tyr Tyr Cys
                85                  90                  95

Ala Arg Asp Ala Pro Tyr Tyr Tyr Asp Ser Ser Gly Tyr Thr Asp Ala
            100                 105                 110

Phe Asp Ile Trp Gly Gln Gly Thr Met Val Thr Val Ser Ser Ala Ser
        115                 120                 125

Thr Lys Gly Pro Ser Val Phe Pro Leu Ala Pro Ser Ser Lys Ser Thr
    130                 135                 140

Ser Gly Gly Thr Ala Ala Leu Gly Cys Leu Val Lys Asp Tyr Phe Pro
145                 150                 155                 160

Glu Pro Val Thr Val Ser Trp Asn Ser Gly Ala Leu Thr Ser Gly Val
                165                 170                 175

His Thr Phe Pro Ala Val Leu Gln Ser Ser Gly Leu Tyr Ser Leu Ser
            180                 185                 190

Ser Val Val Thr Val Pro Ser Ser Ser Leu Gly Thr Gln Thr Tyr Ile
        195                 200                 205

Cys Asn Val Asn His Lys Pro Ser Asn Thr Lys Val Asp Lys Lys Val
    210                 215                 220

Glu Pro Lys Ser Cys Asp Lys Thr His Thr Cys Pro Pro Cys Pro Ala
225                 230                 235                 240

Pro Glu Leu Leu Gly Gly Pro Ser Val Phe Leu Phe Pro Pro Lys Pro
                245                 250                 255

Lys Asp Thr Leu Met Ile Ser Arg Thr Pro Glu Val Thr Cys Val Val
            260                 265                 270

Val Asp Val Ser His Glu Asp Pro Glu Val Lys Phe Asn Trp Tyr Val
        275                 280                 285

Asp Gly Val Glu Val His Asn Ala Lys Thr Lys Pro Arg Glu Glu Gln
    290                 295                 300

Tyr Asn Ser Thr Tyr Arg Val Val Ser Val Leu Thr Val Leu His Gln
305                 310                 315                 320

Asp Trp Leu Asn Gly Lys Glu Tyr Lys Cys Lys Val Ser Asn Lys Ala
                325                 330                 335

Leu Pro Ala Pro Ile Glu Lys Thr Ile Ser Lys Ala Lys Gly Gln Pro
```

```
            340                 345                 350

Arg Glu Pro Gln Val Tyr Thr Leu Pro Pro Ser Arg Asp Glu Leu Thr
        355                 360                 365

Lys Asn Gln Val Ser Leu Thr Cys Leu Val Lys Gly Phe Tyr Pro Ser
    370                 375                 380

Asp Ile Ala Val Glu Trp Glu Ser Asn Gly Gln Pro Glu Asn Asn Tyr
385                 390                 395                 400

Lys Thr Thr Pro Pro Val Leu Asp Ser Asp Gly Ser Phe Phe Leu Tyr
                405                 410                 415

Ser Lys Leu Thr Val Asp Lys Ser Arg Trp Gln Gln Gly Asn Val Phe
            420                 425                 430

Ser Cys Ser Val Met His Glu Ala Leu His Asn His Tyr Thr Gln Lys
        435                 440                 445

Ser Leu Ser Leu Ser Pro
    450


<210> SEQ ID NO 122
<211> LENGTH: 214
<212> TYPE: PRT
<213> ORGANISM: Artificial sequence
<220> FEATURE:
<223> OTHER INFORMATION: an artificially synthesized sequence

<400> SEQUENCE: 122

Asp Ile Gln Met Thr Gln Ser Pro Ser Ser Leu Ser Ala Ser Val Gly
1               5                   10                  15

Asp Ser Val Thr Ile Thr Cys Gln Ala Ser Thr Asp Ile Ser Ser His
            20                  25                  30

Leu Asn Trp Tyr Gln Gln Lys Pro Gly Lys Ala Pro Glu Leu Leu Ile
        35                  40                  45

Tyr Tyr Gly Ser His Leu Leu Ser Gly Val Pro Ser Arg Phe Ser Gly
    50                  55                  60

Ser Gly Ser Gly Thr Asp Phe Thr Phe Thr Ile Ser Ser Leu Glu Ala
65                  70                  75                  80

Glu Asp Ala Ala Thr Tyr Tyr Cys Gly Gln Gly Asn Arg Leu Pro Tyr
                85                  90                  95

Thr Phe Gly Gln Gly Thr Lys Val Glu Ile Glu Arg Thr Val Ala Ala
            100                 105                 110

Pro Ser Val Phe Ile Phe Pro Pro Ser Asp Glu Gln Leu Lys Ser Gly
        115                 120                 125

Thr Ala Ser Val Val Cys Leu Leu Asn Asn Phe Tyr Pro Arg Glu Ala
    130                 135                 140

Lys Val Gln Trp Lys Val Asp Asn Ala Leu Gln Ser Gly Asn Ser Gln
145                 150                 155                 160

Glu Ser Val Thr Glu Gln Asp Ser Lys Asp Ser Thr Tyr Ser Leu Ser
                165                 170                 175

Ser Thr Leu Thr Leu Ser Lys Ala Asp Tyr Glu Lys His Lys Val Tyr
            180                 185                 190

Ala Cys Glu Val Thr His Gln Gly Leu Ser Ser Pro Val Thr Lys Ser
        195                 200                 205

Phe Asn Arg Gly Glu Cys
    210


<210> SEQ ID NO 123
<211> LENGTH: 447
<212> TYPE: PRT
```

```
<213> ORGANISM: Artificial sequence
<220> FEATURE:
<223> OTHER INFORMATION: an artificially synthesized sequence

<400> SEQUENCE: 123

Gln Val Gln Leu Gln Glu Ser Gly Pro Gly Leu Val Lys Pro Ser Glu
1               5                   10                  15

Thr Leu Ser Leu Thr Cys Ala Val Ser Gly His Ser Ile Ser His Asp
            20                  25                  30

His Ala Trp Ser Trp Val Arg Gln Pro Pro Gly Glu Gly Leu Glu Trp
        35                  40                  45

Ile Gly Phe Ile Ser Tyr Ser Gly Ile Thr Asn Tyr Asn Pro Ser Leu
    50                  55                  60

Gln Gly Arg Val Thr Ile Ser Arg Asp Asn Ser Lys Asn Thr Leu Tyr
65                  70                  75                  80

Leu Gln Met Asn Ser Leu Arg Ala Glu Asp Thr Ala Val Tyr Tyr Cys
                85                  90                  95

Ala Arg Ser Leu Ala Arg Thr Thr Ala Met Asp Tyr Trp Gly Glu Gly
            100                 105                 110

Thr Leu Val Thr Val Ser Ser Ala Ser Thr Lys Gly Pro Ser Val Phe
        115                 120                 125

Pro Leu Ala Pro Ser Ser Lys Ser Thr Ser Gly Gly Thr Ala Ala Leu
    130                 135                 140

Gly Cys Leu Val Lys Asp Tyr Phe Pro Glu Pro Val Thr Val Ser Trp
145                 150                 155                 160

Asn Ser Gly Ala Leu Thr Ser Gly Val His Thr Phe Pro Ala Val Leu
                165                 170                 175

Gln Ser Ser Gly Leu Tyr Ser Leu Ser Ser Val Val Thr Val Pro Ser
            180                 185                 190

Ser Ser Leu Gly Thr Gln Thr Tyr Ile Cys Asn Val Asn His Lys Pro
        195                 200                 205

Ser Asn Thr Lys Val Asp Lys Lys Val Glu Pro Lys Ser Cys Asp Lys
    210                 215                 220

Thr His Thr Cys Pro Pro Cys Pro Ala Pro Glu Leu Arg Gly Gly Pro
225                 230                 235                 240

Lys Val Phe Leu Phe Pro Pro Lys Pro Lys Asp Thr Leu Met Ile Ser
                245                 250                 255

Arg Thr Pro Glu Val Thr Cys Val Val Val Asp Val Ser His Glu Asp
            260                 265                 270

Pro Glu Val Lys Phe Asn Trp Tyr Val Asp Gly Val Glu Val His Asn
        275                 280                 285

Ala Lys Thr Lys Pro Arg Glu Glu Gln Tyr Asn Ser Thr Tyr Arg Val
    290                 295                 300

Val Ser Val Leu Thr Val Leu His Gln Asp Trp Leu Asn Gly Lys Glu
305                 310                 315                 320

Tyr Lys Cys Lys Val Ser Asn Lys Ala Leu Pro Ala Pro Ile Glu Lys
                325                 330                 335

Thr Ile Ser Lys Ala Lys Gly Gln Pro Arg Glu Pro Gln Val Tyr Thr
            340                 345                 350

Leu Pro Pro Ser Arg Asp Glu Leu Thr Lys Asn Gln Val Ser Leu Thr
        355                 360                 365

Cys Leu Val Lys Gly Phe Tyr Pro Ser Asp Ile Ala Val Glu Trp Glu
    370                 375                 380

Ser Asn Gly Gln Pro Glu Asn Asn Tyr Lys Thr Thr Pro Pro Val Leu
```

385 390 395 400

Asp Ser Asp Gly Ser Phe Phe Leu Tyr Ser Lys Leu Thr Val Asp Lys
405 410 415

Ser Arg Trp Gln Gln Gly Asn Val Phe Ser Cys Ser Val Met His Glu
420 425 430

Ala Leu His Asn His Tyr Thr Gln Lys Ser Leu Ser Leu Ser Pro
435 440 445

<210> SEQ ID NO 124
<211> LENGTH: 447
<212> TYPE: PRT
<213> ORGANISM: Artificial sequence
<220> FEATURE:
<223> OTHER INFORMATION: an artificially synthesized sequence

<400> SEQUENCE: 124

Gln Val Gln Leu Gln Glu Ser Gly Pro Gly Leu Val Lys Pro Ser Glu
1 5 10 15

Thr Leu Ser Leu Thr Cys Ala Val Ser Gly His Ser Ile Ser His Asp
20 25 30

His Ala Trp Ser Trp Val Arg Gln Pro Pro Gly Glu Gly Leu Glu Trp
35 40 45

Ile Gly Phe Ile Ser Tyr Ser Gly Ile Thr Asn Tyr Asn Pro Ser Leu
50 55 60

Gln Gly Arg Val Thr Ile Ser Arg Asp Asn Ser Lys Asn Thr Leu Tyr
65 70 75 80

Leu Gln Met Asn Ser Leu Arg Ala Glu Asp Thr Ala Val Tyr Tyr Cys
85 90 95

Ala Arg Ser Leu Ala Arg Thr Thr Ala Met Asp Tyr Trp Gly Glu Gly
100 105 110

Thr Leu Val Thr Val Ser Ser Ala Ser Thr Lys Gly Pro Ser Val Phe
115 120 125

Pro Leu Ala Pro Ser Ser Lys Ser Thr Ser Gly Gly Thr Ala Ala Leu
130 135 140

Gly Cys Leu Val Lys Asp Tyr Phe Pro Glu Pro Val Thr Val Ser Trp
145 150 155 160

Asn Ser Gly Ala Leu Thr Ser Gly Val His Thr Phe Pro Ala Val Leu
165 170 175

Gln Ser Ser Gly Leu Tyr Ser Leu Ser Ser Val Val Thr Val Pro Ser
180 185 190

Ser Ser Leu Gly Thr Gln Thr Tyr Ile Cys Asn Val Asn His Lys Pro
195 200 205

Ser Asn Thr Lys Val Asp Lys Lys Val Glu Pro Lys Ser Cys Asp Lys
210 215 220

Thr His Thr Cys Pro Pro Cys Pro Ala Pro Glu Leu Leu Gly Gly Pro
225 230 235 240

Ser Val Phe Leu Phe Pro Pro Lys Pro Lys Asp Thr Leu Met Ile Ser
245 250 255

Arg Thr Pro Glu Val Thr Cys Val Val Val Asp Val Ser His Glu Asp
260 265 270

Pro Glu Val Lys Phe Asn Trp Tyr Val Asp Gly Val Glu Val His Asn
275 280 285

Ala Lys Thr Lys Pro Arg Glu Glu Gln Tyr Asn Ser Thr Tyr Arg Val
290 295 300

Val Ser Val Leu Thr Val Leu His Gln Asp Trp Leu Asn Gly Lys Glu 305 310 315 320

Tyr Lys Cys Lys Val Ser Asn Asp Ala Tyr Pro Ala Pro Ile Glu Lys
325 330 335

Thr Ile Ser Lys Ala Lys Gly Gln Pro Arg Glu Pro Gln Val Tyr Thr
340 345 350

Leu Pro Pro Ser Arg Asp Glu Leu Thr Lys Asn Gln Val Ser Leu Thr
355 360 365

Cys Leu Val Lys Gly Phe Tyr Pro Ser Asp Ile Ala Val Glu Trp Glu
370 375 380

Ser Asn Gly Gln Pro Glu Asn Asn Tyr Lys Thr Thr Pro Pro Val Leu
385 390 395 400

Asp Ser Asp Gly Ser Phe Phe Leu Tyr Ser Lys Leu Thr Val Asp Lys
405 410 415

Ser Arg Trp Gln Gln Gly Asn Val Phe Ser Cys Ser Val Met His Glu
420 425 430

Ala Leu His Asn His Tyr Thr Gln Lys Ser Leu Ser Leu Ser Pro
435 440 445

<210> SEQ ID NO 125
<211> LENGTH: 447
<212> TYPE: PRT
<213> ORGANISM: Artificial sequence
<220> FEATURE:
<223> OTHER INFORMATION: an artificially synthesized sequence

<400> SEQUENCE: 125

Gln Val Gln Leu Gln Glu Ser Gly Pro Gly Leu Val Lys Pro Ser Glu
1 5 10 15

Thr Leu Ser Leu Thr Cys Ala Val Ser Gly His Ser Ile Ser His Asp
20 25 30

His Ala Trp Ser Trp Val Arg Gln Pro Pro Gly Glu Gly Leu Glu Trp
35 40 45

Ile Gly Phe Ile Ser Tyr Ser Gly Ile Thr Asn Tyr Asn Pro Ser Leu
50 55 60

Gln Gly Arg Val Thr Ile Ser Arg Asp Asn Ser Lys Asn Thr Leu Tyr
65 70 75 80

Leu Gln Met Asn Ser Leu Arg Ala Glu Asp Thr Ala Val Tyr Tyr Cys
85 90 95

Ala Arg Ser Leu Ala Arg Thr Thr Ala Met Asp Tyr Trp Gly Glu Gly
100 105 110

Thr Leu Val Thr Val Ser Ser Ala Ser Thr Lys Gly Pro Ser Val Phe
115 120 125

Pro Leu Ala Pro Ser Ser Lys Ser Thr Ser Gly Gly Thr Ala Ala Leu
130 135 140

Gly Cys Leu Val Lys Asp Tyr Phe Pro Glu Pro Val Thr Val Ser Trp
145 150 155 160

Asn Ser Gly Ala Leu Thr Ser Gly Val His Thr Phe Pro Ala Val Leu
165 170 175

Gln Ser Ser Gly Leu Tyr Ser Leu Ser Ser Val Val Thr Val Pro Ser
180 185 190

Ser Ser Leu Gly Thr Gln Thr Tyr Ile Cys Asn Val Asn His Lys Pro
195 200 205

Ser Asn Thr Lys Val Asp Lys Lys Val Glu Pro Lys Ser Cys Asp Lys
210 215 220

Thr His Thr Cys Pro Pro Cys Pro Ala Pro Glu Leu Leu Gly Gly Pro

```
225                 230                 235                 240

Ser Val Phe Leu Phe Pro Pro Lys Pro Lys Asp Thr Leu Met Ile Ser
                245                 250                 255

Arg Thr Pro Glu Val Thr Cys Val Val Val Asp Val Ser His Glu Asp
            260                 265                 270

Pro Glu Val Lys Phe Asn Trp Tyr Val Asp Gly Val Glu Val His Asn
        275                 280                 285

Ala Lys Thr Lys Pro Arg Glu Glu Gln Tyr Asn Ser Thr Tyr Arg Val
    290                 295                 300

Val Ser Val Leu Thr Val Leu His Gln Asp Trp Leu Asn Gly Lys Glu
305                 310                 315                 320

Tyr Lys Cys Lys Val Ser Asn Asp Ala Tyr Pro Ala Pro Ile Glu Lys
                325                 330                 335

Thr Ile Ser Lys Ala Lys Gly Gln Pro Arg Glu Pro Gln Val Tyr Thr
            340                 345                 350

Leu Pro Pro Ser Arg Asp Glu Leu Thr Lys Asn Gln Val Ser Leu Thr
        355                 360                 365

Cys Leu Val Lys Gly Phe Tyr Pro Ser Asp Ile Ala Val Glu Trp Glu
    370                 375                 380

Ser Asn Gly Gln Pro Glu Asn Asn Tyr Lys Thr Thr Pro Pro Val Leu
385                 390                 395                 400

Asp Ser Asp Gly Ser Phe Phe Leu Tyr Ser Lys Leu Thr Val Asp Lys
                405                 410                 415

Ser Arg Trp Gln Gln Gly Asn Val Phe Ser Cys Ser Val Leu His Glu
            420                 425                 430

Ala Leu His Ser His Tyr Thr Gln Lys Ser Leu Ser Leu Ser Pro
        435                 440                 445


<210> SEQ ID NO 126
<211> LENGTH: 454
<212> TYPE: PRT
<213> ORGANISM: Artificial sequence
<220> FEATURE:
<223> OTHER INFORMATION: an artificially synthesized sequence

<400> SEQUENCE: 126

Glu Val Gln Leu Val Glu Ser Gly Gly Gly Leu Val Gln Pro Gly Gly
1               5                   10                  15

Ser Leu Arg Leu Ser Cys Ala Ala Ser Gly Phe Thr Phe Ser Ser Tyr
            20                  25                  30

Glu Met Asn Trp Val Arg Gln Ala Pro Gly Lys Gly Leu Glu Trp Val
        35                  40                  45

Ser Tyr Ile Ser Ser Ser Gly Ser Thr Ile Tyr Tyr Ala Ala Ser Val
    50                  55                  60

Lys Gly Arg Phe Thr Ile Ser Arg Asp Asn Ala Lys Asn Ser Leu Tyr
65                  70                  75                  80

Leu Gln Met Asn Ser Leu Arg Ala Glu Asp Thr Ala Val Tyr Tyr Cys
                85                  90                  95

Ala Arg Asp Ala Pro Tyr Tyr Tyr Asp Ser Ser Gly Tyr Thr Asp Ala
            100                 105                 110

Phe Asp Ile Trp Gly Gln Gly Thr Met Val Thr Val Ser Ser Ala Ser
        115                 120                 125

Thr Lys Gly Pro Ser Val Phe Pro Leu Ala Pro Ser Ser Lys Ser Thr
    130                 135                 140

Ser Gly Gly Thr Ala Ala Leu Gly Cys Leu Val Lys Asp Tyr Phe Pro
```

-continued

```
145                 150                 155                 160

Glu Pro Val Thr Val Ser Trp Asn Ser Gly Ala Leu Thr Ser Gly Val
                165                 170                 175

His Thr Phe Pro Ala Val Leu Gln Ser Ser Gly Leu Tyr Ser Leu Ser
            180                 185                 190

Ser Val Val Thr Val Pro Ser Ser Ser Leu Gly Thr Gln Thr Tyr Ile
        195                 200                 205

Cys Asn Val Asn His Lys Pro Ser Asn Thr Lys Val Asp Lys Lys Val
    210                 215                 220

Glu Pro Lys Ser Cys Asp Lys Thr His Thr Cys Pro Pro Cys Pro Ala
225                 230                 235                 240

Pro Glu Leu Leu Gly Gly Pro Ser Val Phe Leu Phe Pro Pro Lys Pro
                245                 250                 255

Lys Asp Thr Leu Met Ile Ser Arg Thr Pro Glu Val Thr Cys Val Val
            260                 265                 270

Val Asp Val Ser His Glu Asp Pro Glu Val Lys Phe Asn Trp Tyr Val
        275                 280                 285

Asp Gly Val Glu Val His Asn Ala Lys Thr Lys Pro Arg Glu Glu Gln
    290                 295                 300

Tyr Asn Ser Thr Tyr Arg Val Val Ser Val Leu Thr Val Leu His Gln
305                 310                 315                 320

Asp Trp Leu Asn Gly Lys Glu Tyr Lys Cys Lys Val Ser Asn Lys Ala
                325                 330                 335

Leu Pro Ala Pro Ile Glu Lys Thr Ile Ser Lys Ala Lys Gly Gln Pro
            340                 345                 350

Arg Glu Pro Gln Val Tyr Thr Leu Pro Pro Ser Arg Asp Glu Leu Thr
        355                 360                 365

Lys Asn Gln Val Ser Leu Thr Cys Leu Val Lys Gly Phe Tyr Pro Ser
    370                 375                 380

Asp Ile Ala Val Glu Trp Glu Ser Asn Gly Gln Pro Glu Asn Asn Tyr
385                 390                 395                 400

Lys Thr Thr Pro Pro Val Leu Asp Ser Asp Gly Ser Phe Phe Leu Tyr
                405                 410                 415

Ser Lys Leu Thr Val Asp Lys Ser Arg Trp Gln Gln Gly Asn Val Phe
            420                 425                 430

Ser Cys Ser Val Met His Glu Ala Leu His Asn His Tyr Thr Gln Lys
        435                 440                 445

Ser Leu Ser Leu Ser Pro
    450


<210> SEQ ID NO 127
<211> LENGTH: 454
<212> TYPE: PRT
<213> ORGANISM: Artificial sequence
<220> FEATURE:
<223> OTHER INFORMATION: an artificially synthesized sequence

<400> SEQUENCE: 127

Glu Val Gln Leu Val Glu Ser Gly Gly Gly Leu Val Gln Pro Gly Gly
1               5                   10                  15

Ser Leu Arg Leu Ser Cys Ala Ala Ser Gly Phe Thr Phe Ser Ser Tyr
            20                  25                  30

Glu Met Asn Trp Val Arg Gln Ala Pro Gly Lys Gly Leu Glu Trp Val
        35                  40                  45

Ser Tyr Ile Ser Ser Ser Gly Ser Thr Ile Tyr Tyr Ala Asp Ser Val
```

-continued

```
    50                  55                  60

Lys Gly Arg Phe Thr Ile Ser Arg Asp Asn Ala Lys Asn Ser Leu Tyr
65                  70                  75                  80

Leu Gln Met Asn Ser Leu Arg Ala Glu Asp Thr Ala Val Tyr Tyr Cys
                85                  90                  95

Ala Arg Ala Ala Pro Tyr Tyr Tyr Asp Ser Ser Gly Tyr Thr Asp Ala
            100                 105                 110

Phe Asp Ile Trp Gly Gln Gly Thr Met Val Thr Val Ser Ser Ala Ser
        115                 120                 125

Thr Lys Gly Pro Ser Val Phe Pro Leu Ala Pro Ser Ser Lys Ser Thr
    130                 135                 140

Ser Gly Gly Thr Ala Ala Leu Gly Cys Leu Val Lys Asp Tyr Phe Pro
145                 150                 155                 160

Glu Pro Val Thr Val Ser Trp Asn Ser Gly Ala Leu Thr Ser Gly Val
                165                 170                 175

His Thr Phe Pro Ala Val Leu Gln Ser Ser Gly Leu Tyr Ser Leu Ser
            180                 185                 190

Ser Val Val Thr Val Pro Ser Ser Ser Leu Gly Thr Gln Thr Tyr Ile
        195                 200                 205

Cys Asn Val Asn His Lys Pro Ser Asn Thr Lys Val Asp Lys Lys Val
    210                 215                 220

Glu Pro Lys Ser Cys Asp Lys Thr His Thr Cys Pro Pro Cys Pro Ala
225                 230                 235                 240

Pro Glu Leu Leu Gly Gly Pro Ser Val Phe Leu Phe Pro Pro Lys Pro
                245                 250                 255

Lys Asp Thr Leu Met Ile Ser Arg Thr Pro Glu Val Thr Cys Val Val
            260                 265                 270

Val Asp Val Ser His Glu Asp Pro Glu Val Lys Phe Asn Trp Tyr Val
        275                 280                 285

Asp Gly Val Glu Val His Asn Ala Lys Thr Lys Pro Arg Glu Glu Gln
    290                 295                 300

Tyr Asn Ser Thr Tyr Arg Val Val Ser Val Leu Thr Val Leu His Gln
305                 310                 315                 320

Asp Trp Leu Asn Gly Lys Glu Tyr Lys Cys Lys Val Ser Asn Lys Ala
                325                 330                 335

Leu Pro Ala Pro Ile Glu Lys Thr Ile Ser Lys Ala Lys Gly Gln Pro
            340                 345                 350

Arg Glu Pro Gln Val Tyr Thr Leu Pro Pro Ser Arg Asp Glu Leu Thr
        355                 360                 365

Lys Asn Gln Val Ser Leu Thr Cys Leu Val Lys Gly Phe Tyr Pro Ser
    370                 375                 380

Asp Ile Ala Val Glu Trp Glu Ser Asn Gly Gln Pro Glu Asn Asn Tyr
385                 390                 395                 400

Lys Thr Thr Pro Pro Val Leu Asp Ser Asp Gly Ser Phe Phe Leu Tyr
                405                 410                 415

Ser Lys Leu Thr Val Asp Lys Ser Arg Trp Gln Gln Gly Asn Val Phe
            420                 425                 430

Ser Cys Ser Val Met His Glu Ala Leu His Asn His Tyr Thr Gln Lys
        435                 440                 445

Ser Leu Ser Leu Ser Pro
    450

<210> SEQ ID NO 128
```

<211> LENGTH: 454
<212> TYPE: PRT
<213> ORGANISM: Artificial sequence
<220> FEATURE:
<223> OTHER INFORMATION: an artificially synthesized sequence

<400> SEQUENCE: 128

```
Glu Val Gln Leu Val Glu Ser Gly Gly Gly Leu Val Gln Pro Gly Gly
1               5                   10                  15

Ser Leu Arg Leu Ser Cys Ala Ala Ser Gly Phe Thr Phe Ser Ser Tyr
            20                  25                  30

Glu Met Asn Trp Val Arg Gln Ala Pro Gly Lys Gly Leu Glu Trp Val
        35                  40                  45

Ser Tyr Ile Ser Ser Ser Gly Ser Thr Ile Tyr Tyr Ala Asp Ser Val
    50                  55                  60

Lys Gly Arg Phe Thr Ile Ser Arg Asp Asn Ala Lys Asn Ser Leu Tyr
65                  70                  75                  80

Leu Gln Met Asn Ser Leu Arg Ala Glu Asp Thr Ala Val Tyr Tyr Cys
                85                  90                  95

Ala Arg Asp Ala Pro Tyr Tyr Tyr Ala Ser Ser Gly Tyr Thr Asp Ala
            100                 105                 110

Phe Asp Ile Trp Gly Gln Gly Thr Met Val Thr Val Ser Ser Ala Ser
        115                 120                 125

Thr Lys Gly Pro Ser Val Phe Pro Leu Ala Pro Ser Ser Lys Ser Thr
    130                 135                 140

Ser Gly Gly Thr Ala Ala Leu Gly Cys Leu Val Lys Asp Tyr Phe Pro
145                 150                 155                 160

Glu Pro Val Thr Val Ser Trp Asn Ser Gly Ala Leu Thr Ser Gly Val
                165                 170                 175

His Thr Phe Pro Ala Val Leu Gln Ser Ser Gly Leu Tyr Ser Leu Ser
            180                 185                 190

Ser Val Val Thr Val Pro Ser Ser Ser Leu Gly Thr Gln Thr Tyr Ile
        195                 200                 205

Cys Asn Val Asn His Lys Pro Ser Asn Thr Lys Val Asp Lys Lys Val
    210                 215                 220

Glu Pro Lys Ser Cys Asp Lys Thr His Thr Cys Pro Pro Cys Pro Ala
225                 230                 235                 240

Pro Glu Leu Leu Gly Gly Pro Ser Val Phe Leu Phe Pro Pro Lys Pro
                245                 250                 255

Lys Asp Thr Leu Met Ile Ser Arg Thr Pro Glu Val Thr Cys Val Val
            260                 265                 270

Val Asp Val Ser His Glu Asp Pro Glu Val Lys Phe Asn Trp Tyr Val
        275                 280                 285

Asp Gly Val Glu Val His Asn Ala Lys Thr Lys Pro Arg Glu Glu Gln
    290                 295                 300

Tyr Asn Ser Thr Tyr Arg Val Val Ser Val Leu Thr Val Leu His Gln
305                 310                 315                 320

Asp Trp Leu Asn Gly Lys Glu Tyr Lys Cys Lys Val Ser Asn Lys Ala
                325                 330                 335

Leu Pro Ala Pro Ile Glu Lys Thr Ile Ser Lys Ala Lys Gly Gln Pro
            340                 345                 350

Arg Glu Pro Gln Val Tyr Thr Leu Pro Pro Ser Arg Asp Glu Leu Thr
        355                 360                 365

Lys Asn Gln Val Ser Leu Thr Cys Leu Val Lys Gly Phe Tyr Pro Ser
    370                 375                 380
```

Asp Ile Ala Val Glu Trp Glu Ser Asn Gly Gln Pro Glu Asn Asn Tyr
385 390 395 400

Lys Thr Thr Pro Pro Val Leu Asp Ser Asp Gly Ser Phe Phe Leu Tyr
405 410 415

Ser Lys Leu Thr Val Asp Lys Ser Arg Trp Gln Gln Gly Asn Val Phe
420 425 430

Ser Cys Ser Val Met His Glu Ala Leu His Asn His Tyr Thr Gln Lys
435 440 445

Ser Leu Ser Leu Ser Pro
450

<210> SEQ ID NO 129
<211> LENGTH: 454
<212> TYPE: PRT
<213> ORGANISM: Artificial sequence
<220> FEATURE:
<223> OTHER INFORMATION: an artificially synthesized sequence

<400> SEQUENCE: 129

Glu Val Gln Leu Val Glu Ser Gly Gly Gly Leu Val Gln Pro Gly Gly
1 5 10 15

Ser Leu Arg Leu Ser Cys Ala Ala Ser Gly Phe Thr Phe Ser Ser Tyr
20 25 30

Glu Met Asn Trp Val Arg Gln Ala Pro Gly Lys Gly Leu Glu Trp Val
35 40 45

Ser Tyr Ile Ser Ser Ser Gly Ser Thr Ile Tyr Tyr Ala Asp Ser Val
50 55 60

Lys Gly Arg Phe Thr Ile Ser Arg Asp Asn Ala Lys Asn Ser Leu Tyr
65 70 75 80

Leu Gln Met Asn Ser Leu Arg Ala Glu Asp Thr Ala Val Tyr Tyr Cys
85 90 95

Ala Arg Asp Ala Pro Tyr Tyr Tyr Asp Ser Ser Gly Tyr Thr Ala Ala
100 105 110

Phe Asp Ile Trp Gly Gln Gly Thr Met Val Thr Val Ser Ser Ala Ser
115 120 125

Thr Lys Gly Pro Ser Val Phe Pro Leu Ala Pro Ser Ser Lys Ser Thr
130 135 140

Ser Gly Gly Thr Ala Ala Leu Gly Cys Leu Val Lys Asp Tyr Phe Pro
145 150 155 160

Glu Pro Val Thr Val Ser Trp Asn Ser Gly Ala Leu Thr Ser Gly Val
165 170 175

His Thr Phe Pro Ala Val Leu Gln Ser Ser Gly Leu Tyr Ser Leu Ser
180 185 190

Ser Val Val Thr Val Pro Ser Ser Ser Leu Gly Thr Gln Thr Tyr Ile
195 200 205

Cys Asn Val Asn His Lys Pro Ser Asn Thr Lys Val Asp Lys Lys Val
210 215 220

Glu Pro Lys Ser Cys Asp Lys Thr His Thr Cys Pro Pro Cys Pro Ala
225 230 235 240

Pro Glu Leu Leu Gly Gly Pro Ser Val Phe Leu Phe Pro Pro Lys Pro
245 250 255

Lys Asp Thr Leu Met Ile Ser Arg Thr Pro Glu Val Thr Cys Val Val
260 265 270

Val Asp Val Ser His Glu Asp Pro Glu Val Lys Phe Asn Trp Tyr Val
275 280 285

```
Asp Gly Val Glu Val His Asn Ala Lys Thr Lys Pro Arg Glu Glu Gln
    290                 295                 300

Tyr Asn Ser Thr Tyr Arg Val Val Ser Val Leu Thr Val Leu His Gln
305                 310                 315                 320

Asp Trp Leu Asn Gly Lys Glu Tyr Lys Cys Lys Val Ser Asn Lys Ala
                325                 330                 335

Leu Pro Ala Pro Ile Glu Lys Thr Ile Ser Lys Ala Lys Gly Gln Pro
            340                 345                 350

Arg Glu Pro Gln Val Tyr Thr Leu Pro Pro Ser Arg Asp Glu Leu Thr
        355                 360                 365

Lys Asn Gln Val Ser Leu Thr Cys Leu Val Lys Gly Phe Tyr Pro Ser
    370                 375                 380

Asp Ile Ala Val Glu Trp Glu Ser Asn Gly Gln Pro Glu Asn Asn Tyr
385                 390                 395                 400

Lys Thr Thr Pro Pro Val Leu Asp Ser Asp Gly Ser Phe Phe Leu Tyr
                405                 410                 415

Ser Lys Leu Thr Val Asp Lys Ser Arg Trp Gln Gln Gly Asn Val Phe
            420                 425                 430

Ser Cys Ser Val Met His Glu Ala Leu His Asn His Tyr Thr Gln Lys
        435                 440                 445

Ser Leu Ser Leu Ser Pro
    450


<210> SEQ ID NO 130
<211> LENGTH: 454
<212> TYPE: PRT
<213> ORGANISM: Artificial sequence
<220> FEATURE:
<223> OTHER INFORMATION: an artificially synthesized sequence

<400> SEQUENCE: 130

Glu Val Gln Leu Val Glu Ser Gly Gly Gly Leu Val Gln Pro Gly Gly
1               5                   10                  15

Ser Leu Arg Leu Ser Cys Ala Ala Ser Gly Phe Thr Phe Ser Ser Tyr
            20                  25                  30

Glu Met Asn Trp Val Arg Gln Ala Pro Gly Lys Gly Leu Glu Trp Val
        35                  40                  45

Ser Tyr Ile Ser Ser Ser Gly Ser Thr Ile Tyr Tyr Ala Asp Ser Val
    50                  55                  60

Lys Gly Arg Phe Thr Ile Ser Arg Asp Asn Ala Lys Asn Ser Leu Tyr
65                  70                  75                  80

Leu Gln Met Asn Ser Leu Arg Ala Glu Asp Thr Ala Val Tyr Tyr Cys
                85                  90                  95

Ala Arg Asp Ala Pro Tyr Tyr Tyr Asp Ser Ser Gly Tyr Thr Asp Ala
            100                 105                 110

Phe Ala Ile Trp Gly Gln Gly Thr Met Val Thr Val Ser Ser Ala Ser
        115                 120                 125

Thr Lys Gly Pro Ser Val Phe Pro Leu Ala Pro Ser Ser Lys Ser Thr
    130                 135                 140

Ser Gly Gly Thr Ala Ala Leu Gly Cys Leu Val Lys Asp Tyr Phe Pro
145                 150                 155                 160

Glu Pro Val Thr Val Ser Trp Asn Ser Gly Ala Leu Thr Ser Gly Val
                165                 170                 175

His Thr Phe Pro Ala Val Leu Gln Ser Ser Gly Leu Tyr Ser Leu Ser
            180                 185                 190
```

Ser Val Val Thr Val Pro Ser Ser Ser Leu Gly Thr Gln Thr Tyr Ile
195 200 205

Cys Asn Val Asn His Lys Pro Ser Asn Thr Lys Val Asp Lys Lys Val
210 215 220

Glu Pro Lys Ser Cys Asp Lys Thr His Thr Cys Pro Pro Cys Pro Ala
225 230 235 240

Pro Glu Leu Leu Gly Gly Pro Ser Val Phe Leu Phe Pro Pro Lys Pro
245 250 255

Lys Asp Thr Leu Met Ile Ser Arg Thr Pro Glu Val Thr Cys Val Val
260 265 270

Val Asp Val Ser His Glu Asp Pro Glu Val Lys Phe Asn Trp Tyr Val
275 280 285

Asp Gly Val Glu Val His Asn Ala Lys Thr Lys Pro Arg Glu Glu Gln
290 295 300

Tyr Asn Ser Thr Tyr Arg Val Val Ser Val Leu Thr Val Leu His Gln
305 310 315 320

Asp Trp Leu Asn Gly Lys Glu Tyr Lys Cys Lys Val Ser Asn Lys Ala
325 330 335

Leu Pro Ala Pro Ile Glu Lys Thr Ile Ser Lys Ala Lys Gly Gln Pro
340 345 350

Arg Glu Pro Gln Val Tyr Thr Leu Pro Pro Ser Arg Asp Glu Leu Thr
355 360 365

Lys Asn Gln Val Ser Leu Thr Cys Leu Val Lys Gly Phe Tyr Pro Ser
370 375 380

Asp Ile Ala Val Glu Trp Glu Ser Asn Gly Gln Pro Glu Asn Asn Tyr
385 390 395 400

Lys Thr Thr Pro Pro Val Leu Asp Ser Asp Gly Ser Phe Phe Leu Tyr
405 410 415

Ser Lys Leu Thr Val Asp Lys Ser Arg Trp Gln Gln Gly Asn Val Phe
420 425 430

Ser Cys Ser Val Met His Glu Ala Leu His Asn His Tyr Thr Gln Lys
435 440 445

Ser Leu Ser Leu Ser Pro
450

<210> SEQ ID NO 131
<211> LENGTH: 213
<212> TYPE: PRT
<213> ORGANISM: Artificial sequence
<220> FEATURE:
<223> OTHER INFORMATION: an artificially synthesized sequence

<400> SEQUENCE: 131

Glu Ile Val Leu Thr Gln Ser Pro Ala Thr Leu Ser Leu Ser Pro Gly
1 5 10 15

Glu Arg Ala Thr Leu Ser Cys Arg Ala Ser Gln Ser Val Ser Ser Tyr
20 25 30

Leu Ala Trp Tyr Gln Gln Lys Pro Gly Gln Ala Pro Arg Leu Leu Ile
35 40 45

Phe Ala Ala Ser Asn Arg Ala Ala Gly Ile Pro Ala Arg Phe Ser Gly
50 55 60

Ser Gly Ser Gly Thr Asp Phe Thr Leu Thr Ile Ser Ser Leu Glu Pro
65 70 75 80

Glu Asp Phe Ala Val Tyr Tyr Cys Gln Gln Phe Asp Lys Trp Val Thr
85 90 95

Phe Gly Gly Gly Thr Thr Val Glu Ile Arg Arg Thr Val Ala Ala Pro
100 105 110

Ser Val Phe Ile Phe Pro Pro Ser Asp Glu Gln Leu Lys Ser Gly Thr
115 120 125

Ala Ser Val Val Cys Leu Leu Asn Asn Phe Tyr Pro Arg Glu Ala Lys
130 135 140

Val Gln Trp Lys Val Asp Asn Ala Leu Gln Ser Gly Asn Ser Gln Glu
145 150 155 160

Ser Val Thr Glu Gln Asp Ser Lys Asp Ser Thr Tyr Ser Leu Ser Ser
165 170 175

Thr Leu Thr Leu Ser Lys Ala Asp Tyr Glu Lys His Lys Val Tyr Ala
180 185 190

Cys Glu Val Thr His Gln Gly Leu Ser Ser Pro Val Thr Lys Ser Phe
195 200 205

Asn Arg Gly Glu Cys
210

<210> SEQ ID NO 132
<211> LENGTH: 213
<212> TYPE: PRT
<213> ORGANISM: Artificial sequence
<220> FEATURE:
<223> OTHER INFORMATION: an artificially synthesized sequence

<400> SEQUENCE: 132

Glu Ile Val Leu Thr Gln Ser Pro Ala Thr Leu Ser Leu Ser Pro Gly
1 5 10 15

Glu Arg Ala Thr Leu Ser Cys Arg Ala Ser Gln Ser Val Ser Ser Tyr
20 25 30

Leu Ala Trp Tyr Gln Gln Lys Pro Gly Gln Ala Pro Arg Leu Leu Ile
35 40 45

Phe Asp Ala Ser Asn Arg Ala Ala Gly Ile Pro Ala Arg Phe Ser Gly
50 55 60

Ser Gly Ser Gly Thr Asp Phe Thr Leu Thr Ile Ser Ser Leu Glu Pro
65 70 75 80

Glu Asp Phe Ala Val Tyr Tyr Cys Gln Gln Phe Ala Lys Trp Val Thr
85 90 95

Phe Gly Gly Gly Thr Thr Val Glu Ile Arg Arg Thr Val Ala Ala Pro
100 105 110

Ser Val Phe Ile Phe Pro Pro Ser Asp Glu Gln Leu Lys Ser Gly Thr
115 120 125

Ala Ser Val Val Cys Leu Leu Asn Asn Phe Tyr Pro Arg Glu Ala Lys
130 135 140

Val Gln Trp Lys Val Asp Asn Ala Leu Gln Ser Gly Asn Ser Gln Glu
145 150 155 160

Ser Val Thr Glu Gln Asp Ser Lys Asp Ser Thr Tyr Ser Leu Ser Ser
165 170 175

Thr Leu Thr Leu Ser Lys Ala Asp Tyr Glu Lys His Lys Val Tyr Ala
180 185 190

Cys Glu Val Thr His Gln Gly Leu Ser Ser Pro Val Thr Lys Ser Phe
195 200 205

Asn Arg Gly Glu Cys
210

<210> SEQ ID NO 133

<211> LENGTH: 453
<212> TYPE: PRT
<213> ORGANISM: Artificial sequence
<220> FEATURE:
<223> OTHER INFORMATION: an artificially synthesized sequence

<400> SEQUENCE: 133

Gln Val Gln Leu Val Gln Ser Gly Ala Glu Val Lys Lys Pro Gly Ser
1 5 10 15

Ser Val Lys Val Ser Cys Lys Ala Ser Gly Gly Thr Phe Ser Ser Tyr
20 25 30

Ala Ile Ser Trp Val Arg Gln Ala Pro Gly Gln Gly Leu Glu Trp Met
35 40 45

Gly Gly Ile Ile Pro Ile Phe Gly Thr Ala Asn Tyr Ala Gln Lys Phe
50 55 60

Gln Gly Arg Val Thr Ile Thr Ala Asp Glu Ser Thr Ser Thr Ala Tyr
65 70 75 80

Met Glu Leu Ser Ser Leu Arg Ser Glu Asp Thr Ala Val Tyr Tyr Cys
85 90 95

Ala Arg Ala Ala Phe Leu Glu Trp Pro Ile Trp Gly Ser Glu Tyr Phe
100 105 110

Gln His Trp Gly Gln Gly Thr Leu Val Thr Val Ser Ser Ala Ser Thr
115 120 125

Lys Gly Pro Ser Val Phe Pro Leu Ala Pro Ser Ser Lys Ser Thr Ser
130 135 140

Gly Gly Thr Ala Ala Leu Gly Cys Leu Val Lys Asp Tyr Phe Pro Glu
145 150 155 160

Pro Val Thr Val Ser Trp Asn Ser Gly Ala Leu Thr Ser Gly Val His
165 170 175

Thr Phe Pro Ala Val Leu Gln Ser Ser Gly Leu Tyr Ser Leu Ser Ser
180 185 190

Val Val Thr Val Pro Ser Ser Ser Leu Gly Thr Gln Thr Tyr Ile Cys
195 200 205

Asn Val Asn His Lys Pro Ser Asn Thr Lys Val Asp Lys Lys Val Glu
210 215 220

Pro Lys Ser Cys Asp Lys Thr His Thr Cys Pro Pro Cys Pro Ala Pro
225 230 235 240

Glu Leu Leu Gly Gly Pro Ser Val Phe Leu Phe Pro Pro Lys Pro Lys
245 250 255

Asp Thr Leu Met Ile Ser Arg Thr Pro Glu Val Thr Cys Val Val Val
260 265 270

Asp Val Ser His Glu Asp Pro Glu Val Lys Phe Asn Trp Tyr Val Asp
275 280 285

Gly Val Glu Val His Asn Ala Lys Thr Lys Pro Arg Glu Glu Gln Tyr
290 295 300

Asn Ser Thr Tyr Arg Val Val Ser Val Leu Thr Val Leu His Gln Asp
305 310 315 320

Trp Leu Asn Gly Lys Glu Tyr Lys Cys Lys Val Ser Asn Lys Ala Leu
325 330 335

Pro Ala Pro Ile Glu Lys Thr Ile Ser Lys Ala Lys Gly Gln Pro Arg
340 345 350

Glu Pro Gln Val Tyr Thr Leu Pro Pro Ser Arg Asp Glu Leu Thr Lys
355 360 365

Asn Gln Val Ser Leu Thr Cys Leu Val Lys Gly Phe Tyr Pro Ser Asp
370 375 380

```
Ile Ala Val Glu Trp Glu Ser Asn Gly Gln Pro Glu Asn Asn Tyr Lys
385                 390                 395                 400

Thr Thr Pro Pro Val Leu Asp Ser Asp Gly Ser Phe Phe Leu Tyr Ser
                405                 410                 415

Lys Leu Thr Val Asp Lys Ser Arg Trp Gln Gln Gly Asn Val Phe Ser
            420                 425                 430

Cys Ser Val Met His Glu Ala Leu His Asn His Tyr Thr Gln Lys Ser
        435                 440                 445

Leu Ser Leu Ser Pro
    450


<210> SEQ ID NO 134
<211> LENGTH: 214
<212> TYPE: PRT
<213> ORGANISM: Artificial sequence
<220> FEATURE:
<223> OTHER INFORMATION: an artificially synthesized sequence

<400> SEQUENCE: 134

Asp Ile Gln Met Thr Gln Ser Pro Ser Ser Leu Ser Ala Ser Val Gly
1               5                   10                  15

Asp Arg Val Thr Ile Thr Cys Arg Ala Ser Gln Ser Ile Glu Asp Asp
            20                  25                  30

Leu Ala Trp Tyr Gln Gln Lys Pro Gly Lys Ala Pro Lys Leu Leu Ile
        35                  40                  45

Tyr His Ala Ser Ser Leu Gln Ser Gly Val Pro Ser Arg Phe Ser Gly
    50                  55                  60

Ser Gly Ser Gly Thr Asp Phe Thr Leu Thr Ile Ser Ser Leu Gln Pro
65                  70                  75                  80

Glu Asp Phe Ala Thr Tyr Tyr Cys Gln Gln Arg Asp Ser Tyr Pro Leu
                85                  90                  95

Thr Phe Gly Gln Gly Thr Lys Val Glu Ile Lys Arg Thr Val Ala Ala
            100                 105                 110

Pro Ser Val Phe Ile Phe Pro Pro Ser Asp Glu Gln Leu Lys Ser Gly
        115                 120                 125

Thr Ala Ser Val Val Cys Leu Leu Asn Asn Phe Tyr Pro Arg Glu Ala
    130                 135                 140

Lys Val Gln Trp Lys Val Asp Asn Ala Leu Gln Ser Gly Asn Ser Gln
145                 150                 155                 160

Glu Ser Val Thr Glu Gln Asp Ser Lys Asp Ser Thr Tyr Ser Leu Ser
                165                 170                 175

Ser Thr Leu Thr Leu Ser Lys Ala Asp Tyr Glu Lys His Lys Val Tyr
            180                 185                 190

Ala Cys Glu Val Thr His Gln Gly Leu Ser Ser Pro Val Thr Lys Ser
        195                 200                 205

Phe Asn Arg Gly Glu Cys
    210


<210> SEQ ID NO 135
<211> LENGTH: 451
<212> TYPE: PRT
<213> ORGANISM: Artificial sequence
<220> FEATURE:
<223> OTHER INFORMATION: an artificially synthesized sequence

<400> SEQUENCE: 135

Gln Val Gln Leu Val Gln Ser Gly Ala Glu Val Lys Lys Pro Gly Ala
```

-continued

```
1               5                   10                  15

Ser Val Lys Val Ser Cys Lys Ala Ser Gly Tyr Thr Phe Thr Ser Tyr
            20                  25                  30

Gly Ile Ser Trp Val Arg Gln Ala Pro Gly Gln Gly Leu Glu Trp Met
        35                  40                  45

Gly Trp Ile Ser Ala Tyr Asn Gly Asn Thr Asn Tyr Ala Gln Lys Leu
    50                  55                  60

Gln Gly Arg Val Thr Met Thr Thr Asp Thr Ser Thr Ser Thr Ala Tyr
65                  70                  75                  80

Met Glu Leu Arg Ser Leu Arg Ser Asp Asp Thr Ala Val Tyr Tyr Cys
                85                  90                  95

Ala Arg Ala Thr Tyr Tyr Tyr Asp Ser Ser Ala Pro Ala Phe Asp Ile
            100                 105                 110

Trp Gly Gln Gly Thr Met Val Thr Val Ser Ser Ala Ser Thr Lys Gly
        115                 120                 125

Pro Ser Val Phe Pro Leu Ala Pro Ser Ser Lys Ser Thr Ser Gly Gly
    130                 135                 140

Thr Ala Ala Leu Gly Cys Leu Val Lys Asp Tyr Phe Pro Glu Pro Val
145                 150                 155                 160

Thr Val Ser Trp Asn Ser Gly Ala Leu Thr Ser Gly Val His Thr Phe
                165                 170                 175

Pro Ala Val Leu Gln Ser Ser Gly Leu Tyr Ser Leu Ser Ser Val Val
            180                 185                 190

Thr Val Pro Ser Ser Ser Leu Gly Thr Gln Thr Tyr Ile Cys Asn Val
        195                 200                 205

Asn His Lys Pro Ser Asn Thr Lys Val Asp Lys Lys Val Glu Pro Lys
    210                 215                 220

Ser Cys Asp Lys Thr His Thr Cys Pro Pro Cys Pro Ala Pro Glu Leu
225                 230                 235                 240

Leu Gly Gly Pro Ser Val Phe Leu Phe Pro Pro Lys Pro Lys Asp Thr
                245                 250                 255

Leu Met Ile Ser Arg Thr Pro Glu Val Thr Cys Val Val Val Asp Val
            260                 265                 270

Ser His Glu Asp Pro Glu Val Lys Phe Asn Trp Tyr Val Asp Gly Val
        275                 280                 285

Glu Val His Asn Ala Lys Thr Lys Pro Arg Glu Glu Gln Tyr Asn Ser
    290                 295                 300

Thr Tyr Arg Val Val Ser Val Leu Thr Val Leu His Gln Asp Trp Leu
305                 310                 315                 320

Asn Gly Lys Glu Tyr Lys Cys Lys Val Ser Asn Lys Ala Leu Pro Ala
                325                 330                 335

Pro Ile Glu Lys Thr Ile Ser Lys Ala Lys Gly Gln Pro Arg Glu Pro
            340                 345                 350

Gln Val Tyr Thr Leu Pro Pro Ser Arg Asp Glu Leu Thr Lys Asn Gln
        355                 360                 365

Val Ser Leu Thr Cys Leu Val Lys Gly Phe Tyr Pro Ser Asp Ile Ala
    370                 375                 380

Val Glu Trp Glu Ser Asn Gly Gln Pro Glu Asn Asn Tyr Lys Thr Thr
385                 390                 395                 400

Pro Pro Val Leu Asp Ser Asp Gly Ser Phe Phe Leu Tyr Ser Lys Leu
                405                 410                 415

Thr Val Asp Lys Ser Arg Trp Gln Gln Gly Asn Val Phe Ser Cys Ser
            420                 425                 430
```

Val Met His Glu Ala Leu His Asn His Tyr Thr Gln Lys Ser Leu Ser
        435                 440                 445

Leu Ser Pro
    450

<210> SEQ ID NO 136
<211> LENGTH: 214
<212> TYPE: PRT
<213> ORGANISM: Artificial sequence
<220> FEATURE:
<223> OTHER INFORMATION: an artificially synthesized sequence

<400> SEQUENCE: 136

Asp Ile Gln Met Thr Gln Ser Pro Ser Ser Leu Ser Ala Ser Val Gly
1               5                   10                  15

Asp Arg Val Thr Ile Thr Cys Arg Ala Ser Gln Ser Ile Glu Asp Asp
            20                  25                  30

Leu Ala Trp Tyr Gln Gln Lys Pro Gly Lys Ala Pro Lys Leu Leu Ile
        35                  40                  45

Tyr Glu Ala Ser Thr Leu Gln Ser Gly Val Pro Ser Arg Phe Ser Gly
    50                  55                  60

Ser Gly Ser Gly Thr Asp Phe Thr Leu Thr Ile Ser Ser Leu Gln Pro
65                  70                  75                  80

Glu Asp Phe Ala Thr Tyr Tyr Cys Gln Gln His Asp Asp Ser Pro Leu
                85                  90                  95

Thr Phe Gly Gln Gly Thr Lys Val Glu Ile Lys Arg Thr Val Ala Ala
            100                 105                 110

Pro Ser Val Phe Ile Phe Pro Pro Ser Asp Glu Gln Leu Lys Ser Gly
        115                 120                 125

Thr Ala Ser Val Val Cys Leu Leu Asn Asn Phe Tyr Pro Arg Glu Ala
    130                 135                 140

Lys Val Gln Trp Lys Val Asp Asn Ala Leu Gln Ser Gly Asn Ser Gln
145                 150                 155                 160

Glu Ser Val Thr Glu Gln Asp Ser Lys Asp Ser Thr Tyr Ser Leu Ser
                165                 170                 175

Ser Thr Leu Thr Leu Ser Lys Ala Asp Tyr Glu Lys His Lys Val Tyr
            180                 185                 190

Ala Cys Glu Val Thr His Gln Gly Leu Ser Ser Pro Val Thr Lys Ser
        195                 200                 205

Phe Asn Arg Gly Glu Cys
    210

<210> SEQ ID NO 137
<211> LENGTH: 452
<212> TYPE: PRT
<213> ORGANISM: Artificial sequence
<220> FEATURE:
<223> OTHER INFORMATION: an artificially synthesized sequence

<400> SEQUENCE: 137

Glu Val Gln Leu Val Gln Ser Gly Ala Glu Val Lys Lys Pro Gly Ser
1               5                   10                  15

Ser Val Lys Val Ser Cys Lys Ala Ser Gly Gly Thr Phe Ser Ser Tyr
            20                  25                  30

Ala Ile Ser Trp Val Arg Gln Ala Pro Gly Gln Gly Leu Glu Trp Met
        35                  40                  45

Gly Gly Ile Ile Pro Ile Phe Gly Thr Ala Asn Tyr Ala Gln Lys Phe

```
    50                  55                  60

Gln Gly Arg Val Thr Ile Thr Ala Asp Glu Ser Thr Ser Thr Ala Tyr
65                  70                  75                  80

Met Glu Leu Ser Ser Leu Arg Ser Glu Asp Thr Ala Val Tyr Tyr Cys
                85                  90                  95

Ala Arg Asp Arg Gly Ser Gly Phe Asn Trp Gly Asn Tyr Ala Phe Asp
            100                 105                 110

Ile Trp Gly Gln Gly Phe Ser Val Thr Val Ser Ser Ala Ser Thr Lys
        115                 120                 125

Gly Pro Ser Val Phe Pro Leu Ala Pro Ser Ser Lys Ser Thr Ser Gly
    130                 135                 140

Gly Thr Ala Ala Leu Gly Cys Leu Val Lys Asp Tyr Phe Pro Glu Pro
145                 150                 155                 160

Val Thr Val Ser Trp Asn Ser Gly Ala Leu Thr Ser Gly Val His Thr
                165                 170                 175

Phe Pro Ala Val Leu Gln Ser Ser Gly Leu Tyr Ser Leu Ser Ser Val
            180                 185                 190

Val Thr Val Pro Ser Ser Ser Leu Gly Thr Gln Thr Tyr Ile Cys Asn
        195                 200                 205

Val Asn His Lys Pro Ser Asn Thr Lys Val Asp Lys Lys Val Glu Pro
    210                 215                 220

Lys Ser Cys Asp Lys Thr His Thr Cys Pro Pro Cys Pro Ala Pro Glu
225                 230                 235                 240

Leu Leu Gly Gly Pro Ser Val Phe Leu Phe Pro Pro Lys Pro Lys Asp
                245                 250                 255

Thr Leu Met Ile Ser Arg Thr Pro Glu Val Thr Cys Val Val Val Asp
            260                 265                 270

Val Ser His Glu Asp Pro Glu Val Lys Phe Asn Trp Tyr Val Asp Gly
        275                 280                 285

Val Glu Val His Asn Ala Lys Thr Lys Pro Arg Glu Glu Gln Tyr Asn
    290                 295                 300

Ser Thr Tyr Arg Val Val Ser Val Leu Thr Val Leu His Gln Asp Trp
305                 310                 315                 320

Leu Asn Gly Lys Glu Tyr Lys Cys Lys Val Ser Asn Lys Ala Leu Pro
                325                 330                 335

Ala Pro Ile Glu Lys Thr Ile Ser Lys Ala Lys Gly Gln Pro Arg Glu
            340                 345                 350

Pro Gln Val Tyr Thr Leu Pro Pro Ser Arg Asp Glu Leu Thr Lys Asn
        355                 360                 365

Gln Val Ser Leu Thr Cys Leu Val Lys Gly Phe Tyr Pro Ser Asp Ile
    370                 375                 380

Ala Val Glu Trp Glu Ser Asn Gly Gln Pro Glu Asn Asn Tyr Lys Thr
385                 390                 395                 400

Thr Pro Pro Val Leu Asp Ser Asp Gly Ser Phe Phe Leu Tyr Ser Lys
                405                 410                 415

Leu Thr Val Asp Lys Ser Arg Trp Gln Gln Gly Asn Val Phe Ser Cys
            420                 425                 430

Ser Val Met His Glu Ala Leu His Asn His Tyr Thr Gln Lys Ser Leu
        435                 440                 445

Ser Leu Ser Pro
    450
```

<210> SEQ ID NO 138

<211> LENGTH: 214
<212> TYPE: PRT
<213> ORGANISM: Artificial sequence
<220> FEATURE:
<223> OTHER INFORMATION: an artificially synthesized sequence

<400> SEQUENCE: 138

```
Asp Ile Gln Met Thr Gln Ser Pro Ser Ser Leu Ser Ala Ser Val Gly
1               5                   10                  15

Asp Arg Val Thr Ile Thr Cys Arg Ala Ser Gln Ser Ile Glu Asp Asp
            20                  25                  30

Leu Ala Trp Tyr Gln Gln Lys Pro Gly Lys Ala Pro Lys Leu Leu Ile
        35                  40                  45

Tyr Glu Ala Ser Asn Leu Gln Ser Gly Val Pro Ser Arg Phe Ser Gly
    50                  55                  60

Ser Gly Ser Gly Thr Asp Phe Thr Leu Thr Ile Ser Ser Leu Gln Pro
65                  70                  75                  80

Glu Asp Phe Ala Thr Tyr Tyr Cys Gln Gln Tyr Asp Arg Tyr Pro Tyr
                85                  90                  95

Thr Phe Gly Gln Gly Thr Lys Val Glu Ile Lys Arg Thr Val Ala Ala
            100                 105                 110

Pro Ser Val Phe Ile Phe Pro Pro Ser Asp Glu Gln Leu Lys Ser Gly
        115                 120                 125

Thr Ala Ser Val Val Cys Leu Leu Asn Asn Phe Tyr Pro Arg Glu Ala
    130                 135                 140

Lys Val Gln Trp Lys Val Asp Asn Ala Leu Gln Ser Gly Asn Ser Gln
145                 150                 155                 160

Glu Ser Val Thr Glu Gln Asp Ser Lys Asp Ser Thr Tyr Ser Leu Ser
                165                 170                 175

Ser Thr Leu Thr Leu Ser Lys Ala Asp Tyr Glu Lys His Lys Val Tyr
            180                 185                 190

Ala Cys Glu Val Thr His Gln Gly Leu Ser Ser Pro Val Thr Lys Ser
        195                 200                 205

Phe Asn Arg Gly Glu Cys
    210
```

<210> SEQ ID NO 139
<211> LENGTH: 458
<212> TYPE: PRT
<213> ORGANISM: Artificial sequence
<220> FEATURE:
<223> OTHER INFORMATION: an artificially synthesized sequence

<400> SEQUENCE: 139

```
Glu Val Gln Leu Val Gln Ser Gly Ala Glu Val Lys Lys Pro Gly Ser
1               5                   10                  15

Ser Val Lys Val Ser Cys Lys Ala Ser Gly Gly Thr Phe Ser Ser Tyr
            20                  25                  30

Ala Ile Ser Trp Val Arg Gln Ala Pro Gly Gln Gly Leu Glu Trp Met
        35                  40                  45

Gly Gly Ile Ile Pro Ile Phe Gly Thr Ala Asn Tyr Ala Gln Lys Phe
    50                  55                  60

Gln Gly Arg Val Thr Ile Thr Ala Asp Glu Ser Thr Ser Thr Ala Tyr
65                  70                  75                  80

Met Glu Leu Ser Ser Leu Arg Ser Glu Asp Thr Ala Val Tyr Tyr Cys
                85                  90                  95

Ala Arg Ala Ser Ile Tyr Cys Ser Ser Thr Ser Cys Tyr Glu Pro Pro
```

```
            100                 105                 110

Tyr Tyr Tyr Tyr Met Asp Val Trp Gly Lys Gly Thr Met Val Thr Val
        115                 120                 125

Ser Ser Ala Ser Thr Lys Gly Pro Ser Val Phe Pro Leu Ala Pro Ser
    130                 135                 140

Ser Lys Ser Thr Ser Gly Gly Thr Ala Ala Leu Gly Cys Leu Val Lys
145                 150                 155                 160

Asp Tyr Phe Pro Glu Pro Val Thr Val Ser Trp Asn Ser Gly Ala Leu
                165                 170                 175

Thr Ser Gly Val His Thr Phe Pro Ala Val Leu Gln Ser Ser Gly Leu
            180                 185                 190

Tyr Ser Leu Ser Ser Val Val Thr Val Pro Ser Ser Ser Leu Gly Thr
        195                 200                 205

Gln Thr Tyr Ile Cys Asn Val Asn His Lys Pro Ser Asn Thr Lys Val
    210                 215                 220

Asp Lys Lys Val Glu Pro Lys Ser Cys Asp Lys Thr His Thr Cys Pro
225                 230                 235                 240

Pro Cys Pro Ala Pro Glu Leu Leu Gly Gly Pro Ser Val Phe Leu Phe
                245                 250                 255

Pro Pro Lys Pro Lys Asp Thr Leu Met Ile Ser Arg Thr Pro Glu Val
            260                 265                 270

Thr Cys Val Val Val Asp Val Ser His Glu Asp Pro Glu Val Lys Phe
        275                 280                 285

Asn Trp Tyr Val Asp Gly Val Glu Val His Asn Ala Lys Thr Lys Pro
    290                 295                 300

Arg Glu Glu Gln Tyr Asn Ser Thr Tyr Arg Val Val Ser Val Leu Thr
305                 310                 315                 320

Val Leu His Gln Asp Trp Leu Asn Gly Lys Glu Tyr Lys Cys Lys Val
                325                 330                 335

Ser Asn Lys Ala Leu Pro Ala Pro Ile Glu Lys Thr Ile Ser Lys Ala
            340                 345                 350

Lys Gly Gln Pro Arg Glu Pro Gln Val Tyr Thr Leu Pro Pro Ser Arg
        355                 360                 365

Asp Glu Leu Thr Lys Asn Gln Val Ser Leu Thr Cys Leu Val Lys Gly
    370                 375                 380

Phe Tyr Pro Ser Asp Ile Ala Val Glu Trp Glu Ser Asn Gly Gln Pro
385                 390                 395                 400

Glu Asn Asn Tyr Lys Thr Thr Pro Pro Val Leu Asp Ser Asp Gly Ser
                405                 410                 415

Phe Phe Leu Tyr Ser Lys Leu Thr Val Asp Lys Ser Arg Trp Gln Gln
            420                 425                 430

Gly Asn Val Phe Ser Cys Ser Val Met His Glu Ala Leu His Asn His
        435                 440                 445

Tyr Thr Gln Lys Ser Leu Ser Leu Ser Pro
    450                 455


<210> SEQ ID NO 140
<211> LENGTH: 214
<212> TYPE: PRT
<213> ORGANISM: Artificial sequence
<220> FEATURE:
<223> OTHER INFORMATION: an artificially synthesized sequence

<400> SEQUENCE: 140

Asp Ile Gln Met Thr Gln Ser Pro Ser Ser Leu Ser Ala Ser Val Gly
```

```
1               5                   10                  15

Asp Arg Val Thr Ile Thr Cys Arg Ala Ser Gln Ser Ile Ser Ser His
            20                  25                  30

Leu Ala Trp Tyr Gln Gln Lys Pro Gly Lys Ala Pro Lys Leu Leu Ile
        35                  40                  45

Tyr Ala Ala Ser His Leu Gln Ser Gly Val Pro Ser Arg Phe Ser Gly
    50                  55                  60

Ser Gly Ser Gly Thr Asp Phe Thr Leu Thr Ile Ser Ser Leu Gln Pro
65                  70                  75                  80

Glu Asp Phe Ala Thr Tyr Tyr Cys Gln Gln Ser His Asn Tyr Pro Leu
                85                  90                  95

Thr Phe Gly Gln Gly Thr Lys Val Glu Ile Lys Arg Thr Val Ala Ala
            100                 105                 110

Pro Ser Val Phe Ile Phe Pro Pro Ser Asp Glu Gln Leu Lys Ser Gly
        115                 120                 125

Thr Ala Ser Val Val Cys Leu Leu Asn Asn Phe Tyr Pro Arg Glu Ala
    130                 135                 140

Lys Val Gln Trp Lys Val Asp Asn Ala Leu Gln Ser Gly Asn Ser Gln
145                 150                 155                 160

Glu Ser Val Thr Glu Gln Asp Ser Lys Asp Ser Thr Tyr Ser Leu Ser
                165                 170                 175

Ser Thr Leu Thr Leu Ser Lys Ala Asp Tyr Glu Lys His Lys Val Tyr
            180                 185                 190

Ala Cys Glu Val Thr His Gln Gly Leu Ser Ser Pro Val Thr Lys Ser
        195                 200                 205

Phe Asn Arg Gly Glu Cys
    210


<210> SEQ ID NO 141
<211> LENGTH: 447
<212> TYPE: PRT
<213> ORGANISM: Artificial sequence
<220> FEATURE:
<223> OTHER INFORMATION: an artificially synthesized sequence

<400> SEQUENCE: 141

Gln Val Gln Leu Val Gln Ser Gly Ala Glu Val Lys Lys Pro Gly Ser
1               5                   10                  15

Ser Val Lys Val Ser Cys Lys Ala Ser Gly Gly Thr Phe Ser Ser Tyr
            20                  25                  30

Ala Ile Ser Trp Val Arg Gln Ala Pro Gly Gln Gly Leu Glu Trp Met
        35                  40                  45

Gly Gly Ile Ile Pro Ile Phe Gly Thr Ala Asn Tyr Ala Gln Lys Phe
    50                  55                  60

Gln Gly Arg Val Thr Ile Thr Ala Asp Glu Ser Thr Ser Thr Ala Tyr
65                  70                  75                  80

Met Glu Leu Ser Ser Leu Arg Ser Glu Asp Thr Ala Val Tyr Tyr Cys
                85                  90                  95

Met Ile Asn Gly Val Trp Glu Gly Gly Met Asp Val Trp Gly Gln Gly
            100                 105                 110

Thr Thr Val Thr Val Ser Ser Ala Ser Thr Lys Gly Pro Ser Val Phe
        115                 120                 125

Pro Leu Ala Pro Ser Ser Lys Ser Thr Ser Gly Gly Thr Ala Ala Leu
    130                 135                 140

Gly Cys Leu Val Lys Asp Tyr Phe Pro Glu Pro Val Thr Val Ser Trp
```

-continued

```
145                 150                 155                 160

Asn Ser Gly Ala Leu Thr Ser Gly Val His Thr Phe Pro Ala Val Leu
                165                 170                 175

Gln Ser Ser Gly Leu Tyr Ser Leu Ser Ser Val Val Thr Val Pro Ser
            180                 185                 190

Ser Ser Leu Gly Thr Gln Thr Tyr Ile Cys Asn Val Asn His Lys Pro
        195                 200                 205

Ser Asn Thr Lys Val Asp Lys Lys Val Glu Pro Lys Ser Cys Asp Lys
    210                 215                 220

Thr His Thr Cys Pro Pro Cys Pro Ala Pro Glu Leu Leu Gly Gly Pro
225                 230                 235                 240

Ser Val Phe Leu Phe Pro Pro Lys Pro Lys Asp Thr Leu Met Ile Ser
                245                 250                 255

Arg Thr Pro Glu Val Thr Cys Val Val Val Asp Val Ser His Glu Asp
            260                 265                 270

Pro Glu Val Lys Phe Asn Trp Tyr Val Asp Gly Val Glu Val His Asn
        275                 280                 285

Ala Lys Thr Lys Pro Arg Glu Glu Gln Tyr Asn Ser Thr Tyr Arg Val
    290                 295                 300

Val Ser Val Leu Thr Val Leu His Gln Asp Trp Leu Asn Gly Lys Glu
305                 310                 315                 320

Tyr Lys Cys Lys Val Ser Asn Lys Ala Leu Pro Ala Pro Ile Glu Lys
                325                 330                 335

Thr Ile Ser Lys Ala Lys Gly Gln Pro Arg Glu Pro Gln Val Tyr Thr
            340                 345                 350

Leu Pro Pro Ser Arg Asp Glu Leu Thr Lys Asn Gln Val Ser Leu Thr
        355                 360                 365

Cys Leu Val Lys Gly Phe Tyr Pro Ser Asp Ile Ala Val Glu Trp Glu
    370                 375                 380

Ser Asn Gly Gln Pro Glu Asn Asn Tyr Lys Thr Thr Pro Pro Val Leu
385                 390                 395                 400

Asp Ser Asp Gly Ser Phe Phe Leu Tyr Ser Lys Leu Thr Val Asp Lys
                405                 410                 415

Ser Arg Trp Gln Gln Gly Asn Val Phe Ser Cys Ser Val Met His Glu
            420                 425                 430

Ala Leu His Asn His Tyr Thr Gln Lys Ser Leu Ser Leu Ser Pro
        435                 440                 445


<210> SEQ ID NO 142
<211> LENGTH: 214
<212> TYPE: PRT
<213> ORGANISM: Artificial sequence
<220> FEATURE:
<223> OTHER INFORMATION: an artificially synthesized sequence

<400> SEQUENCE: 142

Asp Ile Gln Met Thr Gln Ser Pro Ser Ser Leu Ser Ala Ser Val Gly
1               5                   10                  15

Asp Arg Val Thr Ile Thr Cys Arg Ala Ser Gln Ser Ile His Ser His
            20                  25                  30

Leu Asn Trp Tyr Gln Gln Lys Pro Gly Lys Ala Pro Lys Leu Leu Ile
        35                  40                  45

Tyr His Ala Ser Lys Leu Gln Ser Gly Val Pro Ser Arg Phe Ser Gly
    50                  55                  60

Ser Gly Ser Gly Thr Asp Phe Thr Leu Thr Ile Ser Ser Leu Gln Pro
```

65 70 75 80

Glu Asp Phe Ala Thr Tyr Tyr Cys Gln Gln His Gly Asn Ser Pro Leu
85 90 95

Thr Phe Gly Gln Gly Thr Lys Val Glu Ile Lys Arg Thr Val Ala Ala
100 105 110

Pro Ser Val Phe Ile Phe Pro Pro Ser Asp Glu Gln Leu Lys Ser Gly
115 120 125

Thr Ala Ser Val Val Cys Leu Leu Asn Asn Phe Tyr Pro Arg Glu Ala
130 135 140

Lys Val Gln Trp Lys Val Asp Asn Ala Leu Gln Ser Gly Asn Ser Gln
145 150 155 160

Glu Ser Val Thr Glu Gln Asp Ser Lys Asp Ser Thr Tyr Ser Leu Ser
165 170 175

Ser Thr Leu Thr Leu Ser Lys Ala Asp Tyr Glu Lys His Lys Val Tyr
180 185 190

Ala Cys Glu Val Thr His Gln Gly Leu Ser Ser Pro Val Thr Lys Ser
195 200 205

Phe Asn Arg Gly Glu Cys
210

<210> SEQ ID NO 143
<211> LENGTH: 451
<212> TYPE: PRT
<213> ORGANISM: Artificial sequence
<220> FEATURE:
<223> OTHER INFORMATION: an artificially synthesized sequence

<400> SEQUENCE: 143

Glu Val Gln Leu Val Gln Ser Gly Gly Gly Leu Val Gln Pro Gly Gly
1 5 10 15

Ser Leu Arg Leu Ser Cys Ala Ala Ser Gly Phe Thr Phe Ser Asn Ala
20 25 30

Trp Met Ile Trp Val Arg Gln Ala Pro Gly Lys Gly Leu Glu Trp Val
35 40 45

Gly Arg Ile Lys Ser Lys Val Asp Gly Gly Thr Thr Asp Tyr Ala Ala
50 55 60

Pro Val Lys Gly Arg Phe Thr Ile Ser Arg Asp Asp Ser Lys Asn Thr
65 70 75 80

Leu Tyr Leu Gln Met Asp Ser Leu Lys Thr Glu Asp Thr Ala Val Tyr
85 90 95

Tyr Cys Val Ala Asp Val Pro Ala Ser Asn Pro Tyr Gly Phe Asp Tyr
100 105 110

Trp Gly Gln Gly Thr Leu Val Thr Val Ser Ser Ala Ser Thr Lys Gly
115 120 125

Pro Ser Val Phe Pro Leu Ala Pro Ser Ser Lys Ser Thr Ser Gly Gly
130 135 140

Thr Ala Ala Leu Gly Cys Leu Val Lys Asp Tyr Phe Pro Glu Pro Val
145 150 155 160

Thr Val Ser Trp Asn Ser Gly Ala Leu Thr Ser Gly Val His Thr Phe
165 170 175

Pro Ala Val Leu Gln Ser Ser Gly Leu Tyr Ser Leu Ser Ser Val Val
180 185 190

Thr Val Pro Ser Ser Ser Leu Gly Thr Gln Thr Tyr Ile Cys Asn Val
195 200 205

Asn His Lys Pro Ser Asn Thr Lys Val Asp Lys Lys Val Glu Pro Lys

```
    210                 215                 220

Ser Cys Asp Lys Thr His Thr Cys Pro Pro Cys Pro Ala Pro Glu Leu
225                 230                 235                 240

Leu Gly Gly Pro Ser Val Phe Leu Phe Pro Pro Lys Pro Lys Asp Thr
                245                 250                 255

Leu Met Ile Ser Arg Thr Pro Glu Val Thr Cys Val Val Val Asp Val
            260                 265                 270

Ser His Glu Asp Pro Glu Val Lys Phe Asn Trp Tyr Val Asp Gly Val
        275                 280                 285

Glu Val His Asn Ala Lys Thr Lys Pro Arg Glu Glu Gln Tyr Asn Ser
    290                 295                 300

Thr Tyr Arg Val Val Ser Val Leu Thr Val Leu His Gln Asp Trp Leu
305                 310                 315                 320

Asn Gly Lys Glu Tyr Lys Cys Lys Val Ser Asn Lys Ala Leu Pro Ala
                325                 330                 335

Pro Ile Glu Lys Thr Ile Ser Lys Ala Lys Gly Gln Pro Arg Glu Pro
            340                 345                 350

Gln Val Tyr Thr Leu Pro Pro Ser Arg Asp Glu Leu Thr Lys Asn Gln
        355                 360                 365

Val Ser Leu Thr Cys Leu Val Lys Gly Phe Tyr Pro Ser Asp Ile Ala
    370                 375                 380

Val Glu Trp Glu Ser Asn Gly Gln Pro Glu Asn Asn Tyr Lys Thr Thr
385                 390                 395                 400

Pro Pro Val Leu Asp Ser Asp Gly Ser Phe Phe Leu Tyr Ser Lys Leu
                405                 410                 415

Thr Val Asp Lys Ser Arg Trp Gln Gln Gly Asn Val Phe Ser Cys Ser
            420                 425                 430

Val Met His Glu Ala Leu His Asn His Tyr Thr Gln Lys Ser Leu Ser
        435                 440                 445

Leu Ser Pro
    450


<210> SEQ ID NO 144
<211> LENGTH: 214
<212> TYPE: PRT
<213> ORGANISM: Artificial sequence
<220> FEATURE:
<223> OTHER INFORMATION: an artificially synthesized sequence

<400> SEQUENCE: 144

Asp Ile Gln Met Thr Gln Ser Pro Ser Ser Leu Ser Ala Ser Val Gly
1               5                   10                  15

Asp Arg Val Thr Ile Thr Cys Arg Ala Ser Gln Ser Ile Asn Ser His
            20                  25                  30

Leu Asn Trp Tyr Gln Gln Lys Pro Gly Lys Ala Pro Lys Leu Leu Ile
        35                  40                  45

Tyr Asp Ala Ser His Leu Gln Ser Gly Val Pro Ser Arg Phe Ser Gly
    50                  55                  60

Ser Gly Ser Gly Thr Asp Phe Thr Leu Thr Ile Ser Ser Leu Gln Pro
65                  70                  75                  80

Glu Asp Phe Ala Thr Tyr Tyr Cys Gln Gln His Asn Asn Tyr Pro Leu
                85                  90                  95

Thr Phe Gly Gln Gly Thr Lys Val Glu Ile Lys Arg Thr Val Ala Ala
            100                 105                 110

Pro Ser Val Phe Ile Phe Pro Pro Ser Asp Glu Gln Leu Lys Ser Gly
```

```
        115                 120                 125

Thr Ala Ser Val Val Cys Leu Leu Asn Asn Phe Tyr Pro Arg Glu Ala
    130                 135                 140

Lys Val Gln Trp Lys Val Asp Asn Ala Leu Gln Ser Gly Asn Ser Gln
145                 150                 155                 160

Glu Ser Val Thr Glu Gln Asp Ser Lys Asp Ser Thr Tyr Ser Leu Ser
                165                 170                 175

Ser Thr Leu Thr Leu Ser Lys Ala Asp Tyr Glu Lys His Lys Val Tyr
            180                 185                 190

Ala Cys Glu Val Thr His Gln Gly Leu Ser Ser Pro Val Thr Lys Ser
        195                 200                 205

Phe Asn Arg Gly Glu Cys
    210


<210> SEQ ID NO 145
<211> LENGTH: 447
<212> TYPE: PRT
<213> ORGANISM: Artificial sequence
<220> FEATURE:
<223> OTHER INFORMATION: an artificially synthesized sequence

<400> SEQUENCE: 145

Gln Val Gln Leu Gln Glu Ser Gly Pro Gly Leu Val Lys Pro Ser Glu
1               5                   10                  15

Thr Leu Ser Leu Thr Cys Ala Val Ser Gly His Ser Ile Ser His Asp
            20                  25                  30

His Ala Trp Ser Trp Val Arg Gln Pro Pro Gly Glu Gly Leu Glu Trp
        35                  40                  45

Ile Gly Phe Ile Ser Tyr Ser Gly Ile Thr Asn Tyr Asn Pro Ser Leu
    50                  55                  60

Gln Gly Arg Val Thr Ile Ser Arg Asp Asn Ser Lys Asn Thr Leu Tyr
65                  70                  75                  80

Leu Gln Met Asn Ser Leu Arg Ala Glu Asp Thr Ala Val Tyr Tyr Cys
                85                  90                  95

Ala Arg Ser Leu Ala Arg Thr Thr Ala Met Asp Tyr Trp Gly Glu Gly
            100                 105                 110

Thr Leu Val Thr Val Ser Ser Ala Ser Thr Lys Gly Pro Ser Val Phe
        115                 120                 125

Pro Leu Ala Pro Ser Ser Lys Ser Thr Ser Gly Gly Thr Ala Ala Leu
    130                 135                 140

Gly Cys Leu Val Lys Asp Tyr Phe Pro Glu Pro Val Thr Val Ser Trp
145                 150                 155                 160

Asn Ser Gly Ala Leu Thr Ser Gly Val His Thr Phe Pro Ala Val Leu
                165                 170                 175

Gln Ser Ser Gly Leu Tyr Ser Leu Ser Ser Val Val Thr Val Pro Ser
            180                 185                 190

Ser Ser Leu Gly Thr Gln Thr Tyr Ile Cys Asn Val Asn His Lys Pro
        195                 200                 205

Ser Asn Thr Lys Val Asp Lys Lys Val Glu Pro Lys Ser Cys Asp Lys
    210                 215                 220

Thr His Thr Cys Pro Pro Cys Pro Ala Pro Glu Leu Leu Gly Gly Pro
225                 230                 235                 240

Ser Val Phe Leu Phe Pro Pro Lys Pro Lys Asp Thr Leu Met Ile Ser
                245                 250                 255

Arg Thr Pro Glu Val Thr Cys Val Val Val Asp Val Ser His Glu Asp
```

```
            260                 265                 270

Pro Glu Val Lys Phe Asn Trp Tyr Val Asp Gly Val Glu Val His Asn
        275                 280                 285

Ala Lys Thr Lys Pro Arg Glu Glu Gln Tyr Asn Ser Thr Tyr Arg Val
    290                 295                 300

Val Ser Val Leu Thr Val Leu His Gln Asp Trp Leu Asn Gly Lys Glu
305                 310                 315                 320

Tyr Lys Cys Lys Val Ser Asn Lys Ala Tyr Pro Ala Pro Ile Glu Lys
                325                 330                 335

Thr Ile Ser Lys Ala Lys Gly Gln Pro Arg Glu Pro Gln Val Tyr Thr
            340                 345                 350

Leu Pro Pro Ser Arg Asp Glu Leu Thr Lys Asn Gln Val Ser Leu Thr
        355                 360                 365

Cys Leu Val Lys Gly Phe Tyr Pro Ser Asp Ile Ala Val Glu Trp Glu
    370                 375                 380

Ser Asn Gly Gln Pro Glu Asn Asn Tyr Lys Thr Thr Pro Pro Val Leu
385                 390                 395                 400

Asp Ser Asp Gly Ser Phe Phe Leu Tyr Ser Lys Leu Thr Val Asp Lys
                405                 410                 415

Ser Arg Trp Gln Gln Gly Asn Val Phe Ser Cys Ser Val Met His Glu
            420                 425                 430

Ala Leu His Asn His Tyr Thr Gln Lys Ser Leu Ser Leu Ser Pro
        435                 440                 445


<210> SEQ ID NO 146
<211> LENGTH: 447
<212> TYPE: PRT
<213> ORGANISM: Artificial sequence
<220> FEATURE:
<223> OTHER INFORMATION: an artificially synthesized sequence

<400> SEQUENCE: 146

Gln Val Gln Leu Gln Glu Ser Gly Pro Gly Leu Val Lys Pro Ser Glu
1               5                   10                  15

Thr Leu Ser Leu Thr Cys Ala Val Ser Gly His Ser Ile Ser His Asp
            20                  25                  30

His Ala Trp Ser Trp Val Arg Gln Pro Pro Gly Glu Gly Leu Glu Trp
        35                  40                  45

Ile Gly Phe Ile Ser Tyr Ser Gly Ile Thr Asn Tyr Asn Pro Ser Leu
    50                  55                  60

Gln Gly Arg Val Thr Ile Ser Arg Asp Asn Ser Lys Asn Thr Leu Tyr
65                  70                  75                  80

Leu Gln Met Asn Ser Leu Arg Ala Glu Asp Thr Ala Val Tyr Tyr Cys
                85                  90                  95

Ala Arg Ser Leu Ala Arg Thr Thr Ala Met Asp Tyr Trp Gly Glu Gly
            100                 105                 110

Thr Leu Val Thr Val Ser Ser Ala Ser Thr Lys Gly Pro Ser Val Phe
        115                 120                 125

Pro Leu Ala Pro Ser Ser Lys Ser Thr Ser Gly Gly Thr Ala Ala Leu
    130                 135                 140

Gly Cys Leu Val Lys Asp Tyr Phe Pro Glu Pro Val Thr Val Ser Trp
145                 150                 155                 160

Asn Ser Gly Ala Leu Thr Ser Gly Val His Thr Phe Pro Ala Val Leu
                165                 170                 175

Gln Ser Ser Gly Leu Tyr Ser Leu Ser Ser Val Val Thr Val Pro Ser
```

```
            180                 185                 190

Ser Ser Leu Gly Thr Gln Thr Tyr Ile Cys Asn Val Asn His Lys Pro
        195                 200                 205

Ser Asn Thr Lys Val Asp Lys Lys Val Glu Pro Lys Ser Cys Asp Lys
    210                 215                 220

Thr His Thr Cys Pro Pro Cys Pro Ala Pro Glu Leu Leu Gly Gly Pro
225                 230                 235                 240

Ser Val Phe Leu Phe Pro Pro Lys Pro Lys Asp Thr Leu Met Ile Ser
                245                 250                 255

Arg Thr Pro Glu Val Thr Cys Val Val Val Asp Val Ser His Glu Asp
            260                 265                 270

Pro Glu Val Lys Phe Asn Trp Tyr Val Asp Gly Val Glu Val His Asn
        275                 280                 285

Ala Lys Thr Lys Pro Arg Glu Glu Gln Tyr Asn Ser Thr Tyr Arg Val
    290                 295                 300

Val Ser Val Leu Thr Val Leu His Gln Asp Trp Leu Asn Gly Lys Glu
305                 310                 315                 320

Tyr Lys Cys Lys Val Ser Asn Lys Ala Tyr Pro Ala Pro Ile Glu Lys
                325                 330                 335

Thr Ile Ser Lys Ala Lys Gly Gln Pro Arg Glu Pro Gln Val Tyr Thr
            340                 345                 350

Leu Pro Pro Ser Arg Asp Glu Leu Thr Lys Asn Gln Val Ser Leu Thr
        355                 360                 365

Cys Leu Val Lys Gly Phe Tyr Pro Ser Asp Ile Ala Val Glu Trp Glu
    370                 375                 380

Ser Asn Gly Gln Pro Glu Asn Asn Tyr Lys Thr Thr Pro Pro Val Leu
385                 390                 395                 400

Asp Ser Asp Gly Ser Phe Phe Leu Tyr Ser Lys Leu Thr Val Asp Lys
                405                 410                 415

Ser Arg Trp Gln Gln Gly Asn Val Phe Ser Cys Ser Val Leu His Glu
            420                 425                 430

Ala Leu His Ser His Tyr Thr Gln Lys Ser Leu Ser Leu Ser Pro
        435                 440                 445


<210> SEQ ID NO 147
<211> LENGTH: 447
<212> TYPE: PRT
<213> ORGANISM: Artificial sequence
<220> FEATURE:
<223> OTHER INFORMATION: an artificially synthesized sequence

<400> SEQUENCE: 147

Gln Val Gln Leu Gln Glu Ser Gly Pro Gly Leu Val Lys Pro Ser Glu
1               5                   10                  15

Thr Leu Ser Leu Thr Cys Ala Val Ser Gly His Ser Ile Ser His Asp
            20                  25                  30

His Ala Trp Ser Trp Val Arg Gln Pro Pro Gly Glu Gly Leu Glu Trp
        35                  40                  45

Ile Gly Phe Ile Ser Tyr Ser Gly Ile Thr Asn Tyr Asn Pro Ser Leu
    50                  55                  60

Gln Gly Arg Val Thr Ile Ser Arg Asp Asn Ser Lys Asn Thr Leu Tyr
65                  70                  75                  80

Leu Gln Met Asn Ser Leu Arg Ala Glu Asp Thr Ala Val Tyr Tyr Cys
                85                  90                  95

Ala Arg Ser Leu Ala Arg Thr Thr Ala Met Asp Tyr Trp Gly Glu Gly
```

100 105 110

Thr Leu Val Thr Val Ser Ser Ala Ser Thr Lys Gly Pro Ser Val Phe
115 120 125

Pro Leu Ala Pro Ser Ser Lys Ser Thr Ser Gly Gly Thr Ala Ala Leu
130 135 140

Gly Cys Leu Val Lys Asp Tyr Phe Pro Glu Pro Val Thr Val Ser Trp
145 150 155 160

Asn Ser Gly Ala Leu Thr Ser Gly Val His Thr Phe Pro Ala Val Leu
165 170 175

Gln Ser Ser Gly Leu Tyr Ser Leu Ser Ser Val Val Thr Val Pro Ser
180 185 190

Ser Ser Leu Gly Thr Gln Thr Tyr Ile Cys Asn Val Asn His Lys Pro
195 200 205

Ser Asn Thr Lys Val Asp Lys Lys Val Glu Pro Lys Ser Cys Asp Lys
210 215 220

Thr His Thr Cys Pro Pro Cys Pro Ala Pro Glu Leu Leu Gly Gly Pro
225 230 235 240

Asp Val Phe Leu Phe Pro Pro Lys Pro Lys Asp Thr Leu Met Ile Ser
245 250 255

Arg Thr Pro Glu Val Thr Cys Val Val Val Asp Val Ser His Glu Asp
260 265 270

Pro Glu Val Lys Phe Asn Trp Tyr Val Asp Gly Val Glu Val His Asn
275 280 285

Ala Lys Thr Lys Pro Arg Glu Glu Gln Tyr Asn Ser Thr Tyr Arg Val
290 295 300

Val Ser Val Leu Thr Val Leu His Gln Asp Trp Leu Asn Gly Lys Glu
305 310 315 320

Tyr Lys Cys Lys Val Ser Asn Lys Ala Leu Pro Ala Pro Glu Glu Lys
325 330 335

Thr Ile Ser Lys Ala Lys Gly Gln Pro Arg Glu Pro Gln Val Tyr Thr
340 345 350

Leu Pro Pro Ser Arg Asp Glu Leu Thr Lys Asn Gln Val Ser Leu Thr
355 360 365

Cys Leu Val Lys Gly Phe Tyr Pro Ser Asp Ile Ala Val Glu Trp Glu
370 375 380

Ser Asn Gly Gln Pro Glu Asn Asn Tyr Lys Thr Thr Pro Pro Val Leu
385 390 395 400

Asp Ser Asp Gly Ser Phe Phe Leu Tyr Ser Lys Leu Thr Val Asp Lys
405 410 415

Ser Arg Trp Gln Gln Gly Asn Val Phe Ser Cys Ser Val Leu His Glu
420 425 430

Ala Leu His Ser His Tyr Thr Gln Lys Ser Leu Ser Leu Ser Pro
435 440 445

<210> SEQ ID NO 148
<211> LENGTH: 447
<212> TYPE: PRT
<213> ORGANISM: Artificial sequence
<220> FEATURE:
<223> OTHER INFORMATION: an artificially synthesized sequence

<400> SEQUENCE: 148

Gln Val Gln Leu Gln Glu Ser Gly Pro Gly Leu Val Lys Pro Ser Glu
1 5 10 15

Thr Leu Ser Leu Thr Cys Ala Val Ser Gly His Ser Ile Ser His Asp

-continued

```
            20                  25                  30

His Ala Trp Ser Trp Val Arg Gln Pro Pro Gly Glu Gly Leu Glu Trp
        35                  40                  45

Ile Gly Phe Ile Ser Tyr Ser Gly Ile Thr Asn Tyr Asn Pro Ser Leu
    50                  55                  60

Gln Gly Arg Val Thr Ile Ser Arg Asp Asn Ser Lys Asn Thr Leu Tyr
65                  70                  75                  80

Leu Gln Met Asn Ser Leu Arg Ala Glu Asp Thr Ala Val Tyr Tyr Cys
                85                  90                  95

Ala Arg Ser Leu Ala Arg Thr Thr Ala Met Asp Tyr Trp Gly Glu Gly
            100                 105                 110

Thr Leu Val Thr Val Ser Ser Ala Ser Thr Lys Gly Pro Ser Val Phe
        115                 120                 125

Pro Leu Ala Pro Ser Ser Lys Ser Thr Ser Gly Gly Thr Ala Ala Leu
    130                 135                 140

Gly Cys Leu Val Lys Asp Tyr Phe Pro Glu Pro Val Thr Val Ser Trp
145                 150                 155                 160

Asn Ser Gly Ala Leu Thr Ser Gly Val His Thr Phe Pro Ala Val Leu
                165                 170                 175

Gln Ser Ser Gly Leu Tyr Ser Leu Ser Ser Val Val Thr Val Pro Ser
            180                 185                 190

Ser Ser Leu Gly Thr Gln Thr Tyr Ile Cys Asn Val Asn His Lys Pro
        195                 200                 205

Ser Asn Thr Lys Val Asp Lys Lys Val Glu Pro Lys Ser Cys Asp Lys
    210                 215                 220

Thr His Thr Cys Pro Pro Cys Pro Ala Pro Glu Leu Leu Gly Gly Pro
225                 230                 235                 240

Asp Val Phe Leu Phe Pro Pro Lys Pro Lys Asp Thr Leu Met Ile Ser
                245                 250                 255

Arg Thr Pro Glu Val Thr Cys Val Val Val Asp Val Ser His Glu Asp
            260                 265                 270

Pro Glu Val Lys Phe Asn Trp Tyr Val Asp Gly Val Glu Val His Asn
        275                 280                 285

Ala Lys Thr Lys Pro Arg Glu Glu Gln Tyr Asn Ser Thr Tyr Arg Val
    290                 295                 300

Val Ser Val Leu Thr Val Leu His Gln Asp Trp Leu Asn Gly Lys Glu
305                 310                 315                 320

Tyr Lys Cys Lys Val Ser Asn Lys Ala Leu Pro Ala Pro Glu Glu Lys
                325                 330                 335

Thr Ile Ser Lys Ala Lys Gly Gln Pro Arg Glu Pro Gln Val Tyr Thr
            340                 345                 350

Leu Pro Pro Ser Arg Asp Glu Leu Thr Lys Asn Gln Val Ser Leu Thr
        355                 360                 365

Cys Leu Val Lys Gly Phe Tyr Pro Ser Asp Ile Ala Val Glu Trp Glu
    370                 375                 380

Ser Asn Gly Gln Pro Glu Asn Asn Tyr Lys Thr Thr Pro Pro Val Leu
385                 390                 395                 400

Asp Ser Asp Gly Ser Phe Phe Leu Tyr Ser Lys Leu Thr Val Asp Lys
                405                 410                 415

Ser Arg Trp Gln Gln Gly Asn Val Phe Ser Cys Ser Val Met His Glu
            420                 425                 430

Ala Leu His Asn His Tyr Thr Gln Lys Ser Leu Ser Leu Ser Pro
        435                 440                 445
```

<210> SEQ ID NO 149
<211> LENGTH: 447
<212> TYPE: PRT
<213> ORGANISM: Artificial sequence
<220> FEATURE:
<223> OTHER INFORMATION: an artificially synthesized sequence

<400> SEQUENCE: 149

Gln Val Gln Leu Gln Glu Ser Gly Pro Gly Leu Val Lys Pro Ser Glu
1               5                   10                  15

Thr Leu Ser Leu Thr Cys Ala Val Ser Gly His Ser Ile Ser His Asp
            20                  25                  30

His Ala Trp Ser Trp Val Arg Gln Pro Pro Gly Glu Gly Leu Glu Trp
        35                  40                  45

Ile Gly Phe Ile Ser Tyr Ser Gly Ile Thr Asn Tyr Asn Pro Ser Leu
    50                  55                  60

Gln Gly Arg Val Thr Ile Ser Arg Asp Asn Ser Lys Asn Thr Leu Tyr
65                  70                  75                  80

Leu Gln Met Asn Ser Leu Arg Ala Glu Asp Thr Ala Val Tyr Tyr Cys
                85                  90                  95

Ala Arg Ser Leu Ala Arg Thr Thr Ala Met Asp Tyr Trp Gly Glu Gly
            100                 105                 110

Thr Leu Val Thr Val Ser Ser Ala Ser Thr Lys Gly Pro Ser Val Phe
        115                 120                 125

Pro Leu Ala Pro Ser Ser Lys Ser Thr Ser Gly Gly Thr Ala Ala Leu
    130                 135                 140

Gly Cys Leu Val Lys Asp Tyr Phe Pro Glu Pro Val Thr Val Ser Trp
145                 150                 155                 160

Asn Ser Gly Ala Leu Thr Ser Gly Val His Thr Phe Pro Ala Val Leu
                165                 170                 175

Gln Ser Ser Gly Leu Tyr Ser Leu Ser Ser Val Val Thr Val Pro Ser
            180                 185                 190

Ser Ser Leu Gly Thr Gln Thr Tyr Ile Cys Asn Val Asn His Lys Pro
        195                 200                 205

Ser Asn Thr Lys Val Asp Lys Lys Val Glu Pro Lys Ser Cys Asp Lys
    210                 215                 220

Thr His Thr Cys Pro Pro Cys Pro Ala Pro Glu Leu Leu Gly Gly Pro
225                 230                 235                 240

Ser Val Phe Leu Phe Pro Pro Lys Pro Lys Asp Thr Leu Met Ile Ser
                245                 250                 255

Arg Thr Pro Glu Val Thr Cys Val Val Val Asp Val Ser His Glu Asp
            260                 265                 270

Pro Glu Val Lys Phe Asn Trp Tyr Val Asp Gly Val Glu Val His Asn
        275                 280                 285

Ala Lys Thr Lys Pro Arg Glu Glu Gln Tyr Asn Ser Thr Tyr Arg Val
    290                 295                 300

Val Ser Val Leu Thr Val Leu His Gln Asp Trp Leu Asn Gly Lys Glu
305                 310                 315                 320

Tyr Lys Cys Lys Val Ser Asn Lys Ala Tyr Pro Ala Pro Ile Glu Lys
                325                 330                 335

Thr Ile Ser Lys Ala Lys Gly Gln Pro Arg Glu Pro Gln Val Tyr Thr
            340                 345                 350

Leu Pro Pro Ser Arg Asp Glu Leu Thr Lys Asn Gln Val Ser Leu Thr
        355                 360                 365

Cys Leu Val Lys Gly Phe Tyr Pro Ser Asp Ile Ala Val Glu Trp Glu
370 375 380

Ser Asn Gly Gln Pro Glu Asn Asn Tyr Lys Thr Thr Pro Pro Val Leu
385 390 395 400

Asp Ser Asp Gly Ser Phe Phe Leu Tyr Ser Lys Leu Thr Val Asp Lys
405 410 415

Ser Arg Trp Gln Gln Gly Asn Val Phe Ser Cys Ser Val Met His Glu
420 425 430

Ala Leu His Ala His Tyr Thr Gln Lys Ser Leu Ser Leu Ser Pro
435 440 445

<210> SEQ ID NO 150
<211> LENGTH: 443
<212> TYPE: PRT
<213> ORGANISM: Mus musculus

<400> SEQUENCE: 150

Gln Val Gln Leu Gln Glu Ser Gly Pro Gly Leu Val Lys Pro Ser Glu
1 5 10 15

Thr Leu Ser Leu Thr Cys Ala Val Ser Gly His Ser Ile Ser His Asp
20 25 30

His Ala Trp Ser Trp Val Arg Gln Pro Pro Gly Glu Gly Leu Glu Trp
35 40 45

Ile Gly Phe Ile Ser Tyr Ser Gly Ile Thr Asn Tyr Asn Pro Ser Leu
50 55 60

Gln Gly Arg Val Thr Ile Ser Arg Asp Asn Ser Lys Asn Thr Leu Tyr
65 70 75 80

Leu Gln Met Asn Ser Leu Arg Ala Glu Asp Thr Ala Val Tyr Tyr Cys
85 90 95

Ala Arg Ser Leu Ala Arg Thr Thr Ala Met Asp Tyr Trp Gly Glu Gly
100 105 110

Thr Leu Val Thr Val Ser Ser Ala Lys Thr Thr Pro Pro Ser Val Tyr
115 120 125

Pro Leu Ala Pro Gly Ser Ala Ala Gln Thr Asn Ser Met Val Thr Leu
130 135 140

Gly Cys Leu Val Lys Gly Tyr Phe Pro Glu Pro Val Thr Val Thr Trp
145 150 155 160

Asn Ser Gly Ser Leu Ser Ser Gly Val His Thr Phe Pro Ala Val Leu
165 170 175

Gln Ser Asp Leu Tyr Thr Leu Ser Ser Ser Val Thr Val Pro Ser Ser
180 185 190

Thr Trp Pro Ser Glu Thr Val Thr Cys Asn Val Ala His Pro Ala Ser
195 200 205

Ser Thr Lys Val Asp Lys Lys Ile Val Pro Arg Asp Cys Gly Cys Lys
210 215 220

Pro Cys Ile Cys Thr Val Pro Glu Val Ser Ser Val Phe Ile Phe Pro
225 230 235 240

Pro Lys Pro Lys Asp Val Leu Thr Ile Thr Leu Thr Pro Lys Val Thr
245 250 255

Cys Val Val Val Asp Ile Ser Lys Asp Asp Pro Glu Val Gln Phe Ser
260 265 270

Trp Phe Val Asp Asp Val Glu Val His Thr Ala Gln Thr Gln Pro Arg
275 280 285

Glu Glu Gln Phe Asn Ser Thr Phe Arg Ser Val Ser Glu Leu Pro Ile

```
    290                 295                 300

Met His Gln Asp Trp Leu Asn Gly Lys Glu Phe Lys Cys Arg Val Asn
305                 310                 315                 320

Ser Ala Ala Phe Pro Ala Pro Ile Glu Lys Thr Ile Ser Lys Thr Lys
                325                 330                 335

Gly Arg Pro Lys Ala Pro Gln Val Tyr Thr Ile Pro Pro Pro Lys Glu
            340                 345                 350

Gln Met Ala Lys Asp Lys Val Ser Leu Thr Cys Met Ile Thr Asp Phe
        355                 360                 365

Phe Pro Glu Asp Ile Thr Val Glu Trp Gln Trp Asn Gly Gln Pro Ala
    370                 375                 380

Glu Asn Tyr Lys Asn Thr Gln Pro Ile Met Asp Thr Asp Gly Ser Tyr
385                 390                 395                 400

Phe Val Tyr Ser Lys Leu Asn Val Gln Lys Ser Asn Trp Glu Ala Gly
                405                 410                 415

Asn Thr Phe Thr Cys Ser Val Leu His Glu Gly Leu His Asn His His
            420                 425                 430

Thr Glu Lys Ser Leu Ser His Ser Pro Gly Lys
        435                 440


<210> SEQ ID NO 151
<211> LENGTH: 214
<212> TYPE: PRT
<213> ORGANISM: Mus musculus

<400> SEQUENCE: 151

Asp Ile Gln Met Thr Gln Ser Pro Ser Ser Leu Ser Ala Ser Val Gly
1               5                   10                  15

Asp Ser Val Thr Ile Thr Cys Gln Ala Ser Thr Asp Ile Ser Ser His
            20                  25                  30

Leu Asn Trp Tyr Gln Gln Lys Pro Gly Lys Ala Pro Glu Leu Leu Ile
        35                  40                  45

Tyr Tyr Gly Ser His Leu Leu Ser Gly Val Pro Ser Arg Phe Ser Gly
    50                  55                  60

Ser Gly Ser Gly Thr Asp Phe Thr Phe Thr Ile Ser Ser Leu Glu Ala
65                  70                  75                  80

Glu Asp Ala Ala Thr Tyr Tyr Cys Gly Gln Gly Asn Arg Leu Pro Tyr
                85                  90                  95

Thr Phe Gly Gln Gly Thr Lys Val Glu Ile Glu Arg Ala Asp Ala Ala
            100                 105                 110

Pro Thr Val Ser Ile Phe Pro Pro Ser Ser Glu Gln Leu Thr Ser Gly
        115                 120                 125

Gly Ala Ser Val Val Cys Phe Leu Asn Asn Phe Tyr Pro Lys Asp Ile
    130                 135                 140

Asn Val Lys Trp Lys Ile Asp Gly Ser Glu Arg Gln Asn Gly Val Leu
145                 150                 155                 160

Asn Ser Trp Thr Asp Gln Asp Ser Lys Asp Ser Thr Tyr Ser Met Ser
                165                 170                 175

Ser Thr Leu Thr Leu Thr Lys Asp Glu Tyr Glu Arg His Asn Ser Tyr
            180                 185                 190

Thr Cys Glu Ala Thr His Lys Thr Ser Thr Ser Pro Ile Val Lys Ser
        195                 200                 205

Phe Asn Arg Asn Glu Cys
    210
```

<210> SEQ ID NO 152
<211> LENGTH: 443
<212> TYPE: PRT
<213> ORGANISM: Artificial sequence
<220> FEATURE:
<223> OTHER INFORMATION: an artificially synthesized sequence

<400> SEQUENCE: 152

Gln Val Gln Leu Gln Glu Ser Gly Pro Gly Leu Val Lys Pro Ser Glu
1 5 10 15

Thr Leu Ser Leu Thr Cys Ala Val Ser Gly His Ser Ile Ser His Asp
20 25 30

His Ala Trp Ser Trp Val Arg Gln Pro Pro Gly Glu Gly Leu Glu Trp
35 40 45

Ile Gly Phe Ile Ser Tyr Ser Gly Ile Thr Asn Tyr Asn Pro Ser Leu
50 55 60

Gln Gly Arg Val Thr Ile Ser Arg Asp Asn Ser Lys Asn Thr Leu Tyr
65 70 75 80

Leu Gln Met Asn Ser Leu Arg Ala Glu Asp Thr Ala Val Tyr Tyr Cys
85 90 95

Ala Arg Ser Leu Ala Arg Thr Thr Ala Met Asp Tyr Trp Gly Glu Gly
100 105 110

Thr Leu Val Thr Val Ser Ser Ala Lys Thr Thr Pro Pro Ser Val Tyr
115 120 125

Pro Leu Ala Pro Gly Ser Ala Ala Gln Thr Asn Ser Met Val Thr Leu
130 135 140

Gly Cys Leu Val Lys Gly Tyr Phe Pro Glu Pro Val Thr Val Thr Trp
145 150 155 160

Asn Ser Gly Ser Leu Ser Ser Gly Val His Thr Phe Pro Ala Val Leu
165 170 175

Gln Ser Asp Leu Tyr Thr Leu Ser Ser Ser Val Thr Val Pro Ser Ser
180 185 190

Thr Trp Pro Ser Glu Thr Val Thr Cys Asn Val Ala His Pro Ala Ser
195 200 205

Ser Thr Lys Val Asp Lys Lys Ile Val Pro Arg Asp Cys Gly Cys Lys
210 215 220

Pro Cys Ile Cys Thr Val Pro Glu Val Ser Ser Val Phe Ile Phe Pro
225 230 235 240

Pro Lys Pro Lys Asp Val Leu Thr Ile Thr Leu Thr Pro Lys Val Thr
245 250 255

Cys Val Val Val Asp Ile Ser Lys Asp Asp Pro Glu Val Gln Phe Ser
260 265 270

Trp Phe Val Asp Asp Val Glu Val His Thr Ala Gln Thr Gln Pro Arg
275 280 285

Glu Glu Gln Phe Asn Ser Thr Phe Arg Ser Val Ser Glu Leu Pro Ile
290 295 300

Met His Gln Asp Trp Leu Asn Gly Lys Glu Phe Lys Cys Arg Val Asn
305 310 315 320

Ser Ala Asp Phe Pro Ala Pro Ile Glu Lys Thr Ile Ser Lys Thr Lys
325 330 335

Gly Arg Pro Lys Ala Pro Gln Val Tyr Thr Ile Pro Pro Pro Lys Glu
340 345 350

Gln Met Ala Lys Asp Lys Val Ser Leu Thr Cys Met Ile Thr Asp Phe
355 360 365

```
Phe Pro Glu Asp Ile Thr Val Glu Trp Gln Trp Asn Gly Gln Pro Ala
    370                 375                 380

Glu Asn Tyr Lys Asn Thr Gln Pro Ile Met Asp Thr Asp Gly Ser Tyr
385                 390                 395                 400

Phe Val Tyr Ser Lys Leu Asn Val Gln Lys Ser Asn Trp Glu Ala Gly
                405                 410                 415

Asn Thr Phe Thr Cys Ser Val Leu His Glu Gly Leu His Asn His His
            420                 425                 430

Thr Glu Lys Ser Leu Ser His Ser Pro Gly Lys
        435                 440


<210> SEQ ID NO 153
<211> LENGTH: 443
<212> TYPE: PRT
<213> ORGANISM: Artificial sequence
<220> FEATURE:
<223> OTHER INFORMATION: an artificially synthesized sequence

<400> SEQUENCE: 153

Gln Val Gln Leu Gln Glu Ser Gly Pro Gly Leu Val Lys Pro Ser Glu
1               5                   10                  15

Thr Leu Ser Leu Thr Cys Ala Val Ser Gly His Ser Ile Ser His Asp
            20                  25                  30

His Ala Trp Ser Trp Val Arg Gln Pro Pro Gly Glu Gly Leu Glu Trp
        35                  40                  45

Ile Gly Phe Ile Ser Tyr Ser Gly Ile Thr Asn Tyr Asn Pro Ser Leu
    50                  55                  60

Gln Gly Arg Val Thr Ile Ser Arg Asp Asn Ser Lys Asn Thr Leu Tyr
65                  70                  75                  80

Leu Gln Met Asn Ser Leu Arg Ala Glu Asp Thr Ala Val Tyr Tyr Cys
                85                  90                  95

Ala Arg Ser Leu Ala Arg Thr Thr Ala Met Asp Tyr Trp Gly Glu Gly
            100                 105                 110

Thr Leu Val Thr Val Ser Ser Ala Lys Thr Thr Pro Pro Ser Val Tyr
        115                 120                 125

Pro Leu Ala Pro Gly Ser Ala Ala Gln Thr Asn Ser Met Val Thr Leu
    130                 135                 140

Gly Cys Leu Val Lys Gly Tyr Phe Pro Glu Pro Val Thr Val Thr Trp
145                 150                 155                 160

Asn Ser Gly Ser Leu Ser Ser Gly Val His Thr Phe Pro Ala Val Leu
                165                 170                 175

Gln Ser Asp Leu Tyr Thr Leu Ser Ser Ser Val Thr Val Pro Ser Ser
            180                 185                 190

Thr Trp Pro Ser Glu Thr Val Thr Cys Asn Val Ala His Pro Ala Ser
        195                 200                 205

Ser Thr Lys Val Asp Lys Lys Ile Val Pro Arg Asp Cys Gly Cys Lys
    210                 215                 220

Pro Cys Ile Cys Thr Val Pro Glu Val Ser Asp Val Phe Ile Phe Pro
225                 230                 235                 240

Pro Lys Pro Lys Asp Val Leu Thr Ile Thr Leu Thr Pro Lys Val Thr
                245                 250                 255

Cys Val Val Val Asp Ile Ser Lys Asp Asp Pro Glu Val Gln Phe Ser
            260                 265                 270

Trp Phe Val Asp Asp Val Glu Val His Thr Ala Gln Thr Gln Pro Arg
        275                 280                 285
```

```
Glu Glu Gln Phe Asn Ser Thr Phe Arg Ser Val Ser Glu Leu Pro Ile
    290                 295                 300

Met His Gln Asp Trp Leu Asn Gly Lys Glu Phe Lys Cys Arg Val Asn
305                 310                 315                 320

Ser Ala Asp Phe Pro Ala Pro Ile Glu Lys Thr Ile Ser Lys Thr Lys
                325                 330                 335

Gly Arg Pro Lys Ala Pro Gln Val Tyr Thr Ile Pro Pro Pro Lys Glu
            340                 345                 350

Gln Met Ala Lys Asp Lys Val Ser Leu Thr Cys Met Ile Thr Asp Phe
        355                 360                 365

Phe Pro Glu Asp Ile Thr Val Glu Trp Gln Trp Asn Gly Gln Pro Ala
    370                 375                 380

Glu Asn Tyr Lys Asn Thr Gln Pro Ile Met Asp Thr Asp Gly Ser Tyr
385                 390                 395                 400

Phe Val Tyr Ser Lys Leu Asn Val Gln Lys Ser Asn Trp Glu Ala Gly
                405                 410                 415

Asn Thr Phe Thr Cys Ser Val Leu His Glu Gly Leu His Asn His His
            420                 425                 430

Thr Glu Lys Ser Leu Ser His Ser Pro Gly Lys
        435                 440


<210> SEQ ID NO 154
<211> LENGTH: 119
<212> TYPE: PRT
<213> ORGANISM: Artificial sequence
<220> FEATURE:
<223> OTHER INFORMATION: an artificially synthesized sequence

<400> SEQUENCE: 154

Gln Val Gln Leu Gln Glu Ser Gly Pro Gly Leu Val Lys Pro Ser Glu
1               5                   10                  15

Thr Leu Ser Leu Thr Cys Ala Val Ser Gly His Ser Ile Ser His Asp
            20                  25                  30

His Ala Trp Ser Trp Val Arg Gln Pro Pro Gly Glu Gly Leu Glu Trp
        35                  40                  45

Ile Gly Phe Ile Ser Tyr Ser Gly Ile Thr Asn Tyr Asn Pro Ser Leu
    50                  55                  60

Gln Gly Arg Val Thr Ile Ser Arg Asp Asn Ser Lys Asn Thr Leu Tyr
65                  70                  75                  80

Leu Gln Met Asn Ser Leu Arg Ala Glu Asp Thr Ala Val Tyr Tyr Cys
                85                  90                  95

Ala Arg Ser Leu Ala Arg Thr Thr Ala Met Asp Tyr Trp Gly Glu Gly
            100                 105                 110

Thr Leu Val Thr Val Ser Ser
        115


<210> SEQ ID NO 155
<211> LENGTH: 214
<212> TYPE: PRT
<213> ORGANISM: Artificial sequence
<220> FEATURE:
<223> OTHER INFORMATION: an artificially synthesized sequence

<400> SEQUENCE: 155

Asp Ile Gln Met Thr Gln Ser Pro Ser Ser Leu Ser Ala Ser Val Gly
1               5                   10                  15

Asp Arg Val Thr Ile Thr Cys Arg Ala Ser Gln Asp Ile Ser Ser Tyr
            20                  25                  30
```

```
Leu Asn Trp Tyr Gln Gln Lys Pro Gly Lys Ala Pro Lys Leu Leu Ile
        35                  40                  45

Tyr Tyr Thr Ser Arg Leu His Ser Gly Val Pro Ser Arg Phe Ser Gly
    50                  55                  60

Ser Gly Ser Gly Thr Asp Phe Thr Phe Thr Ile Ser Ser Leu Gln Pro
65                  70                  75                  80

Glu Asp Ile Ala Thr Tyr Tyr Cys Gln Gln Gly Asn Thr Leu Pro Tyr
                85                  90                  95

Thr Phe Gly Gln Gly Thr Lys Val Glu Ile Lys Arg Thr Val Ala Ala
            100                 105                 110

Pro Ser Val Phe Ile Phe Pro Pro Ser Asp Glu Gln Leu Lys Ser Gly
        115                 120                 125

Thr Ala Ser Val Val Cys Leu Leu Asn Asn Phe Tyr Pro Arg Glu Ala
    130                 135                 140

Lys Val Gln Trp Lys Val Asp Asn Ala Leu Gln Ser Gly Asn Ser Gln
145                 150                 155                 160

Glu Ser Val Thr Glu Gln Asp Ser Lys Asp Ser Thr Tyr Ser Leu Ser
                165                 170                 175

Ser Thr Leu Thr Leu Ser Lys Ala Asp Tyr Glu Lys His Lys Val Tyr
            180                 185                 190

Ala Cys Glu Val Thr His Gln Gly Leu Ser Ser Pro Val Thr Lys Ser
        195                 200                 205

Phe Asn Arg Gly Glu Cys
    210


<210> SEQ ID NO 156
<211> LENGTH: 447
<212> TYPE: PRT
<213> ORGANISM: Artificial sequence
<220> FEATURE:
<223> OTHER INFORMATION: an artificially synthesized sequence

<400> SEQUENCE: 156

Gln Val Gln Leu Gln Glu Ser Gly Pro Gly Leu Val Lys Pro Ser Glu
1               5                   10                  15

Thr Leu Ser Leu Thr Cys Ala Val Ser Gly His Ser Ile Ser His Asp
            20                  25                  30

His Ala Trp Ser Trp Val Arg Gln Pro Pro Gly Glu Gly Leu Glu Trp
        35                  40                  45

Ile Gly Phe Ile Ser Tyr Ser Gly Ile Thr Asn Tyr Asn Pro Ser Leu
    50                  55                  60

Gln Gly Arg Val Thr Ile Ser Arg Asp Asn Ser Lys Asn Thr Leu Tyr
65                  70                  75                  80

Leu Gln Met Asn Ser Leu Arg Ala Glu Asp Thr Ala Val Tyr Tyr Cys
                85                  90                  95

Ala Arg Ser Leu Ala Arg Thr Thr Ala Met Asp Tyr Trp Gly Glu Gly
            100                 105                 110

Thr Leu Val Thr Val Ser Ser Ala Ser Thr Lys Gly Pro Ser Val Phe
        115                 120                 125

Pro Leu Ala Pro Ser Ser Lys Ser Thr Ser Gly Gly Thr Ala Ala Leu
    130                 135                 140

Gly Cys Leu Val Lys Asp Tyr Phe Pro Glu Pro Val Thr Val Ser Trp
145                 150                 155                 160

Asn Ser Gly Ala Leu Thr Ser Gly Val His Thr Phe Pro Ala Val Leu
                165                 170                 175
```

```
Gln Ser Ser Gly Leu Tyr Ser Leu Ser Ser Val Val Thr Val Pro Ser
            180                 185                 190

Ser Ser Leu Gly Thr Gln Thr Tyr Ile Cys Asn Val Asn His Lys Pro
        195                 200                 205

Ser Asn Thr Lys Val Asp Lys Lys Val Glu Pro Lys Ser Cys Asp Lys
    210                 215                 220

Thr His Thr Cys Pro Pro Cys Pro Ala Pro Glu Leu Leu Gly Gly Pro
225                 230                 235                 240

Ser Val Phe Leu Phe Pro Pro Lys Pro Lys Asp Thr Leu Met Ile Ser
                245                 250                 255

Arg Thr Pro Glu Val Thr Cys Val Val Val Asp Val Ser His Glu Asp
            260                 265                 270

Pro Glu Val Lys Phe Asn Trp Tyr Val Asp Gly Val Glu Val His Asn
        275                 280                 285

Ala Lys Thr Lys Pro Arg Glu Glu Gln Tyr Asn Ser Thr Tyr Arg Val
    290                 295                 300

Val Ser Val Leu Thr Val Leu His Gln Asp Trp Leu Asn Gly Lys Glu
305                 310                 315                 320

Tyr Lys Cys Lys Val Ser Asn Lys Ala Leu Pro Ala Pro Ile Glu Lys
                325                 330                 335

Thr Ile Ser Lys Ala Lys Gly Gln Pro Arg Glu Pro Gln Val Tyr Thr
            340                 345                 350

Leu Pro Pro Ser Arg Asp Glu Leu Thr Lys Asn Gln Val Ser Leu Thr
        355                 360                 365

Cys Leu Val Lys Gly Phe Tyr Pro Ser Asp Ile Ala Val Glu Trp Glu
    370                 375                 380

Ser Asn Gly Gln Pro Glu Asn Asn Tyr Lys Thr Thr Pro Pro Val Leu
385                 390                 395                 400

Asp Ser Asp Gly Ser Phe Phe Leu Tyr Ser Lys Leu Thr Val Asp Lys
                405                 410                 415

Ser Arg Trp Gln Gln Gly Asn Val Phe Ser Cys Ser Val Met His Glu
            420                 425                 430

Ala Leu His Asn His Tyr Thr Gln Lys Ser Leu Ser Leu Ser Pro
        435                 440                 445


<210> SEQ ID NO 157
<211> LENGTH: 447
<212> TYPE: PRT
<213> ORGANISM: Artificial sequence
<220> FEATURE:
<223> OTHER INFORMATION: an artificially synthesized sequence

<400> SEQUENCE: 157

Gln Val Gln Leu Gln Glu Ser Gly Pro Gly Leu Val Lys Pro Ser Glu
1               5                   10                  15

Thr Leu Ser Leu Thr Cys Ala Val Ser Gly His Ser Ile Ser His Asp
            20                  25                  30

His Ala Trp Ser Trp Val Arg Gln Pro Pro Gly Glu Gly Leu Glu Trp
        35                  40                  45

Ile Gly Phe Ile Ser Tyr Ser Gly Ile Thr Asn Tyr Asn Pro Ser Leu
    50                  55                  60

Gln Gly Arg Val Thr Ile Ser Arg Asp Asn Ser Lys Asn Thr Leu Tyr
65                  70                  75                  80

Leu Gln Met Asn Ser Leu Arg Ala Glu Asp Thr Ala Val Tyr Tyr Cys
                85                  90                  95
```

Ala Arg Ser Leu Ala Arg Thr Thr Ala Met Asp Tyr Trp Gly Glu Gly
100 105 110

Thr Leu Val Thr Val Ser Ser Ala Ser Thr Lys Gly Pro Ser Val Phe
115 120 125

Pro Leu Ala Pro Ser Ser Lys Ser Thr Ser Gly Gly Thr Ala Ala Leu
130 135 140

Gly Cys Leu Val Lys Asp Tyr Phe Pro Glu Pro Val Thr Val Ser Trp
145 150 155 160

Asn Ser Gly Ala Leu Thr Ser Gly Val His Thr Phe Pro Ala Val Leu
165 170 175

Gln Ser Ser Gly Leu Tyr Ser Leu Ser Ser Val Val Thr Val Pro Ser
180 185 190

Ser Ser Leu Gly Thr Gln Thr Tyr Ile Cys Asn Val Asn His Lys Pro
195 200 205

Ser Asn Thr Lys Val Asp Lys Lys Val Glu Pro Lys Ser Cys Asp Lys
210 215 220

Thr His Thr Cys Pro Pro Cys Pro Ala Pro Glu Leu Leu Gly Gly Pro
225 230 235 240

Ser Val Phe Leu Phe Pro Pro Lys Pro Lys Asp Thr Leu Met Ile Ser
245 250 255

Arg Thr Pro Glu Val Thr Cys Val Val Val Asp Val Glu His Glu Asp
260 265 270

Pro Glu Val Lys Phe Asn Trp Tyr Val Asp Gly Val Glu Val His Asn
275 280 285

Ala Lys Thr Lys Pro Arg Glu Glu Gln Tyr Asn Ser Thr Tyr Arg Val
290 295 300

Val Ser Val Leu Thr Val Leu His Gln Asp Trp Leu Asn Gly Lys Glu
305 310 315 320

Tyr Lys Cys Lys Val Ser Asn Lys Ala Phe Pro Ala Pro Ile Glu Lys
325 330 335

Thr Ile Ser Lys Ala Lys Gly Gln Pro Arg Glu Pro Gln Val Tyr Thr
340 345 350

Leu Pro Pro Ser Arg Asp Glu Leu Thr Lys Asn Gln Val Ser Leu Thr
355 360 365

Cys Leu Val Lys Gly Phe Tyr Pro Ser Asp Ile Ala Val Glu Trp Glu
370 375 380

Ser Asn Gly Gln Pro Glu Asn Asn Tyr Lys Thr Thr Pro Pro Val Leu
385 390 395 400

Asp Ser Asp Gly Ser Phe Phe Leu Tyr Ser Lys Leu Thr Val Asp Lys
405 410 415

Ser Arg Trp Gln Gln Gly Asn Val Phe Ser Cys Ser Val Met His Glu
420 425 430

Ala Leu His Asn His Tyr Thr Gln Lys Ser Leu Ser Leu Ser Pro
435 440 445

<210> SEQ ID NO 158
<211> LENGTH: 449
<212> TYPE: PRT
<213> ORGANISM: Artificial sequence
<220> FEATURE:
<223> OTHER INFORMATION: an artificially synthesized sequence

<400> SEQUENCE: 158

Glu Val Gln Leu Val Glu Ser Gly Gly Gly Leu Val Gln Pro Gly Gly
1 5 10 15

-continued

```
Ser Leu Arg Leu Ser Cys Ala Val Ser Gly Tyr Ser Ile Thr Ser Gly
            20                  25                  30

Tyr Ser Trp Asn Trp Ile Arg Gln Ala Pro Gly Lys Gly Leu Glu Trp
        35                  40                  45

Val Ala Ser Ile Thr Tyr Asp Gly Ser Thr Asn Tyr Asn Pro Ser Val
    50                  55                  60

Lys Gly Arg Ile Thr Ile Ser Arg Asp Asp Ser Lys Asn Thr Phe Tyr
65                  70                  75                  80

Leu Gln Met Asn Ser Leu Arg Ala Glu Asp Thr Ala Val Tyr Tyr Cys
                85                  90                  95

Ala Arg Gly Ser His Tyr Phe Gly His Trp His Phe Ala Val Trp Gly
            100                 105                 110

Gln Gly Thr Leu Val Thr Val Ser Ser Ala Ser Thr Lys Gly Pro Ser
        115                 120                 125

Val Phe Pro Leu Ala Pro Ser Ser Lys Ser Thr Ser Gly Gly Thr Ala
    130                 135                 140

Ala Leu Gly Cys Leu Val Lys Asp Tyr Phe Pro Glu Pro Val Thr Val
145                 150                 155                 160

Ser Trp Asn Ser Gly Ala Leu Thr Ser Gly Val His Thr Phe Pro Ala
                165                 170                 175

Val Leu Gln Ser Ser Gly Leu Tyr Ser Leu Ser Ser Val Val Thr Val
            180                 185                 190

Pro Ser Ser Ser Leu Gly Thr Gln Thr Tyr Ile Cys Asn Val Asn His
        195                 200                 205

Lys Pro Ser Asn Thr Lys Val Asp Lys Lys Val Glu Pro Lys Ser Cys
    210                 215                 220

Asp Lys Thr His Thr Cys Pro Pro Cys Pro Ala Pro Glu Leu Leu Gly
225                 230                 235                 240

Gly Pro Ser Val Phe Leu Phe Pro Pro Lys Pro Lys Asp Thr Leu Met
                245                 250                 255

Ile Ser Arg Thr Pro Glu Val Thr Cys Val Val Val Asp Val Ser His
            260                 265                 270

Glu Asp Pro Glu Val Lys Phe Asn Trp Tyr Val Asp Gly Val Glu Val
        275                 280                 285

His Asn Ala Lys Thr Lys Pro Arg Glu Glu Gln Tyr Asn Ser Thr Tyr
    290                 295                 300

Arg Val Val Ser Val Leu Thr Val Leu His Gln Asp Trp Leu Asn Gly
305                 310                 315                 320

Lys Glu Tyr Lys Cys Lys Val Ser Asn Lys Ala Leu Pro Ala Pro Ile
                325                 330                 335

Glu Lys Thr Ile Ser Lys Ala Lys Gly Gln Pro Arg Glu Pro Gln Val
            340                 345                 350

Tyr Thr Leu Pro Pro Ser Arg Asp Glu Leu Thr Lys Asn Gln Val Ser
        355                 360                 365

Leu Thr Cys Leu Val Lys Gly Phe Tyr Pro Ser Asp Ile Ala Val Glu
    370                 375                 380

Trp Glu Ser Asn Gly Gln Pro Glu Asn Asn Tyr Lys Thr Thr Pro Pro
385                 390                 395                 400

Val Leu Asp Ser Asp Gly Ser Phe Phe Leu Tyr Ser Lys Leu Thr Val
                405                 410                 415

Asp Lys Ser Arg Trp Gln Gln Gly Asn Val Phe Ser Cys Ser Val Met
            420                 425                 430
```

His Glu Ala Leu His Asn His Tyr Thr Gln Lys Ser Leu Ser Leu Ser
435 440 445

Pro

<210> SEQ ID NO 159
<211> LENGTH: 218
<212> TYPE: PRT
<213> ORGANISM: Artificial sequence
<220> FEATURE:
<223> OTHER INFORMATION: an artificially synthesized sequence

<400> SEQUENCE: 159

Asp Ile Gln Leu Thr Gln Ser Pro Ser Ser Leu Ser Ala Ser Val Gly
1 5 10 15

Asp Arg Val Thr Ile Thr Cys Arg Ala Ser Gln Ser Val Asp Tyr Asp
20 25 30

Gly Asp Ser Tyr Met Asn Trp Tyr Gln Gln Lys Pro Gly Lys Ala Pro
35 40 45

Lys Leu Leu Ile Tyr Ala Ala Ser Tyr Leu Glu Ser Gly Val Pro Ser
50 55 60

Arg Phe Ser Gly Ser Gly Ser Gly Thr Asp Phe Thr Leu Thr Ile Ser
65 70 75 80

Ser Leu Gln Pro Glu Asp Phe Ala Thr Tyr Tyr Cys Gln Gln Ser His
85 90 95

Glu Asp Pro Tyr Thr Phe Gly Gln Gly Thr Lys Val Glu Ile Lys Arg
100 105 110

Thr Val Ala Ala Pro Ser Val Phe Ile Phe Pro Pro Ser Asp Glu Gln
115 120 125

Leu Lys Ser Gly Thr Ala Ser Val Val Cys Leu Leu Asn Asn Phe Tyr
130 135 140

Pro Arg Glu Ala Lys Val Gln Trp Lys Val Asp Asn Ala Leu Gln Ser
145 150 155 160

Gly Asn Ser Gln Glu Ser Val Thr Glu Gln Asp Ser Lys Asp Ser Thr
165 170 175

Tyr Ser Leu Ser Ser Thr Leu Thr Leu Ser Lys Ala Asp Tyr Glu Lys
180 185 190

His Lys Val Tyr Ala Cys Glu Val Thr His Gln Gly Leu Ser Ser Pro
195 200 205

Val Thr Lys Ser Phe Asn Arg Gly Glu Cys
210 215

<210> SEQ ID NO 160
<211> LENGTH: 449
<212> TYPE: PRT
<213> ORGANISM: Artificial sequence
<220> FEATURE:
<223> OTHER INFORMATION: an artificially synthesized sequence

<400> SEQUENCE: 160

Glu Val Gln Leu Val Glu Ser Gly Gly Gly Leu Val Gln Pro Gly Gly
1 5 10 15

Ser Leu Arg Leu Ser Cys Ala Val Ser Gly Tyr Ser Ile Thr Ser Gly
20 25 30

Tyr Ser Trp Asn Trp Ile Arg Gln Ala Pro Gly Lys Gly Leu Glu Trp
35 40 45

Val Ala Ser Ile Thr Tyr Asp Gly Ser Thr Asn Tyr Asn Pro Ser Val
50 55 60

```
Lys Gly Arg Ile Thr Ile Ser Arg Asp Asp Ser Lys Asn Thr Phe Tyr
65                  70                  75                  80

Leu Gln Met Asn Ser Leu Arg Ala Glu Asp Thr Ala Val Tyr Tyr Cys
                85                  90                  95

Ala Arg Gly Ser His Tyr Phe Gly His Trp His Phe Ala Val Trp Gly
            100                 105                 110

Gln Gly Thr Leu Val Thr Val Ser Ser Ala Ser Thr Lys Gly Pro Ser
        115                 120                 125

Val Phe Pro Leu Ala Pro Ser Ser Lys Ser Thr Ser Gly Gly Thr Ala
    130                 135                 140

Ala Leu Gly Cys Leu Val Lys Asp Tyr Phe Pro Glu Pro Val Thr Val
145                 150                 155                 160

Ser Trp Asn Ser Gly Ala Leu Thr Ser Gly Val His Thr Phe Pro Ala
                165                 170                 175

Val Leu Gln Ser Ser Gly Leu Tyr Ser Leu Ser Ser Val Val Thr Val
            180                 185                 190

Pro Ser Ser Ser Leu Gly Thr Gln Thr Tyr Ile Cys Asn Val Asn His
        195                 200                 205

Lys Pro Ser Asn Thr Lys Val Asp Lys Lys Val Glu Pro Lys Ser Cys
    210                 215                 220

Asp Lys Thr His Thr Cys Pro Pro Cys Pro Ala Pro Glu Leu Leu Gly
225                 230                 235                 240

Gly Pro Ser Val Phe Leu Phe Pro Pro Lys Pro Lys Asp Thr Leu Met
                245                 250                 255

Ile Ser Arg Thr Pro Glu Val Thr Cys Val Val Val Asp Val Glu His
            260                 265                 270

Glu Asp Pro Glu Val Lys Phe Asn Trp Tyr Val Asp Gly Val Glu Val
        275                 280                 285

His Asn Ala Lys Thr Lys Pro Arg Glu Glu Gln Tyr Asn Ser Thr Tyr
    290                 295                 300

Arg Val Val Ser Val Leu Thr Val Leu His Gln Asp Trp Leu Asn Gly
305                 310                 315                 320

Lys Glu Tyr Lys Cys Lys Val Ser Asn Lys Ala Phe Pro Ala Pro Ile
                325                 330                 335

Glu Lys Thr Ile Ser Lys Ala Lys Gly Gln Pro Arg Glu Pro Gln Val
            340                 345                 350

Tyr Thr Leu Pro Pro Ser Arg Asp Glu Leu Thr Lys Asn Gln Val Ser
        355                 360                 365

Leu Thr Cys Leu Val Lys Gly Phe Tyr Pro Ser Asp Ile Ala Val Glu
    370                 375                 380

Trp Glu Ser Asn Gly Gln Pro Glu Asn Asn Tyr Lys Thr Thr Pro Pro
385                 390                 395                 400

Val Leu Asp Ser Asp Gly Ser Phe Phe Leu Tyr Ser Lys Leu Thr Val
                405                 410                 415

Asp Lys Ser Arg Trp Gln Gln Gly Asn Val Phe Ser Cys Ser Val Met
            420                 425                 430

His Glu Ala Leu His Asn His Tyr Thr Gln Lys Ser Leu Ser Leu Ser
        435                 440                 445

Pro
```

<210> SEQ ID NO 161
<211> LENGTH: 447
<212> TYPE: PRT
<213> ORGANISM: Artificial sequence
<220> FEATURE:
<223> OTHER INFORMATION: an artificially synthesized sequence

<400> SEQUENCE: 161

```
Gln Val Gln Leu Gln Glu Ser Gly Pro Gly Leu Val Lys Pro Ser Glu
1               5                   10                  15

Thr Leu Ser Leu Thr Cys Ala Val Ser Gly His Ser Ile Ser His Asp
            20                  25                  30

His Ala Trp Ser Trp Val Arg Gln Pro Pro Gly Glu Gly Leu Glu Trp
        35                  40                  45

Ile Gly Phe Ile Ser Tyr Ser Gly Ile Thr Asn Tyr Asn Pro Ser Leu
    50                  55                  60

Gln Gly Arg Val Thr Ile Ser Arg Asp Asn Ser Lys Asn Thr Leu Tyr
65                  70                  75                  80

Leu Gln Met Asn Ser Leu Arg Ala Glu Asp Thr Ala Val Tyr Tyr Cys
                85                  90                  95

Ala Arg Ser Leu Ala Arg Thr Thr Ala Met Asp Tyr Trp Gly Glu Gly
            100                 105                 110

Thr Leu Val Thr Val Ser Ser Ala Ser Thr Lys Gly Pro Ser Val Phe
        115                 120                 125

Pro Leu Ala Pro Ser Ser Lys Ser Thr Ser Gly Gly Thr Ala Ala Leu
    130                 135                 140

Gly Cys Leu Val Lys Asp Tyr Phe Pro Glu Pro Val Thr Val Ser Trp
145                 150                 155                 160

Asn Ser Gly Ala Leu Thr Ser Gly Val His Thr Phe Pro Ala Val Leu
                165                 170                 175

Gln Ser Ser Gly Leu Tyr Ser Leu Ser Ser Val Val Thr Val Pro Ser
            180                 185                 190

Ser Ser Leu Gly Thr Gln Thr Tyr Ile Cys Asn Val Asn His Lys Pro
        195                 200                 205

Ser Asn Thr Lys Val Asp Lys Lys Val Glu Pro Lys Ser Cys Asp Lys
    210                 215                 220

Thr His Thr Cys Pro Pro Cys Pro Ala Pro Glu Leu Leu Gly Gly Pro
225                 230                 235                 240

Ser Val Phe Leu Phe Pro Pro Lys Pro Lys Asp Thr Leu Tyr Ile Ser
                245                 250                 255

Arg Thr Pro Glu Val Thr Cys Val Val Val Asp Val Ser His Glu Asp
            260                 265                 270

Pro Glu Val Lys Phe Asn Trp Tyr Val Asp Gly Val Glu Val His Asn
        275                 280                 285

Ala Lys Thr Lys Pro Arg Glu Glu Gln Tyr Asn Ser Thr Tyr Arg Val
    290                 295                 300

Val Ser Val Leu Thr Val Leu His Gln Asp Trp Leu Asn Gly Lys Glu
305                 310                 315                 320

Tyr Lys Cys Lys Val Ser Asn Lys Ala Leu Pro Ala Pro Ile Glu Lys
                325                 330                 335

Thr Ile Ser Lys Ala Lys Gly Gln Pro Arg Glu Pro Gln Val Tyr Thr
            340                 345                 350

Leu Pro Pro Ser Arg Asp Glu Leu Thr Lys Asn Gln Val Ser Leu Thr
        355                 360                 365

Cys Leu Val Lys Gly Phe Tyr Pro Ser Asp Ile Ala Val Glu Trp Glu
    370                 375                 380

Ser Asn Gly Gln Pro Glu Asn Asn Tyr Lys Thr Thr Pro Pro Val Leu
385                 390                 395                 400
```

Asp Ser Asp Gly Ser Phe Phe Leu Tyr Ser Lys Leu Thr Val Asp Lys
405 410 415

Ser Arg Trp Gln Gln Gly Asn Val Phe Ser Cys Ser Val Met His Glu
420 425 430

Ala Leu His Tyr His Tyr Thr Gln Lys Ser Leu Ser Leu Ser Pro
435 440 445

<210> SEQ ID NO 162
<211> LENGTH: 447
<212> TYPE: PRT
<213> ORGANISM: Artificial sequence
<220> FEATURE:
<223> OTHER INFORMATION: an artificially synthesized sequence

<400> SEQUENCE: 162

Gln Val Gln Leu Gln Glu Ser Gly Pro Gly Leu Val Lys Pro Ser Glu
1 5 10 15

Thr Leu Ser Leu Thr Cys Ala Val Ser Gly His Ser Ile Ser His Asp
20 25 30

His Ala Trp Ser Trp Val Arg Gln Pro Pro Gly Glu Gly Leu Glu Trp
35 40 45

Ile Gly Phe Ile Ser Tyr Ser Gly Ile Thr Asn Tyr Asn Pro Ser Leu
50 55 60

Gln Gly Arg Val Thr Ile Ser Arg Asp Asn Ser Lys Asn Thr Leu Tyr
65 70 75 80

Leu Gln Met Asn Ser Leu Arg Ala Glu Asp Thr Ala Val Tyr Tyr Cys
85 90 95

Ala Arg Ser Leu Ala Arg Thr Thr Ala Met Asp Tyr Trp Gly Glu Gly
100 105 110

Thr Leu Val Thr Val Ser Ser Ala Ser Thr Lys Gly Pro Ser Val Phe
115 120 125

Pro Leu Ala Pro Ser Ser Lys Ser Thr Ser Gly Gly Thr Ala Ala Leu
130 135 140

Gly Cys Leu Val Lys Asp Tyr Phe Pro Glu Pro Val Thr Val Ser Trp
145 150 155 160

Asn Ser Gly Ala Leu Thr Ser Gly Val His Thr Phe Pro Ala Val Leu
165 170 175

Gln Ser Ser Gly Leu Tyr Ser Leu Ser Ser Val Val Thr Val Pro Ser
180 185 190

Ser Ser Leu Gly Thr Gln Thr Tyr Ile Cys Asn Val Asn His Lys Pro
195 200 205

Ser Asn Thr Lys Val Asp Lys Lys Val Glu Pro Lys Ser Cys Asp Lys
210 215 220

Thr His Thr Cys Pro Pro Cys Pro Ala Pro Glu Leu Leu Gly Gly Asp
225 230 235 240

Ser Val Phe Leu Phe Pro Pro Lys Pro Lys Asp Thr Leu Tyr Ile Ser
245 250 255

Arg Thr Pro Glu Val Thr Cys Val Val Val Asp Val Ser His Glu Asp
260 265 270

Pro Glu Val Lys Phe Asn Trp Tyr Val Asp Gly Val Glu Val His Asn
275 280 285

Ala Lys Thr Lys Pro Arg Glu Glu Gln Tyr Asn Ser Thr Tyr Arg Val
290 295 300

Val Ser Val Leu Thr Val Leu His Gln Asp Trp Leu Asn Gly Lys Glu
305 310 315 320

```
Tyr Lys Cys Lys Val Ser Asn Lys Ala Leu Pro Ala Pro Ile Glu Lys
                325                 330                 335

Thr Ile Ser Lys Ala Lys Gly Gln Pro Arg Glu Pro Gln Val Tyr Thr
            340                 345                 350

Leu Pro Pro Ser Arg Asp Glu Leu Thr Lys Asn Gln Val Ser Leu Thr
        355                 360                 365

Cys Leu Val Lys Gly Phe Tyr Pro Ser Asp Ile Ala Val Glu Trp Glu
    370                 375                 380

Ser Asn Gly Gln Pro Glu Asn Asn Tyr Lys Thr Thr Pro Pro Val Leu
385                 390                 395                 400

Asp Ser Asp Gly Ser Phe Phe Leu Tyr Ser Lys Leu Thr Val Asp Lys
                405                 410                 415

Ser Arg Trp Gln Gln Gly Asn Val Phe Ser Cys Ser Val Met His Glu
            420                 425                 430

Ala Leu His Tyr His Tyr Thr Gln Lys Ser Leu Ser Leu Ser Pro
        435                 440                 445


<210> SEQ ID NO 163
<211> LENGTH: 447
<212> TYPE: PRT
<213> ORGANISM: Artificial sequence
<220> FEATURE:
<223> OTHER INFORMATION: an artificially synthesized sequence

<400> SEQUENCE: 163

Gln Val Gln Leu Gln Glu Ser Gly Pro Gly Leu Val Lys Pro Ser Glu
1               5                   10                  15

Thr Leu Ser Leu Thr Cys Ala Val Ser Gly His Ser Ile Ser His Asp
            20                  25                  30

His Ala Trp Ser Trp Val Arg Gln Pro Pro Gly Glu Gly Leu Glu Trp
        35                  40                  45

Ile Gly Phe Ile Ser Tyr Ser Gly Ile Thr Asn Tyr Asn Pro Ser Leu
    50                  55                  60

Gln Gly Arg Val Thr Ile Ser Arg Asp Asn Ser Lys Asn Thr Leu Tyr
65                  70                  75                  80

Leu Gln Met Asn Ser Leu Arg Ala Glu Asp Thr Ala Val Tyr Tyr Cys
                85                  90                  95

Ala Arg Ser Leu Ala Arg Thr Thr Ala Met Asp Tyr Trp Gly Glu Gly
            100                 105                 110

Thr Leu Val Thr Val Ser Ser Ala Ser Thr Lys Gly Pro Ser Val Phe
        115                 120                 125

Pro Leu Ala Pro Ser Ser Lys Ser Thr Ser Gly Gly Thr Ala Ala Leu
    130                 135                 140

Gly Cys Leu Val Lys Asp Tyr Phe Pro Glu Pro Val Thr Val Ser Trp
145                 150                 155                 160

Asn Ser Gly Ala Leu Thr Ser Gly Val His Thr Phe Pro Ala Val Leu
                165                 170                 175

Gln Ser Ser Gly Leu Tyr Ser Leu Ser Ser Val Val Thr Val Pro Ser
            180                 185                 190

Ser Ser Leu Gly Thr Gln Thr Tyr Ile Cys Asn Val Asn His Lys Pro
        195                 200                 205

Ser Asn Thr Lys Val Asp Lys Lys Val Glu Pro Lys Ser Cys Asp Lys
    210                 215                 220

Thr His Thr Cys Pro Pro Cys Pro Ala Pro Glu Leu Leu Gly Gly Asp
225                 230                 235                 240
```

```
Ser Val Phe Leu Phe Pro Pro Lys Pro Lys Asp Thr Leu Met Ile Ser
                245                 250                 255

Arg Thr Pro Glu Val Thr Cys Val Val Val Asp Val Ser His Glu Asp
            260                 265                 270

Pro Glu Val Lys Phe Asn Trp Tyr Val Asp Gly Val Glu Val His Asn
        275                 280                 285

Ala Lys Thr Lys Pro Arg Glu Glu Gln Tyr Asn Ser Thr Tyr Arg Val
    290                 295                 300

Val Ser Val Leu Thr Val Leu His Gln Asp Trp Leu Asn Gly Lys Glu
305                 310                 315                 320

Tyr Lys Cys Lys Val Ser Asn Lys Ala Leu Pro Ala Pro Ile Glu Lys
                325                 330                 335

Thr Ile Ser Lys Ala Lys Gly Gln Pro Arg Glu Pro Gln Val Tyr Thr
            340                 345                 350

Leu Pro Pro Ser Arg Asp Glu Leu Thr Lys Asn Gln Val Ser Leu Thr
        355                 360                 365

Cys Leu Val Lys Gly Phe Tyr Pro Ser Asp Ile Ala Val Glu Trp Glu
    370                 375                 380

Ser Asn Gly Gln Pro Glu Asn Asn Tyr Lys Thr Thr Pro Pro Val Leu
385                 390                 395                 400

Asp Ser Asp Gly Ser Phe Phe Leu Tyr Ser Lys Leu Thr Val Asp Lys
                405                 410                 415

Ser Arg Trp Gln Gln Gly Asn Val Phe Ser Cys Ser Val Met His Glu
            420                 425                 430

Ala Leu His Asn His Tyr Thr Gln Lys Ser Leu Ser Leu Ser Pro
        435                 440                 445


<210> SEQ ID NO 164
<211> LENGTH: 447
<212> TYPE: PRT
<213> ORGANISM: Artificial sequence
<220> FEATURE:
<223> OTHER INFORMATION: an artificially synthesized sequence

<400> SEQUENCE: 164

Gln Val Gln Leu Gln Glu Ser Gly Pro Gly Leu Val Lys Pro Ser Glu
1               5                   10                  15

Thr Leu Ser Leu Thr Cys Ala Val Ser Gly His Ser Ile Ser His Asp
            20                  25                  30

His Ala Trp Ser Trp Val Arg Gln Pro Pro Gly Glu Gly Leu Glu Trp
        35                  40                  45

Ile Gly Phe Ile Ser Tyr Ser Gly Ile Thr Asn Tyr Asn Pro Ser Leu
    50                  55                  60

Gln Gly Arg Val Thr Ile Ser Arg Asp Asn Ser Lys Asn Thr Leu Tyr
65                  70                  75                  80

Leu Gln Met Asn Ser Leu Arg Ala Glu Asp Thr Ala Val Tyr Tyr Cys
                85                  90                  95

Ala Arg Ser Leu Ala Arg Thr Thr Ala Met Asp Tyr Trp Gly Glu Gly
            100                 105                 110

Thr Leu Val Thr Val Ser Ser Ala Ser Thr Lys Gly Pro Ser Val Phe
        115                 120                 125

Pro Leu Ala Pro Ser Ser Lys Ser Thr Ser Gly Gly Thr Ala Ala Leu
    130                 135                 140

Gly Cys Leu Val Lys Asp Tyr Phe Pro Glu Pro Val Thr Val Ser Trp
145                 150                 155                 160
```

```
Asn Ser Gly Ala Leu Thr Ser Gly Val His Thr Phe Pro Ala Val Leu
                165                 170                 175

Gln Ser Ser Gly Leu Tyr Ser Leu Ser Ser Val Val Thr Val Pro Ser
            180                 185                 190

Ser Ser Leu Gly Thr Gln Thr Tyr Ile Cys Asn Val Asn His Lys Pro
        195                 200                 205

Ser Asn Thr Lys Val Asp Lys Lys Val Glu Pro Lys Ser Cys Asp Lys
    210                 215                 220

Thr His Thr Cys Pro Pro Cys Pro Ala Pro Glu Leu Leu Gly Gly Pro
225                 230                 235                 240

Ser Val Phe Leu Phe Pro Pro Lys Pro Lys Asp Thr Leu Met Ile Ser
                245                 250                 255

Arg Thr Pro Glu Val Thr Cys Val Val Val Asp Val Ser His Glu Asp
            260                 265                 270

Pro Glu Val Lys Phe Asn Trp Tyr Val Asp Gly Val Glu Val His Asn
        275                 280                 285

Ala Lys Thr Lys Pro Arg Glu Glu Gln Tyr Asn Ser Thr Tyr Arg Val
    290                 295                 300

Val Ser Val Leu Thr Val Leu His Gln Asp Trp Leu Asn Gly Lys Glu
305                 310                 315                 320

Tyr Lys Cys Lys Val Ser Asn Lys Ala Leu Pro Ala Pro Ile Glu Lys
                325                 330                 335

Thr Ile Ser Lys Ala Lys Gly Gln Pro Arg Glu Pro Gln Val Tyr Thr
            340                 345                 350

Leu Pro Pro Ser Arg Asp Glu Leu Thr Lys Asn Gln Val Ser Leu Thr
        355                 360                 365

Cys Leu Val Lys Gly Phe Tyr Pro Ser Asp Ile Ala Val Glu Trp Glu
    370                 375                 380

Ser Asn Gly Gln Pro Glu Asn Asn Tyr Lys Thr Thr Pro Pro Val Leu
385                 390                 395                 400

Asp Ser Asp Gly Ser Phe Phe Leu Tyr Ser Lys Leu Thr Val Asp Lys
                405                 410                 415

Ser Arg Trp Gln Gln Gly Asn Val Phe Ser Cys Ser Val Met His Glu
            420                 425                 430

Ala Leu His Asn His Tyr Thr Gln Glu Ser Leu Ser Leu Ser Pro
        435                 440                 445


<210> SEQ ID NO 165
<211> LENGTH: 444
<212> TYPE: PRT
<213> ORGANISM: Artificial sequence
<220> FEATURE:
<223> OTHER INFORMATION: an artificially synthesized sequence

<400> SEQUENCE: 165

Gln Val Gln Leu Gln Glu Ser Gly Pro Gly Leu Val Lys Pro Ser Glu
1               5                   10                  15

Thr Leu Ser Leu Thr Cys Ala Val Ser Gly His Ser Ile Ser His Asp
            20                  25                  30

His Ala Trp Ser Trp Val Arg Gln Pro Pro Gly Glu Gly Leu Glu Trp
        35                  40                  45

Ile Gly Phe Ile Ser Tyr Ser Gly Ile Thr Asn Tyr Asn Pro Ser Leu
    50                  55                  60

Gln Gly Arg Val Thr Ile Ser Arg Asp Asn Ser Lys Asn Thr Leu Tyr
65                  70                  75                  80
```

Leu Gln Met Asn Ser Leu Arg Ala Glu Asp Thr Ala Val Tyr Tyr Cys
85 90 95

Ala Arg Ser Leu Ala Arg Thr Thr Ala Met Asp Tyr Trp Gly Glu Gly
100 105 110

Thr Leu Val Thr Val Ser Ser Ala Ser Thr Lys Gly Pro Ser Val Phe
115 120 125

Pro Leu Ala Pro Cys Ser Arg Ser Thr Ser Glu Ser Thr Ala Ala Leu
130 135 140

Gly Cys Leu Val Lys Asp Tyr Phe Pro Glu Pro Val Thr Val Ser Trp
145 150 155 160

Asn Ser Gly Ala Leu Thr Ser Gly Val His Thr Phe Pro Ala Val Leu
165 170 175

Gln Ser Ser Gly Leu Tyr Ser Leu Ser Ser Val Val Thr Val Pro Ser
180 185 190

Ser Ser Leu Gly Thr Lys Thr Tyr Thr Cys Asn Val Asp His Lys Pro
195 200 205

Ser Asn Thr Lys Val Asp Lys Arg Val Glu Ser Lys Tyr Gly Pro Pro
210 215 220

Cys Pro Pro Cys Pro Ala Pro Glu Phe Leu Gly Gly Pro Ser Val Phe
225 230 235 240

Leu Phe Pro Pro Lys Pro Lys Asp Thr Leu Met Ile Ser Arg Thr Pro
245 250 255

Glu Val Thr Cys Val Val Val Asp Val Ser Gln Glu Asp Pro Glu Val
260 265 270

Gln Phe Asn Trp Tyr Val Asp Gly Val Glu Val His Asn Ala Lys Thr
275 280 285

Lys Pro Arg Glu Glu Gln Phe Asn Ser Thr Tyr Arg Val Val Ser Val
290 295 300

Leu Thr Val Leu His Gln Asp Trp Leu Asn Gly Lys Glu Tyr Lys Cys
305 310 315 320

Lys Val Ser Asn Lys Gly Leu Pro Ser Ser Ile Glu Lys Thr Ile Ser
325 330 335

Lys Ala Lys Gly Gln Pro Arg Glu Pro Gln Val Tyr Thr Leu Pro Pro
340 345 350

Ser Gln Glu Glu Met Thr Lys Asn Gln Val Ser Leu Thr Cys Leu Val
355 360 365

Lys Gly Phe Tyr Pro Ser Asp Ile Ala Val Glu Trp Glu Ser Asn Gly
370 375 380

Gln Pro Glu Asn Asn Tyr Lys Thr Thr Pro Pro Val Leu Asp Ser Asp
385 390 395 400

Gly Ser Phe Phe Leu Tyr Ser Arg Leu Thr Val Asp Lys Ser Arg Trp
405 410 415

Gln Glu Gly Asn Val Phe Ser Cys Ser Val Met His Glu Ala Leu His
420 425 430

Asn His Tyr Thr Gln Lys Ser Leu Ser Leu Ser Leu
435 440

<210> SEQ ID NO 166
<211> LENGTH: 328
<212> TYPE: PRT
<213> ORGANISM: Artificial sequence
<220> FEATURE:
<223> OTHER INFORMATION: an artificially synthesized sequence

<400> SEQUENCE: 166

Ala Ser Thr Lys Gly Pro Ser Val Phe Pro Leu Ala Pro Ser Ser Lys
1 5 10 15

Ser Thr Ser Gly Gly Thr Ala Ala Leu Gly Cys Leu Val Lys Asp Tyr
20 25 30

Phe Pro Glu Pro Val Thr Val Ser Trp Asn Ser Gly Ala Leu Thr Ser
35 40 45

Gly Val His Thr Phe Pro Ala Val Leu Gln Ser Ser Gly Leu Tyr Ser
50 55 60

Leu Ser Ser Val Val Thr Val Pro Ser Ser Ser Leu Gly Thr Gln Thr
65 70 75 80

Tyr Ile Cys Asn Val Asn His Lys Pro Ser Asn Thr Lys Val Asp Lys
85 90 95

Lys Val Glu Pro Lys Ser Cys Asp Lys Thr His Thr Cys Pro Pro Cys
100 105 110

Pro Ala Pro Glu Leu Leu Gly Gly Pro Ser Val Phe Leu Phe Pro Pro
115 120 125

Lys Pro Lys Asp Thr Leu Met Ile Ser Arg Thr Pro Glu Val Thr Cys
130 135 140

Val Val Val Asp Val Ser His Glu Asp Pro Glu Val Lys Phe Asn Trp
145 150 155 160

Tyr Val Asp Gly Val Glu Val His Asn Ala Lys Thr Lys Pro Arg Glu
165 170 175

Glu Gln Tyr Asn Ser Thr Tyr Arg Val Val Ser Val Leu Thr Val Leu
180 185 190

His Gln Asp Trp Leu Asn Gly Lys Glu Tyr Lys Cys Lys Val Ser Asn
195 200 205

Lys Ala Leu Pro Ala Pro Ile Glu Lys Thr Ile Ser Lys Ala Lys Gly
210 215 220

Gln Pro Arg Glu Pro Gln Val Tyr Thr Leu Pro Pro Ser Arg Asp Glu
225 230 235 240

Leu Thr Lys Asn Gln Val Ser Leu Thr Cys Leu Val Lys Gly Phe Tyr
245 250 255

Pro Ser Asp Ile Ala Val Glu Trp Glu Ser Asn Gly Gln Pro Glu Asn
260 265 270

Asn Tyr Lys Thr Thr Pro Pro Val Leu Asp Ser Asp Gly Ser Phe Phe
275 280 285

Leu Tyr Ser Lys Leu Thr Val Asp Lys Ser Arg Trp Gln Gln Gly Asn
290 295 300

Val Phe Ser Cys Ser Val Met His Glu Ala Leu His Asn His Tyr Thr
305 310 315 320

Gln Lys Ser Leu Ser Leu Ser Pro
325

<210> SEQ ID NO 167
<211> LENGTH: 325
<212> TYPE: PRT
<213> ORGANISM: Artificial sequence
<220> FEATURE:
<223> OTHER INFORMATION: an artificially synthesized sequence

<400> SEQUENCE: 167

Ala Ser Thr Lys Gly Pro Ser Val Phe Pro Leu Ala Pro Cys Ser Arg
1 5 10 15

Ser Thr Ser Glu Ser Thr Ala Ala Leu Gly Cys Leu Val Lys Asp Tyr
20 25 30

Phe Pro Glu Pro Val Thr Val Ser Trp Asn Ser Gly Ala Leu Thr Ser
35 40 45

Gly Val His Thr Phe Pro Ala Val Leu Gln Ser Ser Gly Leu Tyr Ser
50 55 60

Leu Ser Ser Val Val Thr Val Pro Ser Ser Ser Leu Gly Thr Lys Thr
65 70 75 80

Tyr Thr Cys Asn Val Asp His Lys Pro Ser Asn Thr Lys Val Asp Lys
85 90 95

Arg Val Glu Ser Lys Tyr Gly Pro Pro Cys Pro Pro Cys Pro Ala Pro
100 105 110

Glu Phe Leu Gly Gly Pro Ser Val Phe Leu Phe Pro Pro Lys Pro Lys
115 120 125

Asp Thr Leu Met Ile Ser Arg Thr Pro Glu Val Thr Cys Val Val Val
130 135 140

Asp Val Ser Gln Glu Asp Pro Glu Val Gln Phe Asn Trp Tyr Val Asp
145 150 155 160

Gly Val Glu Val His Asn Ala Lys Thr Lys Pro Arg Glu Glu Gln Phe
165 170 175

Asn Ser Thr Tyr Arg Val Val Ser Val Leu Thr Val Leu His Gln Asp
180 185 190

Trp Leu Asn Gly Lys Glu Tyr Lys Cys Lys Val Ser Asn Lys Gly Leu
195 200 205

Pro Ser Ser Ile Glu Lys Thr Ile Ser Lys Ala Lys Gly Gln Pro Arg
210 215 220

Glu Pro Gln Val Tyr Thr Leu Pro Pro Ser Gln Glu Glu Met Thr Lys
225 230 235 240

Asn Gln Val Ser Leu Thr Cys Leu Val Lys Gly Phe Tyr Pro Ser Asp
245 250 255

Ile Ala Val Glu Trp Glu Ser Asn Gly Gln Pro Glu Asn Asn Tyr Lys
260 265 270

Thr Thr Pro Pro Val Leu Asp Ser Asp Gly Ser Phe Phe Leu Tyr Ser
275 280 285

Arg Leu Thr Val Asp Lys Ser Arg Trp Gln Glu Gly Asn Val Phe Ser
290 295 300

Cys Ser Val Met His Glu Ala Leu His Asn His Tyr Thr Gln Lys Ser
305 310 315 320

Leu Ser Leu Ser Leu
325

<210> SEQ ID NO 168
<211> LENGTH: 443
<212> TYPE: PRT
<213> ORGANISM: Artificial Sequence
<220> FEATURE:
<223> OTHER INFORMATION: an artificially synthesized sequence

<400> SEQUENCE: 168

Gln Val Gln Leu Val Gln Ser Gly Ala Glu Val Lys Lys Pro Gly Ala
1 5 10 15

Ser Val Thr Val Ser Cys Lys Ala Ser Gly Tyr Thr Phe Thr Asp Tyr
20 25 30

Glu Met His Trp Ile Arg Gln Pro Pro Gly Glu Gly Leu Glu Trp Ile
35 40 45

Gly Ala Ile Asp Pro Lys Thr Gly Asp Thr Ala Tyr Ser Glu Ser Phe
50 55 60

```
Gln Asp Arg Val Thr Leu Thr Ala Asp Lys Ser Thr Ser Thr Ala Tyr
65                  70                  75                  80

Met Glu Leu Ser Ser Leu Thr Ser Glu Asp Thr Ala Val Tyr Tyr Cys
                85                  90                  95

Thr Arg Phe Tyr Ser Tyr Thr Tyr Trp Gly Gln Gly Thr Leu Val Thr
            100                 105                 110

Val Ser Ser Ala Ser Thr Lys Gly Pro Ser Val Phe Pro Leu Ala Pro
        115                 120                 125

Ser Ser Lys Ser Thr Ser Gly Gly Thr Ala Ala Leu Gly Cys Leu Val
    130                 135                 140

Lys Asp Tyr Phe Pro Glu Pro Val Thr Val Ser Trp Asn Ser Gly Ala
145                 150                 155                 160

Leu Thr Ser Gly Val His Thr Phe Pro Ala Val Leu Gln Ser Ser Gly
                165                 170                 175

Leu Tyr Ser Leu Ser Ser Val Val Thr Val Pro Ser Ser Ser Leu Gly
            180                 185                 190

Thr Gln Thr Tyr Ile Cys Asn Val Asn His Lys Pro Ser Asn Thr Lys
        195                 200                 205

Val Asp Lys Lys Val Glu Pro Lys Ser Cys Asp Lys Thr His Thr Cys
    210                 215                 220

Pro Pro Cys Pro Ala Pro Glu Leu Leu Gly Gly Pro Ser Val Phe Leu
225                 230                 235                 240

Phe Pro Pro Lys Pro Lys Asp Thr Leu Met Ile Ser Arg Thr Pro Glu
                245                 250                 255

Val Thr Cys Val Val Val Asp Val Ser His Glu Asp Pro Glu Val Lys
            260                 265                 270

Phe Asn Trp Tyr Val Asp Gly Val Glu Val His Asn Ala Lys Thr Lys
        275                 280                 285

Pro Arg Glu Glu Gln Tyr Asn Ser Thr Tyr Arg Val Val Ser Val Leu
    290                 295                 300

Thr Val Leu His Gln Asp Trp Leu Asn Gly Lys Glu Tyr Lys Cys Lys
305                 310                 315                 320

Val Ser Asn Lys Ala Leu Pro Ala Pro Ile Glu Lys Thr Ile Ser Lys
                325                 330                 335

Ala Lys Gly Gln Pro Arg Glu Pro Gln Val Tyr Thr Leu Pro Pro Ser
            340                 345                 350

Arg Asp Glu Leu Thr Lys Asn Gln Val Ser Leu Thr Cys Leu Val Lys
        355                 360                 365

Gly Phe Tyr Pro Ser Asp Ile Ala Val Glu Trp Glu Ser Asn Gly Gln
    370                 375                 380

Pro Glu Asn Asn Tyr Lys Thr Thr Pro Pro Val Leu Asp Ser Asp Gly
385                 390                 395                 400

Ser Phe Phe Leu Tyr Ser Lys Leu Thr Val Asp Lys Ser Arg Trp Gln
                405                 410                 415

Gln Gly Asn Val Phe Ser Cys Ser Val Met His Glu Ala Leu His Asn
            420                 425                 430

His Tyr Thr Gln Glu Ser Leu Ser Leu Ser Pro
        435                 440
```

<210> SEQ ID NO 169
<211> LENGTH: 219
<212> TYPE: PRT
<213> ORGANISM: Artificial Sequence
<220> FEATURE:
<223> OTHER INFORMATION: an artificially synthesized sequence -continued

<400> SEQUENCE: 169

```
Asp Ile Val Met Thr Gln Ser Pro Leu Ser Leu Pro Val Thr Pro Gly
1               5                   10                  15

Glu Pro Ala Ser Ile Ser Cys Gln Ala Ser Glu Ser Leu Val His Ser
            20                  25                  30

Asn Arg Asn Thr Tyr Leu His Trp Tyr Leu Gln Lys Pro Gly Gln Ser
        35                  40                  45

Pro Gln Leu Leu Ile Tyr Lys Val Ser Asn Arg Phe Ser Gly Val Pro
    50                  55                  60

Asp Arg Phe Ser Gly Ser Gly Ser Gly Thr Asp Phe Thr Leu Lys Ile
65                  70                  75                  80

Ser Arg Val Glu Ala Glu Asp Val Gly Val Tyr Tyr Cys Ser Gln Asn
                85                  90                  95

Thr His Val Pro Pro Thr Phe Gly Gln Gly Thr Lys Val Glu Ile Glu
            100                 105                 110

Arg Thr Val Ala Ala Pro Ser Val Phe Ile Phe Pro Pro Ser Asp Glu
        115                 120                 125

Gln Leu Lys Ser Gly Thr Ala Ser Val Val Cys Leu Leu Asn Asn Phe
    130                 135                 140

Tyr Pro Arg Glu Ala Lys Val Gln Trp Lys Val Asp Asn Ala Leu Gln
145                 150                 155                 160

Ser Gly Asn Ser Gln Glu Ser Val Thr Glu Gln Asp Ser Lys Asp Ser
                165                 170                 175

Thr Tyr Ser Leu Ser Ser Thr Leu Thr Leu Ser Lys Ala Asp Tyr Glu
            180                 185                 190

Lys His Lys Val Tyr Ala Cys Glu Val Thr His Gln Gly Leu Ser Ser
        195                 200                 205

Pro Val Thr Lys Ser Phe Asn Arg Gly Glu Cys
    210                 215
```

METHODS FOR PRODUCING ANTIBODIES PROMOTING DISAPPEARANCE OF ANTIGENS HAVING PLURALITY OF BIOLOGICAL ACTIVITIES

CROSS-REFERENCE TO RELATED APPLICATIONS

This application is a continuation of application Ser. No. 14/347,034, filed on Mar. 25, 2014, now abandoned, which is the National Stage of International Application Serial No. PCT/JP2012/075083, filed on Sep. 28, 2012, which claims the benefit of Japanese Application Serial No. 2011-217043, filed on Sep. 30, 2011.

TECHNICAL FIELD

The present invention relates to antigen-binding molecules that can promote antigen elimination from the blood (serum or plasma), and thereby reduce the in vivo physiological activities of the antigen which are difficult to inhibit in vitro due to multiple physiological activities of the antigen, and pharmaceutical compositions comprising as an active ingredient the antigen-binding molecules.

BACKGROUND ART

There are many known examples of diseases whose onset is caused by disruption of the balance of physiological activities maintained under healthy conditions, due to an excessively increased plasma level of a physiologically active substance (for example, a cytokine) relative to healthy conditions. A possible effective means of treating such diseases is to inhibit the physiological activity of the excessive physiologically active substance. For example, an antibody that binds to an antigen having physiological activity, and thereby neutralizes its physiological activity can be an effective therapeutic agent.

However, when an antigen has two or more physiological activities, normally a single type of neutralizing antibody can inhibit only one physiological activity. It is expected to be difficult for such an antibody to cure a disease caused by the above-described physiologically active substance.

Physiologically active substances that have two or more physiological activities include, for example, high mobility group box 1 (HMGB1). HMGB1 was identified as a member of the HMG family which is a nuclear protein that contributes to the stability of higher-order DNA structure by binding to the DNA. HMGB1 consists of 215 amino acids, and structurally it is composed of three main domains: HMG A box, HMG B box, and an acidic carboxyl-terminal domain. Normally, HMGB1 is present in cells as a DNA-binding protein. However, HMGB1 is released to the outside of inflammatory or necrotic cells through an active or passive mechanism. Released HMGB1 is known to activate a variety of cell surface receptors such as receptor for advanced glycation endproducts (RAGE), Toll-like receptor 4 (TLR4), and IL-1 receptor via binding to various substances such as DNAs, lipopolysaccharide (LPS), and interleukin (IL)-1β, and thereby transmit the signal into cells, which leads to induction of various inflammatory reactions (Non-patent Document 1). Furthermore, HMGB1 has been suggested to play an important role in the onset of sepsis, based on the fact that the blood level of HMGB1 was elevated in sepsis model mice administered with LPS and the mouse mortality rate was decreased by administration of a polyclonal antibody against HMGB1 (Non-patent Document 2). Patent Document 1 discloses preparation of several monoclonal antibodies with high affinity for HMGB1 and that they inhibited the binding of HMGB1 to RAGE or TLR4 and reduced the mortality rate of sepsis model mice. However, there is no description on the acquisition of antibodies that inhibit the HMGB1 activities towards both RAGE and TLR4, suggesting that it is difficult for a single type of antibody to inhibit multiple activities of HMGB1.

Antibodies (IgGs) bind to neonatal Fc receptor (FcRn), and have long plasma retention. The binding of IgG to FcRn is observed only under an acidic condition (pH 6.0), and it is hardly observed under the neutral condition (pH 7.4). Typically, IgG is nonspecifically incorporated into cells via endocytosis, and returns to the cell surface by binding to endosomal FcRn under the acidic condition in the endosome. Then, IgG dissociates from FcRn under the neutral condition in plasma. IgGs that do not bind to FcRn enter the lysosome and are degraded there. When the FcRn binding of an IgG under the acidic condition is eliminated by introducing mutations into its Fc region, the IgG is not recycled from the endosome to the plasma, and as a result the plasma retention of IgG is markedly impaired. For a method of improving the plasma retention of IgG, a method that improves the FcRn binding under acidic conditions has been reported. When the FcRn binding under acidic conditions is improved by introducing an amino acid substitution into an IgG Fc region, the efficiency of recycling from the endosome to the plasma is increased, resulting in an improvement of the plasma retention. Meanwhile, it has been reported that, when the FcRn binding under the neutral condition is enhanced, IgG does not dissociate from FcRn under the neutral condition in plasma even when it returns to the cell surface via binding to FcRn under the acidic condition in the endosome, and consequently the plasma retention remains unaltered or is rather worsened (Non-patent Documents 3 to 5).

Recently, antibodies that bind to antigens in a pH-dependent manner have been reported (Patent Document 2). The antibodies, which strongly bind to antigens under the plasma neutral condition and dissociate from the antigens under the endosomal acidic condition, after being dissociated from the antigen, become again capable of binding to antigens when recycled to the plasma via FcRn. Thus, a single antibody can bind to multiple antigens repeatedly. Plasma retention of an antigen is much shorter than that of an antibody which has the FcRn-mediated recycling mechanism. Therefore, when an antigen is bound to an antibody, the plasma retention of the antigen is normally prolonged, resulting in an increase of antigen concentration in the plasma. On the other hand, it has been reported that the above-described antibodies which bind to antigens in a pH-dependent manner promote antigen elimination from plasma as compared to typical antibodies because they dissociate from the antigens in the endosome during the FcRn-mediated recycling process (Patent Document 2). However, there is no known antibody engineering technique that further improves the above-described effect of promoting antigen elimination from plasma.

PRIOR ART DOCUMENTS

Patent Documents

[Patent Document 1] WO1995/002187
[Patent Document 2] WO2009/125825

Non-Patent Documents

[Non-patent Document 1] Sims G P et al., Annu. Rev. Immunol. (2010) 28, 367-388.

[Non-patent Document 2] Wang H et al., Science (1999) 285, 248-251.

[Non-patent Document 3] Yeung Y A et al., J. Immunol. (2009) 182, 7663-71.

[Non-patent Document 4] Datta-Mannan A et al., J. Biol. Chem. (2007) 282, 1709-17.

[Non-patent Document 5] Dall'Acqua W F et al., J. Immunol. (2002) 169, 5171-80.

SUMMARY OF THE INVENTION

Problems to be Solved by the Invention

The present invention was achieved in view of the above circumstances. An objective of the present invention is to provide antigen-binding molecules that can promote antigen elimination from the blood (serum or plasma) and thereby reduce in vivo the physiological activities of the antigen which are difficult to inhibit with a single type of antigen-binding molecule in vitro because the antigen has two or more physiological activities. Another objective of the present invention is to provide methods for producing the antigen-binding molecules and pharmaceutical compositions comprising the antigen-binding molecules as an active ingredient.

Means for Solving the Problems

The present inventors conducted dedicated studies. As a result, the present inventors newly revealed that an antigen-binding molecule that inhibits some of the physiological activities of antigens with two or more physiological activities but does not inhibit the remaining physiological activities in vitro can promote antigen elimination from blood (serum or plasma), and reduce the physiological activities in vivo, by conferring the antigen-binding molecule with the properties of:

(i) binding to human neonatal Fc receptor (FcRn) under an acidic pH range condition;

(ii) binding to human FcRn and/or human Fcγ receptor more strongly than native human IgG under a neutral pH range condition; and (iii) altering the antigen-binding activity according to the ion concentration condition.

The present invention is based on the above findings, and specifically relates to:

[1] an antigen-binding molecule that reduces plasma antigen concentration, wherein the antigen-binding molecule has characteristics (1) to (6) below:

(1) the antigen-binding molecule comprises an antigen-binding domain and at least one receptor-binding domain;

(2) under an acidic pH range condition, the receptor-binding domain has human neonatal Fc Receptor (FcRn)-binding activity;

(3) under a neutral pH range condition, the human Fc receptor-binding activity of the receptor-binding domain is higher than human Fc receptor-binding activity of native human IgG;

(4) an antigen-binding activity of the antigen-binding domain is altered according to the ion concentration condition;

(5) the antigen has two or more physiological activities; and (6) one or more physiological activities of the antigen are inhibited by binding of the antigen-binding molecule, while at least one type of physiological activity of the antigen is maintained;

[2] the antigen-binding molecule of [1], characterized in that it inhibits the activity of an antigen to bind one or more types of target molecules by binding to the antigen while allowing the antigen to maintain the binding activity to at least one type of target molecule;

[3] the antigen-binding molecule of [1] or [2], wherein the reduction of plasma antigen concentration is due to the promotion of antigen uptake into cells;

[4] the antigen-binding molecule of any one of [1] to [3], characterized in that the decrease of antigen concentration in plasma results in reduction of the physiological activity of the antigen in vivo;

[5] the antigen-binding molecule of any one of [1] to [4], wherein the antigen is high mobility group box 1 (HMGB1);

[6] the antigen-binding molecule of [5], which inhibits the binding between HMGB1 and receptor for advanced glycation endproducts (RAGE);

[7] the antigen-binding molecule of [5] or [6], which inhibits the binding between HMGB1 and Toll-like receptor 4 (TLR4);

[8] the antigen-binding molecule of any one of [1] to [4], wherein the antigen is connective tissue growth factor (CTGF);

[9] the antigen-binding molecule of any one of [1] to [8], wherein the human Fc receptor is human FcRn;

[10] the antigen-binding molecule of [9], wherein the receptor-binding domain comprises an Fc region in which at least one amino acid in the IgG Fc region is altered;

[11] the antigen-binding molecule of [10], wherein the amino acid alteration in the IgG Fc region is an alteration of at least one amino acid selected from positions: 234, 235, 236, 237, 238, 239, 244, 245, 248, 249, 250, 251, 252, 253, 254, 255, 256, 257, 258, 260, 262, 265, 267, 270, 272, 274, 279, 280, 282, 283, 284, 285, 286, 288, 289, 293, 295, 297, 298, 303, 305, 307, 308, 309, 311, 312, 313, 314, 315, 316, 317, 318, 325, 326, 327, 328, 329, 330, 332, 334, 338, 339, 340, 341, 343, 345, 360, 361, 362, 375, 376, 377, 378, 380, 382, 384, 385, 386, 387, 389, 390, 391, 413, 422, 423, 424, 427, 428, 430, 431, 433, 434, 435, 436, 437, 438, 440, and 442 (EU numbering);

[12] the antigen-binding molecule of [11], wherein the amino acid alteration in the IgG Fc region is at least one amino acid alteration selected from the alterations: wherein according to EU numbering, the amino acid at position 234 is Arg;

the amino acid at position 235 is Gly, Lys, or Arg;

the amino acid at position 236 is Ala, Asp, Lys, or Arg;

the amino acid at position 237 is Lys, Met, or Arg;

the amino acid at position 238 is Ala, Asp, Lys, Leu, or Arg;

the amino acid at position 239 is Asp or Lys;

the amino acid at position 244 is Leu;

the amino acid at position 245 is Arg;

the amino acid at position 248 is Ile or Tyr;

the amino acid at position 249 is Pro;

the amino acid at position 250 is Ala, Glu, Phe, Ile, Met, Gln, Ser, Val, Trp, Gly, His, Leu, Asn, or Tyr;

the amino acid at position 251 is Arg, Asp, Glu, or Leu;

the amino acid at position 252 is Phe, Ser, Thr, Trp, or Tyr;

the amino acid at position 253 is Val;

the amino acid at position 254 is Ala, Gly, His, Ile, Gln, Ser, Val, or Thr;

the amino acid at position 255 is Ala, Asp, Phe, His, Ile, Lys, Leu, Met, Asn, Gln, Arg, Gly, Ser, Trp, Tyr, or Glu;

the amino acid at position 256 is Ala, Asp, Glu, Arg, Asn, Pro, Thr, Ser, or Gln;

the amino acid at position 257 is Ala, Gly, Ile, Leu, Met, Asn, Ser, Thr, or Val;

the amino acid at position 258 is Asp or His;
the amino acid at position 260 is Ser;
the amino acid at position 262 is Leu;
the amino acid at position 265 is Ala;
the amino acid at position 267 is Met or Leu;
the amino acid at position 270 is Lys or Phe;
the amino acid at position 272 is Ala, Leu, or Arg;
the amino acid at position 274 is Ala;
the amino acid at position 279 is Leu, Ala, Asp, Gly, His, Met, Asn, Gln, Arg, Ser, Thr, Trp, or Tyr;
the amino acid at position 280 is Ala, Gly, His, Lys, Asn, Gln, Arg, Ser, Thr, or Glu;
the amino acid at position 282 is Ala or Asp;
the amino acid at position 283 is Ala, Asp, Phe, Gly, His, Ile, Lys, Leu, Asn, Pro, Gln, Arg, Ser, Thr, Trp, or Tyr;
the amino acid at position 284 is Lys;
the amino acid at position 285 is Asn;
the amino acid at position 286 is Ala, Asp, Phe, Gly, His, Ile, Lys, Leu, Met, Pro, Gln, Arg, Ser, Thr, Val, Trp, Tyr, or Glu;
the amino acid at position 288 is Ala, Asp, Glu, Phe, Gly, His, Ile, Leu, Met, Asn, Pro, Gln, Arg, Val, Trp, Tyr, or Ser;
the amino acid at position 289 is His;
the amino acid at position 293 is Val;
the amino acid at position 295 is Met;
the amino acid at position 297 is Ala;
the amino acid at position 298 is Gly;
the amino acid at position 303 is Ala;
the amino acid at position 305 is Ala or Thr;
the amino acid at position 307 is Ala, Asp, Glu, Phe, Gly, His, Ile, Lys, Leu, Met, Asn, Pro, Gln, Arg, Ser, Val, Trp, or Tyr;
the amino acid at position 308 is Ala, Phe, Ile, Leu, Met, Pro, Gln, or Thr;
the amino acid at position 309 is Ala, Asp, Glu, Pro, His, or Arg;
the amino acid at position 311 is Ala, His, Glu, Lys, Leu, Met, Ser, Val, Trp, or Ile;
the amino acid at position 312 is Ala, Asp, Pro, or His;
the amino acid at position 313 is Tyr or Phe;
the amino acid at position 314 is Ala, Leu, Lys, or Arg;
the amino acid at position 315 is Ala, Asp, Glu, Phe, Gly, Ile, Lys, Leu, Met, Gln, Arg, Ser, Thr, Val, Trp, Tyr, or His;
the amino acid at position 316 is Ala, Glu, Phe, His, Ile, Lys, Leu, Met, Asn, Pro, Gln, Arg, Ser, Thr, Val, Trp, or Asp;
the amino acid at position 317 is Ala or Pro;
the amino acid at position 318 is Asn or Thr;
the amino acid at position 325 is Ala, Gly, Met, Leu, Ile, or Ser;
the amino acid at position 326 is Asp;
the amino acid at position 327 is Gly;
the amino acid at position 328 is Arg, Asp, Glu, or Tyr;
the amino acid at position 329 is Lys or Arg;
the amino acid at position 330 is Leu;
the amino acid at position 332 is Glu, Phe, His, Lys, Leu, Met, Arg, Ser, Trp, or Val;
the amino acid at position 334 is Leu;
the amino acid at position 338 is Ala;
the amino acid at position 339 is Asn, Thr, or Trp;
the amino acid at position 340 is Ala;
the amino acid at position 341 is Pro;
the amino acid at position 343 is Glu, His, Lys, Gln, Arg, Thr, or Tyr;
the amino acid at position 345 is Ala;
the amino acid at position 360 is His;
the amino acid at position 361 is Ala;
the amino acid at position 362 is Ala;
the amino acid at position 375 is Ala or Arg;
the amino acid at position 376 is Ala, Gly, Ile, Met, Pro, Thr, or Val;
the amino acid at position 377 is Lys;
the amino acid at position 378 is Asp, Asn, or Val;
the amino acid at position 380 is Ala, Asn, Thr, or Ser;
the amino acid at position 382 is Ala, Phe, His, Ile, Lys, Leu, Met, Asn, Gln, Arg, Ser, Thr, Trp, Tyr, or Val;
the amino acid at position 384 is Ala;
the amino acid at position 385 is Ala, Gly, Lys, Ser, Thr, Asp, His, or Arg;
the amino acid at position 386 is Arg, Asp, Ile, Met, Ser, Thr, Lys, or Pro;
the amino acid at position 387 is Ala, Arg, His, Pro, Ser, Thr, or Glu;
the amino acid at position 389 is Ala, Asn, Pro, or Ser;
the amino acid at position 390 is Ala;
the amino acid at position 391 is Ala;
the amino acid at position 413 is Ala;
the amino acid at position 423 is Asn;
the amino acid at position 424 is Ala or Glu;
the amino acid at position 427 is Asn;
the amino acid at position 428 is Ala, Asp, Phe, Gly, His, Ile, Lys, Leu, Met, Asn, Pro, Gln, Ser, Thr, Val, Trp, or Tyr;
the amino acid at position 430 is Ala, Phe, Gly, His, Ile, Lys, Leu, Met, Asn, Gln, Arg, Ser, Thr, Val, or Tyr;
the amino acid at position 431 is His or Asn;
the amino acid at position 433 is Arg, Gln, His, Ile, Pro, Ser, or Lys;
the amino acid at position 434 is Ala, Phe, Gly, Met, His, Ser, Trp, or Tyr;
the amino acid at position 435 is Lys, Arg, or Asn;
the amino acid at position 436 is Ala, His, Ile, Leu, Glu, Phe, Gly, Lys, Met, Asn, Arg, Ser, Thr, Trp, or Val;
the amino acid at position 437 is Arg;
the amino acid at position 438 is Lys, Leu, Thr, or Trp;
the amino acid at position 440 is Lys; and
the amino acid at position 442 is Lys;

[13] the antigen-binding molecule of any one of [10] to [12], wherein the IgG Fc region is the Fc region of a nonhuman animal-derived IgG;

[14] the antigen-binding molecule of any one of [10] to [12], wherein the IgG Fc region is the Fc region of a human-derived IgG;

[15] the antigen-binding molecule of any one of [1] to [8], wherein the human Fc receptor is a human Fcγ receptor;

[16] the antigen-binding molecule of [15], wherein the receptor-binding domain comprises an Fc region in which at least one amino acid in the IgG Fc region is altered;

[17] the antigen-binding molecule of [16], wherein the amino acid alteration in the IgG Fc region is an alteration of at least one amino acid selected from positions: 221, 222, 223, 224, 225, 227, 228, 230, 231, 232, 233, 234, 235, 236, 237, 238, 239, 240, 241, 243, 244, 245, 246, 247, 249, 250, 251, 252, 254, 255, 256, 257, 258, 260, 262, 263, 264, 265, 266, 267, 268, 269, 270, 271, 272, 273, 274, 275, 276, 278, 279, 280, 281, 282, 283, 284, 285, 286, 288, 290, 291, 292, 293, 294, 295, 296, 297, 298, 299, 300, 301, 302, 303, 304, 305, 307, 308, 309, 311, 312, 313, 314, 315, 316, 317, 318, 320, 322, 323, 324, 325, 326, 327, 328, 329, 330, 331, 332, 333, 334, 335, 336, 337, 339, 341, 343, 375, 376, 377, 378, 379, 380, 382, 385, 386, 387, 389, 392, 396, 421, 423, 427, 428, 429, 430, 431, 433, 434, 436, 438, 440; and 442 (EU numbering);

[18] the antigen-binding molecule of [17], wherein the amino acid alteration in the IgG Fc region is at least one amino acid alteration selected from the alterations: wherein, according to EU numbering, the amino acid at position 221 is Lys or Tyr;
the amino acid at position 222 is Phe, Trp, Glu, or Tyr;
the amino acid at position 223 is Phe, Trp, Glu, or Lys;
the amino acid at position 224 is Phe, Trp, Glu, or Tyr;
the amino acid at position 225 is Glu, Lys, or Trp;
the amino acid at position 227 is Glu, Gly, Lys, or Tyr;
the amino acid at position 228 is Glu, Gly, Lys, or Tyr;
the amino acid at position 230 is Ala, Glu, Gly, or Tyr;
the amino acid at position 231 is Glu, Gly, Lys, Pro, or Tyr;
the amino acid at position 232 is Glu, Gly, Lys, or Tyr;
the amino acid at position 233 is Ala, Asp, Phe, Gly, His, Ile, Lys, Leu, Met, Asn, Gln, Arg, Ser, Thr, Val, Trp, or Tyr;
the amino acid at position 234 is Ala, Asp, Glu, Phe, Gly, His, Ile, Lys, Met, Asn, Pro, Gln, Arg, Ser, Thr, Val, Trp, or Tyr;
the amino acid at position 235 is Ala, Asp, Glu, Phe, Gly, His, Ile, Lys, Met, Asn, Pro, Gln, Arg, Ser, Thr, Val, Trp, or Tyr;
the amino acid at position 236 is Ala, Asp, Glu, Phe, His, Ile, Lys, Leu, Met, Asn, Pro, Gln, Arg, Ser, Thr, Val, Trp, or Tyr;
the amino acid at position 237 is Ala, Asp, Glu, Phe, His, Ile, Lys, Leu, Met, Asn, Pro, Gln, Arg, Ser, Thr, Val, Trp, or Tyr;
the amino acid at position 238 is Asp, Glu, Phe, Gly, His, Ile, Lys, Leu, Met, Asn, Gln, Arg, Ser, Thr, Val, Trp, or Tyr;
the amino acid at position 239 is Asp, Glu, Phe, Gly, His, Ile, Lys, Leu, Met, Asn, Pro, Gln, Arg, Thr, Val, Trp, or Tyr;
the amino acid at position 240 is Ala, Ile, Met, or Thr;
the amino acid at position 241 is Asp, Glu, Leu, Arg, Trp, or Tyr;
the amino acid at position 243 is Leu, Glu, Leu, Gln, Arg, Trp, or Tyr;
the amino acid at position 244 is His;
the amino acid at position 245 is Ala;
the amino acid at position 246 is Asp, Glu, His, or Tyr,
the amino acid at position 247 is Ala, Phe, Gly, His, Ile, Leu, Met, Thr, Val, or Tyr;
the amino acid at position 249 is Glu, His, Gln, or Tyr;
the amino acid at position 250 is Glu or Gln;
the amino acid at position 251 is Phe;
the amino acid at position 254 is Phe, Met, or Tyr;
the amino acid at position 255 is Glu, Leu, or Tyr;
the amino acid at position 256 is Ala, Met, or Pro;
the amino acid at position 258 is Asp, Glu, His, Ser, or Tyr;
the amino acid at position 260 is Asp, Glu, His, or Tyr;
the amino acid at position 262 is Ala, Glu, Phe, Ile, or Thr;
the amino acid at position 263 is Ala, Ile, Met, or Thr;
the amino acid at position 264 is Asp, Glu, Phe, Gly, His, Ile, Lys, Leu, Met, Asn, Pro, Gln, Arg, Ser, Thr, Trp, or Tyr;
the amino acid at position 265 is Ala, Glu, Leu, Phe, Gly, His, Ile, Lys, Leu, Met, Asn, Pro, Gln, Arg, Ser, Thr, Val, Trp, or Tyr;
the amino acid at position 266 is Ala, Phe, Ile, Leu, Met, or Thr;
the amino acid at position 267 is Ala, Asp, Glu, Phe, Gly, His, Ile, Lys, Leu, Met, Asn, Pro, Gln, Arg, Thr, Val, Trp, or Tyr;
the amino acid at position 268 is Ala, Asp, Glu, Phe, Gly, Ile, Lys, Leu, Met, Asn, Pro, Gln, Arg, Thr, Val, or Trp;
the amino acid at position 269 is Asp, Phe, Gly, His, Ile, Lys, Leu, Met, Asn, Pro, Arg, Ser, Thr, Val, Trp, or Tyr;
the amino acid at position 270 is Glu, Phe, Gly, His, Ile, Leu, Met, Pro, Gln, Arg, Ser, Thr, Trp, or Tyr;
the amino acid at position 271 is Ala, Asp, Glu, Phe, Gly, His, Ile, Lys, Leu, Met, Asn, Gln, Arg, Ser, Thr, Val, Trp, or Tyr;
the amino acid at position 272 is Asp, Phe, Gly, His, Ile, Lys, Leu, Met, Asn, Pro, Gln, Arg, Ser, Thr, Val, Trp, or Tyr;
the amino acid at position 273 is Phe or Ile;
the amino acid at position 274 is Asp, Glu, Phe, Gly, His, Ile, Leu, Met, Asn, Pro, Arg, Ser, Thr, Val, Trp, or Tyr;
the amino acid at position 275 is Leu or Trp;
the amino acid at position 276 is Asp, Glu, Phe, Gly, His, Ile, Leu, Met, Pro, Arg, Ser, Thr, Val, Trp, or Tyr;
the amino acid at position 278 is Asp, Glu, Gly, His, Ile, Lys, Leu, Met, Asn, Pro, Gln, Arg, Ser, Thr, Val, or Trp;
the amino acid at position 279 is Ala;
the amino acid at position 280 is Ala, Gly, His, Lys, Leu, Pro, Gln, Trp, or Tyr;
the amino acid at position 281 is Asp, Lys, Pro, or Tyr;
the amino acid at position 282 is Glu, Gly, Lys, Pro, or Tyr;
the amino acid at position 283 is Ala, Gly, His, Ile, Lys, Leu, Met, Pro, Arg, or Tyr;
the amino acid at position 284 is Asp, Glu, Leu, Asn, Thr, or Tyr;
the amino acid at position 285 is Asp, Glu, Lys, Gln, Trp, or Tyr;
the amino acid at position 286 is Glu, Gly, Pro, or Tyr;
the amino acid at position 288 is Asn, Asp, Glu, or Tyr;
the amino acid at position 290 is Asp, Gly, His, Leu, Asn, Ser, Thr, Trp, or Tyr;
the amino acid at position 291 is Asp, Glu, Gly, His, Ile, Gln, or Thr;
the amino acid at position 292 is Ala, Asp, Glu, Pro, Thr, or Tyr;
the amino acid at position 293 is Phe, Gly, His, Ile, Leu, Met, Asn, Pro, Arg, Ser, Thr, Val, Trp, or Tyr;
the amino acid at position 294 is Phe, Gly, His, Ile, Lys, Leu, Met, Asn, Pro, Arg, Ser, Thr, Val, Trp, or Tyr;
the amino acid at position 295 is Asp, Glu, Phe, Gly, His, Ile, Lys, Leu, Met, Asn, Pro, Arg, Ser, Thr, Val, Trp, or Tyr;
the amino acid at position 296 is Ala, Asp, Glu, Gly, His, Ile, Lys, Leu, Met, Asn, Gln, Arg, Ser, Thr, or Val;
the amino acid at position 297 is Asp, Glu, Phe, Gly, His, Ile, Lys, Leu, Met, Pro, Gln, Arg, Ser, Thr, Val, Trp, or Tyr;
the amino acid at position 298 is Ala, Asp, Glu, Phe, His, Ile, Lys, Met, Asn, Gln, Arg, Thr, Val, Trp, or Tyr;
the amino acid at position 299 is Ala, Asp, Glu, Phe, Gly, His, Ile, Lys, Leu, Met, Asn, Pro, Gln, Arg, Ser, Val, Trp, or Tyr;
the amino acid at position 300 is Ala, Asp, Glu, Gly, His, Ile, Lys, Leu, Met, Asn, Pro, Gln, Arg, Ser, Thr, Val, or Trp;
the amino acid at position 301 is Asp, Glu, His, or Tyr;
the amino acid at position 302 is Ile;
the amino acid at position 303 is Asp, Gly, or Tyr;
the amino acid at position 304 is Asp, His, Leu, Asn, or Thr;
the amino acid at position 305 is Glu, Ile, Thr, or Tyr;
the amino acid at position 311 is Ala, Asp, Asn, Thr, Val or Tyr;
the amino acid at position 313 is Phe;
the amino acid at position 315 is Leu;
the amino acid at position 317 is Glu or Gln;
the amino acid at position 318 is His, Leu, Asn, Pro, Gln, Arg, Thr, Val, or Tyr;
the amino acid at position 320 is Asp, Phe, Gly, His, Ile, Leu, Asn, Pro, Ser, Thr, Val, Trp, or Tyr;
the amino acid at position 322 is Ala, Asp, Phe, Gly, His, Ile, Pro, Ser, Thr, Val, Trp, or Tyr;
the amino acid at position 323 is Ile, Leu, or Met;
the amino acid at position 324 is Asp, Phe, Gly, His, Ile, Leu, Met, Pro, Arg, Thr, Val, Trp, or Tyr;
the amino acid at position 325 is Ala, Asp, Glu, Phe, Gly, His, Ile, Lys, Leu, Met, Pro, Gln, Arg, Ser, Thr, Val, Trp, or Tyr;

the amino acid at position 326 is Ala, Asp, Glu, Phe, Gly, His, Ile, Leu, Met, Asn, Pro, Gln, Ser, Thr, Val, Trp, or Tyr;
the amino acid at position 327 is Ala, Asp, Glu, Phe, Gly, His, Ile, Lys, Leu, Met, Asn, Pro, Arg, Thr, Val, Trp, or Tyr;
the amino acid at position 328 is Ala, Asp, Glu, Phe, Gly, His, Ile, Lys, Met, Asn, Pro, Gln, Arg, Ser, Thr, Val, Trp, or Tyr;
the amino acid at position 329 is Asp, Glu, Phe, Gly, His, Ile, Lys, Leu, Met, Asn, Gln, Arg, Ser, Thr, Val, Trp, or Tyr;
the amino acid at position 330 is Cys, Glu, Phe, Gly, His, Ile, Lys, Leu, Met, Asn, Pro, Arg, Ser, Thr, Val, Trp, or Tyr;
the amino acid at position 331 is Asp, Phe, His, Ile, Leu, Met, Gln, Arg, Ser, Thr, Val, Trp, or Tyr;
the amino acid at position 332 is Ala, Asp, Glu, Phe, Gly, His, Lys, Leu, Met, Asn, Pro, Gln, Arg, Ser, Thr, Val, Trp, or Tyr;
the amino acid at position 333 is Ala, Asp, Glu, Phe, Gly, His, Ile, Lys, Leu, Met, Pro, Arg, Ser, Thr, Val, or Tyr;
the amino acid at position 334 is Ala, Glu, Phe, His, Ile, Leu, Met, Asn, Pro, Gln, Arg, Ser, Thr, Val, Trp, or Tyr;
the amino acid at position 335 is Asp, Phe, Gly, His, Ile, Leu, Met, Asn, Pro, Arg, Ser, Val, Trp, or Tyr;
the amino acid at position 336 is Glu, Lys, or Tyr;
the amino acid at position 337 is Asp, Glu, His, or Asn;
the amino acid at position 339 is Asp, Phe, Gly, Ile, Lys, Met, Asn, Gln, Arg, Ser, or Thr;
the amino acid at position 376 is Ala or Val;
the amino acid at position 377 is Gly or Lys;
the amino acid at position 378 is Asp;
the amino acid at position 379 is Asn;
the amino acid at position 380 is Ala, Asn, or Ser;
the amino acid at position 382 is Ala or Ile;
the amino acid at position 385 is Glu;
the amino acid at position 392 is Thr;
the amino acid at position 396 is Asp, Glu, Phe, Ile, Lys, Leu, Met, Gln, Arg, or Tyr;
the amino acid at position 421 is Lys;
the amino acid at position 427 is Asn;
the amino acid at position 428 is Phe or Leu;
the amino acid at position 429 is Met;
the amino acid at position 434 is Trp;
the amino acid at position 436 is Ile; and
the amino acid at position 440 is Gly, His, Ile, Leu, or Tyr;

[19] the antigen-binding molecule of any one of [16] to [18], wherein the human Fcγ receptor is FcγRIa, FcγRIIa, FcγRIIb, or FcγRIIIa;

[20] the antigen-binding molecule of [17], wherein the amino acid alteration in the IgG Fc region is an alteration wherein the amino acid at position 238 is Asp and the amino acid at position 271 is Gly according to EU numbering;

[21] the antigen-binding molecule of [20], wherein the IgG Fc region comprises an additional alteration of at least one amino acid selected from positions: 233, 234, 237, 244, 245, 249, 250, 251, 252, 254, 255, 256, 257, 258, 260, 262, 264, 265, 266, 267, 268, 269, 270, 272, 279, 283, 285, 286, 288, 293, 296, 307, 308, 309, 311, 312, 314, 316, 317, 318, 326, 327, 330, 331, 332, 333, 339, 341, 343, 375, 376, 377, 378, 380, 382, 385, 386, 387, 389, 396, 423, 427, 428, 430, 431, 433, 434, 436, 438, 440, and 442 according to EU numbering;

[22] the antigen-binding molecule of [21], wherein the amino acid alteration in the IgG Fc region is at least one amino acid alteration selected from the alterations: wherein according to EU numbering,
the amino acid at position 233 is Asp;
the amino acid at position 234 is Tyr;
the amino acid at position 237 is Asp;
the amino acid at position 264 is Ile;
the amino acid at position 265 is Glu;
the amino acid at position 266 is Phe, Met, or Leu;
the amino acid at position 267 is Ala, Glu, Gly, or Gln;
the amino acid at position 268 is Asp or Glu;
the amino acid at position 269 is Asp;
the amino acid at position 272 is Asp, Phe, Ile, Met, Asn, or Gln;
the amino acid at position 296 is Asp;
the amino acid at position 326 is Ala or Asp;
the amino acid at position 327 is Gly;
the amino acid at position 330 is Lys or Arg;
the amino acid at position 331 is Ser;
the amino acid at position 332 is Thr,
the amino acid at position 333 is Thr, Lys, or Arg; and
the amino acid at position 396 is Asp, Glu, Phe, Ile, Lys, Leu, Met, Gln, Arg, or Tyr;

[23] the antigen-binding molecule of any one of [20] to [22], wherein the IgG Fc region comprises an additional alteration of at least one amino acid selected from positions: 244, 245, 249, 250, 251, 252, 254, 255, 256, 257, 258, 260, 262, 270, 272, 279, 283, 285, 286, 288, 293, 307, 308, 309, 311, 312, 314, 316, 317, 318, 332, 339, 341, 343, 375, 376, 377, 378, 380, 382, 385, 386, 387, 389, 423, 427, 428, 430, 431, 433, 434, 436, 438, 440, and 442 (EU numbering);

[24] the antigen-binding molecule of [23], wherein the amino acid alteration in the IgG Fc region is at least one amino acid alteration selected from the alterations: wherein according to EU numbering,
the amino acid at position 244 is Leu;
the amino acid at position 245 is Arg;
the amino acid at position 249 is Pro;
the amino acid at position 250 is Gln or Glu;
the amino acid at position 251 is Arg, Asp, Glu, or Leu;
the amino acid at position 252 is Phe, Ser, Thr, or Tyr;
the amino acid at position 254 is Ser or Thr;
the amino acid at position 255 is Arg, Gly, Ile, or Leu;
the amino acid at position 256 is Ala, Arg, Asn, Asp, Gln, Glu, Pro, or Thr;
the amino acid at position 257 is Ala, Ile, Met, Asn, Ser, or Val;
the amino acid at position 258 is Asp;
the amino acid at position 260 is Ser;
the amino acid at position 262 is Leu;
the amino acid at position 270 is Lys;
the amino acid at position 272 is Leu or Arg;
the amino acid at position 279 is Ala, Asp, Gly, His, Met, Asn, Gln, Arg, Ser, Thr, Trp, or Tyr;
the amino acid at position 283 is Ala, Asp, Phe, Gly, His, Ile, Lys, Leu, Asn, Pro, Gln, Arg, Ser, Thr, Trp, or Tyr;
the amino acid at position 285 is Asn;
the amino acid at position 286 is Phe;
the amino acid at position 288 is Asn or Pro;
the amino acid at position 293 is Val;
the amino acid at position 307 is Ala, Glu, Gln, or Met;
the amino acid at position 308 is Ile, Pro, or Thr;
the amino acid at position 309 is Pro,
the amino acid at position 311 is Ala, Glu, Ile, Lys, Leu, Met, Ser, Val, or Trp;
the amino acid at position 312 is Ala, Asp, or Pro;
the amino acid at position 314 is Ala or Leu;
the amino acid at position 316 is Lys;
the amino acid at position 317 is Pro;
the amino acid at position 318 is Asn or Thr;
the amino acid at position 332 is Phe, His, Lys, Leu, Met, Arg, Ser, or Trp;
the amino acid at position 339 is Asn, Thr, or Trp;

the amino acid at position 341 is Pro;
the amino acid at position 343 is Glu, His, Lys, Gln, Arg, Thr, or Tyr;
the amino acid at position 375 is Arg;
the amino acid at position 376 is Gly, Ile, Met, Pro, Thr, or Val;
the amino acid at position 377 is Lys;
the amino acid at position 378 is Asp, Asn, or Val;
the amino acid at position 380 is Ala, Asn, Ser, or Thr;
the amino acid at position 382 is Phe, His, Ile, Lys, Leu, Met, Asn, Gln, Arg, Ser, Thr, Val, Trp, or Tyr;
the amino acid at position 385 is Ala, Arg, Asp, Gly, His, Lys, Ser, or Thr;
the amino acid at position 386 is Arg, Asp, Ile, Lys, Met, Pro, Ser, or Thr;
the amino acid at position 387 is Ala, Arg, His, Pro, Ser, or Thr;
the amino acid at position 389 is Asn, Pro, or Ser;
the amino acid at position 423 is Asn;
the amino acid at position 427 is Asn;
the amino acid at position 428 is Leu, Met, Phe, Ser, or Thr;
the amino acid at position 430 is Ala, Phe, Gly, His, Ile, Lys, Leu, Met, Asn, Gln, Arg, Ser, Thr, Val, or Tyr;
the amino acid at position 431 is His or Asn;
the amino acid at position 433 is Arg, Gln, His, Ile, Lys, Pro, or Ser;
the amino acid at position 434 is Ala, Gly, His, Phe, Ser, Trp, or Tyr;
the amino acid at position 436 is Arg, Asn, His, Ile, Leu, Lys, Met, or Thr;
the amino acid at position 438 is Lys, Leu, Thr, or Trp;
the amino acid at position 440 is Lys; and
the amino acid at position 442 is Lys;

[25] the antigen-binding molecule of any one of [16] to [24], wherein the IgG Fc region is an Fc region of nonhuman animal-derived IgG;

[26] the antigen-binding molecule of any one of [16] to [24], wherein the IgG Fc region is an Fc region of human-derived IgG;

[27] the antigen-binding molecule of any one of [1] to [26], wherein the ion concentration is a hydrogen-ion concentration (pH) and the antigen-binding activity is lower under an acidic pH range condition than under a neutral pH range condition;

[28] the antigen-binding molecule of [27], wherein the acidic pH is endosomal pH;

[29] the antigen-binding molecule of [27] or [28], wherein the neutral pH is plasma pH;

[30] the antigen-binding molecule of any one of [27] to [29], wherein the acidic pH is pH 5.5 to 6.5 and the neutral pH is pH 7.0 to 8.0;

[31] the antigen-binding molecule of any one of [27] to [30], wherein the ratio of antigen-binding activity under an acidic pH range condition and a neutral pH range condition is 2 or more in the value of KD (acidic pH)/KD (neutral pH);

[32] the antigen-binding molecule of any one of [27] to [31], wherein at least one amino acid is substituted with histidine and/or at least one histidine is inserted in the antigen-binding domain;

[33] the antigen-binding molecule of any one of [27] to [32], wherein additionally the antigen-binding activity is lower under a low calcium ion concentration condition than under a high calcium ion concentration condition;

[34] the antigen-binding molecule of any one of [1] to [26], wherein the ion concentration is a calcium ion concentration and the antigen-binding activity is lower under a low calcium ion concentration condition than under a high calcium ion concentration condition;

[35] the antigen-binding molecule of [33] or [34], wherein the low calcium ion concentration is a calcium ion concentration in the endosome;

[36] the antigen-binding molecule of any one of [33] to [35], wherein the high calcium ion concentration is a calcium ion concentration in the plasma;

[37] the antigen-binding molecule of any one of [33] to [36], wherein the low calcium ion concentration is calcium ion concentration of 0.1 μM to 30 μM, and the high calcium ion concentration is calcium ion concentration of 100 μM to 10 mM;

[38] the antigen-binding molecule of any one of [33] to [37], wherein the ratio of the antigen-binding activity under a low calcium ion concentration condition and under a high calcium ion concentration is 2 or more in the value of KD (low calcium ion concentration)/KD (high calcium ion concentration);

[39] the antigen-binding molecule of any one of [1] to [38], wherein the antigen-binding domain is obtained from a library;

[40] the antigen-binding molecule of any one of [1] to [39], wherein the antigen-binding molecule is an antibody;

[41] the antigen-binding molecule of [40], wherein the antibody is any one of a chimeric antibody, a humanized antibody, and a human antibody;

[42] a pharmaceutical composition comprising as an active ingredient the antigen-binding molecule of any one of [1] to [41];

[43] the pharmaceutical composition of [42] for treating a disease for which one of the causes is assumed to be the antigen;

[44] the pharmaceutical composition of [43], wherein the antigen is HMGB1;

[45] the pharmaceutical composition of [43] or [44], wherein the disease is sepsis;

[46] the pharmaceutical composition of [43], wherein the antigen is CTGF;

[47] the pharmaceutical composition of [43] or [46], wherein the disease is fibrosis;

[48] a method for producing the antigen-binding molecule of [1], which comprises the steps of:

(a) selecting an antigen having two or more physiological activities;
(b) obtaining an antigen-binding domain;
(c) obtaining at least one receptor-binding domain;
(d) selecting a domain of which antigen-binding activity changes according to the ion concentration condition from the antigen-binding domain obtained in step (b);
(e) selecting from the receptor-binding domain obtained in step (c), a domain that has human FcRn-binding activity under an acidic pH range condition and of which binding activity to human Fc receptor under a neutral pH range condition is higher than the human Fc receptor-binding activity of native human IgG;
(f) preparing an antigen-binding molecule in which the antigen-binding domain selected in step (d) is linked to the receptor-binding domain selected in step (e); and
(g) selecting from the antigen-binding molecule prepared in step (f), an antigen-binding molecule that inhibits one or more physiological activities of the antigen by binding to the antigen while allowing the antigen to maintain at least one type of physiological activity;

[49] the method of [48], wherein step (b) is the step of isolating a domain that binds to the antigen and then altering at least one amino acid in the domain;
[50] the method of [48] or [49], wherein step (c) is the step of isolating a domain that binds to human FcRn and then altering at least one amino acid in the domain;
[51] the method of any one of [48] to [50], wherein step (f) is the step of: (f) constructing a polynucleotide wherein a polynucleotide encoding the antigen-binding domain selected in step (d) is linked to a polynucleotide encoding the receptor-binding domain selected in step (e), and producing an antigen-binding molecule wherein the antigen-binding domain selected in step (d) is linked to the receptor-binding domain selected in step (e) by using the constructed polynucleotide;
[52] the method of any one of [48] to [51], wherein step (g) is the step of (g) selecting from the antigen-binding molecule prepared step (f), an antigen-binding molecule that inhibits one or more binding activities of the antigen to target molecules by binding to the antigen while allowing the antigen to maintain at least one type of binding activity to target molecules; and
[53] the method of any one of [48] to [52], wherein the human Fc receptor is human FcRn or human Fcγ receptor.

The present invention also relates to:
[54] a method for decreasing a plasma antigen concentration by administering the antigen-binding molecule of any one of [1] to [41], or an antigen-binding molecule produced by the production method of any one of [48] to [53];
[55] a method for promoting an antigen uptake into a cell by administering the antigen-binding molecule of any one of [1] to [41], or an antigen-binding molecule produced by the production method of any one of [48] to [53];
[56] a method for reducing the physiological activity of an antigen in vivo by administering the antigen-binding molecule of any one of [1] to [41], or an antigen-binding molecule produced by the production method of any one of [48] to [53];
[57] the method of any one of [54] to [56], wherein the antigen-binding molecule is an antibody;
[58] the method of [57], wherein the antibody is a chimeric antibody, humanized antibody, or human antibody;
[59] an agent for treating a disease, which comprises as an active ingredient the antigen-binding molecule of any one of [1] to [41], or an antigen-binding molecule produced by the production method of any one of [48] to [53];
[60] the therapeutic agent of [59], wherein the antigen is HMGB1;
[61] the therapeutic agent of [59] or [60], wherein the disease is sepsis;
[62] the therapeutic agent of [59], wherein the antigen is CTGF;
[63] the therapeutic agent of [59] or [62], wherein the disease is fibrosis; and
[64] a kit for use in the method of any one of [54] to [58], which comprises the antigen-binding molecule of any one of [1] to [41], or an antigen-binding molecule produced by the production method of any one of [48] to [53].

The present invention further relates to:
[101] a method of screening for an antibody whose antigen-binding activity alters depending on condition, which comprises the steps of:
(a) preparing an antibody-producing cell;
(b) contacting the cell of (a) with an antigen under the first condition;
(c) selecting from the cell of step (b) a cell to which a predetermined amount of antigen or more is bound;
(d) exposing the cell of step (c) to the second condition; and
(e) selecting from the cell of step (d) a cell to which the binding amount of antigen is decreased as compared to step (c);

[102] the method of [101], which comprises the steps of:
(a) preparing an antibody-producing cell;
(b) contacting an antigen with the cell of (a) under the first condition;
(c) contacting an anti-IgG antibody with the cell of step (b);
(d) selecting from the cell of step (c) a cell to which a predetermined amount of antigen or more is bound and a predetermined amount of anti-IgG antibody or more is bound;
(e) exposing the cell of step (d) to the second condition; and
(f) selecting from the cell of step (e) a cell to which the binding amount of antigen is decreased as compared to step (d);

[103] the method of [102], which comprises the steps of:
(a) preparing an antibody-producing cell;
(b) contacting an antigen with the cell of (a) under the first condition;
(c) enriching a cell that is bound to an antigen from the cell of step (b);
(d) contacting an anti-IgG antibody with the cell of step (c);
(e) selecting from the cell of step (d) a cell to which a predetermined amount of antigen or more is bound and a predetermined amount of anti-IgG antibody or more is bound;
(f) exposing the cell of step (e) to the second condition; and
(g) selecting from the cell of step (f) a cell to which the binding amount of antigen is decreased as compared to step (e);

[104] the method of any one of [101] to [103], wherein the first and second conditions are ion concentration conditions;
[105] the method of [104], wherein the first condition is a neutral pH and the second condition is an acidic pH;
[106] the method of [104], wherein the first condition is a high calcium ion concentration and the second condition is a low calcium ion concentration;
[107] the method of [104], wherein the first condition is a neutral pH and a high calcium ion concentration, and the second condition is an acidic pH and a low calcium ion concentration;
[108] the method of [105] or [107], wherein the neutral pH is pH 7.0 to 8.0 and the acidic pH is pH 5.5 to 6.5;
[109] the method of any one of [106] to [108], wherein the high calcium ion concentration is a calcium ion concentration of 100 μM to 10 mM, and the low calcium ion concentration is the same as or lower than the high calcium ion concentration;
[110] the method of any one of [101] to [109], wherein the antibody-producing cell is a cell collected from blood, spleen, and/or lymph node;
[111] the method of any one of [101] to [110], wherein the antibody-producing cell is a B cell;
[112] the method of [111], wherein the antibody-producing cell is a rabbit B cell;
[113] the method of any one of [101] to [112], wherein the antigen and/or anti-IgG antibody is fluorescently labeled;
[114] the method of any one of [101] to [113], wherein the step of selecting a cell is carried out by using FACS; and

[115] the method of any one of [101] to [114], wherein the step of enriching a cell is carried out by using MACS® (Magnetic Activated Cell Sorting).

The present invention also relates to:

[a] methods for treating diseases for which one of the causes might be an antigen that has physiological activities, methods for reducing plasma antigen concentration, methods for promoting antigen uptake into cells, or methods for reducing the physiological activities of an antigen in vivo, which comprise the step of administering an antigen-binding molecule of the present invention;

[b] therapeutic agents for diseases for which one of the causes might be an antigen that has physiological activities, agents for reducing plasma antigen concentration, agents for promoting antigen uptake into cells, or agents for reducing the physiological activities of an antigen in vivo, which comprise an antigen-binding molecule of the present invention as an active ingredient;

[c] antigen-binding molecules of the present invention for use in methods for treating diseases for which one of the causes might be an antigen that has physiological activities, methods for reducing plasma antigen concentration, methods for promoting antigen uptake into cells, or methods for reducing the physiological activities of an antigen in vivo;

[d] use of an antigen-binding molecule of the present invention in producing therapeutic agents for diseases for which one of the causes might be an antigen that has physiological activities, agents for reducing plasma antigen concentration, agents for promoting antigen uptake into cells, or agents for reducing the physiological activities of an antigen in vivo; and

[e] processes for producing therapeutic agents for diseases for which one of the causes might be an antigen that has physiological activities, agents for reducing plasma antigen concentration, agents for promoting antigen uptake into cells, or agents for reducing the physiological activities of an antigen in vivo, which comprise the step of using an antigen-binding molecule of the present invention.

Examples of diseases include diseases for which one of the causes is HMGB1, CTGF, or IgE.

BRIEF DESCRIPTION OF THE DRAWINGS

FIGS. 1A-1B show a result of FACS sorting for B cells that produce anti-HMGB1 antibodies. (A) shows a result of the first sorting under a neutral pH and high calcium ion concentration condition. (B) shows a result of the second sorting under an acidic pH and low calcium ion concentration condition. Numbers (1, 2, and 3) in the diagram indicate gate numbers.

FIGS. 2A-2C show plotted graphs of the HMGB1-binding activity of anti-HMGB1 antibodies. (A), (B), and (C) shows a result of plotting antibodies produced by B cells derived from Gate 1, Gate 2, and Gate 3 in FACS sorting, respectively.

FIG. 4-2 is a continuation diagram of FIG. 4-1. The diagram shows sensorgrams for anti-HMGB1 antibodies (HMG481-IgG1 and HMG487-IgG1) and human HMG1.

MODE FOR CARRYING OUT THE INVENTION

Figure 1:
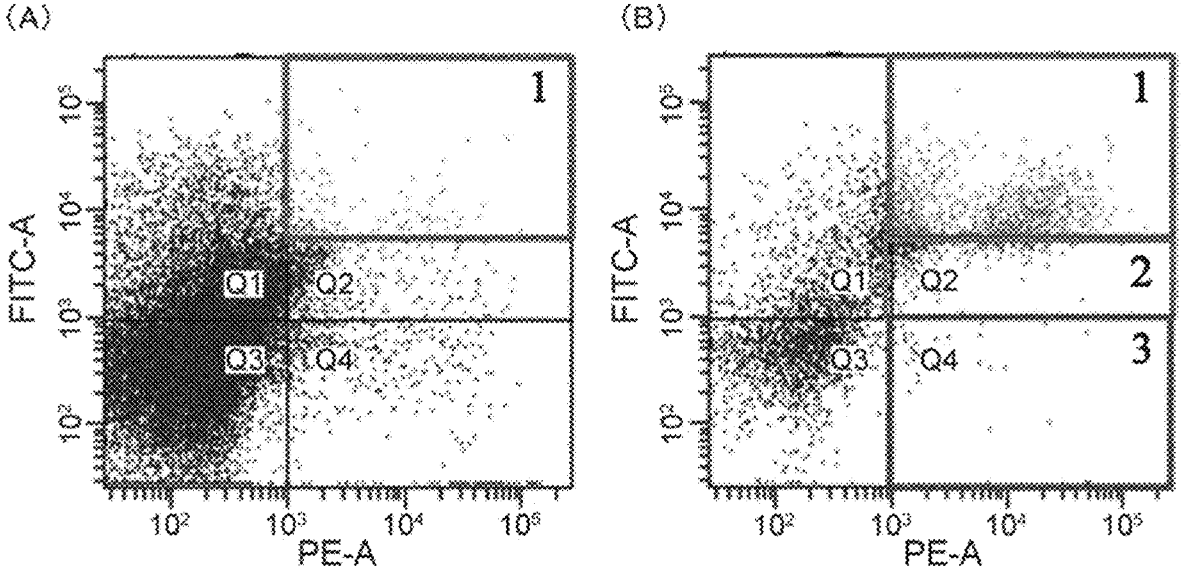
FIG. 4-1 is a diagram showing BIACORE™ sensorgrams for anti-HMGB1 antibodies (HMG233-IgG1 and HMG236-IgG1) and human HMGB1.

The present invention provides antigen-binding molecules that reduce a plasma antigen concentration, which have the properties of (1) to (6) below:

(1) the antigen-binding molecules have an antigen-binding domain(s) and a receptor-binding domain(s);

(2) the receptor-binding domain(s) has human neonatal Fc receptor (FcRn)-binding activity under an acidic pH range condition;

(3) the human Fc receptor-binding activity of the receptor-binding domain(s) is stronger than that of native human IgG under a neutral pH range condition;

(4) the antigen-binding activity of the antigen-binding domain(s) changes depending on the ion concentration condition;

(5) the antigen (as a binding target) has two or more physiological activities; and (6) binding of the antigen-binding molecule inhibits one or more of the physiological activities of the antigen (as a binding target), while at least one physiological activity is maintained.

In the present invention, the physiological activity is a general term for activities that cause quantitative and/or qualitative changes/influence in the living organism, tissue, cell, protein, DNA, RNA, or such; and for example, the activity of regulating a biological function such as metabolism, growth, reproduction, maintenance of homeostasis, mental activity, and biological defense. More specifically, it includes activities of regulating cell proliferation and maturation, metabolism mediated by the endocrine system, signal transduction in the nervous system, blood circulation, wound healing, immune response, and cell migration. Physiological activity can be reworded as biological activity. A physiologically active substance refers to a substance with such physiological activities. Physiologically active substances exert their physiological activities by acting on specific molecules (target molecules) that constitute the living organism, and conferring certain change/influence. In the present invention, physiologically active substances are also referred to as antigens that have physiological activities. Physiologically active substances of the present invention may be any substances as long as they have physiological activities; but preferably, they are polypeptides and modified products thereof that have physiological activities (physiologically active peptides). Preferred target molecules for physiologically active substances to exert physiological activities are cell surface receptors and intracellular receptors. Physiologically active substances exert their physiological activities by binding to a specific receptor and transducing signals into cells. When physiologically active substances result from conversion of precursors without physiological activities into mature types that have physiological activities, enzymes responsible for such conversion are also included in the physiologically active substances of the present invention. In this case, target molecules are substrates (precursors) for the enzymes. Physiologically active substances may be substances produced by organisms (humans or nonhuman organisms) or artificially synthesized substances. Physiologically active substances that might be a cause of disease in organisms (preferably humans) are preferred in the present invention.

Examples of physiologically active peptides include cell growth factors including fibroblast growth factors (FGFs), transforming growth factors (TGFs), bone morphogenetic factors (BMPs), epidermal growth factors (EGFs), platelet-derived growth factor (PDGF), insulin-like growth factor (IGF), nerve growth factor (NGF), vascular endothelial growth factor (VEGF), hepatocyte growth factor (HGF), and bone morphogenetic factor (BMP); cytokines including interferons (IFNs), interleukins (ILs), colony stimulation factors (CSFs), erythropoietin, and tumor necrosis factor (TNF); various hormones such as insulin and parathyroid hormone (PTH); enzymes including proteases such as matrix metalloproteinases (MMPs); and enzyme inhibitory factors such as TIMPs (tissue inhibitor of metalloproteases). Physiologically active substances of the present invention are preferably physiologically active substances derived from mammals, especially preferably physiologically active substances derived from humans.

Physiologically active substances can be obtained, for example, by purifying from a living organism. Alternatively, physiologically active substances can be prepared by chemical synthesis. When physiologically active substances are physiologically active peptides, they can also be prepared as recombinant peptides by using genetic engineering techniques. Specifically, nucleic acids encoding physiologically active peptides can be synthesized based on amino acid sequences of the physiologically active peptides or nucleotide sequences encoding them, by gene cloning methods or nucleotide synthesis methods known to those skilled in the art. After the nucleic acids are inserted into known expression vectors to transform appropriate host cells, physiologically active peptides of interest can be purified from the host cells or culture supernatants by known methods. Such purification can be achieved by using multiple chromatographies such as typical ion chromatographies and affinity chromatographies once or several times in combination or alone. Furthermore, the physiologically active peptides may be prepared as partial peptides, which comprise a portion of a physiologically active peptide, or may be prepared as fusion peptides by fusing with different polypeptides such as peptide tags and Fc fragments, as long as they retain their original physiological activities. Fusion peptides can be prepared by fusing in frame genes encoding two or more desired polypeptide fragments and inserting the resulting fusion genes into expression vectors as described above (Sambrook J et al., Molecular Cloning $2^{nd}$ ed. (1989) 9.47-9.58, Cold Spring Harbor Lab. Press). Target molecules that bind to physiologically active substances can also be obtained by similar methods.

Regarding methods for assaying in vitro physiological activity, physiologically active substances and their target molecules are prepared, and then their in vitro physiological activity can be assayed using methods capable of detecting their binding, for example, ELISA, FACS, and a BIACORE™ system. Alternatively, the physiological activities can be measured by detecting cellular changes (for example, changes in cell proliferation or morphology, and changes in gene or protein expression) after reacting physiologically active substances with receptor-expressing cells. Meanwhile, in vivo physiological activities can be measured by observing changes in animals (for example, changes associated with biological functions such as metabolism, growth, maintenance of homeostasis) after administering physiologically active substances to the animals.

In the present invention, "having two or more physiological activities" means that a physiologically active substance has the property of binding to two or more different target molecules. A physiologically active substance may bind directly to target molecules, or may bind indirectly to target molecules after binding to a substance other than the target molecules that promotes binding to the target molecules. A domain(s) responsible for target molecule binding exists in a physiologically active substance. It is preferable that there are multiple binding domains in a physiologically active substance corresponding to two or more different target molecules. In particular, it is preferable that the binding domains are located in the three-dimensional structure, at positions distant enough not to inhibit all the binding of the physiologically active substance to the target molecules at the same time when an antigen-binding molecule of the present invention binds to the physiologically active substance.

In the present invention, "having an activity" means that measured values are greater than the background value (or a measured value for a negative control) in a system capable of measuring the activity. For example, having a binding activity means that measured values are greater than the background value in a system capable of measuring binding activity such as ELISA, FACS, and a BIACORE™ system. In the present invention, the ratio of a measured value to the background value is preferably twice or more, more preferably three times or more, still more preferably five times or more, and particularly preferably 10 times or more.

In the present invention, "inhibiting activity" means that values measured in a system capable of measuring the activity after adding a substance are lower than values measured before adding the substance (or the measured value when a negative control is added). For example, inhibiting binding activity means that values measured after adding a substance are lower than values measured before adding the substance in a system capable of measuring the binding activity such as ELISA, FACS, and a BIACORE™ system. In the present invention, the ratio of a measured value after adding a substance to a measured value before adding the substance (or a measured value when adding a negative control) is preferably 80% or less, more preferably 50% or less, still more preferably 30% or less, and particularly preferably 10% or less.

In the present invention, "maintaining an activity" means that a measured value after adding a substance is 80% or more of a measured value before adding the substance (or a measured value when a negative control is added) in a system capable of measuring the activity. For example, maintaining a binding activity means that a measured value after adding a substance is 80% or more of a measured value before adding the substance in a system capable of measuring the binding activity such as ELISA, FACS, and a BIACORE™ system. In the present invention, the ratio of a measured value after adding a substance to a measured value before adding the substance (or a measured value when a negative control is added) is preferably 85% or more, more preferably 90% or more, and still more preferably 95% or more.

In the present invention, "reducing plasma antigen concentration" means that plasma antigen concentration when an antigen-binding molecule of the present invention is administered to a subject is lower compared to when a negative control is administered to a subject. The percentage of reduction is not particularly limited; however, the percentage is preferably 80% or less, more preferably 50% or less, still more preferably 30% or less, and most preferably 10% or less. Furthermore, in the present invention, "reducing antigen concentration in plasma" is reworded as "promoting antigen elimination from plasma (clearance)", "shortening antigen retention time in plasma", and "shortening antigen half-life in plasma". Meanwhile, "in plasma" may also be "in serum". Antigen-binding molecules provided by the present invention can be administered to subjects (a living organism) by, for example, intradermal, intravenous, intravitreal, subcutaneous, intraperitoneal, parenteral, or intramuscular injection. Subjects to which antigen-binding molecules of the present invention are administered are preferably animals, more preferably mammals, and still more preferably humans.

The reduction of antigen concentration may be achieved by promoting antigen uptake into cells. Meanwhile, the reduction of antigen concentration preferably results in a decrease of the physiological activity of the antigen in vivo, and particularly preferably results in a decrease of all the physiological activities of the antigen.

Antigen concentration can be measured by appropriately using methods known to those skilled in the art. When an antigen is a physiologically active peptide, the concentration of the physiologically active peptide in a sample of unknown concentration can be determined by preparing standard samples of known concentration and a system that can quantitatively determine their concentration (for example, ELISA or a BIACORE™ system), and creating a standard curve that shows the relationship between measured values and respective concentrations. Samples include plasma from the living organism, cell culture media, and cell extracts.

In the present invention, antigen uptake into cells means that the antigen is incorporated into cells by endocytosis. Whether antigen uptake into cells is promoted can be assessed by, for example, testing whether the antigen concentration in the culture medium is decreased as compared to a control or whether the antigen concentration in cells is increased as compared to a control after the antigen is added to the cell culture medium. Promotion of antigen uptake into cells means promotion of antigen elimination from plasma in the living organism. Thus, whether antigen uptake into cells is promoted can be assessed by, for example, testing whether the antigen concentration in plasma is decreased as compared to a control after the antigen is administered to a living organism.

Antigen-binding molecules provided by the present invention are not particularly limited as long as they have the properties described in (1) to (6) above. However, they are preferably polypeptides having the property of binding specifically to an antigen, human FcRn, and human Fc receptor; and they are more preferably antibodies, and particularly preferably IgGs. Antibodies may be chimeric antibodies, humanized antibodies, human antibodies, and such. Antibodies may also be bispecific antibodies, antibody modification products to which various types of molecules are linked, polypeptides comprising antibody fragments, and such. The antigen-binding molecules provided by the present invention comprise an antigen-binding domain(s) and a receptor-binding domain(s). The above-described domain refers to constitutional units that can be divided in parts and isolated. The size of the domain is not particularly limited. Each domain comprises a polypeptide. The antigen-binding domain of the present invention is not particularly limited as long as it has the property of binding specifically to an antigen; however, preferred examples include antibodies and fragments thereof (variable region, Fab, F(ab')2, Fv, CDR, etc.), antibody-like molecules referred to as scaffold (DARPins (WO2002/020565), Affibody (WO1995/001937), Avimer (WO2004/044011; WO2005/040229), Adnectin (WO2002/032925), etc.), and target molecules (receptors) and fragments thereof (soluble receptors), which bind to physiologically active substances. Particularly preferred examples include antibody variable regions. Meanwhile, receptor-binding domains of the present invention are not particularly limited as long as they have the property of binding specifically to human FcRn and/or human Fc receptor; however, preferred examples include antibodies (IgGs) and fragments thereof (the constant region, Fc, etc.), albumin and fragments thereof (domain 3), anti-FcRn antibody and fragments thereof (variable region, Fab, F(ab')2, Fv, CDR, etc.), anti-FcRn antibody-like molecules (DARPins (WO2002/020565), Affibody (WO1995/001937), Avimer (WO2004/044011; WO2005/040229), Adnectin (WO2002/032925), etc.), and anti-FcRn peptides. More preferred examples include IgG Fc regions. Human Fc receptors of the present invention are not particularly limited as long as human IgG, in particular human IgG Fc region, binds to them; however, preferably they are human FcRn and human Fcγ receptors. IgGs may be derived from nonhuman animals or humans; however, IgGs are preferably human IgGs, particularly preferably human IgG1. As described below, it is preferable that the Fc region of the IgGs has amino acid alterations.

An antigen-binding molecule of the present invention may comprise at least one receptor-binding domain. For example, a single antigen-binding molecule may comprise one antigen-binding domain and one receptor-binding domain, or may comprise one antigen-binding domain and multiple receptor-binding domains. When a single antigen-binding molecule comprises multiple receptor-binding domains, all of the receptor-binding domains may bind to the same type of human Fc receptors, or each of the domains may bind to different types of human Fc receptors. On the other hand, since one of the requirements for antigen-binding molecules of the present invention to fulfill is to have human FcRn-binding activity, it is preferable that at least one receptor-binding domain comprised in an antigen-binding molecule of the present invention binds to human FcRn. Without particular limitation, embodiments where a single antigen-binding molecule comprises two receptor-binding domains include antigen-binding molecules of which two receptor-binding domains both bind to human FcRn, and antigen-binding molecules of which one of the receptor-binding domains binds to human FcRn and the other binds to human Fcγ receptor. Alternatively, when a single antigen-binding molecule comprises one receptor-binding domain, the receptor-binding domain may at least bind to human FcRn and may have the property that the single domain simultaneously binds to other types of human Fc receptors. Such receptor-binding domains include, for example, IgG Fc regions. IgG Fc regions have the property of binding to human FcRn and human Fcγ receptor.

Herein, native human IgG refers to naturally-occurring human IgG. It is desirable that a fucose-containing sugar chain is linked at position 297 (EU numbering) in the Fc region. As a native human IgG, naturally-occurring human IgG1, IgG2, IgG3, and IgG4 can be used. Preferred native human IgG is a naturally-occurring human IgG1. Whether a linked sugar chain is a fucose-containing sugar chain can be assessed, for example, by the method described below. Test human IgG is incubated with N-Glycosidase F (Roche diagnostics) to release its sugar chains (Weitzhandler et al., J. Pharma. Sciences (1994) 83(12): 1670-1675). Then, the reaction solution is deproteinated by reacting ethanol (Schenk et al., J. Clin. Investigation (2001) 108 (11): 1687-1695) and concentrated to dryness, followed by fluorescence labeling with 2-aminopyridin (Bigge et al., Anal. Biochem. (1995) 230 (2): 229-238). Solid extraction is performed using cellulose cartridge to remove the reagents, and the resulting fluorescently 2-AB-labeled sugar chains are analyzed by normal phase chromatography. Whether the sugar chain linked to the Fc region of the test human IgG is a fucose-containing sugar chain can be assessed by observing peaks detected in the chromatogram.

"Chimeric antibodies" are antibodies prepared by combining sequences derived from different animals. Specifically, the chimeric antibody includes, for example, antibodies having heavy and light chain variable (V) regions from a mouse antibody and heavy and light chain constant (C) regions from a human antibody.

"Humanized antibodies", also referred to as reshaped human antibodies, are antibodies in which the complementarity determining regions (CDRs) of an antibody derived from a nonhuman mammal, for example, a mouse, are grafted into the CDRs of a human antibody. Methods for identifying CDRs are known (Kabat et al., Sequence of Proteins of Immunological Interest (1987), National Institute of Health, Bethesda, Md.; Chothia et al., Nature (1989) 342: 877). General genetic recombination technologies suitable for grafting CDRs are also known (see European Patent Application EP 125023; and WO96/02576).

"A bispecific antibody" refers to an antibody that has two variable regions in the same antibody molecule that recognize different epitopes. A bispecific antibody may be an antibody that recognizes two or more different antigens, or an antibody that recognizes two or more different epitopes on a same antigen.

Furthermore, polypeptides comprising antibody fragments include, for example, Fab fragments, F(ab')2 fragments, scFvs (Nat Biotechnol. 2005 September; 23(9): 1126-36), domain antibodies (dAbs) (WO2004/058821; WO2003/002609), scFv-Fc (WO2005/037989), dAb-Fc, and Fc fusion proteins. When a molecule contains an Fc region, the Fc region can be used as the receptor-binding domain. The Fc region refers to a portion of the heavy chain constant region, which starts from the N terminus of the hinge region corresponding to the papain cleavage site in the antibody molecule and contains the hinge, and the CH2 and CH3 domains. The IgG Fc region refers to, for example, from cysteine at position 226 (EU numbering) up to the C terminus, or from proline at position 230 (EU numbering) up to the C terminus; but are not limited thereto. Without particular limitation, examples of the IgG Fc region include the Fc regions of human IgG1 (SEQ ID NO: 49), IgG2 (SEQ ID NO: 50), IgG3 (SEQ ID NO: 51), and IgG4 (SEQ ID NO: 52). The IgG Fc region is preferably the Fc region of human IgG1.

Antibody-like molecule (scaffolding molecule or scaffold molecule) is a general name for molecules that have a common backbone structure and the property of being able to specifically bind to an antigen (Current Opinion in Biotechnology 2006, 17: 653-658; Current Opinion in Biotechnology 2007, 18: 1-10; Current Opinion in Structural Biology 1997, 7: 463-469; Protein Science 2006, 15: 14-27). Antibody-like molecules include, for example, DARPins (WO2002/020565), affibody (WO1995/001937), avimer (WO2004/044011; WO2005/040229), and adnectin (WO2002/032925).

Antibodies may contain modified sugar chains. Antibodies with modified sugar chains include, for example, antibodies with modified glycosylation (WO99/54342), antibodies that are deficient in sugar chain-attached fucose (WO00/61739; WO02/31140; WO2006/067847; WO2006/067913), and antibodies having sugar chains with bisecting GlcNAc (WO02/79255).

The binding between an antigen and an antigen-binding molecule of the present invention, or between a target molecule and an antigen with physiological activities can be measured by using methods known to those skilled in the art such as ELISA, FACS, and a BIACORE™ system. By setting the measurement condition to an extracellular condition or intracellular condition, differences in the binding activity under such conditions can be assessed. Furthermore, such methods can be combined with the above-described methods for measuring the physiological activity of physiologically active substances to assess whether the binding of an antigen-binding molecule of the present invention to an antigen with physiological activities inhibits the physiological activity/activities of the antigen or maintains the physiological activity/activities.

The present invention provides antigen-binding molecules characterized in that they inhibit one or more binding activities of an antigen to its target molecules by binding to the antigen while allowing the antigen to maintain the binding activity to at least one type of its target molecules. Specifically, it is preferable that one or more physiological activities of an antigen having two or more physiological activities are inhibited by binding of an antigen-binding molecule of the present invention to the antigen. Inhibiting one or more physiological activities (or, are inhibited) means inhibiting the activity of an antigen, which has binding activity to multiple target molecules, to bind to one or more types of its target molecules (or, are inhibited). Furthermore, when an antigen-binding molecule of the present invention binds to an antigen having two or more types of physiological activities, it is preferable that the antigen maintains at least one type of physiological activity among its physiological activities (or, at least one type of physiological activity is maintained). Maintaining at least one type of physiological activity (or is maintained) means that an antigen maintains its binding-activity to at least one type of the target molecules (or is maintained) among the binding activities of the antigen to multiple target molecules.

When an antigen with physiological activity that is present in excess in a living organism causes a disease, molecules, for example, neutralizing antibodies which inhibit the physiological activity by binding to the antigen, are expected to be useful in treating the disease. However, when the antigen has two or more types of physiological activities, neutralizing antibodies can inhibit only a single type of physiological activity. On the other hand, antigen-binding molecules of the present invention can ultimately reduce the in vivo physiological activities by promoting antigen elimination from blood (serum or plasma) even when the antigen maintains at least one type of physiological activity. Thus, the antigen-binding molecules of the present invention are very useful as compared to common neutralizing antibodies.

In the present invention, when a human Fc receptor is human FcRn, the receptor-binding domain of antigen-binding molecules is preferably an IgG Fc region, more preferably an Fc region variant in which at least one amino acid in the IgG Fc region is altered. The IgG may be derived from nonhuman animals or humans; however, the IgG is preferably human IgG (IgG1, IgG2, IgG3, or IgG4), and particularly preferably human IgG1. Examples of amino acid alterations include amino acid substitution, insertion, and deletion; however, amino acid substitution is preferred. The number of amino acids to be altered is not particularly limited, and amino acids may be altered at only one site or at two or more sites. In such amino acid alteration, amino acids at any positions may be altered to any amino acids as long as the Fc region variant after alteration has human FcRn-binding activity under acidic and neutral pH range conditions, and the human FcRn-binding activity under a neutral pH range condition is greater than that of human IgG. It is known that in a living organism, generally the extracellular pH (for example, in plasma) is neutral and the intracellular pH (for example, in the endosome) is acidic. It is also known that the binding between IgG and FcRn is detected only under an acidic (intracellular) pH condition and is almost undetectable under a neutral (extracellular) pH condition. For the antigen-binding molecules of the present invention, acidic pH is preferably endosomal pH and neutral pH is preferably plasma pH.

If the receptor-binding domains of antigen-binding molecules provided by the present invention can be conferred with the property of having human FcRn-binding activity under intracellular and extracellular pH conditions and the property that the human FcRn-binding activity under an extracellular pH condition is stronger than that of human IgG, extracellularly antigen-bound antigen-binding molecules of the present invention bind to cell-surface FcRn and are internalized into cells, which results in promotion of antigen uptake into cells from the outside of the cells. When administered to a living organism, such antigen-binding molecules can reduce plasma antigen concentration and decrease the physiological activities of antigens in vivo. Thus, antigen-binding molecules provided by the present invention are useful.

Human FcRn is structurally similar to major histocompatibility complex (MHC) class I polypeptides, and shares 22 to 29% sequence identity with class I MHC molecules (Ghetie et al., Immunol. Today (1997) 18 (12), 592-598). FcRn is expressed as a heterodimer consisting of P2 microglobulin which is a soluble β chain (or light chain), and transmembrane α chain (or heavy chain). FcRn α chain comprises three extracellular domains (α1, α2, and α3). The α1 and α2 domains interact with the FcRn-binding domain of antibody Fc region (Raghavan et al., Immunity (1994) 1, 303-315).

The gene and amino acid sequences for human FcRn are registered under GenBank accession number NM_001136019 (SEQ ID NO: 16) and NP_001129491 (SEQ ID NO: 17), respectively. In addition to human, the gene and amino acid sequences for mouse FcRn are registered under GenBank accession number NM_010189 (SEQ ID NO: 18) and NP_034319 (SEQ ID NO: 19), respectively; the gene and amino acid sequences for rat FcRn are registered under GenBank accession number NM_033351 (SEQ ID NO: 20) and NP_203502 (SEQ ID NO: 21), respectively.

Human FcRn (SEQ ID NO: 17) forms a complex with human β2 microglobulin (SEQ ID NO: 38) in vivo. The complex of soluble human FcRn and β2 microglobulin can be produced using general recombination/expression methods. Such a soluble human FcRn/β2 microglobulin complex can be used to assess the binding activity of receptor-binding domains of the present invention. In the present invention, unless otherwise specified, human FcRn refers to a form capable of binding to receptor-binding domains of the present invention, and includes, for example, a complex of human FcRn and human β2 microglobulin.

Receptor-binding domains that bind to FcRn under a neutral pH range condition more strongly than native human IgG can be produced by altering the amino acids of human IgG Fc region. Examples of alteration include substitution, insertion, and deletion of one or more amino acids. Alternatively, it is possible to use an antigen-binding domain characterized in binding to FcRn as the receptor-binding domain. Whether the FcRn-binding activity of a receptor-binding domain is higher than that of the native human IgG Fc region can be appropriately assessed by the above-described methods.

In the present invention, the human FcRn-binding activity under an acidic pH range condition means the human FcRn-binding activity at pH 4.0 to pH 6.5, preferably at pH 5.0 to pH 6.5, more preferably at any of pH 5.5, 5.6, 5.7, 5.8, 5.9, 6.0, 6.1, 6.2, 6.3, 6.4, and 6.5, and particularly preferably at pH 5.8 to pH 6.0 which is close to the pH of early endosome in vivo. Meanwhile, in the present invention, the human FcRn-binding activity under a neutral pH range condition refers to human FcRn-binding activity at pH 6.7 to pH 10.0, preferably at pH 7.0 to pH 9.0, more preferably at any of pH 7.0, 7.1, 7.2, 7.3, 7.4, 7.5, 7.6, 7.7, 7.8, 7.9, and 8.0, and particularly preferably at pH 7.4 which is close to the pH of plasma in vivo.

When the binding affinity between a receptor-binding domain and human FcRn is very low at pH 7.4 and is difficult to determine accurately, the pH can be 7.0 instead of pH 7.4. Regarding the measurement temperature, the binding affinity between a receptor-binding domain and human FcRn may be measured at any temperature between 10° C. and 50° C. The binding affinity between a receptor-binding domain and human FcRn is preferably determined at 15° C. to 40° C., more preferably at any temperature of 20, 21, 22, 23, 24, 25, 26, 27, 28, 29, 30, 31, 32, 33, 34, and 35° C. Without particular limitation, the 25° C. temperature is a preferred embodiment.

As a receptor-binding domain that binds to human FcRn, an IgG Fc region is altered preferably at sites including, for example, amino acids at positions 221 to 225, 227, 228, 230, 232, 233 to 241, 243 to 260, 262 to 272, 274, 276, 278 to 289, 291 to 320, 324 to 341, 343, 345, 360 to 362, 370, 375 to 378, 380, 382, 384 to 387, 389 to 391, 396, 413, 414, 416, 422, 423, 424, 426 to 438, 440, and 442 (EU numbering). More specifically, such alteration includes, for example, alteration of amino acids shown in Table 1. Such alteration can be used to enhance the human FcRn binding of an IgG Fc region under a neutral pH range condition.

TABLE 1

| POSITION | AMINO ACID ALTERATION |
|---|---|
| 256 | P |
| 280 | K |
| 339 | T |
| 385 | H |
| 428 | L |
| 434 | W, Y, F, A, H |

Meanwhile, an example of alteration that can enhance the human FcRn binding under an acidic pH range condition as compared to native human IgG is shown in Table 2. From among such alterations, appropriate alterations that can also enhance the human FcRn binding under a neutral pH range condition can be selected and used in the present invention. In alteration of IgG Fc region, particularly preferred sites for alteration include, for example, amino acid(s) at position(s) 234, 235, 236, 237, 238, 239, 244, 245, 248, 249, 250, 251, 252, 253, 254, 255, 256, 257, 258, 260, 262, 265, 267, 270, 272, 274, 279, 280, 282, 283, 284, 285, 286, 288, 289, 293, 295, 297, 298, 303, 305, 307, 308, 309, 311, 312, 313, 314, 315, 316, 317, 318, 325, 326, 327, 328, 329, 330, 332, 334, 338, 339, 340, 341, 343, 345, 360, 361, 362, 375, 376, 377, 378, 380, 382, 384, 385, 386, 387, 389, 390, 391, 413, 422, 423, 424, 427, 428, 430, 431, 433, 434, 435, 436, 437, 438, 440, and 442 (EU numbering). Furthermore, preferred site(s) besides those described above include, for example: amino acid(s) at position(s) 252, 254, 256, 309, 311, 315, 433, and/or 434 (EU numbering) and, in combination with those described above, amino acid(s) at position(s) 253, 310, 435, and/or 426 (EU numbering), which are described in WO1997/034631;

amino acid(s) at position(s) 238, 252, 253, 254, 255, 256, 265, 272, 286, 288, 303, 305, 307, 309, 311, 312, 317, 340, 356, 360, 362, 376, 378, 380, 382, 386, 388, 400, 413, 415, 424, 433, 434, 435, 436, 439, and/or 447 (EU numbering), which are described in WO2000/042072; amino acid(s) at position(s) 251, 252, 254, 255, 256, 308, 309, 311, 312, 385, 386, 387, 389, 428, 433, 434, and/or 436 (EU numbering), which are described in WO2002/060919;

amino acid(s) at position(s) 250, 314, and 428 (EU numbering), which are described in WO2004/092219;

amino acid(s) at position(s) 238, 244, 245, 249, 252, 256, 257, 258, 260, 262, 270, 272, 279, 283, 285, 286, 288, 293, 307, 311, 312, 316, 317, 318, 332, 339, 341, 343, 375, 376, 377, 378, 380, 382, 423, 427, 430, 431, 434, 436, 438, 440, and/or 442 (EU numbering), which are described in WO2006/020114; and amino acid(s) at position(s) 251, 252, 307, 308, 378, 428, 430, 434, and/or 436 (EU numbering), which are described in WO2010/045193. At least one amino acid selected from the amino acids described above can be altered to increase the human FcRn-binding activity under a neutral pH range condition. The number of amino acids to be altered is not particularly limited, and amino acids may be altered at only one site or two or more sites.

TABLE 2

| POSITION | AMINO ACID ALTERATION |
|---|---|
| 221 | Y, K |
| 222 | Y |
| 223 | E, K |
| 224 | Y, E |
| 225 | E, K, W |
| 227 | K, E, G |
| 228 | Y, K, G |
| 230 | E, G |
| 232 | K |
| 233 | R, S, M, T, W, Y, G |
| 234 | H, R, E, I, V, F, D, Y, G |
| 235 | Y, V, N, S, T, Q, D |
| 236 | I, V, K, P, E, Q, H, W, Y, D, T, M, A, F, S, N, R |
| 237 | I, W, S, T, E, R, N, Q, K, H, D, P, L, M |
| 238 | A, L, D, S, T, H, W, V, I, G, M, F, E, K |
| 239 | M, R, T, G, V, E, D, L, A |
| 240 | I, M, T |
| 241 | E, W, L |
| 243 | E, W |
| 244 | L |
| 245 | R |
| 246 | Y, H |
| 247 | D |
| 248 | Y |
| 249 | P, Q, Y, H |
| 250 | I, E, Q |
| 251 | T, D |
| 252 | Y, W, Q |
| 254 | H |
| 255 | E, Y, H |
| 256 | A |
| 257 | A, I, M, N, S, V, T, L, Y, C |
| 258 | D, Y, H, A |
| 259 | I, F, N |
| 260 | S, D, E, H, Y |
| 262 | L, E |
| 263 | I |
| 264 | F, A, I, T, N, S, D |
| 265 | R, P, G, A |
| 266 | I |
| 267 | K, E, A |
| 268 | E, M |
| 269 | M, W, K, P, I, S, G, V, F, Y, A |
| 270 | K, S, I, A |
| 271 | A, V, S, Y, I, T |
| 272 | A, L, R, I, D, H, V, W, Y, P, T |
| 274 | M, F, G, E, I, T, N |
| 276 | D, F, H, R, L, V, W, A |
| 278 | R, S, V, M, N, I, L, D |
| 279 | A, D, G, H, M, N, Q, R, S, T, W, Y, C, I |
| 281 | D, Y |
| 282 | G, K, E, Y |
| 283 | A, D, F, G, H, I, K, L, N, P, Q, R, S, T, W, Y |
| 284 | T, L, Q, E |

TABLE 2-continued

| POSITION | AMINO ACID ALTERATION |
|---|---|
| 285 | N, Y, W, Q, K, E, D, Y |
| 286 | F, L, Y, E, P, D, K, A |
| 287 | S, H |
| 288 | N, P, Y, H, D, I, V, C, E, G, L, Q, R |
| 289 | H |
| 291 | Q, H |
| 292 | Y, E, D |
| 293 | V |
| 294 | I, K, G |
| 295 | V, T |
| 296 | E, I, L |
| 298 | F, E, T, H |
| 299 | W, F, H, Y |
| 300 | K, A, G, V, M, Q, N, E |
| 301 | E |
| 302 | I |
| 303 | Y, E, A |
| 304 | N, T |
| 305 | A, H |
| 306 | Y |
| 307 | A, E, M, G, Q, H |
| 308 | A, R, F, C, Y, W, N, H |
| 311 | A, I, K, L, M, V, W, T, H |
| 312 | A, P, H |
| 315 | T, H |
| 316 | K |
| 317 | A, P, H |
| 318 | N, T, R, L, Y |
| 319 | L, I, W, H, M, V, A |
| 320 | L, W, H, N |
| 324 | T, D |
| 325 | F, M, D |
| 326 | A |
| 327 | D, K, M, Y, H, L |
| 328 | G, A, W, R, F |
| 329 | K, R, W |
| 330 | G, W, V, P, H, F |
| 331 | L, F, Y |
| 332 | F, H, K, L, M, R, S, W, T, Q, E, Y, D, N, V |
| 333 | L, F, M, A |
| 334 | A |
| 335 | H, F, N, V, M, W, I, S, P, L |
| 336 | E, K |
| 337 | A |
| 338 | A |
| 339 | N, W |
| 341 | P |
| 343 | E, H, K, Q, R, T, Y |
| 360 | H, A |
| 362 | A |
| 375 | R |
| 376 | A, G, I, M, P, T, V |
| 377 | K |
| 378 | Q, D, N, W |
| 380 | A, N, S, T, Q, R, H |
| 382 | A, F, H, I, K, L, M, N, Q, R, S, T, V, W, Y |
| 385 | N, E |
| 386 | H |
| 387 | H, Q |
| 414 | A |
| 423 | N |
| 424 | A |
| 426 | H, L, V, R |
| 427 | N |
| 428 | F |
| 429 | Q |
| 430 | A, F, G, H, I, K, L, M, N, Q, R, S, T, V, Y |
| 431 | H, K |
| 432 | H |
| 433 | P |
| 434 | G, T, M, S |
| 435 | K |
| 436 | I, L, T |
| 437 | H |
| 438 | K, L, T, W |
| 440 | K |
| 442 | K |

Meanwhile, receptor-binding domains that originally have human FcRn-binding activity under acidic pH range and neutral pH range conditions include, for example, an IgG Fc region, wherein amino acids of the Fc region are selected from:

according to EU numbering, the amino acid at position 234 which is Arg;

the amino acid at position 235 which is Gly, Lys, or Arg;

the amino acid at position 236 which is Ala, Asp, Lys, or Arg;

the amino acid at position 237 which is Lys, Met, or Arg;

the amino acid at position 238 which is Ala, Asp, Lys, Leu, or Arg;

the amino acid at position 239 which is Asp or Lys;

the amino acid at position 244 which is Leu;

the amino acid at position 245 which is Arg;

the amino acid at position 248 which is Ile or Tyr;

the amino acid at position 249 which is Pro;

the amino acid at position 250 which is Ala, Glu, Phe, Ile, Met, Gln, Ser, Val, Trp, Gly, His, Leu, Asn, or Tyr;

the amino acid at position 251 which is Arg, Asp, Glu, or Leu;

the amino acid at position 252 which is Phe, Ser, Thr, Trp, or Tyr;

the amino acid at position 253 which is Val;

the amino acid at position 254 which is Ala, Gly, His, Ile, Gln, Ser, Val, or Thr;

the amino acid at position 255 which is Ala, Asp, Phe, His, Ile, Lys, Leu, Met, Asn, Gln, Arg, Gly, Ser, Trp, Tyr, or Glu;

the amino acid at position 256 which is Ala, Asp, Glu, Arg, Asn, Pro, Thr, Ser, or Gln;

the amino acid at position 257 which is Ala, Gly, Ile, Leu, Met, Asn, Ser, Thr, or Val;

the amino acid at position 258 which is Asp or His;

the amino acid at position 260 which is Ser;

the amino acid at position 262 which is Leu;

the amino acid at position 265 which is Ala;

the amino acid at position 267 which is Met or Leu;

the amino acid at position 270 which is Lys or Phe;

the amino acid at position 272 which is Ala, Leu, or Arg;

the amino acid at position 274 which is Ala;

the amino acid at position 279 which is Leu, Ala, Asp, Gly, His, Met, Asn, Gln, Arg, Ser, Thr, Trp, or Tyr;

the amino acid at position 280 which is Ala, Gly, His, Lys, Asn, Gln, Arg Ser, Thr, or Glu;

the amino acid at position 282 which is Ala or Asp;

the amino acid at position 283 which is Ala, Asp, Phe, Gly, His, Ile, Lys, Leu, Asn, Pro, Gln, Arg, Ser, Thr, Trp, or Tyr;

the amino acid at position 284 which is Lys;

the amino acid at position 285 which is Asn;

the amino acid at position 286 which is Ala, Asp, Phe, Gly, His, Ile, Lys, Leu, Met, Pro, Gln, Arg, Ser, Thr, Val, Trp, Tyr, or Glu;

the amino acid at position 288 which is Ala, Asp, Glu, Phe, Gly, His, Ile, Leu, Met, Asn, Pro, Gln, Arg, Val, Trp, Tyr, or Ser;

the amino acid at position 289 which is His;

the amino acid at position 293 which is Val;

the amino acid at position 295 which is Met;

the amino acid at position 297 which is Ala;

the amino acid at position 298 which is Gly;

the amino acid at position 303 which is Ala;

the amino acid at position 305 which is Ala or Thr;

the amino acid at position 307 which is Ala, Asp, Glu, Phe, Gly, His, Ile, Lys, Leu, Met, Asn, Pro, Gln, Arg, Ser, Val, Trp, or Tyr;

the amino acid at position 308 which is Ala, Phe, Ile, Leu, Met, Pro, Gln, or Thr;

the amino acid at position 309 which is Ala, Asp, Glu, Pro, His, or Arg;

the amino acid at position 311 which is Ala, His, Glu, Lys, Leu, Met, Ser, Val, Trp, or Ile;

the amino acid at position 312 which is Ala, Asp, Pro, or His;

the amino acid at position 313 which is Tyr or Phe;

the amino acid at position 314 which is Ala, Leu, Lys, or Arg;

the amino acid at position 315 which is Ala, Asp, Glu, Phe, Gly, Ile, Lys, Leu, Met, Gln, Arg, Ser, Thr, Val, Trp, Tyr, or His;

the amino acid at position 316 which is Ala, Glu, Phe, His, Ile, Lys, Leu, Met, Asn, Pro, Gln, Arg, Ser, Thr, Val, Trp, or Asp;

the amino acid at position 317 which is Ala or Pro;

the amino acid at position 318 which is Asn or Thr;

the amino acid at position 325 which is Ala, Gly, Met, Leu, Ile, or Ser;

the amino acid at position 326 which is Asp;

the amino acid at position 327 which is Gly;

the amino acid at position 328 which is Arg, Asp, Glu, or Tyr;

the amino acid at position 329 which is Lys or Arg;

the amino acid at position 330 which is Leu;

the amino acid at position 332 which is Glu, Phe, His, Lys, Leu, Met, Arg, Ser, Trp, or Val;

the amino acid at position 334 which is Leu;

the amino acid at position 338 which is Ala;

the amino acid at position 339 which is Asn, Thr, or Trp;

the amino acid at position 340 which is Ala;

the amino acid at position 341 which is Pro;

the amino acid at position 343 which is Glu, His, Lys, Gln, Arg, Thr, or Tyr;

the amino acid at position 345 which is Ala;

the amino acid at position 360 which is His;

the amino acid at position 361 which is Ala;

the amino acid at position 362 which is Ala;

the amino acid at position 375 which is Ala or Arg;

the amino acid at position 376 which is Ala, Gly, Ile, Met, Pro, Thr, or Val;

the amino acid at position 377 which is Lys;

the amino acid at position 378 which is Asp, Asn, or Val;

the amino acid at position 380 which is Ala, Asn, Thr, or Ser;

the amino acid at position 382 which is Ala, Phe, His, Ile, Lys, Leu, Met, Asn, Gln, Arg, Ser, Thr, Trp, Tyr, or Val;

the amino acid at position 384 which is Ala;

the amino acid at position 385 which is Ala, Gly, Lys, Ser, Thr, Asp, His, or Arg;

the amino acid at position 386 which is Arg, Asp, Ile, Met, Ser, Thr, Lys, or Pro;

the amino acid at position 387 which is Ala, Arg, His, Pro, Ser, Thr, or Glu;

the amino acid at position 389 which is Ala, Asn, Pro, or Ser;

the amino acid at position 390 which is Ala;

the amino acid at position 391 which is Ala;

the amino acid at position 413 which is Ala;

the amino acid at position 423 which is Asn;

the amino acid at position 424 which is Ala or Glu;

the amino acid at position 427 which is Asn;

the amino acid at position 428 which is Ala, Asp, Phe, Gly, His, Ile, Lys, Leu, Met, Asn, Pro, Gln, Ser, Thr, Val, Trp, or Tyr;

the amino acid at position 430 which is Ala, Phe, Gly, His, Ile, Lys, Leu, Met, Asn, Gln, Arg, Ser, Thr, Val, or Tyr;

the amino acid at position 431 which is His or Asn;

the amino acid at position 433 which is Arg, Gln, His, Ile, Pro, Ser, or Lys;
the amino acid at position 434 which is Ala, Phe, Gly, Met, His, Ser, Trp, or Tyr;
the amino acid at position 435 which is Lys, Arg, or Asn;
the amino acid at position 436 which is Ala, His, Ile, Leu, Glu, Phe, Gly, Lys, Met, Asn, Arg, Ser, Thr, Trp, or Val;
the amino acid at position 437 which is Arg;
the amino acid at position 438 which is Lys, Leu, Thr, or Trp;
the amino acid at position 440 which is Lys; and
the amino acid at position 442 which is Lys.

Amino acid positions to be selected may be only one, or two or more positions. Combinations of amino acids of two or more positions include, for example, those described in Tables 3, 4-1 to 4-5, and 13-1 to 13-14.

TABLE 3

| COMBINATION OF AMINO ACID ALTERATION |
|---|
| M252Y/S254T/T256E |
| M252Y/S254T/T256E/H433K/N434F/Y436H |
| H433K/N434F/Y436H |
| T307A/E380A |
| T307A/E380A/N434H |
| T307A/E380A/N434A |
| N434H/N315H |
| N434H/T289H |
| N434H/T370A/E380A |
| T250Q/M428L |
| T250Q/N434A |
| M252W/N434A |
| M252Y/N434A |
| T256A/N434A |
| T256D/N434A |
| T256E/N434A |
| T256S/N434A |
| P257I/Q311I |
| T307A/N434A |
| T307E/N434A |
| T307Q/N434A |
| V308P/N434A |
| L309G/N434A |
| Q311H/N434A |
| Q311R/N434A |
| N315D/N434A |
| A378V/N434A |
| E380S/N434A |
| E382V/N434A |
| S424E/N434A |
| M428L/N434A |
| N434A/Y436I |
| T437Q/N434A |
| T437R/N434A |

TABLE 4-1

| COMBINATION OF AMINO ACID ALTERATION |
|---|
| L234I/L235D |
| G236A/V308F/I332E |
| G236R/L328R |
| G236A/I332E/N434S |
| S239E/V264I/A330Y/I332E |
| S239E/V264I/I332E |
| S239E/V264I/S298A/A330Y/I332E |
| S239D/D265H/N297D/I332E |
| S239D/E272Y/I332E |
| S239D/E272S/I332E |
| S239D/E272I/I332E |
| S239D/N297D/I332E |
| S239D/K326T/I332E |
| S239Q/I332Q |
| S239Q/I332N |
| S239D/I332D |
| S239D/I332E |

TABLE 4-1-continued

| COMBINATION OF AMINO ACID ALTERATION |
|---|
| S239Q/I332E |
| S239E/I332E |
| F241W/F243W |
| F241Y/F243Y/V262T/V264T |
| F241W/F243W/V262A/V264A |
| F241L/V262I |
| F243L/V262I/V264W |
| F243L/K288D/R292P/Y300L/V305I/P396L/H435K |
| F243L/K288D/R292P/Y300L/H435K |
| F243L/R292P/Y300L/V305I/P396L/H435K |
| P245G/V308F |
| T250I/V259I/V308F |
| T250I/V308F |
| T250I/V308F/N434S |
| T250Q/V308F/M428L |
| T250Q/M428L |
| L251I/N434S |
| L251N/N434S |
| L251F/N434S |
| L251V/N434S |
| L251M/N434S |
| T252L/T254S/T256F |
| M252Y/S254T/T256E/N434M |
| M252Y/S254T/T256E/M428L/N434S |
| M252Y/S254T/T256E |
| M252Y/S254T/T256E/V308F |
| M252Y/S254T/T256E/N434S |
| M252Y/S254T/T256E/N434A |
| M252Y/S254T/T256E/M428L |
| M252Y/S254T/T256E/T307Q |
| M252F/T256D |
| M252Y/T256Q |
| M252Y/P257L |
| M252Y/P257N |
| M252Y/V259I |
| M252Y/V279Q |
| M252Y/V308P/N434Y |
| M252Q/V308F |
| M252Y/V308F |

Table 4-2 is a continuation table of Table 4-1.

TABLE 4-2

| |
|---|
| M252Q/V308F/N434S |
| M252Y/V308F/M428L |
| M252Y/V308F/N434M |
| M252Y/V308F/N434S |
| M252Y/Y319I |
| M252Q/M428L/N434S |
| M252Y/M428L |
| M252Y/N434M |
| M252Y/N434S |
| M252Y/N434A |
| M252Y/N434Y |
| S254T/V308F |
| R255H/N434A |
| R255Q/N434S |
| R255H/N434S |
| T256V/V308F |
| T256P/Q311I |
| T256P/I332E |
| T256P/I332F/S440Y |
| T256P/E430Q |
| T256P/N434H |
| T256E/N434Y |
| T256P/S440Y |
| P257Y/V279Q |
| P257L/V279E |
| P257N/V279Q |
| P257N/V279E |
| P257N/V279Y |
| P257L/V279Q |
| P257N/^281S |
| P257L/^281S |
| P257N/V284E |

TABLE 4-2-continued

| |
|---|
| P257N/L306Y |
| P257L/V308Y |
| P257L/V308F |
| P257N/V308Y |
| P257I/Q311I/N434H |
| P257L/Q311V |
| P257L/G385N |
| P257L/M428L |
| P257I/E430Q |
| P257I/N434H |
| P257L/N434Y |
| E258H/N434A |
| E258H/N434H |
| V259I/T307Q/V308F |
| V259I/V308F |
| V259I/V308F/Y319L |
| V259I/V308F/Y319I |
| V259A/V308F |
| V259I/V308F/N434M |
| V259I/V308F/N434S |
| V259I/V308F/M428L/N434S |
| V259I/V308F/M428L |
| V259I/Y319I |
| V259I/Y319I/N434S |
| V259I/M428L |
| V259I/M428L/N434S |
| V259I/N434S |

Table 4-3 is a continuation table of Table 4-2.

TABLE 4-3

| |
|---|
| V259I/N434Y |
| V264I/A330L/I332E |
| V264I/I332E |
| D265F/N297E/I332E |
| S267L/A327S |
| E272R/V279L |
| V279E/V284E |
| V279Q/L306Y |
| V279Y/V308F |
| V279Q/V308F |
| V279Q/G385H |
| ˆ281S/V308Y |
| ˆ281S/V308F |
| ˆ281S/N434Y |
| E283F/V284E |
| V284E/V308F |
| V284E/G385H |
| K288A/N434A |
| K288D/H435K |
| K288V/H435D |
| T289H/N434A |
| T289H/N434H |
| L306I/V308F |
| T307P/V308F |
| T307Q/V308F/N434S |
| T307Q/V308F/Y319L |
| T307S/V308F |
| T307Q/V308F |
| T307A/E310A/N434A |
| T307Q/E380A/N434A |
| T307Q/M428L |
| T307Q/N434M |
| T307I/N434S |
| T307V/N434S |
| T307Q/N434S |
| T307Q/N434Y |
| V308T/L309P/Q311S |
| V308F/L309Y |
| V308F/Q311V |
| V308F/Y319F |
| V308F/Y319I/N434M |
| V308F/Y319I |
| V308F/Y319L |
| V308F/Y319I/M428L |
| V308F/Y319I/M428L/N434S |
| V308F/Y319L/N434S |

TABLE 4-3-continued

| |
|---|
| V308F/I332E |
| V308F/G385H |
| V308F/M428L/N434M |
| V308F/M428L |
| V308F/M428L/N434S |
| V308P/N434Y |
| V308F/N434M |
| V308F/N434S |
| V308F/N434Y |
| Q311G/N434S |
| Q311D/N434S |
| Q311E/N434S |
| Q311N/N434S |

Table 4-4 is a continuation table of Table 4-3.

TABLE 4-4

| |
|---|
| Q311Y/N434S |
| Q311F/N434S |
| Q311W/N434S |
| Q311A/N434S |
| Q311K/N434S |
| Q311T/N434S |
| Q311R/N434S |
| Q311L/N434S |
| Q311M/N434S |
| Q311V/N434S |
| Q311I/N434S |
| Q311A/N434Y |
| D312H/N434A |
| D312H/N434H |
| L314Q/N434S |
| L314V/N434S |
| L314M/N434S |
| L314F/N434S |
| L314I/N434S |
| N315H/N434A |
| N315H/N434H |
| Y319I/V308F |
| Y319I/M428L |
| Y319I/M428L/N434S |
| Y319I/N434M |
| Y319I/N434S |
| L328H/I332E |
| L328N/I332E |
| L328E/I332E |
| L328I/I332E |
| L328Q/I332E |
| L328D/I332E |
| L328R/M428L/N434S |
| A330L/I332E |
| A330Y/I332E |
| I332E/D376V |
| I332E/N434S |
| P343R/E345D |
| D376V/E430Q |
| D376V/E430R |
| D376V/N434H |
| E380A/N434A |
| G385R/Q386T/P387R/N389P |
| G385D/Q386P/N389S |
| N414F/Y416H |
| M428L/N434M |
| M428L/N434S |
| M428L/N434A |
| M428L/N434Y |
| M429N/N434S |
| E430D/N434S |
| E430T/N434S |
| E430S/N434S |
| E430A/N434S |
| E430F/N434S |
| E430Q/N434S |
| E430L/N434S |
| E430I/N434S |
| A431T/N434S |

Table 4-5 is a continuation table of Table 4-4.

TABLE 4-5

| |
|---|
| A431S/N434S |
| A431G/N434S |
| A431V/N434S |
| A431N/N434S |
| A431F/N434S |
| A431H/N434S |
| L432F/N434S |
| L432N/N434S |
| L432Q/N434S |
| L432H/N434S |
| L432G/N434S |
| L432I/N434S |
| L432V/N434S |
| L432A/N434S |
| H433K/N434F |
| H433L/N434S |
| H433M/N434S |
| H433A/N434S |
| H433V/N434S |
| H433K/N434S |
| H433S/N434S |
| H433P/N434S |
| N434S/M428L |
| N434S/Y436D |
| N434S/Y436Q |
| N434S/Y436M |
| N434S/Y436G |
| N434S/Y436E |
| N434S/Y436F |
| N434S/Y436T |
| N434S/Y436R |
| N434S/Y436S |
| N434S/Y436H |
| N434S/Y436K |
| N434S/Y436L |
| N434S/Y436V |
| N434S/Y436W |
| N434S/Y436I |
| N434S/T437I |

Herein, higher human FcRn-binding activity than that of native human IgG means that the human FcRn-binding activity is, for example, 105% or more, preferably 110% or higher, 115% or higher, 120% or higher, 125% or higher, particularly preferably 130% or higher, 135% or higher, 140% or higher, 145% or higher, 150% or higher, 155% or higher, 160% or higher, 165% or higher, 170% or higher, 175% or higher, 180% or higher, 185% or higher, 190% or higher, 195% or higher, twice or higher, 2.5 fold or higher, 3 fold or higher, 3.5 fold or higher, 4 fold or higher, 4.5 fold or higher, 5 fold or higher, 7.5 fold or higher, 10 fold or higher, 20 fold or higher, 30 fold or higher, 40 fold or higher, 50 fold or higher, 60 fold or higher, 70 fold or higher, 80 fold or higher, 90 fold or higher, 100 fold or higher than that of native human IgG.

Such amino acid alterations can be appropriately introduced using known methods. For example, alterations in the Fc domain of human IgG1 are described in Drug Metab Dispos. 2007 Jan. 35(1): 86-94; Int Immunol. 2006 Dec. 18, (12): 1759-69; J Biol Chem. 2001 Mar. 2, 276(9): 6591-604; J Biol Chem. (2007) 282(3): 1709-17; J Immunol. (2002) 169(9): 5171-80; J Immunol. (2009) 182(12): 7663-71; Molecular Cell, Vol. 7, 867-877, April, 2001; Nat Biotechnol. 1997 Jul. 15, (7): 637-40; Nat Biotechnol. 2005 Oct. 23, (10): 1283-8; Proc Natl Acad Sci USA. 2006 Dec. 5, 103(49): 18709-14; EP 2154157; US 20070141052; WO2000/042072; WO2002/060919; WO2006/020114; WO2006/031370; WO2010/033279; WO2006/053301; and WO2009/086320.

According to Yeung et al. (The Journal of Immunology, 2009 182: 7663-7671), the human FcRn-binding activity of human IgG1 is KD 1.7 μM under an acidic pH range (pH6.0) condition but is almost undetectable under a neutral pH range condition. Thus, preferred embodiments of antigen-binding molecules provided by the present invention include antigen-binding molecules of which human FcRn-binding activity under an acidic pH range condition is KD 20 μM or stronger and of which human FcRn-binding activity under a neutral pH range condition is comparable to or higher than that of human IgG. More preferred embodiments include antigen-binding molecules of which human FcRn-binding activity under an acidic pH range condition is KD 2.0 μM or stronger and of which human FcRn-binding activity under a neutral pH range condition is KD 40 μM or stronger. Still more preferred embodiments include antigen-binding molecules of which human FcRn-binding activity under an acidic pH range condition is KD 0.5 μM or stronger and of which human FcRn-binding activity under a neutral pH range condition is KD 15 μM or stronger. The above KD values refers to values determined by the method described in The Journal of Immunology, 2009 182: 7663-7671 (antigen-binding molecules are immobilized onto a chip, and human FcRn is injected as an analyte).

In a preferred embodiment, the antigen-binding molecules provided by the present invention have human FcRn-binding activity at pH 7.0 and at 25° C. which is stronger than human IgG. In a more preferred embodiment, human FcRn-binding activity at pH 7.0 and at 25° C. is 28-fold stronger than human IgG or stronger than KD 3.2 μM. In a more preferred embodiment, human FcRn-binding activity at pH 7.0 and at 25° C. is 38-fold stronger than human IgG or stronger than KD 2.3 μM.

KD (dissociation constant) can be used as a value for human FcRn-binding activity. However, the human FcRn-binding activity of human IgG is almost undetectable under a neutral pH range (pH 7.4) condition, and it is difficult to calculate the activity as KD. A method for assessing whether the human FcRn-binding activity at pH 7.4 is higher than that of human IgG is to assess based on the level of binding response in a BIACORE™ system when analytes are injected at the same concentration. Specifically, if the response level when human FcRn is injected into a chip immobilized with an antigen-binding molecule provided by the present invention is greater than the response level when human FcRn is injected into a human IgG-immobilized chip, the human FcRn-binding activity of the antigen-binding molecule is concluded to be higher than that of the human IgG.

Fcγ receptor (FcγR) refers to a receptor capable of binding to the Fc region of IgGs (for example, IgG1, IgG2, IgG3, or IgG4), and practically includes any members belonging to the Fcγ receptor family. In human, the family includes FcγRI (CD64) including isoforms FcγRIa, FcγRIb and FcγRIc; FcγRII (CD32) including isoforms FcγRIIa (including allotype H131 and R131), FcγRIIb (including FcγRIIb-1 and FcγRIIb-2), and FcγRIIc; and FcγRIII (CD16) including isoform FcγRIIIa (including allotype V158 and F158) and FcγRIIIb (including allotype FcγRIIIb-NA1 and FcγRIIIb-NA2); as well as all unidentified human FcγRs, FcγR isoforms, and allotypes thereof. However, Fcγ receptor is not limited to these examples. Without being limited thereto, origin of FcγR includes humans, mice, rats, rabbits, and monkeys. FcγR may be derived from any organisms. Mouse FcγR includes, without being limited to, FcγRI (CD64), FcγRII (CD32), FcγRIII (CD16), and FcγRIII-2 (FcγRIV, CD16-2), as well as all unidentified mouse FcγRs, FcγR isoforms, and allotypes thereof. Such preferred Fcγ receptors include, for example, human FcγRI (CD64), FcγRIIa (CD32), FcγRIIb (CD32), FcγRIIIa (CD16), and/or FcγRIIIb (CD16). The polynucleotide sequence and amino acid sequence of human FcγRI are shown in SEQ ID NOs: 39 (NM_000566.3) and 40 (NP_000557.1), respectively; the polynucleotide sequence and amino acid sequence of human FcγRIIa (allotype H131) are shown in SEQ ID NOs: 41 (BC020823.1) and 42 (AAH20823.1) (allotype R131 is a sequence in which amino acid at position 166 of SEQ ID NO: 42 is substituted with Arg), respectively; the polynucleotide sequence and amino acid sequence of FcγIIb are shown in SEQ ID NOs: 43 (BC146678.1) and 44 (AA146679.1), respectively; the polynucleotide sequence and amino acid sequence of FcγRIIIa are shown in SEQ ID NOs: 45 (BC033678.1) and 46 (AAH33678.1), respectively; and the polynucleotide sequence and amino acid sequence of FcγRIIIb are shown in SEQ ID NOs: 47 (BC128562.1) and 48 (AA128563.1), respectively (RefSeq accession number is shown in each parentheses). Whether an Fcγ receptor has binding activity to the Fc region of an IgG can be assessed by ALPHAscreen® (Amplified Luminescent Proximity Homogeneous Assay) bead-based proximity assay, surface plasmon resonance (SPR)-based BIACORE™ method, and others (Proc. Natl. Acad. Sci. USA (2006) 103(11), 4005-4010), in addition to FACS and ELISA.

Meanwhile, "Fc ligand" or "effector ligand" refers to a molecule and preferably a polypeptide that binds to an antibody Fc region, forming a complex. The molecule may be derived from any organisms. The binding of an Fc ligand to Fc region preferably induces one or more effector functions. Such Fc ligands include, but are not limited to, Fc receptors, FcγR, FcαR, FcεR, FcRn, C1q, and C3, mannan-binding lectin, mannose receptor, *Staphylococcus* Protein A, *Staphylococcus* Protein G, and viral FcγRs. The Fc ligands also include Fc receptor homologs (FcRH) (Davis et al., (2002) Immunological Reviews 190, 123-136), which are a family of Fc receptors homologous to FcγR. The Fc ligands also include unidentified molecules that bind to Fc.

FcγRI (CD64) including FcγRIa, FcγRIb, and FcγRIc, and FcγRIII (CD16) including isoforms FcγRIIIa (including allotypes V158 and F158) and FcγRIIIb (including allotypes FcγRIIIb-NA1 and FcγRIIIb-NA2) is composed of two types of subunits, α chain that binds to the Fc region of IgG and common γ chain having ITAM responsible for transduction of intracellular activation signal. Meanwhile, the cytoplasmic domain of FcγRII (CD32) including isoforms FcγRIIa (including allotypes H131 and R131) and FcγRIIc contains ITAM. These receptors are expressed on many immune cells such as macrophages, mast cells, and antigen-presenting cells. The activation signal transduced upon binding of these receptors to the Fc region of IgG results in enhancement of the phagocytic activity and inflammatory cytokine production of macrophages, mast cell degranulation, and the activation of antigen-presenting cells. Fcγ receptors having the ability to transduce the activation signal as described above are referred to as activating Fcγ receptors.

Meanwhile, the intracytoplasmic domain of FcγRIIb (including FcγRIIb-1 and FcγRIIb-2) contains ITIM responsible for transduction of inhibitory signals. The crosslinking between FcγRIIb and B cell receptor (BCR) on B cells suppresses the activation signal from BCR, which results in suppression of antibody production of B cells. The crosslinking of FcγRIII and FcγRIIb on macrophages suppresses the phagocytic activity and inflammatory cytokine production. Fcγ receptors having the ability to transduce the inhibitory signal as described above are referred to as inhibitory Fcγ receptors.

Receptor-binding domains that bind under a neutral pH range condition to Fcγ receptors more strongly than native human IgG can be produced by altering the amino acids of the Fc region of a human IgG. Such alterations include, for example, substitution, insertion, and deletion of one or more amino acids. Alternatively, an antigen-binding domain that binds to Fcγ receptor may be used as a receptor-binding domain. Such receptor-binding domains include Fab fragments that bind to FcγRIIIa, camel-derived single-domain antibodies, and the single-chain Fvs, described in Protein Eng Des Sel. 2009 March; 22(3): 175-88; Protein Eng Des Sel. 2008 January; 21(1): 1-10; and J Immunol. 2002 Jul. 1; 169(1): 137-44; and FcγRI-binding cyclic peptides described in FASEB J. 2009 February; 23(2): 575-85. Whether the Fcγ receptor-binding activity of a receptor-binding domain is greater than that of the Fc region of native human IgG can be appropriately assessed using the methods described above.

In the present invention, the activity of binding to a human Fcγ receptor under an acidic pH range condition means human Fcγ receptor-binding activity at pH 4.0 to pH 6.5, preferably human Fcγ receptor-binding activity at pH 5.0 to pH 6.5, more preferably human Fcγ receptor-binding activity at any of pH 5.5, 5.6, 5.7, 5.8, 5.9, 6.0, 6.1, 6.2, 6.3, 6.4, and 6.5, and particularly preferably human Fcγ receptor-binding activity at pH 5.8 to pH 6.0, which are close to the pH in the early endosome in vivo. Meanwhile, in the present invention, the binding activity to a human Fcγ receptor under a neutral pH range condition means human Fcγ receptor-binding activity at pH 6.7 to pH 10.0, preferably human Fcγ receptor-binding activity at pH 7.0 to pH 9.0, more preferably human Fcγ receptor-binding activity at any of pH 7.0, 7.1, 7.2, 7.3, 7.4, 7.5, 7.6, 7.7, 7.8, 7.9, and 8.0, and particularly preferably human Fcγ receptor-binding activity at pH 7.4, which is close to the pH of plasma in vivo.

Regarding measurement temperature, the binding affinity between a receptor-binding domain and a human Fcγ receptor may be measured at any temperature between 10° C. and 50° C. The binding affinity between a receptor-binding domain and a human Fcγ receptor is preferably determined at 15° C. to 40° C., more preferably at any of 20, 21, 22, 23, 24, 25, 26, 27, 28, 29, 30, 31, 32, 33, 34, and 35° C. Without being particularly limited, the 25° C. temperature is a preferred embodiment.

Receptor-binding domains of the present invention preferably include, for example, the Fc regions of human IgGs. The origin of such an Fc region is not particularly limited, and the domain can be obtained from any nonhuman animals or from humans. Nonhuman animals preferably include mice, rats, guinea pigs, hamsters, gerbils, cats, rabbits, dogs, goats, sheep, bovines, horses, camels, and nonhuman primates. In another embodiment, the receptor-binding domains can be obtained from cynomolgus monkeys, marmosets, rhesus monkeys, chimpanzees, and humans. The Fc regions are preferably obtained from the Fc region of human IgG1, and are not limited to particular IgG classes. Specifically, the Fc region of human IgG1, IgG2, IgG3, or IgG4 can be suitably used as a receptor-binding domain. Naturally occurring or artificially modified IgG variants include, for example, those described in published documents (Curr. Opin. Biotechnol. (2009) 20 (6), 685-91; Curr. Opin. Immunol. (2008) 20 (4), 460-470; Protein Eng. Des. Sel. (2010) 23 (4), 195-202; WO2009/086320; WO2008/092117; WO2007/041635; and WO2006/105338) but are not limited thereto.

As long as the receptor-binding domain binds under a neutral pH range condition to Fcγ receptor more strongly than native human IgG, amino acids may be altered at any positions. When receptor-binding domains are produced by altering the Fc region of human IgG1, amino acid alterations for increasing the binding activity to an Fcγ receptor under a neutral pH range condition includes, for example, the amino acid alterations described in WO2007/024249, WO2007/021841, WO2006/031370, WO2000/042072, WO2004/029207, WO2004/099249, WO2006/105338, WO2007/041635, WO2008/092117, WO2005/070963, WO2006/020114, WO2006/116260, and WO2006/023403.

Preferred amino acids when modifying the Fc region of IgG for receptor-binding domains that bind to human Fcγ receptor are, for example, at least one or more amino acids selected from the group consisting of the amino acids at positions 221, 222, 223, 224, 225, 227, 228, 230, 231, 232, 233, 234, 235, 236, 237, 238, 239, 240, 241, 243, 244, 245, 246, 247, 249, 250, 251, 252, 254, 255, 256, 257, 258, 260, 262, 263, 264, 265, 266, 267, 268, 269, 270, 271, 272, 273, 274, 275, 276, 278, 279, 280, 281, 282, 283, 284, 285, 286, 288, 290, 291, 292, 293, 294, 295, 296, 297, 298, 299, 300, 301, 302, 303, 304, 305, 307, 308, 309, 311, 312, 313, 314, 315, 316, 317, 318, 320, 322, 323, 324, 325, 326, 327, 328, 329, 330, 331, 332, 333, 334, 335, 336, 337, 339, 341, 343, 375, 376, 377, 378, 379, 380, 382, 385, 386, 387, 389, 392, 396, 421, 423, 427, 428, 429, 430, 431, 433, 434, 436, 438, 440, and 442 according to EU numbering. Alteration of these amino acids increases the activity of an IgG Fc region to bind an Fcγ receptor under a neutral pH range condition.

Particularly preferred alterations for increasing the binding to an Fcγ receptor under a neutral pH range condition include, for example, alteration of at least one or more amino acids selected from the group consisting of:

the amino acid at position 221 which is Lys or Tyr;
the amino acid at position 222 which is Phe, Trp, Glu, or Tyr;
the amino acid at position 223 which is Phe, Trp, Glu, or Lys;
the amino acid at position 224 which is Phe, Trp, Glu, or Tyr;
the amino acid at position 225 which is Glu, Lys, or Trp;
the amino acid at position 227 which is Glu, Gly, Lys, or Tyr;
the amino acid at position 228 which is Glu, Gly, Lys, or Tyr;
the amino acid at position 230 which is Ala, Glu, Gly, or Tyr;
the amino acid at position 231 which is Glu, Gly, Lys, Pro, or Tyr;
the amino acid at position 232 which is Glu, Gly, Lys, or Tyr;
the amino acid at position 233 which is Ala, Asp, Phe, Gly, His, Ile, Lys, Leu, Met, Asn, Gln, Arg, Ser, Thr, Val, Trp, or Tyr;
the amino acid at position 234 which is Ala, Asp, Glu, Phe, Gly, His, Ile, Lys, Met, Asn, Pro, Gln, Arg, Ser, Thr, Val, Trp, or Tyr;
the amino acid at position 235 which is Ala, Asp, Glu, Phe, Gly, His, Ile, Lys, Met, Asn, Pro, Gln, Arg, Ser, Thr, Val, Trp, or Tyr;
the amino acid at position 236 which is Ala, Asp, Glu, Phe, His, Ile, Lys, Leu, Met, Asn, Pro, Gln, Arg, Ser, Thr, Val, Trp, or Tyr;
the amino acid at position 237 which is Ala, Asp, Glu, Phe, His, Ile, Lys, Leu, Met, Asn, Pro, Gln, Arg, Ser, Thr, Val, Trp, or Tyr;
the amino acid at position 238 which is Asp, Glu, Phe, Gly, His, Ile, Lys, Leu, Met, Asn, Gln, Arg, Ser, Thr, Val, Trp, or Tyr;
the amino acid at position 239 which is Asp, Glu, Phe, Gly, His, Ile, Lys, Leu, Met, Asn, Pro, Gln, Arg, Thr, Val, Trp, or Tyr;
the amino acid at position 240 which is Ala, Ile, Met, or Thr;
the amino acid at position 241 which is Asp, Glu, Leu, Arg, Trp, or Tyr;
the amino acid at position 243 which is Leu, Glu, Leu, Gln, Arg, Trp, or Tyr;
the amino acid at position 244 which is His;
the amino acid at position 245 which is Ala;
the amino acid at position 246 which is Asp, Glu, His, or Tyr;
the amino acid at position 247 which is Ala, Phe, Gly, His, Ile, Leu, Met, Thr, Val, or Tyr;
the amino acid at position 249 which is Glu, His, Gln, or Tyr;
the amino acid at position 250 which is Glu or Gln;
the amino acid at position 251 which is Phe;
the amino acid at position 254 which is Phe, Met, or Tyr;
the amino acid at position 255 which is Glu, Leu, or Tyr;
the amino acid at position 256 which is Ala, Met, or Pro;
the amino acid at position 258 which is Asp, Glu, His, Ser, or Tyr;
the amino acid at position 260 which is Asp, Glu, His, or Tyr;
the amino acid at position 262 which is Ala, Glu, Phe, Ile, or Thr;
the amino acid at position 263 which is Ala, Ile, Met, or Thr;
the amino acid at position 264 which is Asp, Glu, Phe, Gly, His, Ile, Lys, Leu, Met, Asn, Pro, Gln, Arg, Ser, Thr, Trp, or Tyr;
the amino acid at position 265 which is Ala, Glu, Leu, Phe, Gly, His, Ile, Lys, Leu, Met, Asn, Pro, Gln, Arg, Ser, Thr, Val, Trp, or Tyr;
the amino acid at position 266 which is Ala, Phe, Ile, Leu, Met, or Thr;
the amino acid at position 267 which is Ala, Asp, Glu, Phe, Gly, His, Ile, Lys, Leu, Met, Asn, Pro, Gln, Arg, Thr, Val, Trp, or Tyr;
the amino acid at position 268 which is Ala, Asp, Glu, Phe, Gly, Ile, Lys, Leu, Met, Asn, Pro, Gln, Arg, Thr, Val, or Trp;
the amino acid at position 269 which is Asp, Phe, Gly, His, Ile, Lys, Leu, Met, Asn, Pro, Arg, Ser, Thr, Val, Trp, or Tyr;
the amino acid at position 270 which is Glu, Phe, Gly, His, Ile, Leu, Met, Pro, Gln, Arg, Ser, Thr, Trp, or Tyr;
the amino acid at position 271 which is Ala, Asp, Glu, Phe, Gly, His, Ile, Lys, Leu, Met, Asn, Gln, Arg, Ser, Thr, Val, Trp, or Tyr;
the amino acid at position 272 which is Asp, Phe, Gly, His, Ile, Lys, Leu, Met, Asn, Pro, Gln, Arg, Ser, Thr, Val, Trp, or Tyr;
the amino acid at position 273 which is Phe or Ile;
the amino acid at position 274 which is Asp, Glu, Phe, Gly, His, Ile, Leu, Met, Asn, Pro, Arg, Ser, Thr, Val, Trp, or Tyr;
the amino acid at position 275 which is Leu or Trp;
the amino acid at position 276 which is Asp, Glu, Phe, Gly, His, Ile, Leu, Met, Pro, Arg, Ser, Thr, Val, Trp, or Tyr;
the amino acid at position 278 which is Asp, Glu, Gly, His, Ile, Lys, Leu, Met, Asn, Pro, Gln, Arg, Ser, Thr, Val, or Trp;
the amino acid at position 279 which is Ala;
the amino acid at position 280 which is Ala, Gly, His, Lys, Leu, Pro, Gln, Trp, or Tyr;
the amino acid at position 281 which is Asp, Lys, Pro, or Tyr;
the amino acid at position 282 which is Glu, Gly, Lys, Pro, or Tyr;
the amino acid at position 283 which is Ala, Gly, His, Ile, Lys, Leu, Met, Pro, Arg, or Tyr;
the amino acid at position 284 which is Asp, Glu, Leu, Asn, Thr, or Tyr;
the amino acid at position 285 which is Asp, Glu, Lys, Gln, Trp, or Tyr;
the amino acid at position 286 which is Glu, Gly, Pro, or Tyr;
the amino acid at position 288 which is Asn, Asp, Glu, or Tyr;

the amino acid at position 290 which is Asp, Gly, His, Leu, Asn, Ser, Thr, Trp, or Tyr;
the amino acid at position 291 which is Asp, Glu, Gly, His, Ile, Gln, or Thr;
the amino acid at position 292 which is Ala, Asp, Glu, Pro, Thr, or Tyr;
the amino acid at position 293 which is Phe, Gly, His, Ile, Leu, Met, Asn, Pro, Arg, Ser, Thr, Val, Trp, or Tyr;
the amino acid at position 294 which is Phe, Gly, His, Ile, Lys, Leu, Met, Asn, Pro, Arg, Ser, Thr, Val, Trp, or Tyr;
the amino acid at position 295 which is Asp, Glu, Phe, Gly, His, Ile, Lys, Leu, Met, Asn, Pro, Arg, Ser, Thr, Val, Trp, or Tyr;
the amino acid at position 296 which is Ala, Asp, Glu, Gly, His, Ile, Lys, Leu, Met, Asn, Gln, Arg, Ser, Thr, or Val;
the amino acid at position 297 which is Asp, Glu, Phe, Gly, His, Ile, Lys, Leu, Met, Pro, Gln, Arg, Ser, Thr, Val, Trp, or Tyr;
the amino acid at position 298 which is Ala, Asp, Glu, Phe, His, Ile, Lys, Met, Asn, Gln, Arg, Thr, Val, Trp, or Tyr;
the amino acid at position 299 which is Ala, Asp, Glu, Phe, Gly, His, Ile, Lys, Leu, Met, Asn, Pro, Gln, Arg, Ser, Val, Trp, or Tyr;
the amino acid at position 300 which is Ala, Asp, Glu, Gly, His, Ile, Lys, Leu, Met, Asn, Pro, Gln, Arg, Ser, Thr, Val, or Trp;
the amino acid at position 301 which is Asp, Glu, His, or Tyr;
the amino acid at position 302 which is Ile;
the amino acid at position 303 which is Asp, Gly, or Tyr;
the amino acid at position 304 which is Asp, His, Leu, Asn, or Thr;
the amino acid at position 305 which is Glu, Ile, Thr, or Tyr;
the amino acid at position 311 which is Ala, Asp, Asn, Thr, Val, or Tyr;
the amino acid at position 313 which is Phe;
the amino acid at position 315 which is Leu;
the amino acid at position 317 which is Glu or Gln;
the amino acid at position 318 which is His, Leu, Asn, Pro, Gln, Arg, Thr, Val, or Tyr,
the amino acid at position 320 which is Asp, Phe, Gly, His, Ile, Leu, Asn, Pro, Ser, Thr, Val, Trp, or Tyr;
the amino acid at position 322 which is Ala, Asp, Phe, Gly, His, Ile, Pro, Ser, Thr, Val, Trp, or Tyr;
the amino acid at position 323 which is Ile, Leu, or Met;
the amino acid at position 324 which is Asp, Phe, Gly, His, Ile, Leu, Met, Pro, Arg, Thr, Val, Trp, or Tyr;
the amino acid at position 325 which is Ala, Asp, Glu, Phe, Gly, His, Ile, Lys, Leu, Met, Pro, Gln, Arg, Ser, Thr, Val, Trp, or Tyr;
the amino acid at position 326 which is Ala, Asp, Glu, Phe, Gly, His, Ile, Leu, Met, Asn, Pro, Gln, Ser, Thr, Val, Trp, or Tyr;
the amino acid at position 327 which is Ala, Asp, Glu, Phe, Gly, His, Ile, Lys, Leu, Met, Asn, Pro, Arg, Thr, Val, Trp, or Tyr;
the amino acid at position 328 which is Ala, Asp, Glu, Phe, Gly, His, Ile, Lys, Met, Asn, Pro, Gln, Arg, Ser, Thr, Val, Trp, or Tyr;
the amino acid at position 329 which is Asp, Glu, Phe, Gly, His, Ile, Lys, Leu, Met, Asn, Gln, Arg, Ser, Thr, Val, Trp, or Tyr;
the amino acid at position 330 which is Cys, Glu, Phe, Gly, His, Ile, Lys, Leu, Met, Asn, Pro, Arg, Ser, Thr, Val, Trp, or Tyr;
the amino acid at position 331 which is Asp, Phe, His, Ile, Leu, Met, Gln, Arg, Ser, Thr, Val, Trp, or Tyr;
the amino acid at position 332 which is Ala, Asp, Glu, Phe, Gly, His, Lys, Leu, Met, Asn, Pro, Gln, Arg, Ser, Thr, Val, Trp, or Tyr;
the amino acid at position 333 which is Ala, Asp, Glu, Phe, Gly, His, Ile, Lys, Leu, Met, Pro, Arg, Ser, Thr, Val, or Tyr;
the amino acid at position 334 which is Ala, Glu, Phe, His, Ile, Leu, Met, Asn, Pro, Gln, Arg, Ser, Thr, Val, Trp, or Tyr;
the amino acid at position 335 which is Asp, Phe, Gly, His, Ile, Leu, Met, Asn, Pro, Arg, Ser, Val, Trp, or Tyr;
the amino acid at position 336 which is Glu, Lys, or Tyr;
the amino acid at position 337 which is Asp, Glu, His, or Asn;
the amino acid at position 339 which is Asp, Phe, Gly, Ile, Lys, Met, Asn, Gln, Arg, Ser, or Thr;
the amino acid at position 376 which is Ala or Val;
the amino acid at position 377 which is Gly or Lys;
the amino acid at position 378 which is Asp;
the amino acid at position 379 which is Asn;
the amino acid at position 380 which is Ala, Asn, or Ser;
the amino acid at position 382 which is Ala or Ile;
the amino acid at position 385 which is Glu;
the amino acid at position 392 which is Thr;
the amino acid at position 396 which is Asp, Glu, Phe, Ile, Lys, Leu, Met, Gln, Arg, or Tyr;
the amino acid at position 421 which is Lys;
the amino acid at position 427 which is Asn;
the amino acid at position 428 which is Phe or Leu;
the amino acid at position 429 which is Met;
the amino acid at position 434 which is Trp;
the amino acid at position 436 which is Ile; and
the amino acid at position 440 is Gly, His, Ile, Leu, or Tyr, according to EU numbering in the Fc region. Further, the number of amino acids to be altered is not particularly limited, and amino acids may be modified at only one site, or two or more sites. Combinations of amino acid alterations at two or more sites include, for example, those described in Tables 5-1 to 5-3.

TABLE 5-1

| AMINO ACID COMBINATION | AMINO ACID COMBINATION |
|---|---|
| K370E/P396L/D270E | S239Q/I332Q |
| Q419H/P396L/D270E | S267D/I332E |
| V240A/P396L/D270E | S267E/I332E |
| R255L/P396L/D270E | S267L/A327S |
| R255L/P396L/D270E | S267Q/A327S |
| R255L/P396L/D270E/R292G | S298A/I332E |
| R255L/P396L/D270E | S304T/I332E |
| R255L/P396L/D270E/Y300L | S324G/I332D |
| F243L/D270E/K392N/P396L | S324G/I332E |
| F243L/R255L/D270E/P396L | S324I/I332D |
| F243L/R292P/Y300L/V305I/P396L | S324I/I332E |
| F243L/R292P/Y300L/P396L | T260H/I332E |
| F243L/R292P/Y300L | T335D/I332E |
| F243L/R292P/P396L | V240I/V266I |
| F243L/R292P/V305I | V264I/I332E |
| F243L/R292P | D265F/N297E/I332E |
| S298A/E333A/K334A | D265Y/N297D/I332E |
| E380A/T307A | F243L/V262I/V264W |
| K326M/E333S | N297D/A330Y/I332E |
| K326A/E333A | N297D/T299E/I332E |
| S317A/K353A | N297D/T299F/I332E |
| A327D/I332E | N297D/T299H/I332E |
| A330L/I332E | N297D/T299I/I332E |
| A330Y/I332E | N297D/T299L/I332E |
| E258H/I332E | N297D/T299V/I332E |
| E272H/I332E | P230A/E233D/I332E |
| E272I/N276D | P244H/P245A/P247V |
| E272R/I332E | S239D/A330L/I332E |
| E283H/I332E | S239D/A330Y/I332E |
| E293R/I332E | S239D/H268E/A330Y |
| F241L/V262I | S239D/I332E/A327A |
| F241W/F243W | S239D/I332E/A330I |

Table 5-2 is a continuation of Table 5-1.

TABLE 5-2

| | |
|---|---|
| F243L/V264I | S239D/N297D/I332E |
| H268D/A330Y | S239D/S298A/I332E |
| H268E/A330Y | S239D/V264I/I332E |
| K246H/I332E | S239E/N297D/I332E |
| L234D/I332E | S239E/V264I/I332E |
| L234E/I332E | S239N/A330L/I332E |
| L234G/I332E | S239N/A330Y/I332E |
| L234I/I332E | S239N/S298A/I332E |
| L234I/L235D | S239Q/V264I/I332E |
| L234Y/I332E | V264E/N297D/I332E |
| L235D/I332E | V264I/A330L/I332E |
| L235E/I332E | V264I/A330Y/I332E |
| L235I/I332E | V264I/S298A/I332E |
| L235S/I332E | Y296D/N297D/I332E |
| L328A/I332D | Y296E/N297D/I332E |
| L328D/I332D | Y296H/N297D/I332E |
| L328D/I332E | Y296N/N297D/I332E |
| L328E/I332D | Y296Q/N297D/I332E |
| L328E/I332E | Y296T/N297D/I332E |
| L328F/I332D | D265Y/N297D/T299L/I332E |
| L328F/I332E | F241E/F243Q/V262T/V264E |
| L328H/I332E | F241E/F243R/V262E/V264R |
| L328I/I332D | F241E/F243Y/V262T/V264R |
| L328I/I332E | F241L/F243L/V262I/V264I |
| L328M/I332D | F241R/F243Q/V262T/V264R |
| L328M/I332E | F241S/F243H/V262T/V264T |
| L328N/I332D | F241W/F243W/V262A/V264A |
| L328N/I332E | F241Y/F243Y/V262T/V264T |
| L328Q/I332D | I332E/A330Y/H268E/A327A |
| L328Q/I332E | N297D/I332E/S239D/A330L |
| L328T/I332D | N297D/S298A/A330Y/I332E |
| L328T/I332E | S239D/A330Y/I332E/K326E |
| L328V/I332D | S239D/A330Y/I332E/K326T |
| L328V/I332E | S239D/A330Y/I332E/L234I |
| L328Y/I332D | S239D/A330Y/I332E/L235D |

Table 5-3 is a continuation of Table 5-2.

TABLE 5-3

| | |
|---|---|
| L328Y/I332E | S239D/A330Y/I332E/V240I |
| N297D/I332E | S239D/A330Y/I332E/V264T |
| N297E/I332E | S239D/A330Y/I332E/V266I |
| N297S/I332E | S239D/D265F/N297D/I332E |
| P227G/I332E | S239D/D265H/N297D/I332E |
| P230A/E233D | S239D/D265I/N297D/I332E |
| Q295E/I332E | S239D/D265L/N297D/I332E |
| R255Y/I332E | S239D/D265T/N297D/I332E |
| S239D/I332D | S239D/D265V/N297D/I332E |
| S239D/I332E | S239D/D265Y/N297D/I332E |
| S239D/I332N | S239D/I332E/A330Y/A327A |
| S239D/I332Q | S239D/I332E/H268E/A327A |
| S239E/D265G | S239D/I332E/H268E/A330Y |
| S239E/D265N | S239D/N297D/I332E/A330Y |
| S239E/D265Q | S239D/N297D/I332E/K326E |
| S239E/I332D | S239D/N297D/I332E/L235D |
| S239E/I332E | S239D/V264I/A330L/I332E |
| S239E/I332N | S239D/V264I/S298A/I332E |
| S239E/I332Q | S239E/V264I/A330Y/I332E |
| S239N/I332D | F241E/F243Q/V262T/V264E/I332E |
| S239N/I332E | F241E/F243R/V262E/V264R/I332E |
| S239N/I332N | F241E/F243Y/V262T/V264R/I332E |
| S239N/I332Q | F241R/F243Q/V262T/V264R/I332E |
| S239Q/I332D | S239D/I332E/H268E/A330Y/A327A |
| S239Q/I332E | S239E/V264I/S298A/A330Y/I332E |
| S239Q/I332N | F241Y/F243Y/V262T/V264T/N297D/I332E |
| S267E/L328F | G236D/S267E |
| S239D/S267E | |

Herein, the activity to bind a human Fcγreceptor is deemed to be greater than that of native human IgG when the activity to bind human Fcγ receptors FcγRI, FcγRIIa, FcγRIIb, FcγRIIIa, and/or FcγRIIIb, is greater than that of native human IgG. This means that, for example, the activity to bind a human Fcγreceptor is 105% or more, preferably 110% or more, 115% or more, 120% or more, 125% or more, particularly preferably 130% or more, 135% or more, 140% or more, 145% or more, 150% or more, 155% or more, 160% or more, 165% or more, 170% or more, 175% or more, 180% or more, 185% or more, 190% or more, 195% or more, twice or more, 2.5 times or more, 3 times or more, 3.5 times or more, 4 times or more, 4.5 times or more, 5 times or more, 7.5 times or more, 10 times or more, 20 times or more, 30 times or more, 40 times or more, 50 times or more, 60 times or more, 70 times or more, 80 times or more, 90 times or more, or 100 times or more than that of native human IgG.

Receptor-binding domains of the present invention may have the property of having a greater binding activity to a specific Fcγ receptor(s) than the binding activity to other Fcγ receptors (selectively binds to a specific Fcγ receptor(s)). Examples include a receptor-binding domain having a greater binding activity to an inhibitory Fcγ receptor than to an activating Fcγ receptor. Such receptor-binding domains preferably include those having a greater binding activity to FcγRIIb (including FcγRIIb-1 and FcγRIIb-2), which is an inhibitory Fcγ receptor, than to an activating Fcγ receptor selected from: FcγRI (CD64) including isoforms FcγRIa, FcγRIb, and FcγRIc; FcγRIII (CD16) including isoforms FcγRIIIa (including allotypes V158 and F158) and FcγRIIIb (including allotypes FcγRIIIb-NA1 and FcγRIIIb-NA2); and FcγRII (CD32) including isoforms FcγRIIa (including allotypes H131 and R131) and FcγRIIc. The receptor-binding domains particularly preferably include those having a greater binding activity to FcγRIIb-1 and/or FcγRIIb-2 than to FcγRIIa (allotype H131).

Whether a receptor-binding domain has the property of selectively binding to a specific Fcγ receptor can be determined by measuring and comparing the KD value of the receptor-binding domain for each Fcγ receptor. For example, when the KD value of a receptor-binding domain to an activating Fcγ receptor divided by its KD value to an inhibitory Fcγ receptor is 1.2 or more, 1.3 or more, 1.4 or more, 1.5 or more, 1.6 or more, 1.7 or more, 1.8 or more, 1.9 or more, 2 or more, 3 or more, 5 or more, 6 or more, 7 or more, 8 or more, 9 or more, 10 or more, 15 or more, 20 or more, 25 or more, 30 or more, 35 or more, 40 or more, 45 or more, 50 or more, 55 or more, 60 or more, 65 or more, 70 or more, 75 or more, 80 or more, 85 or more, 90 or more, 95 or more, 100 or more, 110 or more, 120 or more, 130 or more, 140 or more, 150 or more, 160 or more, 170 or more, 180 or more, 190 or more, 200 or more, 210 or more, 220 or more, 230 or more, 240 or more, 250 or more, 260 or more, 270 or more, 280 or more, 290 or more, 300 or more, 310 or more, 320 or more, 330 or more, 340 or more, 350 or more, 360 or more, 370 or more, 380 or more, 390 or more, 400 or more, 410 or more, 420 or more, 430 or more, 440 or more, 450 or more, 460 or more, 470 or more, 480 or more, 490 or more, 500 or more, 520 or more, 540 or more, 560 or more, 580 or more, 600 or more, 620 or more, 640 or more, 660 or more, 680 or more, 700 or more, 720 or more, 740 or more, 760 or more, 780 or more, 800 or more, 820 or more, 840 or more, 860 or more, 880 or more, 900 or more, 920 or more, 940 or more, 960 or more, 980 or more, 1000 or more, 1500 or more, 2000 or more, 2500 or more, 3000 or more, 3500 or more, 4000 or more, 4500 or more, 5000 or more, 5500 or more, 6000 or more, 6500 or more, 7000 or more, 7500 or more, 8000 or more, 8500 or more, 9000 or more, 9500 or more, 10000 or more, or 100000 or more, it is determined that the receptor-binding domain may bind more selectively to the inhibitory Fcγ receptor than to the activating Fcγ receptor.

Without being particularly limited thereto, receptor-binding domains having a greater binding activity to an inhibitory Fcγ receptor than to an activating Fcγ receptor (selectively binds to an inhibitory Fcγ receptor) preferably include, for example, the IgG Fc region variants described in WO2012/115241, such as Fc regions with alterations of the amino acids at positions 238 and/or 328 (EU numbering) into different amino acids in IgG Fc region, more preferably Fc regions with alteration of the amino acid at position 238 into Asp and/or alteration of the amino acid at position 328 into Glu. Furthermore, it is possible to select appropriate IgG Fc region variants described in US2009/0136485.

At least one different alteration may be added to IgG Fc regions in combination with the above-described alterations. It is preferable that as a result of the alteration, the binding activity to FcγRIIb is increased, and the binding activity to FcγRIIa (allotype H131) and FcγRIIa (allotype R131) is maintained or is reduced. Such alteration improves the binding selectivity for FcγRIIb over FcγRIIa. Alteration that improves the binding selectivity for FcγRIIb over FcγRIIa (allotype R131) is preferred, and alteration that improves the binding selectivity for FcγRIIb over FcγRIIa (allotype R131) and FcγRIIa (allotype H131) is more preferred. Without being particularly limited thereto, such alterations include, for example, at least one or more amino acid alterations selected from the following group:

the amino acid at position 233 is Asp;
the amino acid at position 234 is Trp or Tyr;
the amino acid at position 235 is Phe, Trp, or Tyr;
the amino acid at position 236 is Asp,
the amino acid at position 237 is Ala, Asp, Glu, Phe, Leu, Met, Trp, or Tyr;
the amino acid at position 238 is Phe or Leu;
the amino acid at position 239 is Asp, Glu, Gly, Leu, or Asn;
the amino acid at position 266 is Ile, Leu, or Met;
the amino acid at position 267 is Ala, Asp, Glu, Ile, Met, Gln, or Val;
the amino acid at position 268 is Ala, Asp, Glu, Gly, Asn, or Gln;
the amino acid at position 271 is Gly or Leu;
the amino acid at position 295 is Leu;
the amino acid at position 296 is Asp;
the amino acid at position 300 is Asp, Glu, or Gln;
the amino acid at position 323 is Ile, Leu, or Met;
the amino acid at position 324 is Ile or Val;
the amino acid at position 325 is Met or Ser;
the amino acid at position 326 is Ala, Asp, Glu, Phe, His, Ile, Leu, Met, Asn, Pro, Gln, Ser, Thr, Val, Trp, or Tyr;
the amino acid at position 327 is Asp, Glu, Gly, or Asn;
the amino acid at position 328 is Ala, Asp, Phe, Ile, Met, Gln, Ser, Thr, Val, Trp, or Tyr;
the amino acid at position 330 is Lys, Met, or Arg;
the amino acid at position 331 is Phe, Trp, or Tyr;
the amino acid at position 332 is Phe;
the amino acid at position 333 is Pro;
the amino acid at position 334 is Ala, Trp, Glu, Phe, His, Ile, Leu, Met, Asn, Pro, Gln, Arg, Ser, Thr, Val, or Tyr;
the amino acid at position 335 is Asp; and
the amino acid at position 337 is Asp according to EU numbering.

Among the above, preferred alterations include, for example, at least one or more amino acid alterations selected from the following group:

the amino acid at position 233 is Asp;
the amino acid at position 234 is Trp or Tyr;
the amino acid at position 237 is Ala, Asp, Glu, Phe, Leu, Met, Trp, or Tyr;
the amino acid at position 239 is Asp;
the amino acid at position 267 is Ala, Gln, or Val;
the amino acid at position 268 is Asp, Glu, or Asn;
the amino acid at position 271 is Gly;
the amino acid at position 296 is Asp;
the amino acid at position 323 is Ile, Leu, or Met;
the amino acid at position 326 is Ala, Asp, Glu, Leu, Met, Asn, Gln, Ser, or Thr; and
the amino acid at position 330 is Lys, Met, or Arg according to EU numbering.

The alterations described above may be an alteration at one site, or at two or more sites in combination. Preferred alterations include, for example, the alterations shown in Tables 24 to 25, 27 to 34, and 36 to 37.

Without being particularly limited thereto, one embodiment of the receptor-binding domain included in antigen-binding molecules of the present invention includes altered Fc regions of human IgG1 (SEQ ID NO: 49), IgG2 (SEQ ID NO: 50), IgG3 (SEQ ID NO: 51), and IgG4 (SEQ ID NO: 52). Examples of the altered Fc regions include the Fc regions of human IgGs (IgG1, IgG2, IgG3, and IgG4), in which the amino acid at position 238 (EU numbering) is Asp and the amino acid at position 271 (EU numbering) is Gly. The Fc regions of human IgGs (IgG1, IgG2, IgG3, and IgG4) in which the amino acid at position 238 (EU numbering) is Asp and the amino acid at position 271 is Gly, and antigen-binding molecules containing the Fc regions exhibit a greater binding activity to the inhibitory Fcγ receptor rather than to the activating Fcγ receptor.

In the present invention, at least one different alteration may be added to the Fc region in which the amino acid at position 238 (EU numbering) is Asp and the amino acid at position 271 is Gly (EU numbering). It is preferable that as a result, the binding activity to FcγRIIb-1 and/or FcγRIIb-2 is increased, and the binding activity to FcγRIIa (allotype H131) and FcγRIIa (allotype R131) is maintained or is reduced. It is also preferable that the level of increase in the binding activity to the inhibitory Fcγ receptor (FcγRIIb-1 and/or FcγRIIb-2) is higher than the level of increase in the binding activity to the activating Fcγ receptor (FcγRIa, FcγRIb, FcγRIc, FcγRIIIa (allotype V158), FcγRIIIa (allotype F158), FcγRIIIb (allotype FcγRIIIb-NA1), FcγRIIIb (allotype FcγRIIIb-NA2), FcγRIIa (allotype H131), and FcγRIIa (allotype R131)). Such alteration improves the binding selectivity for FcγRIIb over FcγRIIa.

Without being particularly limited thereto, selective receptor-binding domains include, for example, Fc regions of a human IgG (IgG1, IgG2, IgG3, or IgG4) in which the amino acid at position 238 (EU numbering) is altered to Asp and the amino acid at position 271 is altered to Gly, and in which one or more of the amino acids at positions 233, 234, 237, 244, 245, 249, 250, 251, 252, 254, 255, 256, 257, 258, 260, 262, 264, 265, 266, 267, 268, 269, 270, 272, 279, 283, 285, 286, 288, 293, 296, 307, 308, 309, 311, 312, 314, 316, 317, 318, 326, 327, 330, 331, 332, 333, 339, 341, 343, 375, 376, 377, 378, 380, 382, 385, 386, 387, 389, 396, 423, 427, 428, 430, 431, 433, 434, 436, 438, 440, and 442 according to EU numbering are altered.

Furthermore, without being particularly limited thereto, selective receptor-binding domains include, for example, Fc regions of a human IgG (IgG1, IgG2, IgG3, or IgG4) in which the amino acid at position 238 (EU numbering) is altered to Asp and the amino acid at position 271 is altered to Gly, and in which one or more amino acid alterations selected from the following group are made:

the amino acid at position 233 is Asp;
the amino acid at position 234 is Tyr;

the amino acid at position 237 is Asp;
the amino acid at position 264 is Ile;
the amino acid at position 265 is Glu;
the amino acid at position 266 is Phe, Met, or Leu;
the amino acid at position 267 is Ala, Glu, Gly, or Gln;
the amino acid at position 268 is Asp or Glu;
the amino acid at position 269 is Asp;
the amino acid at position 272 is Asp, Phe, Ile, Met, Asn, or Gln;
the amino acid at position 296 is Asp;
the amino acid at position 326 is Ala or Asp;
the amino acid at position 327 is Gly;
the amino acid at position 330 is Lys or Arg;
the amino acid at position 331 is Ser;
the amino acid at position 332 is Thr;
the amino acid at position 333 is Thr, Lys, or Arg; and
the amino acid at position 396 is Asp, Glu, Phe, Ile, Lys, Leu, Met, Gln, Arg, or Tyr, according to EU numbering.

Without being particularly limited thereto, one embodiment of the above-described Fc regions includes, for example, those described in Tables 6-1 to 6-6.

TABLE 6-1

| ALTERED Fc REGION | ALTERED AMINO ACID (EU NUMBERING) |
|---|---|
| BP208 | E233D/G237D/P238D/H268D/P271G/A330R |
| BP209 | G237D/P238D/H268D/P271G/K326A/A330R |
| BP210 | G237D/P238D/H268D/P271G/A330R |
| BP211 | E233D/P238D/H268D/P271G/K326A/A330R |
| BP212 | E233D/P238D/H268D/P271G/Y296D/A330R |
| BP213 | E233D/P238D/H268D/P271G/A330R |
| BP214 | E233D/L234Y/G237D/P238D/Y296D/K326D/A330K |
| BP215 | G237D/P238D/H268D/P271G/Y296D/A330K |
| BP216 | G237D/P238D/S267Q/H268D/P271G/A330K |
| BP217 | G237D/P238D/S267Q/H268D/P271G/Y296D/A330K |
| BP218 | G237D/P238D/H268D/P271G/K326D/A330K |
| BP219 | L234Y/G237D/P238D/H268D/P271G/A330K |
| BP220 | E233D/G237D/P238D/H268D/P271G/Y296D/A330K |
| BP221 | L234Y/G237D/P238D/Y296D/K326A/A330R |
| BP222 | L234Y/G237D/P238D/P271G/K326A/A330R |
| BP223 | L234Y/G237D/P238D/H268D/P271G/K326A/A330R |
| BP224 | L234Y/G237D/P238D/S267Q/H268D/P271G/K326A/A330R |
| BP225 | L234Y/G237D/P238D/K326D/A330R |
| BP226 | L234Y/G237D/P238D/P271G/K326D/A330R |
| BP227 | L234Y/G237D/P238D/H268D/P271G/K326D/A390R |
| BP228 | L234Y/G237D/P238D/S267Q/H268D/P271G/K326D/A330R |
| BP229 | E233D/L234Y/G237D/P238D/P271G/K326A/A330R |
| BP230 | E233D/G237D/P238D/H268D/P271G/Y296D/A330R |
| BP231 | G237D/P238D/H268D/P271G/Y296D/A330R |
| BP232 | L234Y/G237D/P238D/P271G/K326A/A330K |
| BP233 | L234Y/G237D/P238D/P271G/A330K |
| BP234 | E233D/L234Y/G237D/P238D/S267Q/H268D/P271G/Y296D/K326D/A330K |
| BP235 | E233D/L234Y/G237D/P238D/H268D/P271G/Y296D/K326D/A330R |
| BP236 | E233D/L234Y/G237D/P238D/S267Q/H268D/P271G/Y296D/K326D/A330R |
| BP237 | E233D/L234Y/G237D/P238D/S267Q/H268D/P271G/Y296D/K326A/A330K |

Table 6-2 is a continuation table of Table 6-1.

TABLE 6-2

| ALTERED Fc REGION | ALTERED AMINO ACID (EU NUMBERING) |
|---|---|
| BP238 | E233D/L234Y/G237D/P238D/H268D/P271G/Y296D/K326A/A330R |
| BP239 | E233D/L234Y/G237D/P238D/S267Q/H268D/P271G/Y296D/K326A/A330R |

TABLE 6-2-continued

| ALTERED Fc REGION | ALTERED AMINO ACID (EU NUMBERING) |
|---|---|
| BP240 | E233D/G237D/P238D/S267Q/H268D/P271G/A330R |
| BP241 | E233D/G237D/P238D/H268D/P271G/K326D/A330R |
| BP242 | E233D/G237D/P238D/H268D/P271G/K326A/A330R |
| BP243 | E233D/L234Y/G237D/P238D/H268D/P271G/A330R |
| BP244 | E233D/G237D/P238D/S267Q/E268D/P271G/Y296D/A330R |
| BP245 | E233D/G237D/P238D/S267Q/H268D/P271G/Y296D/K326D/A330R |
| BP246 | E233D/G237D/P238D/S267Q/H268D/P271G/Y296D/K326A/A330R |
| BP247 | E233D/G237D/P238D/H268D/P271G/Y296D/K326D/A330R |
| BP248 | E233D/G237D/P238D/H268D/P271G/Y296D/K326A/A330R |
| BP249 | E233D/L234Y/G237D/P238D/H268D/P271G/Y296D/A330R |
| BP262 | G237D/P238D/H268E/P271G |
| BP264 | E233D/G237D/P238D/H268E/P271G/Y296D/A330R |
| BP265 | G237D/P238D/H268E/P271G/Y296D/A330R |
| BP266 | E233D/G237D/P238D/H268E/P271G/A330R |
| BP267 | E233D/G237D/P238D/H268E/P271G |
| BP268 | E233D/G237D/P238D/H268E/P271G/Y296D |
| BP269 | G237D/P238D/H268E/P271G/Y296D |
| BP300 | E233D/G237D/P238D/V264I/H268E/P271G |
| BP313 | E233D/G237D/P238D/D265E/H268E/P271G |
| BP333 | E233D/G237D/P238D/V266F/H268E/P271G |
| BP338 | E233D/G237D/P238D/V266L/H268E/P271G |
| BP339 | E233D/G237D/P238D/V266M/H268E/P271G |
| BP348 | E233D/G237D/P238D/S267A/H268E/P271G |
| BP350 | E233D/G237D/P238D/S267E/H268E/P271G |
| BP352 | E233D/G237D/P238D/S267G/H268E/P271G |
| BP367 | E233D/G237D/P238D/H268E/E269D/P271G |
| BP384 | E233D/G237D/P238D/H268D/P271G/Y296D/A330R/K334R |
| BP390 | E233D/G237D/P238D/H268D/P271G/Y296D/A330R/I332S |
| BP391 | E233D/G237D/P238D/H268D/P271G/Y296D/A330R/I332T |

Table 6-3 is a continuation table of Table 6-2.

TABLE 6-3

| ALTERED Fc REGION | ALTERED AMINO ACID (EU NUMBERING) |
|---|---|
| BP392 | E233D/G237D/P238D/H268D/P271G/Y296D/A330R/I332K |
| BP393 | E233D/G237D/P238D/H268D/P271G/Y296D/A330R/I332R |
| BP423 | E233D/G237D/P238D/S267A/H268E/P271G/A330R |
| BP425 | E233D/G237D/P238D/V266L/S267A/H268E/P271G/A330R |
| BP426 | E233D/G237D/P238D/S267A/H268E/E269D/P271G/A330R |
| BP427 | E233D/G237D/P238D/S267A/H268E/E269Y/P271G/A330R |
| BP428 | E233D/G237D/P238D/S267G/H268E/P271G/A330R |
| BP429 | E233D/G237D/P238D/V264I/S267G/H268E/P271G/A330R |
| BP430 | E233D/G237D/P238D/V266L/S267G/H268E/P271G/A330R |
| BP431 | E233D/G237D/P238D/S267G/H268E/E269D/P271G/A330R |
| BP432 | E233D/G237D/P238D/S267G/H268E/E269Y/P271G/A330R |
| BP433 | E233D/G237D/P238D/H268D/P271G/Y296D/A330K/I332T |
| BP434 | E233D/G237D/P238D/H268D/P271G/Y296D/K326D/A330R/I332T |
| BP435 | E233D/G237D/P238D/H268D/P271G/Y296D/K326A/A330R/I332T |
| BP436 | E233D/G237D/P238D/S267A/H268E/P271G/Y296D/A330R/I332T |

TABLE 6-3-continued

| ALTERED Fc REGION | ALTERED AMINO ACID (EU NUMBERING) |
|---|---|
| BP437 | G237D/P238D/S267A/H268E/P271G/Y296D/A330R/I332T |
| BP438 | E233D/G237D/P238D/S267A/H268E/P271G/A330R/I332T |
| BP439 | E233D/G237D/P238D/V264I/V266L/S267A/H268E/P271G/A330R |
| BP440 | E233D/G237D/P238D/V264I/H268E/P271G/A330R |
| BP441 | E233D/G237D/P238D/V266L/H268E/P271G/A330R |
| BP442 | E233D/G237D/P238D/H268E/E269D/P271G/A330R |
| BP443 | E233D/G237D/P238D/V266L/H268E/E269D/P271G/A330R |
| BP444 | E233D/G237D/P238D/H268E/E269N/P271G/A330R |
| BP445 | E233D/G237D/P238D/V264I/S267A/H268E/P271G/A330R |
| BP446 | E233D/G237D/P238D/S267A/H268E/E269N/P271G/A330R |
| BP447 | E233D/G237D/P238D/S267A/H268E/P271G/A330R/P396A |
| BP448 | E233D/G237D/P238D/S267A/H268E/P271G/A330R/P396D |
| BP449 | E233D/G237D/P238D/S267A/H268E/P271G/A330R/P396E |
| BP450 | E233D/G237D/P238D/S267A/H268E/P271G/A330R/P396F |
| BP451 | E233D/G237D/P238D/S267A/H268E/P271G/A330R/P396G |
| BP452 | E233D/G237D/P238D/S267A/H268E/P271G/A330R/P396H |

Table 6-4 is a continuation table of Table 6-3.

TABLE 6-4

| ALTERED Fc REGION | ALTERED AMINO ACID (EU NUMBERING) |
|---|---|
| BP453 | E233D/G237D/P238D/S267A/H268E/P271G/A330R/P396I |
| BP454 | E233D/G237D/P238D/S267A/H268E/P271G/A330R/P396K |
| BP455 | E233D/G237D/P238D/S267A/H268E/P271G/A330R/P396L |
| BP456 | E233D/G237D/P238D/S267A/H268E/P271G/A330R/P396M |
| BP457 | E233D/G237D/P238D/S267A/H268E/P271G/A330R/P396N |
| BP458 | E233D/G237D/P238D/S267A/H268E/P271G/A330R/P396Q |
| BP459 | E233D/G237D/P238D/S267A/H268E/P271G/A330R/P396R |
| BP460 | E233D/G237D/P238D/S267A/H268E/P271G/A330R/P396S |
| BP461 | E233D/G237D/P238D/S267A/H268E/P271G/A330R/P396T |
| BP462 | E233D/G237D/P238D/S267A/H268E/P271G/A330R/P396V |
| BP463 | E233D/G237D/P238D/S267A/H268E/P271G/A330R/P396W |
| BP464 | E233D/G237D/P238D/S267A/H268E/P271G/A330R/P396Y |
| BP465 | E233D/G237D/P238D/H268D/P271G/Y296D/A330R/E333K |
| BP466 | E233D/G237D/P238D/H268D/P271G/Y296D/A330R/E333R |
| BP467 | E233D/G237D/P238D/H268D/P271G/Y296D/A330R/E334S |
| BP468 | E233D/G237D/P238D/H268D/P271G/Y296D/A330R/E334T |
| BP469 | E233D/G237D/P238D/H268D/P271G/Y296D/A330R/E333S |
| BP470 | E233D/G237D/P238D/H268D/P271G/Y296D/A330R/E333T |
| BP471 | E233D/G237D/P238D/H268D/P271G/Y296D/A330R/P331S |
| BP472 | E233D/G237D/P238D/H268D/P271G/Y296D/A330S |
| BP473 | E233D/G237D/P238D/H268D/P271G/Y296D/A327G/A330R |
| BP474 | E233D/G237D/P238D/H268D/P271G/Y296D/A330R/P331S |
| BP475 | E233D/G237D/P238D/H268D/P271G/Y296D/A327G/A330S |
| BP476 | E233D/G237D/P238D/H268D/P271G/Y296D/A327G/A330S/P331S |
| BP477 | E233D/G237D/P238D/H268D/P271G/Y296D/A327G/A330R/P331S |
| BP478 | E233D/G237D/P238D/H268D/P271G/Y296D/A330R + S131C/K133R/G137E/G138S/Q196K/I199T/N203D/K214R/P217S + 219-221 DELETION + K222Y/T223G/H224P/T225P |
| BP479 | E233D/G237D/P238D/V264I/V266L/S267A/H268E/P271G |
| BP480 | E233D/G237D/P238D/V266L/H268E/E269D/P271G |
| BP481 | E233D/G237D/P238D/V264I/S267A/H268E/P271G |

Table 6-5 is a continuation table of Table 6-4.

TABLE 6-5

| ALTERED Fc REGION | ALTERED AMINO ACIDS (EU NUMBERING) |
|---|---|
| BP482 | E233D/G237D/P238D/S267A/H268E/E269N/P271G |
| BP483 | E233D/G237D/P238D/V266L/S267A/H268E/P271G |
| BP484 | E233D/G237D/P238D/S267A/H268E/E269D/P271G |
| BP485 | E233D/G237D/P238D/S267A/H268E/E269Y/P271G |
| BP487 | E233D/G237D/P238D/V264I/S267A/H268E/P271G/A330R/P396M |
| BP488 | E233D/G237D/P238D/V264I/S267A/H268E/P271G/Y296D/A330R |
| BP489 | E233D/G237D/P238D/V264I/S267A/H268E/P271G/Y296D/A330R/P396M |
| BP490 | G237D/P238D/V264I/S267A/H268E/P271G/A330R |
| BP491 | G237D/P238D/V264I/S267A/H268E/P271G/Y296D/A330R |
| BP492 | P238D/V264I/S267A/H268E/P271G |
| BP493 | P238D/V264I/S267A/H268E/P271G/Y296D |
| BP494 | G237D/P238D/S267A/H268E/P271G/Y296D/A330R |
| BP495 | G237D/P238D/S267G/H268E/P271G/Y296D/A330R |
| BP496 | E233D/G237D/P238D/V264I/S267A/H268E/P271G/Y296D |
| BP497 | E233D/G237D/P238D/V264I/S267A/H268E/P271G/A327G/A330R |

TABLE 6-5-continued

| ALTERED Fc REGION | ALTERED AMINO ACIDS (EU NUMBERING) |
|---|---|
| BP498 | E233D/G237D/P238D/V264I/S267A/H268E/P271G/A330R/P396L |
| BP499 | E233D/G237D/P238D/V264I/S267A/H268E/P271G/Y296D/A330R/P396L |
| BP500 | G237D/P238D/V264I/S267A/H268E/P271G/Y296D |
| BP501 | G237D/P238D/V264I/S267A/H268E/P271G |
| BP502 | E233D/G237D/P238D/V264I/S267A/H268E/P271G/Y296D/A327G/A330R |
| BP503 | E233D/G237D/P238D/V264I/S267A/H268E/P271G/Y296D/A327G/A330R/P396M |
| BP504 | E233D/G237D/P238D/V264I/S267A/H268E/P271G/E272P |
| BP505 | E233D/G237D/P238D/V264I/S267A/H268E/P271G/E272D |
| BP506 | E233D/G237D/P238D/V264I/S267A/H268E/P271G/E272P/Y296D/A330R |
| BP507 | E233D/G237D/P238D/V264I/S267A/H268E/P271G/E272P/A330R |
| BP508 | E233D/G237D/P238D/V264I/S267A/H268E/P271G/E272P/Y296D |
| BP509 | E233D/G237D/P238D/V264I/S267A/H268E/P271G/E272D/Y296D |
| BP510 | G237D/P238D/V264I/S267A/H268E/P271G/E272P/A330R |
| BP511 | G237D/P238D/V264I/S267A/H268E/P271G/E272P/Y296D/A330R |
| BP513 | E233D/G237D/P238D/H268E/E272D/P271G |

Table 6-6 is a continuation table of Table 6-5.

TABLE 6-6

| ALTERED Fc REGION | ALTERED AMINO ACIDS (EU NUMBERING) |
|---|---|
| BP514 | E233D/G237D/P238D/H268E/E272F/P271G |
| BP517 | E233D/G237D/P238D/H268E/E272I/P271G |
| BP520 | E233D/G237D/P238D/H268E/E272M/P271G |
| BP521 | E233D/G237D/P238D/H268E/E272N/P271G |
| BP523 | E233D/G237D/P238D/H268E/E272Q/P271G |

It is preferable that the above-described receptor-binding domains which bind to human Fcγ receptor further contain amino acid alterations that enhance the FcRn-binding under an acidic pH range condition. Amino acids that can be altered as such include, for example: the amino acids at positions 252, 254, 256, 309, 311, 315, 433, and/or 434 (EU numbering), and in combination with these described above, the amino acids at positions 253, 310, 435, and/or 426 (EU numbering), as described in WO1997/034631;

the amino acids at positions 238, 252, 253, 254, 255, 256, 265, 272, 286, 288, 303, 305, 307, 309, 311, 312, 317, 340, 356, 360, 362, 376, 378, 380, 382, 386, 388, 400, 413, 415, 424, 433, 434, 435, 436, 439, and/or 447 (EU numbering), as described in WO2000/042072;

the amino acids at positions 251, 252, 254, 255, 256, 308, 309, 311, 312, 385, 386, 387, 389, 428, 433, 434, and/or 436 (EU numbering), as described in WO2002/060919;

the amino acids at positions 250, 314, and 428 (EU numbering), as described in WO2004/092219;

the amino acids at positions 238, 244, 245, 249, 252, 256, 257, 258, 260, 262, 270, 272, 279, 283, 285, 286, 288, 293, 307, 311, 312, 316, 317, 318, 332, 339, 341, 343, 375, 376, 377, 378, 380, 382, 423, 427, 430, 431, 434, 436, 438, 440, and/or 442 (EU numbering), as described in WO2006/020114; and the amino acids at positions 251, 252, 307, 308, 378, 428, 430, 434, and/or 436 (EU numbering), as described in WO2010/045193. Alterations of these amino acids enhance the FcRn-binding of IgG Fc regions under an acidic pH range condition.

More specifically, such alterations include, for example, at least one or more amino acid alterations selected from the following group:

the amino acid at position 244 is Leu;
the amino acid at position 245 is Arg;
the amino acid at position 249 is Pro;
the amino acid at position 250 is Gln or Glu;
the amino acid at position 251 is Arg, Asp, Glu, or Leu;
the amino acid at position 252 is Phe, Ser, Thr, or Tyr;
the amino acid at position 254 is Ser or Thr;
the amino acid at position 255 is Arg, Gly, Ile, or Leu;
the amino acid at position 256 is Ala, Arg, Asn, Asp, Gln, Glu, Pro, or Thr;
the amino acid at position 257 is Ala, Ile, Met, Asn, Ser, or Val;
the amino acid at position 258 is Asp;
the amino acid at position 260 is Ser;
the amino acid at position 262 is Leu;
the amino acid at position 270 is Lys;
the amino acid at position 272 is Leu or Arg;
the amino acid at position 279 is Ala, Asp, Gly, His, Met, Asn, Gln, Arg, Ser, Thr, Trp, or Tyr;
the amino acid at position 283 is Ala, Asp, Phe, Gly, His, Ile, Lys, Leu, Asn, Pro, Gln, Arg, Ser, Thr, Trp, or Tyr;
the amino acid at position 285 is Asn;
the amino acid at position 286 is Phe;
the amino acid at position 288 is Asn or Pro;
the amino acid at position 293 is Val;
the amino acid at position 307 is Ala, Glu, Gln, or Met;
the amino acid at position 308 is Ile, Pro, or Thr;
the amino acid at position 309 is Pro;
the amino acid at position 311 is Ala, Glu, Ile, Lys, Leu, Met, Ser, Val, or Trp;
the amino acid at position 312 is Ala, Asp, or Pro;
the amino acid at position 314 is Ala or Leu;
the amino acid at position 316 is Lys;
the amino acid at position 317 is Pro;
the amino acid at position 318 is Asn or Thr;
the amino acid at position 332 is Phe, His, Lys, Leu, Met, Arg, Ser, or Trp;
the amino acid at position 339 is Asn, Thr, or Trp;
the amino acid at position 341 is Pro,
the amino acid at position 343 is Glu, His, Lys, Gln, Arg, Thr, or Tyr;
the amino acid at position 375 is Arg;
the amino acid at position 376 is Gly, Ile, Met, Pro, Thr, or Val;
the amino acid at position 377 is Lys;
the amino acid at position 378 is Asp, Asn, or Val;
the amino acid at position 380 is Ala, Asn, Ser, or Thr;
the amino acid at position 382 is Phe, His, Ile, Lys, Leu, Met, Asn, Gln, Arg, Ser, Thr, Val, Trp, or Tyr;
the amino acid at position 385 is Ala, Arg, Asp, Gly, His, Lys, Ser, or Thr;
the amino acid at position 386 is Arg, Asp, Ile, Lys, Met, Pro, Ser, or Thr;

the amino acid at position 387 is Ala, Arg, His, Pro, Ser, or Thr;

the amino acid at position 389 is Asn, Pro, or Ser;

the amino acid at position 423 is Asn;

the amino acid at position 427 is Asn;

the amino acid at position 428 is Leu, Met, Phe, Ser, or Thr;

the amino acid at position 430 is Ala, Phe, Gly, His, Ile, Lys, Leu, Met, Asn, Gln, Arg, Ser, Thr, Val, or Tyr;

the amino acid at position 431 is His or Asn;

the amino acid at position 433 is Arg, Gln, His, Ile, Lys, Pro, or Ser;

the amino acid at position 434 is Ala, Gly, His, Phe, Ser, Trp, or Tyr;

the amino acid at position 436 is Arg, Asn, His, Ile, Leu, Lys, Met, or Thr;

the amino acid at position 438 is Lys, Leu, Thr, or Trp;

the amino acid at position 440 is Lys; and the amino acid at position 442 is Lys, according to EU numbering.

Alterations that can enhance the binding to human FcRn under an acidic pH range condition as compared to human IgG include, for example, at least one or more alterations selected from the following group:

an alteration comprising the amino acid at position 308 is Ile, the amino acid at position 309 is Pro, and/or the amino acid at position 311 is Glu;

an alteration comprising the amino acid at position 308 is Thr, the amino acid at position 309 is Pro, the amino acid at position 311 is Leu, the amino acid at position 312 is Ala, and/or the amino acid at position 314 is Ala;

an alteration comprising the amino acid at position 308 is Ile or Thr, the amino acid at position 309 is Pro, the amino acid at position 311 is Glu, Leu, or Ser, the amino acid at position 312 is Ala, and/or the amino acid at position 314 is Ala or Leu; and an alteration comprising the amino acid at position 308 is Thr, the amino acid at position 309 is Pro, the amino acid at position 311 is Ser, the amino acid at position 312 is Asp, and/or the amino acid at position 314 is Leu according to EU numbering.

In addition to the above, alterations that can enhance the binding to human FcRn under an acidic pH range condition as compared to human IgG include, for example: an alteration comprising the amino acid at position 251 is Leu, the amino acid at position 252 is Tyr, the amino acid at position 254 is Ser or Thr, the amino acid at position 255 is Arg, and/or the amino acid at position 256 is Glu according to EU numbering.

In addition to the above, alterations that can enhance the binding to human FcRn under an acidic pH range condition as compared to human IgG include, for example, at least one or more alterations selected from the following group:

an alteration comprising the amino acid at position 428 is Leu, Met, Phe, Ser, or Thr, the amino acid at position 433 is Arg, Gln, His, Ile, Lys, Pro, or Ser, the amino acid at position 434 is His, Phe, or Tyr, and/or the amino acid at position 436 is Arg, Asn, His, Lys, Met, or Thr; and an alteration comprising the amino acid at position 428 is His or Met, and/or the amino acid at position 434 is His or Met according to EU numbering.

In addition to the above, alterations that can enhance the binding to human FcRn under an acidic pH range condition as compared to human IgG include, for example, at least one or more alterations selected from the following group:

an alteration comprising the amino acid at position 385 is Arg, the amino acid at position 386 is Thr, the amino acid at position 387 is Arg, and/or the amino acid at position 389 is Pro; and an alteration comprising the amino acid at position 385 is Asp, the amino acid at position 386 is Pro, and/or the amino acid at position 389 is Ser according to EU numbering.

In addition to the above, alterations that can enhance the binding to human FcRn under an acidic pH range condition as compared to human IgG include, for example, at least one or more alterations selected from the following group:

an alteration comprising the amino acid at position 250 is Gln or Glu; and an alteration comprising the amino acid at position 428 is Leu or Phe according to EU numbering.

In addition to the above, alterations that can enhance the binding to human FcRn under an acidic pH range condition as compared to human IgG include, for example, at least one or more alterations selected from the following group:

an alteration comprising the amino acid at position 250 is Gln, and/or the amino acid at position 428 is Leu or Phe; and an alteration comprising the amino acid at position 250 is Glu, and/or the amino acid at position 428 is Leu or Phe according to EU numbering.

In addition to the above, alterations that can enhance the binding to human FcRn under an acidic pH range condition as compared to human IgG include, for example, at least one or more alterations selected from the following group:

an alteration comprising the amino acid at position 307 is Gln and the amino acid at position 434 is Ala or Ser;

an alteration comprising the amino acid at position 308 is Pro and the amino acid at position 434 is Ala;

an alteration comprising the amino acid at position 252 is Tyr and the amino acid at position 434 is Ala;

an alteration comprising the amino acid at position 378 is Val and the amino acid at position 434 is Ala;

an alteration comprising the amino acid at position 428 is Leu and the amino acid at position 434 is Ala;

an alteration comprising the amino acid at position 434 is Ala and the amino acid at position 436 is Ile;

an alteration comprising the amino acid at position 308 is Pro and the amino acid at position 434 is Tyr; and an alteration comprising the amino acid at position 307 is Gln and the amino acid at position 436 is Ile according to EU numbering.

In addition to the above, alterations that can enhance the binding to human FcRn under an acidic pH range condition as compared to human IgG include, for example, at least one or more alterations selected from the following group:

an alteration comprising the amino acid at position 307 is Gln, the amino acid at position 380 is Ala, and the amino acid at position 434 is Ser;

an alteration comprising the amino acid at position 307 is Gln, the amino acid at position 380 is Ala, and the amino acid at position 434 is Ala;

an alteration comprising the amino acid at position 252 is Tyr, the amino acid at position 308 is Pro, and the amino acid at position 434 is Tyr; and an alteration comprising the amino acid at position 251 is Asp, the amino acid at position 307 is Gln, and the amino acid at position 434 is His according to EU numbering.

In addition to the above, alterations that can enhance the binding to human FcRn under an acidic pH range condition as compared to human IgG include, for example, at least one or more alterations selected from the following group:

an alteration comprising the amino acid at position 257 is Ile and the amino acid at position 311 is Ile;

an alteration comprising the amino acid at position 257 is Ile and the amino acid at position 434 is His; and an alteration comprising the amino acid at position 376 is Val and the amino acid at position 434 is His according to EU numbering.

When an antigen-binding molecule of the present invention is produced using the Fc region of human IgG, an antigen-binding molecule containing the Fc region of IgG of the same subclass can be used as a control to assess the effect of the antigen-binding molecule of the present invention. Appropriate human IgG Fc regions that serve as a control include the Fc regions of human IgG1 (SEQ ID NO: 49, which results from adding A to the N terminus of RefSeq accession number AAC82527.1), human IgG2 (SEQ ID NO: 50, which results from adding A to the N terminus of RefSeq accession number AAB59393.1), human IgG3 (SEQ ID NO: 51, RefSeq accession number CAA27268.1), and human IgG4 (SEQ ID NO: 52, which results from adding A to the N terminus of RefSeq accession number AAB59394.1).

In mice, four types of Fcγ receptors have been identified: FcγRI (CD64), FcγRIIb (CD32), FcγRIII (CD16), and FcγRIV (CD16-2 or FcγRIII-2). As is the case in humans, FcγRIIb is believed to be the sole inhibitory Fcγ receptor. FcγRIIb1 and FcγRIIb2 are reported to be splicing variants of FcγRIIb. Both human and mouse FcγRIIb1 have a longer intracellular domain than FcγRIIb2. FcγRIIb1 is confirmed to be expressed in B cells. FcγRIIb2 is confirmed to be expressed in macrophages, mast cells, dendritic cells, basophils, neutrophils, and eosinophils (J. Clin. Immunol. (2005) 25 (1), 1-18).

To date, functional deficiency or reduced expression of FcγRIIb has been reported to have a correlation with the onset of autoimmune diseases in humans. For example, it has been reported that in some SLE patients, the binding of transcription activation factors is impaired due to the effect of genetic polymorphism in the expression promoter region of FcγRIIb, and the expression level of FcγRIIb is reduced (Hum. Genet. (2005) 117, 220-227; J. Immunol. (2004) 172, 7192-7199; J. Immunol. (2004) 172, 7186-7191). Furthermore, it has been reported that in some SLE patients, two types of genetic polymorphism of FcγRIIb are found in which the amino acid at position 233 is Ile or Thr. It has been reported that this site is located within the transmembrane domain of FcγRIIb, and in comparison to Ile, when the amino acid at position 233 is Thr, it becomes difficult for FcγRIIb to be present on lipid rafts, resulting in impairment of the signaling function of FcγRIIb (Nat. Med. (2005) 11, 1056-1058; Hum. Mol. Genet., (2005) 14, 2881-2892). Regarding mice, knockout C57BL/6 mice with the FcγRIIb gene disrupted have been reported to develop SLE-like symptoms such as autoantibody production and glomerulonephritis (Immunity 13 (2000) 277-285; J. Exp. Med. (2002) 195, 1167-1174). In addition, it has been reported that the expression level of FcγRIIb is reduced in mice that have been regarded as a spontaneous SLE onset model (Immunogenetics (2000) 51, 429-435; Int. Immunol. (1999) 11, 1685-1691; Curr. Biol. (2000) 10, 227-230; J. Immunol. (2002) 169, 4340-4346). These findings suggest that FcγRIIb regulates the humoral immunity in mice as is the case in humans.

When an antibody that has an Fc region of the present invention eliminates antigens via FcγRIIb, among the functions of FcγRIIb, the endocytotic function is thought to make the most important contribution. As described above, there are splicing variants of FcγRIIb: FcγRIIb1 and FcγRIIb2. It has been reported that the latter is primarily involved in the endocytosis of the immune complex between antibody and antigen (J. Immunol. (1994), 152 574-585; Science (1992) 256, 1808-1812; Cell (1989) 58, 317-327). To date, mouse FcγRIIb2 is reported to initiate endocytosis when incorporated into clathrin-coated pits (Cell (1989) 58, 317-327). Meanwhile, it has been reported that a dileucine motif is required for the FcγRIIb2-mediated endocytosis, and the dileucine motif is conserved in both humans and mice (EMBO J. (1994) 13 (13), 2963-2969). This finding also suggests that, like mouse, human FcγRIIb2 has endocytotic ability.

On the other hand, unlike FcγRIIb2, FcγRIIb1 is reported not to induce endocytosis. In its intracellular domain, FcγRIIb1 has an insertion sequence which is not found in FcγRIIb2. The sequence is believed to inhibit the incorporation of FcγRIIb1 into clathrin-coated pits, resulting in inhibition of endocytosis (J. Cell. Biol. (1992) 116, 875-888; J. Cell. Biol. (1989) 109, 3291-3302). As in mouse, human FcγRIIb1 contains the insertion sequence, and thus due to a similar mechanism, there expects to be a difference in the endocytotic ability of FcγRIIb1 and FcγRIIb2. Meanwhile, it has been reported that about 40% of the immune complexes on the cell surface are incorporated into cells in 20 minutes both in humans and in mice (Mol. Immunol. (2011) 49, 329-337; Science (1992) 256, 1808-1812). This finding suggests that in humans, FcγRIIb2 internalizes immune complexes into cells at a rate similar to that in mice.

In the Fcγ receptor family, FcγRIIb alone has ITIM inside the cell in both mice and humans, and the distribution of cells expressing FcγRIIb is identical. Thus, its function in the immunological regulation is also assumed to be the same. Furthermore, in light of the fact that immune complexes are taken up into cells at the same rate in humans and mice, the effect of FcγRIIb-mediated antigen elimination by antibody in human is expected to be predictable by using mice. In fact, as shown in the Examples discussed below, as compared to when mIgG1 is administered, antigen clearance is increased when altered molecules (mF44 and mF46) with increased affinity for mouse FcγRIIb and FcγRIII relative to mIgG1 are administered to normal mice.

Furthermore, as shown in the Examples described below, similar experiments were carried out using Fc receptor γ chain-deficient mice. As for mice, it has been reported that FcγRs other than FcγRIIb are expressed only in the copresence of the γ chain. For this reason, Fc receptor γ chain-deficient mice express FcγRIIb alone. The effect on antigen elimination produced when the binding activity to FcγRIIb is selectively increased can be studied by administering mF44 and mF46 to Fc receptor γ chain-deficient mice. The results described in the Examples demonstrate that mF44 and mF46 administered to Fc receptor γ chain-deficient mice increase antigen clearance as compared to when mIgG1 is administered to the same mice. Furthermore, the results described in the Examples demonstrate that even when administered to Fc receptor γ chain-deficient mice, mF44 and mF46 eliminate antigens to almost the same level as that when administered to normal mice.

Furthermore, as shown in the Examples described below, similar experiments were carried out using FcγRIII-deficient mice. mIgG1, mF44, and mF46 bind to only FcγRIIb and FcγRIII among mouse FcγRs. For this reason, the effect on antigen elimination produced when the binding activity to FcγRIIb is selectively increased can be studied by administering these antibodies to FcγRIII-deficient mice. The results described in the Examples demonstrate that when administered to FcγRIII-deficient mice, mF44 and mF46 increase antigen clearance as compared to when mIgG1 is administered to the same mice. Furthermore, the results described in the Examples demonstrate that even when administered to FcγRIII-deficient mice, mF44 and mF46 eliminate antigens to almost the same level as that when administered to normal mice or Fc receptor γ chain-deficient mice.

The results described above reveals that antigen elimination can be accelerated by increasing the binding activity in an FcγRIIb-selective manner without increasing the binding activity to activating Fcγ receptors.

In addition to previous literature reports studied above, the results of studies using mice described above suggest that as is the case in mouse, FcγRIIb-mediated intake of immune complexes into cells occurs in humans, and as a result, antibodies that have an Fc region with increased binding activity to human FcγRIIb in a selective manner can accelerate antigen elimination. Furthermore, as discussed above, since the rate of FcγRIIb-mediated intake of immune complexes into cells is assumed to be comparable between mouse and human, the antigen elimination-accelerating effect comparable to that of antibodies having an Fc region with increased affinity for mouse FcγRIIb can be achieved with antibodies that have an Fc region with increased affinity for human FcγRIIb.

In general, the Kabat numbering system is used to describe residues in the antibody variable regions (roughly, the residues at positions 1 to 107 in the light chain, and the residues at positions 1 to 113 in the heavy chain) (for example, Kabat et al., Sequences of Proteins of Immunological Interest. 5th Ed. Public Health Service, National Institutes of Health, Bethesda, Md. (1991)). "The EU numbering system" or "EU index" is generally used when referring to residues in the heavy chain constant region of an antibody (for example, the EU index reported in Kabat et al., supra). "The EU index of Kabat" refers to residue numbering for human IgG1 EU antibody. In the present specification, unless otherwise specified, the residue numbers in antibody variable regions are described using the Kabat numbering system. In the present specification, unless otherwise specified, the residue numbers in antibody constant regions are described using the EU numbering system (see, for example, WO2006/073941).

Antigen-binding domains of the present invention have antigen-binding activity which is different between intracellular condition and extracellular condition. Intracellular condition and extracellular condition refer to conditions that are different between in and outside of the cell. Categories of conditions include, for example, ion concentration, more specifically, hydrogen ion concentration (pH) and calcium ion concentration. Intracellular condition preferably refers to an environment characteristic to the environment inside the endosome, while extracellular condition preferably refers to an environment characteristic to the environment in plasma.

Antigen-binding domains with the property of having an antigen-binding activity that changes according to ion concentration can be obtained by screening a large number of antigen-binding domains for domains having such property. For example, when antigen-binding molecules of the present invention are antibodies, antibodies with the above-described property can be obtained by producing a large number of antibodies whose sequences are different from one another by a hybridoma method or an antibody library method and measuring their antigen-binding activities at different ion concentrations. The B cell cloning method illustrated in Example 1 of the present specification is particularly suitable as a method of screening for such antibodies. Furthermore, as described below, at least one distinctive amino acid residue that can confer an antigen-binding domain with the property of having an antigen-binding activity that changes according to ion concentration is specified, to prepare as a library of a large number of antigen-binding domains that have different sequences while sharing the distinctive amino acid residues as a common structure. Such a library can be screened to efficiently isolate antigen-binding domains that have the property described above.

In an embodiment of the present invention, the condition of ion concentrations refers to the condition of hydrogen ion concentrations or pH condition. In the present invention, the concentration of proton, i.e., the nucleus of hydrogen atom, is treated as synonymous with hydrogen ion concentration index (pH). When the activity of hydrogen ion in an aqueous solution is represented as aH+, pH is defined as −log 10aH+. When the ionic strength of the aqueous solution is low (for example, lower than $10^{-3}$), aH+ is nearly equal to the hydrogen ion strength. For example, the ionic product of water at 25° C. and 1 atmosphere is Kw=aH+aOH=$10^{-14}$, and therefore in pure water, aH+=aOH=10. In this case, pH=7 is neutral; an aqueous solution whose pH is lower than 7 is acidic or whose pH is greater than 7 is alkaline.

In the present invention, when the pH condition is used as the ion concentration condition, it is desirable that the antigen-binding activity under an acidic pH range (i.e., a high hydrogen ion concentration or low pH) condition is lower than that under a neutral pH range (i.e., a low hydrogen ion concentration or high pH) condition.

Intracellular pH is acidic as compared to extracellular pH. Conversely, extracellular pH is neutral as compared to intracellular pH. The present invention provides antigen-binding molecules in which the extracellular condition is a neutral pH range condition and the intracellular condition is an acidic pH range condition. In the present invention, the acidic pH range is preferably pH 4.0 to pH 6.5, more preferably pH 5.0 to pH 6.5, still more preferably any of pH 5.5, 5.6, 5.7, 5.8, 5.9, 6.0, 6.1, 6.2, 6.3, 6.4, and 6.5, and particularly preferably pH 5.8 to pH 6.0 which is close to the pH in the early endosome in vivo. Meanwhile, in the present invention, the neutral pH range is preferably pH 6.7 to pH 10.0, more preferably pH 7.0 to pH 9.0, still more preferably any of pH 7.0, 7.1, 7.2, 7.3, 7.4, 7.5, 7.6, 7.7, 7.8, 7.9, and 8.0, and particularly preferably pH 7.4 which is close to the pH in plasma (in blood).

When the level of antigen-binding activity is compared between the acidic pH range condition and the neutral pH range condition, it is preferable that the binding of antigen-binding domains of the present invention is stronger under a neutral pH range condition than under an acidic pH range condition. When the level of binding activity is expressed with the dissociation constant (KD), the value of KD (acidic pH)/KD (neutral pH) is preferably 2 or more, more preferably 10 or more, and still more preferably 40 or more. The upper limit of the value of KD (acidic pH)/KD (neutral pH) is not particularly limited, and may be any value such as 100, 400, 1000, or 10000, as long as it can be produced with the techniques of skilled artisans. It is possible to use the dissociation rate constant (kd) instead of KD. When it is difficult to calculate the KD value, the activity may be assessed based on the level of binding response in a BIACORE™ system when analytes are passed at the same concentration. When antigens are passed over a chip immobilized with antigen-binding molecules of the present invention, the binding response under an acidic pH range condition is preferably ½ or less of the binding response under a neutral pH range condition, more preferably ⅓ or less, still more preferably ⅕ or less, and particularly preferably 1/10 or less.

It is known that in general the in vivo extracellular pH (for example, in plasma) is neutral while the intracellular pH (for example, in the endosome) is acidic. When the property of having a lower antigen-binding activity under an intracellular pH condition than under an extracellular pH condition is conferred to the antigen-binding domain of antigen-binding molecules of the present invention, antigens that have bound to the antigen-binding molecule of the present invention outside of the cell dissociate from the antigen-binding molecule of the present invention inside the cell, thereby enhancing antigen incorporation into the cell from the outside of the cell. Such antigen-binding molecules, when administered to the living body, can reduce antigen concentration in plasma and thereby reduce the physiological activity of antigens in vivo. Thus, antigen-binding molecules of the present invention are useful.

Methods for conferring to antigen-binding domains of the present invention the property of binding more weakly to antigens under an acidic pH range condition than binding under a neutral pH range condition are not particularly limited, and the property may be conferred by any methods. Specifically, the methods are described in WO2009/125825, and include a method of substituting at least one amino acid residue with histidine and/or inserting at least one histidine in an antigen-binding domain. In a preferred embodiment, the antigen-binding molecules of the present invention contain a substitution of at least one amino acid residue by histidine and/or an insertion of at least one histidine in their antigen-binding domain. It is already known that the pH-dependent antigen-binding activity can be conferred to antibodies by substituting their amino acid residues with histidine (Ito W et al., FEBS Lett. (1992) 309, 85-88). The site of histidine substitution and/or insertion is not particularly limited, and amino acid residues at any positions may be substituted with histidine, and histidine may be inserted at any sites as long as the antigen-binding activity under an acidic pH range condition is reduced to be lower than that under a neutral pH range condition. Histidine substitution and/or insertion sites preferably include, for example, the site to which an antigen directly binds and portions that contribute to the preservation of the conformation of the site. For example, when the antigen-binding domain is an antibody variable region, the sites include CDRs and regions that contribute to the preservation of their conformation. Specifically, the sites include H27, H31, H32, H33, H35, H50, H58, H59, H61, H62, H63, H64, H65, H99, H100b, and H102 in the heavy chain; and L24, L27, L28, L32, L53, L54, L56, L90, L92, and L94 in the light chain. Among these sites, H32, H61, L53, L90, and L94 are expected to be high in universality (the positions of amino acid residues are indicated according to Kabat numbering (Kabat E A et al., 1991. Sequences of Proteins of Immunological Interest. NIH)). Preferred combinations of substituting multiple sites with histidine include, for example, the combination of H27, H31, and H35; the combination of H27, H31, H32, H35, H58, H62, and H102; the combination of L32 and L53; and the combination of L28, L32, and L53. Furthermore, preferred combinations of substitution sites in the heavy chain and light chain include, for example, the combination of H27, H31, L32, and L53.

Histidine is substituted and/or inserted at random into the antigen-binding domains of antigen-binding molecules of the present invention by a method such as histidine scanning, where histidine is used instead of alanine in an alanine scanning method known to those skilled in the art. It is possible to select from the resulting molecules, antigen-binding domains that bind more weakly to antigens under an acidic pH range condition than under a neutral pH range condition.

The number of histidines to be substituted and/or inserted can be appropriately determined by those skilled in the art. Histidine may be substituted or inserted at only one site. Alternatively, histidine may be substituted or inserted at two or more sites. Alternatively, histidine substitution and histidine insertion may be combined at two or more sites.

It is preferable that the antigen-binding domains have comparable antigen-binding activities before and after histidine substitution and/or insertion. Herein, comparable activity means 10% or more, preferably 30% or more, more preferably 50% or more, still more preferably 80% or more, and particularly preferably 90% or more of the original activity.

When antigen-binding molecules provided by the present invention contain the antibody constant region, methods for conferring to the antigen-binding provided by the present invention the property of binding more weakly to the antigen under an acidic pH range condition than under a neutral pH range condition include methods for altering the antibody constant region. Methods for altering the antibody constant region include, for example, methods in which the constant region is compared among isotypes (IgG1, IgG2, IgG3, and IgG4) to select an isotype with reduced antigen-binding activity under an acidic pH range condition (dissociation rate is accelerated under an acidic pH range condition). Such methods also include methods that reduce the antigen binding activity under an acidic pH range condition (dissociation rate is accelerated under an acidic pH range condition) by introducing amino acid alteration into the amino acid sequence of an isotype (IgG1, IgG2, IgG3, or IgG4). The sequence of the hinge domain of an antibody constant region varies considerably among isotypes (IgG1, IgG2, IgG3, and IgG4). The difference in the amino acid sequence of the hinge domain has great effects on the antigen-binding activity. Thus, the antigen-binding activity under an acidic pH range condition can be reduced by selecting an isotype appropriate for the type of binding antigen. Meanwhile, when an amino acid alteration is introduced into the amino acid sequence of an isotype, the site of introducing an amino acid alteration is preferably within the hinge domain.

A large number of antigen-binding domains is prepared as a library, in which the antigen-binding domains have different sequences while sharing as a common structure the above-described amino acid residues that change the antigen-binding activity according to the hydrogen ion concentration. The library can be screened to efficiently obtain antigen-binding domains with binding activity to a desired antigen, and in which their antigen-binding activity changes according to the hydrogen ion concentration.

For example, a light chain variable region with a framework sequence containing at least one amino acid residue that changes the antigen-binding activity according to the hydrogen ion concentration can be combined with a heavy chain variable region containing a random sequence, to construct a library that contains multiple antigen-binding domains that have different sequences while sharing as a common structure amino acid residues that change the antigen-binding activity according to the hydrogen ion concentration. In a preferred embodiment where such amino acid residues are introduced into the light chain altered region, the amino acid residues may be contained in the CDR1 of the light chain altered region, more preferably at positions 24, 27, 28, 31, 32, and/or 34 according to Kabat numbering in the CDR1 of the light chain variable region. In another preferred embodiment, the amino acid residues may be contained in the CDR2 of the light chain variable region, more preferably at positions 50, 51, 52, 53, 54, 55, and/or 56 according to Kabat numbering in the CDR2 of the light chain variable region. In still another preferred embodiment, the amino acid residues may be contained in the CDR3 of the light chain variable region, more preferably at positions 89, 90, 91, 92, 93, 94, and/or 95A according to Kabat numbering in the CDR3 of the light chain variable region. The amino acid residues may be contained alone, or two or more may be contained in combination as long as they change the antigen-binding activity according to the hydrogen ion concentration.

When the light chain variable region containing at least one amino acid residue that changes the antigen-binding activity according to the hydrogen ion concentration is combined with the heavy chain variable region containing a random sequence to produce an antigen-binding domain, it is possible to design it in such a way that its light chain variable region further contains flexible residues. Such flexible residues are not particularly limited in number and position, as long as the antigen-binding activity of the antigen-binding domain of the present invention is changed according to the hydrogen ion concentration. Specifically, the light chain CDR sequences and/or FR sequences may contain one or more flexible residues. Without being particularly limited thereto, flexible residues that are introduced into the sequence of the light chain variable region include, for example, amino acid residues shown in Tables 7 and 8. Meanwhile, without being particularly limited thereto, the sequence of the light chain variable region, other than flexible residues and amino acid residues that change the antigen-binding activity according to the hydrogen ion concentration, preferably includes germ-line sequences such as Vk1 (SEQ ID NO: 58), Vk2 (SEQ ID NO: 59), Vk3 (SEQ ID NO: 60), and Vk4 (SEQ ID NO: 61).

TABLE 7

| POSITION | AMINO ACID | | | | | | | | |
|---|---|---|---|---|---|---|---|---|---|
| | CDR1 | | | | | | | | |
| 28 | S: 100% | | | | | | | | |
| 29 | I: 100% | | | | | | | | |
| 30 | N: 25% | S: 25% | R: 25% | H: 25% | | | | | |
| 31 | S: 100% | | | | | | | | |
| 32 | H: 100% | | | | | | | | |
| 33 | L: 100% | | | | | | | | |
| 34 | A: 50% | N: 50% | | | | | | | |
| | CDR2 | | | | | | | | |
| 50 | H: 100% | | | | OR | A: 25% | D: 25% | G: 25% | K: 25% |
| 51 | A: 100% | | | | | A: 100% | | | |
| 52 | S: 100% | | | | | S: 100% | | | |
| 53 | K: 33.3% | N: 33.3% | S: 33.3% | | | H: 100% | | | |
| 54 | L: 100% | | | | | L: 100% | | | |
| 55 | Q: 100% | | | | | Q: 100% | | | |
| 56 | S: 100% | | | | | S: 100% | | | |
| | CDR3 | | | | | | | | |
| 90 | Q: 100% | | | | OR | Q: 100% | | | |
| 91 | H: 100% | | | | | S: 33.3% | R: 33.3% | Y: 33.3% | |
| 92 | G: 25% | N: 25% | S: 25% | Y: 25% | | H: 100% | | | |
| 93 | H: 33.3% | N: 33.3% | S: 33.3% | | | H: 33.3% | N: 33.3% | S: 33.3% | |
| 94 | S: 50% | Y: 50% | | | | S: 50% | Y: 50% | | |
| 95 | P: 100% | | | | | P: 100% | | | |
| 96 | L: 50% | Y: 50% | | | | L: 50% | Y: 50% | | |

("POSITION" indicates Kabat numbering)

TABLE 8

| CDR | POSITION | AMINO ACID | | | | |
|---|---|---|---|---|---|---|
| CDR1 | 28 | S: 100% | | | | |
| | 29 | I: 100% | | | | |
| | 30 | H: 30% | N: 10% | S: 50% | R: 10% | |
| | 31 | N: 35% | S: 65% | | | |
| | 32 | H: 40% | N: 20% | Y: 40% | | |
| | 33 | L: 100% | | | | |
| | 34 | A: 70% | N: 30% | | | |
| CDR2 | 50 | A: 25% | D: 15% | G: 25% | H: 30% | K: 5% |
| | 51 | A: 100% | | | | |
| | 52 | S: 100% | | | | |
| | 53 | H: 30% | K: 10% | N: 15% | S: 45% | |
| | 54 | L: 100% | | | | |
| | 55 | Q: 100% | | | | |
| | 56 | S: 100% | | | | |
| CDR3 | 90 | Q: 100% | | | | |
| | 91 | H: 30% | S: 15% | R: 10% | Y: 45% | |
| | 92 | G: 20% | H: 30% | N: 20% | S: 15% | Y: 15% |
| | 93 | H: 30% | N: 25% | S: 45% | | |
| | 94 | S: 50% | Y: 50% | | | |
| | 95 | P: 100% | | | | |
| | 96 | L: 50% | Y: 50% | | | |

("POSITION" indicates Kabat numbering)

Any amino acid residues may be suitably used as an amino acid residue that changes the antigen-binding activity according to the hydrogen ion concentration. Specifically, such amino acid residues include those with a side-chain pKa of 4.0 to 8.0. Such electron-donating amino acids preferably include, for example, native amino acids such as histidine and glutamic acid, and unnatural amino acids such as histidine analogs (US20090035836), m-N02-Tyr (pKa 7.45), 3,5-Br2-Tyr (pKa 7.21), and 3,5-I2-Tyr (pKa 7.38) (Bioorg. Med. Chem. (2003) 11 (17), 3761-2768). The amino acid residues particularly preferably include, for example, those with a side-chain pKa of 6.0 to 7.0. Such electron-donating amino acids preferably include, for example, histidine.

Furthermore, in one embodiment of the present invention, the ion concentration refers to a metal ion concentration.

"Metal ions" refer to ions of group I elements except hydrogen such as alkaline metals and copper group elements, group II elements such as alkaline earth metals and zinc group elements, group III elements except boron, group IV elements except carbon and silicon, group VIII elements such as iron group and platinum group elements, elements belonging to subgroup A of groups V, VI, and VII, and metal elements such as antimony, bismuth, and polonium. Metal atoms have the property of releasing valence electrons to become cations. This is referred to as ionization tendency. Metals with strong ionization tendency are deemed to be chemically active.

In the present invention, preferred metal ions include, for example, calcium ion. Calcium ion is involved in modulation of many biological phenomena, including contraction of muscles such as skeletal, smooth, and cardiac muscles; activation of movement, phagocytosis, and the like of leukocytes; activation of shape change, secretion, and the like of platelets; activation of lymphocytes; activation of mast cells including secretion of histamine; cell responses mediated by catecholamine a receptor or acetylcholine receptor; exocytosis; release of transmitter substances from neuron terminals; and axoplasmic flow in neurons. Known intracellular calcium ion receptors include troponin C, calmodulin, parvalbumin, and myosin light chain, which have several calcium ion-binding sites and are believed to be derived from a common origin in terms of molecular evolution. There are also many known calcium-binding motifs. Such well-known motifs include, for example, cadherin domains, EF-hand of calmodulin, C2 domain of Protein kinase C, Gla domain of blood coagulation protein Factor IX, C-type lectins of acyaroglycoprotein receptor and mannose-binding receptor, A domains of LDL receptors, annexin, thrombospondin type 3 domain, and EGF-like domains.

In the present invention, when the metal ion is calcium ion, it is desirable that the antigen-binding activity is lower under a low calcium ion concentration condition than under a high calcium ion concentration condition.

Meanwhile, the intracellular calcium ion concentration is lower than the extracellular calcium ion concentration. Conversely, the extracellular calcium ion concentration is higher than the intracellular calcium ion concentration. In the present invention, the low calcium ion concentration is preferably 0.1 μM to 30 μM, more preferably 0.5 μM to 10 μM, and particularly preferably 1 μM to 5 μM which is close to the calcium ion concentration in the early endosome in vivo. Meanwhile, in the present invention, the high calcium ion concentration is preferably 100 μM to 10 mM, more preferably 200 μM to 5 mM, and particularly preferably 0.5 mM to 2.5 mM which is close to the calcium ion concentration in plasma (in blood). In the present invention, it is preferable that the low calcium ion concentration is the calcium ion concentration in endosomes, and the high calcium ion concentration is the calcium ion concentration in plasma.

When the level of antigen-binding activity is compared between low and high calcium ion concentrations, it is preferable that the binding of antigen-binding domains of the present invention is stronger at a high calcium ion concentration than at a low calcium ion concentration. In other words, it is preferable that the antigen-binding activity of antigen-binding domains of the present invention is lower at a low calcium ion concentration than at a high calcium ion concentration.

When the level of binding activity is expressed with the dissociation constant (KD), the value of KD (low calcium ion concentration)/KD (high calcium ion concentration) is greater than 1, preferably 2 or more, still more preferably 10 or more, and yet more preferably 40 or more. The upper limit of the value of KD (low calcium ion concentration)/KD (high calcium ion concentration) is not particularly limited, and may be any value such as 100, 400, 1000, or 10000, as long as it can be produced with the techniques of skilled artisans. It is possible to use the dissociation rate constant (kd) instead of KD. When it is difficult to calculate the KD value, the activity may be assessed based on the level of binding response in a BIACORE™ system when analytes are passed at the same concentration. When antigens are passed over a chip immobilized with antigen-binding molecules of the present invention, the binding response at a low calcium concentration is preferably ½ or less of the binding response at a high calcium concentration, more preferably ⅓ or less, still more preferably ⅕ or less, and particularly preferably 1/10 or less.

It is known that in general the in vivo extracellular calcium ion concentration (for example, in plasma) is high, and the intracellular calcium ion concentration (for example, in the endosome) is low. Thus, in the present invention, it is preferable that the extracellular condition is a high calcium ion concentration, and the intracellular condition is a low calcium ion concentration.

When the property that the antigen-binding activity is lower under an intracellular calcium ion concentration condition than under an extracellular calcium ion concentration condition is conferred to the antigen-binding domain of antigen-binding molecules of the present invention, antigens that have bound to antigen-binding molecule of the present invention outside of the cell dissociate from the antigen-binding molecule of the present invention inside the cell, thereby enhancing antigen incorporation into the cell from the outside of the cell. Such antigen-binding molecules, when administered to the living body, can reduce antigen concentration in plasma and reduce the physiological activity of antigens in vivo. Thus, antigen-binding molecules of the present invention are useful.

Methods of screening for antigen-binding domains or antigen-binding molecules having a lower antigen-binding activity under a low calcium ion concentration condition than under a high calcium ion concentration condition include, for example, the method described in WO2012/073992 (for example, paragraphs 0200-0213).

Methods for conferring antigen-binding domains of the present invention with the property of binding more weakly to antigens under a low calcium ion concentration condition than under a high calcium ion concentration condition are not particularly limited, and may be carried out by any methods. Specifically, the methods are described in Japanese Patent Application No. 2011-218006 and include, for example, methods for substituting at least one amino acid residue in an antigen-binding domain with an amino acid residue having metal chelating activity, and/or inserting into an antigen-binding domain at least one amino acid residue having metal chelating activity. Antigen-binding molecules of the present invention in which at least one amino acid residue of the antigen-binding domain has been substituted with an amino acid residue having metal chelating activity and/or at least one amino acid residue having metal chelating activity has been inserted into the antigen-binding domain are a preferred embodiment of antigen-binding molecules of the present invention. Amino acid residues having metal chelating activity preferably include, for example, serine, threonine, asparagine, glutamine, aspartic acid, and glutamic acid.

Furthermore, amino acid residues that change the antigen-binding activity of antigen-binding domains according to the calcium ion concentration preferably include, for example, amino acid residues that form a calcium-binding motif. Calcium-binding motifs are well known to those skilled in the art, and have been described in detail (for example, Springer et al., (Cell (2000) 102, 275-277); Kawasaki and Kretsinger (Protein Prof (1995) 2, 305-490); Moncrief et al., (J. Mol. Evol. (1990) 30, 522-562); Chauvaux et al., (Biochem. J. (1990) 265, 261-265); Bairoch and Cox (FEBS Lett. (1990) 269, 454-456); Davis (New Biol. (1990) 2, 410-419); Schaefer et al., (Genomics (1995) 25, 638 to 643); Economou et al., (EMBO J. (1990) 9, 349-354); Wurzburg et al., (Structure. (2006) 14, 6, 1049-1058)). EF hand in troponin C, calmodulin, parvalbumin, and myosin light chain; C2 domain in protein kinase C; Gla domain in blood coagulation protein factor IX; C-type lectin of acyaroglycoprotein receptor and mannose-binding receptor, ASGPR, CD23, and DC-SIGN; A domain in LDL receptor; annexin domain; cadherin domain; thrombospondin type 3 domain; and EGF-like domain are preferably used as calcium-binding motifs. In addition to the above, the calcium-binding motif in the antigen-binding domain of SEQ ID NO: 57 is preferably used.

Antigen-binding domains of the present invention can contain amino acid residues that change the antigen-binding activity according to the calcium ion concentration, such as the above-described amino acid residues with metal chelating activity and amino acid residues that form a calcium-binding motif. The location of such amino acid residues in the antigen-binding domain is not particularly limited, and they may be located at any position as long as the antigen-binding activity changes according to the calcium ion concentration. Meanwhile, such amino acid residues may be contained alone or in combination of two or more, as long as the antigen-binding activity changes according to the calcium ion concentration. The amino acid residues preferably include, for example, serine, threonine, asparagine, glutamine, aspartic acid, and glutamic acid. When an antigen-binding domain is an antibody variable region, the amino acid residues may be contained in the heavy chain variable region and/or the light chain variable region. In a preferred embodiment, the amino acid residues may be contained in the CDR3 of the heavy chain variable region, more preferably at positions 95, 96, 100a, and/or 101 according to Kabat numbering in the CDR3 of the heavy chain variable region.

In another preferred embodiment, the amino acid residues may be contained in the CDR1 of the light chain variable region, more preferably at positions 30, 31, and/or 32 according to Kabat numbering in the CDR1 of the light chain variable region. In still another preferred embodiment, the amino acid residues may be contained in the CDR2 of the light chain variable region, more preferably at position 50 according to Kabat numbering in the CDR2 of the light chain variable region. In yet another preferred embodiment, the amino acid residues may be contained in the CDR3 of the light chain variable region, more preferably at position 92 according to Kabat numbering in the CDR3 of the light chain variable region.

Furthermore, it is possible to combine the above-described embodiments. For example, the amino acid residues may be contained in two or three CDRs selected from the CDR1, CDR2, and CDR3 of the light chain variable region, more preferably at any one or more of positions 30, 31, 32, 50, and/or 92 according to Kabat numbering in the light chain variable region.

A large number of antigen-binding domains that have different sequences while sharing as a common structure the above-described amino acid residues that change the antigen-biding activity according to the calcium ion concentration are prepared as a library. The library can be screened to efficiently obtain antigen-binding domains with binding activity to a desired antigen, in which their antigen-binding activity changes according to the calcium ion concentration.

When the antigen-binding domain is an antibody variable region, in a particularly preferred embodiment, it is desirable that the framework sequences of the light chain and/or heavy chain variable region have a human germ-line framework sequence. Thus, in an embodiment of the present invention, when the framework sequence is completely a human sequence, the antigen-binding domain of the present invention, when administered to humans (for example, to treat diseases), is expected to induce little or no immunogenic response. In this context, herein, "having a germ-line sequence" means that a portion of the framework sequence of the present invention is identical to a portion of a human germ-line framework sequence. For example, even when an antigen-binding domain of the present invention has a sequence resulting from combining multiple different human germ-line framework sequences, it is an antigen-binding domain of the present invention "having a germ-line sequence".

Without being bound by a particular theory, one reason why the use of a germ-line sequence is expected to result in the elimination of adverse immune responses in most individuals is believed to be as follows. As a result of the process of affinity maturation during normal immune responses, somatic cell mutations occur frequently in the variable region of immunoglobulins. Such mutations also affect residues in the framework region while they primarily occur around CDRs of which sequences are hypervariable. There is no such framework mutation in the germ line sequences, and thus they can be immunogenic in patients. On the other hand, the normal human population is exposed to most framework sequences expressed from the germ line genes. As a result of immunotolerance, the germ line sequences are expected to be only weakly immunogenic or nonimmunogenic in patients. To maximize the possibility of immunotolerance, genes encoding the variable region can be selected from a group of functional germ-line genes (which are expressed normally).

The framework preferably includes, for example, currently known framework region sequences that are completely of the human type. The sequences of such framework regions are shown, for example, on the websites of V-Base (world wide web at vbase.mrc-cpe.cam.ac.uk/). Those framework region sequences can be appropriately used as a germ line sequence contained in an antigen-binding domain of the present invention. The germ line sequences may be categorized according to their similarity (Tomlinson et al. (J. Mol. Biol. (1992) 227, 776-798); Williams and Winter (Eur. J. Immunol. (1993) 23, 1456-1461); Cox et al. (Nat. Genetics (1994) 7, 162-168)). Appropriate germ line sequences can be selected from Vκ, which is grouped into seven subgroups; Vλ, which is grouped into ten subgroups; and VH, which is grouped into seven subgroups.

Fully human VH sequences preferably include, but are not limited to, for example, VH sequences of subgroup VH1 (for example, VH1-2, VH1-3, VH1-8, VH1-18, VH1-24, VH1-45, VH1-46, VH1-58, and VH1-69);

subgroup VH2 (for example, VH2-5, VH2-26, and VH2-70);

subgroup VH3 (VH3-7, VH3-9, VH3-11, VH3-13, VH3-15, VH3-16, VH3-20, VH3-21, VH3-23, VH3-30, VH3-33, VH3-35, VH3-38, VH3-43, VH3-48, VH3-49, VH3-53, VH3-64, VH3-66, VH3-72, VH3-73, and VH3-74);
subgroup VH4 (VH4-4, VH4-28, VH4-31, VH4-34, VH4-39, VH4-59, and VH4-61);
subgroup VH5 (VH5-51);
subgroup VH6 (VH6-1); and
subgroup VH7 (VH7-4 and VH7-81).

These are also described in known documents (Matsuda et al. (J. Exp. Med. (1998) 188, 1973-1975)) and such, and thus persons skilled in the art can appropriately design antigen-binding domains of the present invention based on the information of these sequences. It is also preferable to use other fully human framework regions or framework sub-regions.

Fully human VK sequences preferably include, but are not limited to, for example: A20, A30, L1, L4, L5, L8, L9, L11, L12, L14, L15, L18, L19, L22, L23, L24, O2, O4, O8, O12, O014, and O18, grouped into subgroup Vk1;
A1, A2, A3, A5, A7, A17, A18, A19, A23, 01, and 011, grouped into subgroup Vk2;
A11, A27, L2, L6, L10, L16, L20, and L25, grouped into subgroup Vk3;
B3, grouped into subgroup Vk4;
B2 (herein also referred to as Vk5-2), grouped into subgroup Vk5; and
A10, A14, and A26, grouped into subgroup VK6
(Kawasaki et al. (Eur. J. Immunol. (2001) 31, 1017-1028); Schable and Zachau (Biol. Chem. Hoppe Seyler (1993) 374, 1001-1022); Brensing-Kuppers et al. (Gene (1997) 191, 173-181)).

Fully human VL sequences preferably include, but are not limited to, for example:
V1-2, V1-3, V1-4, V1-5, V1-7, V1-9, V1-11, V1-13, V1-16, V1-17, V1-18, V1-19, V1-20, and V1-22, grouped into subgroup VL1;
V2-1, V2-6, V2-7, V2-8, V2-11, V2-13, V2-14, V2-15, V2-17, and V2-19, grouped into subgroup VL1;
V3-2, V3-3, and V3-4, grouped into subgroup VL3;
V4-1, V4-2, V4-3, V4-4, and V4-6, grouped into subgroup VL4; and
V5-1, V5-2, V5-4, and V5-6, grouped into subgroup VL5 (Kawasaki et al. (Genome Res. (1997) 7, 250-261)).

Normally, these framework sequences are different from one another at one or more amino acid residues. These framework sequences can be used in combination with at least one amino acid residue that alters the antigen-binding activity depending on ion concentrations described above. Other examples of frameworks include, but are not limited to, for example, KOL, NEWM, REI, EU, TUR, TEI, LAY, and POM (for example, Kabat et al. (1991) supra; Wu et al. (J. Exp. Med. (1970) 132, 211-250)).

For example, a light chain variable region that contains in its framework sequence at least one amino acid residue that changes the antigen-binding activity according to the calcium ion concentration can be combined with a heavy chain variable region containing a random sequence to construct a library containing a number of antigen-binding domains that have different sequences while sharing as a common structure the amino acid residues that change the antigen-binding activity according to the calcium ion concentration. Without being particularly limited thereto, a preferred example includes a library of antigen-binding domains resulting from combining the heavy chain variable region containing a random sequence with the light chain variable region that belongs to the Vk5-2 family such as SEQ ID NO: 57 (Vk5-2). Preferred examples also include a library of antigen-binding domains resulting from combining the heavy chain variable region containing a random sequence with the sequence of a light chain variable region in which at least one amino acid residue that changes the antigen-binding activity according to the calcium ion concentration has been substituted for specific amino acid residues in a germ-line sequence such as SEQ ID NO: 58 (Vk1), SEQ ID NO: 59 (Vk2), SEQ ID NO: 60 (Vk3), and SEQ ID NO: 61 (Vk4).

Furthermore, it is possible to design in such a way that flexible residues are contained in the light chain variable region of which framework sequences contain at least one amino acid residue that changes the antigen-binding activity according to the calcium ion concentration. Such flexible residues are not particularly limited in number and position as long as the antigen-binding activity of antigen-binding domains of the present invention changes according to the ion concentration. Specifically, the CDR and/or FR sequences of the heavy chain variable region and/or the light chain variable region may contain one or more flexible residues. Without being particularly limited thereto, flexible residues that are introduced into the light chain variable region of SEQ ID NO: 57 (Vk5-2) include, for example, amino acid residues shown in Tables 9 and 10.

TABLE 9

| CDR | Kabat NUMBERING | 70% AMINO ACID OF THE TOTAL | | | | |
|---|---|---|---|---|---|---|
| CDR1 | 28 | S: 100% | | | | |
| | 29 | I: 100% | | | | |
| | 30 | E: 72% | N: 14% | S: 14% | | |
| | 31 | D: 100% | | | | |
| | 32 | D: 100% | | | | |
| | 33 | L: 100% | | | | |
| | 34 | A: 70% | N: 30% | | | |
| CDR2 | 50 | E: 100% | | | | |
| | 51 | A: 100% | | | | |
| | 52 | S: 100% | | | | |
| | 53 | H: 5% | N: 25% | S: 45% | T: 25% | |
| | 54 | L: 100% | | | | |
| | 55 | Q: 100% | | | | |
| | 56 | S: 100% | | | | |
| CDR3 | 90 | Q: 100% | | | | |
| | 91 | H: 25% | S: 15% | R: 15% | Y: 45% | |
| | 92 | D: 80% | N: 10% | S: 10% | | |
| | 93 | D: 5% | G: 10% | N: 25% | S: 50% | R: 10% |
| | 94 | S: 50% | Y: 50% | | | |
| | 95 | P: 100% | | | | |
| | 96 | L: 50% | Y: 50% | | | |

TABLE 10

| CDR | Kabat NUMBERING | 30% AMINO ACID OF THE TOTAL | | | |
|---|---|---|---|---|---|
| CDR1 | 28 | S: 100% | | | |
| | 29 | I: 100% | | | |
| | 30 | E: 83% | S: 17% | | |
| | 31 | D: 100% | | | |
| | 32 | D: 100% | | | |
| | 33 | L: 100% | | | |
| | 34 | A: 70% | N: 30% | | |
| CDR2 | 50 | H: 100% | | | |
| | 51 | A: 100% | | | |
| | 52 | S: 100% | | | |
| | 53 | H: 5% | N: 25% | S: 45% | T: 25% |
| | 54 | L: 100% | | | |
| | 55 | Q: 100% | | | |
| | 56 | S: 100% | | | |

TABLE 10-continued

| CDR | Kabat NUMBERING | 30% AMINO ACID OF THE TOTAL | | | | |
|---|---|---|---|---|---|---|
| CDR3 | 90 | Q: 100% | | | | |
| | 91 | H: 25% | S: 15% | R: 15% | Y: 45% | |
| | 92 | D: 80% | N: 10% | S: 10% | | |
| | 93 | D: 5% | G: 10% | N: 25% | S: 50% | R: 10% |
| | 94 | S: 50% | Y: 50% | | | |
| | 95 | P: 100% | | | | |
| | 96 | L: 50% | Y: 50% | | | |

Herein, flexible residue refers to an amino acid residue that is present at a position where the type of amino acid varies greatly in the light chain variable regions and heavy chain variable regions when comparing the amino acid sequences of known and/or native antibodies or antigen-binding domains. The positions that vary greatly are generally present in the CDR regions. For example, the data provided as Kabat, Sequences of Proteins of Immunological Interest (National Institute of Health Bethesda Md.) (1987 and 1991) is useful to determine the positions that vary greatly in known and/or native antibodies. Furthermore, various databases on the Internet (world wide web at vbase.mrc-cpe.cam.ac.ukl, world wide web at bioinf.org.uklabs/index.html) provide the collected sequences of many human light chains and heavy chains. The sequence information is useful for determining the positions that vary greatly in the present invention. In the present invention, when at a certain amino acid position, the number of possible variations of amino acids is preferably about 2 to 20, preferably about 3 to 19, preferably about 4 to 18, preferably 5 to 17, preferably 6 to 16, preferably 7 to 15, preferably 8 to 14, preferably 9 to 13, and preferably 10 to 12, such a position is defined as varying greatly. Meanwhile, at a certain position, the number of possible variations of amino acids can be preferably at least about 2, preferably at least about 4, preferably at least about 6, preferably at least about 8, preferably at least about 10, and preferably at least about 12.

In order to produce an antigen-binding domain, when a light chain variable region containing at least one amino acid residue that changes the antigen-binding activity according to the calcium ion concentration is combined with a heavy chain variable region containing a random sequence, it is possible to design it in such a way that its light chain variable region further contains flexible residues. The flexible residues are not particularly limited in number and position as long as the antigen-binding activity changes according to the calcium ion concentration. Specifically, the light chain CDR sequences and/or FR sequences may contain one or more flexible residues. Without being particularly limited, flexible residues that are introduced into the light chain variable region include, for example, amino acid residues shown in Tables 9 and 10.

In the present invention, known methods can be appropriately combined to prepare as a randomized variable region library the heavy chain and/or the light chain variable region that have a random sequence. In an embodiment, immune libraries constructed based on antibody genes derived from the lymphocytes of animals immunized with a specific antigen, humans whose antibody titer in blood has been increased due to vaccination, patients with infection, cancer patients, autoimmune disease patients, and such may be suitably used as a randomized variable region library.

In another embodiment, a synthetic library in which arbitrary CDR sequences of V genes from genomic DNA or functional reshaped V genes are replaced with a set of synthetic oligonucleotides encoding codon sets of an appropriate length can also be preferably used as a randomized variable region library. In this case, it is possible to replace CDR3 sequences alone, since sequence polymorphism is observed in the CDR3 of the heavy chain variable region. When diversifying the amino acid sequence of an antigen-binding molecule, it is preferable to generate variations in the amino acid residues at surface-exposed positions in the antigen-binding molecule. Surface-exposed position refers to a position where surface exposure and/or contact with an antigen is determined to be possible, based on the conformation, structural ensemble, and/or modeled structure of an antigen-binding molecule. In the variable region, such positions are generally the CDRs. Surface-exposed positions can be determined from the coordinates of a three dimensional model of the antigen-binding molecule using computer programs such as the InsightII program (Accelrys). Surface-exposed positions can also be determined using algorithms known in the art (for example, Lee and Richards (J. Mol. Biol. (1971) 55, 379-400); Connolly (J. Appl. Cryst. (1983) 16, 548-558)). Alternatively, the surface-exposed positions can be determined based on the information on the three dimensional structure obtained from antibodies and software suitable for protein modeling. Software that can be used for this purpose preferably includes the SYBYL® Biopolymer Module software (Tripos Associates). When the algorithm requires the input size parameter from the user, the "size" of probe for use in computation is generally set to be about 1.4 Å or less in radius. Furthermore, a method for determining the surface-exposed region or area using PC software is described by Pacios (Comput. Chem. (1994) 18 (4), 377-386; and J. Mol. Model. (1995) 1, 46-53).

In still another embodiment, a naive library constructed from antibody genes derived from lymphocytes of healthy persons can also be particularly preferably used as a randomized variable region library (Gejima et al., (Human Antibodies (2002) 11, 121-129); and Cardoso et al., (Scand. J. Immunol. (2000) 51, 337-344)). Much variation is expected in the repertoire of antibody sequences derived from lymphocytes of healthy persons, because it is unbiased. In the present invention, an amino acid sequence containing a naive sequence refers to an amino acid sequence obtained from such a naive library.

In an embodiment of the present invention, antigen-binding domains of the present invention can be obtained from a library that contains a number of antigen-binding domains with sequences different from one another, which is constructed by combining a light chain variable region having a random sequence with a heavy chain variable region containing at least one amino acid residue that changes the antigen-binding activity according to the calcium ion concentration. Without being particularly limited thereto, the libraries preferably include, for example, libraries of antigen-binding domains in which the heavy chain variable region of SEQ ID NO: 117 (6RL #9-IgG1) or SEQ ID NO: 119 (6KC4-1 #85-IgG1) is combined with a light chain variable region having a random sequence. Alternatively, a light chain variable region having a germ-line sequence may be suitably selected and used instead of the light chain variable region having a random sequence. Without being particularly limited thereto, the libraries preferably include, for example, libraries of antigen-binding domains in which the heavy chain variable region of SEQ ID NO: 117 (6RL #9-IgG1) or SEQ ID NO: 119 (6KC4-1 #85-IgG1) is combined with the light chain variable region having a germ-line sequence.

Furthermore, the above-described heavy chain variable region containing at least one amino acid residue that changes the antigen-binding activity according to the calcium ion concentration can be designed in such a way that it additionally contains flexible residues. The flexible residues are not particularly limited in number and position, as long as the antigen-binding activity of antigen-binding domains of the present invention changes according to the calcium ion concentration. Specifically, the CDR sequences and/or FR sequences of the heavy chain and/or the light chain may contain one or more flexible residues. Without being particularly limited thereto, flexible residues that are introduced into the heavy chain variable region of SEQ ID NO: 117 (6RL #9-IgG1) include, for example, the entire amino acid residues of the heavy chain CDR1 and the heavy chain CDR2, and amino acid residues of the heavy chain CDR3 except for at positions 95, 96, and/or 100a. Meanwhile, flexible residues that are introduced into the heavy chain variable region of SEQ ID NO: 119 (6KC4-1 #85-IgG1) include, for example, the entire amino acid residues of the heavy chain CDR1 and the heavy chain CDR2, and amino acid residues of the heavy chain CDR3 except for at positions 95 and/or 101.

Alternatively, a library that contains multiple antigen-binding domains with sequences different from one another can be constructed by combining a light chain variable region having a random sequence or a light chain variable region having a germ-line sequence with the above-described heavy chain variable region introduced with at least one amino acid residue that changes the antigen-binding activity according to the calcium ion concentration. The libraries preferably include, for example, libraries of antigen-binding domains in which a light chain variable region having a random sequence or a light chain variable region having a germ-line sequence is combined with a heavy chain variable region in which specific amino acid residues in the heavy chain variable region are substituted with at least one amino acid residue that changes the antigen-binding activity according to the calcium ion concentration. Without being particularly limited thereto, the amino acid residues include, for example, amino acid residues of the heavy chain CDR1, amino acid residues of the heavy chain CDR2, and the amino acids at positions 95, 96, 100a, and/or 101 in the heavy chain CDR3. As long as the amino acid residues form a calcium-binding motif and/or the antigen-binding activity changes according to the calcium ion concentration, the amino acid residues may be contained alone or in combination of two or more.

Even when the above-described heavy chain variable region which is introduced with at least one amino acid residue that changes the antigen-binding activity according to the calcium ion concentration is combined with a light chain variable region having a random sequence or a light chain variable region having a germ-line sequence, the heavy chain variable region can be designed in such a way that it also contains flexible residues. The flexible residues are not particularly limited in number and position, as long as the antigen-binding activity of antigen-binding domains of the present invention changes according to the calcium ion concentration. Specifically, the CDR sequences and/or FR sequences of the heavy chain may contain one or more flexible residues. Alternatively, amino acid sequences of the CDR1, CDR2, and/or CDR3 in the heavy chain variable region other than the amino acid residues that change the antigen-binding activity according to the calcium ion concentration may be randomized sequences, as in the above-described synthetic libraries. Without being particularly limited, when used as the light chain variable region, germ-line sequences preferably include, for example, those of SEQ ID NO: 58 (Vk1), SEQ ID NO: 59 (Vk2), SEQ ID NO: 60 (Vk3), and SEQ ID NO: 61 (Vk4).

In the present invention, known methods such as site-directed mutagenesis (Kunkel et al., (Proc. Natl. Acad. Sci. USA (1985) 82, 488-492)) and overlap extension PCR can be appropriately employed to modify amino acids. Furthermore, various known methods can also be used as a method for modifying amino acids into those other than natural amino acids (Annu. Rev. Biophys. Biomol. Struct. (2006) 35, 225-249; Proc. Natl. Acad. Sci. U.S.A. (2003) 100 (11), 6353-6357). For example, one may appropriately use a cell-free translation system (Clover Direct™ (Protein Express)) containing tRNAs linked with an unnatural amino acid on amber suppressor tRNAs, which are complementary to the UAG codon (amber codon) which is a stop codon.

KD values for antigen-binding domains of the present invention can be measured by methods known to those skilled in the art, for example, using a BIACORE™ system (GE healthcare), Scatchard plot, or flow cytometer. Specifically, in the case of a BIACORE™ system, antigen-binding molecules containing an antigen-binding domain of the present invention are immobilized on a chip and an antigen is passed as an analyte to determine KD. The measurement can be carried out under an acidic pH range condition and under a neutral pH range condition to calculate the value of KD (acidic pH)/KD (neutral pH). Meanwhile, the measurement can be carried out under a low calcium ion concentration condition and under a high calcium ion concentration condition to calculate the value of KD (low calcium ion concentration)/KD (high calcium ion concentration).

Antigen-binding domains of the present invention may exhibit, under different types of conditions at the same time, the property that the antigen-binding activity changes according to the ion concentration. For example, antigen-binding domains of the present invention may have the property that their antigen-binding activity is lower under an acidic pH range condition than under a neutral pH range condition, and is lower under a low calcium ion concentration condition than under a high calcium ion concentration condition.

Specifically, antigens of the present invention having two or more types of physiological activities include, for example:

activin, activin A, activin AB, activin B, activin C, activin RIA, activin RIA, Activin receptor-like kinase (ALK)-2, activin RIB ALK-4, activin RIIA, activin RIIB, adiponectin, acidic fibroblast growth factor (aFGF), Advanced glycation end products (AGE), allergen, amyloid β, amyloid immunoglobulin heavy chain variable region, amyloid immunoglobulin light chain variable region, anti-Id, antithrombin III, anthrax, apo A1, apo-serum amyloid A (apo-SAA), β-2-microglobulin, basic fibroblast growth factor (bFGF), B-lymphocyte stimulator (BLyS), BMP, BMP-2 (BMP-2a), BMP-3 (osteogenin), BMP-4 (BMP-2b), BMP-5, BMP-6 (Vg-related (Vgr)-1), BMP-7 (osteogenic protein (OP)-1), BMP-8 (BMP-8a), C10, C1 inhibitory factor, Complement component (C)1q, C3, C3a, C4, C5, C5a (complement 5a), cathepsin A, cathepsin B, cathepsin C/Dipeptidyl-peptidase I (DPPI), cathepsin D, cathepsin E, cathepsin H, cathepsin L, cathepsin O, cathepsin S, cathepsin V, cathepsin X/Z/P, Chemokine (C—C motif) ligand (CCL), CCL1/I-309, CCL11/eotaxin, CCL12/Monocyte chemotactic protein 5

(MCP-5), CCL13/MCP-4, CCL14/Hemofiltrate CC Chemokine-1 (HCC-1), CCL15/HCC-2, CCL16/HCC-4, CCL17/Thymus- and activation-regulated chemokine (TARC), CCL18/Pulmonary- and activation-regulated chemokine (PARC), CCL19/EBI1 ligand chemokine (ELC), CCL2/MCP-1, CCL20/Macrophage inflammatory protein-3 alpha (MIP-3-α), CCL21/secondary lymphoid tissue chemokine (SLC), CCL22/Macrophage-derived chemokine (MDC), CCL23/Myeloid progenitor inhibitory factor 1 (MPIF-1), CCL24/eotaxin-2, CCL25/Thymus-expressed chemokine (TECK), CCL26/eotaxin-3, CCL27/Cutaneous T cell-attracting chemokine (CTACK), CCL28/Mucosae-associated epithelial chemokine (MEC), CCL3/Macrophage inflammatory protein-1 alpha (MIP-1-α), Chemokine (C—C motif) ligand 3-like 1 (CCL3L1)/LD-78-β, CCL4/Macrophage inflammatory protein-1 beta (MIP-1-β), CCL5/Regulated on activation, normal T cell expressed and secreted (RANTES), CCL6/C10, CCL7/MCP-3, CCL8/MCP-2, CCL9/10/Macrophage inflammatory protein-1 gamma (MIP-1-γ), *Clostridium botulinum* toxin, *Clostridium difficile* toxin, *Clostridium perfringens* toxin, connective tissue growth factor (CTGF), Cytotoxic T-lymphocyte-associated protein 4 (CTLA-4), C-X3-C Motif Chemokine Ligand 1 (CX3CL1)/fractalkine, chemokine (C—X—C motif) ligand 1 (CXCL), CXCL1/Growth-regulated oncogene alpha (Gro-α), CXCL10, CXCL11/Interferon-inducible T-cell alpha chemoattractant (1-TAC), CXCL12/stromal cell-derived factor 1-alpha/beta (SDF-1-α/β), CXCL13/B cell-attracting chemokine 1 (BCA-1), CXCL14/Breast and kidney-expressed chemokine (BRAK), CXCL15/lungkine, CXCL16, CXCL16, CXCL2/Growth-regulated oncogene beta (Gro-β), CXCL3/Growth-regulated oncogene gamma (Gro-γ), CXCL3, CXCL4/Platelet factor 4 (PF4), CXCL5/epithelial-derived neutrophil-activating peptide 78 (ENA-78), CXCL6/Granulocyte chemotactic protein-2 (GCP-2), CXCL7/Neutrophil Activating Peptide 2 (NAP-2), CXCL8/Interleukin 8 (IL-8), CXCL9/Monokine induced by gamma interferon (Mig), CXCL10/Interferon gamma-induced protein 10 (IP-10), Dendritic Cell-Specific Intercellular adhesion molecule-3-Grabbing Non-integrin (DC-SIGN), digoxin, Epidermal Growth Factor (EGF) like domain containing protein 7, endotoxin, Respiratory syncytial virus (RSV) F protein, F10, F11, F12, F13, F5, F9, factor Ia, factor IX, factor Xa, factor VII, factor VIII, factor VIIc, FGF, FGF-19, FGF-2, FGF-2 receptor, FGF-3, FGF-8, fibronectin, Growth Regulated Protein/Melanoma Growth Stimulatory Activity (GRO/MGSA), GRO-β, GRO-γ, *Helicobacter pylon* (*H. pylon*), hapten ((NP-epsilon-aminocaproic acid (NP-cap) or NIP-ε-aminocaproic acid (NIP-cap)), Heparin-binding EGF-like growth factor (HB-EGF), Human cytomegalovirus (HCMV) gB envelope glycoprotein, Hep B gp120, *Bacillus anthracis* protective antigen, hepatitis C virus E2 glycoprotein, hepatitis E, hepcidin, herpes simplex virus (HSV) gB glycoprotein, Human Immunodeficiency Virus (HIV) envelope proteins such as GP120, HIV gp 120 V3 loop, Human leukocyte antigen (HLA), Human Leukocyte Antigen—DR isotype (HLA-DR), high mobility group box 1 (HMGB1), Heat shock protein 47 (HSP47), Heat shock protein 90 (Hsp90), HSV gD glycoprotein, human cytomegalovirus (HCMV), human serum albumin, human tissue plasminogen activator (t-PA), Interferon alpha (IFN-α), Interferon beta (IFN-β), Interferon gamma (IFN-γ), Immunoglobulin E (IgE), Insulin-like growth factor (IGF), immunoglobulin immune complex, immunoglobulin, influenza, inhibin, inhibin α, inhibin β, laminin 5, latency-associated peptide, latent TGF-1, latent TGF-1 bp1, Lipopolysaccharide binding protein (LBP), Low-density lipoprotein (LDL), leptin, Lewis-Y antigen, Lewis-Y-related antigen, lymphocyte function-associated antigen (LFA)-1, LFA-3, lipoproteins, L-selectin, type 3 nonstructural protein of hepatitis C virus (NS3), oncostatin M, osteopontin, oxidized LDL, poly glycol chains of different size (for example, Polyethylene glycol (PEG)-20, PEG-30, and PEG40), prekallikrein, prion protein, procalcitonin, proinsulin, prolactin, proprotein convertase PC9, prorelaxin, respiratory syncytial virus (RSV) F, rheumatoid factor, RSV Fgp, Sclerostin, serum amyloid P, serum albumin, Shiga like-toxin II, syndecan-1, tenascin, TGF, TGF-α, TGF-β, TGF-β Pan Specific, TGF-β1, TGF-β2, TGF-β, TGF-β4, TGF-β5, TGF-I, thrombin, thrombopoietin (TPO), thyroxine binding globulin, TNF-α, TNF-β, TNIL-I, toxic metabolite, VEGF, viral antigens, and von Willebrand factor (vWF). Particularly preferred examples include HMGB1, CTGF, and IgE. These antigens are preferably derived from mammals, particularly preferably from humans.

The gene and amino acid sequences of human HMGB1 have been deposited under GenBank accession number NM 002128 (SEQ ID NO: 22) and NP_002119 (SEQ ID NO: 23), respectively. In addition to human, the gene and amino acid sequences of mouse HMGB1 have been deposited under GenBank accession number NM 010439 (SEQ ID NO: 24) and NP_034569 (SEQ ID NO: 25), respectively; and the gene and amino acid sequences of rat HMGB1 have been deposited under GenBank accession number NM_012963 (SEQ ID NO: 26) and NP_037095 (SEQ ID NO: 27), respectively.

The gene and amino acid sequences of human CTGF have been deposited under GenBank accession number NM_001901 (SEQ ID NO: 28) and NP_001892 (SEQ ID NO: 29), respectively. In addition to human, the gene and amino acid sequences of mouse CTGF have been deposited under GenBank accession number NM_010217 (SEQ ID NO: 30) and NP_034347 (SEQ ID NO: 31), respectively; and the gene and amino acid sequences of rat CTGF have been deposited under GenBank accession number NM_022266 (SEQ ID NO: 32) and NP_071602 (SEQ ID NO: 33), respectively.

The gene sequences of the constant region of human IgE and mouse IgE have been deposited under GenBank accession number L00022 (SEQ ID NO: 34) and GenBank accession number X01857 (SEQ ID NO: 35), respectively.

Target molecules to which HMGB1 binds include receptor for advanced glycation endproducts (RAGE), Toll-like receptor 4 (TLR4), IL-1 receptor, Toll-like receptor 2 (TLR2), thrombospondin, triggering receptor expressed on myeloid cells-1 (TREM-1), and CD24. Meanwhile, reported substances that enhance the binding between HMGB1 and the above-described target molecules include DNA, RNA, lipopolysaccharide (LPS), interleukin-1IP (IL-1β), chemokine (C—X—C motif) Ligand 12 (CXCL12), and nucleosomes. Preferred target molecules of the present invention include, for example, RAGE and TLR4.

Reported target molecules to which CTGF binds include insulin-like growth factor-1 (IGF-1), insulin-like growth factor-2 (IGF-2), integrin αvβ3, transforming growth factor-β (TGF-β), bone morphogenetic protein-4 (BMP-4), LDL receptor-related protein-1 (LRP-1), vascular endothelial growth factor (VEGF), Wnt, heparan sulfate proteoglycans (HSPG), integrins, LDL receptor-related protein-5 (LRP-5), and LDL receptor-related protein-6 (LRP-6).

Reported target molecules to which IgE binds include FcεRI and FcεRII. These are also preferred examples of a target molecule of the present invention.

The present invention provides polynucleotides encoding antigen-binding molecules of the present invention. Polynucleotides are primarily constituted with DNA, RNA, other nucleotide analogs, and such.

The present invention provides vectors carrying polynucleotides of the present invention. Vectors for use in the present invention are not particularly limited in type, as long as they can stably carry inserted nucleic acids, and various vectors available in the market can be used. Gene cloning vectors include, for example, M13 vectors and pUC vectors. When vectors are used to produce antigen-binding molecules of the present invention, expression vectors are particularly useful. Expression vectors are not particularly limited, as long as they are capable of expressing polypeptides in vitro, in *E. coli*, in cultured cells, or in individual organisms. For example, vectors for in vitro expression include pBEST vectors (Promega); vectors for expression in *E. coli* include pGEX, pET, and pBluescript vectors (Stratagene); vectors for expression in cultured cells include pME18S-FL3 vector (GenBank Accession No. AB009864); vectors for expression in animal cells include pcDNA; and vectors for expression in individual organisms include pME18S vector (Mol Cell Biol. 8: 466-472 (1988)). Polynucleotides of the present invention can be inserted into vectors, for example, using the IN-FUSION™ Advantage PCR Cloning Kit (Clontech).

The present invention provides host cells retaining vectors of the present invention. Host cells that can be used are not particularly limited, and for example, *E. coli* and various animal cells can be suitably used. Host cells can be used, for example, as a production system to produce or express antigen-binding molecules of the present invention. Such production systems include in vitro and in vivo production systems. The in vitro production systems include production systems using eukaryotic cells and those using prokaryotic cells. Eukaryotic cells that can be used as host cells include, for example, animal cells, plant cells, and fungal cells. Animal cells include, for example, mammalian cells, for example, CHO (J. Exp. Med. (1995) 108: 94.0), COS, HEK293, 3T3, myeloma, BHK (baby hamster kidney), HeLa, and Vero; amphibian cells, for example, *Xenopus* oocytes (Valle et al., Nature (1981) 291: 338-340); and insect cells, for example, Sf9, Sf21, and Tn5. CHO-DG44, CHO-DX11B, COS7, HEK293, and BHK are preferably used. CHO is particularly preferable for large-scale expression. Vectors can be introduced into host cells, for example, by using techniques known to those skilled in the art, such as calcium phosphate methods, DEAE-dextran methods, methods using cationic liposome DOTAP (Boehringer-Mannheim), electroporation, lipofection, and microinjection. Alternatively, the FreeStyle™ 293 Expression System (Invitrogen) may be used to accomplish the process from gene introduction to polypeptide expression.

As plant cells, for example, cells derived from *Nicotiana tabacum* and *Lemna minor* are known as a protein production system. Calluses can be cultured from these cells to produce antigen-binding molecules of the present invention. Fungal cells known as a protein expression system include yeast cells, for example, cells of genus *Saccharomyces* such as *Saccharomyces cerevisiae* and *Saccharomyces pombe*; and cells of filamentous fungi, for example, cells of genus *Aspergillus* such as *Aspergillus niger.*

When prokaryotic cells are used, there are production systems that use bacterial cells. Bacterial cells known as a protein production system include, for example, *Streptococcus, Staphylococcus, Escherichia coli, streptomyces*, and *Bacillus subtilis.*

On the other hand, for example, production systems using animals or plants may be used as systems for producing polypeptides in vivo. A polynucleotide of interest is introduced into an animal or plant and the polypeptide is produced in the body of the animal or plant, and then collected. The hosts of the present invention include such animals and plants.

The production system using animals include those using mammals or insects. It is possible to use mammals such as goats, pigs, sheep, mice, and bovines (Vicki Glaser SPECTRUM Biotechnology Applications (1993)). The mammals may be transgenic animals. For example, a polynucleotide encoding an antigen-binding molecule provided by the present invention is prepared as a fusion gene with a gene encoding a polypeptide specifically produced in milk, such as the goat p casein. Next, goat embryos are injected with polynucleotide fragments containing the fusion gene, and then transplanted to female goats. Desired antigen-binding molecules can be obtained from milk produced by the transgenic goats, which are born from the goats that received the embryos, or their offspring. Hormones may be administered as appropriate to increase the volume of milk containing the antigen-binding molecule produced by the transgenic goats (Ebert et al., Bio/Technology (1994) 12: 699-702).

Insects such as silkworms may be used to produce the antigen-binding molecules provided by the present invention. When silkworms are used, baculoviruses carrying a polynucleotide encoding an antigen-binding molecule of interest can be used to infect silkworms, and the antigen-binding molecule of interest can be obtained from their body fluids.

Furthermore, when plants are used to produce the antigen-binding molecules provided by the present invention, for example, tobacco may be used. When tobacco is used, a polynucleotide encoding an antigen-binding molecule of interest is inserted into a plant expression vector, for example, μMON 530, and then the vector is introduced into bacteria, such as *Agrobacterium tumefaciens*. The bacteria are then allowed to infect tobacco such as *Nicotiana tabacum*, and the desired antigen-binding molecules can be collected from their leaves (Ma et al., Eur. J. Immunol. (1994) 24: 131-138). Alternatively, it is possible to infect duckweed (*Lemna minor*) with similar bacteria. After cloning, the desired antigen-binding molecules can be obtained from the duckweed cells (Cox K M et al., Nat. Biotechnol. 2006 December; 24(12): 1591-1597).

The thus obtained antigen-binding molecules may be isolated from the inside or outside (such as the medium and milk) of host cells, and purified as substantially pure and homogenous molecules. The methods for isolating and purifying antigen-binding molecules provided by the present invention are not particularly limited, and isolation and purification methods usually used for polypeptide purification can be used. Isolation and purification may be performed by appropriately selecting and combining, for example, column chromatographies, filtration, ultrafiltration, salting out, solvent precipitation, solvent extraction, distillation, immunoprecipitation, SDS-polyacrylamide gel electrophoresis, isoelectric focusing, dialysis, and recrystallization.

Chromatography includes, for example, affinity chromatography, ion exchange chromatography, hydrophobic chromatography, gel filtration chromatography, reverse-phase chromatography, and adsorption chromatography (Strategies for Protein Purification and Characterization: A Laboratory Course Manual. Ed Daniel R. Marshak et al., (1996)

Cold Spring Harbor Laboratory Press). Such chromatographic methods can be conducted using liquid phase chromatography such as HPLC and FPLC. Columns used for affinity chromatography include, protein A columns and protein G columns. Columns using protein A include, for example, Hyper D, POROS® column, and Sepharose® F. F. column (Pharmacia).

If needed, an antigen-binding molecule provided by the present invention can be modified arbitrarily, and peptides can be partially deleted by allowing an appropriate protein modification enzyme to act on the antigen-binding molecule. Such protein modification enzymes include, for example, trypsin, chymotrypsin, lysyl endopeptidases, protein kinases, and glucosidases.

The present invention also provides pharmaceutical compositions comprising an antigen-binding molecule of the present invention as an active ingredient. Pharmaceutical compositions can be used to treat diseases. It is preferable that pharmaceutical compositions of the present invention are used to treat diseases for which one of the causes is assumed to be an antigen that has physiological activity. The antigen is preferably an antigen having two or more types of physiological activities that can be reduced in vivo by antigen-binding molecules of the present invention. In the present specification, "treatment" means to obtain pharmacological and/or physiological effects. Such an effect may be preventive in the sense that it completely or partially prevents the symptoms of a disease, or may be therapeutic in the sense that it completely or partially cures the symptoms of a disease. In the present specification, "treatment" includes all of the treatments for diseases in mammals, in particular humans. Furthermore, the "treatment" also includes preventing the onset of diseases in subjects who have not yet been diagnosed with a disease, restraining the progression of symptoms, and reducing the symptoms of diseases.

Pharmaceutical compositions of the present invention can be formulated by methods known to those skilled in the art (for example, Remington's Pharmaceutical Science, latest edition, Mark Publishing Company, Easton, USA). If needed, antigen-binding molecules of the present invention may be formulated in combination with other pharmaceutical ingredients. The pharmaceutical compositions may also comprise, for example, pharmaceutically acceptable carriers and additives. The pharmaceutical compositions of the present invention can also be used parenterally, for example, when they are formulated in a sterile solution or suspension for injection using water or any other pharmaceutically acceptable liquid. Dosage forms for oral and parenteral administration, and methods for producing them are well known to those skilled in the art, and may be produced according to conventional methods by mixing the pharmaceutical compositions of the present invention with pharmaceutically acceptable carriers and such. In the present invention, examples include sterile water, physiological saline, vegetable oils, emulsifiers, surfactants, excipients, vehicles, colorants, flavoring agents, preservatives, antiseptic agents, stabilizers, buffers, suspension agents, isotonizing agents, binders, disintegrating agents, lubricants, fluidity enhancing agents, flavor additives, and corrigents; however, the carriers are not limited to the above example, and other conventional carriers may be appropriately used. Specifically, light anhydrous silicic acid, lactose, crystalline cellulose, mannitol, starch, carmellose calcium, carmellose sodium, hydroxypropylcellulose, hydroxypropyl methylcellulose, polyvinyl acetal diethylaminoacetate, polyvinylpyrrolidone, gelatin, medium chain fatty acid triglyceride, polyoxyethylene hydrogenated castor oil 60, saccharose, carboxymethylcellulose, corn starch, and inorganic salts may be used. Pharmaceutical compositions of the present invention may be formulated by appropriately combining the above-described examples, and mixing them into unit dosage forms required for generally accepted drug manufacture. The amount of active ingredients in these preparations is determined to achieve an adequate dose within the indicated range.

Pharmaceutical compositions of the present invention can be administered orally or parenterally; however, parenteral administration is preferred, which specifically includes injection, transnasal administration, transpulmonary administration, and transdermal administration. Injection includes, for example, intravenous administration, intramuscular administration, intraperitoneal administration, and subcutaneous administration. The dose can be suitably selected from the range of 0.0001 mg to 1000 mg/kg body weight of a patient or within the range of 0.001 mg to 10000 mg/patient; however, the dose is not limited to this example. Subjects to be administered are mammals, preferably humans.

The present invention also provides kits comprising an antigen-binding molecule of the present invention or a pharmaceutical composition of the present invention, and kits for use in various methods of the present invention. The kits of the present invention may additionally contain in a package instruction manuals describing how to use them, as necessary. In addition, the kits of the present invention can be preferably used in: (i) methods for reducing antigen concentration in plasma; (ii) methods for enhancing antigen incorporation into cells; or (iii) methods for reducing the physiological activity of antigens in vivo.

In the present invention, preferred antigens include, for example, HMGB1. Diseases for which one of the causes is assumed to be HMGB1 include sepsis, trauma, acute respiratory distress syndrome (ARDS), ischemia-reperfusion injury in the brain, heart, liver, kidney, and such, pancreatitis, nephritis, hepatitis, colitis, meningitis, endophthalmitis, myopathy, rheumatoid arthritis (RA), systemic lupus erythematosus (SLE), diabetes, multiple sclerosis (MS), colorectal cancer, osteosarcoma, cervical cancer, liver cancer, lymphoma, nasopharyngeal cancer, prostate cancer, skin cancer, urothelial cancer, lung cancer, autism, seizure, sleep apnea syndrome, HIV infection, pulmonary fibrosis, and burn injury. Other preferred antigens include, for example, CTGF. Diseases for which one of the causes is assumed to be CTGF include fibrosis such as pulmonary fibrosis and hepatic fibrosis. Other preferred antigens include, for example, IgE. Diseases for which one of the causes is assumed to be IgE include allergic diseases such as bronchial asthma, atopic dermatitis, and pollinosis.

The present invention also provides methods for producing antigen-binding molecules of the present invention, which comprise the steps of (a) selecting an antigen having two or more types of physiological activities;

(b) obtaining an antigen-binding domain;

(c) obtaining at least one receptor-binding domain;

(d) selecting from antigen-binding domains obtained in step (b) a domain of which antigen-binding activity changes according to the ion concentration;

(e) selecting from receptor-binding domains obtained in step (c) a domain that has human FcRn-binding activity under an acidic pH range condition and of which human Fc receptor-binding activity under a neutral pH range condition is greater than the human Fc receptor-binding activity of native human IgG;

(f) producing an antigen-binding molecule in which the antigen-binding domain selected in step (d) is linked to the receptor-binding domain selected in step (e); and (g) selecting from antigen-binding molecules produced in step (f) an antigen-binding molecule which inhibits one or more types of the physiological activities of the antigen by binding to the antigen while allowing for the antigen to retain at least one type of physiological activity.

Antigen-binding domains of the present invention may be prepared by any methods. For example, when an antigen-binding domain is an antibody or a fragment thereof (such as a variable region, Fab, F(ab')2, Fv, or CDR), it can be prepared by antibody library methods, hybridoma methods, B cell cloning methods (Bernasconi et al., Science (2002) 298, 2199-2202; or WO2008/081008), and such. Meanwhile, antibodies and fragments thereof prepared as described above may be modified at at least one amino acid.

There are a number of known methods for constructing antibody libraries. Regarding phage display libraries, for example, those skilled in the art can prepare them by referring to documents such as Clackson et al., Nature 1991, 352: 624-8; Marks et al., J. Mol. Biol. 1991, 222: 581-97; Waterhouses et al., Nucleic Acids Res. 1993, 21: 2265-6; Griffiths et al., EMBO J. 1994, 13: 324.0-60; Vaughan et al., Nature Biotechnology 1996, 14: 309-14; Kang A S et al., Proc Natl Acad Sci USA (1991) 88, 4363-4366; and Japanese Patent Kohyo Publication No. (JP-A) H10-504970 (unexamined Japanese national phase publication corresponding to a non-Japanese international publication). When the variable regions of antibodies in a phage display library are expressed as single-chain antibodies (scFv) on the surface of phages, phages that bind to antigens can be selected by panning. The genes of selected phages are analyzed to determine the DNA sequences encoding the variable regions of antibodies that bind to the antigens. Once the DNA sequences of the variable regions of antibodies are revealed, they can be linked to the DNAs encoding desired constant regions and inserted into appropriate expression vectors. The resulting vectors are introduced into host cells for expression to produce the antibodies as recombinant proteins. These methods are already well known, and one can refer to the following documents: WO92/01047, WO92/20791, WO93/06213, WO93/11236, WO93/19172, WO95/01438, and WO95/15388. In addition to phage display libraries, it is possible to use known antibody libraries such as ribosome display libraries (Schaffitzel C et al., J. Immunol. Methods (1999) 231, 119-135), cell display libraries (Fuchs P et al., Biotechnology (1991) 9, 1369-1372; Boder E T & Wittrup K D, Nat Biotechnol (1997) 15, 553-557; WO95/15393), nucleotide display libraries (Cull M G et al., Proc Nalt Acad Sci USA (1992) 89, 1865-1869; Roberts R D & Szostak J W, Proc Natl Acad Sci USA (1997) 94, 12297-12302), and eukaryotic virus display libraries (Grabherr R & Ernst W, Comb Chem High Throughput Screen (1991) 4, 185-192).

As a hybridoma method for preparing antibodies, basically known techniques are used. A desired antigen or cells expressing the desired antigen are used as a sensitizing antigen. Immune cells obtained by immunization with the antigen according to a conventional immunization method are fused with known parental cells by a conventional cell fusion method. The resulting cells are screened for cells producing monoclonal antibodies (hybridomas) by a conventional screening method. Furthermore, by using reverse transcriptase, cDNAs encoding the variable regions of the antibodies can be prepared from the mRNA of the obtained hybridomas. The cDNAs are linked to the DNA encoding a desired constant region and inserted into an appropriate expression vector. The resulting vectors are introduced and expressed in host cells to produce the antibodies as recombinant proteins.

More specifically, the sensitizing antigens include, but are not limited to, for example, both complete antigens with immunogenicity, and incomplete antigens without immunogenicity including haptens. For example, the full-length proteins of interest and partial peptides can be used. In addition, it is known that substances composed of polysaccharides, nucleic acids, lipids, and such can serve as an antigen, and are not particularly limited. Antigens can be prepared by methods known to those skilled in the art, for example, according to methods using baculoviruses (for example, WO98/46777). Hybridomas can be produced, for example, according to the method of Milstein et al. (G. Kohler and C. Milstein, Methods Enzymol. 1981, 73: 3-46). When the immunogenicity of an antigen is low, it can be linked to a macromolecule having immunogenicity, such as albumin, and then used for immunization. Alternatively, the antigen may be linked to other molecules, if necessary.

Hybridomas can be obtained by immunizing animals using suitable sensitizing antigens described above. Alternatively, antibody-producing cells can be prepared by in vitro immortalization of lymphocytes capable of producing antibodies. Various mammals can be used for immunization, and such animals generally used include rodents, lagomorphas and primates. Such animals include, for example, rodents such as mice, rats, and hamsters; lagomorphas such as rabbits; and primates such as monkeys including cynomolgus monkeys, rhesus monkeys, hamadryas baboons, and chimpanzees. In addition, transgenic animals with the repertoire of human antibody genes are also known, and such animals can be immunized with a desired antigen to obtain human antibodies (see WO93/12227; WO92/03918; WO94/02602; WO96/34096; WO96/33735; Mendez et al., Nat. Genet. 1997, 15: 146-56). Instead of using such transgenic animals, for example, human lymphocytes can be sensitized in vitro with a desired antigen, and the sensitized lymphocytes can be fused with human myeloma cells, for example, U266 to obtain desired human antibodies with antigen-binding activity (see Japanese Patent Kohyo Publication No. (JP-A) H01-59878 (unexamined Japanese national phase publication corresponding to a non-Japanese international publication)).

Animals are immunized, for example, by appropriately diluting and suspending a sensitizing antigen in phosphate-buffered saline (PBS), physiological saline, or such, and after combining it with an adjuvant and emulsifying if needed, injecting it intraperitoneally or subcutaneously to the animals. Then, the sensitizing antigen combined with Freund's incomplete adjuvant is preferably administered several times every four to 21 days. Antibody production can be confirmed by measuring the titer of antibody of interest in the sera of the animals according to conventional methods.

To produce hybridomas, antibody-producing cells such as lymphocytes obtained from animals immunized with a desired antigen are fused with myeloma cells using conventional fusion agents (for example, polyethylene glycol) (Goding, Monoclonal Antibodies: Principles and Practice, Academic Press, 1986, 59-103). If needed, hybridomas can be cultured and grown, and the binding specificity of antibodies produced by the hybridomas can be measured using known analysis methods, such as immunoprecipitation, radioimmunoassay (RIA), and enzyme-linked immunosorbent assay (ELISA). Then, as necessary, hybridomas producing the antibodies of interest with determined specificity, affinity, or activity can be subcloned by methods such as limiting dilution.

Next, genes encoding antibodies can be cloned from hybridomas or antibody-producing cells (such as sensitized lymphocytes) using probes capable of specifically binding to antibody genes (for example, oligonucleotides complementary to sequences encoding the antibody constant regions). Alternatively, the genes can be cloned from mRNA by RT-PCR. Immunoglobulins are classified into five different classes: IgA, IgD, IgE, IgG, and IgM. These classes are further divided into several subclasses (isotypes) (for example, IgG1, IgG2, IgG3, and IgG4).

Receptor-binding domains of the present invention may be obtained by any methods. For example, when a receptor-binding domain is an anti-FcRn antibody or a fragment thereof (a variable region, Fab, F(ab')2, Fv, CDR, etc.), it can be prepared by the above-described antibody library methods and hybridoma methods. Other examples of receptor-binding domains include the Fc region of an antibody (IgG) and regions containing the Fc region (antibody constant regions and full length antibodies). When a receptor-binding domain is the Fc region of an IgG, it may be modified at at least one amino acid.

Arbitrary amino acids can be added, deleted, and/or substituted in polypeptides by methods known to those skilled in the art, for example, site-directed mutagenesis (Hashimoto-Gotoh T. et al., Gene (1995) 152, 271-275; Zoller M. J. & Smith M., Methods Enzymol (1983) 100, 468-500; Kramer W. et al., Nucleic Acids Res (1987) 12, 9441-9456; Kramer W. & Fritz H. J., Methods Enzymol (1987) 154, 350-367; Kunkel T. A., Proc Natl Acad Sci USA (1985) 82, 488-492).

Methods for producing chimeric antibodies are known, and in the case of a human-mouse chimeric antibody, for example, DNA encoding the variable region of a mouse antibody can be linked to a DNA encoding the constant region of a human antibody and inserted into an expression vector, and then introducing the vector into a host to produce the chimeric antibody.

Humanized antibodies are also referred to as "reshaped human antibodies", and result from grafting the complementarity determining region (CDR) of an antibody derived from a nonhuman mammal, for example, a mouse, into a human antibody at its CDR. Methods for identifying CDRs are known (Kabat et al., Sequence of Proteins of Immunological Interest (1987) National Institute of Health, Bethesda, Md.; Chothia et al., Nature (1989) 342: 877). General genetic recombination techniques for grafting CDRs are also known (see European Patent Application Publication No. EP 125023; WO96/02576). Humanized antibodies can be produced by known methods, for example, with a system using common expression vectors, by determining the CDR of a mouse antibody and preparing a DNA encoding an antibody in which the CDR is linked to the framework region (FR) of a human antibody. Such DNAs can be synthesized by assemble PCR, using as primers several oligonucleotides designed to include overlapping portions at the ends of both the CDR and FR regions (see the method described in WO98/13388). Human antibody FRs linked via CDRs are selected such that the CDRs form a suitable antigen binding site. If required, amino acids in the FRs of an antibody variable region may be altered in such a way that the CDRs of the reshaped human antibody form a suitable antigen binding site (Sato et al., Cancer Res. (1993) 53: 10.01-6). Amino acid residues that can be altered in the FRs include portions that directly bind to an antigen via non-covalent bonds (Amit et al., Science (1986) 233: 747-53), portions that influence or act on the CDR structure (Chothia et al., J. Mol. Biol. (1987) 196: 901-17), and portions involved in the interaction between VH and VL (EP 239400).

In addition to the humanization techniques described above, antibodies may be modified to improve their biological properties, for example, antigen affinity. In the present invention, alteration can be achieved using methods such as site-directed mutagenesis (see, for example, Kunkel (1910.0) Proc. Natl. Acad. Sci. USA 82: 488), PCR mutagenesis, and cassette mutagenesis. In general, mutant antibodies with improved biological properties show amino acid sequence homology and/or similarity of 70% or higher, more preferably 80% or higher, and even more preferably 90% or higher (for example, 95% or higher, 96%, 97%, 98%, 99%, etc.), to the amino acid sequence of the original antibody variable region. In the present specification, sequence homology and/or similarity is defined as the ratio of amino acid residues that are homologous (same residue) and/or similar (residues classified into the same group based on the general properties of amino acid side chains) to the amino acid residues of the original sequence, after the sequence homology value has been maximized by sequence alignment and gap introduction, as necessary. In general, native amino acid residues are classified based on the characteristics of their side chains into the following groups:

(1) hydrophobic: alanine, isoleucine, valine, methionine, and leucine;
(2) neutral, hydrophilic: asparagine, glutamine, cysteine, threonine, and serine;
(3) acidic: aspartic acid and glutamic acid;
(4) basic: arginine, histidine, and lysine;
(5) residues that have influence on chain configuration: glycine and proline; and
(6) aromatic: tyrosine, tryptophan, and phenylalanine.

In methods for producing antigen-binding molecules of the present invention, a number of antigen-binding domains are prepared, and domains of which antigen-binding activity changes according to the ion concentration can be selected from among them; or a number of domains are prepared by modifying an arbitrary antigen-binding domain by adding, deleting, and/or substituting at least one amino acid, and domains of which antigen-binding activity changes according to the ion concentration can be selected from among them. Alternatively, antigen-binding domains that inhibit one or more of the physiological activities of an antigen by binding to the antigen but allow for the antigen to retain at least one type of physiological activity may be appropriately selected from a number of antigen-binding domains.

In methods for producing antigen-binding molecules of the present invention, whether the binding of the antigen-binding molecule or the antigen-binding domain thereof to an antigen inhibits one or more types of the physiological activities of the antigen or allows for the antigen to retain at least one type of physiological activity can also be confirmed, by measuring whether one or more of the activities of the antigen to bind target molecules are inhibited or whether the activity to bind at least one type of target molecule is retained.

In methods for producing antigen-binding molecules of the present invention, a number of receptor-binding domains are prepared, and from among them, domains that have human FcRn-binding activity under an acidic pH range condition, and of which human Fc receptor-binding activity under a neutral pH range condition is greater than that of native human IgG can be selected; or a number of domains are prepared by modifying an arbitrary receptor-binding domain by adding, deleting, and/or substituting at least one amino acid, and from among them, domains that have human FcRn-binding activity under an acidic pH range condition, and of which human Fc receptor-binding activity under a neutral pH range condition is greater than that of native human IgG can be selected.

In methods for producing antigen-binding molecules of the present invention, in order to produce an antigen-binding molecule in which an antigen-binding domain is linked to a receptor-binding domain, polynucleotides encoding the antigen-binding domain and the receptor-binding domain are constructed, linked together in frame, inserted into an expression vector, and expressed in host cells. The antigen-binding domain may be linked directly to the receptor-binding domain, or indirectly using an arbitrary peptide linker that can be introduced by genetic engineering or using a synthetic compound linker (for example, the linkers disclosed in Protein Engineering (1996) 9, 299-305). Such peptide linkers are not particularly limited in length and amino acid sequence; however, peptides of 100 amino acids or less, preferably 50 amino acids or less, more preferably 30 amino acids or less, and particularly preferably 10 amino acids or less are generally used.

The present invention also provides methods of screening for antibodies of which antigen-binding activity changes depending on conditions, which comprise the steps of (a) preparing antibody-producing cells;
(b) contacting an antigen with the cells of (a) under the first condition;
(c) selecting from the cells of step (b), cells bound to a specific amount of antigen or more;
(d) exposing the cells of step (c) to the second condition; and
(e) selecting from the cells of step (d), cells in which the amount of antigen binding has been reduced as compared to step (c).

More preferred embodiments of the above-described method include methods comprising the steps of (a) preparing antibody-producing cells;
(b) contacting an antigen with the cells of (a) under the first condition;
(c) contacting an anti-IgG antibody with the cells of step (b);
(d) selecting from the cells of step (c), cells bound to a specific amount of antigen or more and bound to a specific amount of anti-IgG antibody or more;
(e) exposing the cells of step (d) to the second condition; and
(f) selecting from the cells of step (e), cells in which the amount of antigen binding has been reduced as compared to step (d).

Sill more preferred embodiments of the above-described method include methods comprising the steps of:

(a) preparing antibody-producing cells;
(b) contacting an antigen with the cell of (a) under the first condition;
(c) enriching cells bound to the antigen among the cells of step (b);
(d) contacting an anti-IgG antibody with the cells of step (c);
(e) selecting from the cells of step (d), cells bound to a specific amount of antigen or more and bound to a specific amount of anti-IgG antibody or more;
(f) exposing the cells of step (e) to the second condition; and
(g) selecting from the cells of step (f), cells in which the amount of antigen binding has been reduced as compared to step (e).

In the present invention, "antibody-producing cells" are not particularly limited as long as they contain an antibody gene and express the antibody protein; however, they are preferably naturally-occurring cells producing antibodies within an animal body, more preferably lymphocytes, and still more preferably B cells. Animals can be appropriately selected from various mammals (such as mice, rats, hamsters, rabbits, cynomolgus monkeys, rhesus monkeys, hamadryas baboons, chimpanzees, and humans); however, rabbits are particularly preferable in the present invention. It is also preferable to use animals immunized with desired antigens. Antibody-producing cells may be naturally-occurring cells or artificially produced cells such as hybridomas and genetically modified cells. Antibody-producing cells for use in the present invention preferably have the property that they secrete antibodies to the outside of the cells (secretory antibodies) and/or the property that they present antibodies on the cell membrane (membrane-bound antibodies). Naturally occurring antibody-producing cells in the animal body can be preferably collected, for example, from spleen, lymph nodes, and blood (peripheral blood mononuclear cells). Such methods are known to those skilled in the art, and are also described in the Examples below.

In the present invention, "the first condition" and "the second condition" mean two types of different conditions and arbitrary conditions can be set when one desires to obtain an antibody of which antigen-binding activity varies between the conditions. Preferred examples in the present invention include extracellular condition and intracellular condition. The category of conditions is not particularly limited as long as antibody-producing cells are exposed to the conditions, and examples include temperature, pH, compositions in media, and the concentrations thereof. The conditions preferably include ion concentration, particularly preferably hydrogen ion concentration (pH) and calcium ion concentration. The intracellular condition preferably refers to a condition characteristic of the internal environment of an endosome, and the extracellular condition preferably refers to a condition characteristic of the environment in plasma.

The extracellular pH is neutral as compared to that inside the cell, and conversely the intracellular pH is acidic as compared to that outside the cell. A neutral pH range preferred in the present invention is pH 6.7 to pH 10.0, more preferably pH 7.0 to pH 9.0, still more preferably any of pH 7.0, 7.1, 7.2, 7.3, 7.4, 7.5, 7.6, 7.7, 7.8, 7.9, and 8.0, and particularly preferably pH 7.4 which is close to the pH in plasma (in blood). Meanwhile, an acidic pH range preferred in the present invention is pH 4.0 to pH 6.5, more preferably pH 5.0 to pH 6.5, still more preferably any of pH 5.5, 5.6, 5.7, 5.8, 5.9, 6.0, 6.1, 6.2, 6.3, 6.4, and 6.5, and particularly preferably pH 5.8 to pH 6.0 which is close to the pH in the early endosome in vivo.

Meanwhile, the extracellular calcium ion concentration is higher than that inside the cell, and conversely the intracellular calcium ion concentration is lower than that outside the cell. A high calcium ion concentration preferred in the present invention is 100 μM to 10 mM, more preferably 200 μM to 5 mM, and particularly preferably 0.5 mM to 2.5 mM which is close to the calcium ion concentration in plasma (in blood). Meanwhile, a low calcium ion concentration preferred in the present invention is 0.1 μM to 30 μM, more preferably 0.5 μM to 10 μM, and particularly preferably 1 μM to 5 μM which is close to the calcium ion concentration in the early endosome in vivo. Low calcium ion concentration can also be achieved by adding a chelating agent such as EDTA, instead of reducing the amount of calcium added.

"The first condition" and "the second condition" may include several conditions at the same time. For example, "the first condition" may be a neutral pH condition and a high calcium ion concentration condition, and "the second condition" may be an acidic pH condition and a low calcium ion concentration condition.

Antigens may be any substances as long as it is possible to produce antibodies against them. The type of antigen is not particularly limited, and it preferably comprises polypeptides. Meanwhile, in the above-described antibody screening methods of the present invention, antigens are preferably labeled with certain substances that can be detected with high sensitivity. The labeling substances may be linked directly to antigens, or indirectly to antigens using antigen-antibody reaction or biotin-avidin reaction. The labeling substances include, for example, radioisotopes, chemiluminescent compounds, fluorescent compounds, phosphorescent compounds, magnetic particles, and enzymes, particularly preferably fluorescent compounds. Fluorescent compounds include, for example, fluorescein isothiocyanate (FITC), phycoerythrin (PE), PE-Cyanin5 (PE-Cy5), PE-Cyanin5.5 (PE-Cy5.5), PE-Cyanin7 (PE-Cy5), rhodamine isothiocyanate, Texas Red, PE-Texas Red-x (ECD), allophycocyanin (APC), APC-Cyanin 7 (APC-Cy7, PharRed), Peridinin Chlorophyll Protein (Per-CP), and Per-CP-Cyanin5.5 (PerCP-Cy5.5).

Furthermore, in the above-described antibody screening methods of the present invention, anti-IgG antibodies are also preferably labeled with certain substances that can be detected with high sensitivity. Cells to which anti-IgG antibodies are bound can be selected from antibody-producing cells to increase the percentage of cells expressing IgG subclasses. The presence of IgG expression in B cells namely suggests that class switching to IgG is taking place. To enrich cells producing such matured antibodies is expected to be beneficial from the viewpoint of screening for antibodies with strong binding activity. The labeling substances may be linked directly to antigens, or indirectly to antigens using antigen-antibody reaction or biotin-avidin reaction. The labeling substances include, for example, those described above. When an antigen and an anti-IgG antibody are both used, it is desirable that the labeling substances for them are different from each other and their detection methods are different (each can be detected independently). Antigens and anti-IgG antibodies can be labeled by referring to methods known to those skilled in the art (for example, U.S. Pat. Nos. 5,057,313 and 5,156,840).

In the above-described antibody screening methods provided by the present invention, the step of selecting cells bound to a specific amount of antigen or more and/or a specific amount of anti-IgG antibody or more is preferably achieved by detecting the above-described labeling substances. For example, when an antigen and/or an anti-IgG antibody are each labeled with a different type of fluorescent compound, whether a specific amount of antigen or more and/or a specific amount of anti-IgG antibody or more is bound to cells can be assessed by testing whether the fluorescence emitted from each fluorescent compound is detected to be at a specific lever or higher. The specific level can be set arbitrarily by those skilled in the art depending on the purpose. In the present invention, it is preferable that the selection step is achieved using FACS (Fluorescence Activated Cell Sorting).

In the above-described antibody screening methods provided by the present invention, it is preferable that the step of enriching antigen-bound cells is achieved by detecting the above-described labeling substances. For example, when an antigen is labeled with magnetic particles, antigen-bound cells can be separated from cells not bound by the antigen using magnetic devices. Antigen-bound cells can be enriched by removing cells not bound by the antigen. In the present invention, it is preferable that the enriching step is achieved by using the MACS (Magnetic Activated Cell Sorting (Registered Trademark)).

By using the above-described antibody screening methods provided by the present invention, a large amount of antibody-producing cells can be simply and efficiently screened for antibodies with antigen-binding activity that changes according to condition. As compared to conventional methods, the methods enable one to drastically increase the number of cells that can be screened, and thus greatly raise the probability to find rare antibodies that have been previously undetectable. Thus, the above-described antibody screening methods of the present invention are useful.

The present invention also provides methods for reducing antigen concentration in plasma by administering an antigen-binding molecule of the present invention, methods for enhancing antigen incorporation into cells by administering an antigen-binding molecule of the present invention, and methods for reducing the physiological activity of antigens in vivo by administering an antigen-binding molecule of the present invention.

The present invention also provides therapeutic agents for diseases, which comprise an antigen-binding molecule of the present invention as an active ingredient. The diseases include, for example, diseases for which one of the causes is assumed to be HMGB1, diseases for which one of the causes is assumed to be CTGF, and diseases for which one of the causes is assumed to be IgE.

The present invention also provides kits comprising antigen-binding molecules of the present invention for use in methods for reducing antigen concentration in plasma, methods for enhancing antigen incorporation into cells, and methods for reducing the physiological activity of antigens in vivo.

The present invention also provides methods for treating diseases for which one of the causes is assumed to be an antigen that has physiological activity, methods for reducing antigen concentration in plasma, methods for enhancing antigen incorporation into cells, and methods for reducing the physiological activity of antigens in vivo, which comprise the step of administering antigen-binding molecules of the present invention.

The present invention also provides agents for treating diseases for which one of the causes is assumed to be an antigen that has physiological activity, agents for reducing antigen concentration in plasma, agents for enhancing antigen incorporation into cells, and agents for reducing the physiological activity of antigens in vivo, which comprise an antigen-binding molecule of the present invention as an active ingredient.

The present invention also provides antigen-binding molecules of the present invention for use in methods for treating diseases for which one of the causes is assumed to be an antigen that has physiological activity, methods for reducing antigen concentration in plasma, methods for enhancing antigen incorporation into cells, and methods for reducing the physiological activity of antigens in vivo.

The present invention also provides the use of antigen-binding molecules of the present invention in the production of agents for treating diseases for which one of the causes is assumed to be an antigen that has physiological activity, agents for reducing antigen concentration in plasma, agents for enhancing antigen incorporation into cells, and agents for reducing the physiological activity of antigens in vivo.

The present invention also provides processes for producing agents for treating diseases for which one of the causes is assumed to be an antigen that has physiological activity, agents for reducing antigen concentration in plasma, agents for enhancing antigen incorporation into cells, and agents for reducing the physiological activity of antigens in vivo, which comprise the step of using an antigen-binding molecule of the present invention. Such diseases include, for example, diseases for which one of the causes is assumed to be HMGB1, diseases for which one of the causes is assumed to be CTGF, and diseases for which one of the causes is assumed to be IgE.

Amino acids contained in the amino acid sequences of the present invention may be post-translationally modified (for example, the modification of an N-terminal glutamine into a pyroglutamic acid by pyroglutamylation is well-known to those skilled in the art). Naturally, such post-translationally modified amino acids are included in the amino acid sequences in the present invention.

All prior art documents cited in the specification are incorporated herein by reference.

EXAMPLES

Herein below, the present invention will be specifically described with reference to the Examples, but it is not to be construed as being limited thereto.

[Example 1] Construction of Anti-HMGB1 Antibodies by the Rabbit B Cell Cloning Method

Preparation of HMGB1

HMGB1 was prepared as an antigen by the following procedure. An animal cell expression vector inserted with a DNA sequence encoding human HMGB1 (GenBank accession number NP002119, SEQ ID NO: 7) was constructed and used in combination with FreeStyle™ 293-F cells (Invitrogen) to express the full-length human HMGB1 protein in the culture supernatant. From the resulting culture supernatant, the HMGB1 protein was purified by cation-exchange column chromatography, anion-exchange chromatography, and gel filtration chromatography.

Immunization of Animals with the Antigen

Rabbits were immunized with HMGB1. The initial immunization was carried out by intracutaneously injecting 100 μg of the HMGB1 protein included in complete Freund's adjuvant (CFA). Then, booster immunization was performed with the HMGB1 protein included in incomplete Freund's adjuvant (IFA) at 50 μg each time, twice or more times at intervals of one week or more. Antibody titers were determined to confirm antibody production in the animal bodies.

Tissue Sampling from Immunized Animals and Preparation of Single-Cell Suspensions Animals which had been confirmed to produce antibodies were euthanized to collect their spleens, lymph nodes, and blood. Peripheral blood mononuclear cells (PBMCs) were prepared from the blood. An equal volume of the blood was carefully overlaid onto Histpaque-1077 (Sigma) in a 50-ml centrifuge tube, and centrifuged at 400×g and 25° C. for 30 minutes. After centrifugation, the PBMC layer was carefully collected with a glass Pasteur pipette and transferred into a sterile 50-ml tube. About 10 volumes of RPMI-1640 containing 2% FBS was added to the collected cell suspension. The cells were washed by centrifugation at 1000×g for 5 minutes followed by removing the supernatant. The same washing treatment was carried out again to prepare PBMCs. The PBMCs were stained with trypan blue, and the cell density was determined with a hemocytometer.

The collected spleens and lymph nodes were filtered through 70-μm Cell Strainers (BD Falcon) using the plunger of a 5-ml syringe to prepare single-cell suspensions. The cells were collected into sterile 50-ml tubes using RPMI medium containing 2% FBS. The cells were washed by centrifugation at 1000×g for 5 minutes followed by removing the supernatant. 50 ml of RPMI-1640 containing 2% FBS was added, and the cells were washed again. After the final washing, the cells were stained with trypan blue, and the cell density was determined with a hemocytometer.

Collection of Antigen-Binding B Cells

The single-cell suspensions from the blood, spleens, and lymph nodes prepared by the above method were centrifuged at 1000×g for 5 minutes twice to wash the cells with HBSS (20 mM HEPES, 5.3 mM KCl, 0.4 mM $KH_2PO_4$, 4.2 mM $NaHCO_3$, 0.3 mM $Na_2HPO_4$, 0.10% BSA, 2 mM $CaCl_2$, 5 mM glucose, 138 mM NaCl, pH 7.4). A solution with biotinylated human HMGB1 diluted to 500 nM with HBSS was prepared and added to the cells so that the density is 1E08 cells/100 μl or less, and the cells were suspended. Biotinylated HMGB1 was prepared by labeling the HMGB1 protein using EZ-Link NHS-PEG4-Biotin and Biotinylation Kit (Thermo Scientific) according to the attached protocol, and then dialyzing against TBS/300 mM NaCl (10 mM Tris-HCl/300 mM NaCl) using a Microdialyzer (TOMY). The cell suspensions were incubated on ice for 30 minutes. Then, the cells were washed with 50 ml of HBSS to remove biotinylated HMGB1 that was not bound to the cells. A solution of MACS (Registered Trademark) streptavidin beads (Miltenyi Biotech) diluted 10 times with HBSS was prepared and added to the cells so that the density was 1E08 cells/500 μl or less to suspend them. The cell suspensions were incubated on ice for 30 minutes. After washing with 50 ml of HBSS, the cells were combined with HBSS so that the density was 1E08 cells/500 μl or less, and suspended. From the cell suspensions, fractions of positive cells to which MACS® streptavidin beads were bound were collected using the autoMACS® Pro Separator cell separator.

A solution of biotinylated HMGB1 diluted with HBSS was prepared again, and added to the collected cells so that the density was 1E08 cells/100 μl or less, and the cells were suspended. After incubating the cell suspensions on ice for 30 minutes, the cells were washed with 50 ml of HBSS. This secondary incubation with biotinylated human HMGB1 was omitted in some cases. Solutions of streptavidin-FITC (BD) and mouse anti-rabbit IgG-PE (Southern Biotech) diluted with HBSS were prepared and added to the cells so that the density was 1E08 cells/100 μl or less, and the cells were suspended. After incubating the cell suspensions on ice for 30 minutes, the cells were washed with 50 ml of HBSS. Next, HBSS was added to the cells so that the density was 1E07 cells/100 μl or less and they were suspended. The cell fractions whose FITC and PE fluorescence intensities were both high were collected from the cell suspensions using FACSAria™ cell sorter (BD).

Collection of B Cells that Express Antigen-Binding Antibodies Whose Dissociation Ability is Altered Depending on the Change in pH or $Ca^{2+}$ Ion Concentration B cells that express antibodies whose dissociation ability is altered depending on the change in pH or $Ca^{2+}$ ion concentration were enriched and collected by the following method. The prepared single-cell suspensions from blood, spleens, and lymph nodes were centrifuged at 1000×g for 5 minutes twice to wash the cells with HBSS (20 mM HEPES, 5.3 mM KCl, 0.4 mM $KH_2PO_4$, 4.2 mM $NaHCO_3$, 0.3 mM $Na_2HPO_4$, 0.10% BSA, 2 mM $CaCl_2$, 5 mM glucose, 138 mM NaCl, pH 7.4). A solution of biotinylated HMGB1 diluted to 500 nM with HBSS was prepared and added to the cells so that the density was 1E08 cells/100 μl or less, and the cells were suspended. After incubating the cell suspensions on ice for 30 minutes, the cells were washed with 50 ml of HBSS to remove biotinylated HMGB1 that was not bound to the cells. A solution of MACS® streptavidin beads (Miltenyi Biotech) diluted 10 times with HBSS was prepared and added to the cells so that the density was 1E08 cells/500 μl or less, and the cells were suspended. The cell suspensions were incubated on ice for 30 minutes. After washing with 50 ml of HBSS, HBSS was added to the cells so that the density was 1E08 cells/500 μl or less, and the cells were suspended. Positive fractions of cells to which MACS® streptavidin beads were bound were collected from the cell suspensions using the autoMACS® Pro Separator cell separator.

A solution of biotinylated HMGB1 diluted to 500 nM with HBSS was prepared again and added to the collected cells so that the density was 1E08 cells/100 μl or less, and the cells were suspended. After 30 minutes of incubation on ice, the cells were washed with 50 ml of HBSS. Solutions of streptavidin-FITC (BD) and mouse anti-rabbit IgG-PE (Southern Biotech) diluted with HBSS were prepared, and added to the cells so that the density was 1E08 cells/100 μl or less, and the cells were suspended. After incubating the cell suspensions on ice for 30 minutes, the cells were washed with 50 ml of HBSS. Next, HBSS was added to the cells in such a way that the density was 1E07 cells/100 μl or less, and they were suspended. From the cell suspensions, cells were collected using FACSAria™ cell sorter (BD) with a gate for the fraction whose FITC and PE fluorescence intensities were both high. Upon collection, MBSS (20 mM MES, 5.3 mM KCl, 0.4 mM $KH_2PO_4$, 4.2 mM $NaHCO_3$, 0.3 mM $Na_2HPO_4$, 0.1% BSA, 2 mM EDTA, 5 mM glucose, 138 mM NaCl, pH 5.8) was added to tubes for the collection. Then, this was allowed to stand in the MBSS solution for 30 minutes. In the case of antibodies that readily dissociate from an antigen by decrease in pH or $Ca^{2+}$ ion concentration, when left in MBSS at low pH and in the presence of EDTA, the antigen dissociates, resulting in decreased FITC fluorescence intensity. After being allowed to stand for 30 minutes, the cells were collected using FACSAria™ cell sorter again, while setting a gate for cell populations whose PE fluorescence intensity was the same as the first sorting but the FITC fluorescence intensity was lower than the first sorting. The result is shown in FIG. 1. (A) shows a dot plot result for the first sorting. The cells within the gate indicated as 1 were collected. (B) shows a dot plot result for the second sorting. In the second sorting, the cells were collected separately from gates 1, 2, and 3.

When performing this cell collection method, it is unnecessary to increase the scale of subsequent screening for antibodies whose dissociation ability is altered depending on the change in pH or $Ca^{2+}$ ion concentration. Thus, it is possible to efficiently isolate antibodies whose dissociation ability is altered depending on the change in pH or $Ca^{2+}$ ion concentration.

Culture of B Cells

The collected cells were seeded onto a 96-well microtiter plate at one cell or less/well. Activated rabbit T cell conditioned medium was added at a final concentration of 5%, and EL4 cells (European Collection of Cell Cultures) were added at about 25000 cells/well. The activated rabbit T cell conditioned medium was prepared as follows: thymuses collected from rabbits were filtered through 70 m Cell Strainers (BD Falcon) using the plunger of a 5-ml syringe; the cells thus prepared were cultured in RPMI-1640 containing PHA (Roche), phorbol 12-myristate 13-acetate (Sigma), and 2% FBS; and the culture supernatants were frozen and stored until use at −70° C. or below. The EL4 cells to be used as feeder cells were cultured at 37° C. under 5% $CO_2$ for two hours or more after adding mitomycin C (Sigma) at 10 μg/ml to stop the cell growth. After leaving the culture for 5 to 7 days at 37° C. under 5% $CO_2$, a portion of the supernatants containing secreted antibodies was collected. Using the collected supernatants, the antibodies were assessed for their HMGB1 binding by the method described below. The cells were allowed to stand at 37° C. under 5% $CO_2$ until assessment of the antibodies for their HMGB1 binding.

Screening of Culture Supernatants for Monoclonal Antibodies with Desired Specificity Screening was carried out by the ELISA method for the antigen recognition of an antibody. A streptavidin-coated 384-well plate was prepared and biotinylated HMGB1 was captured. Culture supernatants containing secreted antibodies were added to the plate. After leaving one hour at room temperature, this was washed three times with 80 μl of TBS (TAKARA) containing 2 mM $CaCl_2$ and 0.05% Tween-20, and then a dilution solution prepared by 40000-fold diluting Goat anti-rabbit IgG Fc HRP conjugate (BETHYL) with TBS containing 2 mM $CaCl_2$ was aliquoted thereto, and this was allowed to stand at room temperature for one hour. This was washed three times with 80 μl of TBS (pH 7.4) containing 2 mM $CaCl_2$ and 0.05% Tween-20, and a chromogenic substrate (ABTS® peroxidase substrate (KPL)) was added thereto at 40 μl/well. After one hour of incubation, the absorbance at 405 nm was determined with SpectraMax from Molecular Device. The measurement result for the absorbance at 405 nm was analyzed to determine the wells with secreted antibodies that recognize the HMGB1 protein.

Screening for Antibodies Whose Dissociation Ability is Altered Depending on the Change in pH or $Ca^{2+}$ Ion Concentration ELISA was performed using culture supernatants to assess the presence of pH/Ca-dependent dissociation. A goat anti-rabbit IgG-Fc (BETHYL) diluted to 1 μg/ml with PBS(−) was added to a 384-well MaxiSorp™ plate (Nunc). The plate was allowed to stand at room temperature for one hour or more. Then, the goat anti-rabbit IgG-Fc diluted with PBS(−) was removed from the plate, and TBS (pH 7.4) containing 1% BSA and 2 mM $CaCl_2$ was added thereto. The plate was allowed to stand for one hour or more. TBS (pH 7.4) containing 1% BSA and 2 mM $CaCl_2$) was removed from the plate, and culture supernatants were added thereto. In this step, when assessing antibodies whose dissociation ability is altered depending on the change in pH or $Ca^{2+}$ ion concentration, each type of B cell culture supernatant was aliquoted to two wells in the ELISA plate. Culture supernatants were added, and the plate was allowed to stand at room temperature for one hour or more, or at 4° C. overnight, to allow the goat anti-rabbit IgG-Fc to trap antibodies in the culture supernatants. Then, the plate was washed three times with 80 μl of TBS (pH 7.4) containing 2 mM $CaCl_2$ and 0.05% Tween-20, and biotinylated HMGB1 was added thereto. The plate was allowed to stand at room temperature for one hour or more. This allowed biotinylated HMGB1 to bind to rabbit antibodies trapped by the goat anti-rabbit IgG-Fc. The plate was washed three times with 80 μl of TBS (pH 7.4) containing 2 mM $CaCl_2$ and 0.05% Tween-20 to wash off biotinylated HMGB1 that were not bound to rabbit antibodies. Then, 20 mM MES (pH 7.4) containing 150 mM NaCl and 2 mM $CaCl_2$ (Buffer A) was added to one of the above two wells containing the same culture supernatant, and 20 mM MES (pH 5.8) containing 150 mM NaCl and 2 mM EDTA (Buffer B) was added to the other. The plate was allowed to stand at 37° C. or below for one hour or more. In the presence of Buffer A or Buffer B, biotinylated human HMGB1 dissociated from rabbit antibodies. When, due to its property, an antibody readily dissociates from an antigen at low pH, or $Ca^{2+}$ ion is required to maintain the binding of the antibody to the antigen, the antigen more readily dissociated from the antibody on a well containing Buffer B than a well containing Buffer A. The plate was washed three times with 80 μl of TBS (pH 7.4) containing 2 mM $CaCl_2$ and 0.05% Tween-20. Then, 25 ng/ml of streptavidin-HRP (Genscript) prepared with TBS containing 2 mM $CaCl_2$ was added, and the plate was allowed to stand at room temperature for one hour. Streptavidin-HRP bound to biotinylated HMGB1 that remained without dissociating from the antibody. The plate was washed three times with 80 μl of TBS (pH 7.4) containing 2 mM $CaCl_2$ and 0.05% Tween-20, and a chromogenic substrate (ABTS® peroxidase substrate) was added thereto. After one hour of incubation, the absorbance at 405 nm was measured with SpectraMax from Molecular Device. Based on the analysis of the result of absorbance measurement at 405 nm, when the intensity of color development in the well to which Buffer A was added was greater than that in the well to which Buffer B was added, the antibody in the culture supernatant was thought to be an antibody whose dissociation ability is altered depending on the change in pH or $Ca^{2+}$ ion concentration.

This ELISA system has two features. One is that, for each B cell culture supernatant, two wells of the culture supernatant are prepared in an ELISA plate; and the antibody is allowed to bind to the antigen; and then, for dissociation of the antigen from the antibody, incubation is carried out under a condition at about pH 7.0 or above and a $Ca^{2+}$ ion concentration of about 1 mM or higher in one well, and under a condition at about pH 6.0 or below and a low $Ca^{2+}$ ion concentration in the other well. The presence of this incubation step enables efficient screening for antibodies whose dissociation ability is altered depending on the change in pH or $Ca^{2+}$ ion concentration. The other feature is that rabbit antibodies in the culture supernatant are trapped by the goat anti-rabbit IgG-Fc, and antigens are allowed to bind thereto. When rabbit antibodies are reacted after binding antigens to a plate, an antibody strongly bind to the antigens immobilized onto the plate with the two arms, and the binding reaction is strong. Thus, even antibodies that show pH/Ca-dependent dissociation are less likely to dissociate, and one can only obtain those which exhibit strong dependence. In contrast, when rabbit antibodies in the culture supernatant are trapped by the goat anti-rabbit IgG-Fc and antigens are allowed to bind thereto, the antigen/antibody binding is likely to occur in a one-to-one fashion. In this case, the presence or absence of the pH/Ca dependence can be determined even when the change in the dissociation ability depending on the change in pH or $Ca^{2+}$ ion concentration is small.

Figure 2:
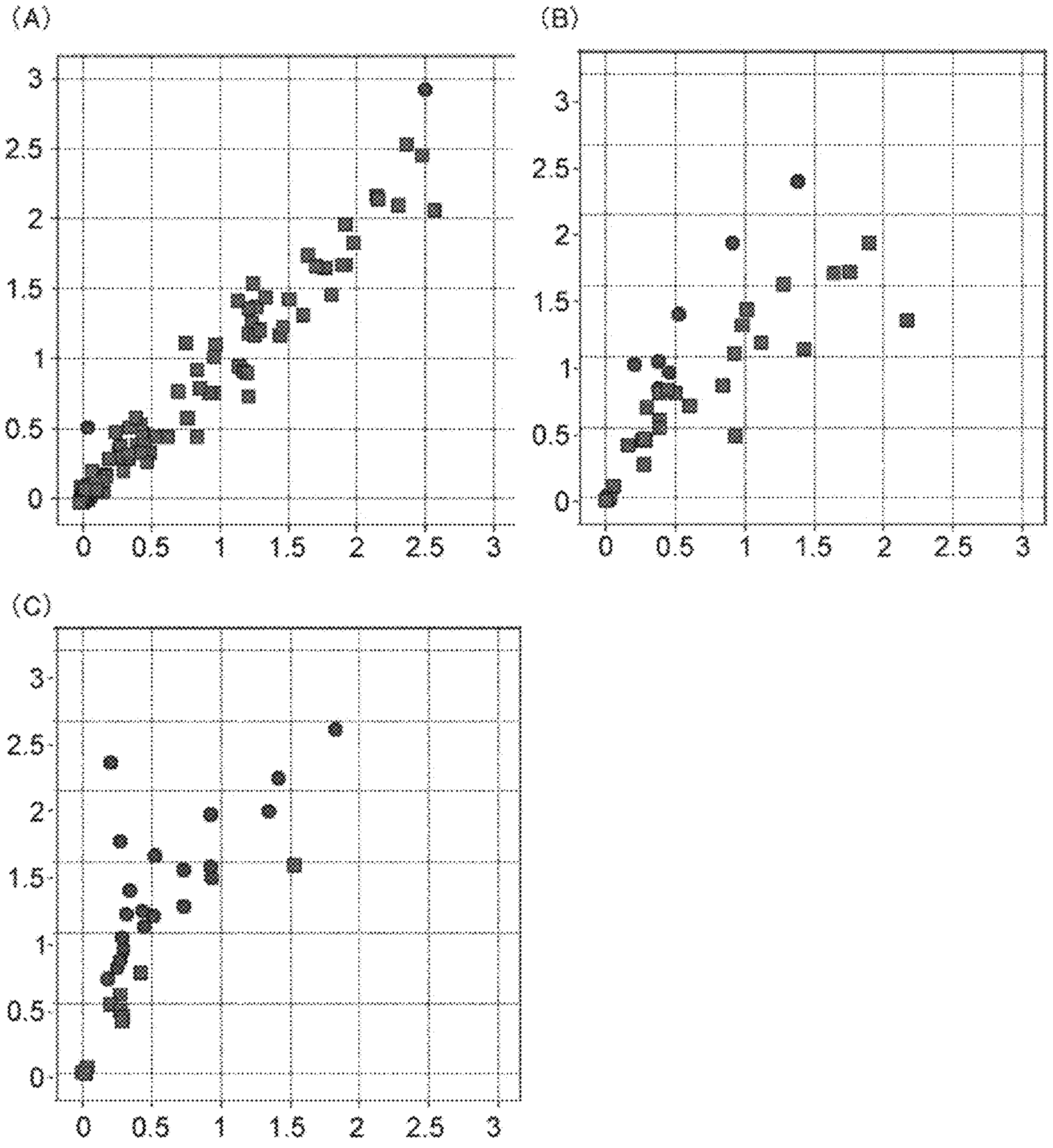
Figure 3:
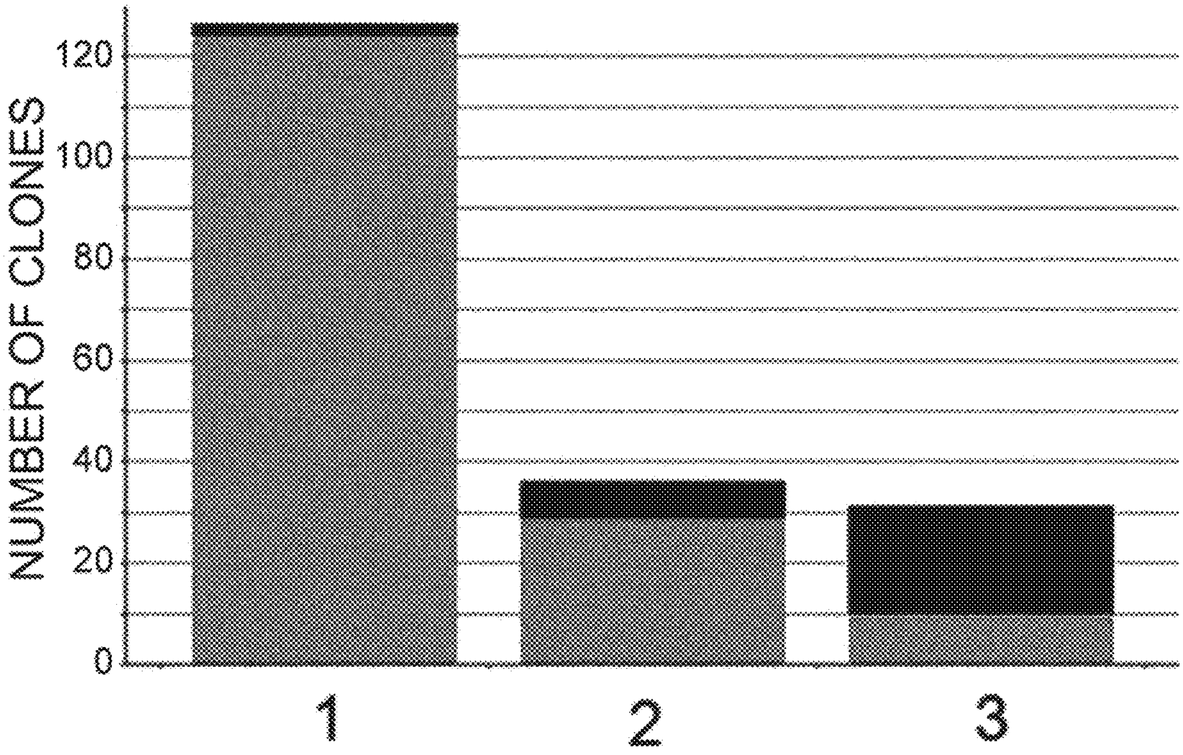
FIG. 3 is a graph showing the number of antibodies whose antigen-binding ability does not depend on pH and/or calcium ion concentration (gray area), and the number of antibodies whose antigen-binding ability depends on pH and/or calcium ion concentration (black area) among antibodies produced by B cells derived from Gate 1, Gate 2, and Gate 3.

The result is shown in FIGS. 2 and 3. FIG. 2 is a dot plot for the result of screening for antibodies whose dissociation ability is altered depending on the change in pH or $Ca^2$ ion concentration. The Y axis indicates OD (405 nm) values under conditions of incubation with 20 mM MES (pH 7.4) containing 150 mM NaCl and 2 mM $CaCl_2$. The X axis indicates OD (405 nm) values under conditions of incubation with 20 mM MES (pH 5.8) containing 150 mM NaCl and 2 mM EDTA. (A) shows the result of screening for antibodies whose dissociation ability is altered depending on the change in pH or $Ca^{2+}$ ion concentration by culturing B cells from gate 1 shown in FIG. 1(B). (B) shows the result of screening for antibodies whose dissociation ability is altered depending on the change in pH or $Ca^{2+}$ ion concentration by culturing B cells from gate 2 shown in FIG. 1(B). (C) shows the result of screening for antibodies whose dissociation ability is altered depending on the change in pH or $Ca^{2+}$ ion concentration by culturing B cells from gate 3 shown in FIG. 1(B). The antibody that readily dissociates from the antigen when incubated at pH 5.8 in the presence of 2 mM EDTA as compared to when incubated at pH 7.4 in the presence of 2 mM $Ca^{2+}$ is indicated by circle. The antibody for which the value is not significantly altered between conditions comprising pH 5.8 and 2 mM EDTA and pH 7.4 and 2 mM $Ca^{2+}$ is indicated by square. FIG. 3 is a graphic representation of the numbers of clones shown in FIGS. 2(A), 2(B), and 2(C). The gray area indicates the number of clones that did not exhibit changes in antibody dissociation from antigens even when pH or the $Ca^{2+}$ ion concentration is altered (indicated by square in (A), (B), and (C)). The dark area indicates the number of clones of antibodies that readily dissociate from antigens when pH or the $Ca^{2+}$ ion concentration is decreased (indicated by circle in (A), (B), and (C)). When antigen-binding B cells are collected, of the antigen-binding antibodies, the proportion of antigen-binding antibodies whose dissociation ability is altered depending on the change in pH or $Ca^{2+}$ ion concentration is about several percent at most, as seen in the result of (A). On the other hand, when B cells expressing antibodies whose dissociation ability is altered depending on the change in pH or $Ca^{2+}$ ion concentration are enriched and collected, the proportion of antigen-binding antibodies whose dissociation ability is altered depending on the change in pH or $Ca^{2+}$ ion concentration, of the antigen-binding antibodies, can be increased up to several tens percent, as seen in the result of (C). This collection method allows efficient isolation of very rare antibodies whose dissociation ability is altered depending on the change in pH or $Ca^{2+}$ ion concentration and which have physiological activity.

Sequence Identification of Variable Region L and H Chains from B Cells and Expression of Recombinant Antibodies Based on the result of screening for monoclonal antibodies having desired specificity, or for antibodies whose dissociation ability is altered depending on the change in pH or $Ca^{2+}$ ion concentration, cells and culture supernatants were collected from a cell culture plate incubated at 37° C. under 5% $CO_2$, and transferred to a fresh 96-well plates by MS2000 (J-Tek). From the plate containing the collected cells and culture supernatants, the supernatants alone were transferred to another 96-well plate. Meanwhile, the plate containing the cells collected by MS2000 was frozen and stored at −70° C. or below. To construct antibody expression vectors, antibody cDNAs were prepared from the cells frozen at −70° C. PCR primers to isolate the cDNAs were designed so that they anneal to the conserved regions in the sequence of rabbit immunoglobulin (the H region and the L region). Antibody cDNAs were obtained by two collection steps using nested PCR. RNA was purified using the MagMax™ 96 RNA Purinfication Kit for microarray (Ambion). Using the purified RNA, reverse transcription and first PCR was carried out with the OneStep RT-PCR Kit (TAKARA). The primer sequences used are shown in Table 11. Then, the product of first PCR was subjected to nested PCR with PrimeSTAR® HS DNA polymerase (TAKARA). The primer sequences used for PCR are shown in Table 11. In the table, R represents a nucleotide mixture of A and G; V represents a nucleotide mixture of A, C, and G; W represents a nucleotide mixture of A and T; and Y represents a nucleotide mixture of C and T.

TABLE 11

| | | | | |
|---|---|---|---|---|
| first PCR | H CHAIN | Forward | AS215 | AGRACCCAGCATGGACAYVA (SEQ ID NO: 8) |
| | | Reverse | AS217 | GGAYRGWATTTATTYGCCACRCACA (SEQ ID NO: 9) |
| | L CHAIN | Forward | AS219 | AGACRCTCACCATGGAGACT (SEQ ID NO: 10) |
| | | Reverse | AS221 | ACTGGCTCCGGGAGGTA (SEQ ID NO: 11) |
| nested PCR | H CHAIN | Forward | AS365 | CACCATGGAGACTGGGC (SEQ ID NO: 12) |
| | | Reverse | AS368 | GGAGGAGACGGTGAC (SEQ ID NO: 13) |
| | L CHAIN | Forward | AS359 | ATGGACACGAGGGCCC (SEQ ID NO: 14) |
| | | Reverse | AS362 | TTTGACCACCACCTCGGTC (SEQ ID NO: 15) |

Cassette vectors were constructed by inserting the sequences of antibody constant regions into an animal cell expression vector, and they were used to construct antibody expression vectors. The following two types of cassette vectors were constructed: a vector carrying the sequence of the H chain constant region of a rabbit antibody; and a vector carrying the sequence of the L chain constant region of a rabbit antibody. The vector carrying the sequence of an H chain constant region has an inserted ampicillin resistance gene, while the vector carrying the sequence of an L chain constant region has an inserted kanamycin resistance gene. These two types of vectors have a partial sequence overlap with the nested PCR primer sequences. Using the In-Fusion PCR™ cloning Kit (Clontech), the nested PCR products are incorporated into the cassette vectors introduced with the sequences of the antibody constant regions to construct expression vectors containing the full-length rabbit antibody genes. The nested PCR products were inserted into vectors using an In-Fusion™ PCR cloning Kit from Clontech, and then transformed into bacteria for plasmid transmission and production. The transformed bacteria were cultured in LB media containing ampicillin or kanamycin. After purification of plasmids from the grown bacteria using the 96-well EndoFree ezFilter Plasmid Miniprep Kit (Biomiga), antibodies were prepared according to Reference Example 1.

[Example 2] Determination of the Affinity and pH/Ca Dependency of Anti-HMGB1 Antibody Preparation of MedG4-IgG1 Antibody MedG4H-IgG1 (SEQ ID NO: 36) and MedG4L-CK (SEQ ID NO: 37) were designed by linking the VH region (WO2007/084253, SEQ ID NO: 19) and VL region (WO2007/084253, SEQ ID NO: 17) of the G4 antibody described in WO2007/084253 to human IgG1 constant region and human Igκ constant region, respectively. To prepare MedG4-IgG1, which is an anti-HMGB1 antibody, DNAs encoding those described above were constructed using genetic engineering techniques, and expressed in animal cells by a method known to those skilled in the art.

Assessment of Prepared Antibodies for the pH- and pH/Ca-Dependent Binding Ability to Human HMGB1

Prepared antibodies were assessed for the presence of pH- and pH/Ca-dependent binding ability using BIACORE™ T100 and T200 systems (GE Healthcare). The plasma condition was set to be pH 7.4 and a calcium ion concentration of 1.2 mM. Two types of intraendosomal conditions were set to be: pH 5.8 and a calcium ion concentration of 1.2 mM; and pH 5.8 and a calcium ion concentration of 3 μM. An appropriate amount of Protein A (Invitrogen) was immobilized onto Sensor chip CM4 (GE Healthcare) by the amine coupling method and antibodies of interest were captured thereon. The antigen used was human HMGB1. Measurements were carried out using three types of running buffers (#1: 20 mmol/l N-(2-acetamido)-2-aminoethanesulfonic acid (ACES), 150 mmol/l NaCl, 0.05% (w/v) polysorbate 20 (Tween20®), 2 mmol/l $CaCl_2$, pH 7.4; #2: 20 mmol/l ACES, 150 mmol/l NaCl, 0.05% (w/v) Tween20®, 2 mmol/l $CaCl_2$), pH 5.8; #3: 20 mmol/l ACES, 150 mmol/l NaCl, 0.05% (w/v) Tween20®, 3 μmol/l $CaCl_2$, pH 5.8). Human HMGB1 was diluted using the respective running buffers.

HMG233-IgG1, HMG236-IgG1, HMG481-IgG1, and HMG487-IgG1

Antibodies diluted with a running buffer were captured onto a sensor chip by injecting at a flow rate of 10 μl/min for one minute. Then, a solution of diluted human HMGB1 (500 nM) and a running buffer (as a reference solution) were injected at a flow rate of 10 μl/min for one minute to interact with the captured antibodies. Then, a running buffer was injected at a flow rate of 10 μl/min for one minute to observe the dissociation of human HMGB1. Finally, 10 mmol/l glycine-HCl (pH 1.5) was injected at a flow rate of 30 μl/min for 30 seconds to regenerate the sensor chip.

Figure 4:
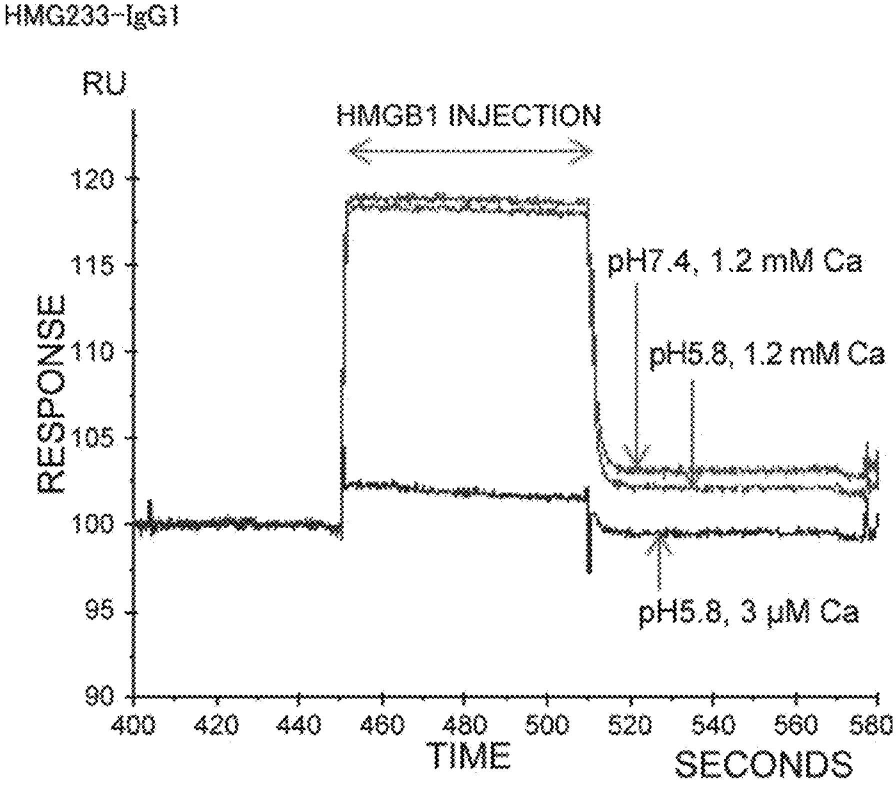
Figure 1:
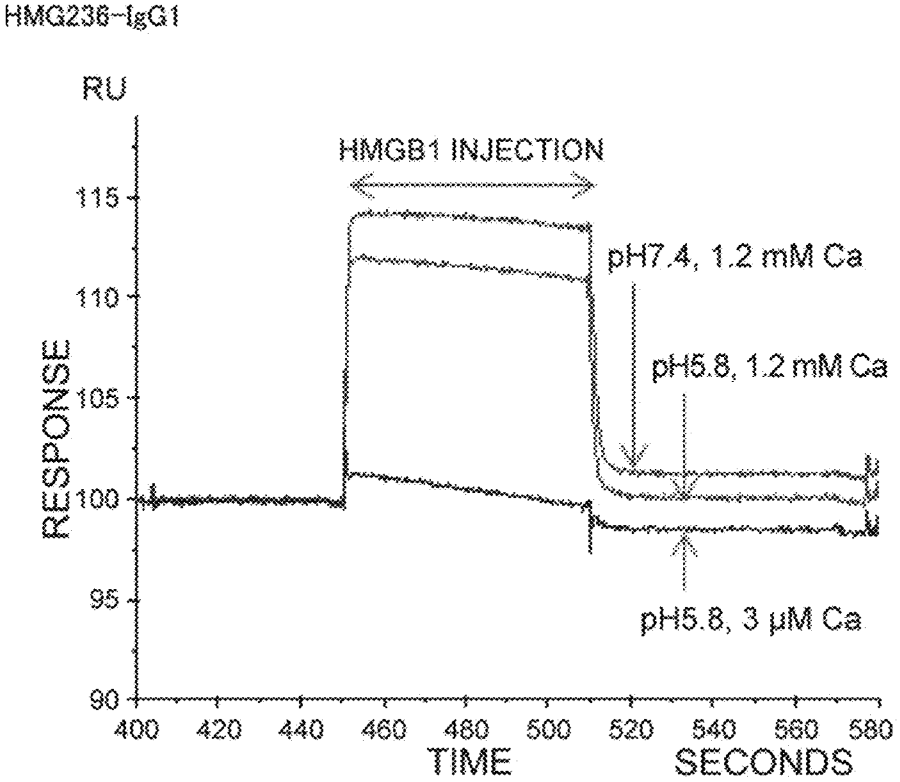
Figure 4:
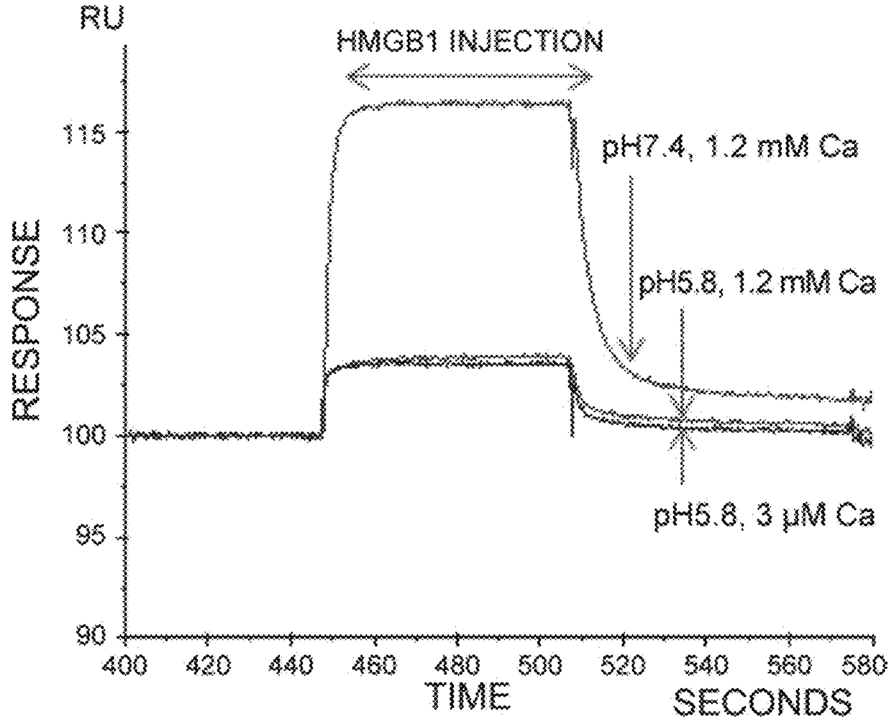
Figure 2:
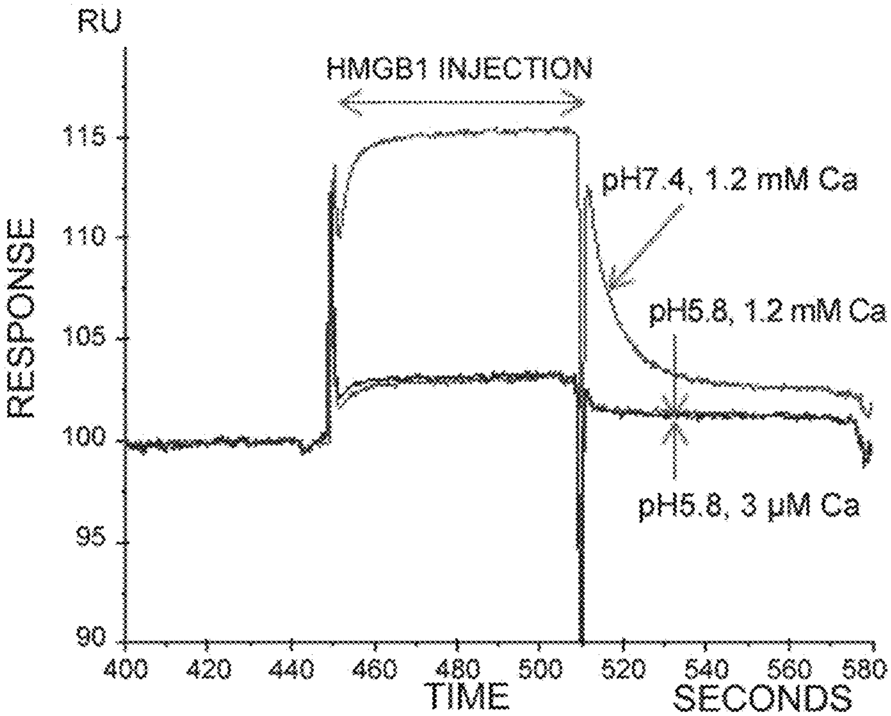

Sensorgrams obtained by the measurement are shown in FIGS. 4-1 and 4-2, in which the quantity of each antibody captured has been converted to 100 RU. Since they are a box-shaped sensorgram with rapid convergence to an equilibrium state, the equilibrium value (i.e., binding amount) during injection of human HMGB1 reflects the dissociation constant KD (M). As to HMG233-IgG1 and HMG236-IgG1, each antibody showed a significant decrease in the amount of binding to human HMGB1 under the condition of pH 5.8 and 3 μM Ca as compared to the conditions of pH 7.4 and 1.2 mM Ca and of pH 5.8 and 1.2 mM Ca. Regarding HMG481-IgG1 and HMG487-IgG1, each antibody exhibited a significant decrease in the amount of binding to human HMGB1 under the conditions of pH 5.8 and 1.2 mM Ca, and of pH 5.8 and 3 μM Ca as compared to the condition of pH 7.4 and 1.2 mM Ca.

HMG446-IgG1 and MedG4-IgG1

With respect to HMG446-IgG1 and MedG4-IgG1, an antibody diluted with a running buffer was captured onto a sensor chip by injecting at a flow rate of 10 μl/min for one minute, and then a solution of diluted human HMGB1 and a running buffer (as a reference solution) were injected at a flow rate of 10 μl/min for one minute to interact with the captured antibody. Next, a running buffer was injected at a flow rate of 10 μl/min for two minutes to observe the dissociation of human HMGB1. Finally, 10 mmol/l glycine-HCl (pH 1.5) was injected at a flow rate of 30 μl/min for 30 seconds to regenerate the sensor chip.

Regarding MedG4-IgG1, a sensorgram obtained by the measurement was analyzed by curve fitting. A 1:1 binding model is used for the reaction model equation. The binding rate constant ka (1/Ms) and dissociation rate constant kd (1/s), which are kinetic parameters, were calculated, and based on the values, the dissociation constant KD (M) was calculated for each antibody for dissociation from human HMGB1. Regarding HMG446-IgG1, the dissociation constant KD (M) was calculated by applying a steady state affinity model to the sensorgram obtained by the measurement. Each parameter was calculated using BIACORE™ T200 Evaluation Software (GE Healthcare). Meanwhile, the pH dependence was determined by dividing KD (M) at pH 5.8 and 1.2 mM Ca by KD (M) at pH 7.4 and 1.2 mM Ca, whereas the pH/Ca dependence was determined by dividing KD (M) at pH 5.8 and 3 μM Ca by KD (M) at pH 7.4 and 1.2 mM.

The analysis result is summarized in Table 12. The KD (M) of HMG446-IgG1 at pH 7.4 and 1.2 mM Ca was calculated to be 220 nM. The KD (M) to human HMGB1 was increased by 50 times (the affinity was reduced by 50 times) by the change from pH 7.4, 1.2 mM Ca to pH 5.8, 1.2 mM Ca, and it was increased by 82 times (the affinity was reduced by 82 times) by the change to pH 5.8, 3 μM Ca. This demonstrates that the affinity for human HMGB1 is reduced under the intraendosomal condition compared to the plasma condition. Meanwhile, the KD (M) of MedG4-IgG1 was calculated to be 96 nM at pH 7.4 and 1.2 mM Ca, and 15 nM at pH 5.8 and 1.2 mM Ca and 3 μM Ca. This demonstrates that the affinity for human HMGB1 is increased under the intraendosomal condition compared to the plasma condition, suggesting that MedG4-IgG1 is less likely to release HMGB1 in the endosome.

TABLE 12

| ANTIBODY NAME | CONDITION | $K_D$(M) | DEPENDENCY |
|---|---|---|---|
| MedG4 | pH 7.4, 1.2 mM Ca | 96 nM | |
| | pH 5.8, 1.2 mM Ca | 15 nM | 0.15 TIMES (pH-DEPENDENT) |
| | pH 5.8, 3 μM Ca | 15 nM | 0.15 TIMES (pH/Ca-DEPENDENT) |
| HMG446 | pH 7.4, 1.2 mM Ca | 220 nM | |
| | pH 5.8, 1.2 mM Ca | 1.1 μM | 50 TIMES (pH-DEPENDENT) |
| | pH 5.8, 3 μM Ca | 1.8 μM | 82 TIMES (pH/Ca-DEPENDENT) |

[Example 3] Assessment for the Binding Between HMGB1 and the Cell Surface Receptor ELISA for the Binding of HMGB1 to RAGE-Fc A solution containing 5 μg/ml recombinant human RAGE-Fc fusion protein (R&D SYSTEMS) in PBS was added to each well of an ELISA plate at 20 μl/well. The plate was incubated at 4° C. overnight. Then, the plate was blocked with 100 μl of 5% skim milk at 37° C. for one hour, and washed four times with PBS/Tween. In another plate, 4 μg/ml HMGB1 was pre-incubated with 100 μg/ml anti-HMGB1 antibody or a buffer in the presence of 2.5% skim milk at room temperature for one hour, and this was transferred to the RAGE-coated, blocked plate. Then, the plate was incubated at 4° C. overnight, and washed four times with PBS/Tween. To detect HMGB1 bound to the immobilized RAGE-Fc, a peroxidase-labeled mouse anti-HMGB1 monoclonal antibody was added to each well, and the plate was incubated at room temperature for two hours. Then, the plate was washed five times, and 20 μl of the chromogenic agent TMB was added thereto. The absorbance at 450 nm in the plate was measured.

It was confirmed that the anti-HMGB1 antibody does not inhibit the binding between HMGB1 and the peroxidase-labeled mouse anti-HMGB1 monoclonal antibody used for detection, by allowing the anti-HMGB1 antibody to compete the peroxidase-labeled mouse anti-HMGB1 monoclonal antibody in an HMGB1-immobilized plate.

ELISA for the Binding of HMGB1 to TLR4/MD-2

A solution of 5 μg/ml recombinant human TLR4/MD-2 protein (R&D SYSTEMS) in PBS was added to each well of an ELISA plate at 20 μl/well. The plate was incubated at 4° C. overnight. Then, the plate was blocked with 100 μl of 5% skim milk at 37° C. for one hour, and washed four times with PBS/Tween. In another plate, 10 μg/ml HMGB1 was pre-incubated with 100 μg/ml anti-HMGB1 antibody or a buffer in the presence of 2.5% skim milk at room temperature for one hour, and this was transferred to the TLR4/MD-2-coated, blocked plate. Then, the plate was incubated at room temperature for two hours, and washed four times with PBS/Tween. To detect HMGB1 bound to the immobilized TLR4/MD-2, 1 μg/ml peroxidase-labeled mouse anti-HMGB1 monoclonal antibody was added to each well, and the plate was incubated at room temperature for two hours. Then, the plate was washed five times with PBS/Tween, and 20 μl of the chromogenic agent TMB was added thereto. The absorbance at 450 nm in the plate was measured.

It was confirmed that the anti-HMGB1 antibody does not inhibit the binding between HMGB1 and the peroxidase-labeled mouse anti-HMGB1 monoclonal antibody used for detection, by allowing the anti-HMGB1 antibody to compete the peroxidase-labeled mouse anti-HMGB1 monoclonal antibody in an HMGB1-immobilized plate.

Results

Both RAGE and TLR4 have been identified as putative receptors for HMGB1. Some anti-HMGB1 antibodies were assessed by ELISA assay for their ability to inhibit the binding between HMGB1 and the RAGE-Fc fusion product or TLR4/MD-2 fusion product.

Figure 5:
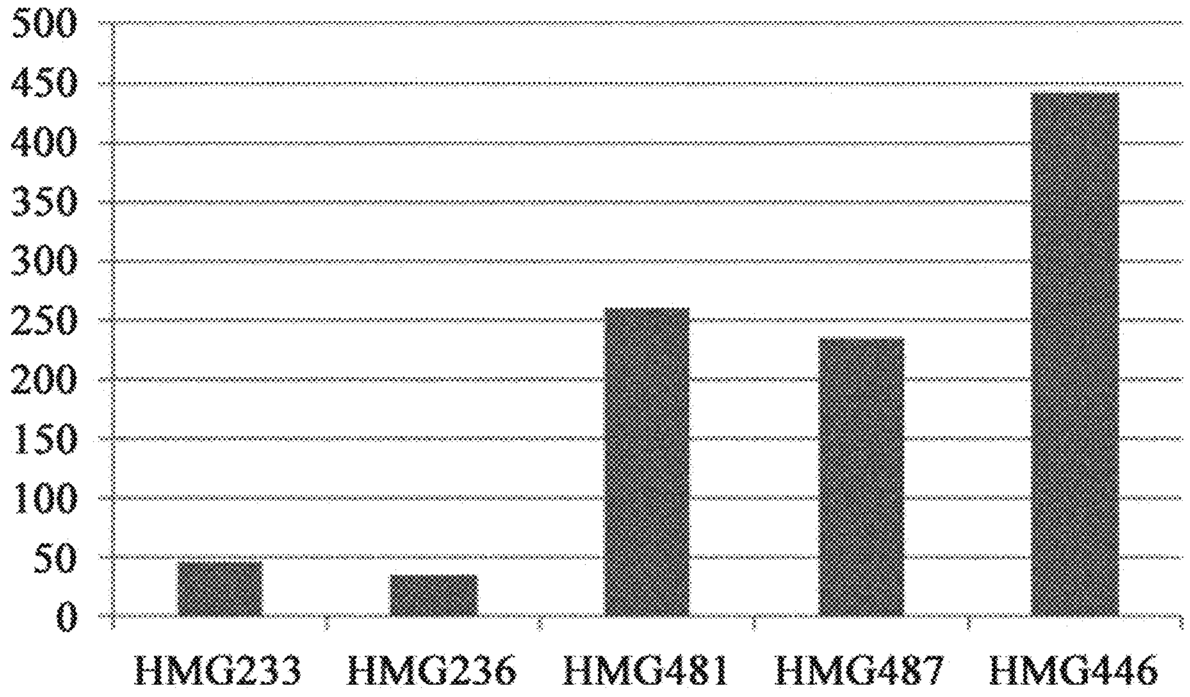
FIG. 5 is a graph showing a result of RAGE ELISA for anti-HMGB1 antibodies (HMG233, HMG236, HMG481, HMG487, and HMG446). The absorbance for each antibody is shown as a relative value to the absorbance of a control in the absence of antibody which is taken as 100.
Figure 6:
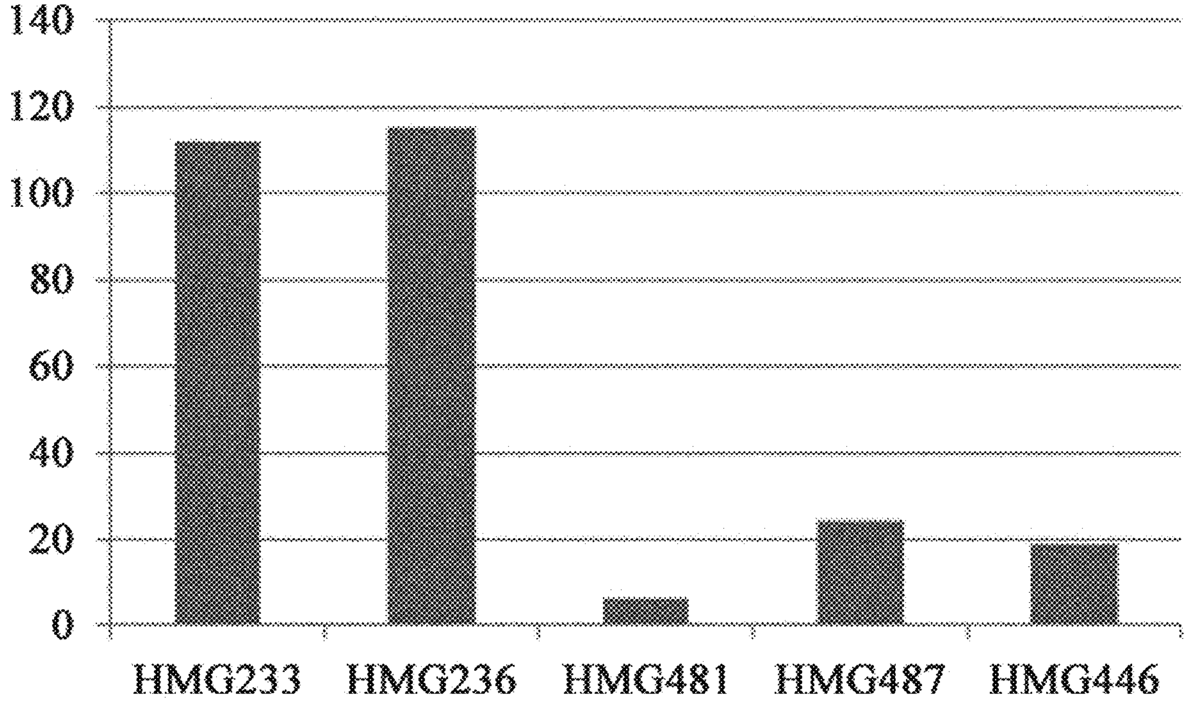
FIG. 6 presents graphs showing a result of TLR4/MD-2 ELISA for anti-HMGB1 antibodies (HMG233, HMG236, HMG481, HMG487, and HMG446). The absorbance for each antibody is shown as a relative value to the absorbance of a control in the absence of antibody which is taken as 100.

By setting the value determined under the condition in the absence of the anti-HMGB1 antibody as 100, a relative value was determined for each of RAGE and TLR4 from the value determined under each condition in the presence of the anti-HMGB1 antibody. The values are shown in FIGS. 5 and 6. Anti-HMGB1 antibodies with a value less than 100 were determined to have the ability to inhibit the binding to each receptor. Of the antibodies subjected to RAGE ELISA, HMG233-IgG1 and HMG236-IgG1 inhibited the binding of HMGB1 to RAGE. The percent inhibition was 53.1% for HMG233-IgG1, and 64.1% for HMG236-IgG1. Of the antibodies subjected to TLR4/MD-2 ELISA, HMG481-

IgG1, HMG487-IgG1, and HMG446-IgG1 inhibited the binding of HMGB1 to TLR4/MD-2. The percent inhibition was 93.5% for HMG481-IgG1, 75.7% for HMG487-IgG1, and 81.3% for HMG446-IgG1. HMG233-IgG1 and HMG236-IgG1 did not inhibit the binding between HMGB1 and TLR4/MD-2. Meanwhile, HMG481-IgG1, HMG487-IgG1, and HMG446-IgG1 did not inhibit the binding between HMGB1 and RAGE.

The present invention demonstrated that, of anti-HMGB1 antibodies, some antibodies inhibited the binding of HMGB1 to RAGE but not the binding to TLR4, and that some antibody inhibited the binding of HMGB1 to TLR4/MD-2 but not the binding to RAGE.

[Example 4] Improvement of the Effect to Accelerate the Elimination of Human HMGB1 by the pH-Dependent Anti-Human HMGB1 Antibody In Vivo Test Using Normal Mice Human HMGB1 and anti-human HMGB1 antibody were simultaneously administered to normal mice (C57BL/6J mouse, Charles River Japan) to assess the in vivo kinetics of human HMGB1 and the anti-human HMGB1 antibody. A mixed solution of human HMGB1 (0.1 mg/ml) and the anti-human HMGB1 antibody (1 mg/ml MedG4-IgG1, 2.05 mg/ml HMG446) was administered at 10 ml/kg once into the tail vein. The antibody concentration in this mixed solution was adopted as a concentration that allows 99.0% or more of human HMGB1 contained in the solution to bind to the antibody. Blood was collected at 5 minutes, 10 minutes, 15 minutes, one hour, 4 hours, 2 days, and 7 days after administration. The collected blood was allowed to stand for two hours, and then centrifuged at 12,000 rpm and 4° C. for 5 minutes to obtain sera. The isolated sera were stored in a freezer set at −20° C. or below until use. Herein, MedG4-IgG1 is sometimes referred to as “med G4”, while HMG446-IgG1 is sometimes referred to as “HMG446-G1”.

Determination of Anti-Human HMGB1 Antibody Concentration in Serum by ELISA

Figure 8:
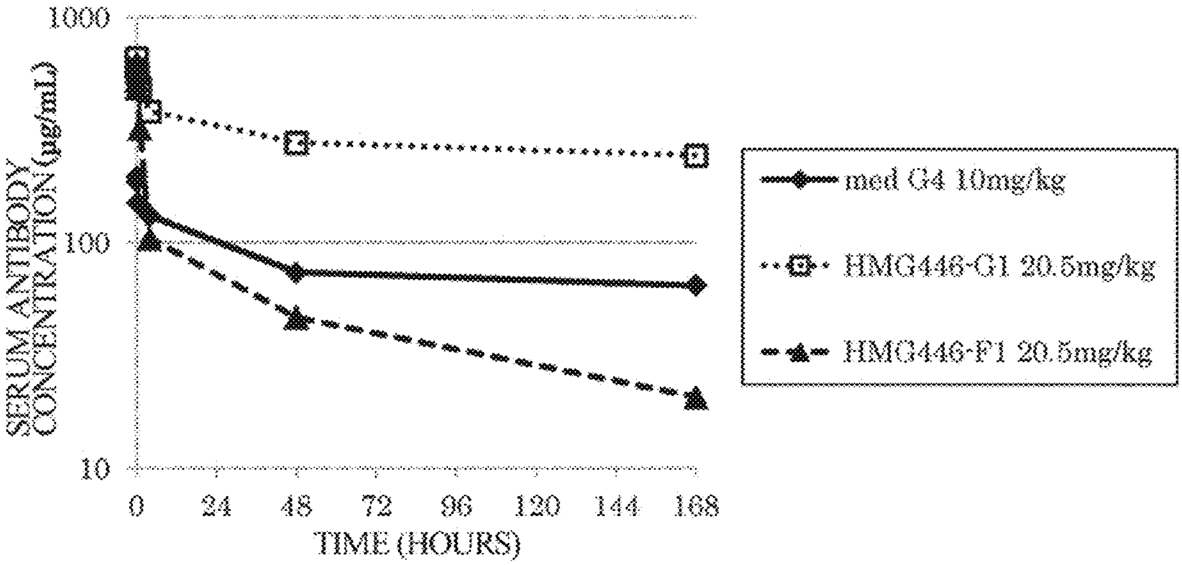
FIG. 8 is a graph showing a time course of serum anti-human HMGB1 antibody concentration in normal mice.

Anti-human HMGB1 antibody concentrations in mouse sera were determined by ELISA. First, to prepare an anti-human IgG-immobilized plate, Anti-Human IgG (γ-chain specific) F(ab')2 Fragment of Antibody (SIGMA) was aliquoted into a Nunc-Immuno Plate, MaxiSorp™ plate (Nalge nunc International), and the plate was allowed to stand at 4° C. overnight. Standard curve samples (serum concentrations of 3.2, 1.6, 0.8, 0.4, 0.2, 0.1, and 0.05 μg/ml) and assay samples of mouse serum diluted 100 times or more were prepared. 150 μl of 2000 ng/ml human HMGB1 was added to 150 μl of the standard curve samples and assay samples. This was allowed to stand at room temperature for one hour, and then aliquoted into the anti-human IgG-immobilized plate. The plate was allowed to stand at room temperature for one hour. Then, Goat Anti-Human IgG (γ chain specific) Biotin (BIOT) Conjugate (Southern Biotech Association) was reacted at room temperature for one hour. Next, Streptavidin-PolyHRP80 (Stereospecific Detection Technologies) was reacted at room temperature for one hour. Chromogenic reaction was performed using TMB One Component HRP Microwell Substrate (BioFX Laboratories) as a substrate. After terminating the reaction with 1N sulfuric acid (Showa Chemical), the absorbance at 450 nm was measured with a microplate reader. The anti-human HMGB1 antibody concentrations in mouse sera were determined based on the absorbance of the standard curve using the analysis software SOFTmax® PRO (Molecular Devices). A time course of anti-human HMGB1 antibody concentration in the sera of mice after intravenous administration, which was measured by the above method, is shown in FIG. 8.

Measurement of Human HMGB1 Concentration in Serum by ELISA

Figure 7:
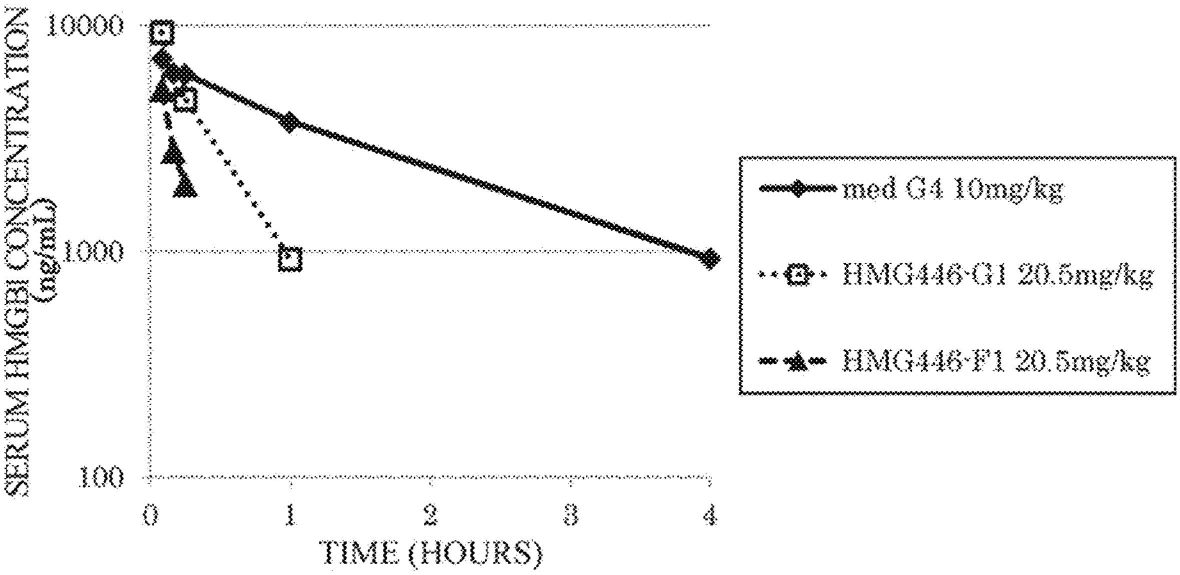
FIG. 7 is a graph showing a time course of serum human HMGB1 concentration in normal mice.

Human HMGB1 concentrations in mouse sera were measured using HMGB1 ELISA Kit II (shino-test). Standard curve samples with a serum concentration of 12800, 6400, 3200, 1600, 800, 400, or 200 μg/ml, and assay samples of mouse sera diluted 100 times or more were prepared, and mixed with an equal volume of 40 μg/ml HMG446 solution (in the presence of HMG446-IgG1 or HMG446-F1) or 20 μg/ml MedG4-IgG1 solution (in the presence of MedG4-IgG1). After one hour of incubation at room temperature, the mixtures were aliquoted in the attached, immobilized plate. The plate was incubated at 37° C. for 20 to 24 hours. Then, the attached, labeled antibody solution was reacted at 25° C. for two hours. After 30 minutes of reaction with a chromogenic reagent, the reaction was stopped by adding a stop solution. Then, the absorbance at 450 nm was measured using a microplate reader. The human HMGB1 concentrations in mouse sera were calculated based on the absorbance of the standard curve using the analysis software SOFTmax® PRO (Molecular Devices). A time course of human HMGB1 concentration in the sera of mice after intravenous administration, which was measured by the above method, is shown in FIG. 7.

The Effect of pH/Ca-Dependent Binding to Human HMGB1

HMG446-IgG1 whose human HMGB1-binding activity is decreased at acidic pH or low calcium ion concentration and MedG4-IgG1 whose human HMGB1-binding activity is not decreased at acidic pH or low calcium ion concentration were tested in vivo, and the results were compared to each other. As shown in FIG. 8, the pharmacokinetics of the two antibodies showed linearity. Meanwhile, as shown in FIG. 7, it was revealed that, when HMGB1 was administered in combination with HMG446-IgG1 that binds to human HMGB1 in a pH-dependent manner, HMG446-IgG1 accelerated the elimination of HMGB1 as compared to when MedG4-IgG1 was administered in combination with HMGB1. Thus, it was demonstrated that, by conferring the pH-dependent human HMGB1-binding ability, the serum HMGB1 concentration can be decreased by about 4.0 times one day after administration.

The Effect of FcRn Binding at Neutral Conditions (pH 7.4)

In addition to HMG446-IgG1, HMG446-F1 resulting from introducing an amino acid substitution into the IgG Fc region of HMG446-IgG1, was tested in vivo using mice. The test result was compared to that for HMG446-IgG1. As shown in FIG. 8, the serum antibody concentration of HMG446-F1 whose mouse FcRn binding was enhanced under a neutral condition (pH 7.4) was lower by about 1.2 times than that of HMG446-IgG1 15 minutes after administration.

As shown in FIG. 7, it was demonstrated that HMGB1, when administered in combination with HMG446-F1 whose mouse FcRn binding was enhanced under a neutral condition (pH 7.4), was eliminated more rapidly as compared to when HMGB1 was administered in combination with HMG446-IgG1. HMG446-F1 reduced the serum HMGB1 concentration by about 2.4 times in 15 minutes as compared to HMG446-IgG1. Thus, it was demonstrated that the serum human HMGB1 concentration can be reduced by conferring the mouse FcRn-binding ability under a neutral condition (pH 7.4). As described above, the antibody concentration in serum was reduced by conferring the ability to bind to mouse FcRn under a neutral condition (pH 7.4). However, the achieved effect to decrease the serum HMGB1 concentration exceeded the decrease in antibody concentration.

The above results suggest that, by administering an antibody whose binding activity to human HMGB1 is reduced under an acidic pH or low calcium ion concentration condition, the elimination of human HMGB1 can be accelerated as compared to when administering an antibody whose binding activity to human HMGB1 is not reduced at an acidic pH or low calcium ion concentration condition, and this effect is enhanced depending on the mouse FcRn-binding ability under a neutral condition (pH 7.4).

[Example 5] Production of Various Antibody Fc Variants with Increased Binding Affinity for Human FcRn at Neutral pH Production of Fc Variants To increase the binding affinity for human FcRn in a neutral pH range, various substitutions were introduced into the antibody Fv4-IgG1 that comprise the H chain and L chain which are, respectively, VH3-IgG1 and VL3-CK described as SEQ ID NOs: 6 and 7 in WO2009/125825. Specifically, the amino acid substitutions shown in Table 13-1 to 13-14 were introduced into the heavy chain constant region of Fv4-IgG1 to create Fc variants (the amino acid numbers for mutation sites are shown according to EU numbering). Amino acid substitutions were introduced according to the method known to those skilled in the art, which is described in Reference Example 1.

Variants containing the prepared heavy chains and the light chain L(WT) described as SEQ ID NO: 5 in WO2009/125825 were expressed and purified by the method known to those skilled in the art, which is described in Reference Example 1.

Assessment of Human FcRn Binding

The binding between the antibody and human FcRn under a neutral condition (pH 7.0) was analyzed with a BIACORE™ system. The results are shown in Table 13-1 to 13-14.

TABLE 13-1

| VARIANT NAME | KD (M) | AMINO ACID SUBSTITUTION |
|---|---|---|
| F1 | 8.10E-07 | N434W |
| F2 | 3.20E-06 | M252Y/S254T/T256E |
| F3 | 2.50E-06 | N434Y |
| F4 | 5.80E-06 | N434S |
| F5 | 6.80E-06 | N434A |
| F7 | 5.60E-06 | M252Y |
| F8 | 4.20E-06 | M252W |
| F9 | 1.40E-07 | M252Y/S254T/T256E/N434Y |
| F10 | 6.90E-08 | M252Y/S254T/T256E/N434W |
| F11 | 3.10E-07 | M252Y/N434Y |
| F12 | 1.70E-07 | M252Y/N434W |
| F13 | 3.20E-07 | M252W/N434Y |
| F14 | 1.80E-07 | M252W/N434W |
| F19 | 4.60E-07 | P257L/N434Y |
| F20 | 4.60E-07 | V308F/N434Y |
| F21 | 3.00E-08 | M252Y/V308P/N434Y |
| F22 | 2.00E-06 | M428L/N434S |
| F25 | 9.20E-09 | M252Y/S254T/T256E/V308P/N434W |
| F26 | 1.00E-06 | I332V |
| F27 | 7.40E-06 | G237M |
| F29 | 1.40E-06 | I332V/N434Y |
| F31 | 2.80E-06 | G237M/V308F |
| F32 | 8.00E-07 | S254T/N434W |
| F33 | 2.30E-06 | S254T/N434Y |
| F34 | 2.80E-07 | T256E/N434W |
| F35 | 8.40E-07 | T256E/N434Y |
| F36 | 3.60E-07 | S254T/T256E/N434W |
| F37 | 1.10E-06 | S254T/T256E/N434Y |

TABLE 13-1-continued

| VARIANT NAME | KD (M) | AMINO ACID SUBSTITUTION |
|---|---|---|
| F38 | 1.00E-07 | M252Y/S254T/N434W |
| F39 | 3.00E-07 | M252Y/S254T/N434Y |
| F40 | 8.20E-08 | M252Y/T256E/N434W |
| F41 | 1.50E-07 | M252Y/T256E/N434Y |
| F42 | 1.00E-06 | M252Y/S254T/T256E/N434A |
| F43 | 1.70E-06 | M252Y/N434A |
| F44 | 1.10E-06 | M252W/N434A |
| F47 | 2.40E-07 | M252Y/T256Q/N434W |
| F48 | 3.20E-07 | M252Y/T256Q/N434Y |
| F49 | 5.10E-07 | M252F/T256D/N434W |
| F50 | 1.20E-06 | M252F/T256D/N434Y |
| F51 | 8.10E-06 | N434F/Y436H |
| F52 | 3.10E-06 | H433K/N434F/Y436H |
| F53 | 1.00E-06 | I332V/N434W |
| F54 | 8.40E-08 | V308P/N434W |
| F56 | 9.40E-07 | I332V/M428L/N434Y |
| F57 | 1.10E-05 | G385D/Q386P/N389S |
| F58 | 7.70E-07 | G385D/Q386P/N389S/N434W |
| F59 | 2.40E-06 | G385D/Q386P/N389S/N434Y |
| F60 | 1.10E-05 | G385H |
| F61 | 9.70E-07 | G385H/N434W |
| F62 | 1.90E-06 | G385H/N434Y |
| F63 | 2.50E-06 | N434F |
| F64 | 5.30E-06 | N434H |
| F65 | 2.90E-07 | M252Y/S254T/T256E/N434F |
| F66 | 4.30E-07 | M252Y/S254T/T256E/N434H |
| F67 | 6.30E-07 | M252Y/N434F |
| F68 | 9.30E-07 | M252Y/N434H |
| F69 | 5.10E-07 | M428L/N434W |
| F70 | 1.50E-06 | M428L/N434Y |
| F71 | 8.30E-08 | M252Y/S254T/T256E/M428L/N434W |
| F72 | 2.00E-07 | M252Y/S254T/T256E/M428L/N434Y |

Table 13-2 is the continuation of Table 13-1.

TABLE 13-2

| | | |
|---|---|---|
| F73 | 1.70E-07 | M252Y/M428L/N434W |
| F74 | 4.60E-07 | M252Y/M428L/N434Y |
| F75 | 1.40E-06 | M252Y/M428L/N434A |
| F76 | 1.00E-06 | M252Y/S254T/T256E/M428L/N434A |
| F77 | 9.90E-07 | T256E/M428L/N434Y |
| F78 | 7.80E-07 | S254T/M428L/N434W |
| F79 | 5.90E-06 | S254T/T256E/N434A |
| F80 | 2.70E-06 | M252Y/T256Q/N434A |
| F81 | 1.60E-06 | M252Y/T256E/N434A |
| F82 | 1.10E-06 | T256Q/N434W |
| F83 | 2.60E-06 | T256Q/N434Y |
| F84 | 2.80E-07 | M252W/T256Q/N434W |
| F85 | 5.50E-07 | M252W/T256Q/N434Y |
| F86 | 1.50E-06 | S254T/T256Q/N434W |
| F87 | 4.30E-06 | S254T/T256Q/N434Y |
| F88 | 1.90E-07 | M252Y/S254T/T256Q/N434W |
| F89 | 3.60E-07 | M252Y/S254T/T256Q/N434Y |
| F90 | 1.90E-08 | M252Y/T256E/V308P/N434W |
| F91 | 4.80E-08 | M252Y/V308P/M428L/N434Y |
| F92 | 1.10E-08 | M252Y/S254T/T256E/V308P/M428L/N434W |
| F93 | 7.40E-07 | M252W/M428L/N434W |
| F94 | 3.70E-07 | P257L/M428L/N434Y |
| F95 | 2.60E-07 | M252Y/S254T/T256E/M428L/N434F |
| F99 | 6.20E-07 | M252Y/T256E/N434H |
| F101 | 1.10E-07 | M252W/T256Q/P257L/N434Y |
| F103 | 4.40E-08 | P238A/M252Y/V308P/N434Y |
| F104 | 3.70E-08 | M252Y/D265A/V308P/N434Y |
| F105 | 7.50E-08 | M252Y/T307A/V308P/N434Y |
| F106 | 3.70E-08 | M252Y/V303A/V308P/N434Y |
| F107 | 3.40E-08 | M252Y/V308P/D376A/N434Y |
| F108 | 4.10E-08 | M252Y/V305A/V308P/N434Y |
| F109 | 3.20E-08 | M252Y/V308P/Q311A/N434Y |
| F111 | 3.20E-08 | M252Y/V308P/K317A/N434Y |
| F112 | 6.40E-08 | M252Y/V308P/E380A/N434Y |
| F113 | 3.20E-08 | M252Y/V308P/E382A/N434Y |
| F114 | 3.80E-08 | M252Y/V308P/S424A/N434Y |
| F115 | 6.60E-06 | T307A/N434A |
| F116 | 8.70E-06 | E380A/N434A |
| F118 | 1.40E-05 | M428L |

TABLE 13-2-continued

| | | |
|---|---|---|
| F119 | 5.40E−06 | T250Q/M428L |
| F120 | 6.30E−08 | P257L/V308P/M428L/N434Y |
| F121 | 1.50E−08 | M252Y/T256E/V308P/M428L/N434W |
| F122 | 1.20E−07 | M252Y/T256E/M428L/N434W |
| F123 | 3.00E−08 | M252Y/T256E/V308P/N434Y |
| F124 | 2.90E−07 | M252Y/T256E/M428L/N434Y |
| F125 | 2.40E−08 | M252Y/S254T/T256E/V308P/M428L/N434Y |
| F128 | 1.70E−07 | P257L/M428L/N434W |
| F129 | 2.20E−07 | P257A/M428L/N434Y |
| F131 | 3.00E−06 | P257G/M428L/N434Y |
| F132 | 2.10E−07 | P257I/M428L/N434Y |
| F133 | 4.10E−07 | P257M/M428L/N434Y |
| F134 | 2.70E−07 | P257N/M428L/N434Y |
| F135 | 7.50E−07 | P257S/M428L/N434Y |
| F136 | 3.80E−07 | P257T/M428L/N434Y |
| F137 | 4.60E−07 | P257V/M428L/N434Y |
| F139 | 1.50E−08 | M252W/V308P/N434W |
| F140 | 3.60E−08 | S239K/M252Y/V308P/N434Y |
| F141 | 3.50E−08 | M252Y/S298G/V308P/N434Y |
| F142 | 3.70E−08 | M252Y/D270F/V308P/N434Y |
| F143 | 2.00E−07 | M252Y/V308A/N434Y |
| F145 | 5.30E−08 | M252Y/V308F/N434Y |

Table 13-3 is the continuation of Table 13-2.

TABLE 13-3

| | | |
|---|---|---|
| F147 | 2.40E−07 | M252Y/V308I/N434Y |
| F149 | 1.90E−07 | M252Y/V308L/N434Y |
| F150 | 2.00E−07 | M252Y/V308M/N434Y |
| F152 | 2.70E−07 | M252Y/V308Q/N434Y |
| F154 | 1.80E−07 | M252Y/V308T/N434Y |
| F157 | 1.50E−07 | P257A/V308P/M428L/N434Y |
| F158 | 5.90E−08 | P257T/V308P/M428L/N434Y |
| F159 | 4.40E−08 | P257V/V308P/M428L/N434Y |
| F160 | 8.50E−07 | M252W/M428I/N434Y |
| F162 | 1.60E−07 | M252W/M428Y/N434Y |
| F163 | 4.20E−07 | M252W/M428F/N434Y |
| F164 | 3.70E−07 | P238A/M252W/N434Y |
| F165 | 2.90E−07 | M252W/D265A/N434Y |
| F166 | 1.50E−07 | M252W/T307Q/N434Y |
| F167 | 2.90E−07 | M252W/V303A/N434Y |
| F168 | 3.20E−07 | M252W/D376A/N434Y |
| F169 | 2.90E−07 | M252W/V305A/N434Y |
| F170 | 1.70E−07 | M252W/Q311A/N434Y |
| F171 | 1.90E−07 | M252W/D312A/N434Y |
| F172 | 2.20E−07 | M252W/K317A/N434Y |
| F173 | 7.70E−07 | M252W/E380A/N434Y |
| F174 | 3.40E−07 | M252W/E382A/N434Y |
| F175 | 2.70E−07 | M252W/S424A/N434Y |
| F176 | 2.90E−07 | S239K/M252W/N434Y |
| F177 | 2.80E−07 | M252W/S298G/N434Y |
| F178 | 2.70E−07 | M252W/D270F/N434Y |
| F179 | 3.10E−07 | M252W/N325G/N434Y |
| F182 | 6.60E−08 | P257A/M428L/N434W |
| F183 | 2.20E−07 | P257T/M428L/N434W |
| F184 | 2.70E−07 | P257V/M428L/N434W |
| F185 | 2.60E−07 | M252W/I332V/N434Y |
| F188 | 3.00E−06 | P257I/Q311I |
| F189 | 1.90E−07 | M252Y/T307A/N434Y |
| F190 | 1.10E−07 | M252Y/T307Q/N434Y |
| F191 | 1.60E−07 | P257L/T307A/M428L/N434Y |
| F192 | 1.10E−07 | P257A/T307A/M428L/N434Y |
| F193 | 8.50E−08 | P257T/T307A/M428L/N434Y |
| F194 | 1.20E−07 | P257V/T307A/M428L/N434Y |
| F195 | 5.60E−08 | P257L/T307Q/M428L/N434Y |
| F196 | 3.50E−08 | P257A/T307Q/M428L/N434Y |
| F197 | 3.30E−08 | P257T/T307Q/M428L/N434Y |
| F198 | 4.80E−08 | P257V/T307Q/M428L/N434Y |
| F201 | 2.10E−07 | M252Y/T307D/N434Y |
| F203 | 2.40E−07 | M252Y/T307F/N434Y |
| F204 | 2.10E−07 | M252Y/T307G/N434Y |
| F205 | 2.00E−07 | M252Y/T307H/N434Y |
| F206 | 2.30E−07 | M252Y/T307I/N434Y |
| F207 | 9.40E−07 | M252Y/T307K/N434Y |
| F208 | 3.90E−07 | M252Y/T307L/N434Y |
| F209 | 1.30E−07 | M252Y/T307M/N434Y |
| F210 | 2.90E−07 | M252Y/T307N/N434Y |

TABLE 13-3-continued

| | | |
|---|---|---|
| F211 | 2.40E−07 | M252Y/T307P/N434Y |
| F212 | 6.80E−07 | M252Y/T307R/N434Y |
| F213 | 2.30E−07 | M252Y/T307S/N434Y |
| F214 | 1.70E−07 | M252Y/T307V/N434Y |
| F215 | 9.60E−08 | M252Y/T307W/N434Y |
| F216 | 2.30E−07 | M252Y/T307Y/N434Y |
| F217 | 2.30E−07 | M252Y/K334L/N434Y |
| F218 | 2.60E−07 | M252Y/G385H/N434Y |
| F219 | 2.50E−07 | M252Y/T289H/N434Y |
| F220 | 2.60E−07 | M252Y/Q311H/N434Y |

Table 13-4 is the continuation of Table 13-3.

TABLE 13-4

| | | |
|---|---|---|
| F221 | 3.10E−07 | M252Y/D312H/N434Y |
| F222 | 3.40E−07 | M252Y/N315H/N434Y |
| F223 | 2.70E−07 | M252Y/K360H/N434Y |
| F225 | 1.50E−06 | M252Y/L314R/N434Y |
| F226 | 5.40E−07 | M252Y/L314K/N434Y |
| F227 | 1.20E−07 | M252Y/N286E/N434Y |
| F228 | 2.30E−07 | M252Y/L309E/N434Y |
| F229 | 5.10E−07 | M252Y/R255E/N434Y |
| F230 | 2.50E−07 | M252Y/P387E/N434Y |
| F236 | 8.90E−07 | K248I/M428L/N434Y |
| F237 | 2.30E−07 | M252Y/M428A/N434Y |
| F238 | 7.40E−07 | M252Y/M428D/N434Y |
| F240 | 7.20E−07 | M252Y/M428F/N434Y |
| F241 | 1.50E−06 | M252Y/M428G/N434Y |
| F242 | 8.50E−07 | M252Y/M428H/N434Y |
| F243 | 1.80E−07 | M252Y/M428I/N434Y |
| F244 | 1.30E−06 | M252Y/M428K/N434Y |
| F245 | 4.70E−07 | M252Y/M428N/N434Y |
| F246 | 1.10E−06 | M252Y/M428P/N434Y |
| F247 | 4.40E−07 | M252Y/M428Q/N434Y |
| F249 | 6.40E−07 | M252Y/M428S/N434Y |
| F250 | 2.90E−07 | M252Y/M428T/N434Y |
| F251 | 1.90E−07 | M252Y/M428V/N434Y |
| F252 | 1.00E−06 | M252Y/M428W/N434Y |
| F253 | 7.10E−07 | M252Y/M428Y/N434Y |
| F254 | 7.50E−08 | M252W/T307Q/M428Y/N434Y |
| F255 | 1.10E−07 | M252W/Q311A/M428Y/N434Y |
| F256 | 5.40E−08 | M252W/T307Q/Q311A/M428Y/N434Y |
| F257 | 5.00E−07 | M252Y/T307A/M428Y/N434Y |
| F258 | 3.20E−07 | M252Y/T307Q/M428Y/N434Y |
| F259 | 2.80E−07 | M252Y/D270F/N434Y |
| F260 | 1.30E−07 | M252Y/T307A/Q311A/N434Y |
| F261 | 8.40E−08 | M252Y/T307Q/Q311A/N434Y |
| F262 | 1.90E−07 | M252Y/T307A/Q311H/N434Y |
| F263 | 1.10E−07 | M252Y/T307Q/Q311H/N434Y |
| F264 | 2.80E−07 | M252Y/E382A/N434Y |
| F265 | 6.80E−07 | M252Y/E382A/M428Y/N434Y |
| F266 | 4.70E−07 | M252Y/T307A/E382A/M428Y/N434Y |
| F267 | 3.20E−07 | M252Y/T307Q/E382A/M428Y/N434Y |
| F268 | 6.30E−07 | P238A/M252Y/M428F/N434Y |
| F269 | 5.20E−07 | M252Y/V305A/M428F/N434Y |
| F270 | 6.60E−07 | M252Y/N325G/M428F/N434Y |
| F271 | 6.90E−07 | M252Y/D376A/M428F/N434Y |
| F272 | 6.80E−07 | M252Y/E380A/M428F/N434Y |
| F273 | 6.50E−07 | M252Y/E382A/M428F/N434Y |
| F274 | 7.60E−07 | M252Y/E380A/E382A/M428F/N434Y |
| F275 | 4.20E−08 | S239K/M252Y/V308P/E382A/N434Y |
| F276 | 4.10E−08 | M252Y/D270F/V308P/E382A/N434Y |
| F277 | 1.30E−07 | S239K/M252Y/V308P/M428Y/N434Y |
| F278 | 3.00E−08 | M252Y/T307Q/V308P/E382A/N434Y |
| F279 | 6.10E−08 | M252Y/V308P/Q311H/E382A/N434Y |
| F280 | 4.10E−08 | S239K/M252Y/D270F/V308P/N434Y |
| F281 | 9.20E−08 | M252Y/V308P/E382A/M428F/N434Y |
| F282 | 2.90E−08 | M252Y/V308P/E382A/M428L/N434Y |
| F283 | 1.00E−07 | M252Y/V308P/E382A/M428Y/N434Y |
| F284 | 1.00E−07 | M252Y/V308P/M428Y/N434Y |
| F285 | 9.90E−08 | M252Y/V308P/M428F/N434Y |
| F286 | 1.20E−07 | S239K/M252Y/V308P/E382A/M428Y/N434Y |
| F287 | 1.00E−07 | M252Y/V308P/E380A/E382A/M428F/N434Y |
| F288 | 1.90E−07 | M252Y/T256E/E382A/N434Y |
| F289 | 4.80E−07 | M252Y/T256E/M428Y/N434Y |

Table 13-5 is the continuation of Table 13-4.

TABLE 13-5

| | | |
|---|---|---|
| F290 | 4.60E−07 | M252Y/T256E/E382A/M428Y/N434Y |
| F292 | 2.30E−08 | S239K/M252Y/V308P/E382A/M428I/N434Y |
| F293 | 5.30E−08 | M252Y/V308P/E380A/E382A/M428I/N434Y |
| F294 | 1.10E−07 | S239K/M252Y/V308P/M428F/N434Y |
| F295 | 6.80E−07 | S239K/M252Y/E380A/E382A/M428F/N434Y |
| F296 | 4.90E−07 | M252Y/Q311A/M428Y/N434Y |
| F297 | 5.10E−07 | M252Y/D312A/M428Y/N434Y |
| F298 | 4.80E−07 | M252Y/Q311A/D312A/M428Y/N434Y |
| F299 | 9.40E−08 | S239K/M252Y/V308P/Q311A/M428Y/N434Y |
| F300 | 8.30E−08 | S239K/M252Y/V308P/D312A/M428Y/N434Y |
| F301 | 7.20E−08 | S239K/M252Y/V308P/Q311A/D312A/M428Y/N434Y |
| F302 | 1.90E−07 | M252Y/T256E/T307P/N434Y |
| F303 | 6.70E−07 | M252Y/T307P/M428Y/N434Y |
| F304 | 1.60E−08 | M252W/V308P/M428Y/N434Y |
| F305 | 2.70E−08 | M252Y/T256E/V308P/E382A/N434Y |
| F306 | 3.60E−08 | M252W/V308P/E382A/N434Y |
| F307 | 3.60E−08 | S239K/M252W/V308P/E382A/N434Y |
| F308 | 1.90E−08 | S239K/M252W/V308P/E382A/M428Y/N434Y |
| F310 | 9.40E−08 | S239K/M252W/V308P/E382A/M428I/N434Y |
| F311 | 2.80E−08 | S239K/M252W/V308P/M428F/N434Y |
| F312 | 4.50E−07 | S239K/M252W/E380A/E382A/M428F/N434Y |
| F313 | 6.50E−07 | S239K/M252Y/T307P/M428Y/N434Y |
| F314 | 3.20E−07 | M252Y/T256E/Q311A/D312A/M428Y/N434Y |
| F315 | 6.80E−07 | S239K/M252Y/M428Y/N434Y |
| F316 | 7.00E−07 | S239K/M252Y/D270F/M428Y/N434Y |
| F317 | 1.10E−07 | S239K/M252Y/D270F/V308P/M428Y/N434Y |
| F318 | 1.80E−08 | S239K/M252Y/V308P/M428I/N434Y |
| F320 | 2.00E−08 | S239K/M252Y/V308P/N325G/E382A/M428I/N434Y |
| F321 | 3.20E−08 | S239K/M252Y/D270F/V308P/N325G/N434Y |
| F322 | 9.20E−08 | S239K/M252Y/D270F/T307P/V308P/N434Y |
| F323 | 2.70E−08 | S239K/M252Y/T256E/D270F/V308P/N434Y |
| F324 | 2.80E−08 | S239K/M252Y/D270F/T307Q/V308P/N434Y |
| F325 | 2.10E−08 | S239K/M252Y/D270F/T307Q/V308P/Q311A/N434Y |
| F326 | 7.50E−08 | S239K/M252Y/D270F/T307Q/Q311A/N434Y |
| F327 | 6.50E−08 | S239K/M252Y/T256E/D270F/T307Q/Q311A/N434Y |
| F328 | 1.90E−08 | S239K/M252Y/D270F/V308P/M428I/N434Y |
| F329 | 1.20E−08 | S239K/M252Y/D270F/N286E/V308P/N434Y |
| F330 | 3.60E−08 | S239K/M252Y/D270F/V308P/L309E/N434Y |
| F331 | 3.00E−08 | S239K/M252Y/D270F/V308P/P387E/N434Y |
| F333 | 7.40E−08 | S239K/M252Y/D270F/T307Q/L309E/Q311A/N434Y |
| F334 | 1.90E−08 | S239K/M252Y/D270F/V308P/N325G/M428I/N434Y |
| F335 | 1.50E−08 | S239K/M252Y/T256E/D270F/V308P/M428I/N434Y |
| F336 | 1.40E−08 | S239K/M252Y/D270F/T307Q/V308P/Q311A/ M428I/N434Y |
| F337 | 5.60E−08 | S239K/M252Y/D270F/T307Q/Q311A/M428I/N434Y |
| F338 | 7.70E−09 | S239K/M252Y/D270F/N286E/V308P/M428I/N434Y |
| F339 | 1.90E−08 | S239K/M252Y/D270F/V308P/L309E/M428I/N434Y |
| F343 | 3.20E−08 | S239K/M252Y/D270F/V308P/M428L/N434Y |
| F344 | 3.00E−08 | S239K/M252Y/V308P/M428L/N434Y |
| F349 | 1.50E−07 | S239K/M252Y/V308P/L309P/M428L/N434Y |
| F350 | 1.70E−07 | S239K/M252Y/V308P/L309R/M428L/N434Y |
| F352 | 6.00E−07 | S239K/M252Y/L309P/M428L/N434Y |
| F353 | 1.10E−06 | S239K/M252Y/L309R/M428L/N434Y |
| F354 | 2.80E−08 | S239K/M252Y/T307Q/V308P/M428L/N434Y |
| F356 | 3.40E−08 | S239K/M252Y/D270F/V308P/L309E/P387E/N434Y |
| F357 | 1.60E−08 | S239K/M252Y/T256E/D270F/V308P/N325G/ M428I/N434Y |
| F358 | 1.00E−07 | S239K/M252Y/T307Q/N434Y |
| F359 | 4.20E−07 | P257V/T307Q/M428I/N434Y |
| F360 | 1.30E−06 | P257V/T307Q/M428V/N434Y |
| F362 | 5.40E−08 | P257V/T307Q/N325G/M428L/N434Y |
| F363 | 4.10E−08 | P257V/T307Q/Q311A/M428L/N434Y |
| F364 | 3.50E−08 | P257V/T307Q/Q311A/N325G/M428L/N434Y |

Table 13-6 is the continuation of Table 13-5.

TABLE 13-6

| | | |
|---|---|---|
| F365 | 5.10E−08 | P257V/V305A/T307Q/M428L/N434Y |
| F367 | 1.50E−08 | S239K/M252Y/E258H/D270F/T307Q/V308P/Q311A/ N434Y |
| F368 | 2.00E−08 | S239K/M252Y/D270F/V308P/N325G/E382A/M428I/ N434Y |
| F369 | 7.50E−08 | M252Y/P257V/T307Q/M428I/N434Y |
| F372 | 1.30E−08 | S239K/M252W/V308P/M428Y/N434Y |
| F373 | 1.10E−08 | S239K/M252W/V308P/Q311A/M428Y/N434Y |

TABLE 13-6-continued

| | | |
|---|---|---|
| F374 | 1.20E−08 | S239K/M252W/T256E/V308P/M428Y/N434Y |
| F375 | 5.50E−09 | S239K/M252W/N286E/V308P/M428Y/N434Y |
| F376 | 9.60E−09 | S239K/M252Y/T256E/D270F/N286E/V308P/N434Y |
| F377 | 1.30E−07 | S239K/M252W/T307P/M428Y/N434Y |
| F379 | 9.00E−09 | S239K/M252W/T256E/V308P/Q311A/M428Y/N434Y |
| F380 | 5.60E−09 | S239K/M252W/T256E/N286E/V308P/M428Y/N434Y |
| F381 | 1.10E−07 | P257V/T307A/Q311A/M428L/N434Y |
| F382 | 8.70E−08 | P257V/V305A/T307A/M428L/N434Y |
| F386 | 3.20E−08 | M252Y/V308P/L309E/N434Y |
| F387 | 1.50E−07 | M252Y/V308P/L309D/N434Y |
| F388 | 7.00E−08 | M252Y/V308P/L309A/N434Y |
| F389 | 1.70E−08 | M252W/V308P/L309E/M428Y/N434Y |
| F390 | 6.80E−08 | M252W/V308P/L309D/M428Y/N434Y |
| F391 | 3.60E−08 | M252W/V308P/L309A/M428Y/N434Y |
| F392 | 6.90E−09 | S239K/M252Y/N286E/V308P/M428I/N434Y |
| F393 | 1.20E−08 | S239K/M252Y/N286E/V308P/N434Y |
| F394 | 5.30E−08 | S239K/M252Y/T307Q/Q311A/M428I/N434Y |
| F395 | 2.40E−08 | S239K/M252Y/T256E/V308P/N434Y |
| F396 | 2.00E−08 | S239K/M252Y/D270F/N286E/T307Q/Q311A/M428I/ N434Y |
| F397 | 4.50E−08 | S239K/M252Y/D270F/T307Q/Q311A/P387E/M428I/ N434Y |
| F398 | 4.40E−09 | S239K/M252Y/D270F/N286E/T307Q/V308P/Q311A/ M428I/N434Y |
| F399 | 6.50E−09 | S239K/M252Y/D270F/N286E/T307Q/V308P/M428I/ N434Y |
| F400 | 6.10E−09 | S239K/M252Y/D270F/N286E/V308P/Q311A/M428I/ N434Y |
| F401 | 6.90E−09 | S239K/M252Y/D270F/N286E/V308P/P387E/M428I/ N434Y |
| F402 | 2.30E−08 | P257V/T307Q/M428L/N434W |
| F403 | 5.10E−08 | P257V/T307A/M428L/N434W |
| F404 | 9.40E−08 | P257A/T307Q/L309P/M428L/N434Y |
| F405 | 1.70E−07 | P257V/T307Q/L309P/M428L/N434Y |
| F406 | 1.50E−07 | P257A/T307Q/L309R/M428L/N434Y |
| F407 | 1.60E−07 | P257V/T307Q/L309R/M428L/N434Y |
| F408 | 2.50E−07 | P257V/N286E/M428L/N434Y |
| F409 | 2.00E−07 | P257V/P387E/M428L/N434Y |
| F410 | 2.20E−07 | P257V/T307H/M428L/N434Y |
| F411 | 1.30E−07 | P257V/T307N/M428L/N434Y |
| F412 | 8.80E−08 | P257V/T307G/M428L/N434Y |
| F413 | 1.20E−07 | P257V/T307P/M428L/N434Y |
| F414 | 1.10E−07 | P257V/T307S/M428L/N434Y |
| F415 | 5.60E−08 | P257V/N286E/T307A/M428L/N434Y |
| F416 | 9.40E−08 | P257V/T307A/P387E/M428L/N434Y |
| F418 | 6.20E−07 | S239K/M252Y/T307P/N325G/M428Y/N434Y |
| F419 | 1.60E−07 | M252Y/T307A/Q311H/K360H/N434Y |
| F420 | 1.50E−07 | M252Y/T307A/Q311H/P387E/N434Y |
| F421 | 1.30E−07 | M252Y/T307A/Q311H/M428A/N434Y |
| F422 | 1.80E−07 | M252Y/T307A/Q311H/E382A/N434Y |
| F423 | 8.40E−08 | M252Y/T307W/Q311H/N434Y |
| F424 | 9.40E−08 | S239K/P257A/V308P/M428L/N434Y |
| F425 | 8.00E−08 | P257A/V308P/L309E/M428L/N434Y |
| F426 | 8.40E−08 | P257V/T307Q/N434Y |
| F427 | 1.10E−07 | M252Y/P257V/T307Q/M428V/N434Y |
| F428 | 8.00E−08 | M252Y/P257V/T307Q/M428L/N434Y |
| F429 | 3.70E−08 | M252Y/P257V/T307Q/N434Y |
| F430 | 8.10E−08 | M252Y/P257V/T307Q/M428Y/N434Y |
| F431 | 6.50E−08 | M252Y/P257V/T307Q/M428F/N434Y |
| F432 | 9.20E−07 | P257V/T307Q/Q311A/N325G/M428V/N434Y |

Table 13-7 is the continuation of Table 13-6.

TABLE 13-7

| | | |
|---|---|---|
| F433 | 6.00E−08 | P257V/T307Q/Q311A/N325G/N434Y |
| F434 | 2.00E−08 | P257V/T307Q/Q311A/N325G/M428Y/N434Y |
| F435 | 2.50E−08 | P257V/T307Q/Q311A/N325G/M428F/N434Y |
| F436 | 2.50E−07 | P257A/T307Q/M428V/N434Y |
| F437 | 5.70E−08 | P257A/T307Q/N434Y |
| F438 | 3.60E−08 | P257A/T307Q/M428Y/N434Y |
| F439 | 4.00E−08 | P257A/T307Q/M428F/N434Y |
| F440 | 1.50E−08 | P257V/N286E/T307Q/Q311A/N325G/M428L/N434Y |
| F441 | 1.80E−07 | P257A/Q311A/M428L/N434Y |
| F442 | 2.00E−07 | P257A/Q311H/M428L/N434Y |
| F443 | 5.50E−08 | P257A/T307Q/Q311A/M428L/N434Y |
| F444 | 1.40E−07 | P257A/T307A/Q311A/M428L/N434Y |
| F445 | 6.20E−08 | P257A/T307Q/Q311H/M428L/N434Y |

TABLE 13-7-continued

| | | |
|---|---|---|
| F446 | 1.10E−07 | P257A/T307A/Q311H/M428L/N434Y |
| F447 | 1.40E−08 | P257A/N286E/T307Q/M428L/N434Y |
| F448 | 5.30E−08 | P257A/N286E/T307A/M428L/N434Y |
| F449 | 5.70E−07 | S239K/M252Y/D270F/T307P/N325G/M428Y/N434Y |
| F450 | 5.20E−07 | S239K/M252Y/T307P/L309E/N325G/M428Y/N434Y |
| F451 | 1.00E−07 | P257S/T307A/M428L/N434Y |
| F452 | 1.40E−07 | P257M/T307A/M428L/N434Y |
| F453 | 7.80E−08 | P257N/T307A/M428L/N434Y |
| F454 | 9.60E−08 | P257I/T307A/M428L/N434Y |
| F455 | 2.70E−08 | P257V/T307Q/M428Y/N434Y |
| F456 | 3.40E−08 | P257V/T307Q/M428F/N434Y |
| F457 | 4.00E−08 | S239K/P257V/V308P/M428L/N434Y |
| F458 | 1.50E−08 | P257V/T307Q/V308P/N325G/M428L/N434Y |
| F459 | 1.30E−08 | P257V/T307Q/V308P/Q311A/N325G/M428L/N434Y |
| F460 | 4.70E−08 | P257V/T307A/V308P/N325G/M428L/N434Y |
| F462 | 8.50E−08 | P257A/V308P/N325G/M428L/N434Y |
| F463 | 1.30E−07 | P257A/T307A/V308P/M428L/N434Y |
| F464 | 5.50E−08 | P257A/T307Q/V308P/M428L/N434Y |
| F465 | 2.10E−08 | P257V/N286E/T307Q/N325G/M428L/N434Y |
| F466 | 3.50E−07 | T256E/P257V/N434Y |
| F467 | 5.70E−07 | T256E/P257T/N434Y |
| F468 | 5.70E−08 | S239K/P257T/V308P/M428L/N434Y |
| F469 | 5.60E−08 | P257T/V308P/N325G/M428L/N434Y |
| F470 | 5.40E−08 | T256E/P257T/V308P/N325G/M428L/N434Y |
| F471 | 6.60E−08 | P257T/V308P/N325G/E382A/M428L/N434Y |
| F472 | 5.40E−08 | P257T/V308P/N325G/P387E/M428L/N434Y |
| F473 | 4.50E−07 | P257T/V308P/L309P/N325G/M428L/N434Y |
| F474 | 3.50E−07 | P257T/V308P/L309R/N325G/M428L/N434Y |
| F475 | 4.30E−08 | T256E/P257V/T307Q/M428L/N434Y |
| F476 | 5.50E−08 | P257V/T307Q/E382A/M428L/N434Y |
| F477 | 4.30E−08 | P257V/T307Q/P387E/M428L/N434Y |
| F480 | 3.90E−08 | P257L/V308P/N434Y |
| F481 | 5.60E−08 | P257T/T307Q/N434Y |
| F482 | 7.00E−08 | P257V/T307Q/N325G/N434Y |
| F483 | 5.70E−08 | P257V/T307Q/Q311A/N434Y |
| F484 | 6.20E−08 | P257V/V305A/T307Q/N434Y |
| F485 | 9.70E−08 | P257V/N286E/T307A/N434Y |
| F486 | 3.40E−07 | P257V/T307Q/L309R/Q311H/M428L/N434Y |
| F488 | 3.50E−08 | P257V/V308P/N325G/M428L/N434Y |
| F490 | 7.50E−08 | S239K/P257V/V308P/Q311H/M428L/N434Y |
| F492 | 9.80E−08 | P257V/V305A/T307A/N325G/M428L/N434Y |
| F493 | 4.90E−07 | S239K/D270F/T307P/N325G/M428Y/N434Y |
| F497 | 3.10E−06 | P257T/T307A/M428V/N434Y |
| F498 | 1.30E−06 | P257A/M428V/N434Y |
| F499 | 5.20E−07 | P257A/T307A/M428V/N434Y |
| F500 | 4.30E−08 | P257S/T307Q/M428L/N434Y |
| F506 | 1.90E−07 | P257V/N297A/T307Q/M428L/N434Y |

Table 13-8 is the continuation of Table 13-7.

TABLE 13-8

| | | |
|---|---|---|
| F507 | 5.10E−08 | P257V/N286A/T307Q/M428L/N434Y |
| F508 | 1.10E−07 | P257V/T307Q/N315A/M428L/N434Y |
| F509 | 5.80E−08 | P257V/T307Q/N384A/M428L/N434Y |
| F510 | 5.30E−08 | P257V/T307Q/N389A/M428L/N434Y |
| F511 | 4.20E−07 | P257V/N434Y |
| F512 | 5.80E−07 | P257T/N434Y |
| F517 | 3.10E−07 | P257V/N286E/N434Y |
| F518 | 4.20E−07 | P257T/N286E/N434Y |
| F519 | 2.60E−08 | P257V/N286E/T307Q/N434Y |
| F521 | 1.10E−08 | P257V/N286E/T307Q/M428Y/N434Y |
| F523 | 2.60E−08 | P257V/V305A/T307Q/M428Y/N434Y |
| F526 | 1.90E−08 | P257T/T307Q/M428Y/N434Y |
| F527 | 9.40E−09 | P257V/T307Q/V308P/N325G/M428Y/N434Y |
| F529 | 2.50E−08 | P257T/T307Q/M428F/N434Y |
| F533 | 1.20E−08 | P257A/N286E/T307Q/M428F/N434Y |
| F534 | 1.20E−08 | P257A/N286E/T307Q/M428Y/N434Y |
| F535 | 3.90E−08 | T250A/P257V/T307Q/M428L/N434Y |
| F538 | 9.90E−08 | T250F/P257V/T307Q/M428L/N434Y |
| F541 | 6.00E−08 | T250I/P257V/T307Q/M428L/N434Y |
| F544 | 3.10E−08 | T250M/P257V/T307Q/M428L/N434Y |
| F549 | 5.40E−08 | T250S/P257V/T307Q/M428L/N434Y |
| F550 | 5.90E−08 | T250V/P257V/T307Q/M428L/N434Y |
| F551 | 1.20E−07 | T250W/P257V/T307Q/M428L/N434Y |
| F552 | 1.10E−07 | T250Y/P257V/T307Q/M428L/N434Y |
| F553 | 1.70E−07 | M252Y/Q311A/N434Y |
| F554 | 2.80E−08 | S239K/M252Y/S254T/V308P/N434Y |

TABLE 13-8-continued

| | | |
|---|---|---|
| F556 | 1.50E−06 | M252Y/T307Q/Q311A |
| F559 | 8.00E−08 | M252Y/S254T/N286E/N434Y |
| F560 | 2.80E−08 | M252Y/S254T/V308P/N434Y |
| F561 | 1.40E−07 | M252Y/S254T/T307A/N434Y |
| F562 | 8.30E−08 | M252Y/S254T/T307Q/N434Y |
| F563 | 1.30E−07 | M252Y/S254T/Q311A/N434Y |
| F564 | 1.90E−07 | M252Y/S254T/Q311H/N434Y |
| F565 | 9.20E−08 | M252Y/S254T/T307A/Q311A/N434Y |
| F566 | 6.10E−08 | M252Y/S254T/T307Q/Q311A/N434Y |
| F567 | 2.20E−07 | M252Y/S254T/M428I/N434Y |
| F568 | 1.10E−07 | M252Y/T256E/T307A/Q311H/N434Y |
| F569 | 2.00E−07 | M252Y/T256Q/T307A/Q311H/N434Y |
| F570 | 1.30E−07 | M252Y/S254T/T307A/Q311H/N434Y |
| F571 | 8.10E−08 | M252Y/N286E/T307A/Q311H/N434Y |
| F572 | 1.00E−07 | M252Y/T307A/Q311H/M428I/N434Y |
| F576 | 1.60E−06 | M252Y/T256E/T307Q/Q311H |
| F577 | 1.30E−06 | M252Y/N286E/T307A/Q311A |
| F578 | 5.70E−07 | M252Y/N286E/T307Q/Q311A |
| F580 | 8.60E−07 | M252Y/N286E/T307Q/Q311H |
| F581 | 7.20E−08 | M252Y/T256E/N286E/N434Y |
| F582 | 7.50E−07 | S239K/M252Y/V308P |
| F583 | 7.80E−07 | S239K/M252Y/V308P/E382A |
| F584 | 6.30E−07 | S239K/M252Y/T256E/V308P |
| F585 | 2.90E−07 | S239K/M252Y/N286E/V308P |
| F586 | 1.40E−07 | S239K/M252Y/N286E/V308P/M428I |
| F587 | 1.90E−07 | M252Y/N286E/M428L/N434Y |
| F592 | 2.00E−07 | M252Y/S254T/E382A/N434Y |
| F593 | 3.10E−08 | S239K/M252Y/S254T/V308P/M428I/N434Y |
| F594 | 1.60E−08 | S239K/M252Y/T256E/V308P/M428I/N434Y |
| F595 | 1.80E−07 | S239K/M252Y/M428I/N434Y |
| F596 | 4.00E−07 | M252Y/D312A/E382A/M428Y/N434Y |
| F597 | 2.20E−07 | M252Y/E382A/P387E/N434Y |
| F598 | 1.40E−07 | M252Y/D312A/P387E/N434Y |
| F599 | 5.20E−07 | M252Y/P387E/M428Y/N434Y |

Table 13-9 is the continuation of Table 13-8.

TABLE 13-9

| | | |
|---|---|---|
| F600 | 2.80E−07 | M252Y/T256Q/E382A/N434Y |
| F601 | 9.60E−09 | M252Y/N286E/V308P/N434Y |
| F608 | | G236A/S239D/I332E |
| F611 | 2.80E−07 | M252Y/V305T/T307P/V308I/L309A/N434Y |
| F612 | 3.60E−07 | M252Y/T307P/V308I/L309A/N434Y |
| F613 | | S239D/A330L/I332E |
| F616 | | S239D/K326D/L328Y |
| F617 | 7.40E−07 | S239K/N434W |
| F618 | 6.40E−07 | S239K/V308F/N434Y |
| F619 | 3.10E−07 | S239K/M252Y/N434Y |
| F620 | 2.10E−07 | S239K/M252Y/S254T/N434Y |
| F621 | 1.50E−07 | S239K/M252Y/T307A/Q311H/N434Y |
| F622 | 3.50E−07 | S239K/M252Y/T256Q/N434Y |
| F623 | 1.80E−07 | S239K/M252W/N434W |
| F624 | 1.40E−08 | S239K/P257A/N286E/T307Q/M428L/N434Y |
| F625 | 7.60E−08 | S239K/P257A/T307Q/M428L/N434Y |
| F626 | 1.30E−06 | V308P |
| F629 | 3.90E−08 | M252Y/V279L/V308P/N434Y |
| F630 | 3.70E−08 | S239K/M252Y/V279L/V308P/N434Y |
| F633 | 2.40E−08 | M252Y/V282D/V308P/N434Y |
| F634 | 3.20E−08 | S239K/M252Y/V282D/V308P/N434Y |
| F635 | 4.50E−08 | M252Y/V284K/V308P/N434Y |
| F636 | 4.80E−08 | S239K/M252Y/V284K/V308P/N434Y |
| F637 | 1.50E−07 | M252Y/K288S/V308P/N434Y |
| F638 | 1.40E−07 | S239K/M252Y/K288S/V308P/N434Y |
| F639 | 2.70E−08 | M252Y/V308P/G385R/N434Y |
| F640 | 3.60E−08 | S239K/M252Y/V308P/G385R/N434Y |
| F641 | 3.00E−08 | M252Y/V308P/Q386K/N434Y |
| F642 | 3.00E−08 | S239K/M252Y/V308P/Q386K/N434Y |
| F643 | 3.20E−08 | L235G/G236R/S239K/M252Y/V308P/N434Y |
| F644 | 3.00E−08 | G236R/S239K/M252Y/V308P/N434Y |
| F645 | 3.30E−08 | S239K/M252Y/V308P/L328R/N434Y |
| F646 | 3.80E−08 | S239K/M252Y/N297A/V308P/N434Y |
| F647 | 2.90E−08 | P238D/M252Y/V308P/N434Y |
| F648 | | P238D |
| F649 | 1.20E−07 | S239K/M252Y/N286E/N434Y |
| F650 | 1.70E−07 | S239K/M252Y/T256E/N434Y |
| F651 | 1.80E−07 | S239K/M252Y/Q311A/N434Y |
| F652 | 2.40E−07 | P238D/M252Y/N434Y |

TABLE 13-9-continued

| | | |
|---|---|---|
| F654 | 3.20E−08 | L235K/S239K/M252Y/V308P/N434Y |
| F655 | 3.40E−08 | L235R/S239K/M252Y/V308P/N434Y |
| F656 | 3.30E−08 | G237K/S239K/M252Y/V308P/N434Y |
| F657 | 3.20E−08 | G237R/S239K/M252Y/V308P/N434Y |
| F658 | 3.20E−08 | P238K/S239K/M252Y/V308P/N434Y |
| F659 | 3.00E−08 | P238R/S239K/M252Y/V308P/N434Y |
| F660 | 3.10E−08 | S239K/M252Y/V308P/P329K/N434Y |
| F661 | 3.40E−08 | S239K/M252Y/V308P/P329R/N434Y |
| F663 | 6.40E−09 | S239K/M252Y/N286E/T307Q/V308P/Q311A/N434Y |
| F664 | 3.90E−08 | M252Y/N286A/V308P/N434Y |
| F665 | 2.00E−08 | M252Y/N286D/V308P/N434Y |
| F666 | 2.10E−08 | M252Y/N286F/V308P/N434Y |
| F667 | 3.00E−08 | M252Y/N286G/V308P/N434Y |
| F668 | 4.00E−08 | M252Y/N286H/V308P/N434Y |
| F669 | 3.50E−08 | M252Y/N286I/V308P/N434Y |
| F670 | 2.10E−07 | M252Y/N286K/V308P/N434Y |
| F671 | 2.20E−08 | M252Y/N286L/V308P/N434Y |
| F672 | 2.40E−08 | M252Y/N286M/V308P/N434Y |
| F673 | 2.30E−08 | M252Y/N286P/V308P/N434Y |
| F674 | 3.20E−08 | M252Y/N286Q/V308P/N434Y |
| F675 | 5.10E−08 | M252Y/N286R/V308P/N434Y |

Table 13-10 is the continuation of Table 13-9.

TABLE 13-10

| | | |
|---|---|---|
| F676 | 3.20E−08 | M252Y/N286S/V308P/N434Y |
| F677 | 4.70E−08 | M252Y/N286T/V308P/N434Y |
| F678 | 3.30E−08 | M252Y/N286V/V308P/N434Y |
| F679 | 1.70E−08 | M252Y/N286W/V308P/N434Y |
| F680 | 1.50E−08 | M252Y/N286Y/V308P/N434Y |
| F681 | 4.90E−08 | M252Y/K288A/V308P/N434Y |
| F682 | 8.20E−08 | M252Y/K288D/V308P/N434Y |
| F683 | 5.00E−08 | M252Y/K288E/V308P/N434Y |
| F684 | 5.10E−08 | M252Y/K288F/V308P/N434Y |
| F685 | 5.30E−08 | M252Y/K288G/V308P/N434Y |
| F686 | 4.60E−08 | M252Y/K288H/V308P/N434Y |
| F687 | 4.90E−08 | M252Y/K288I/V308P/N434Y |
| F688 | 2.80E−08 | M252Y/K288L/V308P/N434Y |
| F689 | 4.10E−08 | M252Y/K288M/V308P/N434Y |
| F690 | 1.00E−07 | M252Y/K288N/V308P/N434Y |
| F691 | 3.20E−07 | M252Y/K288P/V308P/N434Y |
| F692 | 3.90E−08 | M252Y/K288Q/V308P/N434Y |
| F693 | 3.60E−08 | M252Y/K288R/V308P/N434Y |
| F694 | 4.70E−08 | M252Y/K288V/V308P/N434Y |
| F695 | 4.00E−08 | M252Y/K288W/V308P/N434Y |
| F696 | 4.40E−08 | M252Y/K288Y/V308P/N434Y |
| F697 | 3.10E−08 | S239K/M252Y/V308P/N325G/N434Y |
| F698 | 2.20E−08 | M252Y/N286E/T307Q/Q311A/N434Y |
| F699 | 2.30E−08 | S239K/M252Y/N286E/T307Q/Q311A/N434Y |
| F700 | 5.20E−08 | M252Y/V308P/L328E/N434Y |
| F705 | 7.10E−09 | M252Y/N286E/V308P/M428I/N434Y |
| F706 | 1.80E−08 | M252Y/N286E/T307Q/Q311A/M428I/N434Y |
| F707 | 5.90E−09 | M252Y/N286E/T307Q/V308P/Q311A/N434Y |
| F708 | 4.10E−09 | M252Y/N286E/T307Q/V308P/Q311A/M428I/N434Y |
| F709 | 2.00E−08 | S239K/M252Y/N286E/T307Q/Q311A/M428I/N434Y |
| F710 | 1.50E−08 | P238D/M252Y/N286E/T307Q/Q311A/M428I/N434Y |
| F711 | 6.50E−08 | S239K/M252Y/T307Q/Q311A/N434Y |
| F712 | 6.00E−08 | P238D/M252Y/T307Q/Q311A/N434Y |
| F713 | 2.00E−08 | P238D/M252Y/N286E/T307Q/Q311A/N434Y |
| F714 | 2.30E−07 | P238D/M252Y/N325S/N434Y |
| F715 | 2.30E−07 | P238D/M252Y/N325M/N434Y |
| F716 | 2.70E−07 | P238D/M252Y/N325L/N434Y |
| F717 | 2.60E−07 | P238D/M252Y/N325I/N434Y |
| F718 | 2.80E−07 | P238D/M252Y/Q295M/N434Y |
| F719 | 7.40E−08 | P238D/M252Y/N325G/N434Y |
| F720 | 2.40E−08 | M252Y/T307Q/V308P/Q311A/N434Y |
| F721 | 1.50E−08 | M252Y/T307Q/V308P/Q311A/M428I/N434Y |
| F722 | 2.70E−07 | P238D/M252Y/A327G/N434Y |
| F723 | 2.80E−07 | P238D/M252Y/L328D/N434Y |
| F724 | 2.50E−07 | P238D/M252Y/L328E/N434Y |
| F725 | 4.20E−08 | L235K/G237R/S239K/M252Y/V308P/N434Y |
| F726 | 3.70E−08 | L235K/P238K/S239K/M252Y/V308P/N434Y |
| F729 | 9.20E−07 | T307A/Q311A/N434Y |
| F730 | 6.00E−07 | T307Q/Q311A/N434Y |
| F731 | 8.50E−07 | T307A/Q311H/N434Y |
| F732 | 6.80E−07 | T307Q/Q311H/N434Y |
| F733 | 3.20E−07 | M252Y/L328E/N434Y |

TABLE 13-10-continued

| | | |
|---|---|---|
| F734 | 3.10E−07 | G236D/M252Y/L328E/N434Y |
| F736 | 3.10E−07 | M252Y/S267M/L328E/N434Y |
| F737 | 3.10E−07 | M252Y/S267L/L328E/N434Y |
| F738 | 3.50E−07 | P238D/M252Y/T307P/N434Y |
| F739 | 2.20E−07 | M252Y/T307P/Q311A/N434Y |
| F740 | 2.90E−07 | M252Y/T307P/Q311H/N434Y |
| F741 | 3.10E−07 | P238D/T250A/M252Y/N434Y |
| F744 | 9.90E−07 | P238D/T250F/M252Y/N434Y |

Table 13-11 is the continuation of Table 13-10.

TABLE 13-11

| | | |
|---|---|---|
| F745 | 6.60E−07 | P238D/T250G/M252Y/N434Y |
| F746 | 6.00E−07 | P238D/T250H/M252Y/N434Y |
| F747 | 2.80E−07 | P238D/T250I/M252Y/N434Y |
| F749 | 5.10E−07 | P238D/T250L/M252Y/N434Y |
| F750 | 3.00E−07 | P238D/T250M/M252Y/N434Y |
| F751 | 5.30E−07 | P238D/T250N/M252Y/N434Y |
| F753 | 1.80E−07 | P238D/T250Q/M252Y/N434Y |
| F755 | 3.50E−07 | P238D/T250S/M252Y/N434Y |
| F756 | 3.70E−07 | P238D/T250V/M252Y/N434Y |
| F757 | 1.20E−06 | P238D/T250W/M252Y/N434Y |
| F758 | 1.40E−06 | P238D/T250Y/M252Y/N434Y |
| F759 | | L235K/S239K |
| F760 | | L235R/S239K |
| F761 | 1.10E−06 | P238D/N434Y |
| F762 | 3.60E−08 | L235K/S239K/M252Y/N286E/T307Q/Q311A/N434Y |
| F763 | 3.50E−08 | L235R/S239K/M252Y/N286E/T307Q/Q311A/N434Y |
| F764 | 6.30E−07 | P238D/T307Q/Q311A/N434Y |
| F765 | 8.50E−08 | P238D/M252Y/T307Q/L309E/Q311A/N434Y |
| F766 | 6.00E−07 | T307A/L309E/Q311A/N434Y |
| F767 | 4.30E−07 | T307Q/L309E/Q311A/N434Y |
| F768 | 6.40E−07 | T307A/L309E/Q311H/N434Y |
| F769 | 4.60E−07 | T307Q/L309E/Q311H/N434Y |
| F770 | 3.00E−07 | M252Y/T256A/N434Y |
| F771 | 4.00E−07 | M252Y/E272A/N434Y |
| F772 | 3.80E−07 | M252Y/K274A/N434Y |
| F773 | 3.90E−07 | M252Y/V282A/N434Y |
| F774 | 4.00E−07 | M252Y/N286A/N434Y |
| F775 | 6.20E−07 | M252Y/K338A/N434Y |
| F776 | 3.90E−07 | M252Y/K340A/N434Y |
| F777 | 3.90E−07 | M252Y/E345A/N434Y |
| F779 | 3.90E−07 | M252Y/N361A/N434Y |
| F780 | 3.90E−07 | M252Y/Q362A/N434Y |
| F781 | 3.70E−07 | M252Y/S375A/N434Y |
| F782 | 3.50E−07 | M252Y/Y391A/N434Y |
| F783 | 4.00E−07 | M252Y/D413A/N434Y |
| F784 | 5.00E−07 | M252Y/L309A/N434Y |
| F785 | 7.40E−07 | M252Y/L309H/N434Y |
| F786 | 2.80E−08 | M252Y/S254T/N286E/T307Q/Q311A/N434Y |
| F787 | 8.80E−08 | M252Y/S254T/T307Q/L309E/Q311A/N434Y |
| F788 | 4.10E−07 | M252Y/N315A/N434Y |
| F789 | 1.50E−07 | M252Y/N315D/N434Y |
| F790 | 2.70E−07 | M252Y/N315E/N434Y |
| F791 | 4.40E−07 | M252Y/N315F/N434Y |
| F792 | 4.40E−07 | M252Y/N315G/N434Y |
| F793 | 3.30E−07 | M252Y/N315I/N434Y |
| F794 | 4.10E−07 | M252Y/N315K/N434Y |
| F795 | 3.10E−07 | M252Y/N315L/N434Y |
| F796 | 3.40E−07 | M252Y/N315M/N434Y |
| F798 | 3.50E−07 | M252Y/N315Q/N434Y |
| F799 | 4.10E−07 | M252Y/N315R/N434Y |
| F800 | 3.80E−07 | M252Y/N315S/N434Y |
| F801 | 4.40E−07 | M252Y/N315T/N434Y |
| F802 | 3.30E−07 | M252Y/N315V/N434Y |
| F803 | 3.60E−07 | M252Y/N315W/N434Y |
| F804 | 4.00E−07 | M252Y/N315Y/N434Y |
| F805 | 3.00E−07 | M252Y/N325A/N434Y |
| F806 | 3.10E−07 | M252Y/N384A/N434Y |
| F807 | 3.20E−07 | M252Y/N389A/N434Y |
| F808 | 3.20E−07 | M252Y/N389A/N390A/N434Y |
| F809 | 2.20E−07 | M252Y/S254T/T256S/N434Y |

Table 13-12 is the continuation of Table 13-11.

TABLE 13-12

| | | |
|---|---|---|
| F810 | 2.20E−07 | M252Y/A378V/N434Y |
| F811 | 4.90E−07 | M252Y/E380S/N434Y |
| F812 | 2.70E−07 | M252Y/E382V/N434Y |
| F813 | 2.80E−07 | M252Y/S424E/N434Y |
| F814 | 1.20E−07 | M252Y/N434Y/Y436I |
| F815 | 5.50E−07 | M252Y/N434Y/T437R |
| F816 | 3.60E−07 | P238D/T250V/M252Y/T307P/N434Y |
| F817 | 9.80E−08 | P238D/T250V/M252Y/T307Q/Q311A/N434Y |
| F819 | 1.40E−07 | P238D/M252Y/N286E/N434Y |
| F820 | 3.40E−07 | L235K/S239K/M252Y/N434Y |
| F821 | 3.10E−07 | L235R/S239K/M252Y/N434Y |
| F822 | 1.10E−06 | P238D/T250Y/M252Y/W313Y/N434Y |
| F823 | 1.10E−06 | P238D/T250Y/M252Y/W313F/N434Y |
| F828 | 2.50E−06 | P238D/T250V/M252Y/I253V/N434Y |
| F831 | 1.60E−06 | P238D/T250V/M252Y/R255A/N434Y |
| F832 | 2.60E−06 | P238D/T250V/M252Y/R255D/N434Y |
| F833 | 8.00E−07 | P238D/T250V/M252Y/R255E/N434Y |
| F834 | 8.10E−07 | P238D/T250V/M252Y/R255F/N434Y |
| F836 | 5.00E−07 | P238D/T250V/M252Y/R255H/N434Y |
| F837 | 5.60E−07 | P238D/T250V/M252Y/R255I/N434Y |
| F838 | 4.30E−07 | P238D/T250V/M252Y/R255K/N434Y |
| F839 | 3.40E−07 | P238D/T250V/M252Y/R255L/N434Y |
| F840 | 4.20E−07 | P238D/T250V/M252Y/R255M/N434Y |
| F841 | 1.10E−06 | P238D/T250V/M252Y/R255N/N434Y |
| F843 | 6.60E−07 | P238D/T250V/M252Y/R255Q/N434Y |
| F844 | 1.30E−06 | P238D/T250V/M252Y/R255S/N434Y |
| F847 | 3.40E−07 | P238D/T250V/M252Y/R255W/N434Y |
| F848 | 8.30E−07 | P238D/T250V/M252Y/R255Y/N434Y |
| F849 | 3.30E−07 | M252Y/D280A/N434Y |
| F850 | 2.90E−07 | M252Y/D280E/N434Y |
| F852 | 3.30E−07 | M252Y/D280G/N434Y |
| F853 | 3.20E−07 | M252Y/D280H/N434Y |
| F855 | 3.20E−07 | M252Y/D280K/N434Y |
| F858 | 3.20E−07 | M252Y/D280N/N434Y |
| F860 | 3.30E−07 | M252Y/D280Q/N434Y |
| F861 | 3.20E−07 | M252Y/D280R/N434Y |
| F862 | 3.00E−07 | M252Y/D280S/N434Y |
| F863 | 2.70E−07 | M252Y/D280T/N434Y |
| F867 | 2.80E−07 | M252Y/N384A/N389A/N434Y |
| F868 | 2.00E−08 | G236A/S239D/M252Y/N286E/T307Q/Q311A/N434Y |
| F869 | | G236A/S239D |
| F870 | 7.30E−08 | L235K/S239K/M252Y/T307Q/Q311A/N434Y |
| F871 | 7.10E−08 | L235R/S239K/M252Y/T307Q/Q311A/N434Y |
| F872 | 1.30E−07 | L235K/S239K/M252Y/N286E/N434Y |
| F873 | 1.20E−07 | L235R/S239K/M252Y/N286E/N434Y |
| F875 | 4.80E−07 | M252Y/N434Y/Y436A |
| F877 | 8.30E−07 | M252Y/N434Y/Y436E |
| F878 | 1.90E−07 | M252Y/N434Y/Y436F |
| F879 | 9.20E−07 | M252Y/N434Y/Y436G |
| F880 | 3.90E−07 | M252Y/N434Y/Y436H |
| F881 | 3.10E−07 | M252Y/N434Y/Y436K |
| F882 | 1.30E−07 | M252Y/N434Y/Y436L |
| F883 | 2.10E−07 | M252Y/N434Y/Y436M |
| F884 | 4.00E−07 | M252Y/N434Y/Y436N |
| F888 | 4.80E−07 | M252Y/N434Y/Y436S |
| F889 | 2.20E−07 | M252Y/N434Y/Y436T |
| F890 | 1.10E−07 | M252Y/N434Y/Y436V |
| F891 | 1.70E−07 | M252Y/N434Y/Y436W |
| F892 | 7.10E−08 | M252Y/S254T/N434Y/Y436I |
| F893 | 9.80E−08 | L235K/S239K/M252Y/N434Y/Y436I |

Table 13-13 is the continuation of Table 13-12.

TABLE 13-13

| | | |
|---|---|---|
| F894 | 9.20E−08 | L235R/S239K/M252Y/N434Y/Y436I |
| F895 | 2.10E−08 | L235K/S239K/M252Y/N286E/T307Q/Q311A/N315E/N434Y |
| F896 | 2.00E−08 | L235R/S239K/M252Y/N286E/T307Q/Q311A/N315E/N434Y |
| F897 | 9.70E−08 | M252Y/N315D/N384A/N389A/N434Y |
| F898 | 1.70E−07 | M252Y/N315E/N384A/N389A/N434Y |
| F899 | 1.10E−07 | M252Y/N315D/G316A/N434Y |
| F900 | 1.70E−07 | M252Y/N315D/G316D/N434Y |
| F901 | 1.30E−07 | M252Y/N315D/G316E/N434Y |
| F902 | 2.20E−07 | M252Y/N315D/G316F/N434Y |
| F903 | 2.30E−07 | M252Y/N315D/G316H/N434Y |
| F904 | 1.00E−07 | M252Y/N315D/G316I/N434Y |
| F905 | 1.30E−07 | M252Y/N315D/G316K/N434Y |
| F906 | 1.50E−07 | M252Y/N315D/G316L/N434Y |
| F907 | 1.30E−07 | M252Y/N315D/G316M/N434Y |
| F908 | 1.50E−07 | M252Y/N315D/G316N/N434Y |
| F909 | 1.30E−07 | M252Y/N315D/G316P/N434v |
| F910 | 1.40E−07 | M252Y/N315D/G316Q/N434Y |
| F911 | 1.30E−07 | M252Y/N315D/G316R/N434Y |
| F912 | 1.20E−07 | M252Y/N315D/G316S/N434Y |
| F913 | 1.10E−07 | M252Y/N315D/G316T/N434Y |
| F914 | 1.50E−07 | M252Y/N315D/G316V/N434Y |
| F915 | 2.30E−07 | M252Y/N315D/G316W/N434Y |
| F917 | 2.50E−07 | M252Y/N286S/N434Y |
| F918 | 2.80E−07 | M252Y/D280E/N384A/N389A/N434Y |
| F919 | 3.30E−07 | M252Y/D280G/N384A/N389A/N434Y |
| F920 | 2.50E−07 | M252Y/N286S/N384A/N389A/N434Y |
| F921 | 1.20E−07 | M252Y/N286E/N384A/N389A/N434Y |
| F922 | 5.90E−08 | L235K/S239K/M252Y/N286E/N434Y/Y436I |
| F923 | 6.00E−08 | L235R/S239K/M252Y/N286E/N434Y/Y436I |
| F924 | 3.40E−08 | L235K/S239K/M252Y/T307Q/Q311A/N434Y/Y436I |
| F925 | 3.20E−08 | L235R/S239K/M252Y/T307Q/Q311A/N434Y/Y436I |
| F926 | 1.10E−07 | L235K/S239K/M252Y/S254T/N434Y/Y436I |
| F927 | 1.00E−07 | L235R/S239K/M252Y/S254T/N434Y/Y436I |
| F928 | 2.90E−08 | M252Y/T307Q/Q311A/N434Y/Y436I |
| F929 | 2.90E−08 | M252Y/S254T/T307Q/Q311A/N434Y/Y436I |
| F930 | 1.40E−07 | P238D/T250V/M252Y/N286E/N434Y |
| F931 | 1.20E−07 | P238D/T250V/M252Y/N434Y/Y436I |
| F932 | 3.20E−07 | T250V/M252Y/N434Y |
| F933 | 3.00E−07 | L234R/P238D/M250V/M252Y/N434Y |
| F934 | 3.10E−07 | G236K/P238D/T250V/M252Y/N434Y |
| F935 | 3.20E−07 | G237K/P238D/T250V/M252Y/N434Y |
| F936 | 3.20E−07 | G237R/P238D/T250V/M252Y/N434Y |
| F937 | 3.10E−07 | P238D/S239K/T250V/M252Y/N434Y |
| F938 | 1.60E−07 | L235K/S239K/M252Y/N434Y/Y436V |
| F939 | 1.50E−07 | L235R/S239K/M252Y/N434Y/Y436V |
| F940 | 1.50E−07 | P238D/T250V/M252Y/N434Y/Y436V |
| F941 | 1.20E−08 | M252Y/N286E/T307Q/Q311A/N434Y/Y436V |
| F942 | 4.20E−08 | L235K/S239K/M252Y/T307Q/Q311A/N434Y/Y436V |
| F943 | 4.00E−08 | L235R/S239K/M252Y/T307Q/Q311A/N434Y/Y436V |
| F944 | 1.70E−07 | T250V/M252Y/N434Y/Y436V |
| F945 | 1.70E−08 | T250V/M252Y/V308P/N434Y/Y436V |
| F946 | 4.30E−08 | T250V/M252Y/T307Q/Q311A/N434Y/Y436V |
| F947 | 1.10E−08 | T250V/M252Y/T307Q/V308P/Q311A/N434Y/Y436V |
| F954 | 5.30E−07 | M252Y/N434Y/H435K/Y436V |
| F957 | 7.70E−07 | M252Y/N434Y/H435N/Y436V |
| F960 | 8.00E−07 | M252Y/N434Y/H435R/Y436V |
| F966 | 3.10E−07 | M252Y/S254A/N434Y |
| F970 | 2.50E−06 | M252Y/S254G/N434Y |
| F971 | 2.60E−06 | M252Y/S254H/N434Y |
| F972 | 2.60E−07 | M252Y/S254I/N434Y |

Table 13-14 is the continuation of Table 13-13.

TABLE 13-14

| | | |
|---|---|---|
| F978 | 1.30E−06 | M252Y/S254Q/N434Y |
| F980 | 1.80E−07 | M252Y/S254V/N434Y |
| F987 | 4.00E−08 | P238D/T250V/M252Y/T307Q/Q311A/N434Y/Y436V |
| F988 | 6.90E−08 | P238D/T250V/M252Y/N286E/N434Y/Y436V |
| F989 | 1.40E−08 | L235R/S239K/M252Y/V308P/N434Y/Y436V |
| F990 | 9.40E−09 | L235R/S239K/M252Y/T307Q/V308P/Q311A/N434Y/Y436V |
| F991 | 1.30E−08 | L235R/S239K/M252Y/N286E/T307Q/Q311A/N434Y/Y436V |
| F992 | 5.10E−08 | L235R/S239K/M252Y/T307Q/Q311A/M428I/N434Y/Y436V |
| F993 | 3.80E−08 | M252Y/T307Q/Q311A/N434Y/Y436V |

TABLE 13-14-continued

| | | |
|---|---|---|
| F994 | 2.80E−07 | M252Y/N325G/N434Y |
| F995 | 2.90E−07 | L235R/P238D/S239K/M252Y/N434Y |
| F996 | 1.30E−07 | L235R/P238D/S239K/M252Y/N434Y/Y436V |
| F997 | 3.80E−07 | K248I/T250V/M252Y/N434Y/Y436V |
| F998 | 8.50E−07 | K248Y/T250V/M252Y/N434Y/Y436V |
| F999 | 2.10E−07 | T250V/M252Y/E258H/N434Y/Y436V |
| F1005 | | N325G |
| F1008 | 1.70E−07 | L235R/S239K/T250V/M252Y/N434Y/Y436V |
| F1009 | 1.20E−08 | L235R/S239K/T250V/M252Y/T307Q/V308P/Q311A/N434Y/Y436V |
| F1010 | 1.90E−07 | L235R/S239K/M252Y/T307A/Q311H/N434Y |
| F1011 | 4.50E−08 | T250V/M252Y/V308P/N434Y |
| F1012 | 4.70E−08 | L235R/S239K/T250V/M252Y/V308P/N434Y |
| F1013 | 3.00E−08 | T250V/M252Y/T307Q/V308P/Q311A/N434Y |
| F1014 | 3.20E−08 | L235R/S239K/T250V/M252Y/T307Q/V308P/Q311A/N434Y |
| F1015 | 2.20E−08 | L235R/S239K/M252Y/T307Q/V308P/Q311A/N434Y |
| F1016 | 3.80E−09 | T250V/M252Y/N286E/T307Q/V308P/Q311A/N434Y/Y436V |
| F1017 | 4.20E−09 | L235R/S239K/T250V/M252Y/N286E/T307Q/V308P/Q311A/N434Y/Y436V |
| F1018 | 3.20E−09 | L235R/S239K/M252Y/N286E/T307Q/V308P/Q311A/N434Y/Y436V |
| F1019 | 3.40E−07 | P238D/T250V/M252Y/N325G/N434Y |
| F1020 | 8.50E−08 | P238D/T250V/M252Y/T307Q/Q311A/N325G/N434Y |
| F1021 | 3.30E−07 | P238D/T250V/M252Y/N325A/N434Y |
| F1022 | | K326D/L328Y |
| F1023 | 4.40E−08 | S239D/T250V/M252Y/T307Q/Q311A/N434Y/Y436V |
| F1024 | 4.00E−08 | T250V/M252Y/T307Q/Q311A/K326D/L328Y/N434Y/Y436V |
| F1025 | 3.60E−08 | S239D/T250V/M252Y/T307Q/Q311A/K326D/L328Y/N434Y/Y436V |
| F1026 | 8.40E−08 | M252Y/T307A/Q311H/N434Y/Y436V |
| F1027 | 8.60E−08 | L235R/S239K/M252Y/T307A/Q311H/N434Y/Y436V |
| F1028 | 4.60E−08 | G236A/S239D/T250V/M252Y/T307Q/Q311A/N434Y/Y436V |
| F1029 | 5.10E−08 | T250V/M252Y/T307Q/Q311A/I332E/N434Y/Y436V |
| F1030 | | I332E |
| F1031 | 5.30E−08 | G236A/S239D/T250V/M252Y/T307Q/Q311A/I332E/N434Y/Y436V |
| F1032 | 4.30E−08 | P238D/T250V/M252Y/T307Q/Q311A/N325G/N434Y/Y436V |
| F1033 | 1.00E−06 | P238D/N434W |
| F1034 | 1.50E−08 | L235K/S239K/M252Y/V308P/N434Y/Y436V |
| F1035 | 1.00E−08 | L235K/S239K/M252Y/T307Q/V308P/Q311A/N434Y/Y436V |
| F1036 | 1.40E−08 | L235K/S239K/M252Y/N286E/T307Q/Q311A/N434Y/Y436V |
| F1037 | 6.10E−08 | L235K/S239K/M252Y/T307Q/Q311A/M428I/N434Y/Y436V |
| F1038 | 2.80E−07 | L235K/P238D/S239K/M252Y/N434Y |
| F1039 | 1.30E−07 | L235K/P238D/S239K/M252Y/N434Y/Y436V |
| F1040 | 2.00E−07 | L235K/S239K/T250V/M252Y/N434Y/Y436V |
| F1041 | 1.40E−08 | L235K/S239K/T250V/M252Y/T307Q/V308P/Q311A/N434Y/Y436V |
| F1042 | 2.00E−07 | L235K/S239K/M252Y/T307A/Q311H/N434Y |
| F1043 | 5.20E−08 | L235K/S239K/T250V/M252Y/V308P/N434Y |
| F1044 | 3.50E−08 | L235K/S239K/T250V/M252Y/T307Q/V308P/Q311A/N434Y |
| F1045 | 2.50E−08 | L235K/S239K/M252Y/T307Q/V308P/Q311A/N434Y |
| F1046 | 4.50E−09 | L235K/S239K/T250V/M252Y/N286E/T307Q/V308P/Q311A/N434Y/Y436V |
| F1047 | 3.40E−09 | L235K/S239K/M252Y/N286E/T307Q/V308P/Q311A/N434Y/Y436V |
| F1048 | 9.90E−08 | L235K/S239K/M252Y/T307A/Q311H/N434Y/Y436V |
| F1050 | 3.50E−09 | T250V/M252Y/N286E/T307Q/V308P/Q311A/M428I/N434Y/Y436V |
| F1051 | 3.90E−09 | L235R/S239K/T250V/M252Y/N286E/T307Q/V308P/Q311A/M428I/N434Y/Y436V |
| F1052 | 3.20E−09 | L235R/S239K/M252Y/N286E/T307Q/V308P/Q311A/M428I/N434Y/Y436V |

[Reference Example 1] Construction of Antibody Expression Vectors; and Expression and Purification of Antibodies Synthesis of full-length genes encoding the nucleotide sequences of the H chain and L chain of the antibody variable regions was carried out by production methods known to those skilled in the art using Assemble PCR and such. Introduction of amino acid substitutions was carried out by methods known to those skilled in the art using PCR or such. The obtained plasmid fragment was inserted into an animal cell expression vector, and the H-chain expression vector and L-chain expression vector were produced. The nucleotide sequence of the obtained expression vector was determined by methods known to those skilled in the art. The produced plasmids were introduced transiently into the HEK293H cell line derived from human embryonic kidney cancer cells (Invitrogen) or into FreeStyle™ 293-F cells (Invitrogen) for antibody expression. The obtained culture supernatant was collected, and then passed through a 0.22 m MILLEX®-GV filter (Millipore), or through a 0.45 m MILLEX®-GV filter (Millipore) to obtain the culture supernatant. Antibodies were purified from the obtained culture supernatant by methods known to those skilled in the art using rProtein A Sepharose™ Fast Flow affinity medium (GE Healthcare) or Protein G Sepharose™ 4 Fast Flow affinity medium (GE Healthcare). For the concentration of the purified antibodies, their absorbance at 280 nm was measured using a spectrophotometer. From the obtained value, the extinction coefficient calculated by the methods such as PACE was used to calculate the antibody concentration (Protein Science 1995; 4: 2411-2423).

[Reference Example 2] Method for Preparing FcγR and Method for Analyzing the Interaction Between an Altered Antibody and FcγR Extracellular domains of FcγRs were prepared by the following method. First, a gene of the extracellular domain of FcγR was synthesized by a method well known to those skilled in the art. At that time, the sequence of each FcγR was produced based on the information registered at NCBI. Specifically, FcγRI was produced based on the sequence of NCBI Accession No. NM_000566 (Version No.

NM_000566.3), FcγRIIa was produced based on the sequence of NCBI Accession No. NM_001136219 (Version No. NM_001136219.1), FcγRIIb was produced based on the sequence of NCBI Accession No. NM_004001 (Version No. NM_004001.3), FcγRIIIa was produced based on the sequence of NCBI Accession No. NM_001127593 (Version No. NM_001127593.1), and FcγRIIIb was produced based on the sequence of NCBI Accession No. NM_000570 (Version No. NM_000570.3), and a His tag was attached to the C terminus. Furthermore, the presence of polymorphism is known for FcγRIIa, FcγRIIIa, and FcγRIIIb, and the polymorphic sites were produced by referring to Warmerdam et al. (J. Exp. Med., 1990, 172: 19-25) for FcγRIIa; Wu et al. (J. Clin. Invest., 1997, 100 (5): 1059-1070) for FcγRIIIa; and Ory et al. (J. Clin. Invest., 1989, 84, 1688-1691) for FcγRIIIb.

The obtained gene fragments were inserted into an animal cell expression vector, and expression vectors were produced. The produced expression vectors were introduced transiently into human embryonic kidney cancer cell-derived FreeStyle™ 293-F cells (Invitrogen) to express the proteins of interest. Regarding FcγRIIb used for crystal structure analysis, the protein of interest was expressed in the presence of Kifunesine at a final concentration of 10 g/mL, so that the sugar chain added to FcγRIIb will be the high-mannose type. Cells were cultured, and after collection of the obtained culture supernatant, this was passed through a 0.22 m filter to obtain the culture supernatant. In principle, the obtained culture supernatants were purified in the following four steps. The steps carried out were, cation exchange column chromatography (SP Sepharose™ FF ion exchange chromatography) in step 1, affinity column chromatography (HisTrap™ HP column) for His tag in step 2, gel filtration column chromatography (Superdex® 200 gel filtration column) in step 3, and aseptic filtration in step 4. However, for FcγRI, anion exchange column chromatography using Q Sepharose™ FF was performed as step 1. The purified proteins were subjected to absorbance measurements at 280 nm using a spectrophotometer; and from the obtained values, the concentrations of the purified proteins were calculated using the absorption coefficient calculated using methods such as PACE (Protein Science 1995; 4: 2411-2423).

Analysis of interaction between each altered antibody and the Fcγ receptor prepared as mentioned above was carried out using a BIACORE™ T100 surface plasmon resonance system (GE Healthcare), a BIACORE™ T200 surface plasmon resonance system (GE Healthcare), a BIACORE™ A100 surface plasmon resonance system, and a BIACORE™ 4000 surface plasmon resonance system. HBS-EP+(GE Healthcare) was used as the running buffer, and the measurement temperature was set to 25° C. Chips produced by immobilizing the antigen peptide, Protein A (Thermo Scientific), Protein A/G (Thermo Scientific), and Protein L (ACTIGEN® protein (Alltech) or BioVision) by the amine coupling method to a Series S sensor Chip CM5 (GE Healthcare) or Series S sensor Chip CM4 (GE Healthcare), or alternatively, chips produced by allowing preliminarily biotinylated antigen peptides to interact with and immobilize onto a Series S Sensor Chip SA (certified) (GE Healthcare) were used.

After capturing of antibodies of interest onto these sensor chips, an Fcγ receptor diluted with the running buffer was allowed to interact, the amount bound to an antibody was measured, and compared among the antibodies. However, since the amount of Fcγ receptor bound depends on the amount of the captured antibodies, the amount of Fcγ receptor bound was divided by the amount of each antibody captured to obtain corrected values, and these values were compared. Furthermore, antibodies captured onto the sensor chips were washed by reaction with 10 mM glycine-HCl, pH 1.5, and the chips were regenerated and used repeatedly.

Kinetic analyses for calculating the KD values of each altered antibody for FcγR were performed according to the following method. First, antibodies of interest were captured onto the above-mentioned sensor chips, and an Fcγ receptor diluted with the running buffer was allowed to interact. The BIACORE™ Evaluation Software was used to globally fit the measured results regarding the obtained sensorgram using the 1:1 Langmuir binding model, and the association rate constant ka (L/mol/s) and the dissociation rate constant kd (1/s) were calculated; and from those values the dissociation constants KD (mol/L) were calculated.

When the interaction between each of the altered antibodies and FcγR was weak, and correct analysis was determined to be impossible by the above-mentioned kinetic analysis, the KD for such interactions were calculated using the following 1:1 binding model equation described in the BIACORE™ T100 Software Handbook BR1006-48 Edition AE.

The behavior of interacting molecules according to the 1:1 binding model on a BIACORE™ system can be described by Equation 1 shown below.

$$R_{eq}=C \cdot R_{max}/(KD+C)+RI \quad \text{[Equation 1]}$$

Req: a plot of steady state binding levels against analyte concentration

C: concentration

RI: bulk refractive index contribution in the sample

Rmax: analyte binding capacity of the surface

When this equation is rearranged, KD can be expressed as Equation 2 shown below.

$$KD=C \cdot R_{max}/(R_{eq}-RI)-C \quad \text{[Equation 2]}$$

KD can be calculated by substituting the values of Rmax, RI, and C into this equation. The values of RI and C can be determined from the sensorgram of the measurement results and measurement conditions. Rmax was calculated according to the following method. As a target of comparison, for antibodies that had sufficiently strong interactions as evaluated simultaneously in the same round of measurement, the Rmax value was obtained through global fitting using the 1:1 Langmuir binding model, and then it was divided by the amount of the comparison antibody captured onto the sensor chip, and multiplied by the captured amount of an altered antibody to be evaluated.

[Reference Example 3] Preparation of Soluble Human IL-6 Receptor (hsIL-6R)

Recombinant human IL-6 receptor which is an antigen was prepared in the manner described below. A CHO line that constantly expresses soluble human IL-6 receptor composed of an amino acid sequence consisting of the 1st to 357th amino acid from the N terminus as reported in J. Immunol. (1994) 152, 4958-4968 (hereinafter referred to as hsIL-6R) was constructed using a method known among persons with ordinary skill in the art. hsIL-6R was expressed by culturing this CHO line. hsIL-6R was purified from culture supernatant of the resulting CHO line by the two steps of Blue Sepharose™ 6 FF column chromatography and gel filtration column chromatography. The fraction that eluted as the main peak in the final step was used as the final purified product.

[Reference Example 4] Elimination of Target Antigen from Plasma by pH-Dependent Binding Antibody Having Human FcRn-Binding Activity Under a Neutral pH Range Condition When a conventional neutralizing antibody against a soluble antigen is administered, the plasma retention of the antigen is expected to be prolonged by binding to the antibody. In general, antibodies have a long half-life (one week to three weeks) while the half-life of antigen is generally short (one day or less). Meanwhile, antibody-bound antigens have a significantly longer half-life in plasma as compared to when the antigens are present alone. For this reason, administration of existing neutralizing antibody results in an increased antigen concentration in plasma. Such cases have been reported with various neutralizing antibodies that target soluble antigens including, for example, IL-6 (J Immunotoxicol. 2005, 3: 131-9), amyloid beta (mAbs, 2010, 2: 5, 1-13), MCP-1 (ARTHRITIS & RHEUMATISM 2006, 54: 2387-92), hepcidin (AAPS J. 2010, 4, 646-57), and sIL-6 receptor (Blood. 2008 Nov. 15; 112(10): 3959-64). Administration of existing neutralizing antibodies has been reported to increase the total plasma antigen concentration to about 10 to 1000 times (the level of increase varies depending on antigen) from the base line. Herein, the total plasma antigen concentration refers to a concentration as a total amount of antigen present in plasma, i.e., the sum of concentrations of antibody-bound and antibody-unbound antigens. An increase in the total plasma antigen concentration is undesirable for such antibody pharmaceuticals that target a soluble antigen. The reason is that the plasma antibody concentration has to be higher than at least the total plasma antigen concentration to neutralize the soluble antigen. Specifically, "the total plasma antigen concentration is increased to 10 to 1,000 times" means that, in order to neutralize the antigen, the plasma antibody concentration (i.e., antibody dose) has to be 10 to 1,000 times higher as compared to when increase in the total plasma antigen concentration does not occur. Conversely, if the total plasma antigen concentration can be reduced by 10 to 1,000 times as compared to the existing neutralizing antibody, the antibody dose can also be reduced to similar extent. Thus, antibodies capable of decreasing the total plasma antigen concentration by eliminating the soluble antigen from plasma are highly useful as compared to existing neutralizing antibodies.

The examination described in PCT/JP2011/001888 demonstrated that antigen-binding molecules (IL-6 receptor-binding antibodies) with enhanced FcRn binding at pH 7.4 can reduce the total antigen concentration in plasma by eliminating the soluble antigen, and the effect to eliminate the soluble antigen is improved by conferring the property of binding to the antigen in a pH-dependent manner (binding to the antigen at pH 7.4 in plasma and dissociating from the antigen at pH 6.0 in the endosome). To reduce the total antigen concentration in plasma by administering an antigen-binding molecule, it is desirable that the antigen-binding molecule comprises an antigen-binding domain and a human FcRn-binding domain, and the human FcRn-binding domain has human FcRn binding activity under an acidic condition and under a neutral condition, and the human FcRn binding activity is 3200 nM or greater under a neutral condition. In this case, a control antigen-binding molecule has the same antigen-binding domain, and its human FcRn-binding domain is a native human IgG Fc region.

Figure 9:
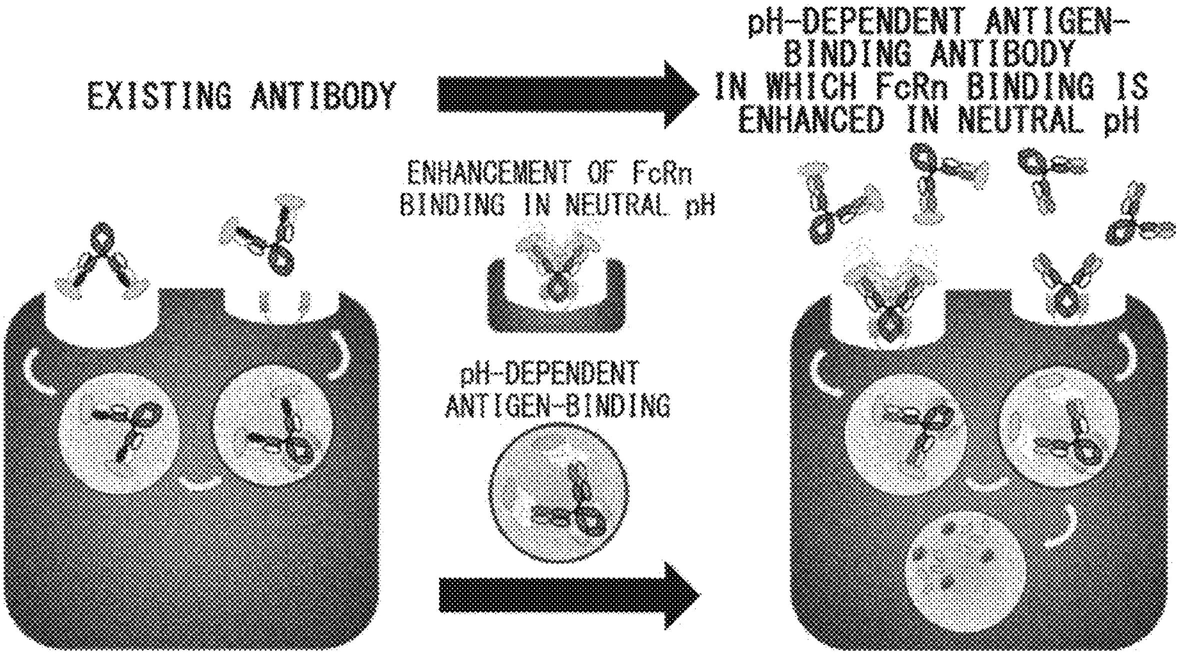
FIG. 9 is a diagram showing that antigens can be eliminated from plasma by using antibodies that bind to target antigens in a pH-dependent manner and have FcRn-binding activity in a neutral pH range.

FIG. 9 shows a mechanism in which soluble antigens are eliminated from plasma by administering a pH-dependent antigen-binding antibody that has increased FcRn-binding activity at neutral pH as compared to a conventional neutralizing antibody. After binding to the soluble antigen in plasma, the existing neutralizing antibody that does not have the pH-dependent antigen-binding ability is slowly incorporated into cells by non-specific interaction with the cells. The complex between the neutralizing antibody and soluble antigen incorporated into the cell is transferred to the acidic endosome and then recycled to plasma by FcRn. Meanwhile, the pH-dependent antigen-binding antibody that has the increased FcRn-binding activity under the neutral condition is, after binding to the soluble antigen in plasma, rapidly incorporated into cells expressing FcRn on their cell membrane. Then, the soluble antigen bound to the pH-dependent antigen-binding antibody is dissociated from the antibody in the acidic endosome due to the pH-dependent binding ability. The soluble antigen dissociated from the antibody is transferred to the lysosome and degraded by proteolytic activity. Meanwhile, the antibody dissociated from the soluble antigen is recycled onto cell membrane by FcRn and then released to plasma again. The free antibody, recycled as described above, can again bind to other soluble antigens. By repeating such cycle: FcRn-mediated uptake into cells; dissociation and degradation of the soluble antigen; and antibody recycling, such pH-dependent antigen-binding antibodies as described above having the increased FcRn binding activity under the neutral condition can transfer a large amount of soluble antigen to the lysosome and thereby decrease the total antigen concentration in plasma.

[Reference Example 5] Demonstration of the In Vivo Pharmaceutical Effect of an Antibody without Neutralizing Activity In Vitro by Eliminating Target Antigens from Plasma It has been believed that, to exhibit the in vivo pharmaceutical effect to neutralize target antigens, antigen-binding molecules must have an in vitro activity of neutralizing the target antigens. The reason is that, if ordinary antigen-binding molecules do not have in vitro neutralizing activity, they cannot exhibit the in vivo pharmaceutical effect by neutralizing target antigens.

Meanwhile, Reference Example 4 shows that, when administered in vivo, pH-dependent binding antibodies that have human FcRn-binding activity under a neutral pH range condition can eliminate target antigens from plasma. The present inventors conceived that, if a target antigen was eliminated from plasma by administering an antibody, the action of the target antigen can be substantially blocked even when the antibody does not have antigen-neutralizing activity.

Isolation of the pH-Dependent Antibody 6RKE02-IgG1 Against Human IL-6 Receptor from Human Naive Library A human antibody phage display library consisting of multiple phages that display Fab domains of different human antibody sequences was constructed according to a method known to those skilled in the art using as a template poly A RNA prepared from human PBMCs or commercially-available human poly A RNA.

The first selection from the constructed naive human antibody phage display library was performed by enriching only antibody fragments with antigen-binding ability. A biotin-labeled human IL-6 receptor was used as an antigen.

Phages were produced by *E. coli* containing the constructed phage display phagemids. To precipitate the phages, 2.5 M NaCl/10% PEG was added to the *E. coli* culture media of phage production. The phages were diluted with TBS to prepare a phage library solution. Then, BSA and $CaCl_2$ were added at a final concentration of 4% BSA and a final calcium ion concentration of 1.2 mM respectively to the phage library solution. Regarding the panning method, the present inventors referred to general panning methods using antigens immobilized onto magnetic beads (J. Immunol. Methods. (2008) 332 (1-2), 2-9, J. Immunol. Methods. (2001) 247 (1-2), 191-203, Biotechnol. Prog. (2002) 18(2) 212-20, Mol. Cell Proteomics (2003) 2 (2), 61-9). The magnetic beads used were NeutrAvidin™ coated beads (Sera-Mag Speed-Beads™ NeutrAvidin™-coated) and Streptavidin coated beads (Dynabeads™ M-280 Streptavidin).

Specifically, 250 pmol of biotin-labeled antigen was added to the prepared phage library solution to contact it with the phage library solution at room temperature for 60 minutes. BSA-blocked magnetic beads were added thereto and allowed to bind to antigen/phage complexes at room temperature for 15 minutes. The beads were washed once with 1 ml of 1.2 mM $CaCl_2$)/TBS (TBS containing 1.2 mM $CaCl_2$). Then, a phage solution was collected according to a general method. The collected phage solution was added to 10 ml of *E. coli* strain TG1 in the logarithmic growth phase (OD600 of 0.4-0.5). The *E. coli* was infected with the phages by culturing them while gently stirring at 37° C. for one hour. The infected *E. coli* was seeded in a 225 mm×225 mm plate. Then, the phages were collected from the culture medium of the seeded *E. coli* to prepare a phage library solution.

To enrich the phages, the second and subsequent pannings were performed using the pH-dependent binding ability as an indicator. Specifically, 40 pmol of the biotin-labeled antigen was added to the prepared phage library solution, and contacted it with the phage library at room temperature for 60 minutes. BSA-blocked magnetic beads were added thereto and allowed to bind to antigen/phage complexes at room temperature for 15 minutes. The beads were washed with 1 ml of 1.2 mM $CaCl_2$/TBST (TBS containing 1.2 mM $CaCl_2$ and 0.1% Tween 20) and with 1.2 mM $CaCl_2$)/TBS. Then, the beads combined with 0.1 ml of 50 mM MES/1.2 mM $CaCl_2$/150 mM NaCl (pH 5.5) were suspended at room temperature, and immediately separated using a magnetic stand to collect a phage solution. The collected phage solution was added to 10 ml of *E. coli* strain TG1 in the logarithmic growth phase (OD600 of 0.4-0.5). The *E. coli* was infected with the phages by culturing them while gently stirring at 37° C. for one hour. The infected *E. coli* was seeded in a 225 mm×225 mm plate. Then, the phages were collected from the culture medium of the seeded *E. coli* to prepare a phage library solution. The panning using the pH-dependent binding ability as an indicator was performed repeatedly several times.

After repeating the panning twice, three times, or four times, phage-containing culture supernatants were collected according to a conventional method (Methods Mol. Biol. (2002) 178, 133-145) from single colonies of *E. coli* obtained by the method described above.

To the phage-containing culture supernatants, BSA and $CaCl_2$ were added at a final concentration of 4% BSA and at a final calcium ion concentration of 1.2 mM, respectively. The phage-containing culture supernatants were subjected to ELISA by the following procedure. A StreptaWell 96 microtiter plate (Roche) was coated overnight with 100 µl of PBS containing the biotin-labeled antigen. After washing each well of the plate with PBST to remove the antigen, the wells were blocked with 250 µl of 4% BSA/TBS for one hour or more. After removing 4% BSA/TBS from the wells, the culture supernatants prepared as mentioned above were added thereto. The antibodies presented on the phages were allowed to bind to the antigens on each well by incubating the plate at 37° C. for one hour. The wells were washed with 1.2 mM $CaCl_2$/TBST, and 1.2 mM $CaCl_2$/TBS (pH 7.6) or 1.2 mM $CaCl_2$/TBS (pH 5.5) was added thereto. The plate was incubated by being allowed to stand at 37° C. for 30 minutes. After washing with 1.2 mM $CaCl_2$)/TBST (pH 7.6), an HRP-linked anti-M13 antibody (Amersham Pharmacia Biotech) diluted with TBS containing BSA at a final concentration of 4% and ionized calcium at a final concentration of 1.2 mM was added to each well. The plate was incubated for one hour. After washing with 1.2 mM $CaCl_2$/TBST, TMB single solution (ZYMED) was added thereto. The chromogenic reaction in the solution of each well was stopped by adding sulfuric acid, and then the absorbance at 450 nm was measured to assess the color development.

Furthermore, the genes amplified with specific primers using as a template the clones subjected to phage ELISA were analyzed for their nucleotide sequence.

Based on the results of the above-mentioned phage ELISA and sequence analysis, selection was performed using pooled libraries containing many antibody fragments which were considered to have the ability to bind to the antigen in a pH-dependent manner.

Expression of Antibodies

Antibody genes from pooled libraries containing many clones that were considered to have the ability to bind to the antigen in a pH-dependent manner based on the result of phage ELISA, were inserted into animal cell expression plasmids. Antibody expression was carried out using the method described below. The FreeStyle™ 293-F cell line (Invitrogen) derived from human fetal kidney cells were suspended in FreeStyle™ 293 Expression Medium (Invitrogen), and plated at a cell density of $2.63\times10^5$ cells/ml in 190 µl to each well of a 96-well plate. The prepared plasmids were introduced into the cells by a lipofection method. The cells were cultured in a $CO_2$ incubator (37° C., 8% $CO_2$) for four days.

Analysis and Assessment of Interaction Using a BIACORE™ A100 Surface Plasmon Resonance System Antibodies isolated by the above-described method were analyzed using a BIACORE™ A100 surface plasmon resonance (GE Healthcare) for the interaction between IL-6R and the antibodies of interest. The running buffer used was: 10 mM ACES, 150 mM NaCl, 1.2 mM $CaCl_2$, 0.05% Tween20®, pH 7.4, or 10 mM ACES, 150 mM NaCl, 1.2 mM $CaCl_2$, 0.05% Tween20®, pH 6.0. The measurement temperature was 25° C. The chip used was a Series S Sencor Chip CM5 (GE Healthcare) immobilized with Protein A/G (Thermo Scientific) by an amine coupling method. Antibodies of interest were captured onto the chip, and allowed to interact with IL-6R diluted with the running buffer. The antibodies captured onto the chip were washed off by reacting 10 mM glycine-HCl (pH 1.5), and the chip was regenerated for repeated use.

The IL-6R-binding activity of each antibody was assessed mainly using as an indicator the binding amount of IL-6R to the antibody. The amount of change (RU) in sensorgram upon interaction of the captured antibody with IL-6R, divided by the amount of change (RU) upon capturing the antibody onto the chip, was used as the binding amount of IL-6R to the antibody.

Expression and Purification of Antibodies

Clones that were determined to have the ability to bind to the antigen in a pH-dependent manner, based on the result of screening with a BIACORE™ A100 surface plasmon resonance system, were expressed again to perform the assessment. Antibodies were prepared using the method described in Reference Example 1.

Assessment of 6RKE02-IgG1 for its pH-Dependent Binding to Soluble Human IL-6 Receptor The above method yielded 6RKE02-IgG1 having 6RKE02H-IgG1 (SEQ ID NO: 1) as the heavy chain and 6RKE02L-k0 (SEQ ID NO: 2) as the light chain. 6RKE02-IgG1 was analyzed for its interaction with IL-6R using a BIACORE™ T100 surface plasmon resonance system (GE Healthcare), and the dissociation constant (KD) was calculated.

The running buffer used was 10 mM ACES (pH 7.4) containing 150 mM NaCl and 0.05% Tween20®. The measurement temperature was 37° C. The chip used was a Series S Sencor Chip CM4 (GE Healthcare) immobilized with Protein A/G (Thermo Scientific) by an amine coupling method. Antibodies of interest were captured onto the chip, and allowed to interact with IL-6R diluted with the running buffer to 800, 400, 200, 100, 50, 25, and 12.5 nM, and the running buffer at a flow rate of 2 μl/minute for 15 minutes. The antibodies captured onto the chip were washed off by reacting 10 mM glycine-HCl (pH 1.5), and the chip was regenerated for repeated use.

From the sensorgrams obtained as a result of the BIACORE™ system measurement, the dissociation constant KD (mol/l) of 6RKE02-IgG1 for IL-6R was calculated by performing steady state affinity analysis using BIACORE™ Evaluation Software. The dissociation constant (KD) between 6RKE02-IgG1 and IL-6R at pH 7.4, calculated by this method, was 1.4E-7 (M).

Next, the pH dependence of the binding of 6RKE02-IgG1 to hIL-6R was assessed using a BIACORE T100 surface plasmon resonance system. The running buffer used was: 10 mM ACES, 150 mM NaCl, 0.05% Tween20®, pH 7.4; and 10 mM ACES, 150 mM NaCl, 0.05% Tween20®, pH 6.0. The measurement temperature was 37° C. The chip used was a Series S Sencor Chip CM4 (GE Healthcare) immobilized with Protein A/G (Thermo Scientific) by an amine coupling method. Antibodies of interest were captured onto the chip, and allowed to interact with hIL-6R diluted with the running buffer to 1000, 250, and 62.5 nM, and the running buffer.

Figure 10:
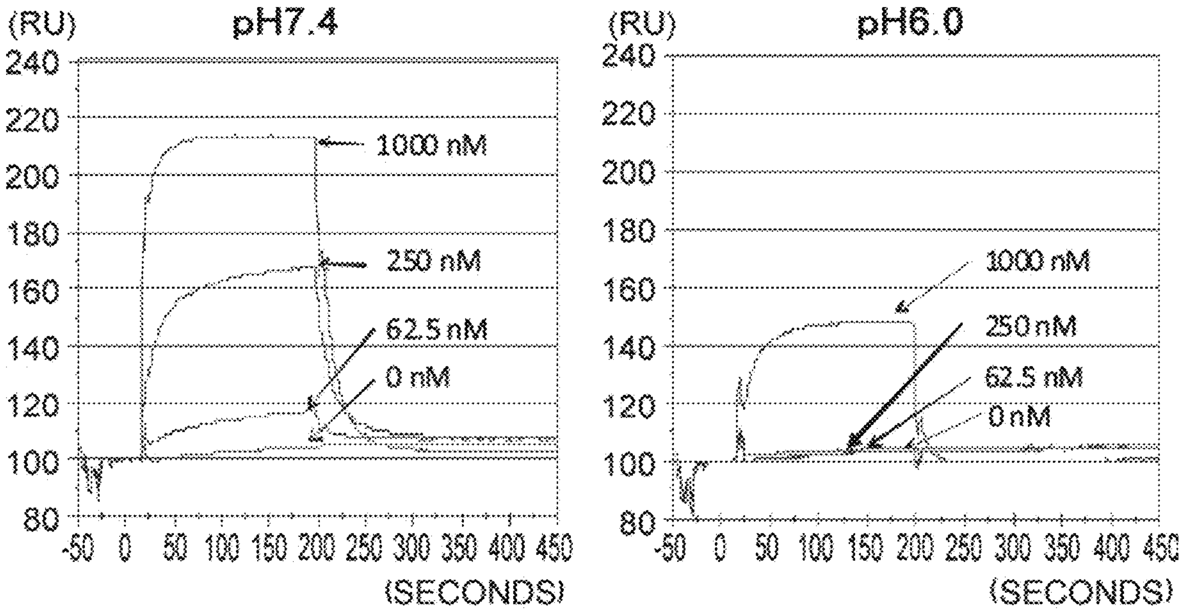
FIG. 10 is a diagram showing sensorgrams for 6RKE02-IgG1 to hsIL-6R at pH 7.4 and pH 6.0.

Sensorgrams obtained by the measurement at pH 7.4 and pH 6.0 using this method are shown in FIG. 10. The captured amount of antibody has been normalized to be 100 RU, and the binding phase and dissociation phase of 6RKE02-IgG1 for hIL-6R are shown. A comparison of the results shown in FIG. 10 revealed that the binding of 6REK02-IgG1 to hIl-6R was reduced at pH 6.0 as compared to pH 7.4.

Assessment for Biological Activity Using BaF3 Cells Expressing Human Gp130 (BaF/Gp130)

Figure 11:
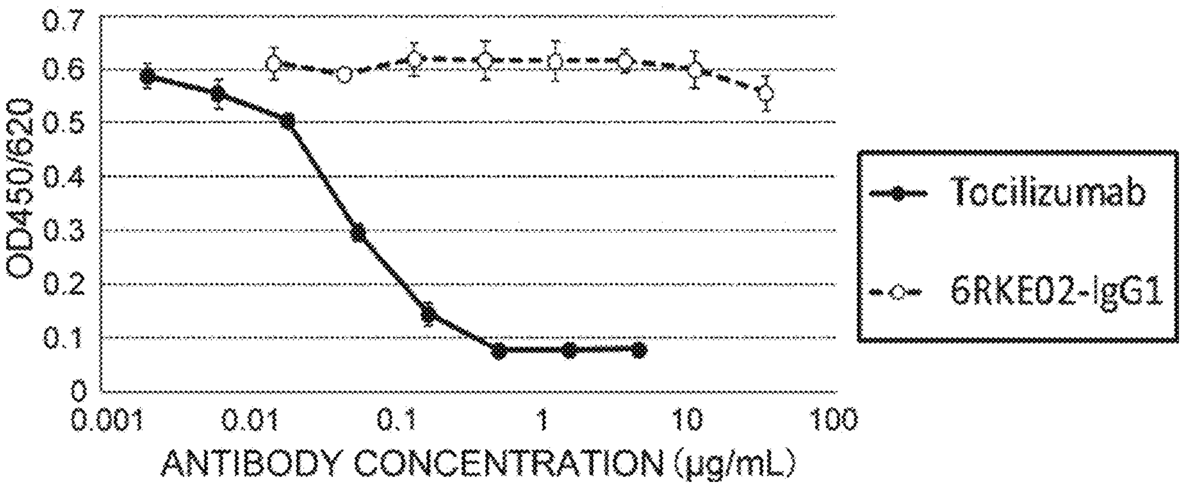
FIG. 11 is a graph showing a result of biological activity evaluation using BaF3 cells expressing human gp130 (BaF/gp130).

6RKE02-IgG1 and Tocilizumab were assessed for their IL-6 receptor-neutralizing activity using BaF3/gp130 that shows human IL-6/soluble human IL-6 receptor-dependent growth. After washing three times with RPMI1640 medium containing 10% FBS, BaF3/gp130 was suspended in RPMI1640 medium containing 10% FBS and prepared at $1.5\times10^5$ cells/ml with a final concentration of 15 ng/ml for both human interleukin-6 (R&D Systems) and soluble human IL-6 receptor. This was aliquoted at 50 μl to each well of a 96 well-plate (CORNING). Then, the purified antibodies were serially diluted with PBS, and then diluted 20 times with RPMI1640 medium containing 10% FBS, and added at 50 μl to each well. The cells were cultured at 37° C. under 5% $CO_2$ for three days, and WST-8 reagent (Cell Counting Kit-8, DOJINDO LABORATORIES) diluted twice with PBS was added thereto at 20 μl/well. After four hours of incubation, the absorbance at 450 nm (reference wavelength of 620 nm) was measured with microplate reader xMark (Bio-Rad Laboratories) to assess the IL-6 receptor-neutralizing activity. The result is shown in FIG. 11. 6RKE02-IgG1 did not inhibit the human IL-6/soluble human IL-6 receptor-dependent growth of BaF3/gp130. Thus, it was shown that 6RKE02-IgG1 does not have the neutralizing activity.

Preparation of 6RKE02-IgG1 with Increased FcRn-Binding Activity in a Neutral pH Range To confer the mouse FcRn-binding activity under a neutral pH range condition to 6RKE02-IgG1, amino acid mutations were introduced into 6RKE02H-IgG1, which is the heavy chain constant region of 6RKE02-IgG1. Specifically, 6RKE02H-F29 (SEQ ID NO: 3) was constructed by introducing into 6RKE02H-IgG1 an amino acid substitution of Val for Ile at position 332 (EU numbering) and an amino acid substitution of Tyr for Asn at position 434 (EU numbering), using the method described in Reference Example 1. 6RKE02-F29, which contains 6RKE02H-F29 as the heavy chain and 6RKE02L-k0 as the light chain, was constructed using the method described in Reference Example 1.

Kinetic Analysis for the Binding to Mouse FcRn

VH3/L(WT)-IgG1 comprising VH3-IgG1 (SEQ ID NO: 4) and L(WT)-CK (SEQ ID NO: 5), and VH3/L(WT)-F29 comprising VH3-F29 (SEQ ID NO: 6) and L(WT)-CK (SEQ ID NO: 5) were constructed to assess the mouse FcRn-binding activity of 6RKE02-F29.

Using VH3/L(WT)-IgG1 and VH3/L(WT)-F29, the mouse FcRn-binding activity was assessed as follows.

Mouse FcRn and antibodies were kinetically analyzed using a BIACORE™ T100 surface plasmon resonance system (GE Healthcare). An appropriate amount of protein L (ACTIGEN® protein (Alltech)) was immobilized onto a Sensor chip CM4 (GE Healthcare) by an amine coupling method, and antibodies of interest were captured onto the chip. Then, a diluted mouse FcRn solution and a running buffer as a blank were injected, and mouse FcRn was allowed to interact with the antibodies captured onto the sensor chip. The running buffer used was 50 mmol/l sodium phosphate, 150 mmol/l NaCl, 0.05% (w/v) Tween20®, pH 7.0. The buffer was also used to dilute mouse FcRn. 10 mmol/l glycine-HCl (pH 1.5) was used for regeneration. All measurements were carried out at 25° C. The binding rate constant ka (1/Ms) and dissociation rate constant kd (1/s), which are kinetic parameters, were calculated from the sensorgrams obtained by the measurement, and the KD (M) of each antibody for mouse FcRn was calculated based on the values. Each parameter was calculated using BIACORE™ T100 or T200 Evaluation Software (GE Healthcare).

The result is shown in Table 14 (KD of human IgG1 or F29 for mouse FcRn). F29 was demonstrated to have increased mouse FcRn-binding activity under a neutral pH range condition (pH 7.0).

TABLE 14

| ANTIBODY | mFcRn KD (M) | AMINO ACID SUBSTITUTION |
|---|---|---|
| HUMAN IgG1 | ND | |
| F29 | 8.5E−08 | I332V/N434Y |

In Vivo Infusion Test Using Normal Mouse

An infusion pump (MODEL2004, alzet MINI-OSMOTIC PUMP), filled with soluble human IL-6 receptor, was subcutaneously implanted into the back of a normal mouse (C57BL/6J mouse, Charles River Japan) to create an animal model with plasma concentration of soluble human IL-6 receptor maintained in the steady state. In the animal model, the anti-human IL-6 receptor antibody was administered to assess the in vivo kinetics of soluble human IL-6 receptor after antibody administration. To suppress the production of neutralizing antibodies against soluble human IL-6 receptor, an anti-mouse CD4 monoclonal antibody (in-house preparation) was administered once at 20 mg/kg into the tail vein. Then, an infusion pump containing 92.8 μg/ml soluble human IL-6 receptor was implanted subcutaneously on the back of mice. Three days after implantation of the infusion pump, 6RKE02-IgG1 and 6RKE02-F29 were administered once at 1 mg/kg subcutaneously on the back of the normal mice. Blood was collected at appropriate time points after administration of the anti-human IL-6 receptor antibody. The blood samples obtained were immediately centrifuged at 15,000 rpm for 15 minutes at 4° C. to separate plasma. The separated plasma was stored in a freezer set to −20° C. or lower until the time of measurement.

hsIL-6R concentration in mouse plasma was determined using electrochemiluminescence method. An hsIL-6R calibration curve sample prepared at 2,000, 1,000, 500, 250, 125, 62.5, or 31.25 pg/mL, and a mouse plasma measurement sample diluted by 50-fold or above, were mixed with a monoclonal anti-human IL-6R antibody (R&D) ruthenated with SULFO-TAG NHS Ester (Meso Scale Discovery), a biotinylated anti-human IL-6R antibody (R&D), and tocilizumab, followed by overnight reaction at 37° C. Tocilizumab was prepared at a final concentration of 333 μg/mL. Subsequently, the reaction solution was dispensed into an MA400 PR Streptavidin Plate (Meso Scale Discovery). In addition, after washing off the reaction solution that was allowed to react at room temperature for 1 hour, Read Buffer T (×4) (Meso Scale Discovery) was dispensed. Subsequently, the reaction solution was immediately subjected to measurement using a SECTOR PR 400 Reader (Meso Scale Discovery). The concentration of hsIL-6R was calculated from the response of the calibration curve using the SOFTmax® PRO analysis software (Molecular Devices).

Figure 12:
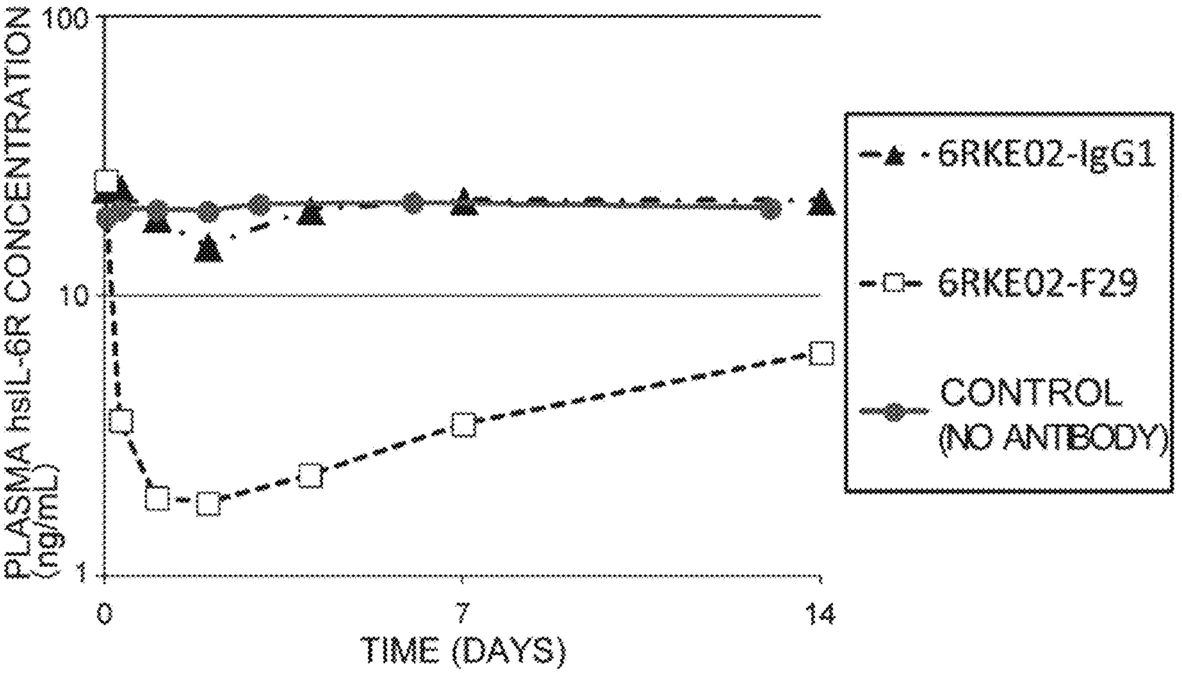
FIG. 12 shows a time course of plasma hsIL-6R concentration after antibody administration in an infusion test using normal mice.

The time course of the monitored human IL-6 receptor concentration is shown in FIG. 12. The plasma hsIL-6R concentration was not reduced in the antibody non-administered group and the 6RKE02-IgG1 administered group. By contrast, the plasma hsIL-6R concentration was found to be markedly reduced in the group administered with 6RKE02-F29 that binds to the IL-6 receptor in a pH-dependent manner and has the activity of binding mouse FcRn in a neutral range.

In Vivo Drug Efficacy Test Using Normal Mice (Test 1)

Whether 6RKE02-F29 that has no neutralizing activity in vitro can achieve the in vivo pharmaceutical effect by eliminating hsIL-6R from the plasma was assessed by using a normal mice model (C57BL/6J Jcl mice). It is known that, when a mixed solution of hIL-6 and hsIL-6R is administered to mice, the following two kinds of signaling are triggered: trans-signaling by the binding of hIL-6/hsIL-6R complexes to mouse gp130; and classical-signaling by the binding of hIL-6 to mouse membrane IL-6R followed by binding to mouse gp130; thus, the production of serum amyloid A (SAA) is induced, resulting in an increase of the plasma SAA concentration.

6RKE02-F29 was intravenously administered at 0, 1, 10, and 30 mg/kg to C57BL/6J Jcl mice (female), and, one hour after administration, hIL-6 and hsIL-6R were intravenously administered at 4 μg/kg and 7 μg/kg, respectively, as a mixture. Six hours after the second intravenous administration, blood was collected to determine the plasma SAA concentration by ELISA. To rule out the effect of endogenous mouse IL-6R on the plasma SAA concentration, MR16-1 (rat anti-mouse IL-6R antibody) was intravenously administered at 20 mg/kg to all mice simultaneously with the test substance. Since the trans-signaling alone is induced by administering hIL-6/hsIL-6R, it is possible to assess whether the in vivo pharmaceutical effect can be achieved through eliminating hsIL-6R from the plasma. Exclusion of the effect of endogenous mouse IL-6R was confirmed by intravenously administering hIL-6 at 4 μg/kg to the vehicle-administered group that was intravenously administered with MR16-1 at 20 mg/kg.

Figure 13:
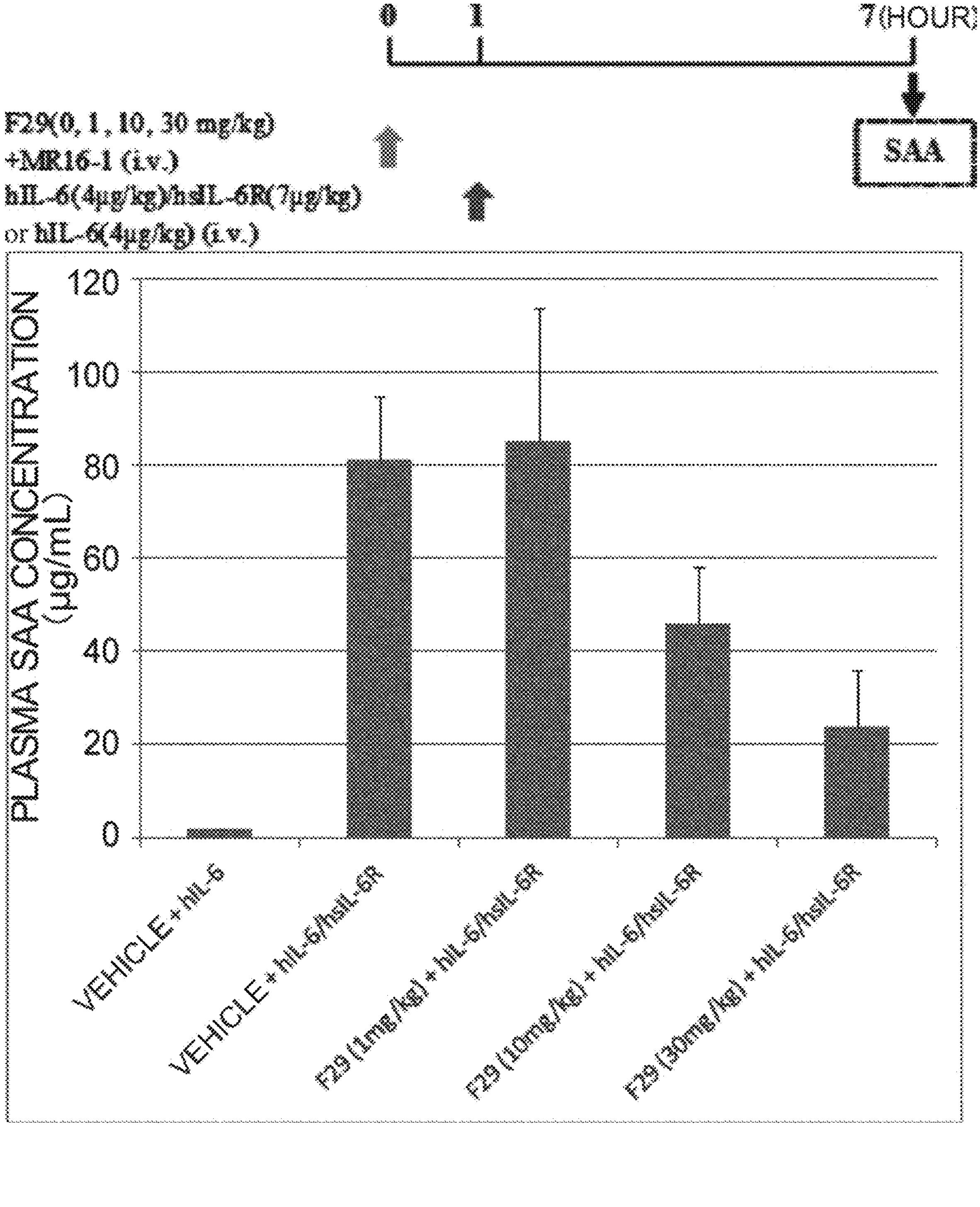
FIG. 13 shows a protocol of in vivo drug efficacy test (Test 1) using normal mice and the SAA inhibitory effect (mean±SE) of antibody administration.

The plasma SAA concentration was measured using the SAA Mouse ELISA Kit (catalog NO. KMA0021, Life Technologies Corporation) according to the protocol attached to the kit. The plasma SAA concentration six hours after antibody administration is shown in FIG. 13. Meanwhile, the plasma hsIL-6R concentration six hours after antibody administration is shown in Table 15.

TABLE 15

| samples | ng/mL |
|---|---|
| 6RKE02-F29 (F29) 30 mg/kg | N.D. |
| 6RKE02-F29 (F29) 10 mg/kg | 0.38 |
| 6RKE02-F29 (F29) 1 mg/kg | 3.22 |
| IL6/IL6R | 17.35 |
| IL6 | N.D. |

It was confirmed that 6RKE02-F29 reduced the plasma hsIL-6R concentration in a dose-dependent manner and thus had the effect to reduce the plasma SAA concentration.

In Vivo Drug Efficacy Test Using Normal Mice (Test 2)

6RKE02-F29 was intravenously administered at 0, 10, and 30 mg/kg to C57BL/6J Jcl mice (female). In test 2, 24 hours after administration, hIL-6 and hsIL-6R were intravenously administered at 4 μg/kg and 7 μg/kg, respectively, as a mixture. Six hours after the second intravenous administration, the blood was collected to determine the plasma SAA concentration by ELISA. To rule out the effect of endogenous mouse IL-6R on the plasma SAA concentration, MR16-1 (rat anti-mouse IL-6R antibody) was intravenously administered at 20 mg/kg to all mice simultaneously with the test substance. Exclusion of the effect of endogenous mouse IL-6R was confirmed by intravenously administering hIL-6 at 4 μg/kg to the vehicle-administered group that was intravenously administered with MR16-1 at 20 mg/kg.

Figure 14:
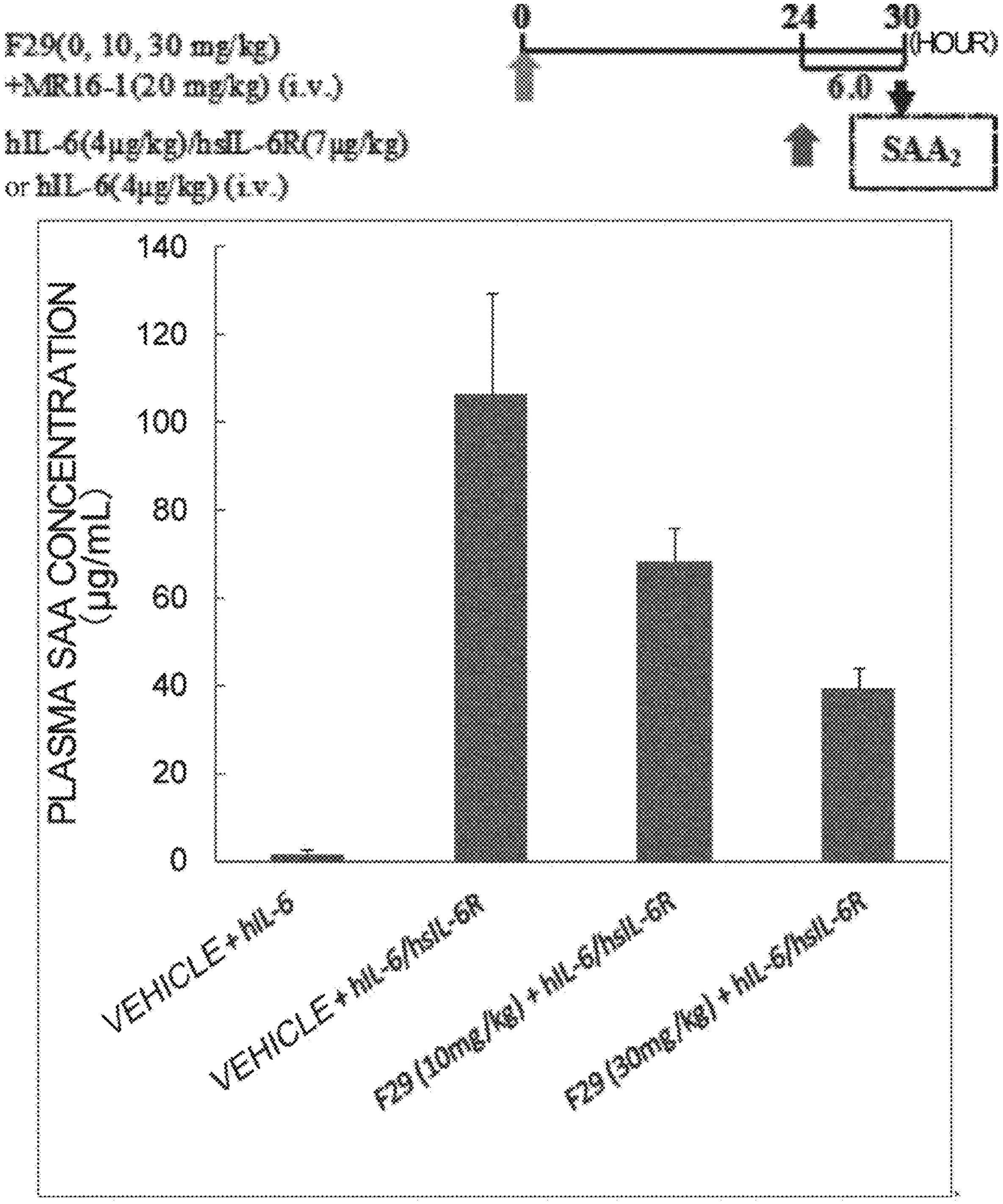
FIG. 14 is a diagram showing a protocol of in vivo drug efficacy test (Test 2) using normal mice and the SAA inhibitory effect (mean±SE) of antibody administration.

The plasma SAA concentration six hours after antibody administration is shown in FIG. 14. Meanwhile, the plasma hsIL-6R concentration six hours after antibody administration is shown in Table 16.

TABLE 16

| samples | ng/mL |
|---|---|
| 6RKE02-F29 (F29) 30 mg/kg | 0.22 |
| 6RKE02-F29 (F29) 10 mg/kg | 0.82 |
| IL6/IL6R | 27.50 |
| IL6 | N.D. |

It was confirmed that 6RKE02-F29 reduced the plasma hsIL-6R concentration in a dose-dependent manner and thus had the effect to reduce the plasma SAA concentration.

Tests 1 and 2 revealed that, although 6RKE02-F29 does not have in vitro inhibitory activity against the hsIL-6R- mediated trans-signaling, it can exhibit the in vivo inhibitory effect against the trans-signaling by eliminating hsIL-6R from the plasma.

Based on this finding, it can be said that, when using an antibody that binds to a target antigen in a pH-dependent manner and which has FcRn-binding activity in a neutral pH range, even if the antibody does not have the neutralizing activity to a specific epitope in vitro, the in vivo pharmaceutical effect (inhibitory effect) can be exhibited by eliminating the target antigen from the plasma. Ordinary antigen-binding molecules including monoclonal antibodies can only bind to a single epitope. Meanwhile, in certain antigens, there are several antigenic sites to be neutralized; ordinary monoclonal antibodies can neutralize the action of a single epitope, but cannot neutralize the action of other epitopes of such antigens. Even in this case, as shown in this Example, the action of all epitopes can be substantially inhibited when eliminating the antigen from the plasma by using a monoclonal antibody that binds to the target antigen in a pH-dependent manner and which has FcRn-binding activity in a neural pH range.

[Reference Example 6] Preparation of Antigen-Binding Molecules Whose Mouse FcγR-Binding Activity Under a Neutral pH Range Condition is Higher than the Binding Activity of Native Human IgG Fc Region (6-1) pH-Dependent Human IL-6 Receptor-Binding Antibodies H54/L28-IgG1 which comprises H54-IgG1 (SEQ ID NO: 113) and L28-CK (SEQ ID NO: 114) described in WO2009/125825 is a humanized anti-IL-6 receptor antibody. Meanwhile, Fv4-IgG1 which comprises VH3-IgG1 (SEQ ID NO: 4) and VL3-CK (SEQ ID NO: 122) is a humanized anti-IL-6 receptor antibody resulting from conferring, to H54/L28-IgG1, the property of binding to soluble human IL-6 receptor in a pH-dependent manner (which binds at pH 7.4 and dissociates at pH 5.8). The in vivo mouse test described in WO2009/125825 demonstrated that, in the group administered with a mixture of Fv4-IgG1 and soluble human IL-6 receptor as the antigen, the elimination of soluble human IL-6 receptor from plasma was significantly accelerated as compared to the group administered with a mixture of H54/L28-IgG1 and soluble human IL-6 receptor as the antigen.

Figure 15:
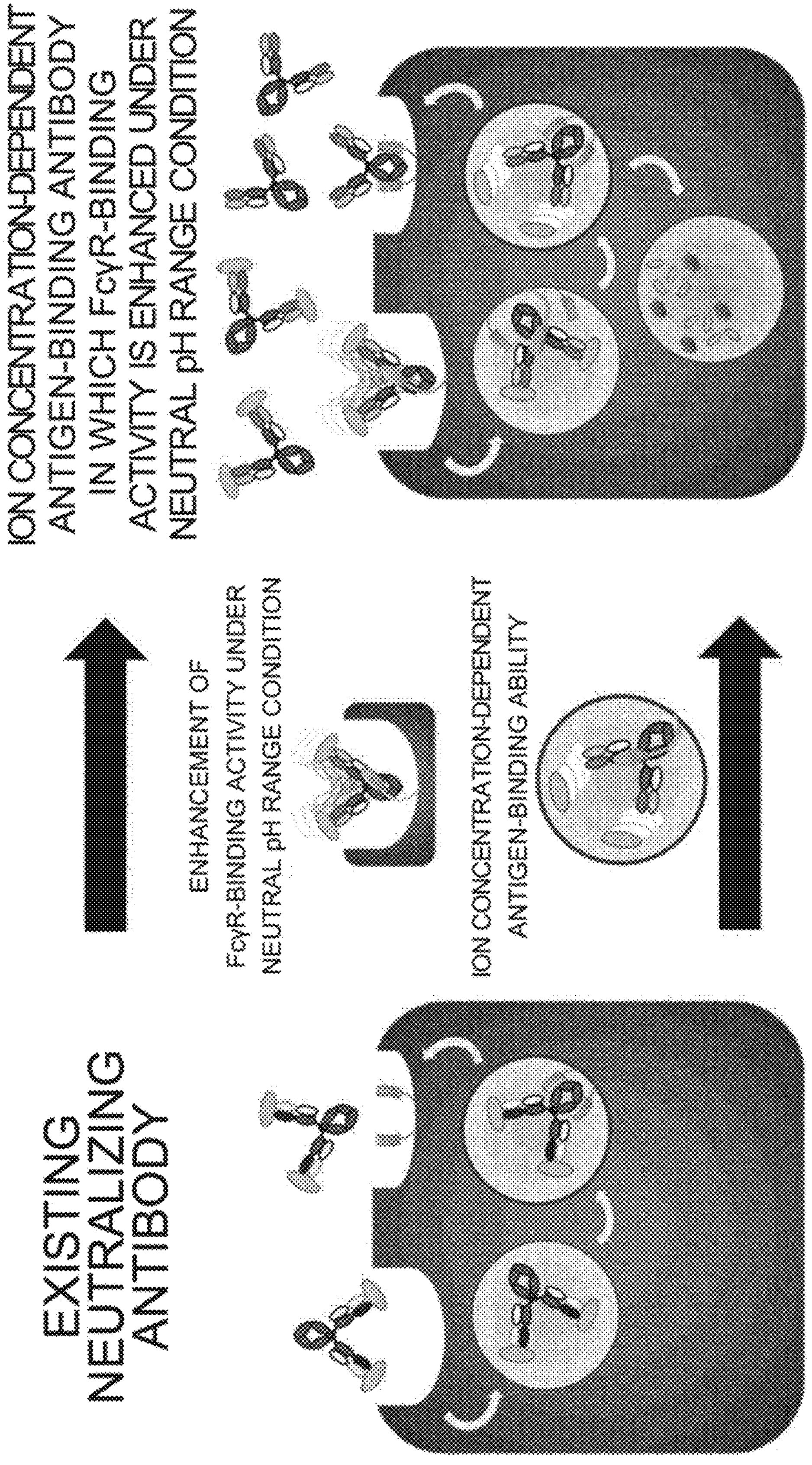
FIG. 15 shows a non-limiting action mechanism for the elimination of soluble antigen from plasma by administering an antibody that binds to an antigen in an ion concentration-dependent manner and whose Fcγ receptor binding is enhanced at a neutral pH as compared to existing neutralizing antibodies.

The soluble human IL-6 receptor bound to H54/L28-IgG1 is, together with the antibody, recycled to plasma by FcRn. Meanwhile, Fv4-IgG1 dissociates soluble human IL-6 receptor under the acidic condition in the endosome, and the dissociated soluble human IL-6 receptor is degraded in the lysosomes, thus this enables considerable acceleration of the elimination of soluble human IL-6 receptor. After binding to FcRn in the endosome, Fv4-IgG1 is recycled to the plasma. Since the recycled antibody can bind to soluble human IL-6 receptor again, the antibody repeatedly binds to the antigen (soluble human IL-6 receptor) and is recycled by FcRn to the plasma. It is thought that, as a result, a single antibody molecule can bind repeatedly several times to soluble human IL-6 receptor (FIG. 15).

(6-2) Preparation of an Anti-Human IL-6 Receptor Antibody with Enhanced Mouse FcγR Binding and Anti-Human IL-6 Receptor Antibody without Mouse FcγR Binding VH3-IgG1-F1022 (SEQ ID NO: 124), an antigen-binding molecule with enhanced mouse FcγR binding, was prepared by substituting Asp for Lys at position 326 (EU numbering) and Tyr for Leu at position 328 (EU numbering) in VH3-IgG1. Fv4-IgG1-F1022 containing VH3-IgG1-F1022 as the heavy chain and VL3-CK as the light chain was produced using the method described in Reference Example 1.

Meanwhile, VH3-IgG1-F760 (SEQ ID NO: 123), an antigen-binding molecule without mouse FcγR binding, was prepared by substituting Arg for Leu at position 235 and Lys for Ser at position 239 (EU numbering) in VH3-IgG1. Fv4-IgG1-F760 containing VH3-IgG1-F760 as the heavy chain and VL3-CK as the light chain was produced using the method described in Reference Example 1.

(6-3) Assessment of Mouse FcγR-Binding Activity

VH3/L(WT)-IgG1, VH3/L(WT)-IgG1-F1022, and VH3/L(WT)-IgG1-F760, which contain VH3-IgG1, VH3-IgG1-F1022, and VH3-IgG1-F760 as the heavy chain, respectively, and L(WT)-CK (SEQ ID NO: 5) as the light chain, were produced using the method described in Reference Example 1. These antibodies were kinetically analyzed for their mouse FcγR binding as described below.

(6-4) Kinetic Analysis of Mouse FcγR Binding

The binding of antibodies to mouse FcγRI, FcγRIIb, FcγRIII, and FcγRIV (hereinafter, referred to as mouse FcγRs) (R&D systems, Sino Biological, or prepared by the method described in Reference Example 2) was kinetically analyzed using BIACORE™ T100 and T200 surface plasmon resonance systems (GE Healthcare). An appropriate amount of protein L (ACTIGEN® protein (Alltech) or BioVision) was immobilized onto a Sensor chip CM4 (GE Healthcare) by an amine coupling method, and antibodies of interest were captured thereto. Then, diluted solutions of mouse FcγRs and a running buffer as a blank were injected, and the mouse FcγRs were allowed to interact with antibodies captured onto the sensor chip. The running buffer used was 20 mmol/l ACES, 150 mmol/l NaCl, 0.05% (w/v) Tween20®, pH 7.4. This buffer was also used to dilute the mouse FcγRs. The sensor chip was regenerated using 10 mmol/l glycine-HCl, pH 1.5. All measurements were carried out at 25° C. The binding rate constant ka (1/Ms) and dissociation rate constant kd (1/s), which are kinetic parameters, were calculated from the sensorgrams obtained by the measurement. KD (M) of each antibody for human FcγR was calculated based on the values. Each parameter was calculated using BIACORE™ T100 or T200 Evaluation Software (GE Healthcare).

The result shown in Table 17 was obtained by the measurement. VH3/L (WT)-IgG1-F1022 was demonstrated to have increased binding activity to mFcγRI, mFcγRIIb, and mFcγRIII as compared to VH3/L (WT)-IgG1. Regarding VH3/L (WT)-IgG1-F760, the binding to the various mouse FcγRs was undetectable, demonstrating that VH3/L (WT)-IgG1-F760 lacks the binding activity to the various mouse FcγRs. In the table, VH3/L (WT)-IgG1 is abbreviated as IgG1; VH3/L (WT)-IgG1-F1022 is abbreviated as F1022; and VH3/L (WT)-IgG1-F760 is abbreviated as F760.

TABLE 17

| VARIANT | KD (M) | | | |
|---|---|---|---|---|
| NAME | mFcγRI | mFcγRII | mFcγRIIII | mFcγRIV |
| IgG1 | 5.3E−08 | 9.8E−07 | 2.4E−06 | 8.6E−08 |
| F1022 | 7.6E−09 | 1.0E−08 | 5.5E−09 | 1.4E−07 |
| F760 | NOT DETECTED | NOT DETECTED | NOT DETECTED | NOT DETECTED |

(6-5) Preparation of Antibodies with Low Fucose Content

Known methods for increasing the FcγR-binding activity of antibodies include methods for making sugar chains linked to an antibody be sugar chains with low fucose content (J. Biol. Chem. (2003) 278, 3466-3473) in addition to methods for introducing an amino acid alteration into the Fc region of an antibody. An Fv4-IgG1 with low fucose content (hereinafter, abbreviated as Fv4-IgG1-Fuc) was produced by expressing Fv4-IgG1 using fucose transporter gene-deficient CHO cells (WO2006/067913) as host cells according to the method described in Reference Example 1. It has been reported that, of the mFcγRs (mouse Fcγ receptors), antibodies with low fucose content have selectively increased FcγRIV-binding activity (Science, 2005, 310 (5753) 1510-1512).

[Reference Example 7] Effect of Eliminating Antigens from Plasma by Antigen-Binding Molecules Whose FcγR-Binding Activity is Higher than the Binding Activity of Native Human IgG Fc Region (7-1) Effect of H54/L28-IgG1 and Fv4-IgG1 to Eliminate Antigens from Plasma H54/L28-IgG1, which is an anti-human IL-6 receptor antibody, and Fv4-IgG1 having the property of binding to human IL-6 receptor in a pH-dependent manner were produced by the method described in Reference Example 1. In vivo infusion tests were carried out using the produced H54/L28-IgG1 and Fv4-IgG1 by the method described below.

(7-1-1) In Vivo Infusion Tests Using Human FcRn Transgenic Mice

An animal model in which the soluble human IL-6 receptor concentration is maintained constant in plasma was created by implanting an infusion pump (MINI-OSMOTIC PUMP MODEL2004, alzet) containing soluble human IL-6 receptor under the skin on the back of human FcRn transgenic mice (B6.mFcRn−/−.hFcRn Tg line 32+/+mouse, Jackson Laboratories, Methods Mol Biol. (2010) 602, 93-104). The in vivo dynamics after administration of an anti-human IL-6 receptor antibody was assessed in the animal model. To suppress the production of neutralizing antibodies against soluble human IL-6 receptor, an anti-mouse CD4 monoclonal antibody (prepared by a known method) was administered once at 20 mg/kg into the tail vein. Then, an infusion pump containing 92.8 μg/ml soluble human IL-6 receptor was subcutaneously implanted on the back of the mice. Three days after implantation of the infusion pump, an anti-human IL-6 receptor antibody was administered once at 1 mg/kg into the tail vein. The blood was collected from the mice 15 minutes, seven hours, one day, two days, four days, and seven days after administration of the anti-human IL-6 receptor antibody. Immediately, the collected blood was centrifuged at 15,000 rpm and 4° C. for 15 minutes to prepare plasma. The isolated plasma was stored in a freezer set at −20° C. or below until use.

(7-1-2) Determination of the Soluble Human IL-6 Receptor (hsIL-6R) Concentration in Plasma by an Electrochemiluminescent Method The hsIL-6R concentrations in mouse plasma were determined by an electrochemiluminescent method. hsIL-6R standard curve samples prepared at 2000, 1000, 500, 250, 125, 62.5, and 31.25 μg/ml and assay samples of mouse plasma diluted 50 times or more were mixed with Monoclonal Anti-human IL-6R Antibody (R&D) which had been ruthenated with SULFO-TAG NHS Ester (Meso Scale Discovery), Biotinylated Anti-human IL-6 R Antibody (R&D), and Tocilizumab. The mixtures were incubated at 37° C. overnight. Tocilizumab was prepared at a final concentration of 333 μg/ml. Then, the reaction mixtures were aliquoted in an MA400 PR Streptavidin Plate (Meso Scale Discovery). The solution reacted at room temperature for one hour was washed out, and then Read Buffer T (×4) (Meso Scale Discovery) was aliquoted. Immediately thereafter, the measurement was carried out using SECTOR PR 400 Reader (Meso Scale Discovery). The concentration of hsIL-6R was determined based on the response of the standard curve using analysis software SOFTmax® PRO (Molecular Devices).

Figure 16:
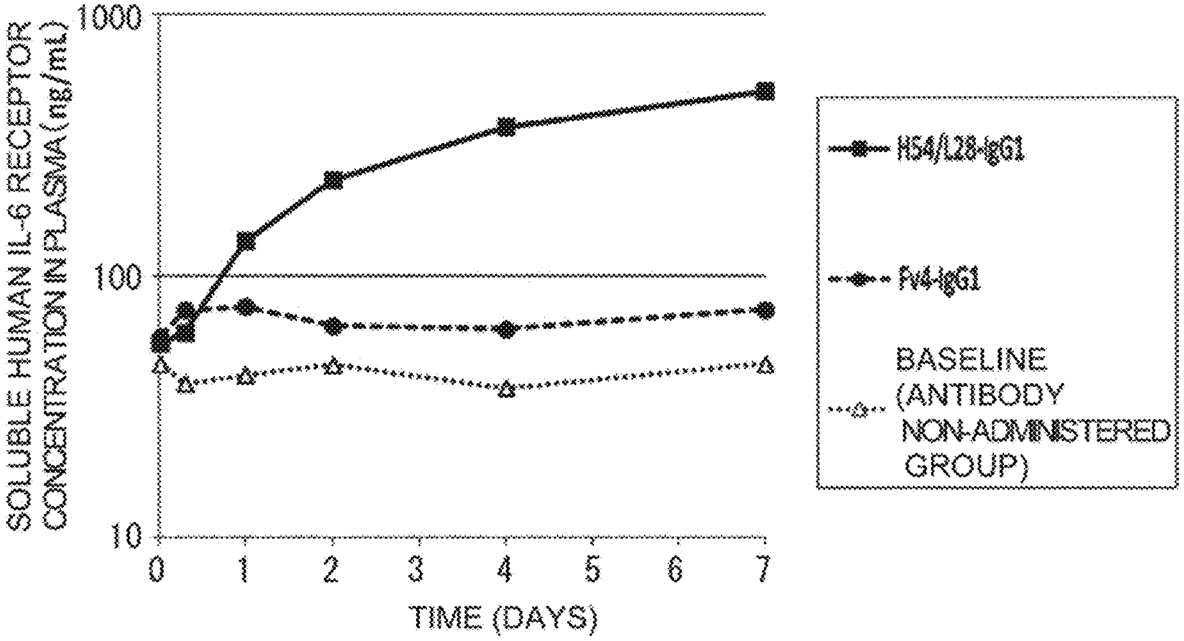
FIG. 16 shows a time course of human IL-6 receptor concentration in the plasma of human FcRn transgenic mice administered with Fv4-IgG1 which binds to human IL-6 receptor in a pH-dependent manner or H54/L28-IgG1.

A time course of the monitored human IL-6 receptor concentration is shown in FIG. 16. As compared to H54/L28-IgG1, Fv4-IgG1 that binds to human IL-6 receptor in a pH-dependent manner could reduce the human IL-6 receptor concentration, but could not reduce it below the baseline without antibody administration. That is, the administered antibody which binds to an antigen in a pH-dependent manner could not reduce the antigen concentration in plasma below the level prior to antibody administration.

(7-2) The Effect of Eliminating an Antigen from Plasma by an Antibody with Increased or Reduced FcγR-binding Activity Whether the time course of human IL-6 receptor concentration is influenced by increasing or reducing the FcγR-binding activity of Fv4-IgG1, which is a pH-dependent human IL-6 receptor-binding antibody, was assessed by the method described below. Using Fv4-IgG1, Fv4-IgG1-F760, Fv4-IgG1-F1022, and Fv4-IgG1-Fuc prepared as described in Reference Example 6, in vivo infusion tests were performed by the method described below.

(7-2-1) In Vivo Infusion Tests Using Human FcRn Transgenic Mice

A animal model in which the soluble human IL-6 receptor concentration is maintained constant in plasma was created by implanting an infusion pump (MINI-OSMOTIC PUMP MODEL2004, alzet) containing soluble human IL-6 receptor under the skin on the back of human FcRn transgenic mice (B6.mFcRn−/−.hFcRn Tg line 32+/+mouse, Jackson Laboratories, Methods Mol Biol. (2010) 602, 93-104). In the animal model, an anti-human IL-6 receptor antibody was administered simultaneously with Sanglopor (CSL Behring) which is a human immunoglobulin preparation, to assess the in vivo dynamics of the soluble human IL-6 receptor after antibody administration. To suppress the production of neutralizing antibodies against soluble human IL-6 receptor, an anti-mouse CD4 monoclonal antibody (prepared by a known method) was administered once at 20 mg/kg into the tail vein. Then, an infusion pump containing 92.8 μg/ml soluble human IL-6 receptor was subcutaneously implanted on the back of the mice. Three days after implantation of the infusion pump, an anti-human IL-6 receptor antibody and Sanglopor were administered once at 1 mg/kg and 1000 mg/kg, respectively, into the tail vein. The blood was collected from the mice 15 minutes, seven hours, one day, two days, four days, seven days, 14 days, and 21 days after administration of the anti-human IL-6 receptor antibody. The blood was collected from the mice 15 minutes, seven hours, one day, two days, three days, seven days, 14 days, and 21 days after administration of the anti-human IL-6 receptor antibody. Immediately, the collected blood was centrifuged at 15,000 rpm and 4° C. for 15 minutes to prepare the plasma. The isolated plasma was stored in a freezer set at −20° C. or below until use.

(7-2-2) Determination of the Soluble Human IL-6 Receptor (hsIL-6R) Concentration in Plasma by an Electrochemiluminescent Method The hsIL-6R concentrations in mouse plasma were determined by the same electrochemiluminescent method as described in (7-1-2).

Figure 17:
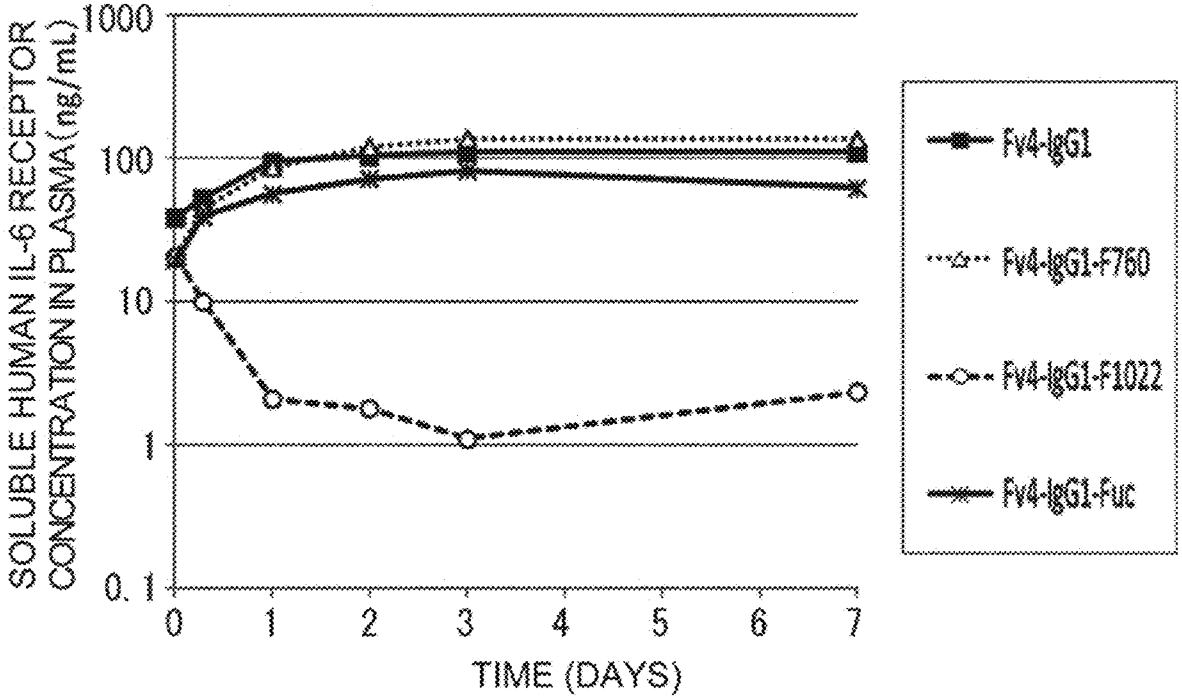
FIG. 17 shows a time course of human IL-6 receptor concentration in the plasma of human FcRn transgenic mice administered with Fv4-IgG1 which binds to human IL-6 receptor in a pH-dependent manner, Fv4-IgG1-F760 which is an Fv4-IgG1 variant that lacks mouse FcγR binding, Fv4-IgG1-F1022 which is an Fv4-IgG1 variant with enhanced mouse FcγR binding, or Fv4-IgG1-Fuc which is an Fv4-IgG1 antibody with low fucose content.

The result is shown in FIG. 17. The time course of human IL-6 receptor concentration in plasma of mice administered with Fv4-IgG1-F760, from which the mouse FcγR binding of Fv4-IgG1 is deleted, was demonstrated to be comparable to that in mice administered with Fv4-IgG1. The cytotoxic activity to a membrane antigen depends on the FcγR binding, and thus the cytotoxic activity is lost when eliminating the FcγR binding. On the other hand, even when administering an antibody, from which mouse FcγR binding is deleted, against human IL-6 receptor which is a soluble antigen, there was no effect on the time course of human IL-6 receptor concentration in the plasma of the administered mice. Thus, it would be thought that the FcγR binding of an antibody against the soluble antigen has no contribution to the time course of antigen concentration in the plasma of mice administered with the antibody.

Surprisingly, however, the human IL-6 receptor concentration in the plasma of mice administered with Fv4-IgG1-F1022 with enhanced mouse FcγR binding was considerably reduced as compared to the human IL-6 receptor concentration in the plasma of mice administered with Fv4-IgG1. As to the degree of reduction, the concentration was confirmed to be decreased below the base-line human IL-6 receptor concentration without antibody administration. In particular, the human IL-6 receptor concentration in the plasma of mice administered with Fv4-IgG1-F1022 was reduced down to about 1/100 three days after administration as compared to the case of Fv4-IgG1 administration. This finding demonstrates that, by administering to mice an antibody that binds to human IL-6 receptor in a pH-dependent manner and whose FcγR binding has been enhanced, the human IL-6 receptor concentration in the plasma of the mice can be significantly reduced, and as to the degree of reduction, the antigen concentration in plasma can be reduced below the level before antibody administration.

Furthermore, it was also demonstrated that, as compared to mice administered with Fv4-IgG1, the human IL-6 receptor concentration in plasma was reduced in mice administered with Fv4-IgG1-Fuc which has sugar chains with low fucose content and with increased mouse FcγR IV-binding activity. In particular, the human IL-6 receptor concentration in the plasma of mice administered with Fv4-IgG1-Fuc was reduced down to about 1/2 seven days after administration as compared to the case of Fv4-IgG1 administration. The above finding demonstrates that, by administering to mice a pH-dependent antigen-binding molecule that binds to human IL-6 receptor in a pH-dependent manner and whose FcγR binding has been enhanced, the soluble antigen concentration in the plasma of the mice can be reduced. Methods for enhancing the FcγR binding are not particularly limited to introduction of amino acid alterations. It was demonstrated that such enhancement can be achieved, for example, by using a human IgG Fc region to which a sugar chain with low fucose content is linked at position 297 (EU numbering); however, the effect of Fv4-IgG1-Fuc to reduce antigen concentration was smaller than Fv4-F1022. Thus, it would be thought that, of several FcγRs (FcγRI, II, III, and IV for mouse), mFcγIV, to which the binding of Fv4-IgG1-Fuc is enhanced, does not have a large contribution to the reduction of antigen concentration as an FcγR.

Thus, it was revealed that, by administering to an individual an antibody that binds to a soluble antigen in a pH-dependent manner and whose FcγR binding has been enhanced, the soluble antigen concentration in the plasma of the individual can be markedly reduced.

Without being bound by a particular theory, the unexpected reduction of soluble antigen concentration in plasma, which was observed when administering an antigen-binding molecule whose FcγR binding has been enhanced and that comprises an antigen-binding domain whose antigen-binding activity is altered depending on the ion concentration condition such as pH and an FcRn-binding domain that has FcRn-binding activity under an acidic pH range condition, can be explained as follows.

IgG antibodies that are non-specifically incorporated into cells return to the cell surface by binding to FcRn under the acidic condition in the endosome, and then dissociate from FcRn under the neutral condition in plasma. In such a case, when an antibody that neutralizes the function of a soluble antigen by binding to the antigen is administered to mice in which the concentration of the soluble antigen is maintained constant in plasma, the soluble antigen in plasma forms a complex with the antibody. The soluble antigen incorporated into cells while remaining as the complex is thought to be recycled, in a state bound to the antibody, to the plasma together with the antibody, because the Fc region of the antibody binds to FcRn under the acidic condition in the endosome.

Meanwhile, when the antibody against the soluble antigen is an antibody that binds to the antigen in a pH-dependent manner (i.e., an antibody that dissociates the soluble antigen under the acidic condition in the endosome), the soluble antigen that is non-specifically incorporated into cells while remaining as a complex with the antibody, is dissociated from the antibody in the endosome and degraded in the lysosome; thus, the soluble antigen is not recycled to the plasma. That is, it is thought that Fv4-IgG1 incorporated as a complex with the soluble antigen into cells can dissociate the soluble antigen in the endosome and thus accelerate the elimination of the soluble antigen.

As described above, antigen-binding molecules such as Fv4-IgG1, which contain an antigen-binding domain whose antigen-binding activity is altered depending on the ion concentration, are thought to be capable of binding to antigens repeatedly several times. The effect to accelerate the elimination of soluble antigens from the plasma by dissociating them in the endosome is thought to depend on the rate of incorporation of the antigen/antigen-binding molecule complex into the endosome. An antigen-binding molecule whose binding activity to various FcγRs has been increased and that contains an antigen-binding domain whose antigen-binding activity is altered depending on the condition of ion concentration, is actively incorporated into cells by binding to various FcγRs expressed on the cell membrane, and can be shuttled back to plasma by recycling via the binding between FcRn and the FcRn-binding domain comprised in the molecule, which has FcRn-binding activity under an acidic pH range condition. That is, it is thought that, since the above antigen-binding molecule which forms a complex with a soluble antigen in plasma is actively incorporated into cells via FcγR expressed on the cell membrane, its effect to accelerate the elimination of the soluble antigen from plasma is more markedly shown than antigen-binding molecules whose binding activity to various FcγRs has not been increased.

The FcγR-binding activity of an antibody that binds to a membrane antigen plays an important role in the cytotoxic activity of the antibody. Thus, when it is necessary for an antibody used as a pharmaceutical agent to have cytotoxic activity, a human IgG1 isotype with strong FcγR-binding activity is used. In addition, techniques to enhance the cytotoxic activity of such antibodies by increasing the FcγR-binding activity of the antibodies are used commonly in the art.

Meanwhile, the role of the FcγR-binding activity of antibodies that bind to soluble antigens and which are used as pharmaceutical agents has not been known in the art. There has been no sufficient assessment on what difference in the effect on the living organism administered with the antibodies is caused by the difference in the FcγR-binding activity between human IgG1 with high FcγR-binding activity and human IgG2 and human IgG4 with low FcγR-binding activity. Actually, it was demonstrated in the present Example that there was no influence on the time course of soluble antigen concentration in the plasma of the individuals administered with an antibody that lacks FcγR-binding activity. Meanwhile, in the present invention, it was revealed that the soluble antigen concentration was significantly reduced in the plasma of the individuals administered with an antigen-binding molecule whose FcγR-binding activity has been increased and which contains an antigen-binding domain whose soluble antigen-binding activity is altered depending on the ion concentration condition. Specifically, it can be said that the present inventors revealed for the first time the benefit of the enhancement of FcγR binding by combining an FcRn-binding domain that has FcRn-binding activity under an acidic pH range condition with an antigen-binding domain whose soluble antigen binding is altered depending on the ion concentration condition, comprised in an antigen-binding molecule targeted to a soluble antigen.

[Reference Example 8] Effect of Eliminating Antigens from Plasma by Antigen-Binding Molecules Whose FcγR-Binding Activity is Greater than that of Native Human IgG Fc Region and Whose Human FcRn-Binding Activity has been Increased Under an Acidic pH Range Condition (8-1) Preparation of Antigen-Binding Molecules Whose FcγR-Binding Activity is Greater than the Binding Activity of Native Human IgG Fc Region and Whose Human FcRn-Binding Activity has been Increased Under an Acidic pH Range Condition A reported method for improving the retention of IgG antibody in plasma is to improve the FcRn binding under an acidic pH range condition. It is thought that, when the FcRn binding under an acidic pH range condition is improved by introducing an amino acid substitution into the Fc region of an IgG antibody, this increases the recycling efficiency from the endosome to plasma, resulting in an improvement of the plasma retention of the IgG antibody.

There are many reports on amino acid alterations to improve the plasma retention by improving the human FcRn-binding activity under an acidic pH range condition. Such alterations include, for example: the method for substituting Leu for Met at position 428 and Ser for Asn at position 434 (EU numbering) in an IgG antibody (Nat. Biotechnol, (2010) 28, 157-159); the method for substituting Ala for Asn at position 434 (Drug. Metab. Dispos. (2010) 38 (4), 600-605); the method for substituting Tyr for Met at position 252, Thr for Ser at position 254, and Glu for Thr at position 256 (J. Biol. Chem. (2006) 281, 23514-23524); the method for substituting Gln for Thr at position 250 and Leu for Met at position 428 (J. Immunol. (2006) 176 (1) 346-356); the method for substituting His for Asn at position 434 (Clin. Pharm. & Ther. (2011) 89 (2) 283-290); and WO2010/106180; WO2010/045193; WO2009/058492; WO2008/022152; WO2006/050166, WO2006/053301, WO2006/031370; WO2005/123780; WO2005/047327; WO2005/037867; WO2004/035752; and WO2002/060919.

VH3-IgG1-F1093 (SEQ ID NO: 125) with a substitution of Leu for Met at position 428 and Ser for Asn at position 434 (EU numbering) in VH3-IgG1-F1022 was prepared to improve the pharmacokinetics of Fv4-IgG1-F1022 that was demonstrated to produce, when administered, the effect of significantly reducing the soluble antigen concentration in plasma, as described in Reference Example 7. Fv4-IgG1-F1093 comprising VH3-IgG1-F1093 as the heavy chain and VL3-CK as the light chain was constructed using the method described in Reference Example 1.

(8-2) Effect of Eliminating Antigens from Plasma by Antigen-Binding Molecules Whose FcγR-Binding Activity is Greater than that of Native Human IgG Fc Region and Whose Human FcRn-Binding Activity has been Increased Under an Acidic pH Range Condition An in vivo infusion test was carried out for Fv4-IgG1-F1093 by the same method as described in (7-1-1) using human FcRn transgenic mice in which the soluble human IL-6 receptor concentration is maintained constant in plasma. Soluble human IL-6 receptor concentrations in the plasma of the mice were determined by the method described in (7-1-2). The result is shown in FIG. 18.

(8-2-1) Determination of the Anti-Human IL-6 Receptor Antibody Concentration in Plasma by ELISA Anti-human IL-6 receptor antibody concentrations in the plasma of the mice were determined by ELISA. First, an anti-Fv4 ideotype antibody (in-house preparation) was aliquoted in a Nunc-Immuno Plate, MaxiSorp™ plate (Nalge nunc International). The plate was allowed to stand at 4° C. overnight to prepare a plate immobilized with the anti-Fv4 ideotype antibody. Standard curve samples with a concentration of 6.4, 3.2, 1.6, 0.8, 0.4, 0.2, or 0.1 μg/ml plasma, and assay samples of mouse plasma diluted 100 times or more were prepared. 100 μl of the standard curve and plasma assay samples were mixed with 200 μl of 20 ng/ml hsIL-6R and 2 mg/ml Sanglopor. This was allowed to stand at one hour at room temperature, and then aliquoted into a plate immobilized with an anti-Fv4 ideotype antibody. The plate was allowed to stand at room temperature for one hour. Then, Biotinylated Anti-human IL-6 R Antibody (R&D) was reacted at room temperature for one hour. Next, Streptavidin-PolyHRP80 (Stereospecific Detection Technologies) was reacted at room temperature for one hour. Chromogenic reaction was performed using TMB One Component HRP Microwell Substrate (BioFX Laboratories) as a substrate. After terminating the reaction with TN sulfuric acid (Showa Chemical), the absorbance at 450 nm was measured with a microplate reader. The concentrations in mouse plasma were determined based on the absorbance of the standard curve using the analysis software SOFTmax® PRO (Molecular Devices). The result is shown in FIG. 19.

Figure 19:
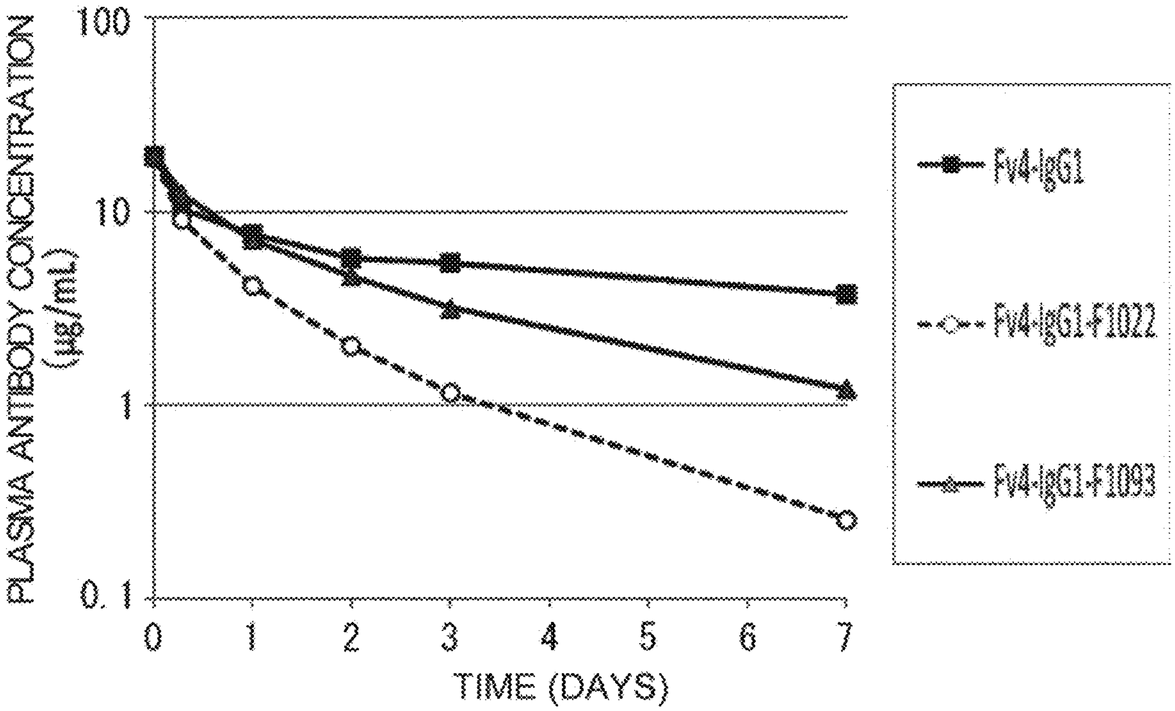
FIG. 19 shows a concentration time course of the administered antigen-binding molecules in the plasma of human FcRn transgenic mice administered with Fv4-IgG1 or antigen-binding molecules comprising as the heavy chain, VH3-IgG1-F1022 or VH3-IgG1-F1093 which is a VH3-IgG1-F1022 variant with improved FcRn binding in an acidic pH range.

(8-3) Improvement of Pharmacokinetics by Increasing the Human FcRn-Binding Activity Under an Acidic pH Range Condition As shown in FIG. 19, in the group administered with Fv4-IgG1-F1022 resulting from the enhancement of the FcγR-binding activity of Fv4-IgG1 under a neutral pH range condition, the plasma retention of the administered antibody was demonstrated to be reduced as compared to the group administered with Fv4-IgG1. Meanwhile, in the group administered with Fv4-IgG1-F1093 resulting from the enhancement of the human FcRn-binding activity of Fv4-IgG1-F1022 under an acidic pH range condition, the plasma retention of the administered antibody was demonstrated to be significantly improved as compared to the group administered with Fv4-IgG1-F1022.

Figure 18:
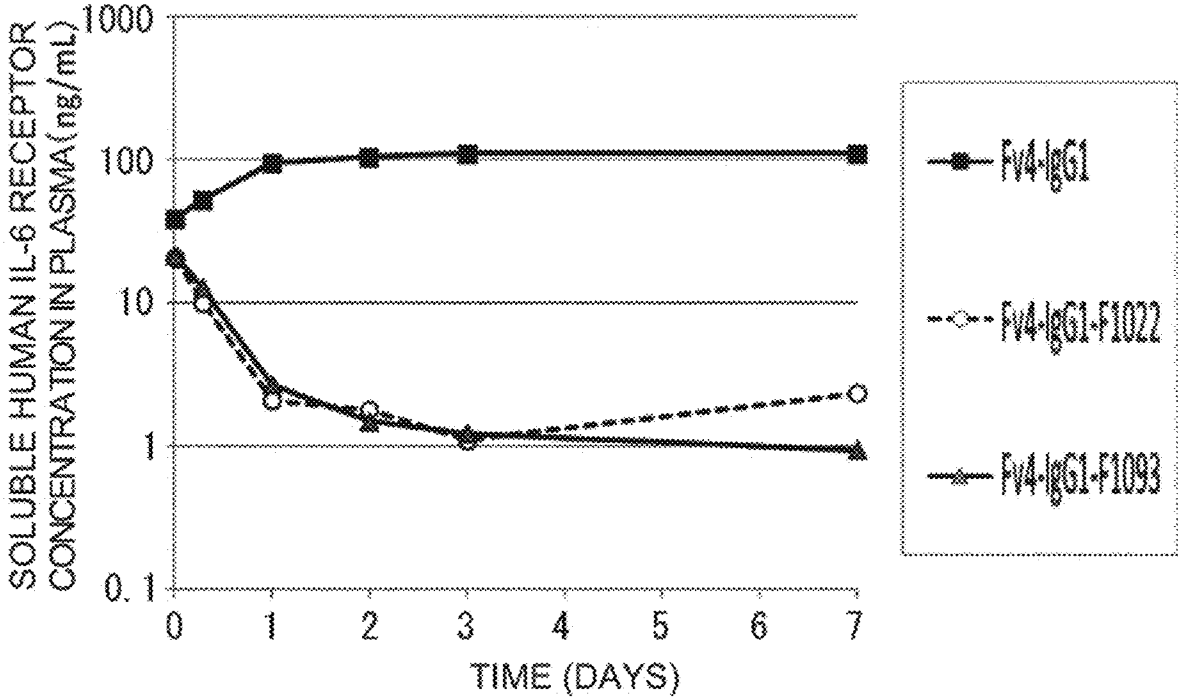
FIG. 18 shows a time course of human IL-6 receptor concentration in the plasma of human FcRn transgenic mice administered with Fv4-IgG1 or antigen-binding molecules comprising as the heavy chain, VH3-IgG1-F1022 or VH3-IgG1-F1093 which is a VH3-IgG1-F1022 variant with improved FcRn binding in an acidic pH range.

Furthermore, as shown in FIG. 18, the time course of the soluble human IL-6 receptor concentration in the plasma of the Fv4-IgG1-F1022-administered group was equivalent to that of the Fv4-IgG1-F1093-administered group, up to three days after antibody administration. On day three after administration, as compared to the Fv4-IgG1-administered group, the soluble human IL-6 receptor concentration in plasma was reduced as much as 100 times in both of the Fv4-IgG1-F1022 and Fv4-IgG1-F1093-administered groups. However, on day seven after antibody administration, the soluble human IL-6 receptor concentration in plasma was observed to be elevated in the Fv4-IgG1-F1022-administered group as compared to on day three after administration. On the other hand, in the Fv4-IgG1-F1093-administered group, an increase in the plasma concentration of soluble human IL-6 receptor was not observed, showing that the effect to reduce the soluble human IL-6 receptor concentration was sustained in this administration group.

Specifically, Fv4-IgG1-F1093, when administered, reduced the soluble human IL-6 receptor concentration in the plasma of the administered individual down to about 1/100 as compared to Fv4-IgG1, and in addition, it sustained this condition for a long period. Thus, Fv4-IgG1-F1093 was demonstrated to be a highly excellent antigen-binding molecule. Without being bound by a particular theory, the phenomenon observed herein can be explained as follows. Fv4-IgG1-F1022 in which the FcγR-binding activity of Fv4-IgG1 has been increased under a neutral pH range condition is thought to be incorporated in a large amount mainly into cells expressing FcγR on the cell membrane. The incorporated antibody is transferred into the endosome, and by binding to FcRn in the endosome, the antibody is recycled to the plasma. When the FcRn-binding activity of the antibody is not high enough under the condition at acidic pH in the endosome, the antibody incorporated into the endosome is thought to be incapable of sufficient recycling. Specifically, a possible reason for the reduced plasma retention of Fv4-IgG1-F1022 relative to Fv4-IgG1 would be that the FcRn-binding activity under an acidic pH range condition is insufficient for sufficient recycling of the endosome-incorporated antibody to the plasma by FcRn binding, and the antibody that was not recycled was degraded in the lysosome.

On the other hand, as with Fv4-IgG1-F1022, Fv4-IgG1-F1093 resulting from the enhancement of the human FcRn-binding activity of Fv4-IgG1-F1022 under an acidic pH range condition is thought to be incorporated in a large amount mainly into cells expressing FcγR on the cell membrane. An antibody incorporated and transferred into the endosome is recycled to the plasma by binding to FcRn in the endosome. Since its human FcRn-binding activity under an acidic pH range condition is enhanced, Fv4-IgG1-F1093 is thought to have sufficient FcRn-binding activity in the endosome. Thus, after incorporation into cells, most of Fv4-IgG1-F1093 is recycled to the plasma. Thus, it would be thought that the plasma retention of Fv4-IgG1-F1093 was improved in administered individuals as compared to Fv4-IgG1-F1022.

On the other hand, it has been known that the plasma retention of ordinary antibodies is improved when their FcRn-binding activity is improved under an acidic pH range condition. However, it is thought that, when the antibody retention in plasma is improved, the plasma retention of antibody-bound antigens is also improved, and this results in an increase of the antigen concentration in plasma. In actual, as described in WO2010/088444, Antibody 18E introduced with the alteration YTE into Antibody 18, which is a human IgG1 antibody against IL-6, to increase the FcRn-binding activity under an acidic pH range condition, showed improved antibody retention in the plasma of cynomolgus monkeys, and at the same time, the concentration of the IL-6 antigen was also elevated in the plasma.

Surprisingly, however, when administering Fv4-IgG1-F1093 introduced with an alteration similar to YTE for increasing the FcRn-binding activity under an acidic pH range condition into Fv4-IgG1-F1022 that binds to the antigen in a pH-dependent manner and has increased FcγR-binding activity, the plasma retention of the antibody was significantly improved in the administered individuals without increasing the concentration of soluble human IL-6 receptor which is the antigen. Rather, on day seven after antibody administration, the soluble human IL-6 receptor concentration remained low in the individuals administered with Fv4-IgG1-F1093 as compared to those administered with Fv4-IgG1-F1022.

Without being bound by a particular theory, the phenomenon observed herein can be explained as follows. When administered to a living organism, an antibody without pH-dependent antigen binding is non-specifically incorporated into cells. Antigens that remain to be bound to the antibody are recycled to the plasma in the same extent as the antibody. Meanwhile, for an antibody with increased FcRn-binding activity under an acidic pH range condition, the extent of recycling to the plasma in a living organism administered with the antibody is higher than that of an antibody without increased FcRn-binding activity, and this results in an increased extent of recycling of antigens bound to the antigen to the plasma in the living organism. Thus, due to the improved plasma retention of the antibody administered in the living organism, the plasma concentration of the antigen to which the antibody binds is thought to be also increased in the living organism.

Meanwhile, when administered to a living organism, an antibody that binds to an antigen in a pH-dependent manner and which has increased FcγR-binding activity is mainly incorporated into cells expressing FcγR on the cell membrane, and this worsens the plasma retention. Furthermore, after being incorporated into the cells while bound to the antibody, the antigen is dissociated from the antibody in the endosome and then degraded in the lysosome, resulting in a decrease of the antigen concentration in plasma in the living organism. When the FcRn-binding activity is increased under an acidic pH range condition, the antibody retention in plasma, even if worsened due to increased FcγR-binding activity, is improved by an increase in the rate of recycling by FcRn. In this case, since the antigen bound to the antibody that binds to the antigen in a pH-dependent manner is dissociated from the antibody in the endosome and directly degraded in the lysosome, it is not thought that the antigen concentration is increased in the plasma. Furthermore, the improved plasma retention of the antibody administered to the living organism is thought to allow the antigen elimination effect of the antibody to be sustained, and the antigen concentration to be maintained low for a longer period.

The above findings demonstrate that the plasma retention of an administered antibody is improved in a living organism administered with the antibody in which the human FcRn-binding activity under an acidic pH range condition is enhanced in an antigen-binding molecule whose FcγR-binding activity is higher than that of native human IgG Fc region. Furthermore, it was revealed that, in this case, the antibody retention in plasma is improved without deteriorating the antigen-elimination effect.

[Reference Example 9] Further Assessment of the Effect of Eliminating Antigens from Plasma by Antigen-Binding Molecules Whose FcγR-Binding Activity is Greater than that of Native Human IgG Fc Region and Whose Human FcRn-Binding Activity has been Increased Under an Acidic pH Range Condition (9-1) The Antigen Elimination Effect of an Antibody with Increased FcγR-Binding Activity As described in Reference Example 7, the antigen concentration in plasma was significantly reduced in the group administered with Fv4-IgG1-F1022 with enhanced mouse FcγR binding. Meanwhile, as shown in Reference Example 8, the reduced plasma retention observed in the Fv4-IgG1-F1022-administered group was markedly improved by increasing the human FcRn-binding activity of Fv4-IgG1-F1022 under an acidic pH range condition. Next, the effect of eliminating soluble antigens from plasma by enhancing mouse FcγR binding and the effect of improving the plasma antibody retention by enhancing the human FcRn binding activity under an acidic pH range condition were further assessed as described below.

(9-2) Preparation of an Anti-Human IL-6 Receptor Antibody with Enhanced Mouse FcγR Binding VH3-IgG1-F1087 (SEQ ID NO: 145) resulting from substituting Asp for Lys at position 326 (EU numbering) in VH3-IgG1, and VH3-IgG1-F1182 (SEQ ID NO: 148) resulting from substituting Asp for Ser at position 239 and Glu for Ile at position 332 (EU numbering) in VH3-IgG1, were prepared as antigen-binding molecules with enhanced mouse FcγR binding. Fv4-IgG1-F1087 that contains VH3-IgG1-F1087 as the heavy chain and VL3-CK as the light chain, and Fv4-IgG1-F1182 that contains VH3-IgG1-F1182 as the heavy chain and VL3-CK as the light chain, were produced using the method described in Reference Example 1.

(9-3) Assessment of Mouse FcγR-Binding Activity

VH3/L (WT)-IgG1-F1087 and VH3/L (WT)-IgG1-F1182 which contain VH3-IgG1-F1087 and VH3-IgG1-F1182 as the heavy chain, respectively, and L (WT)-CK (SEQ ID NO: 5) as the light chain, were prepared by the method described in Reference Example 1. These antibodies, VH3/L (WT)-IgG1-F1022, and VH3/L (WT)-IgG1 were assessed for their mouse FcγR-binding activity by the method described in Reference Example 2. The result is shown in Table 18. In addition, the ratio of the increase in the mouse FcγR-binding activity of each variant relative to the IgG1 before alteration is shown in Table 19. In the table, VH3/L (WT)-IgG1 is abbreviated as IgG1; VH3/L (WT)-IgG1-F1022 is abbreviated as F1022; VH3/L (WT)-IgG1-F1087 is abbreviated as F1087; and VH3/L (WT)-IgG1-F1182 is abbreviated as F1182.

TABLE 18

| VARIANT | KD (M) | | | |
|---|---|---|---|---|
| NAME | mFcγRI | mFcγRIIb | mFcγRIII | mFcγRIV |
| IgG1 | 5.3E−08 | 9.8E−07 | 2.4E−06 | 8.6E−08 |
| F1022 | 7.6E−09 | 1.0E−08 | 5.5E−09 | 1.4E−07 |
| F1087 | 2.9E−08 | 5.6E−08 | 5.2E−08 | 3.3E−07 |
| F1182 | 2.4E−09 | 1.1E−07 | 4.8E−07 | 5.3E−10 |

TABLE 19

| | RATIO OF BINDING TO IgG1 | | | |
|---|---|---|---|---|
| VARIANT NAME | mFcγRI | mFcγRIIb | mFcγRIII | mFcγRIV |
| IgG1 | 1.0 | 1.0 | 1.0 | 1.0 |
| F1022 | 7.0 | 93.6 | 440.5 | 0.6 |
| F1087 | 1.8 | 17.5 | 46.2 | 0.3 |
| F1182 | 22.1 | 9.1 | 5.0 | 162.3 |

As shown in Table 19, it was demonstrated that F1087 and F1022 had increased binding activity to mouse FcγRI, mouse FcγRIIb, and mouse FcγRIII as compared to IgG1, whereas their mouse FcγRIV-binding activity was not increased. Regarding the binding activity of F1087 to mouse FcγRI, mouse FcγRIIb, mouse FcγRIII, and mouse FcγRIV, the extent of its increase was revealed to be smaller than that of F1022. Meanwhile, it was shown that the binding activity of F1182 to mouse FcγRI and mouse FcγRIV was considerably increased, whereas the extent of increase in its binding activity to FcγRIIb and FcγRIII was smaller than those of F1022 and F1087. As mentioned above, these three types of variants showed enhanced binding to some mouse FcγRs; however, it was shown that the FcγR to which the binding activity is selectively increased and the extent of the increase vary depending on the variant.

(9-4) The Effect of Eliminating Antigens from Plasma by Fv4-IgG1-F1087 and Fv4-IgG1-F1182

Figure 20:
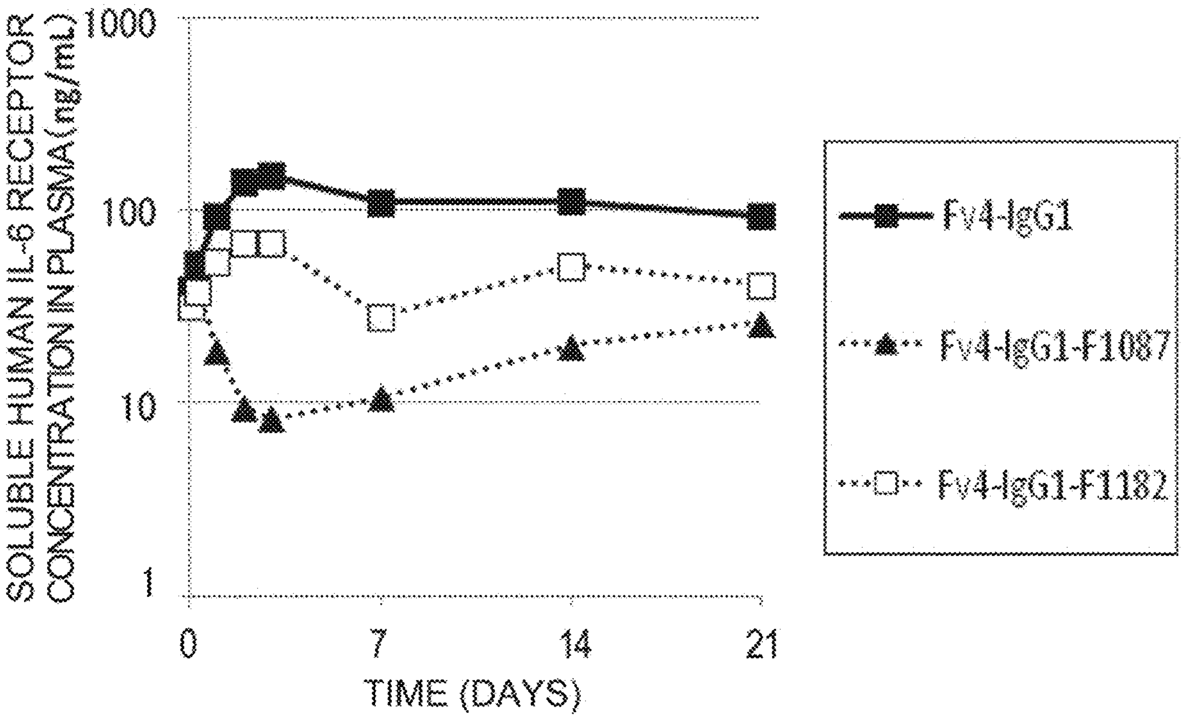
FIG. 20 shows a time course of human IL-6 receptor concentration in the plasma of human FcRn transgenic mice administered with Fv4-IgG1, Fv4-IgG1-F1087 which is an Fv4-IgG1 variant with enhanced mouse FcγR binding (in particular, enhanced mouse FcγRIIb binding and mouse FcγRIII binding), and Fv4-IgG1-F1182 which is an Fv4-IgG1 variant with enhanced mouse FcγR binding (in particular, enhanced mouse FcγRI binding and mouse FcγRIV binding).

By the same method as described in Reference Example 7, in vivo infusion tests using human FcRn transgenic mice were carried out to determine the soluble human IL-6 receptor concentrations in the plasma of the mice. The result is shown in FIG. 20.

In both of the groups administered with Fv4-IgG1-F1087 and Fv4-IgG1-F1182 in vivo, which have increased mouse FcγR-binding activity as compared to Fv4-IgG1, the in vivo plasma concentration of soluble human IL-6 receptor was able to be reduced as compared to the group administered with Fv4-IgG1. The effect to reduce the plasma concentration of soluble human IL-6 receptor was high especially in the group administered with Fv4-IgG1-F1087 which has enhanced binding to mouse FcγRII and mouse FcγRIII. Meanwhile, the effect of F1182 administration to reduce the plasma concentration of soluble human IL-6 receptor was small in the group administered with F1182 in vivo which has considerably increased binding activity to mouse FcγRI and mouse FcγRIV (as well as several-fold enhanced binding to mouse FcγRII and mouse FcγRIII). It was thought from these results that the mouse FcγRs that more significantly contribute to the efficient decrease of the antigen concentration in mouse plasma by administration of a pH-dependent antigen-binding antibody, are mouse FcγRII and/or mouse FcγRIII. Specifically, it is thought that the plasma antigen concentration can be more efficiently reduced in vivo by administering into a living organism a pH-dependent antigen-binding antibody with enhanced binding to mouse FcγRII and/or mouse FcγRIII.

(9-5) Preparation of Antigen-Binding Molecules Whose FcγR-Binding Activity is Greater than the Binding Activity of Native Human IgG Fc Region and which have Increased Human FcRn-Binding Activity Under an Acidic pH Range Condition As described in Reference Example 8, when compared to human FcRn transgenic mice administered with Fv4-IgG1-F1022, the plasma antibody retention is markedly improved in human FcRn transgenic mice administered with Fv4-IgG1-F1093 resulting from increasing the human FcRn-binding activity under an acidic pH range condition of Fv4-IgG1-F1022 in which the mouse FcγR-binding activity has been increased. Whether this effect is also observed in human FcRn transgenic mice administered with Fv4-IgG1-F1087 and Fv4-IgG1-F1182, and whether the same effect is observed in mice administered with variants which have increased human FcRn-binding activity under an acidic pH range condition by addition of an alteration distinct from the alteration assessed in Reference Example 8 were assessed as follows.

VH3-IgG1-F1180 (SEQ ID NO: 146) and VH3-IgG1-F1181 (SEQ ID NO: 147) were prepared by substituting Leu for Met at position 428 and Ser for Asn at position 434 (EU numbering) in the heavy chains VH3-IgG1-F1087 and VH3-IgG1-F1182, respectively, in order to increase their human FcRn-binding activity of Fv4-IgG1-F1087 and Fv4-IgG1-F1182 under an acidic pH range condition. Furthermore, VH3-IgG1-F1412 (SEQ ID NO: 149) was prepared by substituting Ala for Asn at position 434 (EU numbering) in the heavy chain VH3-IgG1-F1087, in order to increase the human FcRn-binding activity of Fv4-IgG1-F1087 under an acidic pH range condition. Fv4-IgG1-F1180, Fv4-IgG1-F1181, and Fv4-IgG1-F1412, which contain the above heavy chains and VL3-CK as the light chain, were prepared using the method described in Reference Example 1.

Figure 21:
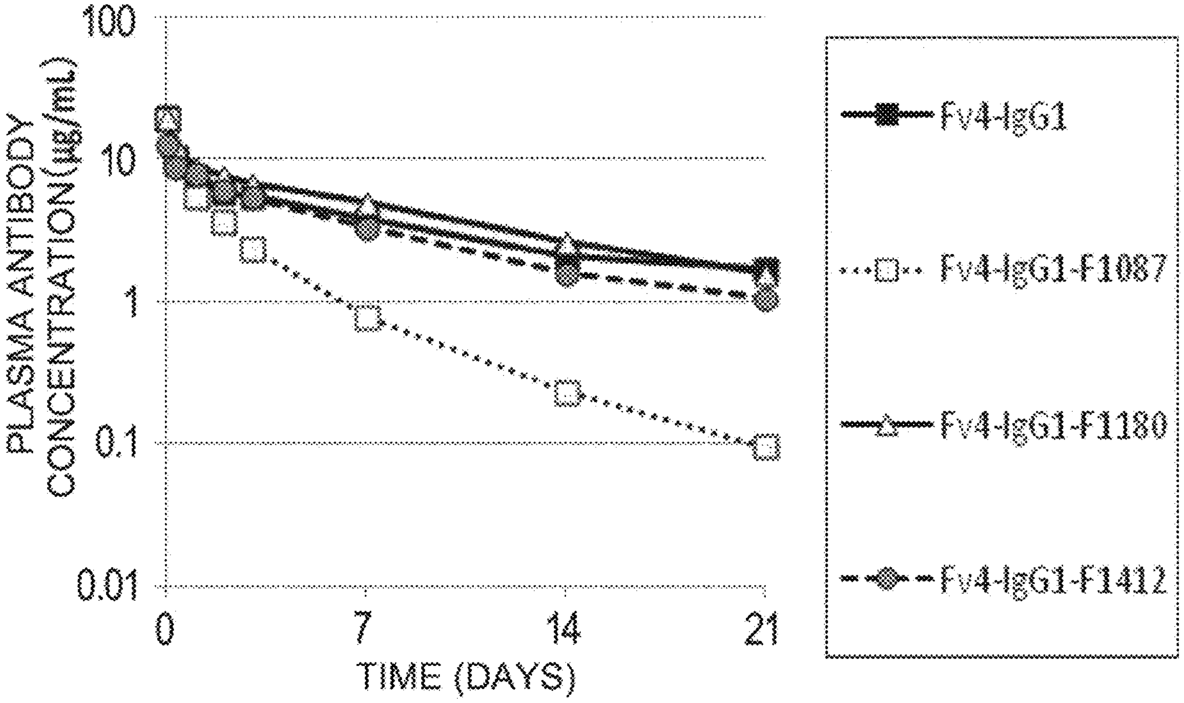
FIG. 21 shows a concentration time course of the administered antigen-binding molecules in the plasma of human FcRn transgenic mice administered with Fv4-IgG1, Fv4-IgG1-F1087, and Fv4-IgG1-F1180 and Fv4-IgG1-F1412 which are Fv4-IgG1-F1087 variants with improved FcRn binding in an acidic pH range.
Figure 22:
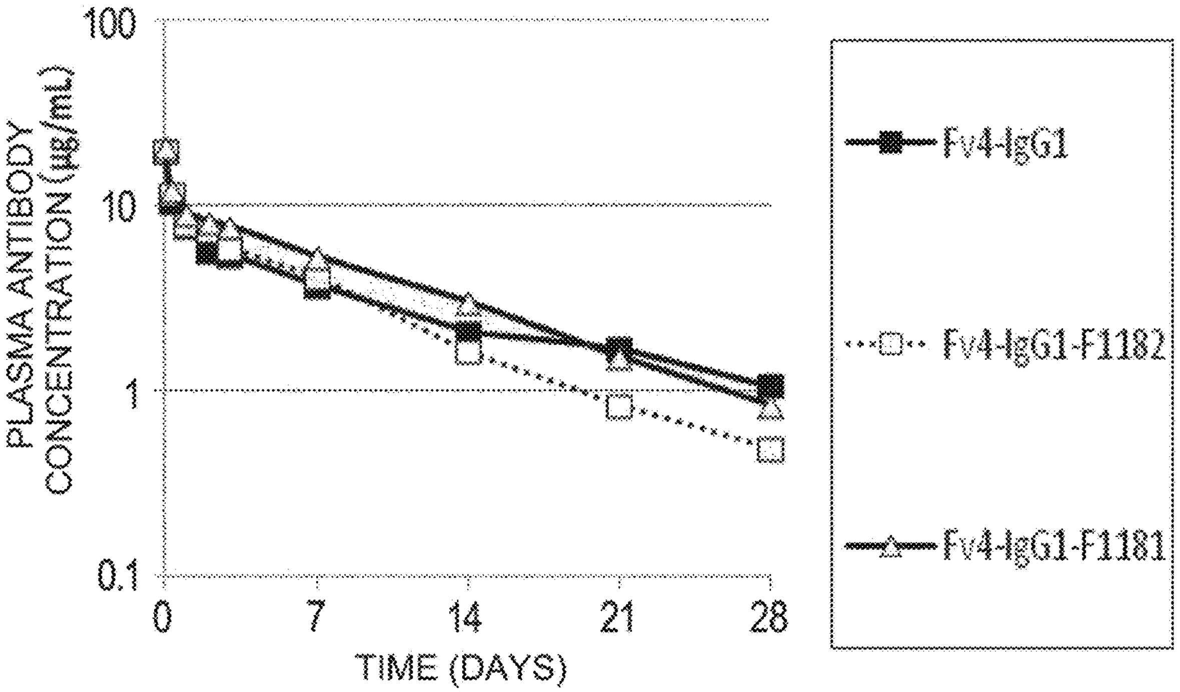
FIG. 22 shows a concentration time course of the administered antigen-binding molecules in the plasma of human FcRn transgenic mice administered with Fv4-IgG1, Fv4-IgG1-F1182, and Fv4-IgG1-F1181 which is an Fv4-IgG1-F1182 variant with improved FcRn binding in an acidic pH range.
Figure 23:
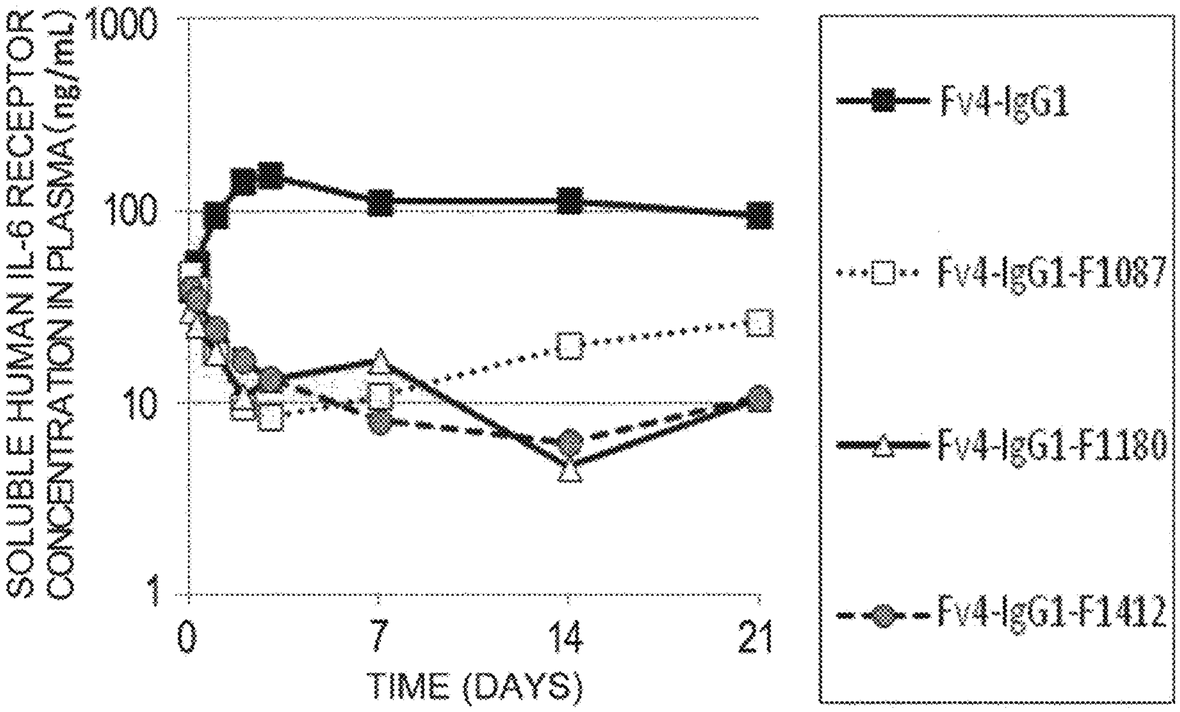
FIG. 23 shows a time course of human IL-6 receptor concentration in the plasma of human FcRn transgenic mice administered with Fv4-IgG1, Fv4-IgG1-F1087, and Fv4-IgG1-F1180 and Fv4-IgG1-F1412 which are Fv4-IgG1-F1087 variants with improved FcRn binding in an acidic pH range.
Figure 24:
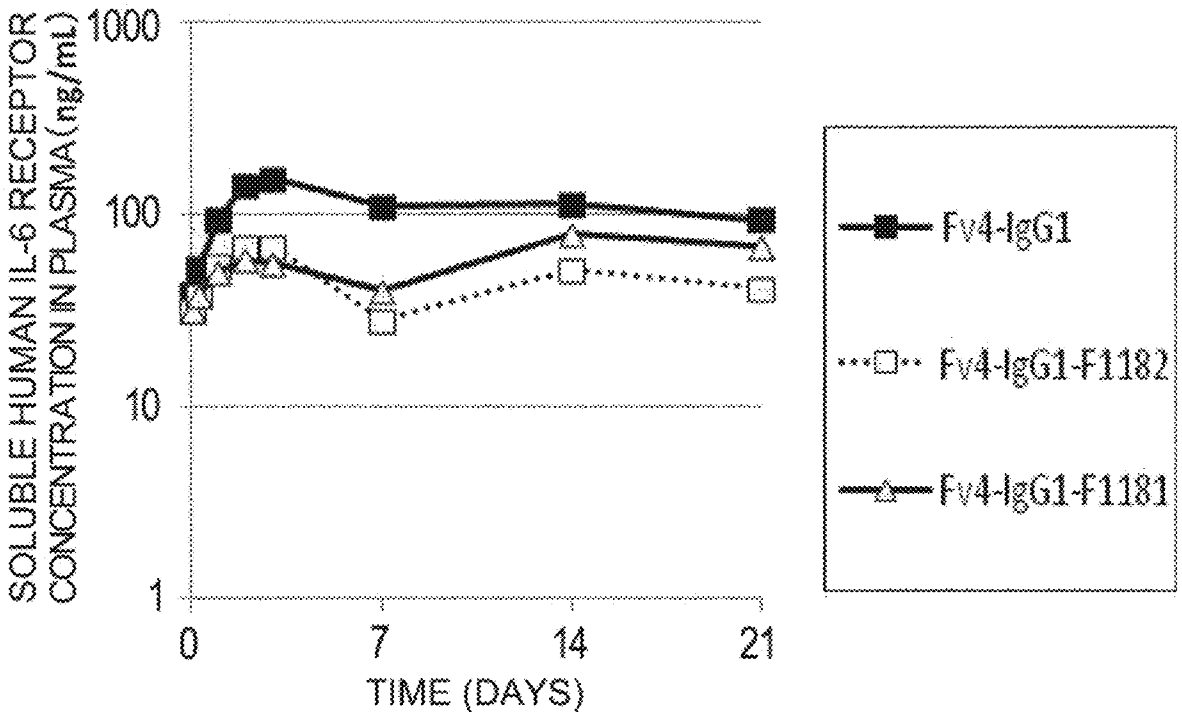
FIG. 24 shows a time course of human IL-6 receptor concentration in the plasma of human FcRn transgenic mice administered with Fv4-IgG1, Fv4-IgG1-F1182, and Fv4-IgG1-F1181 which is an Fv4-IgG1-F1182 variant with improved FcRn binding in an acidic pH range.

(9-6) Improvement of Pharmacokinetics by Increasing the Human FcRn-Binding Activity Under an Acidic pH Range Condition In vivo infusion tests were carried out by administering Fv4-IgG1-F1180, Fv4-IgG1-F1181, and Fv4-IgG1-F1412 to human FcRn transgenic mice according to the same method as described in Reference Example 7 to determine the soluble human IL-6 receptor concentrations in the plasma of the mice. The results on the soluble human IL-6 receptor concentrations in the plasma of the mouse groups administered with Fv4-IgG1-F1087, Fv4-IgG1-F1180, Fv4-IgG1-F1412, and Fv4-IgG1 are shown in FIG. 23. The results on the soluble human IL-6 receptor concentrations in the plasma of the mouse groups administered with Fv4-IgG1-F1182, Fv4-IgG1-F1181, and Fv4-IgG1 are shown in FIG. 24. Meanwhile, the plasma antibody concentrations in the mouse groups were measured by the method described in Reference Example 8. The results on the plasma antibody concentrations of Fv4-IgG1-F1087, Fv4-IgG1-F1180, Fv4-IgG1-F1412, and Fv4-IgG1 in the mouse groups are shown in FIG. 21; and the results on the plasma antibody concentrations of Fv4-IgG1-F1182, Fv4-IgG1-F1181, and Fv4-IgG1 are shown in FIG. 22.

It was confirmed that, as compared to the group of mice administered with Fv4-IgG1-F1182, the plasma antibody retention was improved in the group of mice administered with Fv4-IgG1-F1181 resulting from increasing the human FcRn-binding activity of Fv4-IgG1-F1182 in an acidic pH range. Meanwhile, the soluble human IL-6 receptor concentration in the plasma of the mouse groups administered with Fv4-IgG1-F1181 was comparable to that in the group of mice administered with Fv4-IgG1-F1182. When compared to the mouse groups administered with Fv4-IgG1, the soluble human IL-6 receptor concentration in the plasma was decreased in both groups.

On the other hand, as compared to the group of mice administered with Fv4-IgG1-F1087, the plasma antibody retention was improved in both groups of mice administered with Fv4-IgG1-F1180 and Fv4-IgG1-F1412 resulting from increasing the human FcRn-binding activity of Fv4-IgG1-F1087 in an acidic pH range, and surprisingly, the plasma retention was improved up to a level comparable to that of the mouse groups administered with Fv4-IgG1. Furthermore, the sustainability of the effect of reducing the soluble human IL-6 receptor concentration in plasma was improved by the improvement of the plasma antibody retention in the groups of administered mice. Specifically, in the groups of administered mice, the soluble human IL-6 receptor concentrations in plasma 14 days and 21 days after administration of Fv4-IgG1-F1180 and Fv4-IgG1-F1412 were significantly reduced as compared to the concentrations 14 days and 21 days after administration of Fv4-IgG1-F1087.

In view of the above, as for the groups of mice administered with the four examples of antibodies, Fv4-IgG1-F1093, Fv4-IgG1-F1181, Fv4-IgG1-F1180, and Fv4-IgG1-F1412, it was demonstrated that the plasma retention can be improved in a living organism administered with an antibody in which the human FcRn-binding activity under an acidic pH range condition is enhanced in an antigen-binding molecule whose FcγR-binding activity is higher than the binding activity of native human IgG Fc region. It was also demonstrated that, in the living organism administered with the antigen-binding molecule, the plasma retention is improved without deteriorating the effect of eliminating antigens from the living organism, and rather, the antigen elimination effect can be sustained.

It was shown that the alteration that increases the human FcRn-binding activity under an acidic pH range condition can be achievable by not only a method for substituting Leu for Met at position 428 and Ser for Asn at position 434 (EU numbering), but also a method for substituting Ala for Asn at position 434 (EU numbering). Thus, alterations used for increasing the human FcRn-binding activity under an acidic pH range condition are not particularly limited, and include: the method for substituting Leu for Met at position 428 and Ser for Asn at position 434 (EU numbering) in an IgG antibody (Nat. Biotechnol. (2010) 28, 157-159); the method for substituting Ala for Asn at position 434 (Drug Metab. Dispos. (2010) 38 (4) 600-605); the method for substituting Tyr for Met at position 252, Thr for Ser at position 254, and Glu for Thr at position 256 (J. Biol. Chem. (2006) 281, 23514-23524); the method for substituting Gln for Thr at position 250 and Leu for Met at position 428 (J. Immunol. (2006) 176 (1), 346-356); and the method for substituting His for Asn at position 434 (Clin. Pharmcol. Ther. (2011) 89 (2) 283-290); and the alterations described in WO2010/106180, WO2010/045193, WO2009/058492, WO2008/022152, WO2006/050166; WO2006/053301, WO2006/031370, WO2005/123780, WO2005/047327, WO2005/037867, WO2004/035752, and WO2002/060919, etc.

(9-7) Preparation of Antigen-Binding Molecules with Increased Human FcRn-Binding Activity Under an Acidic pH Range Condition and Suppressed Binding to a Rheumatoid Factor In recent years, an antibody molecule resulting from substituting His for Asn at position 434 (EU numbering) in a humanized anti-CD4 antibody to improve the plasma retention by increasing its human FcRn-binding activity under an acidic pH range condition, has been reported to bind to the rheumatoid factor (RF) (Clin. Pharmacol. Ther. (2011) 89 (2), 283-290). This antibody has a human IgG1 Fc region and a substitution of His for Asn at position 434 (EU numbering) in the FcRn-binding site. The rheumatoid factor has been demonstrated to recognize and bind to the substituted portion.

As shown in (9-6), various alterations have been reported to increase the human FcRn-binding activity under an acidic pH range condition. There is the possibility that the binding activity to the rheumatoid factor that recognizes the site is increased by introducing such alterations into the FcRn-binding site of the Fc region.

However, antigen-binding molecules that have increased human FcRn-binding activity under an acidic pH range condition but do not have the binding to the rheumatoid factor can be produced by introducing into the site of the Fc region an alteration that reduces the rheumatoid factor-binding activity alone without reducing the FcRn-binding activity under an acidic pH range condition.

Such alterations used for reducing the rheumatoid factor-binding activity include alterations at positions 248-257, 305-314, 342-352, 380-386, 388, 414-421, 423, 425-437, 439, and 441-444 (EU numbering), preferably those at positions 387, 422, 424, 426, 433, 436, 438, and 440 (EU numbering), and particularly preferably, an alteration that substitutes Glu or Ser for Val at position 422, an alteration that substitutes Arg for Ser at position 424, an alteration that substitutes Asp for His at position 433, an alteration that substitutes Thr for Tyr at position 436, an alteration that substitutes Arg or Lys for Gln at position 438, and an alteration that substitutes Glu or Asp for Ser at position 440 (EU numbering). These alterations may be used alone or in combination.

Alternatively, it is possible to introduce N-type glycosylation sequences to reduce the rheumatoid factor-binding activity. Specifically, known N-type glycosylation sequences include Asn-Xxx-Ser/Thr (Xxx represents an arbitrary amino acid other than Pro). This sequence can be introduced into the Fc region to add an N-type sugar chain, and the binding to RF can be inhibited by the steric hindrance of the N-type sugar chain. Alterations used for adding an N-type sugar chain preferably include an alteration that substitutes Asn for Lys at position 248, an alteration that substitutes Asn for Ser at position 424, an alteration that substitutes Asn for Tyr at position 436 and Thr for Gln at position 438, and an alteration that substitutes of Asn for Qln at position 438, according to EU numbering, particularly preferably an alteration that substitutes Asn for Ser at position 424 (EU numbering).

[Reference Example 10] Effect of Eliminating Antigens from Plasma by Antigen-Binding Molecules Whose FcγR-Binding Activity is Higher than the Binding Activity of Native Mouse IgG Fc Region (10-1) The Antigen Elimination Effect of Mouse Antibodies with Increased FcγR-Binding Activity As described in Reference Examples 6 to 9, it was demonstrated that the elimination of soluble human IL-6 receptor from mouse plasma is accelerated in the groups of human FcRn transgenic mice administered with antigen-binding molecules resulting from increasing the mouse FcγR-binding activity of antigen-binding molecules that have a human antibody Fc region and the property of binding to human IL-6 receptor in a pH-dependent manner. Whether this effect is also achieved in normal mice having mouse FcRn that was administered with antigen-binding molecules that have a mouse antibody Fc region and the property of binding to human IL-6 receptor in a pH-dependent manner, was assessed as follows.

(10-2) Preparation of Mouse Antibodies with Increased FcγR-Binding Activity

For a mouse IgG1 antibody having the property of binding to human IL-6 receptor in a pH-dependent manner, the heavy chain VH3-mIgG1 (SEQ ID NO: 150) and the light chain VL3-mk1 (SEQ ID NO: 151) were constructed using the method described in Reference Example 1. Meanwhile, to increase the mouse FcγR-binding activity of VH3-mIgG1, VH3-mIgG1-mF44 (SEQ ID NO: 152) was produced by substituting Asp for Ala at position 327 (EU numbering). Likewise, VH3-mIgG1-mF46 (SEQ ID NO: 153) was produced by substituting Asp for Ser at position 239 and Asp for Ala at position 327, according to EU numbering, in VH3-mIgG1. Fv4-mIgG1, Fv4-mIgG1-mF44, and Fv4-mIgG1-mF46, which contain VH3-mIgG1, VH3-mIgG1-mF44, and VH3-mIgG1-mF46, respectively, as the heavy chain, and VL3-mk1 as the light chain, were prepared using the method described in Reference Example 1.

(10-3) Assessment of Mouse FcγR-Binding Activity

VH3/L (WT)-mIgG1, VH3/L (WT)-mIgG1-mF44, and VH3/L (WT)-mIgG1-mF46, which contain VH3-mIgG1, VH3-mIgG1-mF44, and VH3-mIgG1-mF46, respectively, as the heavy chain, and L (WT)-CK (SEQ ID NO: 5) as the light chain, were prepared by the method described in Reference Example 1. These antibodies were assessed for their mouse FcγR-binding activity by the method described in Reference Example 2. The result is shown in Table 20. In addition, the ratio of the increase in the mouse FcγR-binding activity of each variant relative to the mIgG1 before alteration is shown in Table 21. In the table, VH3/L (WT)-mIgG1 is abbreviated as mIgG1; VH3/L (WT)-mIgG1-mF44 is abbreviated as mF44; and VH3/L (WT)-mIgG1-mF46 is abbreviated as mF46.

TABLE 20

| VARIANT | KD (M) | | | |
|---|---|---|---|---|
| NAME | mFcγRI | mFcγRIIb | mFcγRIII | mFcγRIV |
| mIgG1 | NOT DETECTED | 1.1E−07 | 2.1E−07 | NOT DETECTED |
| mF44 | NOT DETECTED | 8.9E−09 | 6.7E−09 | NOT DETECTED |
| mF46 | NOT DETECTED | 1.2E−09 | 3.6E−09 | NOT DETECTED |

TABLE 21

| VARIANT | RATIO OF BINDING TO mIgG1 | | | |
|---|---|---|---|---|
| NAME | mFcγRI | mFcγRIIb | mFcγRIII | mFcγRIV |
| mIgG1 | NOT DETECTED | 1.0 | 1.0 | NOT DETECTED |
| mF44 | NOT DETECTED | 11.9 | 31.0 | NOT DETECTED |
| mF46 | NOT DETECTED | 91.4 | 57.5 | NOT DETECTED |

The assessment result of Reference Example 9 showing that VH3/L (WT)-mIgG1 having the Fc region of native mouse IgG1 antibody only binds to mouse FcγRIIb and mouse FcγRIII but not to mouse FcγRI and mouse FcγRIV, suggests that mouse FcγRs important for the reduction of antigen concentration are mouse FcγRII and/or mouse FcγRIII. VH3/L (WT)-mIgG-mF44 and VH3/L (WT)-mIgG1-mF46 introduced with an alteration that is thought to increase the FcγR-binding activity of VH3/L (WT)-mIgG1 was demonstrated to have increased binding activity to both of mouse FcγRIIb and mouse FcγRIII.

(10-4) Assessment of the Effect to Reduce the Soluble Human IL-6 Receptor Concentration in the Plasma of Normal Mice The effect to eliminate soluble human IL-6 receptor from the plasma of normal mice administered with the anti-human IL-6 receptor antibody Fv4-mIgG1, Fv4-mIgG1-mF44, or Fv4-mIgG1mF46 was assessed as follows.

An animal model where the soluble human IL-6 receptor concentration is maintained in a steady state in plasma was created by implanting an infusion pump (MINI-OSMOTIC PUMP MODEL2004, alzet) containing soluble human IL-6 receptor under the skin on the back of normal mice (C57BL/6J mouse, Charles River Japan). The in vivo kinetics of soluble human IL-6 receptor after administration of the anti-human IL-6 receptor antibody was assessed in the animal model. To suppress the production of antibodies against soluble human IL-6 receptor, an anti-mouse CD4 monoclonal antibody was administered once at 20 mg/kg into the tail vein. Then, an infusion pump containing 92.8 μg/ml soluble human IL-6 receptor was subcutaneously implanted on the back of the mice. Three days after implantation of the infusion pump, the anti-human IL-6 receptor antibody was administered once at 1 mg/kg into the tail vein. The blood was collected from the mice 15 minutes, seven hours, one day, two days, four days, seven days, 14 days (or 15 days), and 21 days (or 22 days) after administration of the anti-human IL-6 receptor antibody. Immediately thereafter, the collected blood was centrifuged at 15,000 rpm and 4° C. for 15 minutes to prepare the plasma. The isolated plasma was stored in a freezer set at −20° C. or below until use.

Figure 25:
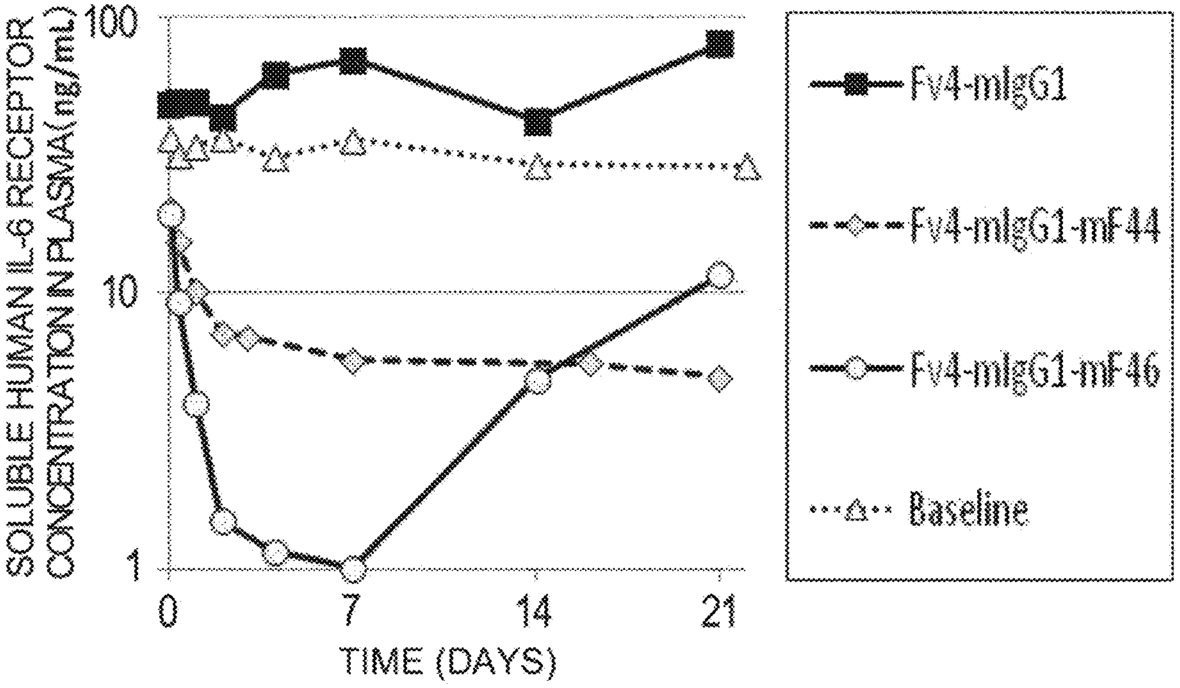
FIG. 25 shows a time course of human IL-6 receptor concentration in the plasma of normal mice administered with Fv4-mIgG1, Fv4-mIgG1-mF44 which is an Fv4-mIgG1 variant with enhanced mouse FcγRIIb binding and mouse FcγRIII binding, and Fv4-mIgG1-mF46 which is an Fv4-mIgG1 variant with further enhanced mouse FcγRIIb binding and mouse FcγRIII binding.

The soluble human IL-6 receptor concentrations in plasma were determined by the method described in (7-1-2). The result is shown in FIG. 25.

Surprisingly, it was demonstrated that, in mice administered with mF44 and mF46 introduced with an alteration to increase the binding activity of mIgG1 (native mouse IgG1) to mouse FcγRIIb and mouse FcγRIII, the plasma IL-6 receptor concentration was markedly reduced as compared to mice administered with mIgG1. In particular, even on day 21 after administration of mF44, the plasma IL-6 receptor concentration in the mF44-administered group was reduced by about 6 times as compared to the plasma IL-6 receptor concentration in the group without antibody administration, and about 10 times as compared to the mIgG1-administered group. On the other hand, on day seven after administration of mF46, the plasma IL-6 receptor concentration in the mF46-administered group was markedly reduced by about 30 times as compared to the plasma IL-6 receptor concentration in the group without antibody administration, and about 50 times as compared to the mIgG1-administered group.

The above findings demonstrate that the elimination of soluble human IL-6 receptor from plasma was also accelerated in mice administered with antibodies in which the mouse FcγR-binding activity of an antigen-binding molecule having the Fc regions of mouse IgG1 antibody is increased, as with antibodies in which the mouse FcγR-binding activity of an antigen-binding molecule having the Fc region of human IgG1 antibody is increased. Without being bound by a particular theory, the phenomenon observed as described above can be explained as follows.

When administered to mice, antibodies that bind to a soluble antigen in a pH-dependent manner and have increased FcγR-binding activity are actively incorporated mainly into cells expressing FcγR on the cell membrane. The incorporated antibodies dissociate the soluble antigen under an acidic pH condition in the endosome, and then recycled to plasma via FcRn. Thus, a factor that achieves the effect of eliminating the plasma soluble antigen of such an antibody is the FcγR-binding activity level of the antibody. Specifically, as the FcγR-binding activity is greater, the incorporation into FcγR-expressing cells occurs more actively, and this makes the elimination of soluble antigens from plasma more rapid. Furthermore, as long as the FcγR-binding activity has been increased, the effect can be assessed in the same manner regardless of whether the Fc region contained in an antibody originates from human or mouse IgG1. Specifically, the assessment can be achieved for an Fc region of any animal species, such as any of human IgG1, human IgG2, human IgG3, human IgG4, mouse IgG1, mouse IgG2a, mouse IgG2b, mouse IgG3, rat IgG, monkey IgG, and rabbit IgG, as long as the binding activity to the FcγR of the animal species to be administered has been increased.

[Reference Example 11] the Antigen Elimination Effect by Antibodies with the Binding Activity Increased in a FcγRIIb-Selective Manner (11-1) The Antigen Elimination Effect of Antibodies in which the FcγRIIb-Binding Activity has been Selectively Increased FcγRIII-deficient mice (B6.129P2-FcgrR3tm1Sjv/J mouse, Jackson Laboratories) express mouse FcγRI, mouse FcγRIIb, and mouse FcγRIV, but not mouse FcγRIII. Meanwhile, Fc receptor γ chain-deficient mice (Fcer1g mouse, Taconic, Cell (1994) 76, 519-529) express mouse FcγRIIb alone, but not mouse FcγRI, mouse FcγRIII, and mouse FcγRIV.

As described in Reference Example 10, it was demonstrated that mF44 and mF46 with increased FcγR-binding activity of native mouse IgG1 show selectively enhanced binding to mouse FcγRIIb and mouse FcγRIII. It was conceived that, using the selectively increased binding activity of the antibodies, the condition under which an antibody with selectively enhanced mouse FcγRIIb binding is administered can be mimicked by administering mF44 and mF46 to mouse FcγRIII-deficient mice or Fc receptor γ chain-deficient mice which do not express mouse FcγRIII.

Figure 26:
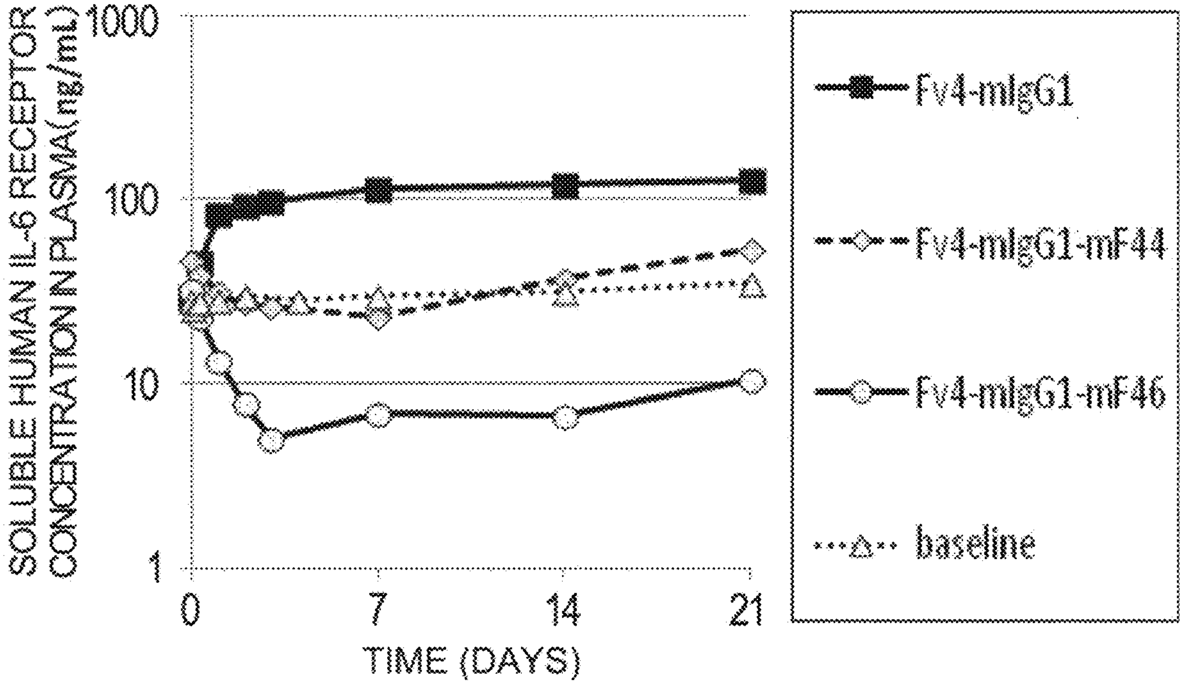
FIG. 26 shows a time course of human IL-6 receptor concentration in the plasma of FcγRIII-deficient mice administered with Fv4-mIgG1, Fv4-mIgG1-mF44 which is an Fv4-mIgG1 variant with enhanced mouse FcγRIIb binding and mouse FcγRIII binding, and Fv4-mIgG1-mF46 which is an Fv4-mIgG1 variant with further enhanced mouse FcγRIIb binding and mouse FcγRIII binding.

(11-2) Assessment of the Antigen Elimination Effect by the Mouse FcγRIIb-Selective Enhancement of Binding Using FcγRIII-Deficient Mice The effect to eliminate soluble human IL-6 receptor from plasma in FcγRIII-deficient mice administered with the anti-human IL-6 receptor antibody Fv4-mIgG1, Fv4-mIgG1-mF44, or Fv4-mIgG1-mF46 was assessed by the same method described in Reference Example 10. The soluble human IL-6 receptor concentrations in the plasma of the mice were determined by the method described in (7-1-2). The result is shown in FIG. 26.

Surprisingly, it was demonstrated that, the plasma IL-6 receptor concentrations in FcγRIII-deficient mice administered with mF44 and mF46, which mimic the condition under which the mouse FcγRIIb-binding activity of mIgG1 (native mouse IgG1) is selectively increased, were markedly reduced as compared to the plasma IL-6 receptor concentration in mice administered with mIgG1. In particular, the plasma IL-6 receptor concentration of the mF44-administered group was reduced by about three times as compared to that of the mIgG1-administered group and the accumulation of antigen concentration due to antibody administration was suppressed. Meanwhile, on day three after administration, the plasma IL-6 receptor concentration of the mF46-administered group was markedly reduced by about six times as compared to the plasma IL-6 receptor concentration of the group without antibody administration, and about 25 times as compared to the plasma IL-6 receptor concentration of the mIgG1-administered group. This result shows that, as the mouse FcγRIIb-binding activity of an anti-human IL-6 receptor antibody that binds to the antigen in a pH-dependent manner is greater, the IL-6 receptor concentration can be reduced more in the plasma of mice administered with the antibody.

Figure 27:
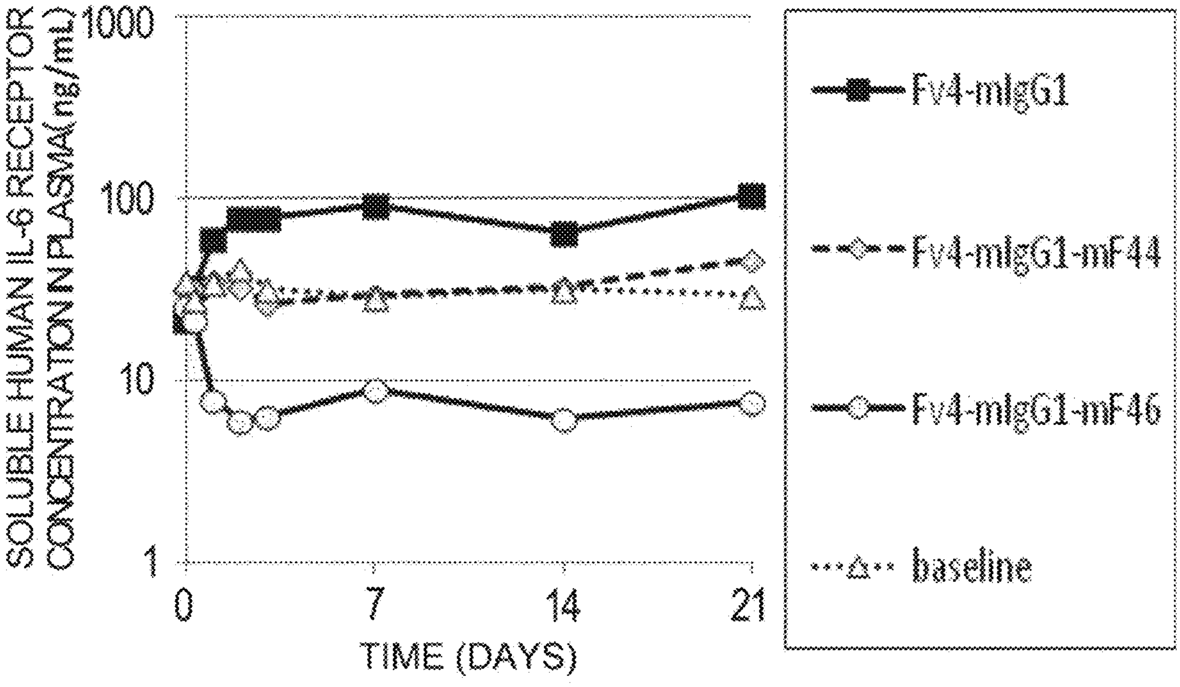
FIG. 27 shows a time course of human IL-6 receptor concentration in the plasma of Fc receptor γ chain-deficient mice administered with Fv4-mIgG1, Fv4-mIgG1-mF44 which is an Fv4-mIgG1 variant with enhanced mouse FcγRIIb binding and mouse FcγRIII binding, and Fv4-mIgG1-mF46 which is an Fv4-mIgG1 variant with further enhanced mouse FcγRIIb binding and mouse FcγRIII binding.

(11-3) Assessment of the Antigen Elimination Effect by the Selective Enhancement of Mouse FcγRIIb Binding Using Fc Receptor γ Chain-Deficient Mice The effect to eliminate soluble human IL-6 receptor from the plasma of Fc receptor γ chain-deficient mice administered with the anti-human IL-6 receptor antibody Fv4-mIgG1, Fv4-mIgG1-mF44, or Fv4-mIgG1mF46, was assessed by the same method as described in Reference Example 10. The soluble human IL-6 receptor concentrations in the plasma of the mice were determined by the method described in (7-1-2). The result is shown in FIG. 27.

As with the case where mF44 and mF46 were administered to FcγRIII-deficient mice, the plasma IL-6 receptor concentration in Fc receptor γ chain-deficient mice administered with mF44 and mF46, which mimic the condition resulting from the selective increase in the mouse FcγRIIb-binding activity of mIgG1 (native mouse IgG1), was demonstrated to be markedly reduced as compared to the plasma IL-6 receptor concentration in Fc receptor γ chain-deficient mice administered with mIgG1. In particular, the plasma IL-6 receptor concentration in the mF44-administered group was reduced to about three times that in the mIgG1-administered group, and the accumulation of antigen concentration due to antibody administration was suppressed. Meanwhile, on day three after administration, the plasma IL-6 receptor concentration in the mF46-administered group was markedly reduced by about five times as compared to that in the group without antibody administration, and about 15 times as compared to that in the mIgG1-administered group.

The results described in (11-2) and (11-3) show that the soluble antigen concentration in the plasma is markedly reduced in the group administered with an antibody that binds to a soluble antigen in a pH-dependent manner and has selectively increased mouse FcγRIIb-binding activity.

[Reference Example 12] the Antigen Elimination Effect of Antibodies with FcγRIII-Selective Binding Enhancement (12-1) The Antigen Elimination Effect of Antibodies with Selectively Enhanced FcγRIII Binding FcγRIIb-deficient mice (Fcgr2b (FcγRII) mouse, Taconic) (Nature (1996) 379 (6563), 346-349) express mouse FcγRI, mouse FcγRIII, and mouse FcγRIV, but not mouse FcγRIIb. As described in Reference Example 10, it was demonstrated that mF44 and mF46 resulting from increasing the FcγR-binding activity of native mouse IgG1 show selectively enhanced binding to mouse FcγRIIb and mouse FcγRIII. It was conceived that, based on the use of the selectively increased binding activity of the antibodies, the condition of administration of an antibody with selectively enhanced binding to mouse FcγRIII can be mimicked by administering mF44 or mF46 to mouse FcγRIIb-deficient mice which do not express mouse FcγRIIb.

As described in Reference Example 11, the soluble antigen concentration was reduced in the plasma of FcγRIII-deficient mice, which mimic the condition of administration of an antibody with selectively increased mouse FcγRIIb-binding activity. Meanwhile, whether the soluble antigen concentration is reduced in the plasma of FcγRIIb-deficient mice, which mimic the condition of administration of an antibody with selectively increased mouse FcγRIII-binding activity, was assessed by the test described below.

Figure 28:
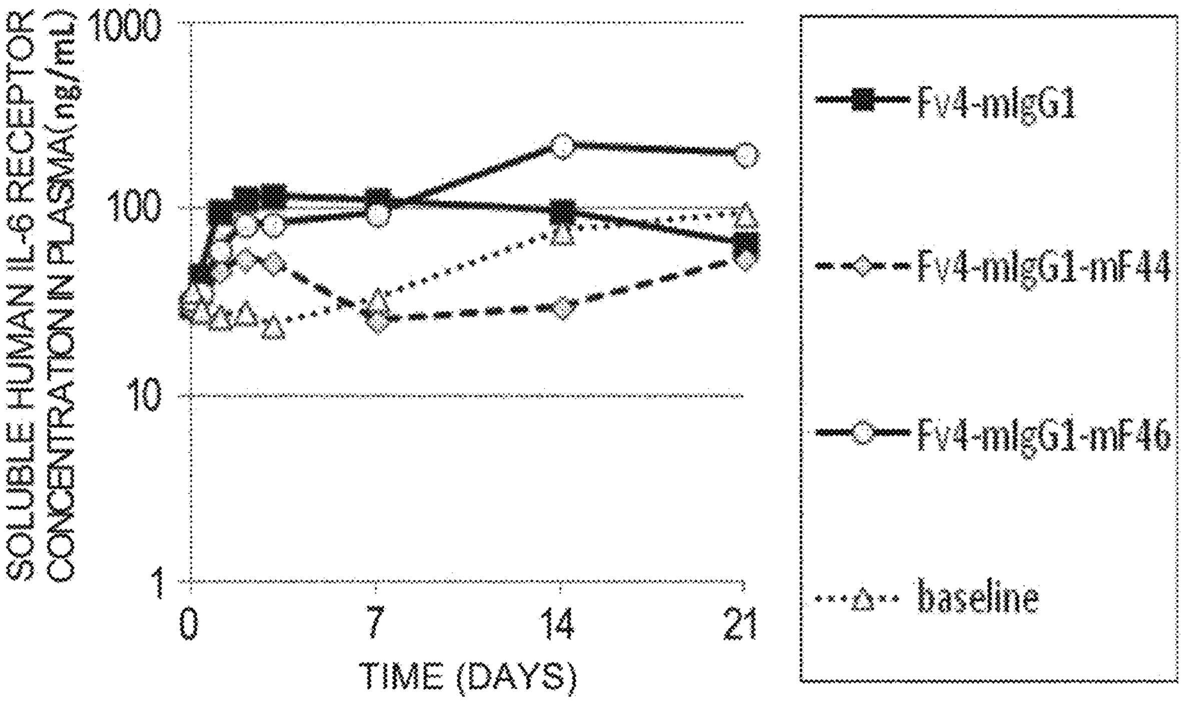
FIG. 28 shows a time course of human IL-6 receptor concentration in the plasma of FcγRIIb-deficient mice administered with Fv4-mIgG1, Fv4-mIgG1-mF44 which is an Fv4-mIgG1 variant with enhanced mouse FcγRIIb binding and mouse FcγRIII binding, and Fv4-mIgG1-mF46 which is an Fv4-mIgG1 variant with further enhanced mouse FcγRIIb binding and mouse FcγRIII binding.

(12-2) Assessment of the Antigen Elimination Effect by Selective Enhancement of Mouse FcγRIII Binding Using FcγRIIb-Deficient Mice The effect to eliminate soluble human IL-6 receptor from the plasma of FcγRIIb-deficient mice administered with the anti-human IL-6 receptor antibody Fv4-mIgG1, Fv4-mIgG1-mF44, or Fv4-mIgG1mF46, was assessed by the same method as described in Reference Example 10. The soluble human IL-6 receptor concentrations in plasma were determined by the method described in (7-1-2). The result is shown in FIG. 28.

Surprisingly, in the groups administered with mF44 and mF46, which mimic selective increase of the mouse FcγRIII-binding activity of mIgG1 (native mouse IgG1), the plasma IL-6 receptor concentration was reduced, but the reduction was not as significant as that shown in Reference Example 11.

Without being bound by a particular theory, based on the results described in Reference Examples 10, 11, and 12, the following discussion is possible. The elimination of soluble human IL-6 receptor from plasma was found to be markedly accelerated in normal mice expressing both mouse FcγRIIb and mouse FcγRIII that were administered with mF44 and mF46 with selectively increased binding activity of mIgG1 (native mouse IgG1) to mouse FcγRIIb and mouse FcγRIII. Furthermore, it was revealed that, when mF44 and mF46 were administered to mice that express mouse FcγRIIb but not mouse FcγRIII (i.e., FcγRIII-deficient mice and Fc receptor γ chain-deficient mice), the elimination of soluble human IL-6 receptor from plasma was also accelerated markedly in the mice. Meanwhile, when mF44 and mF46 were administered to mice that express mouse FcγRIII but not mouse FcγRIIb (i.e., FcγRII-deficient mice), the elimination of soluble human IL-6 receptor from plasma was not markedly accelerated in the mice.

From the above findings, it is thought that, the antibodies mF44 and mF46 in which the binding activity of mIgG1 (native mouse IgG1) to mouse FcγRIIb and mouse FcγRIII is selectively increased, are incorporated into FcγR-expressing cells mainly by mouse FcγRIIb, and thus the soluble antigen in the plasma that binds to the antibodies is eliminated. Meanwhile, the FcγRIII-mediated incorporation of antibody/antigen complexes into FcγR-expressing cells is thought not to significantly contribute to the elimination of the soluble antigen from plasma.

Furthermore, as shown in Reference Example 9, the plasma concentration of soluble human IL-6 receptor was markedly reduced in mice administered with Fv4-IgG1-F1087 having increased binding activity to mouse FcγRIIb and mouse FcγRIII, in particular. Meanwhile, the effect to eliminate soluble human IL-6 receptor from the plasma of mice administered with Fv4-IgG1-F1182 with increased binding activity to mouse FcγRI and mouse FcγRIV, in particular, was smaller than that of Fv4-IgG1-F1087.

Furthermore, as shown in Reference Example 7, in mice administered with Fv4-IgG1-Fuc whose mouse FcγRIV-binding activity has been considerably increased by having sugar chains with low fucose content (Science (2005) 310 (5753) 1510-1512), the plasma concentration of soluble human IL-6 receptor was reduced as compared to that in mice administered with Fv4-IgG1; however, the reduction effect was as small as about twice. Thus, mouse FcγRIV-mediated incorporation of antibodies into FcγR-expressing cells is thought not to significantly contribute to the elimination of soluble antigens from plasma.

The above demonstrates that, in mice, of multiple mouse FcγRs, mouse FcγRIIb plays a major role in the incorporation of antibodies into FcγR-expressing cells. Thus, mutations to be introduced into the mouse Fcγreceptor-binding domain are particularly preferably, but are not particularly limited to, mutations that enhance the binding to mouse FcγRIIb.

By this assessment using mice, it was demonstrated that, when an antigen-binding molecule that binds to a soluble antigen in a pH-dependent manner and has increased FcγR-binding activity is administered to accelerate the elimination of the soluble antigen from plasma in the administered living organism, it is more preferable to increase the FcγRIIb-binding activity of the antibody to be administered. Specifically, it was revealed that, when administered to the living organism, antigen-binding molecules that bind to a soluble antigen in a pH-dependent manner and have increased FcγRIIb-binding activity can effectively reduce the plasma concentration of the soluble antigen by accelerating the elimination of the soluble antigen from plasma, and thus such antigen-binding molecules exhibit highly effective action.

[Reference Example 13] Assessment of the Platelet Aggregatory Ability of Antibodies Containing an Fc Region Introduced with an Existing Alteration that Enhances the FcγRIIb Binding (13-1) Preparation of Antibodies Containing an Fc Region Introduced with an Existing Alteration that Enhances the FcγRIIb Binding As described in Reference Example 12, antigens can be efficiently eliminated from the plasma of the living organism by administering antibodies with selectively increased FcγRIIb-binding activity to the living organism. Furthermore, the administration of antibodies containing an Fc region with selectively increased FcγRIIb-binding activity is thought to be preferred from the viewpoint of safety and side effects in the living organism administered with such antibodies.

However, the mouse FcγRIIb binding and mouse FcγRIII binding are both enhanced in mF44 and mF46, and thus the binding enhancement is not selective for mouse FcγRIIb. Since the homology between mouse FcγRIIb and mouse FcγRIII is high, it would be difficult to find an alteration that enhances the mouse FcγRIIb-selective binding while distinguishing the two. Moreover, there is no previous report on Fc regions with selectively enhanced mouse FcγRIIb binding. In addition, the homology between human FcγRIIb and human FcγRIIa (allotypes H131 and R131) is also known to be high. Furthermore, it has been reported that antibodies with enhanced FcγRIIa binding have increased platelet aggregatory activity, and can increase the risk of developing thrombosis in the living organism administered with them (Meyer et al., (J. Thromb. Haemost. (2009), 7 (1), 171-181), Robles-Carrillo et al., (J. Immunol. (2010), 185 (3), 1577-1583)). Thus, whether antibodies with enhanced FcγRIIa binding have increased platelet aggregatory activity was assessed as follows.

(13-2) Assessment of the Human FcγR-Binding Activity of Antibodies Containing an Fc Region Introduced with an Existing Alteration that Enhances the FcγRIIb Binding Antibodies containing an Fc region introduced with an existing alteration that enhances the human FcγRIIb binding were analyzed for their affinity for human FcγRIa, R-type and H-type FcγRIIa, FcγRIIb, and FcγRIIIa by the following procedure. An H chain was constructed to have, as the antibody H chain variable region, the antibody variable region IL6R-H (SEQ ID NO: 154) against human IL-6 receptor which is disclosed in WO2009/125825, and as the antibody H chain constant region, IL6R-G1d (SEQ ID NO: 156) that has G1d resulting from removing the C-terminal Gly and Lys from human IgG1. Then, IL6R-G1d-v3 (SEQ ID NO: 157) was constructed by altering the Fc region of IL6R-G1d by the substitution of Glu for Ser at position 267 (EU numbering) and Phe for Leu at position 328 (EU numbering), as described in Seung et al., (Mol. Immunol. (2008) 45, 3926-3933). IL6R-L (SEQ ID NO: 155) which is the L chain of anti-human IL-6 receptor antibody was used as a common antibody L chain, and expressed in combination with respective H chains according to the method described in Reference Example 1, and the resulting antibodies were purified. Hereinafter, antibodies containing IL6R-G1d and IL6R-G1d-v3 as the heavy chain are referred to as IgG1 and IgG1-v3, respectively.

Then, the interaction between FcγR and the above antibodies was kinetically analyzed using a BIACORE™ T100 surface plasmon resonance system (GE Healthcare). The assay for the interaction was carried out at 25° C. using HBS-EP+(GE Healthcare) as a running buffer. The chip used was a Series S Sencor Chip CM5 (GE Healthcare) immobilized with Protein A by an amine coupling method. Each FcγR diluted with the running buffer was allowed to interact with the antibodies of interest captured onto the chip to measure the binding of the antibodies to each FcγR. After measurement, 10 mM glycine-HCl (pH 1.5) was reacted to the chip to wash off the captured antibodies to repeatedly use the regenerated chip. A sensorgram obtained as a result of the measurement was analyzed using 1:1 Langmuir binding model with BIACORE™ Evaluation Software, and binding rate constant ka (L/mol/s) and dissociation rate constant kd (1/s) were calculated, and the dissociation constant KD (mol/l) was calculated from these values. The KD values of IgG1 and IgG1-v3 to each FcγR are shown in Table 22 (the KD values of each antibody to each FcγR), while the relative KD values of IgG1-v3, which are obtained by dividing KD of IgG1 to each FcγR by KD of IgG1-v3 to each FcγR, are shown in Table 23.

TABLE 22

| | KD (M) | | | | |
|---|---|---|---|---|---|
| ANTIBODY | FcγRIa | FcγRIIaR | FcγRIIaH | FcγRIIb | FcγRIIIa |
| IgG1 | 3.4E−10 | 1.2E−06 | 7.7E−07 | 5.3E−06 | 3.1E−06 |
| IgG1-v3 | 1.9E−10 | 2.3E−09 | 1.5E−06 | 1.3E−08 | 8.8E−06 |

TABLE 23

| | FcγRIa | FcγRIIaR | FcγRIIaH | FcγRIIb | FcγRIIIa |
|---|---|---|---|---|---|
| KD VALUE RATIO | 1.8 | 522 | 0.51 | 408 | 0.35 |

The above results show that, as compared to the antibody containing the Fc region of IgG1, the antibody containing an altered Fc region (Mol. Immunol. (2008) 45, 3926-3933) with the substitution of Glu for Ser at position 267 and Phe for Leu at position 328 (EU numbering) in the Fc region of IgG1, its affinity for FcγRIIb has been increased by 408 times; its affinity for H-type FcγRIIa has been reduced to 0.51 times; and its affinity for R-type FcγRIIa has been increased by 522 times.

(13-3) Assessment of the Ability to Aggregate Platelets

Next, whether the increased/reduced FcγRIIa affinity of the antibody containing the Fc region with the substitution of Glu for Ser at position 267 and Phe for Leu at position 328 (EU numbering) in the Fc region of IgG1 changes the platelet aggregatory ability, was assessed using platelets derived from donors with H-type or R-type FcγRIIa. The antibody comprising as the light chain omalizumab_VL-CK (SEQ ID NO: 159) and omalizumab_VH-G1d (SEQ ID NO: 158) that contains the heavy chain variable region of hIgG1 antibody (human IgG1 constant region) that binds to IgE and the G1d heavy chain constant region, was constructed using the method described in Reference Example 1. Furthermore, omalizumab_VH-G1d-v3 (SEQ ID NO: 160) was constructed by substituting Glu for Ser at position 267 and Phe for Leu at position 328 (EU numbering) in omalizumab_VH-G1d. Omalizumab-G1d-v3, which contains omalizumab_VH-G1d-v3 as the heavy chain and omalizumab_VL-CK as the light chain, was prepared using the method described in Reference Example 1. This antibody was assessed for the platelet aggregatory ability.

Platelet aggregation was assayed using the platelet aggregometer HEMA TRACER 712 (LMS Co.). First, about 50 ml of whole blood was collected at a fixed amount into 4.5-ml evacuated blood collection tubes containing 0.5 ml of 3.8% sodium citrate, and this was centrifuged at 200 g for 15 minutes. The resultant supernatant was collected and used as platelet-rich plasma (PRP). After PRP was washed with buffer A (137 mM NaCl, 2.7 mM KCl, 12 mM $NaHCO_3$, 0.42 mM $NaH_2PO_4$, 2 mM $MgCl_2$, 5 mM HEPES, 5.55 mM dextrose, 1.5 U/ml apyrase, 0.35% BSA), the buffer was replaced with buffer B (137 mM NaCl, 2.7 mM KCl, 12 mM $NaHCO_3$, 0.42 mM $NaH_2PO_4$, 2 mM $MgCl_2$, 5 mM HEPES, 5.55 mM dextrose, 2 mM $CaCl_2$, 0.35% BSA). This yielded washed platelets at a density of about 300,000/μl. 156 μl of the washed platelets was aliquoted into assay cuvettes containing a stir bar in the platelet aggregometer. The platelets were stirred at 1000 rpm with the stir bar in the cuvettes maintained at 37.0° C. in the platelet aggregometer. 44 μl of the immune complex of omalizumab-G1d-v3 and IgE at a molar ratio of 1:1, prepared at final concentrations of 600 μg/ml and 686 μg/ml, respectively, was added to the cuvettes. The platelets were reacted with the immune complex for five minutes. Then, at a concentration that does not allow secondary platelet aggregation, adenosine diphosphate (ADP, SIGMA) was added to the reaction mixture to test whether the aggregation is enhanced.

Figure 29:
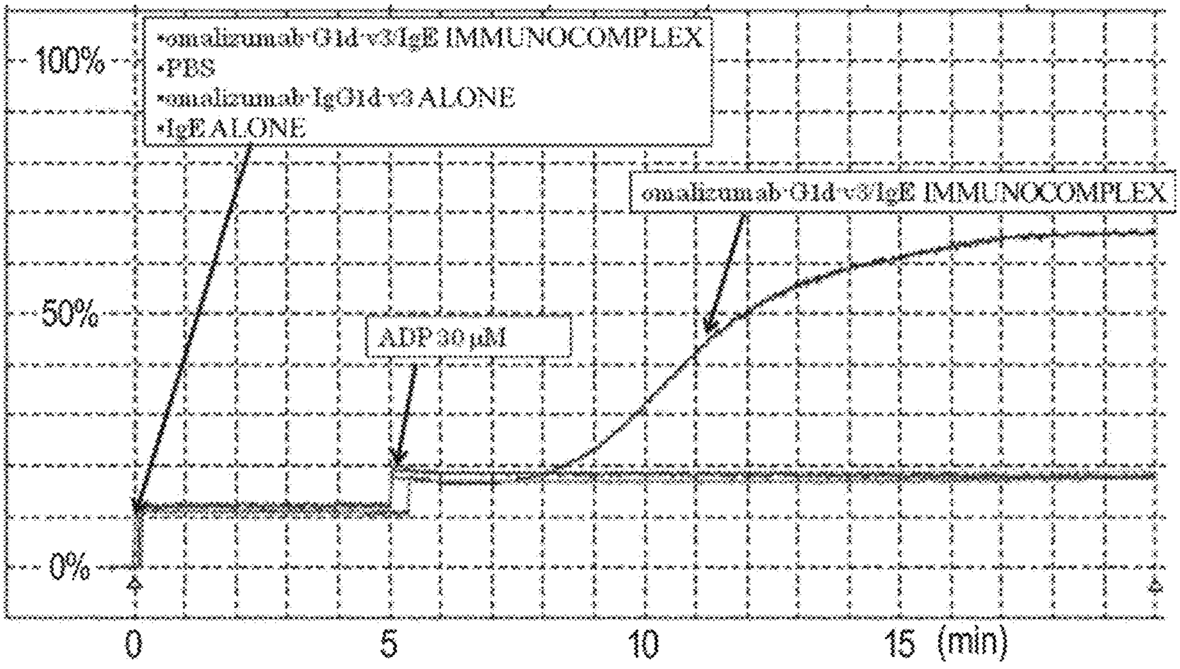
FIG. 29 shows a result of evaluating the platelet aggregation ability of the omalizumab-G1d-v3/IgE immunocomplex by platelet aggregation assay using platelets derived from donors with FcγRIIa allotype (R/H).
Figure 30:
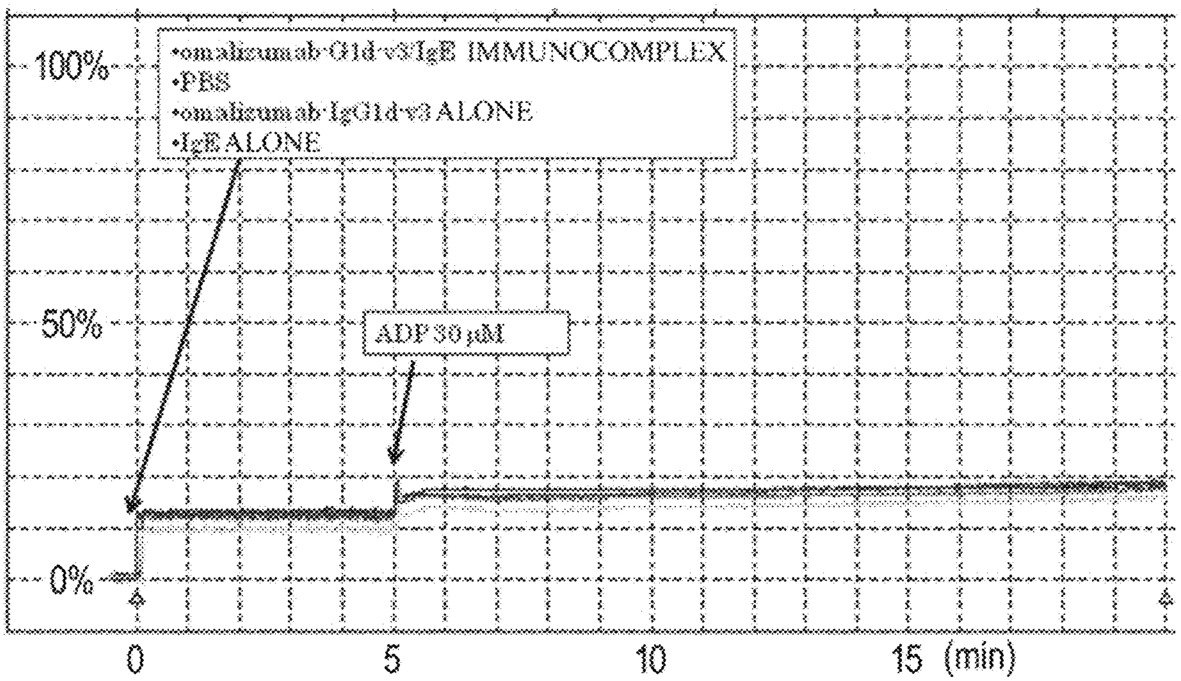
FIG. 30 shows a result of evaluating the platelet aggregation ability of the omalizumab-G1d-v3/IgE immunocomplex by platelet aggregation assay using platelets derived from donors with FcγRIIa allotype (H/H).

The result of platelet aggregation for each donor with an FcγRIIa polymorphic form (H/H or R/H) obtained from the above assay is shown in FIGS. 29 and 30. The result in FIG. 29 shows that platelet aggregation is enhanced when the immune complex is added to the platelets of a donor with the FcγRIIa polymorphic form (R/H). Meanwhile, as shown in FIG. 30, platelet aggregation was not enhanced when the immune complex is added to the platelets of a donor with the FcγRIIa polymorphic form (H/H). Next, platelet activation was assessed using activation markers. Platelet activation can be measured based on the increased expression of an activation marker such as CD62p (p-selectin) or active integrin on the platelet membrane surface. 2.3 μl of the immune complex was added to 7.7 μl of the washed platelets prepared by the method described above. After five minutes of reaction at room temperature, activation was induced by adding ADP at a final concentration of 30 μM, and whether the immune complex enhances the ADP-dependent activation was assessed. A sample added with phosphate buffer (pH 7.4) (Gibco), instead of the immune complex, was used as a negative control. Staining was performed by adding, to each post-reaction sample, PE-labeled anti-CD62 antibody (BECTON DICKINSON), PerCP-labeled anti-CD61 antibody, and FITC-labeled PAC-1 antibody (BD bioscience). Fluorescence intensity for each stain was measured using a flow cytometer (FACS CantoII, BD bioscience).

Figure 31:
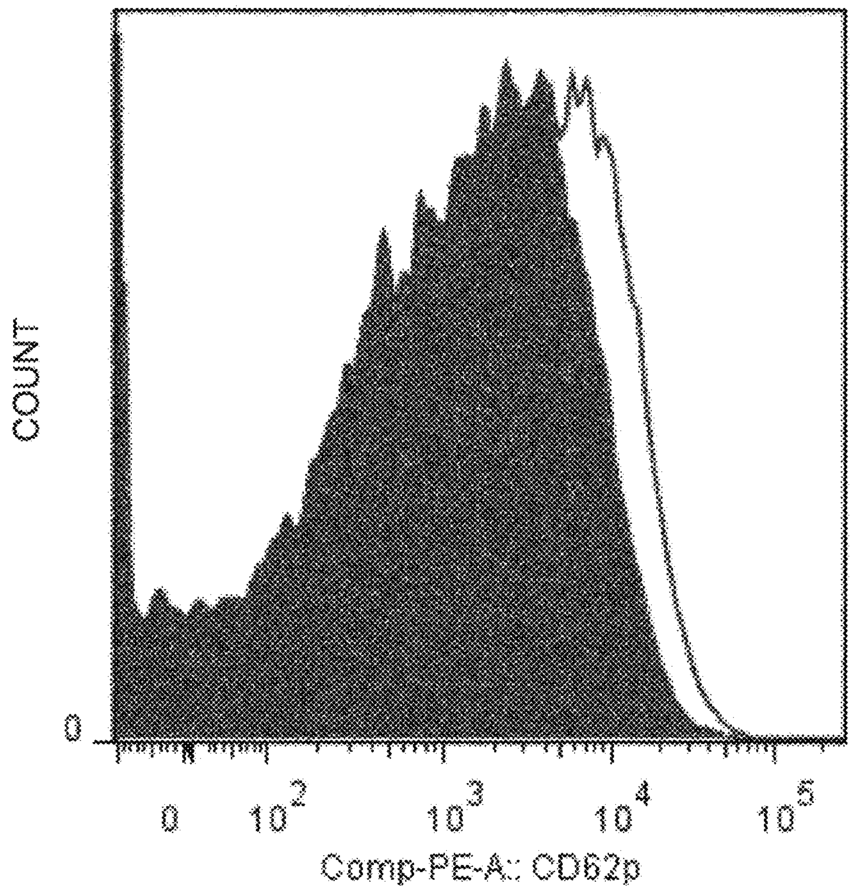
FIG. 31 shows a result of assessing CD62p expression on the membrane surface of washed platelets. The black-filled area in the graph indicates a result of ADP stimulation after reaction with PBS. The area that is not filled in the graph indicates a result of ADP stimulation after reaction with the immunocomplex.
Figure 32:
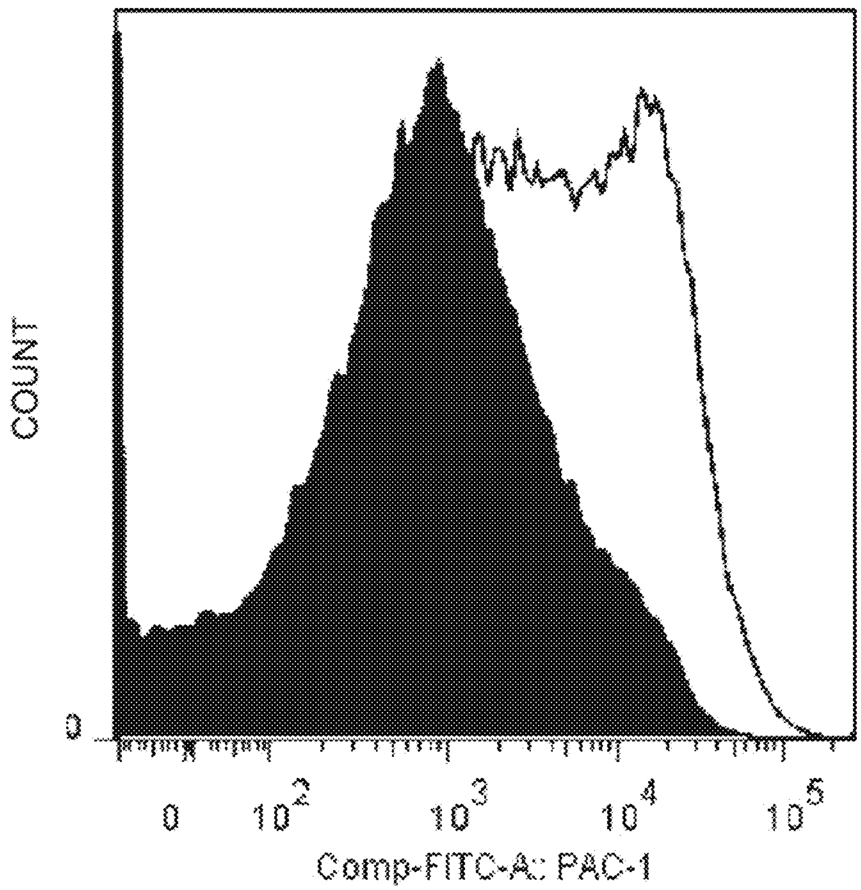
FIG. 32 shows a result of assessing the expression of active integrin on the membrane surface of washed platelets. The black-filled area in the graph indicates a result of ADP stimulation after reaction with PBS. The area that is not filled in the graph indicates a result of ADP stimulation after reaction with the immunocomplex.

The result on CD62p expression, obtained by the above assay method, is shown in FIG. 31. The result on the activated integrin expression is shown in FIG. 32. The washed platelets used were obtained from a healthy person with the FcγRIIa polymorphic form R/H. The expression of both CD62p and active integrin on platelet membrane surface, which is induced by ADP stimulation, was enhanced in the presence of the immune complex.

The above results demonstrate that the antibody having the Fc region introduced with an existing alteration that enhances the human FcγRIIb binding, which is the substitution of Glu for Ser at position 267 and Phe for Leu at position 328 (EU numbering) in the Fc region of IgG1, promotes the aggregation of platelets with the FcγRIIa allotype in which the amino acid at position 131 is R, as compared to platelets with the FcγRIIa polymorphic form in which the amino acid at position 131 is H. That is, it was suggested that the risk of developing thrombosis due to platelet aggregation can be increased when an antibody containing an Fc region introduced with an existing alteration that enhances the human FcγRIIb binding is administered to humans having R-type FcγRIIa. It was shown that the antigen-binding molecules containing an Fc region of the present invention that enhances the FcγRIIb binding more selectively not only improves the antigen retention in plasma, but also possibly solves the above problems. Thus, the usefulness of the antigen-binding molecules of the present invention is obvious.

[Reference Example 14] Comprehensive Analysis of FcγRIIb Binding of Variants Introduced with an Alteration at the Hinge Portion in Addition to the P238D Alteration In an Fc produced by substituting Pro at position 238 (EU numbering) with Asp in a naturally-occurring human IgG1, an anticipated combinatorial effect could not be obtained even by combining it with another alteration predicted to further increase FcγRIIb binding from the analysis of naturally-occurring antibodies. Therefore, in order to find variants that further enhance FcγRIIb binding, alterations were comprehensively introduced into the altered Fc produced by substituting Pro at position 238 (EU numbering) with Asp. IL6R-F11 (SEQ ID NO: 161) was produced by introducing an alteration of substituting Met at position 252 (EU numbering) with Tyr and an alteration of substituting Asn at position 434 (EU numbering) with Tyr in IL6R-G1d (SEQ ID NO: 156) which was used as the antibody H chain. Furthermore, IL6R-F652 (SEQ ID NO: 162) was prepared by introducing an alteration of substituting Pro at position 238 (EU numbering) with Asp into IL6R-F11. Expression plasmids containing an antibody H chain sequence were prepared for each of the antibody H chain sequences produced by substituting the region near the residue at position 238 (EU numbering) (positions 234 to 237, and 239 (EU numbering)) in L6R-F652 each with 18 amino acids excluding the original amino acid and Cys. IL6R-L (SEQ ID NO: 155) was utilized as an antibody L chain. These variants were expressed and purified by the method of Reference Example 1. These Fc variants are called PD variants. Interactions of each PD variant with FcγRIIa type R (allotype R131) and FcγRIIb were comprehensively evaluated by the method of Reference Example 2.

Figure 33:
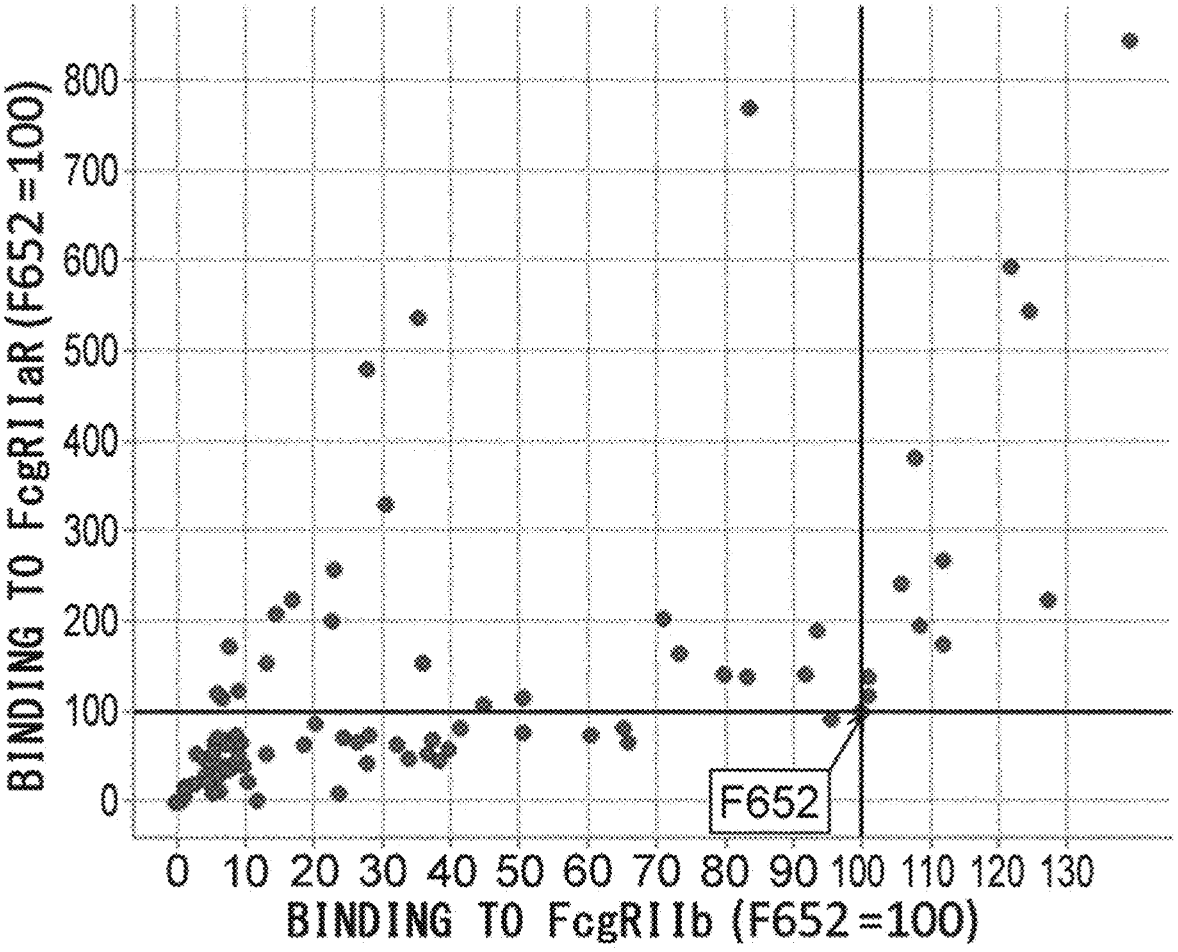
FIG. 33 shows a graph in which the horizontal axis shows the relative value of FcγRIIb-binding activity of each PD variant, and the vertical axis shows the relative value of FcγRIIa type R-binding activity of each PD variant. The value for the amount of binding of each PD variant to each FcγR was divided by the value for the amount of binding of IL6R-F652 (SEQ ID NO: 162)/IL6R-L, which is a control antibody prior to introduction of the alteration (IL6R-F652 is an antibody heavy chain comprising an altered Fc with substitution of Pro at position 238 (EU numbering) with Asp), to each FcγR; and then the obtained value was multiplied by 100, and used as the relative binding activity value for each PD variant to each FcγR. The F652 plot in the figure shows the value for IL6R-F652/IL6R-L.

A figure that shows the results of analyzing the interaction with the respective FcγRs was produced according to the following method. The value obtained by dividing the value for the amount of binding of each PD variant to each FcγR by the value for the amount of FcγR binding of the pre-altered antibody which is used as the control (IL6R-F652/IL6R-L, which has an alteration of substituting Pro at position 238 (EU numbering) with Asp) and then multiplying the result by 100, was shown as the relative binding activity value of each PD variant to each FcγR. The horizontal axis shows relative values of the FcγRIIb-binding activity of each PD variant, and the vertical axis shows relative values of the FcγRIIa type R-binding activity of each PD variant (FIG. 33).

As a result, it was found that the FcγRIIb binding of eleven types of alterations were enhanced compared with the antibody before introducing alterations, and they have the effects of maintaining or enhancing FcγRIIa type R-binding. The activities of these eleven variants to bind FcγRIIb and FcγRIIa type R are summarized in Table 24. In the table, alteration refers to the alteration introduced into IL6R-F11 (SEQ ID NO: 161).

TABLE 24

| VARIANT NAME | ALTERATION | RELATIVE BINDING ACTIVITY TO FcγRIIb | RELATIVE BINDING ACTIVITY TO FcγRIIaR |
|---|---|---|---|
| IL6R-F652/IL6R-L | P238D | 100 | 100 |
| IL6R-PD042/IL6R-L | P238D/L234W | 106 | 240 |
| IL6R-PD043/IL6R-L | P238D/L234Y | 112 | 175 |
| IL6R-PD079/IL6R-L | P238D/G237A | 101 | 138 |
| IL6R-PD080/IL6R-L | P238D/G237D | 127 | 222 |
| IL6R-PD081/IL6R-L | P238D/G237E | 101 | 117 |
| IL6R-PD082/IL6R-L | P238D/G237F | 108 | 380 |
| IL6R-PD086/IL6R-L | P238D/G237L | 112 | 268 |
| IL6R-PD087/IL6R-L | P238D/G237M | 109 | 196 |
| IL6R-PD094/IL6R-L | P238D/G237W | 122 | 593 |
| IL6R-PD095/IL6R-L | P238D/G237Y | 124 | 543 |
| IL6R-PD097/IL6R-L | P238D/S239D | 139 | 844 |

Figure 34:
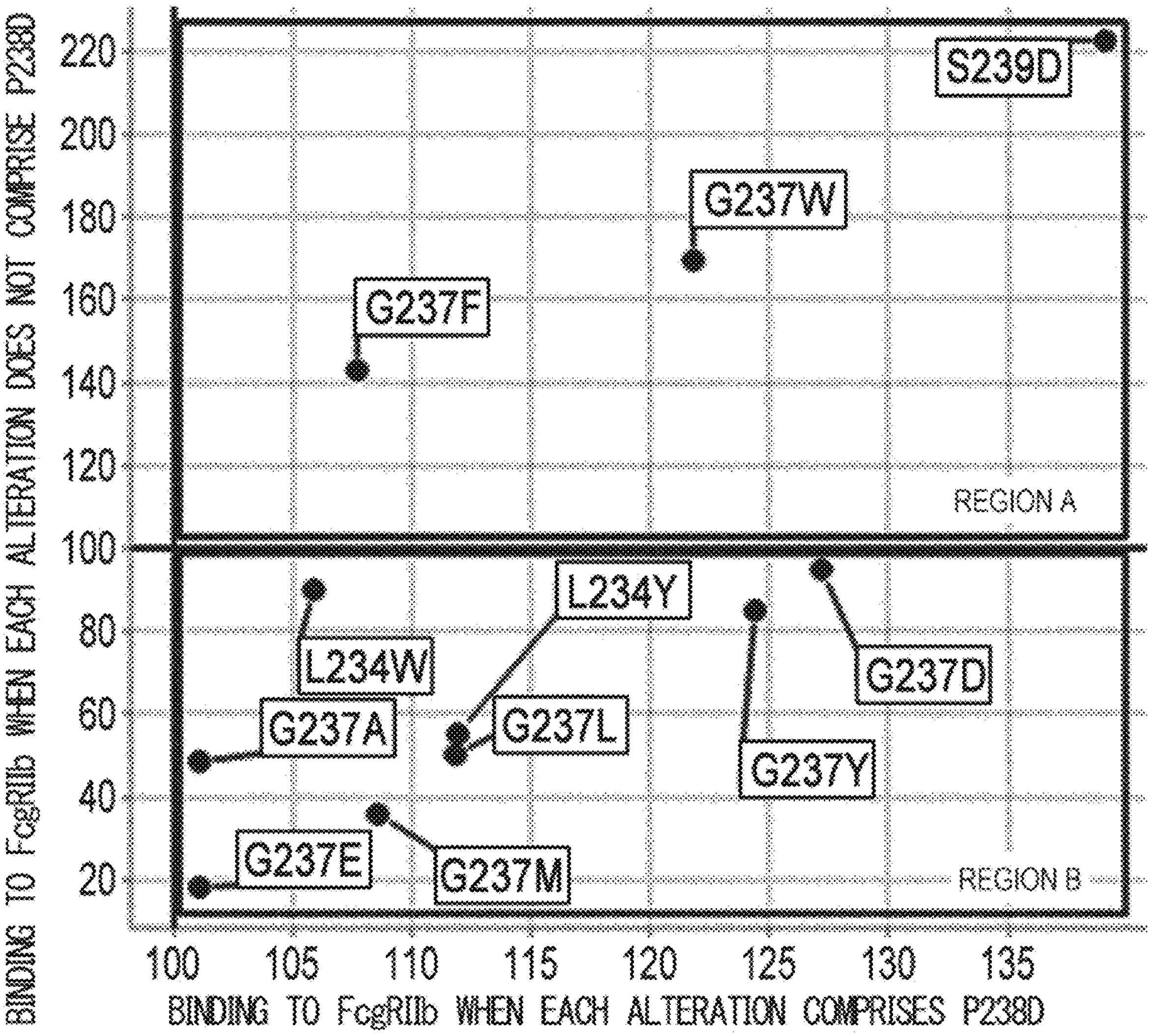
FIG. 34 shows a graph in which the vertical axis shows the relative value of FcγRIIb-binding activity of variants produced by introducing each alteration into GpH7-B3 (SEQ ID NO: 168)/GpL16-k0 (SEQ ID NO: 169) which does not have the P238D alteration, and the horizontal axis shows the relative value of FcγRIIb-binding activity of variants produced by introducing each alteration into IL6R-F652 (SEQ ID NO: 162)/IL6R-L which has the P238D alteration. The value for the amount of FcγRIIb binding of each variant was divided by the value for the amount of FcγRIIb binding of the pre-altered antibody; and then the obtained value was multiplied by 100, and used as the value of relative binding activity. Here, region A contains alterations that exhibit the effect of enhancing FcγRIIb binding in both cases where an alteration is introduced into GpH7-B3/GpL16-k0 which does not have P238D and where an alteration is introduced into IL6R-F652/IL6R-L which has P238D. Region B contains alterations that exhibit the effect of enhancing FcγRIIb binding when introduced into GpH7-B3/GpL16-k0 which does not have P238D, but do not exhibit the effect of enhancing FcγRIIb binding when introduced into IL6R-F652/IL6R-L which has P238D.

FIG. 34 shows relative values for the FcγRIIb-binding activity of a variant obtained by additionally introducing the above eleven alterations into a variant carrying the P238D alteration, and relative values for the FcγRIIb-binding activity of a variant obtained by introducing the alterations into an Fc that does not contain the P238D. These eleven alterations enhanced the amount of FcγRIIb binding compared with before introduction when they were further introduced into the P238D variant. On the contrary, the effect of lowering FcγRIIb binding was observed for eight of those alterations except G237F, G237W, and S239D, when they were introduced into the variant that does not contain P238D (data not shown).

These results showed that, based on the effects of introducing alterations into a naturally-occurring IgG1, it is difficult to predict the effects of combining and introducing the same alterations into the variant containing the P238D alteration. In other words, it would not have been possible to discover these eight alterations identified this time without this investigation that the same alterations are combined and introduced into the variant containing the P238D alteration.

The results of measuring KD values of the variants indicated in Table 24 for FcγRIa, FcγRIIaR (allotype R131), FcγRIIaH (allotype H131), FcγRIIb, and FcγRIIIaV (allotype V158) by the method of Reference Example 2 are summarized in Table 25. In the table, alteration refers to the alteration introduced into IL6R-F11 (SEQ ID NO: 161). The template used for producing IL6R-F11, IL6R-G1d/IL6R-L, is indicated with an asterisk (*). Furthermore, KD (IIaR)/KD (IIb) and KD (IIaH)/KD (IIb) in the table respectively show the value obtained by dividing the KD value of each variant for FcγRIIaR by the KD value of each variant for FcγRIIb, and the value obtained by dividing the KD value of each variant for FcγRIIaH by the KD value of each variant for FcγRIIb. KD (IIb) of the parent polypeptide/KD (IIb) of the variant refers to a value obtained by dividing the KD value of the parent polypeptide for FcγRIIb by the KD value of each variant for FcγRIIb. In addition, Table 25 shows KD values for the stronger of the FcγRIIaR- and FcγRIIaH-binding activities of each variant/KD values for the stronger of the FcγRIIaR- and FcγRIIaH-binding activities of the parent polypeptide. Here, parent polypeptide refers to a variant which has IL6R-F11 (SEQ ID NO: 161) as the H chain. For some variants, the binding of FcγR to IgG was too weak to analyze accurately by kinetic analysis, and thus the cells with bolded, italicized numerals in Table 25 show values calculated by using Equation 2 of Reference Example 2.

$$KD=C\cdot R_{max}/(R_{eq}-RI)-C \qquad \text{[Equation 2]}$$

Table 25 shows that all variants improved their affinity for FcγRIIb in comparison with IL6R-F11, and the range of improvement was 1.9 fold to 5.0 fold. The ratio of KD value of each variant for FcγRIIaR/KD value of each variant for FcγRIIb, and the ratio of KD value of each variant for FcγRIIaH/KD value of each variant for FcγRIIb represent an FcγRIIb-binding activity relative to the FcγRIIaR-binding activity and FcγRIIaH-binding activity, respectively. That is, these values show the degree of binding selectivity of each variant for FcγRIIb, and a larger value indicates a higher binding selectivity for FcγRIIb. For the parent polypeptide IL6R-F11/IL6R-L, the ratio of KD value for FcγRIIaR/KD value for FcγRIIb and the ratio of KD value for FcγRIIaH/KD value for FcγRIIb are both 0.7, and accordingly all variants in Table 25 showed improvement of binding selectivity for FcγRIIb in comparison with the parent polypeptide. When the KD value for the stronger of the FcγRIIaR- and FcγRIIaH-binding activities of a variant/KD value for the stronger of the FcγRIIaR- and FcγRIIaH-binding activities of the parent polypeptide is 1 or more, this means that the stronger of the FcγRIIaR- and FcγRIIaH-binding activities of a variant has equivalent or reduced binding compared with the binding by the stronger of the FcγRIIaR- and FcγRIIaH-binding activities of the parent polypeptide. Since this value was 0.7 to 5.0 for the variants obtained this time, one may say that binding by the stronger of the FcγRIIaR- and FcγRIIaH-binding activities of the variants obtained this time was nearly the same or decreased in comparison with the parent polypeptide. These results showed that compared with the parent polypeptide, the variants obtained this time have maintained or decreased binding activities to FcγRIIa type R and type H and enhanced binding activity to FcγRIIb, and thus have improved selectivity for FcγRIIb. Furthermore, compared with IL6R-F11, all variants had lower affinity to FcγRIa and FcγRIIIaV

TABLE 25

| ALTERATION | KD (mol/L) FcγRIa | FcγRIIaR | FcγRIIaH | FcγRIIb | FcγRIIIaV | KD (IIaR)/ KD (IIb) | KD (IIaH)/ KD (IIb) | KD (IIb) OF PARENT POLYPEPTIDE/ KD (IIb) OF ALTERED POLYPEPTIDE | KD VALUE FOR THE STRONGER OF THE BINDING ACTIVITIES OF A VARIANT TO FcγRIIaR AND FcγRIIaH/KD VALUE FOR THE STRONGER OF THE BINDING ACTIVITIES OF THE PARENT POLYPEPTIDE TO FcγRIIaR AND FcγRIIaH |
|---|---|---|---|---|---|---|---|---|---|
| * | 3.2E−10 | 1.0E−06 | 6.7E−07 | 2.6E−06 | 3.5E−07 | 0.4 | 0.3 | 2.6 | 0.1 |
| | 9.0E−10 | 5.0E−06 | 5.0E−06 | 6.8E−06 | **1.5E-06** | 0.7 | 0.7 | 1.0 | 1.0 |
| L234W/P238D | 6.3E−08 | 1.6E−05 | *1.9E-05* | 2.0E−06 | **3.7E-05** | 8.1 | 9.5 | 3.4 | 3.2 |
| L234Y/P238D | 7.5E−08 | 2.6E−05 | *2.3E-05* | 1.6E−06 | **4.5E-05** | 15.9 | 14.4 | 4.2 | 4.6 |
| G237A/P238D | 1.4E−07 | 3.2E−05 | *2.1E-05* | 3.0E−06 | **3.7E-05** | 10.5 | 7.0 | 2.3 | 4.2 |
| G237D/P238D | 1.4E−07 | 2.1E−05 | *2.5E-05* | 2.0E−06 | **4.3E-05** | 10.7 | 12.8 | 3.5 | 4.2 |
| G237E/P238D | 3.4E−07 | 3.8E−05 | *2.5E-05* | 3.6E−06 | **4.1E-05** | 10.6 | 7.0 | 1.9 | 5.0 |
| G237F/P238D | 5.2E−08 | 1.4E−05 | *1.6E-05* | 3.4E−06 | **4.3E-05** | 4.1 | 4.7 | 2.0 | 2.8 |
| G237L/P238D | 1.2E−07 | 1.8E−05 | *1.8E-05* | 2.6E−06 | **4.1E-05** | 6.9 | 7.1 | 2.7 | 3.5 |
| G237M/P238D | 5.2E−08 | 2.2E−05 | *2.0E-05* | 2.9E−06 | **3.7E-05** | 7.7 | 7.0 | 2.4 | 4.0 |
| G237W/P238D | 3.6E−08 | 7.2E−06 | **1.2E-05** | 2.3E−06 | **3.8E-05** | 3.1 | 5.2 | 2.9 | 1.4 |
| G237Y/P238D | 9.3E−08 | 7.9E−06 | **1.5E-05** | 2.3E−06 | **4.2E-05** | 3.4 | 6.4 | 2.9 | 1.6 |
| P238D/S239D | 4.9E−09 | 3.5E−06 | **1.5E-06** | 1.4E−06 | **1.7E-05** | 2.6 | 14.0 | 5.0 | 0.7 |

[Reference Example 15] X-Ray Crystal Structure Analysis of a Complex Formed Between an Fc Containing P238D and an Extracellular Region of FcγRIIb As indicated earlier in Reference Example 14, even though an alteration that is predicted from the analysis of naturally-occurring IgG1 antibodies to improve FcγRIIb-binding activity or selectivity for FcγRIIb is introduced into an Fc containing P238D, the FcγRIIb-binding activity was found to decrease, and the reason for this may be that the structure at the interacting interface between Fc and FcγRIIb is changed due to introduction of P238D. Therefore, to pursue the reason for this phenomena, the three-dimensional structure of the complex formed between an IgG1 Fc containing the P238D mutation (hereinafter, referred to as Fc (P238D)) and the extracellular region of FcγRIIb was elucidated by X-ray crystal structure analysis, and this was compared to the three-dimensional structure of the complex formed between the Fc of a naturally-occurring IgG1 (hereinafter, referred to as Fc (WT)) and the extracellular region of FcγRIIb, and the binding modes were compared. Multiple reports have been made on the three-dimensional structure of a complex formed between an Fc and an FcγR extracellular region; and the three-dimensional structures of the Fc (WT)/FcγRIIIb extracellular region complex (Nature (2000) 400, 267-273; J. Biol. Chem. (2011) 276, 16469-16477), the Fc (WT)/FcγRIIIa extracellular region complex (Proc. Natl. Acad. Sci. USA (2011) 108, 12669-126674), and the Fc (WT)/FcγRIIa extracellular region complex (J. Immunol. (2011) 187, 3208-3217) have been analyzed. While the three-dimensional structure of the Fc (WT)/FcγRIIb extracellular region complex has not been analyzed, the three-dimensional structure of a complex formed with Fc (WT) is known for FcγRIIa, and the extracellular regions of FcγRIIa and FcγRIIb match 93% in amino acid sequence and have very high homology. Thus, the three-dimensional structure of the Fc (WT)/FcγRIIb extracellular region complex was predicted by modeling using the crystal structure of the Fc (WT)/FcγRIIa extracellular region complex.

Figure 35:
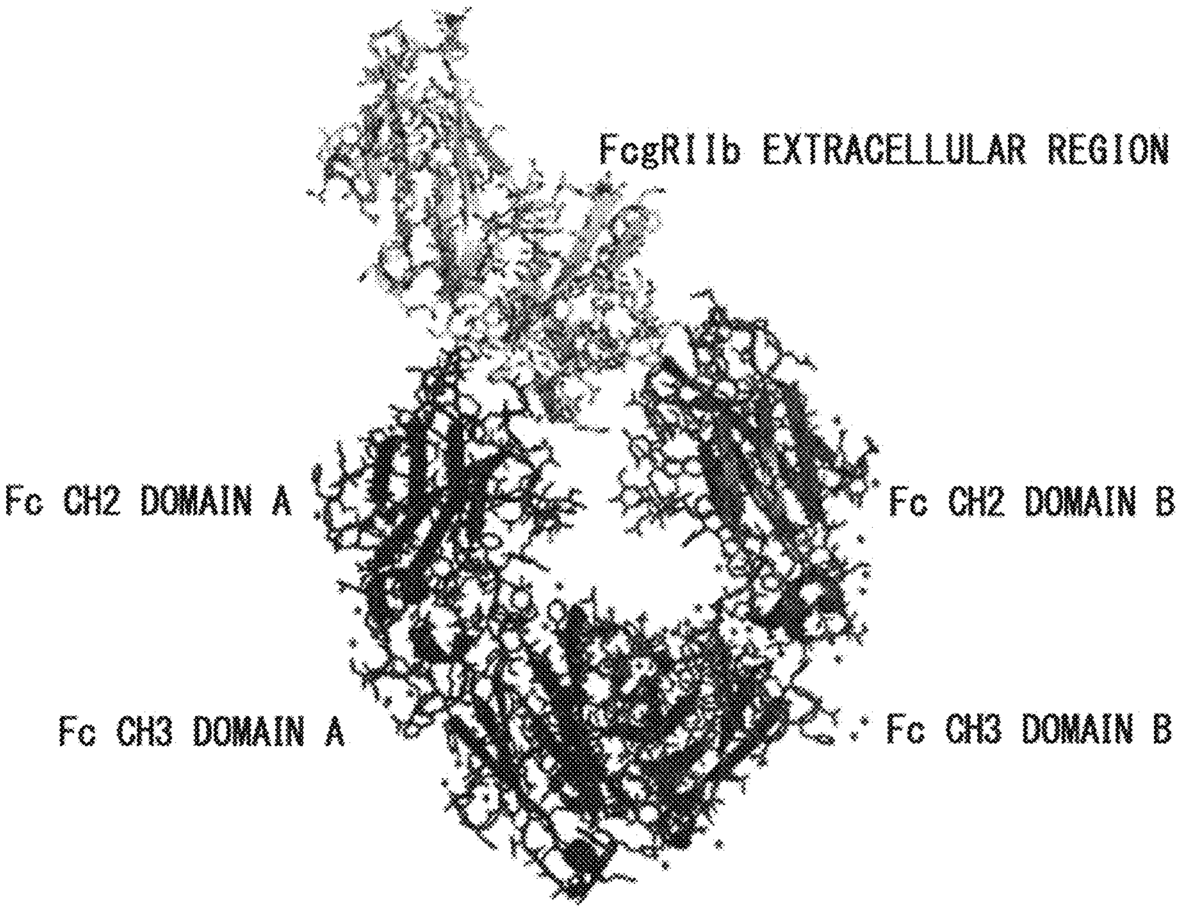
FIG. 35 shows a crystal structure of the Fc (P238D)/FcγRIIb extracellular region complex.
Figure 36:
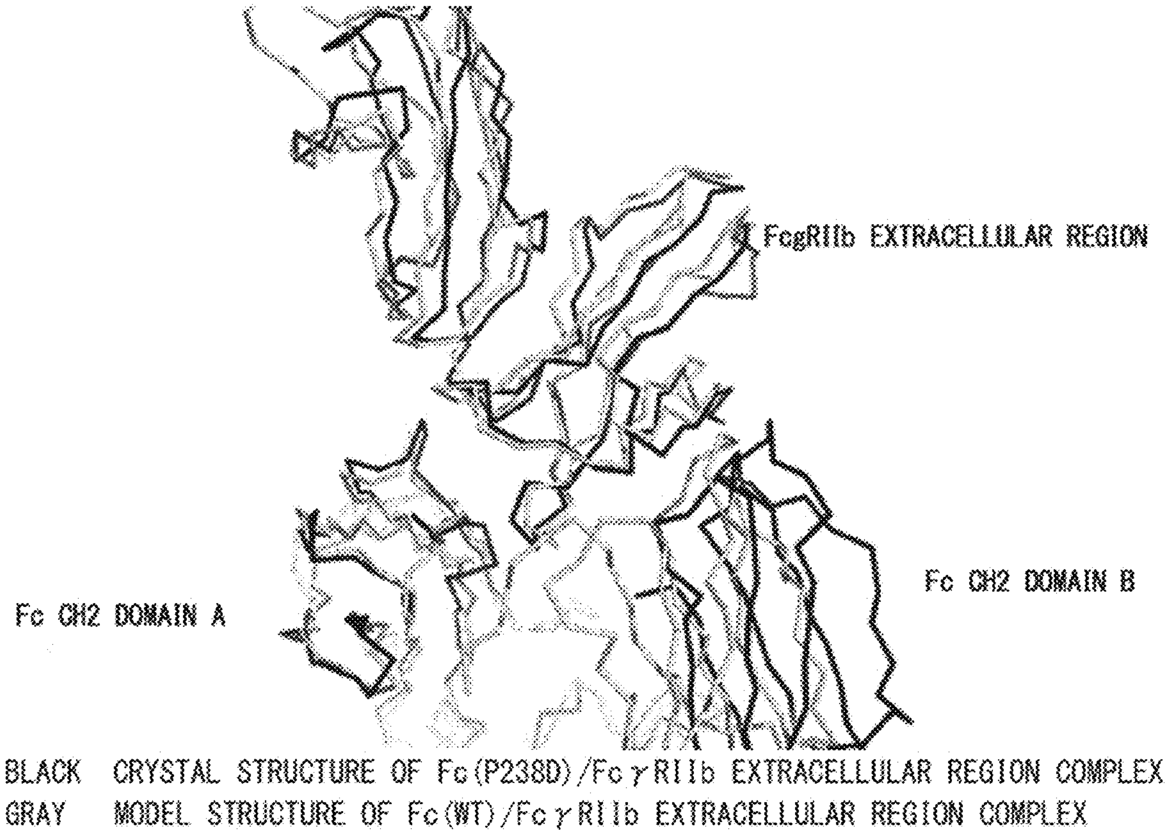
FIG. 36 shows an image of superimposing the crystal structure of the Fc (P238D)/FcγRIIb extracellular region complex and the model structure of the Fc (WT)/FcγRIIb extracellular region complex, with respect to the FcγRIIb extracellular region and the Fc CH2 domain A by the least squares fitting based on the Cα atom pair distances.

The three-dimensional structure of the Fc (P238D)/FcγRIIb extracellular region complex was determined by X-ray crystal structure analysis at 2.6 Å resolution. The structure obtained as a result of this analysis is shown in FIG. 35. The FcγRIIb extracellular region is bound between two Fc CH2 domains, and this was similar to the three-dimensional structures of complexes formed between Fc (WT) and the respective extracellular region of FcγRIIIa, FcγRIIIb, or FcγRIIa analyzed so far. Next, for detailed comparison, the crystal structure of the Fc (P238D)/FcγRIIb extracellular region complex and the model structure of the Fc (WT)/FcγRIIb extracellular region complex were superimposed by the least squares fitting based on the Cα atom pair distances with respect to the FcγRIIb extracellular region and the Fc CH2 domain A (FIG. 36). In that case, the degree of overlap between Fc CH2 domains B was not satisfactory, and conformational differences were found in this portion. Furthermore, using the crystal structure of the Fe (P238D)/FcγRIIb extracellular region complex and the model structure of the Fc (WT)/FcγRIIb extracellular region complex, pairs of atoms that have a distance of 3.7 Å or less between the FcγRIIb extracellular region and Fc CH2 domain B were extracted and compared in order to compare the interatomic interaction between FcγRIIb and Fc (WT) CH2 domain B with the interatomic interaction between FcγRIIb and Fc (P238D) CH2 domain B. As shown in Table 26, the interatomic interactions between Fc CH2 domain B and FcγRIIb in Fc (P238D) and Fc (WT) did not match.

TABLE 26

| FcγRIIb ATOM | | | Fc (P238D) CH2 DOMAIN B INTERACTION PARTNER (DISTANCE BETWEEN ATOMS, Å) | | | | Fc (WT) CH2 DOMAIN B INTERACTION PARTNER (DISTANCE BETWEEN ATOMS, Å) | | | |
|---|---|---|---|---|---|---|---|---|---|---|
| Val | 116 | CG2 | | | | | Asp | 265 | OD2 | (3.47) |
| | | | | | | | Gly | 237 | O | (3.65) |
| Ser | 126 | OG | Ser | 298 | N | (3.31) | | | | |
| | | | Ser | 298 | CB | (3.32) | | | | |
| | | | Tyr | 296 | O | (3.05) | | | | |
| Lys | 128 | CA | Ser | 298 | OG | (3.50) | | | | |
| Phe | 129 | CB | Ser | 298 | O | (3.36) | | | | |
| Phe | 129 | CD2 | | | | | Asn | 297 | CB | (3.50) |
| | | | | | | | Asn | 297 | CG | (3.43) |
| Lys | 128 | C | Ser | 298 | O | (3.47) | | | | |
| Phe | 129 | N | Ser | 298 | OG | (3.30) | | | | |
| Phe | 129 | O | Ser | 267 | OG | (3.54) | | | | |
| Arg | 131 | CB | | | | | Val | 266 | O | (3.02) |
| Arg | 131 | CG | | | | | Val | 266 | O | (3.22) |
| Arg | 131 | CD | | | | | Val | 266 | CG1 | (3.45) |
| | | | | | | | Val | 266 | C | (3.55) |
| | | | | | | | Val | 266 | O | (3.10) |
| Arg | 131 | NE | Ala | 327 | O | (3.60) | Val | 266 | C | (3.66) |
| | | | | | | | Val | 266 | O | (3.01) |
| | | | | | | | Val | 266 | N | (3.49) |
| Arg | 131 | CZ | Asp | 270 | CG | (3.64) | Val | 266 | N | (3.13) |
| | | | Asp | 270 | OD2 | (3.22) | | | | |
| | | | Asp | 270 | OD1 | (3.27) | | | | |
| | | | Ala | 327 | CB | (3.63) | | | | |
| Arg | 131 | NH1 | Asp | 270 | CG | (3.19) | Val | 266 | CG1 | (3.47) |
| | | | Asp | 270 | OD2 | (2.83) | Val | 266 | N | (3.43) |
| | | | Asp | 270 | OD1 | (2.99) | Thr | 299 | OG1 | (3.66) |
| | | | Ser | 267 | CB | (3.56) | Ser | 298 | O | (3.11) |
| Arg | 131 | NH2 | Asp | 270 | CG | (3.20) | Asp | 265 | CA | (3.16) |
| | | | Asp | 270 | OD2 | (2.80) | Val | 266 | N | (3.37) |
| | | | Asp | 270 | OD1 | (2.87) | | | | |
| | | | Ala | 327 | CB | (3.66) | | | | |
| Tyr | 157 | CE1 | | | | | Leu | 234 | CG | (3.64) |
| | | | | | | | Leu | 234 | CD1 | (3.61) |
| Tyr | 157 | OH | | | | | Gly | 236 | O | (3.62) |
| | | | | | | | Leu | 234 | CA | (3.48) |
| | | | | | | | Leu | 234 | CG | (3.45) |

Figure 37:
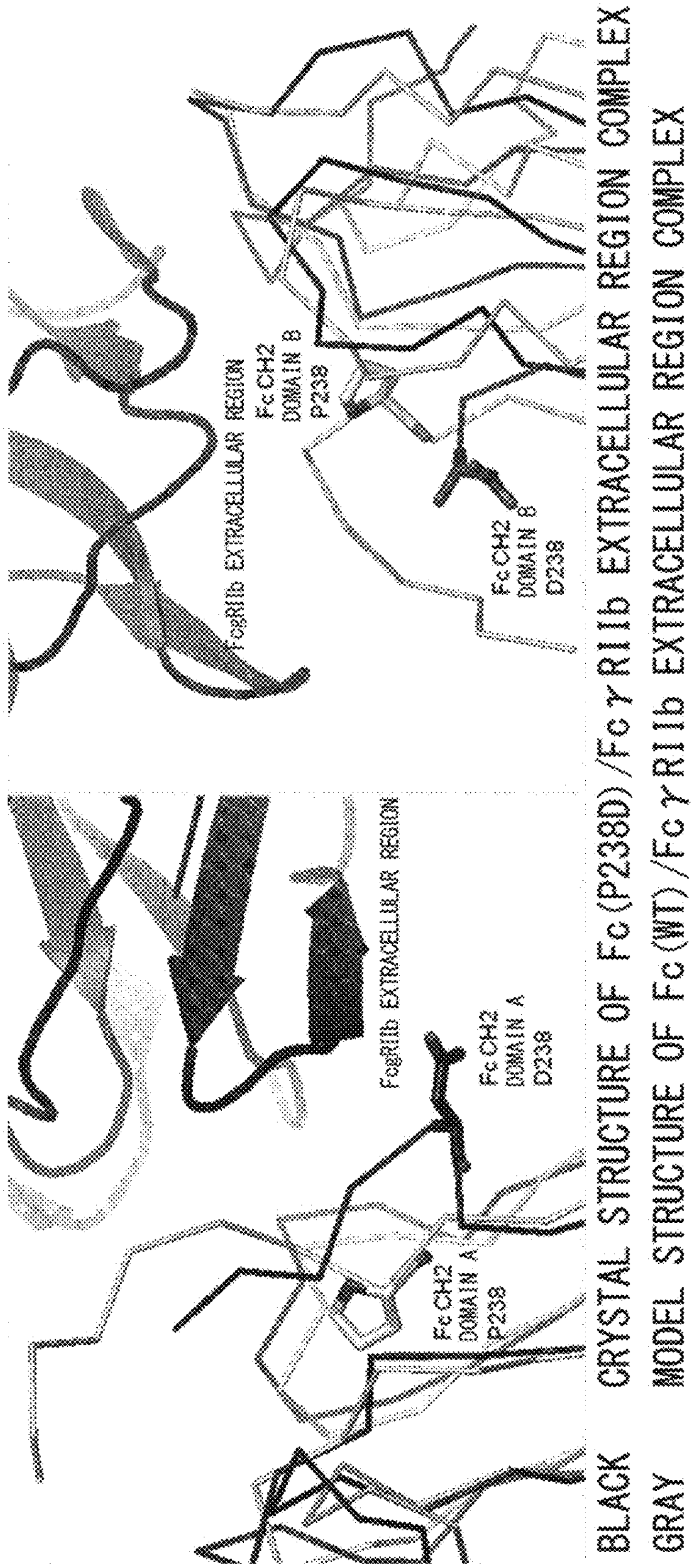
FIG. 37 shows comparison of the detailed structure around P238D after superimposing the crystal structure of the Fc (P238D)/FcγRIIb extracellular region complex and the model structure of the Fc (WT)/FcγRIIb extracellular region complex with respect to the only Fc CH2 domain A or the only Fc CH2 domain B by the least squares fitting based on the Cα atom pair distances.

Furthermore, the detailed structures around P238D were compared by superposing the X-ray crystal structure of Fc (P238D)/FcγRIIb extracellular region complex on the model structure of the Fc (WT)/FcγRIIb extracellular region complex using the least squares method based on the Cα atomic distance between Fc CH2 domains A and B alone. As the position of the amino acid residue at position 238 (EU numbering), i.e., a mutagenesis position of Fc (P238D), is altered from Fe (WT), the loop structure around the amino acid residue at position 238 following the hinge region is found to be different between Fc (P238D) and Fc (WT) (FIG. 37). Pro at position 238 (EU numbering) is originally located inside Fc (WT), forming a hydrophobic core with residues around position 238. However, if Pro at position 238 (EU numbering) is altered to highly hydrophilic and charged Asp, the presence of the altered Asp residue in a hydrophobic core is energetically disadvantageous in terms of desolvation. Therefore, in Fc (P238D), to cancel this energetically disadvantageous situation, the amino acid residue at position 238 (EU numbering) may have changed its orientation to face the solvent side, and this may have caused the change in the loop structure near the amino acid residue at position 238. Furthermore, since this loop is not far from the hinge region crosslinked by an S—S bond, its structural change will not be limited to a local change, and will affect the relative positioning of the Fc CH2 domain A and domain B. As a result, the interatomic interactions between FcγRIIb and Fc CH2 domain B have been changed. Therefore, predicted effects could not be observed when alterations that improve selectivity and binding activity towards FcγRIIb in a naturally-occurring IgG were combined with an Fc containing the P238D alteration.

Figure 38:
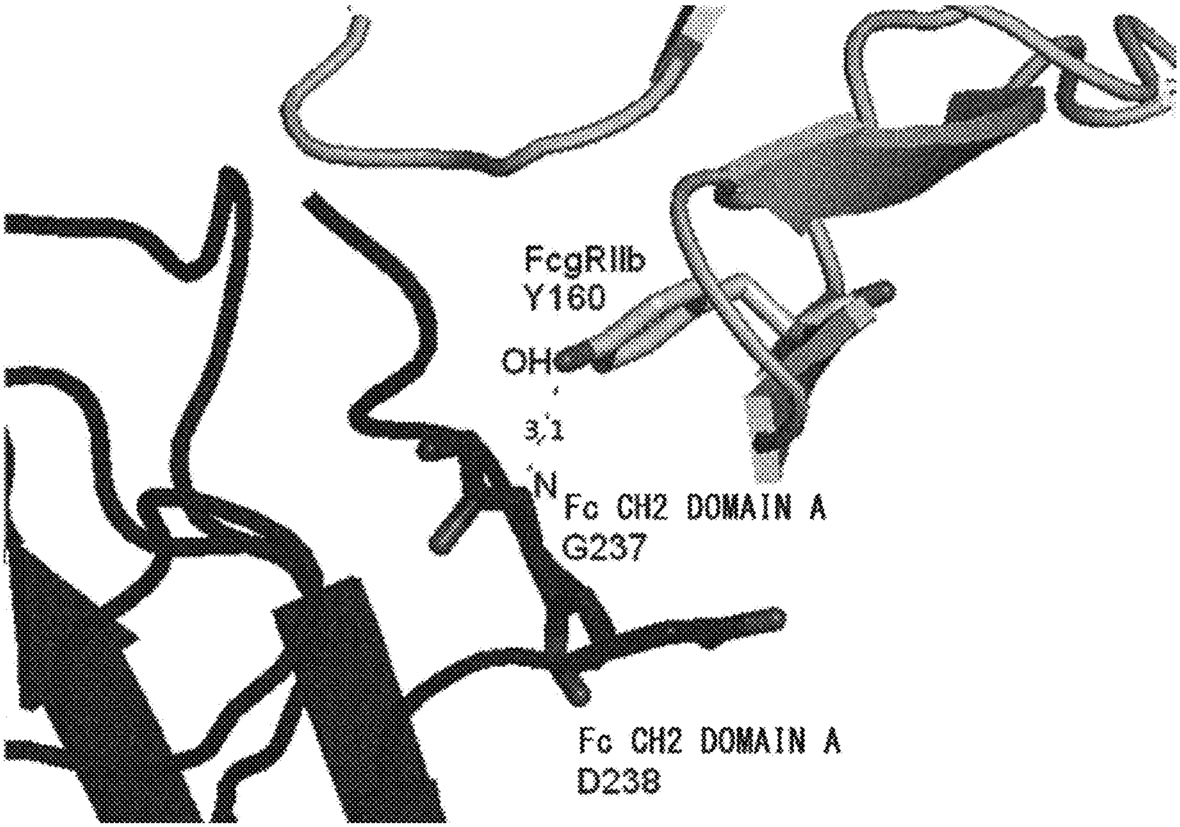
FIG. 38 shows that a hydrogen bond can be found between the main chain of Gly at position 237 (EU numbering) in Fc CH2 domain A, and Tyr at position 160 in FcγRIIb in the crystal structure of the Fc (P238D)/FcγRIIb extracellular region complex.
Figure 39:
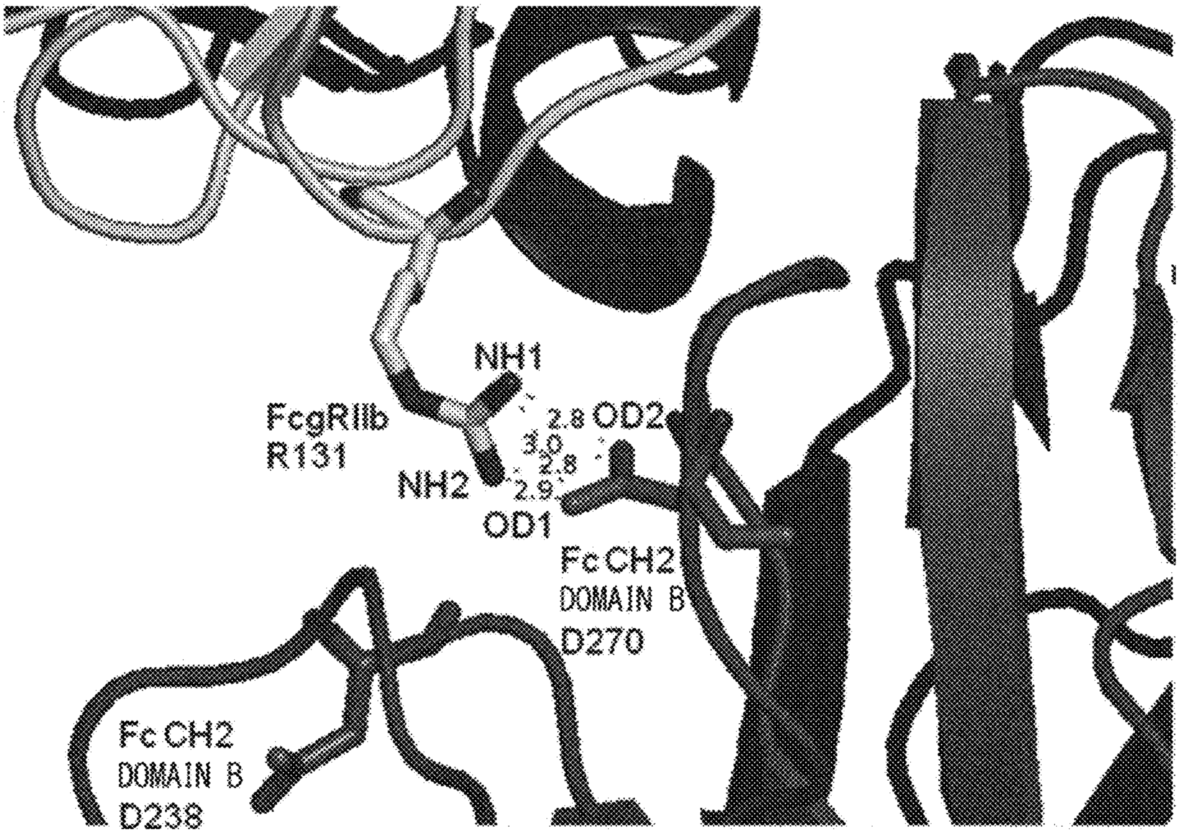
FIG. 39 shows that an electrostatic interaction can be found between Asp at position 270 (EU numbering) in Fc CH2 domain B, and Arg at position 131 in FcγRIIb in the crystal structure of the Fc (P238D)/FcγRIIb extracellular region complex.

Furthermore, as a result of structural changes due to introduction of P238D in Fc CH2 domain A, a hydrogen bond has been found between the main chain of Gly at position 237 (EU numbering), which is adjacent to P238D mutated, and Tyr at position 160 in FcγRIIb (FIG. 38). The residue in FcγRIIa that corresponds to this Tyr 160 is Phe; and when the binding is to FcγRIIa, this hydrogen bond is not formed. Considering that the amino acid at position 160 is one of the few differences between FcγRIIa and FcγRIIb at the interface of interaction with Fc, the presence of this hydrogen bond which is specific to FcγRIIb is presumed to have led to improvement of FcγRIIb-binding activity and decrease of FcγRIIa-binding activity in Fc (P238D), and improvement of its selectivity. Furthermore, in Fc CH2 domain B, an electrostatic interaction is observed between Asp at position 270 (EU numbering) and Arg at position 131 in FcγRIIb (FIG. 39). In FcγRIIa type H, which is one of the allotypes of FcγRIIa, the residue corresponding to Arg at position 131 of FcγRIIb is His, and therefore cannot form this electrostatic interaction. This can explain why the Fc (P238D)-binding activity is lowered in FcγRIIa type H compared with FcγRIIa type R. Observations based on such results of X-ray crystal structure analysis showed that the change of the loop structure beside P238D due to P238D introduction and the accompanying change in the relative domain positioning could cause formation of new interactions which is not found in the binding of the naturally-occurring IgG and FcγR, and this could lead to a selective binding profile of P238D variants for FcγRIIb.

[Expression and Purification of Fc (P238D)]

An Fc containing the P238D alteration was prepared as follows. First, Cys at position 220 (EU numbering) of hIL6R-IgG1-v1 (SEQ ID NO: 163) was substituted with Ser. Then, genetic sequence of Fc (P238D) from Glu at position 236 (EU numbering) to its C terminal was cloned by PCR. Using this cloned genetic sequence, production of expression vectors, and expression and purification of Fc (P238D) were carried out according to the method of Reference Example 1. Cys at position 220 (EU numbering) forms a disulfide bond with Cys of the L chain in general IgG1. The L chain is not co-expressed when Fc alone is prepared, and therefore, the Cys residue was substituted with Ser to avoid formation of unnecessary disulfide bonds.

[Expression and Purification of the FcγRIIb Extracellular Region]

The FcγRIIb extracellular region was prepared according to the method of Reference Example 2.

[Purification of the Fc (P238D)/FcγRIIb Extracellular Region Complex]

To 2 mg of the FcγRIIb extracellular region sample obtained for use in crystallization, 0.29 mg of Endo F1 (Protein Science (1996) 5: 2617-2622) expressed and purified from *Escherichia coli* as a glutathione S-transferase fusion protein was added. This was allowed to remain at room temperature for three days in 0.1 M Bis-Tris buffer at pH 6.5, and the N-linked oligosaccharide was cleaved, except for N-acetylglucosamine directly bound to Asn of the FcγRIIb extracellular region. Next, the FcγRIIb extracellular region sample subjected to carbohydrate cleavage treatment, which was concentrated by ultrafiltration with 5000 MWCO, was purified by gel filtration chromatography (Superdex® 200 10/300 gel filtration column) using a column equilibrated in 20 mM HEPS at pH 7.5 containing 0.05 M NaCl. Furthermore, to the obtained carbohydrate-cleaved FcγRIIb extracellular region fraction, Fc (P238D) was added so that the molar ratio of the FcγRIIb extracellular region would be present in slight excess. The mixture concentrated by ultrafiltration with 10,000 MWCO was subjected to purification by gel filtration chromatography (Superdex® 200 10/300 gel filtration column) using a column equilibrated in 20 mM HEPS at pH 7.5 containing 0.05 M NaCl. Thus, a sample of the Fc (P238D)/FcγRIIb extracellular region complex was obtained.

[Crystallization of the Fc (P238D)/FcγRIIb Extracellular Region Complex]

Using the sample of the Fc (P238D)/FcγRIIb extracellular region complex which was concentrated to approximately 10 mg/mL by ultrafiltration with 10,000 MWCO, crystallization of the complex was carried out by the sitting drop vapor diffusion method. Hydra II Plus One (MATRIX) was used for crystallization; and for a reservoir solution containing 100 mM Bis-Tris pH 6.5, 17% PEG3350, 0.2 M ammonium acetate, and 2.7% (w/v) D-Galactose, a crystallization drop was produced by mixing at a ratio of reservoir solution: crystallization sample=0.2 μL: 0.2 μL. The crystallization drop after sealing was allowed to remain at 20° C., and thus thin plate-like crystals were obtained.

[Measurement of X-Ray Diffraction Data from an Fc (P238D)/FcγRIIb Extracellular Region Complex Crystal]

One of the obtained single crystals of the Fc (P238D)/FcγRIIb extracellular region complex was soaked into a solution of 100 mM Bis-Tris pH 6.5, 20% PEG3350, ammonium acetate, 2.7% (w/v) D-Galactose, 22.5% (v/v) ethylene glycol. The single crystal was fished out of the solution using a pin with attached tiny nylon loop, and frozen in liquid nitrogen. Then, the X-ray diffraction data of the crystal was measured at synchrotron radiation facility Photon Factory BL-1A in High Energy Accelerator Research Organization. During the measurement, the crystal was constantly placed in a nitrogen stream at −178° C. to maintain in a frozen state, and a total of 225 X-ray diffraction images were collected using Quantum 270 CCD detector (ADSC) attached to a beam line with rotating the crystal 0.8° at a time. Determination of cell parameters, indexing of diffraction spots, and diffraction data processing from the obtained diffraction images were performed using the Xia2 program (CCP4 Software Suite), XDS Package (Walfgang Kabsch) and Scala (CCP4 Software Suite); and finally, diffraction intensity data of the crystal up to 2.46 Å resolution was obtained. The crystal belongs to the space group P21, and has the following cell parameters; a=48.85 Å, b=76.01 Å, c=115.09 Å, α=90°, β=100.700, γ=900.

[X-Ray Crystal Structure Analysis of the Fc (P238D)/FcγRIIb Extracellular Region Complex]

Crystal structure of the Fc (P238D)/FcγRIIb extracellular region complex was determined by the molecular replacement method using the program Phaser (CCP4 Software Suite). From the size of the obtained crystal lattice and the molecular weight of the Fc (P238D)/FcγRIIb extracellular region complex, the number of complexes in the asymmetric unit was predicted to be one. From the structural coordinates of PDB code: 3SGJ which is the crystal structure of the Fc (WT)/FcγRIIIa extracellular region complex, the amino acid residue portions of the A chain positions 239-340 and the B chain positions 239-340 were taken out as separate coordinates, and they were set respectively as models for searching the Fc CH2 domains. The amino acid residue portions of the A chain positions 341-444 and the B chain positions 341-443 were taken out as a single set of coordinates from the same structural coordinates of PDB code: 3SGJ; and this was set as a model for searching the Fc CH3 domains. Finally, from the structural coordinates of PDB code: 2FCB which is a crystal structure of the FcγRIIb extracellular region, the amino acid residue portions of the A chain positions 6-178 was taken out and set as a model for searching the FcγRIIb extracellular region. The orientation and position of each search model in the crystal lattice were determined in the order of Fc CH3 domain, FcγRIIb extracellular region, and Fc CH2 domain, based on the rotation function and translation function to obtain the initial model for the crystal structure of the Fc (P238D)/FcγRIIb extracellular region complex. When rigid body refinement which moves the two Fc CH2 domains, the two Fc CH3 domains, and the FcγRIIb extracellular region was performed on the obtained initial model, the crystallographic reliability factor, R value became 40.4%, and the Free R value became 41.9% to diffraction intensity data from 25 Å to 3.0 Å at this point. Furthermore, structural refinement using the program Refmac5 (CCP4 Software Suite), and revision of the model to observe the electron density maps whose coefficient have 2Fo-Fc or Fo-Fc, which are calculated based on the experimentally determined structural factor Fo, the calculated structural factor Fc and the calculated phase using the model, was carried out by the Coot program (Paul Emsley). Model refinement was carried out by repeating these steps. Finally, as a result of incorporation of water molecules into the model based on the electron density maps which use 2Fo-Fc or Fo-Fc as the coefficient, and the following refinement, the crystallographic reliability factor, R values and the Free R value of the model containing 4846 non-hydrogen atoms became 23.7% and 27.6% to 24291 diffraction intensity data from 25 Å to 2.6 Å resolution, respectively.

[Production of a Model Structure of the Fc (WT)/FcγRIIb Extracellular Region Complex]

Based on the structural coordinates of PDB code: 3RY6 which is a crystal structure of the Fc (WT)/FcγRIIa extracellular region complex, the Build Mutants function of the Discovery Studio 3.1 program (Accelrys) was used to introduce mutations to match the amino acid sequence of FcγRIIb into FcγRIIa in this structural coordinates. In that case, the Optimization Level was set to High, Cut Radius was set to 4.5, five models were generated, and the one with the best energy score from among them was set as the model structure for the Fc (WT)/FcγRIIb extracellular region complex.

[Reference Example 16] Analysis of FcγR Binding of Fc Variants Whose Alteration Sites were Determined Based on Crystal Structures Based on the results of X-ray crystal structure analysis on the complex formed between Fc (P238D) and the FcγRIIb extracellular region obtained in Reference Example 15, variants were constructed by comprehensively introducing alterations into sites on the altered Fc having substitution of Pro at position 238 (EU numbering) with Asp that were predicted to affect interaction with FcγRIIb (residues of positions 233, 240, 241, 263, 265, 266, 267, 268, 271, 273, 295, 296, 298, 300, 323, 325, 326, 327, 328, 330, 332, and 334 (EU numbering)), and whether combinations of alterations that further enhance FcγRIIb binding in addition to the P238D alteration can be obtained, was examined.

IL6R-B3 (SEQ ID NO: 164) was produced by introducing into IL6R-G1d (SEQ ID NO: 156), the alteration produced by substituting Lys at position 439 (EU numbering) with Glu. Next, IL6R-BF648 was produced by introducing into IL6R-B3, the alteration produced by substituting Pro at position 238 (EU numbering) with Asp. IL6R-L (SEQ ID NO: 155) was utilized as the common antibody L chain. These antibody variants expressed were purified according to the method of Reference Example 1. The binding of these antibody variants to each of the FcγRs (FcγRIa, FcγRIIa type H, FcγRIIa type R, FcγRIIb, and FcγRIIIa type V) was comprehensively evaluated by the method of Reference Example 2.

A figure was produced according to the following method to show the results of analyzing the interactions with the respective FcγRs. The value for the amount of binding of each variant to each FcγR was divided by the value for the amount of binding of the pre-altered control antibody (IL6R-BF648/IL6R-L, alteration by substituting Pro at position 238 (EU numbering) with Asp) to each FcγR, and the obtained was then multiplied by 100 and shown as the relative binding activity value of each variant to each FcγR. The horizontal axis shows the relative binding activity value of each variant to FcγRIIb, and the vertical axis shows the relative binding activity value of each variant to FcγRIIa type R (FIG. 40).

Figure 40:
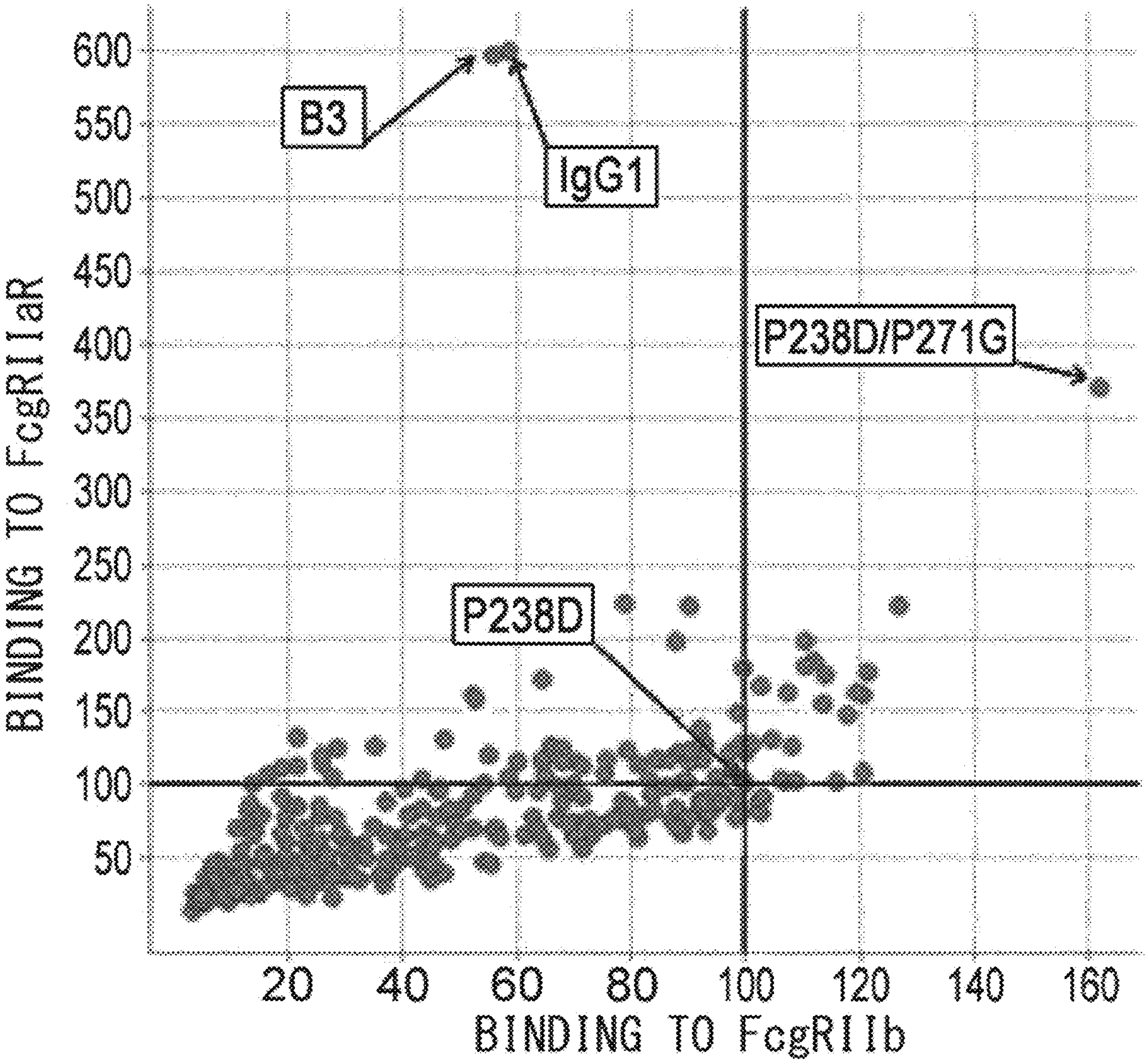
FIG. 40 shows a graph in which the horizontal axis shows the relative value of FcγRIIb-binding activity of each 2B variant, and the vertical axis shows the relative value of FcγRIIa type R-binding activity of each 2B variant. The value for the amount of binding of each 2B variant to each FcγR was divided by the value for the amount of binding of a control antibody prior to alteration (altered Fc with substitution of Pro at position 238 (EU numbering) with Asp) to each FcγR; and then the obtained value was multiplied by 100, and used as the value of relative binding activity of each 2B variant towards each FcγR.

As shown in FIG. 40, the results show that of all the alterations, 24 types of alterations were found to maintain or enhance FcγRIIb binding in comparison with the pre-altered antibody. The binding of these variants to each of the FcγRs are shown in Table 27. In the table, alteration refers to the alteration introduced into IL6R-B3 (SEQ ID NO: 164). The template used for producing IL6R-B3, IL6R-G1d/IL6R-L, is indicated with an asterisk (*).

TABLE 27

| | | RELATIVE BINDING | | | | |
|---|---|---|---|---|---|---|
| VARIANT NAME | ALTERATION | FcγRIa | FcγRIIaR | FcγRIIaH | FcγRIIb | FcγRIIIa |
| IL6R-G1d/IL6R-L | * | 140 | 650 | 1670 | 62 | 3348 |
| IL6R-B3/IL6R-L | | 145 | 625 | 1601 | 58 | 3264 |
| IL6R-BF648/IL6R-L | P238D | 100 | 100 | 100 | 100 | 100 |
| IL6R-2B002/IL6R-L | P238D/E233D | 118 | 103 | 147 | 116 | 147 |
| IL6R-BP100/IL6R-L | P238D/S267A | 121 | 197 | 128 | 110 | 138 |
| IL6R-BP102/IL6R-L | P238D/S267Q | 104 | 165 | 66 | 106 | 86 |
| IL6R-BP103/IL6R-L | P238D/S267V | 56 | 163 | 69 | 107 | 77 |
| IL6R-BP106/IL6R-L | P238D/H268D | 127 | 150 | 110 | 116 | 127 |
| IL6R-BP107/IL6R-L | P238D/H268E | 123 | 147 | 114 | 118 | 129 |
| IL6R-BP110/IL6R-L | P238D/H268N | 105 | 128 | 127 | 101 | 127 |
| IL6R-BP112/IL6R-L | P238D/P271G | 119 | 340 | 113 | 157 | 102 |
| IL6R-2B128/IL6R-L | P238D/Y296D | 95 | 87 | 37 | 103 | 96 |
| IL6R-2B169/IL6R-L | P238D/V323I | 73 | 92 | 83 | 104 | 94 |
| IL6R-2B171/IL6R-L | P238D/V323L | 116 | 117 | 115 | 113 | 122 |
| IL6R-2B172/IL6R-L | P238D/V323M | 140 | 244 | 179 | 132 | 144 |
| IL6R-BP136/IL6R-L | P238D/K326A | 117 | 159 | 103 | 119 | 102 |
| IL6R-BP117/IL6R-L | P238D/K326D | 124 | 166 | 96 | 118 | 105 |

TABLE 27-continued

| VARIANT NAME | ALTERATION | RELATIVE BINDING FcγRIa | FcγRIIaR | FcγRIIaH | FcγRIIb | FcγRIIIa |
|---|---|---|---|---|---|---|
| IL6R-BP120/IL6R-L | P238D/K326E | 125 | 175 | 92 | 114 | 103 |
| IL6R-BP126/IL6R-L | P238D/K326L | 113 | 167 | 132 | 103 | 146 |
| IL6R-BP119/IL6R-L | P238D/K326M | 117 | 181 | 133 | 110 | 145 |
| IL6R-BP142/IL6R-L | P238D/K326N | 98 | 103 | 97 | 106 | 102 |
| IL6R-BP121/IL6R-L | P238D/K326Q | 118 | 155 | 135 | 113 | 157 |
| IL6R-BP118/IL6R-L | P238D/K326S | 101 | 132 | 128 | 104 | 144 |
| IL6R-BP116/IL6R-L | P238D/K326T | 110 | 126 | 110 | 108 | 114 |
| IL6R-BP911/IL6R-L | P238D/A330K | 52 | 101 | 108 | 119 | 120 |
| IL6R-BP078/IL6R-L | P238D/A330M | 106 | 101 | 89 | 105 | 91 |
| IL6R-BP912/IL6R-L | P238D/A330R | 60 | 81 | 93 | 103 | 97 |

The results of measuring KD values of the variants shown in Table 27 for FcγRIa, FcγRIIaR, FcγRIIaH, FcγRIIb, and FcγRIIIa V by the method of Reference Example 2 are summarized in Table 28. In the table, alteration refers to the alteration introduced into IL6R-B3 (SEQ ID NO: 164). The template used for producing IL6R-B3, IL6R-G1d/IL6R-L, is indicated with an asterisk (*). Furthermore, KD (IIaR)/KD (IIb) and KD (IIaH)/KD (IIb) in the table respectively represent the value obtained by dividing the KD value of each variant for FcγRIIaR by the KD value of each variant for FcγRIIb, and the value obtained by dividing the KD value of each variant for FcγRIIaH by the KD value of each variant for FcγRIIb. KD (IIb) of the parent polypeptide/KD (IIb) of the altered polypeptide refers to the value obtained by dividing the KD value of the parent polypeptide for FcγRIIb by the KD value of each variant for FcγRIIb. In addition, the KD value for the stronger of the FcγRIIaR- and FcγRIIaH-binding activities of each variant/KD value for the stronger of the FcγRIIaR- and FcγRIIaH-binding activities of the parent polypeptide are shown in Table 28. Here, parent polypeptide refers to the variant which has IL6R-B3 (SEQ ID NO: 164) as the H chain. For some variants, the binding of FcγR to IgG was too weak to analyze accurately by kinetic analysis, and thus the cells with bolded, italicized numerals in Table 28 show values calculated by using Equation 2 of Reference Example 2.

$$KD=C\cdot R_{max}/(R_{eq}-RI)-C \quad \text{[Equation 2]}$$

TABLE 28

| VARIANT NAME | ALTERATION | KD (mol/L) FcγRIa | FcγRIIaR | FcγRIIaH | FcγRIIb | FcγRIIIaV | KD (IIaR)/ KD (IIb) |
|---|---|---|---|---|---|---|---|
| IL6R-G1d/IL6R-L | * | 3.2E−10 | 1.0E−06 | 6.7E−07 | 2.6E−06 | 3.5E−07 | 0.4 |
| IL6R-B3/IL6R-L | | 4.2E−10 | 1.1E−06 | 7.7E−07 | 3.1E−06 | 3.3E−07 | 0.3 |
| IL6R-BF648/IL6R-L | P238D | 1.1E−08 | 1.5E−05 | ***4.0E-05*** | 1.2E−06 | ***7.1E-05*** | 13.0 |
| IL6R-2B002/IL6R-L | P238D/E233D | 6.4E−09 | ***1.9E-05*** | ***8.6E-05*** | 9.3E−07 | ***5.3E-05*** | 20.4 |
| IL6R-BP100/IL6R-L | P238D/S267A | 1.1E−09 | 7.8E−06 | ***4.6E-05*** | 1.1E−06 | ***5.9E-05*** | 7.3 |
| IL6R-BP102/IL6R-L | P238D/S267Q | 8.2E−09 | 8.4E−06 | ***6.1E-05*** | 9.0E−07 | ***8.2E-05*** | 9.4 |
| IL6R-BP103/IL6R-L | P238D/S267V | 3.5E−08 | 1.1E−05 | ***9.9E-05*** | 1.2E−06 | ***1.1E-04*** | 9.0 |
| IL6R-BP106/IL6R-L | P238D/H268D | 4.0E−09 | 1.1E−05 | ***3.6E-05*** | 9.3E−07 | ***5.5E-05*** | 11.6 |
| IL6R-BP107/IL6R-L | P238D/H268E | 1.5E−09 | 1.2E−05 | ***5.2E-05*** | 9.3E−07 | ***6.3E-05*** | 12.7 |
| IL6R-BP110/IL6R-L | P238D/H268N | 7.3E−09 | 1.7E−05 | ***4.7E-05*** | 1.5E−06 | ***6.4E-05*** | 11.7 |
| IL6R-BP112/IL6R-L | P238D/P271G | 6.5E−09 | 3.5E−06 | ***3.5E-05*** | 3.2E−07 | ***6.9E-05*** | 11.0 |
| IL6R-2B128/IL6R-L | P238D/Y296D | 1.3E−08 | 2.6E−05 | ***3.4E-05*** | 1.4E−06 | ***7.2E-05*** | 17.7 |
| IL6R-2B169/IL6R-L | P238D/V323I | 2.5E−08 | 1.9E−05 | ***4.8E-05*** | 1.2E−06 | ***7.5E-05*** | 15.8 |
| IL6R-2B171/IL6R-L | P238D/V323L | 9.1E−09 | 1.6E−05 | ***3.4E-05*** | 1.1E−06 | ***5.7E-05*** | 15.0 |
| IL6R-2B172/IL6R-L | P238D/V323M | 3.0E−09 | 6.1E−06 | ***2.1E-05*** | 7.7E−07 | ***4.8E-05*** | 8.0 |
| IL6R-BP136/IL6R-L | P238D/K326A | 6.6E−09 | 9.1E−06 | ***3.8E-05*** | 8.0E−07 | ***5.9E-05*** | 11.4 |
| IL6R-BP117/IL6R-L | P238D/K326D | 4.1E−09 | 9.2E−06 | ***4.1E-05*** | 8.0E−07 | ***5.7E-05*** | 11.6 |
| IL6R-BP120/IL6R-L | P238D/K326E | 6.6E−09 | 9.6E−06 | ***6.5E-05*** | 1.0E−06 | ***7.9E-05*** | 9.3 |
| IL6R-BP126/IL6R-L | P238D/K326L | 7.4E−09 | 1.1E−05 | ***4.5E-05*** | 1.4E−06 | ***5.6E-05*** | 7.8 |
| IL6R-BP119/IL6R-L | P238D/K326M | 7.0E−09 | 9.9E−06 | ***4.5E-05*** | 1.1E−06 | ***5.6E-05*** | 8.7 |
| IL6R-BP142/IL6R-L | P238D/K326N | 5.3E−09 | 1.8E−05 | ***9.3E-05*** | 1.2E−06 | ***1.1E-04*** | 15.5 |
| IL6R-BP121/IL6R-L | P238D/K326Q | 1.1E−08 | 1.3E−05 | ***4.4E-05*** | 1.1E−06 | ***5.2E-05*** | 11.7 |
| IL6R-BP118/IL6R-L | P238D/K326S | 1.2E−08 | 1.5E−05 | ***4.6E-05*** | 1.2E−06 | ***5.6E-05*** | 13.2 |
| IL6R-BP116/IL6R-L | P238D/K326T | 2.6E−09 | 1.5E−05 | ***5.4E-05*** | 1.1E−06 | ***7.2E-05*** | 13.3 |
| IL6R-BP911/IL6R-L | P238D/A330K | 4.9E−08 | 1.6E−05 | ***3.7E-05*** | 8.9E−07 | ***5.9E-05*** | 18.5 |

TABLE 28-continued

| | | | | | | | |
|---|---|---|---|---|---|---|---|
| IL6R-BP078/IL6R-L | P238D/A330M | 8.2E−09 | 1.5E−05 | 4.5E-05 | 1.1E−06 | ***7.9E-05*** | 13.4 |
| IL6R-BP912/IL6R-L | P238D/A330R | 3.8E−08 | 2.6E−05 | 3.8E-05 | 1.5E−06 | ***7.9E-05*** | 17.8 |

| VARIANT NAME | KD (IIaH)/ KD (IIb) | KD (IIb) OF THE PARENT POLYPEPTIDE/ KD (IIb) OF ALTERED POLYPEPTIDE | KD VALUE FOR THE STRONGER OF THE FcγRIIaR- AND FcγRIIaH-BINDING ACTIVITIES OF THE VARIANT/KD VALUE FOR THE STRONGER OF THE FcγRIIaR- AND FcγRIIaH-BINDING ACTIVITIES OF THE PARENT POLYPEPTIDE |
|---|---|---|---|
| IL6R-G1d/IL6R-L | 0.3 | 1.2 | 0.9 |
| IL6R-B3/IL6R-L | 0.2 | 1.0 | 1.0 |
| IL6R-BF648/IL6R-L | 33.9 | 2.6 | 19.9 |
| IL6R-2B002/IL6R-L | 92.3 | 3.3 | 24.7 |
| IL6R-BP100/IL6R-L | 42.6 | 2.9 | 10.2 |
| IL6R-BP102/IL6R-L | 67.6 | 3.4 | 11.0 |
| IL6R-BP103/IL6R-L | 71.5 | 2.5 | 14.4 |
| IL6R-BP106/IL6R-L | 38.7 | 3.3 | 14.0 |
| IL6R-BP107/IL6R-L | 56.1 | 3.3 | 15.3 |
| IL6R-BP110/IL6R-L | 31.5 | 2.1 | 22.6 |
| IL6R-BP112/IL6R-L | 109.4 | 9.7 | 4.6 |
| IL6R-2B128/IL6R-L | 23.6 | 2.1 | 33.1 |
| IL6R-2B169/IL6R-L | 40.7 | 2.6 | 24.3 |
| IL6R-2B171/IL6R-L | 31.8 | 2.9 | 20.8 |
| IL6R-2B172/IL6R-L | 27.3 | 4.0 | 8.0 |
| IL6R-BP136/IL6R-L | 47.6 | 3.9 | 11.8 |
| IL6R-BP117/IL6R-L | 51.4 | 3.9 | 12.0 |
| IL6R-BP120/IL6R-L | 63.1 | 3.0 | 12.5 |
| IL6R-BP126/IL6R-L | 31.7 | 2.2 | 14.4 |
| IL6R-BP119/IL6R-L | 39.5 | 2.7 | 12.8 |
| IL6R-BP142/IL6R-L | 79.5 | 2.6 | 23.5 |
| IL6R-BP121/IL6R-L | 40.4 | 2.8 | 16.6 |
| IL6R-BP118/IL6R-L | 40.0 | 2.7 | 19.7 |
| IL6R-BP116/IL6R-L | 48.2 | 2.8 | 19.4 |
| IL6R-BP911/IL6R-L | 41.7 | 3.5 | 21.3 |
| IL6R-BP078/IL6R-L | 41.3 | 2.8 | 19.0 |
| IL6R-BP912/IL6R-L | 25.9 | 2.1 | 34.0 |

Table 28 shows that in comparison with IL6R-B3, all variants showed improvement of affinity for FcγRIIb, and the range of improvement was 2.1 fold to 9.7 fold. The ratio of KD value of each variant for FcγRIIaR/KD value of each variant for FcγRIIb, and the ratio of KD value of each variant for FcγRIIaH/KD value of each variant for FcγRIIb represent an FcγRIIb-binding activity relative to the FcγRIIaR-binding activity and FcγRIIaH-binding activity, respectively. That is, these values show the degree of binding selectivity of each variant for FcγRIIb, and a greater value indicates a higher binding selectivity for FcγRIIb. Since the ratio of KD value for FcγRIIaR/KD value for FcγRIIb, and the ratio of KD value for FcγRIIaH/KD value for FcγRIIb in the parent polypeptide IL6R-B3/IL6R-L were 0.3 and 0.2, respectively, all variants in Table 28 showed improvement of binding selectivity for FcγRIIb in comparison with the parent polypeptide. When the KD value for the stronger of the FcγRIIaR- and FcγRIIaH-binding activities of a variant/KD value for the stronger of the FcγRIIaR- and FcγRIIaH-binding activities of the parent polypeptide is 1 or more, this means that the stronger of the FcγRIIaR- and FcγRIIaH-binding activities of a variant has equivalent or decreased binding compared with the binding by the stronger of the FcγRIIaR- and FcγRIIaH-binding activities of the parent polypeptide. Since this value was 4.6 to 34.0 for the variants obtained this time, one may say that in comparison with the parent polypeptide, the variants obtained this time had reduced binding by the stronger of the FcγRIIaR- and FcγRIIaH-binding activities. These results showed that compared with the parent polypeptide, the variants obtained this time have maintained or decreased FcγRIIa type R- and type H-binding activities, enhanced FcγRIIb-binding activity, and improved selectivity for FcγRIIb. Furthermore, compared with IL6R-B3, all variants had lower affinity to FcγRIa and FcγRIIIaV.

Figure 41:
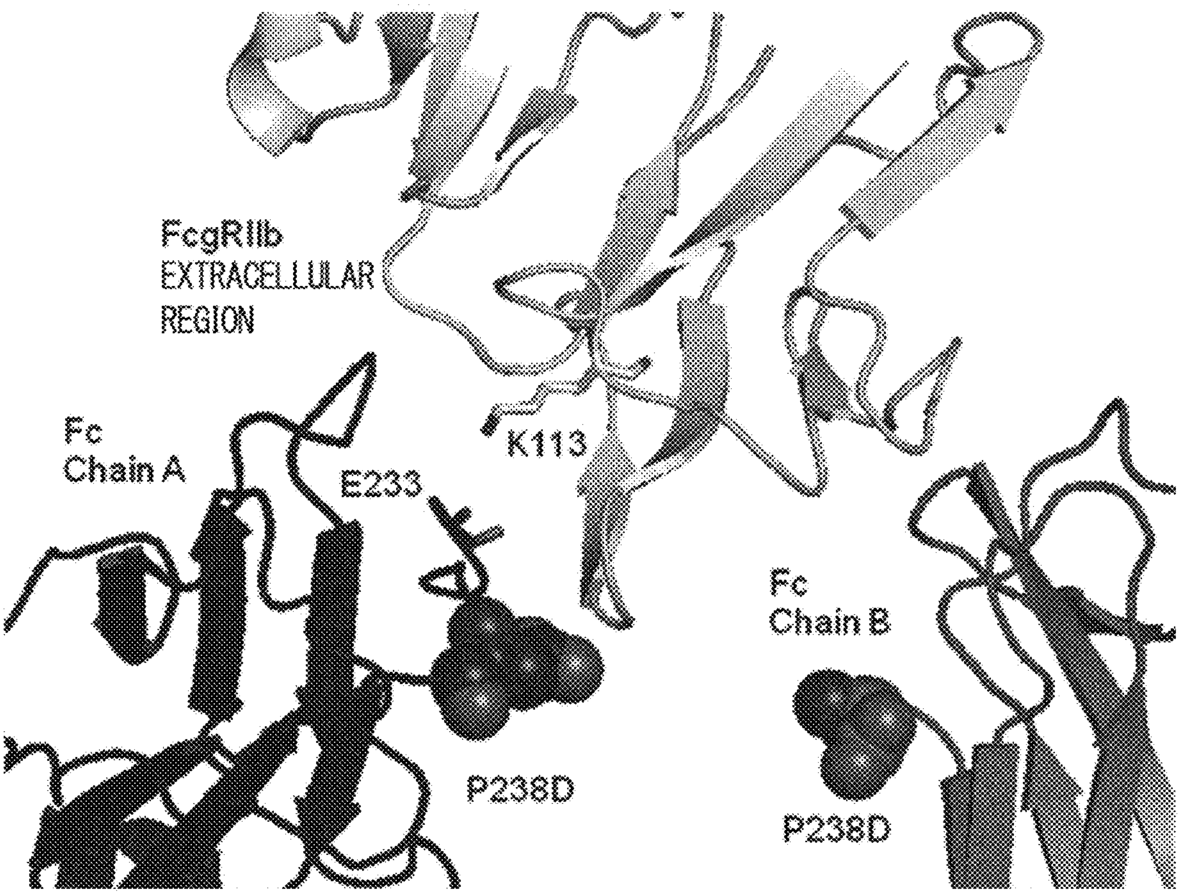
FIG. 41 shows Glu at position 233 (EU numbering) in Fc Chain A and the surrounding residues in the extracellular region of FcγRIIb in the crystal structure of the Fc (P238D)/FcγRIIb extracellular region complex.

With regard to the promising variants among the obtained combination variants, the factors leading to their effects were studied using the crystal structure. FIG. 41 shows the crystal structure of the Fc (P238D)/FcγRIIb extracellular region complex. In this figure, the H chain positioned on the left side is Fc Chain A, and the H chain positioned on the right side is Fc Chain B. Here, one can see that the site at position 233 (EU numbering) in Fc Chain A is located near Lys at position 113 of FcγRIIb. However, in this crystal structure, the E233 side chain is in a condition of considerably high mobility, and its electron density is not well observed. Therefore, the alteration produced by substituting Glu at position 233 (EU numbering) with Asp leads to decrease in the degree of freedom of the side chain since the side chain becomes one carbon shorter. As a result, the entropy loss when forming an interaction with Lys at position 113 of FcγRIIb may be decreased, and consequently this is speculated to contribute to improvement of binding free energy.

Figure 42:
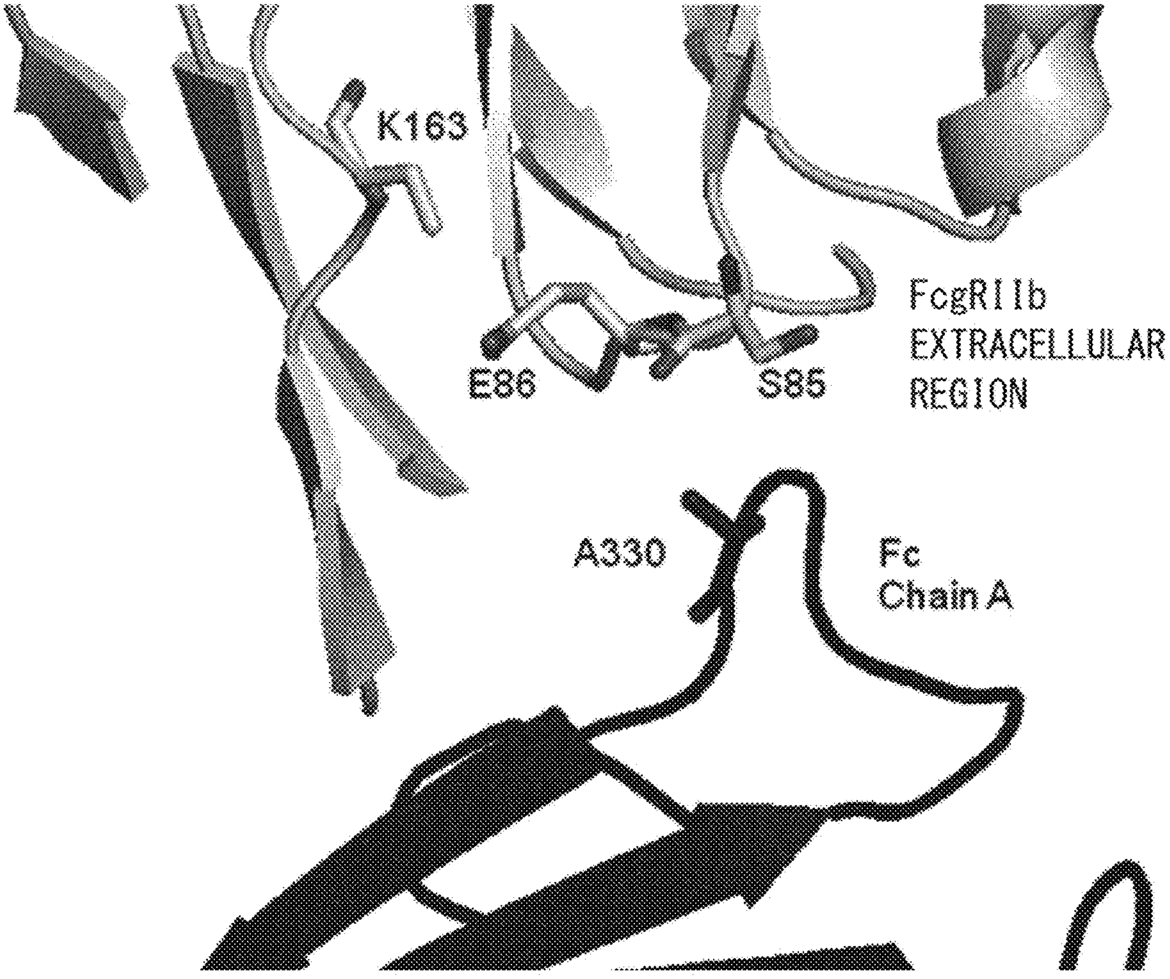
FIG. 42 shows Ala at position 330 (EU numbering) in Fc Chain A and the surrounding residues in the extracellular region of FcγRIIb in the crystal structure of the Fc (P238D)/FcγRIIb extracellular region complex.

Similarly, FIG. 42 shows the environment near the site at position 330 (EU numbering) in the structure of the Fe (P238D)/FcγRIIb extracellular region complex. This figure shows that the environment around the site at position 330 (EU numbering) of Fc Chain A of Fc (P238D) is a hydrophilic environment composed of Ser at position 85, Glu at position 86, Lys at position 163, and such of FcγRIIb. Therefore, the alteration produced by substituting Ala at position 330 (EU numbering) with Lys or Arg is speculated to contribute to strengthening the interaction with Ser at position 85 or Glu at position 86 in FcγRIIb.

Figure 43:
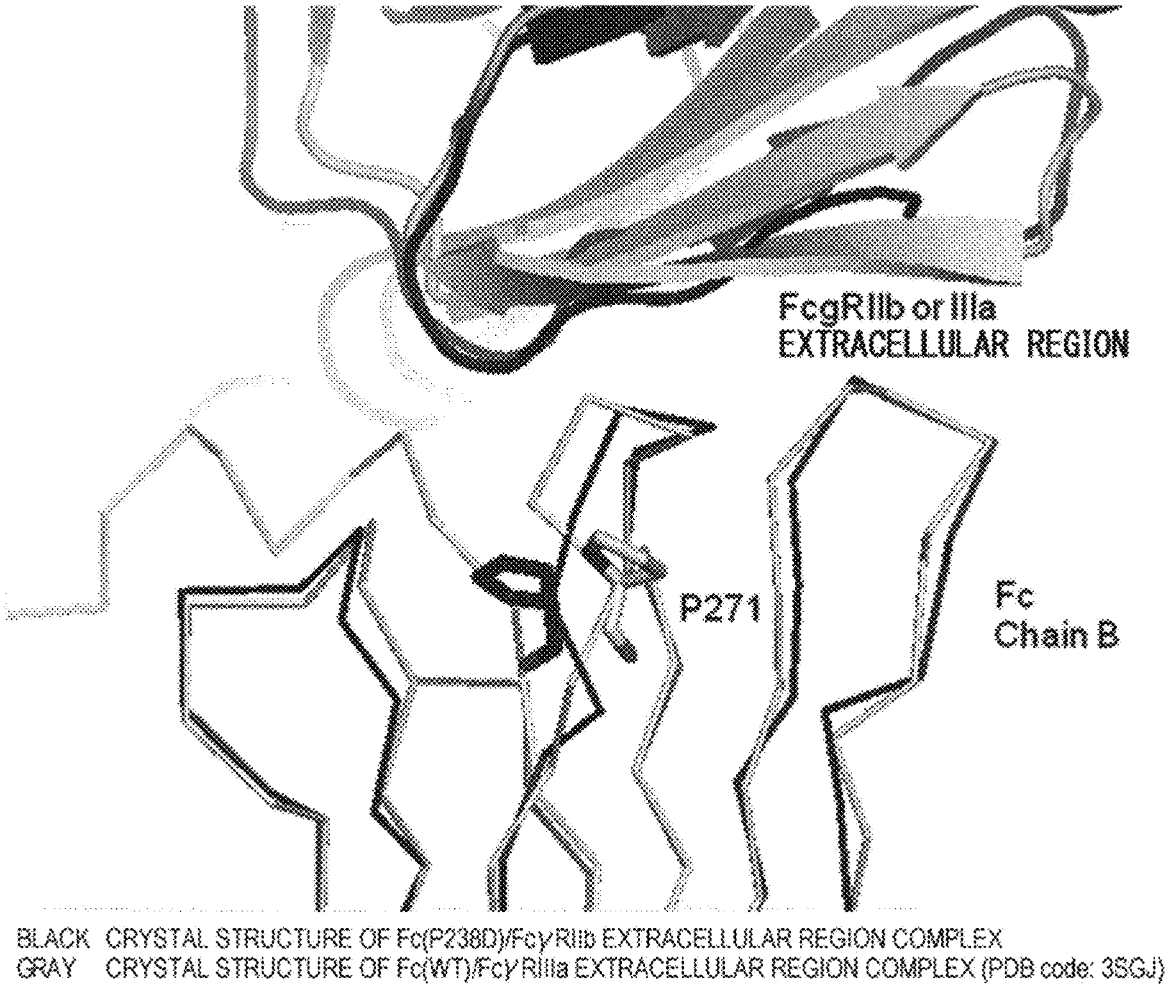
FIG. 43 shows the structures of Pro at position 271 (EU numbering) of Fc Chain B after superimposing the crystal structures of the Fc (P238D)/FcγRIIb extracellular region complex and the Fc (WT)/FcγRIIIa extracellular region complex by the least squares fitting based on the Cα atom pair distances with respect to Fc Chain B.

FIG. 43 depicts the structures of Pro at position 271 (EU numbering) of Fc Chain B after superimposing the crystal structures of the Fc (P238D)/FcγRIIb extracellular region complex and the Fc (WT)/FcγRIIIa extracellular region complex by the least squares fitting based on the Cα atom pair distances with respect to Fc Chain B. These two structures match well, but have different three-dimensional structures of Pro at position 271 (EU numbering). When the weak electron density around this area in the crystal structure of the Fc (P238D)/FcγRIIb extracellular region complex is also taken into consideration, it is suggested that there is possibility that Pro at position 271 (EU numbering) in Fc (P238D)/FcγRIIb causes a large strain on the structure, thus disturbing the loop structure to attain an optimal structure. Therefore, the alteration produced by substituting Pro at position 271 (EU numbering) with Gly is speculated to give flexibility to this loop structure, and contribute to enhancement of binding by reducing the energetic barrier for attaining an optimum structure when interacting with FcγRIIb.

[Reference Example 17] Examination of the Combinatorial Effect of Alterations that Enhance FcγRIIb Binding when Combined with P238D Of the alterations obtained in Reference Examples 14 and 16, those that showed effects of enhancing FcγRIIb binding or maintaining FcγRIIb binding and suppressing binding to other FcγRs were combined with each other, and its effect was examined.

Particularly good alterations selected from Tables 24 and 28 were introduced into the antibody H chain IL6R-BF648 in a similar manner to the method of Reference Example 16. IL6R-L was utilized as the antibody L chain, and the expressed antibodies were purified according to the method of Reference Example 1. The binding to each of the FcγRs (FcγRIa, FcγRIIa H type, FcγRIIa R type, FcγRIIb, and FcγRIIIa V type) was comprehensively evaluated by the method of Reference Example 2.

According to the following method, relative binding activities were calculated for the results of analyzing interactions with the respective FcγRs. The value for the amount of binding of each variant to each FcγR was divided by the value for the amount of binding of the pre-altered control antibody (IL6R-BF648/IL6R-L with substitution of Pro at position 238 (EU numbering) with Asp) to each FcγR, and multiplied by 100; and then the value was shown as the relative binding activity value of each van ant to each FcγR (Tables 29-1 to 29-2). In the table, alteration refers to the alteration introduced into IL6R-B3 (SEQ ID NO: 164). The template used for producing IL6R-B3, IL6R-G1 d/IL6R-L, is indicated with an asterisk (*).

TABLE 29-1

| | | RELATIVE BINDING ACTIVITY | | | | |
|---|---|---|---|---|---|---|
| VARIANT NAME | ALTERATION | FcgRIa | FcgRIIaR | FcgRIIaH | FcgRIIb | FcgRIIIaV |
| IL6R-G1d/IL6R-L | * | 140 | 650 | 1670 | 52 | 3348 |
| IL6R-B3/IL6R-L | | 145 | 625 | 1601 | 58 | 3264 |
| IL6R-BF648/IL6R-L | P238D | 100 | 100 | 100 | 100 | 100 |
| IL6R-2B253/IL6R-L | E233D/P238D/V323M | 155 | 288 | 207 | 156 | 126 |
| IL6R-2B261/IL6R-L | E233D/P238D/Y296D | 100 | 94 | 91 | 115 | 87 |
| IL6R-BP082/IL6R-L | E233D/P238D/A330K | 74 | 126 | 106 | 136 | 87 |
| IL6R-BP083/IL6R-L | P238D/Y296D/A330K | 50 | 87 | 91 | 122 | 107 |
| IL6R-BP084/IL6R-L | P238D/V323M/A330K | 109 | 203 | 162 | 141 | 106 |
| IL6R-BP085/IL6R-L | G237D/P238D/A330K | 19 | 279 | 158 | 152 | 104 |
| IL6R-BP086/IL6R-L | P238D/K326A/A330K | 72 | 155 | 116 | 137 | 123 |
| IL6R-BP087/IL6R-L | L234Y/P238D/A330K | 33 | 163 | 179 | 137 | 158 |
| IL6R-BP088/IL6R-L | G237D/P238D/K326A/A330K | 25 | 377 | 166 | 161 | 122 |
| IL6R-BP089/IL6R-L | L234Y/P238D/K326A/A330K | 43 | 222 | 186 | 147 | 136 |
| IL6R-BP129/IL6R-L | E233D/P238D/Y296D/A330K | 68 | 111 | 98 | 138 | 95 |
| IL6R-BP130/IL6R-L | E233D/P238D/V323M/A330K | 104 | 272 | 224 | 160 | 115 |
| IL6R-BP131/IL6R-L | E233D/G237D/P238D/A330K | 33 | 364 | 253 | 160 | 118 |
| IL6R-BP132/IL6R-L | E233D/P238D/K326A/A330K | 91 | 191 | 130 | 150 | 120 |
| IL6R-BP133/IL6R-L | E233D/L234Y/P238D/A330K | 41 | 174 | 151 | 137 | 114 |
| IL6R-BP143/IL6R-L | L234Y/P238D/K326A | 86 | 238 | 143 | 133 | 114 |
| IL6R-BP144/IL6R-L | G237D/P238D/K326A | 64 | 204 | 108 | 121 | 128 |
| IL6R-BP145/IL6R-L | L234Y/G237D/P238D | 41 | 350 | 224 | 152 | 153 |
| IL6R-BP146/IL6R-L | L234Y/G237D/P238D/K326A | 50 | 445 | 203 | 156 | 180 |
| IL6R-BP147/IL6R-L | L234Y/G237D/P238D/K326A/A330K | 24 | 650 | 582 | 177 | 209 |
| IL6R-BP148/IL6R-L | E233D/L234Y/G237D/P238D/K326A/A330K | 33 | 603 | 462 | 176 | 227 |
| IL6R-BP149/IL6R-L | E233D/L234Y/G237D/P238D/Y296D/K326A/A330K | 29 | 539 | 401 | 173 | 186 |
| IL6R-BP150/IL6R-L | L234Y/G237D/P238D/K326A/A330R | 30 | 757 | 770 | 183 | 204 |
| IL6R-BP151/IL6R-L | E233D/L234Y/G237D/P238D/K326A/A330R | 39 | 705 | 621 | 180 | 221 |
| IL6R-BP152/IL6R-L | E233D/L234Y/G237D/P238D/Y296D/K326A/A330R | 34 | 638 | 548 | 178 | 146 |
| IL6R-BP176/IL6R-L | E233D/P238D/K326D/A330K | 102 | 201 | 128 | 147 | 131 |
| IL6R-BP177/IL6R-L | E233D/L234Y/G237D/P238D/P271G/K326D/A330K | 57 | 691 | 409 | 177 | 186 |
| IL6R-BP178/IL6R-L | E233D/G237D/P238D/P271G/A330K | 51 | 653 | 259 | 179 | 110 |
| IL6R-BP179/IL6R-L | G237D/P238D/P271G/K326A/A330K | 39 | 570 | 226 | 177 | 125 |
| IL6R-BP180/IL6R-L | G237D/P238D/P271G/A330K | 29 | 602 | 203 | 179 | 100 |
| IL6R-BP181/IL6R-L | E233D/P238D/P271G/K326A/A330K | 108 | 362 | 150 | 170 | 122 |

Table 29-2 is a continuation table of Table 29-1.

TABLE 29-2

| | | | | | | |
|---|---|---|---|---|---|---|
| IL6R-BP181/IL6R-L | E233D/P238D/P271G/K326A/A330K | 108 | 362 | 150 | 170 | 122 |
| IL6R-BP182/IL6R-L | E233D/P238D/P271G/Y296D/A330K | 95 | 413 | 139 | 173 | 120 |

TABLE 29-2-continued

| | | | | | | |
|---|---|---|---|---|---|---|
| IL6R-BP183/IL6R-L | E233D/L234Y/P238D/P271G/K326A/A330K | 83 | 423 | 191 | 164 | 113 |
| IL6R-BP184/IL6R-L | E233D/P236D/P271G/A330K | 96 | 436 | 131 | 171 | 106 |
| IL6R-BP185/IL6R-L | E233D/L234Y/G237D/P238D/P271G/K326A/A330K | 47 | 670 | 446 | 179 | 191 |
| IL6R-BP186/IL6R-L | E233D/L234Y/G237D/P238D/P271G/Y296D/K326A/A330K | 43 | 614 | 363 | 175 | 143 |
| IL6R-BP187/IL6R-L | L234Y/P238D/P271G/K326A/A330K | 68 | 387 | 205 | 157 | 124 |
| IL6R-BP188/IL6R-L | E233D/G237D/P238D/H268D/P271G/A330K | 74 | 636 | 234 | 179 | 121 |
| IL6R-BP189/IL6R-L | G237D/P238D/H268D/P271G/K326A/A330K | 56 | 557 | 183 | 177 | 141 |
| IL6R-BP190/IL6R-L | G237D/P238D/H268D/P271G/A330K | 50 | 615 | 224 | 181 | 155 |
| IL6R-BP191/IL6R-L | E233D/P238D/H268D/P271G/K326A/A330K | 125 | 382 | 145 | 170 | 142 |
| IL6R-BP192/IL6R-L | E233D/P238D/H268D/P271G/Y296D/A330K | 109 | 406 | 122 | 172 | 118 |
| IL6R-BP193/IL6R-L | E233D/P238D/H268D/P271G/A330K | 113 | 449 | 154 | 173 | 135 |
| IL6R-BP194/IL6R-L | E233D/L234Y/G237D/P238D/H268D/P271G/K326A/A330K | 69 | 672 | 395 | 178 | 249 |
| IL6R-BP195/IL6R-L | E233D/L234Y/G237D/P238D/H268D/P271G/Y296D/K326A/A330K | 66 | 661 | 344 | 181 | 221 |
| IL6R-BP196/IL6R-L | L234Y/P238D/H268D/P271G/K326A/A330K | 89 | 402 | 195 | 157 | 137 |
| IL6R-BP197/IL6R-L | E233D/L234Y/G237D/P238D/H268D/P271G/Y296D/K326D/A330K | 71 | 642 | 294 | 179 | 206 |
| IL6R-BP198/IL6R-L | E233D/L234Y/P238D/H268D/P271G/K326A/A330K | 104 | 449 | 188 | 164 | 157 |
| IL6R-BP199/IL6R-L | E233D/P238D/K326D/A330K | 112 | 172 | 116 | 144 | 103 |
| IL6R-BP200/IL6R-L | E233D/L234Y/G237D/P238D/P271G/K326A/A330R | 60 | 754 | 517 | 188 | 164 |
| IL6R-BP201/IL6R-L | E233D/G237D/P238D/P271G/A330R | 57 | 696 | 359 | 186 | 121 |
| IL6R-BP202/IL6R-L | G237D/P238D/P271G/K326A/A330R | 43 | 615 | 285 | 185 | 108 |
| IL6R-BP203/IL6R-L | G237D/P238D/P271G/A330R | 35 | 637 | 255 | 185 | 88 |
| IL6R-BP204/IL6R-L | E233D/P238D/P271G/K326A/A330R | 110 | 301 | 137 | 165 | 121 |
| IL6R-BP205/IL6R-L | E233D/P238D/P271G/Y296D/A330R | 97 | 335 | 108 | 167 | 93 |
| IL6R-BP206/IL6R-L | E233D/P238D/P271G/A330R | 101 | 362 | 123 | 168 | 92 |
| IL6R-BP207/IL6R-L | E233D/P238D/A330R | 74 | 103 | 103 | 124 | 97 |
| IL6R-BP208/IL6R-L | E233D/G237D/P238D/H268D/P271G/A330R | 81 | 690 | 310 | 188 | 118 |
| IL6R-BP209/IL6R-L | G237D/P238D/H268D/P271G/K326A/A330R | 68 | 625 | 267 | 186 | 153 |
| IL6R-BP210/IL6R-L | G237D/P238D/H268D/P271G/A330R | 57 | 661 | 279 | 187 | 135 |
| IL6R-BP211/IL6R-L | E233D/P238D/H268D/P271G/K326A/A330R | 128 | 312 | 111 | 165 | 87 |
| IL6R-BP212/IL6R-L | E233D/P238D/H268D/P271G/Y296D/A330R | 117 | 363 | 135 | 173 | 122 |
| IL6R-BP213/IL6R-L | E233D/P238D/H268D/P271G/A330R | 118 | 382 | 123 | 169 | 100 |
| IL6R-BP214/IL6R-L | E233D/L234Y/G237D/P238D/Y296D/K326D/A330K | 36 | 498 | 285 | 174 | 165 |

The results of measuring KD values of the variants shown in Tables 29-1 and 29-2 for FcγRIa, FcγRIIaR, FcγRIIaH, FcγRIIb, and FcγRIIIaV by the method of Reference Example 2 are summarized in Tables 30-1 and 30-2. In the table, alteration refers to the alteration introduced into IL6R-B3 (SEQ ID NO: 164). The template used for producing IL6R-B3, IL6R-G1d/IL6R-L, is indicated with an asterisk (*). Furthermore, KD (IIaR)/KD (IIb) and KD (IIaH)/KD (IIb) in the table respectively represent the value obtained by dividing the KD value of the variant for FcγRIIaR by the KD value of the variant for FcγRIIb, and the value obtained by dividing the KD value of the variant for FcγRIIaH by the KD value of each variant for FcγRIIb. KD (IIb) of the parent polypeptide/KD (IIb) of the altered polypeptide refers to the value obtained by dividing the KD value of the parent polypeptide for FcγRIIb by the KD value of each variant for FcγRIIb. In addition, the KD value for the stronger of the FcγRIIaR- and FcγRIIaH-binding activities of each variant/KD value for the stronger of the FcγRIIaR- and FcγRIIaH-binding activities of the parent polypeptide are shown in Tables 30-1 and 30-2. Here, parent polypeptide refers to the variant which has IL6R-B3 (SEQ ID NO: 164) as the H chain. For some variants, the binding of FcγR to IgG was too weak to analyze accurately by kinetic analysis, and thus the cells with bolded, italicized numerals in Tables 30-1 and 30-2 show values calculated by using Equation 2 of Reference Example 2.

$$KD=C\cdot R_{max}/(R_{eq}-RI)-C \qquad \text{[Equation 2]}$$

Tables 30-1 and 30-2 show that in comparison with IL6R-B3, all variants showed improvement of affinity for FcγRIIb, and the range of improvement was 3.0 fold to 99.0 fold. The ratio of KD value of each variant for FcγRIIaR/KD value of each variant for FcγRIIb, and the ratio of KD value of each variant for FcγRIIaH/KD value of each variant for FcγRIIb represent an FcγRIIb-binding activity relative to the FcγRIIaR-binding activity and FcγRIIaH-binding activity, respectively. That is, those values show the degree of binding selectivity of each variant for FcγRIIb, and a greater value indicates a higher binding selectivity for FcγRIIb. Since the ratio of KD value for FcγRIIaR/KD value for FcγRIIb, and the ratio of KD value for FcγRIIaH/KD value for FcγRIIb of the parent polypeptide IL6R-B3/IL6R-L were 0.3 and 0.2, respectively, all variants in Tables 30-1 and 30-2 showed improvement of binding selectivity for FcγRIIb in comparison with the parent polypeptide. When the KD value for the stronger of the FcγRIIaR- and FcγRIIaH-binding activities of a variant/KD value for the stronger of the FcγRIIaR- and FcγRIIaH-binding activities of the parent polypeptide is 1 or more, this means that the stronger of the FcγRIIaR- and FcγRIIaH-binding activities of a variant has equivalent or decreased binding compared with the binding by the stronger of the FcγRIIaR- and FcγRIIaH-binding activities of the parent polypeptide. Since this value was 0.7 to 29.9 for the variants obtained this time, one may say that binding by the stronger of the FcγRIIaR- and FcγRIIaH-binding activities of the variants obtained this time was nearly equivalent or decreased compared with that of the parent polypeptide. These results showed that compared with the parent polypeptide, the variants obtained this time have maintained or decreased FcγRIIa type R- and type H-binding activities, enhanced FcγRIIb-binding activity, and improved selectivity for FcγRIIb. Furthermore, compared with IL6R-B3, all variants had lower affinity for FcγRIa and FcγRIIIaV.

TABLE 30-1

| VARIANT NAME | ALTERATION | KD (mol/L) FcγRIa | FcγRIIaR | FcγRIIaH | FcγRIIb | FcγRIIIaV | KD (IIaR)/ KD (IIb) | KD (IIaH)/ KD (IIb) | KD (IIb) OF THE PARENT POLYPEPTIDE/ KD (IIb) OF ALTERED POLYPEPTIDE | KD VALUE FOR THE STRONGER OF THE FcγRIIaR- FcγRIIaH-BINDING AND ACTIVITIES OF THE VARIANT/KD VALUE FOR THE STRONGER OF THE FcγRIIaR- AND FcγRIIaH- BINDING ACTIVITIES OF THE PARENT POLYPEPTIDE |
|---|---|---|---|---|---|---|---|---|---|---|
| IL6R-G1d/IL6R-L | | 3.2E−10 | 1.0E−06 | 6.7E−07 | 2.6E−06 | 3.5E−07 | 0.4 | 0.3 | 1.2 | 0.9 |
| IL6R-B3/IL6R-L | | 4.2E−10 | 1.1E−06 | 7.7E−07 | 3.1E−06 | 3.3E−07 | 0.3 | 0.2 | 1.0 | 1.0 |
| IL6R-BP648/IL6R-L | P238D | 1.1E−08 | 1.5E−06 | **4.0E-05** | 1.2E−06 | **7.1E-05** | 13.0 | 33.9 | 2.5 | 19.9 |
| IL6R-2B253/IL6R-L | E233D/P238D/V323M | 1.4E−09 | 5.0E−06 | **1.3E-05** | 4.5E−07 | **5.0E-05** | 11.5 | 30.1 | 7.2 | 6.5 |
| IL6R-2B261/IL6R-L | E233D/P238D/Y296D | 9.0E−09 | 2.2E−06 | **3.3E-05** | 1.0E−06 | **7.3E-05** | 21.8 | 32.4 | 3.0 | 28.8 |
| IL6R-BP082/IL6R-L | E233D/P238D/A330K | 1.8E−08 | 1.2E−05 | **1.7E-05** | 5.4E−07 | **8.1E-05** | 22.8 | 69.0 | 5.8 | 15.8 |
| IL6R-BP083/IL6R-L | P238D/Y296D/A330K | 3.8E−08 | 2.3E−05 | **4.4E-05** | 7.9E−07 | **6.6E-05** | 29.0 | 55.5 | 3.9 | 29.9 |
| IL6R-BP084/IL6R-L | P238D/V323M/A330K | 7.0E−09 | 7.2E−06 | **1.4E-05** | 5.0E−07 | **6.7E-05** | 14.3 | 47.6 | 6.1 | 9.4 |
| IL6R-BP085/IL6R-L | G237D/P238D/A330K | 2.9E−07 | 4.2E−06 | **2.4E-05** | 3.2E−07 | **6.8E-05** | 13.1 | 74.5 | 9.6 | 5.5 |
| IL6R-BP086/IL6R-L | P238D/K326A/A330K | 2.7E−08 | 9.7E−06 | **3.4E-05** | 5.7E−07 | **5.7E-05** | 17.1 | 59.9 | 5.4 | 12.6 |
| IL6R-BP087/IL6R-L | L234Y/P238D/A330K | 3.8E−08 | 9.7E−06 | **2.1E-05** | 6.1E−07 | **4.4E-05** | 16.0 | 34.7 | 5.1 | 12.6 |
| IL6R-BP088/IL6R-L | G237D/P238D/K326A/A330K | 3.9E−07 | 2.9E−06 | **2.3E-05** | 2.2E−07 | **5.7E-05** | 13.3 | 106.5 | 14.3 | 3.7 |
| IL6R-BP089/IL6R-L | L234Y/P238D/K326A/A330K | 6.3E−08 | 6.4E−06 | **2.0E-05** | 3.9E−07 | **5.1E-05** | 16.6 | 51.9 | 8.0 | 8.3 |
| IL6R-BP129/IL6R-L | E233D/P238D/Y296D/A330K | 2.5E−08 | 1.5E−05 | **4.0E-05** | 5.2E−07 | **7.5E-05** | 29.3 | 77.5 | 6.0 | 19.6 |
| IL6R-BP130/IL6R-L | E233D/P238D/V323M/A330K | 1.8E−09 | 5.3E−06 | **2.6E-05** | 3.0E−07 | **7.1E-05** | 17.5 | 85.5 | 10.2 | 6.9 |
| IL6R-BP131/IL6R-L | E233D/G237D/P238D/A330K | 1.2E−07 | 3.1E−06 | **1.4E-05** | 2.5E−07 | **5.9E-05** | 12.5 | 56.9 | 12.6 | 4.0 |
| IL6R-BP132/IL6R-L | E233D/P238D/K326A/A330K | 1.5E−08 | 8.0E−06 | **3.0E-05** | 3.7E−07 | **5.8E-05** | 21.5 | 81.1 | 8.4 | 10.3 |
| IL6R-BP133/IL6R-L | E233D/L234Y/P238D/A330K | 1.3E−07 | 8.6E−06 | **2.6E-05** | 5.6E−07 | **6.2E-05** | 15.5 | 46.8 | 5.6 | 11.2 |
| IL6R-BP143/IL6R-L | L234Y/P238D/K236A | 1.6E−08 | 5.7E−06 | **2.7E-05** | 5.7E−07 | **8.2E-05** | 10.0 | 47.1 | 5.4 | 7.5 |
| IL6R-BP144/IL6R-L | G237D/P238D/K326A | 3.7E−08 | 6.9E−06 | **3.6E-05** | 7.9E−07 | **5.5E-05** | 8.7 | 45.8 | 3.9 | 8.9 |
| IL6R-BP145/IL6R-L | L234Y/G237D/P238D | 1.2E−07 | 3.4E−06 | **1.7E-05** | 3.4E−07 | **4.5E-05** | 9.9 | 49.9 | 9.1 | 4.4 |
| IL6R-BP146/IL6R-L | L234Y/G237D/P238D/K326A | 7.4E−08 | 2.1E−06 | **1.8E-05** | 2.3E−07 | **3.9E-06** | 9.3 | 80.0 | 13.7 | 2.7 |
| IL6R-BP147/IL6R-L | L234Y/G237D/P238D/K326A/A330K | 1.4E−07 | 8.9E−07 | **5.1E-06** | 6.6E−08 | **3.3E-05** | 13.6 | 77.7 | 47.1 | 1.2 |
| IL6R-BP148/IL6R-L | E233D/L234Y/G237D/P238D/K326A/A330K | 8.9E−08 | 1.1E−06 | **7.0E-06** | 7.5E−08 | **3.0E-05** | 14.5 | 93.8 | 41.4 | 1.4 |
| IL6R-BP149/IL6R-L | E233D/L234Y/G237D/P238D/Y296D/K326A/A330K | 1.2E−07 | 1.4E−06 | **8.4E-06** | 9.3E−08 | **3.7E-05** | 15.0 | 89.9 | 33.1 | 1.8 |
| IL6R-BP150/IL6R-L | L234Y/G237D/P238D/K326A/A330K | 3.2E−07 | 5.5E−07 | **3.4E-06** | 3.1E−08 | **1.4E-05** | 17.7 | 109.0 | 99.0 | 0.7 |
| IL6R-BP151/IL6R-L | E233D/L234Y/G237D/P238D/K326A/A330K | 8.4E−08 | 6.7E−07 | **4.7E-06** | 4.0E−08 | **3.1E-05** | 16.9 | 117.8 | 77.4 | 0.9 |
| IL6R-BP152/IL6R-L | E233D/L234Y/G237D/P238D/Y296D/K326A/A330K | 7.3E−08 | 8.1E−07 | **5.6E-06** | 4.1E−08 | **4.8E-05** | 19.5 | 135.9 | 75.0 | 1.0 |
| IL6R-BP176/IL6R-L | E233D/P238D/K326D/A330K | 7.3E−09 | 6.9E−06 | **3.0E-05** | 3.6E−07 | **5.4E-05** | 19.1 | 83.1 | 8.6 | 8.9 |
| IL6R-BP177/IL6R-L | E233D/L234Y/G237D/P238D/P271G/K326D/A330K | 3.3E−08 | 7.1E−07 | **9.2E-06** | 5.2E−08 | **3.7E-05** | 13.8 | 159.2 | 60.0 | 0.9 |
| IL6R-BP178/IL6R-L | E233D/G237D/P238D/P271G/A330K | 4.3E−08 | 9.3E−07 | **1.4E-05** | 5.1E−08 | **6.3E-05** | 18.1 | 272.4 | 60.1 | 1.2 |
| IL6R-BP179/IL6R-L | G237D/P238D/P271G/K326A/A330K | 6.4E−08 | 1.4E−06 | **1.6E-05** | 8.4E−05 | **5.6E-05** | 16.7 | 190.9 | 36.9 | 1.8 |
| IL6R-BP180/IL6R-L | G237D/P238D/P271G/A330K | 9.8E−08 | 1.2E−06 | **1.6E-05** | 6.2E−08 | **7.0E-05** | 18.6 | 190.8 | 49.9 | 1.5 |
| IL6R-BP181/IL6R-L | E233D/P238D/P271G/K326A/A330K | 7.5E−09 | 3.2E−06 | **2.6E-06** | 1.6E−07 | **5.7E-05** | 20.3 | 162.5 | 19.3 | 4.2 |
| IL6R-BP182/IL6R-L | E233D/P238D/P271G/Y296D/A330K | 1.0E−08 | 2.6E−06 | **2.8E-05** | 1.1E−07 | **5.9E-05** | 23.5 | 256.9 | 28.3 | 3.3 |

Table 30-2 is a continuation table of Table 30-1.

TABLE 30-2

| | | | | | | | | | | |
|---|---|---|---|---|---|---|---|---|---|---|
| IL6R-BP183/IL6R-L | E233D/L234Y/P238D/P271G/K326A/A330K | 1.7E−08 | 2.6E−06 | ***1.5E-05*** | 2.4E−07 | ***5.6E-05*** | 10.7 | 62.5 | 12.9 | 3.3 |
| IL6R-BP184/IL6R-L | E233D/P238D/P271G/A330K | 1.1E−08 | 2.3E−06 | ***3.0E-05*** | 1.3E−07 | ***5.6E-05*** | 18.2 | 238.1 | 24.5 | 3.0 |
| IL6R-BP185/IL6R-L | E233D/L234Y/G237D/P238D/P271G/K326A/A330K | 6.3E−08 | 8.8E−07 | ***7.3E-06*** | 6.9E−08 | ***3.6E-05*** | 12.6 | 105.2 | 44.5 | 1.1 |
| IL6R-BP186/IL6R-L | E233D/L234Y/G237D/P238D/P271G/Y296D/K326A/A330K | 4.5E−08 | 9.6E−07 | ***9.3E-06*** | 6.1E−08 | ***4.9E-05*** | 15.8 | 152.5 | 50.7 | 1.3 |
| IL6R-BP187/IL6R-L | L234Y/P238D/P271G/K326A/A330K | 2.5E−08 | 2.8E−06 | ***1.8E-05*** | 2.9E−07 | ***5.6E-05*** | 9.7 | 62.3 | 10.7 | 3.6 |
| IL6R-BP188/IL6R-L | E233D/G237D/P238D/H268D/P271G/A330K | 2.1E−08 | 1.0E−06 | ***1.6E-05*** | 4.6E−08 | ***5.8E-05*** | 21.9 | 350.1 | 67.6 | 1.3 |
| IL6R-BP189/IL6R-L | G237D/P238D/H268D/P271G/K326A/A330K | 4.2E−08 | 1.4E−06 | ***2.1E-05*** | 7.4E−08 | ***4.9E-05*** | 18.5 | 283.8 | 41.8 | 1.8 |
| IL6R-BP190/IL6R-L | G237D/P238D/H268D/P271G/A330K | 6.3E−08 | 1.1E−06 | ***1.7E-05*** | 5.8E−08 | ***4.5E-05*** | 12.3 | 292.6 | 53.2 | 1.5 |
| IL6R-BP191/IL6R-L | E233D/P238D/H268D/P271G/K326A/A330K | 4.0E−09 | 3.0E−06 | ***2.7E-05*** | 1.5E−07 | ***4.9E-05*** | 20.3 | 184.9 | 21.2 | 3.8 |
| IL6R-BP192/IL6R-L | E233D/P238D/H268D/P271G/Y296D/A330K | 6.6E−09 | 2.6E−06 | ***3.2E-05*** | 1.1E−07 | ***5.9E-05*** | 23.1 | 263.2 | 27.3 | 3.4 |
| IL6R-BP193/IL6R-L | E233D/P238D/H268D/P271G/A330K | 6.3E−09 | 2.2E−06 | ***3.5E-05*** | 1.2E−07 | ***5.2E-05*** | 18.3 | 206.6 | 25.5 | 2.9 |
| IL6R-BP194/IL6R-L | L233D/L234Y/G237D/P238D/H268D/P271G/K326A/A330K | 2.4E−08 | 8.2E−07 | ***8.5E-06*** | 5.2E−08 | ***2.7E-05*** | 15.8 | 163.5 | 59.4 | 1.1 |
| IL6R-BP195/IL6R-L | E233D/L234Y/G237D/P238D/H268D/P271G/Y296D/K326A/ A330K | 2.3E−08 | 9.1E−07 | ***1.0E-05*** | 5.0E−08 | ***3.1E-05*** | 18.2 | 200.8 | 62.0 | 1.2 |
| IL6R-BP196/IL6R-L | L234Y/P238D/H268D/P271G/K326A/A330K | 1.4E−08 | 3.0E−06 | ***1.9E-05*** | 2.2E−07 | ***5.1E-05*** | 13.4 | 85.2 | 13.9 | 3.9 |
| IL6R-BP197/IL6R-L | E233D/L234Y/G237D/P238D/H268D/P271G/Y296D/K326D/ A330K | 1.9E−08 | 9.8E−07 | ***1.2E-05*** | 5.8E−08 | ***3.3E-05*** | 17.1 | 208.7 | 53.7 | 1.3 |
| IL6R-BP198/IL6R-L | E233D/L234Y/P238D/H268D/P271G/K326A/A330K | 1.1E−08 | 2.2E−06 | ***2.0E-05*** | 2.0E−07 | ***4.4E-05*** | 11.0 | 101.5 | 15.7 | 2.6 |
| IL6R-BP199/IL6R-L | E233D/P238D/K326D/A330K | 6.4E−09 | 8.6E−06 | ***2.6E-05*** | 4.9E−07 | ***6.1E-05*** | 17.5 | 53.0 | 6.3 | 11.1 |
| IL6R-BP200/IL6R-L | E233D/L234Y/G237D/P238D/P271G/K326D/A330K | 3.3E−08 | 6.3E−07 | ***4.2E-06*** | 3.4E−08 | ***3.0E-05*** | 18.6 | 123.9 | 91.2 | 0.8 |
| IL6R-BP201/IL6R-L | E233D/G237D/P238D/P271G/A330R | 5.1E−08 | 8.4E−07 | ***6.9E-06*** | 4.0E−08 | ***5.2E-05*** | 21.0 | 172.1 | 77.1 | 1.1 |
| IL6R-BP202/IL6R-L | G237D/P238D/P271G/K326A/A330K | 9.5E−08 | 1.2E−06 | ***3.7E-06*** | 6.4E−08 | ***5.9E-05*** | 19.2 | 144.0 | 48.4 | 1.6 |
| IL6R-BP203/IL6R-L | G237D/P238D/P271G/A330K | 1.8E−07 | 9.9E−07 | ***1.1E-05*** | 4.9E−08 | ***7.2E-05*** | 20.5 | 226.8 | 63.7 | 1.3 |
| IL6R-BP204/IL6R-L | E233D/P238D/P271G/K326A/A330R | 7.6E−09 | 4.5E−06 | ***2.1E-05*** | 2.5E−07 | ***5.2E-05*** | 17.6 | 82.7 | 12.2 | 5.8 |
| IL6R-BP205/IL6R-L | E233D/P238D/P271G/Y296D/A330K | 7.7E−09 | 3.5E−06 | ***2.8E-05*** | 1.6E−07 | ***6.8E-05*** | 21.8 | 176.1 | 19.4 | 4.5 |
| IL6R-BP206/IL6R-L | E233D/P238D/P271G/A330R | 8.2E−09 | 3.1E−06 | ***2.4E-05*** | 2.0E−07 | ***5.9E-05*** | 16.1 | 123.1 | 15.8 | 4.1 |
| IL6R-BP207/IL6R-L | E233D/P238D/A330R | 2.2E−08 | 1.9E−05 | ***2.9E-05*** | 8.4E−07 | ***6.5E-05*** | 23.0 | 34.5 | 3.7 | 25.1 |
| IL6R-BP208/IL6R-L | E233D/G237D/P238D/H268D/P271G/A330R | 1.9E−08 | 8.5E−07 | ***8.3E-06*** | 3.2E−08 | ***5.3E-05*** | 26.3 | 256.2 | 95.4 | 1.1 |
| IL6R-BP209/IL6R-L | G237D/P238D/H268D/P271G/K326A/A330R | 3.9E−08 | 1.2E−06 | ***1.0E-05*** | 5.1E−08 | ***4.1E-05*** | 22.7 | 195.3 | 60.4 | 1.5 |
| IL6R-BP210/IL6R-L | G237D/P238D/H268D/P271G/A330R | 6.5E−08 | 1.0E−06 | ***9.5E-06*** | 3.9E−05 | ***4.6E-05*** | 25.4 | 241.1 | 78.4 | 1.3 |
| IL6R-BP211/IL6R-L | E233D/P238D/H268D/P271G/K326A/A330R | 4.2E−09 | 4.1E−06 | ***2.7E-05*** | 2.2E−07 | ***7.3E-05*** | 18.5 | 120.5 | 13.8 | 5.4 |
| IL6R-BP212/IL6R-L | E233D/P238D/H268D/P271G/Y296D/A330R | 5.2E−09 | 3.5E−06 | ***2.2E-05*** | 1.7E−07 | ***5.2E-05*** | 21.1 | 133.3 | 18.7 | 4.5 |
| IL6R-BP213/IL6R-L | E233D/P238D/H268D/P271G/A330R | 4.1E−09 | 3.1E−06 | ***2.4E-05*** | 1.8E−07 | ***6.3E-05*** | 17.7 | 136.4 | 17.6 | 4.0 |
| IL6R-BP214/IL6R-L | E233D/L234Y/G237D/P238D/Y296D/K326D/A330R | 5.9E−08 | 1.7E−06 | ***9.2E-06*** | 1.2E−07 | ***3.9E-05*** | 14.5 | 78.0 | 26.2 | 2.2 |

[Reference Example 18] Preparation of Variants with Enhanced FcγRIIb Binding

As shown in Reference Example 13, when enhancing the FcγRIIb binding, it is preferable that the FcγRIIb binding is enhanced while maximally suppressing the binding to other activating FcγRs. Thus, the present inventors additionally produced variants with enhanced FcγRIIb binding or improved selectivity to FcγRIIb by combining alterations that enhance the FcγRIIb binding or improve the selectivity to FcγRIIb. Specifically, the alterations described in Reference Examples 14, 16, and 17 which were found to be effective when combined with alteration P238D, were combined with one another, on the basis of the P238D alteration which showed the excellent effect to enhance the FcγRIIb binding and to improve the selectivity to FcγRIIb.

Variants were produced by combining the Fc regions of IL6R-G1d (SEQ ID NO: 156) and IL6R-B3 (SEQ ID NO: 164) with alterations E233D, L234Y, G237D, S267Q, H268D, P271G, Y296D, K326D, K326A, A330R, and A330K described in Reference Examples 14, 16, and 17 which were found to be effective when combined with alteration P238D. Using IL6R-L (SEQ ID NO: 155) as the antibody L chain, antibodies comprising the above-described variants in the heavy chain were expressed and purified according to the method described in Reference Example 1. The resulting variants were respectively assessed for the binding to each FcγR (FcγRIa, FcγRIIaH, FcγRIIaR, FcγRIIb, or FcγRIIIaV) by the method described in Reference Example 2.

The KD value of each variant to each FcγR is shown in Table 31. "Alteration" refers to an alteration introduced into IL6R-B3 (SEQ ID NO: 164). IL6R-B3/IL6R-L which is used as the template to produce each variant is indicated by asterisk (*). KD (IIaR)/KD (IIb) in the table shows the value obtained by dividing the KD value of each variant for FcγRIIaR by the KD value of each variant for FcγRIIb. The greater the value, the higher the selectivity to FcγRIIb. KD (IIb) of parent polypeptide/KD (IIb) of altered polypeptide shows the value obtained by dividing the KD value of IL6R-B3/IL6R-L for FcγRIIb by the KD value of each variant for FcγRIIb. Meanwhile, KD (IIaR) of parent polypeptide/KD (IIaR) of altered polypeptide shows the value obtained by dividing the KD value of IL6R-B3/IL6R-L for FcγRIIaR by the KD value of each variant for FcγRIIaR. In Table 31, a bolded, italicized value indicates that the binding of FcγR to IgG was concluded to be too weak to analyze correctly by kinetic analysis and thus was calculated using:

$$KD = C \cdot R_{max}/(R_{eq} - RI) - C \quad \text{[Equation 2]}$$

described in Reference Example 2.

TABLE 31

| VARIANT NAME | ALTERATION | KD AGAINST FcγRIa (mol/L) | KD AGAINST FcγRIIaR (mol/L) | KD AGAINST FcγRIIaH (mol/L) | KD AGAINST FcγRIIb (mol/L) | KD AGAINST FcγRIIIaV (mol/L) | KD(IIaR)/ KD(IIb) | KD(IIb) OF PARENT POLYPEPTIDE/ KD(IIb) OF ALTERED POLYPEPTIDE | KD(IIaR) OF PARENT POLYPEPTIDE/ KD(IIaR) OF ALTERED POLYPEPTIDE |
|---|---|---|---|---|---|---|---|---|---|
| IL6R-G1d/IL6R-L | | 3.20E−10 | 1.00E−06 | 6.70E−07 | 2.60E−06 | 3.50E−07 | 0.4 | 1.2 | 1.1 |
| IL6R-B3/IL6R-L | * | 4.20E−10 | 1.10E−06 | 7.70E−07 | 3.10E−06 | 3.30E−07 | 0.3 | 1.0 | 1.0 |
| IL6R-BF648/IL6R-L | P238D | 1.10E−08 | 1.50E−05 | ***4.00E−05*** | 1.20E−06 | ***7.10E−05*** | 12.5 | 2.6 | 0.1 |
| IL6R-BP215/IL6R-L | G237D/P238D/H268D/P271G/Y296D/A330K | 4.30E−08 | 1.30E−06 | ***1.40E−05*** | 4.10E−08 | ***6.70E−05*** | 31.7 | 75.6 | 0.8 |
| IL6R-BP216/IL6R-L | G237D/P238D/S267Q/H268D/P271G/A330K | 6.20E−07 | 2.90E−06 | ***2.60E−05*** | 1.40E−07 | ***5.30E−05*** | 20.7 | 22.1 | 0.4 |
| IL6R-BP217/IL6R-L | G237D/P238D/S267Q/H268D/P271G/Y296D/A330K | 2.80E−06 | 3.60E−06 | ***2.80E−05*** | 1.50E−07 | ***6.00E−05*** | 24.0 | 20.7 | 0.3 |
| IL6R-BP218/IL6R-L | G237D/P238D/H268D/P271G/K326D/A330K | 3.70E−08 | 1.50E−06 | ***1.20E−05*** | 7.60E−08 | ***3.80E−05*** | 19.7 | 40.8 | 0.7 |
| IL6R-BP219/IL6R-L | L234Y/G273D/P238D/H268D/P271G/A330K | 4.60E−08 | 6.10E−07 | ***2.50E−06*** | 3.40E−08 | ***2.90E−05*** | 17.9 | 91.2 | 1.8 |
| IL6R-BP220/IL6R-L | E233D/G237D/P238D/H268D/P271G/Y296D/A330K | 2.00E−08 | 1.10E−06 | ***1.20E−05*** | 3.60E−08 | ***5.80E−05*** | 30.6 | 86.1 | 1.0 |
| IL6R-BP221/IL6R-L | L234Y/G237D/P238D/Y296D/K326A/A330R | 1.30E−07 | 7.10E−07 | ***2.50E−06*** | 2.80E−08 | ***4.60E−05*** | 25.4 | 110.7 | 1.5 |
| IL6R-BP222/IL6R-L | L234Y/G237D/P238D/P271G/K326A/A330R | 5.10E−08 | 7.10E−07 | ***2.60E−06*** | 3.40E−08 | ***4.70E−05*** | 20.9 | 91.2 | 1.5 |
| IL6R-BP223/IL6R-L | L234Y/G237D/P238D/H268D/P271G/K326A/A330R | 2.70E−08 | 6.00E−07 | ***2.80E−06*** | 2.50E−08 | ***3.20E−05*** | 24.0 | 124.0 | 1.8 |
| IL6R-BP224/IL6R-L | L234Y/G237D/P238D/S267Q/H268D/P271G/K326A/A330R | 6.20E−09 | 4.50E−07 | ***9.50E−06*** | 3.50E−08 | ***4.10E−05*** | 12.9 | 88.6 | 2.4 |
| IL6R-BP225/IL6R-L | L234Y/G237D/P238D/K326D/A330R | 9.50E−08 | 6.90E−07 | ***2.80E−06*** | 3.50E−08 | ***3.20E−05*** | 19.7 | 88.6 | 1.6 |
| IL6R-BP226/IL6R-L | L234Y/G237D/P238D/P271G/K326D/A330R | 5.20E−08 | 5.70E−07 | ***2.40E−06*** | 3.30E−08 | ***3.60E−05*** | 17.3 | 93.9 | 1.9 |
| IL6R-BP227/IL6R-L | L234Y/G237D/P238D/H268D/P271G/K326D/A330R | 2.70E−08 | 6.20E−07 | ***2.90E−06*** | 3.20E−08 | ***2.60E−05*** | 19.4 | 96.9 | 1.8 |
| IL6R-BP228/IL6R-L | L234Y/G237D/P238D/S257Q/H268D/P271G/K326D/A330R | 5.50E−09 | 4.20E−07 | ***1.10E−05*** | 4.00E−08 | ***3.20E−05*** | 10.5 | 77.5 | 2.6 |
| IL6R-BP229/IL6R-L | E233D/L234Y/G237D/P238D/P271G/K326A/A330R | 5.60E−08 | 8.10E−07 | ***3.30E−06*** | 4.20E−08 | ***3.70E−05*** | 19.3 | 73.8 | 1.4 |
| IL6R-BP230/IL6R-L | E233D/G237D/P238D/H268D/P271G/Y296D/A330R | 1.40E−08 | 5.70E−07 | ***9.60E−06*** | 2.10E−08 | ***6.70E−05*** | 27.1 | 147.6 | 1.9 |
| IL6R-BP231/IL6R-L | G237D/P238D/H268D/P271G/Y296D/A330R | 9.40E−09 | 7.40E−07 | ***1.10E−05*** | 2.30E−08 | ***4.00E−05*** | 32.2 | 134.8 | 1.5 |
| IL6R-BP232/IL6R-L | L234Y/G237D/P238D/P271G/K326A/A330K | 7.60E−08 | 8.40E−07 | ***3.30E−06*** | 5.60E−08 | ***4.50E−05*** | 15.0 | 55.4 | 1.3 |
| IL6R-BP233/IL6R-L | L234Y/G237D/P238D/P271G/A330K | 7.00E−08 | 6.90E−07 | ***2.80E−06*** | 3.70E−08 | ***5.10E−05*** | 18.6 | 83.8 | 1.6 |
| IL6R-BP234/IL6R-L | E233D/L234Y/G237D/P238D/S267Q/H268D/P271G/Y296D/K326D/A330K | 6.50E−09 | 1.20E−06 | ***2.00E−05*** | 1.20E−07 | ***3.10E−05*** | 10.0 | 25.8 | 0.9 |

TABLE 31-continued

| VARIANT NAME | ALTERATION | KD AGAINST FcγRIa (mol/L) | KD AGAINST FcγRIIaR (mol/L) | KD AGAINST FcγRIIaH (mol/L) | KD AGAINST FcγRIIb (mol/L) | KD AGAINST FcγRIIIaV (mol/L) | KD(IIaR)/KD(IIb) | KD(IIb) OF PARENT POLYPEPTIDE/KD(IIb) OF ALTERED POLYPEPTIDE | KD(IIaR) OF PARENT POLYPEPTIDE/KD(IIaR) OF ALTERED POLYPEPTIDE |
|---|---|---|---|---|---|---|---|---|---|
| IL6R-BP235/IL6R-L | E233D/L234Y/G237D/P238D/H268D/P271G/Y296D/K326D/A330R | 3.50E−09 | 6.80E−07 | ***7.50E−06*** | 4.40E−08 | ***2.50E−05*** | 15.5 | 70.5 | 1.6 |
| IL6R-BP236/IL6R-L | E233D/L234Y/G237D/P238D/S267Q/H268D/P271G/Y296D/K326D/A330R | 7.70E−09 | 8.40E−07 | ***1.90E−05*** | 6.50E−08 | ***3.90E−05*** | 12.9 | 47.7 | 1.3 |
| IL6R-BP237/IL6R-L | E233D/L234Y/G237D/P238D/S267Q/H268D/P271G/Y296D/K326A/A330K | 4.10E−09 | 1.10E−06 | ***1.90E−05*** | 1.00E−07 | ***3.50E−05*** | 11.0 | 31.0 | 1.0 |
| IL6R-BP238/IL6R-L | E233D/L234Y/G237D/P238D/H268D/P271G/Y296D/K326A/A330R | 2.40E−09 | 6.40E−07 | ***7.00E−06*** | 3.60E−08 | ***2.70E−05*** | 17.8 | 86.1 | 1.7 |
| IL6R-BP239/IL6R-L | E233D/L234Y/G237D/P238D/S267Q/H268D/P271G/Y296D/K326A/A330R | 7.60E−09 | 8.10E−07 | ***1.70E−05*** | 6.00E−08 | ***4.80E−05*** | 13.5 | 51.7 | 1.4 |
| IL6R-BP240/IL6R-L | E233D/G237D/P238D/S267Q/H268D/P271G/A330R | 7.60E−09 | 1.50E−06 | ***2.60E−05*** | 9.50E−08 | ***5.20E−05*** | 15.8 | 32.6 | 0.7 |
| IL6R-BP241/IL6R-L | E233D/G237D/P238D/H268D/P271G/K326D/A330R | 1.10E−09 | 6.80E−07 | ***9.00E−06*** | 4.50E−08 | ***3.10E−05*** | 15.1 | 68.9 | 1.6 |
| IL6R-BP242/IL6R-L | E233D/G237D/P238D/H268D/P271G/K326A/A330R | 1.90E−09 | 7.50E−07 | ***8.60E−06*** | 5.10E−08 | ***2.90E−05*** | 14.7 | 60.8 | 1.5 |
| IL6R-BP243/IL6R-L | E233D/L234Y/G237D/P238D/H268D/P271G/A330R | 3.00E−09 | 5.40E−07 | ***6.00E−06*** | 3.60E−08 | ***2.50E−05*** | 15.0 | 86.1 | 2.0 |
| IL6R-BP244/IL6R-L | E233D/G237D/P238D/S267Q/H268D/P271G/Y296D/A330R | 7.80E−09 | 1.80E−06 | ***2.60E−05*** | 1.10E−07 | ***4.60E−05*** | 16.4 | 28.2 | 0.6 |
| IL6R-BP245/IL6R-L | E233D/G237D/P238D/S267Q/H268D/P271G/Y296D/K326D/A330R | 6.30E−09 | 1.40E−06 | ***2.50E−05*** | 8.30E−08 | ***3.90E−05*** | 16.9 | 37.3 | 0.8 |
| IL6R-BP246/IL6R-L | E233D/G237D/P238D/S267Q/H268D/P271G/Y296D/K326A/A330R | 8.00E−09 | 1.60E−06 | ***2.30E−05*** | 9.20E−08 | ***4.40E−05*** | 17.4 | 33.7 | 0.7 |
| IL6R-BP247/IL6R-L | E233D/G237D/P238D/H268D/P271G/Y296D/K326D/A330R | 7.50E−09 | 8.10E−07 | ***1.20E−05*** | 3.70E−08 | ***4.40E−05*** | 21.9 | 83.8 | 1.4 |
| IL6R-BP248/IL6R-L | E233D/G237D/P238D/H268D/P271G/Y296D/K326A/A330R | 1.70E−09 | 8.20E−07 | ***1.10E−05*** | 3.50E−08 | ***4.40E−05*** | 23.4 | 88.6 | 1.3 |
| IL6R-BP249/IL6R-L | E233D/L234Y/G237D/P238D/H268D/P271G/Y296D/A330R | 7.00E−09 | 6.20E−07 | ***7.20E−06*** | 3.70E−08 | ***2.80E−05*** | 16.8 | 83.8 | 1.8 |

When taking the binding to each FcγR by IL6R-B3/IL6R-L resulting from introducing the K439E alteration into IL6R-G1d/IL6R-L containing the sequence of native human IgG1 as 1, the binding of IL6R-G1d/IL6R-L to FcγRIa was 1.3 times; the binding of IL6R-G1d/IL6R-L to FcγRIIaR was 1.1 times; the binding of IL6R-G1d/IL6R-L to FcγRIIaH was 1.1 times, the binding of IL6R-G1d/IL6R-L to FcγRIIb was 1.2 times, and the binding of IL6R-G1d/IL6R-L to FcγRIIIaV was 0.9 times. Thus, for any given FcγR type, the binding of IL6R-B3/IL6R-L to FcγR was comparable to the binding of IL6R-G1d/IL6R-L to FcγR. Thus, the comparison of the binding of each variant to each FcγR with that of IL6R-B3/IL6R-L prior to introduction of the alteration is assumed to be equivalent to the comparison of the binding of each variant to each FcγR with the binding to each FcγR by IL6R-G1d/IL6R-L containing the sequence of native human IgG1. For this reason, in the subsequent Examples below, the binding activity of each variant to each FcγR will be compared to the binding to each FcγR by IL6R-B3/IL6R-L prior to introduction of the alteration. Table 31 shows that all the variants have increased FcγRIIb binding activity as compared to IL6R-B3 prior to introduction of the alteration. The binding activity of IL6R-BF648/IL6R-L, which was the lowest, was increased by 2.6 times, while the binding activity of IL6R-BP230/IL6R-L, which was the highest, was increased by 147.6 times. Regarding the value of KD (IIaR)/KD (IIb) that represents the selectivity, the value for IL6R-BP234/IL6R-L, which was the lowest, was 10.0, while the value for IL6R-BP231/IL6R-L, which was the highest, was 32.2. Compared to 0.3 for IL6R-B3/IL6R-L prior to introduction of the alteration, the values imply that all the variants have improved selectivity. All the variants showed lower binding activity to FcγRIa, FcγRIIaH, and FcγRIIIaV than IL6R-B3/IL6R-L prior to introduction of the alteration.

[Reference Example 19] X-Ray Crystal Structure Analysis of the Complexes of FcγRIIb Extracellular Region or FcγRIIaR Extracellular Region and Fc Region with Enhanced FcγRIIb Binding As shown in Reference Example 18, the FcγRIIb binding of variant IL6R-BP230/IL6R-L, whose FcγRIIb binding was enhanced most, was enhanced to about 150 times as compared to IL6R-B3/IL6R-L prior to introduction of the alteration, while the enhancement of its FcγRIIaR binding was suppressed to an extent of about 1.9 times. Thus, IL6R-BP230/IL6R-L is a variant excellent in both FcγRIIb binding and selectivity. However, the present inventors sought a possibility to create more preferable variants with further enhanced FcγRIIb binding while suppressing the FcγRIIaR binding as possible.

As shown in FIG. 39 described in Reference Example 15, in the Fc region with alteration P238D, Asp at position 270 (EU numbering) in its CH2 domain B forms a tight electrostatic interaction with Arg at position 131 in FcγRIIb. This amino acid residue at position 131 is His in FcγRIIIa and FcγRIIaH, while it is Arg in FcγRIIaR like in FcγRIIb. Thus, there is no difference between FcγRIIaR and FcγRIIb in terms of the interaction of the amino acid residue at position 131 with Asp at position 270 (EU numbering) in the CH2 domain B. This is assumed to be a major factor for the poor selectivity between the FcγRIIb binding and FcγRIIaR binding of the Fc region.

On the other hand, the extracellular regions of FcγRIIa and FcγRIIb are 93% identical in amino acid sequence, and thus they share very high homology. Based on the crystal structure analysis of the complex of the Fc region of native IgG1 (hereinafter abbreviated as Fc (WT)) and the extracellular region of FcγRIIaR (J. Imunol. (2011) 187, 3208-3217), a difference found around the interface of their interaction was only three amino acids (Gln127, Leu132, Phe160) between FcγRIIaR and FcγRIIb. Thus, the present inventors predicted that it was extremely difficult to improve the selectivity of the Fc region between the FcγRIIb binding and FcγRIIaR binding.

In this context, the present inventors conceived that, in order to further enhance the FcγRIIb-binding activity of the Fc region and to improve the selectivity of its FcγRIIaR binding, it was important to clarify subtle differences between Fc region-FcγRIIb interaction and Fc region-FcγRIIaR interaction by analyzing not only the three-dimensional structure of the complex of the Fc region with enhanced FcγRIIb binding and the extracellular region of FcγRIIb but also the three-dimensional structure of the complex of the Fc region with enhanced FcγRIIb binding and the extracellular region of FcγRIIaR. First, the present inventors analyzed the X-ray crystal structure of the complex of the extracellular region of FcγRIIb or FcγRIIaR and Fc (P208) resulting from eliminating the K439E alteration from the Fc region of IL6R-BP208/IL6R-L created as described in Reference Example 17, which was the variant used as the basis in producing IL6R-BP230/IL6R-L.

(19-1) X-Ray Crystal Structure Analysis of the Complex of Fc (P208) and the Extracellular Region of FcγRIIb

[Expression and Purification of Fc (P208)]

Fc (P208) was prepared as described below. First, IL6R-P208 was produced by substituting Lys for Glu at position 439 (EU numbering) in IL6R-BP208, as is in the case of the sequence of native human IgG1. Then, the gene sequence of Fc (P208) spanning from Glu at position 216 (EU numbering) to the C terminus was cloned by PCR using as a template a DNA encoding a variant with a substitution of Ser for Cys at position 220 (EU numbering). Expression vector construction, expression, and purification were achieved according to the method described in Reference Example 1. Meanwhile, Cys at position 220 (EU numbering) in ordinary IgG1 forms a disulfide bond to a Cys in the L chain. When preparing the Fc region alone, the L chain is not coexpressed. Thus, Cys at position 220 was substituted by Ser to avoid unnecessary disulfide bond formation.

[Expression and Purification of the Extracellular Region of FcγRIIb]

The extracellular region of FcγRIIb was prepared according to the method described in Reference Example 2.

[Purification of the Fc (P208)/FcγRIIb Extracellular Region Complex]

0.15 mg of the purified product of Endo F1 (Protein Science (1996) 5, 2617-2622) expressed in *E. coli* as a fusion protein with glutathione S-transferase was added 1.5 mg of a crystallization sample of the extracellular region of FcγRIIb. This added sample in 0.1 M Bis-Tris buffer (pH 6.5) was allowed to stand at room temperature for three days to cleave off N-type sugar chains except N-acetylglucosamine directly linked to the Asn in the sample of the extracellular region of FcγRIIb. Then, the sample of the extracellular region of FcγRIIb subjected to the sugar chain cleavage treatment was concentrated with a 5000 MWCO ultrafiltration filter, and purified by chromatography with a gel filtration column (Superdex® 200 10/300 gel filtration column) equilibrated with 20 mM HEPES (pH7.5)/0.1 M NaCl. Next, Fc (P208) was added in such a way that the extracellular region of FcγRIIb is present in a slightly excessive molar ratio. After concentrating with a 10000

MWCO ultrafiltration filter, the purified fraction of the extracellular region of FcγRIIb subjected to the sugar chain cleavage was purified by chromatography with a gel filtration column (Superdex® 200 10/300 gel filtration column) equilibrated with 25 mM HEPES (pH 7.5)/0.1 M NaCl. The purified fraction prepared as described above was used as a sample of Fc (P208)/FcγRIIb extracellular region complex in the subsequent assessment.

[Crystallization of the Complex of Fc (P208)/FcγRIIb Extracellular Region]

A sample of Fc (P208)/FcγRIIb extracellular region complex concentrated to about 10 mg/ml with a 10000 MWCO ultrafiltration filter was crystallized using the hanging drop vapor diffusion method in combination with the seeding method. VDXm plate (Hampton Research) was used for crystallization. Using a reservoir solution of 0.1 M Bis-Tris (pH 6.5)/19% (w/v) PEG3350/0.2 M potassium phosphate dibasic, crystallization drops were prepared at a mixing ratio of reservoir solution: crystallization sample=0.85 μl:0.85 μl. Crystals of the complex obtained under the same condition were crushed with Seed Bead (Hampton Research) to prepare a seed crystal solution. The crystallization drops were added with 0.15 μl of a diluted solution prepared from the seed solution and allowed to stand at 20° C. in sealed reservoir wells. This yielded plate-like crystals.

[X-Ray Diffraction Data Measurements from an Fc (P208)/FcγRIIb Extracellular Region Complex Crystal]

A single crystal of Fc (P208)/FcγRIIb extracellular region complex prepared as described above was soaked into a solution of 0.1 M Bis-Tris (pH 6.5)/24% (w/v) PEG3350/0.2 M potassium phosphate dibasic/20% (v/v) ethylene glycol. Then, the single crystal was fished out of the solution using a pin with attached tiny nylon loop, and frozen in liquid nitrogen. X-ray diffraction data of the single crystal was collected with Spring-8 BL32XU. During the measurement, the crystal was constantly placed in a nitrogen stream at −178° C. to maintain in a frozen state. A total of 300 X-ray diffraction images of the single crystal were collected using CCD detector MX-225HE (RAYONIX) attached to a beam line with rotating the single crystal 0.6° at a time. Based on the obtained diffraction images, lattice constant determination, diffraction spot indexing, and diffraction data processing were performed using programs Xia2 (J. Appl. Cryst. (2010) 43, 186-190), XDS Package (Acta Cryst. (2010) D66, 125-132) and Scala (Acta Cryst. (2006) D62, 72-82). Finally, diffraction intensity data up to 2.81 Å resolution was obtained. The crystal belongs to the space group $C222_1$ with lattice constant a=156.69 Å, b=260.17 Å, c=56.85 Å, α=90°, β=90°, and γ=90°.

[X-Ray Crystal Structure Analysis of Fc (P208)/FcγRIIb Extracellular Region Complex]

The structure of Fc (P208)/FcγRIIb extracellular region complex was determined by a molecular replacement method using program Phaser (J. Appl. Cryst. (2007) 40, 658-674). The number of complexes in an asymmetrical unit was estimated to be one from the size of the obtained crystal lattice and the molecular weight of Fc (P208)/FcγRIIb extracellular region complex. The segments spanning the amino acid residues at positions 239-340 of the A chain and at positions 239-340 of the B chain, which were retrieved as an independent coordinate from the structural coordinate of PDB code: 3SGJ for the crystal structure of Fc (WT)/FcγRIIIa extracellular region complex, were used as a model for searching the CH2 domain of the Fc region. Likewise, the segments spanning the amino acid residues at positions 341-444 of the A chain and at positions 341-443 of the B chain, which were retrieved as a coordinate from the structural coordinate of PDB code: 3SGJ, were used as a model for searching the CH3 domain of the Fc region. Finally, the segment spanning the amino acid residues at positions 6-178 of the A chain, which was retrieved from the structural coordinate of PDB code: 2FCB for the crystal structure of the extracellular region of FcγRIIb, was used as a model for searching Fc (P208). The present inventors tried to determine the orientations and positions of the respective search models of the CH3 domain of the Fc region, the extracellular region of FcγRIIb, and the CH2 domain of the Fc region in the crystal lattices based on the rotation function and translation function, but failed to determine the position of one of the CH2 domains. Then, with reference to the crystal structure of the complex of Fc (WT)/FcγRIIIa extracellular region, the position of the last CH2 domain A was determined from an electron density map that was calculated based on the phase determined for the remaining three parts. Thus, the present inventors obtained an initial model for the crystal structure of the complex of Fc (P208)/FcγRIIb extracellular region. The crystallographic reliability factor R value of the structural model for the data of diffracted intensity at 25 to 3.0 Å was 42.6% and Free R value was 43.7% after rigid body refinement where the two CH2 domains and two CH3 domains of the Fc region, and the extracellular region of FcγRIIb were allowed to deviate from the obtained initial structural model. Then, structural model refinement was achieved by repeating structural refinement using program REFMAC5 (Acta Cryst. (2011) D67, 355-367) followed by revision of the structural model performed using program Coot (Acta Cryst. (2010) D66, 486-501) with reference to the electron density maps where the coefficients 2Fo-Fc and Fo-Fc were calculated using experimentally determined structural factor Fo, structural factor Fc calculated according to the structural model, and the phases calculated according to the structural model. Then, further refinement was carried out based on the electron density maps with coefficients of 2Fo-Fc and Fo-Fc by integrating water molecules into the structural model. With 27259 diffracted intensity data at 25 to 2.81 Å resolution, ultimately the crystallographic reliability factor R value was 24.5% and free R value was 28.2% for the structural model comprising 4786 non-hydrogen atoms.

Figure 44:
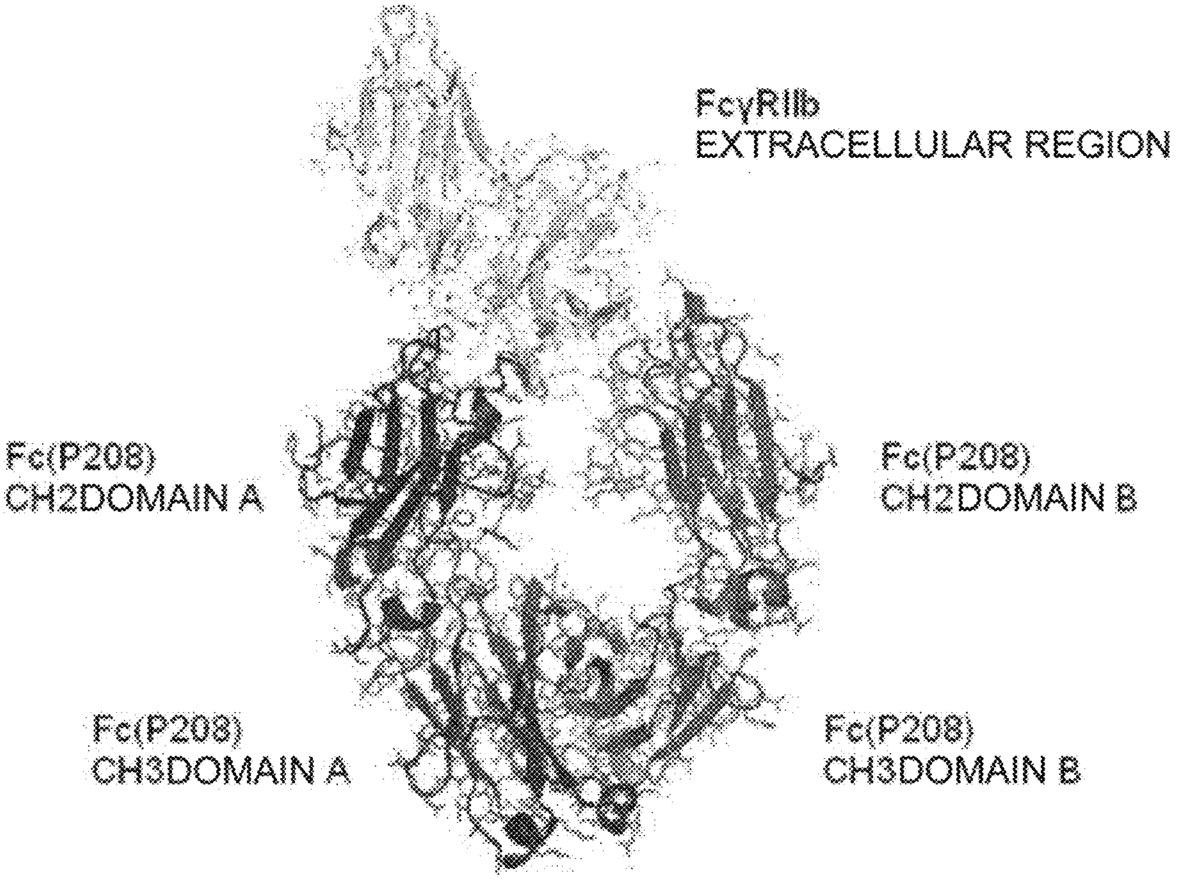
FIG. 44 shows an image of the Fc (P208)/FcγRIIb extracellular region complex determined by X-ray crystal structure analysis. For each of the CH2 and CH3 domains in the Fc portion, those on the left side are referred to as domain A and those on the right side are referred to as domain B.

The three-dimensional structure of the complex of Fc (P208)/FcγRIIb extracellular region was determined at a resolution of 2.81 Å by structure analysis. The structure obtained by the analysis is shown in FIG. 44. FcγRIIb extracellular region was revealed to be bound and sandwiched between the two CH2 domains of the Fc region, which resembles the three-dimensional structures of the previously analyzed complexes of Fc (WT), which is the Fc of native IgG, and each of the extracellular regions of FcγRIIIa (Proc. Natl. Acad. Sci. USA (2011) 108, 12669-126674), FcγRIIIb (Nature (2000) 400, 267-273; J. Biol. Chem. (2011) 276, 16469-16477), and FcγRIIa (J. Immunol. (2011) 187 (6), 3208-3217).

Figure 45:
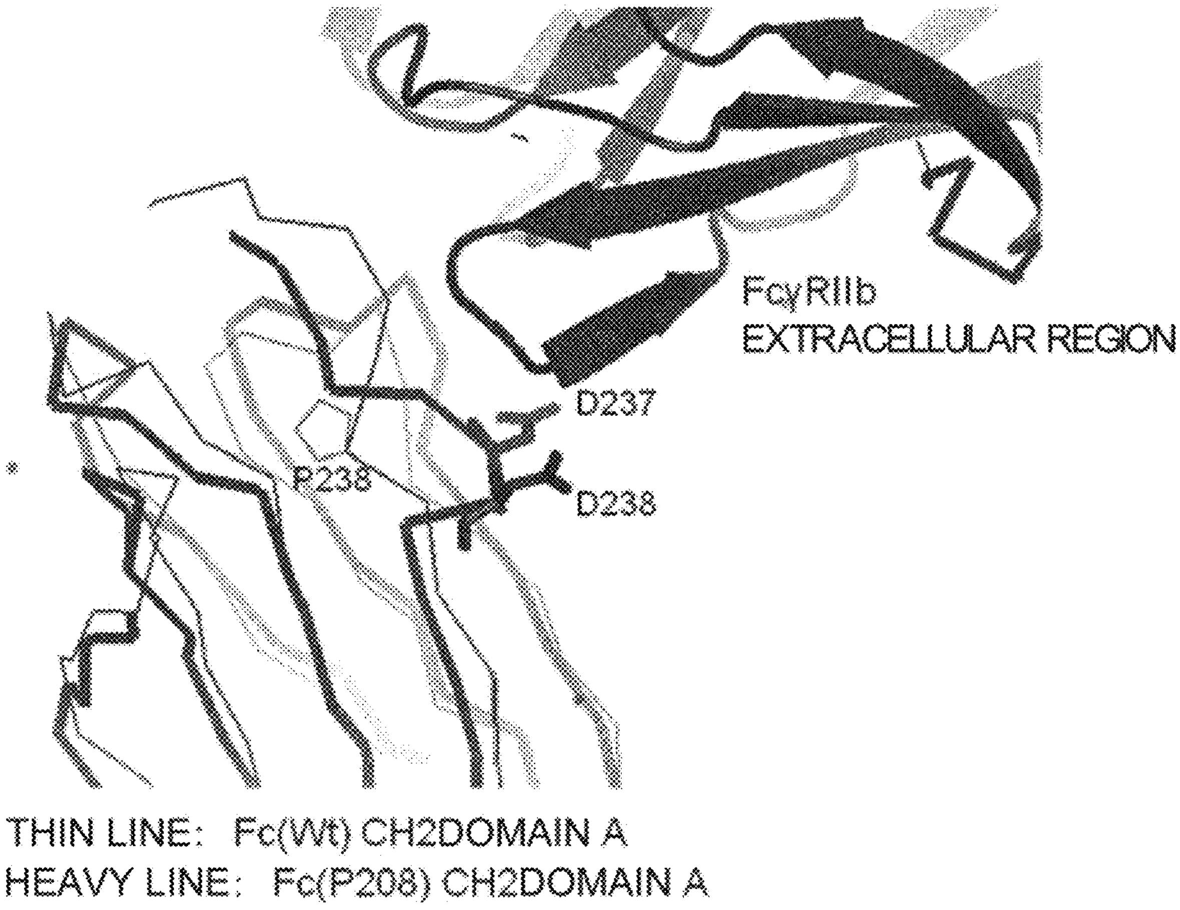
FIG. 45 shows comparison after superimposing the structures of Fc (P208)/FcγRIIb extracellular region complex and Fc (WT)/FcγRIIa extracellular region complex (PDB code: 3RY6) determined by X-ray crystal structure analysis with respect to the CH2 domain A of the Fc portion by the least squares fitting based on the Cα atom pair distances. In the diagram, the structure drawn with heavy line shows the Fc (P208)/FcγRIIb extracellular region complex, while the structure drawn with thin line indicates the structure of Fc (WT)/FcγRIIa extracellular region complex. Only the CH2 domain A of the Fc portion is drawn for the Fc (WT)/FcγRIIa extracellular region complex.
Figure 46:
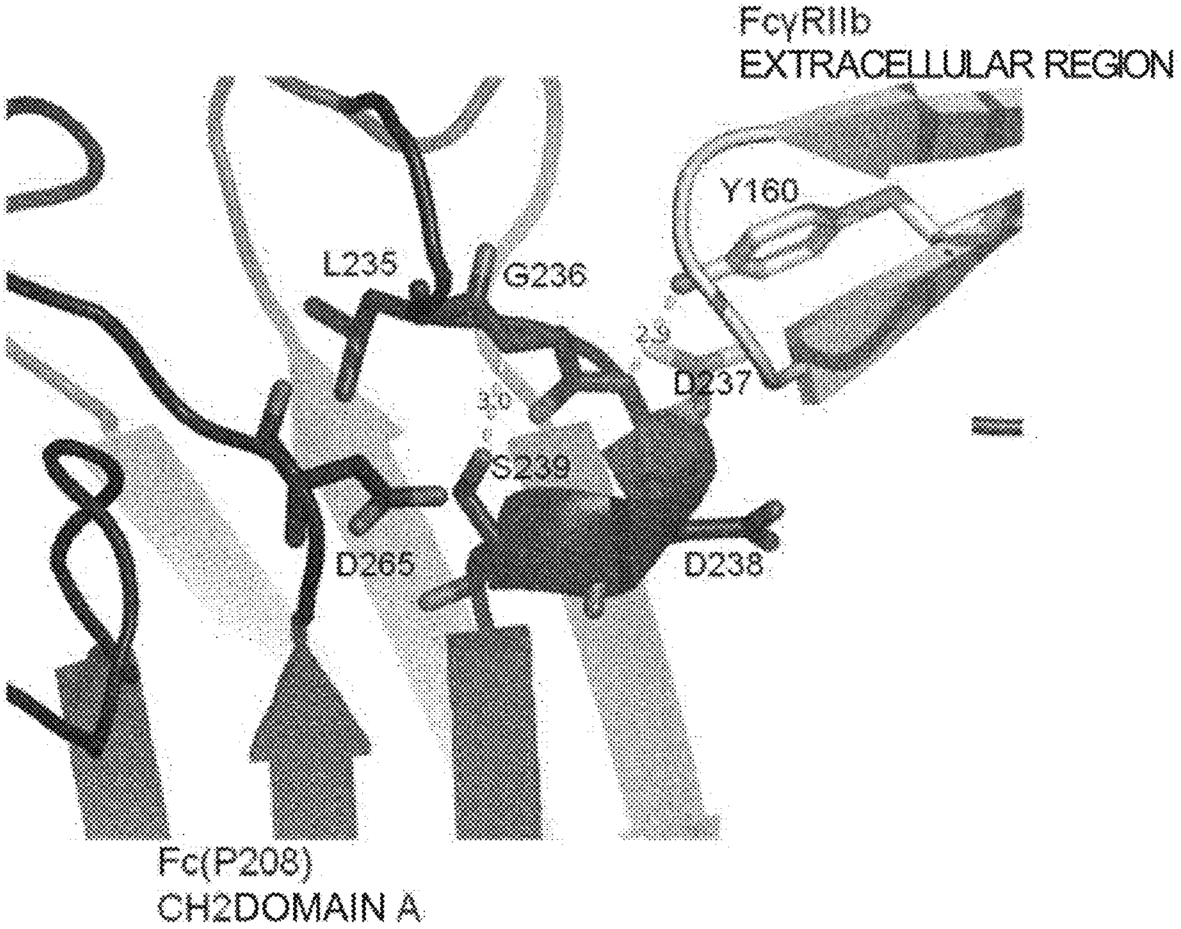
FIG. 46 shows in the X-ray crystal structure of the Fe (P208)/FcγRIIb extracellular region complex, a detailed structure around Asp at position 237 (EU numbering) in the CH2 domain A of the Fc portion, which forms a hydrogen bond with Tyr at position 160 in FcγRIIb at the main chain moiety.

A close observation of the complex of Fc (P208)/FcγRIIb extracellular region revealed a change in the loop structure at positions 233 to 239 (EU numbering) following the hinge region in the CH2 domain A of the Fc region due to an influence of the introduced the G237D and P238D alterations as compared to the complex of Fc (WT)/FcγRIIaR extracellular region (FIG. 45). This leads to that the main chain of Asp at position 237 (EU numbering) in Fc (P208) formed a tight hydrogen bond to the side chain of Tyr at position 160 in FcγRIIb (FIG. 46). In both FcγRIIaH and FcγRIIaR, the amino acid residue at position 160 is Phe, which is incapable of forming such a hydrogen bond. This suggests that the above described hydrogen bond has important contribution to the enhancement of the FcγRIIb binding and the acquisition of the FcγRIIa binding selectivity of Fc (P208), i.e., improvement of the FcγRIIb-binding activity and reduction of FcγRIIa-binding activity of Fc (P208).

Figure 47:
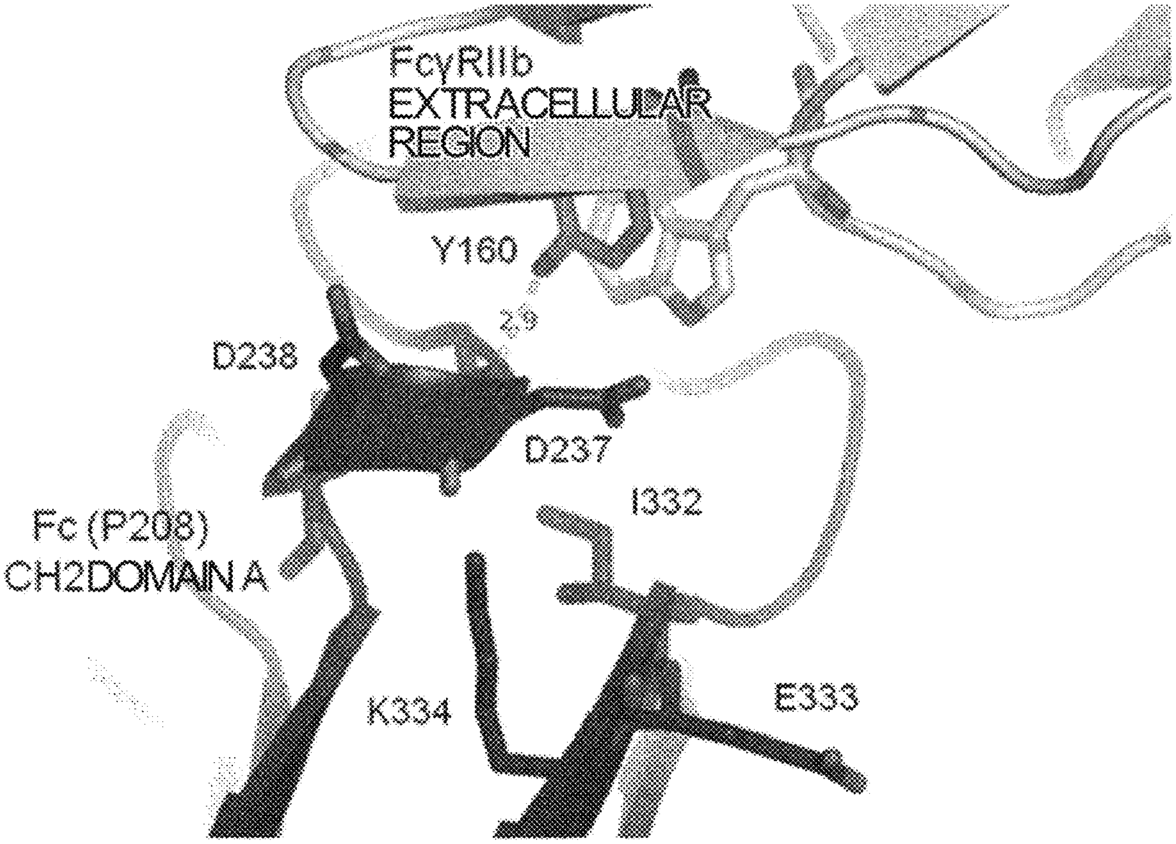
FIG. 47 shows in the X-ray crystal structure of the Fc (P208)/FcγRIIb extracellular region complex, the structure of amino acid residues around Asp at position 237 (EU numbering) in the CH2 domain A of the Fc portion, which forms a hydrogen bond with Tyr at position 160 in FcγRIIb at the main chain moiety.

On the other hand, the side chain of Asp at position 237 (EU numbering) in Fc (P208) forms neither particularly significant interaction in the FcγRIIb binding nor interaction with other residues within the Fc region. Ile at position 332, Glu at position 333, and Lys at position 334 (EU numbering) in the Fc region are located close to Asp at position 237 (EU numbering) (FIG. 47). When the amino acid residues of these positions are substituted by hydrophilic residues to form an interaction with the side chain of Asp at position 237 (EU numbering) in Fc (P208) and the loop structure can be stabilized by the interaction, this can lead to reduction of the entropic energy loss due to the hydrogen bonding between the Fc region and Tyr at position 160 in FcγRIIb and thereby to an increase in the binding free energy, i.e., an increase in the binding activity.

Figure 48:
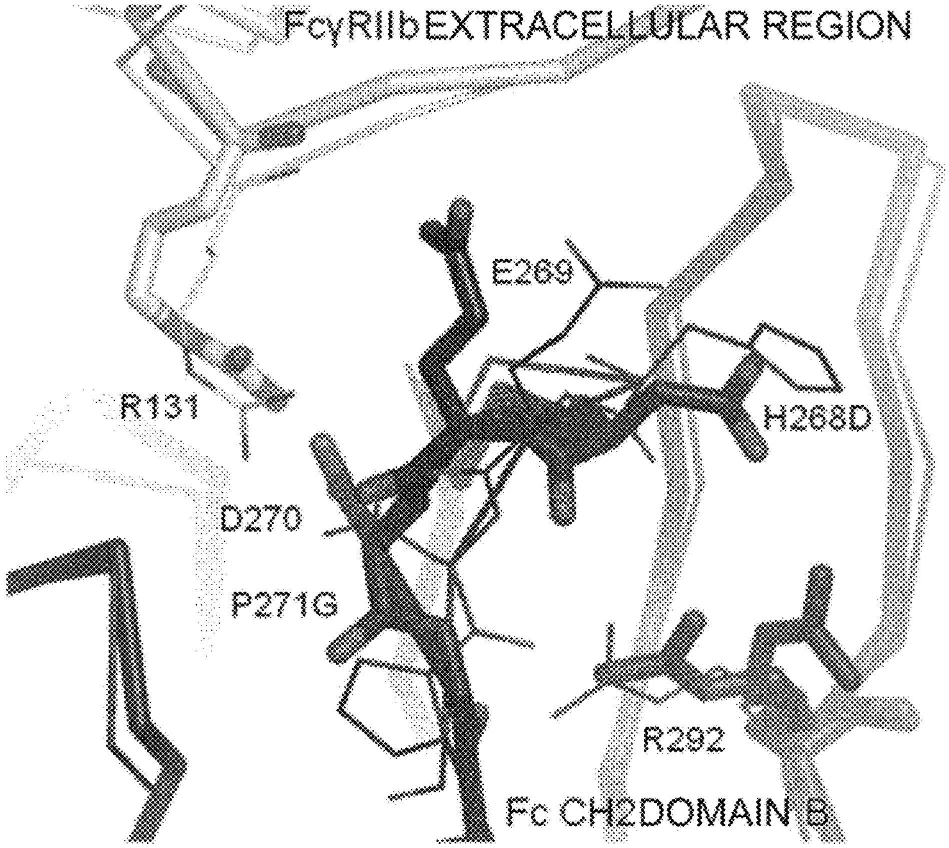
FIG. 48 shows comparison around the loop at positions 266 to 271 (EU numbering) after superimposing the X-ray crystal structure of the Fc (P238D)/FcγRIIb extracellular region complex shown in Reference Example 15 and the Fc (P208)/FcγRIIb extracellular region complex with respect to the CH2 domain B of the Fc portion by the least squares fitting based on the Cα atom pair distances. When compared to Fc (P238D), Fc (P208) has the H268D alteration at position 268 and the P271G alteration at position 271 (EU numbering) in the loop.

When the X-ray crystal structure of the complex of Fc (P238D) with the P238D alteration and FcγRIIb extracellular region described in Reference Example 15 is compared to the X-ray crystal structure of the complex of Fc (P208) and FcγRIIb extracellular region, deviations are observed at five portions in Fc (P208) as compared to Fc (P238D) and most of the changes are seen only at the side chain level. Meanwhile, a positional deviation at the main chain level due to the Pro-to-Gly alteration at position 271 (EU numbering) is also observed in the CH2 domain B of the Fc region, and in addition there is a structural change in the loop at positions 266 to 270 (EU numbering) (FIG. 48). As described in Reference Example 16, it is suggested that, when Asp at position 270 (EU numbering) in Fc (P238D) forms a tight electrostatic interaction with Arg at position 131 in FcγRIIb, the interaction can induce stereochemical stress at Pro at position 271 (EU numbering). The experiment described herein suggests that the structural change observed with the alteration to Gly for the amino acid at position 271 (EU numbering) is assumed to be a result of elimination of the structural distortion accumulated at Pro prior to the alteration and the elimination results in an increase in the free energy for the FcγRIIb binding, i.e., an increase in the binding activity.

Furthermore, it was demonstrated that, due to the change of the loop structure at positions 266 to 271 (EU numbering), Arg at position 292 (EU numbering) underwent a structural change while being in two states. In this case, the electrostatic interaction (FIG. 48) formed between Arg at position 292 (EU numbering) and Asp at position 268 (EU numbering) which is an altered residue in Fc (P208) can contribute to the stabilization of the loop structure. Since the electrostatic interaction formed between Asp at position 270 (EU numbering) in the loop and Arg at position 131 in FcγRIIb largely contribute to the binding activity of Fc (P208) to FcγRIIb, the stabilization of the loop structure in the binding conformation was likely to reduce the entropic energy loss upon binding. Thus, the alteration is expected to result in an increase in the binding free energy, i.e., an increase in the binding activity.

Figure 49:
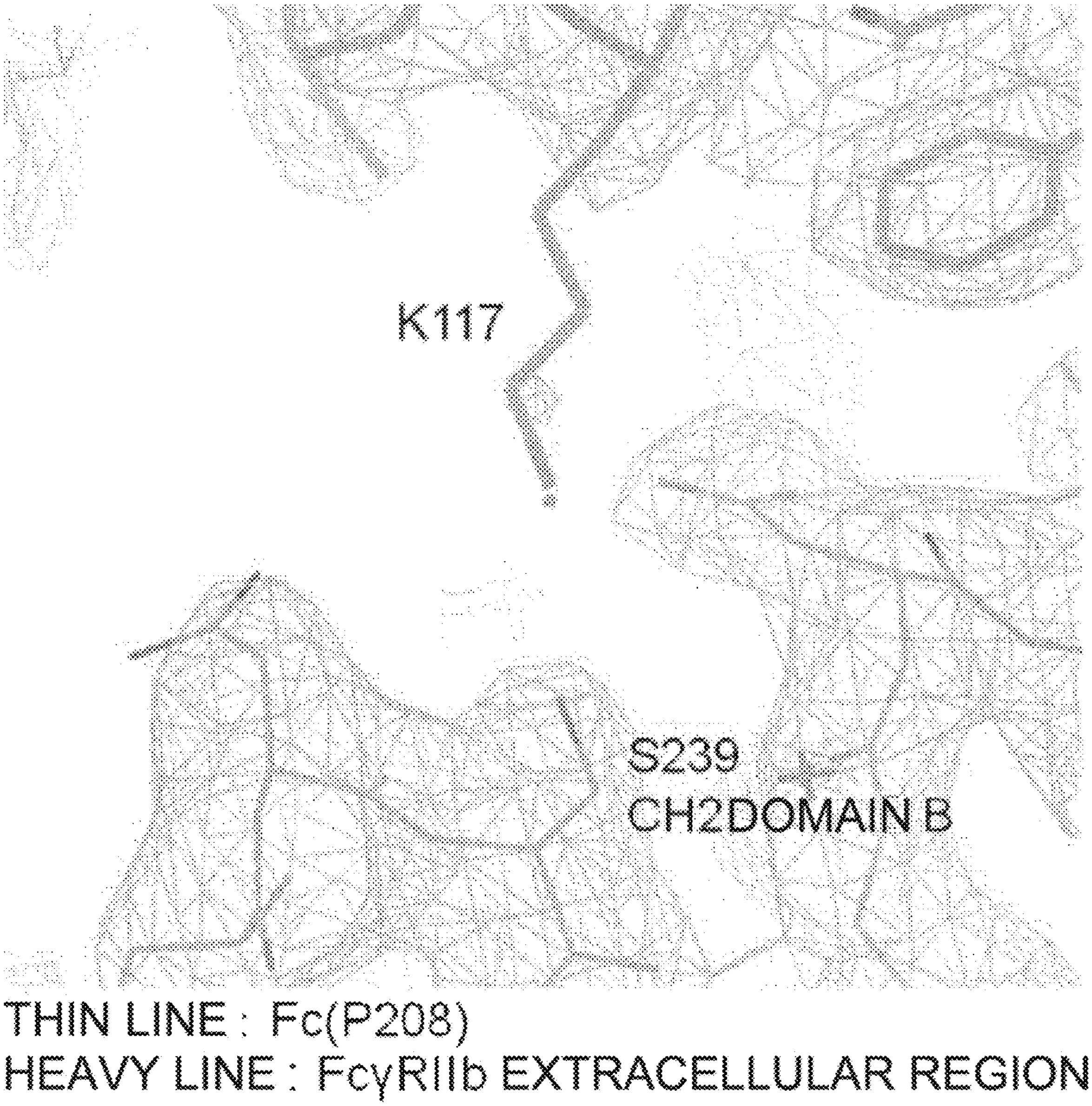
FIG. 49 is a diagram showing the structure around Ser239 in the CH2 domain B of the Fc portion in the X-ray crystal structure of the Fc (P208)/FcγRIIb extracellular region complex, along with the electron density determined by X-ray crystal structure analysis with 2Fo-Fc coefficient.

Moreover, the possibility of alteration to further increase the activity was scrutinized based on the result of structural analysis. Ser at position 239 (EU numbering) was found as a candidate for the site to introduce alteration. As shown in FIG. 49, Ser at position 239 (EU numbering) in the CH2 domain B is present at the position toward which Lys at position 117 in FcγRIIb extends most naturally in structure. However, since the electron density was not observed for Lys at position 117 in FcγRIIb by the analysis described above, the Lys has no definite structure. In this situation, Lys117 is likely to have only a limited effect on the interaction with Fc (P208). When Ser at position 239 (EU numbering) in the CH2 domain B is substituted with negatively charged Asp or Glu, such an alteration is expected to cause an electrostatic interaction with the positively charged Lys at position 117 in FcγRIIb, thereby resulting in improved FcγRIIb-binding activity.

On the other hand, an observation of the structure of Ser at position 239 (EU numbering) in the CH2 domain A revealed that, by forming a hydrogen bond to the main chain of Gly at position 236 (EU numbering), the side chain of this Ser stabilized the loop structure at positions 233 to 239, including Asp at position 237 (EU numbering) that forms a hydrogen bond to the side chain of Tyr at position 160 in FcγRIIb, following the hinge region (FIG. 46). The stabilization of the loop structure in the binding conformation can reduce the entropic energy loss upon binding, and result in an increase in the binding free energy, i.e., an improvement of the binding activity. Meanwhile, when Ser at position 239 (EU numbering) in the CH2 domain A is substituted with Asp or Glu, the loop structure can become unstable due to loss of the hydrogen bond to the main chain of Gly at position 236 (EU numbering). In addition, the alteration can result in electrostatic repulsion to Asp at position 265 (EU numbering) in close proximity, leading to further destabilization of the loop structure. The energy for the destabilization corresponds to loss of free energy for the FcγRIIb binding, which can result in reduction in the binding activity.

(19-2) X-Ray Crystal Structure Analysis of the Complex of Fc (P208) and FcγRIIaR Extracellular Region

[Expression and Purification of the Extracellular Region of FcγRIIaR]

The extracellular region of FcγRIIaR was prepared according to the method described in Reference Example 2.

[Purification of the Complex of Fc (P208)/FcγRIIaR Extracellular Region]

1.5 mg of purified sample of the extracellular region of FcγRIIaR was added with 0.15 mg of the purified product of Endo F1 (Protein Science (1996) 5, 2617-2622) expressed in *E. coli* as a fusion protein with glutathione S-transferase, 20 μl of 5 U/ml Endo F2 (QA-bio), and 20 μl of 5 U/ml Endo F3 (QA-bio). After 9 days of incubation at room temperature in 0.1 M Na acetate buffer (pH 4.5), the sample was further added with 0.07 mg of the above-described Endo F1, 7.5 μl of the above-described Endo F2, and 7.5 μl of the above-described Endo F3, and was incubated for three days to cleave off N-type sugar chains except N-acetylglucosamine directly linked to the Asn in the sample of the extracellular region of FcγRIIa R. Then, the sample of the extracellular region of FcγRIIaR concentrated with a 10000 MWCO ultrafiltration filter and subjected to the above-described sugar chain cleavage treatment was purified by chromatography with a gel filtration column (Superdex® 200 10/300 gel filtration column) equilibrated with 25 mM HEPES (pH 7)/0.1M NaCl. Next, Fc (P208) was added in such a way that the extracellular region of FcγRIIaR is present in a slightly excessive molar ratio. After concentrating with a 10000 MWCO ultrafiltration filter, the purified fraction of the extracellular region of FcγRIIaR subjected to the above-described sugar chain cleavage treatment was purified by chromatography with a gel filtration column (Superdex® 200 10/300 gel filtration column) equilibrated with 25 mM HEPES (pH 7)/0.1 M NaCl. The purified fraction prepared as described above was used as a sample of Fc (P208)/FcγRIIaR extracellular region complex in the subsequent assessment.

[Crystallization of the Complex of Fc (P208)/FcγRIIaR Extracellular Region]

A sample of Fc (P208)/FcγRIIa R extracellular region complex concentrated to about 10 mg/ml with a 10000 MWCO ultrafiltration filter was crystallized using the sitting drop vapor diffusion method. Using a reservoir solution of 0.1 M Bis-Tris (pH 7.5)/26% (w/v) PEG3350/0.2 M ammonium sulfate, crystallization drops were prepared at a mixing ratio of reservoir solution: crystallization sample=0.8 μl: 1.0 μl. The drops were tight sealed and allowed to stand at 20° C. This yielded plate-like crystals.

[X-Ray Diffraction Data Measurement from Fc (P208)/FcγRIIaR Extracellular Region Complex Crystal]

A single crystal of Fc (P208)/FcγRIIaR extracellular region complex prepared as described above was soaked into a solution of 0.1 M Bis-Tris (pH 7.5)/27.5% (w/v) PEG3350/0.2 M ammonium sulfate/20% (v/v) glycerol. Then, the crystal was fished out of the solution using a pin with attached tiny nylon loop, and frozen in liquid nitrogen. X-ray diffraction data of the single crystal was collected from Photon Factory BL-17A of the synchrotron radiation institution in the High Energy Accelerator Research Organization. The crystal was constantly placed in a nitrogen stream at −178° C. to maintain in a frozen state during the measurement. A total of 225 X-ray diffraction images of the single crystal were collected using CCD detector Quantum 315r (ADSC) equipped to the beam line with rotating the single crystal at 0.6° at a time. Based on the obtained diffraction images, lattice constant determination, diffraction spot indexing, and diffraction data processing were performed using programs Xia2 (J. Appl. Cryst. (2010) 43, 186-190), XDS Package (Acta Cryst. (2010) D66, 125-132), and Scala (Acta Cryst. (2006) D62, 72-82). Finally, diffraction intensity data up to 2.87 Å resolution was obtained. The crystal belongs to the space group $C222_1$ with lattice constant a=154.31 Å, b=257.61 Å, c=56.19 Å, α=90°, β=90°, and γ=90°.

[X-Ray Crystal Structure Analysis of Fc (P208)/FcγRIIaR Extracellular Region Complex]

The structure of Fc (P208)/FcγRIIaR extracellular region complex was determined by a molecular replacement method using program Phaser (J. Appl. Cryst. (2007) 40, 658-674). The number of complexes in an asymmetrical unit was estimated to be one from the size of the obtained crystal lattice and the molecular weight of Fc (P208)/FcγRIIaR extracellular region complex. Using, as a search model, the crystallographic structure of Fc (P208)/FcγRIIb extracellular region complex obtained as described in (19-1), the orientation and position of Fc (P208)/FcγRIIaR extracellular region complex in the crystal lattices were determined based on the rotation function and translation function. The crystallographic reliability factor R value of the structural model for the data of diffracted intensity at 25 to 3.0 Å was 38.4% and Free R value was 30.0% after rigid body refinement where the two CH2 domains and two CH3 domains of the Fc region, and the extracellular region of FcγRIIaR were allowed to independently deviate from the obtained initial structural model. Then, structural model refinement was achieved by repeating structural refinement using program REFMAC5 (Acta Cryst. (2011) D67, 355-367) followed by revision of the structural model performed using program Coot (Acta Cryst. (2010) D66, 486-501) with reference to the electron density maps where the coefficients Fo-Fc and 2Fo-Fc were calculated using experimentally determined structural factor Fo, structural factor Fc calculated according to the model, and the phases calculated according to the model. Finally, further refinement was carried out based on the electron density maps with coefficients Fo-Fc and 2Fo-Fc by integrating water molecules into the structural model. With 24838 diffracted intensity data at 25 to 2.87 Å resolution, ultimately the crystallographic reliability factor R value was 26.3% and free R value was 38.0% for the structural model comprising 4758 non-hydrogen atoms.

Figure 50:
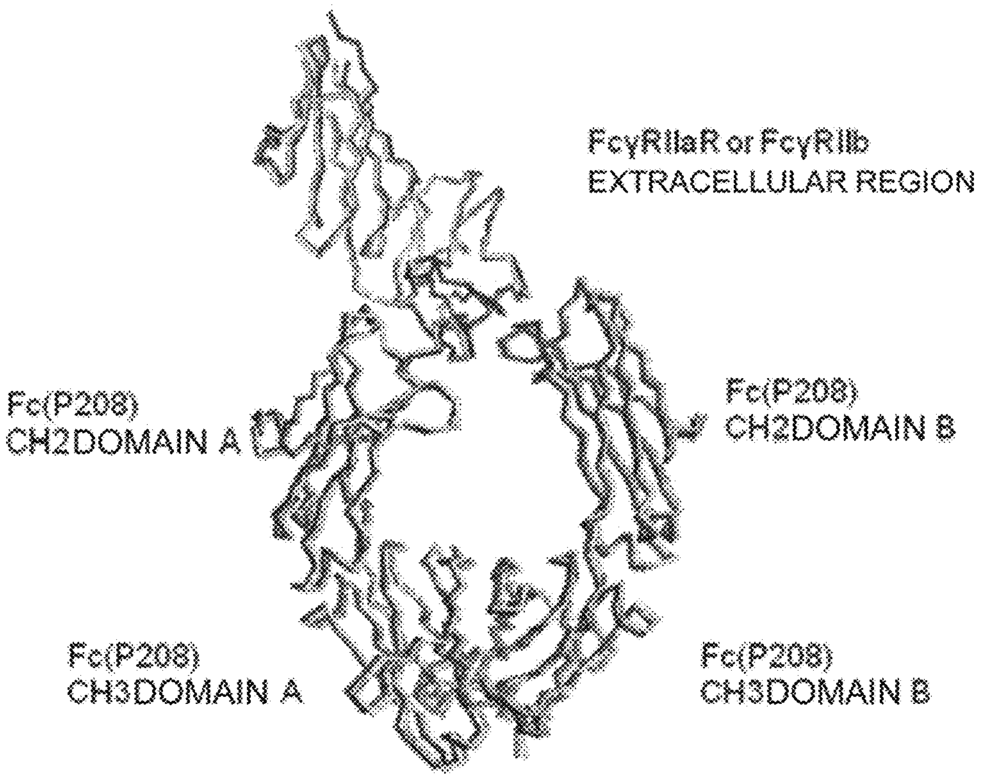
FIG. 50 shows comparison after superimposing the three-dimensional structures of the Fc (P208)/FcγRIIaR extracellular region complex and Fc (P208)/FcγRIIb extracellular region complex determined by X-ray crystal structure analysis by the least squares fitting based on the Cα atom pair distances.

The three-dimensional structure of the complex of Fc (P208)/FcγRIIaR extracellular region was determined at a resolution of 2.87 Å by structure analysis. A comparison of the crystal structure between the complex of Fc (P208)/FcγRIIaR extracellular region and the complex of Fc (P208)/FcγRIIb extracellular region described in (19-1) detected almost no difference at the level of overall structure (FIG. 50), reflecting the very high amino acid identity between the two Fcγ receptors.

Figure 51:
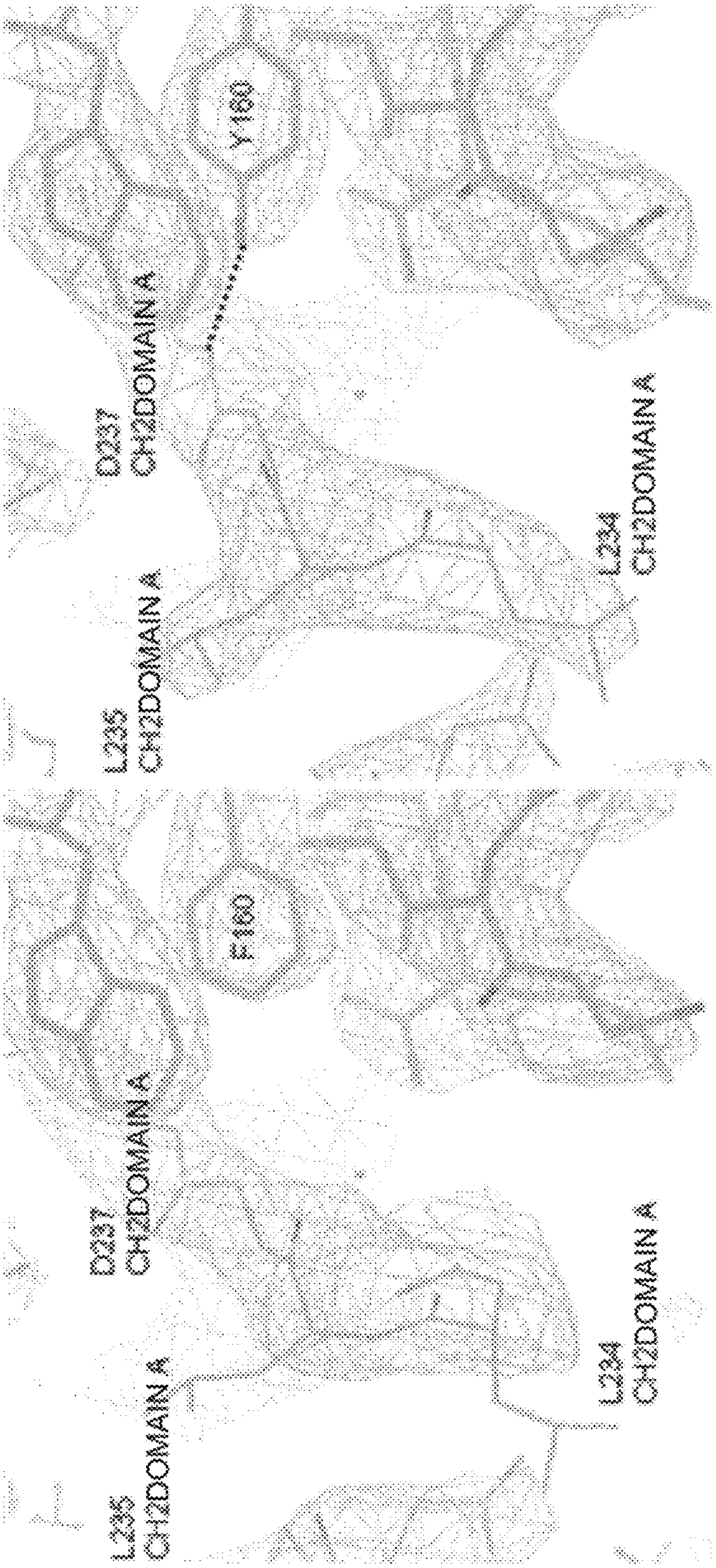
FIG. 51 shows comparison around Asp at position 237 (EU numbering) in the CH2 domain A of the Fc portion between the X-ray crystal structures of the Fc (P208)/FcγRIIaR extracellular region complex and the Fc (P208)/FcγRIIb extracellular region complex, along with the electron density determined by X-ray crystal structure analysis with 2Fo-Fc coefficient.
Figure 52:
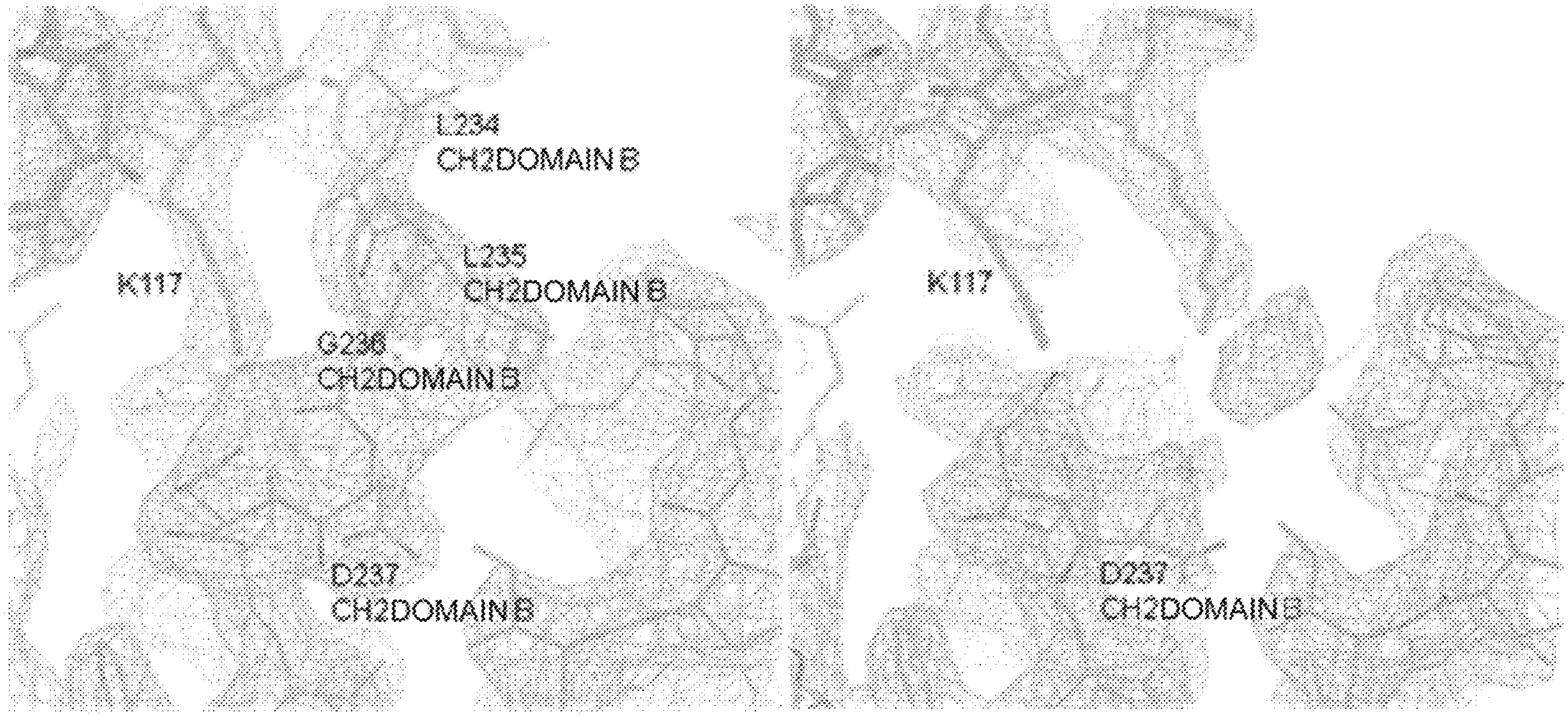
FIG. 52 shows comparison around Asp at position 237 (EU numbering) in the CH2 domain B of the Fc portion between the X-ray crystal structures of the Fc (P208)/FcγRIIaR extracellular region complex and the Fc (P208)/FcγRIIb extracellular region complex, along with the electron density determined by X-ray crystal structure analysis with 2Fo-Fc coefficient.

However, a precise observation of the structures at the electron density level detected some differences that can lead to improvement of the selectivity between the FcγRIIb binding and the FcγRIIaR binding of the Fc region. The amino acid residue at position 160 in FcγRIIaR is not Tyr but Phe. As shown in FIG. 51, the hydrogen bond between the main chain of the amino acid residue at position 237 (EU numbering) in the CH2 domain A of the Fc region and Tyr at position 160 in FcγRIIb, though formed upon binding between FcγRIIb and the Fc region with alteration P238D, is expected not to be formed upon binding between FcγRIIaR and the Fc region with alteration P238D. The absence of the hydrogen bond formation can be a major factor for improving the selectivity between the FcγRIIb binding and the FcγRIIaR binding of the Fc region introduced with alteration P238D. Further comparison at the electron density level showed that, in the Fc region/FcγRIIb complex, electron density was clearly observable for the side chains of Leu at positions 235 and 234 (EU numbering), whereas the electron density of the side chains was unclear in the Fc region/FcγRIIaR complex. This suggests that the loop near position 237 (EU numbering) fluctuates due to the reduced FcγRIIaR interaction around this position. Meanwhile, a structural comparison of the CH2 domain B of the Fc region (FIG. 52) in same region revealed that, in the complex of the Fc region and FcγRIIb, electron density was observable up to Asp at position 237 (EU numbering), whereas, in the complex of the Fc region and FcγRIIaR, electron density was observable up to three residues prior to Asp at position 237 (EU numbering), i.e., up to around Leu at position 234 (EU numbering), suggesting that FcγRIIaR binding forms an interaction over a larger region as compared to the FcγRIIb binding. The finding described above suggests the possibility that, in the CH2 domain A of the Fc region, the region from position 234 to 238 (EU numbering) has a large contribution to the binding between the Fc region and FcγRIIb, while in the CH2 domain B of the Fc region the region from position 234 to 238 (EU numbering) has a large contribution to the binding between the Fc region and FcγRIIaR.

[Reference Example 20] Fc Variants for which Alteration Sites were Determined Based on Crystal Structure As described in Reference Example 19, Asp at position 268 (EU numbering) was suggested to electrostatically interact with Arg at position 292 (EU numbering) (FIG. 48) as a result of the local structural change due to introduction of the alteration P271G in domain B of the variant with enhanced FcγRIIb binding (P208). There is a possibility that the loop structure at positions 266 to 271 (EU numbering) is stabilized by the formation of the interaction, resulting in enhancement of the FcγRIIb binding. Thus, the present inventors assessed whether the FcγRIIb binding of the variant could be enhanced by additional stabilization of its loop structure due to enhancement of the electrostatic interaction by substituting Glu for Asp at position 268 (EU numbering) in the variant. On the other hand, as shown in FIG. 47, Tyr at position 160 in FcγRIIb interacts with the main chain of Asp at position 237 (EU numbering) in domain A of P208. Meanwhile, the side chain of Asp at position 237 (EU numbering) is located close to Ile at position 332, Glu at position 333, and Lys at position 334 (EU numbering) in the molecule without forming any particularly significant interaction. Thus, the present inventors also assessed whether the interaction with Tyr at position 160 in FcγRIIb can be enhanced through stabilization of the loop structure at positions 266 to 271 (EU numbering) due to increased interaction with the side chain of Asp at position 237 (EU numbering) by substituting hydrophilic amino acid residues at the positions described above.

Variants were produced by introducing each of alterations H268E, I332T, I332S, I332E, I332K, E333K, E333R, E333S, E333T, K334S, K334T, and K334E into IL6R-BP230/IL6R-L produced as described in Reference Example 18. IL6R-L (SEQ ID NO: 155) was used as the antibody L chain. Antibodies containing the light chain of IL6R-L and the above-described heavy chain variants were expressed and purified according to the method described in Reference Example 1. The purified antibodies were assessed for their binding to each FcγR (FcγRIa, FcγRIIaH, FcγRIIaR, FcγRIIb, or FcγRIIIaV) by the method described in Reference Example 2.

The KD value of each variant to each FcγR is shown in Table 32. In the table, "alteration" refers to an alteration introduced into IL6R-BP230. IL6R-B3/IL6R-L which is used as the template to produce IL6R-BP230 is indicated by asterisk (*). KD (IIb) of parent polypeptide/KD (IIb) of altered polypeptide in the table shows the value obtained by dividing the KD value of IL6R-B3/IL6R-L for FcγRIIb by the KD value of each variant for FcγRIIb. Meanwhile, KD (IIaR) of parent polypeptide/KD (IIaR) of altered polypeptide shows the value obtained by dividing the KD value of IL6R-B3/IL6R-L for FcγR IIaR by the KD value of each variant for FcγR IIaR. KD (IIaR)/KD (IIb) shows the value obtained by dividing the KD value of each variant for FcγRIIaR by the KD value of the variant for FcγRIIb. The greater the value, the higher the selectivity to FcγRIIb. In Table 32, a bolded, italicized numeral indicates that the binding of FcγR to IgG was concluded to be too weak to analyze correctly by kinetic analysis and thus was calculated using:

$$KD=C\cdot R_{max}(R_{eq}-RI)-C \qquad \text{[Equation 2]}$$

described in Reference Example 2.

TABLE 32

| VARIANT NAME | ALTERATION INTRO-DUCED INTO IL6R-BP230 | KD AGAINST FcγRIa (mol/L) | KD AGAINST FcγRIIaR (mol/L) | KD AGAINST FcγRIIaH (mol/L) | KD AGAINST FcγRIIb (mol/L) | KD AGAINST FcγRIIIaV (mol/L) | KD (IIaR)/ KD (IIb) | KD (IIb) OF PARENT POLYPEPTIDE/ KD (IIb) OF ALTERED POLYPEPTIDE | KD (IIaR) OF PARENT POLYPEPTIDE/ KD (IIaR) OF ALTERED POLYPEPTIDE |
|---|---|---|---|---|---|---|---|---|---|
| IL6R-G1d/IL6R-L | | 3.2E−10 | 1.0E−06 | 6.7E−07 | 2.6E−06 | 3.5E−07 | 0.4 | 1.1 | 1.2 |
| IL6R-B3/IL6R-L | * | 4.2E−10 | 1.1E−06 | 7.7E−07 | 3.1E−06 | 3.3E−07 | 0.3 | 1.0 | 1.0 |
| IL6R-BP230/IL6R-L | | 1.4E−08 | 5.7E−07 | ***9.6E-06*** | 2.1E−08 | ***6.7E-05*** | 27.5 | 1.9 | 149.0 |
| IL6R-BP264/IL6R-L | H268E | 6.5E−09 | 4.8E−07 | ***9.2E-06*** | 1.2E−08 | ***5.2E-05*** | 40.6 | 2.3 | 265.0 |
| IL6R-BP384/IL6R-L | K334R | 3.0E−09 | 1.3E−06 | ***1.8E-05*** | 7.1E−08 | ***4.5E-05*** | 17.7 | 0.9 | 43.5 |
| IL6R-BP390/IL6R-L | I332S | 1.6E−09 | 4.9E−07 | ***7.3E-06*** | 2.1E−08 | ***2.9E-05*** | 22.9 | 2.2 | 144.9 |
| IL6R-BP391/IL6R-L | I332T | 9.6E−10 | 3.4E−07 | ***4.4E-06*** | 1.3E−08 | ***1.9E-05*** | 26.6 | 3.2 | 242.2 |
| IL6R-BP392/IL6R-L | I332K | 7.9E−09 | 7.3E−06 | ***2.8E-05*** | 9.9E−07 | ***2.9E-05*** | 7.3 | 0.2 | 3.1 |
| IL6R-BP393/IL6R-L | I332R | 1.1E−08 | 3.9E−06 | ***4.6E-05*** | 2.7E−06 | ***4.8E-05*** | 1.4 | 0.3 | 1.2 |
| IL6R-BP465/IL6R-L | E333K | 1.6E−08 | 6.1E−07 | ***1.5E-05*** | 2.1E−08 | ***6.7E-05*** | 29.8 | 1.8 | 151.2 |
| IL6R-BP466/IL6R-L | E333R | 1.5E−08 | 5.2E−07 | ***1.1E-05*** | 1.7E−08 | ***2.9E-05*** | 30.4 | 2.1 | 181.3 |
| IL6R-BP467/IL6R-L | K334S | 8.9E−10 | 1.1E−06 | ***1.2E-05*** | 4.1E−08 | ***3.2E-05*** | 25.8 | 1.0 | 75.4 |
| IL6R-BP468/IL6R-L | K334T | 9.7E−10 | 1.1E−06 | ***9.7E-06*** | 4.0E−08 | ***2.7E-05*** | 26.3 | 1.0 | 77.7 |
| IL6R-BP469/IL6R-L | E333S | 1.3E−08 | 6.0E−07 | ***1.2E-05*** | 2.3E−08 | ***3.7E-05*** | 26.4 | 1.8 | 136.6 |
| IL6R-BP470/IL6R-L | E333T | 1.5E−08 | 4.9E−07 | ***1.0E-05*** | 1.6E−08 | ***3.7E-05*** | 30.6 | 2.2 | 192.5 |

Both FcγRIIb-binding activity and FcγRIIb selectivity of IL6R-BP264/IL6R-L, IL6R-BP465/IL6R-L, IL6R-BP466/IL6R-L, and IL6R-BP470, resulting from introducing alterations H268E, E333K, E333R, and E333T, respectively, into IL6R-BP230/IL6R-L were increased as compared to those of IL6R-BP230/IL6R-L. The FcγRIIb selectivity of IL6R-BP391/IL6R-L introduced with the I332T alteration was reduced while its FcγRIIb-binding activity was increased as compared to IL6R-BP230/IL6R-L.

[Reference Example 21] Exhaustive Introduction of Alterations at Amino Acid Residues Around Position 271 (EU Numbering)

In the structural comparison between Fc (P208)/FcγRIIb and Fc (P238D)/FcγRIIb, the most significant difference is found in the structure around position 271 (EU numbering) in the CH2 domain B of the Fc region (FIG. 48). As described in Reference Example 16, it is suggested that, when, in the structure of Fc (P238D)/FcγRIIb, Asp at position 270 (EU numbering) forms a tight electrostatic interaction with Arg at position 131 in FcγRIIb, the interaction can induce stereochemical stress at Pro at position 271 (EU numbering). In the structure of Fc (P208)/FcγRIIb, due to the substitution of Gly for Pro at position 271 (EU numbering), a positional deviation occurred at the main chain level so as to eliminate the structural distortion, resulting in a large structural change around position 271. There is a possibility that additional stabilization of the structure changed around position 271 further reduces the entropic energy loss caused by the binding upon formation of an electrostatic interaction with Arg at position 131 in FcγRIIb. Thus, alterations that enhance the FcγRIIb binding or increase the FcγRIIb selectivity of the Fc region were sought by exhaustive introduction of alterations at amino acid residues around position 271 (EU numbering).

IL6R-BP267 was constructed as a template in exhaustive introduction of alterations by introducing alterations E233D, G237D, P238D, H268E, and P271G into IL6R-B3 (SEQ ID NO: 164). IL6R-L (SEQ ID NO: 155) was used as the antibody L chain. Antibodies containing the light chain of IL6R-L and the above-described heavy chain variants were expressed and purified according to the method described in Reference Example 1. The purified antibodies were assessed for their binding to each FcγR (FcγRIa, FcγRIIaH, FcγRIIaR, FcγRIIb, or FcγRIIIaV) by the method described in Reference Example 2. The amino acids at positions 264, 265, 266, 267, 269, and 272 (EU numbering) in IL6R-BP267 were substituted with each of 18 types of amino acids, except Cys and the amino acid prior to substitution. IL6R-L (SEQ ID NO: 155) was used as the antibody L chain. Antibodies containing the light chain of IL6R-L and the above-described heavy chain variants were expressed and purified according to the method described in Reference Example 1. The purified antibodies were assessed for their binding to each FcγR (FcγRIa, FcγRIIaH, FcγRIIaR, FcγRIIb, or FcγRIIIaV) by the method described in Reference Example 2. Variants whose FcγRIIb binding has been enhanced or FcγRIIb selectivity has been increased as compared to the FcγRIIb binding or FcγRIIb selectivity of IL6R-BP267/IL6R-L prior to introduction of the alterations are shown in Table 33.

TABLE 33

| VARIANT NAME | ALTERATION INTRODUCED INTO IL6R-BP230 | KD AGAINST FcγRIa (mol/L) | KD AGAINST FcγRIIaR (mol/L) | KD AGAINST FcγRIIaH (mol/L) | KD AGAINST FcγRIIb (mol/L) | KD AGAINST FcγRIIIaV (mol/L) | KD (IIaR)/ KD (IIb) | KD (IIaR) OF PARENT POLYPEPTIDE/ KD (IIaR) OF ALTERED POLYPEPTIDE | KD (IIb) OF PARENT POLYPEPTIDE/ KD (IIb) OF ALTERED POLYPEPTIDE |
|---|---|---|---|---|---|---|---|---|---|
| IL6R-B3/IL6R-L | * | 3.2E−10 | 1.0E−06 | 6.7E−07 | 2.6E−06 | 3.5E−07 | 0.4 | 1.0 | 1.0 |
| IL6R-BP267/ IL6R-L | | 4.0E−09 | 1.7E−06 | ***1.9E-05*** | 1.3E−07 | ***5.3E-05*** | 13.0 | 0.6 | 20.5 |
| IL6R-BP348/ IL6R-L | S267A | 5.5E−10 | 7.0E−07 | ***2.2E-05*** | 4.6E−08 | ***2.7E-05*** | 15.3 | 1.4 | 56.9 |
| IL6R-BP300/ IL6R-L | V261I | 9.6E−09 | 6.9E−07 | ***2.2E-05*** | 5.8E−08 | ***5.6E-05*** | 11.9 | 1.4 | 44.8 |
| IL6R-BP367/ IL6R-L | E269D | 3.1E−09 | 1.2E−06 | ***4.6E-05*** | 1.0E−07 | ***5.3E-05*** | 11.7 | 0.8 | 25.7 |
| IL6R-BP350/ IL6R-L | S267E | 8.9E−10 | 1.5E−07 | ***8.3E-05*** | 1.0E−07 | ***8.9E-05*** | 1.5 | 6.5 | 25.2 |
| IL6R-BP333/ IL6R-L | V266F | 9.1E−09 | 1.5E−06 | ***3.4E-05*** | 1.2E−07 | ***5.9E-05*** | 12.5 | 0.7 | 22.2 |
| IL6R-BP352/ IL6R-L | S267G | 1.8E−09 | 1.9E−06 | ***2.8E-05*** | 1.2E−07 | ***4.3E-05*** | 15.7 | 0.5 | 21.3 |
| IL6R-BP339/ IL6R-L | V266M | 4.6E−09 | 1.4E−06 | ***1.8E-05*** | 1.3E−07 | ***2.4E-05*** | 11.3 | 0.7 | 20.6 |
| IL6R-BP520/ IL6R-L | E272M | 3.9E−09 | 3.0E−06 | ***3.1E-05*** | 1.7E−07 | ***4.7E-05*** | 17.5 | 0.3 | 14.9 |
| IL6R-BP523/ IL6R-L | E272Q | 3.7E−09 | 2.7E−06 | ***2.9E-05*** | 1.7E−07 | ***4.1E-05*** | 15.9 | 0.4 | 15.5 |
| IL6R-BP313/ IL6R-L | D265E | 2.6E−08 | 1.3E−05 | ***4.7E-05*** | 8.4E−07 | ***3.8E-05*** | 15.6 | 0.1 | 3.1 |
| IL6R-BP513/ IL6R-L | E272D | 3.8E−09 | 1.7E−06 | ***3.9E-05*** | 1.1E−07 | ***7.5E-05*** | 15.4 | 0.6 | 23.6 |
| IL6R-BP521/ IL6R-L | E272N | 3.6E−09 | 2.9E−06 | ***4.4E-05*** | 1.9E−07 | ***9.9E-05*** | 15.2 | 0.3 | 13.5 |
| IL6R-BP338/ IL6R-L | V266L | 1.5E−08 | 2.2E−06 | ***2.2E-05*** | 1.5E−07 | ***2.5E-05*** | 15.0 | 0.5 | 17.9 |
| IL6R-BP517/ IL6R-L | E272I | 3.2E−09 | 2.1E−06 | ***2.2E-05*** | 1.4E−07 | ***3.5E-05*** | 14.7 | 0.5 | 18.1 |
| IL6R-BP514/ IL6R-L | E272F | 4.3E−09 | 3.0E−05 | ***6.4E-05*** | 2.1E−07 | ***9.1E-05*** | 14.0 | 0.3 | 12.3 |

The KD value of each variant to each FcγR is shown in Table 33. In the table, "alteration" refers to an alteration introduced into IL6R-BP267, which was used as a template. IL6R-B3/IL6R-L which is used as the template to produce IL6R-BP267 is indicated by asterisk (*). In the table, KD (IIb) of parent polypeptide/KD (IIb) of altered polypeptide shows the value obtained by dividing the KD value of IL6R-B3/IL6R-L for FcγRIIb by the KD value of each variant for FcγRIIb. Meanwhile, KD (IIaR) of parent polypeptide/KD (IIaR) of altered polypeptide shows the value obtained by dividing the KD value of IL6R-B3/IL6R-L for FcγRIIaR by the KD value of each variant for FcγR IIaR. KD (IIaR)/KD (IIb) shows the value obtained by dividing the KD value of each variant for FcγRIIaR by the KD value of the variant for FcγRIIb. The greater the value, the higher the selectivity to FcγRIIb. In Table 33, a bolded, italicized numeral indicates that the binding of FcγR to IgG was concluded to be too weak to analyze correctly by kinetic analysis and thus was calculated using:

$$KD=C\cdot R_{max}/(R_{eq}-RI)-C \quad \text{[Equation 2]}$$

described in Reference Example 2.

All the binding activities of variants shown in Table 33 to FcγRIa, FcγRIIaH, and FcγRIIIaV were comparable or reduced as compared to that of IL6R-B3/IL6R-L. Meanwhile, the FcγRIIb-binding activity of variants resulting from adding alterations S267A, V264I, E269D, S267E, V266F, S267G, and V266M, respectively, to IL6R-BP267/IL6R-L were increased as compared to that of IL6R-BP267/IL6R-L prior to addition of alteration. Meanwhile, the KD (IIaR)/KD (IIb) values of variants resulting from adding the S267A, S267G, E272M, E272Q, D265E, E272D, E272N, V266L, E272I, and E272F alterations, respectively, to IL6R-BP267/IL6R-L were increased as compared to that of IL6R-BP267/IL6R-L prior to addition of alteration. This demonstrates that the S267A, S267G, E272M, E272Q, D265E, E272D, E272N, V266L, E272I, and E272F alterations produce the effect to improve the FcγRIIb selectivity.

[Reference Example 22] Enhancement of the FcγRIIb Binding by Introduction of Alterations into CH3 Region A substitution alteration of Leu for Pro at position 396 (EU numbering) has been reported to enhance the FcγRIIb binding (Cancer Res. (2007) 67, 8882-8890). The amino acid at position 396 (EU numbering) is present at a position which is not directly involved in the interaction with FcγR. However, the amino acid can be assumed to have an effect on the interaction with FcγR by changing the antibody structure. Thus, the present inventors assessed whether the FcγRIIb binding of the Fc region is enhanced or its FcγRIIb selectivity is increased by exhaustive introduction of amino acid alterations at position 396 (EU numbering) in the Fc region.

IL6R-BP423 was constructed as a template in exhaustive introduction of alterations by introducing alterations E233D, G237D, P238D, S267A, H268E, P271G, and A330R into IL6R-B3 (SEQ ID NO: 164). Variants, in which the amino acid at position 396 (EU numbering) in IL6R-BP423 was substituted with each of 18 types of amino acids, except Cys and the amino acid prior to substitution, were constructed. IL6R-L (SEQ ID NO: 155) was used as the antibody L chain. Antibodies containing the light chain of IL6R-L and the above-described heavy chain variants were expressed and purified according to the method described in Reference Example 1. The purified antibodies were assessed for their binding to each FcγR (FcγRIa, FcγRIIaH, FcγRIIaR, FcγRIIb, or FcγRIIIaV) by the method described in Reference Example 2. The binding of the resulting variants to each FcγR is shown in Table 34.

TABLE 34

| VARIANT NAME | ALTERATION INTRODUCED INTO IL6R-BP423 | KD AGAINST FcγRIa (mol/L) | KD AGAINST FcγRIIaR (mol/L) | KD AGAINST FcγRIIaH (mol/L) | KD AGAINST FcγRIIb (mol/L) | KD AGAINST FcγRIIIaV (mol/L) | KD (IIaR)/ KD (IIb) | KD (IIaR) OF PARENT POLYPEPTIDE/ KD (IIaR) OF ALTERED POLYPEPTIDE | KD (IIb) OF PARENT POLYPEPTIDE/ KD (IIb) OF ALTERED POLYPEPTIDE |
|---|---|---|---|---|---|---|---|---|---|
| IL6R-G1d/IL6R-L |  | 3.2E−10 | 1.0E−06 | 6.7E−07 | 2.6E−06 | 3.5E−07 | 0.4 | 1.1 | 1.2 |
| IL6R-B3/IL6R-L | * | 4.2E−10 | 1.1E−06 | 7.7E−07 | 3.1E−06 | 3.3E−07 | 0.3 | 1.0 | 1.0 |
| IL6R-BP423/IL6R-L |  | 7.7E−10 | 1.8E−07 | *2.0E−06* | 5.1E−09 | *1.6E−06* | 34.2 | 6.3 | 604 |
| IL6R-BP447/IL6R-L | P396A | 9.0E−10 | 1.6E−07 | *2.0E−06* | 5.3E−09 | *2.5E−06* | 29.7 | 7.0 | 584 |
| IL6R-BP448/IL6R-L | P396D | 7.5E−10 | 1.3E−07 | *1.4E−06* | 4.1E−09 | *9.7E−06* | 31.7 | 8.5 | 759 |
| IL6R-BP449/IL6R-L | P396E | 9.1E−10 | 1.4E−07 | *1.5E−06* | 4.6E−09 | *1.2E−06* | 29.8 | 8.0 | 667 |
| IL6R-BP450/IL6R-L | P396F | 8.4E−10 | 1.2E−07 | *1.3E−06* | 4.1E−09 | *9.6E−06* | 29.4 | 9.2 | 763 |
| IL6R-BP451/IL6R-L | P396G | 9.8E−10 | 1.8E−07 | *2.0E−06* | 6.2E−09 | *1.2E−05* | 29.2 | 6.1 | 499 |
| IL6R-BP452/IL6R-L | P396H | 7.5E−10 | 1.3E−07 | *1.5E−06* | 5.1E−09 | *1.1E−05* | 25.9 | 8.3 | 602 |
| IL6R-BP453/IL6R-L | P396I | 7.5E−10 | 1.2E−07 | *9.3E−06* | 4.6E−09 | *7.4E−06* | 25.5 | 9.4 | 675 |
| IL6R-BP454/IL6R-L | P396K | 8.2E−09 | 1.3E−07 | *1.4E−06* | 4.8E−09 | *9.1E−06* | 27.5 | 8.4 | 649 |
| IL6R-BP455/IL6R-L | P396L | 7.5E−10 | 1.3E−07 | *1.6E−06* | 4.0E−09 | *8.5E−06* | 31.8 | 8.6 | 767 |
| IL6R-BP456/IL6R-L | P396M | 6.0E−10 | 1.2E−07 | *2.0E−06* | 3.5E−09 | *9.2E−06* | 35.3 | 8.9 | 888 |
| IL6R-BP457/IL6R-L | P396N | 9.1E−10 | 1.5E−07 | *2.6E−06* | 5.2E−09 | *1.3E−05* | 28.9 | 7.3 | 591 |
| IL6R-BP458/IL6R-L | P396Q | 7.8E−10 | 1.4E−07 | *1.4E−06* | 4.5E−09 | *1.1E−05* | 31.1 | 7.9 | 687 |
| IL6R-BP459/IL6R-L | P396R | 1.1E−09 | 1.5E−07 | *1.4E−06* | 5.1E−09 | *1.2E−05* | 28.9 | 7.5 | 607 |
| IL6R-BP460/IL6R-L | P396S | 8.7E−10 | 1.6E−07 | *3.2E−06* | 6.5E−09 | *1.4E−05* | 25.2 | 6.7 | 478 |
| IL6R-BP461/IL6R-L | P396T | 1.3E−09 | 1.3E−07 | *1.5E−06* | 5.1E−09 | *9.9E−06* | 24.4 | 8.8 | 602 |
| IL6R-BP462/IL6R-L | P396V | 9.7E−10 | 1.3E−07 | *1.4E−06* | 5.2E−09 | *9.0E−06* | 25.0 | 8.5 | 593 |
| IL6R-BP463/IL6R-L | P396W | 1.3E−09 | 1.6E−07 | *1.9E−06* | 5.6E−09 | *1.2E−05* | 28.1 | 7.0 | 554 |
| IL6R-BP464/IL6R-L | P396Y | 1.1E−09 | 1.3E−07 | *2.1E−06* | 4.0E−09 | *9.9E−06* | 31.5 | 8.7 | 773 |

In the table, "alteration introduced into IL6R-BP423" refers to an alteration introduced into IL6R-BP423, which was used as a template. IL6R-B3/IL6R-L which is used as the template to produce IL6R-BP423 is indicated by asterisk (*). In the table, KD (IIb) of parent polypeptide/KD (IIb) of altered polypeptide shows the value obtained by dividing the KD value of IL6R-B3/IL6R-L for FcγRIIb by the KD value of each variant for FcγRIIb. Meanwhile, KD (IIaR) of parent polypeptide/KD (IIaR) of altered polypeptide shows the value obtained by dividing the KD value of IL6R-B3/IL6R-L for FcγR IIaR by the KD value of each variant for FcγR IIaR. KD (IIaR)/KD (IIb) shows the value obtained by dividing the KD value of each variant for FcγRIIaR by the KD value of the variant for FcγRIIb. The greater the value, the higher the selectivity to FcγRIIb. In Table 34, a bolded, italicized numeral indicates that the binding of FcγR to IgG was concluded to be too weak to analyze correctly by kinetic analysis and thus was calculated using:

$$KD=C\cdot R_{max}/(R_{eq}-RI)-C \quad \text{[Equation 2]}$$

described in Reference Example 2.

The result shown in Table 34 demonstrates that: the FcγRIIb-binding activity of IL6R-BP456/IL6R-L resulting from introducing alteration P396M into IL6R-BP423/IL6R-L, IL6R-BP455/IL6R-L resulting from introducing alteration P396L into IL6R-BP423/IL6R-L, IL6R-BP464/IL6R-L resulting from introducing alteration P396Y into IL6R-BP423/IL6R-L, IL6R-BP450/IL6R-L resulting from introducing alteration P396F into IL6R-BP423/IL6R-L, IL6R-BP448/IL6R-L resulting from introducing alteration P396D into IL6R-BP423/IL6R-L, IL6R-BP458/IL6R-L resulting from introducing alteration P396Q into IL6R-BP423/IL6R-L, IL6R-BP453/IL6R-L resulting from introducing alteration P396I into IL6R-BP423/IL6R-L, IL6R-BP449/IL6R-L resulting from introducing alteration P396E into IL6R-BP423/IL6R-L, IL6R-BP454/IL6R-L resulting from introducing alteration P396K into IL6R-BP423/IL6R-L, and IL6R-BP459/IL6R-L resulting from introducing alteration P396R into IL6R-BP423/IL6R-L was all increased as compared to that of IL6R-BP423/IL6R-L prior to introduction of the alterations. Meanwhile, the KD (IIaR)/KD (IIb) value of IL6R-BP456/IL6R-L resulting from introducing alteration P396M into IL6R-BP423/IL6R-L was larger as compared to that of IL6R-BP423/IL6R-L prior to introduction of the alteration, demonstrating the improved FcγRIIb selectivity. As seen in Table 34, the binding activity of the prepared variants to FcγRIa, FcγRIIaH, and FcγRIIIaV was all lower than that of IL6R-B3/IL6R-L, which was the parent polypeptide.

[Reference Example 23] Preparation of Variants with Enhanced FcγRIIb Binding Using Subclass Sequences The FcγR binding profile varies depending on the subclass of human IgG. The present inventors assessed whether the difference in the binding activity to each FcγR between IgG1 and IgG4 could be utilized to increase the FcγRIIb-binding activity and/or improve the selectivity. First, IgG1 and IgG4 were analyzed for their binding activity to each FcγR. IL6R-G4d (SEQ ID NO: 165) containing G4d was constructed as the antibody H chain. G4d is an Fc region that lacks the C-terminal Gly and Lys and contains a substitution of Pro for Ser at position 228 (EU numbering) in human IgG4. IL6R-L (SEQ ID NO: 155) was used as the antibody L chain. Antibodies containing the light chain of IL6R-L and the heavy chain of IL6R-G1d or IL6R-G4d were expressed and purified according to the method described in Reference Example 1. The purified antibodies were assessed for their binding to each FcγR (FcγRIa, FcγRIIaH, FcγRIIaR, FcγRIIb, or FcγRIIIaV) by the method described in Reference Example 2. The binding of the resulting variants to each FcγR is summarized in Table 35.

TABLE 35

| VARIANT NAME | KD AGAINST FcγRIa (mol/L) | KD AGAINST FcγRIIaR (mol/L) | KD AGAINST FcγRIIaH (mol/L) | KD AGAINST FcγRIIb (mol/L) | KD AGAINST FcγRIIIaV (mol/L) |
|---|---|---|---|---|---|
| IL6R-G1d/IL6R-L | 1.20E−10 | 9.70E−07 | 6.50E−07 | 3.90E−06 | 4.20E−07 |
| IL6R-G4d/IL6R-L | 6.60E−10 | 2.10E−06 | 3.40E−06 | 2.60E−06 | 3.40E−06 |

It was demonstrated that the FcγRIIb binding of IL6R-G4d/IL6R-L was 1.5 times stronger than that of IL6R-G1d/IL6R-L whereas the FcγRIIaR binding of IL6R-G4d/IL6R-L was 2.2 times weaker than that of IL6R-G1d/IL6R-L. Meanwhile, the binding activity of IL6R-G4d/IL6R-L to FcγRIa, FcγRIIaH, and FcγRIIIaV was lower than that of IL6R-G1d/IL6R-L. The result described above revealed that IL6R-G4d had preferable characteristics as compared to IL6R-G1d in terms of both FcγRIIb-binding activity and selectivity.

Figure 53:
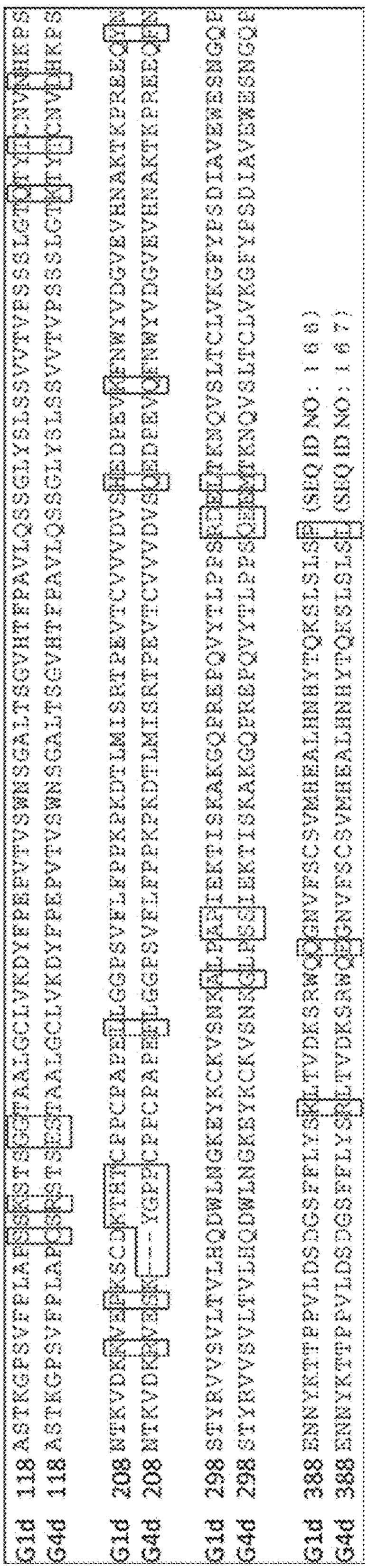
FIG. 53 shows comparison between the constant-region sequences of G1d and G4d. In the diagram, the amino acids boxed with thick-frame indicate positions with different amino acid residues between G1d and G4d.

FIG. 53 is an alignment to compare the sequences from CH1 to the C terminus (positions 118 to 445 (EU numbering)) of G1d and G4d. In FIG. 53, amino acid residues that are different between G1 d and G4d are boxed with thick line. The present inventors assessed whether the FcγRIIb binding could be further increased and/or the FcγRIIb selectivity could be further improved by selecting, from the above-described different amino acids, some portions that are predicted to be involved in the interaction with FcγR, and grafting at least one amino acid residue or more of the G4d sequence, which confers a property preferable from the viewpoint of both FcγRIIb-binding activity and selectivity, to a variant with enhanced FcγRIIb binding.

Specifically, the present inventors produced: IL6R-BP473 resulting from introducing alteration A327G into IL6R-BP230; IL6R-BP472 resulting from introducing alteration A330S into IL6R-BP230; IL6R-BP471 resulting from introducing alteration P331S into IL6R-BP230; IL6R-BP474 resulting from introducing alterations A330S and P331S into IL6R-BP230; IL6R-BP475 resulting from introducing alterations A327G and A330S into IL6R-BP230; IL6R-BP476 resulting from introducing alterations A327G, A330S, and P331S into IL6R-BP230; and IL6R-BP477 resulting from introducing alterations A327G and P331S into IL6R-BP230. Furthermore, to construct IL6R-BP478, the amino acids from Ala at position 118 to Thr at position 225 (EU numbering) in IL6R-BP230 was substituted with the amino acids from Ala at position 118 to Pro at position 222 (EU numbering) in G4d. IL6R-L (SEQ ID NO: 155) was used as the antibody L chain. Antibodies containing the light chain of IL6R-L and the heavy chain variants described above were purified according to the method described in Reference Example 1. The purified antibodies were assessed for their binding activity to each FcγR (FcγRIa, FcγRIIaH, FcγRIIaR, FcγRIIb, or FcγRIIIaV) by the method described in Reference Example 2.

The KD value of each variant to each FcγR is shown in Table 36. KD (IIb) of parent polypeptide/KD (IIb) of altered polypeptide in the table shows the value obtained by dividing the KD value of IL6R-B3/IL6R-L for FcγRIIb by the KD value of each variant for FcγRIIb. In the table, "alteration introduced into IL6R-BP230" refers to an alteration introduced into IL6R-BP230. IL6R-B3/IL6R-L used as the template to produce IL6R-BP230 is indicated by *1. Meanwhile, IL6R-BP478, in which the segment from Ala at position 118 up to Pro at position 222 (EU numbering) in G4d has been substituted for the segment from Ala at position 118 up to Thr at position 225 (EU numbering) in IL6R-BP230, is indicated by *2. KD (IIaR) of parent polypeptide/KD (IIaR) of altered polypeptide shows the value obtained by dividing the KD value of IL6R-B3/IL6R-L for FcγR IIaR by the KD value of each variant for FcγR IIaR. KD (IIaR)/KD (IIb) shows the value obtained by dividing the KD value of each variant for FcγRIIaR by the KD value of the variant for FcγRIIb. The greater the value, the higher the selectivity to FcγRIIb. In Table 36, a bolded, italicized numeral indicates that the binding of FcγR to IgG was concluded to be too weak to analyze correctly by kinetic analysis and thus was calculated using:

$$KD=C\cdot R_{max}/(R_{eq}-RI)-C \quad \text{[Equation 2]}$$

described in Reference Example 2.

to be effective in enhancing the FcγRIIb binding and/or improving the FcγRIIb selectivity were introduced in combination into IL6R-B3 (SEQ ID NO: 164). Furthermore, existing alterations S267E and L328F that enhance the FcγRIIb binding (Seung et al., (Mol. Immunol. (2008) 45, 3926-3933)) were introduced into IL6R-B3 to produce IL6R-BP253 as a comparison control. IL6R-L (SEQ ID NO: 155) was used as the antibody L chain. Antibodies containing the light chain of IL6R-L and the above-described heavy chain variants were expressed and purified according to the method as described in Reference Example 1. The purified antibodies were assessed for their binding to each FcγR (FcγRIa, FcγRIIaH, FcγRIIaR, FcγRIIb, or FcγRIIIaV) by the method described in Reference Example 2.

TABLE 36

| VARIANT NAME | ALTERATION INTRODUCED INTO IL6R-BP230 | KD AGAINST FcγRIa (mol/L) | KD AGAINST FcγRIIaR (mol/L) | KD AGAINST FcγRIIaH (mol/L) | KD AGAINST FcγRIIb (mol/L) | KD AGAINST FcγRIIIaV (mol/L) | KD (IIaR)/ KD (IIb) | KD (IIaR) OF PARENT POLYPEPTIDE/ KD (IIaR) OF ALTERED POLYPEPTIDE | KD (IIb) OF PARENT POLYPEPTIDE/ KD (IIb) OF ALTERED POLYPEPTIDE |
|---|---|---|---|---|---|---|---|---|---|
| IL6R-G1d/IL6R-L | | 3.2E−10 | 1.0E−06 | 6.7E−07 | 2.6E−06 | 3.5E−07 | 0.4 | 1.1 | 1.2 |
| IL6R-B3/IL6R-L | *1 | 4.2E−10 | 1.1E−06 | 7.7E−07 | 3.1E−06 | 3.3E−07 | 0.3 | 1.0 | 1.0 |
| IL6R-BP230/ IL6R-L | | 1.4E−08 | 5.7E−07 | ***9.6E−06*** | 2.1E−08 | ***6.7E−05*** | 27.5 | 1.9 | 149.0 |
| IL6R-BP471/ IL6R-L | P331S | 7.3E−09 | 8.0E−07 | ***1.2E−05*** | 3.5E−08 | ***7.1E−05*** | 22.7 | 1.4 | 88.1 |
| IL6R-BP472/ IL6R-L | A330S | 5.2E−09 | 3.3E−06 | ***2.4E−05*** | 1.5E−07 | ***3.8E−05*** | 21.5 | 0.3 | 20.3 |
| IL6R-BP473/ IL6R-L | A327G | 6.2E−09 | 3.8E−07 | ***4.8E−06*** | 1.8E−08 | ***3.6E−05*** | 21.1 | 2.9 | 172.2 |
| IL6R-BP474/ IL6R-L | A330S/P331S | 4.1E−09 | 3.0E−06 | ***3.7E−05*** | 1.8E−07 | ***5.5E−05*** | 16.6 | 0.4 | 16.9 |
| IL6R-BP475/ IL6R-L | A327G/A330S | 4.9E−09 | 1.0E−06 | ***1.5E−05*** | 1.1E−07 | ***4.6E−05*** | 9.7 | 1.1 | 29.2 |
| IL6R-BP476/ IL6R-L | A327G/ A330S/P331S | 5.9E−09 | 1.3E−06 | ***1.9E−05*** | 1.3E−07 | ***4.9E−05*** | 9.7 | 0.9 | 23.7 |
| IL6R-BP477/ IL6R-L | A327G/P331S | 9.2E−09 | 5.1E−07 | ***7.6E−06*** | 3.7E−08 | ***5.6E−05*** | 14.0 | 2.2 | 84.9 |
| IL6R-BP478/ IL6R-L | *2 | 7.7E−09 | 5.4E−07 | ***6.7E−06*** | 1.9E−08 | ***3.5E−05*** | 28.0 | 2.0 | 160.6 |

Among the variants shown in Table 36, IL6R-BP473/IL6R-L introduced with alteration A327G had 1.2 times enhanced FcγRIIb binding as compared to that of IL6R-BP230/IL6R-L. Regarding IL6R-BP478/IL6R-L, resulting from substituting the amino acids of Ala at position 118 up to Thr at position 225 (EU numbering) in IL6R-BP230 with the amino acids of Ala at position 118 up to Pro at position 222 (EU numbering) in G4d, its FcγRIIb binding is enhanced by 1.1 times as compared to that of IL6R-BP230/IL6R-L, while FcγRIIaR binding of IL6R-BP478/IL6R-L is reduced by 0.9 times as compared to that of IL6R-BP230/IL6R-L. All the variants also showed lower binding activity to FcγRIa, FcγRIIaH, and FcγRIIIaV as compared to parent polypeptide IL6R-B3/IL6R-L.

[Reference Example 24] Assessment of Combinations of Alterations that Enhance the FcγRIIb Binding or Improve the FcγRIIb Selectivity Additional combinations of the alterations described herein in the sections up to and including "Reference Example 23", which alterations had been found to be effective in the aspect of enhancement of the FcγRIIb binding or the improvement of the FcγRIIb selectivity, were assessed. Specifically, the alterations that had been assessed The KD value of each variant to each FcγR is shown in Table 37. In the table, "alteration" refers to an alteration introduced into IL6R-B3 (SEQ ID NO: 164). IL6R-B3/IL6R-L which is used as the template to produce each variant is indicated by asterisk (*). KD (IIb) of parent polypeptide/KD (IIb) of altered polypeptide shows the value obtained by dividing the KD value of IL6R-B3/IL6R-L for FcγRIIb by the KD value of each variant for FcγRIIb. Meanwhile, KD (IIaR) of parent polypeptide/KD (IIaR) of altered polypeptide shows the value obtained by dividing the KD value of IL6R-B3/IL6R-L for FcγR IIaR by the KD value of each variant for FcγRIIaR. KD (IIaR)/KD (IIb) shows the value obtained by dividing the KD value of each variant for FcγRIIaR by the KD value of the variant for FcγRIIb. The greater the value, the higher the selectivity to FcγRIIb as compared to FcγRIIaR. Meanwhile, KD (IIaH)/KD (IIb) shows the value obtained by dividing the KD value of each variant for FcγRIIaH by the KD value of the variant for FcγRIIb. The greater the value, the higher the selectivity to FcγRIIb as compared to FcγRIIaH. In Table 37, a bolded, italicized numeral indicates that the binding of FcγR to IgG was concluded to be too weak to analyze correctly by kinetic analysis and thus was calculated using:

$$KD=C\cdot R_{max}/(R_{eq}-RI)-C \quad \text{[Equation 2]}$$

described in Reference Example 2.

TABLE 37

| VARIANT NAME | ALTERATION | KD AGAINST FcgRIa (mol/L) | KD AGAINST FcgRIIaR (mol/L) | KD AGAINST FcgRIIaH (mol/L) | KD AGAINST FcgRIIb (mol/L) | KD AGAINST FcgRIIIaV (mol/L) | KD (IIaR)/ KD (IIb) | KD (IIaH)/ KD (IIb) | KD (IIaR) OF PARENT POLYPEPTIDE/ KD (IIaR) OF ALTERED POLYPEPTIDE | KD (IIb) OF PARENT POLYPEPTIDE/ KD (IIb) OF ALTERED POLYPEPTIDE |
|---|---|---|---|---|---|---|---|---|---|---|
| IL6R-G1d/IL6R-L | | 3.2E−10 | 1.0E−06 | 6.7E−07 | 2.6E−06 | 3.5E−07 | 0.4 | 0.3 | 1.1 | 1.2 |
| IL6R-B3/IL6R-L | * | 4.2E−10 | 1.1E−06 | 7.7E−07 | 3.1E−06 | 3.3E−07 | 0.3 | 0.2 | 1.0 | 1.0 |
| IL6R-BP253/IL6R-L | S267E/L328F | 6.7E−11 | 2.1E−09 | 1.2E−06 | 1.1E−08 | 3.6E−06 | 0.2 | 107.1 | 528.8 | 276.8 |
| IL6R-BP265/IL6R-L | G237D/P238D/H268E/P271G/Y296D/A330R | 2.3E−08 | 6.3E−07 | **1.2E−05** | 1.5E−08 | **9.6E−05** | 41.2 | 789.5 | 1.8 | 203.9 |
| IL6R-BP266/IL6R-L | E233D/G237D/P238D/H268E/P271G/A330R | 1.4E−08 | 3.2E−07 | **1.3E−05** | 1.8E−08 | **4.0E−05** | 18.0 | 621.5 | 3.4 | 175.1 |
| IL6R-BP423/IL6R-L | E233D/G237D/P238D/S267A/H268E/P271G/A330R | 7.7E−10 | 1.8E−07 | **2.0E−06** | 5.1E−09 | **1.6E−05** | 34.2 | 390.6 | 6.3 | 605.5 |
| IL6R-BP425/IL6R-L | E233D/G237D/P238D/V266L/S267A/H268E/P271G/A330R | 4.1E−09 | 2.2E−07 | **1.5E−05** | 9.1E−09 | **4.2E−05** | 23.6 | 1644.7 | 5.1 | 339.9 |
| IL6R-BP426/IL6R-L | E233D/G237D/P238D/S267A/H268E/E269D/P271G/A330R | 1.0E−09 | 1.6E−07 | **1.9E−05** | 5.9E−09 | **4.1E−05** | 27.6 | 8361.8 | 6.8 | 529.0 |
| IL6R-BP428/IL6R-L | E233D/G237D/P238D/S267G/H268E/P271G/A330R | 4.9E−09 | 3.9E−07 | **3.2E−05** | 1.4E−08 | **3.6E−05** | 28.0 | 3000.0 | 2.8 | 221.4 |
| IL6R-BP429/IL6R-L | E233D/G237D/P238D/V264I/S267G/H268E/P271G/A330R | 6.2E−09 | 1.7E−07 | **3.5E−06** | 5.4E−09 | **6.8E−05** | 31.5 | 648.1 | 6.5 | 574.1 |
| IL6R-BP430/IL6R-L | E233D/G237D/P238D/V266L/S267G/H268E/P271G/A330R | 1.7E−08 | 2.2E−07 | **3.8E−05** | 1.2E−08 | **3.5E−05** | 18.5 | 909.1 | 4.9 | 256.2 |
| IL6R-BP431/IL6R-L | E233D/G237D/P238D/S267G/H268E/E269D/P271G/A330R | 3.6E−09 | 4.1E−07 | **7.6E−06** | 1.2E−08 | **3.2E−05** | 34.6 | 649.6 | 2.7 | 265.0 |
| IL6R-BP433/IL6R-L | E233D/G237D/P238D/H268D/P271G/Y296D/A330K/I332T | 7.5E−10 | 6.8E−07 | **7.3E−06** | 3.4E−08 | **2.6E−05** | 20.0 | 216.0 | 1.6 | 91.7 |
| IL6R-BP434/IL6R-L | E233D/G237D/P238D/H268D/P271G/Y296D/K326D/A330R/I332T | 5.5E−10 | 3.4E−07 | **4.1E−06** | 1.2E−08 | **2.5E−05** | 27.2 | 333.3 | 3.3 | 252.0 |
| IL6R-BP435/IL6R-L | E233D/G237D/P238D/H268D/P271G/Y296D/K326A/A330R/I332T | 1.0E−09 | 4.2E−07 | **3.4E−06** | 1.6E−08 | **2.2E−05** | 27.1 | 217.9 | 2.6 | 198.7 |
| IL6R-BP436/IL6R-L | E233D/G237D/P238D/S267A/H268E/P271G/Y296D/A330R/I332T | 2.6E−10 | 2.2E−07 | **2.1E−06** | 5.1E−09 | **2.3E−05** | 43.8 | 411.0 | 4.9 | 606.7 |
| IL6R-BP437/IL6R-L | G237D/P238D/S267A/H268E/P271G/Y296D/A330R/I332T | 7.5E−10 | 2.2E−07 | **1.4E−06** | 5.9E−09 | **1.1E−05** | 37.7 | 236.5 | 4.9 | 523.6 |
| IL6R-BP438/IL6R-L | E233D/G237D/P238D/S267A/H268E/P271G/A330R/I332T | 2.1E−10 | 1.8E−07 | **1.6E−06** | 5.5E−09 | **6.8E−06** | 32.7 | 293.6 | 6.2 | 568.8 |
| IL6R-BP439/IL6R-L | E233D/G237D/P238D/V264I/V266L/S267A/H268E/P271G/A330R | 8.7E−09 | 1.3E−07 | **2.8E−06** | 6.1E−09 | **6.6E−05** | 20.9 | 460.5 | 8.7 | 509.9 |
| IL6R-BP440/IL6R-L | E233D/G237D/P238D/V264I/H268E/P271G/A330R | 8.7E−09 | 1.3E−07 | **1.6E−06** | 5.2E−09 | **2.8E−05** | 24.0 | 307.1 | 8.8 | 595.0 |
| IL6R-BP441/IL6R-L | E233D/G237D/P238D/V266L/H268E/P271G/A330R | 1.7E−09 | 3.6E−07 | **8.8E−06** | 1.5E−08 | **3.7E−05** | 24.0 | 582.8 | 3.0 | 205.3 |
| IL6R-BP442/IL6R-L | E233D/G237D/P238D/H268E/E269D/P271G/A330R | 4.5E−09 | 3.8E−07 | **4.7E−06** | 1.2E−08 | **2.5E−05** | 30.6 | 379.0 | 2.9 | 250.0 |
| IL6R-BP443/IL6R-L | E233D/G237D/P238D/V266L/H268E/E269D/P271G/A330R | 1.8E−09 | 5.1E−07 | **9.5E−06** | 2.3E−08 | **2.3E−05** | 21.7 | 406.0 | 2.2 | 132.5 |
| IL6R-BP445/IL6R-L | E233D/G237D/P238D/V264I/S267A/H268E/P271G/A330R | 2.0E−09 | 8.0E−08 | **1.5E−06** | 2.6E−09 | **2.4E−05** | 31.0 | 581.4 | 13.8 | 1201.6 |
| IL6R-BP262/IL6R-L | G237D/P238D/H268E/P271G | 1.0E−08 | 2.0E−06 | **4.5E−05** | 1.2E−07 | **5.6E−05** | 17.0 | 375.0 | 0.5 | 25.8 |
| IL6R-BP264/IL6R-L | E233D/G237D/P238D/H268E/P271G/Y296D/A330R | 7.4E−09 | 3.5E−07 | **2.8E−06** | 1.2E−08 | **2.6E−05** | 28.3 | 227.6 | 3.2 | 252.0 |
| IL6R-BP268/IL6R-L | E233D/G237D/P238D/H268E/P271G/Y296D | 4.5E−09 | 1.8E−06 | **2.1E−05** | 9.2E−08 | **2.8E−05** | 19.6 | 228.3 | 0.6 | 33.7 |
| IL6R-BP269/IL6R-L | G237D/P238D/H268E/P271G/Y296D | 1.4E−08 | 2.2E−06 | **7.2E−05** | 1.1E−07 | **1.4E−04** | 19.6 | 637.2 | 0.5 | 27.4 |
| IL6R-BP479/IL6R-L | E233D/G237D/P238D/V264I/V266L/S267A/H268E/P271G | 5.3E−09 | 9.0E−07 | **1.5E−05** | 5.6E−08 | **4.0E−05** | 16.1 | 268.3 | 1.2 | 55.5 |
| IL6R-BP480/IL6R-L | E233D/G237D/P238D/V266L/H268E/E269D/P271G | 1.3E−08 | 6.3E−06 | **2.1E−05** | 2.0E−07 | **4.6E−05** | 32.1 | 107.7 | 0.2 | 15.9 |
| IL6R-BP481/IL6R-L | E233D/G237D/P238D/V264I/S267A/H268E/P271G | 1.0E−09 | 4.0E−07 | **6.8E−06** | 1.9E−08 | **2.4E−05** | 20.5 | 350.5 | 2.8 | 159.8 |
| IL6R-BP483/IL6R-L | E233D/G237D/P238D/V266L/S267A/H268E/P271G | 1.3E−09 | 1.3E−06 | **1.8E−05** | 7.8E−08 | **2.5E−05** | 16.8 | 230.8 | 0.8 | 39.7 |
| IL6R-BP484/IL6R-L | E233D/G237D/P238D/S267A/H268E/E269D/P271G | 8.2E−10 | 7.8E−07 | **1.1E−05** | 4.6E−08 | **2.5E−05** | 17.1 | 240.7 | 1.4 | 67.8 |
| IL6R-BP487/IL6R-L | E233D/G237D/P238D/V264I/S267A/H268E/P271G/A330R/P396M | 1.2E−09 | 3.9E−08 | **8.4E−07** | 1.2E−09 | **1.0E−05** | 33.8 | 730.4 | 28.3 | 2695.7 |
| IL6R-BP488/IL6R-L | E233D/G237D/P238D/V264I/S267A/H268E/P271G/Y296D/A330R | 2.2E−09 | 7.4E−08 | **1.6E−06** | 1.9E−09 | **2.0E−05** | 40.1 | 864.9 | 14.8 | 1675.7 |
| IL6R-BP489/IL6R-L | E233D/G237D/P238D/V264I/S267A/H268E/P271G/Y296D/ A330R/P396M | 1.3E−09 | 4.3E−08 | **8.7E−07** | 1.0E−09 | **1.2E−05** | 42.8 | 870.0 | 25.7 | 3100.0 |

TABLE 37-continued

| VARIANT NAME | ALTERATION | KD AGAINST FcgRIa (mol/L) | KD AGAINST FcgRIIaR (mol/L) | KD AGAINST FcgRIIaH (mol/L) | KD AGAINST FcgRIIb (mol/L) | KD AGAINST FcgRIIIaV (mol/L) | KD (IIaR)/ KD (IIb) | KD (IIaH)/ KD (IIb) | KD (IIaR) OF PARENT POLYPEPTIDE/ KD (IIaR) OF ALTERED POLYPEPTIDE | KD (IIb) OF PARENT POLYPEPTIDE/ KD (IIb) OF ALTERED POLYPEPTIDE |
|---|---|---|---|---|---|---|---|---|---|---|
| IL6R-BP490/IL6R-L | G237D/P238D/V264I/S267A/H268E/P271G/A330R | 4.5E−09 | 1.1E−07 | 2.4E−06 | 2.4E−09 | **2.3E−05** | 46.7 | 1000.0 | 9.8 | 1291.7 |
| IL6R-BP491/IL6R-L | G237D/P238D/V264I/S267A/H268E/P271G/Y296D/A330R | 5.3E−09 | 1.2E−07 | 2.2E−06 | 3.0E−09 | **2.1E−05** | 38.8 | 723.7 | 9.3 | 1019.7 |
| IL6R-BP492/IL6R-L | P238D/V264I/S267A/H268E/P271G | 7.9E−10 | 9.2E−07 | 1.6E−05 | 2.4E−08 | **3.6E−05** | 38.8 | 678.0 | 1.2 | 131.4 |
| IL6R-BP493/IL6R-L | P238D/V264I/S267A/H268E/P271G/Y296D | 8.2E−10 | 1.1E−06 | 1.9E−05 | 2.1E−08 | **3.5E−05** | 52.1 | 900.5 | 1.0 | 146.9 |
| IL6R-BP494/IL6R-L | G237D/P238D/S267A/H268E/P271G/Y296D/A330R | 3.9E−09 | 2.5E−07 | 5.4E−06 | 6.6E−09 | **4.0E−05** | 38.6 | 820.7 | 4.3 | 471.1 |
| IL6R-BP495/IL6R-L | G237D/P238D/S267G/H268E/P271G/Y296D/A330R | 8.3E−09 | 4.9E−07 | 1.2E−05 | 9.7E−09 | **3.3E−05** | 50.9 | 1243.5 | 2.2 | 321.2 |
| IL6R-BP496/IL6R-L | E233D/G237D/P238D/V264I/S267A/H268E/P271G/Y296D | 1.2E−09 | 4.7E−07 | 3.7E−06 | 1.8E−08 | **3.0E−05** | 25.5 | 201.1 | 2.3 | 168.5 |
| IL6R-BP497/IL6R-L | E233D/G237D/P238D/V264I/S267A/H268E/P271G/A327G/A330R | 2.1E−09 | 8.5E−08 | 9.6E−07 | 4.1E−09 | **2.8E−05** | 21.0 | 236.5 | 12.9 | 763.5 |
| IL6R-BP498/IL6R-L | E233D/G237D/P238D/V264I/S267A/H268E/P271G/A330R/P396L | 1.3E−09 | 5.1E−08 | 9.3E−07 | 1.7E−09 | **1.0E−05** | 30.8 | 563.6 | 21.7 | 1878.8 |
| IL6R-BP499/IL6R-L | E233D/G237D/P238D/V264I/S267A/H268E/P271G/Y296D/A330R/ P396L | 1.2E−09 | 4.9E−08 | 1.0E−06 | 1.5E−09 | **1.2E−05** | 33.8 | 684.9 | 22.3 | 2123.3 |
| IL6R-BP500/IL6R-L | G237D/P238D/V264I/S267A/H268E/P271G/Y296D | 2.3E−09 | 7.2E−07 | 2.5E−05 | 2.4E−08 | **3.9E−05** | 29.9 | 1033.1 | 1.5 | 128.1 |
| IL6R-BP501/IL6R-L | G237D/P238D/V264I/S267A/H268E/P271G | 2.1E−09 | 6.3E−07 | 1.4E−05 | 2.5E−08 | **1.9E−05** | 25.1 | 555.6 | 1.7 | 123.0 |
| IL6R-BP502/IL6R-L | E233D/G237D/P238D/V264I/S267A/H268E/P271G/Y296D/A327G/ A330R | 2.1E−09 | 1.1E−07 | 1.3E−06 | 3.7E−09 | **2.4E−05** | 29.5 | 352.3 | 10.1 | 810.1 |
| IL6R-BP503/IL6R-L | E233D/G237D/P238D/V264I/S267A/H268E/P271G/Y296D/A327G/ A330R/P396M | 1.2E−09 | 5.7E−08 | 8.6E−07 | 1.7E−09 | **2.1E−05** | 33.2 | 502.9 | 19.4 | 1812.8 |
| IL6R-BP504/IL6R-L | E233D/G237D/P238D/V264I/S267A/H268E/P271G/E272P | 1.4E−09 | 4.5E−07 | 1.6E−05 | 2.4E−08 | **3.4E−05** | 18.5 | 658.4 | 2.4 | 127.0 |
| IL6R-BP505/IL6R-L | E233D/G237D/P238D/V264I/S267A/H268E/P271G/E272D | 1.1E−09 | 4.3E−07 | 1.1E−05 | 2.1E−08 | **3.8E−05** | 20.0 | 514.0 | 2.6 | 144.9 |
| IL6R-BP506/IL6R-L | E233D/G237D/P238D/V264I/S267A/H268E/P271G/E272P/Y296D/ A330R | 3.1E−09 | 1.2E−07 | 2.5E−06 | 3.4E−09 | **5.5E−05** | 35.1 | 731.0 | 9.2 | 906.4 |
| IL6R-BP507/IL6R-L | E233D/G237D/P238D/V264I/S267A/H268E/P271G/E272P/A330R | 2.6E−09 | 1.0E−07 | 1.8E−06 | 2.9E−09 | **2.6E−05** | 34.2 | 618.6 | 11.1 | 1065.3 |
| IL6R-BP508/IL6R-L | E233D/G237D/P238D/V264I/S267A/H268E/P271G/E272P/Y296D | 1.4E−09 | 5.4E−07 | 2.0E−05 | 2.1E−08 | **6.1E−05** | 26.0 | 961.5 | 2.0 | 149.0 |
| IL6R-BP509/IL6R-L | E233D/G237D/P238D/V264I/S267A/H268E/P271G/E272D/Y296D | 1.1E−09 | 5.2E−07 | 7.9E−06 | 1.8E−08 | **2.3E−05** | 29.2 | 443.8 | 2.1 | 174.2 |
| IL6R-BP510/IL6R-L | G237D/P238D/V264I/S267A/H268E/P271G/E272P/A330R | 6.0E−09 | 1.7E−07 | 4.0E−06 | 3.8E−09 | **2.5E−05** | 43.5 | 1041.7 | 6.6 | 807.3 |
| IL6R-BP511/IL6R-L | G237D/P238D/V264I/S267A/H268E/P271G/E272P/Y296D/A330R | 6.0E−09 | 1.8E−07 | 4.3E−06 | 3.5E−09 | **7.1E−05** | 50.6 | 1235.6 | 6.3 | 890.8 |

Among the variants shown in Table 37, IL6R-BP253/IL6R-L added with the existing alterations that enhance the FcγRIIb binding exhibited FcγRIIb- and FcγRIIaR-binding activities increased to 277 times and 529 times those of IL6R-B3/IL6R-L prior to introduction of the alterations, respectively. Furthermore, the FcγRIa-binding activity of IL6R-BP253/IL6R-L was also greater than that of IL6R-B3/IL6R-L. Meanwhile, the FcγRIIaH binding and FcγRIIIaV binding of IL6R-BP253/IL6R-L were reduced as compared to those of IL6R-B3/IL6R-L. Among other variants, IL6R-BP436/IL6R-L and IL6R-BP438/IL6R-L showed an FcγRIa binding slightly enhanced as compared to that of IL6R-B3/IL6R-L prior to introduction of the alterations. All other variants showed a reduced FcγRIa binding. In addition, all the variants exhibited reduced FcγRIIaH binding and FcγRIIIaV binding as compared to those of IL6R-B3/IL6R-L.

Regarding IL6R-BP489/IL6R-L, IL6R-BP487/IL6R-L, IL6R-BP499/IL6R-L, IL6R-BP498/IL6R-L, IL6R-BP503/IL6R-L, IL6R-BP488/IL6R-L, IL6R-BP490/IL6R-L, IL6R-BP445/IL6R-L, IL6R-BP507/IL6R-L, IL6R-491/IL6R-L, IL6R-BP506/IL6R-L, IL6R-BP511/IL6R-L, IL6R-BP502/IL6R-L, IL6R-BP510/IL6R-L, IL6R-BP497/IL6R-L, IL6R-BP436/IL6R-L, IL6R-BP423/IL6R-L, IL6R-BP440/IL6R-L, IL6R-BP429/IL6R-L, IL6R-BP438/IL6R-L, IL6R-BP426/IL6R-L, IL6R-BP437/IL6R-L, IL6R-BP439/IL6R-L, IL6R-BP494/IL6R-L, IL6R-BP425/IL6R-L, and IL6R-BP495/IL6R-L, their FcγRIIb binding was stronger than that of IL6R-BP253/IL6R-L added with the existing alterations that enhance the FcγRIIb binding. Among these, when taking the binding of IL6R-B3/IL6R-L as 1, the enhancement level ranges from 321 times to 3100 times, corresponding to from IL6R-BP495/IL6R-L which showed the weakest FcγRIIb binding to IL6R-BP489/IL6R-L which showed the strongest binding.

The KD (IIaR)/KD (IIb) value of IL6R-BP479/IL6R-L, which was the lowest, was 16.1, while the value of IL6R-BP493/IL6R-L, which was the highest, was 52.1. Thus, the values of the two variants are higher than 0.2 of IL6R-BP253/IL6R-L. Meanwhile, the KD (IIaH)/KD (IIb) value of IL6R-BP480/IL6R-L, which was the lowest, was 107.7, while the value of IL6R-BP426/IL6R-L, which was the highest, was 8362. Thus, the values of the two variants are higher than 107.1 of IL6R-BP253/IL6R-L. The results described above demonstrate that the FcγRIIb-binding activity of all the variants shown in Table 37 has been increased as compared to the variants added with the existing alterations that enhance the FcγRIIb binding. Furthermore, regardless of whether the FcγR IIa is FcγR IIaR or FcγR IIaH, the FcγRIIb selectivity of the variants shown in Table 37 has been improved relative to the variants added with the existing alterations.

[Reference Example 25] Acquisition of Antibodies that Bind to IL-6 Receptor in Ca-Dependent Manner from a Human Antibody Library Using Phage Display Technology

(25-1) Preparation of a Phage Display Library for Naive Human Antibodies

A phage display library for human antibodies, consisting of multiple phages presenting the Fab domains of mutually different human antibody sequences, was constructed according to a method known to those skilled in the art using a poly A RNA prepared from human PBMC, and commercial human poly A RNA as a template.

(25-2) Acquisition of Antibody Fragments that Bind to Antigen in Ca-Dependent Manner from the Library by Bead Panning The constructed phage display library for naive human antibodies was subjected to initial selection through concentration of only antibody fragments having an antigen (IL-6 receptor)-binding ability or concentration of antibody fragments using a Ca concentration-dependent antigen (IL-6 receptor)-binding ability as an indicator. Concentration of antibody fragments using a Ca concentration-dependent antigen (IL-6 receptor)-binding ability as an indicator were conducted through elution of the phage library phages bound to IL-6 receptor in the presence of Ca ions with EDTA that chelates the Ca ions Biotinylated IL-6 receptor was used as an antigen.

Phages were produced from *Escherichia coli* carrying the constructed phage display phagemid. A phage library solution was obtained by diluting with TBS a phage population precipitated by adding 2.5 M NaCl/10% PEG to the *E. coli* culture solution in which the phages were produced. Subsequently, BSA and $CaCl_2$) were added to the phage library solution at a final concentration of 4% BSA and 1.2 mM of calcium ion concentration. A common panning method using an antigen immobilized on magnetic beads was referred to as a panning method (J. Immunol. Methods. (2008) 332 (1-2), 2-9; J. Immunol. Methods. (2001) 247 (1-2), 191-203; Biotechnol. Prog. (2002) 18(2) 212-20; Mol. Cell Proteomics (2003) 2 (2), 61-9). NeutrAvidin™ coated beads (Sera-Mag SpeedBeads™ NeutrAvidin™-coated) or Streptavidin coated beads (Dynabeads™ M-280 Streptavidin) were used as magnetic beads.

Specifically, 250 pmol of the biotin-labeled antigen was added to the prepared phage library solution to allow the contact of said phage library solution with the antigen at room temperature for 60 minutes. Magnetic beads, blocked with BSA, were added to be bound to antigen-phage complexes at room temperature for 15 minutes. The beads were washed once with 1 mL of 1.2 mM $CaCl_2$/TBS (TBS containing 1.2 mM $CaCl_2$). Subsequently, a phage solution was recovered by a general elution method to concentrate an antibody fragment having an IL-6 receptor-binding ability, or by elution from beads suspended in 2 mM EDTA/TBS (TBS containing 2 mM EDTA) to concentrate an antibody fragment using an IL-6 receptor-binding ability in a Ca concentration-dependent manner as an indicator. The recovered phage solution was added to 10 mL of the *E. coli* strain TG1 in a logarithmic growth phase (OD600 of 0.4-0.7). The *E. coli* was cultured with gentle stirring at 37° C. for 1 hour to allow the phages to infect the *E. coli*. The infected *E. coli* was inoculated into a 225 mm×225 mm plate. Subsequently, the phages were recovered from the culture medium of the *E. coli* after inoculation to prepare a phage library solution.

In the second and subsequent panning, the phages were enriched using the Ca-dependent binding ability as an indicator. Specifically, 40 pmol of the biotin-labeled antigen was added to the prepared phage library solution to allow the contact of the phage library with the antigen at room temperature for 60 minutes. Magnetic beads, blocked with BSA, were added to be bound to antigen-phage complexes at room temperature for 15 minutes. The beads were washed with 1 mL of 1.2 mM $CaCl_2$)/TBST and 1.2 mM $CaCl_2$)/TBS. Subsequently, the beads, to which 0.1 mL of 2 mM EDTA/TBS was added, were suspended at room temperature. Immediately after that, the beads were separated using a magnetic stand to collect a phage solution. The recovered phage solution was added to 10 mL of the *E. coli* strain TG1 in a logarithmic growth phase (OD600 of 0.4-0.7). The *E.*

*coli* was cultured with gentle stirring at 37° C. for 1 hour to allow the phages to infect the *E. coli*. The infected *E. coli* was inoculated into a 225 mm×225 mm plate. Subsequently, the phages were recovered from the culture medium of the *E. coli* after inoculation to collect a phage library solution. The panning using the Ca-dependent binding ability as an indicator was repeated several times.

(25-3) Examination by Phage ELISA

A phage-containing culture supernatant was collected according to a routine method (Methods Mol. Biol. (2002) 178, 133-145) from a single colony of *E. coli*, obtained as described above.

A culture supernatant containing phages, to which BSA and $CaCl_2$ were added at a final concentration of 4% BSA and 1.2 mM of calcium ion concentration was subjected to ELISA as described below. A StreptaWell 96 microtiter plate (Roche) was coated overnight with 100 μL of PBS containing the biotin-labeled antigen. Each well of said plate was washed with PBST to remove the antigen, and then the wells were blocked with 250 μL of 4% BSA-TBS for 1 hour or longer. Said plate with the prepared culture supernatant added to each well, from which the 4% BSA-TBS was removed, was allowed to stand undisturbed at 37° C. for 1 hour, allowing the binding of phage-presenting antibody to the antigen present in each well. To each well washed with 1.2 mM $CaCl_2$/TBST, 1.2 mM $CaCl_2$/TBS or 1 mM EDTA/TBS was added. The plate was allowed to stand undisturbed for 30 minutes at 37° C. for incubation. After washing with 1.2 mM $CaCl_2$/TBST, an HRP-conjugated anti-M13 antibody (Amersham Pharmacia Biotech) diluted with TBS at a final concentration of 4% BSA and 1.2 mM of ionized calcium concentration was added to each well, and the plate was incubated for 1 hour. After washing with 1.2 mM $CaCl_2$/TBST, the chromogenic reaction of the solution in each well with a TMB single solution (ZYMED) added was stopped by adding sulfuric acid. Subsequently, said developed color was measured by measuring absorbance at 450 nm.

As a result of the above phage ELISA, the base sequence of a gene amplified with specific primers and an antibody fragment identified as having a Ca-dependent antigen-binding ability as a template was analyzed.

(25-4) Antibody Expression and Purification

As a result of the above phage ELISA, a clone identified as having a Ca-dependent antigen-binding ability was introduced into an expression plasmid for animal cells. Antibodies were expressed as described below. FreeStyle™ 293-F strain (Invitrogen) derived from human fetal kidney cells was suspended in FreeStyle™ 293 Expression Medium (Invitrogen), followed by inoculation of 3 mL into each well of a 6-well plate at a cell density of $1.33\times10^6$ cells/mL. The prepared plasmid was introduced into the cells by lipofection. The cells were cultured for 4 days in a $CO_2$ incubator (37° C., 8% $CO_2$, 90 rpm). Antibodies were purified from the culture supernatant obtained above by a method known in the art using rProtein A Sepharose™ Fast Flow (Amersham Biosciences). Absorbance of the purified antibody solution was measured at 280 nm using a spectrophotometer. Antibody concentration was calculated from the measurements obtained using an extinction coefficient calculated by the PACE method (Protein Science (1995) 4, 2411-2423).

[Reference Example 26] Examination of Ca-Dependent Binding Ability of the Obtained Antibodies to Human IL-6 Receptor To examine whether or not the binding activities of antibodies 6RL #9-IgG1 [heavy chain SEQ ID NO: 117; light chain SEQ ID NO: 118] and FH4-IgG1 [heavy chain SEQ ID NO: 115; light chain SEQ ID NO: 116], obtained in Reference Example 25, to human IL-6 receptor are Ca-dependent, the kinetic analysis of the antigen-antibody reactions of these antibodies with human IL-6 receptor was conducted using a BIACORE™ T100 surface plasmon resonance system (GE Healthcare). H54/L28-IgG1 [heavy chain SEQ ID NO: 113; light chain SEQ ID NO: 114], described in WO 2009/125825, was used as a control antibody that has no Ca-dependent binding activity to human IL-6 receptor. The kinetic analysis of the antigen-antibody reactions was conducted in solutions with 2 mM and 3 μM calcium ion concentrations, set as high and low calcium ion concentration conditions, respectively. The antibody of interest was captured on Sensor chip CM4 (GE Healthcare) on which an appropriate amount of Protein A (Invitrogen) was immobilized by an amine coupling method. Two buffers [10 mM ACES, 150 mM NaCl, 0.05% (w/v) Tween 20, and 2 mM $CaCl_2$ (pH 7.4) or 10 mM ACES, 150 mM NaCl, 0.05% (w/v) Tween 20, and 3 μmol/L $CaCl_2$ (pH 7.4)] were used as running buffers. These buffers were used for diluting human IL-6 receptor. All the measurements were conducted at 37° C.

In the kinetic analysis of antigen-antibody reaction using H54L28-IgG1 antibody, the H54L28-IgG1 antibody captured on the sensor chip was allowed to interact with IL-6 receptor by injecting a diluent of IL-6 receptor and running buffer (blank) at a flow rate of 20 μL/min for 3 minutes. Subsequently, after the dissociation of IL-6 receptor was observed using running buffer at a flow rate of 20 μL/min for 10 minutes, the sensor chip was regenerated by injecting 10 mM glycine-HCl (pH 1.5) at a flow rate 30 μL/min for 30 seconds. Kinetics parameters, binding rate constant (ka) (1/Ms) and dissociation rate constant (kd) (1/s), were calculated from the sensorgrams obtained in the measurement. These values were used to calculate the dissociation constant (KD) (M) of the H54L28-IgG1 antibody for human IL-6 receptor. Each parameter was calculated using the BIACORE™ T100 Evaluation Software (GE Healthcare).

In the kinetic analysis of antigen-antibody reaction using FH4-IgG1 and 6RL #9-IgG1 antibodies, the FH4-IgG1 or 6RL #9-IgG1 antibody captured on the sensor chip was allowed to interact with IL-6 receptor by injecting a diluent of IL-6 receptor and running buffer (blank) at a flow rate of 5 μL/min for 15 minutes. Subsequently, the sensor chip was regenerated by injecting 10 mM glycine-HCl (pH 1.5) at a flow rate 30 μL/min for 30 seconds. Dissociation constants (KD) (M) were calculated from the sensorgrams obtained in the measurement, using a steady-state affinity model. Each parameter was calculated using the BIACORE™ T100 Evaluation Software (GE Healthcare).

The dissociation constants (KD) between each antibody and IL-6 receptor in the presence of 2 mM $CaCl_2$, determined by the above method, are shown in Table 38.

TABLE 38

| ANTIBODY | H54/L28-IgG1 | FH4-IgG1 | 6RL#9-IgG1 |
|---|---|---|---|
| kD (M) | 1.9E−9 | 5.9E−7 | 2.6E−7 |

The KD value of the H54/L28-IgG1 antibody under the condition of 3 μM Ca concentration can be calculated in the same manner as in the presence of 2 mM Ca concentration. Under the condition of 3 μM Ca concentration, FH4-IgG1 and 6RL #9-IgG1 antibodies were barely observed to be bound to IL-6 receptor, thus the calculation of KD values by the method described above is difficult. However, the KD values of these antibodies under the condition of 3 μM Ca concentration can be estimated using Equation 1 (BIACORE™ T100 Software Handbook, BR-1006-48, AE 01/2007) described below.

$$R_{eq}=C\times R\max/(KD+C)+RI \quad \text{[Equation 1]}$$

The meaning of each parameter in the aforementioned [Equation 1] is as follows:

Req (RU): Steady state binding levels
Rmax (RU): Analyte binding capacity of the surface
RI (RU): Bulk refractive index contribution in the sample
C (M): Analyte concentration
KD (M): Equilibrium dissociation constant The approximate results of dissociation constant KD values for the antibodies and IL-6 receptor at a Ca concentration of 3 μM, estimated using the above-described [Equation 1], are shown in Table 39. In Table 39, the Req, Rmax, RI, and C values are estimated based on the assay result.

TABLE 39

| ANTIBODY | H54/L28-IgG1 | FH4-IgG1 | 6RL#9-IgG1 |
|---|---|---|---|
| Req (RU) | | 5 | 10 |
| Rmax (RU) | | 39 | 72 |
| RI (RU) | | 0 | 0 |
| C (M) | | 5E−06 | 5E−06 |
| KD (M) | 2.2E−9 | 3.4E−05 | 3.1E−05 |

Based on the findings described above, it was predicted that the KD between IL-6 receptor and FH4-IgG1 antibody or 6RL #9-IgG1 antibody was increased by about 60 or 120 times (the affinity was reduced by 60 or 120 times or more) when the concentration of $CaCl_2$ in the buffer was decreased from 2 mM to 3 μM.

Table 40 summarizes the KD values to IL-6 receptor at $CaCl_2$ concentrations of 2 mM and 3 μM and the Ca dependency for the three types of antibodies H54/L28-IgG1, FH4-IgG1, and 6RL #9-IgG1.

TABLE 40

| ANTIBODY | H54/L28-IgG1 | FH4-IgG1 | 6RL#9-IgG1 |
|---|---|---|---|
| KD (M) (2 mM $CaCl_2$) | 1.9E−9 | 5.9E−7 | 2.6E−7 |
| KD (M) (3 μM $CaCl_2$) | 2.2E−9 | 3.4E−5 OR MORE | 3.1E−5 OR MORE |
| Ca DEPENDENCY | ABOUT THE SAME | ABOUT 60 TIMES OR MORE | ABOUT 120 TIMES OR MORE |

No difference in the binding of the H54/L28-IgG1 antibody to IL-6 receptor due to the difference in Ca concentration was observed. On the other hand, the binding of FH4-IgG1 and 6RL #9-IgG1 antibodies to IL-6 receptor was observed to be significantly attenuated under the condition of the low Ca concentration (Table 40).

[Reference Example 27] Examination of Calcium Ion Binding to the Antibody Obtained Subsequently, the intermediate temperature of thermal denaturation (Tm value) was measured by differential scanning calorimetry (DSC) as an indicator for examining calcium ion binding to the antibody (MicroCal VP-Capillary DSC, MicroCal). The intermediate temperature of thermal denaturation (Tm value) is an indicator of stability. The intermediate temperature of thermal denaturation (Tm value) becomes higher when a protein is stabilized through calcium ion binding, as compared with no calcium ion binding (J. Biol. Chem. (2008) 283, 37, 25140-25149). The binding activity of calcium ion to antibody was examined by examining changes in the Tm value of the antibody depending on the changes in the calcium ion concentration of the antibody solution. The purified antibody was subjected to dialysis (EasySEP, TOMY) using an external solution of 20 mM Tris-HCl, 150 mM NaCl, and 2 mM $CaCl_2$ (pH 7.4), or 20 mM Tris-HCl, 150 mM NaCl, and 3 μM $CaCl_2$ (pH 7.4). DSC measurement was conducted at a heating rate of 240° C./hr from 20 to 115° C. using an antibody solution prepared at about 0.1 mg/mL with the dialysate as a test substance. The intermediate temperatures of thermal denaturation (Tm values) of the Fab domains of each antibody, calculated based on the denaturation curve obtained by DSC, are shown in Table 41.

TABLE 41

| | CALCIUM ION CONCENTRATION | | ΔTm (° C.) |
|---|---|---|---|
| ANTIBODY | 3 μM | 2 mM | 2 mM − 3 μM |
| H54/L28-IgG1 | 92.87 | 92.87 | 0.00 |
| FH4-IgG1 | 74.71 | 78.97 | 4.26 |
| 6RL#9-IgG1 | 77.77 | 78.98 | 1.21 |

From the results shown in Table 41, it is indicated that the Tm values of the Fab of the FH4-IgG1 and 6RL #9-IgG1 antibodies, which show a calcium-dependent binding ability, varied with changes in the calcium ion concentration, while the Tm value of the Fab of the H54/L28-IgG1 antibody which shows no calcium-dependent binding ability did not vary with changes in the calcium ion concentration. The variation in the Tm values of the Fab of the FH4-IgG1 and 6RL #9-IgG1 antibodies demonstrates that calcium ions bound to these antibodies to stabilize the Fab portions. The above results show that calcium ions bound to the FH4-IgG1 and 6RL #9-IgG1 antibodies, while no calcium ion bound to the H54/L28-IgG1 antibody.

[Reference Example 28] Identification of Calcium Ion-Binding Site in Antibody 6RL #9 by X-Ray Crystal Structure Analysis (28-1) X-Ray Crystal Structure Analysis As described in Reference Example 27, the measurements of thermal denaturation temperature Tm suggested that antibody 6RL #9 binds to calcium ion. However, it was unpredictable which portion of antibody 6RL #9 binds to calcium ion. Then, by using the technique of X-ray crystal structure analysis, residues of antibody 6RL #9 that interact with calcium ion were identified.

(28-2) Expression and Purification of Antibody 6RL #9

Antibody 6RL #9 was expressed and purified for X-ray crystal structure analysis. Specifically, animal expression plasmids constructed to be capable of expressing the heavy chain (SEQ ID NO: 117) and light chain (SEQ ID NO: 118) of antibody 6RL #9 were introduced transiently into animal cells. The constructed plasmids were introduced by the lipofection method into cells of human fetal kidney cell-derived FreeStyle™ 293-F cells (Invitrogen) suspended in 800 ml of the FreeStyle™ 293 Expression Medium (Invitrogen) (final cell density: $1\times10^6$ cells/mL). The plasmid-introduced cells were cultured in a $CO_2$ incubator (37° C., 8% $CO_2$, 90 rpm) for five days. From the culture supernatant obtained as described above, antibodies were purified by a method known to those skilled in the art using the rProtein A Sepharose™ Fast Flow (Amersham Biosciences). Absorbance at 280 nm of purified antibody solutions was measured using a spectrophotometer. Antibody concentrations were calculated from the measured values using an extinction coefficient calculated by the PACE method (Protein Science (1995) 4, 2411-2423).

(28-3) Purification of Antibody 6RL #9 Fab Fragment

Antibody 6RL #9 was concentrated to 21 mg/ml using an ultrafilter with a molecular weight cutoff of 10,000 MWCO. A 5 mg/mL antibody sample (2.5 mL) was prepared by diluting the antibody solution using 4 mM L-cysteine/5 mM EDTA/20 mM sodium phosphate buffer (pH 6.5). 0.125 mg of papain (Roche Applied Science) was added to the sample. After stirring, the sample was incubated at 35° C. for two hours. After incubation, a tablet of Protease Inhibitor Cocktail Mini, EDTA-free (Roche Applied Science) was dissolved in 10 ml of 25 mM MES buffer (pH 6) and added to the sample. The sample was incubated on ice to stop the papain proteolytic reaction. Then, the sample was loaded onto a 1-ml cation-exchange column HiTrap SP HP (GE Healthcare) equilibrated with 25 mM MES buffer (pH 6), downstream of which a 1-ml HiTrap MabSelect Sure Protein A column (GE Healthcare) was connected in tandem. A purified fraction of the Fab fragment of antibody 6RL #9 was obtained by performing elution with a linear NaCl concentration gradient up to 300 mM in the above-described buffer. Then, the resulting purified fraction was concentrated to about 0.8 ml using a 5000 MWCO ultrafilter. The concentrate was loaded onto a gel filtration column Superdex® 200 10/300 GL (GE Healthcare) equilibrated with 100 mM HEPES buffer (pH 8) containing 50 mM NaCl. The purified Fab fragment of antibody 6RL #9 for crystallization was eluted from the column using the same buffer. All the column treatments described above were carried out at a low temperature of 6 to 7.5° C.

(28-4) Crystallization of the Antibody 6RL #9 Fab Fragment in the Presence of Ca Seed crystals of the 6RL #9 Fab fragment were prepared in advance under general conditions. Then, the purified Fab fragment of antibody 6RL #9 in 5 mM $CaCl_2$ was concentrated to 12 mg/ml with a 5000 MWCO ultrafilter. Next, the sample concentrated as described above was crystallized by the hanging drop vapor diffusion method using 100 mM HEPES buffer (pH 7.5) containing 20% to 29% PEG4000 as a reservoir solution. The above-described seed crystals were crushed in 100 mM HEPES buffer (pH 7.5) containing 29% PEG4000 and 5 mM $CaCl_2$, and serially diluted to 100 to 10,000 folds. Then, 0.2 μL of diluted solutions were combined with a mixture of 0.8 μL of the reservoir solution and 0.8 μL of the concentrated sample to prepare crystallization drops on a glass cover slide. The crystallization drops were allowed to stand at 20° C. for two to three days to prepare thin plate-like crystals. X-ray diffraction data were collected using the crystals.

(28-5) Crystallization of the Antibody 6RL #9 Fab Fragment in the Absence of Ca

The purified Fab fragment of antibody 6RL #9 was concentrated to 15 mg/ml using a 5000 MWCO ultrafilter. Then, the sample concentrated as described above was crystallized by the hanging drop vapor diffusion method using 100 mM HEPES buffer (pH 7.5) containing 18% to 25% PEG4000 as a reservoir solution. Crystals of the antibody 6RL #9 Fab fragment obtained in the presence of Ca were crushed in 100 mM HEPES buffer (pH 7.5) containing 25% PEG4000, and serially diluted to 100 to 10,000 folds. Then, 0.2 μL of diluted solutions were combined with a mixture of 0.8 μL of the reservoir solution and 0.8 μL of the concentrated sample to prepare crystallization drops on a glass cover slide. The crystallization drops were allowed to stand at 20° C. for two to three days to prepare thin plate-like crystals. X-ray diffraction data were collected using the crystals.

(28-6) X-Ray Diffraction Data Measurement of Fab Fragment Crystal from Antibody 6RL #9 in the Presence of Ca Crystals of the Fab fragment of antibody 6RL #9 prepared in the presence of Ca were soaked into 100 mM HEPES buffer (pH 7.5) solution containing 35% PEG4000 and 5 mM $CaCl_2$). The single crystal was fished out of the exterior solution using a pin with attached tiny nylon loop, and frozen in liquid nitrogen. X-ray diffraction data of the frozen crystal was collected from beam line BL-17A of the Photon Factory in the High Energy Accelerator Research Organization. The frozen crystal was constantly placed in a nitrogen stream at −178° C. to maintain in a frozen state during the measurement. A total of 180 diffraction images were collected using the CCD detector Quantum315r (ADSC) attached to the beam line with rotating the crystal 1° at a time. Lattice constant determination, diffraction spot indexing, and diffraction data analysis were performed using programs Xia2 (CCP4 Software Suite), XDS Package (Walfgang Kabsch), and Scala (CCP4 Software Suite). Finally, diffraction intensity data up to 2.2 Å resolution was obtained. The crystal belongs to the space group $P2_12_12_1$ with lattice constant a=45.47 Å, b=79.86 Å, c=116.25 Å, α=90°, β=90°, and γ=90°.

(28-7) X-Ray Diffraction Data Measurement of the Fab Fragment Crystal from Antibody 6RL #9 in the Absence of Ca Crystals of the Fab fragment of antibody 6RL #9 prepared in the absence of Ca were soaked in 100 mM HEPES buffer (pH 7.5) solution containing 35% PEG4000. The single crystal was fished out of the exterior solution using a pin with attached tiny nylon loop, and frozen in liquid nitrogen. X-ray diffraction data of the frozen crystal was collected from beam line BL-5A of the Photon Factory in the High Energy Accelerator Research Organization. The frozen crystal was constantly placed in a nitrogen stream at −178° C. to maintain in a frozen state during the measurement. A total of 180 diffraction images were collected using the CCD detector Quantum210r (ADSC) attached to the beam line with rotating the crystal 1° at a time. Lattice constant determination, diffraction spot indexing, and diffraction data analysis were performed using programs Xia2 (CCP4 Software Suite), XDS Package (Walfgang Kabsch), and Scala (CCP4 Software Suite). Finally, diffraction intensity data up to 2.3 Å resolution was obtained. The crystal belongs to the space group $P2_12_12_1$ with lattice constant a=45.40 Å, b=79.63 Å, c=116.07 Å, α=90°, β=90°, γ=90°, and thus is structurally identical to the crystal prepared in the presence of Ca.

(28-8) Structural Analysis of the Fab Fragment Crystal from Antibody 6RL #9 in the Presence of Ca The crystal structure of the antibody 6RL #9 Fab fragment in the presence of Ca was determined by a molecular replacement method using the Phaser program (CCP4 Software Suite). The number of molecules in an asymmetrical unit was estimated to be one from the size of crystal lattice and molecular weight of the antibody 6RL #9 Fab fragment. Based on the primary sequence homology, a portion of amino acid positions 112 to 220 from A chain and a portion of amino acid positions 116 to 218 from B chain in the conformational coordinate of PDB code 1ZA6 were used as model molecules for analyzing the CL and CH1 regions.

Then, a portion of amino acid positions 1 to 115 from B chain in the conformational coordinate of PDB code 1ZA6 was used as a model molecule for analyzing the VH region. Finally, a portion of amino acid positions 3 to 147 of the light chain in the conformational coordinate of PDB code 2A9M was used as a model molecule for analyzing the VL region. Based on this order, an initial structure model for the antibody 6RL #9 Fab fragment was obtained by determining from translation and rotation functions the positions and orientations of the model molecules for analysis in the crystal lattice. The crystallographic reliability factor R for the reflection data at 25 to 3.0 Å resolution was 46.9% and Free R was 48.6% after rigid body refinement where the VH, VL, CH1, and CL domains were each allowed to deviate from the initial structure model. Then, model refinement was achieved by repeating structural refinement using program Refmac5 (CCP4 Software Suite) followed by model revision performed using program Coot (Paul Emsley) with reference to the Fo-Fc and 2Fo-Fc electron density maps where the coefficients Fo-Fc and 2Fo-Fc were calculated using experimentally determined structural factor Fo, structural factor Fc calculated based on the model, and the phases. The final refinement was carried out using program Refmac5 (CCP4 Software Suite) based on the Fo-Fc and 2Fo-Fc electron density maps by adding water molecule and Ca ion into the model. With 21,020 reflection data at 25 to 2.2 Å resolution, eventually the crystallographic reliability factor R became 20.0% and free R became 27.9% for the model consisting of 3440 atoms.

(28-9) Structural Analysis of the Fab Fragment Crystal from Antibody 6RL #9 in the Absence of Ca The crystal structure of the antibody 6RL #9 Fab fragment in the absence of Ca was determined based on the structure of the crystal prepared in the presence of Ca. Water and Ca ion molecules were omitted from the conformational coordinate of the crystal of the antibody 6RL #9 Fab fragment prepared in the presence of Ca. The crystallographic reliability factor R for the data of reflection at 25 to 3.0 Å resolution was 30.3% and Free R was 31.7% after the rigid body refinement where the VH, VL, CHI, and CL domains were each allowed to deviate. Then, model refinement was achieved by repeating structural refinement using program Refmac5 (CCP4 Software Suite) followed by model revision performed using program Coot (Paul Emsley) with reference to the Fo-Fc and 2Fo-Fc electron density maps where the coefficients Fo-Fc and 2Fo-Fc were calculated using experimentally determined structural factor Fo, structural factor Fc calculated based on the model, and the phases. The final refinement was carried out using program Refmac5 (CCP4 Software Suite) based on the Fo-Fc and 2Fo-Fc electron density maps by adding water molecule into the model. With 18,357 reflection data at 25 to 2.3 Å resolution, eventually the crystallographic reliability factor R became 20.9% and free R became 27.7% for the model consisting of 3351 atoms.

Figure 54:
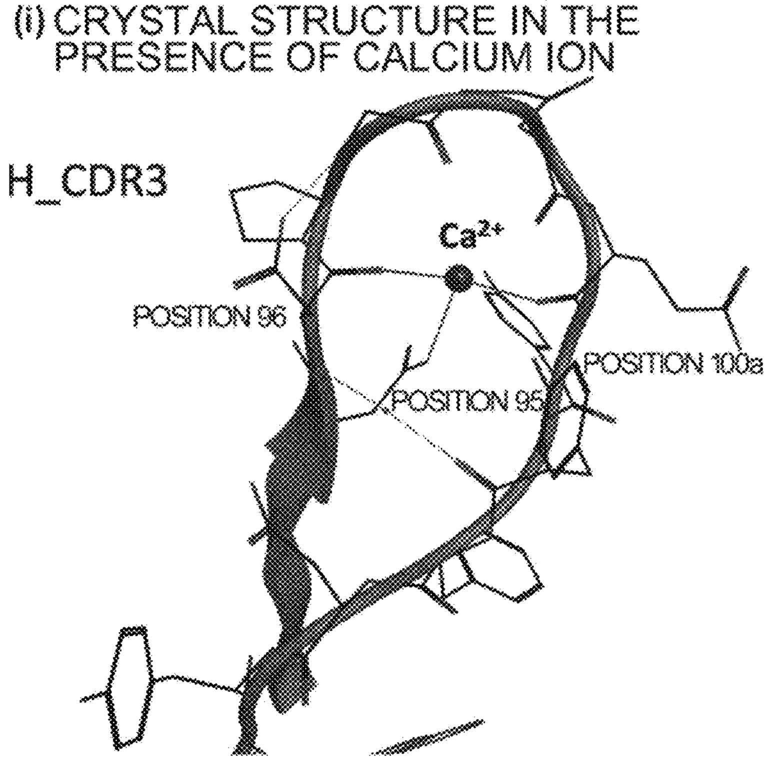
FIG. 54 shows the structure of the heavy chain CDR3 of the 6RL #9 antibody Fab fragment determined by X-ray crystal structure analysis. (i) shows the crystal structure of the heavy chain CDR3 obtained under a crystallization condition in the presence of calcium ion. (ii) shows the crystal structure of the heavy chain CDR3 obtained under a crystallization condition in the absence of calcium ion.
Figure 54:
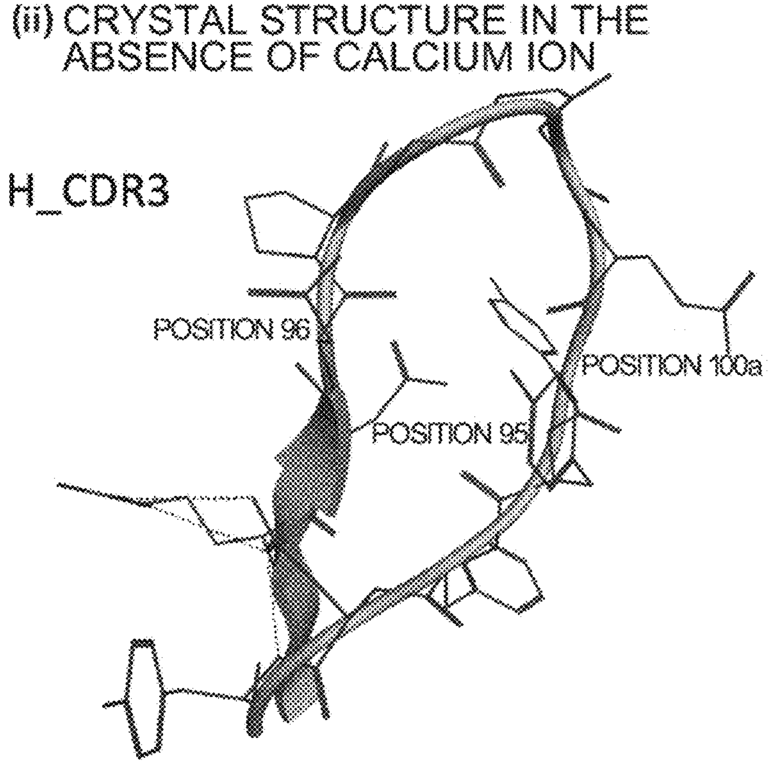

(28-10) Comparison of X-Ray Crystallographic Diffraction Data of the Fab Fragments of Antibody 6RL #9 Between in the Presence and Absence of Ca When the crystal structures of the Fab fragments of antibody 6RL #9 are compared between in the presence and absence of Ca, significant changes are seen in the heavy chain CDR3. The structure of the heavy chain CDR3 of the antibody 6RL #9 Fab fragment determined by X-ray crystal structure analysis is shown in FIG. 54. Specifically, a calcium ion resided at the center of the heavy chain CDR3 loop region of the antibody 6RL #9 Fab fragment crystal prepared in the presence of Ca. The calcium ion was assumed to interact with positions 95, 96, and 100a (Kabat numbering) of the heavy chain CDR3. It was believed that the heavy chain CDR3 loop which is important for the antigen binding was stabilized by calcium binding in the presence of Ca, and became an optimum structure for antigen binding. There is no report demonstrating that calcium binds to the antibody heavy chain CDR3. Thus, the calcium-bound structure of the antibody heavy chain CDR3 is a novel structure.

The calcium-binding motif present in the heavy chain CDR3, revealed in the structure of the Fab fragment of the 6RL #9 antibody may also become a new design element for the Ca library for obtaining antigen-binding domain included in the antigen-binding molecule of the present invention whose antigen-binding activity varies depending on the calcium ion concentration. The calcium-binding motif was introduced into a light chain variable region in later-described Reference Examples 38 and 39, and for example, a library containing the heavy chain CDR3 of the 6RL #9 antibody and flexible residues in other CDRs including the light chain is thought to be possible.

[Reference Example 29] Preparation of Antibodies that Bind to IL-6 in a Ca-Dependent Manner from a Human Antibody Library Using Phage Display Techniques (29-1) Construction of a Phage Display Library of Naive Human Antibodies A human antibody phage display library containing multiple phages that display various human antibody Fab domain sequences was constructed by a method known to those skilled in the art using, as a template, polyA RNA prepared from human PBMC, commercially available human polyA RNA, and such.

(29-2) Preparation of Antibody Fragments that Bind to the Antigen in a Ca-Dependent Manner from Library by Bead Panning Primary selection from the constructed phage display library of naive human antibodies was carried out by enriching antibody fragments that have antigen (IL-6)-binding activity. The antigen used was biotin-labeled IL-6.

Phages were produced from *E. coli* carrying the constructed phagemid for phage display. To precipitate the phages produced by *E. coli,* 2.5 M NaCl/10% PEG was added to the *E. coli* culture medium. The phage fraction was diluted with TBS to prepare a phage library solution. Then, BSA and $CaCl_2$ were added the phage library solution at final concentrations of 4% BSA and 1.2 mM calcium ion concentration, respectively. The panning method used was a conventional panning method using antigen-immobilized magnetic beads (J. Immunol. Methods. (2008) 332(1-2): 2-9; J. Immunol. Methods. (2001) 247(1-2): 191-203; Biotechnol. Prog. (2002) 18(2): 212-20; Mol. Cell Proteomics (2003) 2(2): 61-9). The magnetic beads used were NeutrAvidin™-coated beads (Sera-Mag SpeedBeads™ NeutrAvidin™-coated) and Streptavidin-coated beads (Dynabeads™ M-280 Streptavidin).

Specifically, 250 pmol of the biotin-labeled antigen was added to the prepared phage library solution. Thus, the solution was contacted with the antigen at room temperature for 60 minutes. Magnetic beads blocked with BSA were added, and the antigen-phage complex was allowed to bind to the magnetic beads at room temperature for 15 minutes. The beads were washed three times with 1.2 mM $CaCl_2$/TBST (TBST containing 1.2 mM $CaCl_2$), and then twice with 1 ml of 1.2 mM $CaCl_2$/TBS (TBS containing 1.2 mM $CaCl_2$). Thereafter, 0.5 ml of 1 mg/ml trypsin was added to the beads. After 15 minutes of dispersion at room temperature, the beads were immediately separated using a magnetic stand to collect a phage solution. The prepared phage solution was added to 10 ml of *E. coli* of stain TG1 at the logarithmic growth phase (OD600=0.4 to 0.7). The *E. coli* was cultured with gentle stirring at 37° C. for one hour to infect the phages. The infected *E. coli* was seeded in a plate (225 mm×225 mm). Then, phages were collected from the culture medium of the seeded *E. coli* to prepare a phage library solution.

In the second round and subsequent panning, phages were enriched using the Ca-dependent binding activity as an indicator. Specifically, 40 pmol of the biotin-labeled antigen was added to the prepared phage library solution. Thus, the phage library was contacted with the antigen at room temperature for 60 minutes. Magnetic beads blocked with BSA were added, and the antigen-phage complex was allowed to bind to the magnetic beads at room temperature for 15 minutes. The beads were washed with 1 ml of 1.2 mM $CaCl_2$/TBST and 1.2 mM $CaCl_2$/TBS. Next, 0.1 ml of 2 mM EDTA/TBS was added to the beads. After dispersion at room temperature, the beads were immediately separated using a magnetic stand to collect a phage solution. The pIII protein (helper phage-derived protein pIII) was cleaved from phages that did not display Fab by adding 5 μl of 100 mg/ml trypsin to the collected phage solution to eliminate the ability of phages displaying no Fab to infect *E. coli*. Phages collected from the trypsinized phage solution were added to 10 ml of *E. coli* cells of the TG1 strain at the logarithmic growth phase (OD600=0.4 to 0.7). The *E. coli* was cultured while gently stirring at 37° C. for one hour to infect phage. The infected *E. coli* was seeded in a plate (225 mm×225 mm). Then, phages were collected from the culture medium of the seeded *E. coli* to prepare a phage library solution. Panning was performed three times using the Ca-dependent binding activity as an indicator.

(29-3) Assessment by Phage ELISA

Culture supernatants containing phages were collected from single colonies of *E. coli* obtained by the method described above according to a conventional method (Methods Mol. Biol. (2002) 178, 133-145).

BSA and $CaCl_2$ were added at final concentrations of 4% BSA and 1.2 mM calcium ion concentration, respectively, to the phage-containing culture supernatants. The supernatants were subjected to ELISA by the following procedure. A StreptaWell 96-well microtiter plate (Roche) was coated overnight with 100 μl of PBS containing the biotin-labeled antigen. The antigen was removed by washing each well of the plate with PBST. Then, the wells were blocked with 250 μl of 4% BSA-TBS for one hour or more. After removal of 4% BSA-TBS, the prepared culture supernatants were added to the each well. The plate was incubated at 37° C. for one hour so that the antibody-displaying phages were allowed to bind to the antigen on each well. After each well was washed with 1.2 mM $CaCl_2$/TBST, 1.2 mM $CaCl_2$/TBS or 1 mM EDTA/TBS was added. The plate was left for incubation at 37° C. for 30 minutes. After washing with 1.2 mM $CaCl_2$/TBST, an HRP-conjugated anti-M13 antibody (Amersham Pharmacia Biotech) diluted with TBS containing BSA and calcium ion at final concentrations of 4% BSA and 1.2 mM calcium ion concentration was added to each well, and the plate was incubated for one hour. After washing with 1.2 mM $CaCl_2$/TBST, the TMB single solution (ZYMED) was added to each well. The chromogenic reaction in the solution of each well was stopped by adding sulfuric acid. Then, the developed color was assessed by measuring absorbance at 450 nm.

From the isolated 96 clones, antibody 6KC4-1 #85 having Ca-dependent IL-6-binding activity was obtained by phage ELISA. Using antibody fragments that were predicted to have a Ca-dependent antigen-binding activity based on the result of the phage ELISA described above as a template, genes were amplified with specific primers and their sequences were analyzed. The heavy-chain and light-chain variable region sequences of antibody 6KC4-1 #85 are shown in SEQ ID NOs: 119 and 120, respectively. The polynucleotide encoding the heavy-chain variable region of antibody 6KC4-1 #85 (SEQ ID NO: 119) was linked to a polynucleotide encoding an IgG1-derived sequence by PCR method. The resulting DNA fragment was inserted into an animal cell expression vector to construct an expression vector for the heavy chain of SEQ ID NO: 121. A polynucleotide encoding the light-chain variable region of antibody 6KC4-1 #85 (SEQ ID NO: 120) was linked to a polynucleotide encoding the constant region of the natural Kappa chain (SEQ ID NO: 54) by PCR. The linked DNA fragment was inserted into an animal cell expression vector. Sequences of the constructed variants were confirmed by a method known to those skilled in the art.

(29-4) Expression and Purification of Antibodies

Clone 6KC4-1 #85 that was predicted to have a Ca-dependent antigen-binding activity based on the result of phage ELISA was inserted into animal cell expression plasmids. Antibody expression was carried out by the following method. Human fetal kidney cell-derived FreeStyle™ 293-F cells (Invitrogen) were suspended in the FreeStyle™ 293 Expression Medium (Invitrogen), and plated at a cell density of $1.33\times10^6$ cells/ml (3 ml) into each well of a 6-well plate. The prepared plasmids were introduced into cells by a lipofection method. The cells are cultured for four days in a $CO_2$ incubator (37° C., 8% $CO_2$, 90 rpm). From the culture supernatants, antibodies were purified using the rProtein A Sepharose™ Fast Flow (Amersham Biosciences) by a method known to those skilled in the art. Absorbance at 280 nm of the purified antibody solutions was measured using a spectrophotometer. Antibody concentrations were calculated from the determined values using an extinction coefficient calculated by the PACE method (Protein Science (1995) 4: 2411-2423).

[Reference Example 30] Assessment of Antibody 6KC4-1 #85 for Calcium Ion Binding Calcium-dependent antigen-binding antibody 6KC4-1 #85 which was isolated from a human antibody library was assessed for its calcium binding. Whether the measured Tm value varies depending on the ionized calcium concentration condition was assessed according to the method described in Reference Example 27.

Tm values for the Fab domain of antibody 6KC4-1 #85 are shown in Table 42. As shown in Table 42, the Tm value of the 6KC4-1 #85 antibody Fab domain varied depending on the calcium ion concentration. This demonstrates that antibody 6KC4-1 #85 binds to calcium.

TABLE 42

| | CALCIUM ION CONCENTRATION | | ΔTm (° C.) |
|---|---|---|---|
| ANTIBODY | 3 μM | 2 mM | 2 mM − 3 μM |
| 6KC4-1#85 | 71.49 | 75.39 | 3.9 |

[Reference Example 31] Identification of Calcium Ion-Binding Site in Antibody 6KC4-1 #85

As demonstrated in Reference Example 30, antibody 6KC4-1 #85 binds to calcium ion. However, 6KC4-1 #85 does not have a calcium-binding motif such as the hVk5-2 sequence which was revealed from assessment to have a calcium-binding motif. Then, whether calcium ion binds to either or both of the heavy chain and the light chain of antibody 6KC4-1 #85 was confirmed by assessing the calcium ion binding of altered antibodies resulting from exchanging the heavy chain and light chain of 6KC4-1 #85 respectively with those of an anti-glypican 3 antibody (heavy chain sequence GC_H (SEQ ID NO: 55), light chain sequence GC_L (SEQ ID NO: 56)) which does not bind calcium ion. The Tm values of altered antibodies measured according to the method described in Reference Example 27 are shown in Table 43. The result suggests that the heavy chain of antibody 6KC4-1 #85 binds to calcium, because the Tm values of the altered antibody having the heavy chain of antibody 6KC4-1 #85 changed depending on calcium ion concentration.

TABLE 43

| | | CALCIUM ION CONCENTRATION | | ΔTm (° C.) 2 mM − |
|---|---|---|---|---|
| HEAVY CHAIN | LIGHT CHAIN | 3 μM | 2 mM | 3 μM |
| 6KC4-1#85 | 6KC4-1#85 | 71.46 | 75.18 | 3.72 |
| 6KC4-1#85 | GC_L | 78.87 | 80.01 | 1.14 |
| GC_H | 6KC4-1#85 | 75.69 | 75.94 | 0.25 |
| GC_H | GC_L | 79.94 | 80.01 | 0.07 |

Thus, to further identify residues responsible for the calcium ion binding of the heavy chain of antibody 6KC4-1 #85, altered heavy chains (6_H1-11 (SEQ ID NO: 126), 6_H1-12 (SEQ ID NO: 127), 6_H1-13 (SEQ ID NO: 128), 6_H1-14 (SEQ ID NO: 129), 6_H1-15 (SEQ ID NO: 130)) or altered light chains (6_L1-5 (SEQ ID NO: 131) and 6_L1-6 (SEQ ID NO: 132)) were constructed by substituting an Asp (D) residue in the CDR of antibody 6KC4-1 #85 with an Ala (A) residue which does not participate in the binding or chelation of calcium ion. By the method described in Reference Example 29, altered antibodies were purified from the culture media of animal cells introduced with expression vectors carrying the altered antibody genes. The purified altered antibodies were assessed for their calcium binding according to the method described in Reference Example 27. The measurement result is shown in Table 44. As shown in Table 44, substitution of an Ala residue for the residue at position 95 or 101 (Kabat numbering) in the heavy chain CDR3 of antibody 6KC4-1 #85 resulted in loss of the calcium-binding activity of antibody 6KC4-1 #85. This suggests that these residues are responsible for calcium binding. The calcium-binding motif located at the base of the CDR3 loop in the heavy chain of antibody 6KC4-1 #85, which was found based on the calcium binding capacity of the antibody altered from antibody 6KC4-1 #85, can be a new factor for designing Ca libraries which are used to obtain antigen-binding domains whose antigen-binding activity changes depending on calcium ion concentration and which are to be contained in antigen-binding molecules of the present invention. In Reference Examples 38 and 39 below, calcium-binding motifs were introduced into the light chain variable region. Meanwhile, such libraries include, for example, those containing the heavy chain CDR3 from antibody 6KC4-1 #85 and flexible residues in the CDRs other than the heavy chain CDR3 but including the light chain CDRs.

TABLE 44

| | | | CALCIUM ION CONCENTRATION | | Δ Tm (° C.) |
|---|---|---|---|---|---|
| HEAVY CHAIN | LIGHT CHAIN | ALTERED RESIDUE | 3 μM | 2 mM | 2 mM − 3 μM |
| 6KC4-1#85 | 6KC4-1#85 | WILD-TYPE | 71.49 | 75.39 | 3.9 |
| 6H1-11 | 6KC4-1#85 | H CHAIN POSITION 61 (Kabat NUMBERING) | 71.73 | 75.56 | 3.83 |
| 6H1-12 | 6KC4-1#85 | H CHAIN POSITION 95 (Kabat NUMBERING) | 72.9 | 73.43 | 0.53 |
| 6H1-13 | 6KC4-1#85 | H CHAIN POSITION 100a (Kabat NUMBERING) | 70.94 | 76.25 | 5.31 |
| 6H1-14 | 6KC4-1#85 | H CHAIN POSITION 100g (Kabat NUMBERING) | 73.95 | 75.14 | 1.19 |
| 6H1-15 | 6KC4-1#85 | H CHAIN POSITION 101 (Kabat NUMBERING) | 65.37 | 66.25 | 0.87 |
| 6KC4-1#85 | 6L1-5 | L CHAIN POSITION 50 (Kabat NUMBERING) | 71.92 | 76.08 | 4.16 |
| 6KC4-1#85 | 6L1-6 | L CHAIN POSITION 92 (Kabat NUMBERING) | 72.13 | 78.74 | 6.61 |

[Reference Example 32] Examination of Effects of Ca-Dependent Binding Antibody on Plasma Retention of Antigen Using Normal Mice (32-1) In Vivo Test Using Normal Mice To a normal mouse (C57BL/6J mouse, Charles River Japan), hsIL-6R (soluble human IL-6 receptor prepared in Reference Example 3) alone was administered, or hsIL-6R and anti-human IL-6 receptor antibody were administered simultaneously to examine the kinetics of the hsIL-6R and anti-human IL-6 receptor antibody in vivo. A single dose (10 mL/kg) of the hsIL-6R solution (5 µg/mL) or a mixture of hsIL-6R and anti-human IL-6 receptor antibody was administered into the tail vein. The above H54/L28-IgG1, 6RL #9-IgG1, and FH4-IgG1 were used as anti-human IL-6 receptor antibodies.

The hsIL-6R concentration in all the mixtures is 5 µg/mL. The concentrations of anti-human IL-6 receptor antibody vary with the antibodies: 0.1 mg/mL for H54/L28-IgG1 and 10 mg/mL for 6RL #9-IgG1 and FH4-IgG1. At this time, it was thought that most of the hsIL-6Rs bind to the antibody because the anti-human IL-6 receptor antibody exists in a sufficient or excessive amount for hsIL-6R. Blood samples were collected at 15 minutes, 7 hours and 1, 2, 4, 7, 14, 21, and 28 days after the administration. The blood samples obtained were immediately centrifuged for 15 minutes at 4° C. and 12,000 rpm to separate plasma. The separated plasma was stored in a freezer set to −20° C. or lower until the time of measurement.

Figure 55:
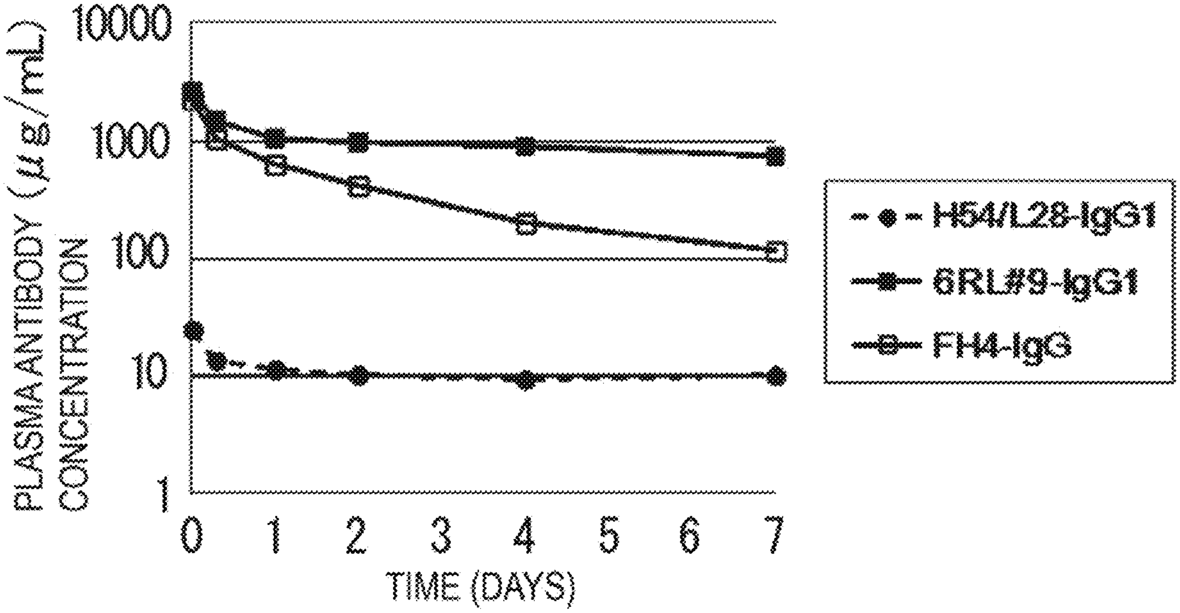
FIG. 55 shows a time course of the plasma concentration of each antibody in normal mice administered with antibody H54/L28-IgG1, FH4-IgG1, or 6RL #9-IgG1.

(32-2) Determination of Plasma Anti-Human IL-6 Receptor Antibody Concentration in Normal Mice by ELISA The plasma concentration of anti-human IL-6 receptor antibody in a mouse was determined by ELISA. First, Anti-Human IgG (γ-chain specific) F(ab')2 Fragment of Antibody (SIGMA) was dispensed into a Nunc-Immuno Plate, MaxiSorp™ plate (Nalge Nunc International), and was allowed to stand undisturbed overnight at 4° C. to prepare an anti-human IgG-immobilized plate. Calibration curve samples at a plasma concentration of 0.64, 0.32, 0.16, 0.08, 0.04, 0.02, or 0.01 µg/mL, and mouse plasma measurement samples diluted by 100-fold or above were each dispensed into the anti-human IgG-immobilized plate, followed by incubation for 1 hour at 25° C. Subsequently, the plate was allowed to react with a biotinylated anti-human IL-6 R antibody (R&D) for 1 hour at 25° C., followed by reaction with Streptavidin-PolyHRP80 (Stereospecific Detection Technologies) for 0.5 hours at 25° C. The chromogenic reaction was conducted using TMB One Component HRP Microwell Substrate (BioFX Laboratories) as a substrate. After the chromogenic reaction was stopped by adding 1N-sulfuric acid (Showa Chemical), absorbance at 450 nm of the colored solution was measured using a microplate reader. The plasma concentration in the mouse was calculated from the absorbance of the calibration curve using the SOFTmax® PRO analysis software (Molecular Devices). Changes in the plasma concentrations of antibodies, H54/L28-IgG1, 6RL #9-IgG1, and FH4-IgG1, in the normal mice after intravenous administration, measured as described above, are shown in FIG. 55.

Figure 56:
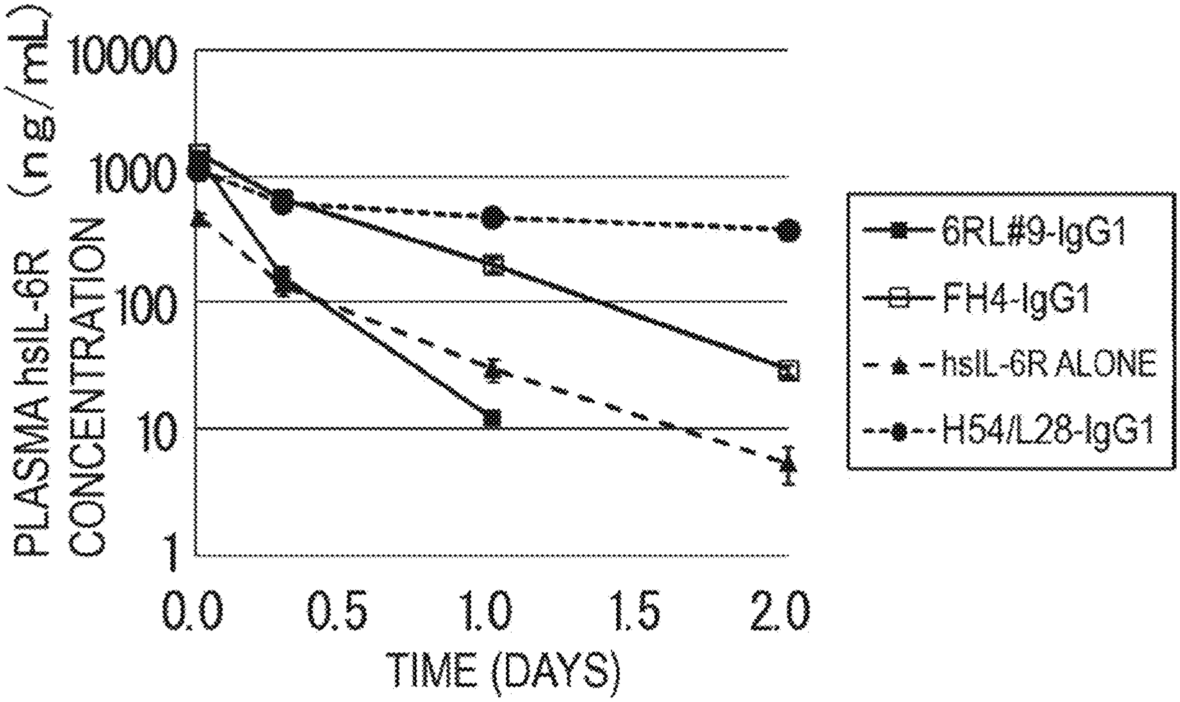
FIG. 56 shows a time course of the plasma concentration of soluble human IL-6 receptor (hsIL-6R) in normal mice administered with antibody H54/L28-IgG1, FH4-IgG1, or 6RL #9-IgG1.

(32-3) Determination of Plasma hsIL-6R Concentration by an Electrochemiluminescence Method The plasma concentration of hsIL-6R in a mouse was determined by an electrochemiluminescence method. A hsIL-6R calibration curve sample prepared at 2,000, 1,000, 500, 250, 125, 62.5, or 31.25 pg/mL, and a mouse plasma measurement sample diluted by 50-fold or above, were mixed with a monoclonal anti-human IL-6R antibody (R&D) ruthenated with SULFO-TAG NHS Ester (Meso Scale Discovery), a biotinylated anti-human IL-6 R antibody (R&D), and tocilizumab (heavy chain SEQ ID NO: 111, light chain SEQ ID NO: 112), followed by overnight reaction at 4° C. At that time, the assay buffer contained 10 mM EDTA to reduce the free Ca concentration in the sample and dissociate almost all the hsIL-6Rs in the sample from 6RL #9-IgG1 or FH4-IgG1 to be bound to the added tocilizumab. Subsequently, said reaction solution was dispensed into an MA400 PR Streptavidin Plate (Meso Scale Discovery). In addition, after washing each well of the plate that was allowed to react for 1 hour at 25° C., Read Buffer T (×4) (Meso Scale Discovery) was dispensed into each well. Immediately, the reaction solution was subjected to measurement using a SECTOR PR 400 reader (Meso Scale Discovery). The concentration of hsIL-6R was calculated from the response of the calibration curve using the SOFTmax® PRO analysis software (Molecular Devices). Changes in the plasma concentration of hsIL-6R in the normal mouse after intravenous administration, determined as described above, are shown in FIG. 56.

As a result, the disappearance of hsIL-6R was very rapid when hsIL-6R was administered alone, while the disappearance of hsIL-6R was significantly delayed when hsIL-6R was administered simultaneously with H54/L28-IgG1, a conventional antibody having no Ca-dependent binding ability to soluble human IL-6 receptor. In contrast, the disappearance of hsIL-6R was significantly accelerated when hsIL-6R was administered simultaneously with 6RL #9-IgG1 or FH4-IgG1 having 100-fold or higher Ca-dependent binding ability to hsIL-6R. The plasma concentrations of hsIL-6R one day after soluble human IL-6 receptor was administered simultaneously with 6RL #9-IgG1 and FH4-IgG1 were reduced 39-fold and 2-fold, respectively, as compared with simultaneous administration with H54/L28-IgG1. Thus, the calcium-dependent binding antibodies were confirmed to be able to accelerate antigen disappearance from the plasma.

[Reference Example 33] Exploration of Human Germline Sequences that Bind to Calcium Ion (33-1) Antibody that Binds to Antigen in a Calcium-Dependent Manner Antibodies that bind to an antigen in a calcium-dependent manner (calcium-dependent antigen-binding antibodies) are those whose interactions with antigen change with calcium concentration. A calcium-dependent antigen-binding antibody is thought to bind to an antigen through calcium ion. Thus, amino acids that form an epitope on the antigen side are negatively charged amino acids that can chelate calcium ions or amino acids that can be a hydrogen-bond acceptor. These properties of amino acids that form an epitope allows targeting of an epitope other than antigen-binding molecules, which are generated by introducing histidines and bind to an antigen in a pH-dependent manner. Furthermore, the use of antigen-binding molecules having calcium- and pH-dependent antigen-binding properties is thought to allow the formation of antigen-binding molecules that can individually target various epitopes having broad properties. Thus, if a population of molecules containing a calcium-binding motif (Ca library) is constructed, from which antigen-binding molecules are obtained, calcium-dependent antigen-binding molecules are thought to be effectively obtained.

(33-2) Acquisition of Human Germline Sequences

An example of the population of molecules containing a calcium-binding motif is an example in which said molecules are antibodies. In other words, an antibody library containing a calcium-binding motif may be a Ca library.

Calcium ion-binding antibodies containing human germline sequences have not been reported. Thus, each antibody having human germline sequences were cloned using as a template cDNA prepared from Human Fetal Spleen Poly RNA (Clontech) to assess whether antibodies having human germline sequences bind to calcium ion. Cloned DNA fragments were inserted into animal cell expression vectors. The nucleotide sequences of the constructed expression vectors were determined by a method known to those skilled in the art. The SEQ IDs are shown in Table 45. By PCR, polynucleotides encoding SEQ ID NO: 58 (Vk1), SEQ ID NO: 59 (Vk2), SEQ ID NO: 60 (Vk3), SEQ ID NO: 61 (Vk4), and SEQ ID NO: 62 (Vk5-2) were linked to a polynucleotide encoding the natural Kappa chain constant region (SEQ ID NO: 54). The linked DNA fragments were inserted into animal cell expression vectors. Furthermore, heavy chain variable region polynucleotides encoding SEQ ID NO: 63, SEQ ID NO: 64, SEQ ID NO: 65, SEQ ID NO: 66, and SEQ ID NO: 67 were linked by PCR to a polynucleotide encoding an IgG1 of SEQ ID NO: 53 (having a deletion of two amino acids at the C terminus of natural sequence). The resulting DNA fragments were inserted into animal cell expression vectors. The sequences of the constructed variants were confirmed by a method known to those skilled in the art.

TABLE 45

| LIGHT CHAIN GERMLINE SEQUENCE | HEAVY CHAIN (VARIABLE REGION) SEQ ID NO | LIGHT CHAIN VARIABLE REGION SEQ ID NO |
|---|---|---|
| Vk1 | 63 | 58 |
| Vk2 | 64 | 59 |
| Vk3 | 65 | 60 |
| Vk4 | 66 | 61 |
| Vk5 | 67 | 62 |

(33-3) Expression and Purification of Antibodies

The constructed animal cell expression vectors inserted with the DNA fragments having the five types of human germline sequences were introduced into animal cells. Antibody expression was carried out by the following method. Cells of human fetal kidney cell-derived FreeStyle™ 293-F cells (Invitrogen) were suspended in the FreeStyle™ 293 Expression Medium (Invitrogen), and plated at a cell density of $1.33\times10^6$ cells/ml (3 ml) into each well of a 6-well plate. The prepared plasmids are introduced into cells by a lipofection method. The cells were cultured for four days in a $CO_2$ incubator (37° C., 8% $CO_2$, 90 rpm). From the culture supernatants prepared as described above, antibodies were purified using the rProtein A Sepharose™ Fast Flow (Amersham Biosciences) by a method known to those skilled in the art. Absorbance at 280 nm of the purified antibody solutions was measured using a spectrophotometer. Antibody concentrations were calculated from the determined values using an extinction coefficient calculated by the PACE method (Protein Science (1995) 4: 2411-2423).

(33-4) Assessment of Antibodies Having Human Germline Sequences for their Calcium Ion-Binding Activity The purified antibodies were assessed for their calcium ion-binding activity. The intermediate temperature of thermal denaturation (Tm value) was measured by differential scanning calorimetry (DSC) as an indicator for examining calcium ion binding to the antibody (MicroCal VP-Capillary DSC, MicroCal). The intermediate temperature of thermal denaturation (Tm value) is an indicator of stability. It becomes higher when a protein is stabilized through calcium ion binding, as compared with the case where no calcium ion is bound (J. Biol. Chem. (2008) 283, 37, 25140-25149). The binding activity of calcium ion to antibody was evaluated by examining changes in the Tm value of the antibody depending on the changes in the calcium ion concentration in the antibody solution. The purified antibody was subjected to dialysis (EasySEP, TOMY) using an external solution of 20 mM Tris-HCl, 150 mM NaCl, and 2 mM $CaCl_2$ (pH 7.4) or 20 mM Tris-HCl, 150 mM NaCl, and 3 μM $CaCl_2$ (pH 7.4). DSC measurement was conducted at a heating rate of 240° C./hr from 20 to 115° C. using as a test substance an antibody solution prepared at about 0.1 mg/mL with the dialysate. The intermediate temperatures of thermal denaturation (Tm values) of the Fab domains of each antibody, calculated from the denaturation curve obtained by DSC, are shown in Table 46.

TABLE 46

| LIGHT CHAIN | CALCIUM ION CONCENTRATION | | ΔTm (° C.) |
|---|---|---|---|
| GERMLINE SEQUENCE | 3 μM | 2 mM | 2 mM − 3 μM |
| hVk1 | 80.32 | 80.78 | 0.46 |
| hVk2 | 80.67 | 80.61 | −0.06 |
| hVk3 | 81.64 | 81.36 | −0.28 |
| hVk4 | 70.74 | 70.74 | 0 |
| hVk5 | 71.52 | 74.17 | 2.65 |

The result showed that the Tm values of the Fab domains of antibodies having the hVk1, hVk2, hVk3, or hVk4 sequence did not vary depending on the calcium ion concentration in the Fab domain-containing solutions. Meanwhile, the Tm value for the antibody Fab domain having the hVk5 sequence varied depending on the calcium ion concentration in the Fab domain-containing solution. This demonstrates that the hVk5 sequence binds to calcium ion.

(33-5) Assessment of hVk5-2 Sequence for Calcium Binding

In (33-2), Vk5-2 variant 1 (SEQ ID NO: 68) and Vk5-2 variant 2 (SEQ ID NO: 69) were obtained in addition to Vk5-2 (SEQ ID NO: 57), all of which are classified as Vk5-2. These variants were assessed for their calcium binding. DNA fragments for Vk5-2, Vk5-2 variant 1, and Vk5-2 variant 2 were each inserted into animal cell expression vectors. The nucleotide sequences of the constructed expression vectors were determined by a method known to those skilled in the art. By the method described in (33-3), the animal cell expression vectors inserted with DNA fragments for Vk5-2, Vk5-2 variant 1, and Vk5-2 variant 2 were introduced, in combination with animal expression vector carrying an insert to express CIM_H (SEQ ID NO: 67) as a heavy chain, into animal cells and antibodies were purified. The purified antibodies were assessed for their calcium ion-binding activity. The purified antibodies were dialyzed (EasySEP, TOMY) against 20 mM Tris-HCl/150 mM NaCl (pH 7.5) (in Table 47, indicated as 0 mM calcium ion concentration) or 20 mM Tris-HCl/150 mM NaCl/2 mM $CaCl_2$ (pH 7.5). DSC measurement was carried out at a rate of temperature increase of 240° C./hr from 20 to 115° C. using as a test substance an antibody solution prepared at a concentration of about 0.1 mg/mL with the same solution as used for dialysis. Based on the obtained DSC denaturation curve, the intermediate temperature of thermal denaturation (Tm value) was calculated for the Fab domain of each antibody. The Tm values are shown in Table 47.

TABLE 47

| | CALCIUM ION CONCENTRATION | | Δ Tm (° C.) |
|---|---|---|---|
| LIGHT CHAIN | 0 mM | 2 mM | 2 mM − 0 mM |
| Vk5-2 | 71.65 | 74.38 | 2.73 |
| Vk5-2 VARIANT 1 | 65.75 | 72.24 | 6.49 |
| Vk5-2 VARIANT 2 | 66.46 | 72.24 | 5.78 |

The result showed that the Tm value for the Fab domains of antibodies having the sequence of Vk5-2, Vk5-2 variant 1, or Vk5-2 variant 2 varied depending on the calcium ion concentration in solutions containing antibodies having the Fab domains. This demonstrates that antibodies having a sequence classified as Vk5-2 bind to calcium ion.

[Reference Example 34] Assessment of the Human Vk5 (hVk5) Sequence (34-1) hVk5 Sequence The only hVk5 sequence registered in Kabat database is hVk5-2 sequence. Herein, hVk5 and hVk5-2 are used synonymously. WO2010/136598 discloses that the abundance ratio of the hVk5-2 sequence in the germline sequence is 0.4%. Other reports have been also made in which the abundance ratio of the hVk5-2 sequence in the germline sequence is 0-0.06% (J. Mol. Biol. (2000) 296, 57-86; Proc. Natl. Acad. Sci. USA (2009) 106, 48, 20216-20221). As described above, since the hVk5-2 sequence is a sequence of low appearance frequency in the germline sequence, it was thought to be inefficient to obtain a calcium-binding antibody from an antibody library consisting of human germline sequences or B cells obtained by immunizing a mouse expressing human antibodies. Thus, it is possible to design Ca libraries containing the sequence of human hVk5-2. Meanwhile, reported synthetic antibody libraries (WO2010/105256 and WO2010/136598) did not contain the sequence of hVk5. In addition, realization of the possibility is unknown because no report has been published on the physical properties of the hVk5-2 sequence.

(34-2) Construction, Expression, and Purification of a Non-Glycosylated Form of the hVk5-2 Sequence The hVk5-2 sequence has a sequence for N-type glycosylation at position 20 amino acid (Kabat numbering). Sugar chains attached to proteins exhibit heterogeneity. Thus, it is desirable to lose the glycosylation from the viewpoint of substance homogeneity. In this context, variant hVk5-2_L65 (SEQ ID NO: 70) in which the Asn (N) residue at position 20 (Kabat numbering) is substituted with Thr (T) was constructed. Amino acid substitution was carried out by a method known to those skilled in the art using the QuikChange Site-Directed Mutagenesis Kit (Stratagene). A DNA encoding the variant hVk5-2_L65 was inserted into an animal expression vector. The animal expression vector inserted with the constructed DNA encoding variant hVk5-2_L65, in combination with an animal expression vector having an insert to express CIM_H (SEQ ID NO: 67) as a heavy chain, was introduced into animal cells by the method described in Reference Example 25. The antibody comprising hVk5-2_L65 and CIM_H, which was expressed in animal cells introduced with the vectors, was purified by the method described in Reference Example 33.

Figure 57:
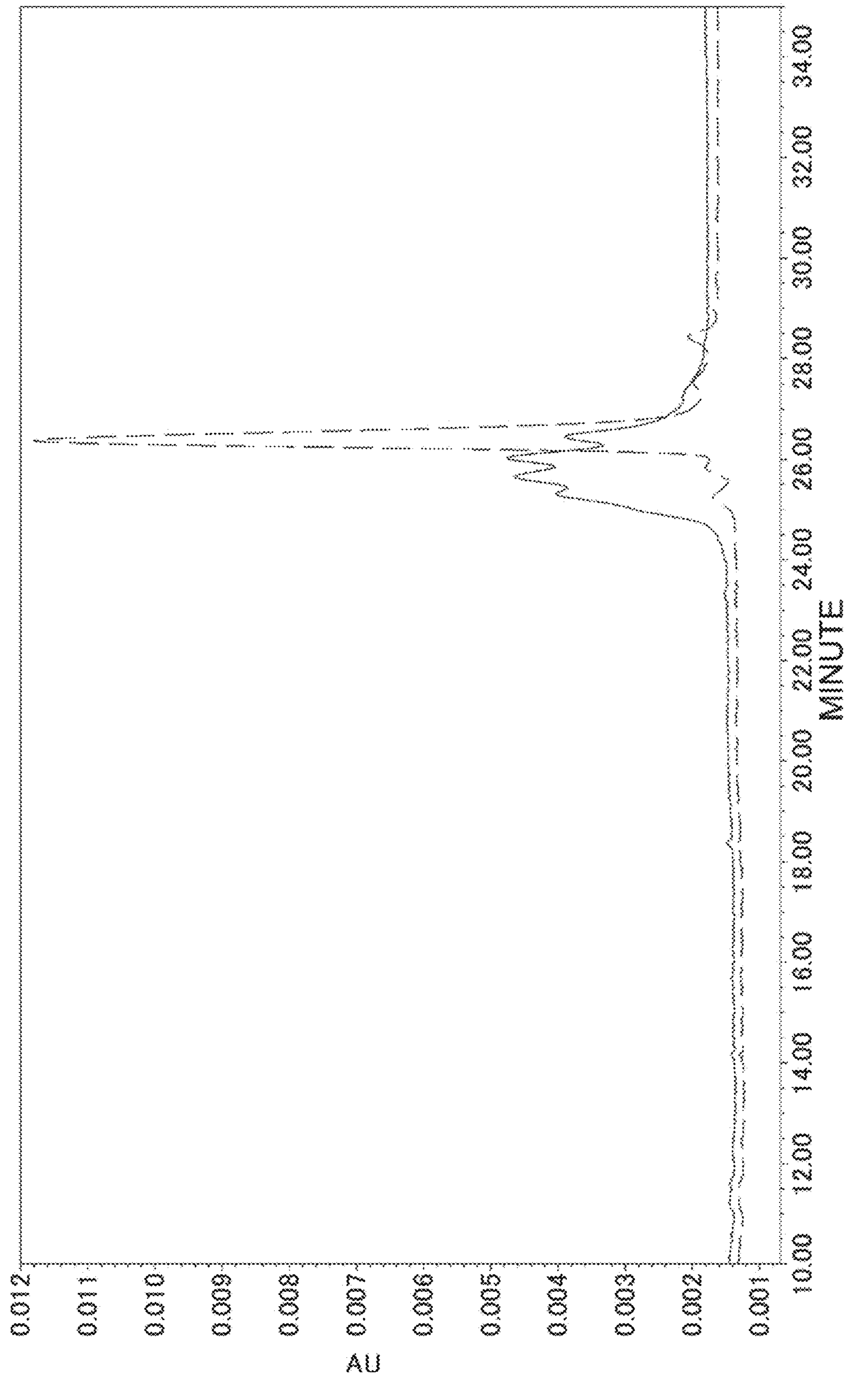
FIG. 57 shows ion-exchange chromatograms for an antibody having human Vk5-2 sequence and an antibody having h Vk5-2_L65 sequence which has an altered glycosylation sequence in the human Vk5-2 sequence. Solid line indicates a chromatogram for an antibody having human Vk5-2 sequence (heavy chain: CIM_H (SEQ ID NO: 67); light chain: hVk5-2 (SEQ ID NO: 57)); broken line indicates a chromatogram for an antibody having hVk5-2_L65 sequence (heavy chain: CIM_H (SEQ ID NO: 67); light chain: hVk5-2_L65 (SEQ ID NO: 70)).
Figure 58A:
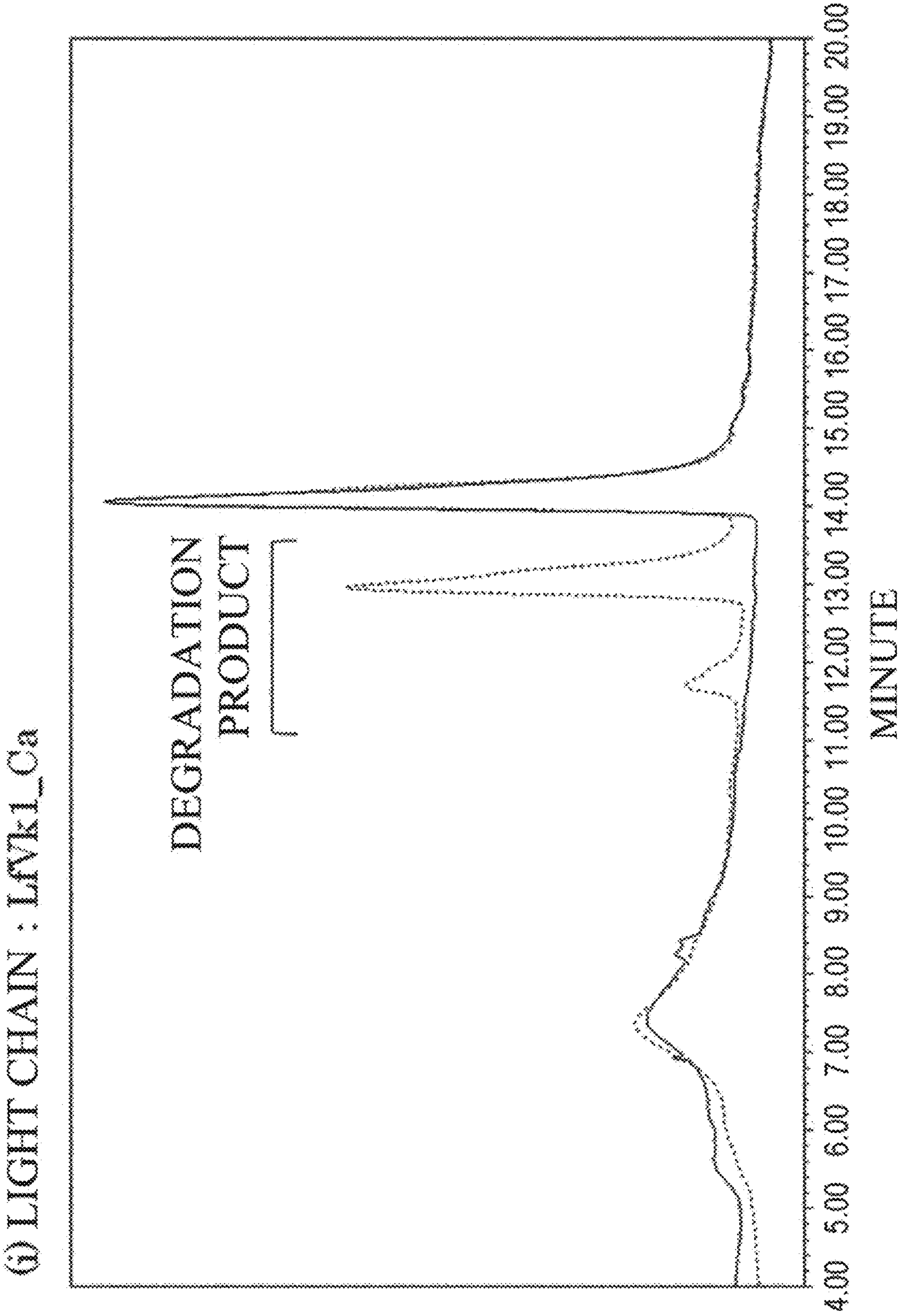
FIG. 58A shows ion-exchange chromatograms for an antibody having LfVk1_Cα sequence (heavy chain: GC_H (SEQ ID NO: 55); light chain: LfVk1_Cα (SEQ ID NO: 83)) and an antibody having a sequence in which Asp (D) in the LfVk1_Cα sequence is substituted with Ala (A) after storage at 5° C. (solid line) or 50° C. (dotted line). After storage at 5° C., the highest peak in the chromatogram for each antibody is defined as a main peak, and the y axis of each ion-exchange chromatogram was normalized to the main peak. The graph shows a chromatogram for an antibody having LfVk1_Cα (SEQ ID NO: 83) as the light chain.
Figure 58B:
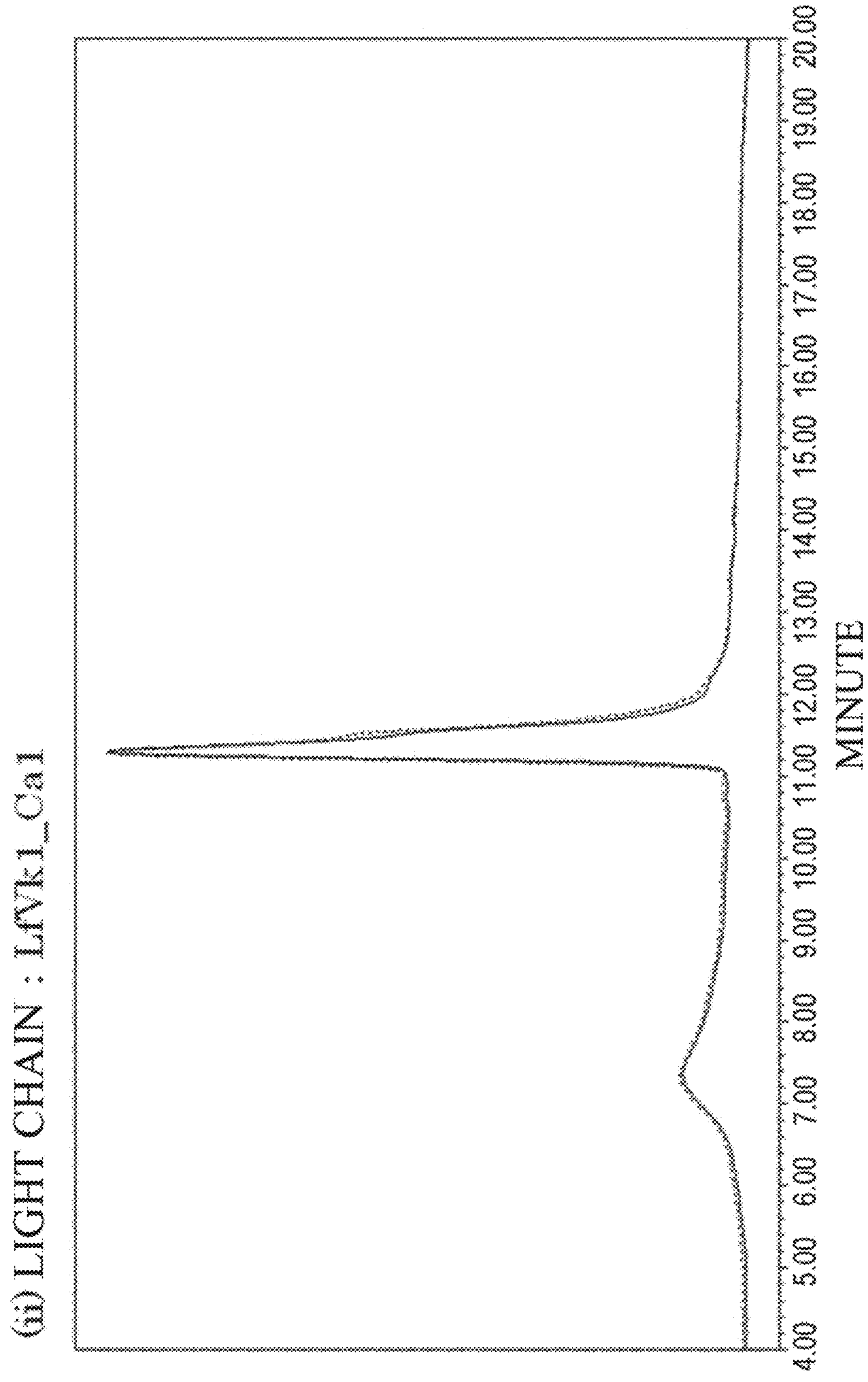
FIG. 58B shows a chromatogram for an antibody having LfVk1_Cα1 (SEQ ID NO: 85) as the light chain.
Figure 58C:
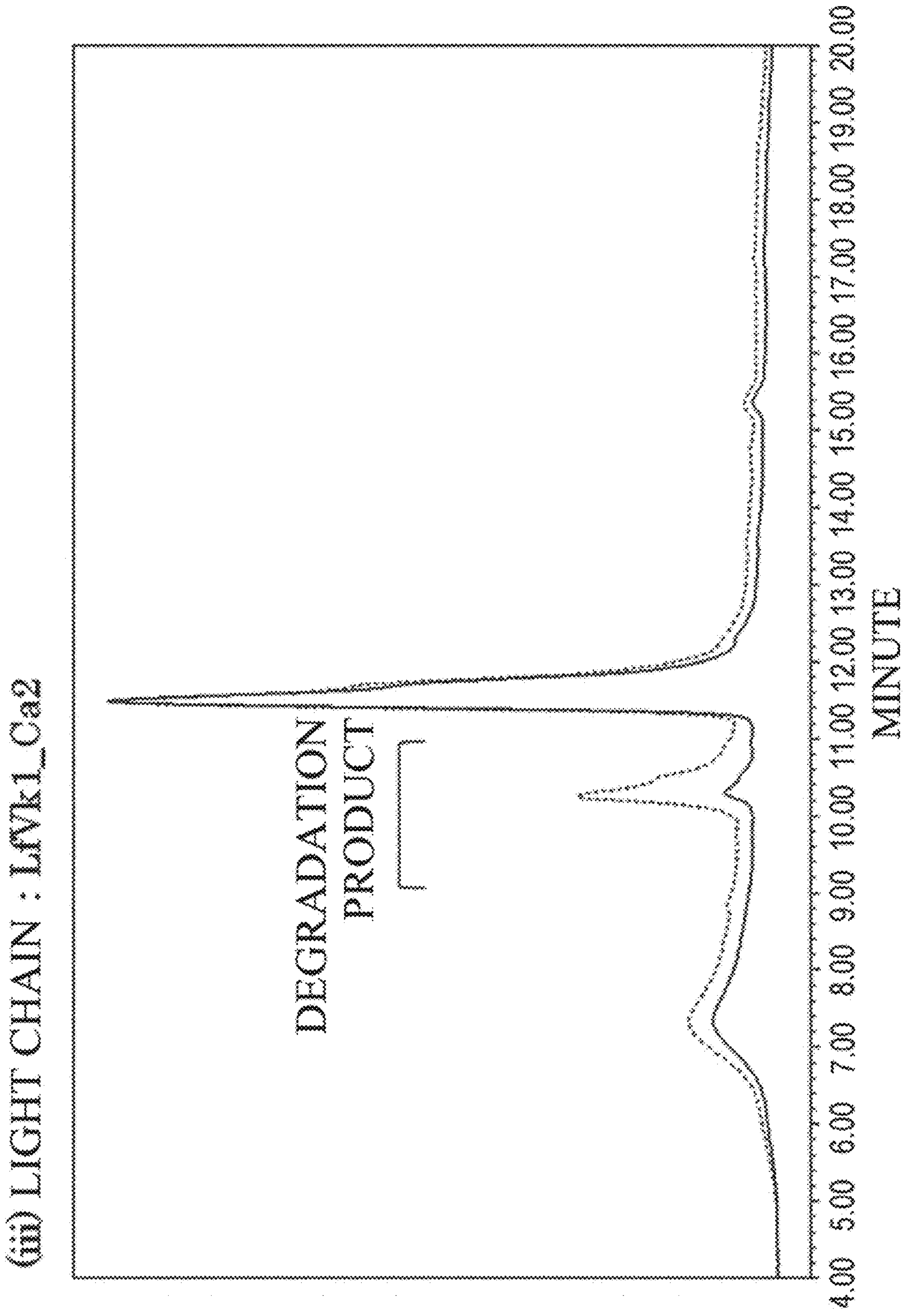
FIG. 58C shows a chromatogram for an antibody having LfVk1_Cα2 (SEQ ID NO: 86) as the light chain.
Figure 58D:
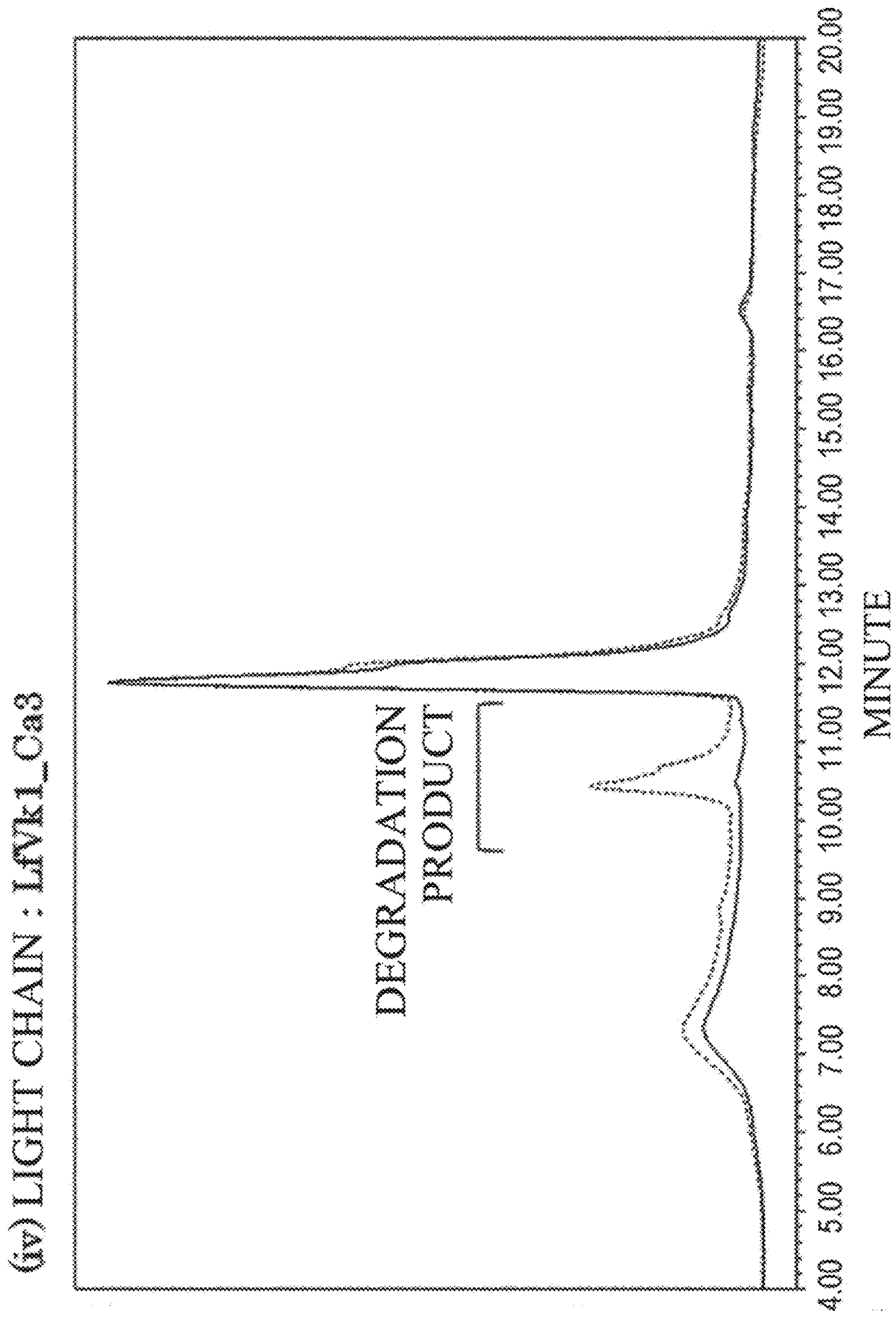
FIG. 58D shows a chromatogram for an antibody having LfVk1_Cα3 (SEQ ID NO: 87) as the light chain.

(34-3) Assessment of the Antibody Having the Non-Glycosylated hVk5-2 Sequence for Physical Properties The isolated antibody having the modified sequence hVk5-2_L65 was analyzed by ion-exchange chromatography to test whether it is less heterogeneous than the antibody having the original sequence hVk5-2 before alteration. The procedure of ion-exchange chromatography is shown in Table 48. The analysis result showed that hVk5-2_L65 modified at the glycosylation site was less heterogeneous than the original sequence hVk5-2, as shown in FIG. 57.

TABLE 48

| | CONDITION |
|---|---|
| COLUMN | TOSOH TSKgel DEAE-NPR |
| MOBILE PHASE | A; 10 mM Tris-HCl, 3 μM $CaCl_2$ (pH 8.0)<br>B; 10 mM Tris-HCl, 500 mM NaCl, 3 μM $CaCl_2$ (pH 8.0) |
| GRADIENT SCHEDULE | % B = 0-(5 min)-0-2%/1 min |
| COLUMN TEMPERATURE | 40° C. |
| DETECTION | 280 nm |
| INJECTION VOLUME | 100 μL (5 μg) |

Next, whether the less-heterogeneous hVk5-2_L65 sequence-comprising antibody binds to calcium ion was assessed by the method described in Reference Example 33. The result showed that the Tm value for the Fab domain of the antibody having hVk5-2_L65 with altered glycosylation site also varied depending on the calcium ion concentration in the antibody solutions, as shown in Table 49. Specifically, it was demonstrated that the Fab domain of the antibody having hVk5-2_L65 with altered glycosylation site binds to calcium ion.

TABLE 49

| | GLYCOSYLATED | CALCIUM ION CONCENTRATION | | Δ Tm (° C.) 2 mM − |
|---|---|---|---|---|
| LIGHT CHAIN | SEQUENCE | 3 μM | 2 mM | 3 μM |
| hVk5-2 | YES | 71.52 | 74.17 | 2.65 |
| hVk5-2_L65 | NO | 71.51 | 73.66 | 2.15 |

[Reference Example 35] Assessment of the Calcium Ion-Binding Activity of Antibody Molecules Having CDR Sequence of the hVk5-2 Sequence (35-1) Construction, Expression, and Purification of Modified Antibodies Having a CDR Sequence from the hVk5-2 Sequence The hVk5-2_L65 sequence is a sequence with altered amino acids at a glycosylation site in the framework of human Vk5-2 sequence. As described in Reference Example 34, it was demonstrated that calcium ion bound even after alteration of the glycosylation site. Meanwhile, from the viewpoint of immunogenicity, it is generally desirable that the framework sequence is a germline sequence. Thus, the present inventors assessed whether an antibody framework sequence could be substituted with the framework sequence of a non-glycosylated germline sequence while maintaining the calcium ion-binding activity of the antibody.

Polynucleotides encoding chemically synthesized sequences in which framework sequence of the hVk5-2 sequence is altered with hVk1, hVk2, hVk3, or hVk4 (CaVk1 (SEQ ID NO: 71), CaVk2 (SEQ ID NO: 72), CaVk3 (SEQ ID NO: 73), or CaVk4 (SEQ ID NO: 74), respectively) were linked by PCR to a polynucleotide encoding the constant region (SEQ ID NO: 54) of the natural Kappa chain. The linked DNA fragments were inserted into animal cell expression vectors. Sequences of the constructed variants were confirmed by a method known to those skilled in the art. Each plasmid constructed as described above was introduced into animal cells in combination with a plasmid inserted with a polynucleotide encoding CIM_H (SEQ ID NO: 67) by the method described in Reference Example 33. The expressed antibody molecules of interest were purified from culture media of the animal cells introduced with the plasmids.

(35-2) Assessment of Altered Antibodies Having the CDR Sequence of the hVk5-2 Sequence for their Calcium Ion-Binding Activity Whether calcium ion binds to altered antibodies having the CDR sequence of the hVK5-2 sequence and the framework sequences of germline sequences other than hVk5-2 (hVk1, hVk2, hVk3, and hVk4) was assessed by the method described in Reference Example 25. The assessment result is shown in Table 50. The Tm value of the Fab domain of each altered antibody was revealed to vary depending on the calcium ion concentration in the antibody solutions. This demonstrates that antibodies having a framework sequence other than the hVk5-2 sequence also bind to calcium ion.

TABLE 50

| GERMLINE (LIGHT CHAIN FRAMEWORK SEQUENCE) | CALCIUM ION CONCENTRATION 3 μM | 2 mM | Δ Tm (° C.) 2 mM − 3 μM |
|---|---|---|---|
| hVk1 | 77.51 | 79.79 | 2.28 |
| hVk2 | 78.46 | 80.37 | 1.91 |
| hVk3 | 77.27 | 79.54 | 2.27 |
| hVk4 | 80.35 | 81.38 | 1.03 |
| hVk5-2 | 71.52 | 74.17 | 2.65 |

The thermal denaturation temperature (Tm value), as an indicator of thermal stability, of the Fab domain of each antibody altered to have the CDR sequence of the hVK5-2 sequence and the framework sequence of a germline sequence other than the hVk5-2 sequence (hVk1, hVk2, hVk3, or hVk4) was demonstrated to be greater than that of the Fab domain of the original antibody having the hVk5-2 sequence. This result shows that antibodies having the CDR sequence of the hVk5-2 sequence and the framework sequence of hVk1, hVk2, hVk3, or hVk4 not only have calcium ion-binding activity but also are excellent molecules from the viewpoint of thermal stability.

[Reference Example 36] Identification of the Calcium Ion-Binding Site in Human Germline hVk5-2 Sequence (36-1) Design of Mutation Site in the CDR Sequence of the hVk5-2 Sequence As described in Reference Example 35, antibodies having the light chain resulting from introduction of the CDR sequence of the hVk5-2 sequence into the framework sequence of a different germline sequence were also demonstrated to bind to calcium ion. This result suggests that in hVk5-2 a calcium ion-binding site is localized within its CDR sequence. Amino acids that bind to calcium ion, i.e., chelate calcium ion, include negatively charged amino acids and amino acids that can be a hydrogen bond acceptor. Thus, it was tested whether antibodies having a mutant hVk5-2 sequence with a substitution of an Ala (A) residue for an Asp (D) or Glu (E) residue in the CDR sequence of the hVk5-2 sequence bind to calcium ion.

(36-2) Construction of Variant hVk5-2 Sequences with Ala Substitution, and Expression and Purification of Antibodies Antibody molecules were prepared to comprise a light chain with substitution of an Ala residue for Asp and/or Glu residue in the CDR sequence of the hVk5-2 sequence. As described in Reference Example 34, non-glycosylated variant hVk5-2_L65 exhibited calcium ion binding and was assumed to be equivalent to the hVk5-2 sequence in terms of calcium ion binding. In this Example, amino acid substitutions were introduced into hVk5-2_L65 as a template sequence. Constructed variants are shown in Table 51. Amino acid substitutions were carried out by methods known to those skilled in the art such as using the QuikChange Site-Directed Mutagenesis Kit (Stratagene), PCR, or the In fusion Advantage PCR Cloning Kit (TAKARA) to construct expression vectors for altered light chains having an amino acid substitution.

TABLE 51

| LIGHT CHAIN VARIANT NAME | ALTERED POSITION (Kabat NUMBERING) | SEQ ID NO |
|---|---|---|
| hVk5-2_L65 | WILDTYPE | 70 |
| hVk5-2_L66 | 30 | 75 |
| hVk5-2_L67 | 31 | 76 |
| hVk5-2_L68 | 32 | 77 |
| hVk5-2_L69 | 50 | 78 |
| hVk5-2_L70 | 30, 32 | 79 |
| hVk5-2_L71 | 30, 50 | 80 |
| hVk5-2_L72 | 30, 32, 50 | 81 |
| hVk5-2_L73 | 92 | 82 |

Nucleotide sequences of the constructed expression vectors were confirmed by a method known to those skilled in the art. The expression vectors constructed for the altered light chains were transiently introduced, in combination with an expression vector for the heavy chain CIM_H (SEQ ID NO: 67), into cells of the human fetal kidney cell-derived HEK293H line (Invitrogen) or FreeStyle™ 293 cells (Invitrogen) to express antibodies. From the obtained culture supernatants, antibodies were purified using the rProtein A Sepharose™ Fast Flow (GE Healthcare) by a method known to those skilled in the art. Absorbance at 280 nm of the purified antibody solutions was measured using a spectrophotometer. Antibody concentrations were calculated from the determined values using an extinction coefficient calculated by the PACE method (Protein Science (1995) 4: 2411-2423).

(36-3) Assessment of the Calcium Ion-Binding Activity of Antibodies Having an Ala Substitution in the hVk5-2 Sequence Whether the obtained purified antibodies bind to calcium ion was tested by the method described in Reference Example 33. The result is shown in Table 52. Some antibodies having substitution of an Asp or Glu residue in the CDR sequence of the hVk5-2 sequence with an Ala residue which cannot be involved in calcium ion binding or chelation were revealed to have an Fab domain whose Tm did not vary by the calcium ion concentration in the antibody solutions. The substitution sites at which Ala substitution did not alter the Tm (positions 32 and 92 (Kabat numbering)) were demonstrated to be greatly important for the calcium ion-antibody binding.

TABLE 52

| LIGHT CHAIN VARIANT NAME | ALTERED POSITION (Kabat NUMBERING) | CALCIUM ION CONCENTRATION 0 μM | 2 mM | Δ Tm (° C.) 2 mM − 0 μM |
|---|---|---|---|---|
| hVk5-2_L65 | WILDTYPE | 71.71 | 73.69 | 1.98 |
| hVk5-2_L66 | 30 | 71.65 | 72.83 | 1.18 |
| hVk5-2_L67 | 31 | 71.52 | 73.30 | 1.78 |
| hVk5-2_L68 | 32 | 73.25 | 74.03 | 0.78 |
| hVk5-2_L69 | 50 | 72.00 | 73.97 | 1.97 |
| hVk5-2_L70 | 30, 32 | 73.42 | 73.60 | 0.18 |
| hVk5-2_L71 | 30, 50 | 71.84 | 72.57 | 0.73 |
| hVk5-2_L72 | 30, 32, 50 | 75.04 | 75.17 | 0.13 |
| hVk5-2_L73 | 92 | 75.23 | 75.04 | −0.19 |

[Reference Example 37] Assessment of the Antibodies Having hVk1 Sequence with Calcium Ion-Binding Motif (37-1) Construction of an hVk1 Sequence with Calcium Ion-Binding Motif, and Expression and Purification of Antibodies The result described in Reference Example 36 on the calcium-binding activity of the Ala substitute demonstrates that Asp or Glu residues in the CDR sequence of the hVk5-2 sequence were important for calcium binding. Thus, the present inventors assessed whether an antibody can bind to calcium ion when the residues at positions 30, 31, 32, 50, and 92 (Kabat numbering) alone were introduced into a different germline variable region sequence. Specifically, variant LfVk1_Ca (SEQ ID NO: 83) was constructed by substituting the residues at positions 30, 31, 32, 50, and 92 (Kabat numbering) in the hVk5-2 sequence for the residues at positions 30, 31, 32, 50, and 92 (Kabat numbering) in the hVk1 sequence (a human germline sequence). Specifically, it was tested whether antibodies having an hVk1 sequence introduced with only 5 residues from the hVk5-2 sequence can bind to calcium. The variants were produced by the same method as described in Reference Example 36. The resulting light chain variant LfVk1_Ca and LfVk1 having the light-chain hVk1 sequence (SEQ ID NO: 84) were co-expressed with the heavy chain CIM_H (SEQ ID NO: 67). Antibodies were expressed and purified by the same method as described in Reference Example 36.

(37-2) Assessment of the Calcium Ion-Binding Activity of Antibodies Having a Human hVk1 Sequence with Calcium Ion-Binding Motif Whether the purified antibody prepared as described above binds to calcium ion was assessed by the method described in Reference Example 33. The result is shown in Table 53. The Tm value of the Fab domain of the antibody having LfVk1 with an hVk1 sequence did not vary depending on the calcium concentration in the antibody solutions. Meanwhile, Tm of the antibody having the LfVk1_Ca sequence was shifted by 1° C. or more upon change in the calcium concentration in the antibody solutions. Thus, it was shown that the antibody having LfVk1_Ca binds to calcium. The result described above demonstrates that the entire CDR sequence of hVk5-2 is not required, while the residues introduced for construction of the LfVk1_Ca sequence alone are sufficient for calcium ion binding.

TABLE 53

| LIGHT CHAIN VARIANT | CALCIUM ION CONCENTRATION 3 μM | 2 mM | Δ Tm (° C.) 2 mM − 3 μM |
|---|---|---|---|
| LfVk1 | 83.18 | 83.81 | 0.63 |
| LfVk1_Ca | 79.83 | 82.24 | 2.41 |

(37-3) Construction, Expression, and Purification of Degradation-Resistant LfVk1 Ca Sequence As described in (37-1), variant LfVk1_Ca (SEQ ID NO: 83) was constructed to have substitution of residues at positions 30, 31, 32, 50, and 92 (Kabat numbering) in the hVk5-2 sequence for residues at positions 30, 31, 32, 50, and 92 (Kabat numbering) in the hVk1 sequence (a human germline sequence). The variant was demonstrated to bind to calcium ion. Thus, it is possible to design Ca libraries containing LfVk1_Ca sequence. Meanwhile, there is no report on the properties of LfVk1_Ca sequence, and thus its feasibility was unknown. LfVk1_Ca sequence has Asp at positions 30, 31, and 32 (Kabat numbering). Thus, the Asp-Asp sequence which has been reported to be degraded under acidic condition is contained in the CDR1 sequence (J. Pharm. Biomed. Anal. (2008) 47(1), 23-30). It is desirable to avoid the degradation at acidic conditions from the viewpoint of the storage stability of antibody. Then, variants LfVk1 Ca1 (SEQ ID NO: 85), LfVk1 Ca2 (SEQ ID NO: 86), and LfVk1_Ca3 (SEQ ID NO: 87) were constructed to have substitution of Ala (A) residues for Asp (D) residues that are possibly sensitive to degradation. Amino acid substitution was carried out by a method known to those skilled in the art using the QuikChange Site-Directed Mutagenesis Kit (Stratagene). DNAs encoding the variants were inserted into animal expression vectors. In combination with an animal expression vector having an insert to express GC_H (SEQ ID NO: 55) as the heavy chain, the constructed animal expression vectors carrying DNA inserts for the variants were introduced into animal cells by the method described in Reference Example 33. The antibodies expressed in the animal cells introduced with the vectors were purified by the method described in Reference Example 33.

(37-4) Stability Assessment of Antibodies Having the Degradation-Resistant LfVk1 Ca Sequence Whether the antibodies prepared as described in (37-3) were more resistant to degradation in solutions at pH 6.0 than the original antibodies having the LfVk1_Ca sequence provided for alteration was assessed by comparing the heterogeneity between respective antibodies after thermal acceleration. Each antibody was dialyzed against a solution of 20 mM Histidine-HCl, 150 mM NaCl (pH 6.0) under a condition of 4° C. overnight. Dialyzed antibodies were adjusted to 0.5 mg/mL and stored at 5° C. or 50° C. for three days. Each antibody after storage was subjected to ion-exchange chromatography using the method described in Reference Example 34. As shown in FIG. 58, the analysis result demonstrates that LfVk1_Ca1 with an alteration at degradation site was less heterogeneous and much more resistant to degradation from thermal acceleration than the original LfVk1_Ca sequence. Specifically, it was demonstrated that degradation occurred at the Asp (D) residue of position 30 in the LfVk1_Ca sequence but it could be prevented by amino acid alteration.

(37-5) Construction of a Light Chain LVk1_Ca Sequence Resistant to Degradation at the Asp Residue of Position 30, and Expression and Purification of Antibodies The result described in (37-4) on the degradation resistance of the Ala-substituted form demonstrates that under acidic conditions the LfVk1_Ca sequence was degraded at the Asp (D) residue of position 30 (Kabat numbering) in its CDR sequence and the degradation could be prevented in the case of substitution of a different amino acid (in (37-4), an Ala (A) residue) for the Asp (D) residue at position 30 (Kabat numbering). Then, the present inventors tested whether even a sequence with a substitution of Ser (S), a main residue capable of chelating calcium ion, for the residue at position 30 (Kabat numbering) (referred to as LfVk1_Ca6; SEQ ID NO: 88) was resistant to degradation. Variants were prepared by the same method as described in Reference Example 29. The altered light chains LfVk1_Ca6 and LfVk1_Ca sequences were expressed in combination with a heavy chain GC_H (SEQ ID NO: 55). Antibodies were expressed and purified by the same method as described in Reference Example 36.

(37-6) Assessment of a Light Chain LVk1_Ca Sequence Resistant to Degradation at Asp Residue at Position 30

Figure 59A:
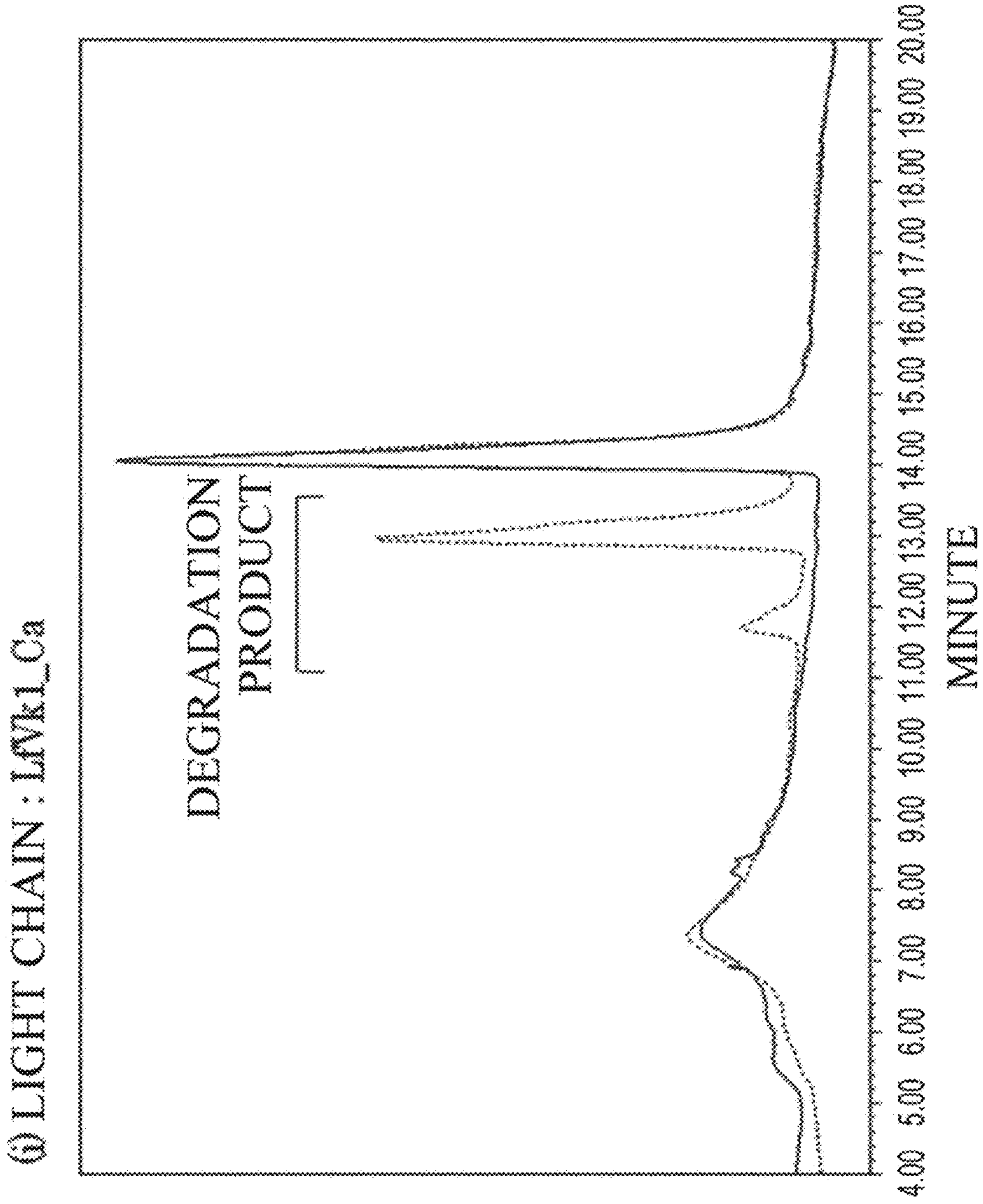
FIG. 59A shows ion-exchange chromatograms for an antibody having LfVk1_Cα sequence (heavy chain: GC_H (SEQ ID NO: 55); light chain: LfVk1_Cα (SEQ ID NO: 83)) and an antibody having LfVk1_Cα6 sequence (heavy chain: GC_H (SEQ ID NO: 55); light chain: LfVk1_Cα6 (SEQ ID NO: 88)) in which Asp (D) at position 30 (Kabat numbering) in the LfVk1_Cα sequence is substituted with Ser (S) after storage at 5° C. (solid line) or 50° C. (dotted line). After storage at 5° C., the highest peak in the chromatogram for each antibody is defined as a main peak, and the y axis of each ion-exchange chromatogram was normalized to the main peak. The graph shows a chromatogram for an antibody having LfVk1_Cα (SEQ ID NO: 83) as the light chain.
Figure 59B:
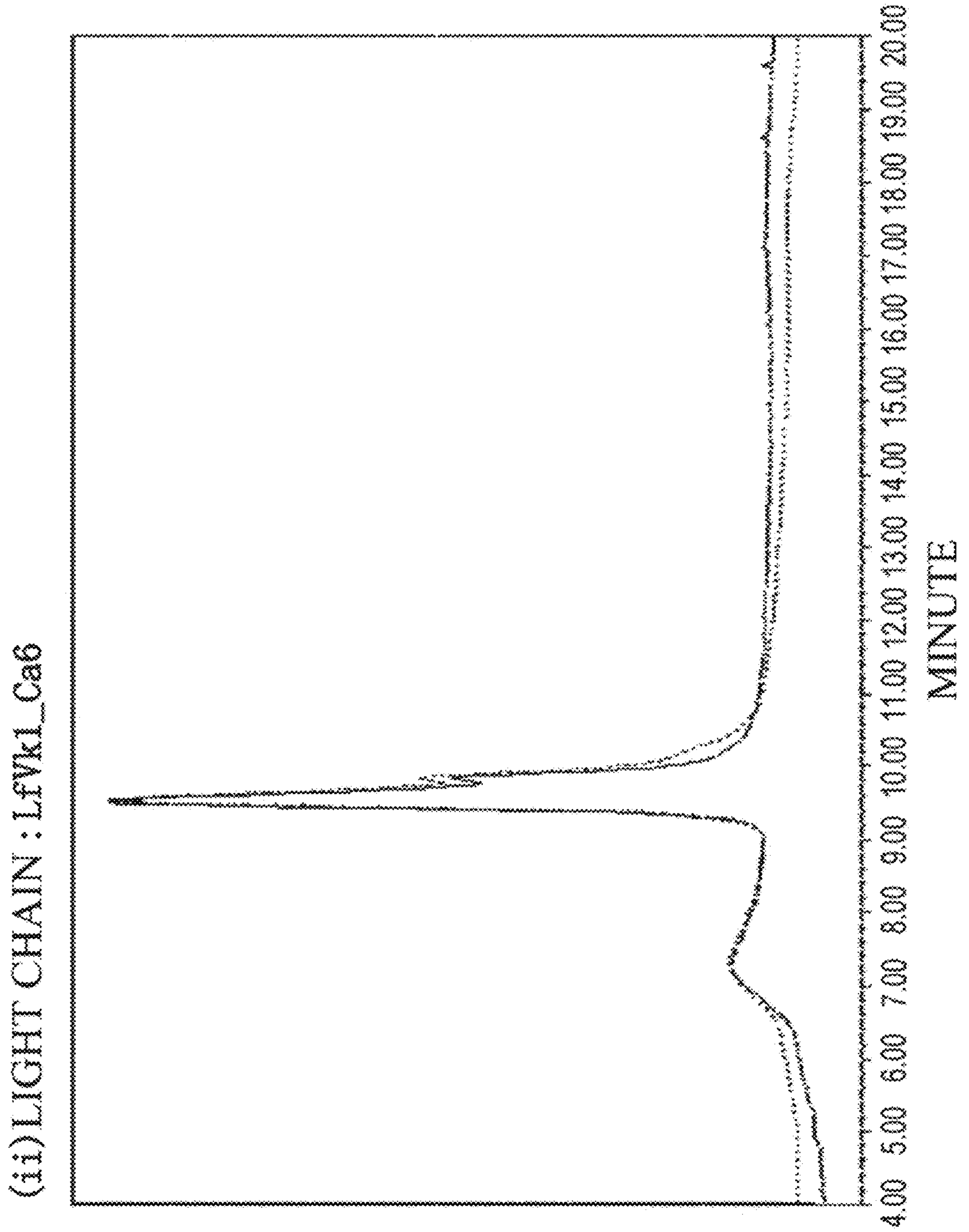
FIG. 59B shows a chromatogram for an antibody having LfVk1_Cα6 (SEQ ID NO: 88) as the light chain.

Purified antibodies prepared as described above were assessed for their storage stability under acidic conditions by the method described in (37-4). The result demonstrates that antibodies having the LfVk1_Ca6 sequence are more resistant to degradation than those having the original LfVk1_Ca sequence, as shown in FIG. 59.

Then, whether antibodies having the LfVk1_Ca sequence and antibodies having the LfVk1_Ca6 sequence bind to calcium ion was tested by the method described in Reference Example 33. The result is shown in Table 54. The Tm values of the Fab domains of antibodies having LfVk1_Ca sequence and antibodies having the degradation-resistant LfVk1_Ca6 sequence were shifted by 1° C. or more upon change in the calcium concentration in antibody solutions.

TABLE 54

| LIGHT CHAIN | CALCIUM ION CONCENTRATION | | Δ Tm (° C.) |
|---|---|---|---|
| VARIANT | 3 μM | 2 mM | 2 mM − 3 μM |
| LfVk1_Ca | 78.45 | 80.06 | 1.61 |
| LfVk1_Ca6 | 78.44 | 79.74 | 1.30 |

[Reference Example 38] Design of a Population of Antibody Molecules (Ca Library) with a Calcium Ion-Binding Motif Introduced into the Variable Region to Effectively Obtain Antibodies that Bind to Antigen in a Ca Concentration-Dependent Manner Preferred calcium-binding motifs include, for example, the hVk5-2 sequence and its CDR sequence, as well as residues at positions 30, 31, 32, 50, and 92 (Kabat numbering) thereof. Other calcium binding motifs include the EF-hand motif possessed by calcium-binding proteins (e.g., calmodulin) and C-type lectin (e.g., ASGPR).

The Ca library consists of heavy and light chain variable regions. A human antibody sequence was used for the heavy chain variable region, and a calcium-binding motif was introduced into the light chain variable region. The hVk1 sequence was selected as a template sequence of the light chain variable region for introducing a calcium-binding motif. An antibody containing an LfVk1_Ca sequence obtained by introducing the CDR sequence of hVk5-2 (one of calcium-binding motifs) into the hVk1 sequence was shown to bind to calcium ions, as shown in Reference Example 36. Multiple amino acids were allowed to appear in the template sequence to diversify antigen-binding molecules that constitute the library. Positions exposed on the surface of a variable region which is likely to interact with the antigen were selected as those where multiple amino acids are allowed to appear. Specifically, positions 30, 31, 32, 34, 50, 53, 91, 92, 93, 94, and 96 (Kabat numbering) were selected as flexible residues.

The type and appearance frequency of amino acid residues that were subsequently allowed to appear were determined. The appearance frequency of amino acids in the flexible residues of the hVk1 and hVk3 sequences registered in the Kabat database (KABAT, E. A. ET AL.: 'Sequences of proteins of immunological interest', vol. 91, 1991, NIH PUBLICATION) was analyzed. Based on the analysis results, the type of amino acids that were allowed to appear in the Ca library were selected from those with higher appearance frequency at each position. At this time, amino acids whose appearance frequency was determined to be low based on the analysis results were also selected to avoid the bias of amino acid properties. The appearance frequency of the selected amino acids was determined in reference to the analysis results of the Kabat database.

A Ca library containing a calcium-binding motif with emphasis on the sequence diversity as to contain multiple amino acids at each residue other than the motif were designed as a Ca library in consideration of the amino acids and appearance frequency set as described above. The detailed designs of the Ca library are shown in Tables 9 and 10 (with the positions in each table representing the Kabat numbering). In addition, in Tables 9 and 10, if position 92 represented by the Kabat numbering is Asn (N), position 94 may be Leu (L) instead of Ser (S).

[Reference Example 39] Ca Library Preparation

A gene library of antibody heavy-chain variable regions was amplified by PCR using a poly A RNA prepared from human PBMC, and commercial human poly A RNA, etc. as a template. As described in Reference Example 38, for the light chain variable regions of antibody, light chain variable regions of antibody that increase appearance frequency of antibodies which maintain a calcium-binding motif and can bind to an antigen in a calcium concentration-dependent manner were designed. In addition, for amino acid residues other than those with a calcium-binding motif introduced, a library of antibody light chain variable regions with evenly distributed amino acids of high appearance frequency in natural human antibodies as flexible residues was designed with reference to the information of amino acid appearance frequency in natural human antibodies (KABAT, E. A. ET AL.: 'Sequences of proteins of immunological interest', vol. 91, 1991, NIH PUBLICATION). A combination of the gene libraries of antibody heavy-chain and light-chain variable regions generated as described above, was inserted into a phagemid vector to construct a human antibody phage display library that presents Fab domains consisting of human antibody sequences (Methods Mol Biol. (2002) 178, 87-100).

Figure 60:
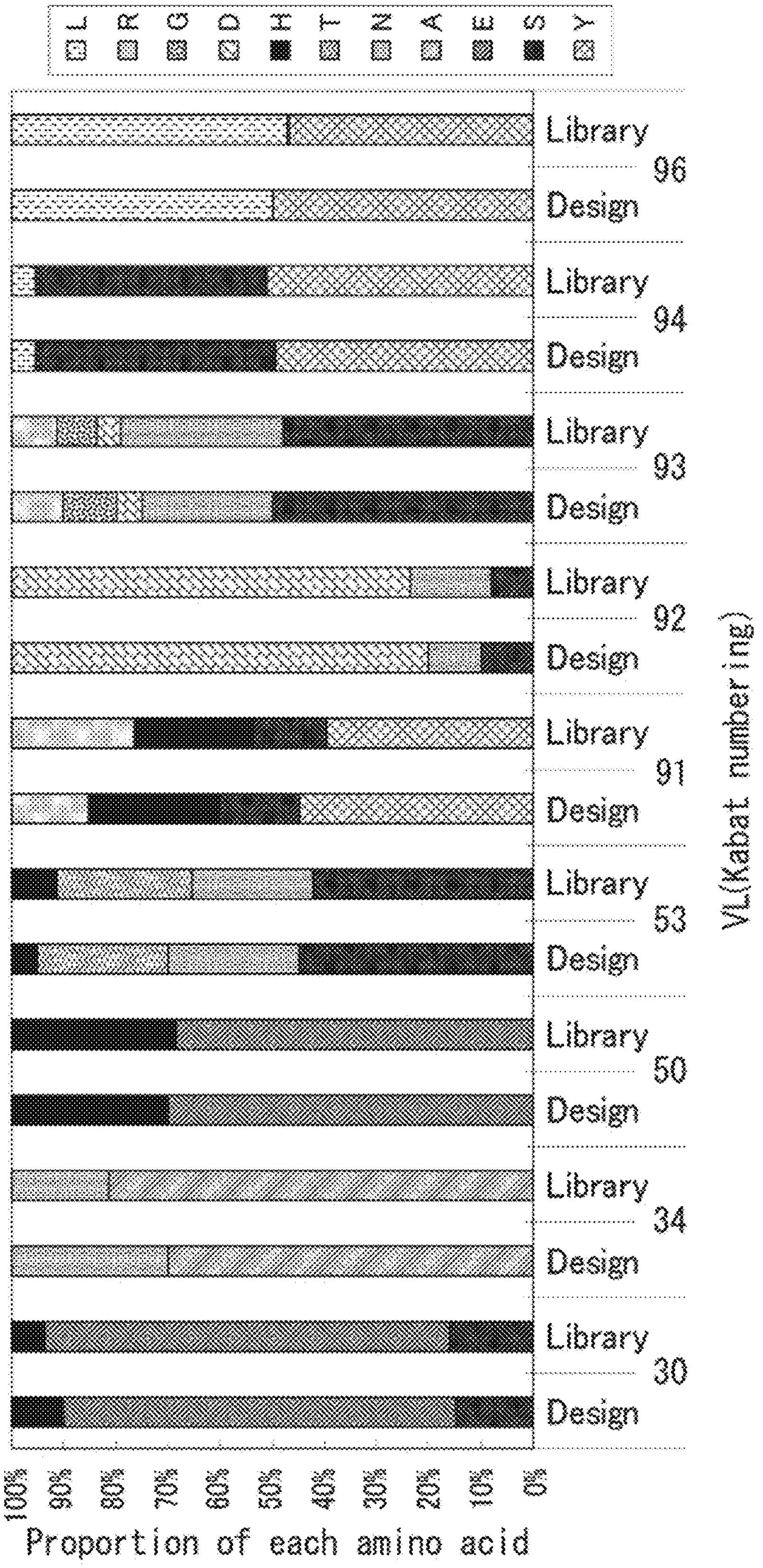
FIG. 60 shows the relationship between designed amino acid distribution (indicated with “Design”) and amino acid distribution for sequence information on 290 clones isolated from *E. coli* introduced with a gene library of antibodies that bind to antigens in a Ca-dependent manner (indicated with “Library”). The horizontal axis indicates amino acid position (Kabat numbering). The vertical axis indicates percentage in amino acid distribution.

The sequences of antibody genes isolated from *E. coli* introduced with an antibody gene library were determined according to the method described in Reference Example 43 below. The amino acid distribution in the sequences of isolated 290 clones and a designed amino acid distribution are shown in FIG. 60.

[Reference Example 40] Examination of the Calcium Ion-Binding Activity of Molecules Contained in the Ca Library (40-1) Calcium Ion-Binding Activity of Molecules Contained in the Ca Library As described in Reference Example 34, the hVk5-2 sequence that was demonstrated to bind to calcium ions is a sequence of low appearance frequency in the germline sequence. Thus, it was thought to be inefficient to obtain a calcium-binding antibody from an antibody library consisting of human germline sequences or from B cells obtained by immunizing a mouse expressing human antibodies. As a result, a Ca library was constructed. The presence or absence of a clone showing calcium binding in the constructed Ca library was examined.

(40-2) Expression and Purification of Antibodies

Clones contained in the Ca library were introduced into animal cell expression plasmids. Antibodies were expressed using the method described below. Cells of human fetal kidney cell-derived FreeStyle™ 293-F line (Invitrogen) were suspended in FreeStyle™ 293 Expression Medium (Invitrogen), and plated at a cell density of $1.33\times10^6$ cells/ml (3 ml) to each well of a 6-well plate. The prepared plasmids were introduced into the cells by a lipofection method. The cells were cultured in a $CO_2$ incubator (37° C., 8% $CO_2$, 90 rpm) for four days. By a method known to those skilled in the art, antibodies were purified using rProtein A Sepharose™ Fast Flow (Amersham Biosciences) from culture supernatants obtained as described above. The absorbance of solutions of purified antibodies was measured at 280 nm using a spectrophotometer. Antibody concentrations were calculated from the measured values by using the extinction coefficient determined by PACE method (Protein Science (1995) 4, 2411-2423).

(40-3) Assessment of Prepared Antibodies for their Calcium Ion Binding

Antibodies purified as described above were assessed for their calcium ion binding by the method described in Reference Example 26. The result is shown in Table 55. The Tm of the Fab domains of multiple antibodies contained in the Ca library changed depending on calcium ion concentration, suggesting that the library contains molecules that bind to calcium ion.

TABLE 55

| | SEQ ID NO | | CALCIUM ION CONCENTRATION | | ΔTm (° C.) |
|---|---|---|---|---|---|
| ANTIBODY | HEAVY CHAIN | LIGHT CHAIN | 3 μM | 2 mM | 2 mM − 3 μM |
| Ca_B01 | 89 | 100 | 70.88 | 71.45 | 0.57 |
| Ca_E01 | 90 | 101 | 84.31 | 84.95 | 0.64 |
| Ca_H01 | 91 | 102 | 77.87 | 79.49 | 1.62 |
| Ca_D02 | 92 | 103 | 78.94 | 81.1 | 2.16 |
| Ca_E02 | 93 | 104 | 81.41 | 83.18 | 1.77 |
| Ca_H02 | 94 | 105 | 72.84 | 75.13 | 2.29 |
| Ca_D03 | 95 | 106 | 87.39 | 86.78 | −0.61 |
| Ca_C01 | 96 | 107 | 74.74 | 74.92 | 0.18 |
| Ca_G01 | 97 | 108 | 65.21 | 65.87 | 0.66 |
| Ca_A03 | 98 | 109 | 80.64 | 81.89 | 1.25 |
| Ca_B03 | 99 | 110 | 93.02 | 93.75 | 0.73 |

[Reference Example 41] Isolation of Antibodies that Bind to IL-6 Receptor in a Ca-Dependent Manner (41-1) Isolation of Antibody Fragments, which Bind to Antigens in a Ca-Dependent Manner, from Library by Bead Panning The first selection from the constructed library of antibodies that bind in a Ca-dependent manner was performed by enriching only antibody fragments having the ability to bind to the antigen (IL-6 receptor).

Phages were produced by *E. coli* containing the constructed phagemids for phage display. To precipitate the phages, 2.5 M NaCl/10% PEG was added to the *E. coli* culture media of phage production. The precipitated phage population was diluted with TBS to prepare a phage library solution. Then, BSA and $CaCl_2$ were added to the phage library solution to adjust the final BSA concentration to 4% and the final calcium ion concentration to 1.2 mM. Regarding the panning method, the present inventors referred to general panning methods using antigens immobilized onto magnetic beads (J. Immunol. Methods. (2008) 332 (1-2), 2-9; J. Immunol. Methods. (2001) 247 (1-2), 191-203; Biotechnol. Prog. (2002) 18(2) 212-20; Mol. Cell Proteomics (2003) 2 (2), 61-9). The magnetic beads used were NeutrAvidin™ coated beads (Sera-Mag SpeedBeads™ NeutrAvidin™-coated) or Streptavidin coated beads (Dynabeads™ M-280 Streptavidin).

Specifically, 250 pmol of biotin-labeled antigen was added to the prepared phage library solution to allow the contact of the phage library solution with the antigen at room temperature for 60 minutes. BSA-blocked magnetic beads were added and allowed to bind to antigen/phage complexes at room temperature for 15 minutes. The beads were washed three times with 1 ml of 1.2 mM $CaCl_2$)/TBST (TBST containing 1.2 mM $CaCl_2$)) and then twice with 1 ml of 1.2 mM $CaCl_2$/TBS (TBST containing 1.2 mM $CaCl_2$). Then, the beads combined with 0.5 ml of 1 mg/ml trypsin were suspended at room temperature for 15 minutes, and immediately followed by separation of beads using a magnetic stand to collect a phage solution. The collected phage solution was added to 10 ml of *E. coli* strain ER2738 in a logarithmic growth phase (OD600 of 0.4-0.7). The *E. coli* was infected with the phages by culturing them while gently stirring at 37° C. for one hour. The infected *E. coli* was plated in a 225 mm×225 mm plate. Then, the phages were collected from the culture medium of the plated *E. coli* to prepare a phage library solution.

In the second-round panning, phages were enriched using the antigen-binding ability or the Ca-dependent binding ability as an indicator.

Specifically, when the enrichment was carried out using the antigen-binding ability as an indicator, 40 pmol of biotin-labeled antigen was added to the prepared phage library solution to allow the contact of the phage library solution with the antigen at room temperature for 60 minutes. BSA-blocked magnetic beads were added and allowed to bind to antigen/phage complexes at room temperature for 15 minutes. The beads were washed three times with 1 ml of 1.2 mM $CaCl_2$/TBST and then twice with 1.2 mM $CaCl_2$/TBS. Then, the beads added with 0.5 ml of 1 mg/ml trypsin were suspended at room temperature for 15 minutes. Then immediately, the beads were separated using a magnetic stand to collect a phage solution. To eliminate the ability from phages displaying no Fab to infect *E. coli*, the pIII protein (helper phage-derived pIII protein) of phages displaying no Fab was cleaved by adding 5 μl of 100 mg/ml trypsin to the collected phage solution. The recovered phage solution was added to 10 mL of the *E. coli* strain ER2738 in a logarithmic growth phase (OD600 of 0.4-0.7). The *E. coli* was cultured with gentle stirring at 37° C. for 1 hour to allow the phages to infect the *E. coli*. The infected *E. coli* was inoculated into a 225 mm×225 mm plate. Subsequently, the phages were recovered from the culture medium of the *E. coli* after inoculation to collect a phage library solution.

When the enrichment was carried out using the Ca-dependent binding ability as an indicator, 40 pmol of biotin-labeled antigen was added to the prepared phage library solution to allow the contact of the phage library solution with the antigen at room temperature for 60 minutes. BSA-blocked magnetic beads were added and allowed to bind to antigen/phage complexes at room temperature for 15 minutes. The beads were washed with 1 ml of 1.2 mM $CaCl_2$/TBST and 1.2 mM $CaCl_2$/TBS. Then, the beads added with 0.1 ml of 2 mM EDTA/TBS (TBS containing 2 mM EDTA) were suspended at room temperature. Then immediately, the beads were separated using a magnetic stand to collect a phage solution. To eliminate the ability from phages displaying no Fab to infect *E. coli*, the pIII protein (helper phage-derived pIII protein) of phages displaying no Fab was cleaved by adding 5 μl of 100 mg/ml trypsin to the collected phage solution. The recovered phage solution was added to 10 mL of the *E. coli* strain ER2738 in a logarithmic growth phase (OD600 of 0.4-0.7). The *E. coli* was cultured with gentle stirring at 37° C. for 1 hour to allow the phages to infect the *E. coli*. The infected *E. coli* was inoculated into a 225 mm×225 mm plate. Subsequently, the phages were recovered from the culture medium of the *E. coli* after inoculation to collect a phage library solution.

(41-2) Examination by Phage ELISA

A phage-containing culture supernatant was collected according to a routine method (Methods Mol. Biol. (2002) 178, 133-145) from a single colony of *E. coli*, obtained as described above.

A culture supernatant containing phages, to which BSA and $CaCl_2$ were added was subjected to ELISA as described below. A StreptaWell 96 microtiter plate (Roche) was coated overnight with 100 μL of PBS containing the biotin-labeled antigen. Each well of said plate was washed with PBST to remove the antigen, and then the wells were blocked with 250 μL of 4% BSA-TBS for 1 hour or longer. Said plate with the prepared culture supernatant added to each well, from which the 4% BSA-TBS was removed, was allowed to stand undisturbed at 37° C. for 1 hour, allowing the binding of phage-presenting antibody to the antigen present in each well. To each well washed with 1.2 mM $CaCl_2$/TBST, 1.2 mM $CaCl_2$/TBS or 1 mM EDTA/TBS was added. The plate was allowed to stand undisturbed for 30 minutes at 37° C. for incubation. After washing with 1.2 mM $CaCl_2$/TBST, an HRP-conjugated anti-M13 antibody (Amersham Pharmacia Biotech) diluted with TBS at a concentration of 1.2 mM of ionized calcium concentration was added to each well, and the plate was incubated for 1 hour. After washing with 1.2 mM $CaCl_2$/TBST, the chromogenic reaction of the solution in each well with a TMB single solution (ZYMED) added was stopped by adding sulfuric acid. Subsequently, said developed color was measured by measuring absorbance at 450 nm.

The base sequences of genes amplified with specific primers were analyzed for the clones subjected to phage ELISA.

The result of phage ELISA and sequence analysis is shown in Table 56.

TABLE 56

| | LIBRARY | |
|---|---|---|
| ENRICHMENT INDEX | Ca LIBRARY ANTIGEN-BINDING ABILITY | Ca LIBRARY DEPENDENT ANTIGEN-BINDING ABILITY |
| NUMBER OF PANNING | 2 | 2 |
| NUMBER OF EXAMINED CLONES | 85 | 86 |
| ELISA-POSITIVE | 77 | 75 |
| TYPES OF ELISA-POSITIVE CLONE SEQUENCES | 74 | 72 |
| TYPES OF Ca-DEPENDENT BINDING CLONE SEQUENCES | 13 | 47 |

(41-3) Expression and Purification of Antibodies

Clones that are determined to have Ca-dependent antigen binding ability as a result of phage ELISA were inserted into animal cell expression plasmids. Antibodies were expressed by the following method. Human fetal kidney cell-derived FreeStyle™ 293-F cells (Invitrogen) were suspended in FreeStyle™ 293 Expression Medium (Invitrogen), and plated at a cell density of $1.33\times10^6$ cells/ml (3 ml) into each well of a 6-well plate. The prepared plasmids were introduced into cells by a lipofection method. The cells were cultured for four days in a $CO_2$ incubator (37° C., 8% $CO_2$, 90 rpm). From the culture supernatants prepared as described above, antibodies were purified using the rProtein A Sepharose™ Fast Flow (Amersham Biosciences) by a method known to those skilled in the art. Absorbance at 280 nm of purified antibody solutions was measured using a spectrophotometer. Antibody concentrations were calculated from the determined values using an extinction coefficient calculated by the PACE method (Protein Science (1995) 4: 2411-2423).

(41-4) Assessment of Isolated Antibodies for their Ca-Dependent Binding Ability to Human IL-6 Receptor Antibodies 6RC1IgG_010 (heavy chain SEQ ID NO: 133; light chain SEQ ID NO: 134), 6RC1IgG_012 (heavy chain SEQ ID NO: 135; light chain SEQ ID NO: 136), and 6RC1IgG_019 (heavy chain SEQ ID NO: 137; light chain SEQ ID NO: 138) isolated as described above were assessed for the Ca dependency of their human IL-6 receptor-binding activity by analyzing the interaction between the antibodies and human IL-6 receptor using a BIACORE™ T100 surface plasmon resonance system (GE Healthcare). Tocilizumab (heavy chain SEQ ID NO: 111; light chain SEQ ID NO: 112) was used as a control antibody that does not have Ca-dependent binding activity to human IL-6 receptor. The interaction was analyzed in solutions at 1.2 mM and 3 μM calcium ion concentration, corresponding to high and low calcium ion concentration conditions, respectively. An appropriate amount of Protein A/G (Invitrogen) was immobilized onto a Sensor chip CM5 (GE Healthcare) by an amine coupling method, and antibodies of interest were captured onto the chip. The two types of running buffers used were: 20 mM ACES/150 mM NaCl/0.05% (w/v) Tween20®/1.2 mM $CaCl_2$) (pH 7.4); and 20 mM ACES/150 mM NaCl/0.05% (w/v) Tween20®/3 μM $CaCl_2$ (pH 7.4). These buffers were each used to dilute human IL-6 receptor. All measurements were carried out at 37° C.

In the interaction analysis of the antigen-antibody reaction using antibody tocilizumab as a control antibody, and antibodies 6RC1IgG_010, 6RC1IgG_012, and 6RC1IgG_019, a diluted IL-6 receptor solution and a running buffer as a blank were injected at a flow rate of 5 l/min for three minutes to allow IL-6 receptor to interact with antibodies tocilizumab, 6RC1IgG_010, 6RC1IgG_012, and 6RC1IgG_019 captured onto the sensor chip. Then, 10 mM glycine-HCl (pH 1.5) was injected at a flow rate of 30 μl/min for 30 seconds to regenerate the sensor chip.

Figure 61:
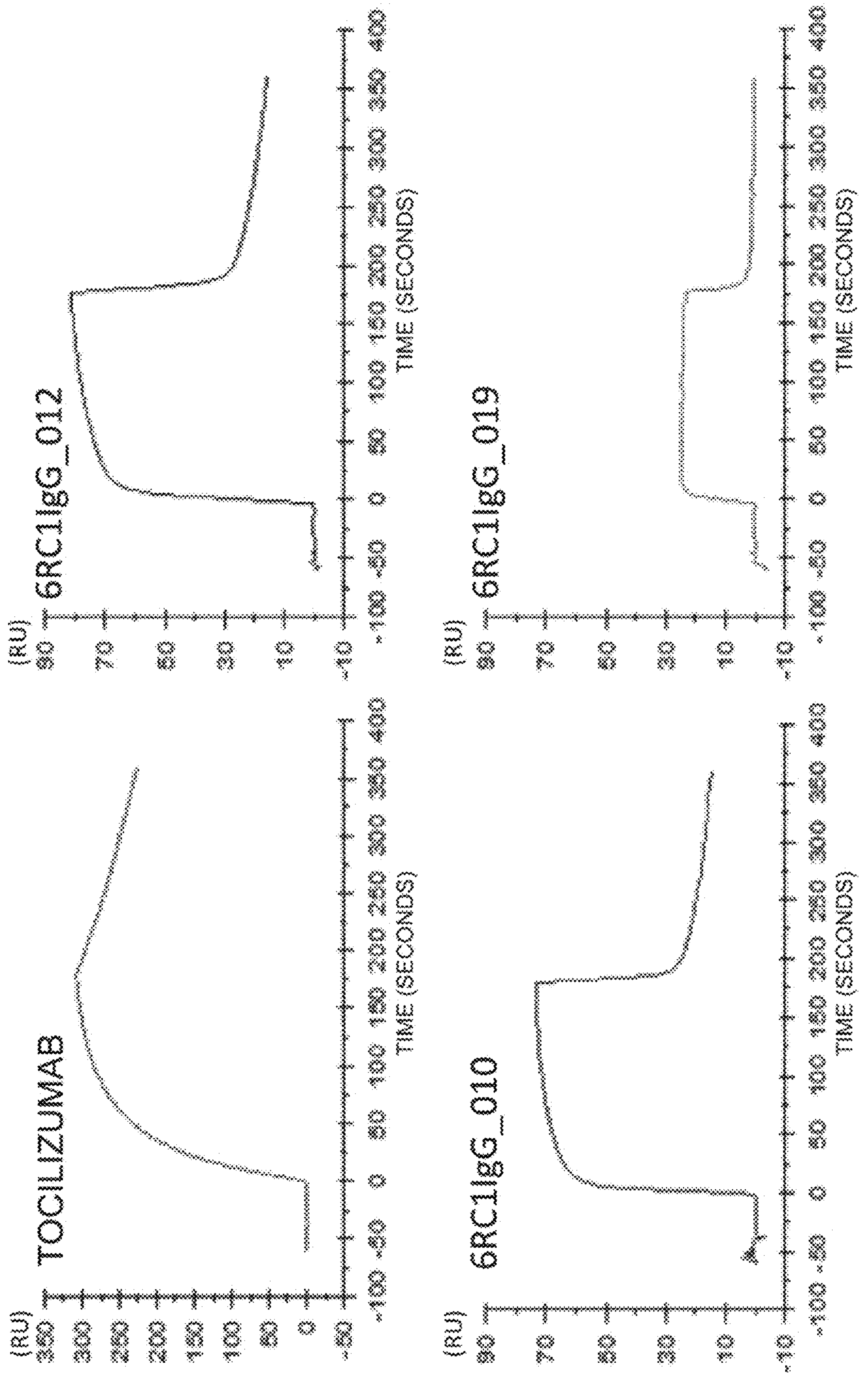
FIG. 61 shows sensorgrams for anti-IL-6R antibody (tocilizumab), antibody 6RC1IgG_010, antibody 6RC1IgG_012, and antibody 6RC1IgG_019 under a high calcium ion concentration (1.2 mM) condition. The horizontal axis shows time, and the vertical axis shows RU value.

Sensorgrams at the high calcium ion concentration obtained by the measurement using the above-described method are shown in FIG. 61.

Figure 62:
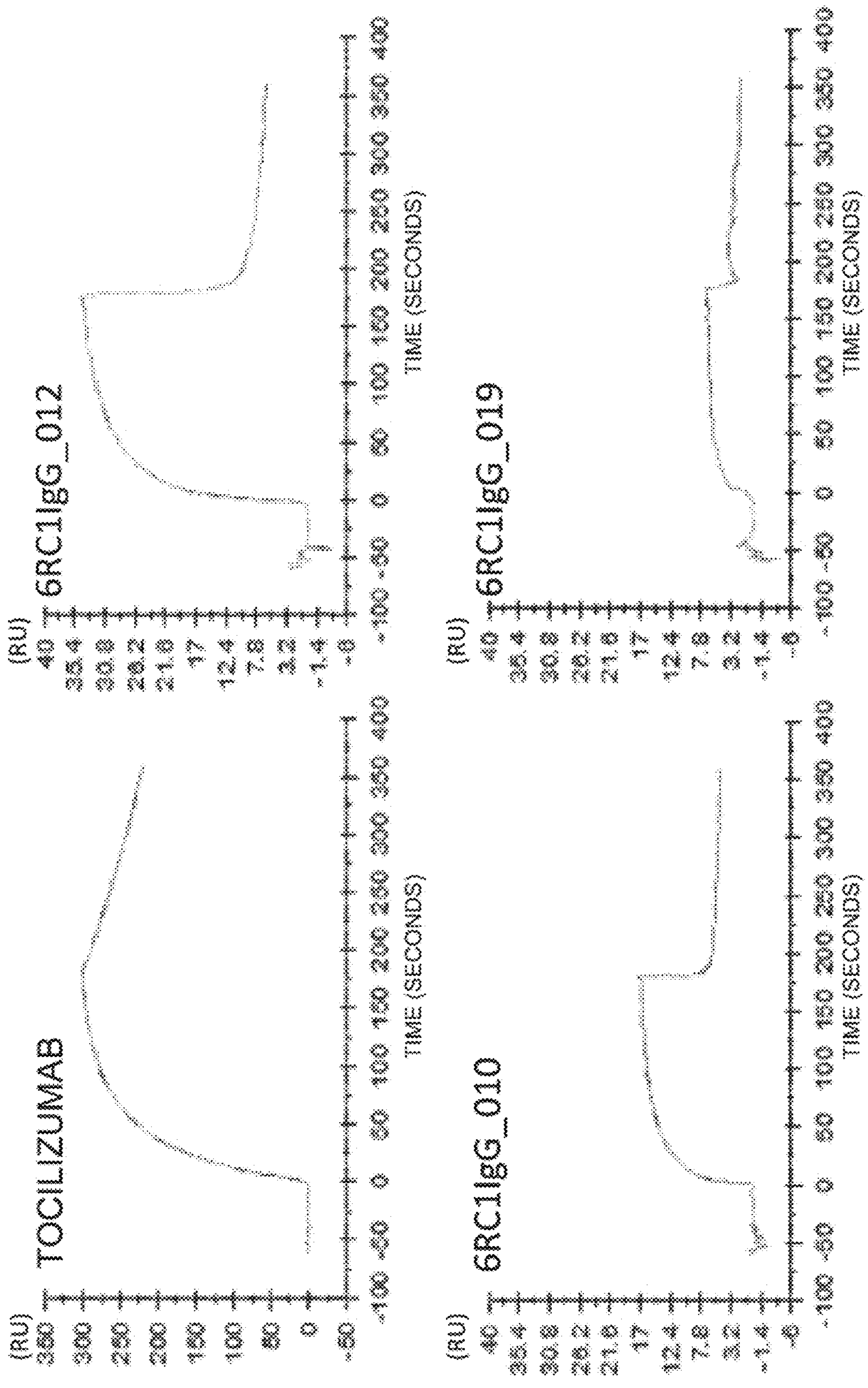
FIG. 62 shows sensorgrams for anti-IL-6R antibody (tocilizumab), antibody 6RC1IgG_010, antibody 6RC1IgG_012, and antibody 6RC1IgG_019 under a low calcium ion concentration (3 μM) condition. The horizontal axis shows time, and the vertical axis shows RU value.

Under the low calcium ion concentration condition, sensorgrams of antibodies tocilizumab, 6RC1IgG_010, 6RC1IgG_012, and 6RC1IgG_019 were also obtained by the same method. Sensorgrams at the low calcium ion concentration are shown in FIG. 62.

The result described above shows that the IL6 receptor-binding ability of antibodies 6RC1IgG_010, 6RC1IgG_012, and 6RC1IgG_019 was significantly reduced when the calcium ion concentration in the buffer was shifted from 1.2 mM to 3 μM.

[Reference Example 42] Design of pH-Dependent Binding Antibody Library (42-1) Method for Acquiring pH-Dependent Binding Antibodies WO2009/125825 discloses a pH-dependent antigen-binding molecule whose properties are changed in neutral pH and acidic pH ranges by introducing a histidine into an antigen-binding molecule. The disclosed pH-dependent antigen-binding molecule is obtained by alteration to substitute a part of the amino acid sequence of the antigen-binding molecule of interest with a histidine. To obtain a pH-dependent antigen-binding molecule more efficiently without preliminarily obtaining the antigen-binding molecule of interest to be modified, one method may be obtaining an antigen-binding molecule that binds to a desired antigen from a population of antigen-binding molecules (referred to as His library) with a histidine introduced into the variable region (more preferably, a position potentially involved in antigen binding). It may be possible to efficiently obtain an antigen-binding molecule having desired properties from a His library, because histidine appears more frequently in antigen-binding molecules from His library than those from conventional antibody libraries.

(42-2) Design of a Population of Antibody Molecules (his Library) with Histidine Residue Introduced into their Variable Region to Effectively Acquire Antibodies that Bind to Antigen in a pH-Dependent Manner First, positions for introducing a histidine were selected in a His library. WO 2009/125825 discloses generation of pH-dependent antigen-binding molecules by substituting amino acid residues in the sequences of IL-6 receptor antibodies, IL-6 antibodies, and IL-31 receptor antibodies with a histidine. In addition, an egg white lysozyme antibody (FEBS Letter 11483, 309, 1, 85-88) and hepcidin antibody (WO2009/139822) having a pH-dependent antigen-binding ability were generated by substituting the amino acid sequence of the antigen-binding molecule with histidines. Positions where histidines were introduced in the IL-6 receptor antibody, IL-6 antibody, IL-31 receptor antibody, egg white lysozyme antibody, and hepcidin antibody are shown in Table 57. Positions shown in Table 57 may be listed as candidate positions that can control the antigen-antibody binding. In addition, besides the positions shown in Table 57, positions that are likely to have contact with antigen were also considered to be suitable for introduction of histidines.

TABLE 57

| ANTIBODY | CHAIN | POSITION (Kabat) | | | | | | | | |
|---|---|---|---|---|---|---|---|---|---|---|
| IL-6 RECEPTOR | H | 27 | 31 | 32 | 35 | 50 | 58 | 62 | 100B | 102 |
| ANTIBODY | L | 28 | 31 | 32 | 53 | 56 | 92 | | | |
| IL-6 ANTIBODY | H | 32 | 59 | 61 | 99 | | | | | |
| | L | 53 | 54 | 90 | 94 | | | | | |
| IL-31 RECEPTOR | H | 33 | | | | | | | | |
| ANTIBODY | L | | | | | | | | | |
| EGG-WHILE LYSOZYME | H | 33 | 98 | | | | | | | |
| ANTIBODY | L | 54 | | | | | | | | |
| HEPCIDIN ANTIBODY | H | 52 | 57 | 99 | 107 | | | | | |
| | L | 27 | 89 | | | | | | | |

In the His library consisting of heavy-chain and light-chain variable regions, a human antibody sequence was used for the heavy chain variable region, and histidines were introduced into the light chain variable region. The positions listed above and positions that may be involved in antigen binding, i.e., positions 30, 32, 50, 53, 91, 92, and 93 (Kabat numbering, Kabat E A et al. 1991. Sequence of Proteins of Immunological Interest. NIH) in the light chain were selected as positions for introducing histidines in the His library. In addition, the hVk1 sequence was selected as a template sequence of the light chain variable region for introducing histidines. Multiple amino acids were allowed to appear in the template sequence to diversify antigen-binding molecules that constitute the library. Positions exposed on the surface of a variable region that is likely to interact with the antigen were selected as those where multiple amino acids are allowed to appear. Specifically, positions 30, 31, 32, 34, 50, 53, 91, 92, 93, 94, and 96 of the light chain (Kabat numbering, Kabat E A et al. 1991. Sequence of Proteins of Immunological Interest. NIH) were selected as flexible residues.

The type and appearance frequency of amino acid residues that were subsequently allowed to appear were determined. The appearance frequency of amino acids in the flexible residues in the hVk1 and hVk3 sequences registered in the Kabat database (KABAT, E. A. ET AL.: 'Sequences of proteins of immunological interest', vol. 91, 1991, NIH PUBLICATION) was analyzed. Based on the analysis results, the type of amino acids that were allowed to appear in the His library were selected from those with higher appearance frequency at each position. At this time, amino acids whose appearance frequency was determined to be low based on the analysis results were also selected to avoid the bias of amino acid properties. The appearance frequency of the selected amino acids was determined in reference to the analysis results of the Kabat database.

As His libraries, His library 1 which is fixed to necessarily incorporate a single histidine into each CDR, and His library 2 which is more emphasized on sequence diversity than the His library 1 were designed by taking the amino acids and appearance frequency set as described above into consideration. The detailed designs of His libraries 1 and 2 are shown in Tables 7 and 8 (with the positions in each table representing the Kabat numbering). In Tables 7 and 8, Ser (S) at position 94 can be excluded if position 92 represented by the Kabat numbering is Asn (N).

Figure 63:
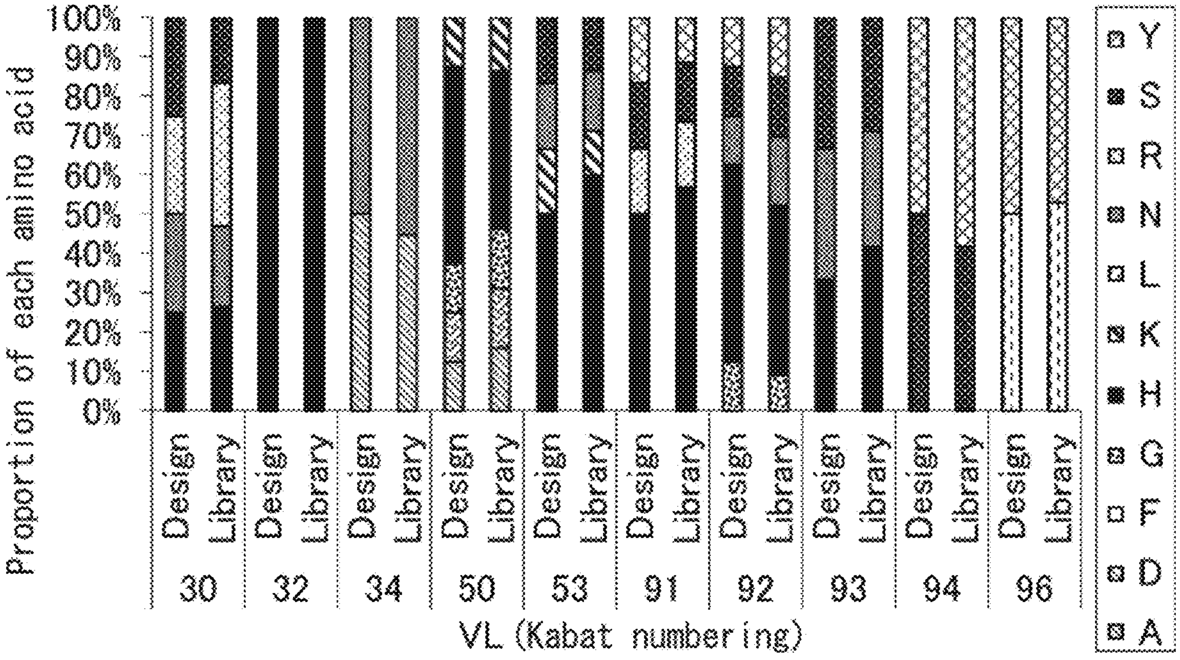
FIG. 63 shows the relationship between designed amino acid distribution (indicated with “Design”) and amino acid distribution for sequence information on 132 clones isolated from *E. coli* introduced with a gene library of antibodies that bind to antigens in a pH-dependent manner (indicated with “Library”). The horizontal axis shows amino acid position (Kabat numbering). The vertical axis indicates percentage in amino acid distribution.

[Reference Example 43] Preparation of a Phage Display Library for Human Antibodies (his Library 1) to Obtain an Antibody that Binds to Antigen in a pH-Dependent Manner A gene library of antibody heavy-chain variable regions was amplified by PCR using a poly A RNA prepared from human PBMC, and commercial human poly A RNA as a template. A gene library of antibody light-chain variable regions designed as His library 1 as described in Reference Example 42 was amplified using PCR. A combination of the gene libraries of antibody heavy-chain and light-chain variable regions generated as described above was inserted into a phagemid vector to construct a human antibody phage display library which presents Fab domains consisting of human antibody sequences. For the construction method, Methods Mol Biol. (2002) 178, 87-100 was used as a reference. For the construction of the library, the sequences of a phage display library with a trypsin cleavage sequence inserted into a linker region connecting the phagemid Fab to the phage pIII protein, and between the N2 and CT domains of the helper phage pIII protein gene were used. Sequences of the antibody genes isolated from *E. coli* into which the antibody gene library was introduced were identified, and sequence information was obtained for 132 clones. The designed amino acid distribution and the amino acid distribution of the identified sequences are shown in FIG. 63. A library containing various sequences corresponding to the designed amino acid distribution was constructed.

[Reference Example 44] Isolation of Antibodies that Bind to IL-6R in a pH-Dependent Manner (44-1) Isolation of Antibody Fragments, which Bind to Antigens in a pH-Dependent Manner, from the Library by Bead Panning The first selection from the constructed His library 1 was performed by enriching only antibody fragments with antigen (IL-6R) binding ability.

Phages were produced by *E. coli* containing the constructed phagemids for phage display. To precipitate the phages, 2.5 M NaCl/10% PEG was added to the *E. coli* culture media of phage production. The precipitated phage population was diluted with TBS to prepare a phage library solution. BSA and $CaCl_2$ were added to the phage library solution to adjust the final BSA concentration to 4% and the final calcium ion concentration to 1.2 mM. Regarding the panning method, the present inventors referred to general panning methods using antigens immobilized onto magnetic beads (J. Immunol. Methods. (2008) 332 (1-2), 2-9; J. Immunol. Methods. (2001) 247 (1-2), 191-203; Biotechnol. Prog. (2002) 18(2) 212-20, Mol. Cell Proteomics (2003) 2 (2), 61-9). The magnetic beads used were NeutrAvidin™ coated beads (Sera-Mag SpeedBeads™ NeutrAvidint-coated) or Streptavidin coated beads (Dynabeads™ M-280 Streptavidin).

Specifically, 250 pmol of biotin-labeled antigen was added to the prepared phage library solution to allow the contact of the phage library solution with the antigen at room temperature for 60 minutes. BSA-blocked magnetic beads were added and allowed to bind to antigen/phage complexes at room temperature for 15 minutes. The beads were washed three times with 1 ml of 1.2 mM $CaCl_2$/TBST (TBS containing 1.2 mM $CaCl_2$ and 0.1% Tween20®) and then twice with 1 ml of 1.2 mM $CaCl_2$/TBS (pH 7.6). Then, the beads added with 0.5 ml of 1 mg/ml trypsin were suspended at room temperature for 15 minutes, and then immediately separated using a magnetic stand to collect a phage solution. The collected phage solution was added to 10 ml of *E. coli* strain ER2738 in a logarithmic growth phase (OD600 of 0.4-0.7). The *E. coli* was infected with the phages by culturing them while gently stirring at 37° C. for one hour. The infected *E. coli* was plated in a 225 mm×225 mm plate. Then, the phages were collected from the culture medium of the plated *E. coli* to prepare a phage library solution.

To enrich the phages, the second and subsequent rounds of panning were performed using the antigen-binding ability or the pH-dependent binding ability as an indicator. Specifically, 40 pmol of the biotin-labeled antigen was added to the prepared phage library solution to allow the contact of the phage library solution with the antigen at room temperature for 60 minutes. BSA-blocked magnetic beads were added and allowed to bind to antigen/phage complexes at room temperature for 15 minutes. The beads were washed multiple times with 1 ml of 1.2 mM $CaCl_2$/TBST and 1.2 mM $CaCl_2$/TBS. Then, when the phages were enriched using the antigen-binding ability as an indicator, the beads added with 0.5 ml of 1 mg/ml trypsin were suspended at room temperature for 15 minutes, and then immediately separated using a magnetic stand to collect a phage solution. Alternatively, when the phages were enriched using the pH-dependent antigen-binding ability as an indicator, the beads added with 0.1 ml of 50 mM MES/1.2 mM $CaCl_2$)/150 mM NaCl (pH 5.5) were suspended at room temperature, and then immediately separated using a magnetic stand to collect a phage solution. To eliminate the ability from phages displaying no Fab to infect *E. coli*, the pIII protein (helper phage-derived pIII protein) of phages displaying no Fab was cleaved by adding 5 µl of 100 mg/ml trypsin to the collected phage solution. The collected phages were added to 10 ml of *E. coli* strain ER2738 in a logarithmic growth phase (OD600 of 0.4-0.7). The *E. coli* was infected with the phages by culturing them while gently stirring at 37° C. for one hour. The infected *E. coli* was plated in a 225 mm×225 mm plate. Then, the phages were collected from the culture medium of the plated *E. coli* to collect a phage library solution. The panning using the antigen-binding ability or the pH-dependent binding ability as an indicator was repeated twice.

(44-2) Assessment by Phage ELISA

Phage-containing culture supernatants were collected according to a conventional method (Methods Mol. Biol. (2002) 178, 133-145) from single colonies of *E. coli* obtained by the method described above.

To the phage-containing culture supernatants, BSA and $CaCl_2$ were added at a final concentration of 4% BSA and at a final calcium ion concentration of 1.2 mM. These phage-containing culture supernatants were subjected to ELISA by the following procedure. A StreptaWell 96 microtiter plate (Roche) was coated overnight with 100 µl of PBS containing the biotin-labeled antigen. After washing each well of the plate with PBST (PBS containing 0.1% Tween20®) to remove the antigen, the wells were blocked with 250 µl of 4% BSA/TBS for one hour or more. After removing 4% BSA/TBS, the prepared culture supernatants were added to each well. The antibodies presented on the phages were allowed to bind to the antigens on each well by incubating the plate at 37° C. for one hour. Following wash with 1.2 mM $CaCl_2$/TBST, 1.2 mM $CaCl_2$/TBS (pH 7.6) or 1.2 mM $CaCl_2$/TBS (pH 5.5) was added to each well. The plate was incubated at 37° C. for 30 minutes. After washing with 1.2 mM $CaCl_2$)/TBST, HRP-coupled anti-M13 antibody (Amersham Pharmacia Biotech) diluted with TBS containing 4% BSA and 1.2 mM ionized calcium was added to each well. The plate was incubated for one hour. After washing with 1.2 mM $CaCl_2$)/TBST, TMB single solution (ZYMED) was added to each well. The chromogenic reaction in the solution of each well was stopped by adding sulfuric acid, and then the absorbance at 450 nm was measured to assess the color development.

When enrichment was carried out using the antigen-binding ability as an indicator, phage ELISA following two rounds of panning showed that 17 of 96 clones were ELISA positive in an antigen-specific manner. Thus, clones were analyzed after three rounds of panning. Meanwhile, when enrichment was carried out using the pH-dependent antigen-binding ability as an indicator, phage ELISA following two rounds of panning showed that 70 of 94 clones were positive in ELISA. Thus, clones were analyzed after two rounds of panning.

The base sequences of genes amplified with specific primers were analyzed for the clones subjected to phage ELISA. The results of phage ELISA and sequence analysis are shown in Table 58 below.

TABLE 58

| | LIBRARY | |
|---|---|---|
| ENRICHMENT INDEX | His LIBRARY 1 ANTIGEN-BINDING ABILITY | His LIBRARY 1 pH-DEPENDENT ANTIGEN-BINDING ABILITY |
| NUMBER OF PANNING | 3 | 2 |
| NUMBER OF EXAMINED CLONES | 80 | 94 |
| ELISA-POSITIVE | 76 | 70 |
| TYPES OF ELISA-POSITIVE CLONE SEQUENCES | 30 | 67 |
| TYPES OF pH-DEPENDENT BINDING CLONE SEQUENCES | 22 | 47 |

By the same method, antibodies with pH-dependent antigen-binding ability were isolated from the naive human antibody phage display library. When enrichment was carried out using the antigen-binding ability as an indicator, 13 types of pH-dependent binding antibodies were isolated from 88 clones tested. Meanwhile, when enrichment was carried out using the pH-dependent antigen-binding ability as an indicator, 27 types of pH-dependent binding antibodies were isolated from 83 clones tested.

The result described above demonstrated that the variation of clones with pH-dependent antigen-binding ability isolated from the His library 1 was larger as compared to the naive human antibody phage display library.

(44-3) Expression and Purification of Antibodies

Clones assumed to have pH-dependent antigen-binding ability based on the result of phage ELISA were introduced into animal cell expression plasmids. Antibodies were expressed using the method described below. Human fetal kidney cell-derived FreeStyle™ 293-F cell line (Invitrogen) were suspended in FreeStyle™ 293 Expression Medium (Invitrogen), and plated at a cell density of $1.33\times10^6$ cells/ml (3 ml) to each well of a 6-well plate. The prepared plasmids were introduced into the cells by a lipofection method. The cells were cultured in a $CO_2$ incubator (37° C., 8% $CO_2$, 90 rpm) for four days. By a method known to those skilled in the art, antibodies were purified using rProtein A Sepharose™ Fast Flow (Amersham Biosciences) from culture supernatants obtained as described above. The absorbance of solutions of purified antibodies was measured at 280 nm using a spectrophotometer. Antibody concentrations were calculated from the measured values by using the extinction coefficient determined by PACE method (Protein Science (1995) 4, 2411-2423).

(44-4) Assessment of Isolated Antibodies for their pH-Dependent Binding Ability to Human IL-6 Receptor Antibodies 6RpH #01 (heavy chain SEQ ID NO: 139; light chain SEQ ID NO: 140), 6RpH #02 (heavy chain SEQ ID NO: 141; light chain SEQ ID NO: 142), and 6RpH #03 (heavy chain SEQ ID NO: 143; light chain SEQ ID NO: 144) isolated as described in (44-3) were assessed for the pH dependency of their human IL-6 receptor-binding activity by analyzing the interaction between the antibodies and human IL-6 receptor using a BIACORE™ T100 surface plasmon resonance system (GE Healthcare). Tocilizumab (heavy chain SEQ ID NO: 111; light chain SEQ ID NO: 112) was used as a control antibody that does not have pH-dependent binding activity to human IL-6 receptor. The interaction for the antigen-antibody reaction was analyzed in solutions at pH 7.4 and pH 6.0, corresponding to a neutral pH and acidic pH conditions, respectively. An appropriate amount of Protein A/G (Invitrogen) was immobilized onto a Sensor chip CM5 (GE Healthcare) by an amine coupling method, and about 300 RU each of antibodies of interest were captured onto the chip. The two types of running buffers used were: 20 mM ACES/150 mM NaCl/0.05% (w/v) Tween20®/1.2 mM $CaCl_2$ (pH 7.4); and 20 mM ACES/150 mM NaCl/0.05% (w/v) Tween20®/1.2 mM $CaCl_2$) (pH 6.0). These buffers were each used to dilute human IL-6 receptor. All measurements were carried out at 37° C.

In the interaction analysis of the antigen-antibody reaction using tocilizumab as a control antibody, and antibodies 6RpH #01, 6RpH #02, and 6RpH #03, a diluted IL-6 receptor solution and a running buffer as a blank were injected at a flow rate of 5 μl/min for three minutes to allow IL-6 receptor to interact with antibodies tocilizumab, 6RpH #01, 6RpH #02, and 6RpH #03 captured onto the sensor chip. Then, 10 mM glycine-HCl (pH 1.5) was injected at a flow rate of 30 μl/min for 30 seconds to regenerate the sensor chip.

Figure 64:
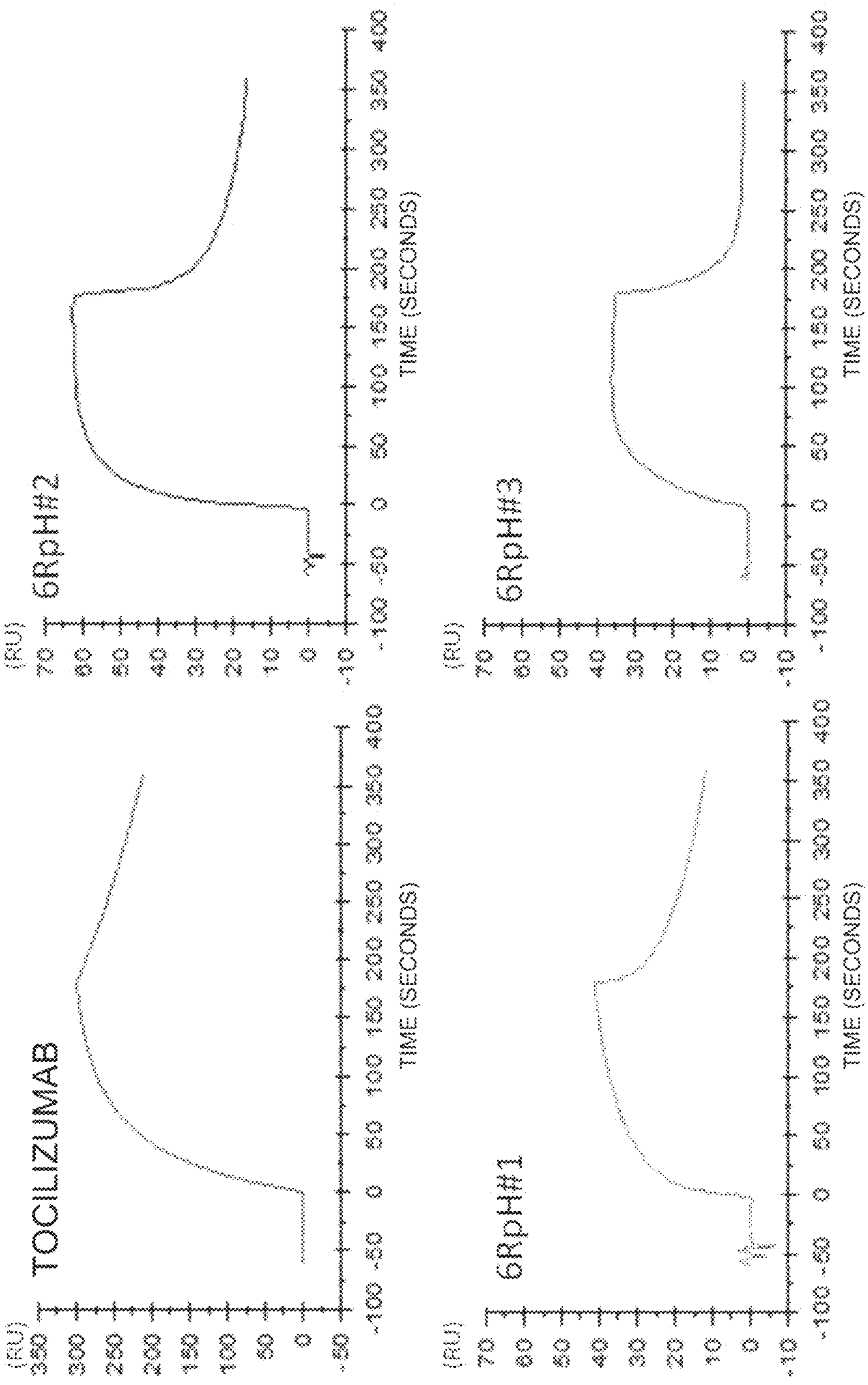
FIG. 64 shows sensorgrams for anti-IL-6R antibody (tocilizumab), antibody 6RpH #01, antibody 6RpH #02, and antibody 6RpH #03 at pH 7.4. The horizontal axis shows time, and the vertical axis shows RU value.
Figure 65:
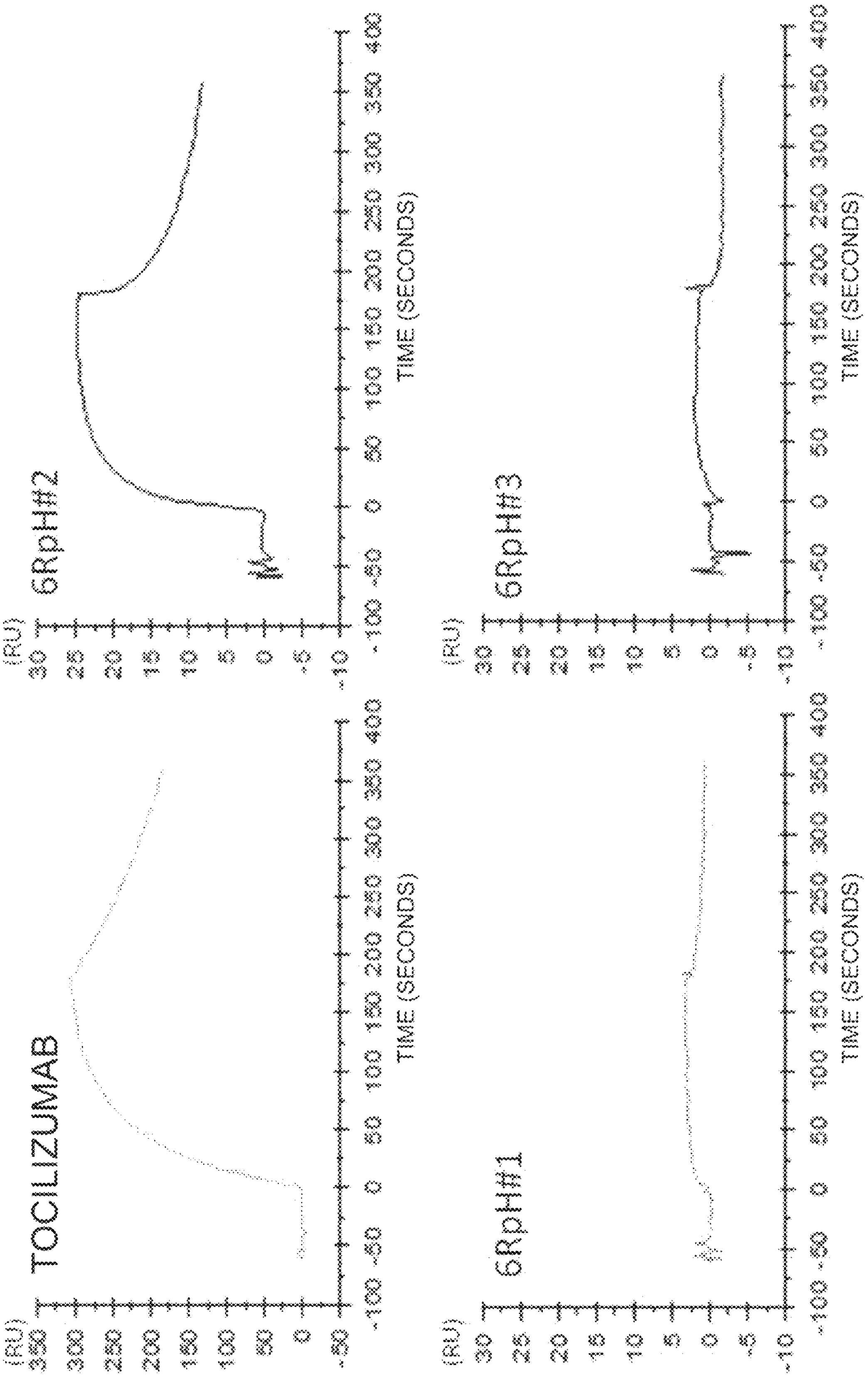
FIG. 65 shows sensorgrams for anti-IL-6R antibody (tocilizumab), antibody 6RpH #01, antibody 6RpH #02, and antibody 6RpH #03 at pH 6.0. The horizontal axis shows time, and the vertical axis shows RU value.

Sensorgrams at pH 7.4 obtained by the measurement using the method described above are shown in FIG. 64. Sensorgrams under the condition of pH 6.0 obtained by the same method are shown in FIG. 65.

The result described above shows that the IL-6 receptor-binding ability of antibodies 6RpH #01, 6RpH #02, and 6RpH #03 was significantly reduced when the buffer pH was shifted from pH 7.4 to pH 6.0.

INDUSTRIAL APPLICABILITY

The present invention has successfully obtained antigen-binding molecules that promote antigen elimination from blood (from serum or plasma), wherein the physiological activities of an antigen having two or more physiological activities which are difficult to inhibit in vitro with a single type of antigen-binding molecule can be reduced with a single type of antigen-binding molecule in vivo. Diseases that are caused by an antigen with multiple physiological activities have been difficult to treat with a single type of pharmaceutical agent alone. The present invention can provide effective pharmaceutical agents for such diseases.

The invention claimed is:

1. A method for producing an antibody comprising an antigen binding domain and an Fc region, the method comprising:

(a) selecting an antigen comprising (i) a first target molecule binding domain that, when bound to a first target molecule, produces a first physiological activity, and (ii) a second target molecule binding domain that, when bound to a second target molecule, produces a second physiological activity, wherein the first and second target molecule binding domains are at different locations on the antigen, wherein the first and second target molecules are different, wherein the first and second physiological activities are different, and wherein the antigen cannot bind to both of the target molecules simultaneously;

(b) identifying one or more antigen-binding domains that bind to the antigen and, when bound to the antigen, inhibit the antigen's ability to bind to the first target molecule but do not inhibit the antigen's ability to bind to the second target molecule;

(c) selecting, from the one or more antigen-binding domains of (b), an antigen-binding domain whose antigen-binding activity varies with pH as described in (i) below, or with calcium ion concentration as described in (ii) below, or with both:

(i) the antigen-binding activity is lower at pH 6.0 than at pH 7.4, wherein the ratio of the KD value for antigen binding at pH 6.0 to the KD value for antigen binding at pH 7.4 (KD (pH 6)/KD (pH 7.4)) is 2 or more when KD values are determined using a surface plasmon resonance technique in which a polypeptide comprising the antigen-binding domain is immobilized, the antigen serves as analyte, and the following conditions are used: 10 mM N-2-amino-ethanesulfonic acid (ACES), 150 mM NaCl, 0.05% polysorbate 20, 37° C., and either pH 6.0 or pH 7.4;

(ii) the antigen-binding activity is lower at a calcium ion concentration of 3 μM than at a second calcium ion concentration of 2 mM, wherein the ratio of the KD value for antigen binding at a calcium ion concentration of 3 μM to the KD value for antigen binding at a calcium ion concentration of 2 mM (KD (3 μM Ca++)/KD (2 mM Ca++)) is 2 or more when KD values are determined using a surface plasmon resonance technique in which a polypeptide comprising the antigen-binding domain is immobilized, the antigen serves as analyte, and the following conditions are used: 10 mM ACES, 150 mM NaCl, 0.05% (w/v) polysorbate 20, 37° C., pH 7.4, and either 3 μM $CaCl_2$) or 2 mM $CaCl_2$);

(d) identifying an IgG Fc region that (i) differs from the Fc region of a native human IgG by amino acid substitution, insertion, or deletion at one or more positions, (ii) binds to a human neonatal Fc receptor (FcRn) at pH 6, and (iii) binds, at pH 7.4, to a human Fc receptor with greater affinity than the affinity with which the native human IgG binds to the human Fc receptor, wherein the native human IgG is of the same isotype as the identified IgG Fc region, and the native human IgG is a native human IgG1, a native human IgG2, a native human IgG3, or a native human IgG4; and (e) preparing an antibody comprising the antigen-binding domain selected in (c) and the IgG Fc region identified in (d).

2. The method of claim 1, wherein the amino acid sequence of the identified IgG Fc region is not identical to the amino acid sequence of any naturally occurring IgG Fc region.

3. The method of claim 1, wherein (e) comprises expressing DNA encoding the antibody, thereby producing the antibody.

4. The method of claim 1, wherein the human Fc receptor of (d)(iii) is the human FcRn.

5. The method of claim 4, wherein the human Fc receptor of (d)(iii) is a human Fcγ receptor.

6. The method of claim 1, wherein introduction of the antibody into an individual whose plasma comprises the antigen reduces the concentration of the antigen in the plasma of the individual.

7. The method of claim 1, wherein the antigen-binding domain selected in (c) comprises at least one histidine residue.

8. The method of claim 4, wherein the one or more positions are selected from the following positions (all by EU numbering): 234, 235, 236, 237, 238, 239, 244, 245, 248, 249, 250, 251, 252, 253, 254, 255, 256, 257, 258, 260, 262, 265, 267, 270, 272, 274, 279, 280, 282, 283, 284, 285, 286, 288, 289, 293, 295, 297, 298, 303, 305, 307, 308, 309, 311, 312, 313, 314, 315, 316, 317, 318, 325, 326, 327, 328, 329, 330, 332, 334, 338, 339, 340, 341, 343, 345, 360, 361, 362, 375, 376, 377, 378, 380, 382, 384, 385, 386, 387, 389, 390, 391, 413, 422, 423, 424, 427, 428, 430, 431, 433, 434, 435, 436, 437, 438, 440, and 442.

9. The method of claim 8, wherein the one or more positions include at least one from the following positions (all by EU numbering), substituted with the indicated amino acid:

position 234: Arg;
position 235: Gly, Lys, or Arg;
position 236: Ala, Asp, Lys, or Arg;
position 237: Lys, Met, or Arg;
position 238: Ala, Asp, Lys, Leu, or Arg;
position 239: Asp or Lys;
position 244: Leu;
position 245: Arg;
position 248: Ile or Tyr;
position 249: Pro;
position 250: Ala, Glu, Phe, Ile, Met, Gln, Ser, Val, Trp, Gly, His, Leu, Asn, or Tyr;
position 251: Arg, Asp, Glu, or Leu;
position 252: Phe, Ser, Thr, Trp, or Tyr;
position 253: Val,
position 254: Ala, Gly, His, Le, Gin, Ser, Val, or Thr;
position 255: Ala, Asp, Phe, His, le, Lys, Leu, Met, Asn, Gin, Arg, Gly, Ser, Trp, Tyr, or Glu;
position 256: Ala, Asp, Glu, Arg, Asn, Pro, Thr, Ser, or Gin;
position 257: Ala, Gly, Ile, Leu, Met, Asn, Ser, Thr, or Val;
position 258: Asp or His;
position 260: Ser;
position 262: Leu;
position 265: Ala;
position 267: Met or Leu;
position 270: Lys or Phe;
position 272: Ala, Leu, or Arg;
position 274: Ala;
position 279: Leu, Ala, Asp, Gly, His, Met, Asn, Gin, Arg, Ser, Thr, Trp, or Tyr;
position 280: Ala, Gly, His, Lys, Asn, Gin, Arg, Ser, Thr, or Glu;
position 282: Ala or Asp;
position 283: Ala, Asp, Phe, Gly, His, Ile, Lys, Leu, Asn, Pro, Gin, Arg, Ser, Thr, Trp, or Tyr;
position 284: Lys;
position 285: Asn;
position 286: Ala, Asp, Phe, Gly, His, Ile, Lys, Leu, Met, Pro, Gin, Arg, Ser, Thr, Val, Trp, Tyr, or Glu;
position 288: Ala, Asp, Glu, Phe, Gly, His, Ile, Leu, Met, Asn, Pro, Gin, Arg, Val, Trp, Tyr, or Ser;
position 289: His;
position 293: Val;
position 295: Met;
position 297: Ala;
position 298: Gly;
position 303: Ala;
position 305: Ala or Thr;
position 307: Ala, Asp, Glu, Phe, Gly, His, Ile, Lys, Leu, Met, Asn, Pro, Gin, Arg, Ser, Val, Trp, or Tyr;
position 308: Ala, Phe, lie, Leu, Met, Pro, Gin, or Thr;
position 309: Ala, Asp, Glu, Pro, His, or Arg;
position 311: Ala, His, Glu, Lys, Leu, Met, Ser, Val, Trp, or Ile;
position 312: Ala, Asp, Pro, or His;
position 313: Tyr or Phe;
position 314: Ala, Leu, Lys, or Arg;
position 315: Ala, Asp, Glu, Phe, Gly, lie, Lys, Leu, Met, Gin, Arg, Ser, Thr, Val, Trp, Tyr, or His;
position 316: Ala, Glu, Phe, His, lie, Lys, Leu, Met, Asn, Pro, Gin, Arg, Ser, Thr, Val, Trp, or Asp;
position 317: Ala or Pro;
position 318: Asn or Thr;
position 325: Ala, Gly, Met, Leu, Ile, or Ser;
position 326: Asp;
position 327: Gly;
position 328: Arg, Asp, Glu, or Tyr;
position 329: Lys or Arg;
position 330: Leu;
position 332: Glu, Phe, His, Lys, Leu, Met, Arg, Ser, Trp, or Val;
position 334: Leu;
position 338: Ala;
position 339: Asn, Thr, or Trp;
position 340: Ala;
position 341: Pro;
position 343: Glu, His, Lys, Gin, Arg, Thr, or Tyr;
position 345: Ala;
position 360: His;
position 361: Ala;
position 362: Ala;
position 375: Ala or Arg;
position 376: Ala, Gly, le, Met, Pro, Thr, or Val;
position 377: Lys;
position 378: Asp, Asn, or Val;
position 380: Ala, Asn, Thr, or Ser;
position 382: Ala, Phe, His, Ile, Lys, Leu, Met, Asn, Gin, Arg, Ser, Thr, Trp, Tyr, or Val;

position 384: Ala;
position 385: Ala, Gly, Lys, Ser, Thr, Asp, His, or Arg;
position 386: Arg, Asp, Ile, Met, Ser, Thr, Lys, or Pro;
position 387: Ala, Arg, His, Pro, Ser, Thr, or Glu;
position 389: Ala, Asn, Pro, or Ser;
position 390: Ala;
position 391: Ala;
position 413: Ala;
position 423: Asn;
position 424: Ala or Glu;
position 427: Asn;
position 428: Ala, Asp, Phe, Gly, His, Ile, Lys, Leu, Met, Asn, Pro, Gln, Ser, Thr, Val, Trp, or Tyr;
position 430: Ala, Phe, Gly, His, Ile, Lys, Leu, Met, Asn, Gln, Arg, Ser, Thr, Val, or Tyr;
position 431: His or Asn;
position 433: Arg, Gin, His, Ile, Pro, Ser, or Lys;
position 434: Ala, Phe, Gly, Met, His, Ser, Trp, or Tyr;
position 435: Lys, Arg, or Asn;
position 436: Ala, His, Ile, Leu, Glu, Phe, Gly, Lys, Met, Asn, Arg, Ser, Thr, Trp, or Val;
position 437: Arg;
position 438: Lys, Leu, Thr, or Trp;
position 440: Lys; and
position 442: Lys.

10. The method of claim 5, wherein the one or more positions are selected from the following positions (all by EU numbering): 221, 222, 223, 224, 225, 227, 228, 230, 231, 232, 233, 234, 235, 236, 237, 238, 239, 240, 241, 243, 244, 245, 246, 247, 249, 250, 251, 252, 254, 255, 256, 257, 258, 260, 262, 263, 264, 265, 266, 267, 268, 269, 270, 271, 272, 273, 274, 275, 276, 278, 279, 280, 281, 282, 283, 284, 285, 286, 288, 290, 291, 292, 293, 294, 295, 296, 297, 298, 299, 300, 301, 302, 303, 304, 305, 307, 308, 309, 311, 312, 313, 314, 315, 316, 317, 318, 320, 322, 323, 324, 325, 326, 327, 328, 329, 330, 331, 332, 333, 334, 335, 336, 337, 339, 341, 343, 375, 376, 377, 378, 379, 380, 382, 385, 386, 387, 389, 392, 396, 421, 423, 427, 428, 429, 430, 431, 433, 434, 436, 438, 440, and 442.

11. The method of claim 10, wherein the one or more positions include at least one of the following positions (all by EU numbering), substituted with the indicated amino acid:

position 221: Lys or Tyr;
position 222: Phe, Trp, Glu, or Tyr;
position 223: Phe, Trp, Glu, or Lys;
position 224: Phe, Trp, Glu, or Tyr;
position 225: Glu, Lys, or Trp;
position 227: Glu, Gly, Lys, or Tyr;
position 228: Glu, Gly, Lys, or Tyr;
position 230: Ala, Glu, Gly, or Tyr;
position 231: Glu, Gly, Lys, Pro, or Tyr;
position 232: Glu, Gly, Lys, or Tyr;
position 233: Ala, Asp, Phe, Gly, His, Ile, Lys, Leu, Met, Asn, Gln, Arg, Ser, Thr, Val, Trp, or Tyr;
position 234: Ala, Asp, Glu, Phe, Gly, His, Ile, Lys, Met, Asn, Pro, Gln, Arg, Ser, Thr, Val, Trp, or Tyr;
position 235: Ala, Asp, Glu, Phe, Gly, His, lie, Lys, Met, Asn, Pro, Gin, Arg, Ser, Thr, Val, Trp, or Tyr;
position 236: Ala, Asp, Glu, Phe, His, lie, Lys, Leu, Met, Asn, Pro, Gin, Arg, Ser, Thr, Val, Trp, or Tyr;
position 237: Ala, Asp, Glu, Phe, His, lie, Lys, Leu, Met, Asn, Pro, Gin, Arg, Ser, Thr, Val, Trp, or Tyr;
position 238: Asp, Glu, Phe, Gly, His, Ile, Lys, Leu, Met, Asn, Gin, Arg, Ser, Thr, Val, Trp, or Tyr;
position 239: Asp, Glu, Phe, Gly, His, Ile, Lys, Leu, Met, Asn, Pro, Gin, Arg, Thr, Val, Trp, or Tyr;

position 240: Ala, Ile, Met, or Thr;
position 241: A sp, Glu, Leu, Arg, Trp, or Tyr;
position 243: Leu, Glu, Leu, Gin, Arg, Trp, or Tyr;
position 244: His;
position 245: Ala;
position 246: Asp, Glu, His, or Tyr;
position 247: Ala, Phe, Gly, His, Ile, Leu, Met, Thr, Val, or Tyr;
position 249: Glu, His, Gin, or Tyr;
position 250: Glu or Gin;
position 251: Phe;
position 254: Phe, Met, or Tyr;
position 255: Glu, Leu, or Tyr;
position 256: Ala, Met, or Pro;
position 258: Asp, Glu, His, Ser, or Tyr;
position 260: Asp, Glu, His, or Tyr;
position 262: Ala, Glu, Phe, lie, or Thr;
position 263: Ala, Ile, Met, or Thr;
position 264: Asp, Glu, Phe, Gly, His, Ile, Lys, Leu, Met, Asn, Pro, Gin, Arg, Ser, Thr, Trp, or Tyr;
position 265: Ala, Glu, Leu, Phe, Gly, His, Ile, Lys, Leu, Met, Asn, Pro, Gin, Arg, Ser, Thr, Val, Trp, or Tyr;
position 266: Ala, Phe, Ile, Leu, Met, or Thr;
position 267: Ala, Asp, Glu, Phe, Gly, His, lie, Lys, Leu, Met, Asn, Pro, Gin, Arg, Thr, Val, Trp, or Tyr;
position 268: Ala, Asp, Glu, Phe, Gly, Ile, Lys, Leu, Met, Asn, Pro, Gin, Arg, Thr, Val, or Trp;
position 269: Asp, Phe, Gly, His, Ile, Lys, Leu, Met, Asn, Pro, Arg, Ser, Thr, Val, Trp, or Tyr;
position 270: Glu, Phe, Gly, His, lie, Leu, Met, Pro, Gin, Arg, Ser, Thr, Trp, or Tyr;
position 271: Ala, Asp, Glu, Phe, Gly, His, Ile, Lys, Leu, Met, Asn, Gin, Arg, Ser, Thr, Val, Trp, or Tyr;
position 272: Asp, Phe, Gly, His, Ile, Lys, Leu, Met, Asn, Pro, Gin, Arg, Ser, Thr, Val, Trp, or Tyr;
position 273: Phe or Ile;
position 274: Asp, Glu, Phe, Gly, His, Ile, Leu, Met, Asn, Pro, Arg, Ser, Thr, Val, Trp, or Tyr;
position 275: Leu or Trp;
position 276: Asp, Glu, Phe, Gly, His, Ile, Leu, Met, Pro, Arg, Ser, Thr, Val, Trp, or Tyr;
position 278: Asp, Glu, Gly, His, Ile, Lys, Leu, Met, Asn, Pro, Gin, Arg, Ser, Thr, Val, or Trp;
position 279: Ala;
position 280: Ala, Gly, His, Lys, Leu, Pro, Gin, Trp, or Tyr;
position 281: Asp, Lys, Pro, or Tyr;
position 282: Glu, Gly, Lys, Pro, or Tyr;
position 283: Ala, Gly, His, Ile, Lys, Leu, Met, Pro, Arg, or Tyr;
position 284: Asp, Glu, Leu, Asn, Thr, or Tyr;
position 285: Asp, Glu, Lys, Gin, Trp, or Tyr;
position 286: Glu, Gly, Pro, or Tyr;
position 288: Asn, Asp, Glu, or Tyr;
position 290: Asp, Gly, His, Leu, Asn, Ser, Thr, Trp, or Tyr;
position 291: Asp, Glu, Gly, His, Lie, Gin, or Thr;
position 292: Ala, Asp, Glu, Pro, Thr, or Tyr;
position 293: Phe, Gly, His, lie, Leu, Met, Asn, Pro, Arg, Ser, Thr, Val, Trp, or Tyr;
position 294: Phe, Gly, His, lie, Lys, Leu, Met, Asn, Pro, Arg, Ser, Thr, Val, Trp, or Tyr;
position 295: Asp, Glu, Phe, Gly, His, Ile, Lys, Leu, Met, Asn, Pro, Arg, Ser, Thr, Val, Trp, or Tyr;
position 296: Ala, Asp, Glu, Gly, His, Ile, Lys, Leu, Met, Asn, Gin, Arg, Ser, Thr, or Val;

position 297: Asp, Glu, Phe, Gly, His, Ile, Lys, Leu, Met, Pro, Gin, Arg, Ser, Thr, Val, Trp, or Tyr;
position 298: Ala, Asp, Glu, Phe, His, Ile, Lys, Met, Asn, Gin, Arg, Thr, Val, Trp, or Tyr;
position 299: Ala, Asp, Glu, Phe, Gly, His, Ile, Lys, Leu, Met, Asn, Pro, Gin, Arg, Ser, Val, Trp, or Tyr;
position 300: Ala, Asp, Glu, Gly, His, Ile, Lys, Leu, Met, Asn, Pro, Gin, Arg, Ser, Thr, Val, or Trp;
position 301: Asp, Glu, His, or Tyr;
position 302: Ile;
position 303: Asp, Gly, or Tyr;
position 304: Asp, His, Leu, Asn, or Thr;
position 305: Glu, Ile, Thr, or Tyr;
position 311: Ala, Asp, Asn, Thr, Val or Tyr;
position 313: Phe;
position 315: Leu;
position 317: Glu or Gin;
position 318: His, Leu, Asn, Pro, Gin, Arg, Thr, Val, or Tyr;
position 320: Asp, Phe, Gly, His, Ile, Leu, Asn, Pro, Ser, Thr, Val, Trp, or Tyr;
position 322: Ala, Asp, Phe, Gly, His, Ile, Pro, Ser, Thr, Val, Trp, or Tyr;
position 323: Ile, Leu, or Met;
position 324: Asp, Phe, Gly, His, Ile, Leu, Met, Pro, Arg, Thr, Val, Trp, or Tyr;
position 325: Ala, Asp, Glu, Phe, Gly, His, Ile, Lys, Leu, Met, Pro, Gin, Arg, Ser, Thr, Val, Trp, or Tyr;
position 326: Ala, Asp, Glu, Phe, Gly, His, lie, Leu, Met, Asn, Pro, Gin, Ser, Thr, Val, Trp, or Tyr;
position 327: Ala, Asp, Glu, Phe, Gly, His, lie, Lys, Leu, Met, Asn, Pro, Arg, Thr, Val, Trp, or Tyr;
position 328: Ala, Asp, Glu, Phe, Gly, His, Ile, Lys, Met, Asn, Pro, Gin, Arg, Ser, Thr, Val, Trp, or Tyr;
position 329: Asp, Glu, Phe, Gly, His, Ile, Lys, Leu, Met, Asn, Gin, Arg, Ser, Thr, Val, Trp, or Tyr;
position 330: Cys, Glu, Phe, Gly, His, Ile, Lys, Leu, Met, Asn, Pro, Arg, Ser, Thr, Val, Trp, or Tyr;
position 331: Asp, Phe, His, Ile, Leu, Met, Gin, Arg, Ser, Thr, Val, Trp, or Tyr;
position 332: Ala, Asp, Glu, Phe, Gly, His, Lys, Leu, Met, Asn, Pro, Gin, Arg, Ser, Thr, Val, Trp, or Tyr;
position 333: Ala, Asp, Glu, Phe, Gly, His, Ile, Lys, Leu, Met, Pro, Arg, Ser, Thr, Val, or Tyr;
position 334: Ala, Glu, Phe, His, le, Leu, Met, Asn, Pro, Gin, Arg, Ser, Thr, Val, Trp, or Tyr;
position 335: Asp, Phe, Gly, His, Ile, Leu, Met, Asn, Pro, Arg, Ser, Val, Trp, or Tyr;
position 336: Glu, Lys, or Tyr;
position 337: Asp, Glu, His, or Asn;
position 339: Asp, Phe, Gly, lie, Lys, Met, Asn, Gin, Arg, Ser, or Thr;
position 376: Ala or Val;
position 377: Gly or Lys;
position 378: Asp;
position 379: Asn;
position 380: Ala, Asn, or Ser;
position 382: Ala or Ile;
position 385: Glu;
position 392: Thr;
position 396: Asp, Glu, Phe, lie, Lys, Leu, Met, Gin, Arg, or Tyr;
position 421: Lys;
position 427: Asn;
position 428: Phe or Leu;
position 429: Met;
position 434: Trp;
position 436: Ile;
position 440: Gly, His, lie, Leu, or Tyr.

12. The method of claim 5, wherein the human Fcγ receptor is selected from FcγRIa, FcγRIIa, FcγRIIb, and FcγRIIIa.

13. The method of claim 10, wherein the one or more positions include position 238 (EU numbering) substituted with Asp and position 271 (EU numbering) substituted with Gly.

14. The method of claim 13, wherein the one or more positions also include at least one position from the following group of positions (all by EU numbering): 233, 234, 237, 244, 245, 249, 250, 251, 252, 254, 255, 256, 257, 258, 260, 262, 264, 265, 266, 267, 268, 269, 270, 272, 279, 283, 285, 286, 288, 293, 296, 307, 308, 309, 311, 312, 314, 316, 317, 318, 326, 327, 330, 331, 332, 333, 339, 341, 343, 375, 376, 377, 378, 380, 382, 385, 386, 387, 389, 396, 423, 427, 428, 430, 431, 433, 434, 436, 438, 440, and 442.

15. The method of claim 14, wherein at least one position from the following positions (all by EU numbering) is substituted with the indicated amino acid:
position 233: Asp;
position 234: Tyr;
position 237: Asp;
position 264: Ile;
position 265: Glu;
position 266: Phe, Met, or Leu;
position 267: Ala, Glu, Gly, or Gln;
position 268: Asp or Glu;
position 269: Asp;
position 272: Asp, Phe, Ile, Met, Asn, or Gln;
position 296: Asp;
position 326: Ala or Asp;
position 327: Gly;
position 330: Lys or Arg;
position 331: Ser;
position 332: Thr;
position 333: Thr, Lys, or Arg;
position 396: Asp, Glu, Phe, lie, Lys, Leu, Met, Gin, Arg, or Tyr.

16. The method of claim 13, wherein the one or more positions also include at least one from the following group of positions (all by EU numbering): 244, 245, 249, 250, 251, 252, 254, 255, 256, 257, 258, 260, 262, 270, 272, 279, 283, 285, 286, 288, 293, 307, 308, 309, 311, 312, 314, 316, 317, 318, 332, 339, 341, 343, 375, 376, 377, 378, 380, 382, 385, 386, 387, 389, 423, 427, 428, 430, 431, 433, 434, 436, 438, 440, and 442.

17. The method of claim 16, wherein at least one position from the following positions (all by EU numbering) is substituted with the indicated amino acid:
position 244: Leu;
position 245: Arg;
position 249: Pro;
position 250: Gln or Glu;
position 251: Arg, Asp, Glu, or Leu;
position 252: Phe, Ser, Thr, or Tyr;
position 254: Ser or Thr;
position 255: Arg, Gly, Ile, or Leu;
position 256: Ala, Arg, Asn, Asp, Gin, Glu, Pro, or Thr;
position 257: Ala, Ile, Met, Asn, Ser, or Val;
position 258: Asp;
position 260: Ser;
position 262: Leu;
position 270: Lys;
position 272: Leu or Arg;

position 279: Ala, Asp, Gly, His, Met, Asn, Gin, Arg, Ser, Thr, Trp, or Tyr;
position 283: Ala, Asp, Phe, Gly, His, Ile, Lys, Leu, Asn, Pro, Gin, Arg, Ser, Thr, Trp, or Tyr;
position 285: Asn;
position 286: Phe;
position 288: Asn or Pro;
position 293: Val;
position 307: Ala, Glu, Gin, or Met;
position 308: Ile, Pro, or Thr;
position 309: Pro,
position 311: Ala, Glu, Ile, Lys, Leu, Met, Ser, Val, or Trp;
position 312: Ala, Asp, or Pro;
position 314: Ala or Leu;
position 316: Lys;
position 317: Pro;
position 318: Asn or Thr;
position 332: Phe, His, Lys, Leu, Met, Arg, Ser, or Trp;
position 339: Asn, Thr, or Trp,
position 341: Pro;
position 343: Glu, His, Lys, Gin, Arg, Thr, or Tyr;
position 375: Arg;
position 376: Gly, Ile, Met, Pro, Thr, or Val;
position 377: Lys;
position 378: Asp, Asn, or Val;
position 380: Ala, Asn, Ser, or Thr;
position 382: Phe, His, Ile, Lys, Leu, Met, Asn, Gin, Arg, Ser, Thr, Val, Trp, or Tyr;
position 385: Ala, Arg, Asp, Gly, His, Lys, Ser, or Thr;
position 386: Arg, Asp, Ile, Lys, Met, Pro, Ser, or Thr;
position 387: Ala, Arg, His, Pro, Ser, or Thr;
position 389: Asn, Pro, or Ser;
position 423: Asn;
position 427: Asn;
position 428: Leu, Met, Phe, Ser, or Thr;
position 430: Ala, Phe, Gly, His, Lie, Lys, Leu, Met, Asn, Gln, Arg, Ser, Thr, Val, or Tyr;
position 431: His or Asn;
position 433: Arg, Gln, His, Ile, Lys, Pro, or Ser;
position 434: Ala, Gly, His, Phe, Ser, Trp, or Tyr;
position 436: Arg, Asn, His, Ile, Leu, Lys, Met, or Thr;
position 438: Lys, Leu, Thr, or Trp;
position 440: Lys;
position 442: Lys.

18. The method of claim 1, wherein the first and second target molecules are cell surface receptors.

19. The method of claim 1, wherein the antigen-binding domain binds to the first binding domain of the antigen and thereby blocks binding of the first binding domain to the first target molecule.

20. The method of claim 1, wherein the antigen is selected from the group consisting of: activin, activin A, activin AB, activin B, activin C, activin RIA, activin RIA ALK-2, activin RIB ALK-4, activin RIIA, activin RIB, adiponectin, aFGF, AGE, allergen, amyloid β, amyloid immunoglobulin heavy chain variable region, amyloid immunoglobulin light chain variable region, anti-Id, antithrombin III, anthrax, apo A1, apo-serum amyloid A, β-2-microglobulin, bFGF, B-lymphocyte stimulator (BLyS), BMP, BMP-2 (BMP-2a), BMP-3 (osteogenin), BMP-4 (BMP-2b), BMP-5, BMP-6 (Vgr-1), BMP-7 (OP-1), BMP-8 (BMP-8a), C10, C1 inhibitory factor, C1q, C3, C3a, C4, C5, C5a (complement 5a), cathepsin A, cathepsin B, cathepsin C/DPPI, cathepsin D, cathepsin E, cathepsin H, cathepsin L, cathepsin O, cathepsin S, cathepsin V, cathepsin X/Z/P, CCL, CCL1/I-309, CCL11/eotaxin, CCL12/MCP-5, CCL13/MCP-4, CCL14/HCC-1, CCL15/HCC-2, CCL16/HCC-4, CCL17/TARC, CCL18/PARC, CCL19/ELC, CCL2/MCP-1, CCL20/MIP-3-α, CCL21/SLC, CCL22/MDC, CCL23/MPIF-1, CCL24/eotaxin-2, CCL25/TECK, CCL26/eotaxin-3, CCL27/CTACK, CCL28/MEC, CCL3/M1P-1-α, CCL3L1/LD-78-D, CCL4/MIP-1-β, CCL5/RANTES, CCL6/C10, CCL7/MCP-3, CCL8/MCP-2, CCL9/10/MIP-1-γ, *Clostridium botulinum* toxin, *Clostridium difficile* toxin, *Clostridium perfringens* toxin, connective tissue growth factor (CTGF), CTLA-4, CX3CL1/fractalkine, CXCL, CXCL1/Gro-α, CXCL10, CXCL11/I-TAC, CXCL12/SDF-1-α/β, CXCL13/BCA-1, CXCL14/BRAK, CXCL15/lungkine, CXCL16, CXCL2/Gro-β CXCL3/Gro-γ, CXCL4/PF4, CXCL5/ENA-78, CXCL6/GCP-2, CXCL7/NAP-2, CXCL8/IL-8, CXCL9/Mig, CXCL10/IP-10, DC-SIGN, digoxin, EGF like domain containing protein 7, endotoxin, RSV F protein, F10, F11, F12, F13, F5, F9, factor Ia, factor IX, factor Xa, factor VII, factor VIII, factor VIIIc, FGF, FGF-19, FGF-2, FGF-2 receptor, FGF-3, FGF-8, fibronectin, GRO/MGSA, GRO-β, GRO-γ, *Helicobacter pylori* (*H. pylori*), hapten (NP-cap or NIP-cap), HB-EGF, HCMV gB envelope glycoprotein, Hep B gp120*, Bacillus anthracis* protective antigen, hepatitis C virus E2 glycoprotein, hepatitis E, hepcidin, herpes simplex virus (HSV) gB glycoprotein, HIV envelope protein GP120, HIV gp 120 V3 loop, HLA, HLA-DR, high mobility group box 1 (HMGB1), HSP47, Hsp90, HSV gD glycoprotein, human cytomegalovirus (HCMV), human serum albumin, human tissue plasminogen activator (t-PA), IFN-α, IFN-β, IFN-γ, IgE, IGF, immunoglobulin immune complex, immunoglobulin, influenza, inhibin, inhibin α, inhibin β, laminin 5, latency-associated peptide, latent TGF-1, latent TGF-1 bp1, LBP, LDL, leptin, Lewis-Y antigen, Lewis-Y-related antigen, LFA-1, LFA-3, lipoproteins, L-selectin, type 3 nonstructural protein of hepatitis C virus (NS3), oncostatin M, osteopontin, oxidized LDL, PEG-20, PEG-30, PEG40, prekallikrein, prion protein, procalcitonin, proinsulin, prolactin, proprotein convertase PC9, prorelaxin, respiratory syncytial virus (RSV) F, rheumatoid factor, RSV Fgp, Sclerostin, serum amyloid P, serum albumin, Shiga like-toxin II, syndecan-1, tenascin, TGF, TGF-α, TGF-β, TGF-β1, TGF-β2, TGF-β, TGF-β4, TGF-β5, TGF-I, thrombin, thrombopoietin (TPO), thyroxine binding globulin, TNF-α, TNF-β, TNIL-I, toxic metabolite, VEGF, viral antigens, and von Willebrand factor (vWF).

* * * * *

UNITED STATES PATENT AND TRADEMARK OFFICE
CERTIFICATE OF CORRECTION

PATENT NO. : 11,827,699 B2
APPLICATION NO. : 16/028140
DATED : November 28, 2023
INVENTOR(S) : Tomoyuki Igawa et al.

Page 1 of 5

It is certified that error appears in the above-identified patent and that said Letters Patent is hereby corrected as shown below:

In the Claims

Column 520, Lines 47 and 48: In Claim 1, delete "N-2-amino-ethanesulfonic acid (ACES)," and insert -- N-(2-Acetamido)-2-aminoethanesulfonic acid --.

Column 520, Line 63: In Claim 1, "CaCl$_2$)" and insert -- CaCl$_2$ --.

Column 520, Line 63: In Claim 1, "CaCl$_2$);" and insert -- CaCl$_2$; --.

Column 521, Line 22: In Claim 5, delete "claim 4," and insert -- claim 1, --.

Column 521, Line 60: In Claim 9, delete "Val," and insert -- Val; --.

Column 521, Line 61: In Claim 9, delete "Le, Gin," and insert -- Ile, Gln, --.

Column 521, Line 62: In Claim 9, delete "le," and insert -- Ile, --.

Column 521, Line 63: In Claim 9, delete "Gin," and insert -- Gln, --.

Column 521, Line 65: In Claim 9, delete "Gin;" and insert -- Gln; --.

Column 522, Line 8: In Claim 9, delete "Gin," and insert -- Gln, --.

Column 522, Line 10: In Claim 9, delete "Gin," and insert -- Gln, --.

Column 522, Line 14: In Claim 9, delete "Gin," and insert -- Gln, --.

Column 522, Line 18: In Claim 9, delete "Gin," and insert -- Gln, --.

Signed and Sealed this
Twenty-ninth Day of April, 2025

Coke Morgan Stewart
*Acting Director of the United States Patent and Trademark Office*

CERTIFICATE OF CORRECTION (continued)
U.S. Pat. No. 11,827,699 B2

Column 522, Line 20: In Claim 9, delete "Gin," and insert -- Gln, --.

Column 522, Line 29: In Claim 9, delete "Gin," and insert -- Gln, --.

Column 522, Line 30: In Claim 9, delete "lie," and insert -- Ile, --.

Column 522, Line 30: In Claim 9, delete "Gin," and insert -- Gln, --.

Column 522, Line 37: In Claim 9, delete "lie," and insert -- Ile, --.

Column 522, Line 38: In Claim 9, delete "Gin," and insert -- Gln, --.

Column 522, Line 39: In Claim 9, delete "lie," and insert -- Ile, --.

Column 522, Line 40: In Claim 9, delete "Gin," and insert -- Gln, --.

Column 522, Line 56: In Claim 9, delete "Gin," and insert -- Gln, --.

Column 522, Line 62: In Claim 9, delete "le," and insert -- Ile, --.

Column 522, Line 66: In Claim 9, delete "Gin," and insert -- Gln, --.

Column 523, Line 17: In Claim 9, delete "Gin," and insert -- Gln, --.

Column 523, Line 58: In Claim 11, delete "lie," and insert -- Ile, --.

Column 523, Line 59: In Claim 11, delete "Gin," and insert -- Gln, --.

Column 523, Line 60: In Claim 11, delete "lie," and insert -- Ile, --.

Column 523, Line 61: In Claim 11, delete "Gin," and insert -- Gln, --.

Column 523, Line 62: In Claim 11, delete "lie," and insert -- Ile, --.

Column 523, Line 63: In Claim 11, delete "Gin," and insert -- Gln, --.

Column 523, Line 65: In Claim 11, delete "Gin," and insert -- Gln, --.

Column 523, Line 67: In Claim 11, delete "Gin," and insert -- Gln, --.

Column 524, Line 2: In Claim 11, delete "A sp," and insert -- Asp, --.

Column 524, Line 3: In Claim 11, delete "Gin," and insert -- Gln, --.

Column 524, Line 10 (approx.): In Claim 11, delete "Gin," and insert -- Gln, --.

CERTIFICATE OF CORRECTION (continued)
U.S. Pat. No. 11,827,699 B2

Column 524, Line 11 (approx.): In Claim 11, delete "Gin;" and insert -- Gln; --.

Column 524, Line 18 (approx.): In Claim 11, delete "lie," and insert -- Ile, --.

Column 524, Line 21: In Claim 11, delete "Gin," and insert -- Gln, --.

Column 524, Line 23: In Claim 11, delete "Gin," and insert -- Gln, --.

Column 524, Line 25: In Claim 11, delete "lie," and insert -- Ile, --.

Column 524, Line 26: In Claim 11, delete "Gin," and insert -- Gln, --.

Column 524, Line 28: In Claim 11, delete "Gin," and insert -- Gln, --.

Column 524, Line 31: In Claim 11, delete "lie," and insert -- Ile, --.

Column 524, Line 31: In Claim 11, delete "Gin," and insert -- Gln, --.

Column 524, Line 34: In Claim 11, delete "Gin," and insert -- Gln, --.

Column 524, Line 36: In Claim 11, delete "Gin," and insert -- Gln, --.

Column 524, Line 44: In Claim 11, delete "Gin," and insert -- Gln, --.

Column 524, Line 46: In Claim 11, delete "Gin," and insert -- Gln, --.

Column 524, Line 53: In Claim 11, delete "Gin," and insert -- Gln, --.

Column 524, Line 58: In Claim 11, delete "Lie, Gin," and insert -- Ile, Gln, --.

Column 524, Line 60: In Claim 11, delete "lie," and insert -- Ile, --.

Column 524, Line 62: In Claim 11, delete "lie," and insert -- Ile, --.

Column 524, Line 67: In Claim 11, delete "Gin," and insert -- Gln, --.

Column 525, Line 2: In Claim 11, delete "Gin," and insert -- Gln, --.

Column 525, Line 4: In Claim 11, delete "Gin," and insert -- Gln, --.

Column 525, Line 6: In Claim 11, delete "Gin," and insert -- Gln, --.

Column 525, Line 8: In Claim 11, delete "Gin," and insert -- Gln, --.

Column 525, Line 17: In Claim 11, delete "Gin," and insert -- Gln, --.

CERTIFICATE OF CORRECTION (continued)
U.S. Pat. No. 11,827,699 B2

Column 525, Line 18: In Claim 11, delete "Gin," and insert -- Gln, --.

Column 525, Line 28: In Claim 11, delete "Gin," and insert -- Gln, --.

Column 525, Line 29: In Claim 11, delete "lie," and insert -- Ile, --.

Column 525, Line 30: In Claim 11, delete "Gin," and insert -- Gln, --.

Column 525, Line 31: In Claim 11, delete "lie," and insert -- Ile, --.

Column 525, Line 34: In Claim 11, delete "Gin," and insert -- Gln, --.

Column 525, Line 36: In Claim 11, delete "Gin," and insert -- Gln, --.

Column 525, Line 39: In Claim 11, delete "Gin," and insert -- Gln, --.

Column 525, Line 42: In Claim 11, delete "Gin," and insert -- Gln, --.

Column 525, Line 45: In Claim 11, delete "le," and insert -- Ile, --.

Column 525, Line 46: In Claim 11, delete "Gin," and insert -- Gln, --.

Column 525, Line 51: In Claim 11, delete "lie," and insert -- Ile, --.

Column 525, Line 51: In Claim 11, delete "Gin," and insert -- Gln, --.

Column 525, Line 61: In Claim 11, delete "lie," and insert -- Ile, --.

Column 525, Line 61: In Claim 11, delete "Gin," and insert -- Gln, --.

Column 526, Line 2: In Claim 11, delete "lie," and insert -- Ile, --.

Column 526, Line 40: In Claim 15, delete "lie," and insert -- Ile, --.

Column 526, Line 40: In Claim 15, delete "Gin," and insert -- Gln, --.

Column 526, Line 61: In Claim 17, delete "Gin," and insert -- Gln, --.

Column 527, Line 1: In Claim 17, delete "Gin," and insert -- Gln, --.

Column 527, Line 4: In Claim 17, delete "Gin," and insert -- Gln, --.

Column 527, Line 9: In Claim 17, delete "Gin," and insert -- Gln, --.

Column 527, Line 19: In Claim 17, delete "Trp," and insert -- Trp; --.

CERTIFICATE OF CORRECTION (continued)
U.S. Pat. No. 11,827,699 B2

Column 527, Line 21: In Claim 17, delete "Gin," and insert -- Gln, --.

Column 527, Line 27: In Claim 17, delete "Gin," and insert -- Gln, --.

Column 527, Line 36: In Claim 17, delete "Lie," and insert -- Ile, --.

Column 527, Line 54: In Claim 20, delete "RIB," and insert -- RIIB, --.

Column 528, Line 23 (approx.): In Claim 20, delete "Gro-β" and insert -- Gro-β, --.

Column 528, Line 45 (approx.): In Claim 20, delete "PEG40," and insert -- PEG-40, --.

Column 528, Line 51 (approx.): In Claim 20, delete "TGF-β," and insert -- TGF-β3, --.